US011917910B2

(12) United States Patent
Lee et al.

(10) Patent No.: US 11,917,910 B2
(45) Date of Patent: Feb. 27, 2024

(54) ORGANIC COMPOUND AND ORGANIC ELECTROLUMINESCENT DEVICE USING THE SAME

(71) Applicant: SOLUS ADVANCED MATERIALS CO., LTD., Iksan-si (KR)

(72) Inventors: Yong Hwan Lee, Yongin-si (KR); Min Sik Eum, Yongin-si (KR); Jae Yi Sim, Yongin-si (KR); Woo Jae Park, Yongin-si (KR); Song Ie Han, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 397 days.

(21) Appl. No.: 16/626,134

(22) PCT Filed: May 18, 2018

(86) PCT No.: PCT/KR2018/005746
§ 371 (c)(1),
(2) Date: Dec. 23, 2019

(87) PCT Pub. No.: WO2019/004599
PCT Pub. Date: Jan. 3, 2019

(65) Prior Publication Data
US 2020/0251659 A1 Aug. 6, 2020

(30) Foreign Application Priority Data
Jun. 30, 2017 (KR) .................. 10-2017-0083739

(51) Int. Cl.
H01L 51/00 (2006.01)
C07D 403/10 (2006.01)
C09K 11/06 (2006.01)
C07D 405/14 (2006.01)
C07D 409/14 (2006.01)
C07D 401/14 (2006.01)
C07D 403/14 (2006.01)
C07D 413/14 (2006.01)
C07D 471/04 (2006.01)
C07F 9/6558 (2006.01)
C07D 487/04 (2006.01)
H10K 85/60 (2023.01)
H10K 50/11 (2023.01)
H10K 50/15 (2023.01)
H10K 50/17 (2023.01)
H10K 50/16 (2023.01)
H10K 101/10 (2023.01)

(52) U.S. Cl.
CPC ......... H10K 85/654 (2023.02); C07D 401/14 (2013.01); C07D 403/10 (2013.01); C07D 403/14 (2013.01); C07D 405/14 (2013.01); C07D 409/14 (2013.01); C07D 413/14 (2013.01); C07D 471/04 (2013.01); C07D 487/04 (2013.01); C07F 9/65583 (2013.01); C09K 11/06 (2013.01); H10K 85/615 (2023.02); H10K 85/622 (2023.02); H10K 85/624 (2023.02); H10K 85/626 (2023.02); H10K 85/636 (2023.02); H10K 85/657 (2023.02); H10K 85/6572 (2023.02); H10K 85/6574 (2023.02); H10K 85/6576 (2023.02); C09K 2211/1018 (2013.01); H10K 50/11 (2023.02); H10K 50/15 (2023.02); H10K 50/166 (2023.02); H10K 50/17 (2023.02); H10K 50/171 (2023.02); H10K 2101/10 (2023.02)

(58) Field of Classification Search
None
See application file for complete search history.

(56) References Cited

U.S. PATENT DOCUMENTS

2012/0104941 A1    5/2012  Jung et al.
2017/0186964 A1    6/2017  Cho et al.
2018/0114917 A1*   4/2018  Lee .................. C07D 403/10
2020/0317654 A1*  10/2020  Jang ................. C07D 407/14

FOREIGN PATENT DOCUMENTS

| CN | 103261171 A | 8/2013 |
| CN | 109096217 A | 12/2018 |
| CN | 109312230 A | 2/2019 |
| JP | 2006510732 A | 3/2006 |
| JP | 2014507383 A | 3/2014 |
| JP | 2014532302 A | 12/2014 |
| JP | 10-2016-0078251 A | 7/2016 |
| JP | 2019006767 A | 1/2019 |
| KR | 1020120140603 A | 12/2012 |
| KR | 10-2013-0130777 A | 12/2013 |

(Continued)

OTHER PUBLICATIONS

Machine English translation of Lee et al. (WO 2017/069442 A1). Mar. 29, 2023.*
International Search Report for PCT/KR2018/005746 dated Aug. 27, 2018 [PCT/ISA/210].
Written Opinion for PCT/KR2018/005746 dated Aug. 27, 2018 [PCT/ISA/210].

Primary Examiner — Jay Yang
(74) Attorney, Agent, or Firm — Sughrue Mion, PLLC

(57) ABSTRACT

The present invention relates to a novel organic compound and an organic electroluminescent device using the same, and more particularly, to a novel compound having excellent electron transport capability and light emitting capability, and an organic electroluminescent device improved in terms of luminous efficiency, driving voltage, lifespan, etc. by including the novel compound in one or more organic layers.

4 Claims, No Drawings

(56) References Cited

FOREIGN PATENT DOCUMENTS

| | | |
|---|---|---|
| KR | 10-2016-0090262 A | 7/2016 |
| KR | 10-1847347 B1 | 4/2018 |
| WO | 2016204375 A1 | 12/2016 |
| WO | 2016204406 A1 | 12/2016 |
| WO | WO-2016/204375 A1 * | 12/2016 |
| WO | 2017055264 A1 | 4/2017 |
| WO | 2017069442 A1 | 4/2017 |
| WO | 2018012718 A1 | 1/2018 |

* cited by examiner

ORGANIC COMPOUND AND ORGANIC ELECTROLUMINESCENT DEVICE USING THE SAME

CROSS REFERENCE TO RELATED APPLICATIONS

This application is a National Stage of International Application No. PCT/KR2018/005746 filed May 18, 2018, claiming priority based on Korean Patent Application No. 10-2017-0083739 filed Jun. 30, 2017.

TECHNICAL FIELD

The present invention relates to a novel organic compound and an organic electroluminescent device using the same, and more particularly, to a compound having excellent electron transport capability and light emitting capability, and an organic electroluminescent device improved in terms of luminous efficiency, driving voltage, lifespan, etc. by including the compound in one or more organic layers.

BACKGROUND ART

Starting from Bernanose's observation of light emission from organic thin films in the 1950s, the study of organic electroluminescent devices led to blue electroluminescence using anthracene monocrystals in 1965, and Tang suggested in 1987 an organic electroluminescent device in a stack structure which may be divided into functional layers of hole and light-emitting layers. Then, in order to develop high efficiency, long life span organic electroluminescent devices, organic layers each having distinctive characteristics have been introduced in the electroluminescent devices, leading to the development of specialized materials used therein.

In the organic electroluminescent device, upon application of voltage between two electrodes, holes are injected from an anode and electrons are injected from a cathode into the organic layer. Injected holes and electrons meet each other to form excitons, and light emission occurs when the excitons fall to a ground state. In such a case, materials used for the organic layer may be classified into, for example, luminescent materials, hole injection materials, hole transporting materials, electron transporting materials and electron injection materials according to their function.

Materials forming a light-emitting layer of an organic electroluminescent device may be classified into blue, green and red luminescent materials according to their emission colors. Besides, yellow and orange luminescent materials may be used as a luminescent material for implementing better natural colors. In addition, a host/dopant system may be employed in the luminescent material to increase color purity and luminous efficiency through energy transfer.

Dopant materials may be classified into fluorescent dopants using organic materials and phosphorescent dopants using metal complex compounds that include heavy atoms such as Ir and Pt. The developed phosphorescent materials may improve the luminous efficiency theoretically up to four times as compared to fluorescent materials, so attention is given to phosphorescent dopants as well as phosphorescent host materials.

To date, NPB, BCP and $Alq_3$, for example, are widely known as materials used in the hole injection layer, the hole transporting layer, the hole blocking layer and the electron transporting layer, and anthracene derivatives have been reported as fluorescent dopant/host materials for luminescent materials. Particularly, metal complex compounds, such as Flrpic, $Ir(ppy)_3$, and $Ir(btp)_2(acac)$, which include Ir are used as blue, green and red dopant materials for the phosphorescent materials having great advantages in terms of efficiency improvement among luminescent materials. Up to this day, CBP has shown excellent properties as a phosphorescent host material.

However, conventional luminescent materials have low glass transition temperatures and poor thermal stability, despite of their advantageous luminous characteristics, and thus are not satisfactory in terms of lifespan for organic electroluminescent devices. Accordingly, there is a demand for development of luminescent materials having excellent performance.

* Prior art document: Japanese Patent Laid-Open No. 2001-160489.

DETAILED DESCRIPTION OF THE INVENTION

Technical Problem

In order to solve the above-described problems, the present invention is directed to providing a novel organic compound, applicable to organic electroluminescent devices, that is excellent in electron transport capability and light emitting capability by satisfying, for example, the required, proper range of energy level, electrochemical stability and thermal stability.

The present invention is also directed to providing an organic electroluminescent device that shows a low driving voltage and high luminous efficiency and has an improved life span, by including the novel organic compound.

TECHNICAL SOLUTION

In order to achieve the above object, the present invention provides a compound represented by the following Chemical Formula 1:

[Chemical Formula 1]

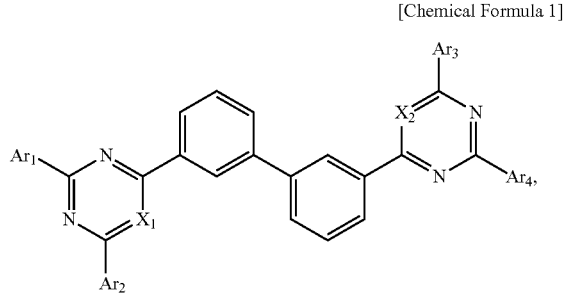

where $X_1$ and $X_2$ are the same as or different from each other and are each independently $CR_1$ or N, wherein when $X_1$ and $X_2$ are both $CR_1$, the plurality of $R_1$ are the same as or different from each other, $R_1$ is selected from the group consisting of hydrogen, deuterium, halogen, a cyano group, a $C_1$ to $C_{40}$ alkyl group, a $C_6$ to $C_{60}$ aryl group and a heteroaryl group having 5 to 60 nuclear atoms;

$Ar_1$ to $Ar_4$ are the same as or different from each other and are each independently a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, wherein a case where all of $Ar_1$ to $Ar_4$ are the same as each other is excluded; and the alkenyl group, the alkynyl group, the cycloalkyl group, the heterocycloalkyl group, the alkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $Ar_1$ to $Ar_4$ are each independently substituted or unsubstituted with one or more kinds of substituents selected from the group consisting of deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, wherein when the substituents are plural in number, the substituents are the same as or different from each other.

In addition, the present invention also provides an organic electroluminescent device including an anode, a cathode and one or more organic layers interposed between the anode and the cathode. At least one of the one or more organic layers includes the compound represented by Chemical Formula 1.

The organic layer including the compound represented by Chemical Formula 1 may be selected from the group consisting of: a hole injection layer, a hole transporting layer, an auxiliary light-emitting layer, a light-emitting layer, an electron transporting layer, an auxiliary electron transporting layer and an electron injection layer.

In such a case, the compound represented by Chemical Formula 1 may be used as a phosphorescent host material of a light-emitting layer, and a material of an electron transporting layer and an auxiliary electron transporting layer.

Effects of the Invention

The compound represented by Chemical Formula 1 may be used as a material of an organic layer of an organic electroluminescent device by virtue of its thermal stability and excellent light emitting properties.

In particular, when the compound represented by Chemical Formula 1 of the present invention is used as a phosphorescent host material or an electron transporting material, an organic electroluminescent device that has a lower driving voltage and higher current efficiency may be manufactured, as compared to the case of using conventional host materials or electron transporting materials. In addition, it is possible to manufacture a full color display panel with improved performance and lifespan.

MODE FOR CARRYING OUT THE INVENTION

Hereinafter, the present invention will be described in detail.

1. Organic Compound

A novel organic compound according to the present invention has a structure, as a base skeleton, in which two electron-withdrawing groups (EWGs) are connected to each other through a linker (or linking group). In such an embodiment, the two EWGs are pyrimidine and triazine, and the linker is m,m-biphenylene. A compound in which various substituents are introduced into such a base skeleton is represented by Chemical Formula 1.

Since the compound represented by Chemical Formula 1 has a structure in which two 6-membered heterocycles (pyrimidine and triazine) having excellent electron withdrawing properties are linked to each other through a linker, it is electrochemically stable and has excellent electron transport properties as well as high triplet energy, high glass transition temperature and excellent thermal stability. Accordingly, the compound represented by Chemical Formula 1 has excellent electron transport capability and light emitting characteristics and thus may be used as a material of one of a light-emitting layer, an electron transporting layer and an electron injection layer, which are organic layers of the organic electroluminescent device. Preferably, the compound may be used as a material of one of a light-emitting layer, an electron transporting layer and an auxiliary electron transporting layer that is laminated additionally to the electron transporting layer, and more particularly, as a material of the electron transporting layer or the auxiliary electron transporting layer.

The compound represented by Chemical Formula 1 may have an improved glass transition temperature by having a significantly increased molecular weight of the compound, and accordingly, may have a higher thermal stability than the conventional single 6-membered heterocyclic compound.

In addition, the compound represented by Chemical Formula 1 may also exhibit effects of inhibiting crystallization of the organic layer by using the m,m-biphenylene linker. For this reason, an organic electroluminescent device to which the compound represented by Chemical Formula 1 is applied may have significantly improved durability and lifespan characteristics. In such a case, the organic electroluminescent device to which the compound represented by Chemical Formula 1 that has m,m-biphenylene as the linker is applied may exhibit excellent driving voltage, light emission peak and current efficiency, as compared to organic electroluminescent devices to which a compound that has p,p-biphenylene or m,p-biphenylene as the linker is applied.

In addition, the compound represented by Chemical Formula 1 may have an improved glass transition temperature by having a significantly increased molecular weight of the compound due to a variety of substituents (e.g., an aromatic cycle and a heterocycle) introduced into the base skeleton, such that durability and lifespan characteristics of the organic electroluminescent device may be significantly improved. The compound represented by Chemical Formula 1 may be used as a material of an organic layer of the organic electroluminescent device, and in particular, as a material of an electron transporting layer and a light-emitting layer.

Accordingly, when the compound represented by Chemical Formula 1 is used in an organic electroluminescent device, not only excellent thermal stability and carrier transporting capability (particularly, electron transport capability and light emitting capability) may be expected, but also the driving voltage, efficiency and lifespan, for example, of the device may be improved.

In addition, the compound represented by Chemical Formula 1 shows long lifespan characteristics while being very advantageous for electron transporting. The excellent electron transport capability of such a compound may achieve high efficiency and speedy mobility in the organic electroluminescent device and may easily control the HOMO and LUMO energy level according to the direction or location of the substituent. Accordingly, excellent electron transporting property may be exhibited in the organic electroluminescent device using such a compound.

Specifically, the compound represented by Chemical Formula 1 according to the present invention may be represented by the following Chemical Formula 2 or 3.

[Chemical Formula 2]

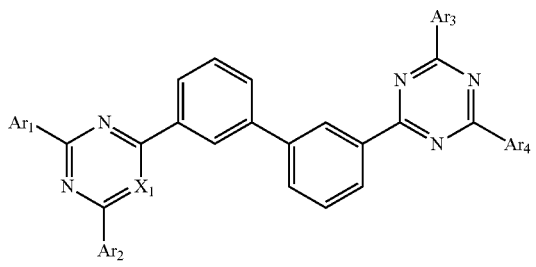

[Chemical Formula 3]

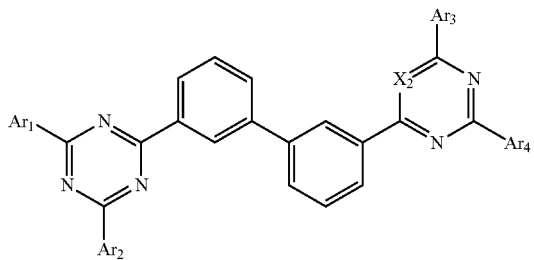

In Chemical Formulas 2 and 3, $X_1$ and $X_2$ and $Ar_1$ to $Ar_4$ are the same as those defined in Chemical Formula 1, respectively.

In an embodiment according to the present invention, at least one of $X_1$ and $X_2$ may be preferably N.

More preferably, one of $X_1$ and $X_2$ may be $CR_1$ and the other thereof may be N.

In addition, preferably, in an embodiment according to the present invention, $Ar_1$ to $Ar_4$ may be the same as or different from each other and may each be independently selected from a $C_1$ to $C_{40}$ alkyl group, a $C_6$ to $C_{60}$ aryl group, a heteroaryl group having 5 to 60 nuclear atoms, $C_6$ to $C_{60}$ aryloxy group, a $C_6$ to $C_{60}$ arylphosphine oxide group and a $C_6$ to $C_{60}$ arylamine group.

More preferably, $Ar_1$ to $Ar_4$ may be the same as or different from each other and may each independently be a $C_6$ to $C_{60}$ aryl group and/or a heteroaryl group having 5 to 60 nuclear atoms. As a specific example, when one of $Ar_1$ to $Ar_4$ is a $C_6$ to $C_{60}$ aryl group, the other three may each be a $C_6$ to $C_{60}$ aryl group and/or a heteroaryl group having 5 to 60 nuclear atoms. As another example, when two of $Ar_1$ to $Ar_4$ are $C_6$ to $C_{60}$ aryl groups, the other two may each be a $C_6$ to $C_{60}$ aryl group and/or a heteroaryl group having 5 to 60 nuclear atoms. As another example, when three of $Ar_1$ to $Ar_4$ are $C_6$ to $C_{60}$ aryl groups, the other one may be a $C_6$ to $C_{60}$ aryl group and/or a heteroaryl group having 5 to 60 nuclear atoms. As another example, all of $Ar_1$ to $Ar_4$ may each be a $C_6$ to $C_{60}$ aryl group.

Preferably, in an embodiment according to the present invention, the alkyl group, the aryl group, the heteroaryl group, the aryloxy group, the arylphosphine oxide group and the arylamine group of $Ar_1$ to $Ar_4$ may each independently be substituted or unsubstituted with one or more kinds of substituents selected from the group consisting of: deuterium, halogen, a cyano group, a nitro group, a $C_1$ to $C_{40}$ alkyl group, a $C_6$ to $C_{60}$ aryl group, a heteroaryl group having 5 to 60 nuclear atoms, a $C_6$ to $C_{60}$ aryloxy group, a $C_6$ to $C_{60}$ arylphosphine oxide group and a $C_6$ to $C_{60}$ arylamine group, and when the substituents are plural in number, they may be the same as or different from each other.

Except the case where all of $Ar_1$ to $Ar_4$ are the same as each other, $Ar_1$ to $Ar_4$ may each independently be embodied into a substituent selected from the following Constitutional Formulas:

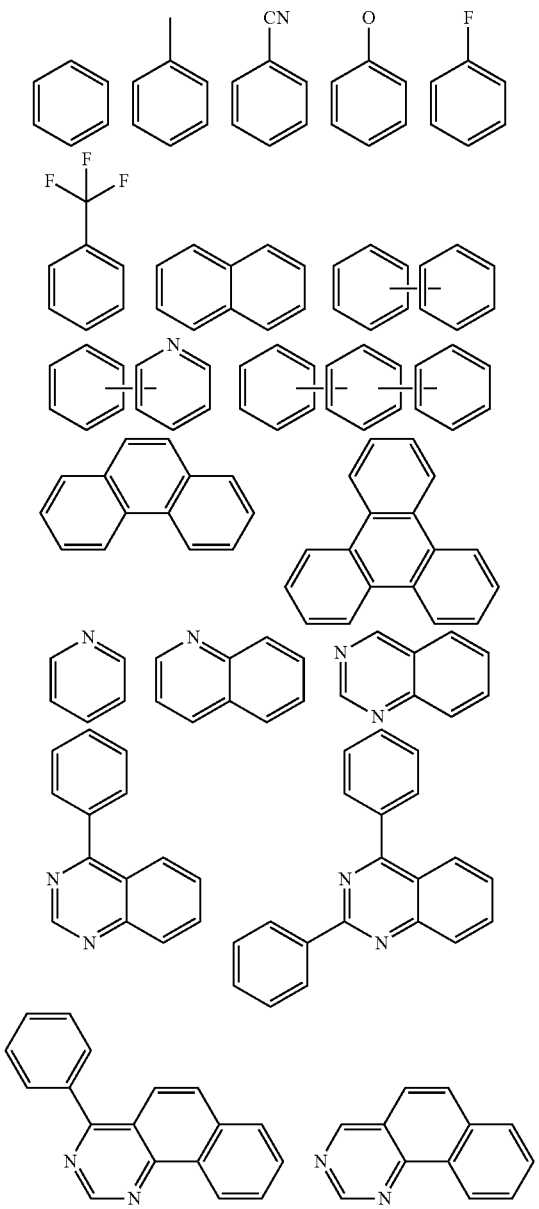

-continued
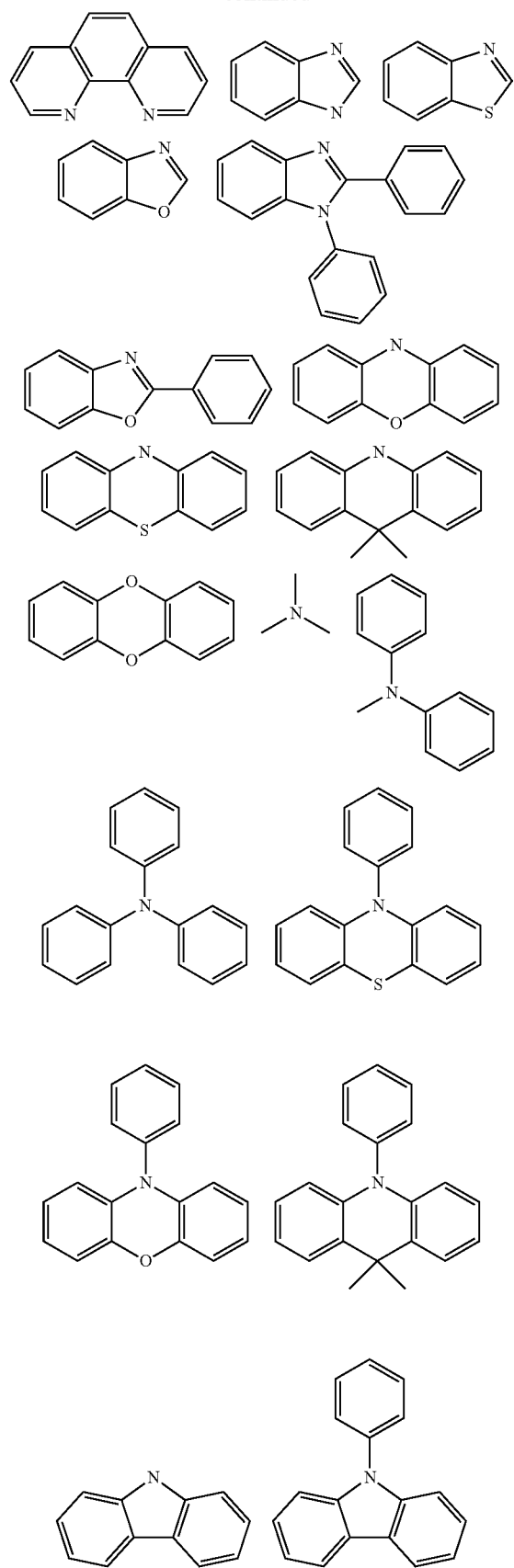
-continued
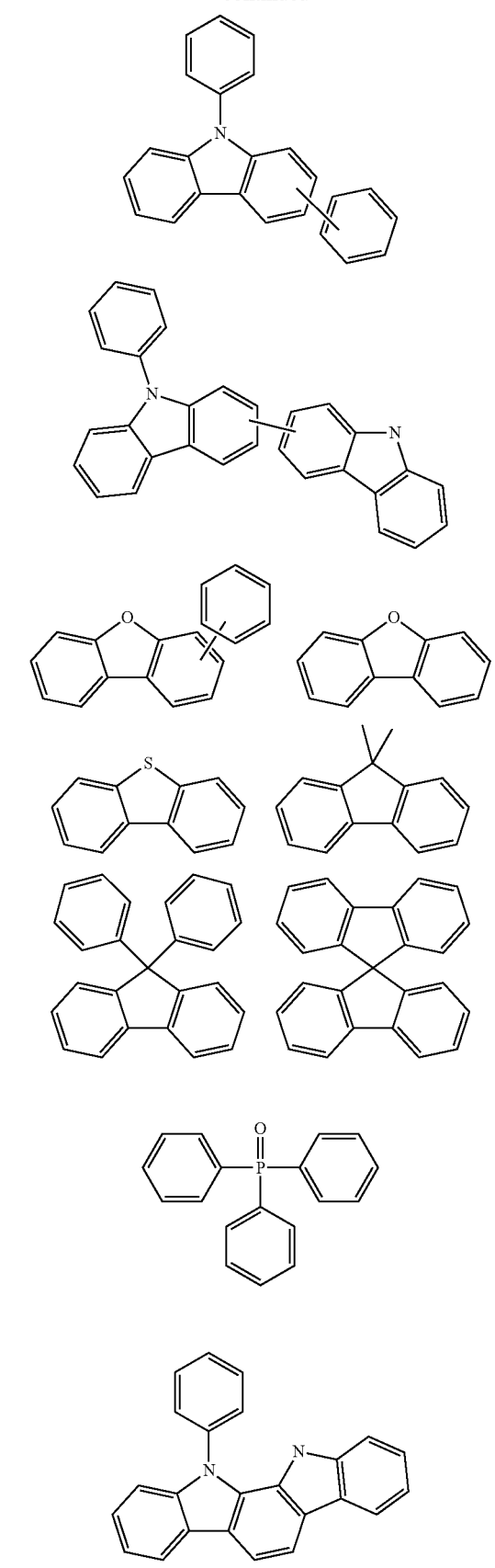

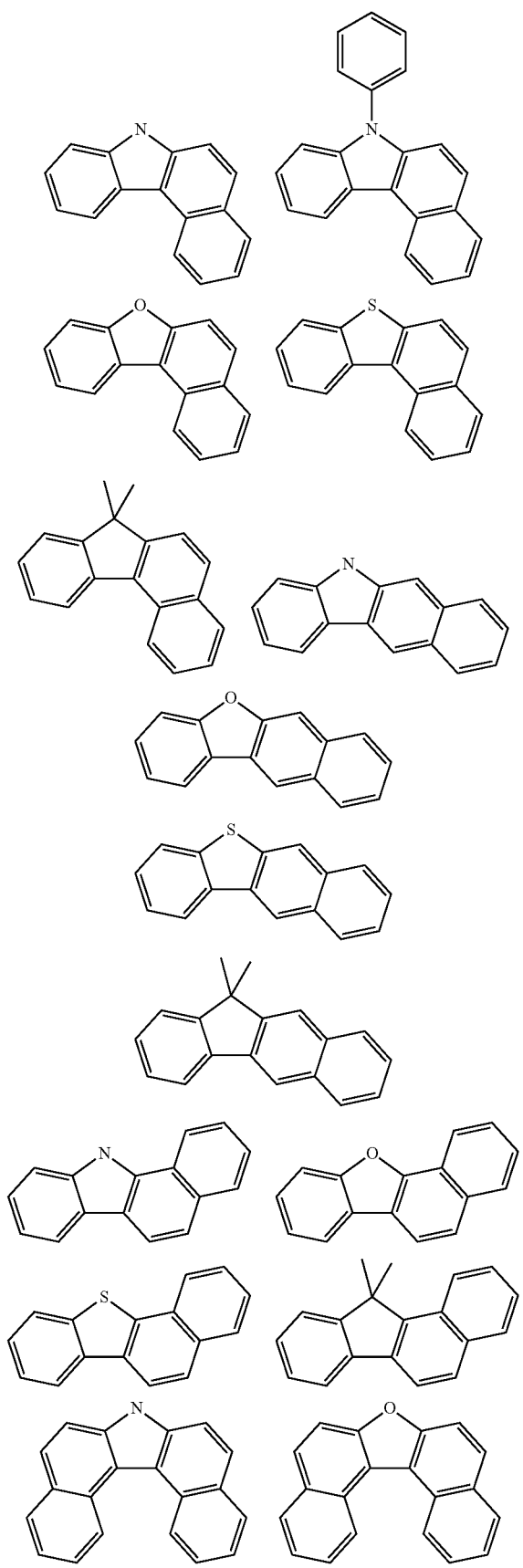
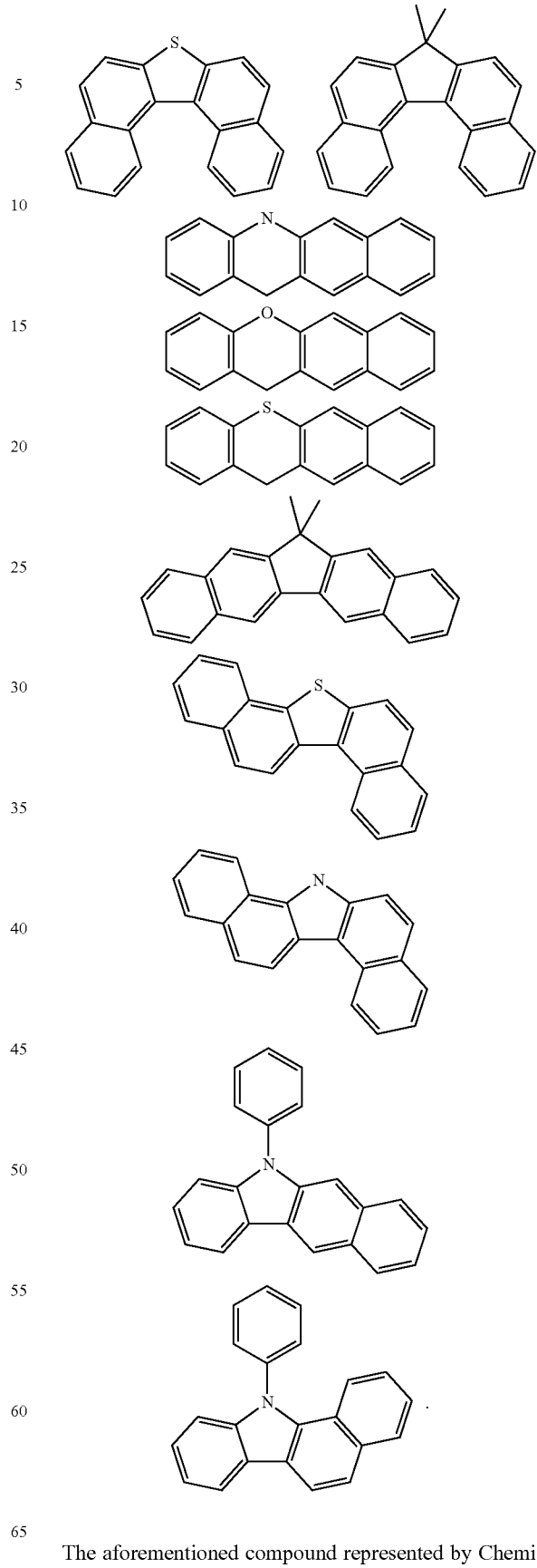
The aforementioned compound represented by Chemical Formula 1 according to the present invention may be more specifically embodied into any one of compounds represented by Compounds 1 to 696 exemplified below. However, the compound represented by Chemical Formula 1 of the present invention is not limited to those illustrated below.
1
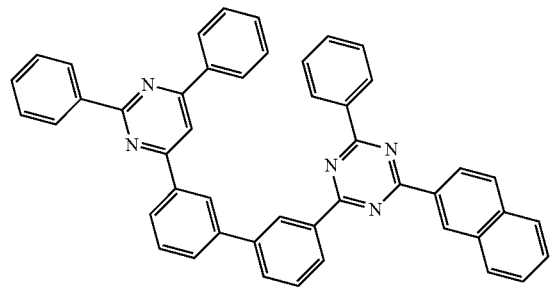
2
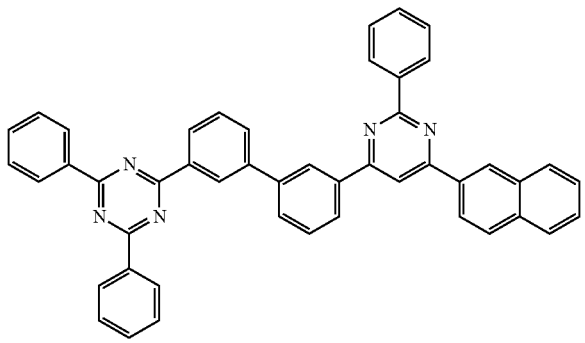
3
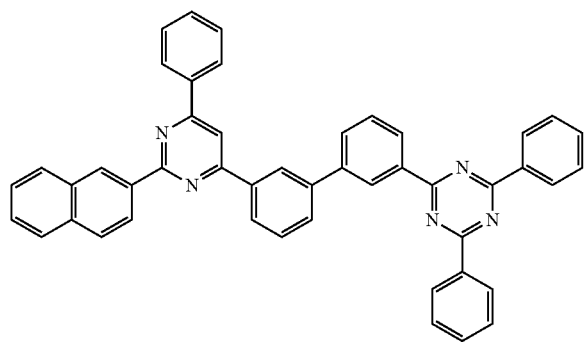
4
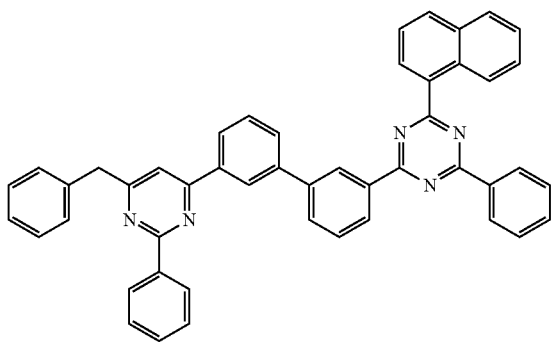
5
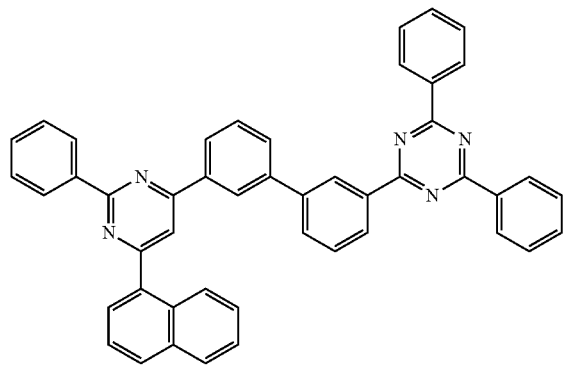
6
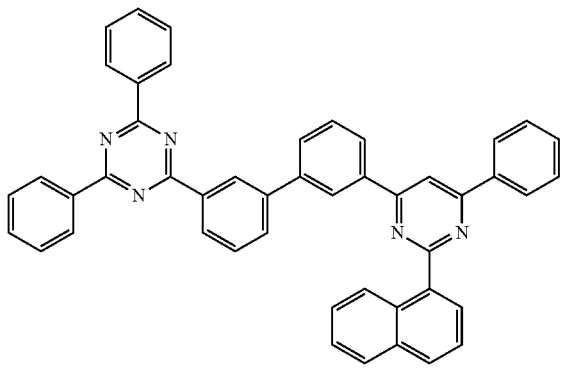
7
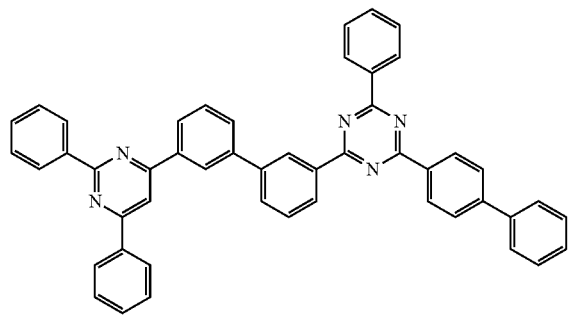
8
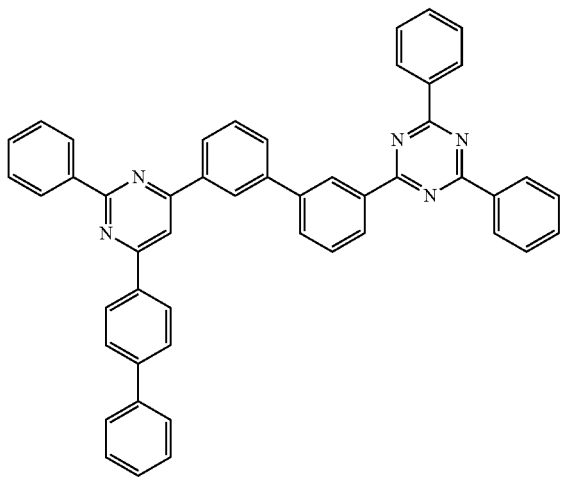

-continued
9
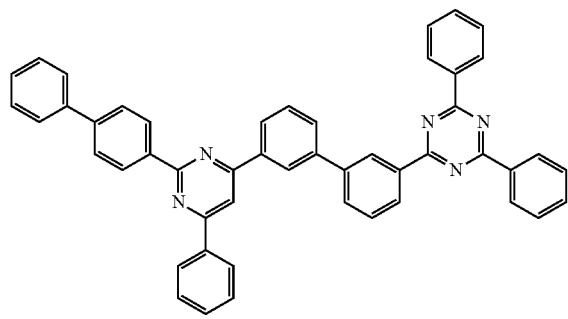
10
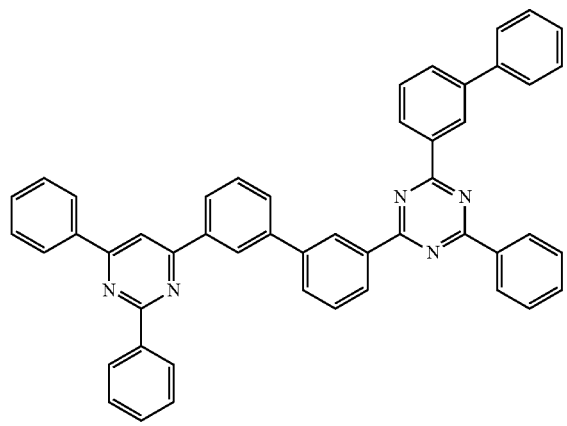
11
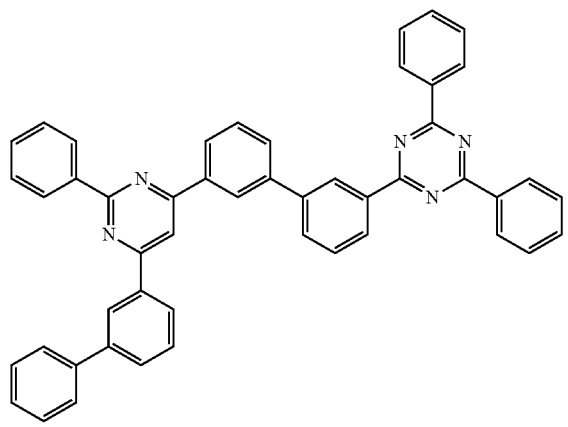
12
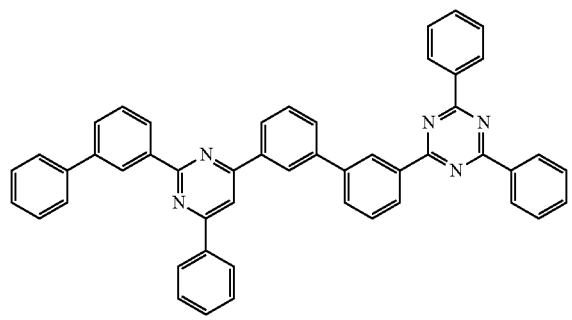
13
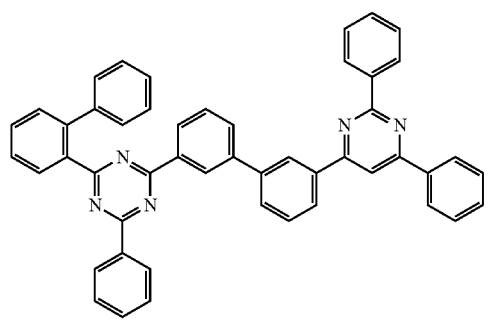
14
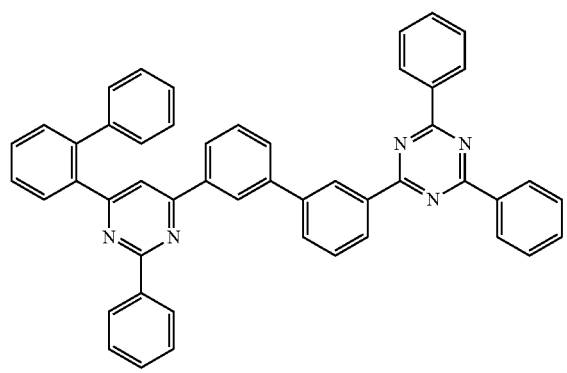

-continued
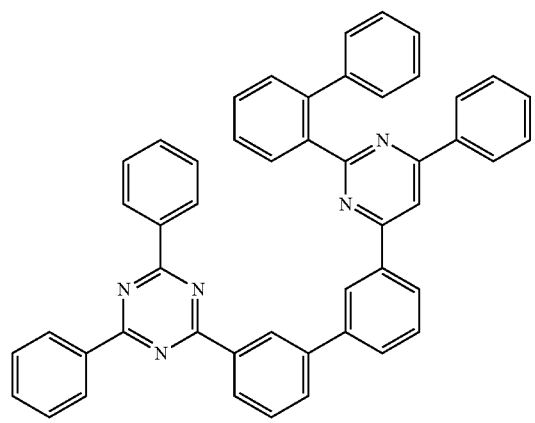
15
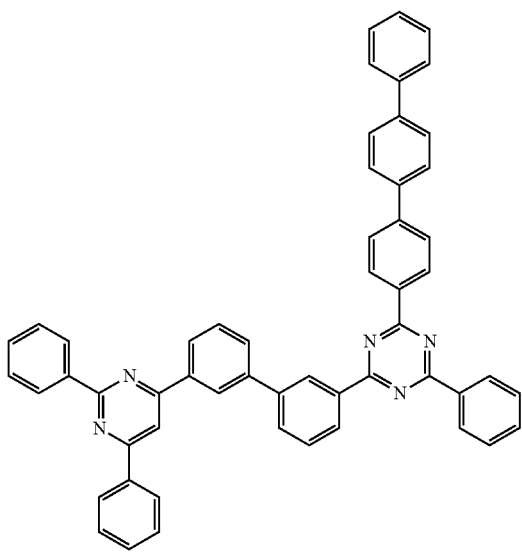
16
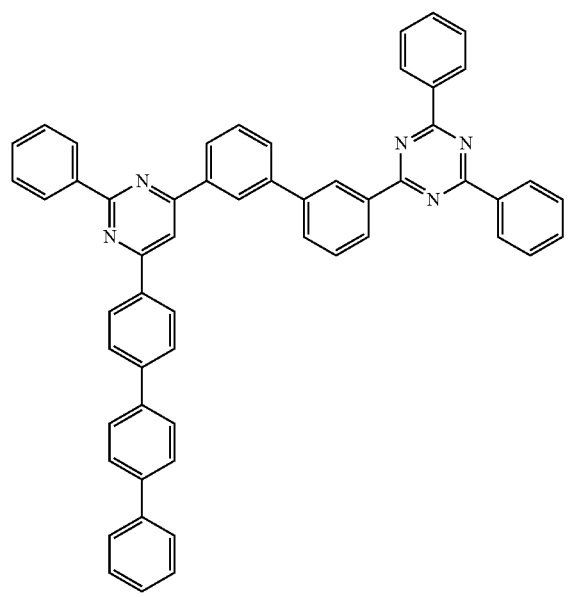
17
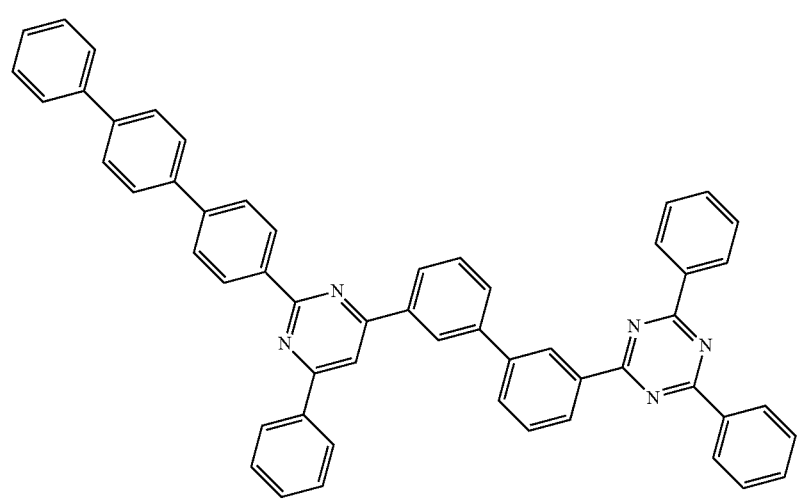
18

-continued
19
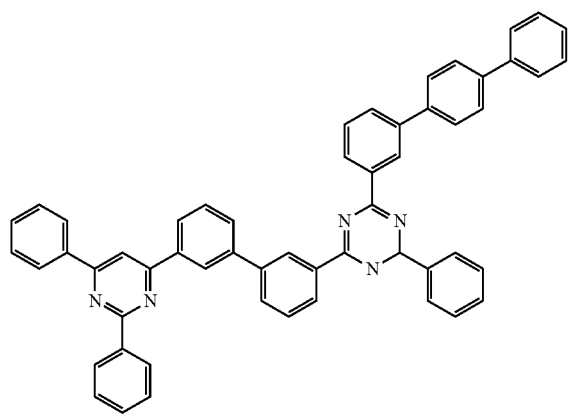
20
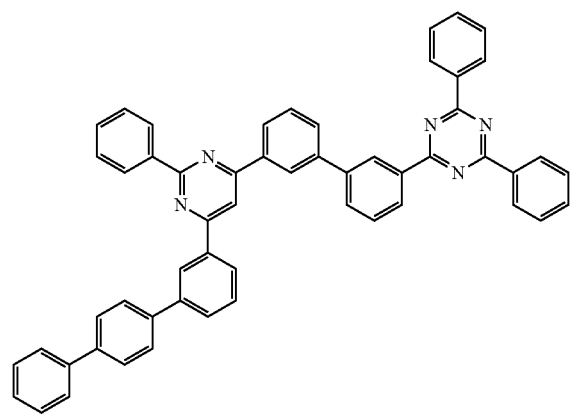
21
22
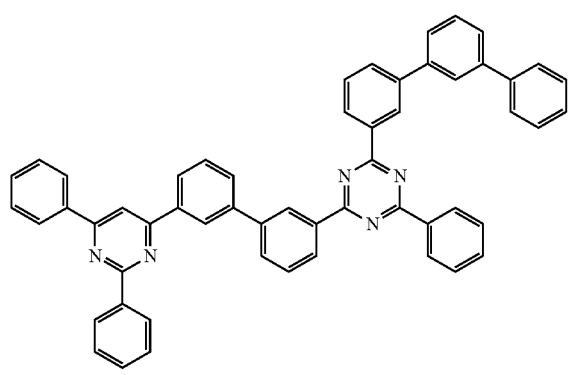
23
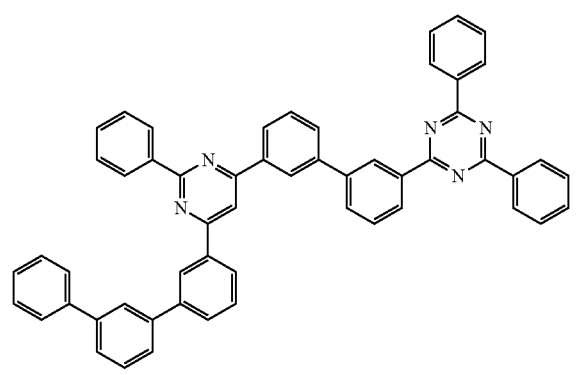
24
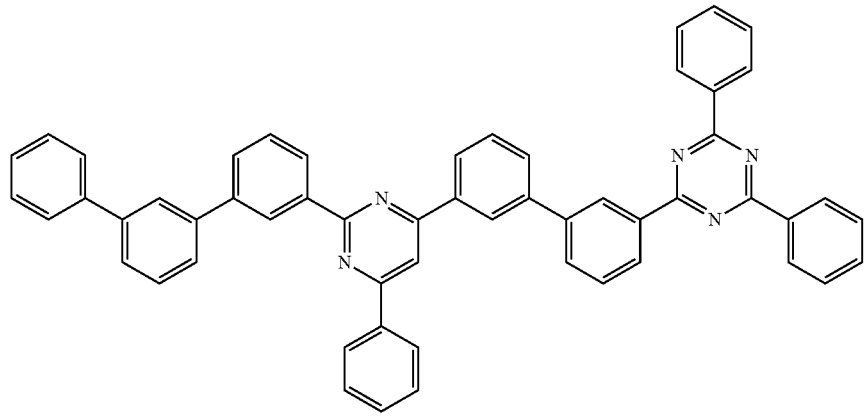

-continued
25
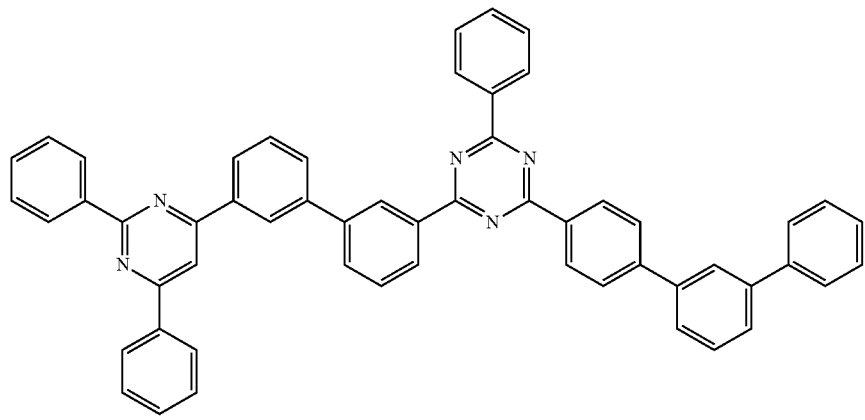
26
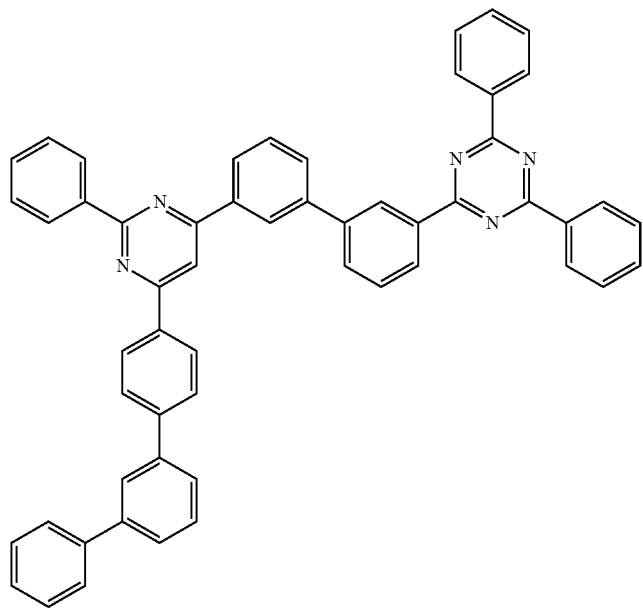
27
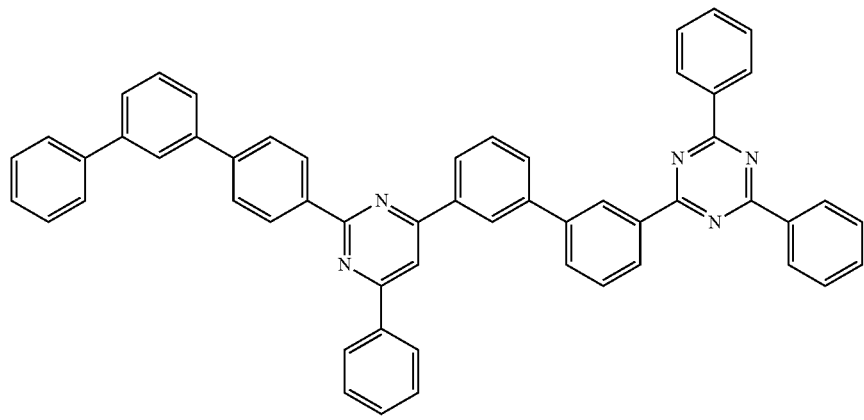

-continued
28
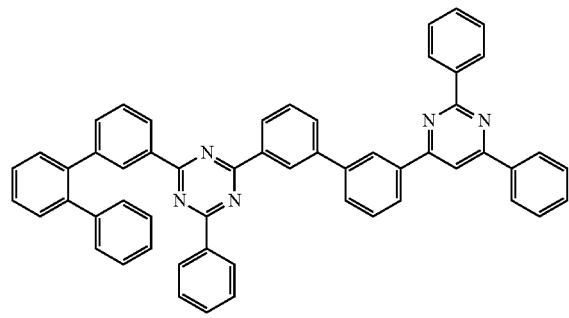
29
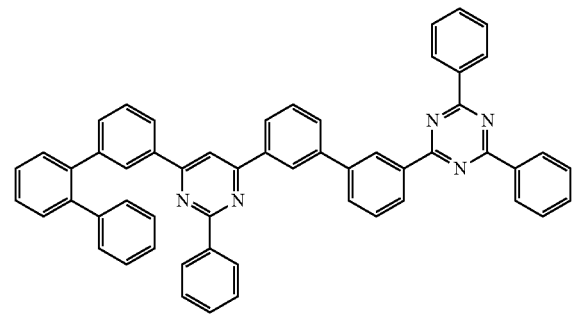
30
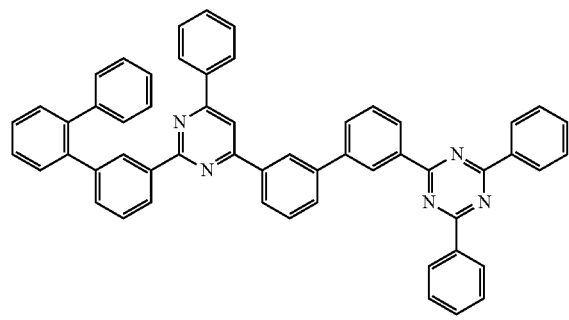
31
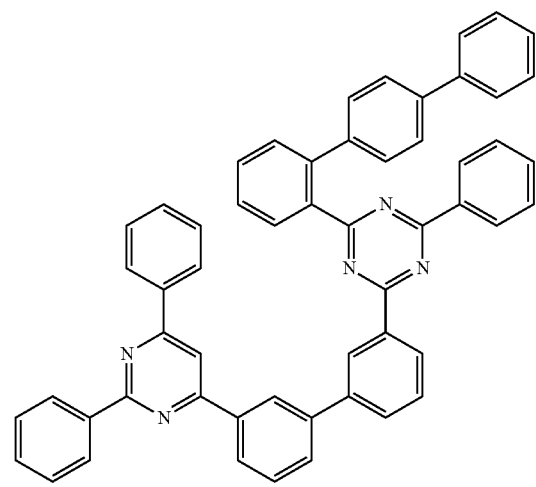
32
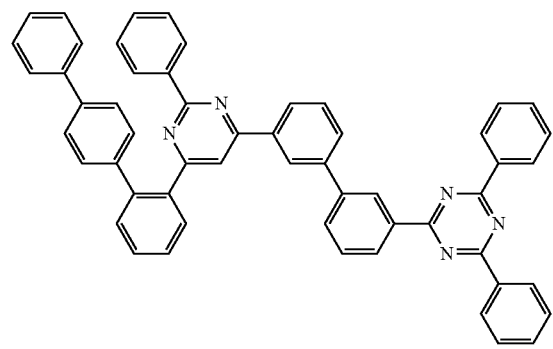
33
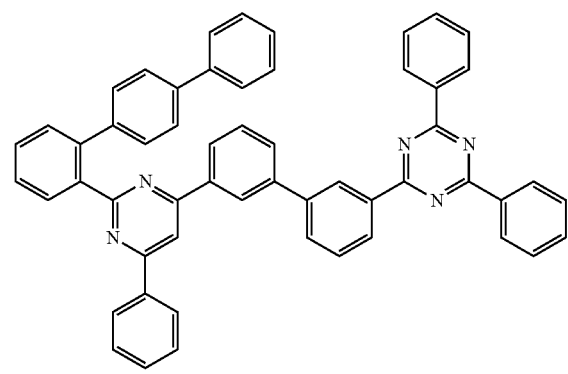

-continued
34
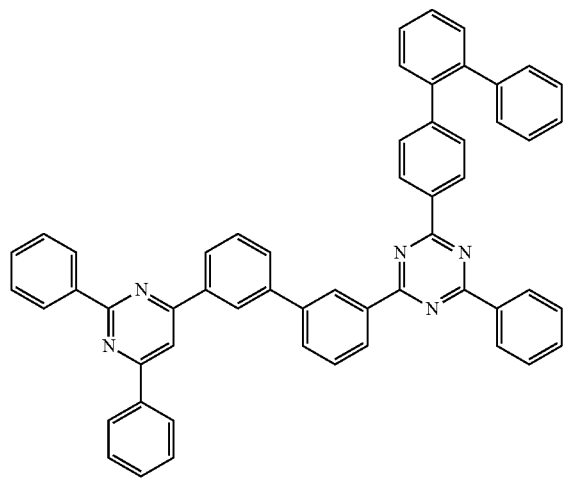
35
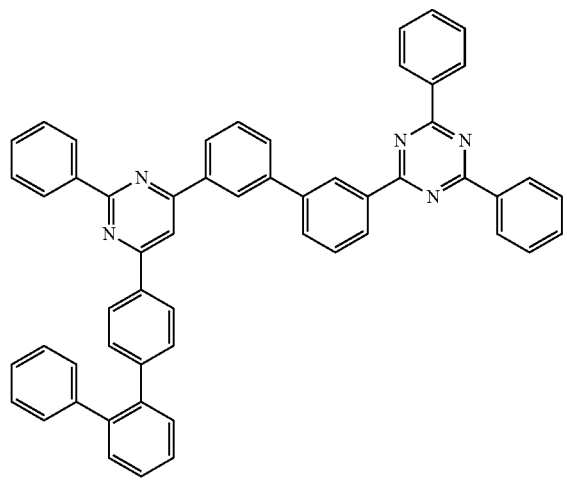
36
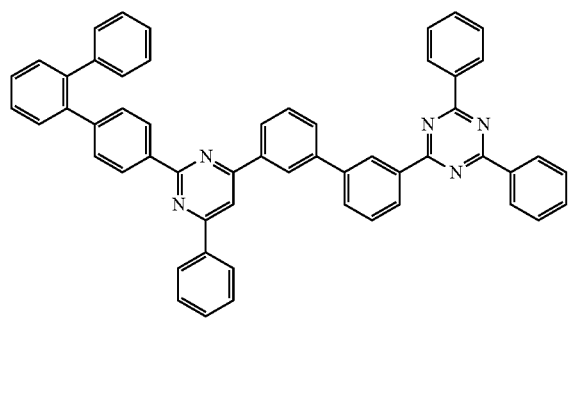
37
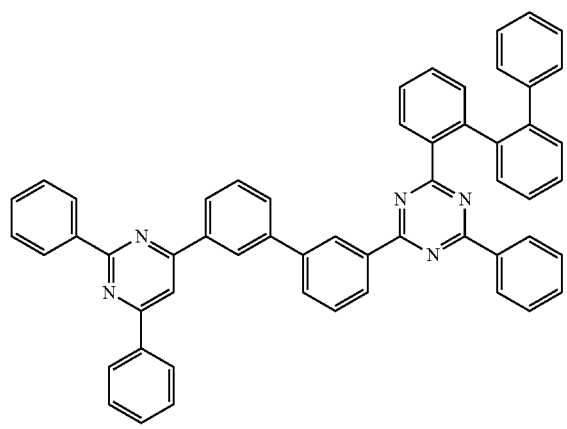
38
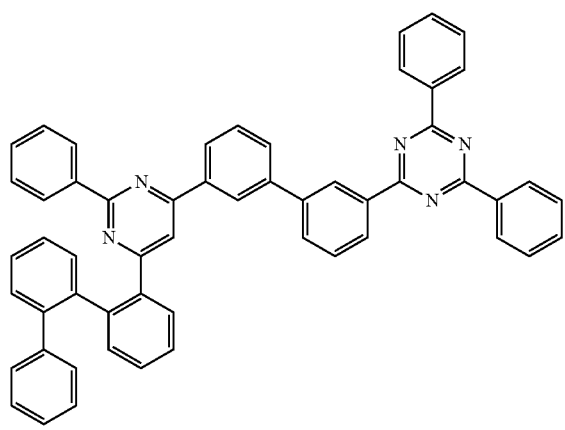
39
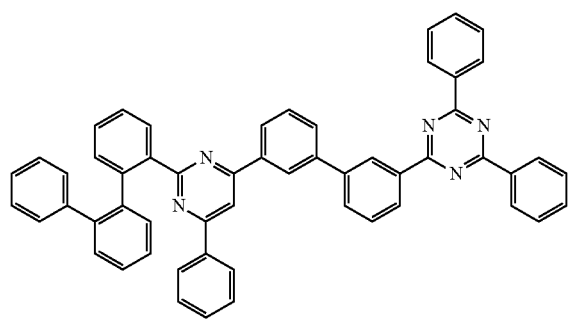

-continued
40
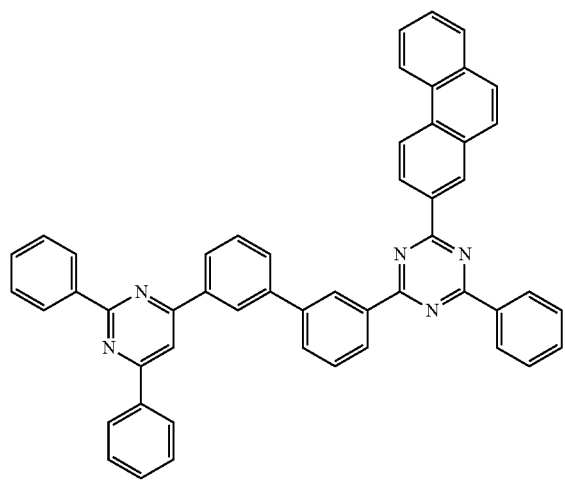
41
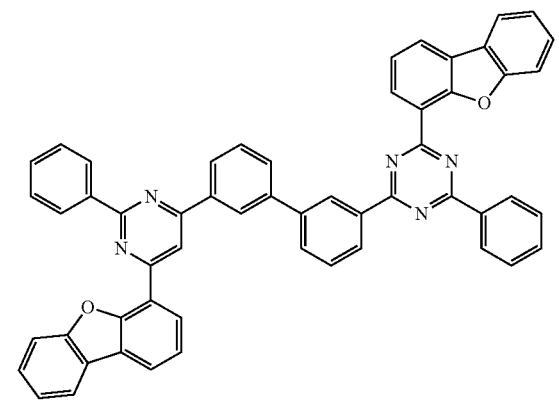
42
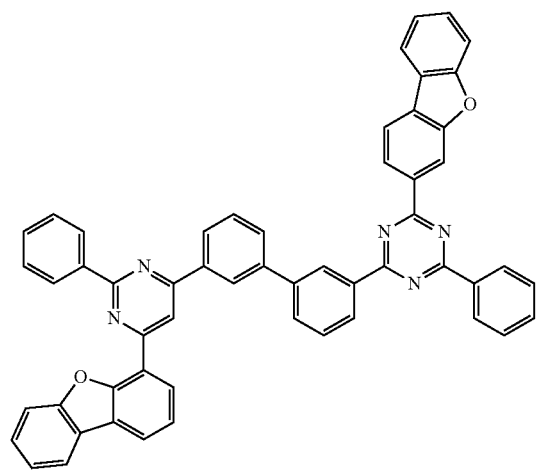
43
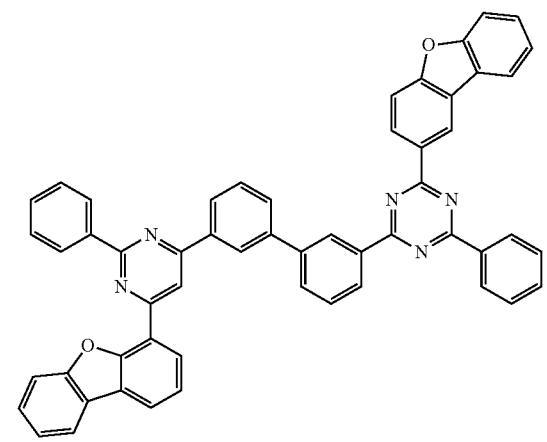
44
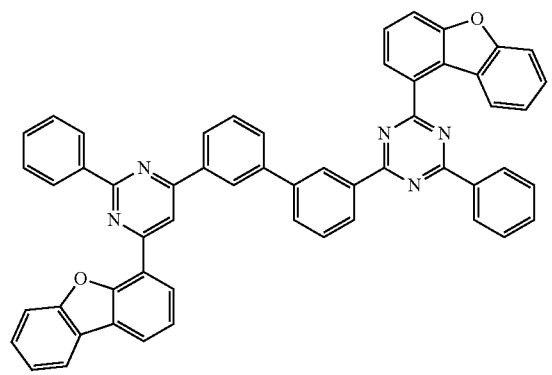
45
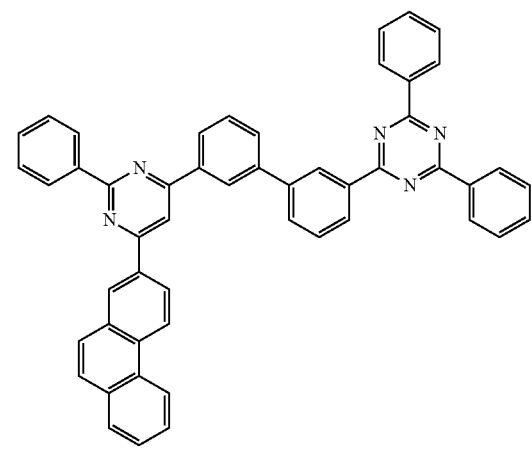

-continued
46
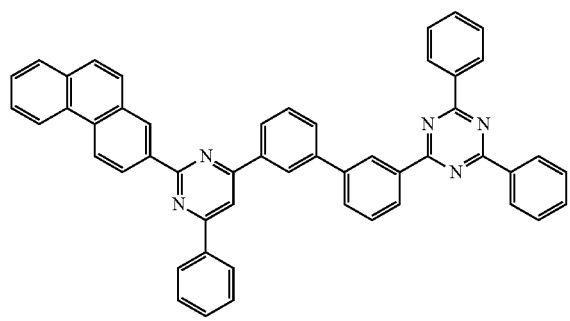
47
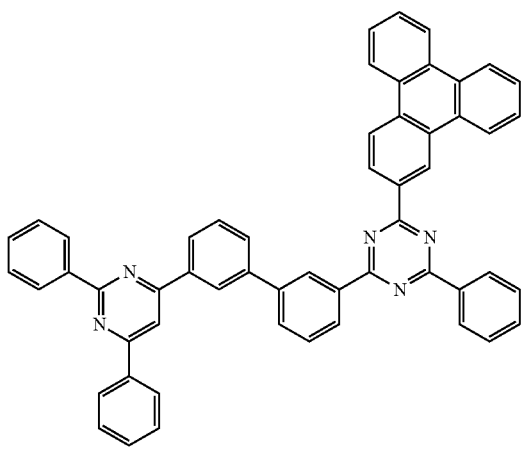
48
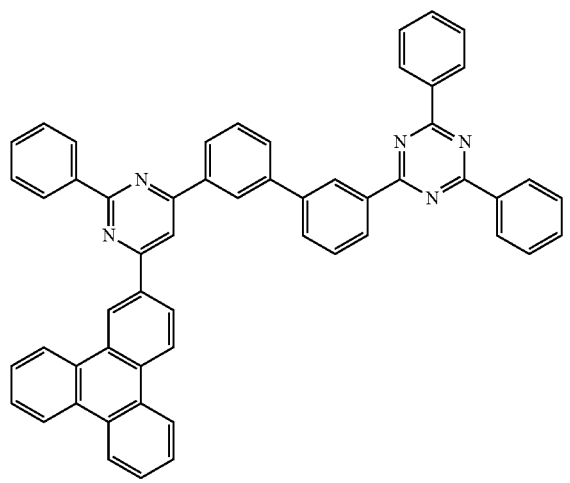
49
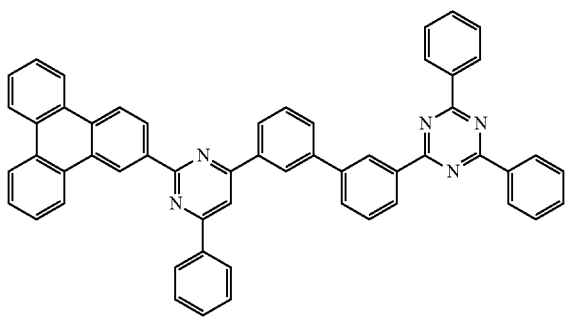
50
51
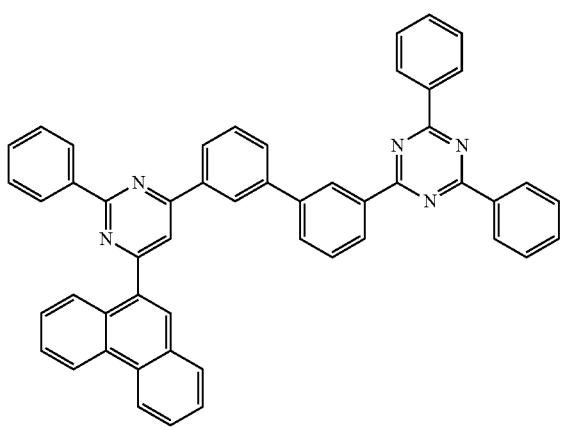

52
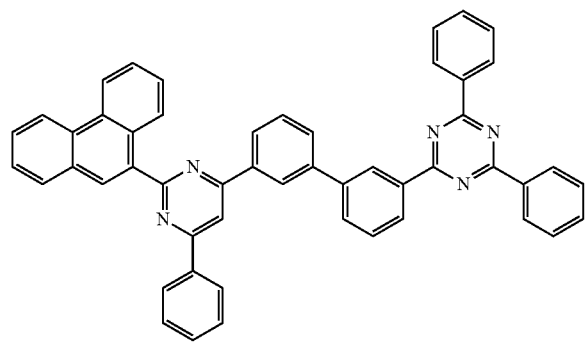
53
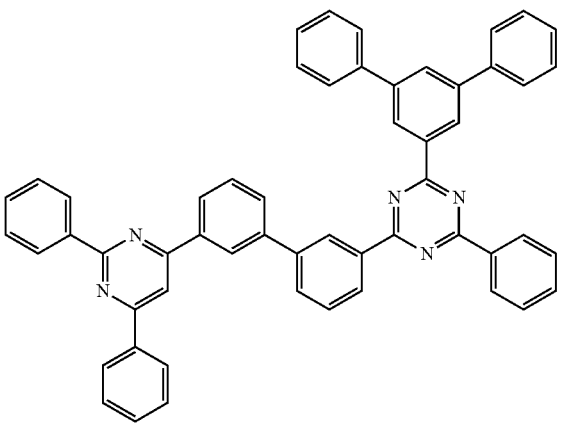
54
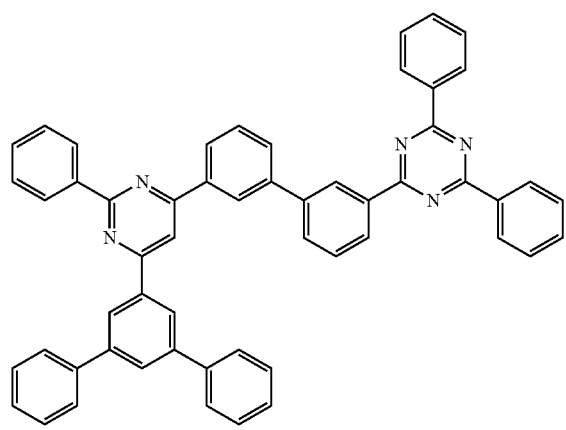
55
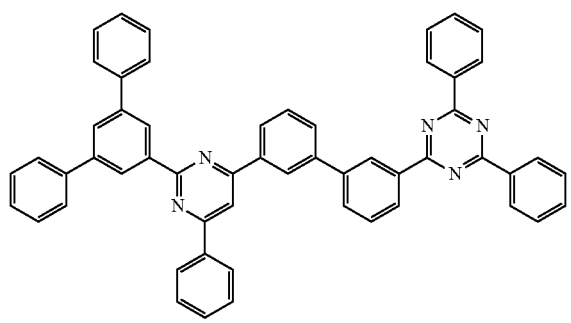
56
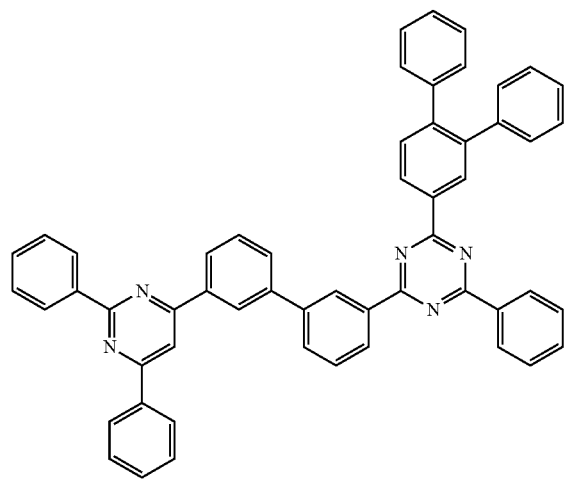
57
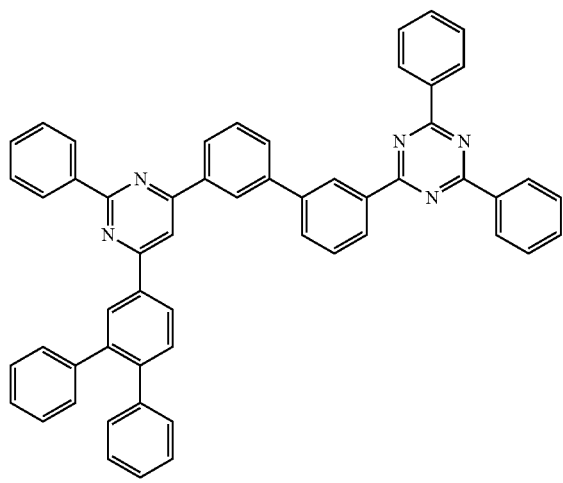

-continued
58
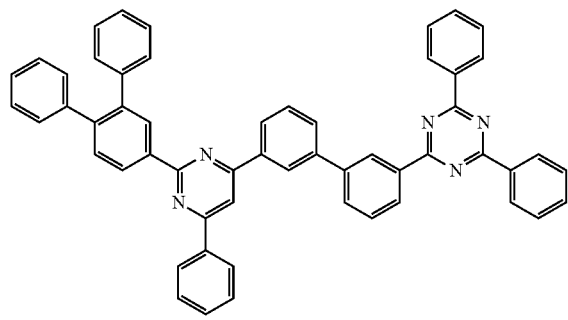
59
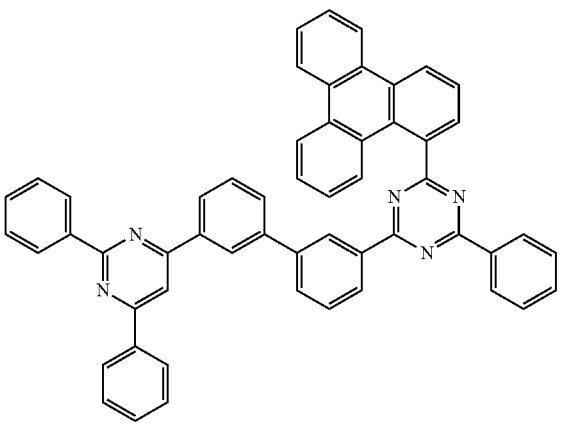
60
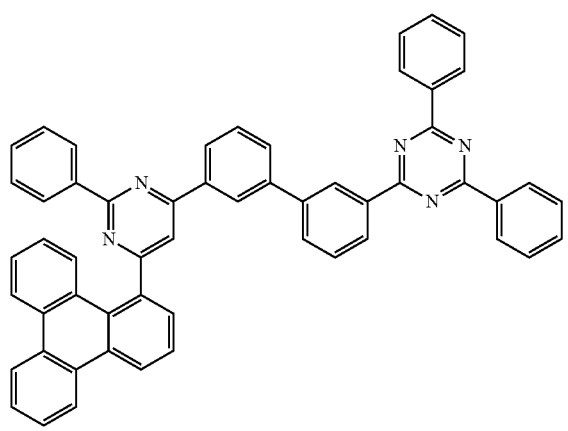
61
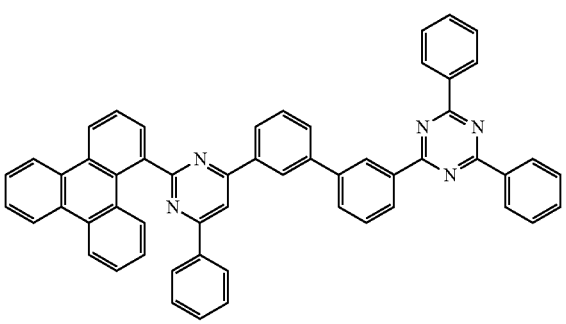
62
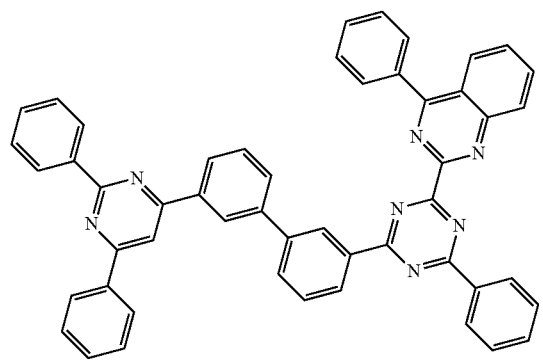
63
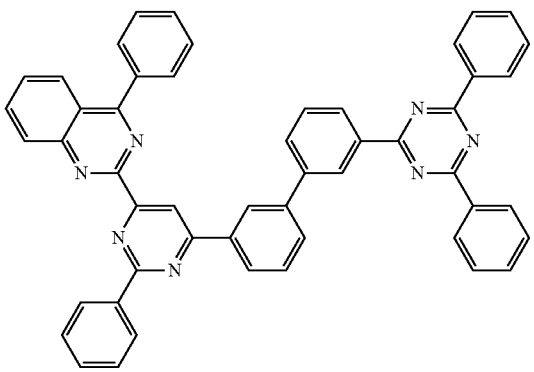
64
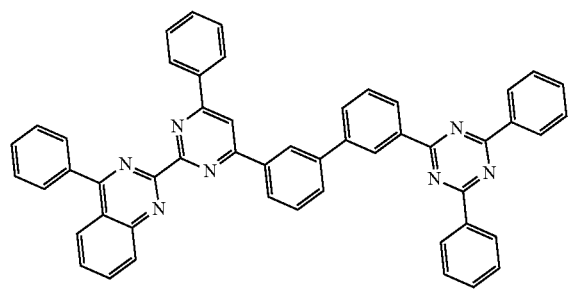
65
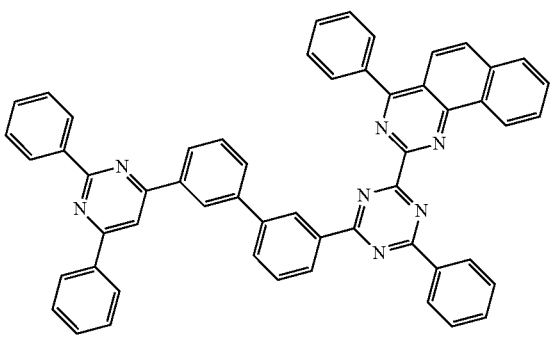

-continued
66
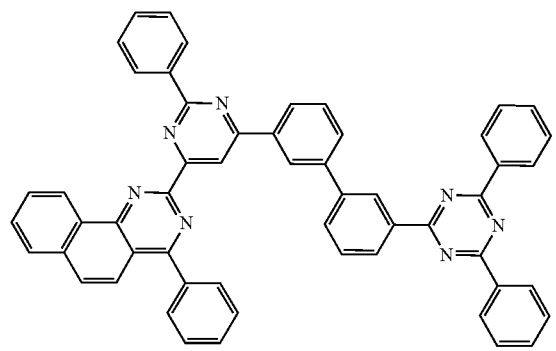
67
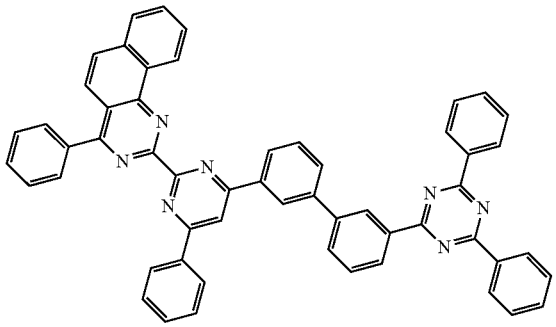
68
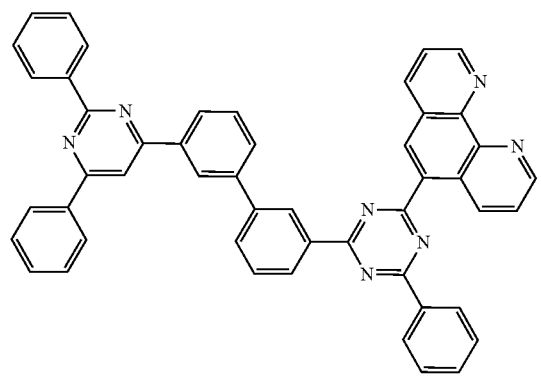
69
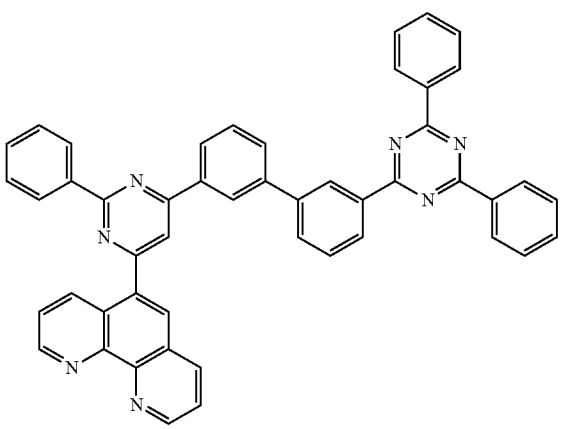
70
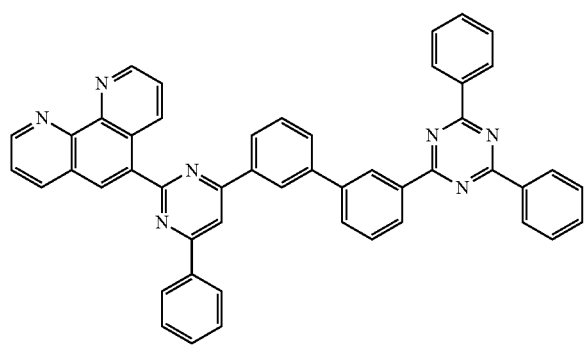
71
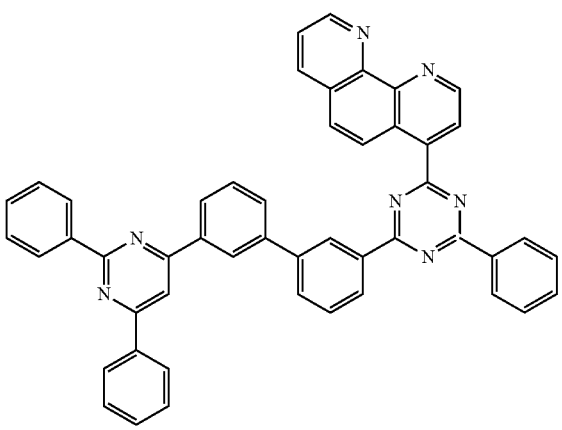

-continued
72
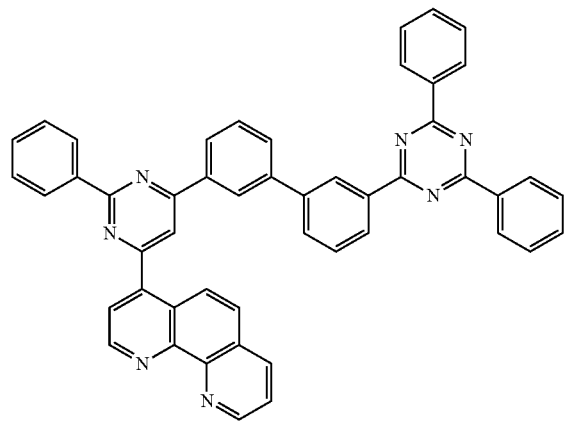
73
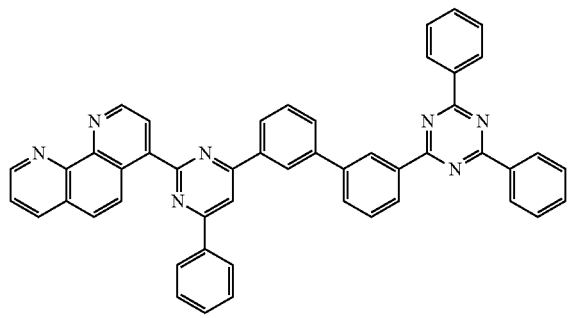
74
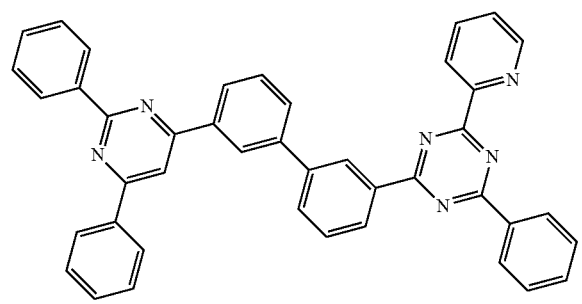
75
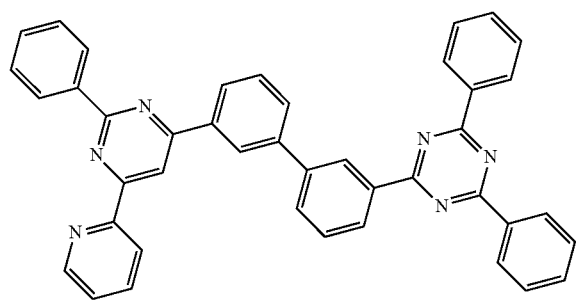
76
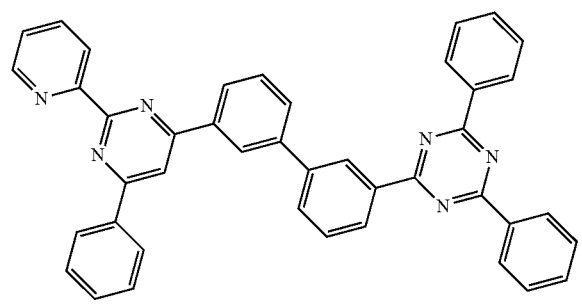
77
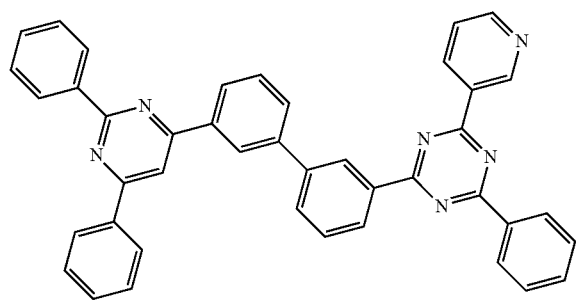
78
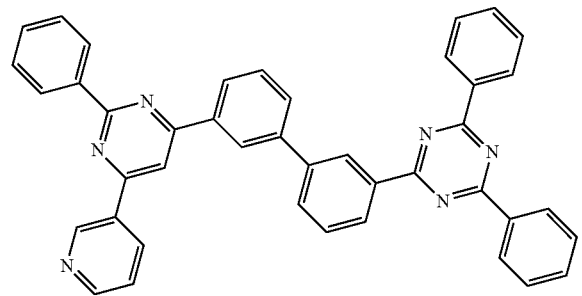
79
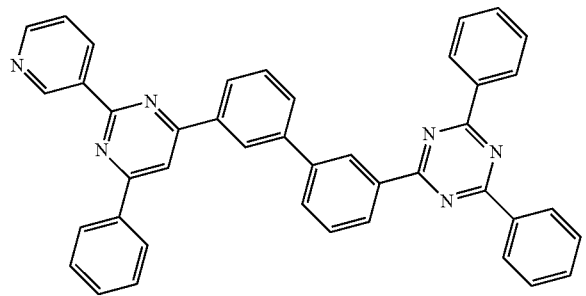

-continued
80
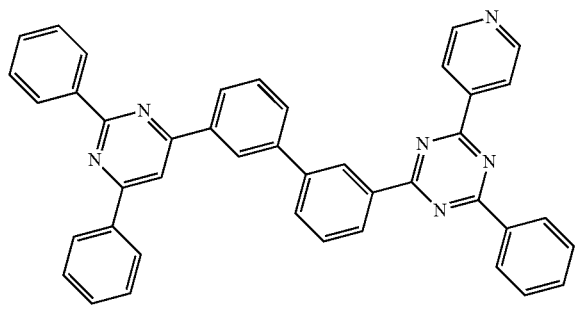
81
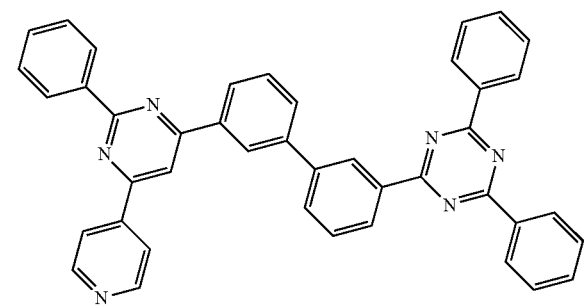
82
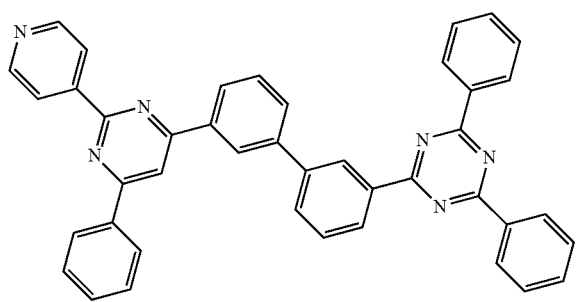
83
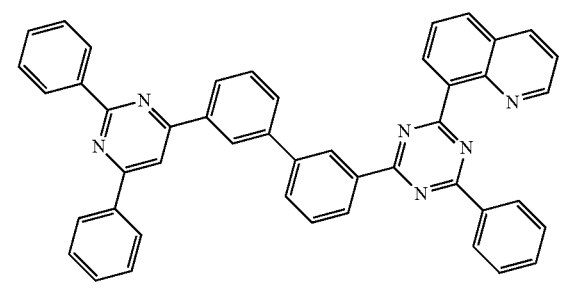
84
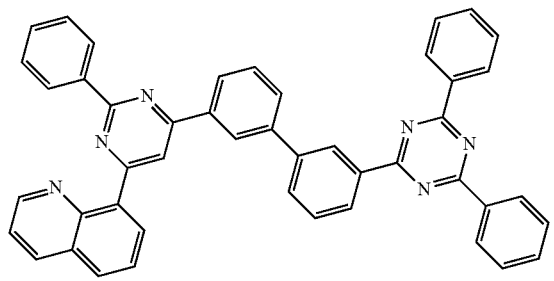
85
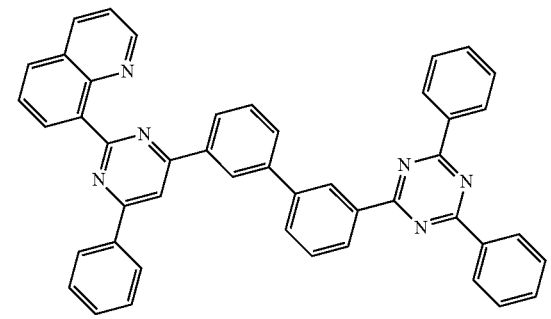
86
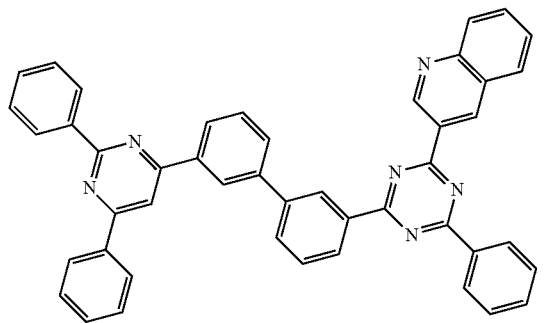
87
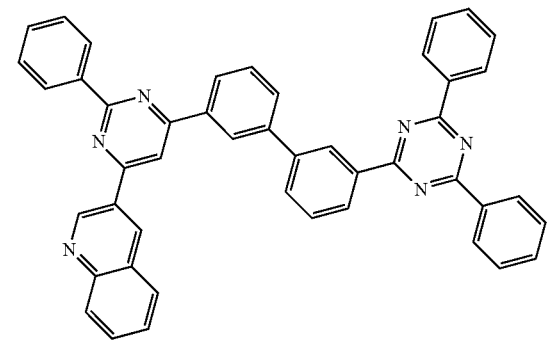

-continued
88
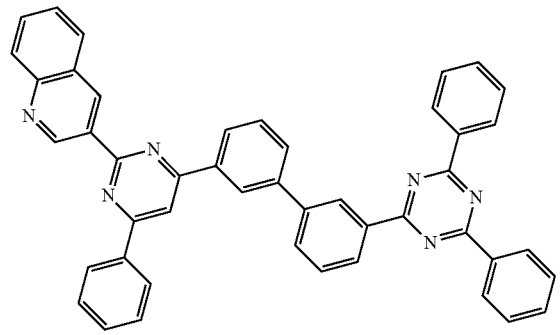
89
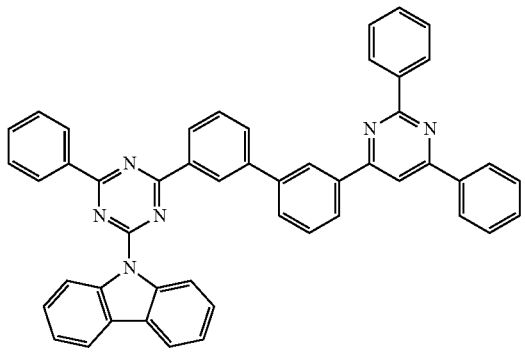
90
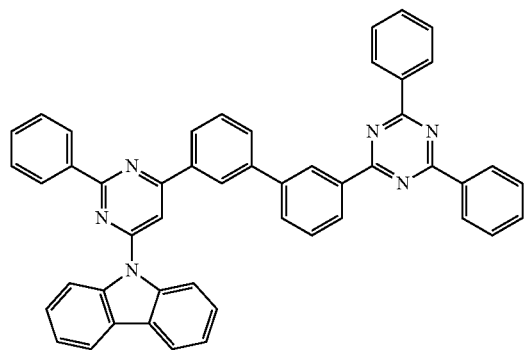
91
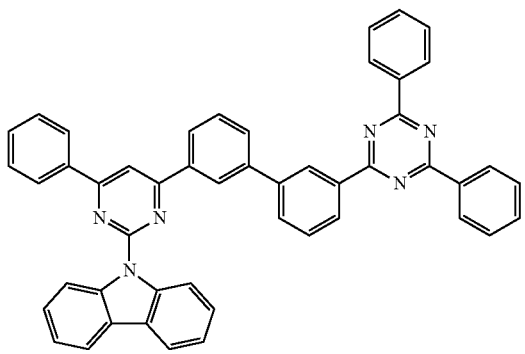
92
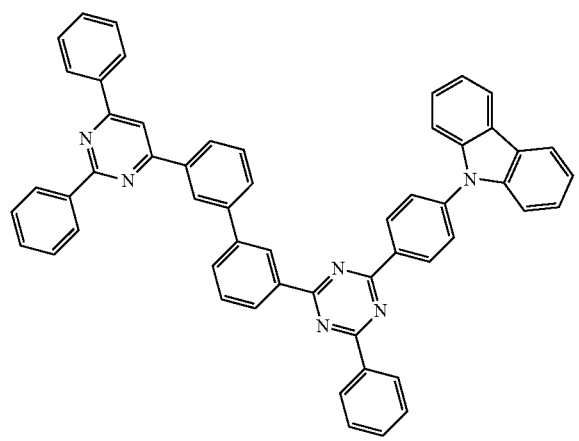
93
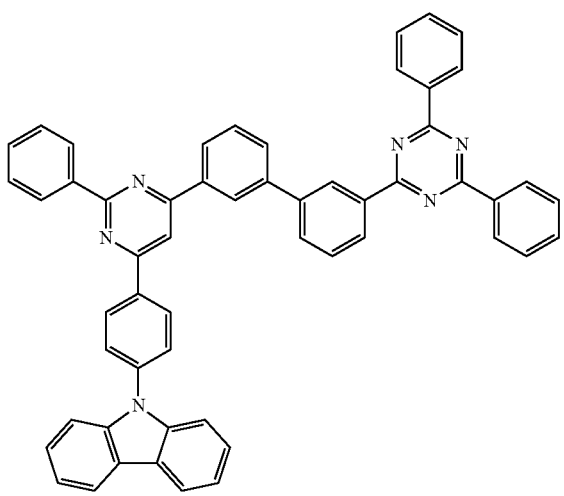

-continued
94
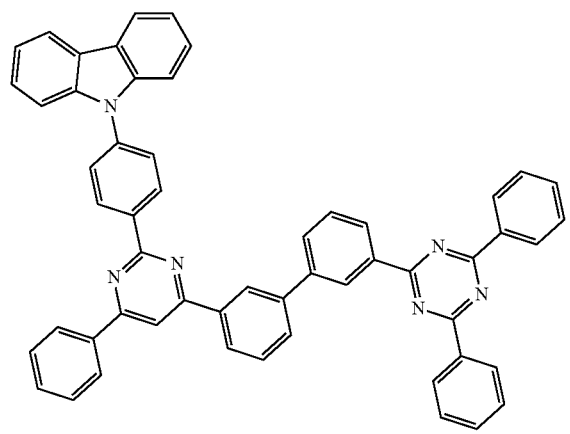
95
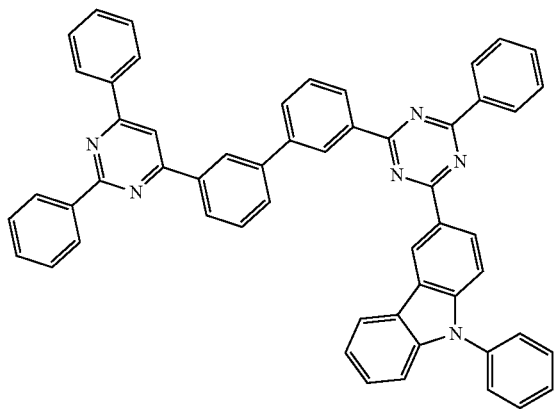
96
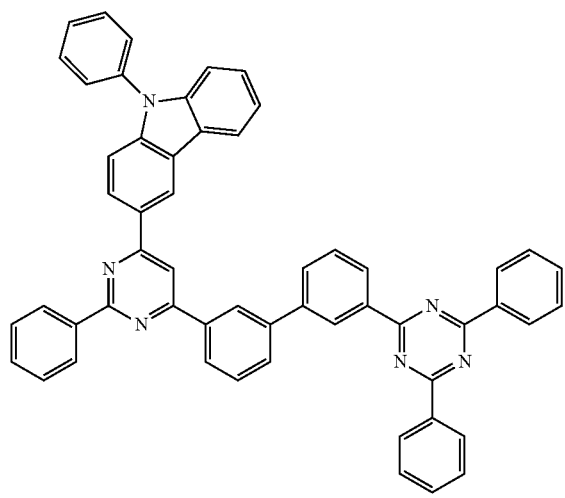
97
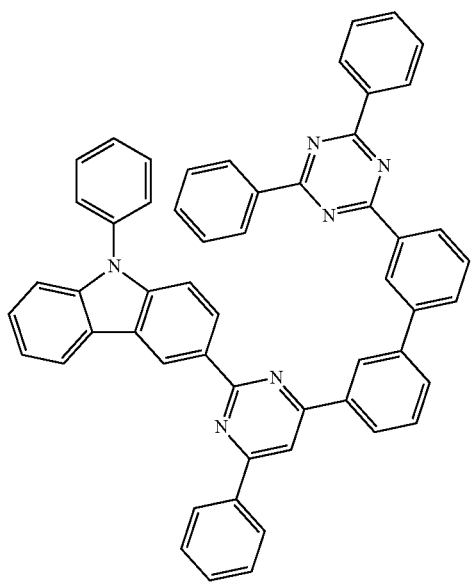
98
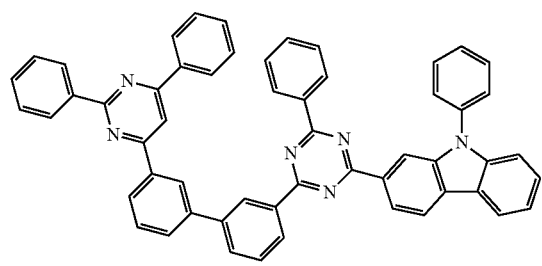
99
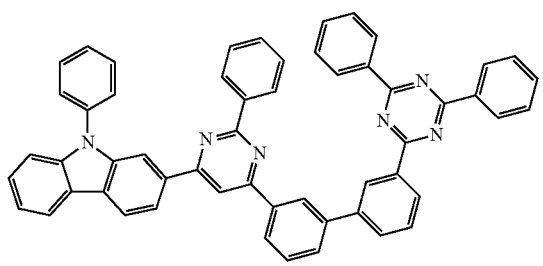

-continued
100
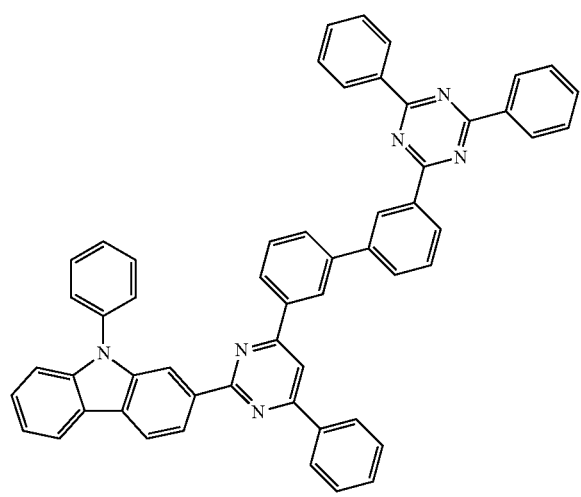
101
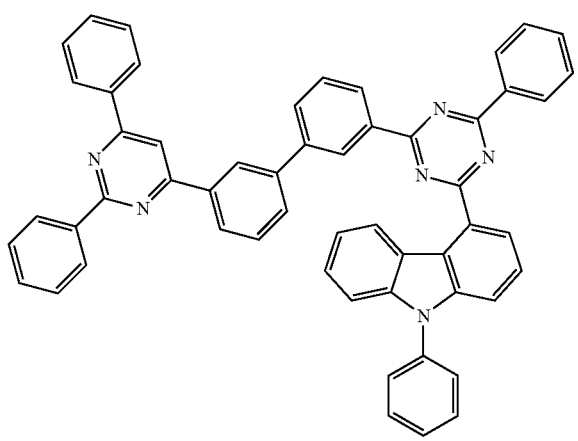
102
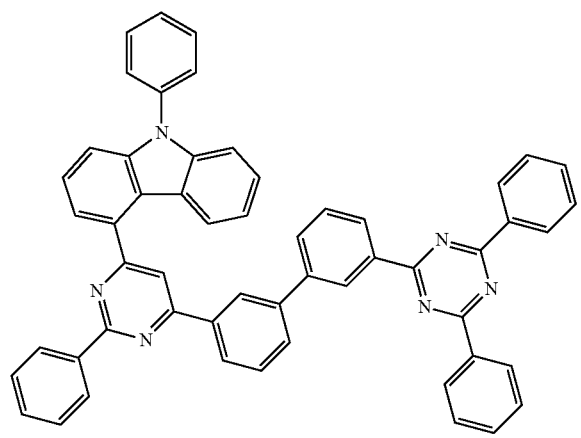
103
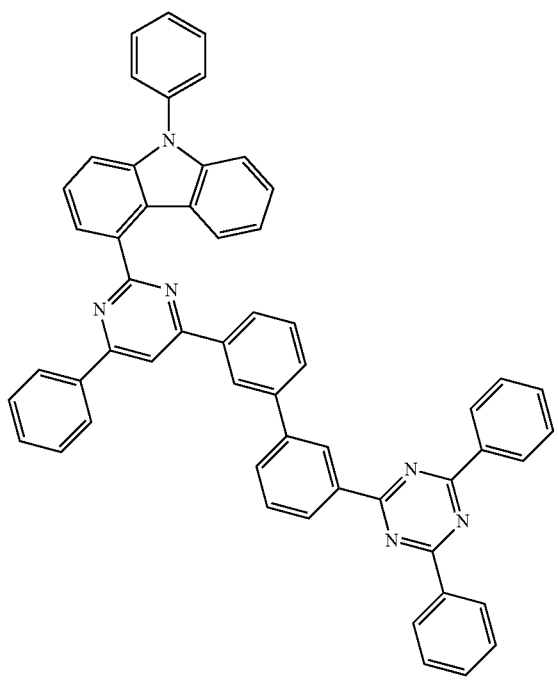
104
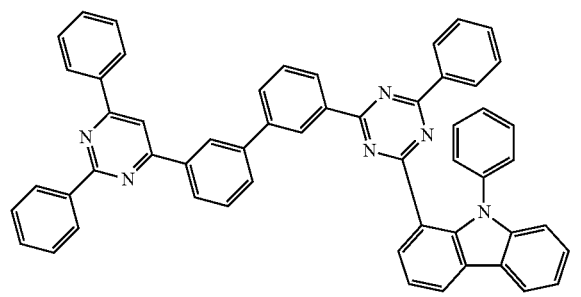
105
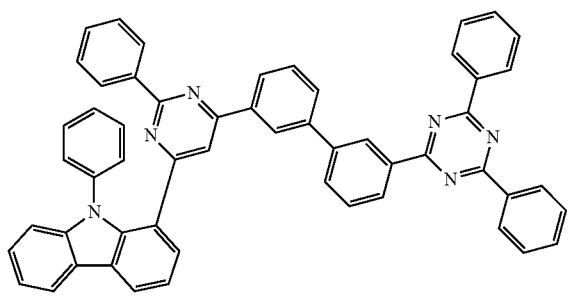

-continued
106
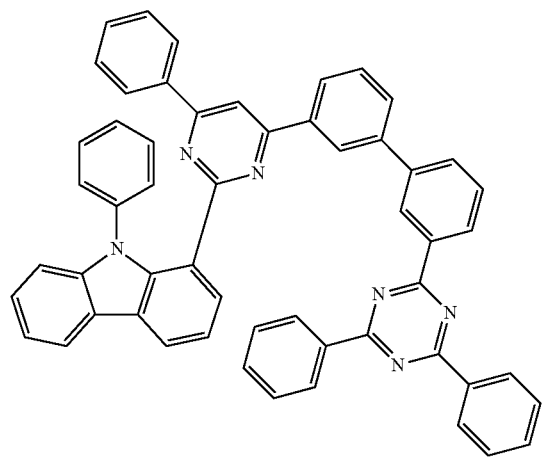
107
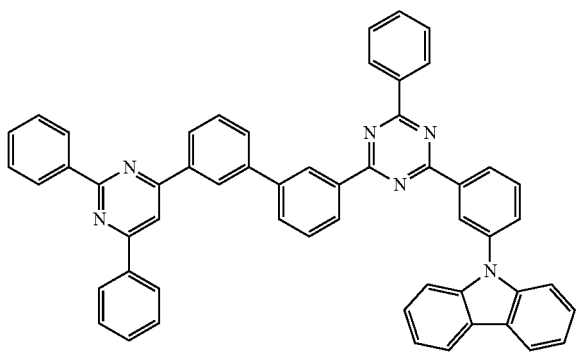
108
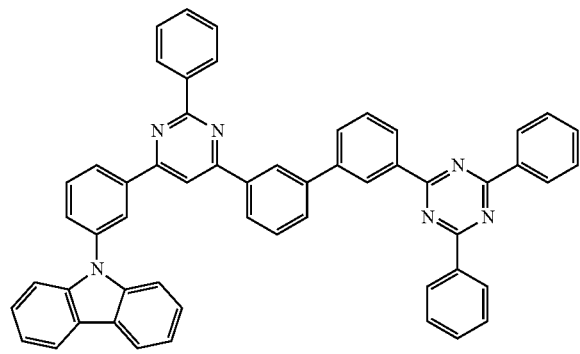
109
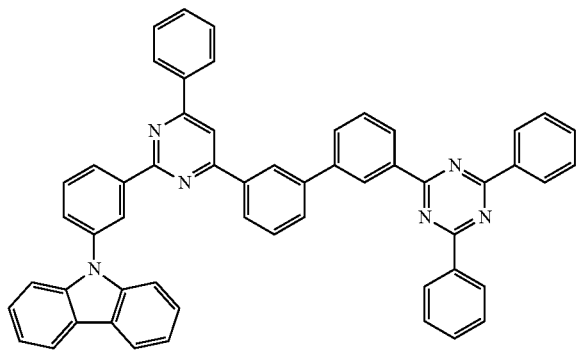
110
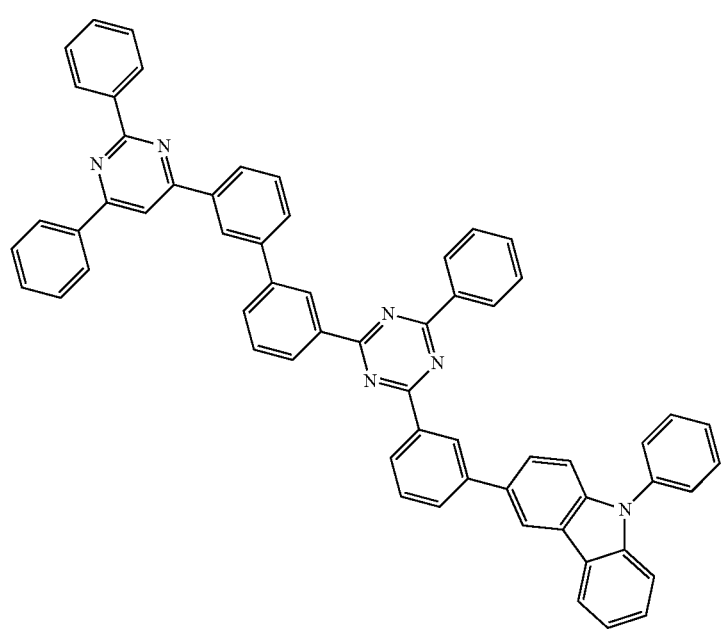

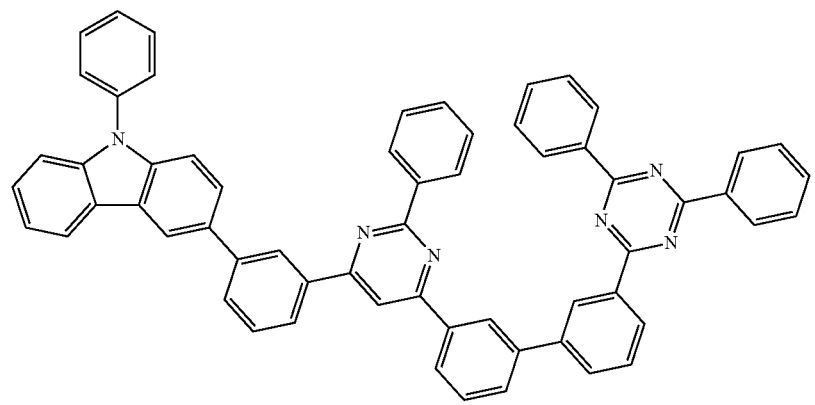
111
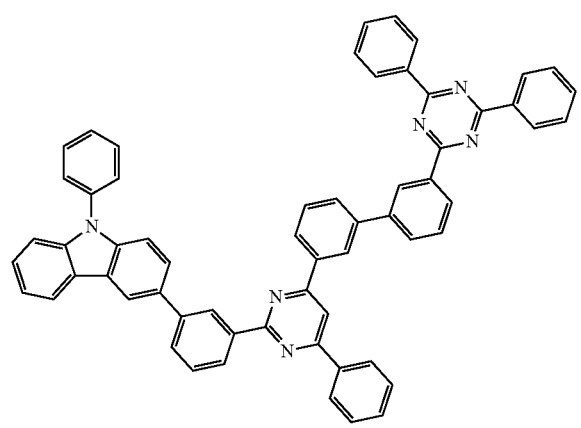
112
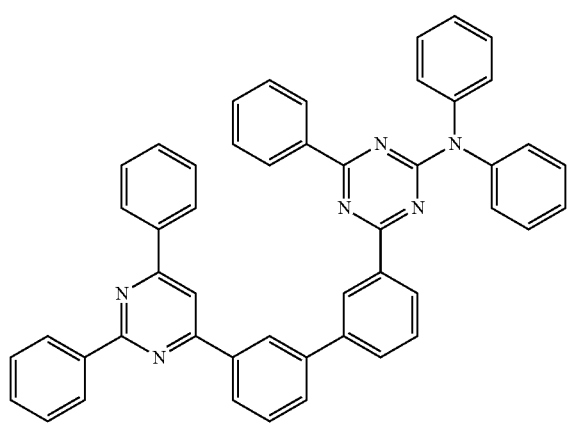
113
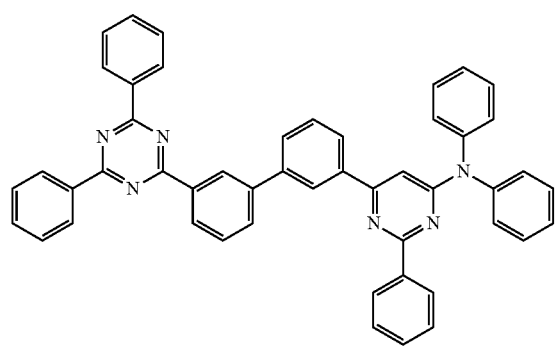
114
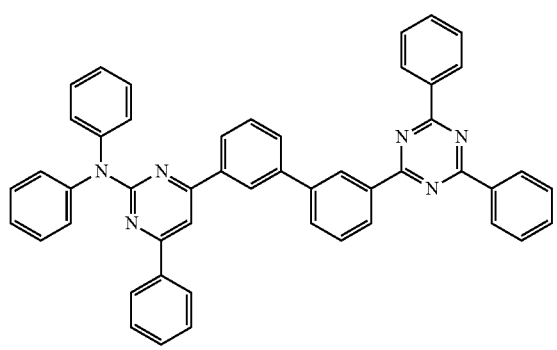
115

116
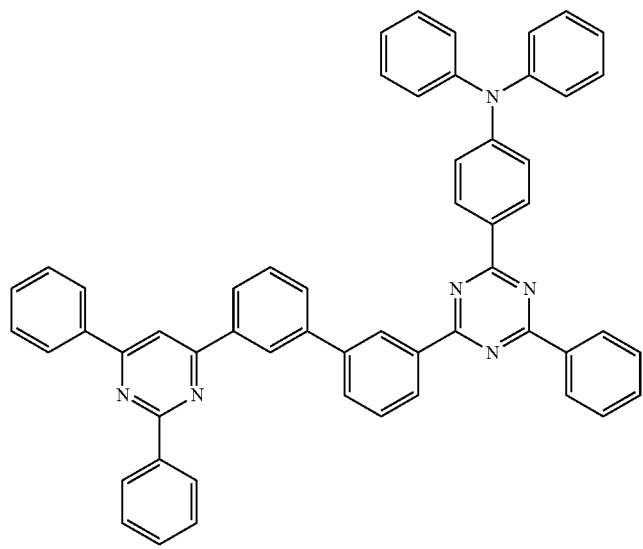
117
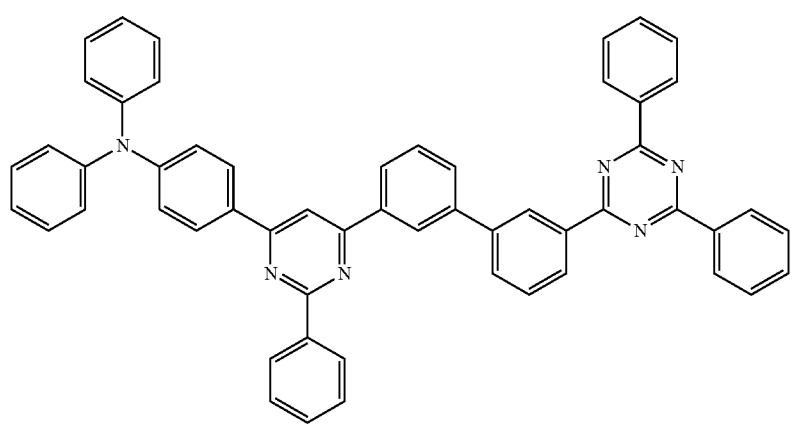
118
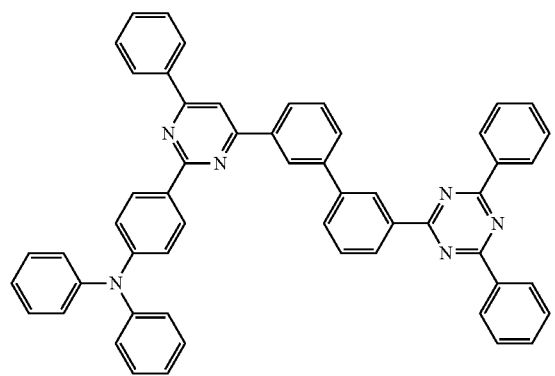
119
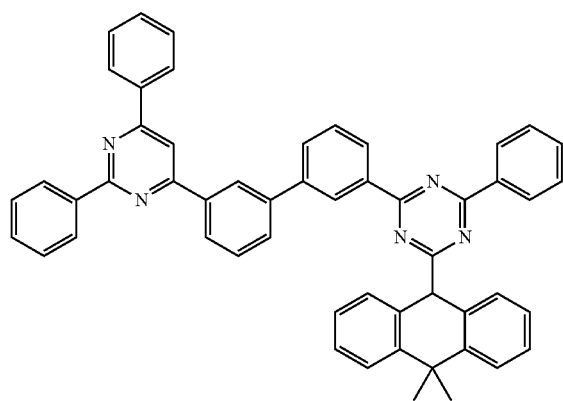

-continued
120
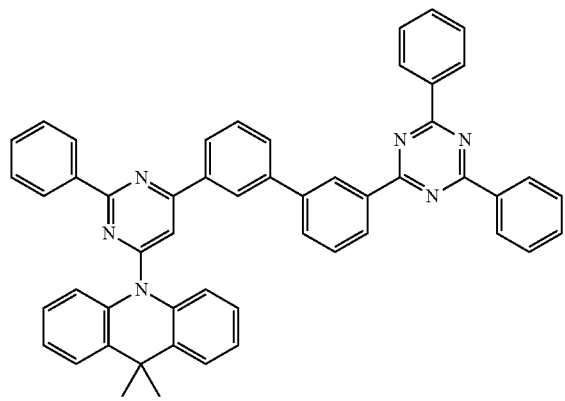
121
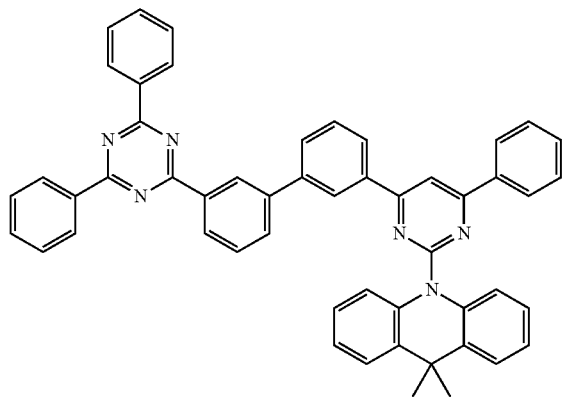
122
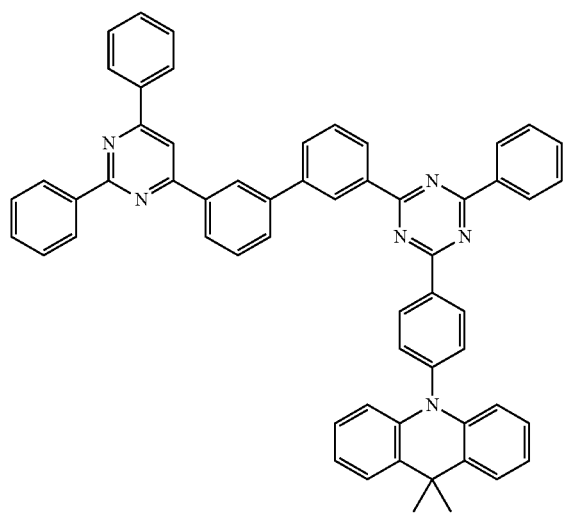
123
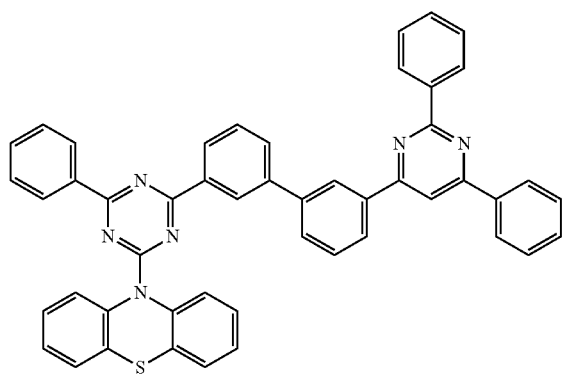
124
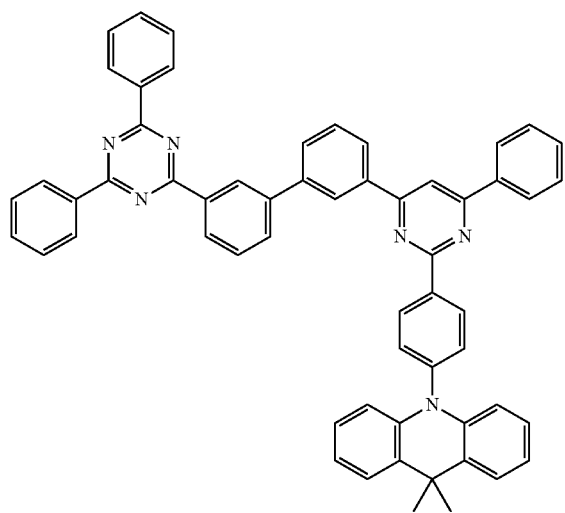
125

-continued
126
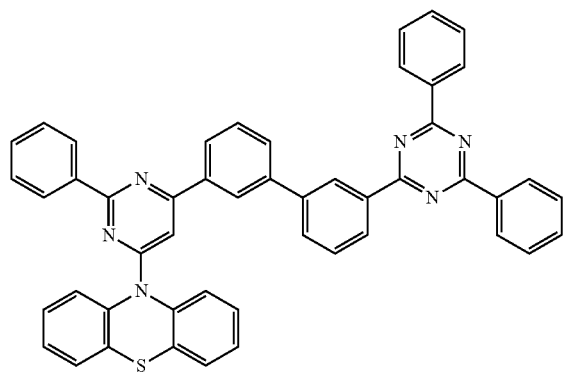
127
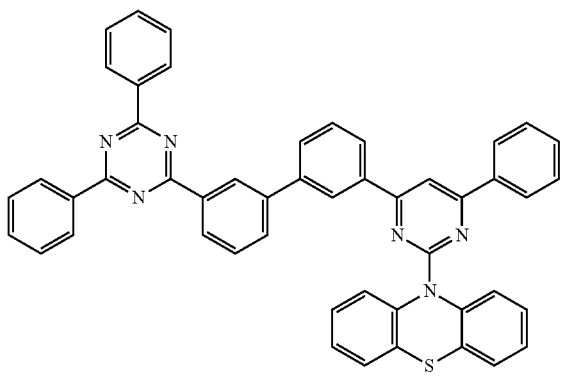
128
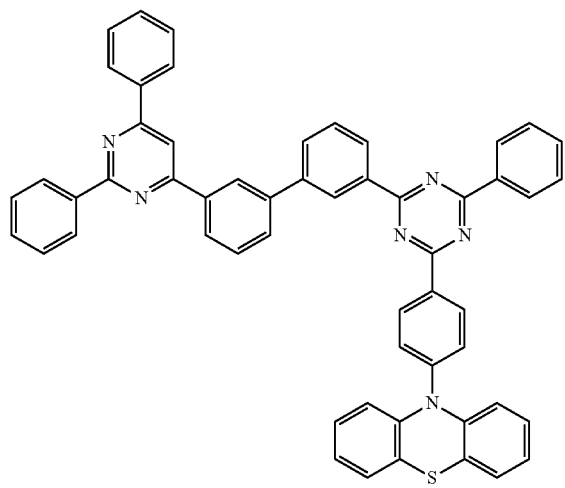
129
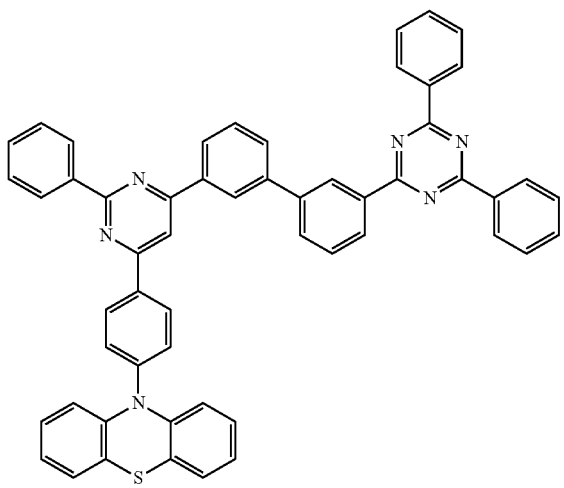
130
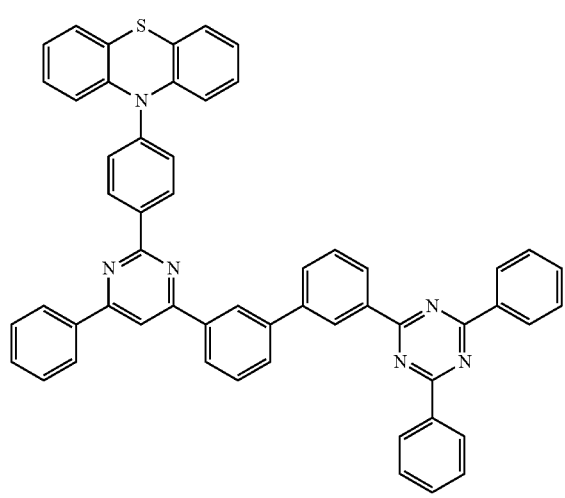
131
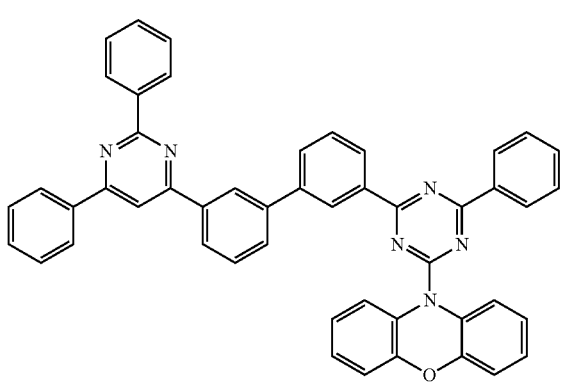

-continued
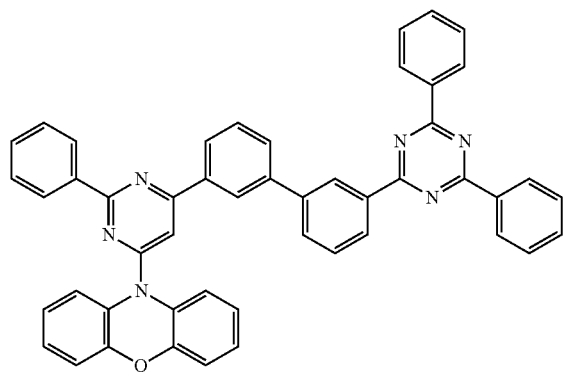
132
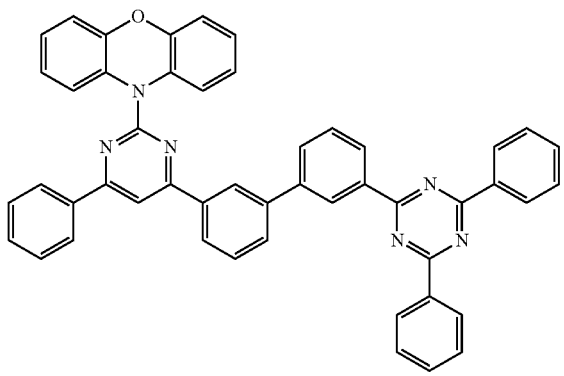
133
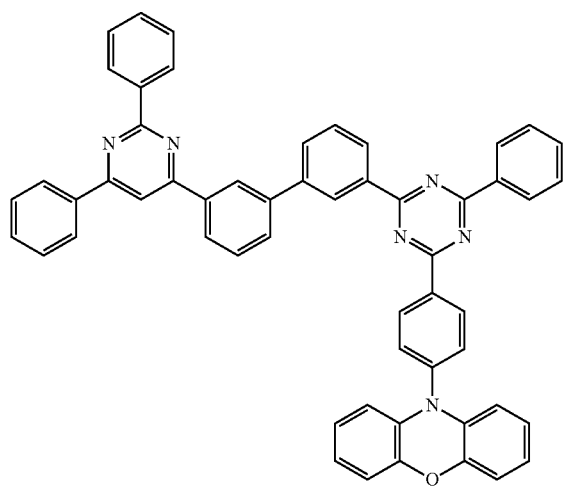
134
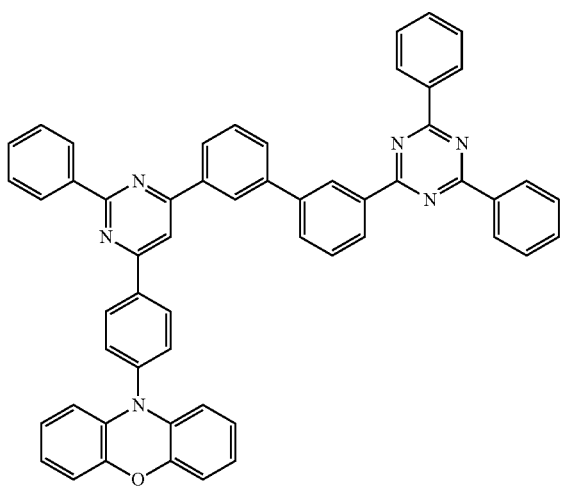
135
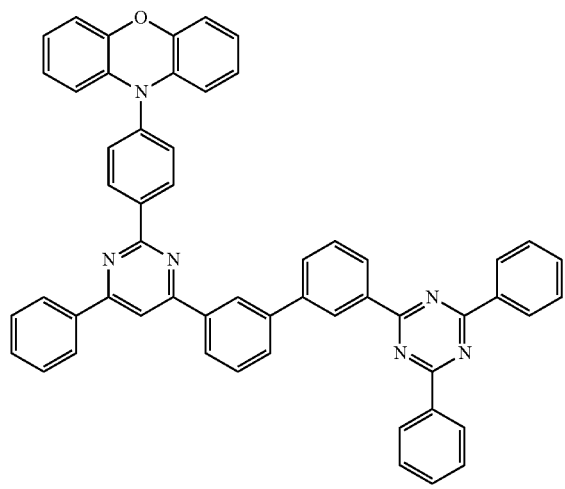
136
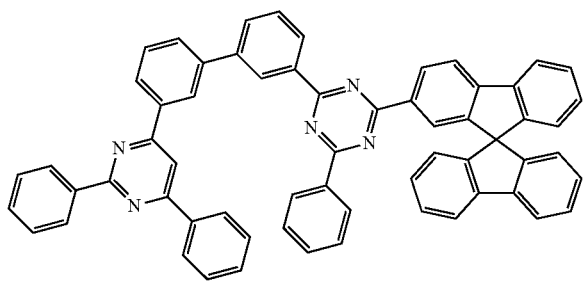
137

-continued
138
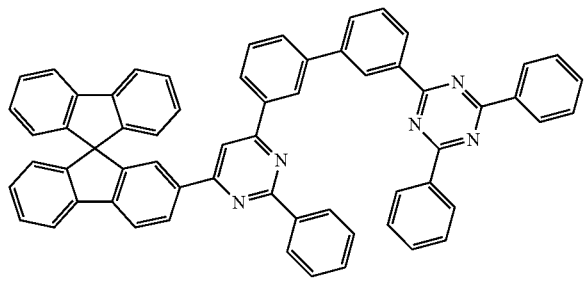
139
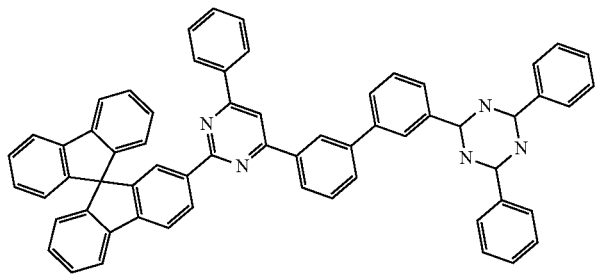
140
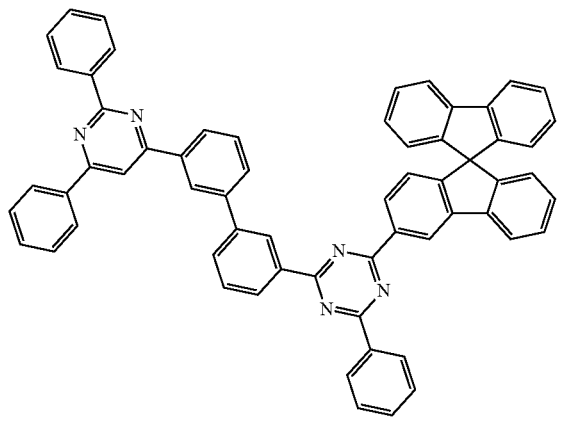
141
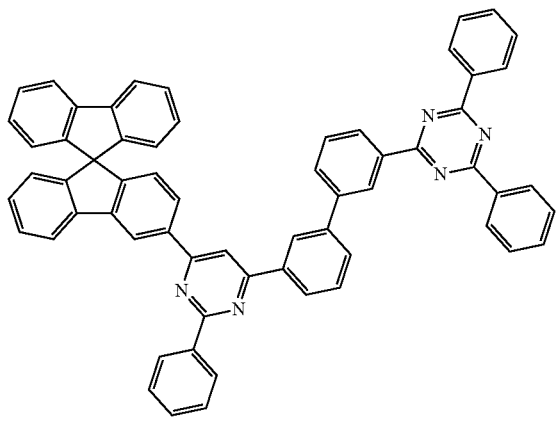
142
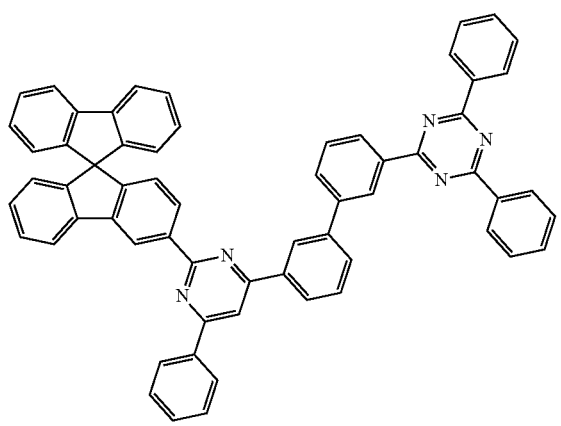
143
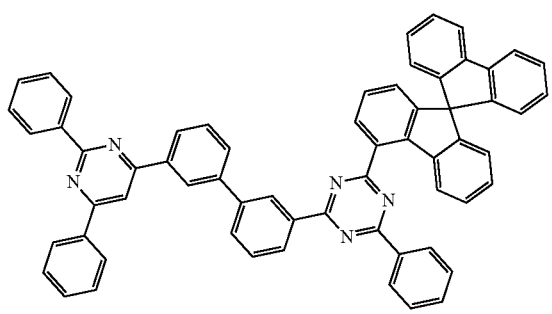
144
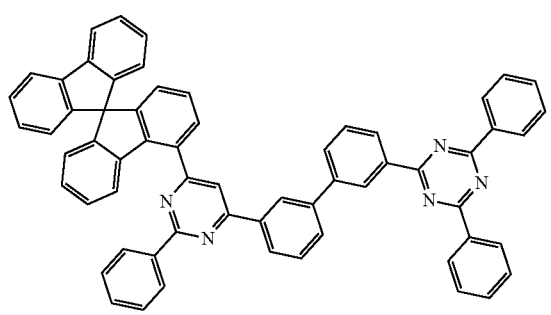
145
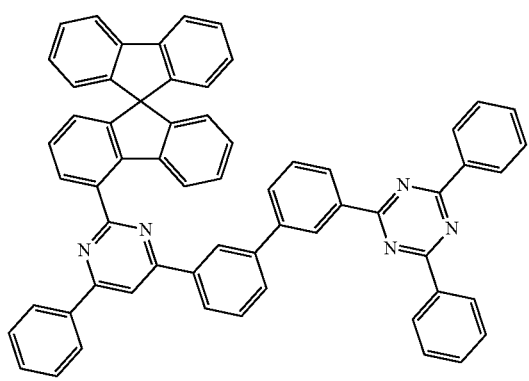

-continued
146
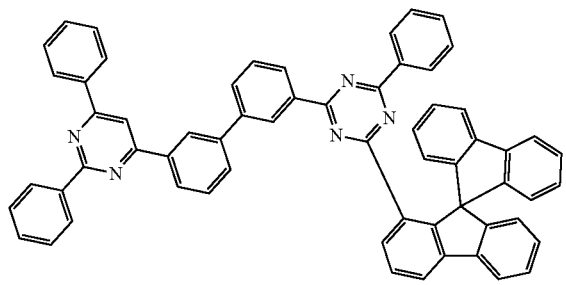
147
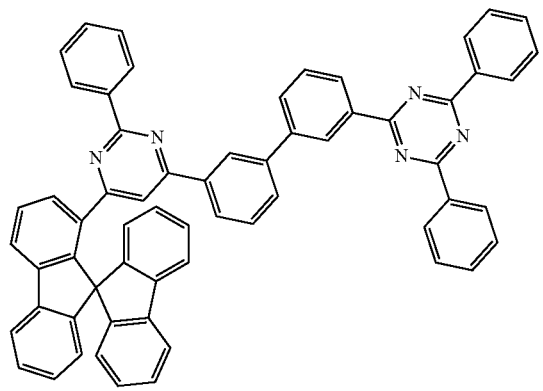
148
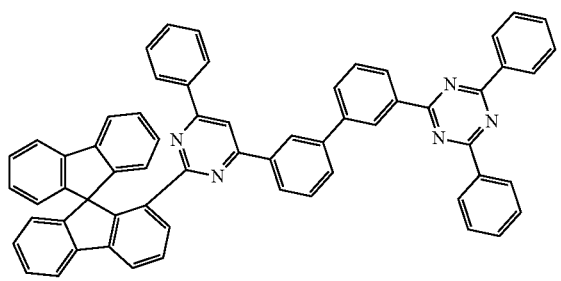
149
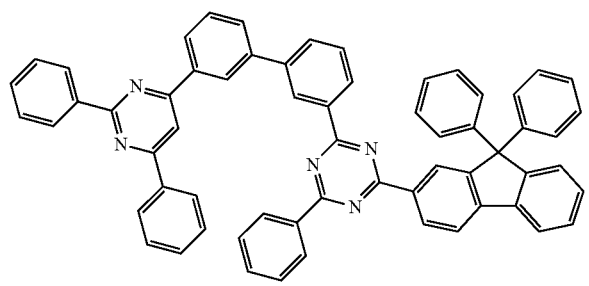
150
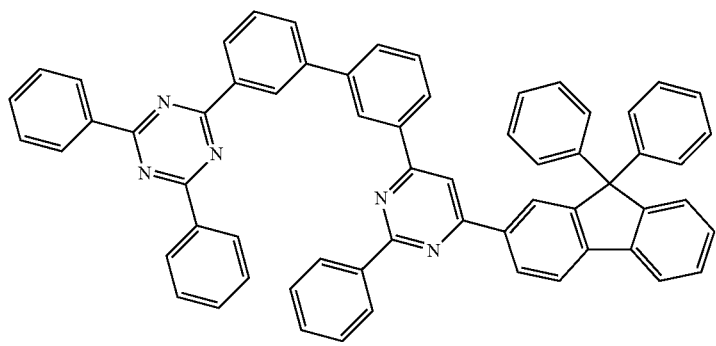
151
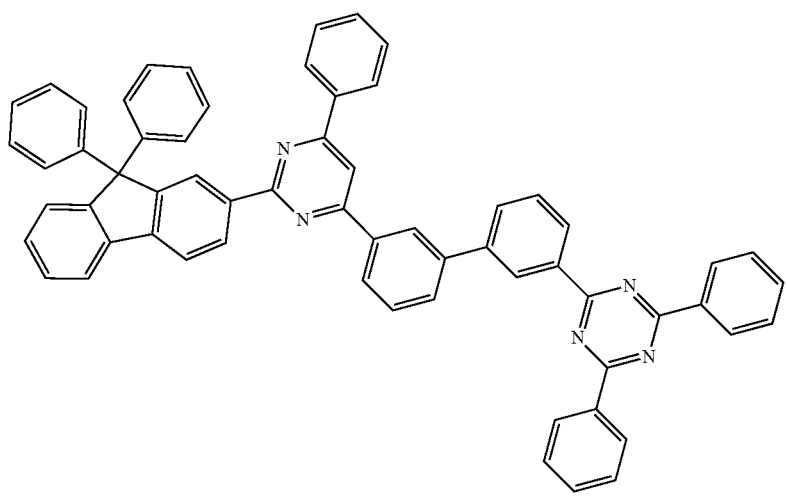

-continued
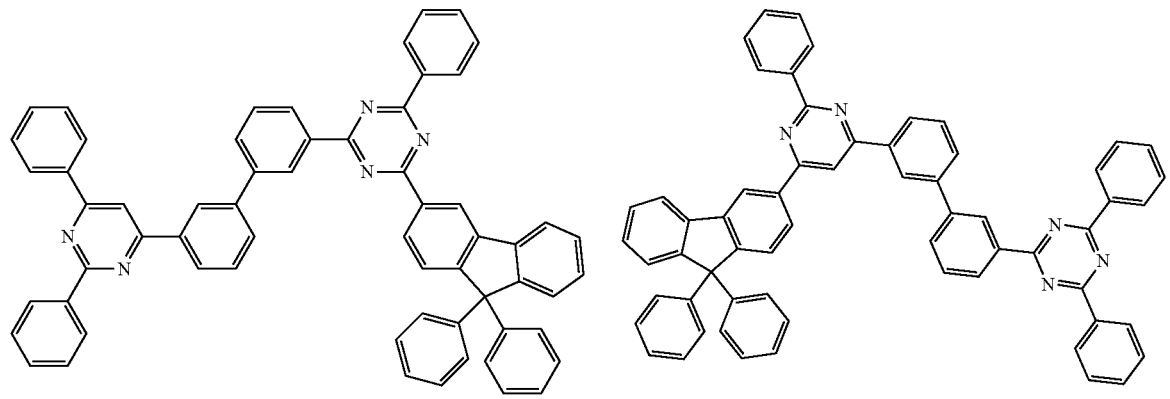
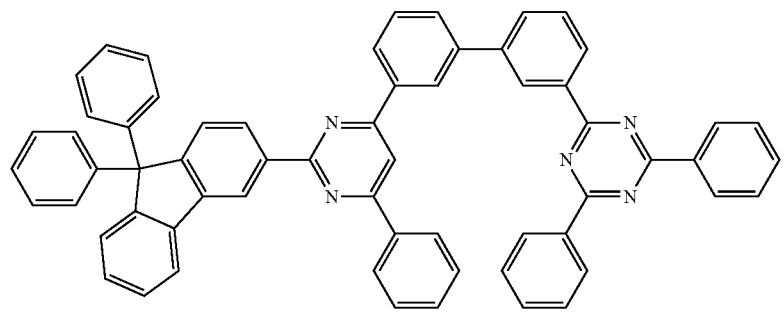
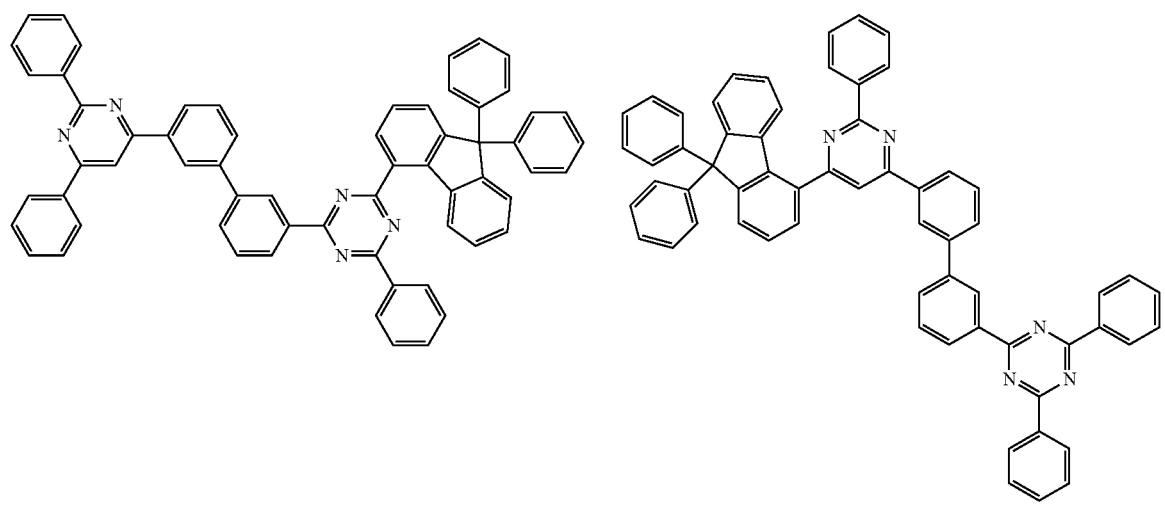

-continued
157
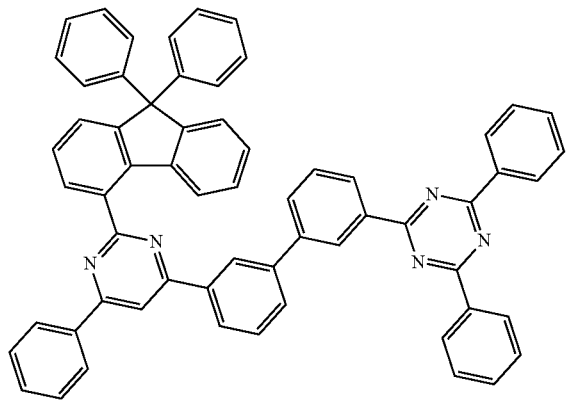
158
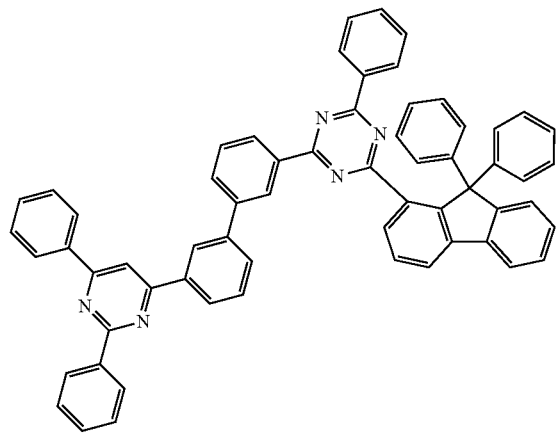
159
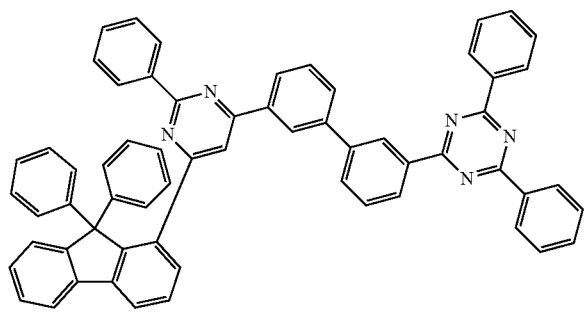
160
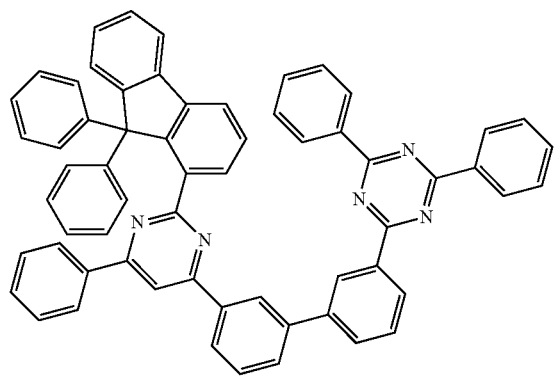
161
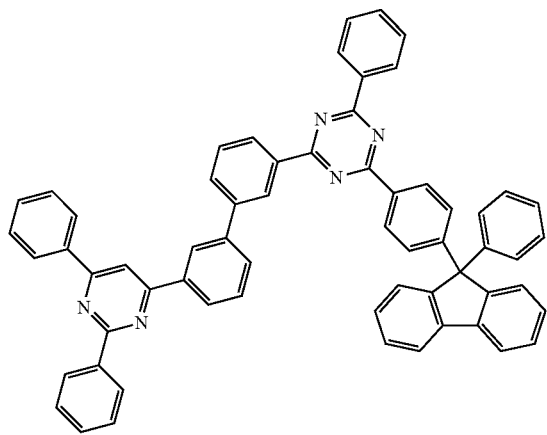
162
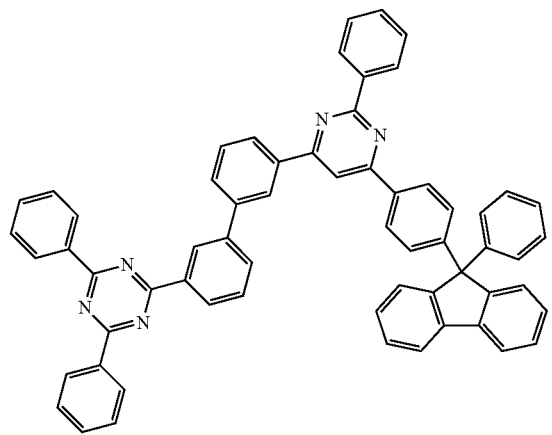

-continued
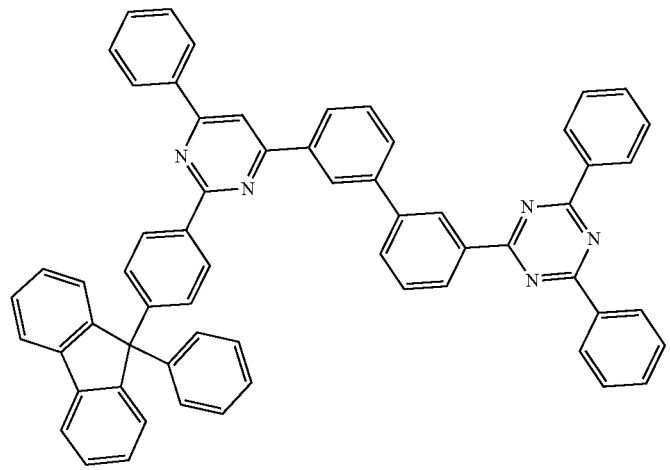
163
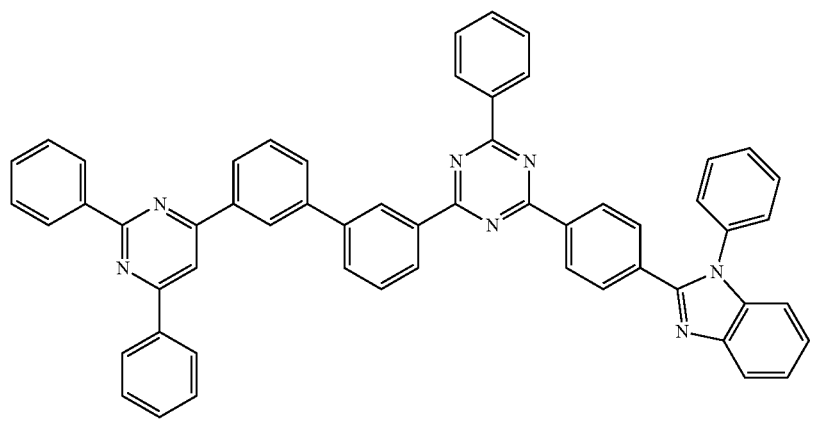
164
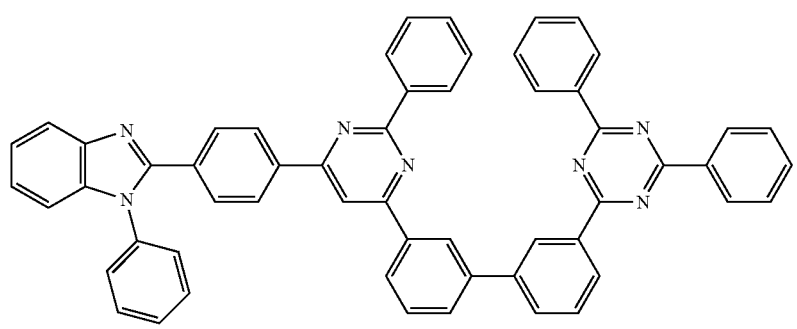
165

-continued
166
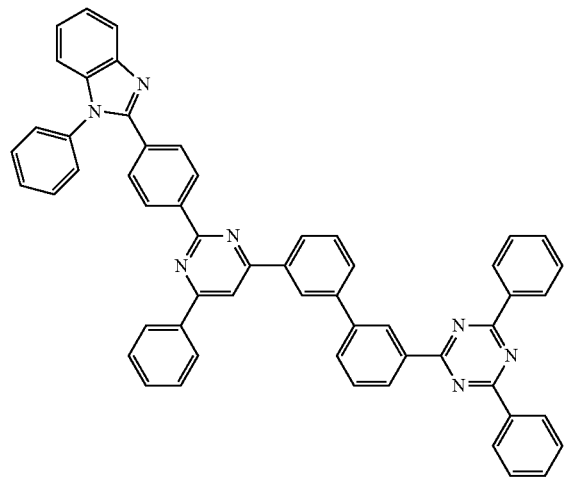
167
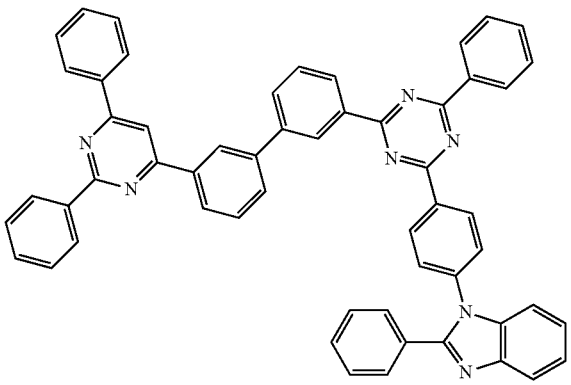
168
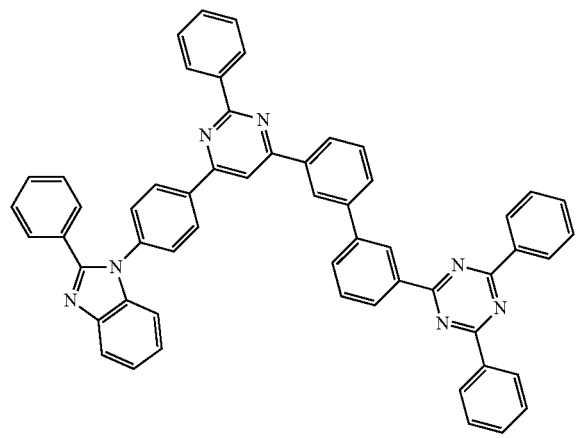
169
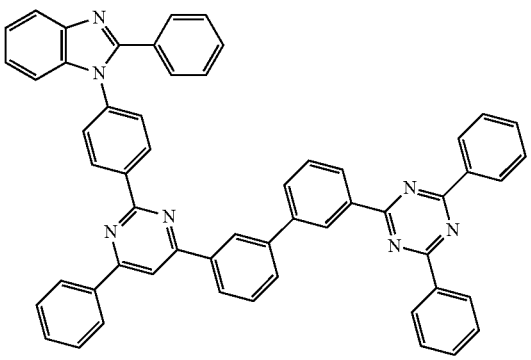
170
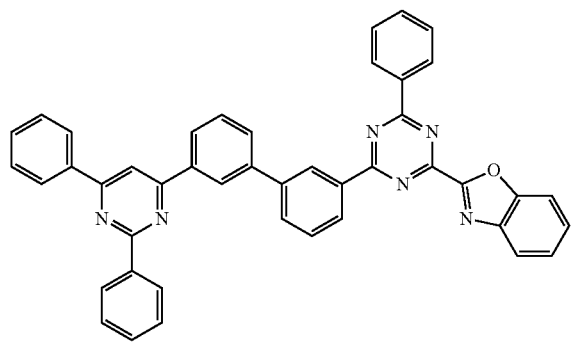
171
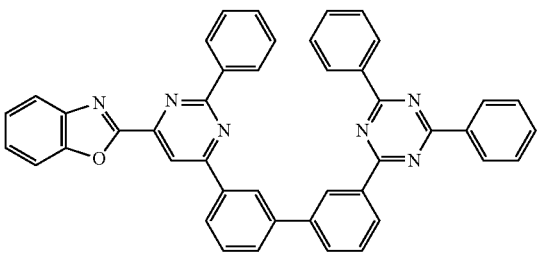

-continued
172
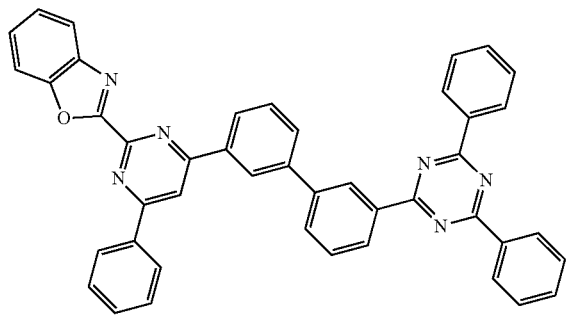
173
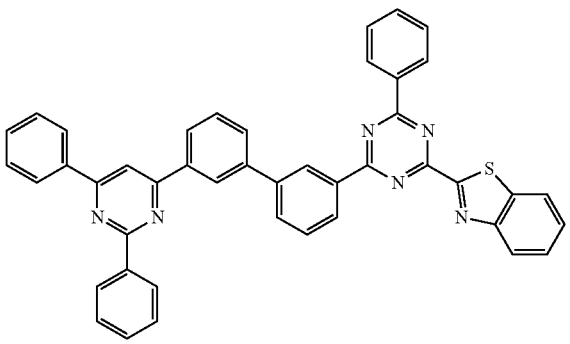
174
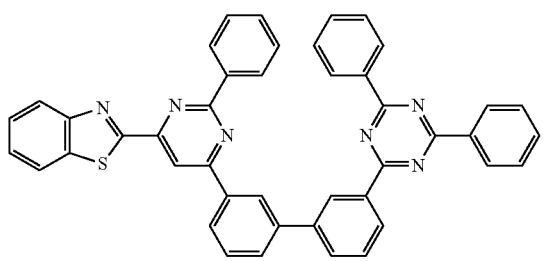
175
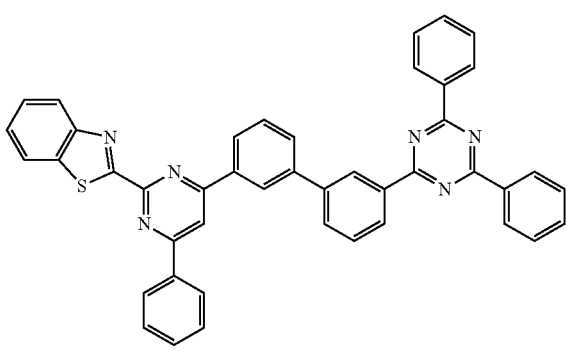
176
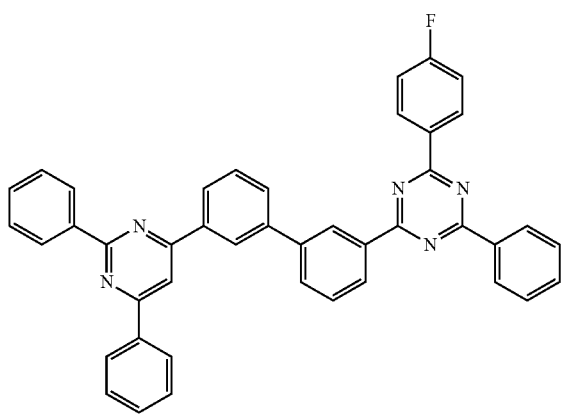
177
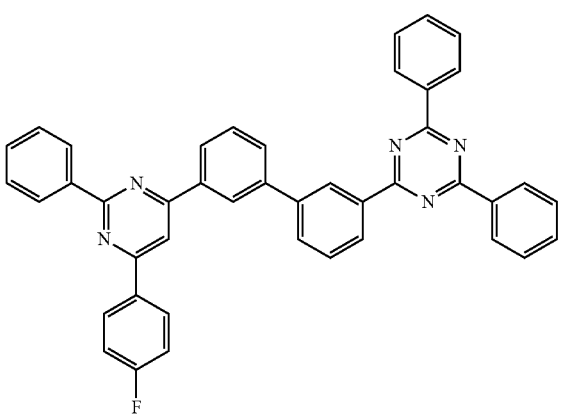
178
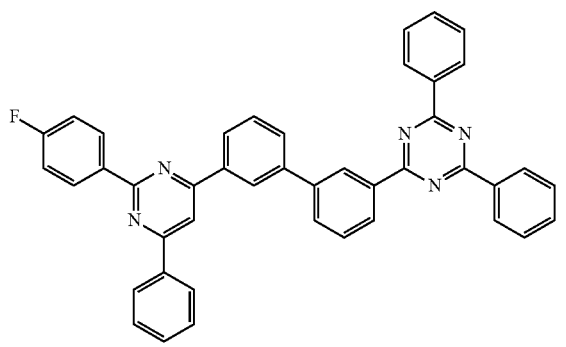
179
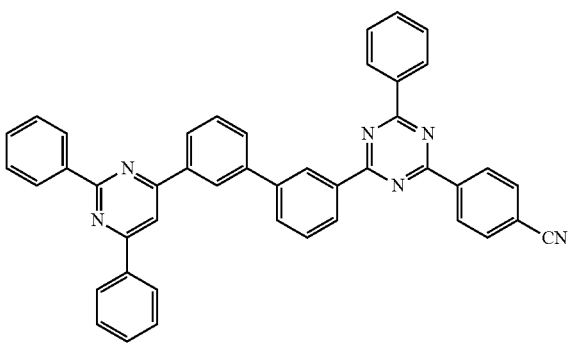

-continued
180
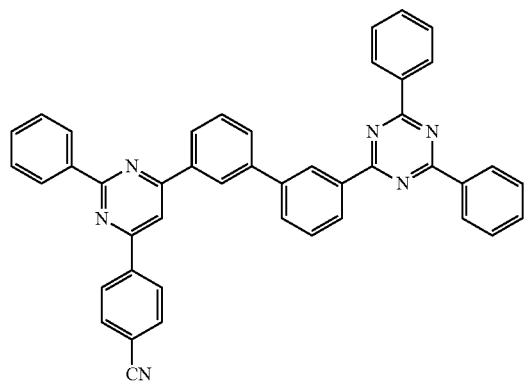
181
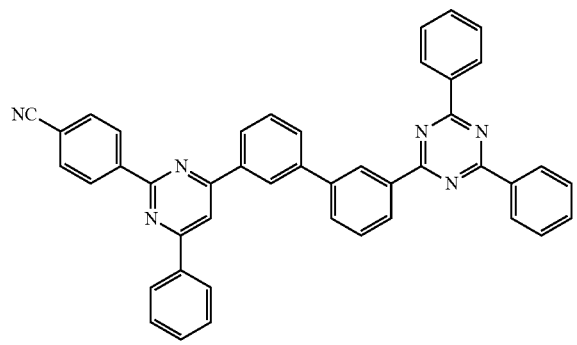
182
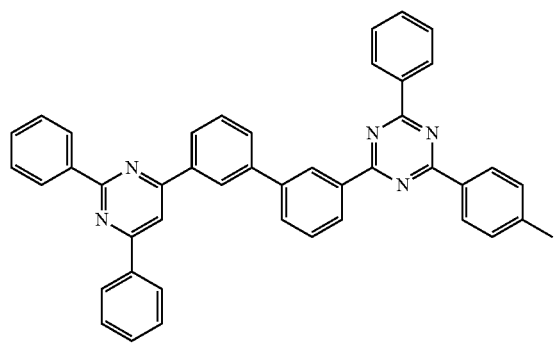
183
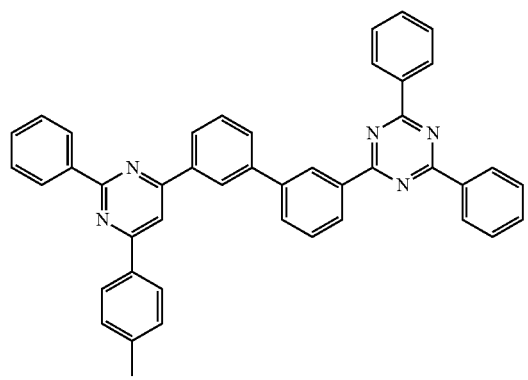
184
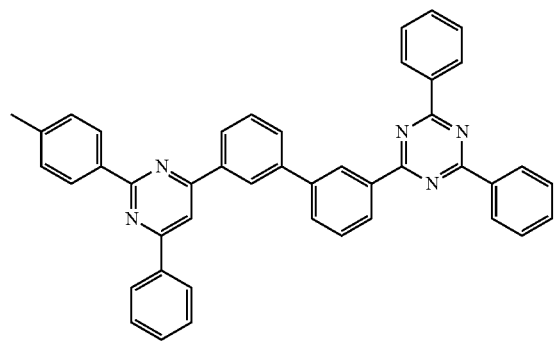
185
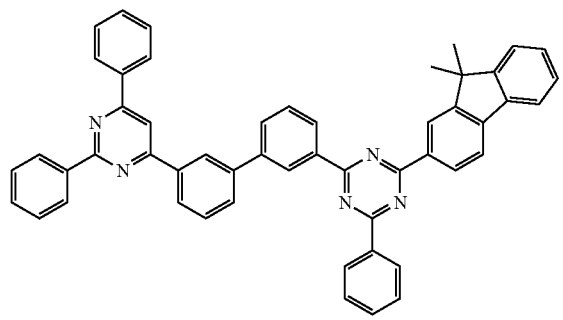
186
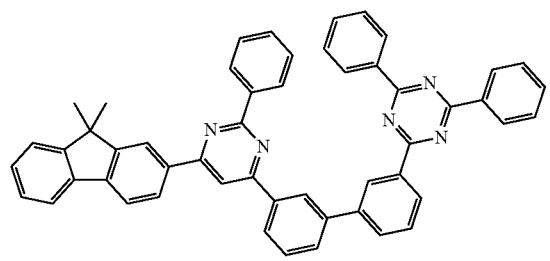
187
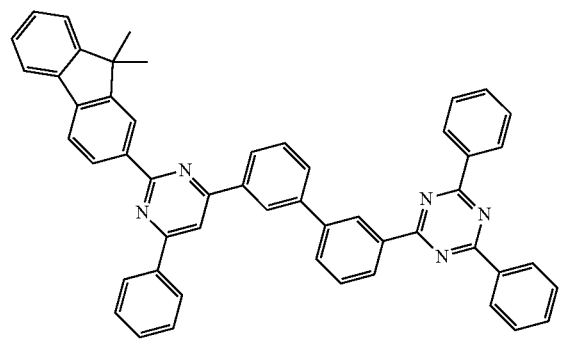

-continued
188
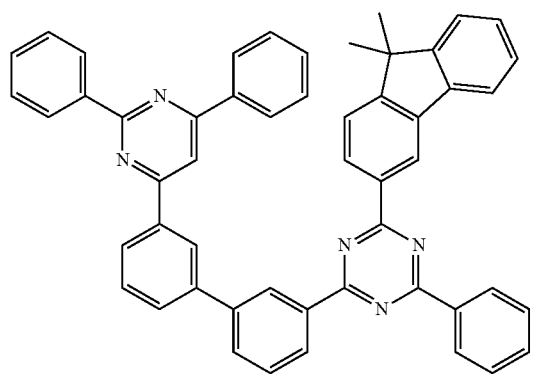
189
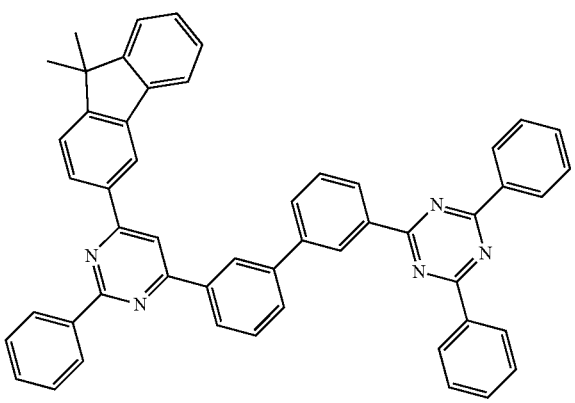
190
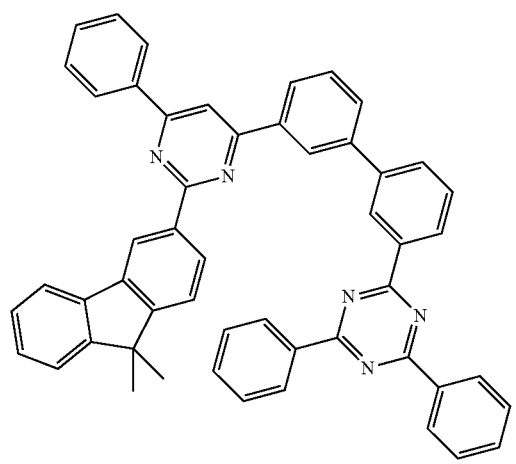
191
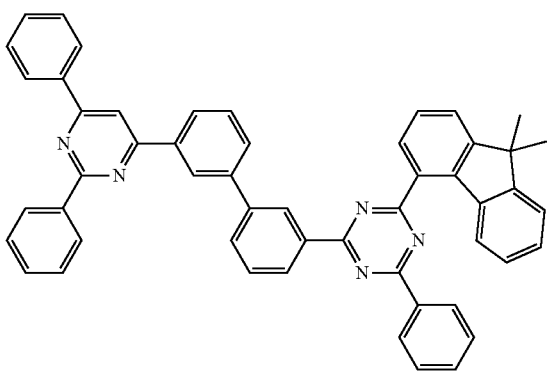
192
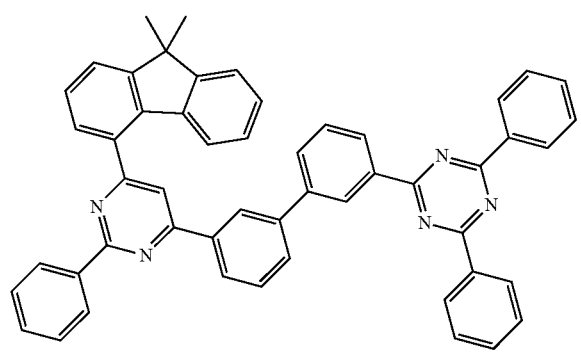
193
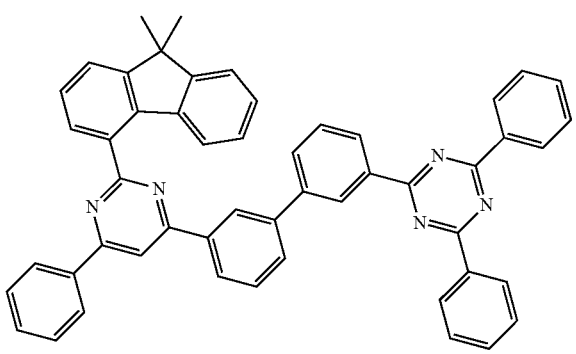

-continued
194
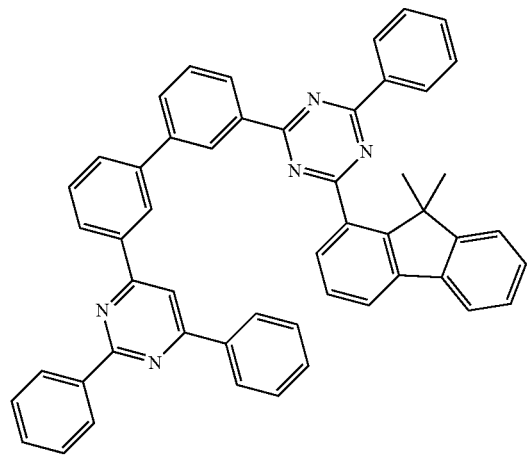
195
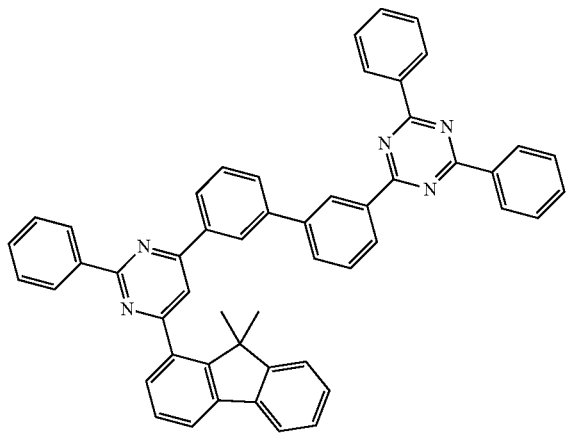
196
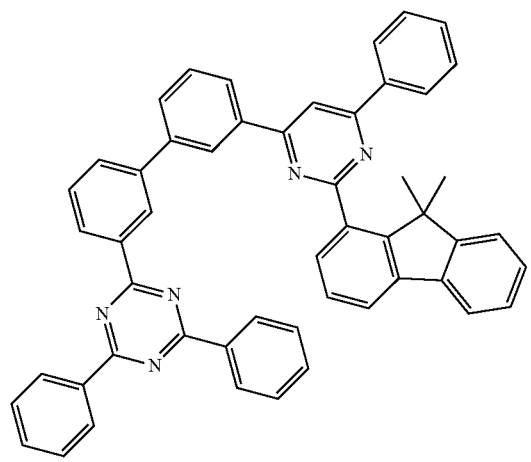
197
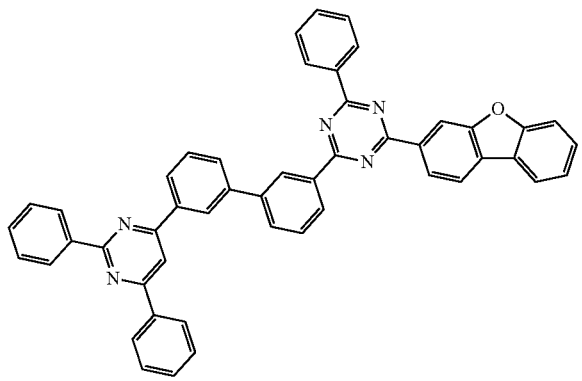
198
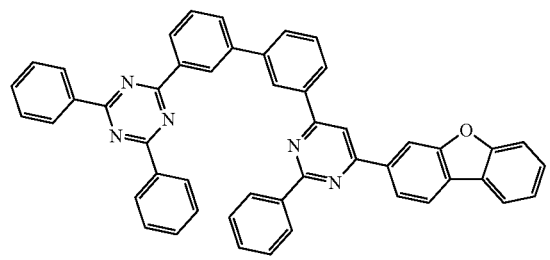
199
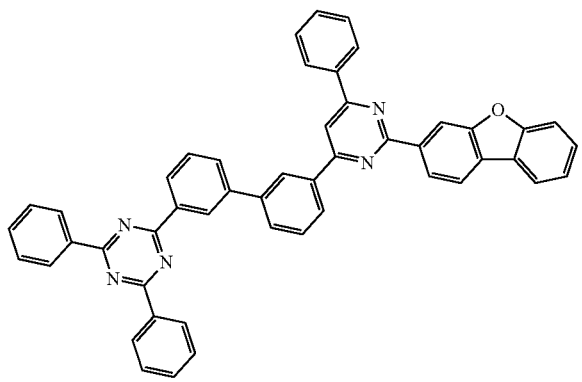

-continued
200
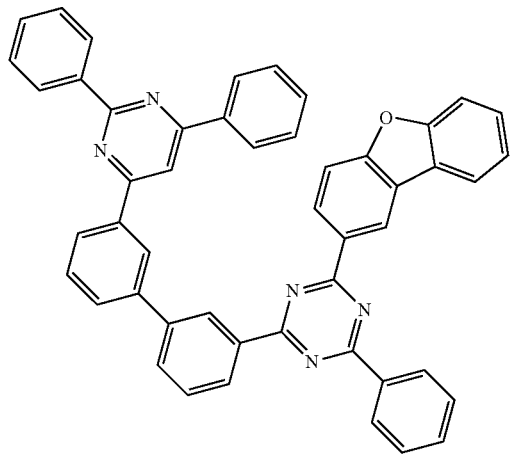
201
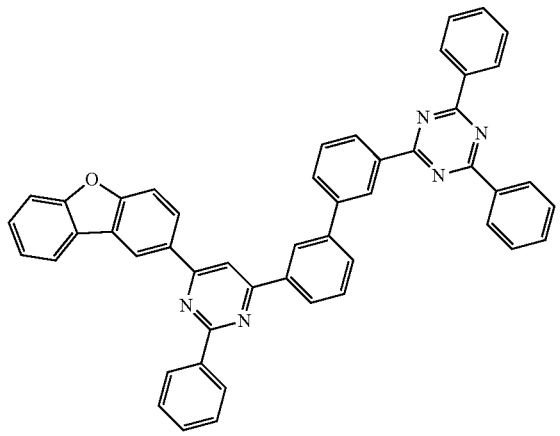
202
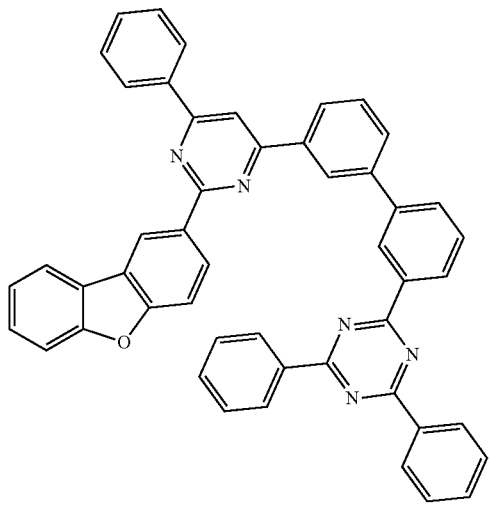
203
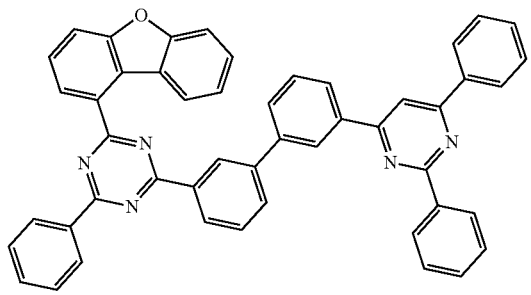
204
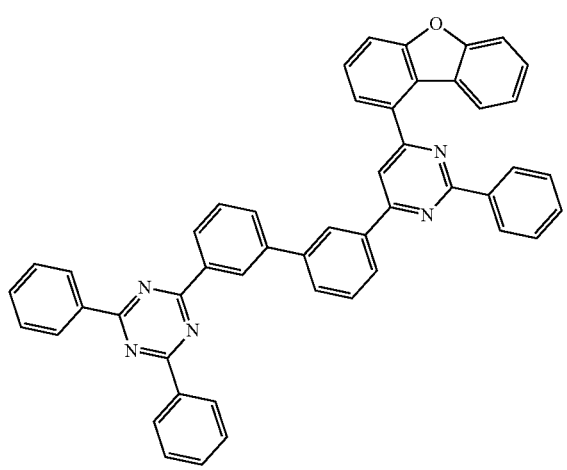
205
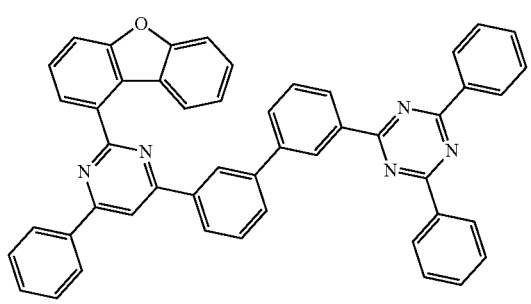

-continued
206
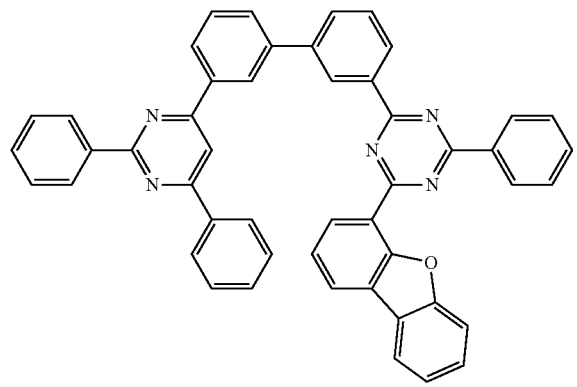
207
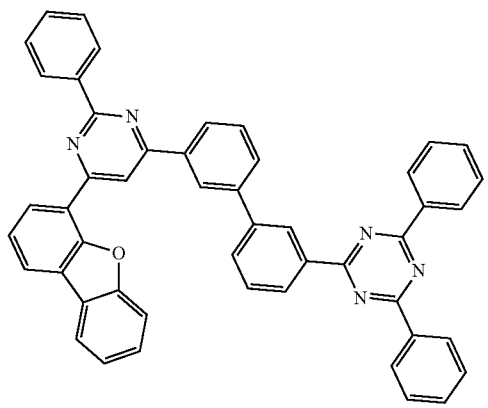
208
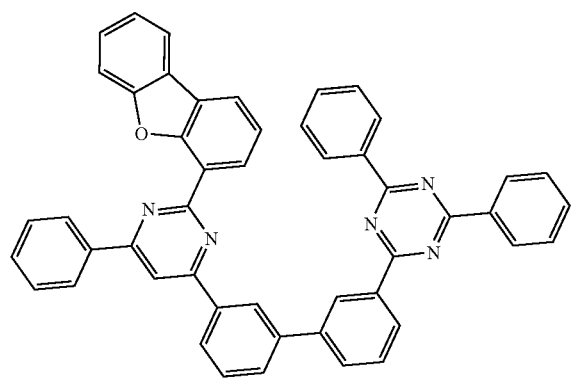
209
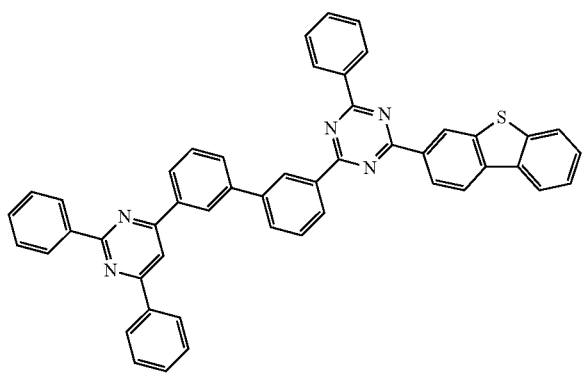
210
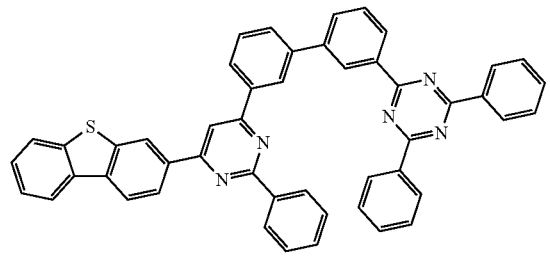
211
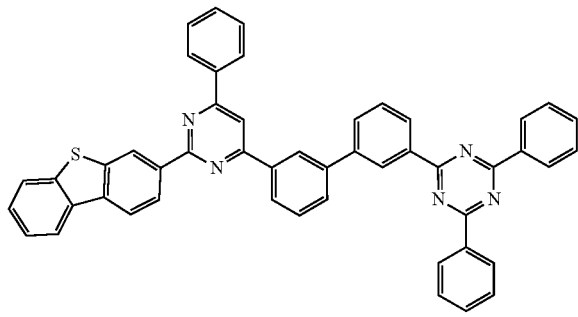
212
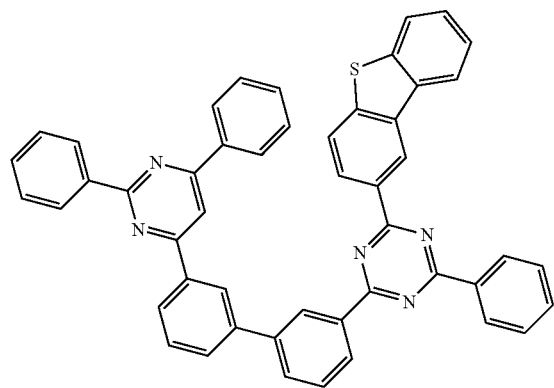
213
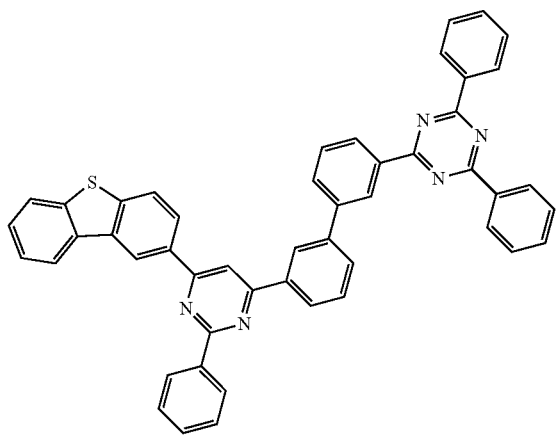

-continued
214
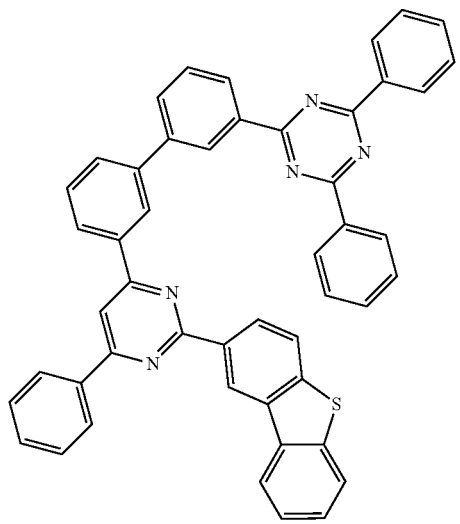
215
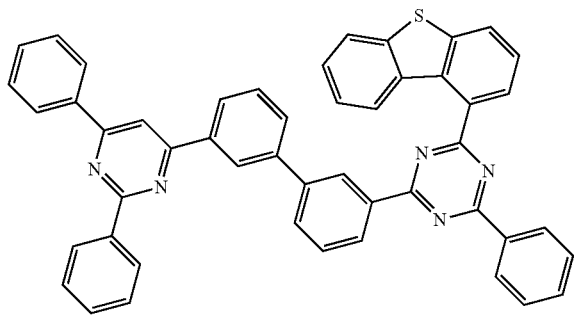
216
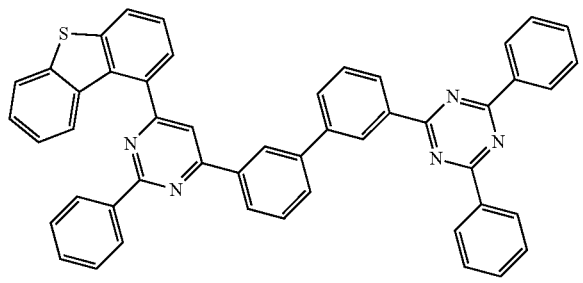
217
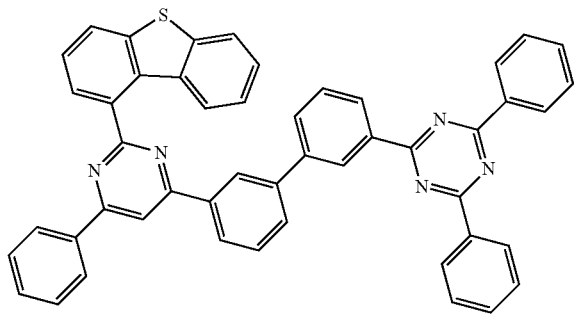
218
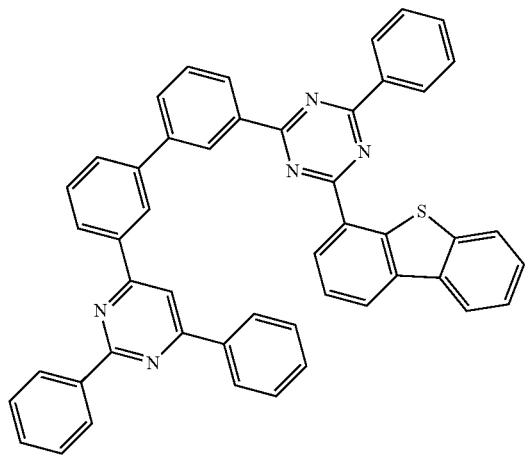
219
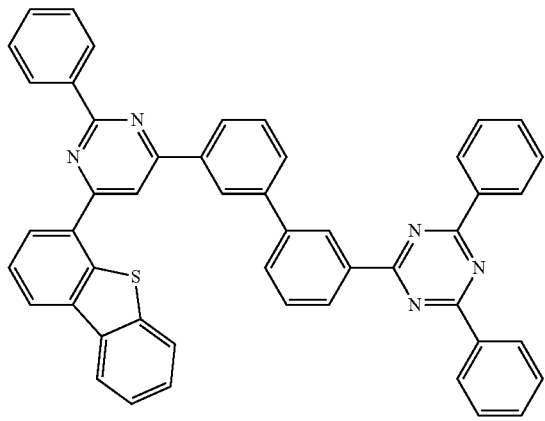

220
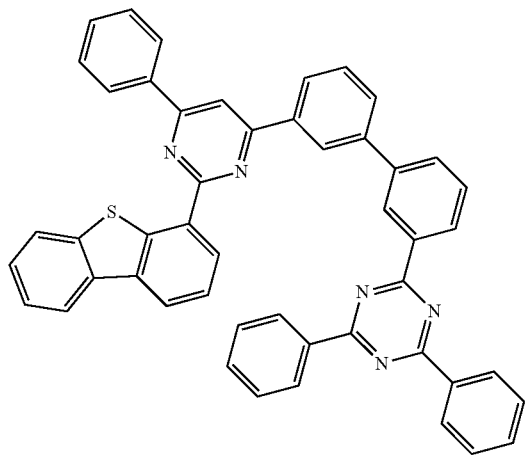
221
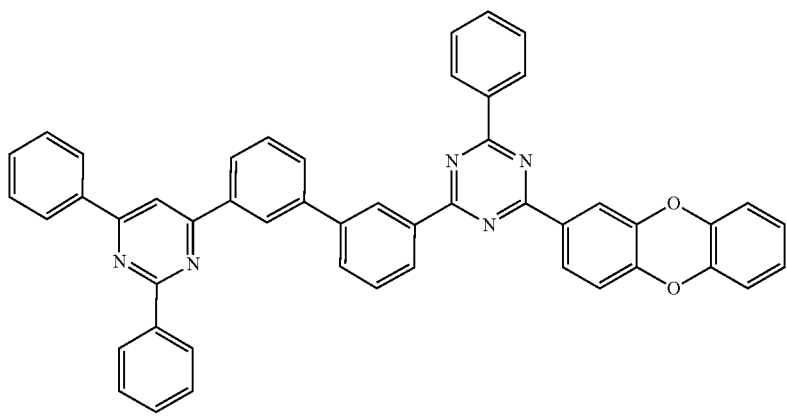
222
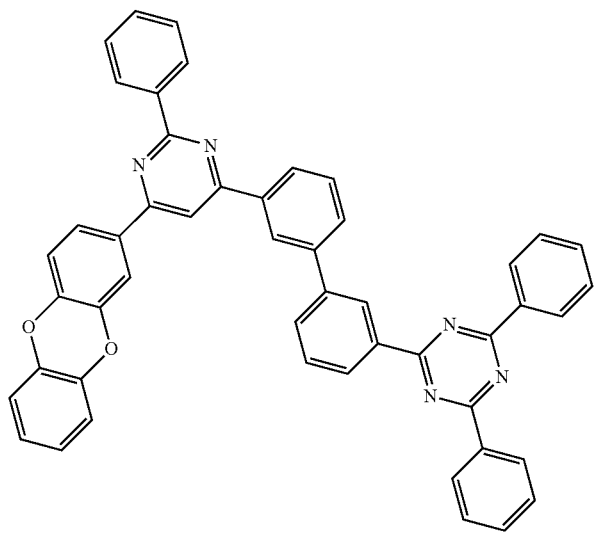

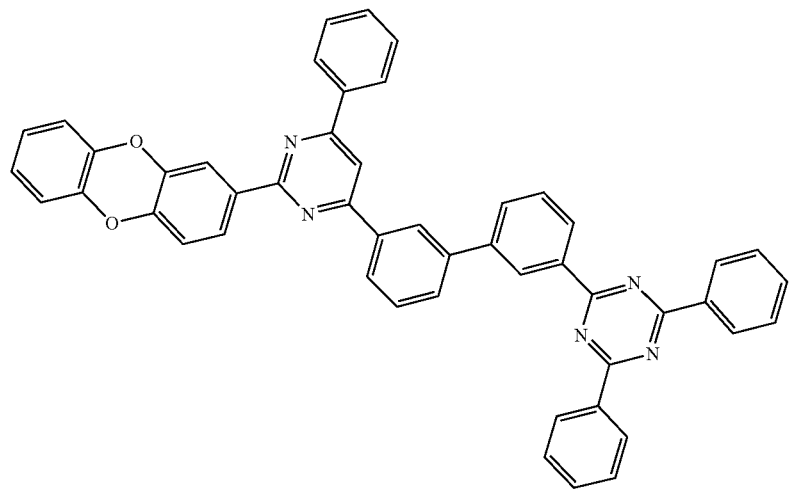
223
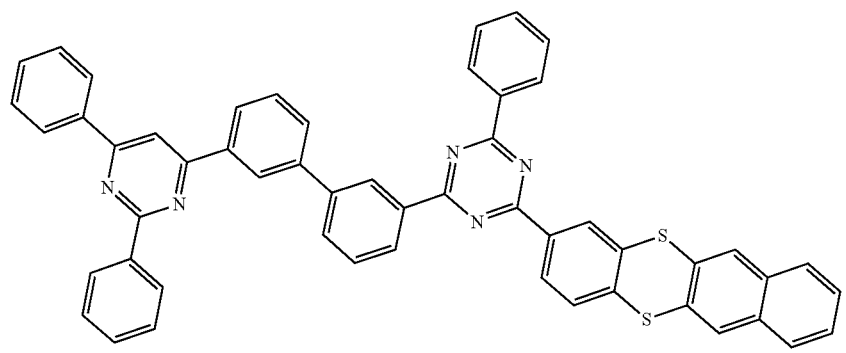
224
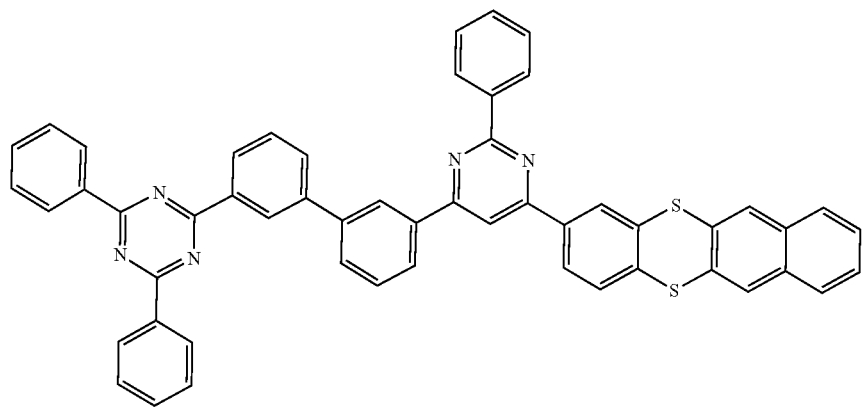
225

226
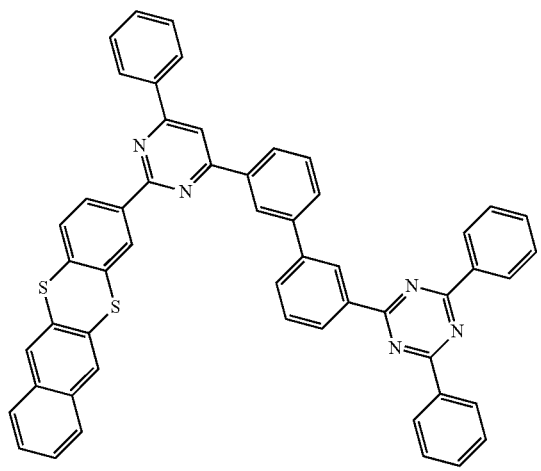
227
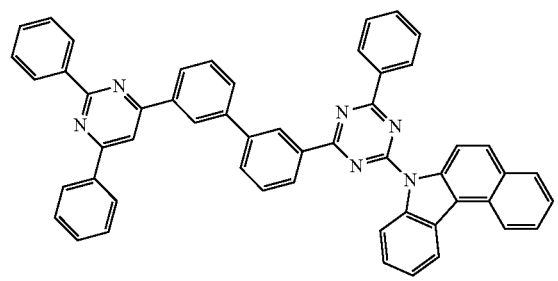
228
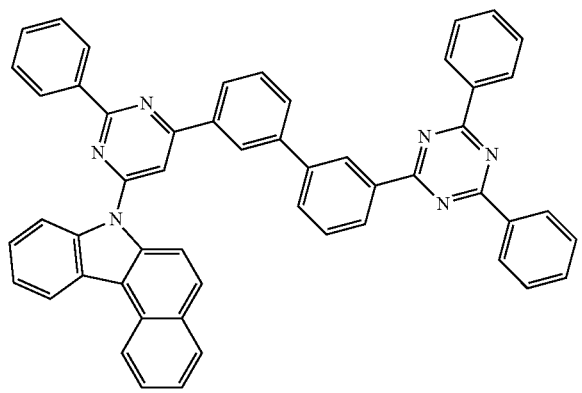
229
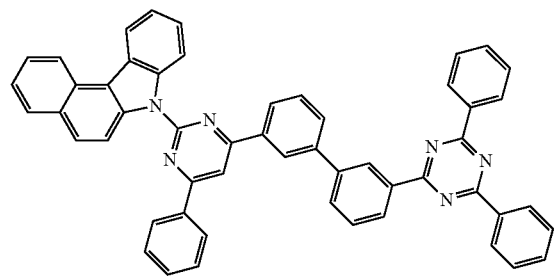
230
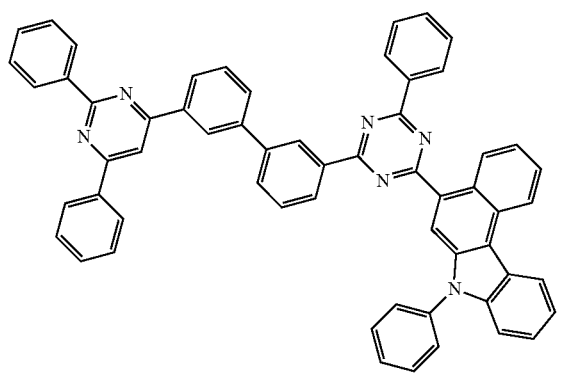
231
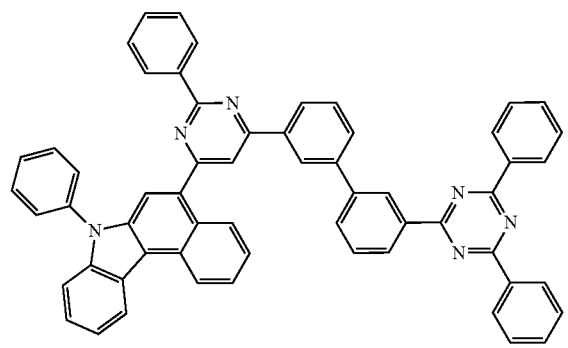

-continued
232
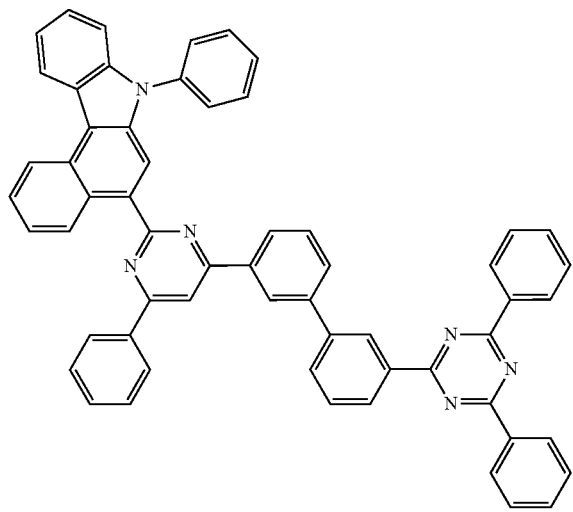
233
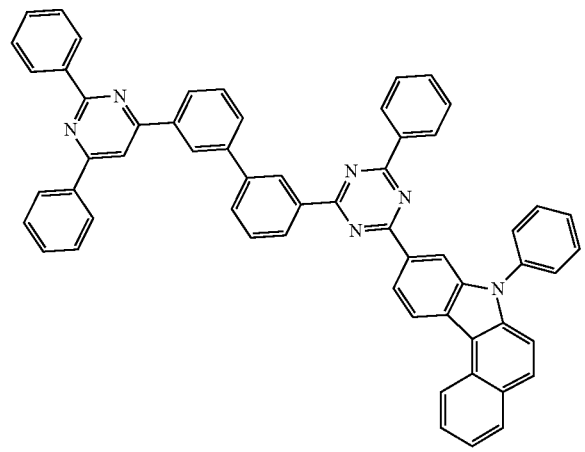
234
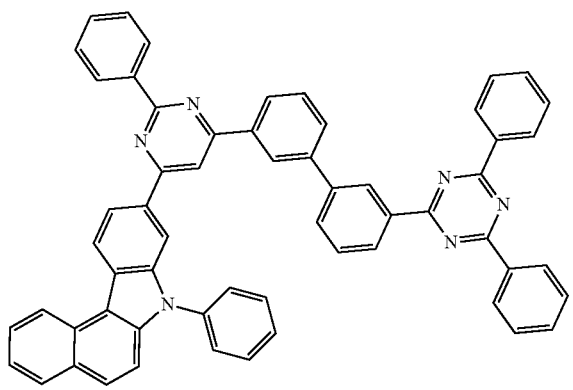
235
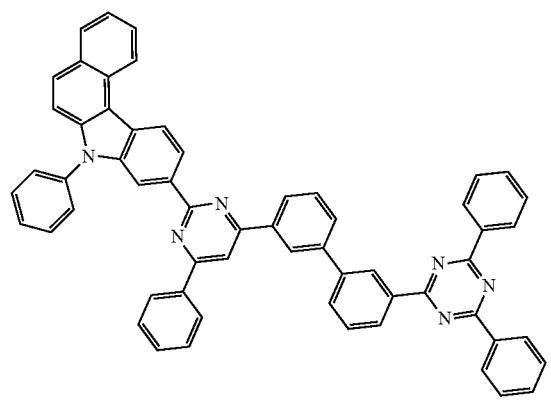
236
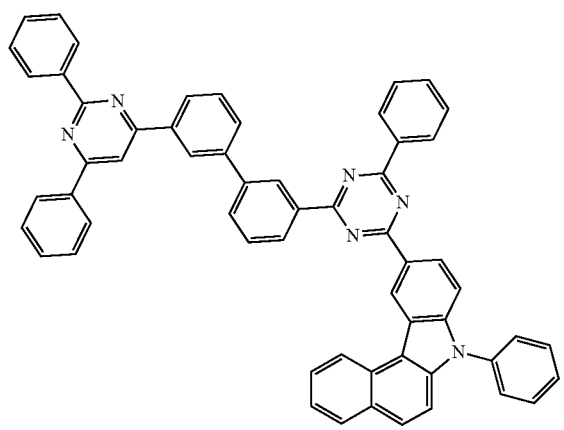
237
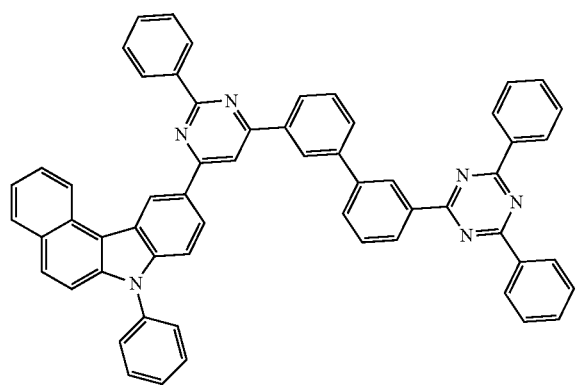

238
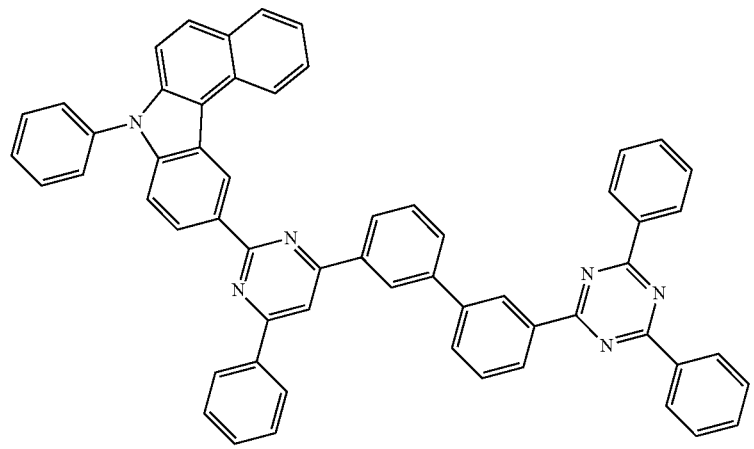
239
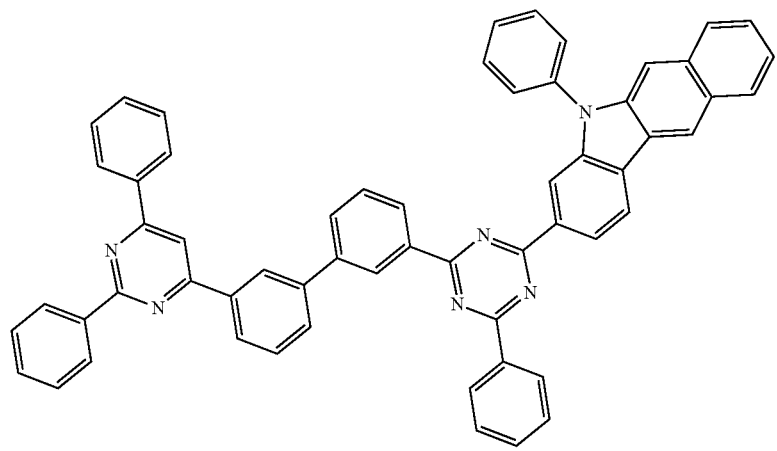
240
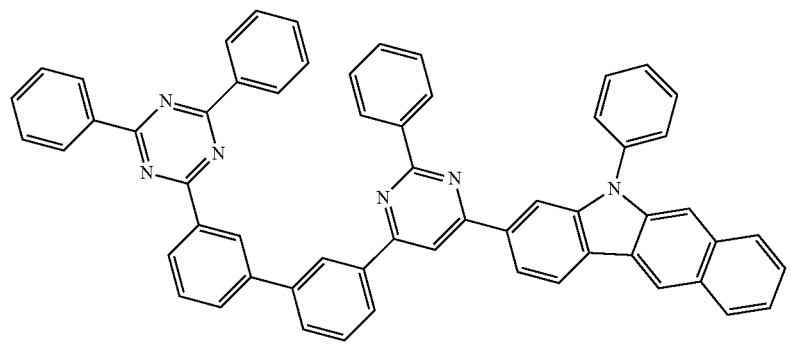

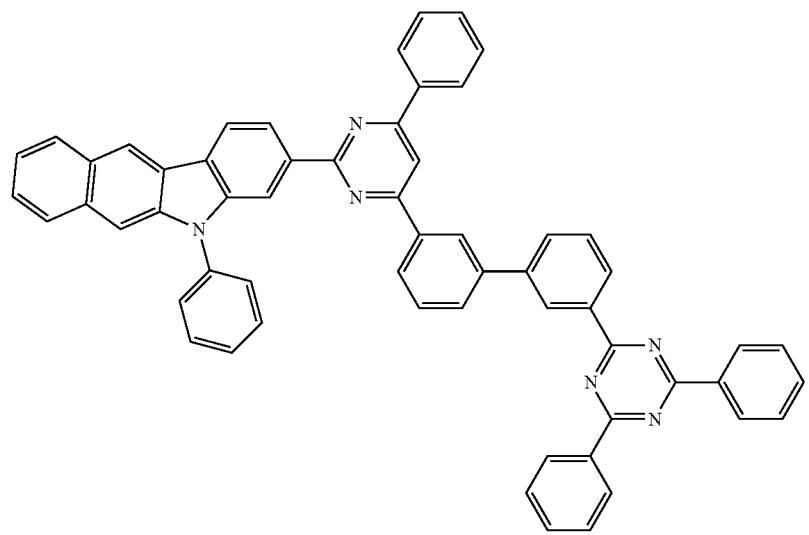
241
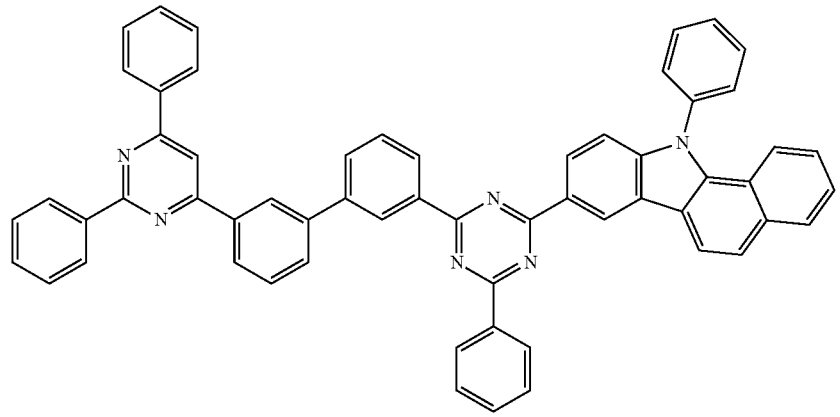
242
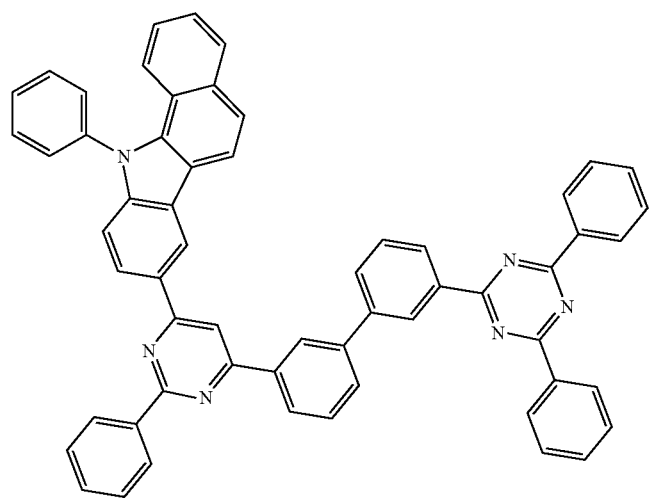
243

244
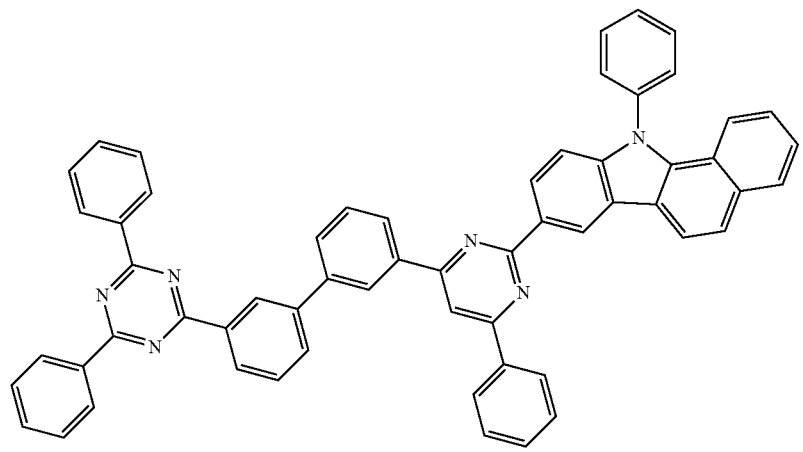
245 246
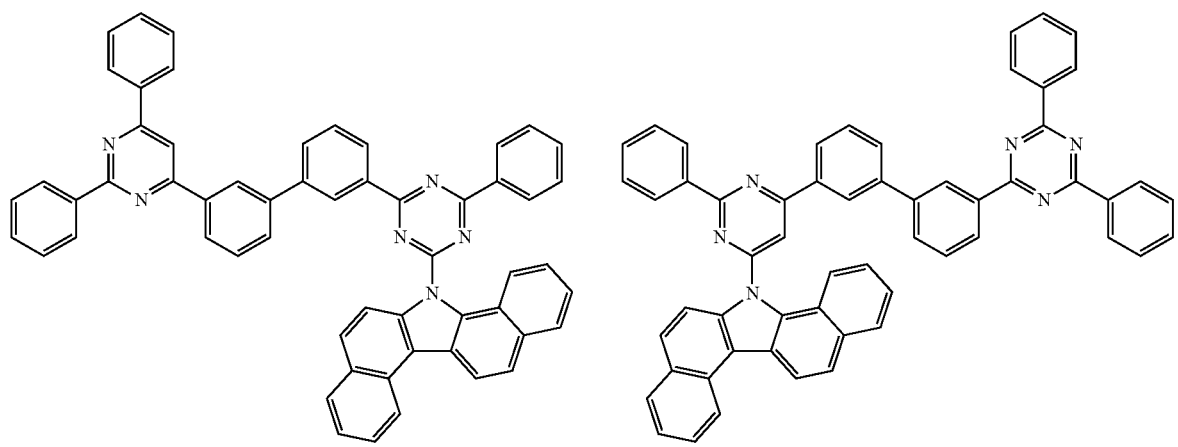
247 248
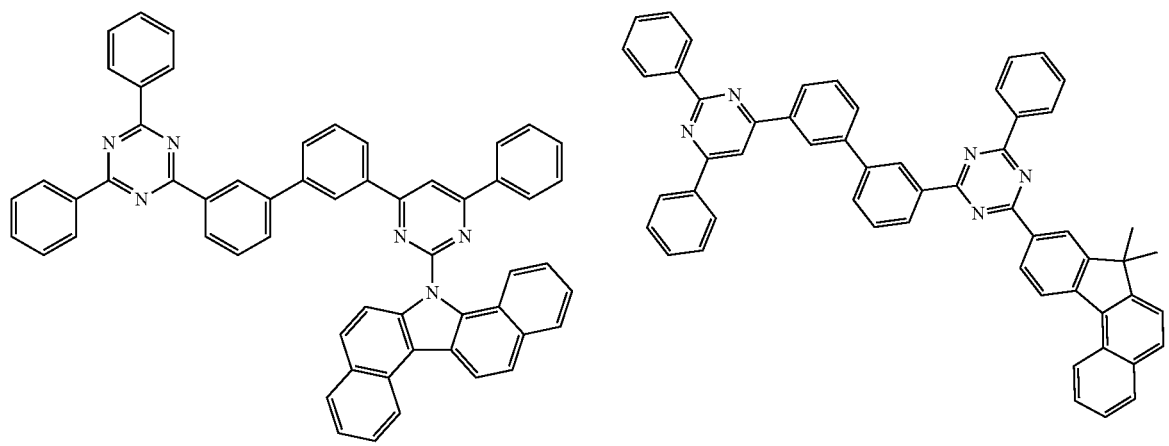

-continued
249
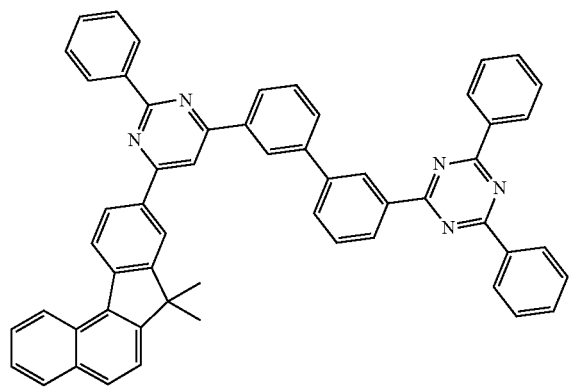
250
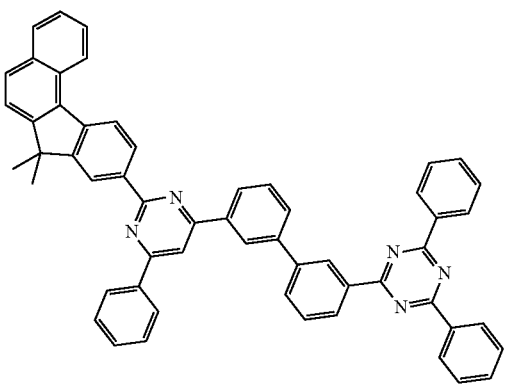
251
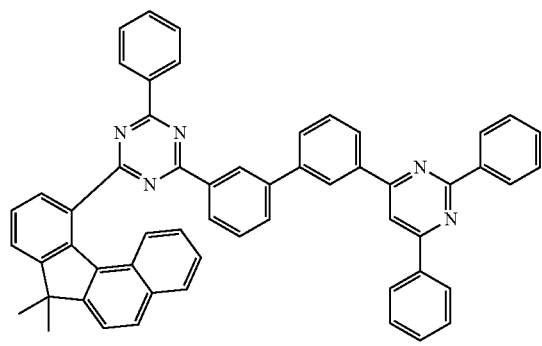
252
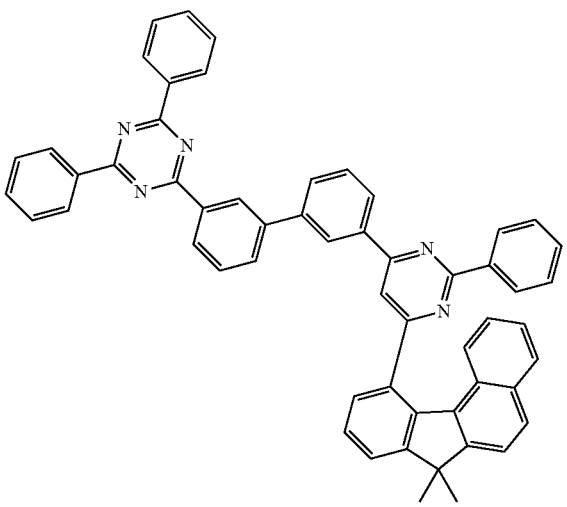
253
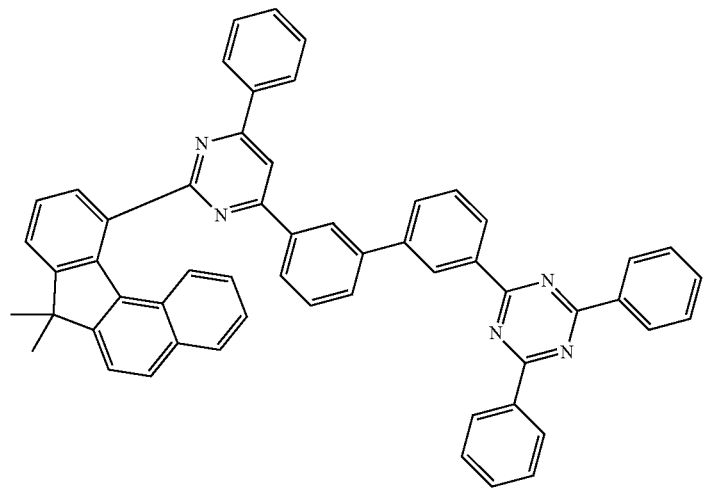

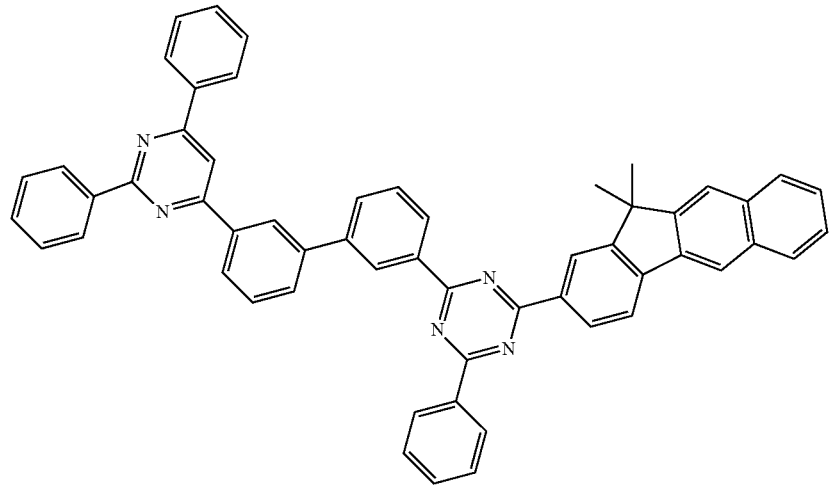
254
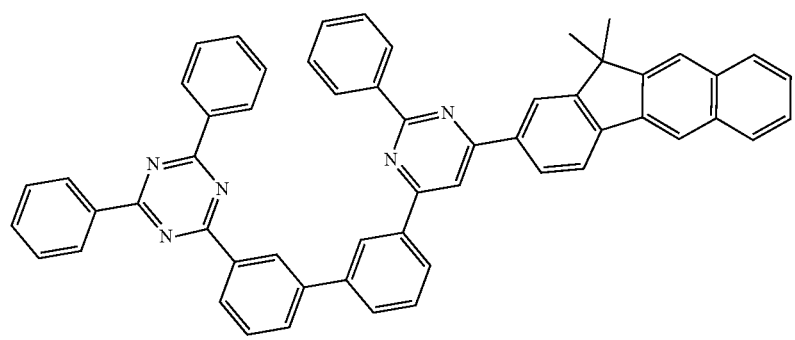
255
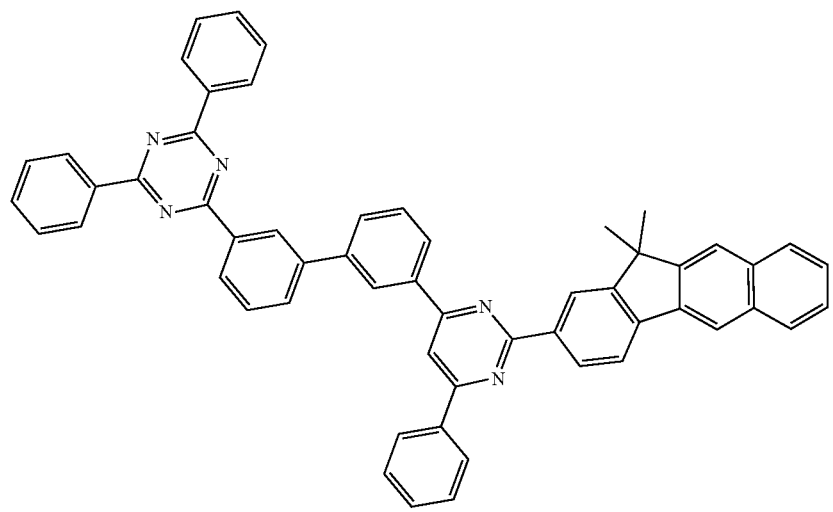
256

257
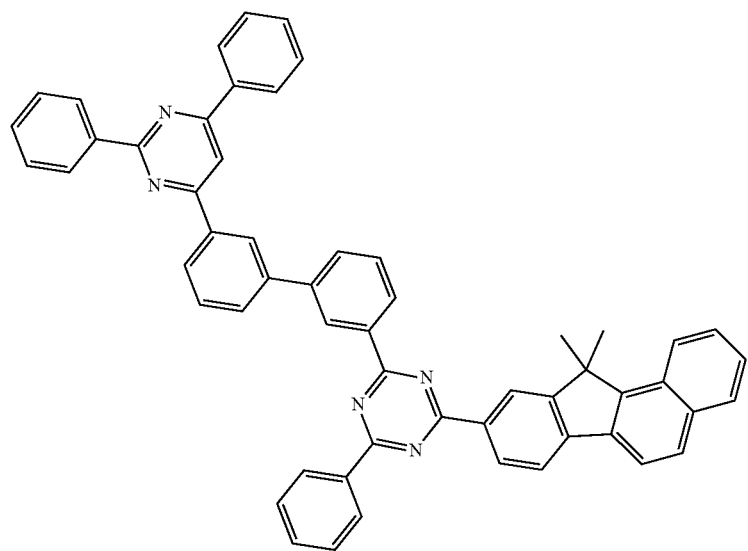
258
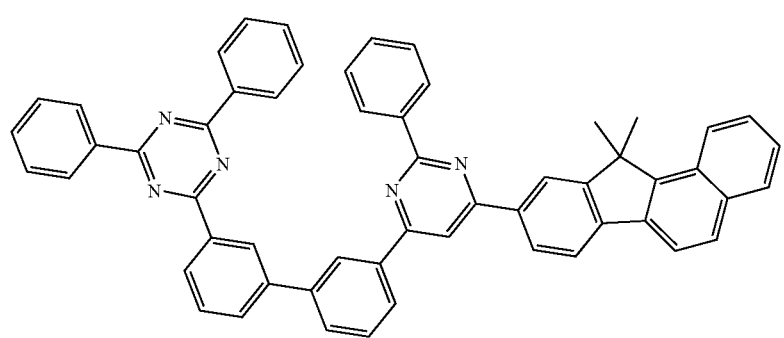
259
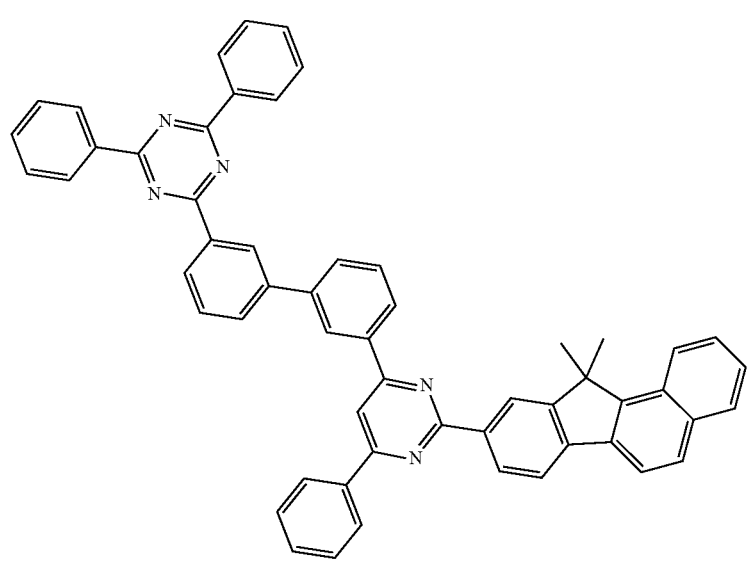

260
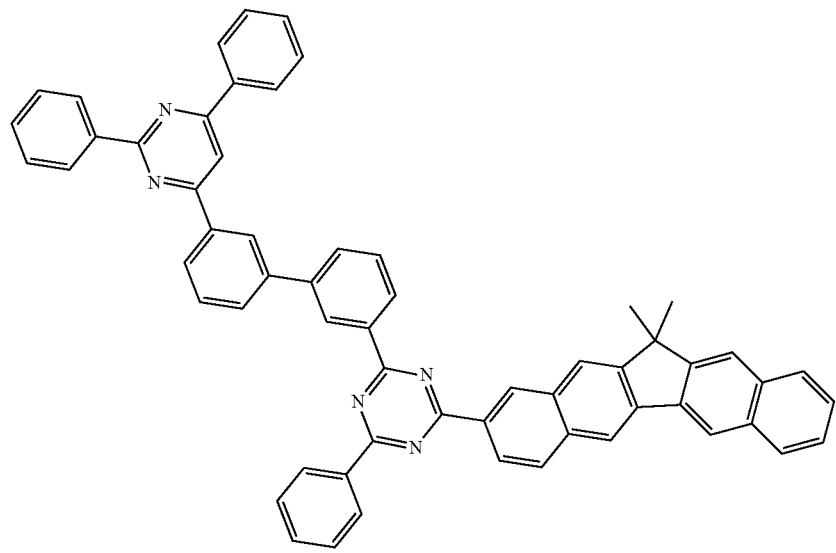
261
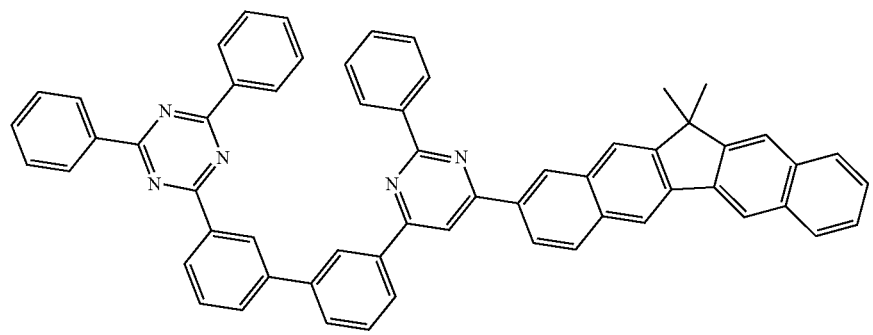
262
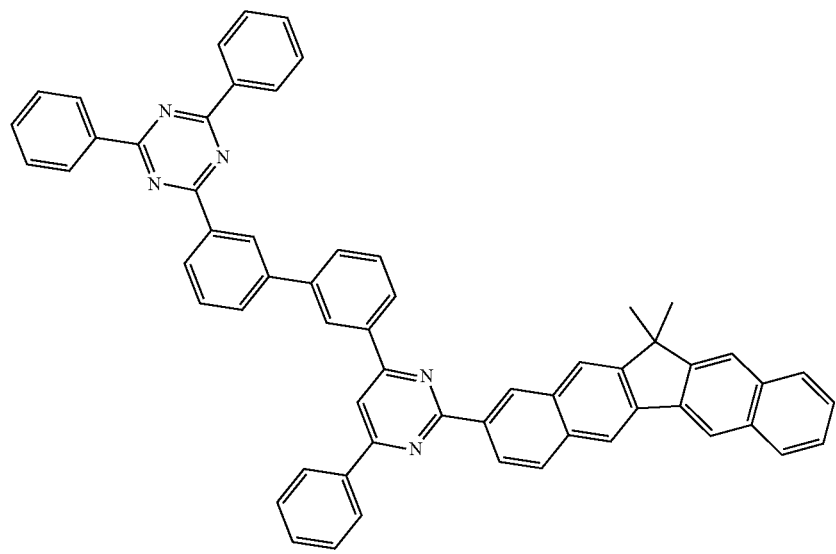

-continued
263
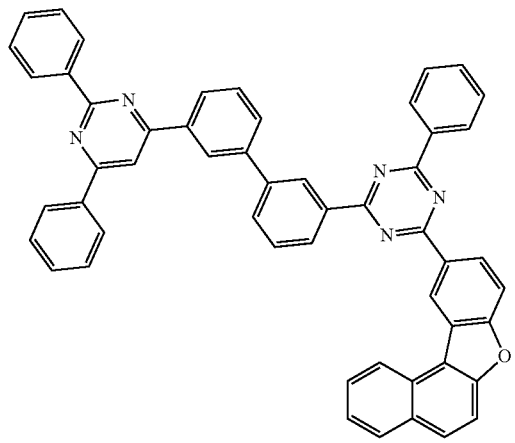
264
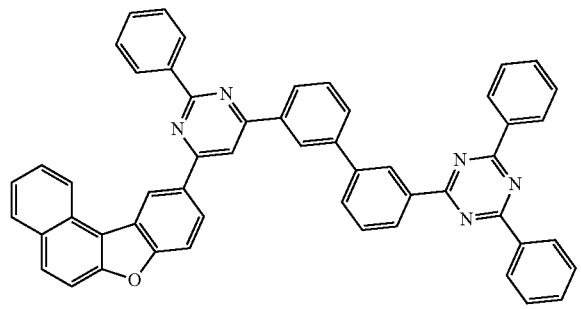
265
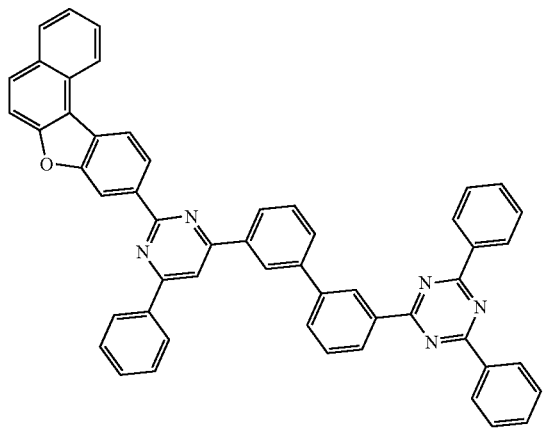
266
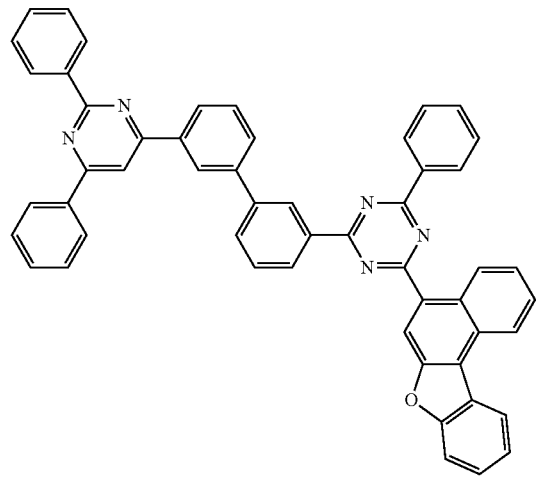
267
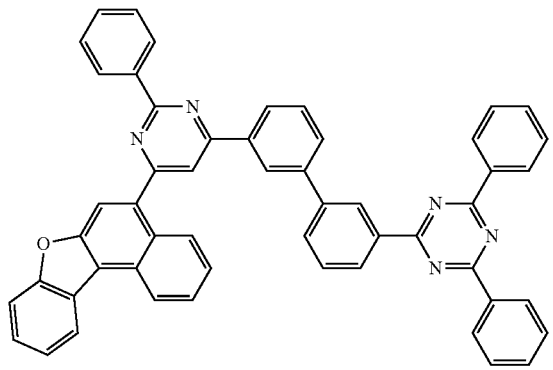
268
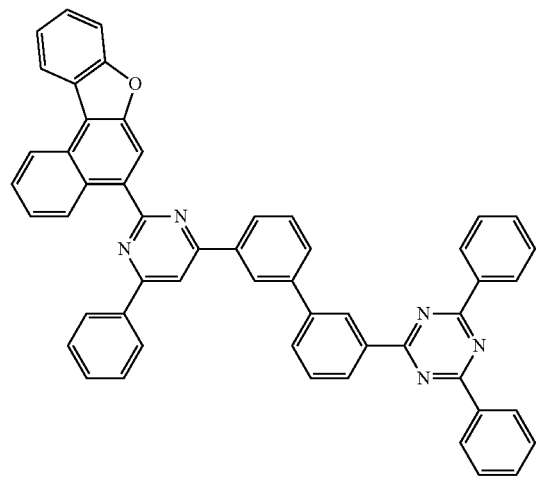

-continued
269 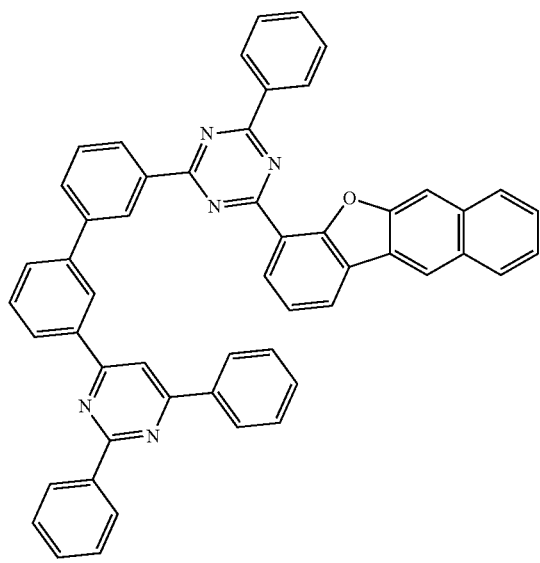
270 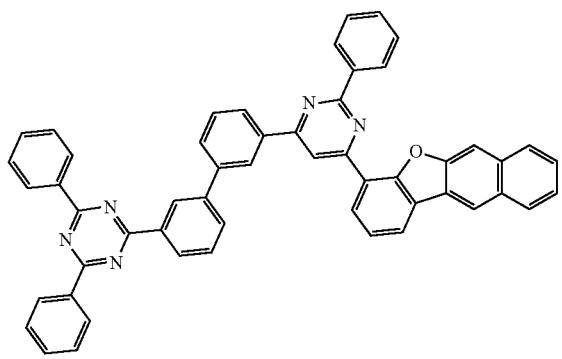
271 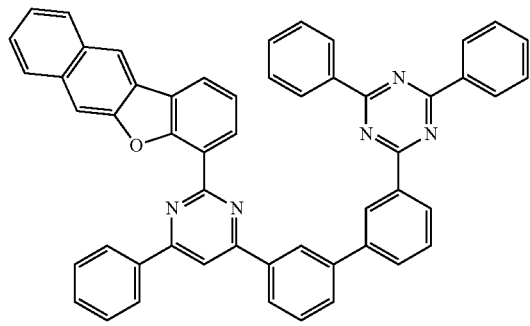
272 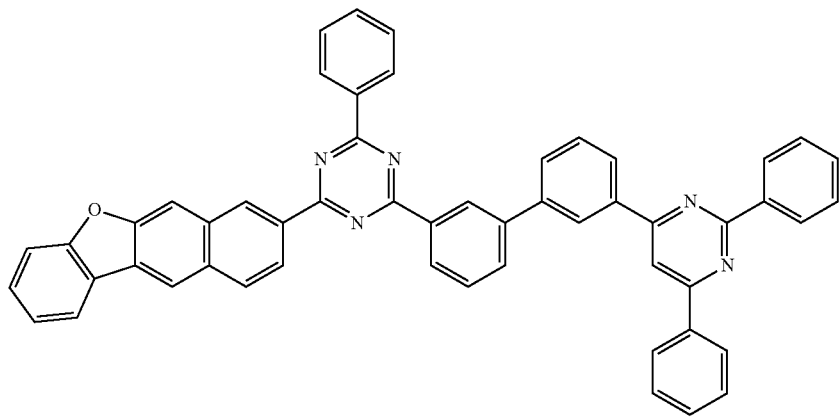

273
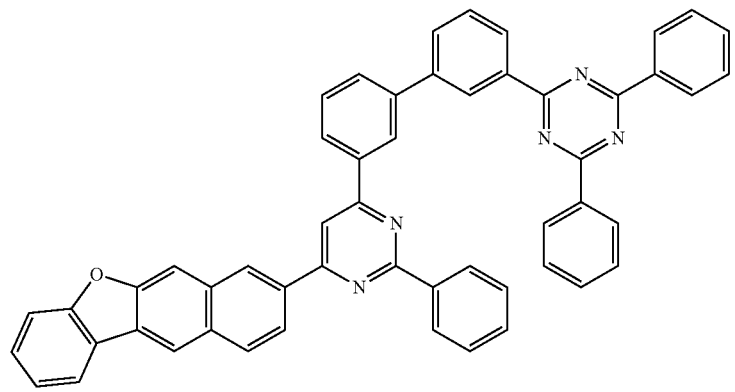
274
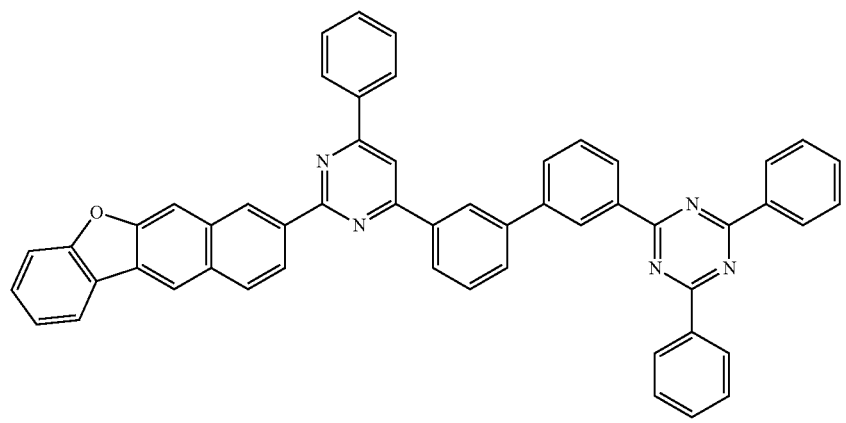
275
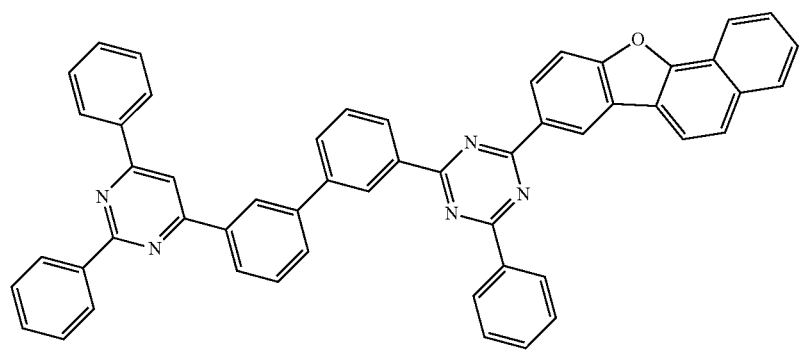
276
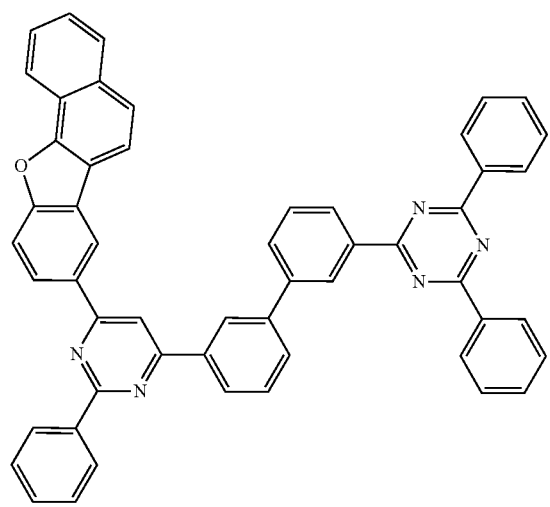

277
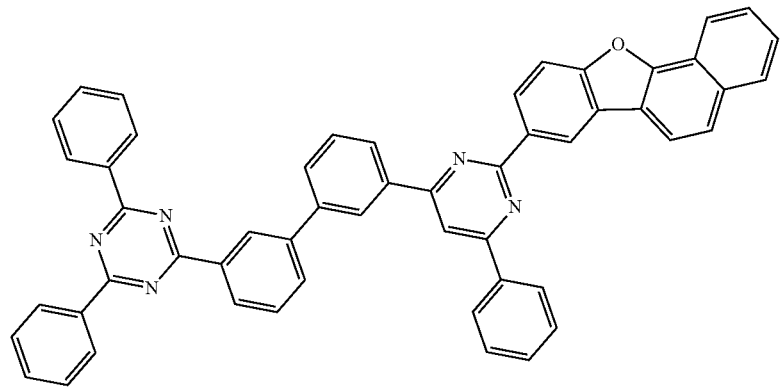
278 279
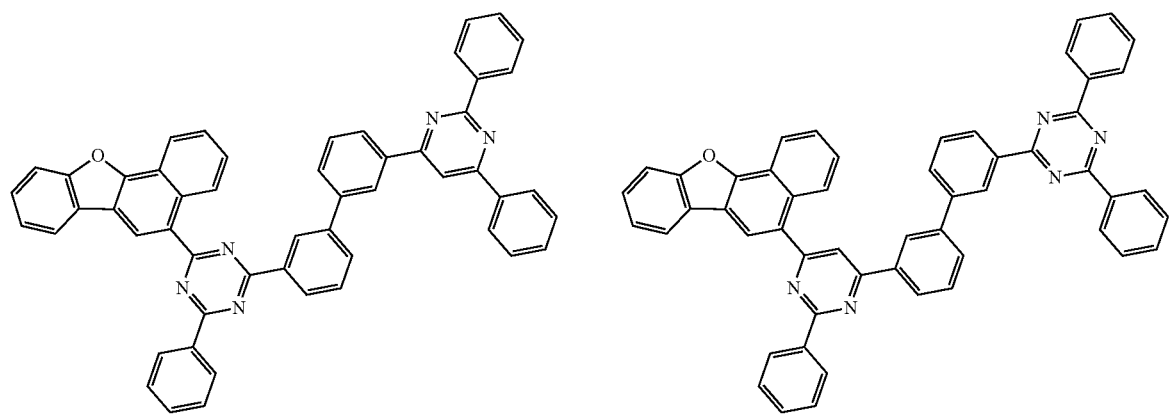
280 281
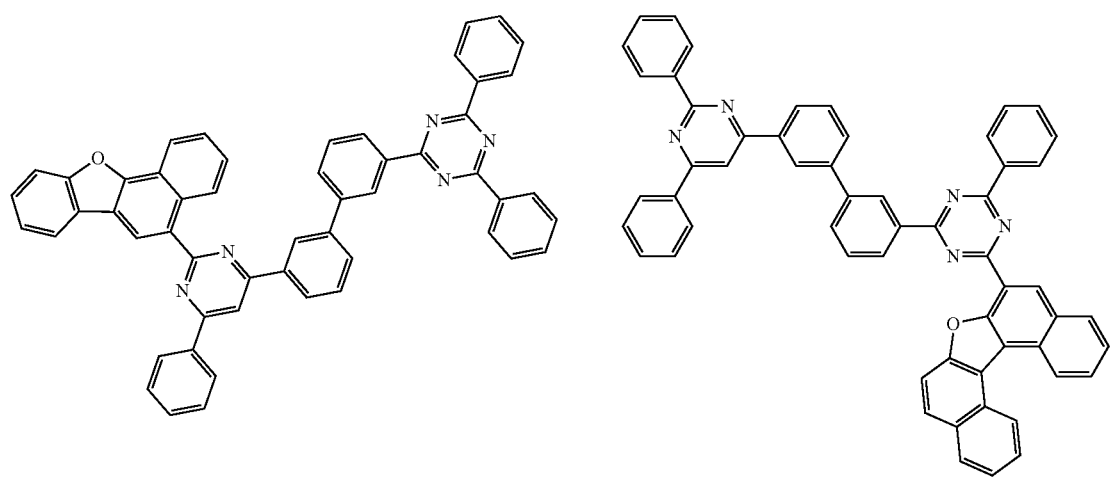

-continued
282
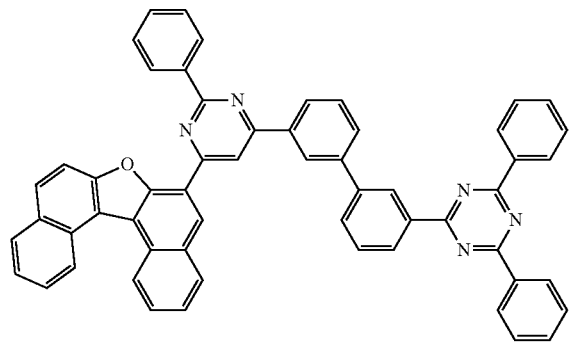
283
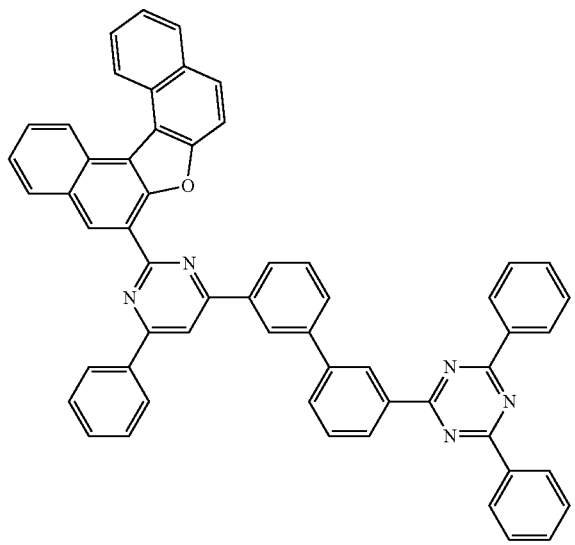
284
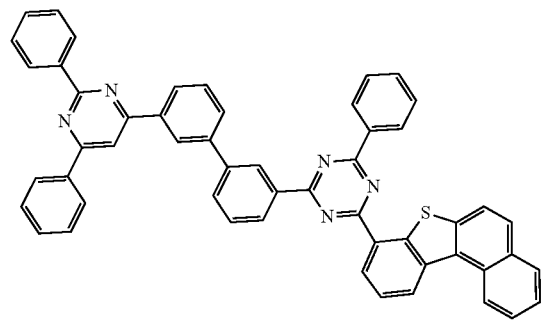
285
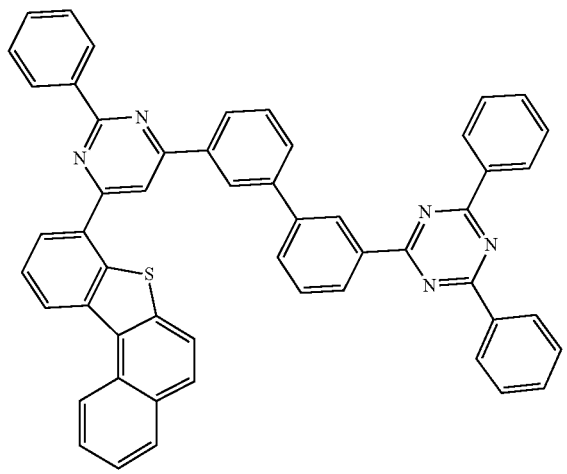
286
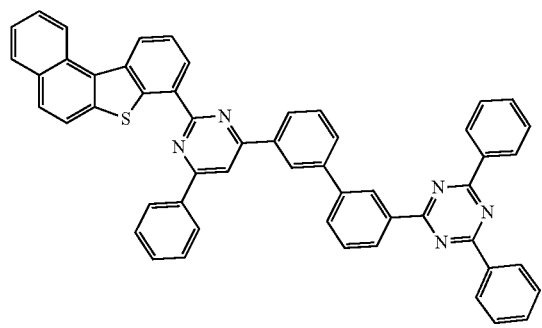
287
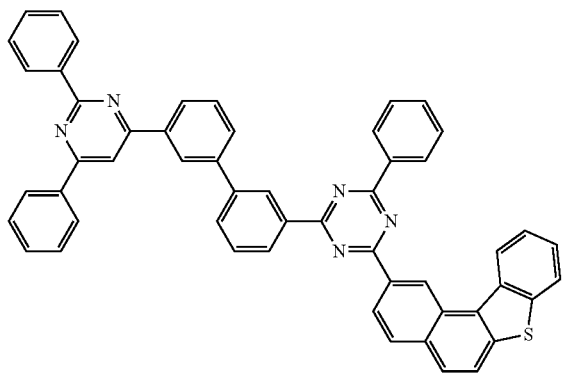

288
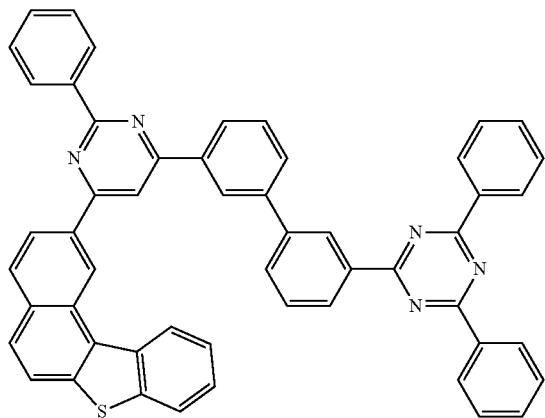
289 290
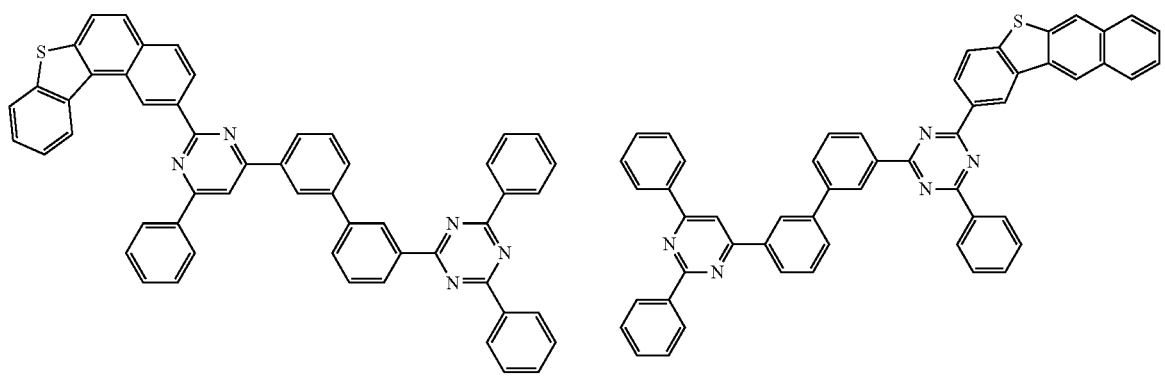
291 292
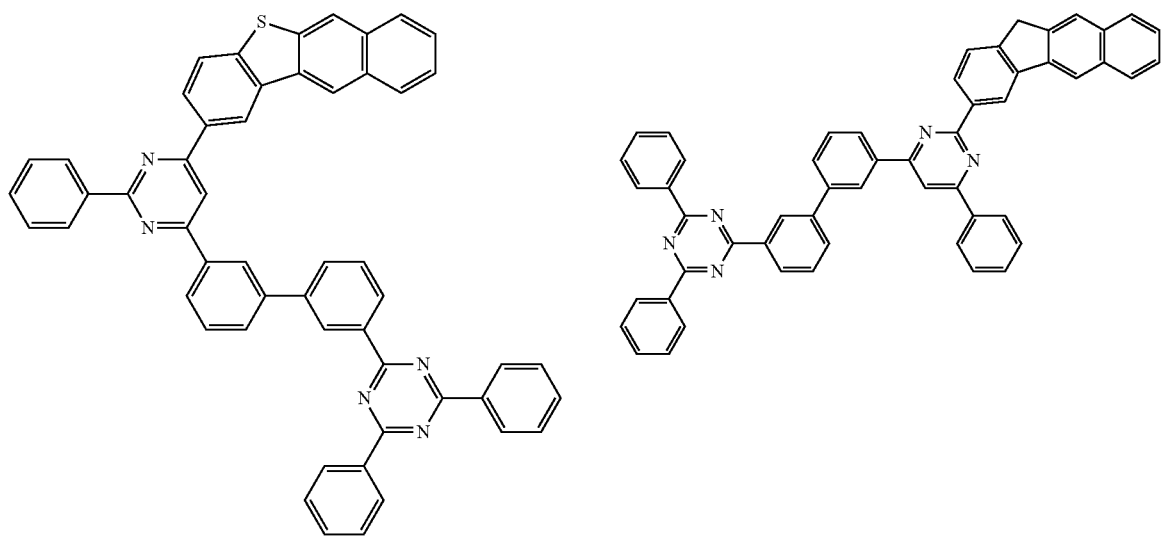

293
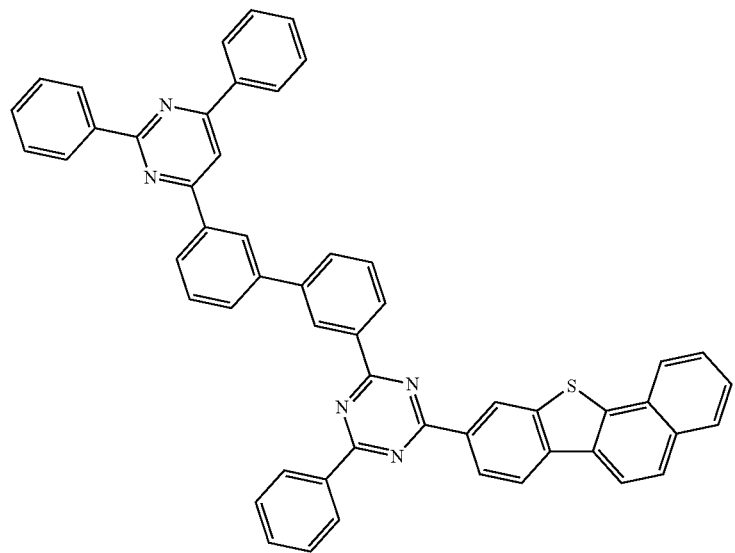
294
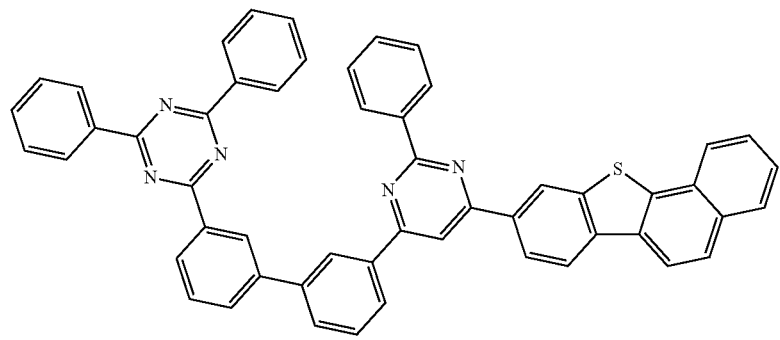
295
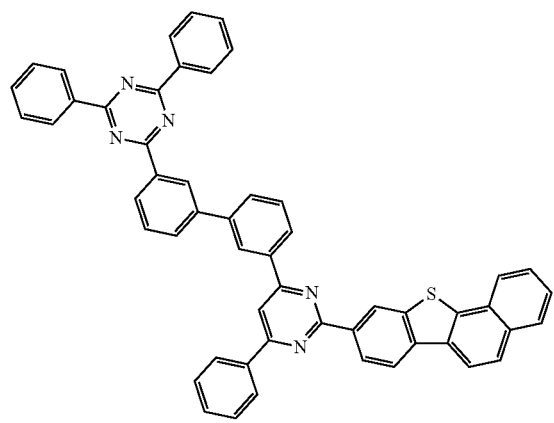
296
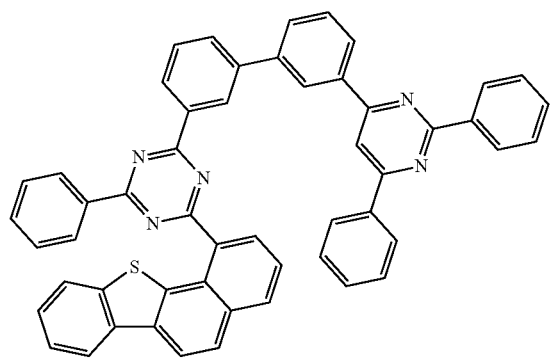

-continued
297
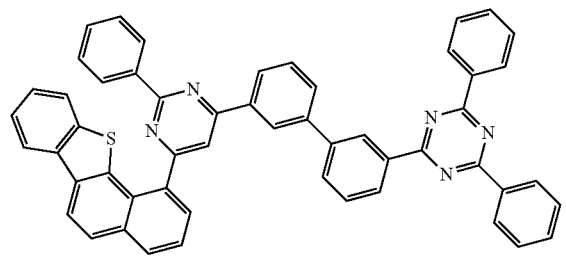
298
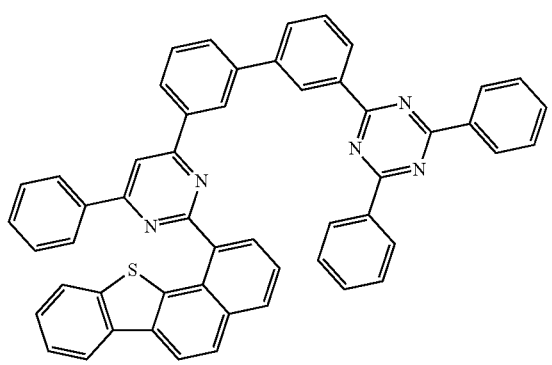
299
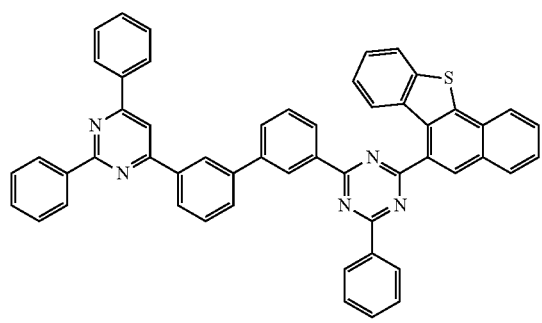
300
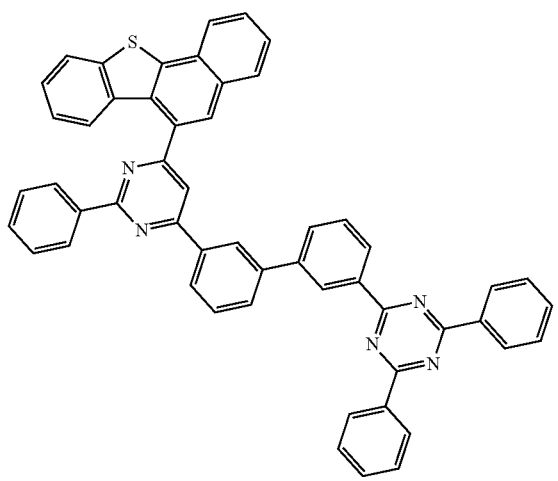
301
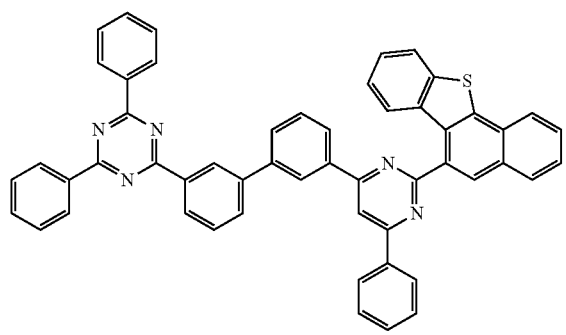
302
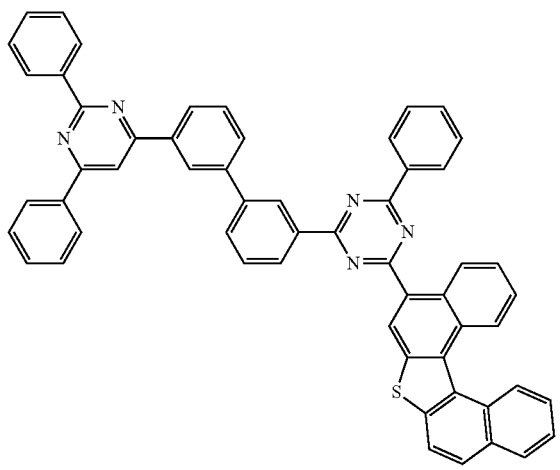

303
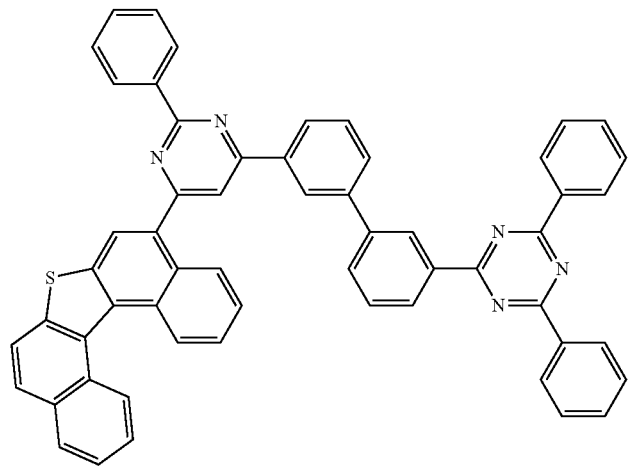
304
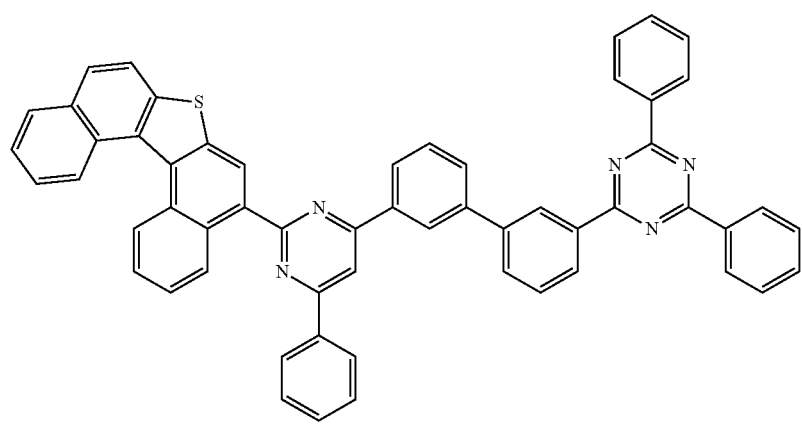
305
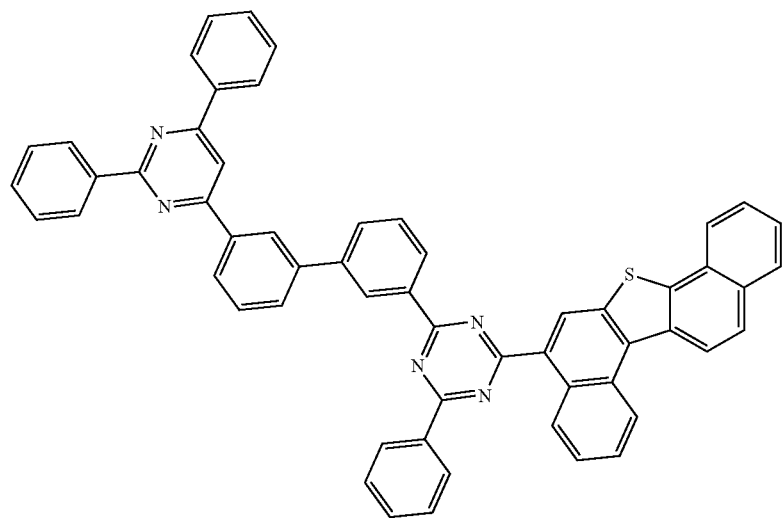

306
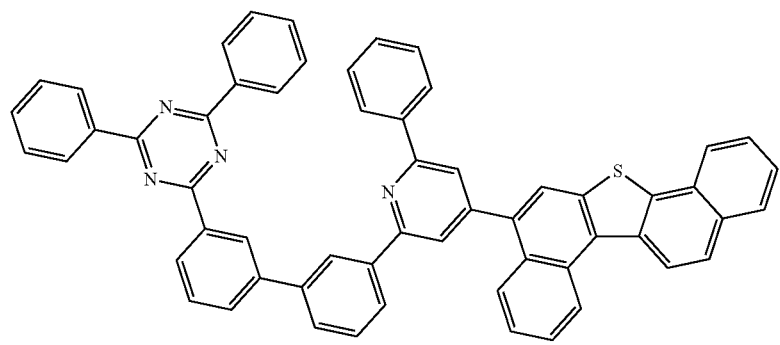
307
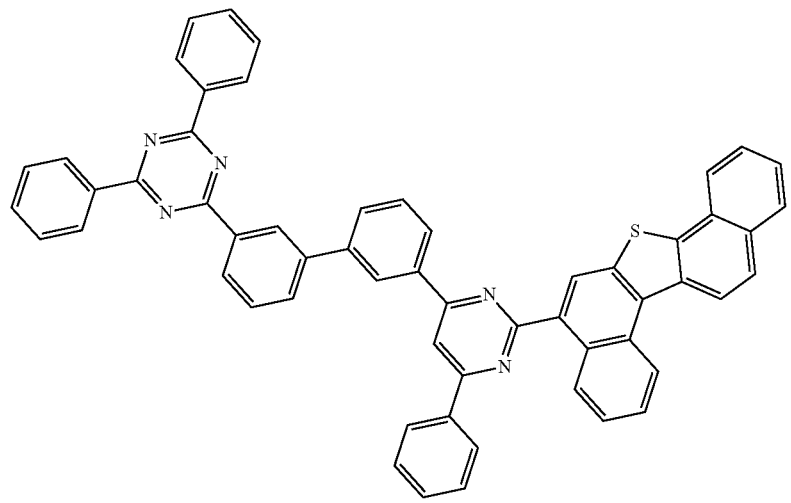
308
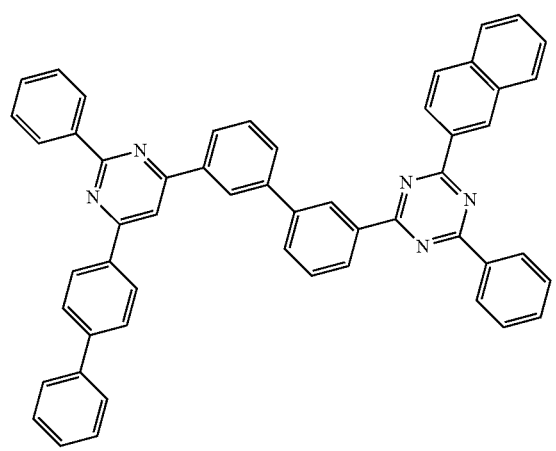
309
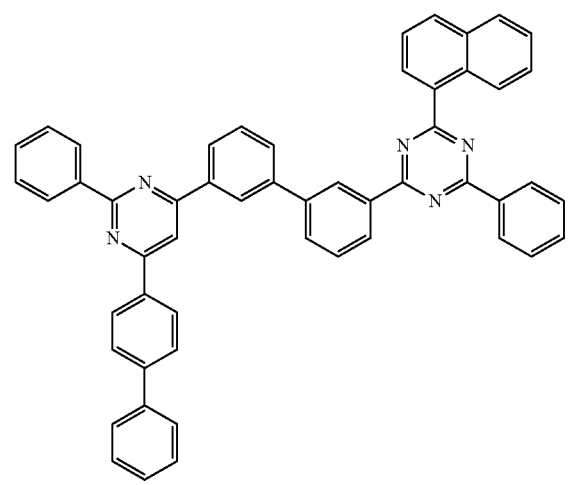

-continued
310
311
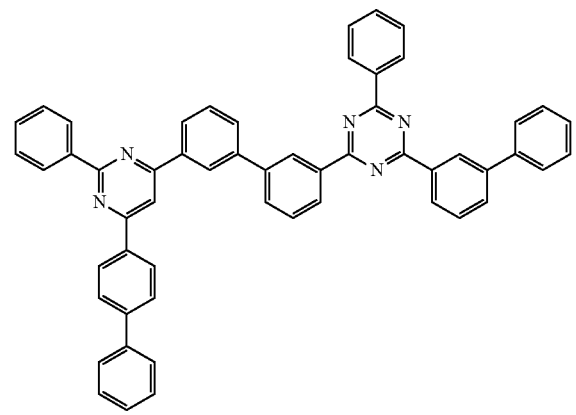
312
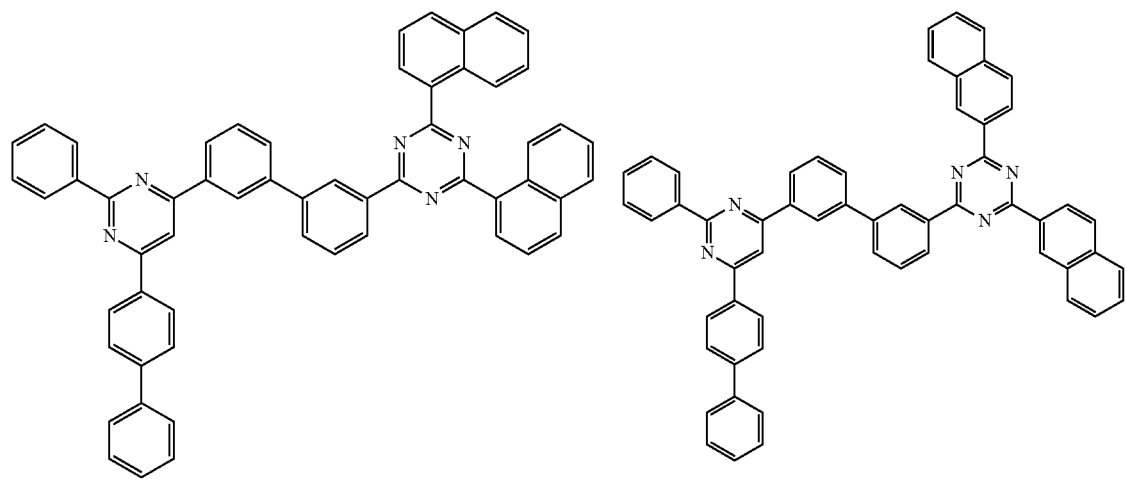
313
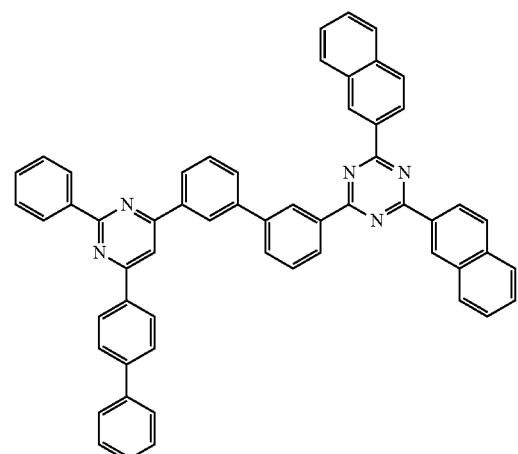
314
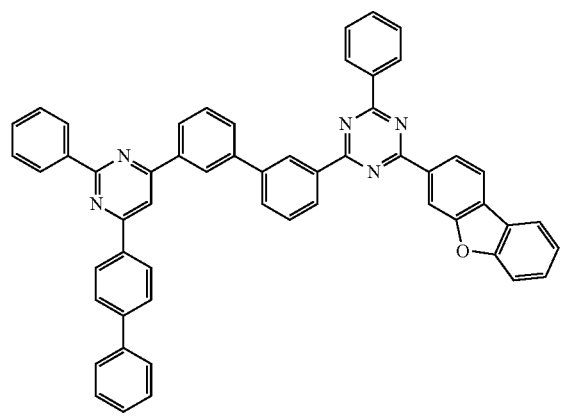
315
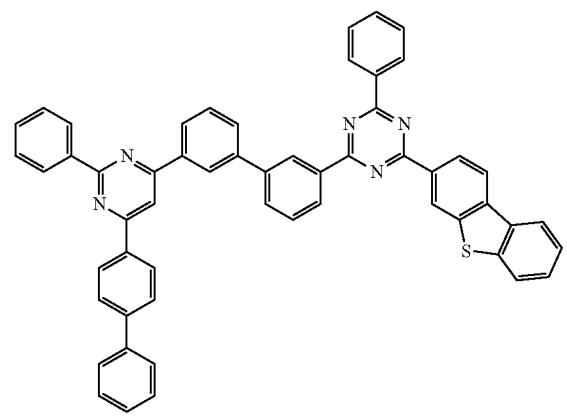

-continued
316
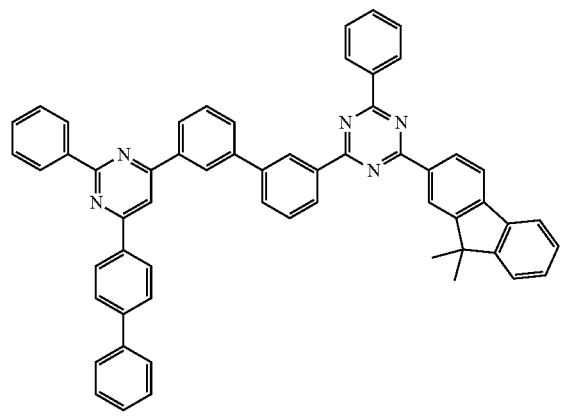
317
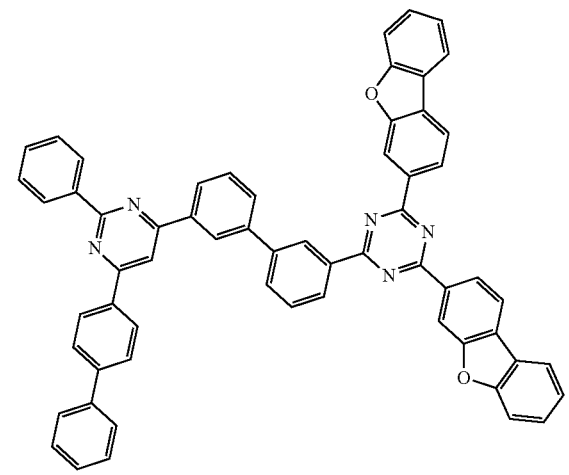
318
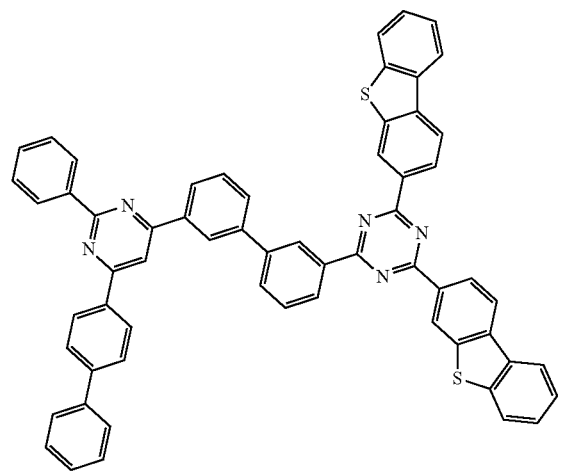
319
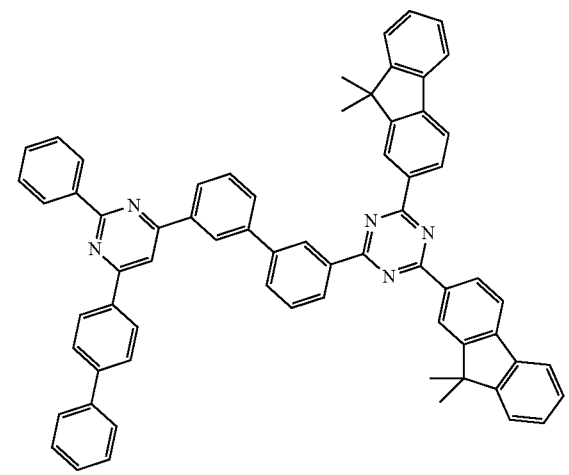
320
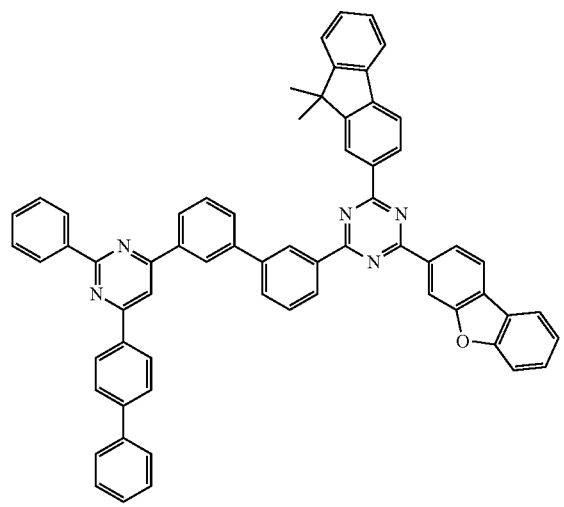
321
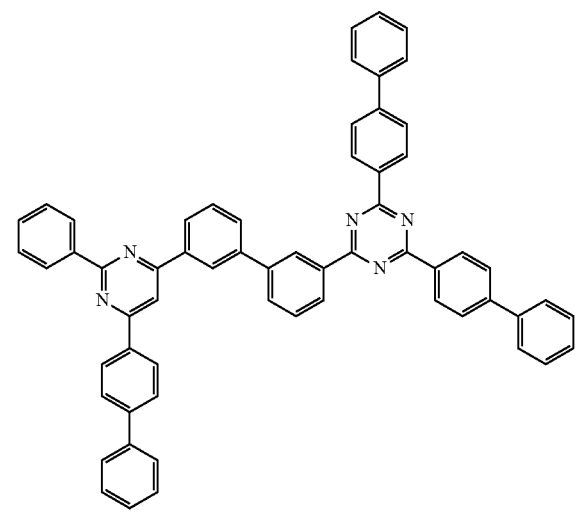

-continued
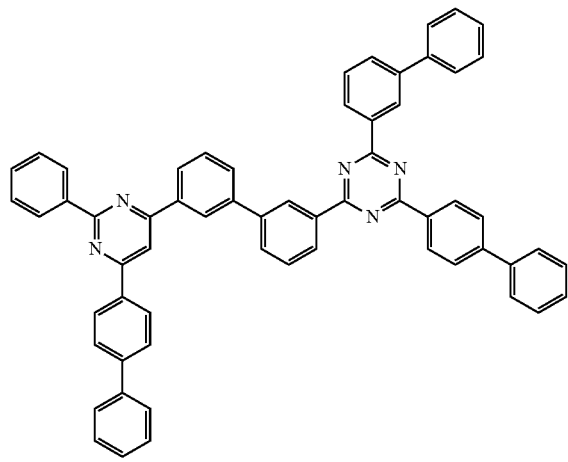
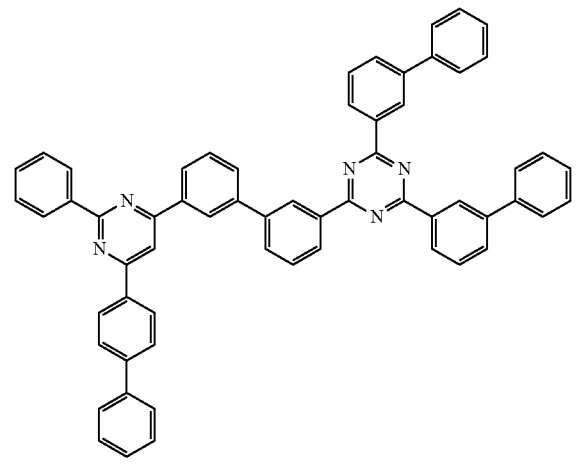
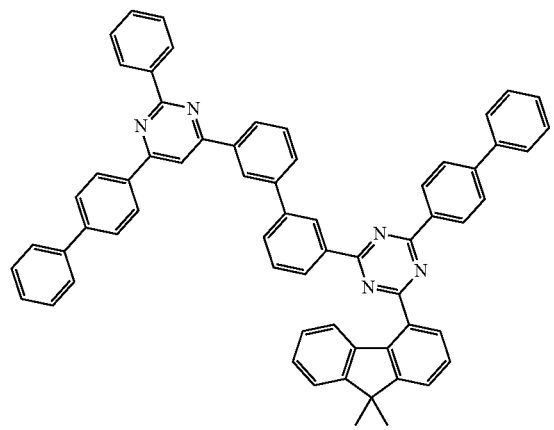
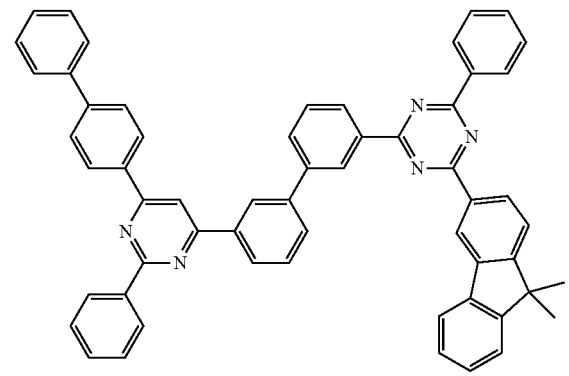
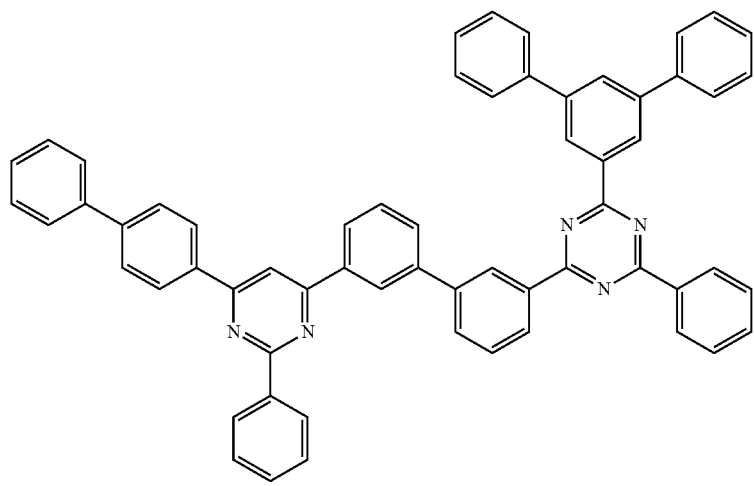

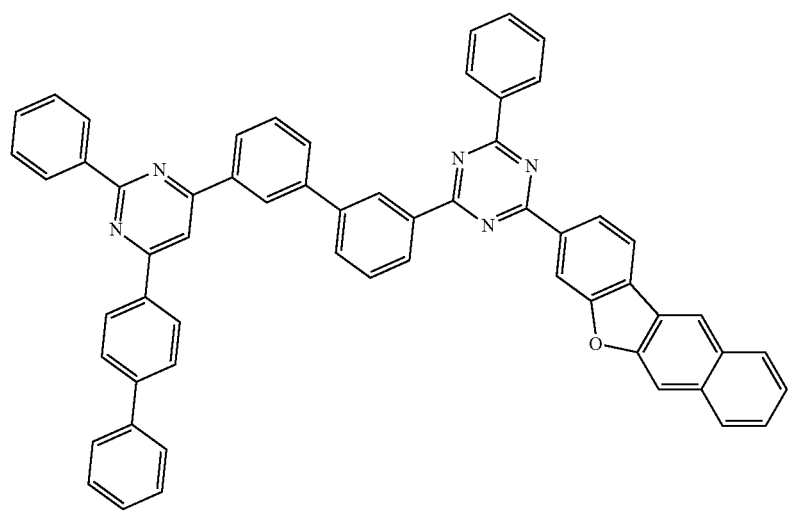
327
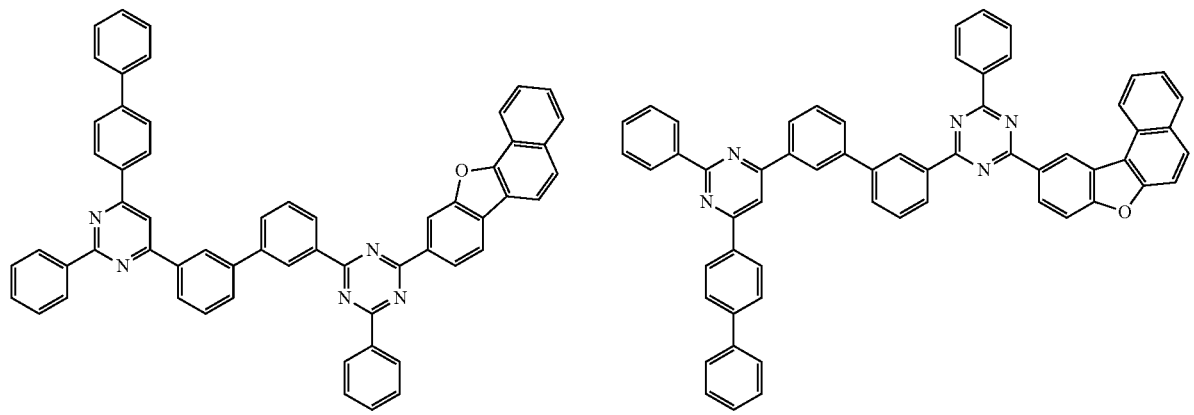
328 329
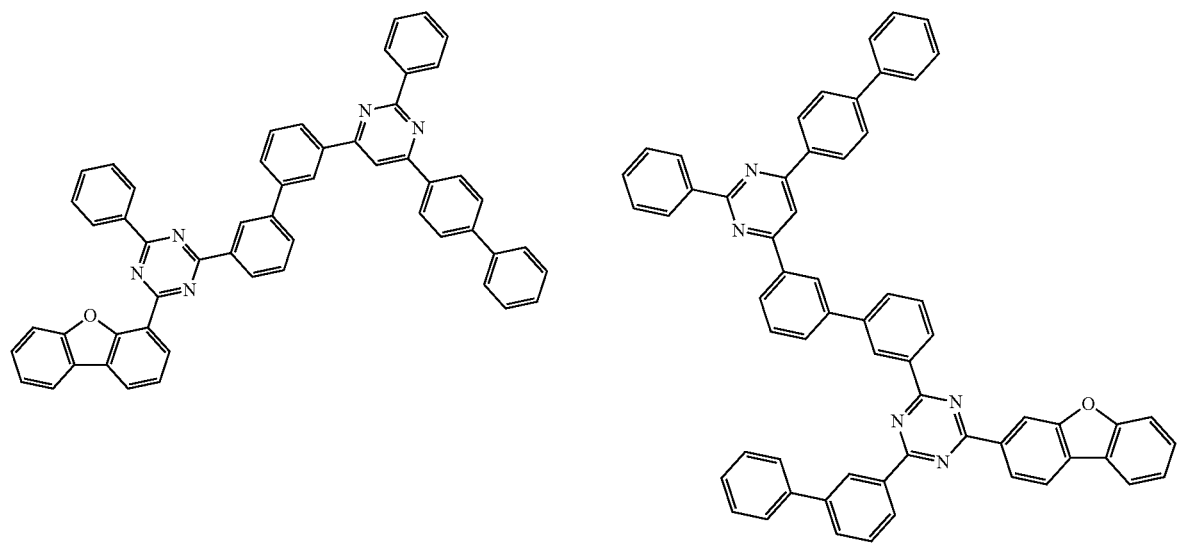
330 331

332
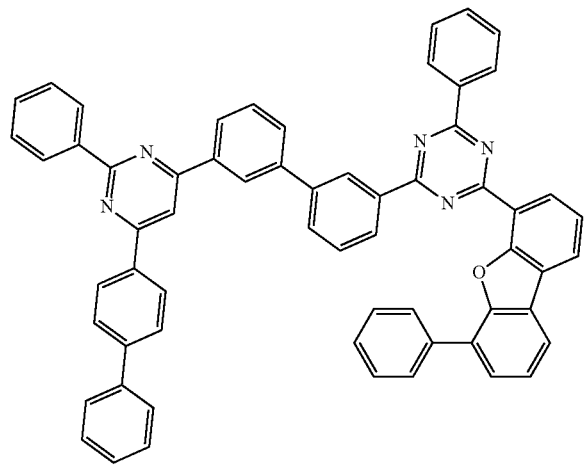
333
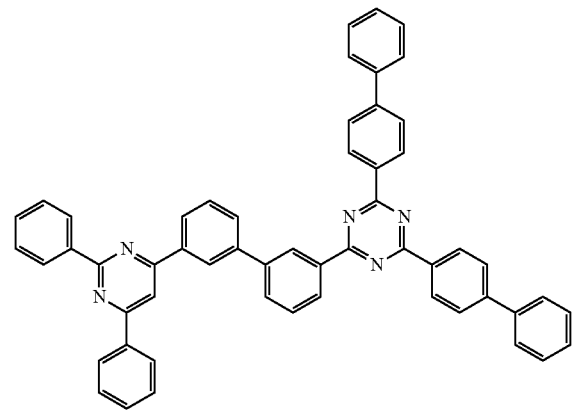
334
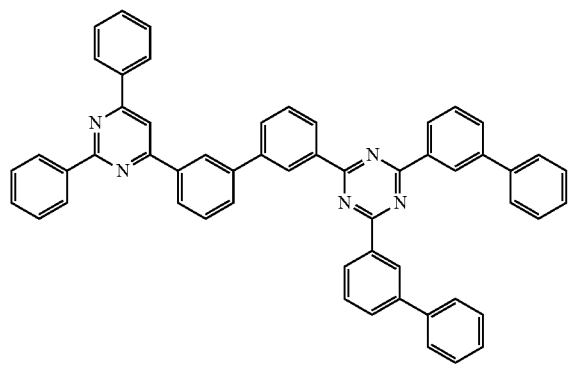
335
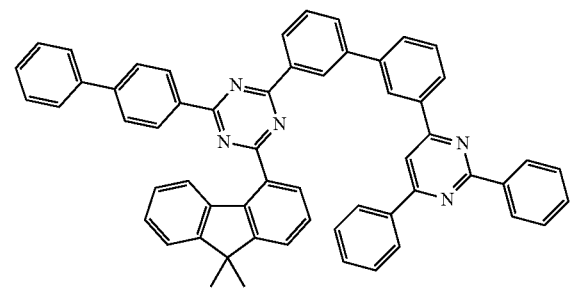
336
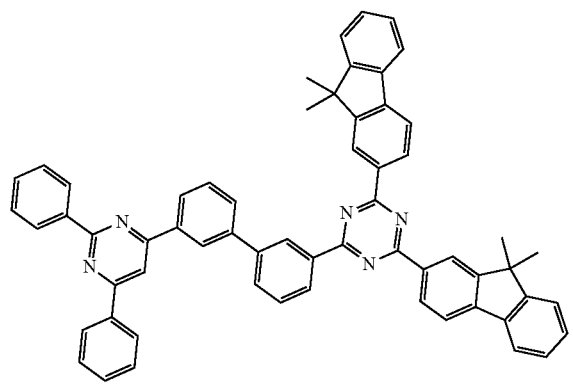
337
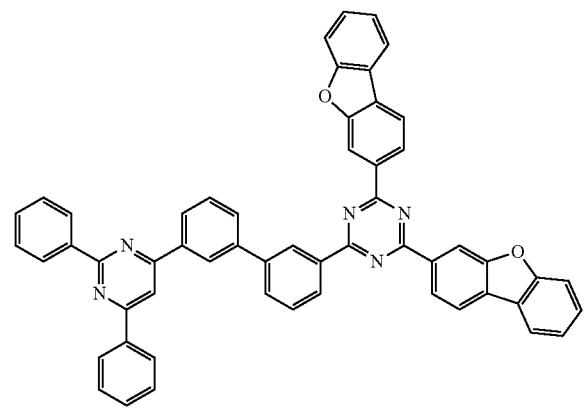

338
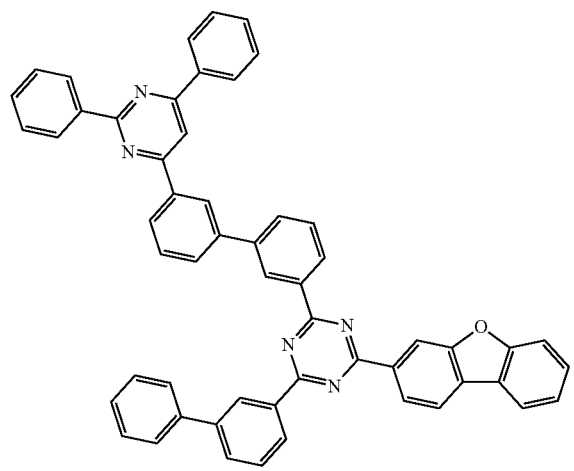
339
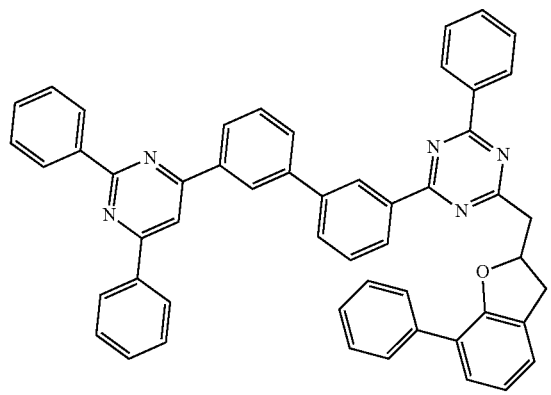
340
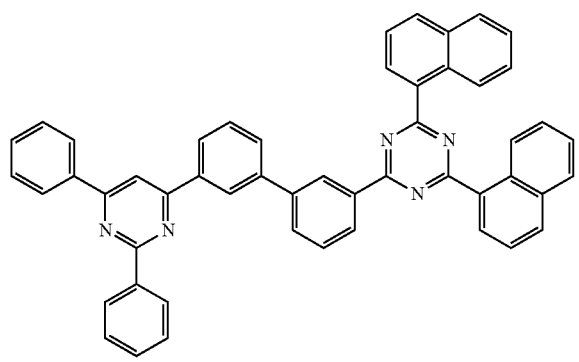
341
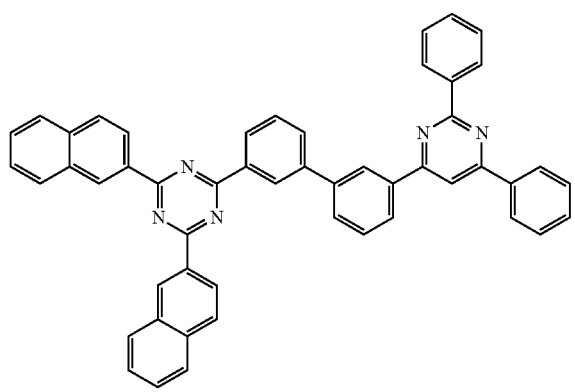
342
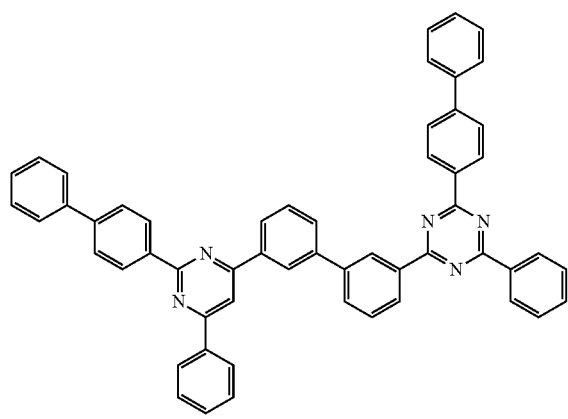
343
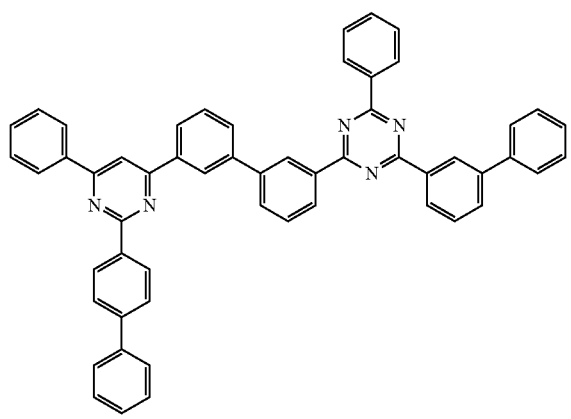

-continued
344
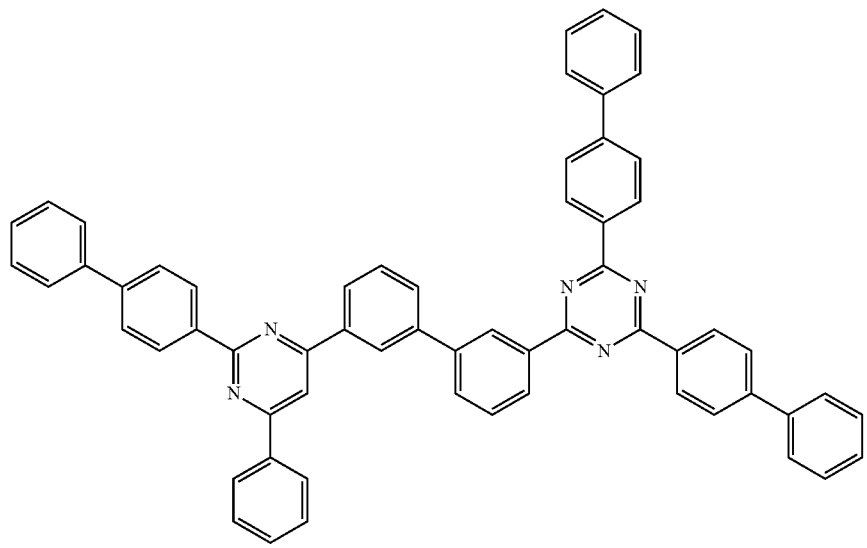
345
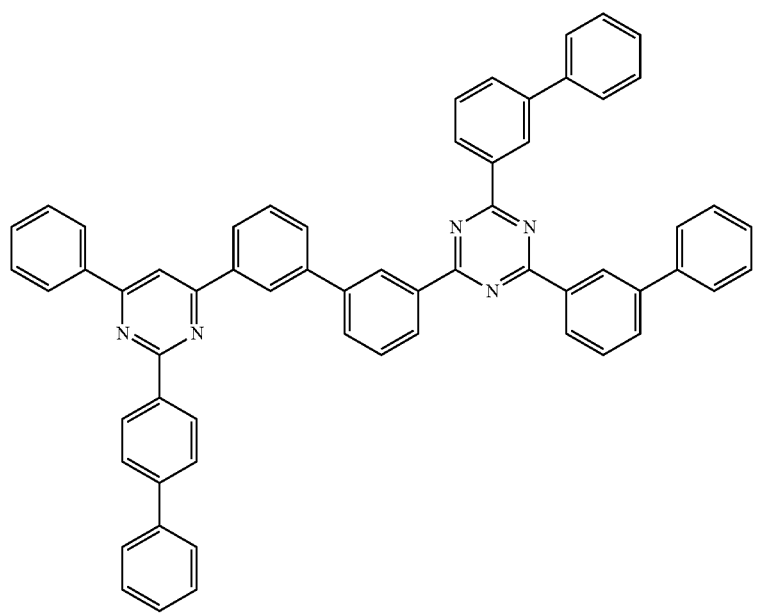
346
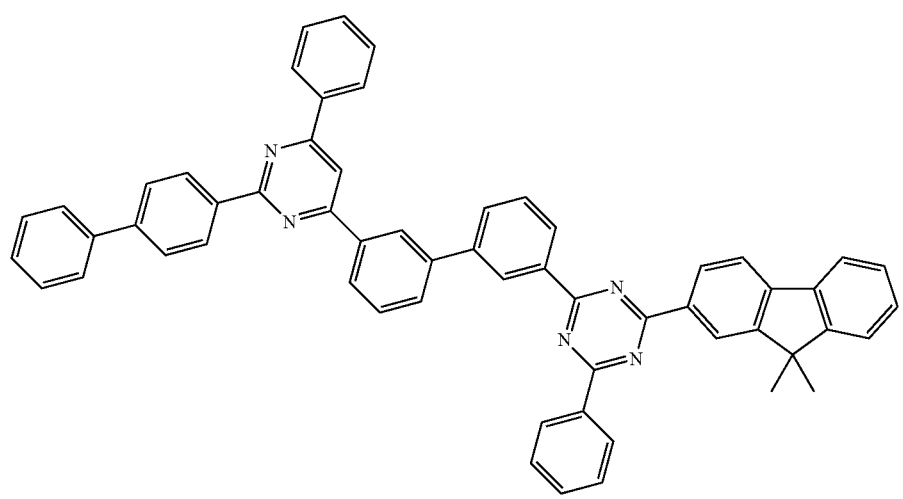

-continued
347
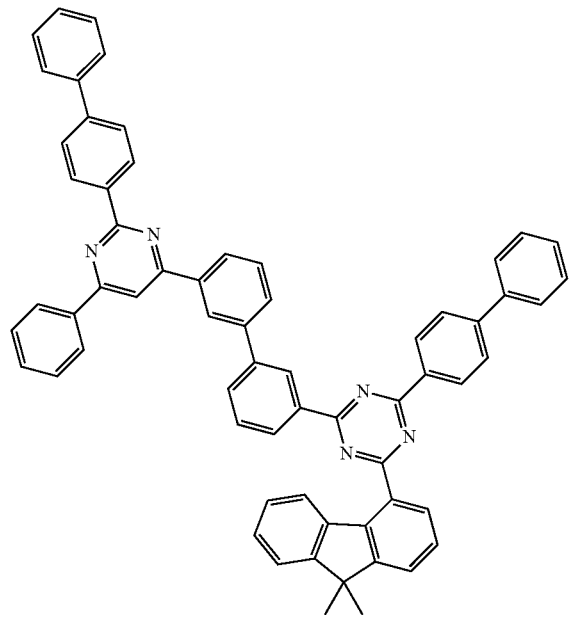
348
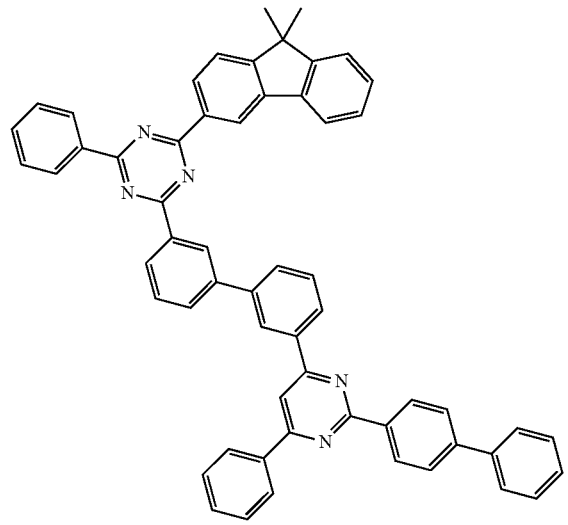
349
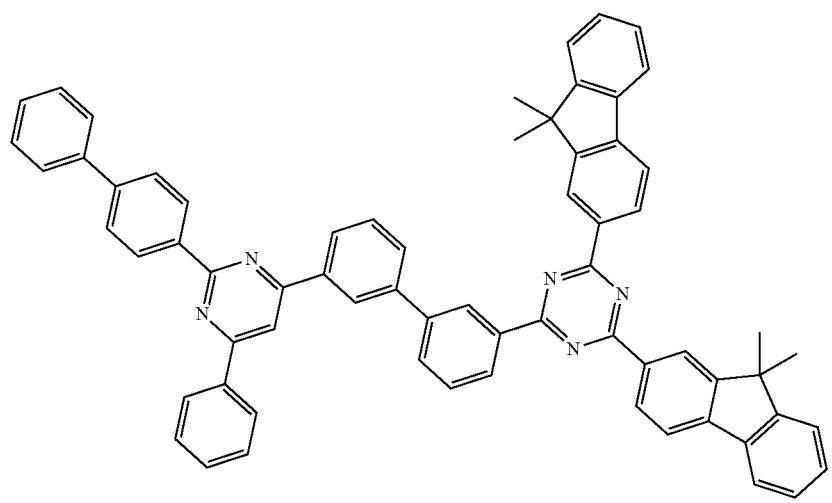
350
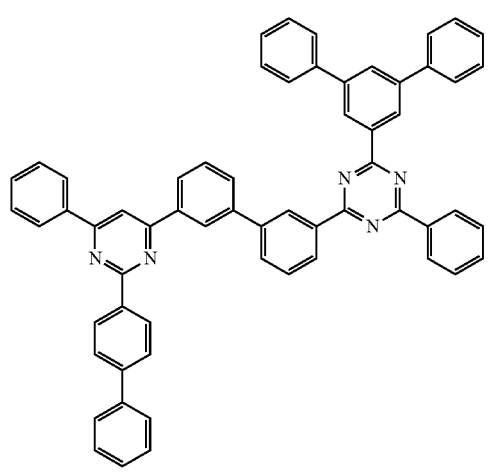
351
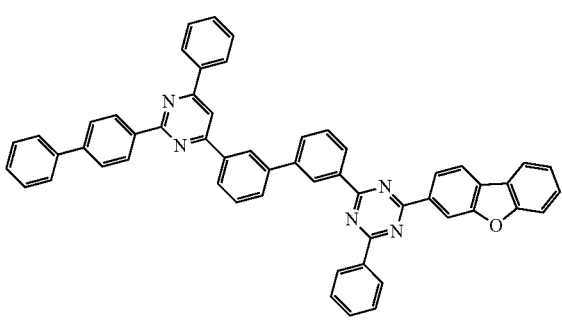

-continued
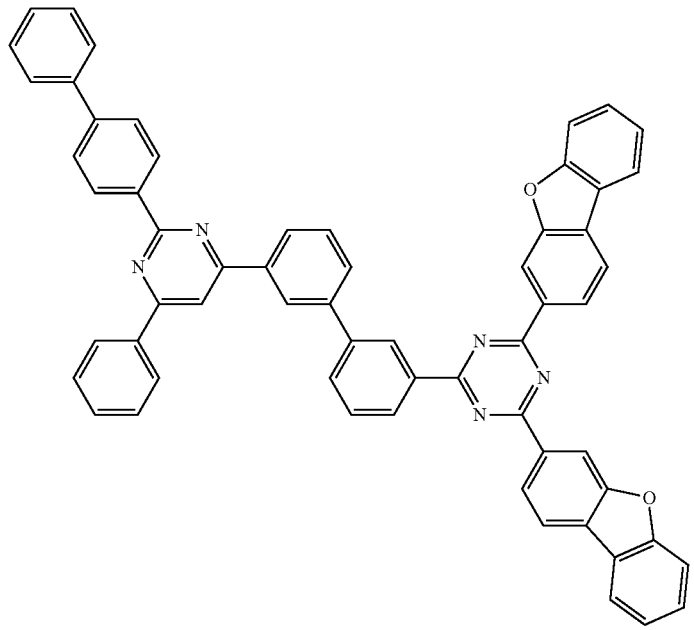
352
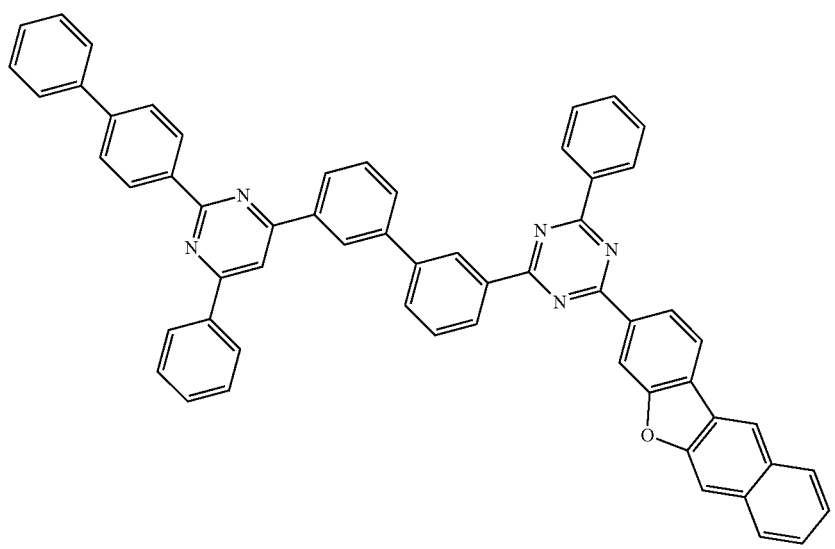
353

354
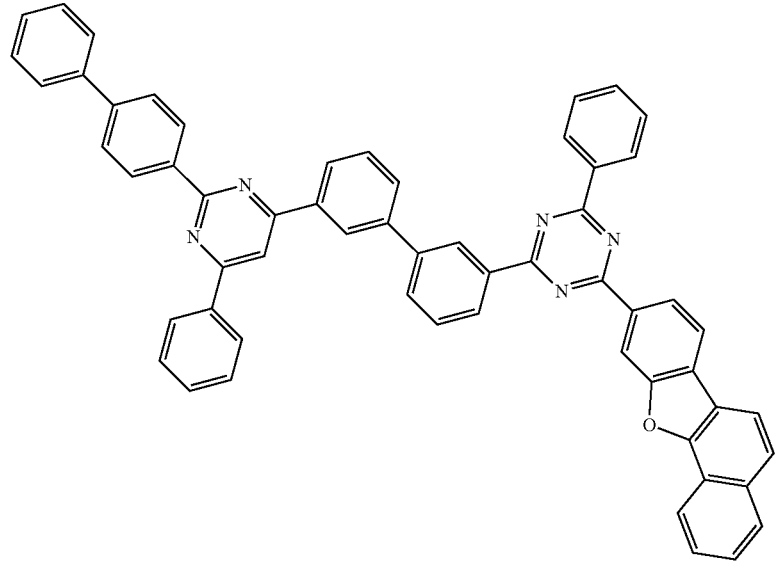
355
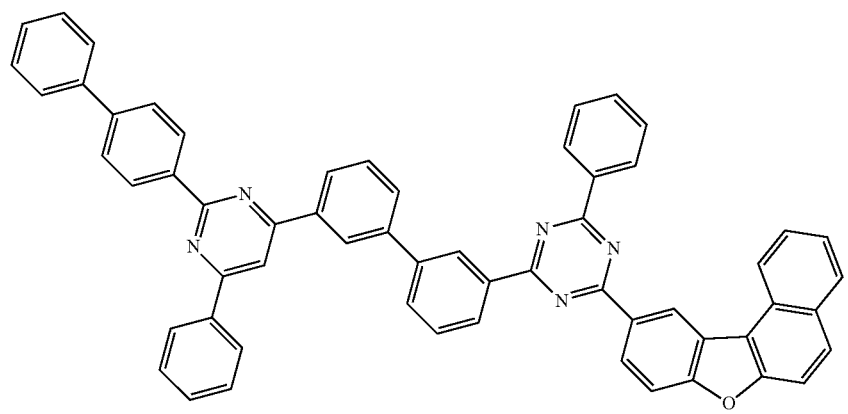
356
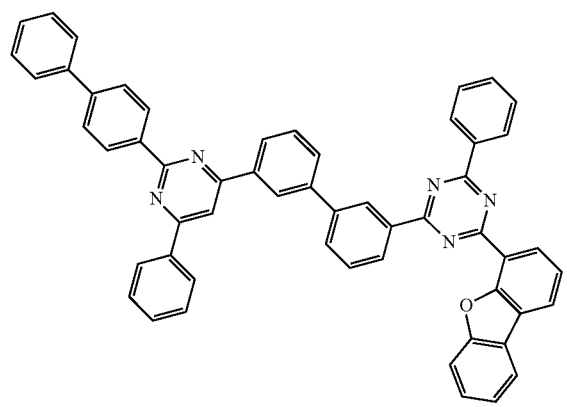
357
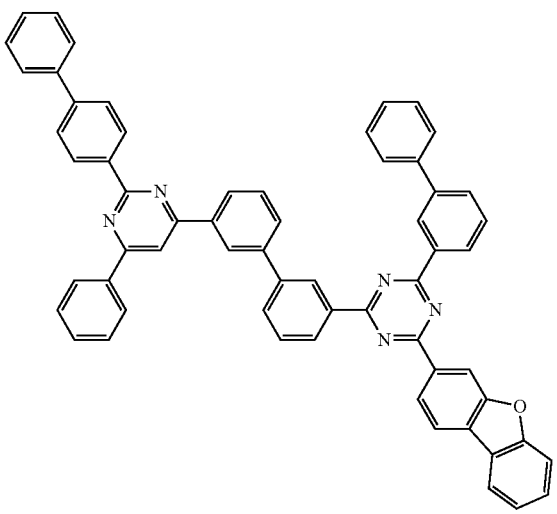

358
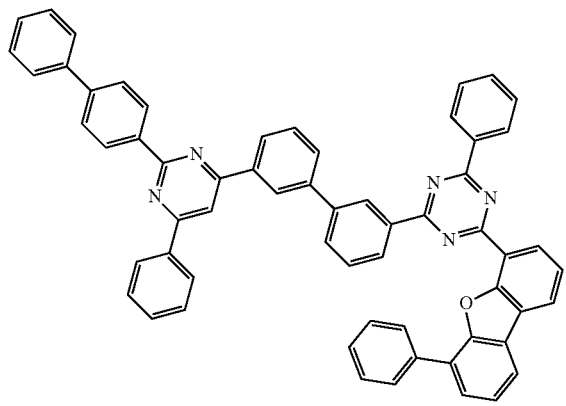
359
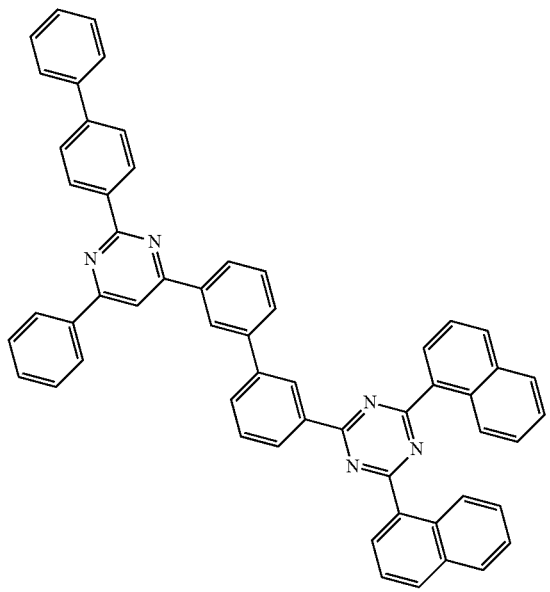
360
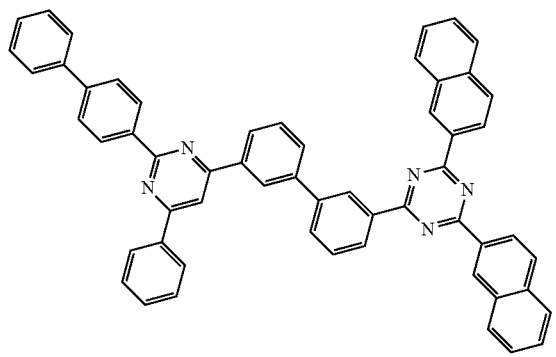
361
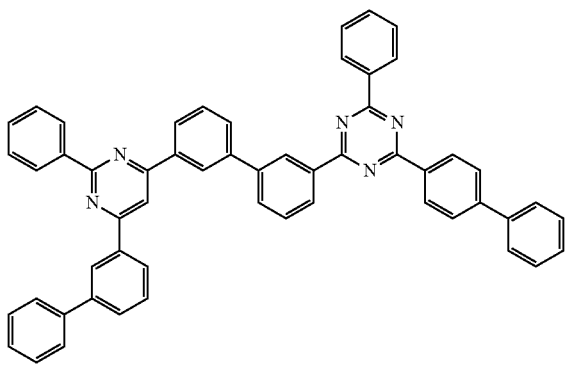
362
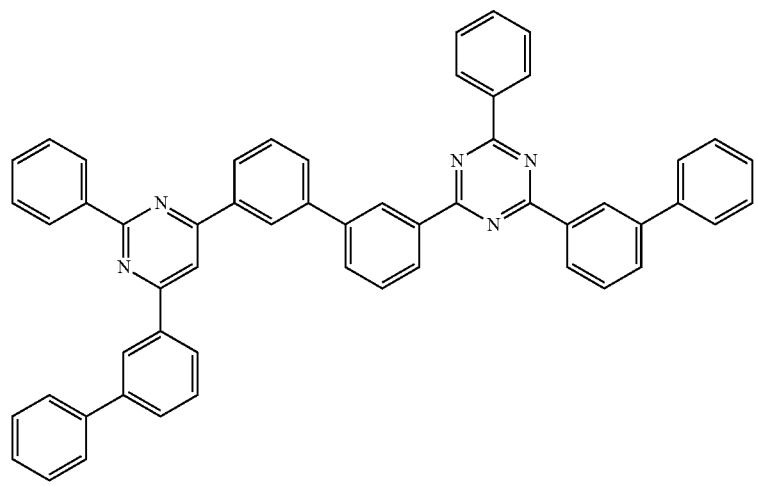

363
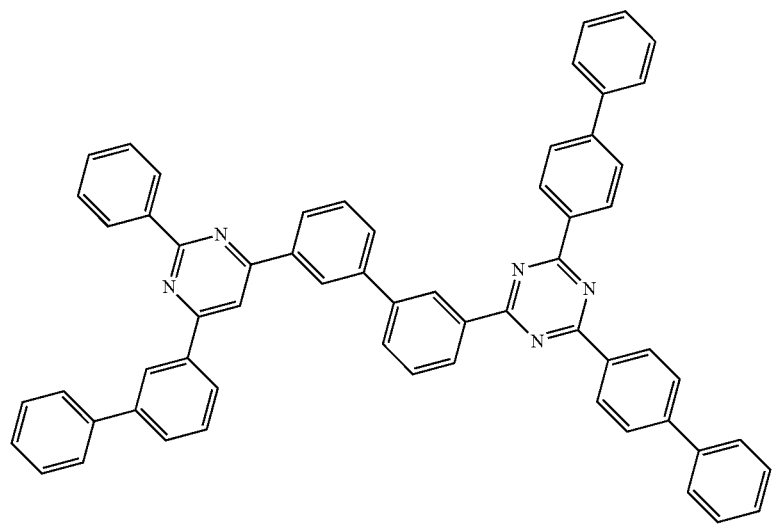
364
365
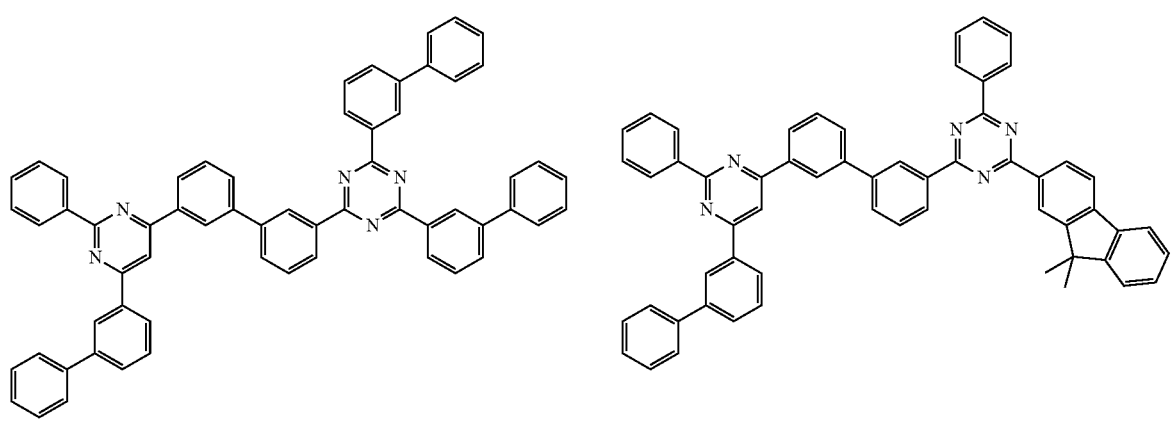
366
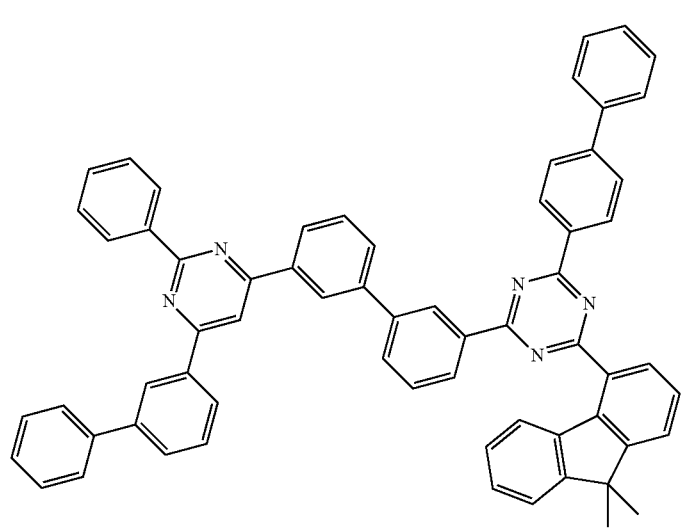

367
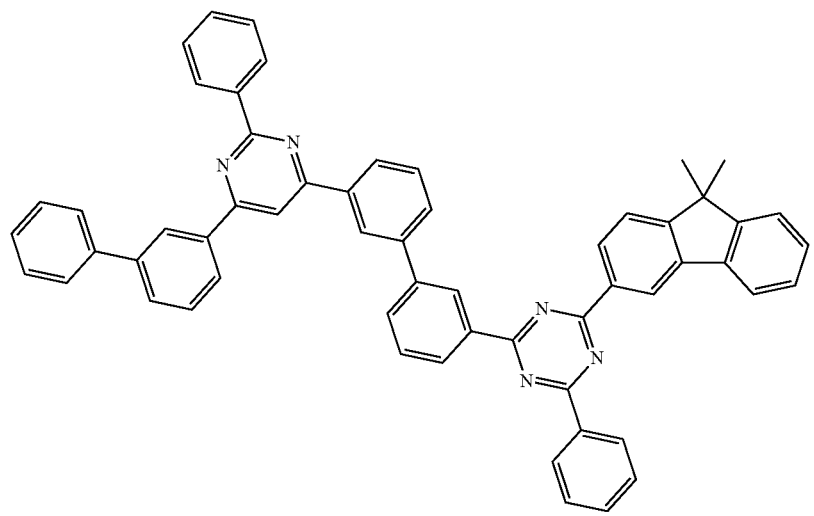
368
369
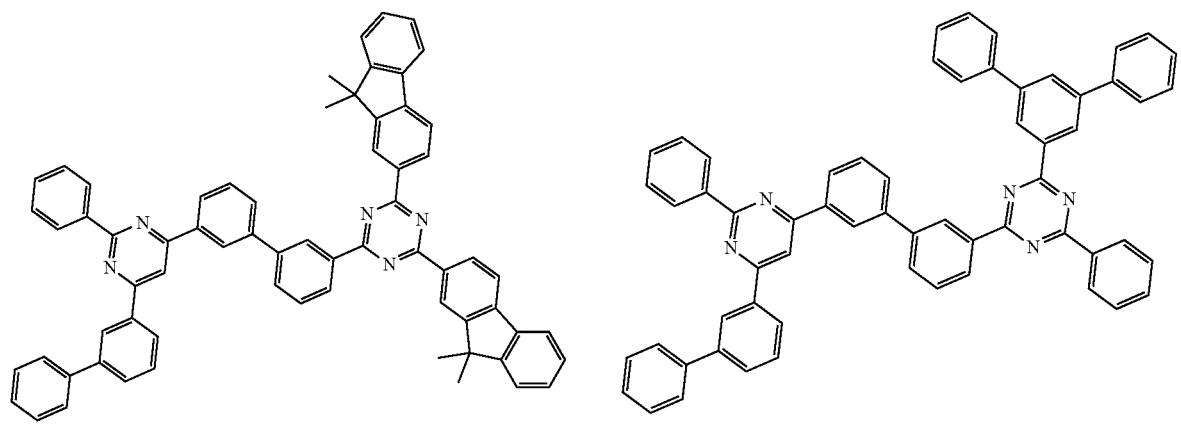
370
371
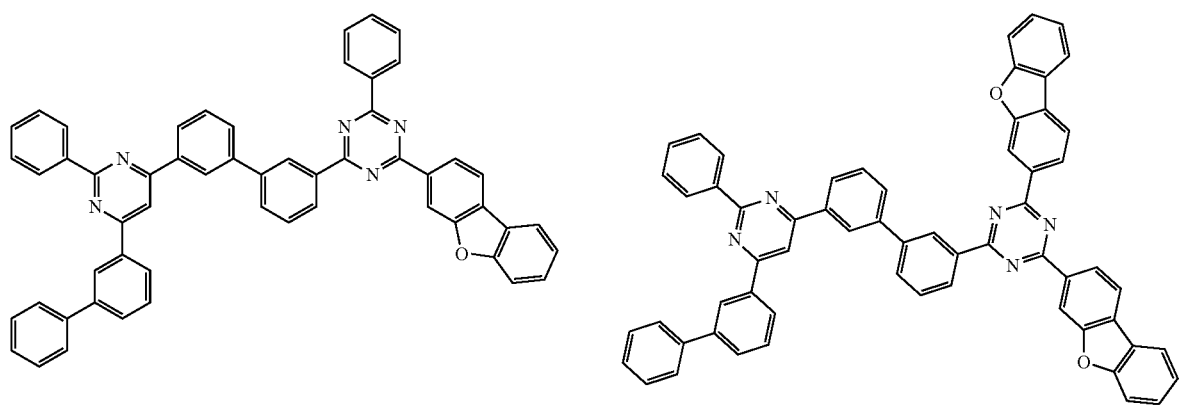

-continued
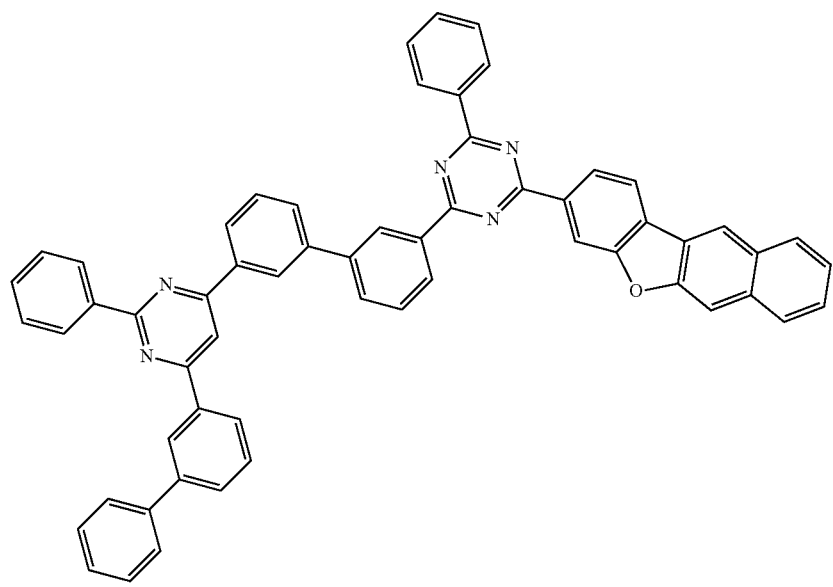
372
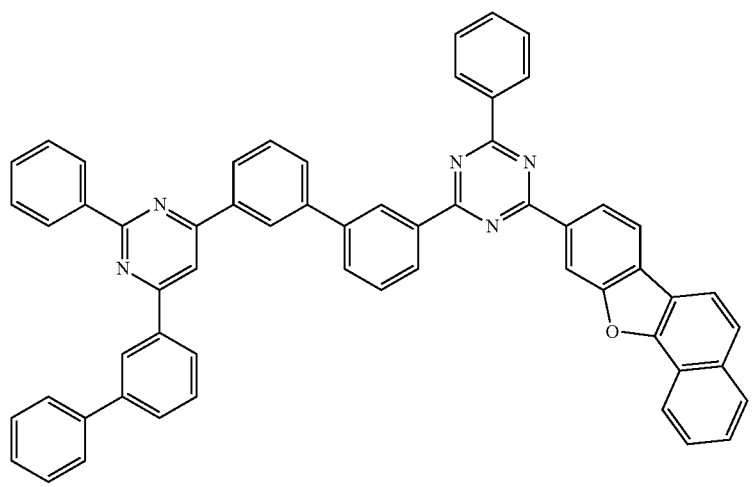
373
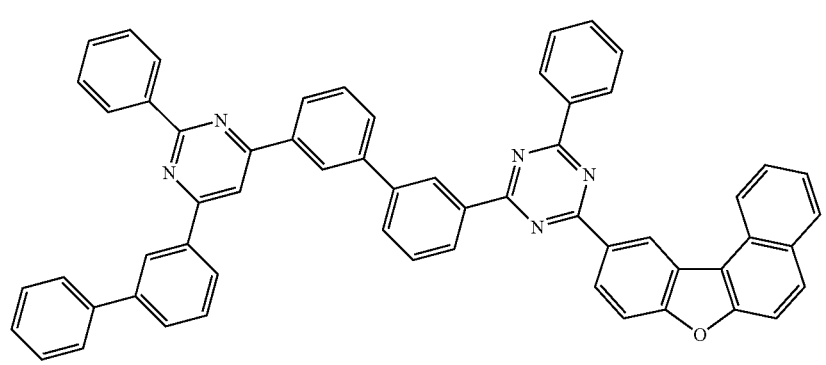
374

375
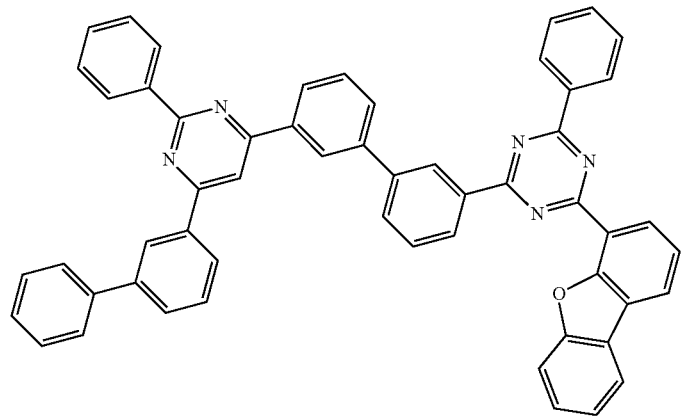
376
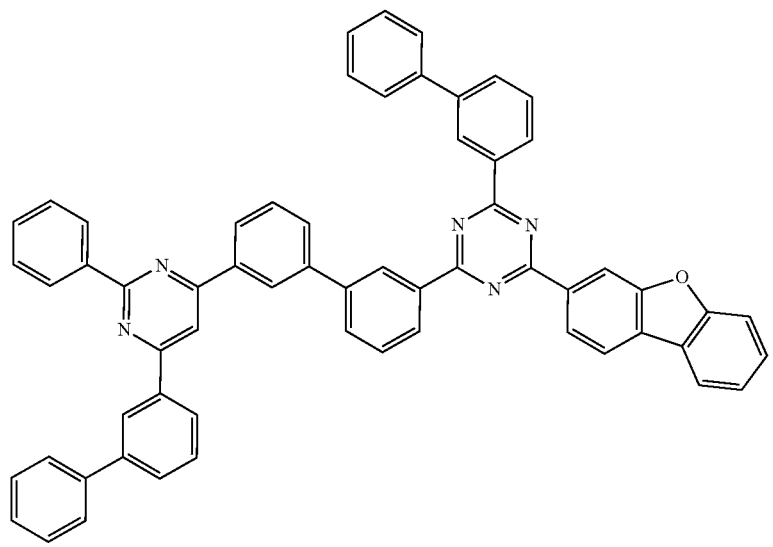
377 378
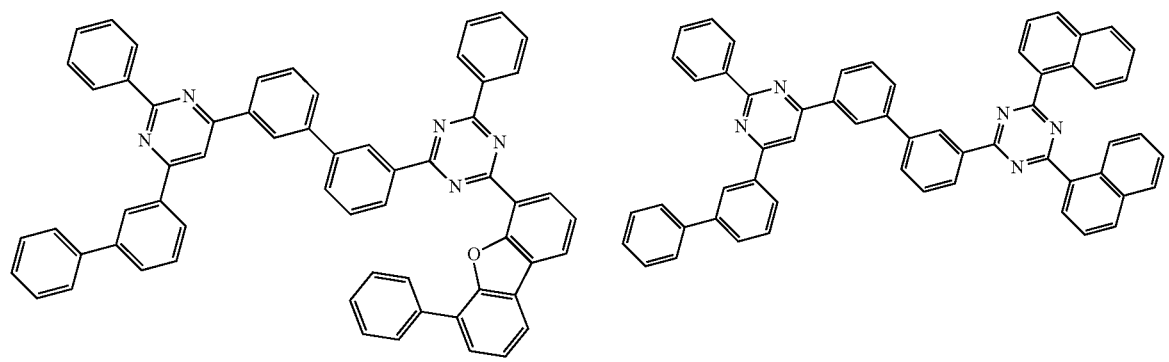

-continued
379
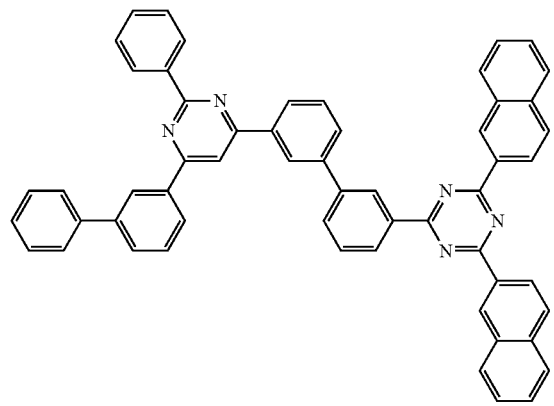
380
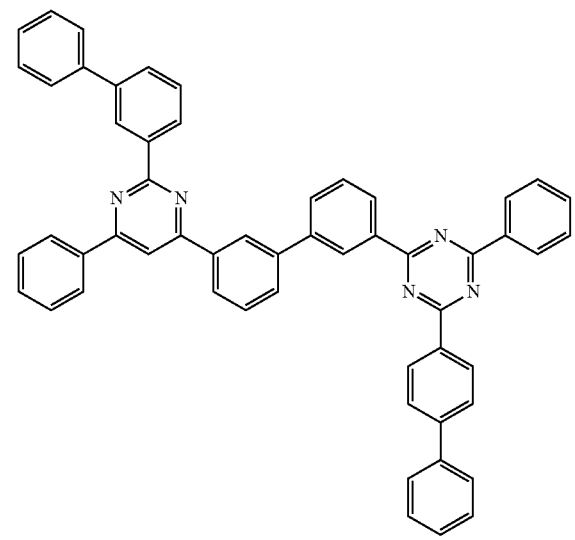
381
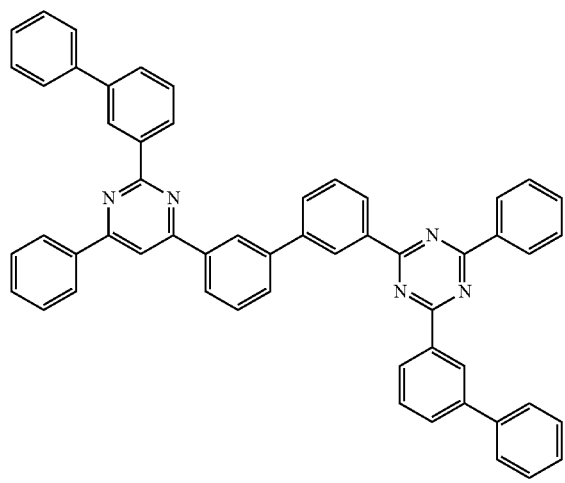
382
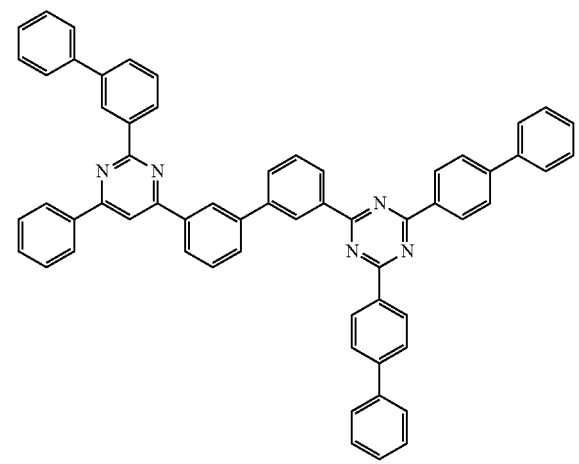
383
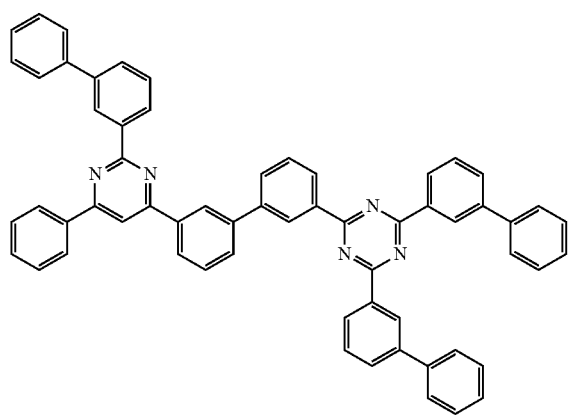
384
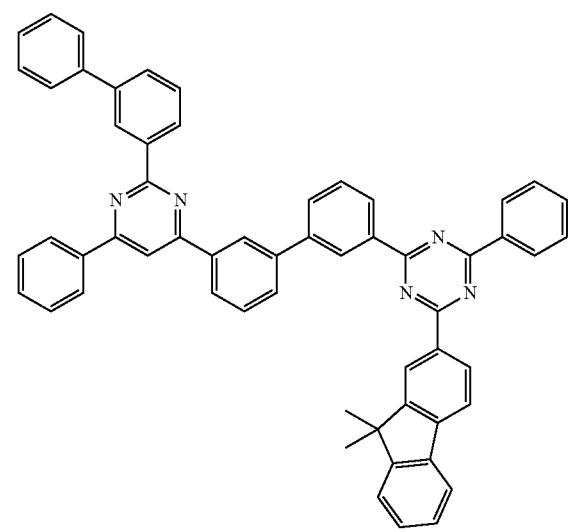

385
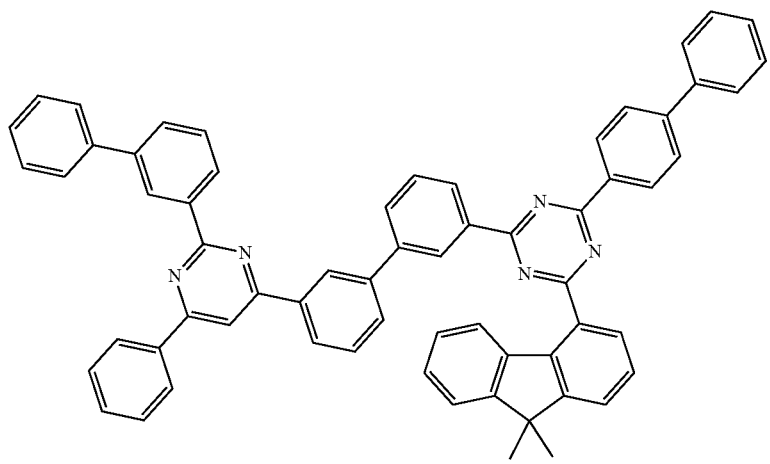
386
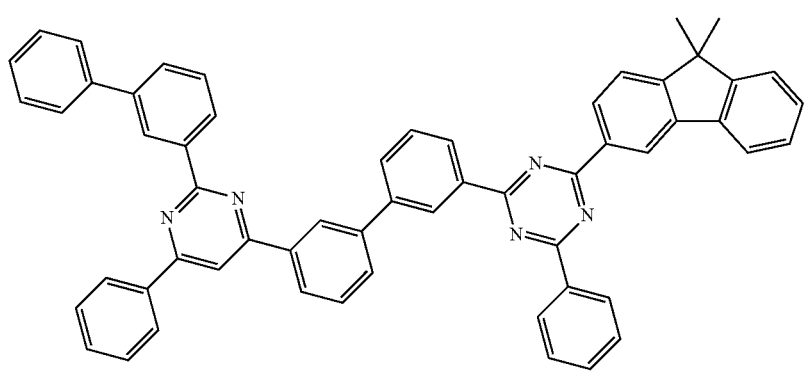
387
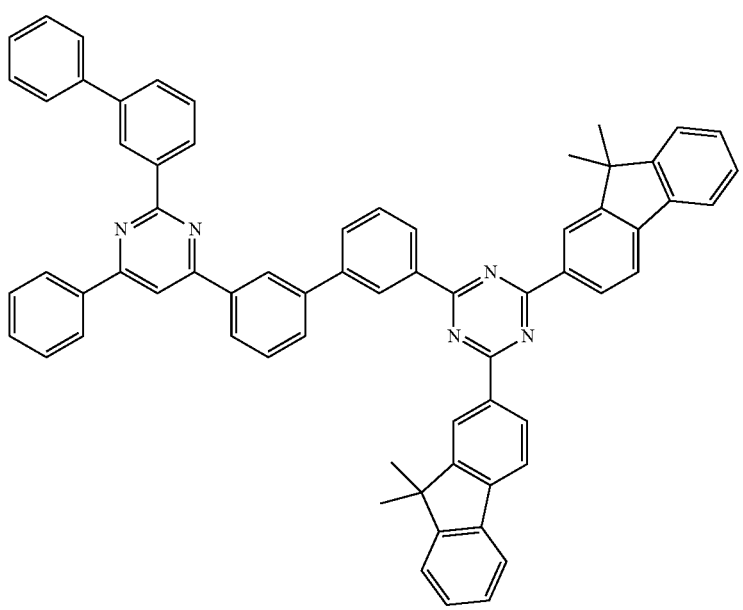

-continued
388
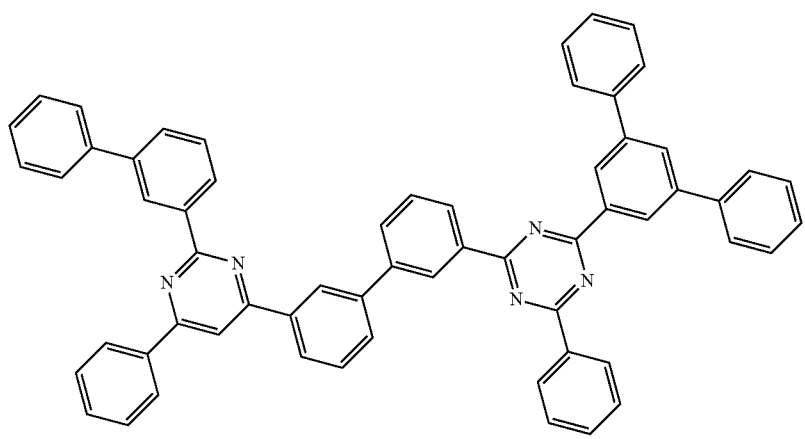
389
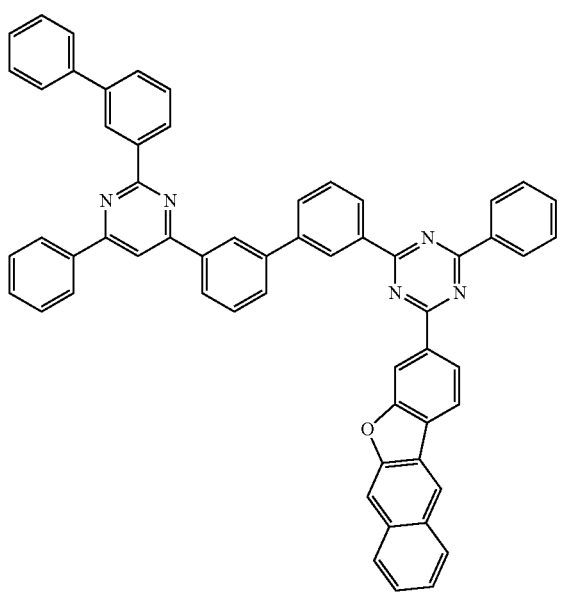
390
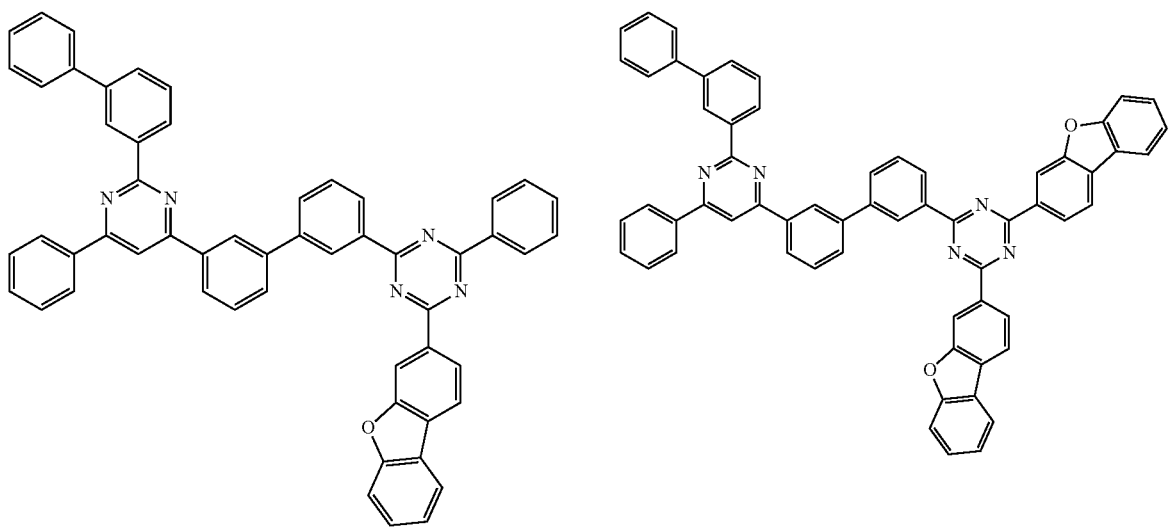
391
392
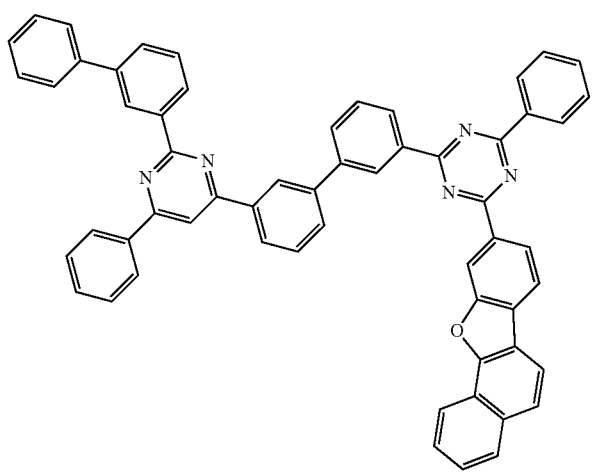

393
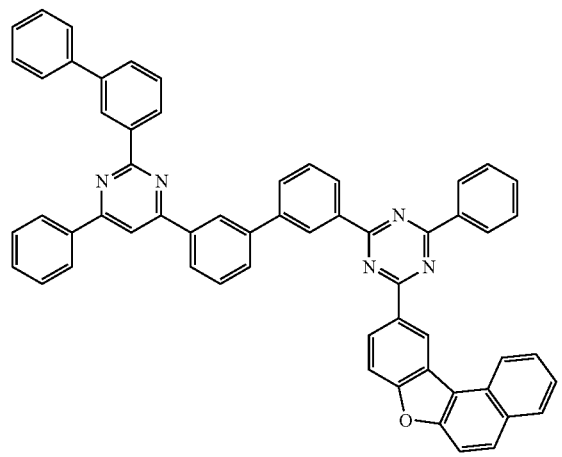
394
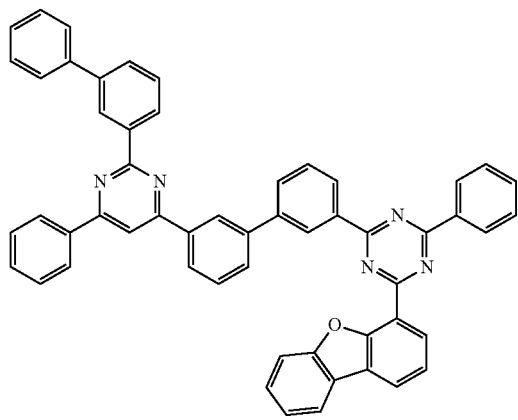
395
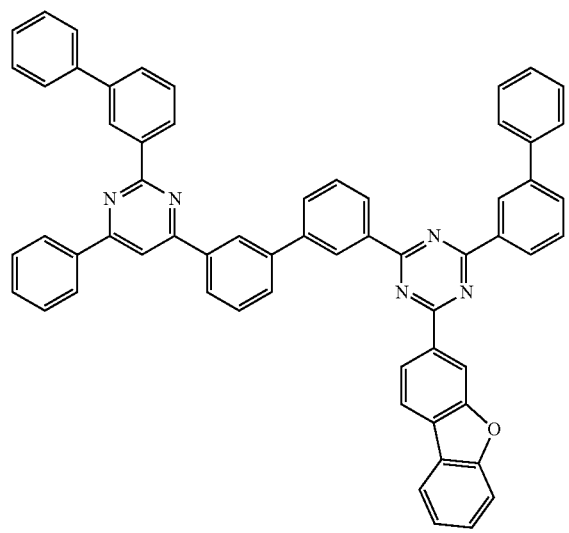
396
397
398
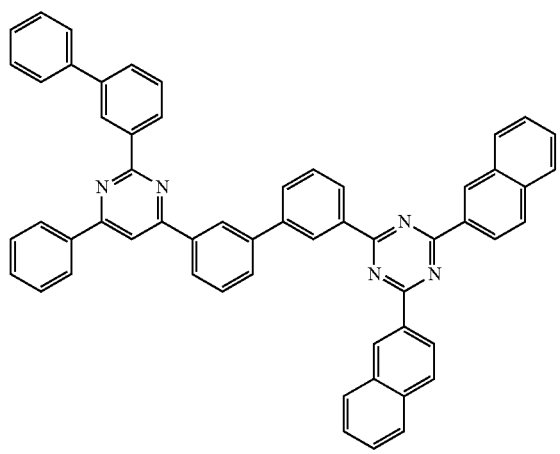

399
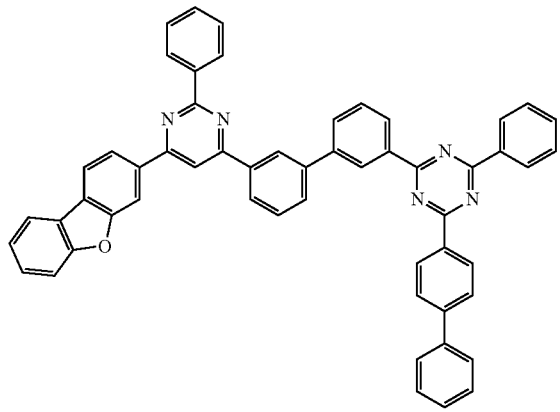
400
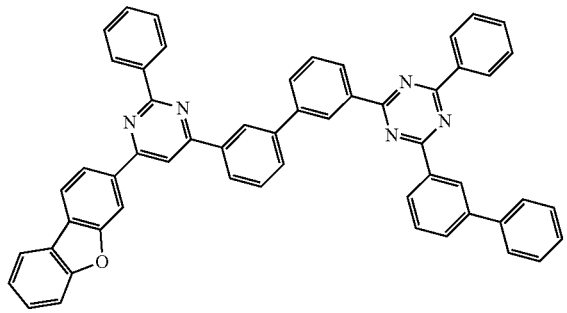
401
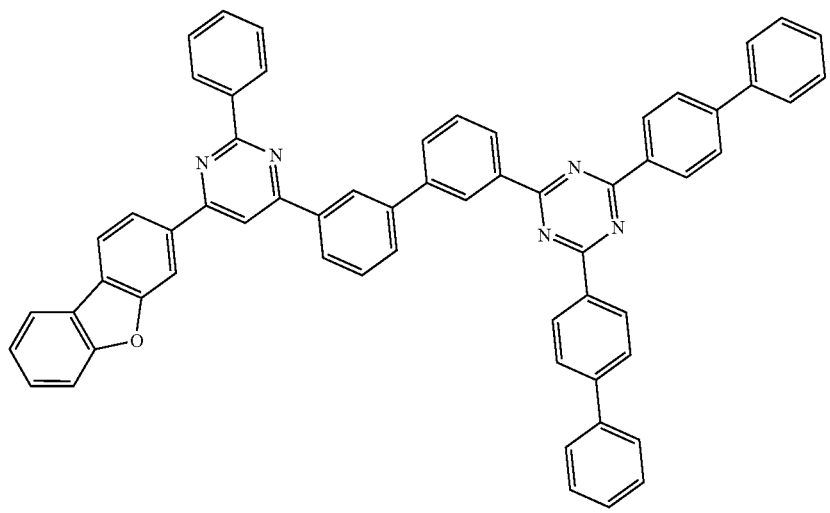
402
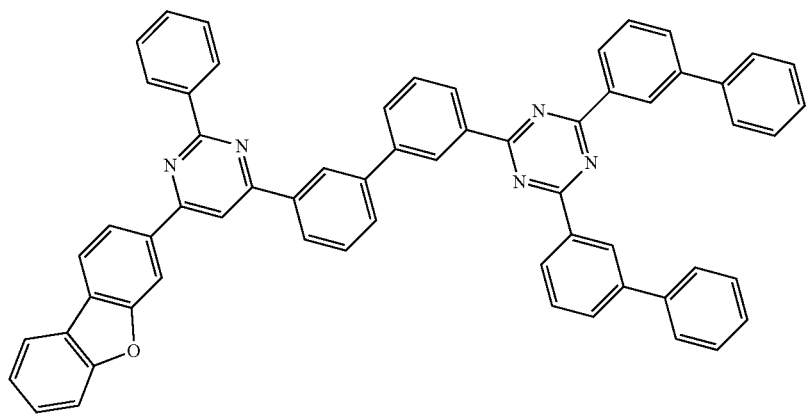

403
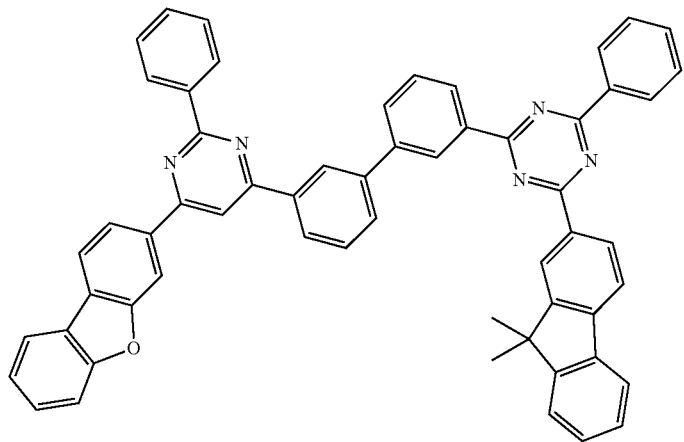
404
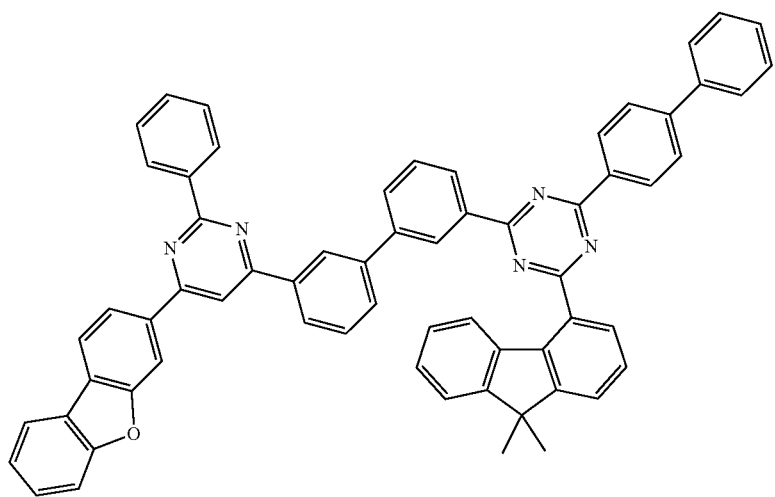
405
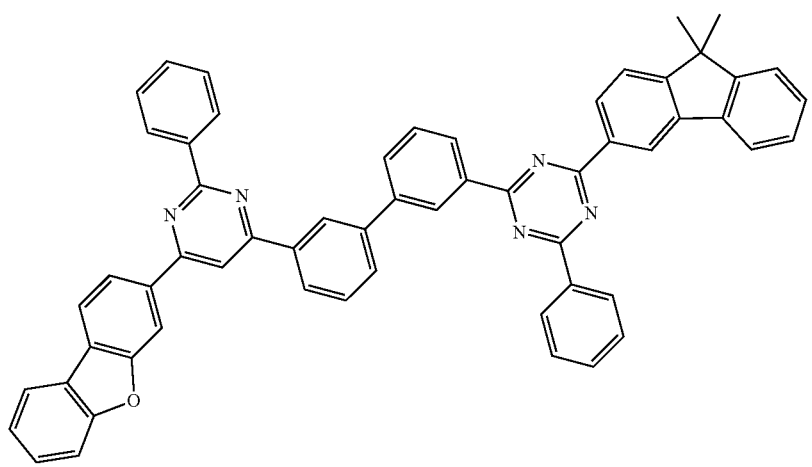

406
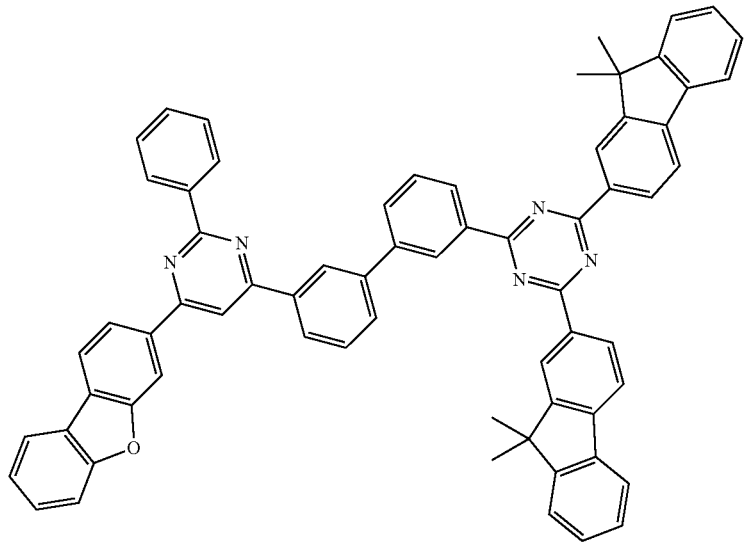
407
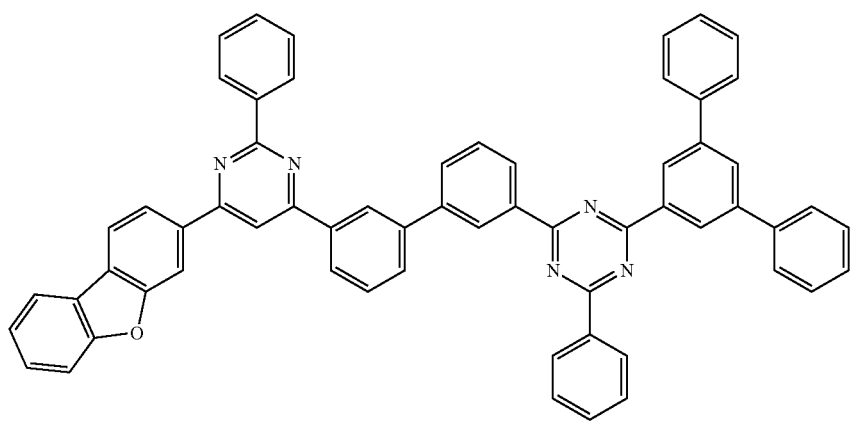
408
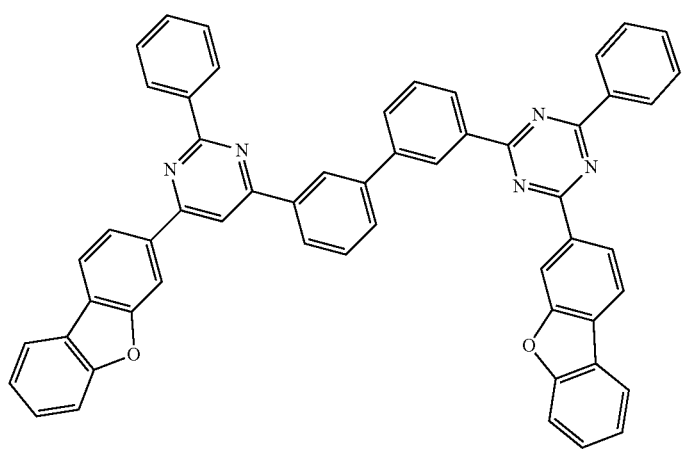

409
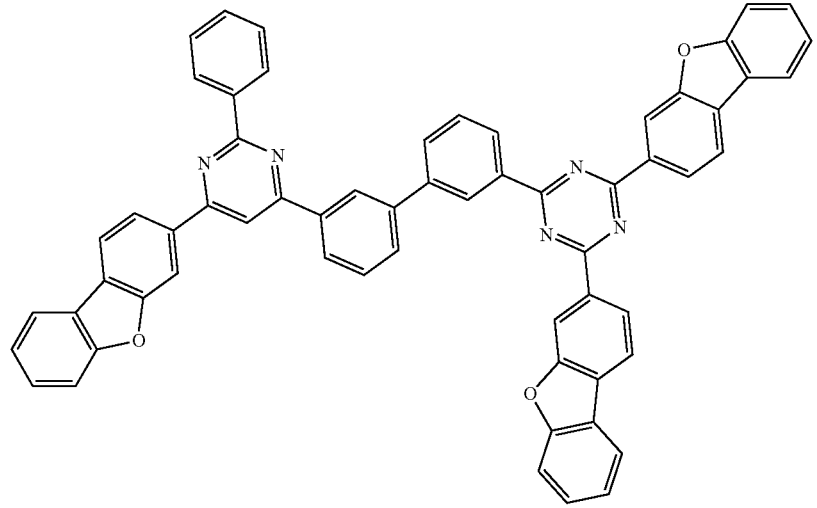
410
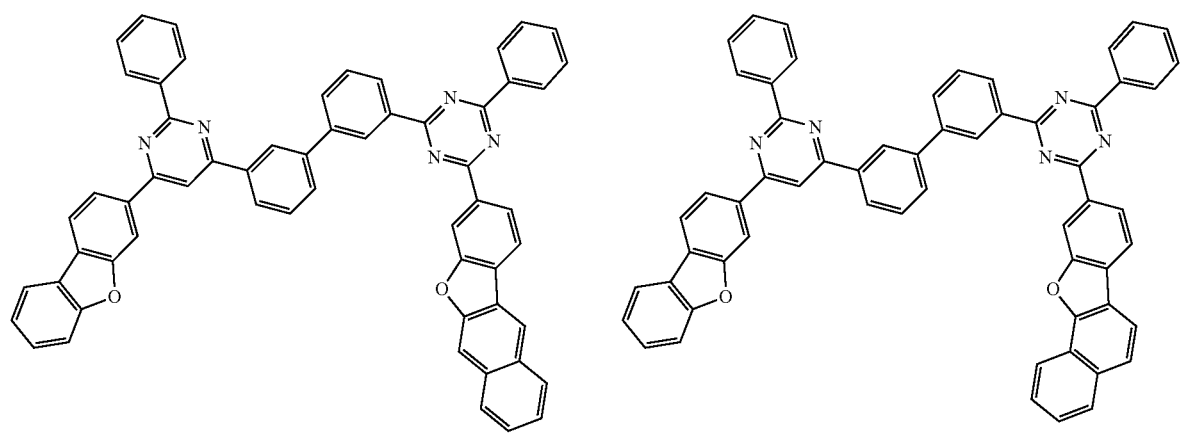
411
412
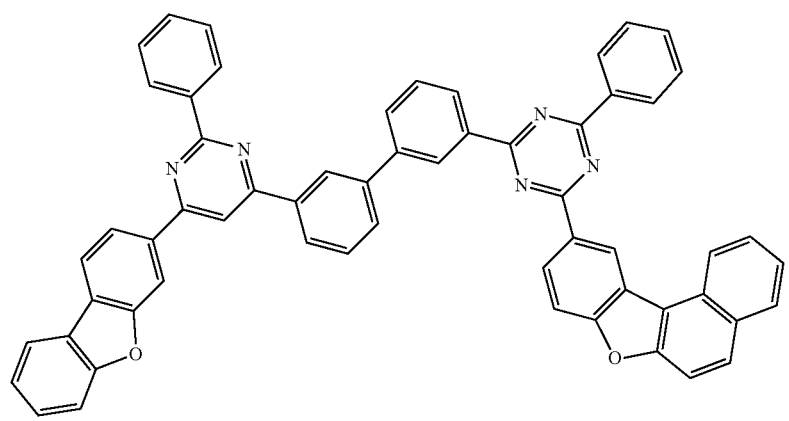

-continued
413
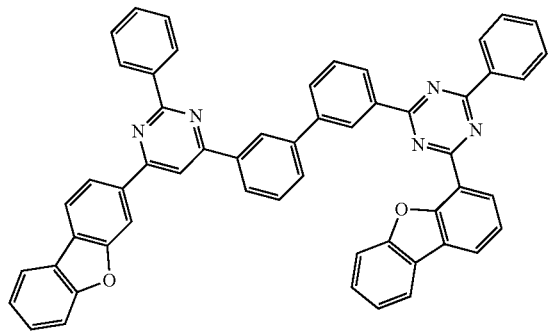
414
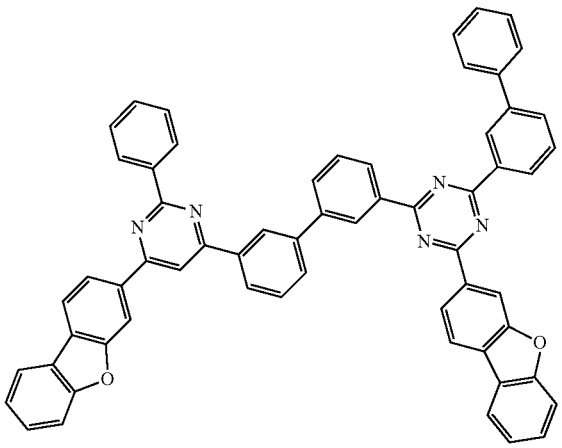
415
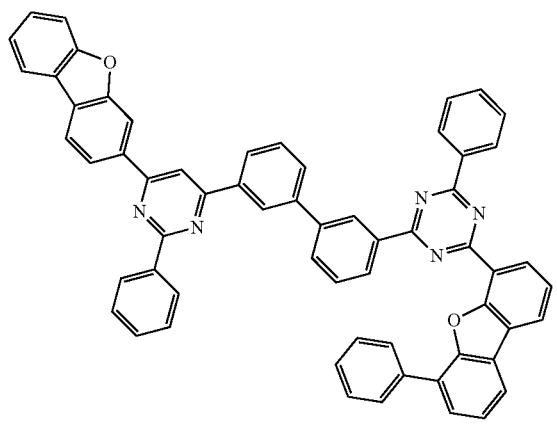
416
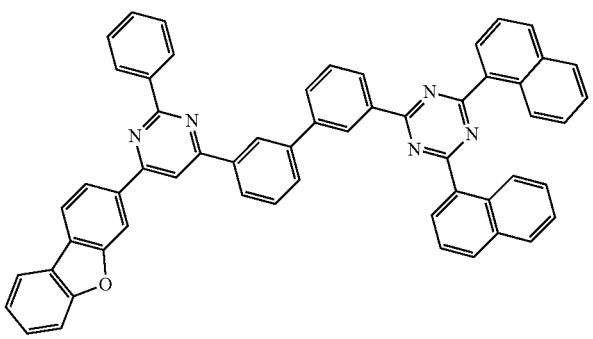
417
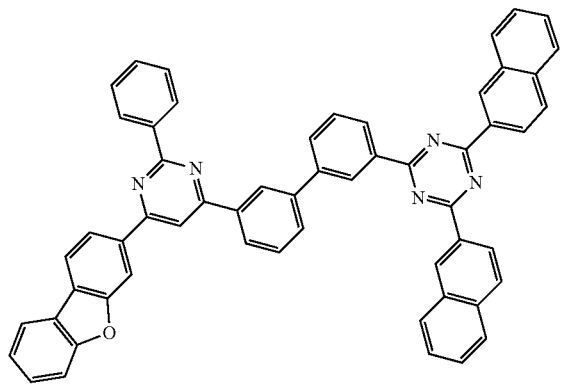
418
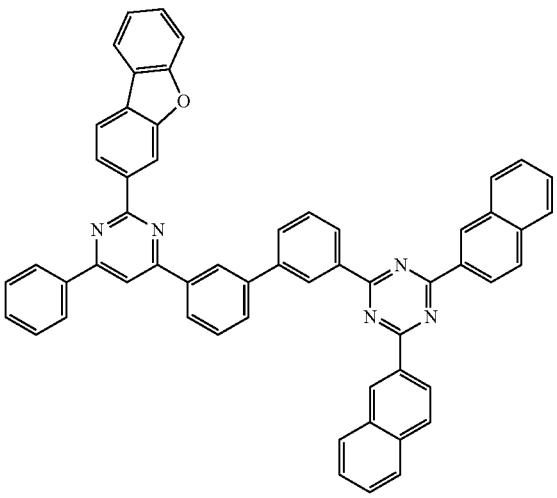

419
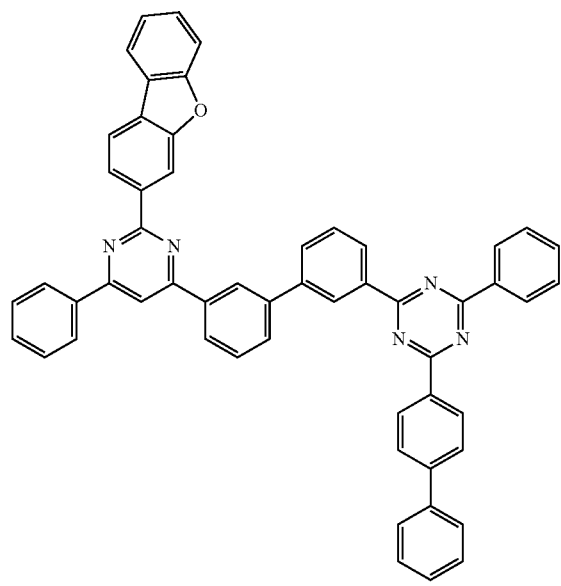
420
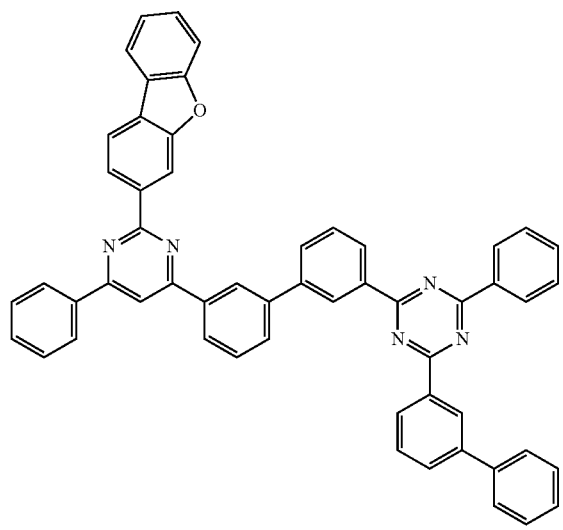
421
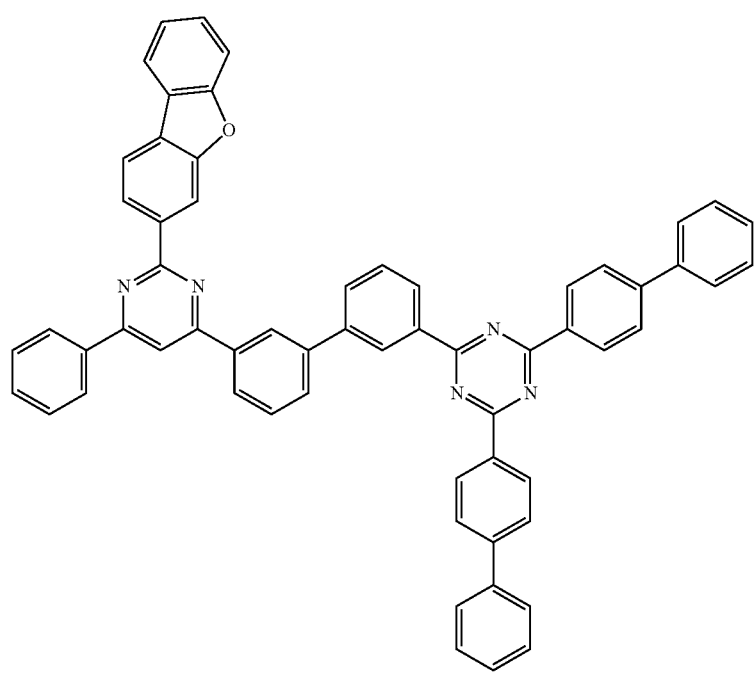

422
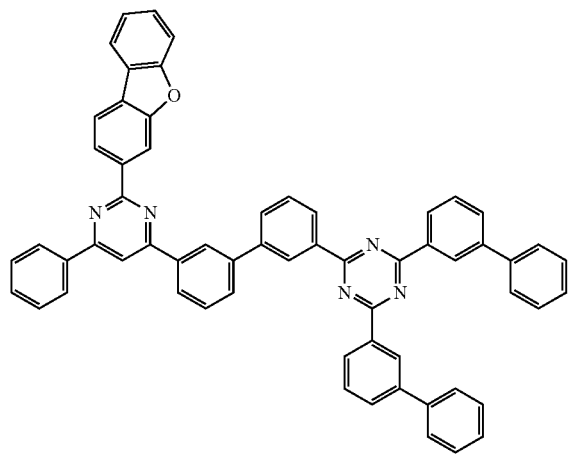
423
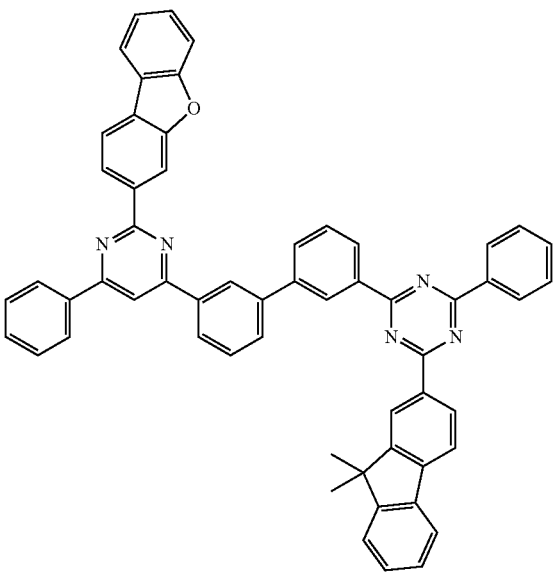
424
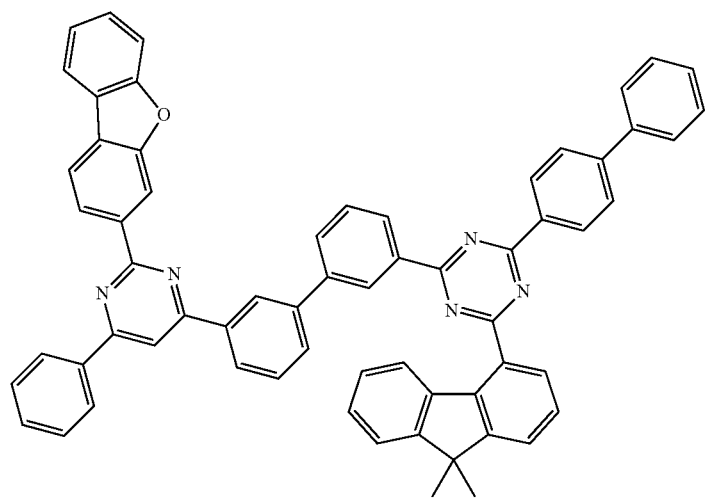
425
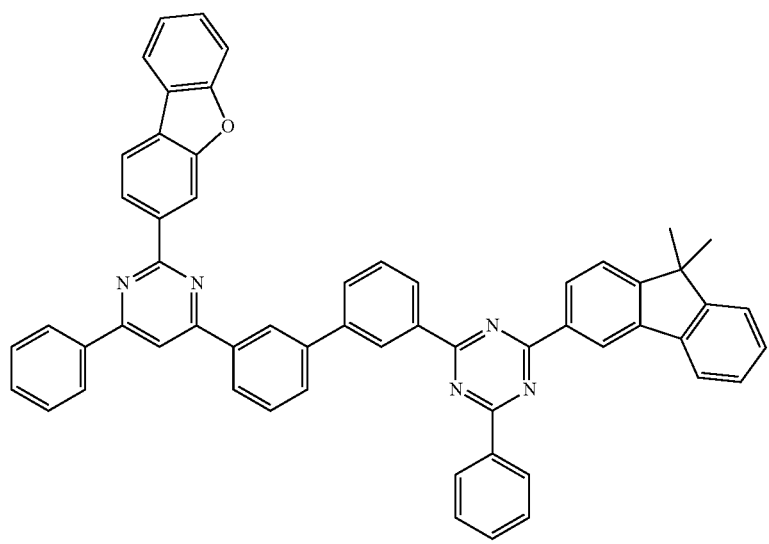

-continued
426
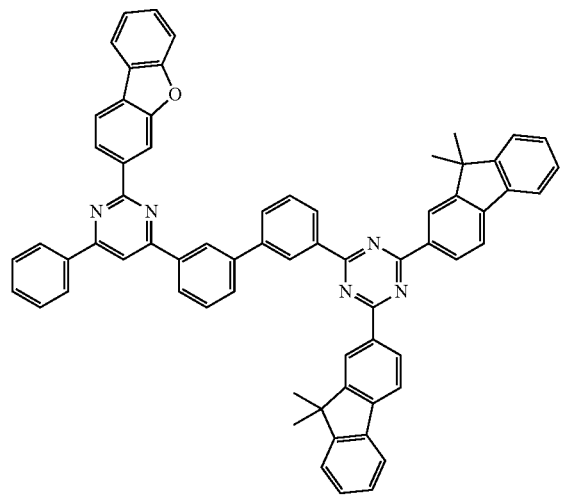
427
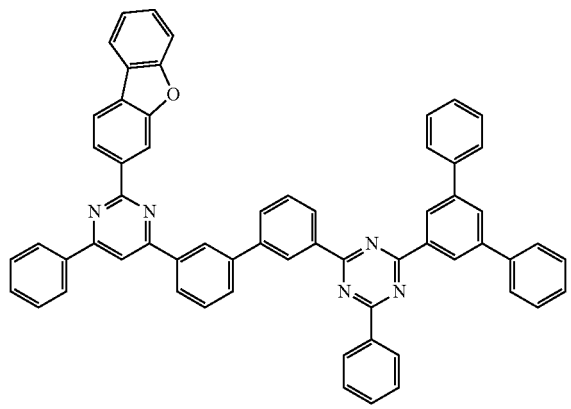
428
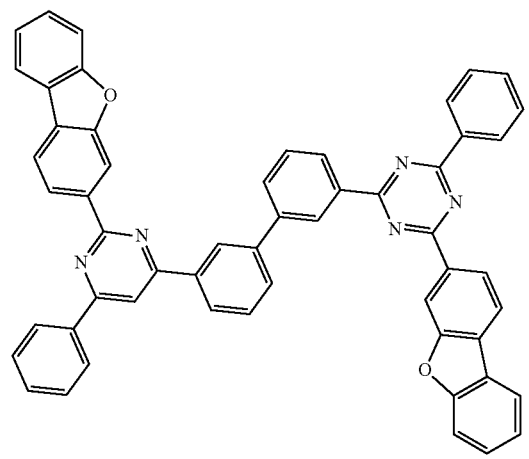
429
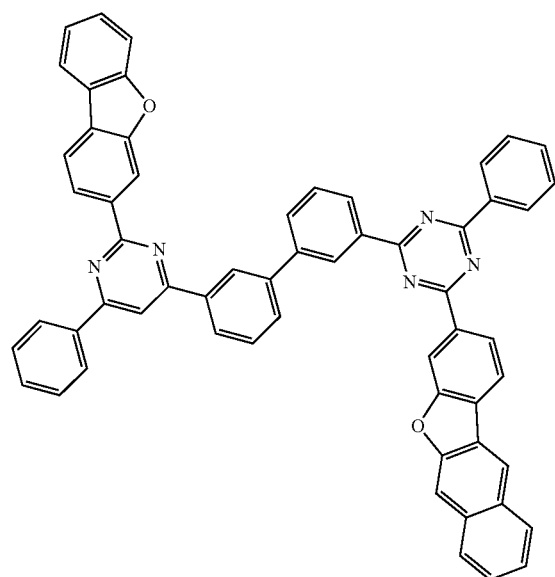
430
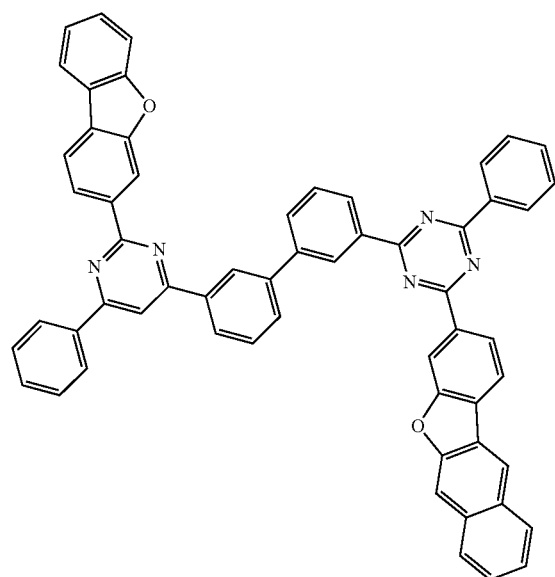
431
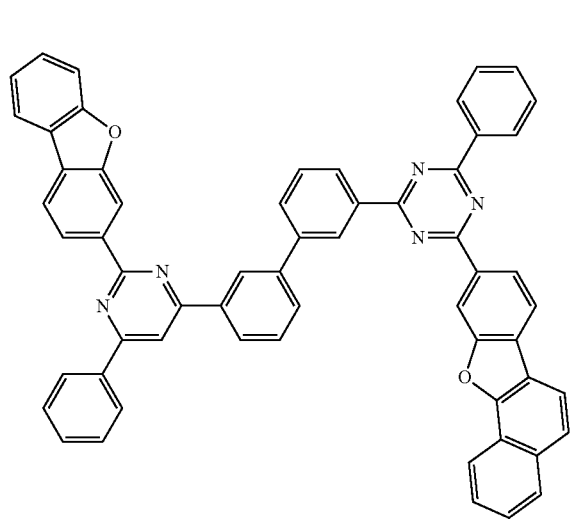

-continued
432
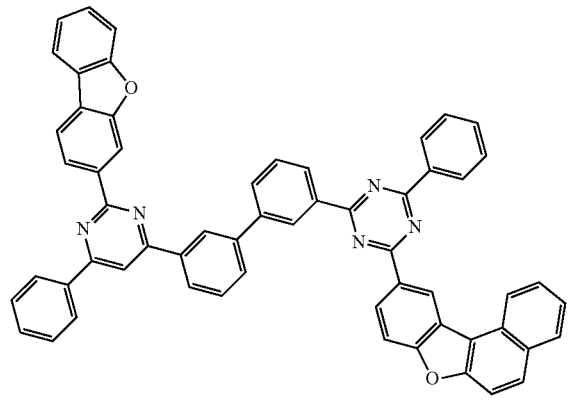
433
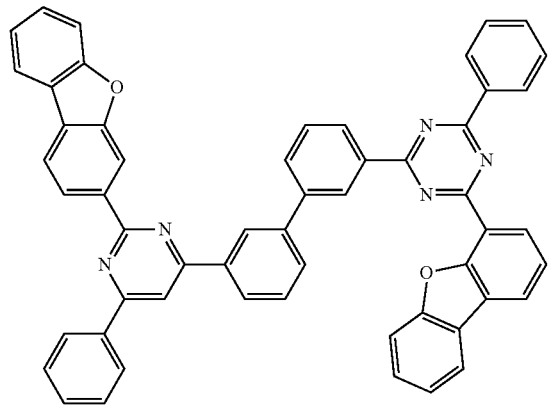
434
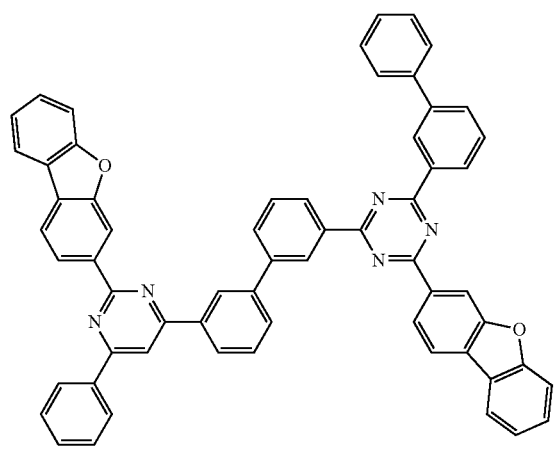
435
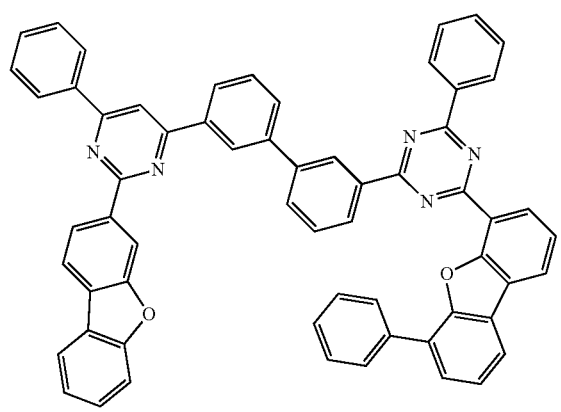
436
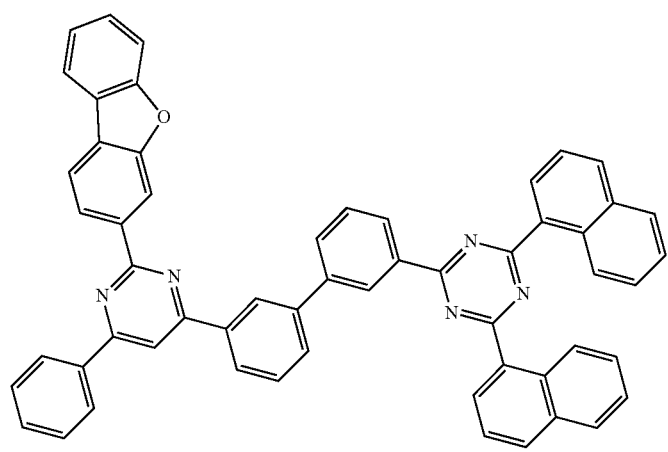

437
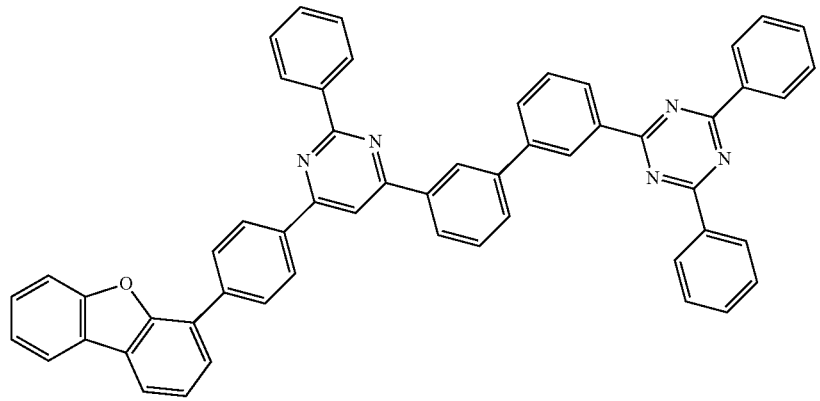
438
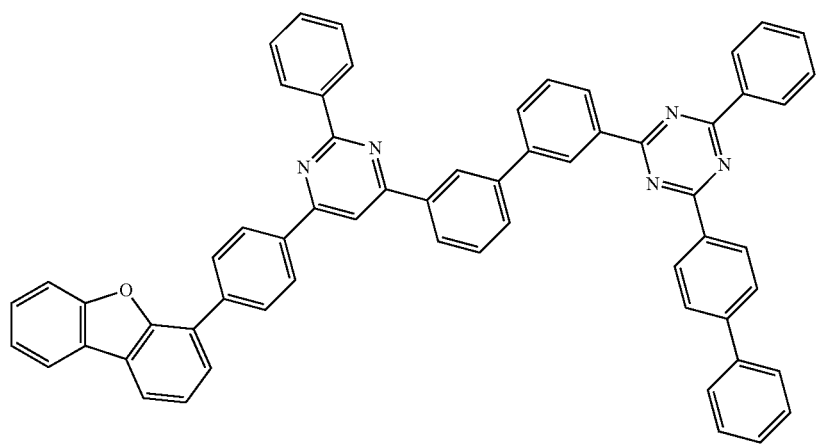
439
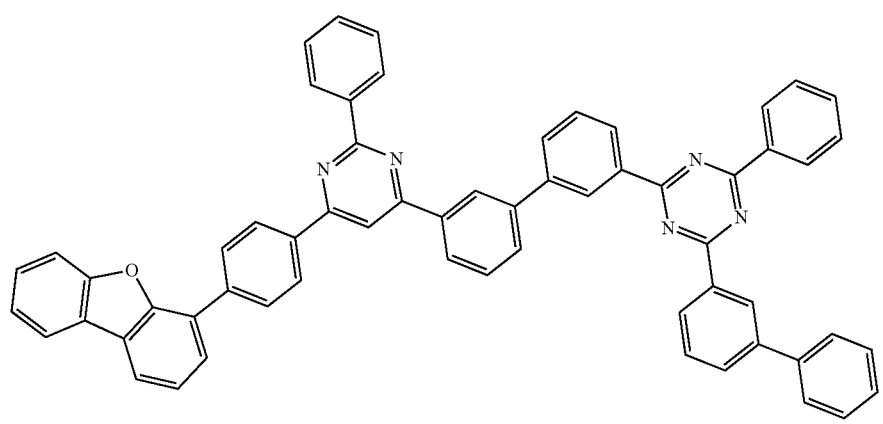

440
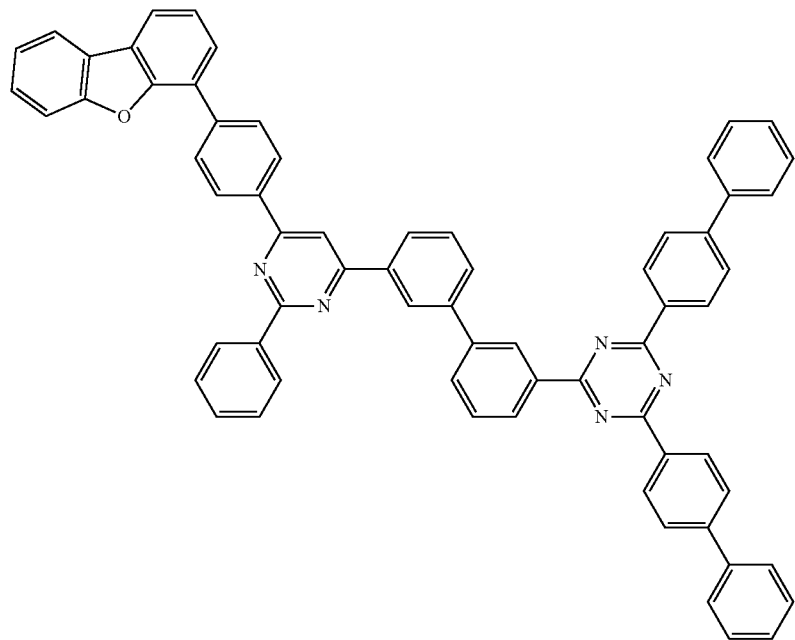
441
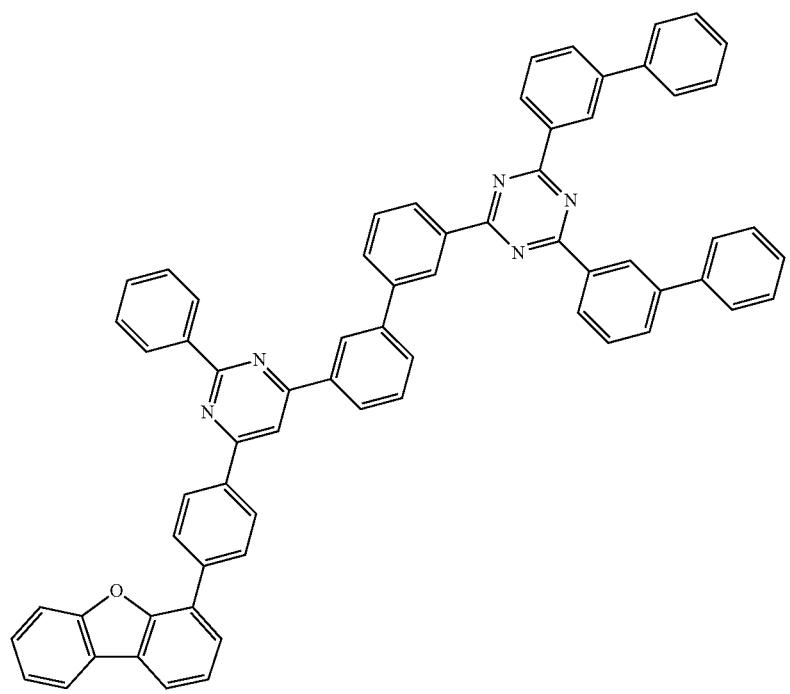

-continued
442
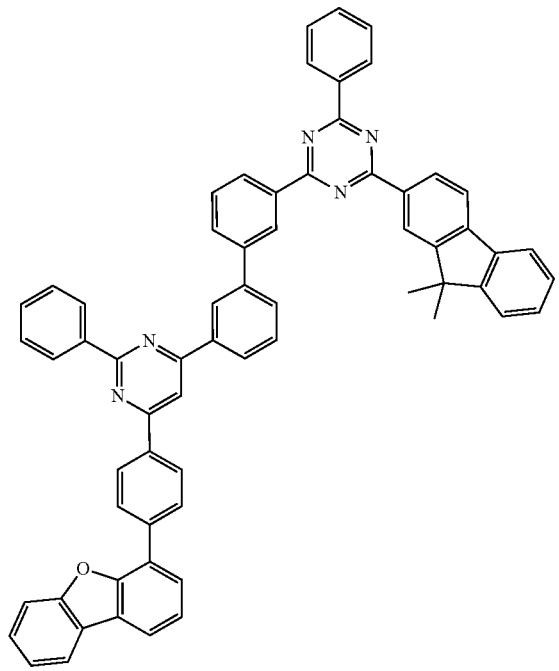
443
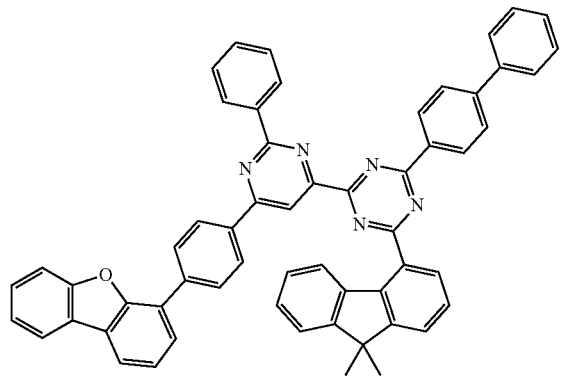
444
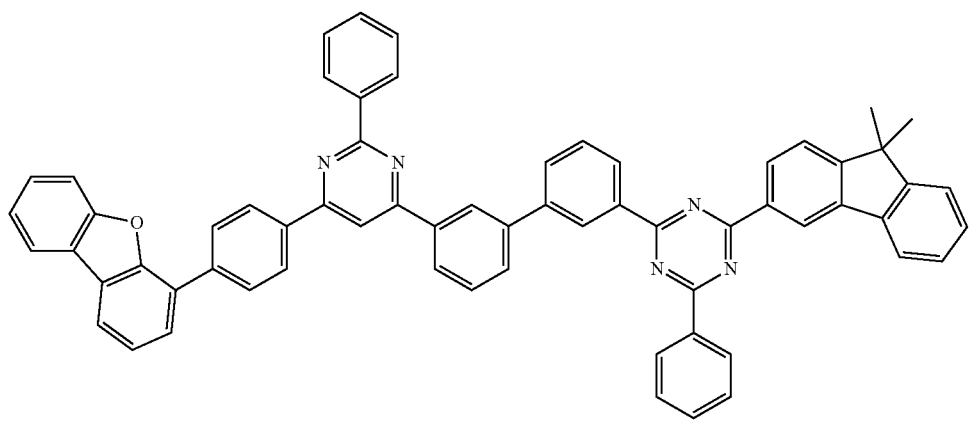
445
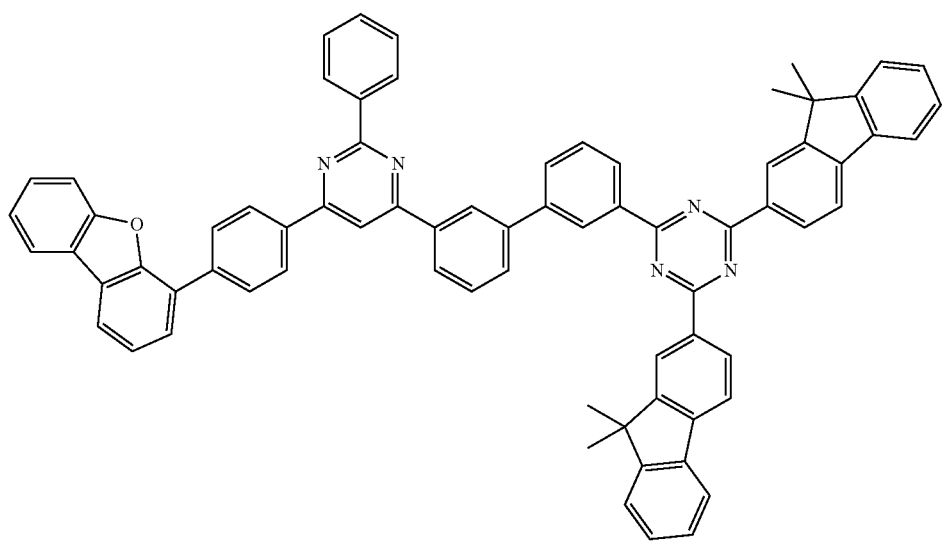

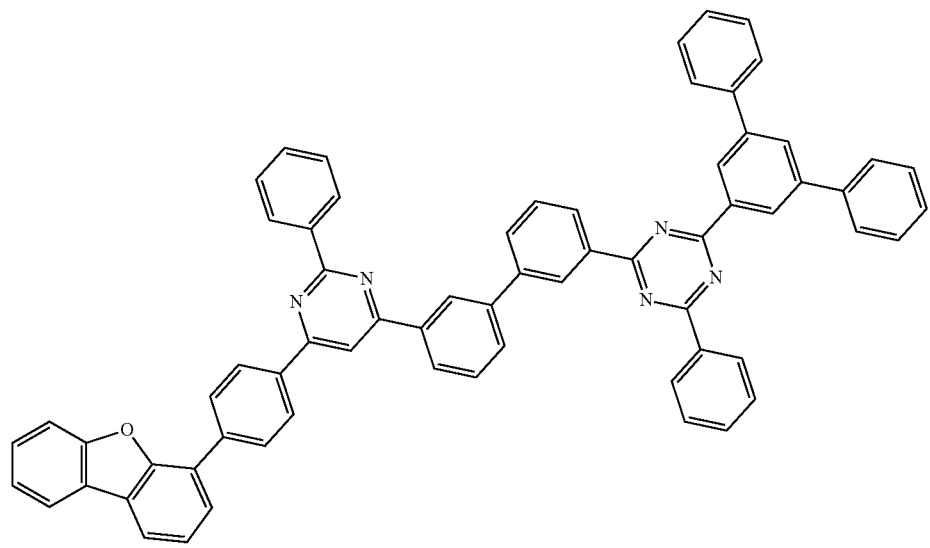
446
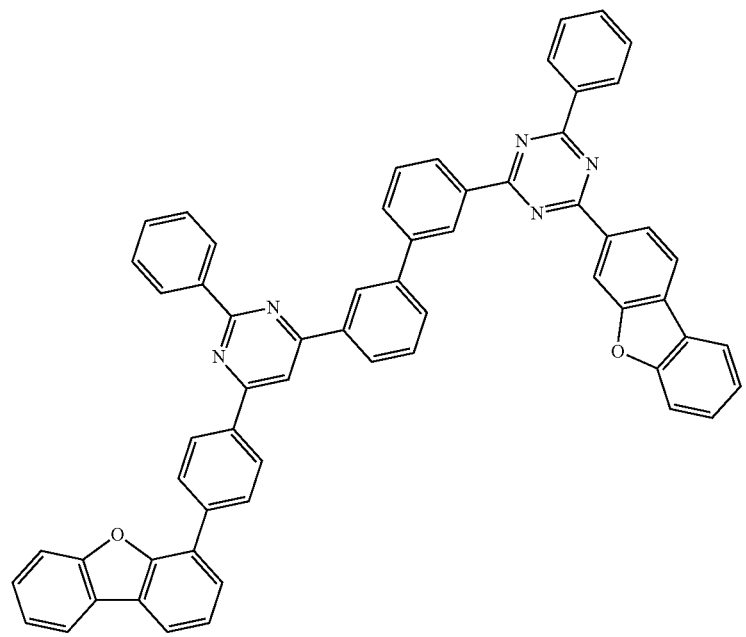
447

448
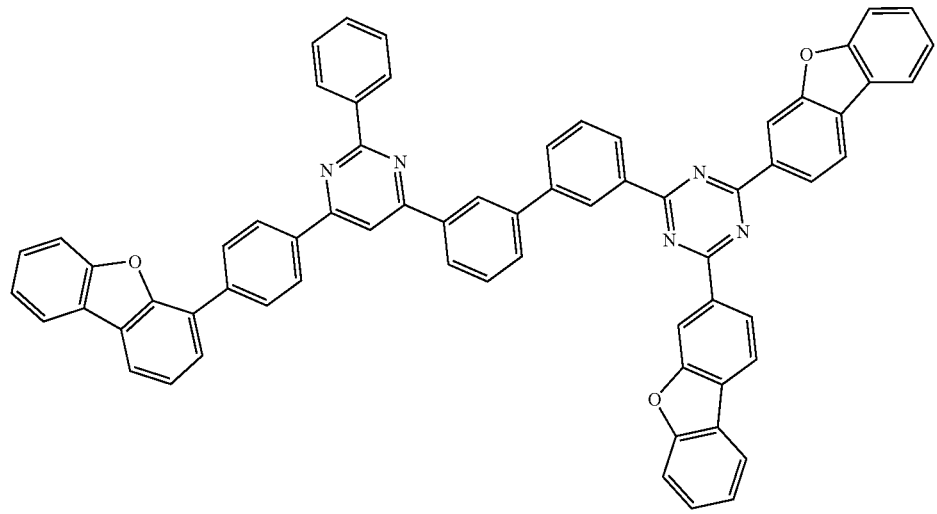
449
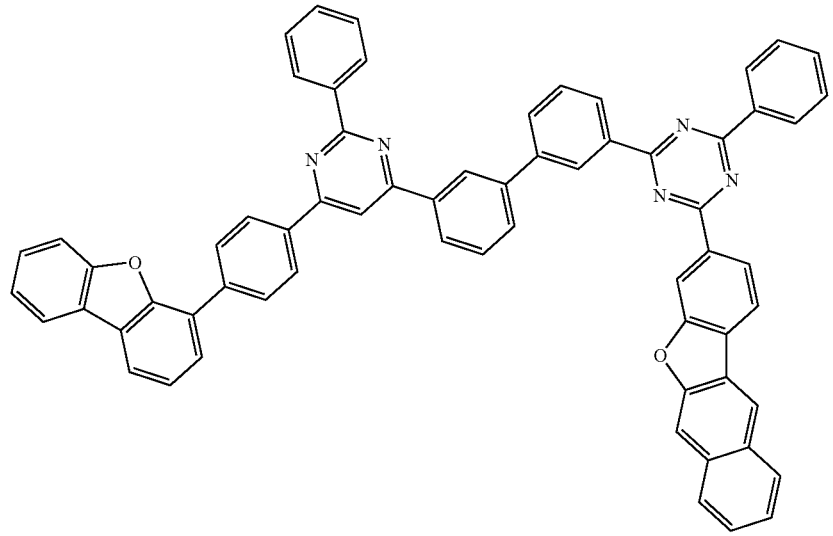
450
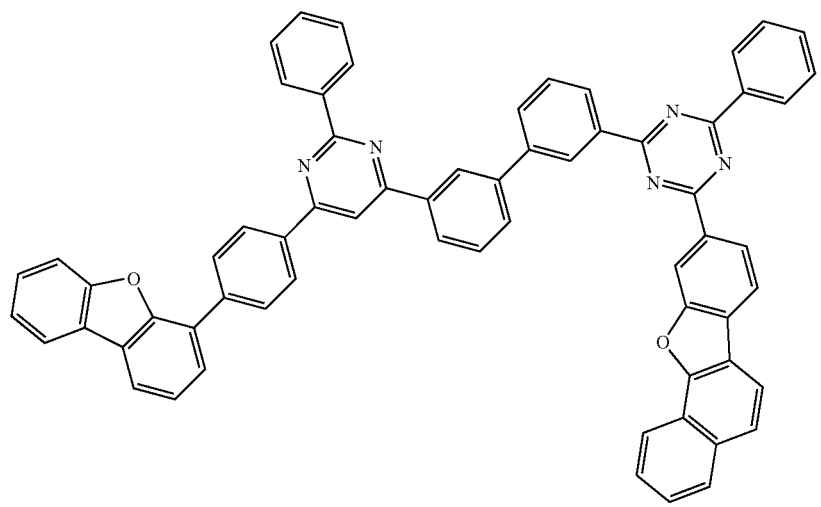

-continued
451
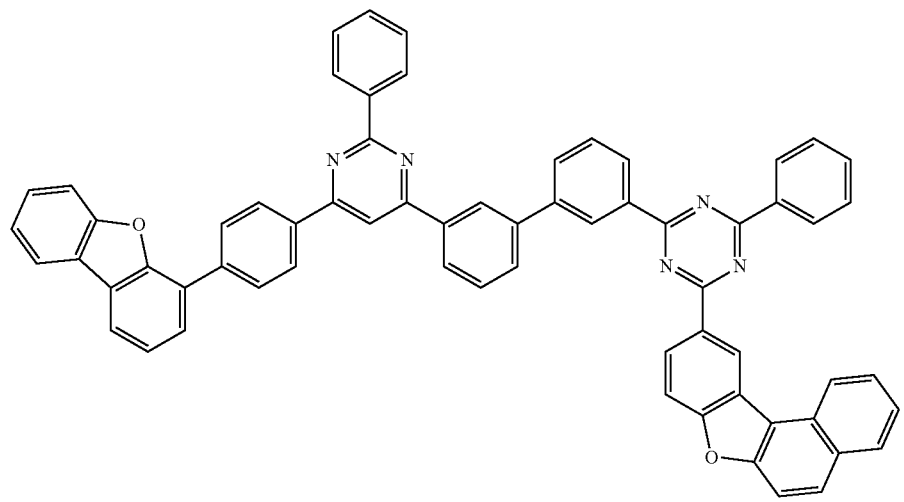
452
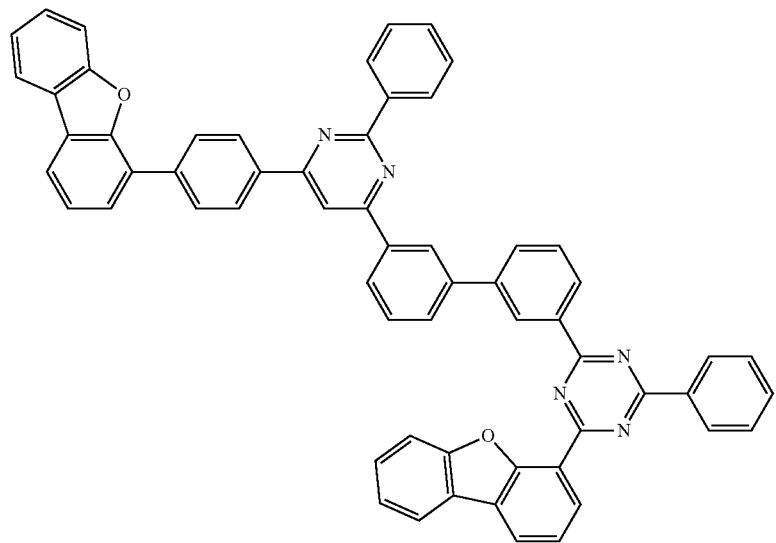
453
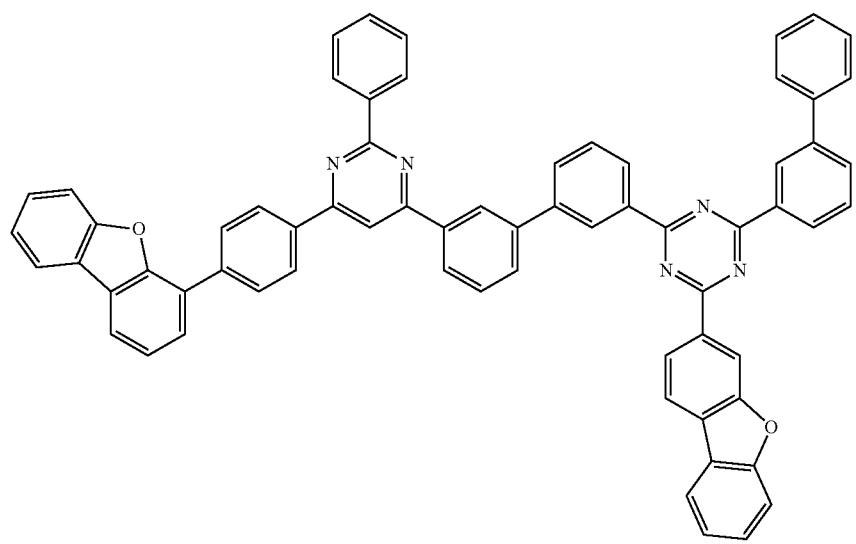

-continued
454
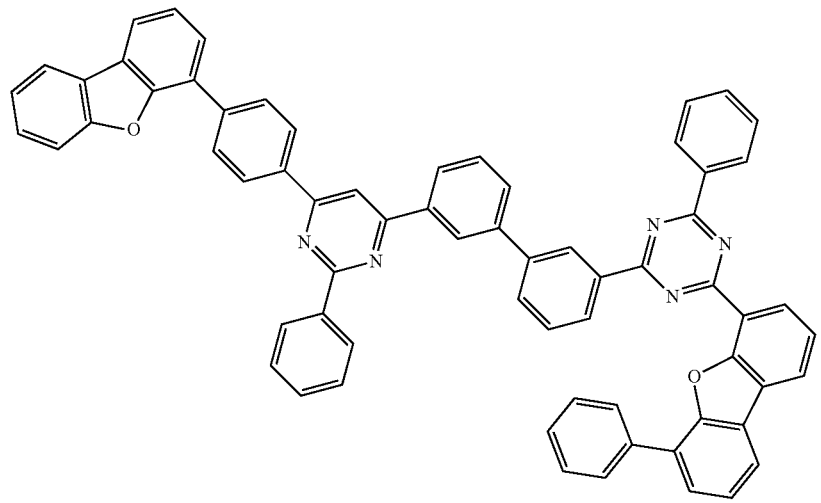
455
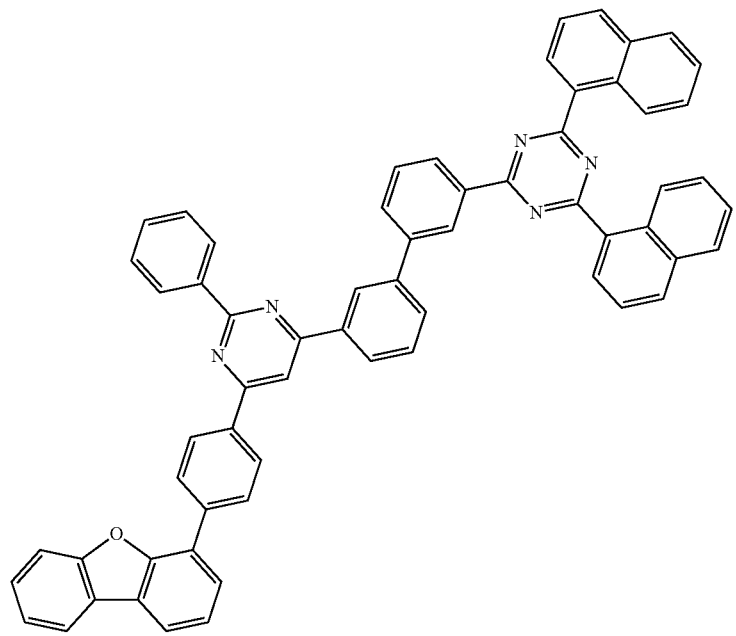
456
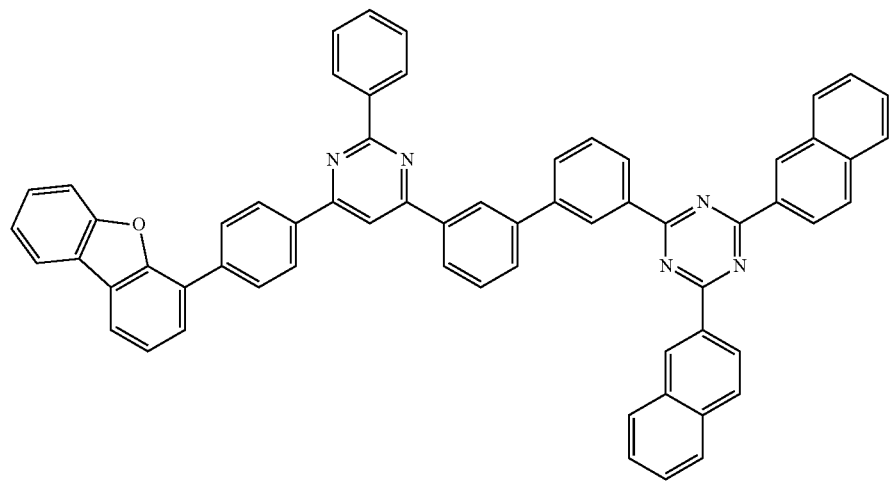

457
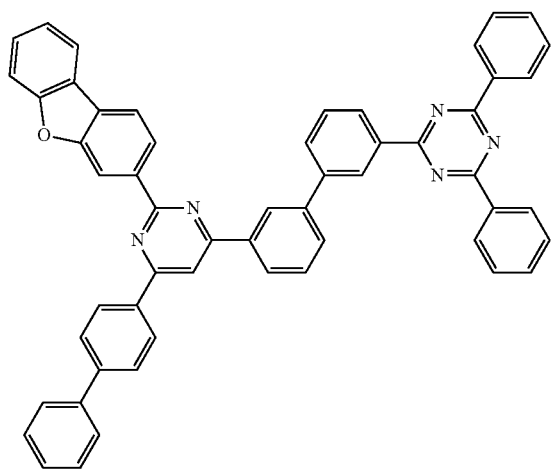
458
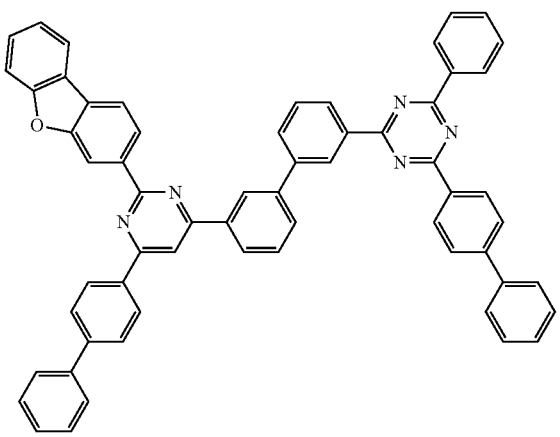
459
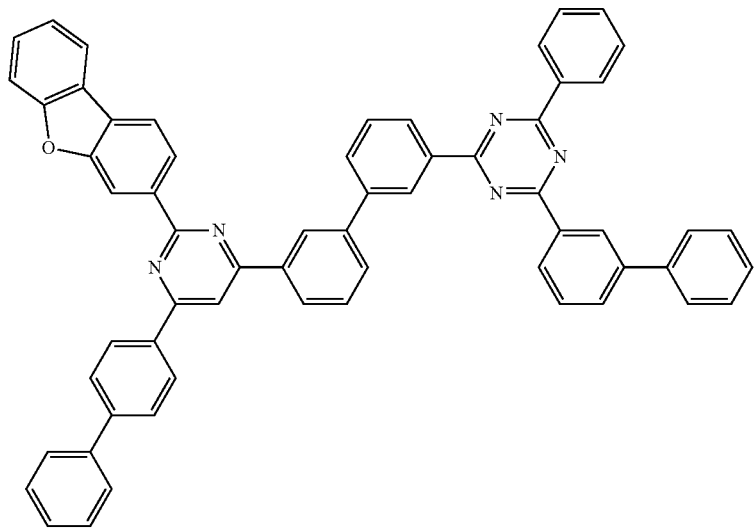
460
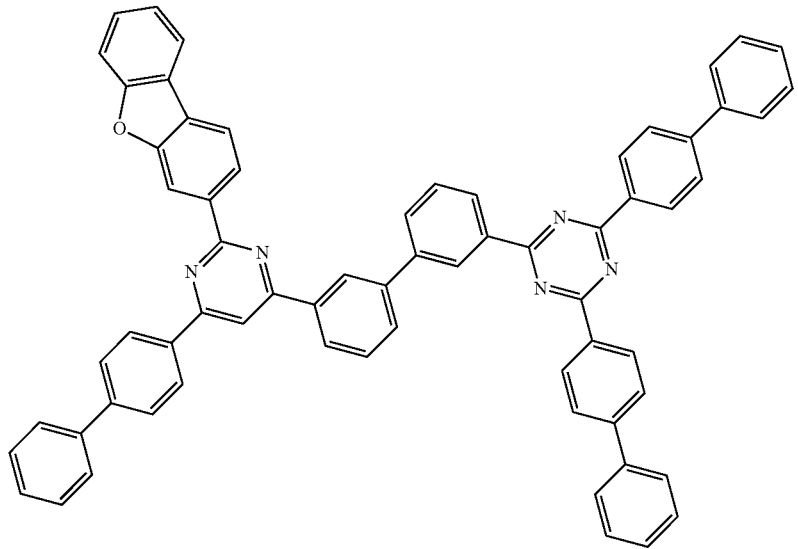

461
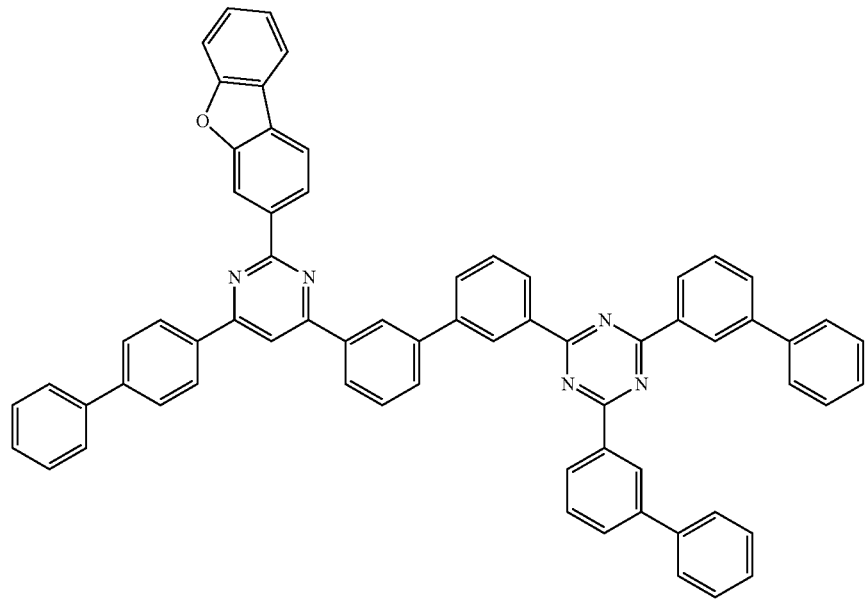
462
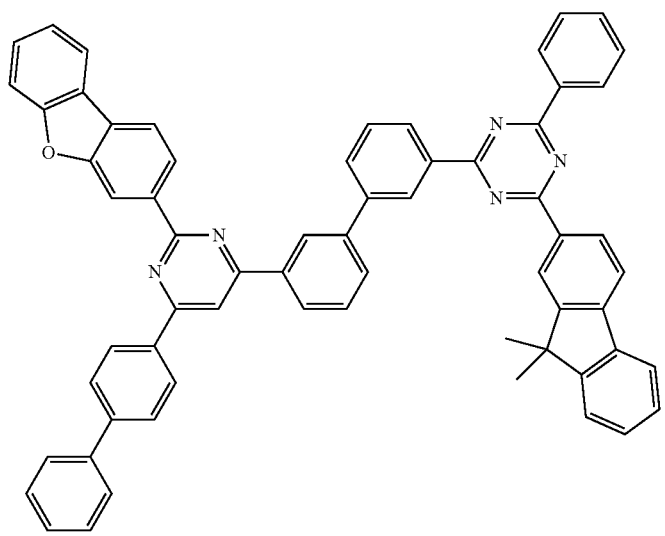
463
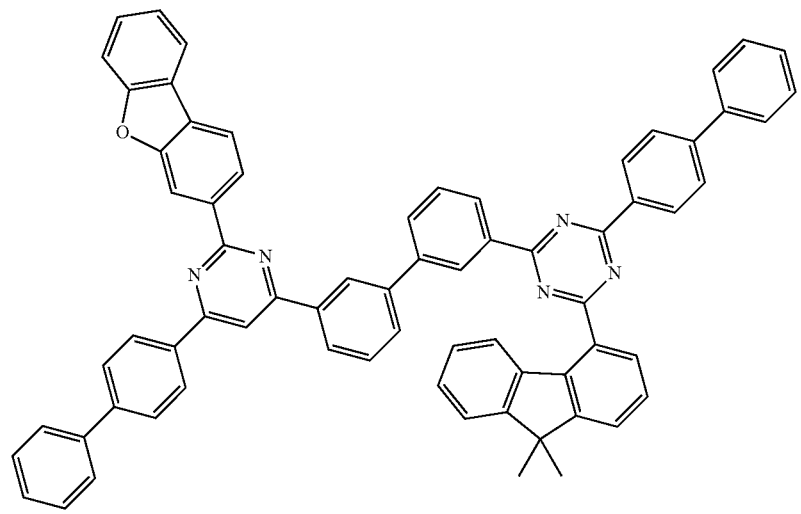

-continued
464
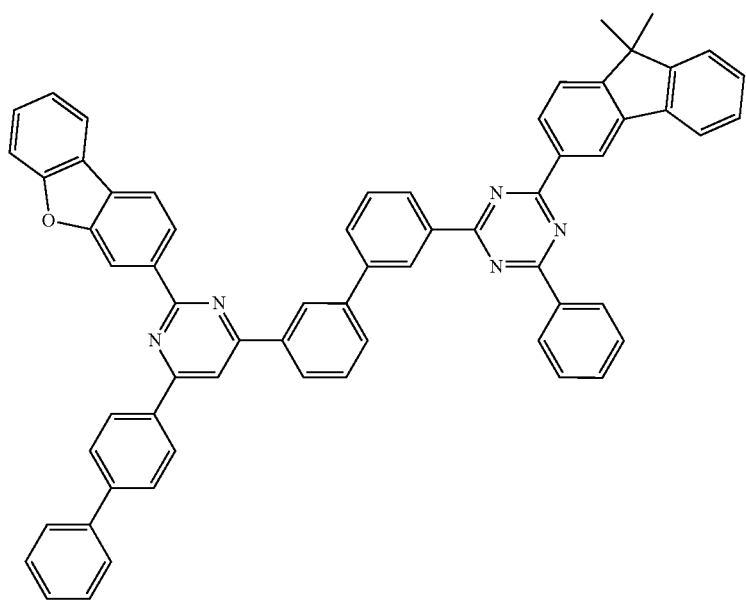
465
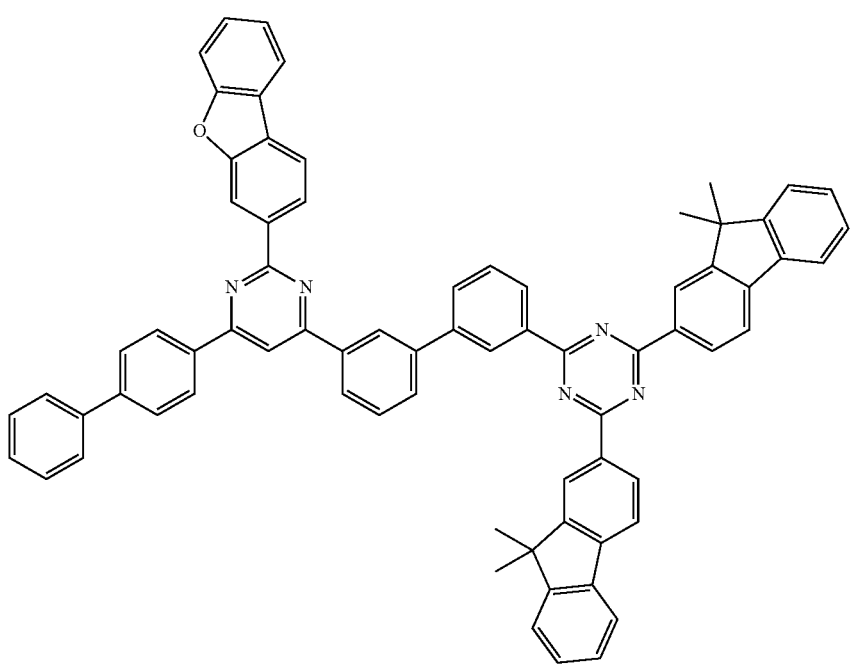

-continued
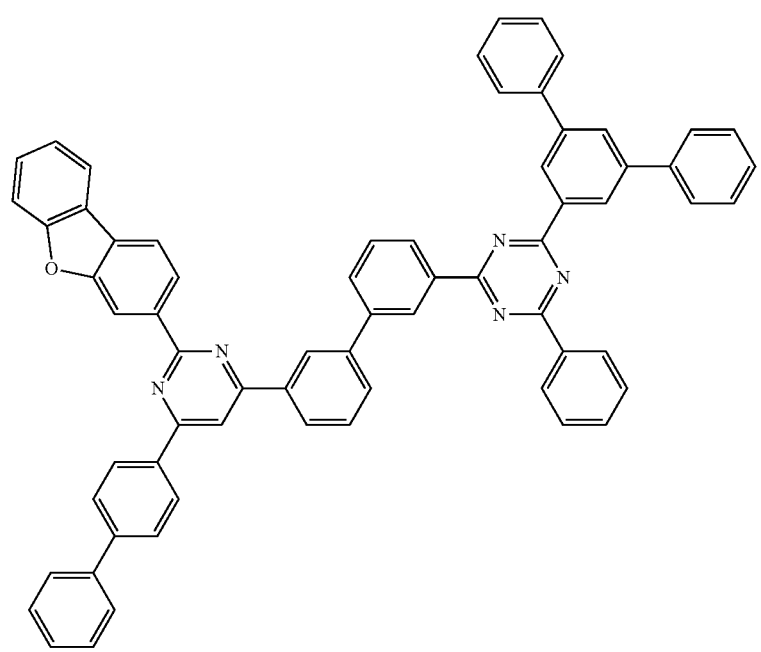
466
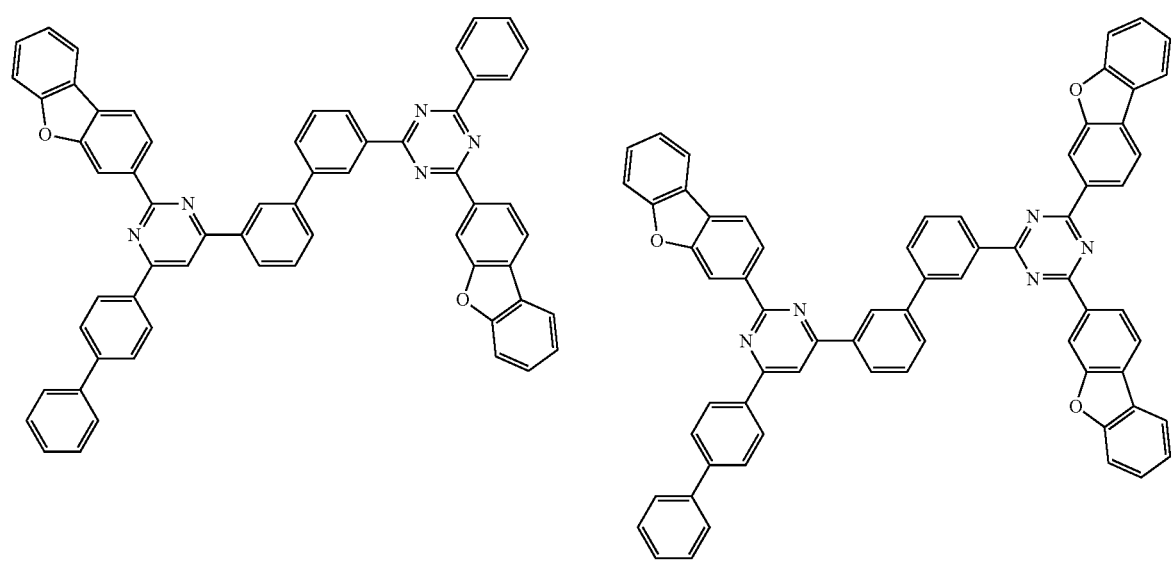

-continued
469
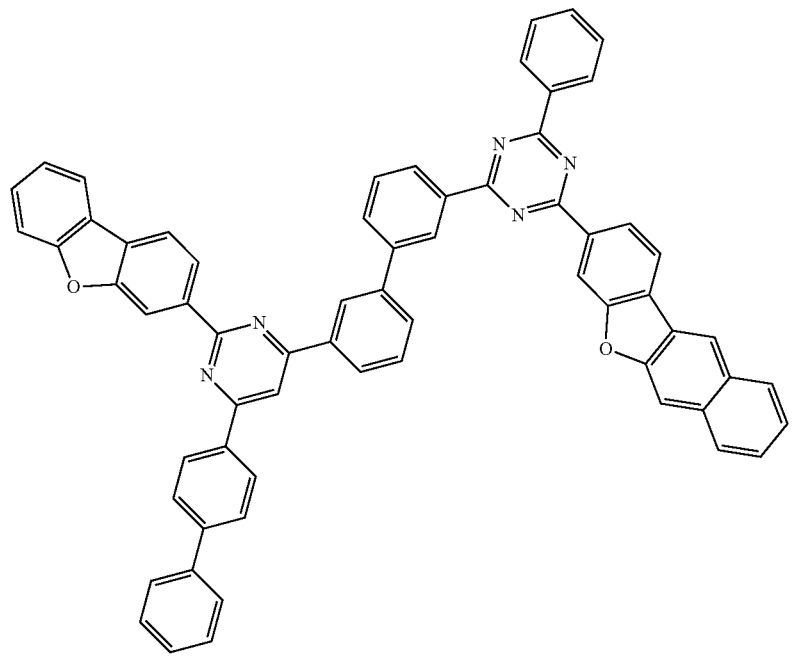
470
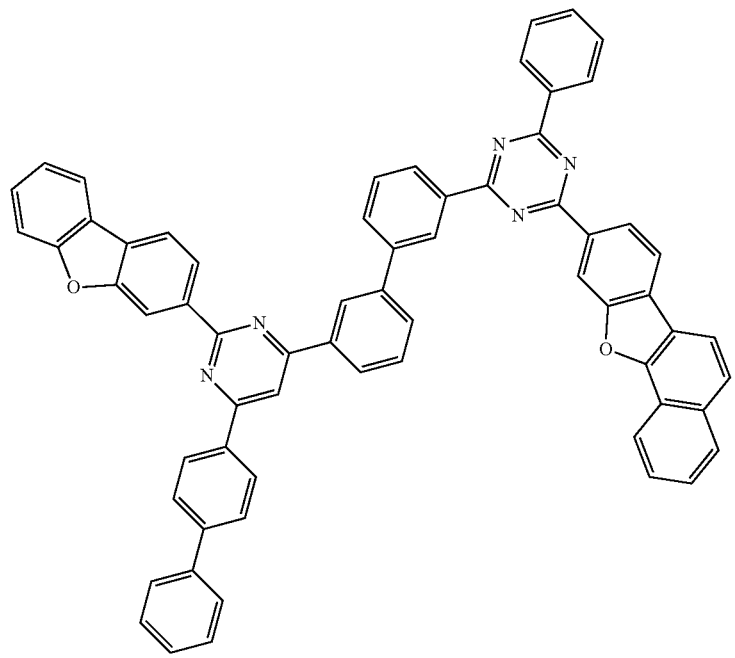

205
-continued
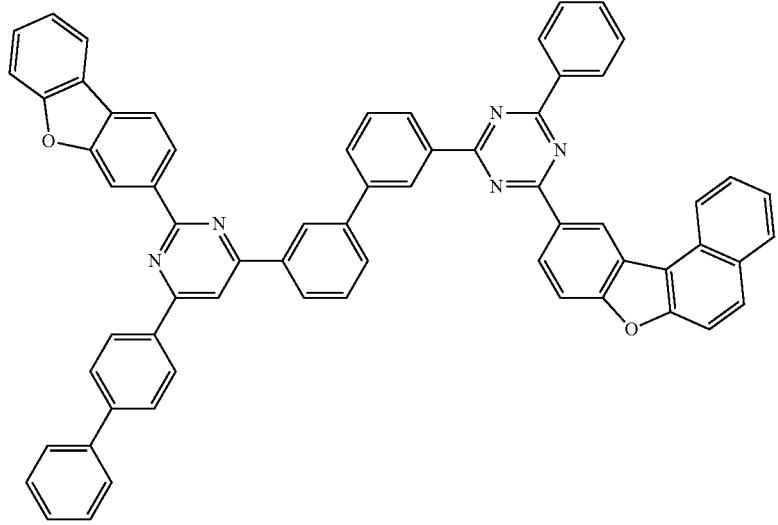
471
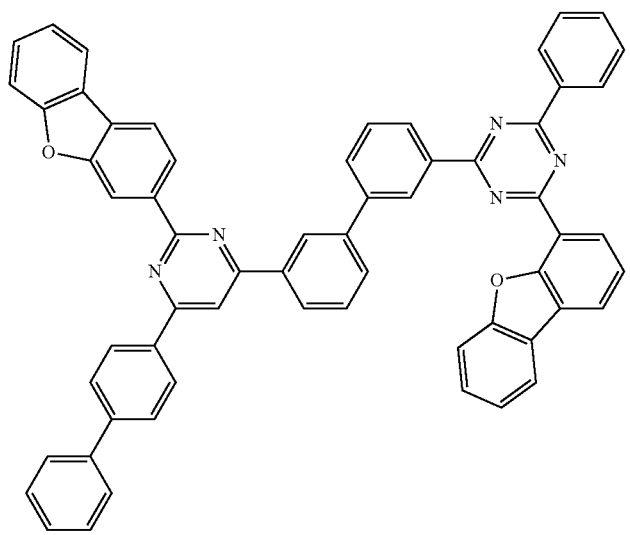
472
473 474
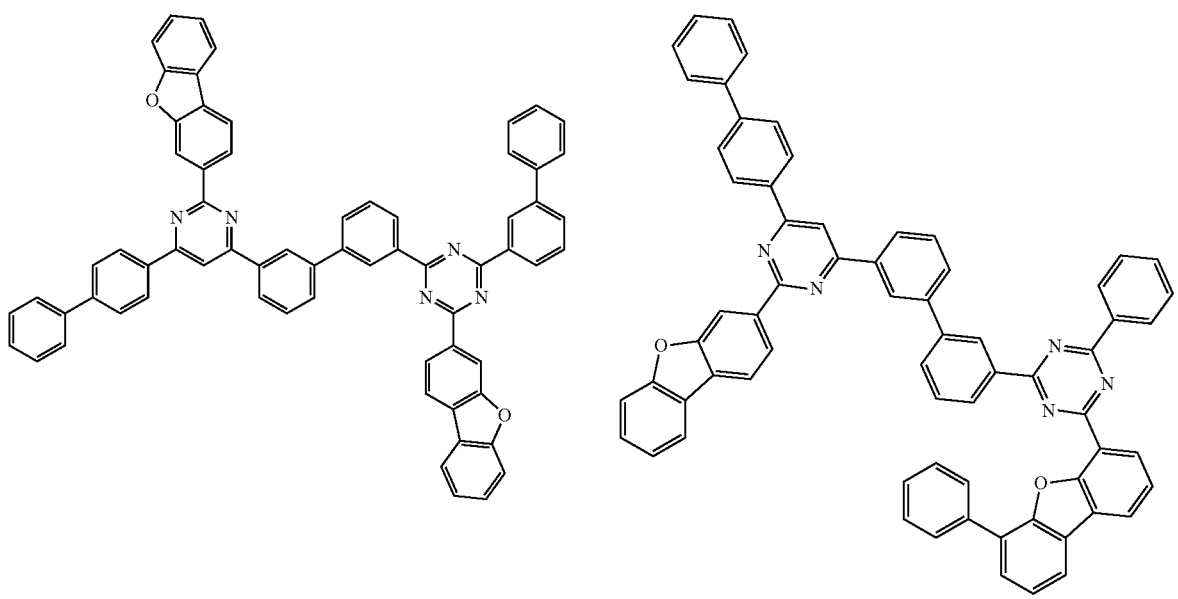
206

475
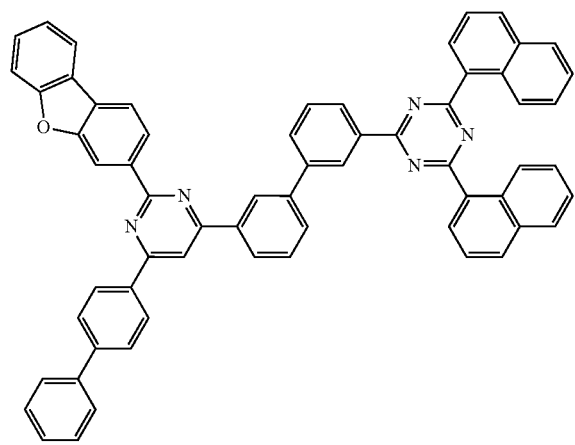
476
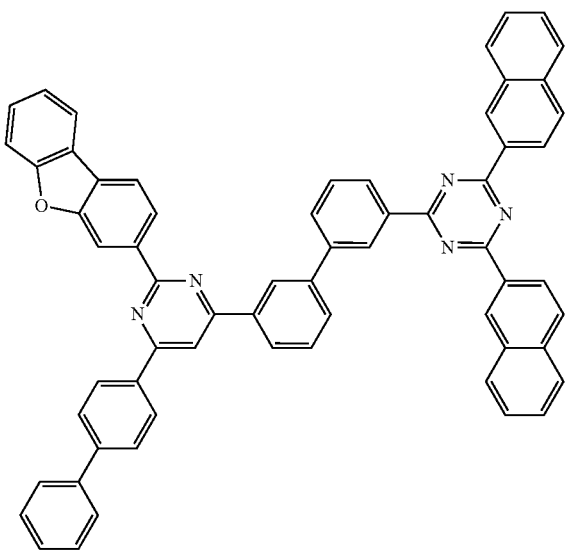
477
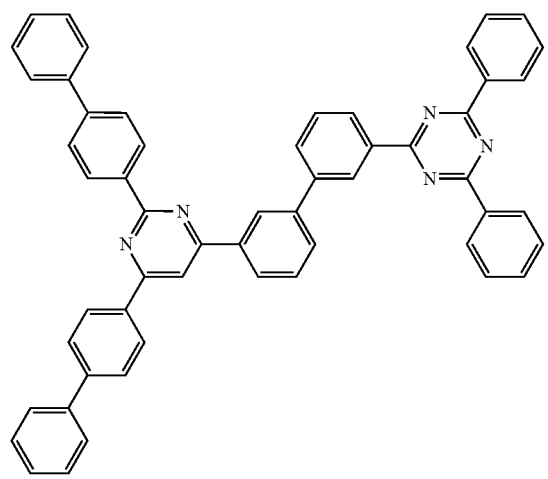
478
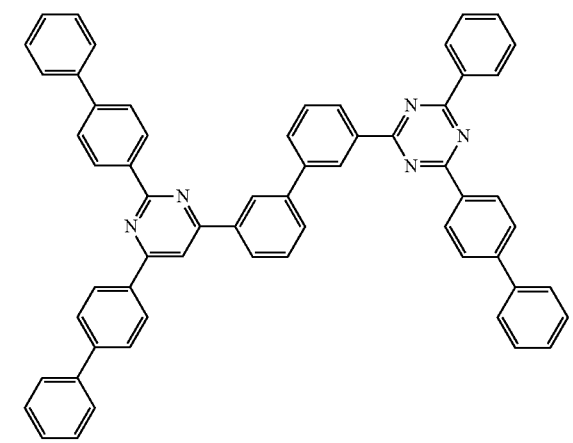
479
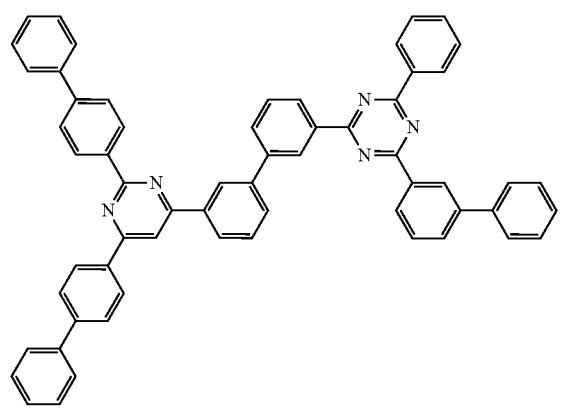
480
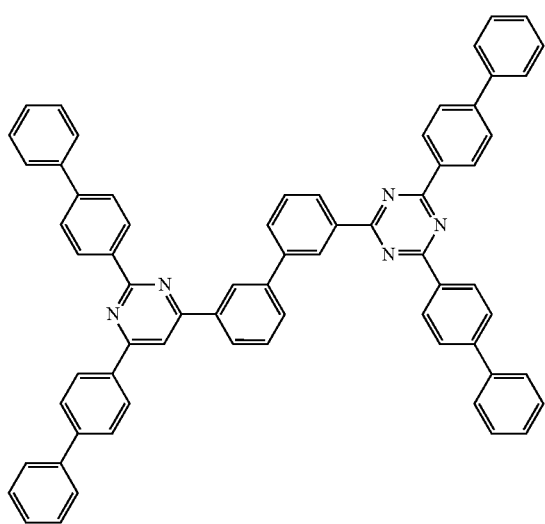

-continued
481
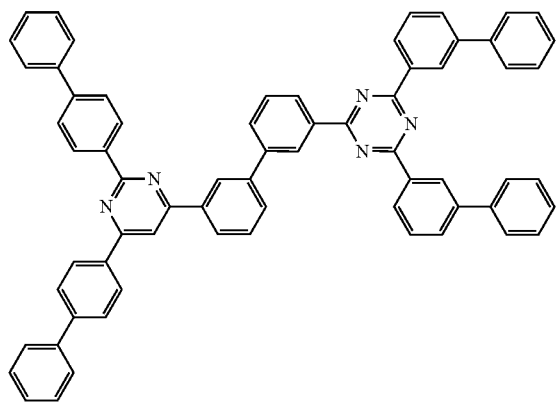
482
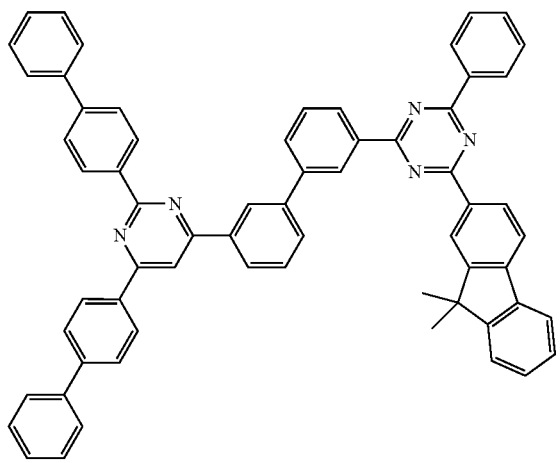
483
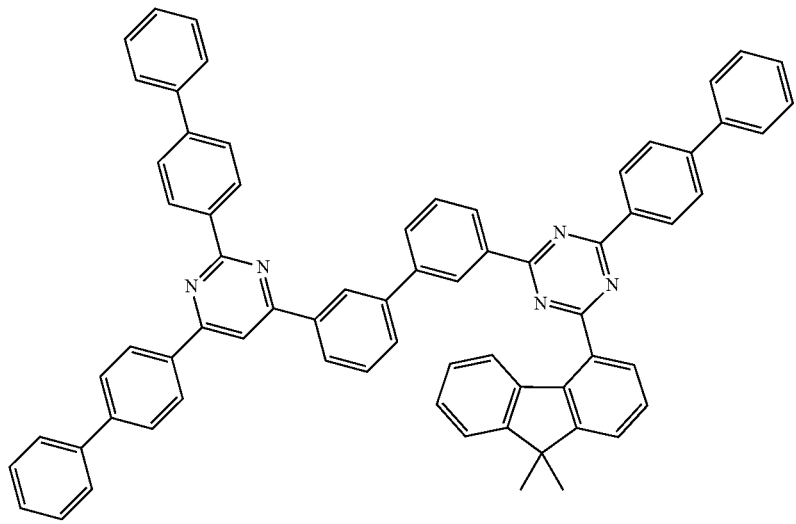
484
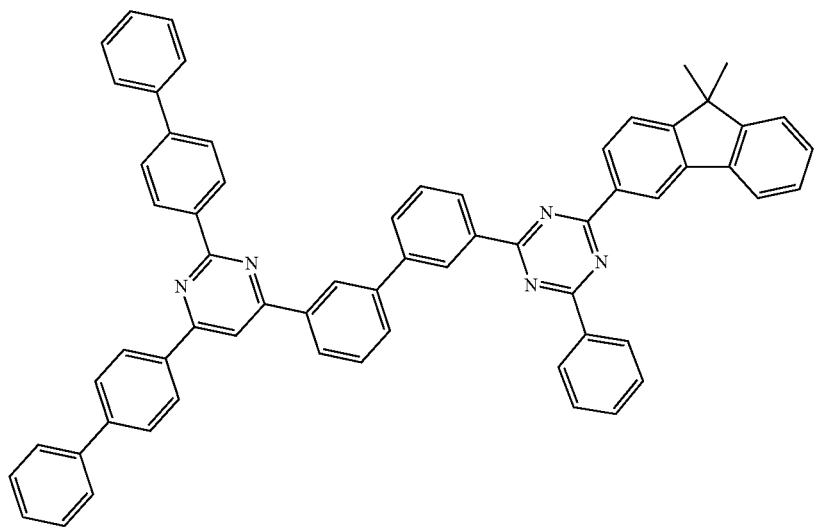

485
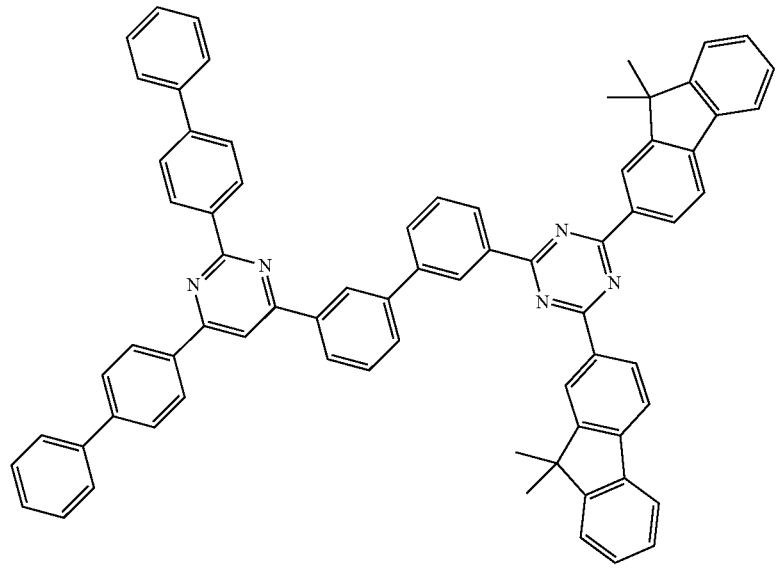
486
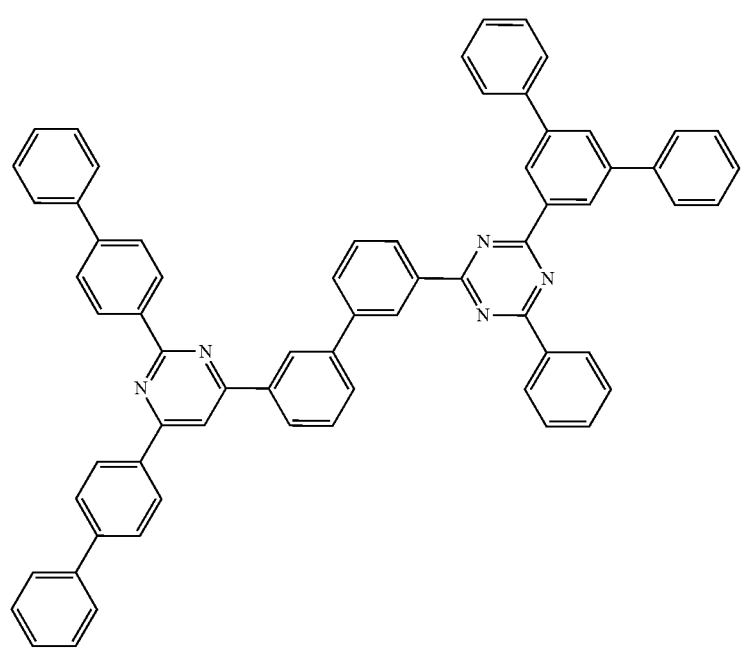

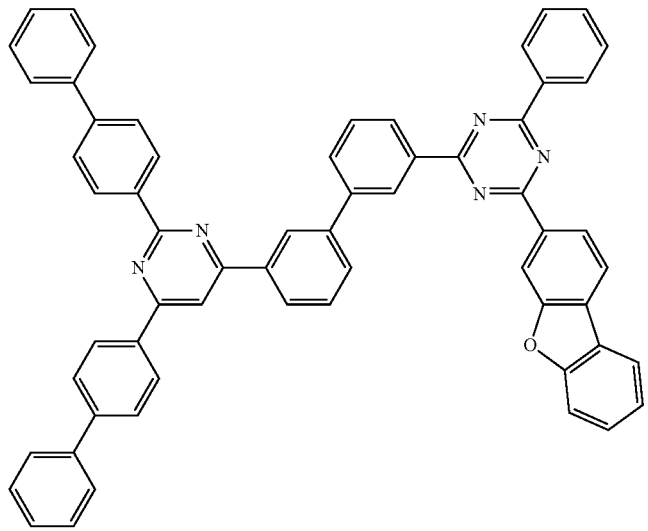
487
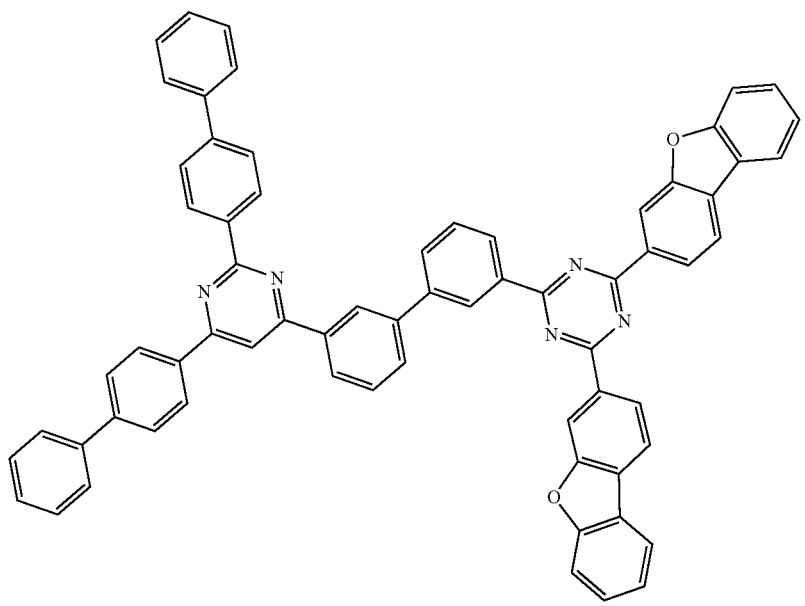
488

-continued
489
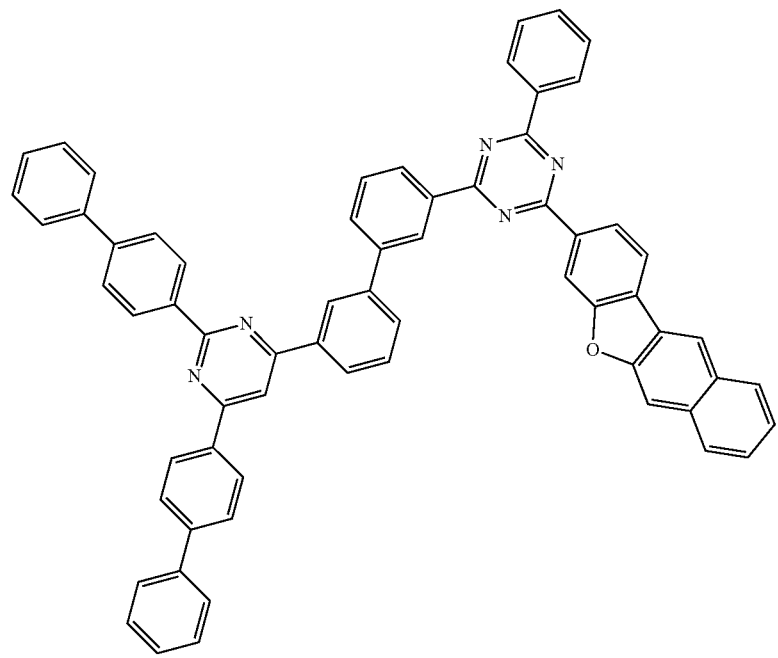
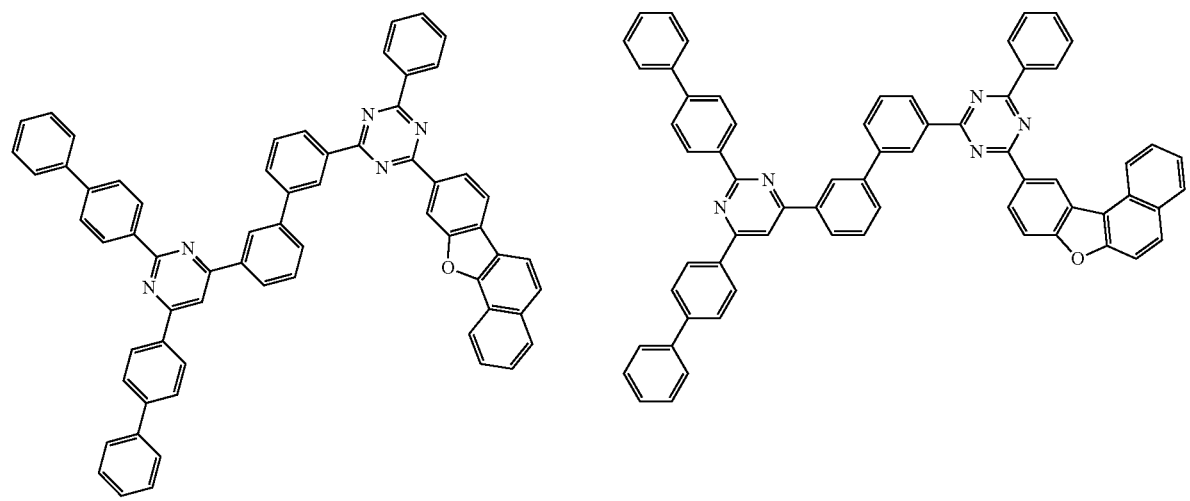

-continued
492
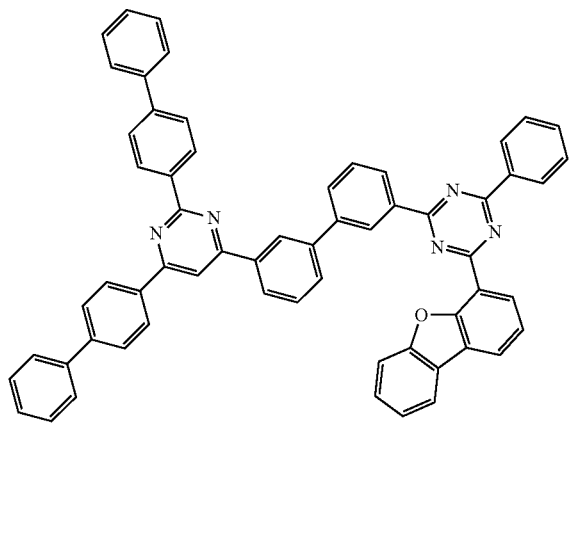
493
494
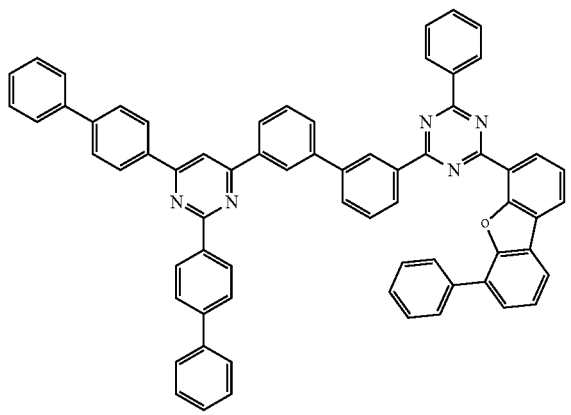
495
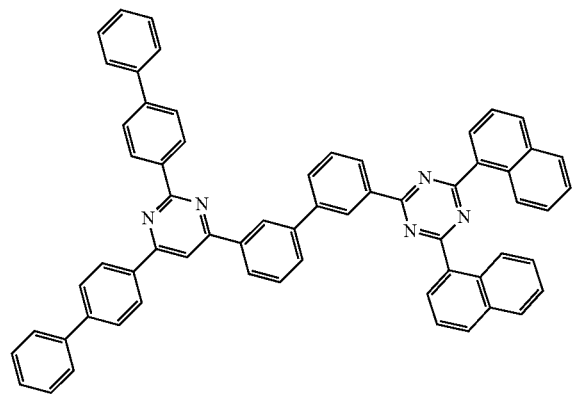
496
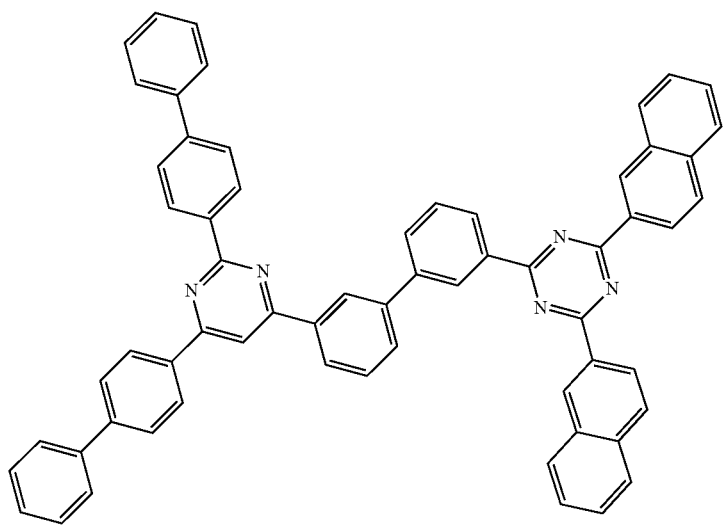

497
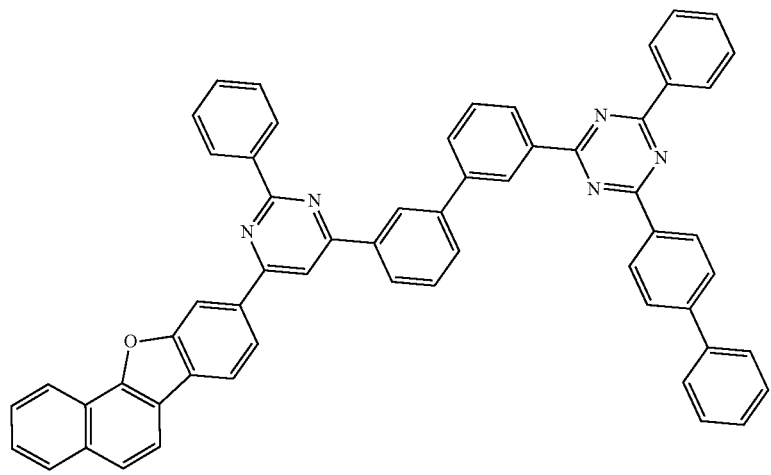
498
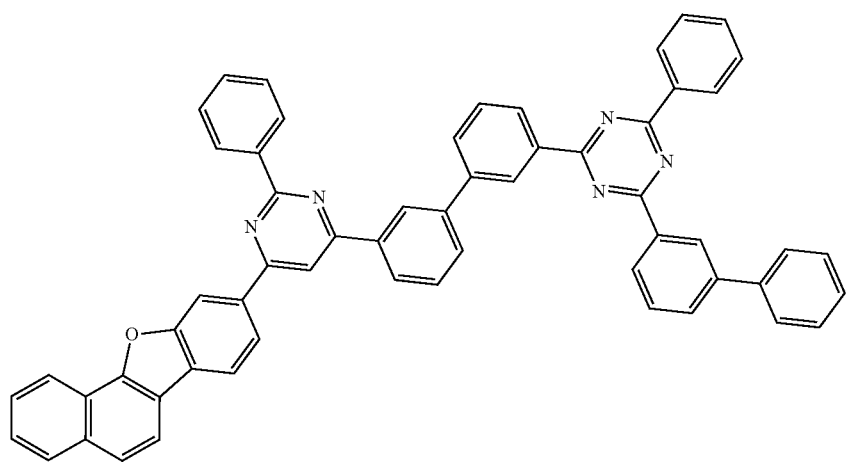
499
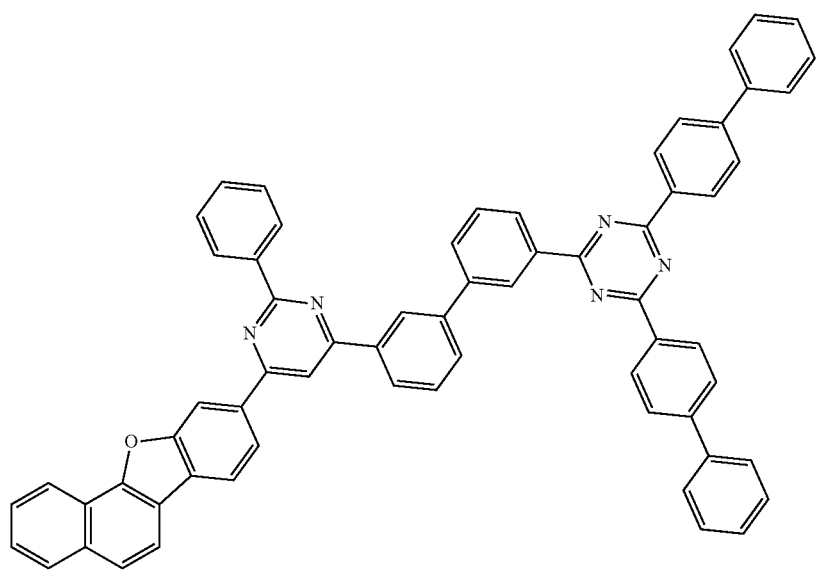

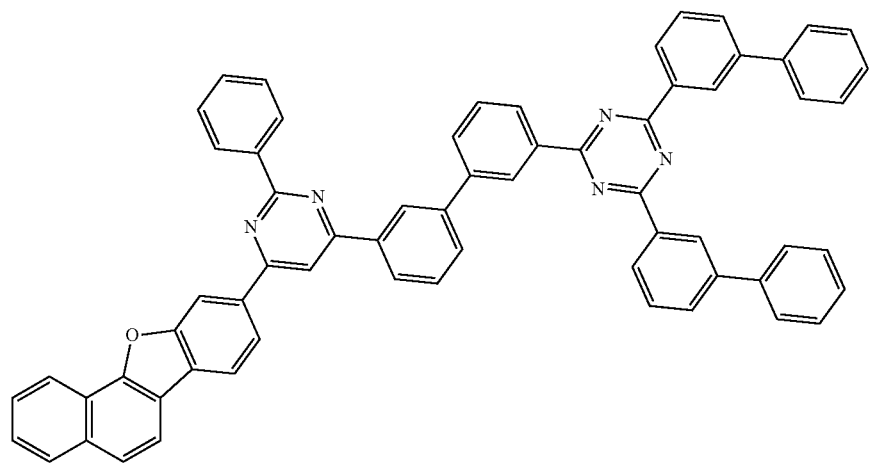
500
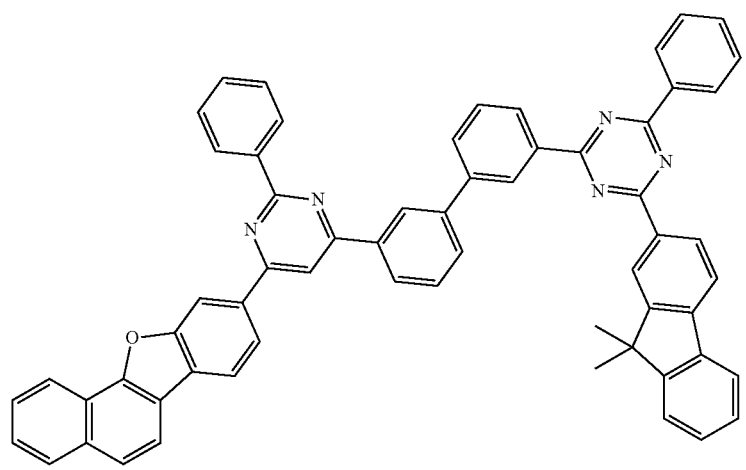
501
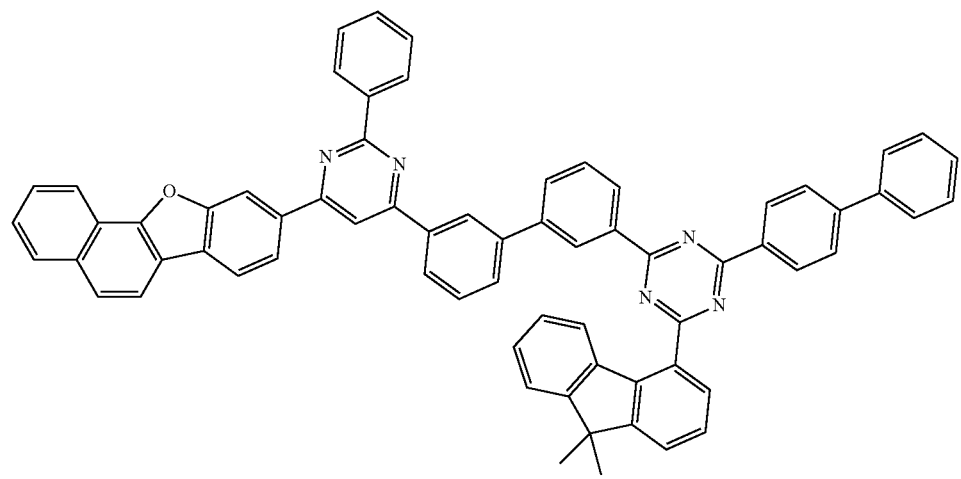
502

-continued
503
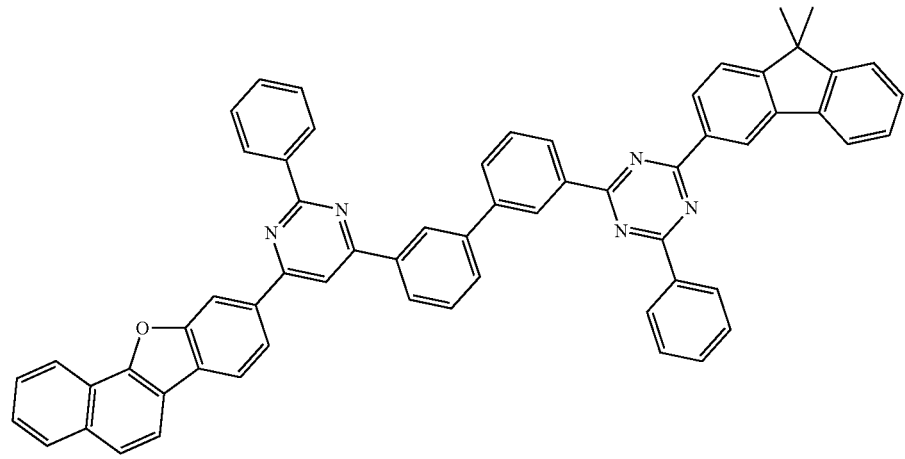
504
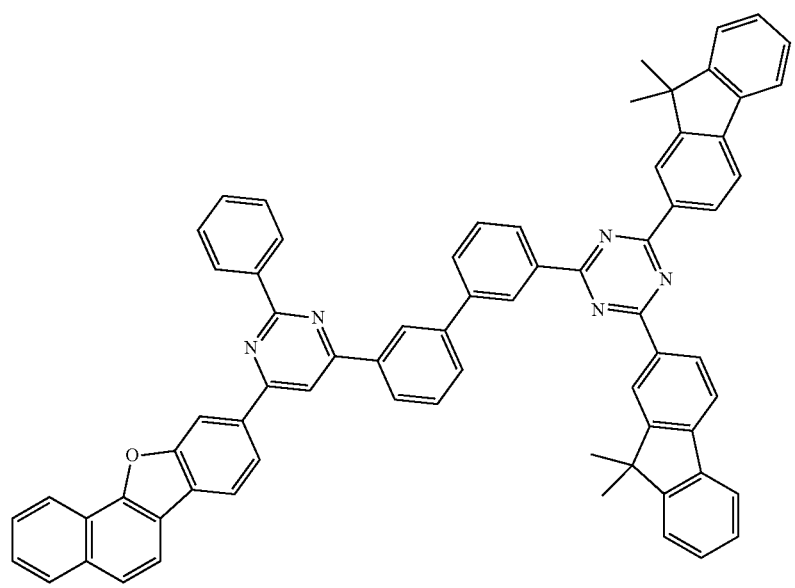
505
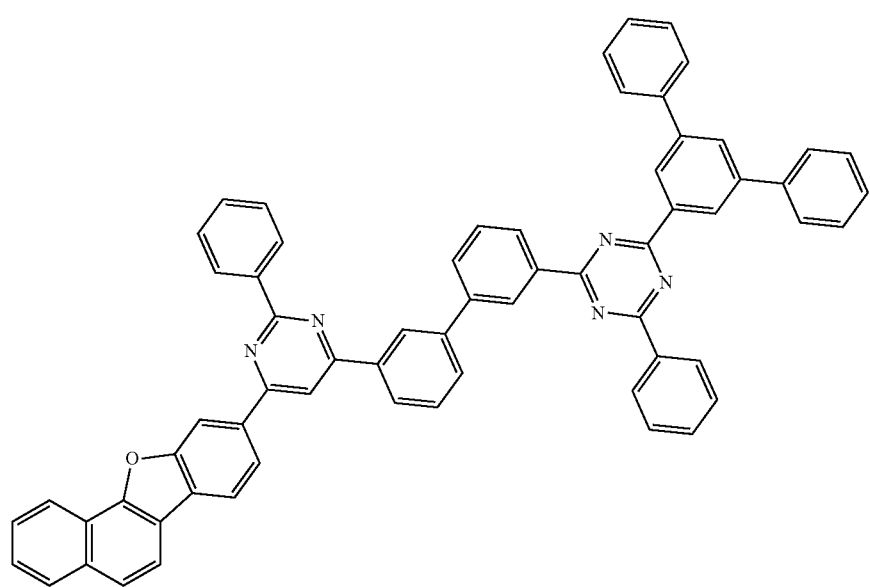

506
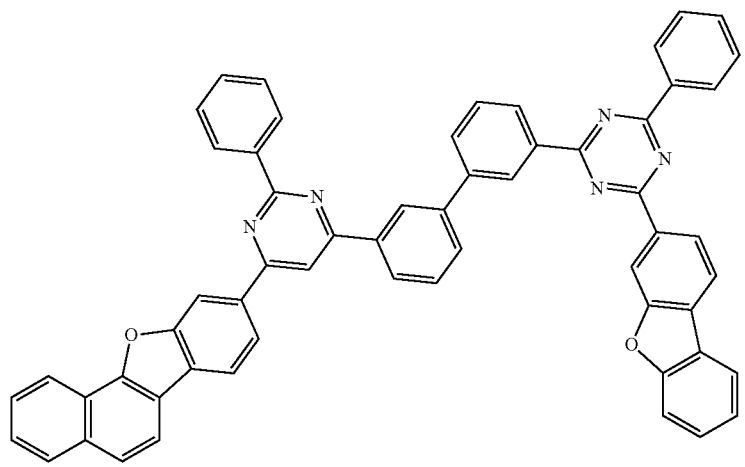
507
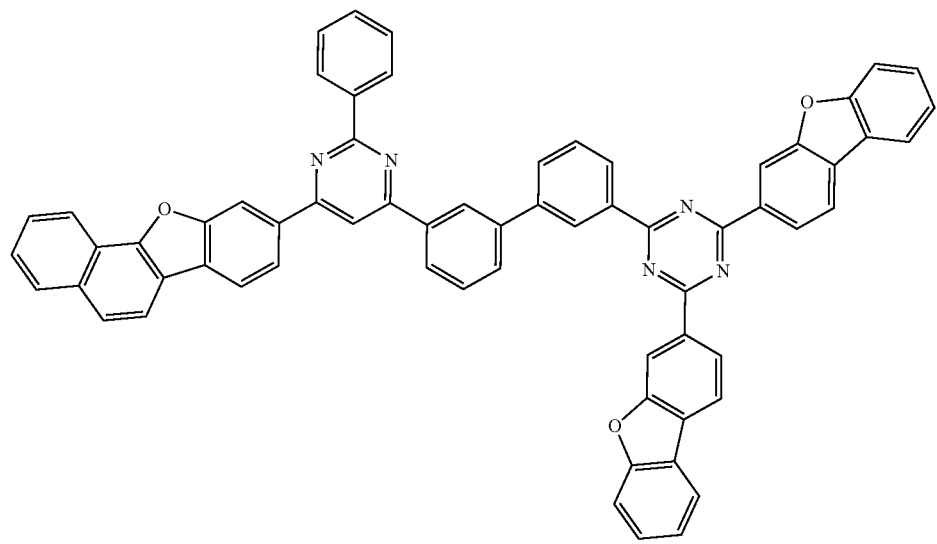
508
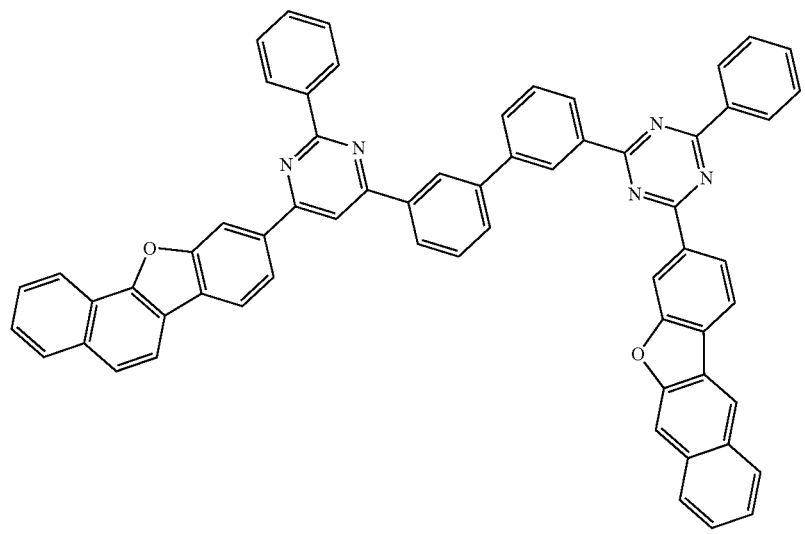

-continued
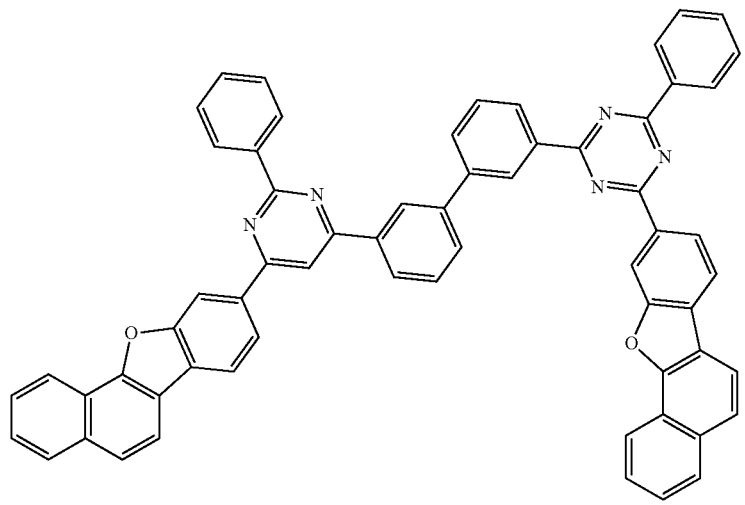
509
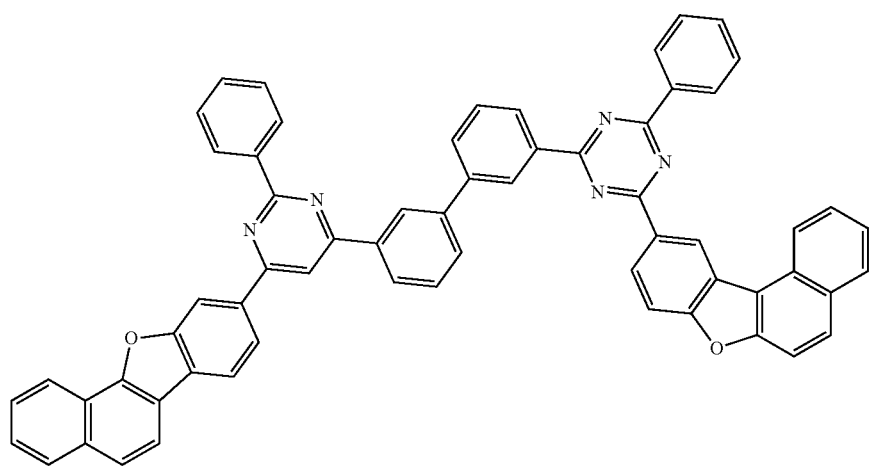
510
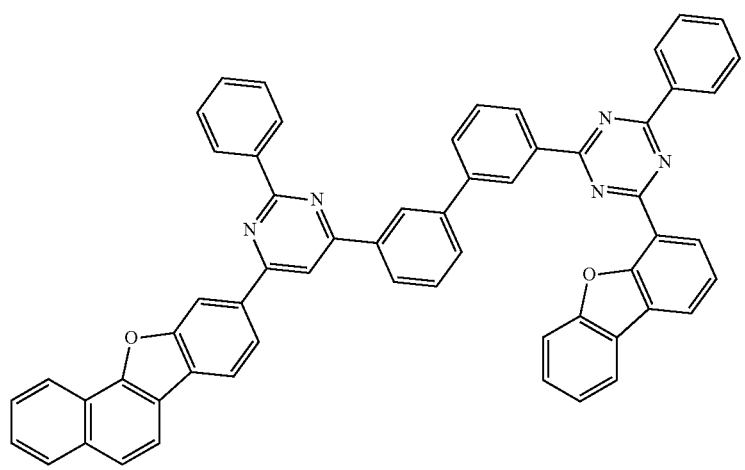
511

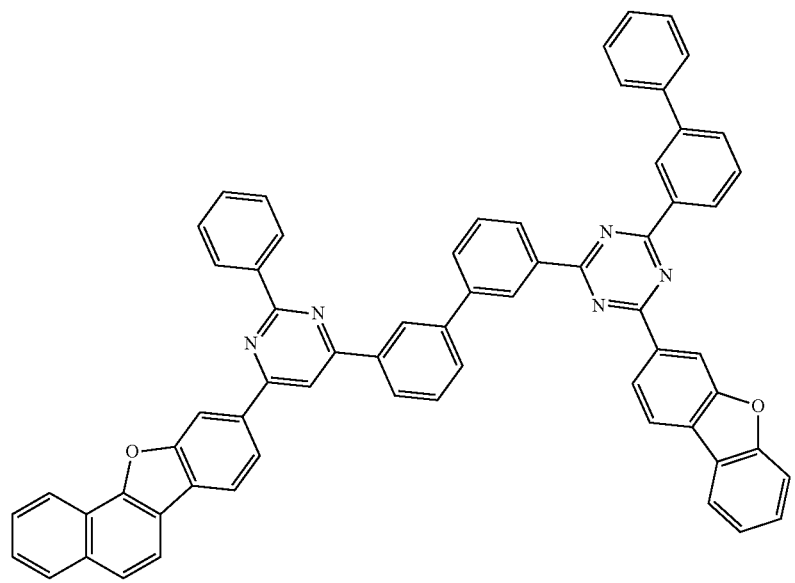
512
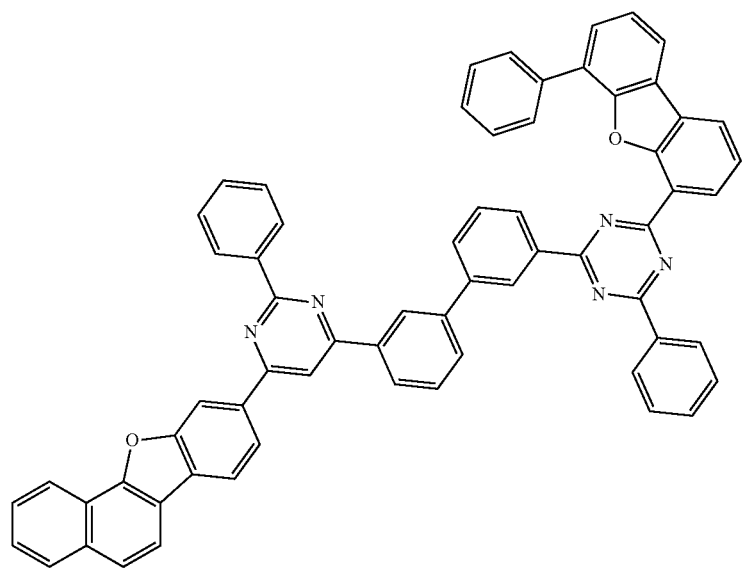
513
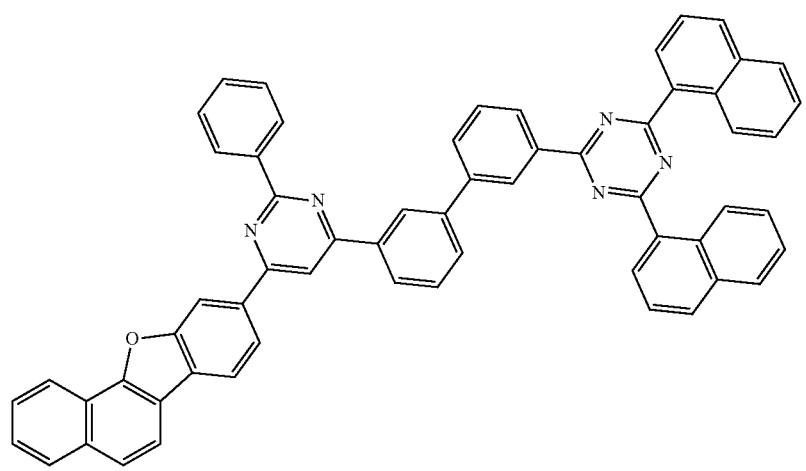
514

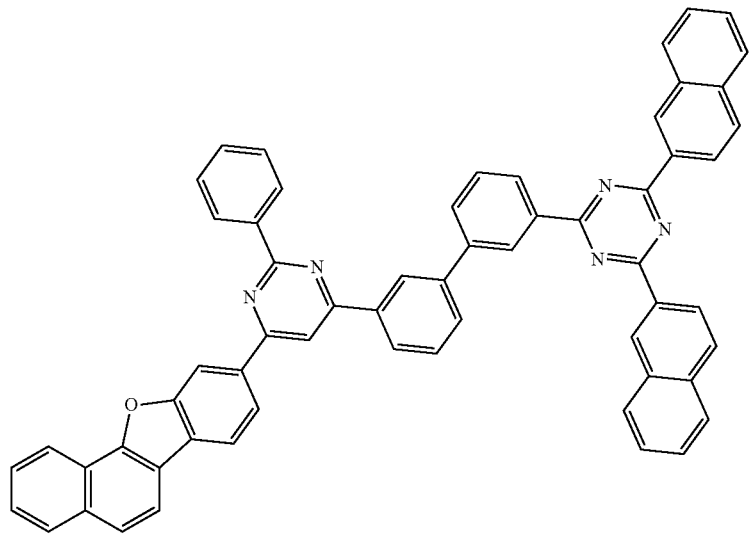
515
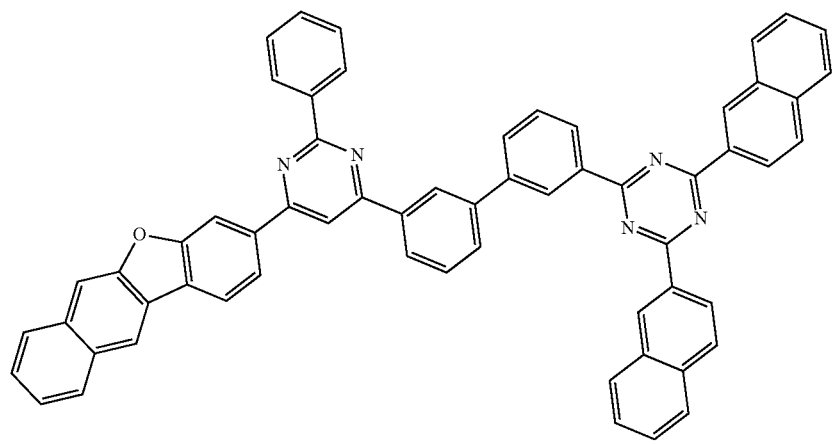
516
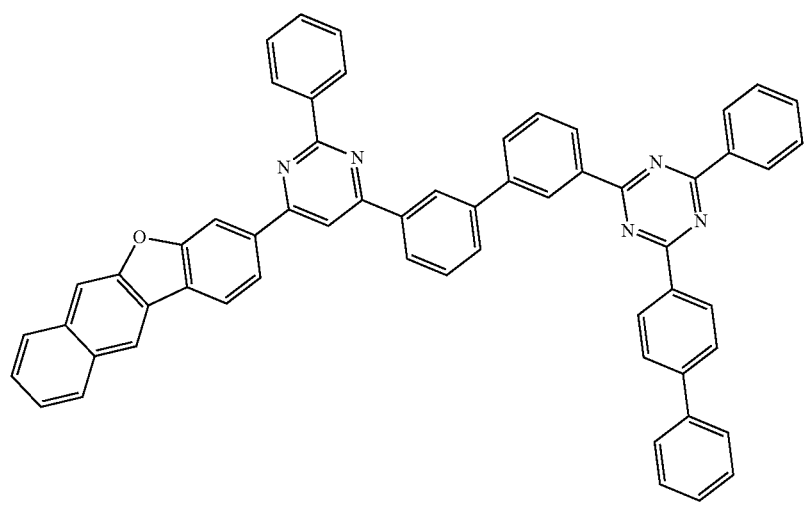
517

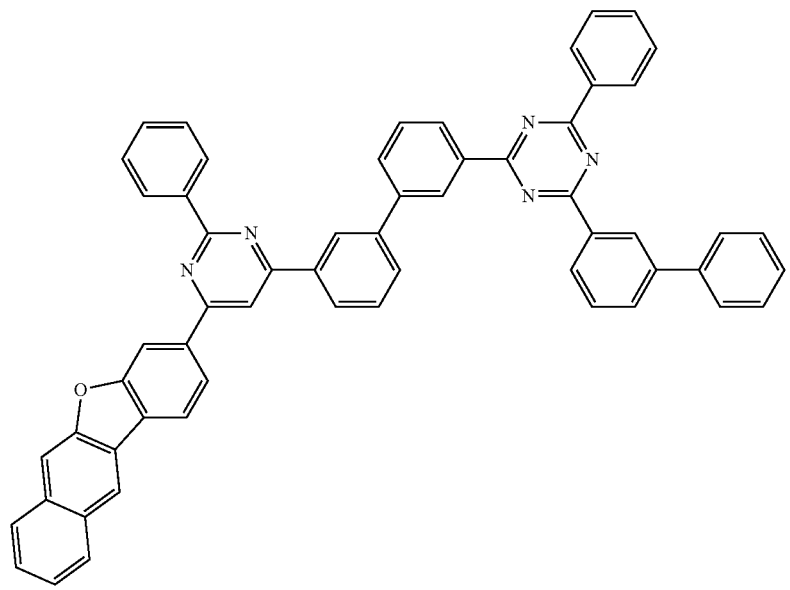
518
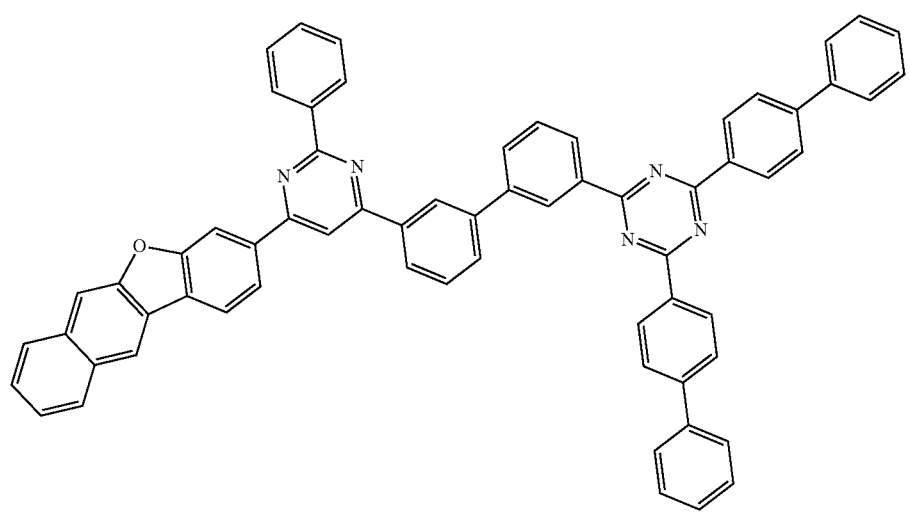
519
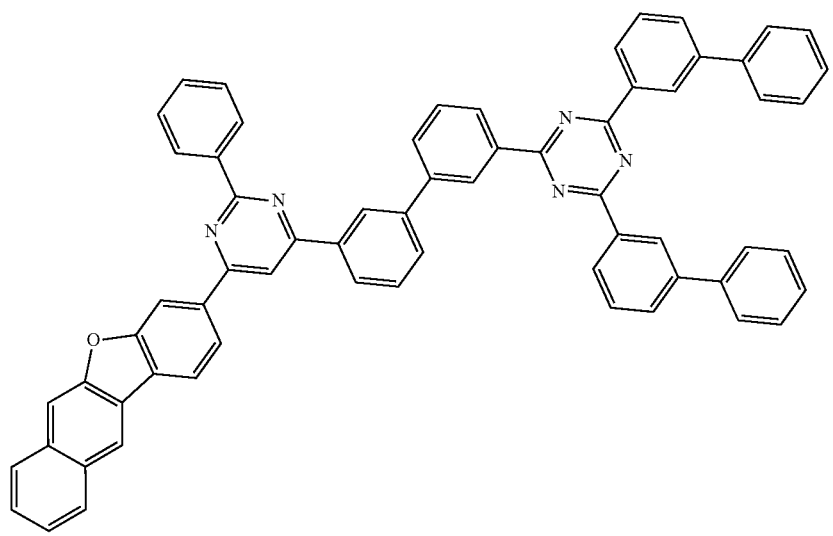
520

-continued
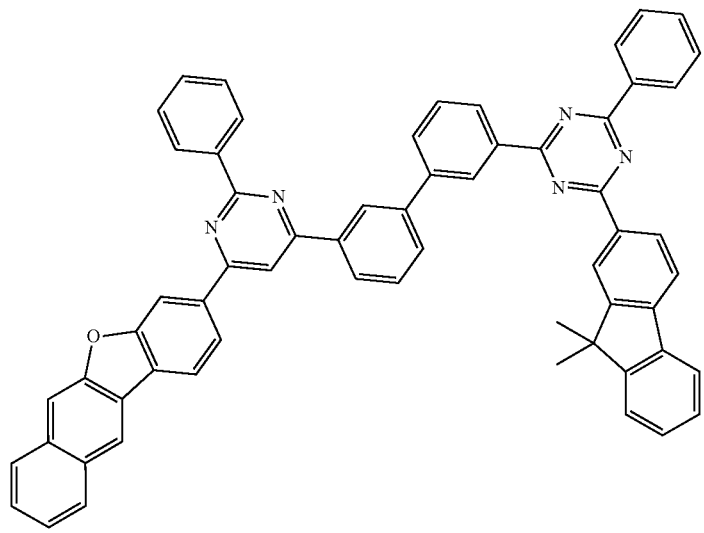
521
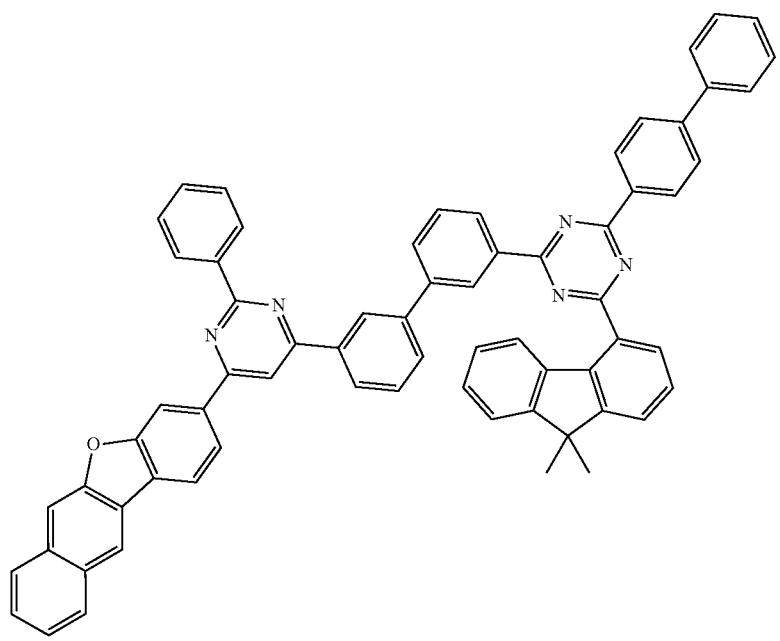
522

523
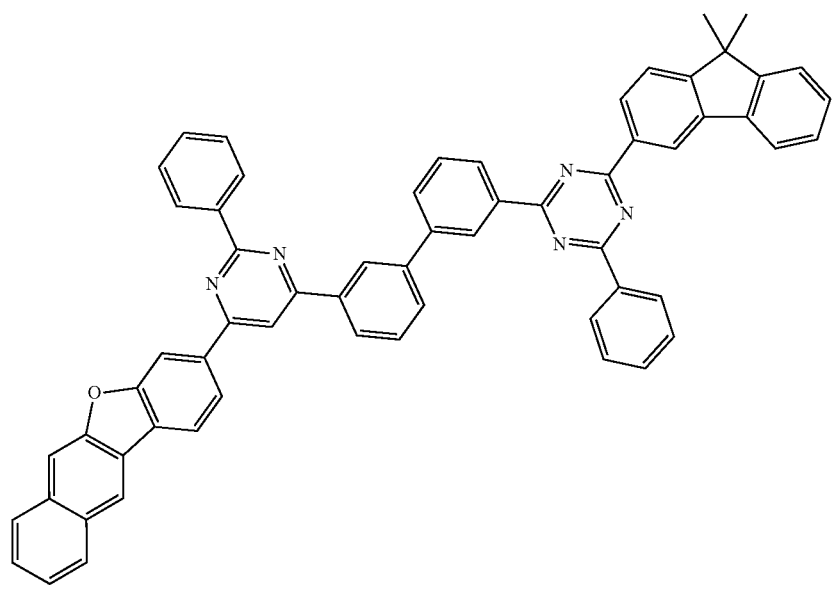
524
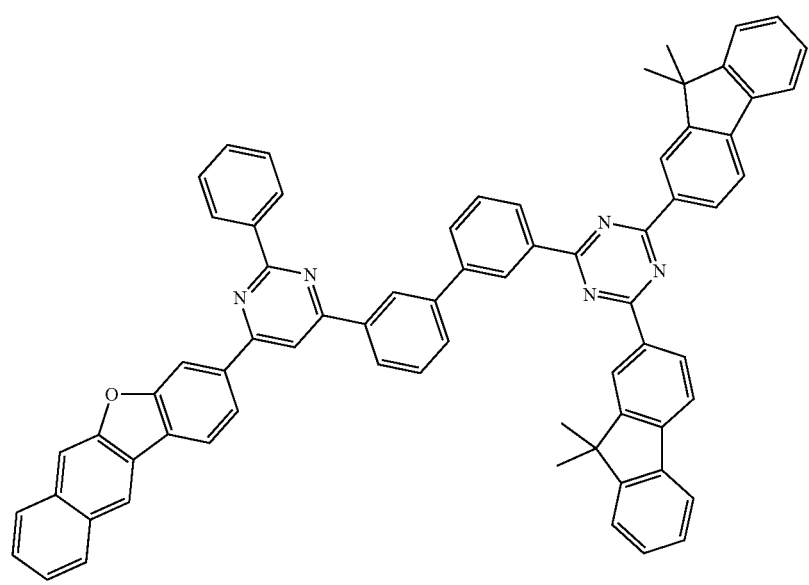

525
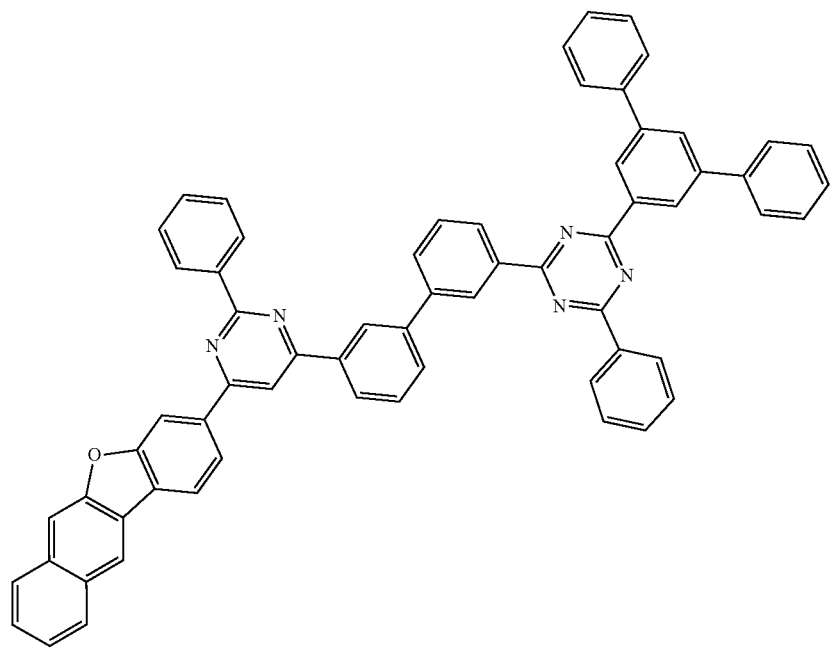
526
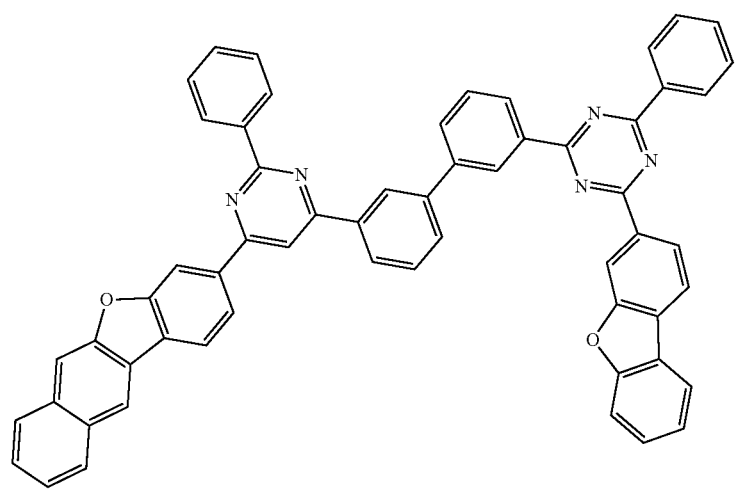
527
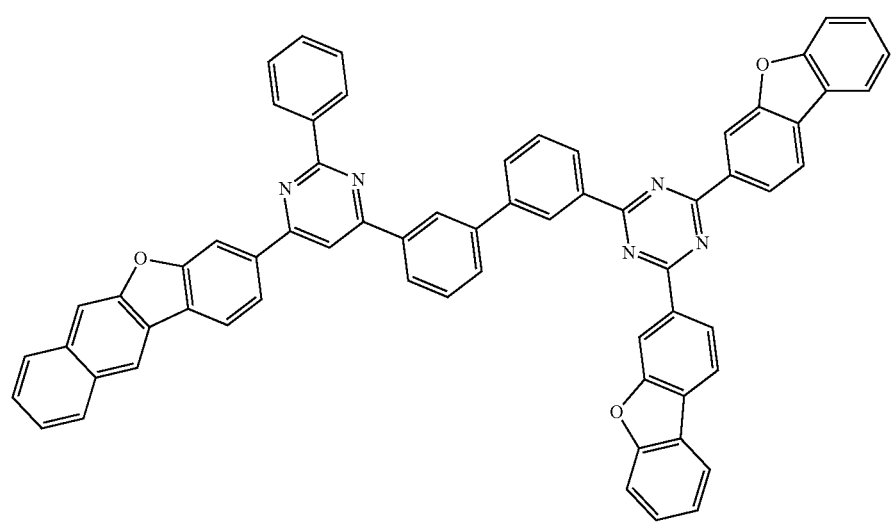

-continued
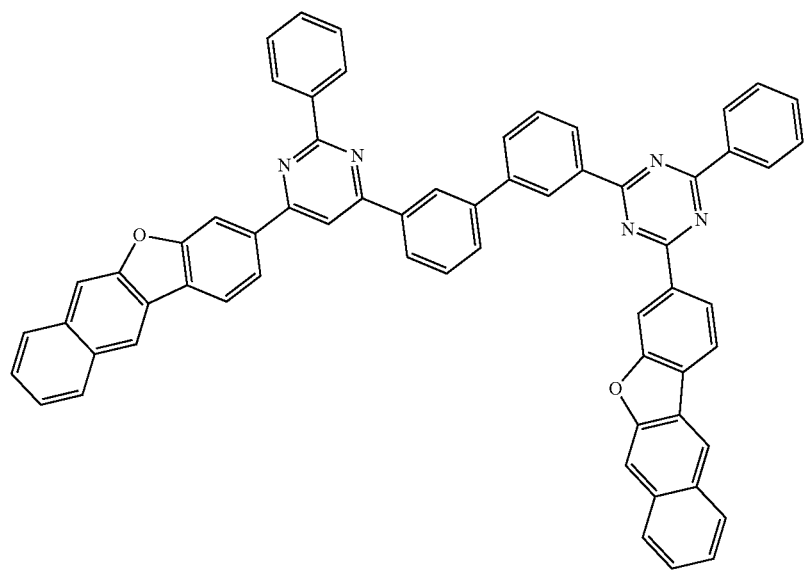
528
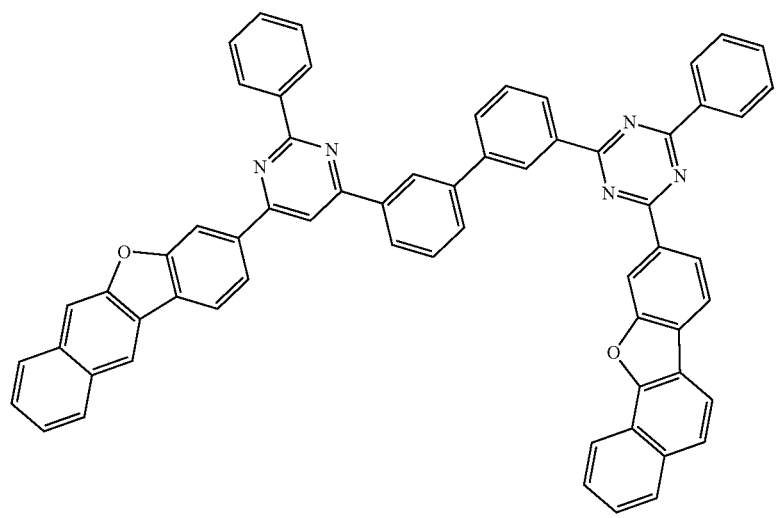
529
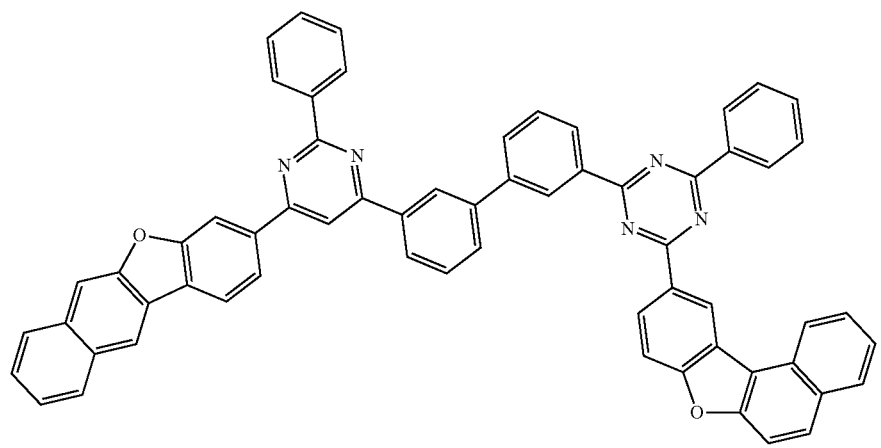
530

531
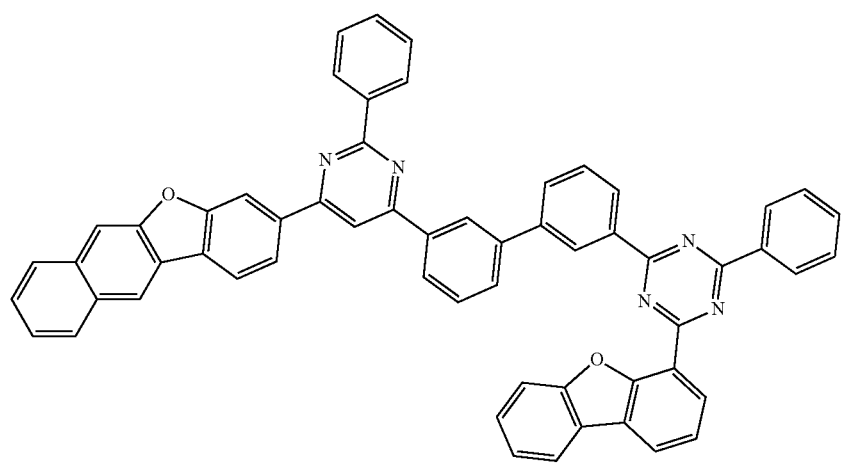
532
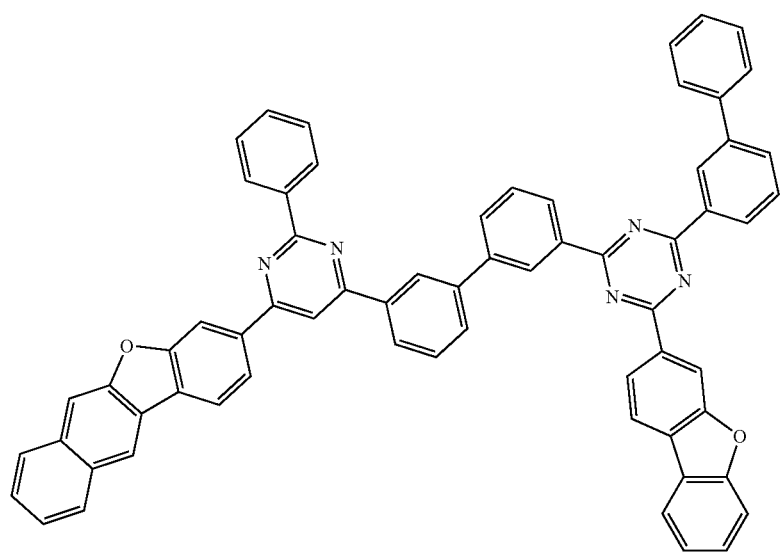
533
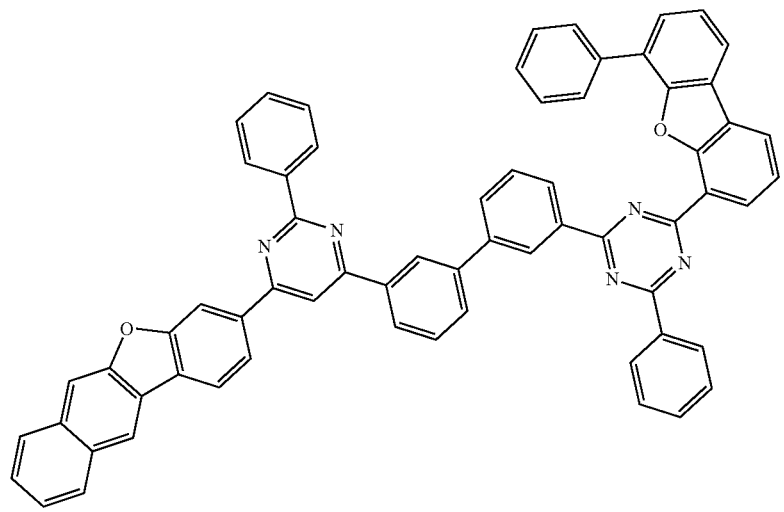

534
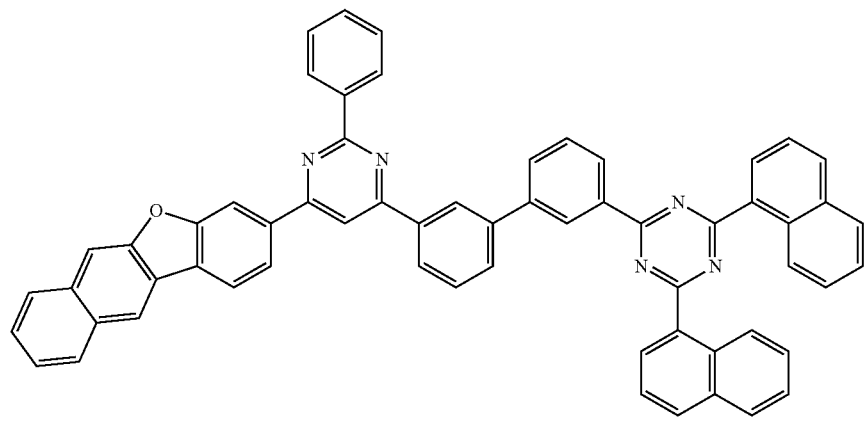
535 536
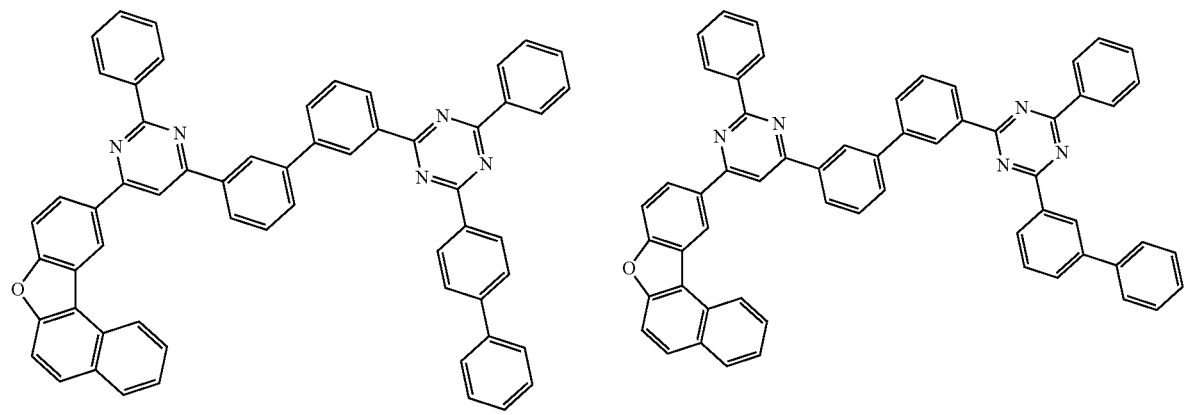
537
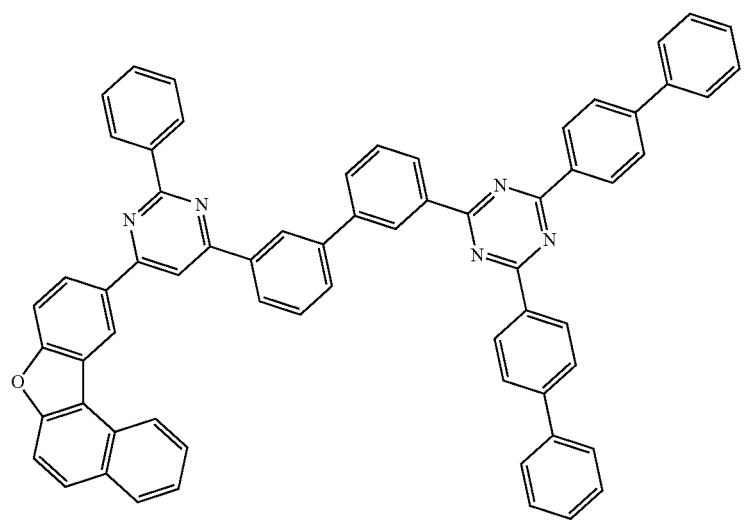

538
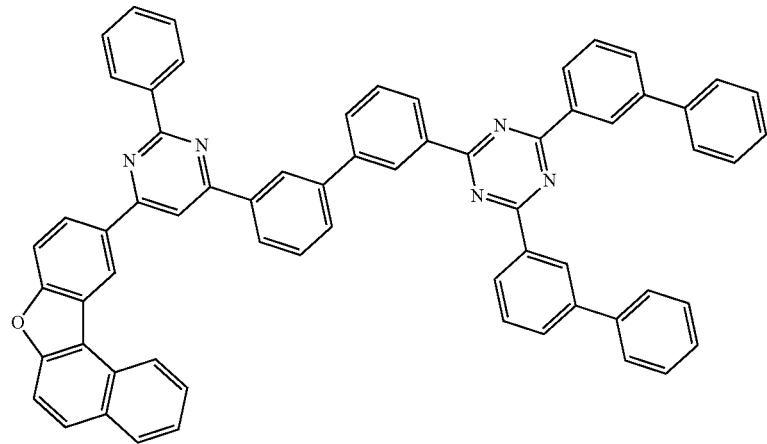
539 540
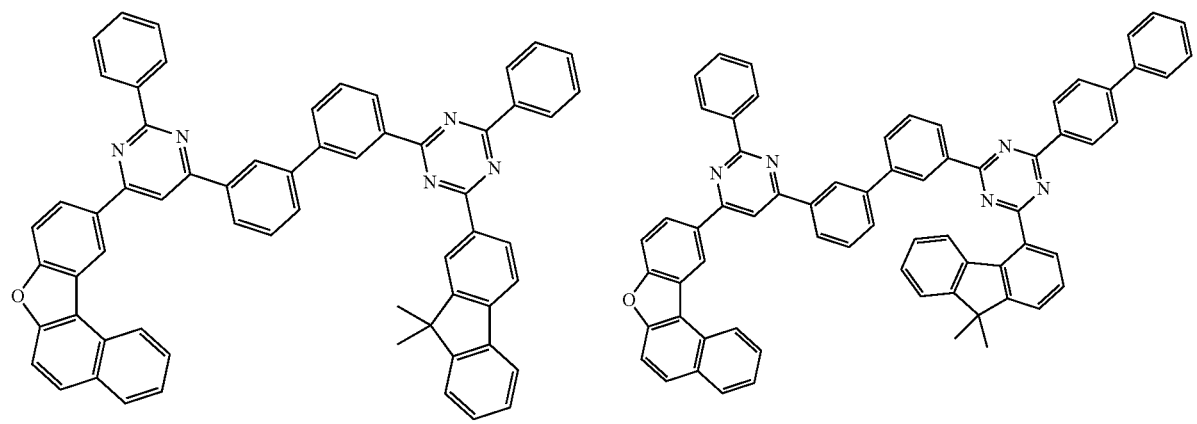
541 542
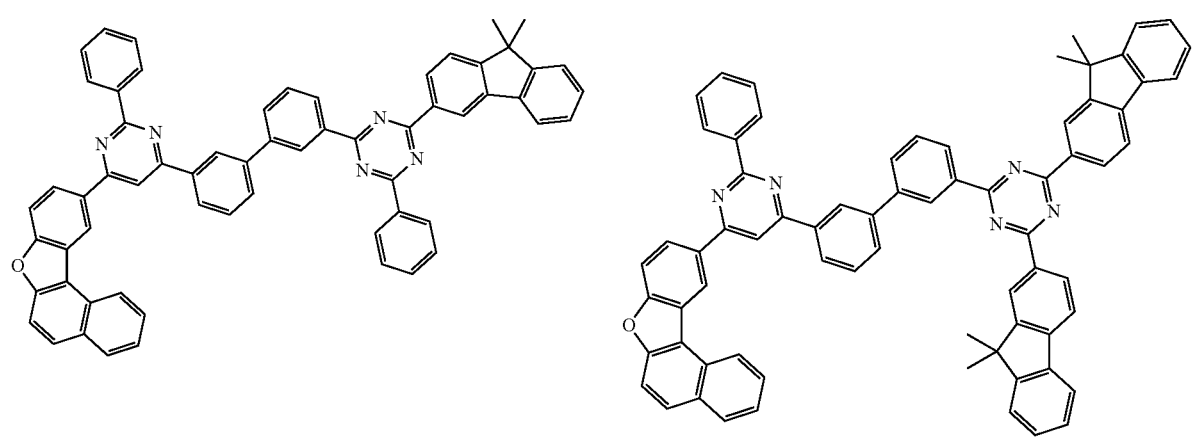

-continued
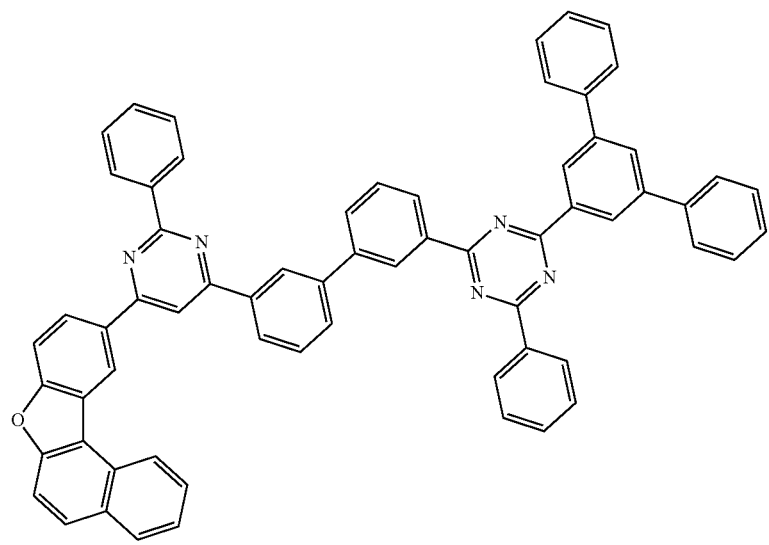
543
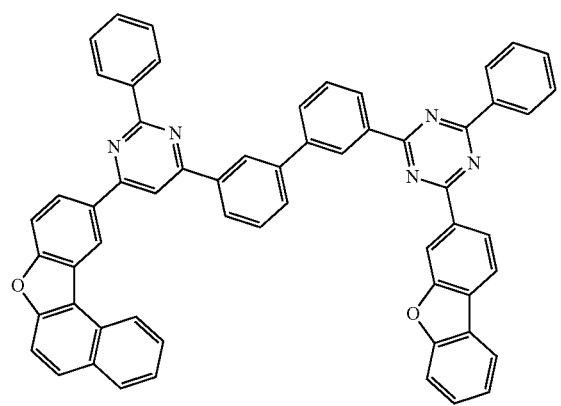
544
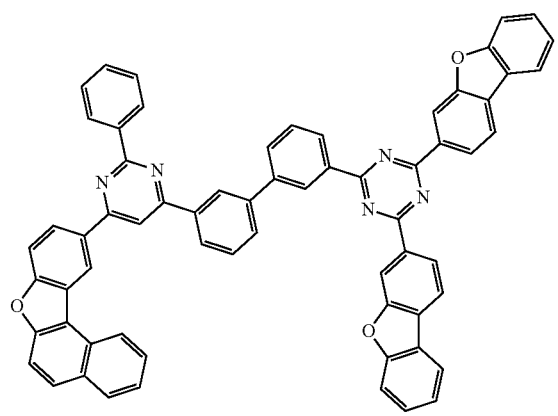
545
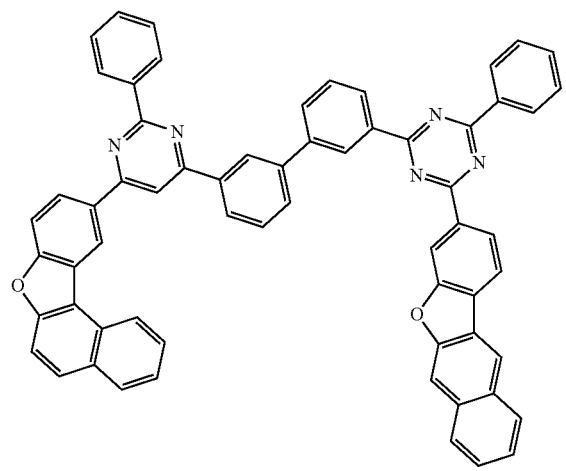
546
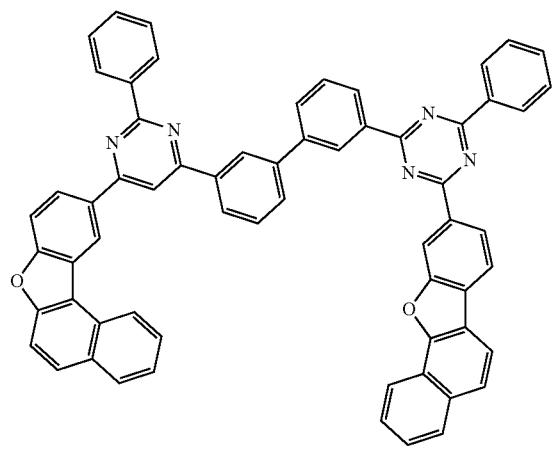
547

548
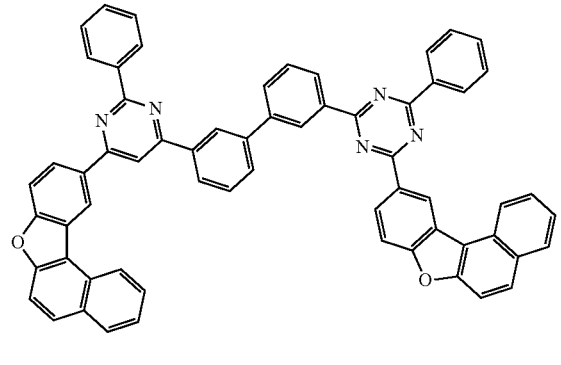
549
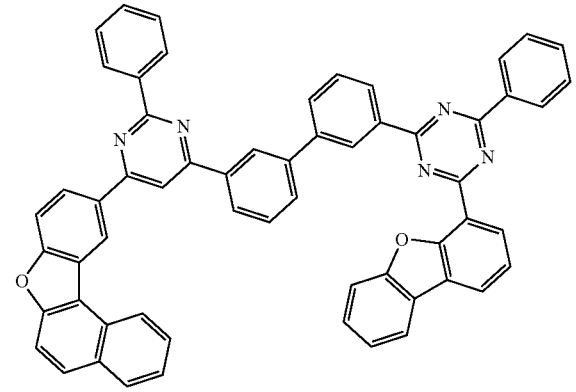
550
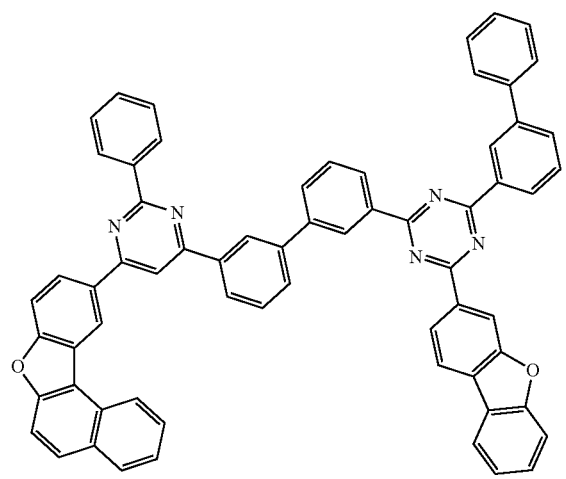
551
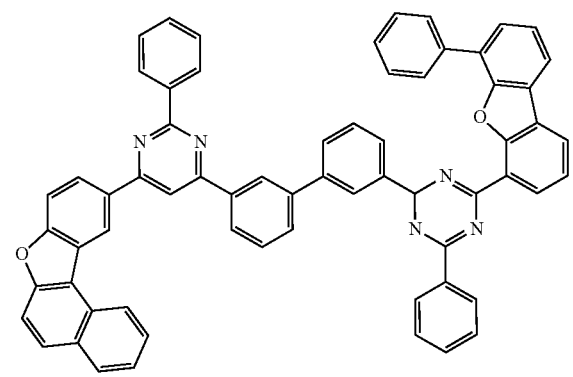
552
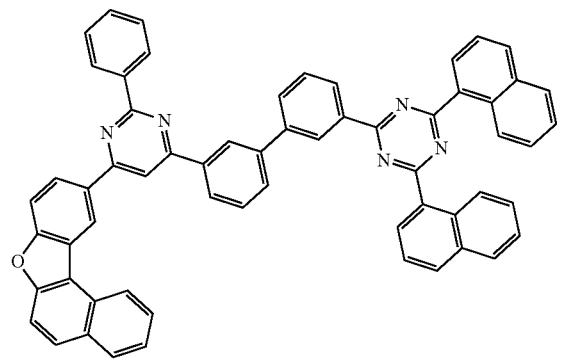
553
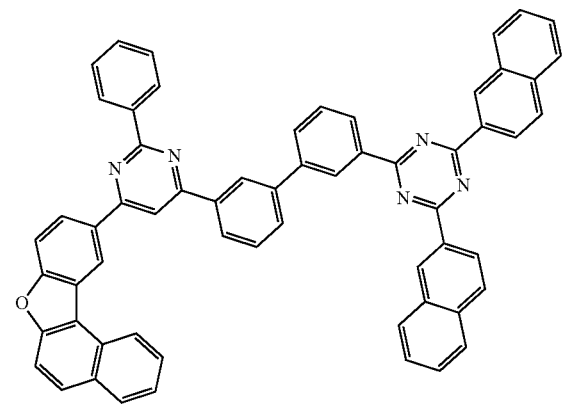

-continued
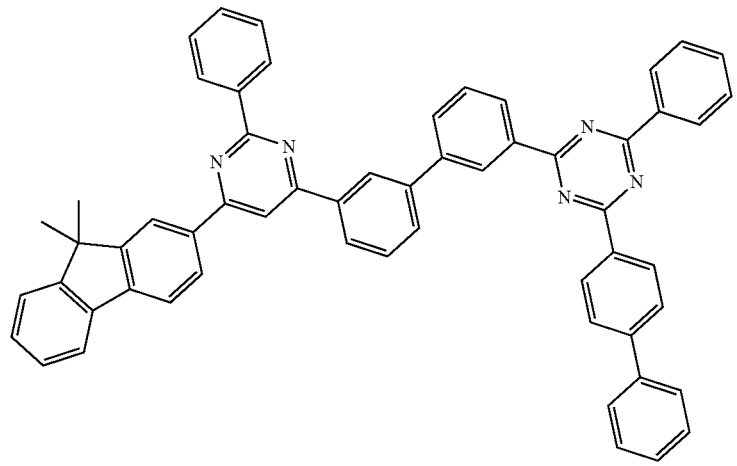
554
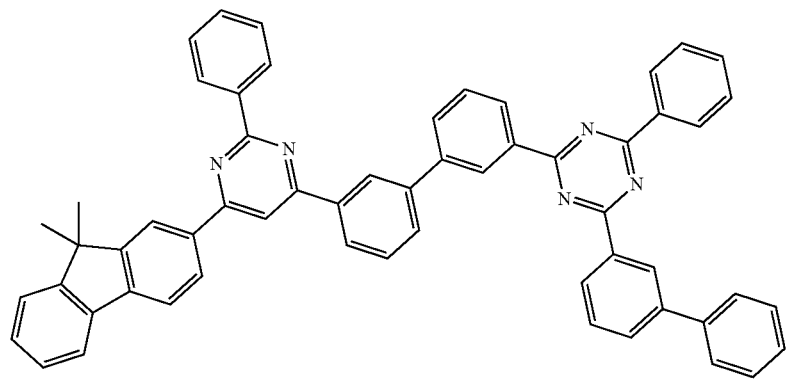
555
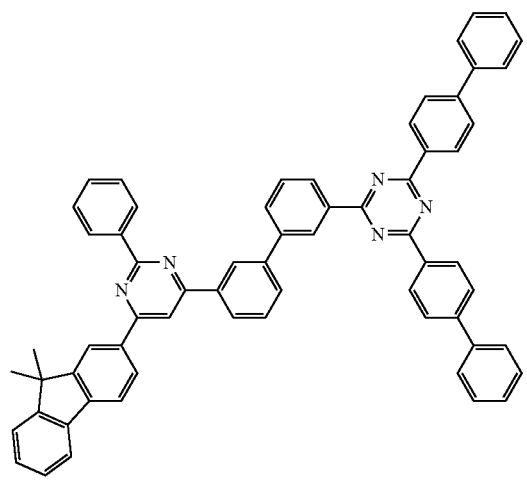
556
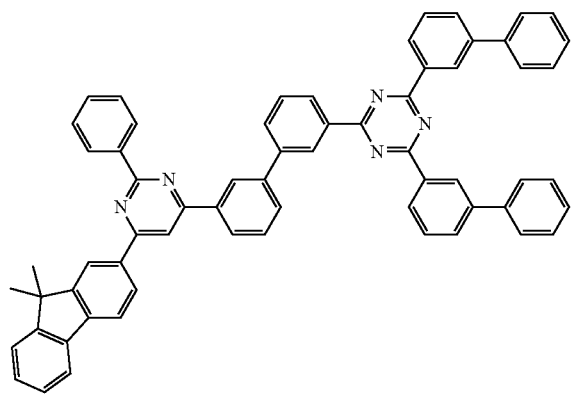
557

558
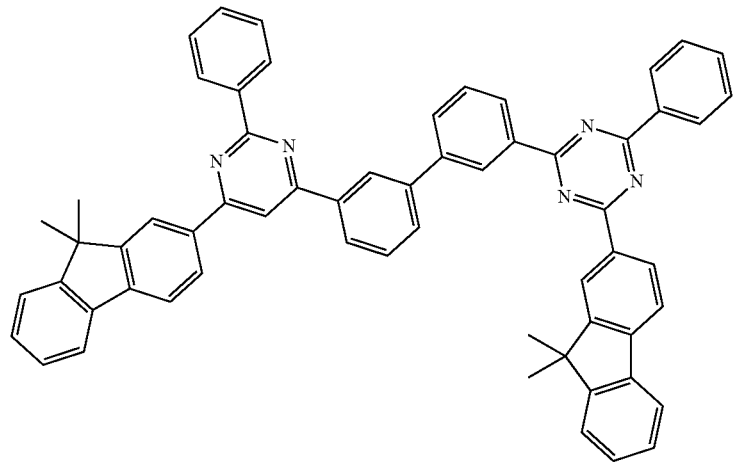
559
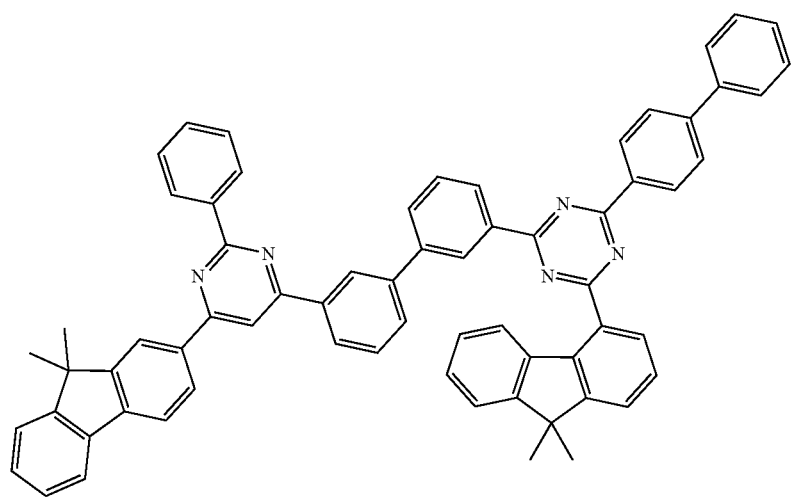
560
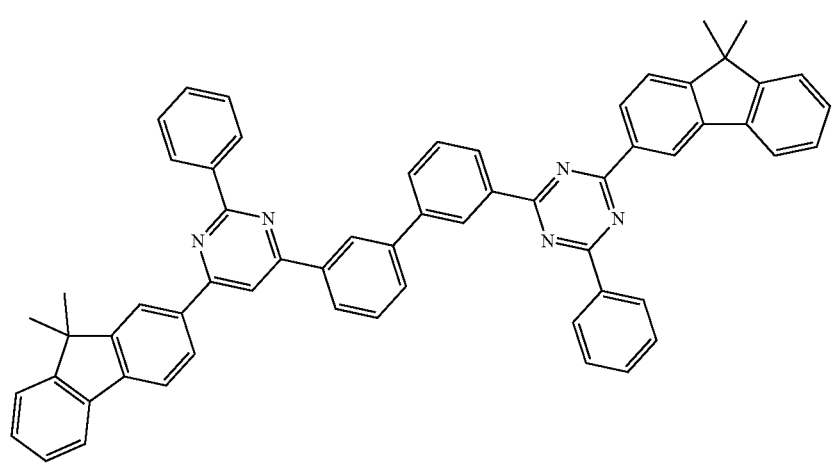

-continued
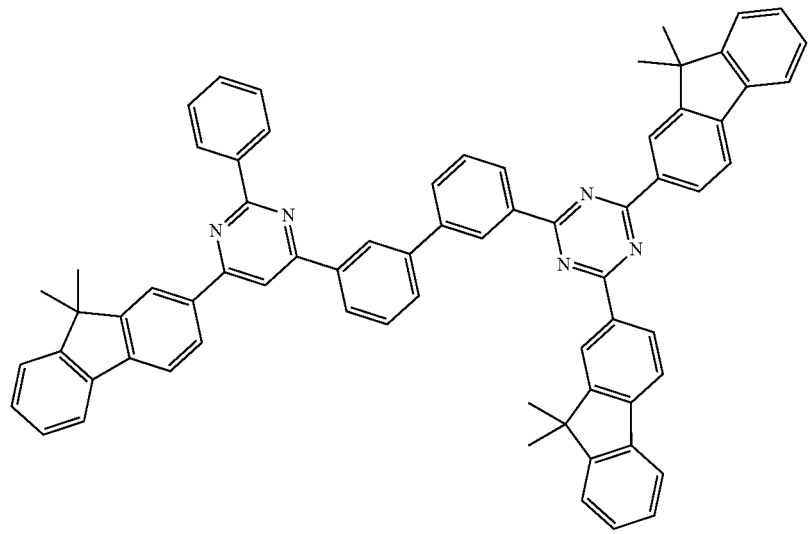
561
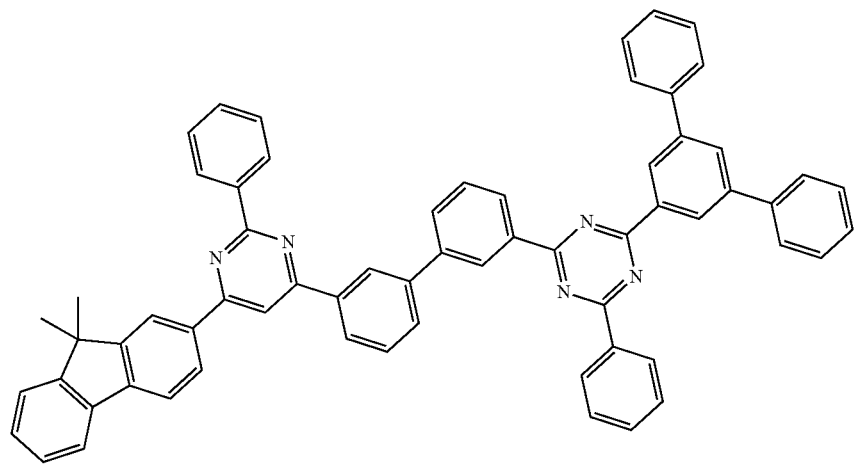
562
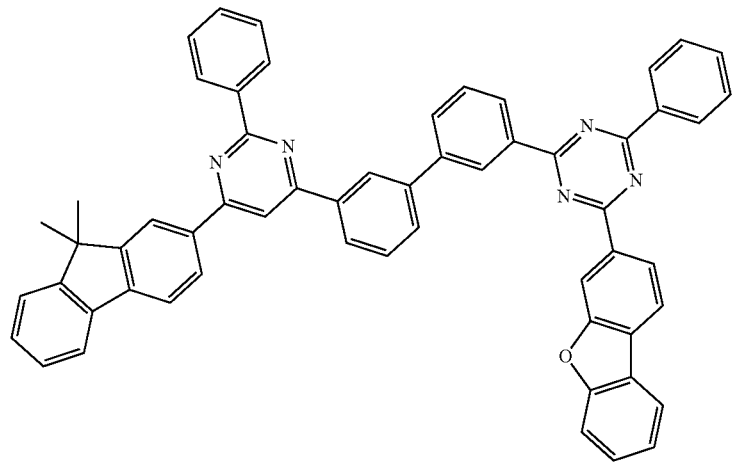
563

564
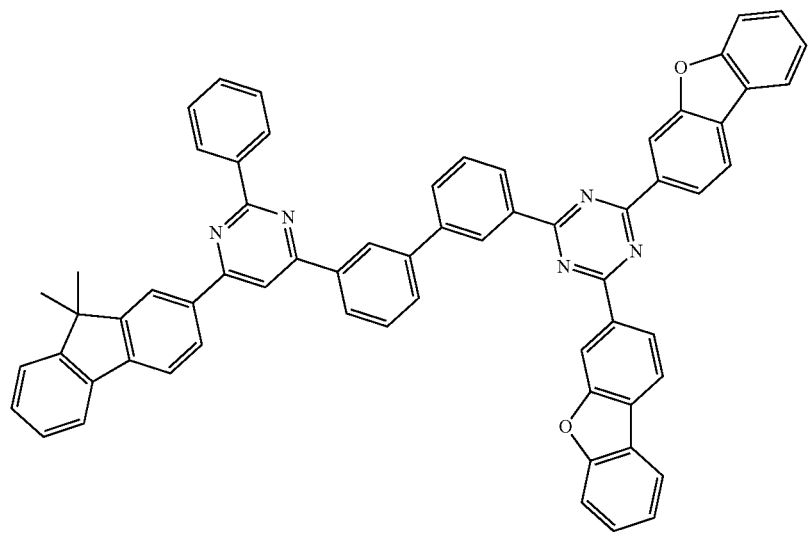
565
566
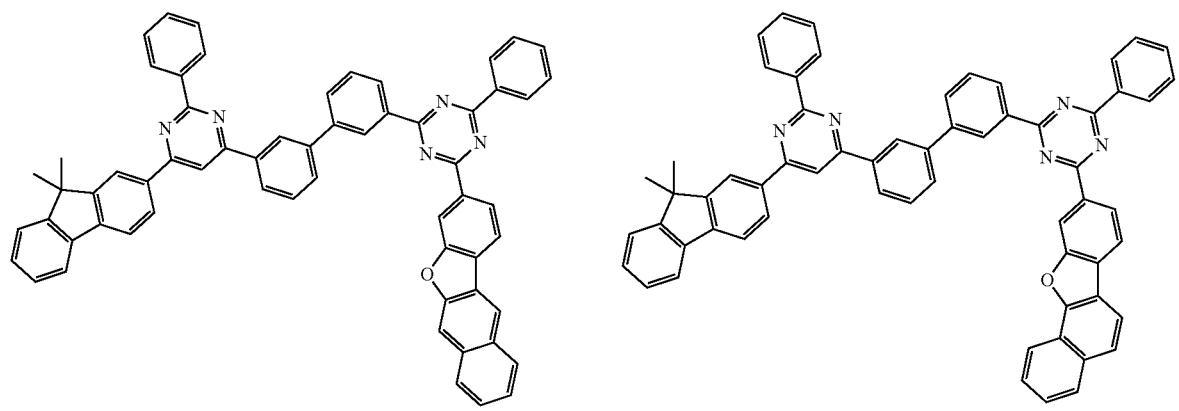
567
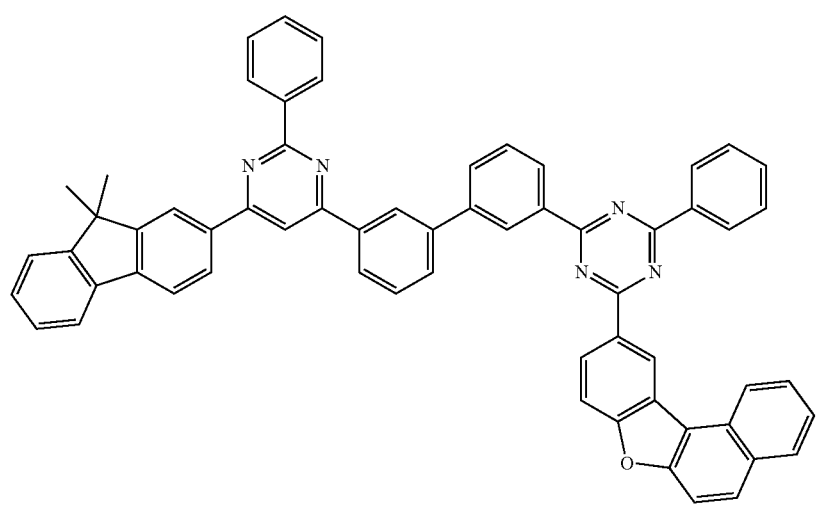

-continued
568
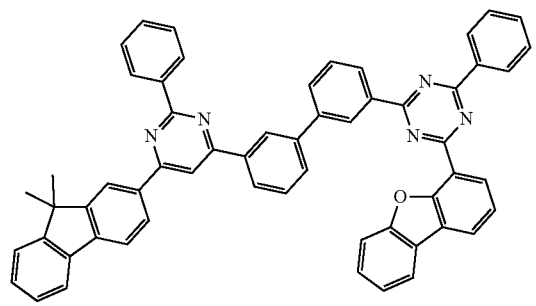
569
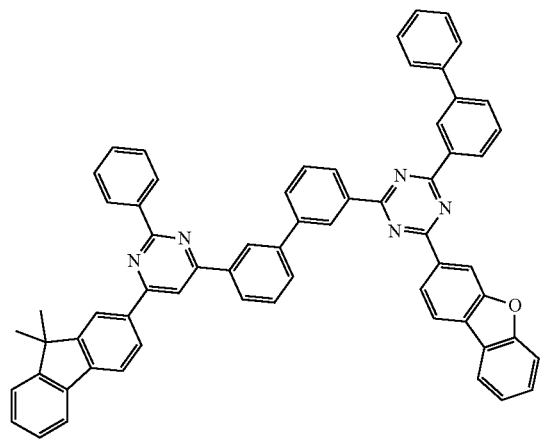
570
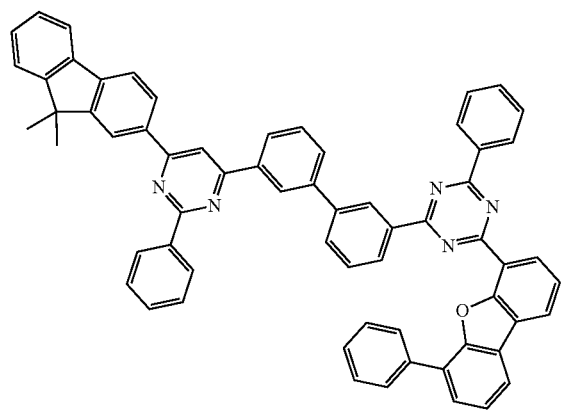
571
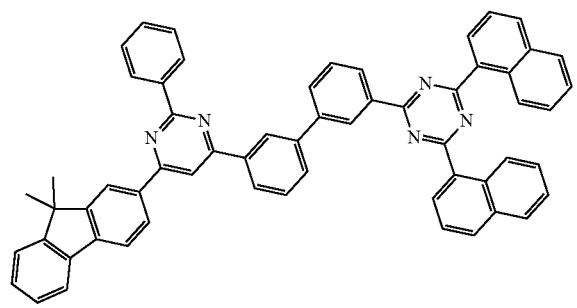
572
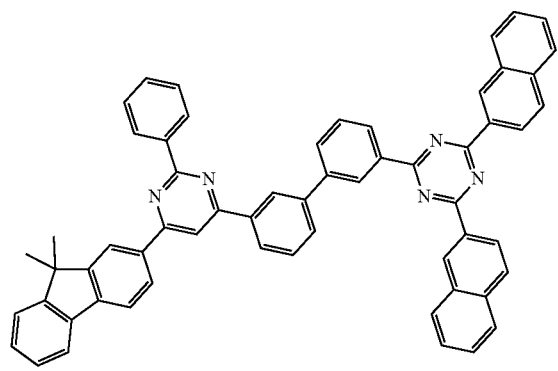
573
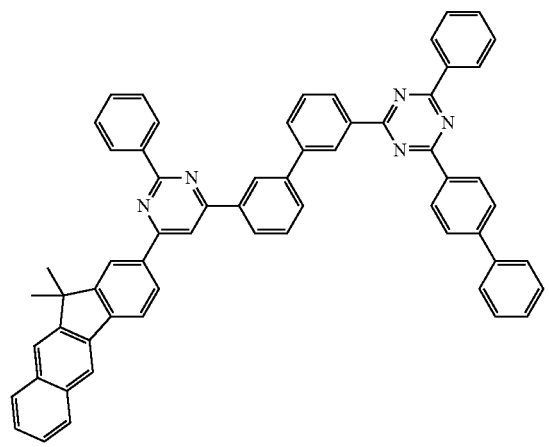

574
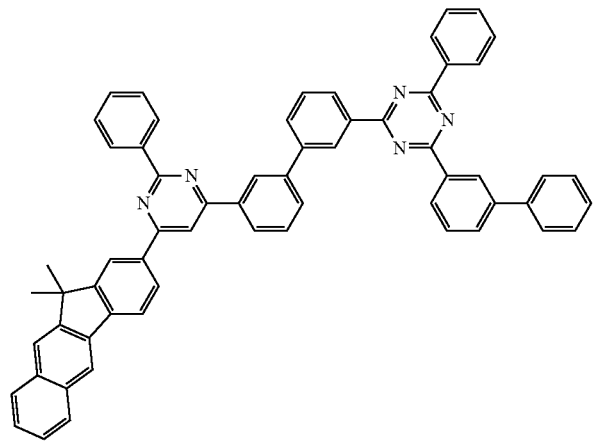
575
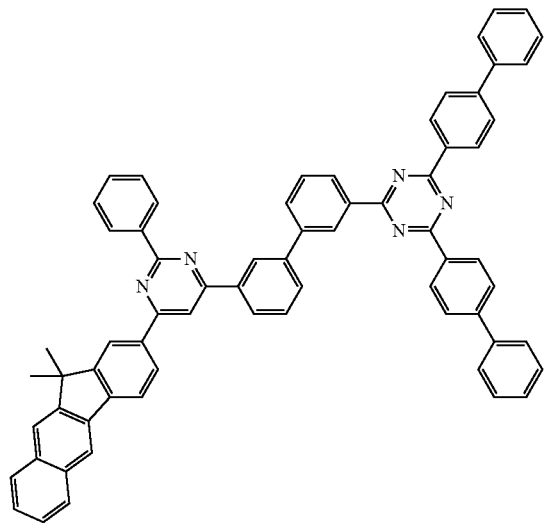
576
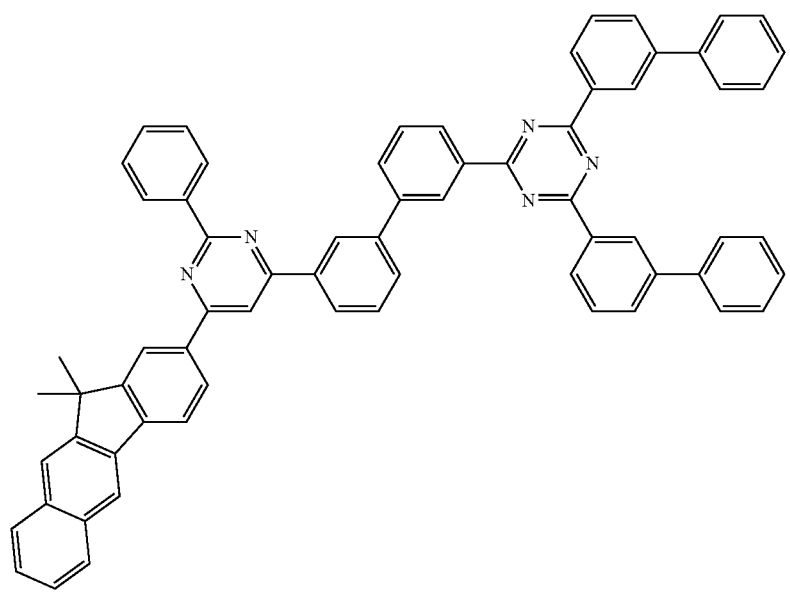

577
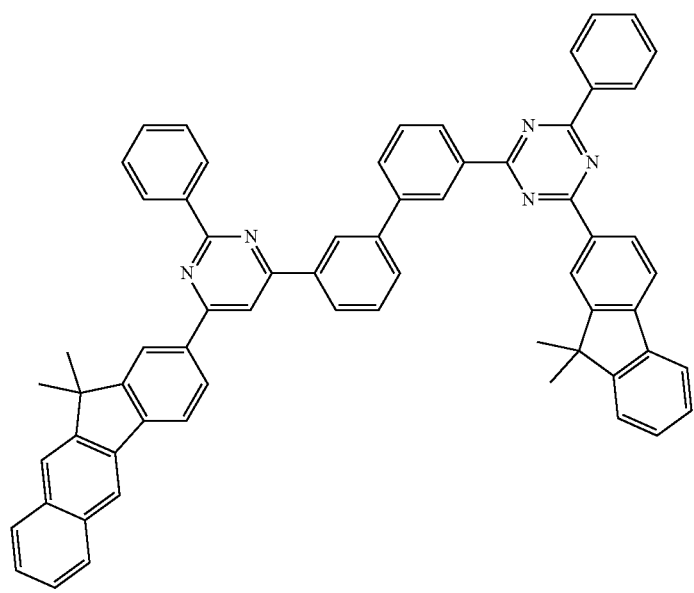
578
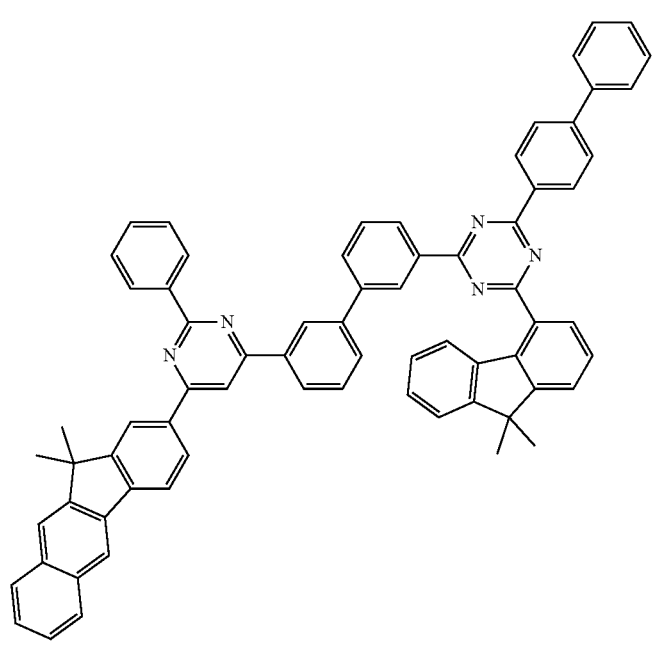

579
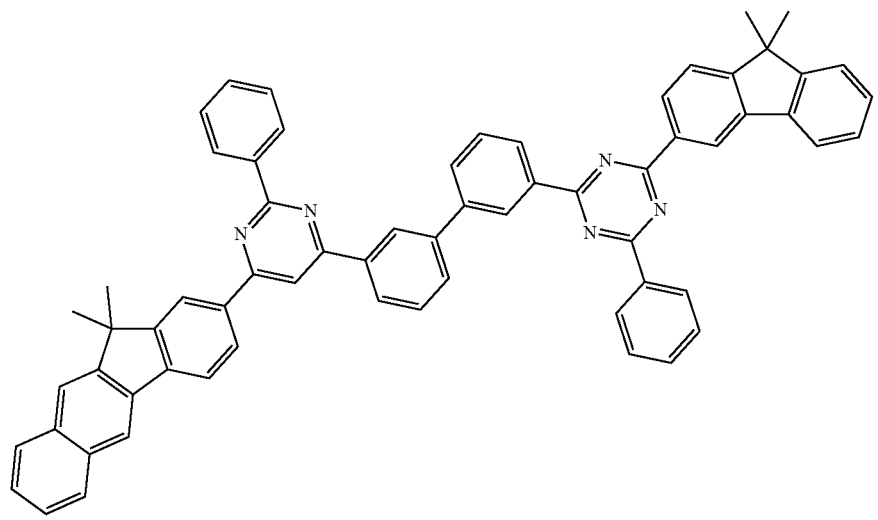
580
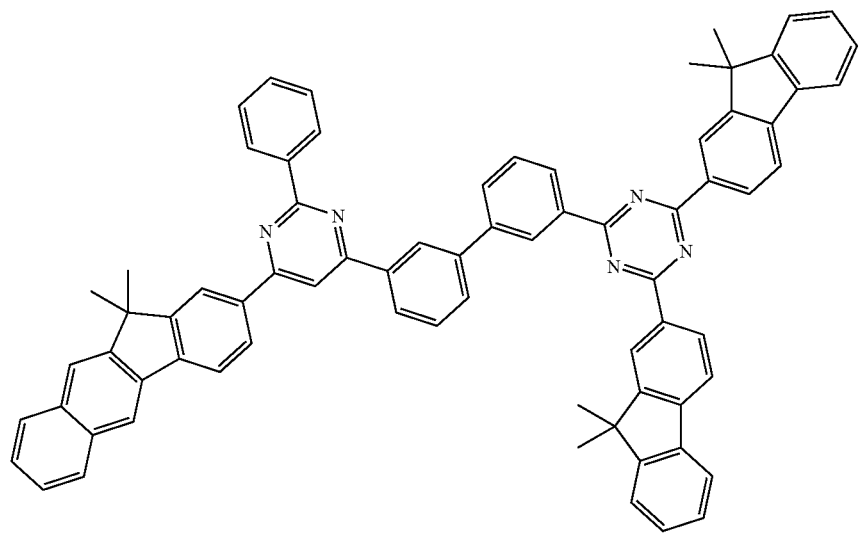

581
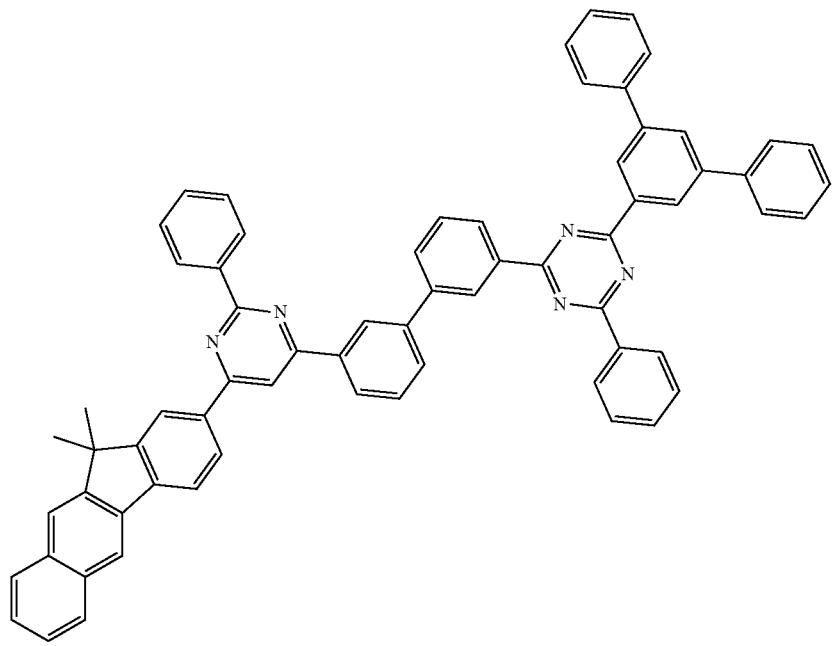
582
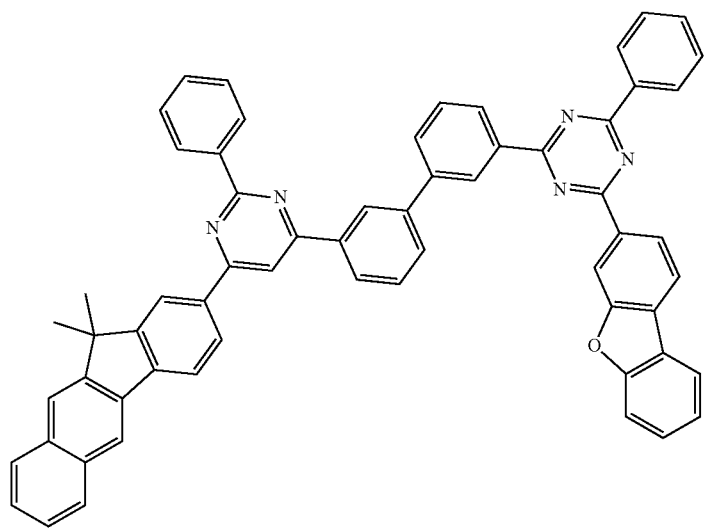

583
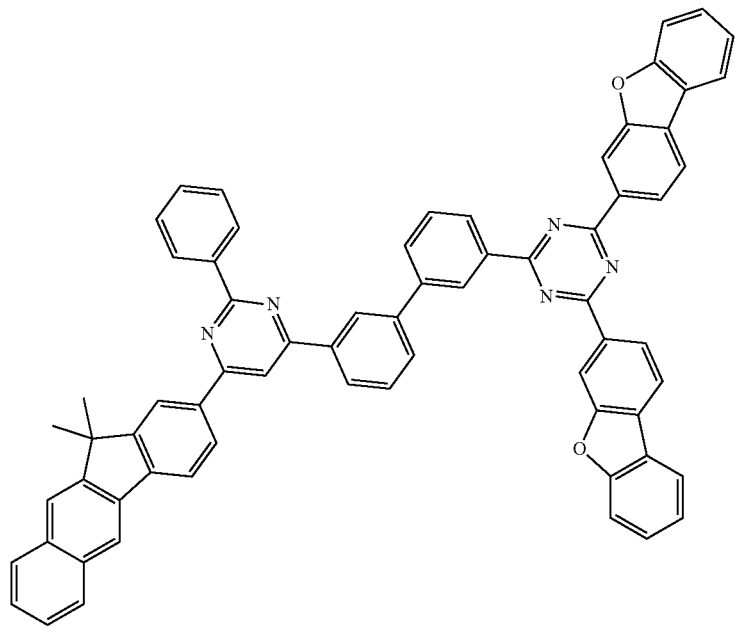
584
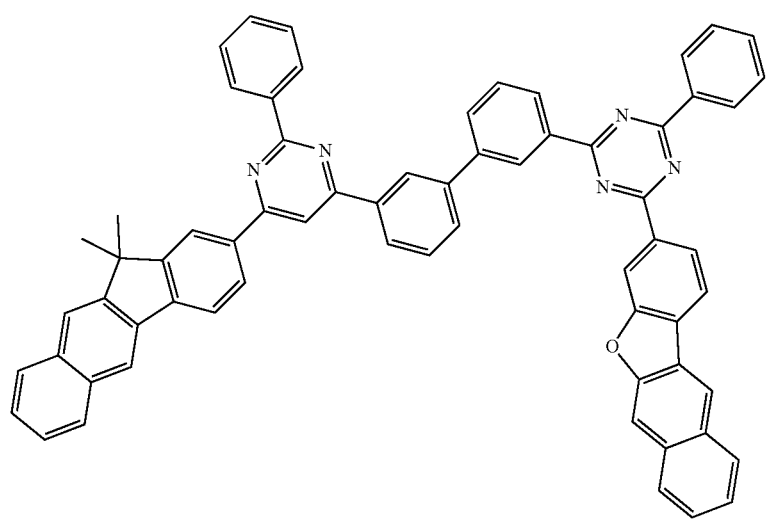

585
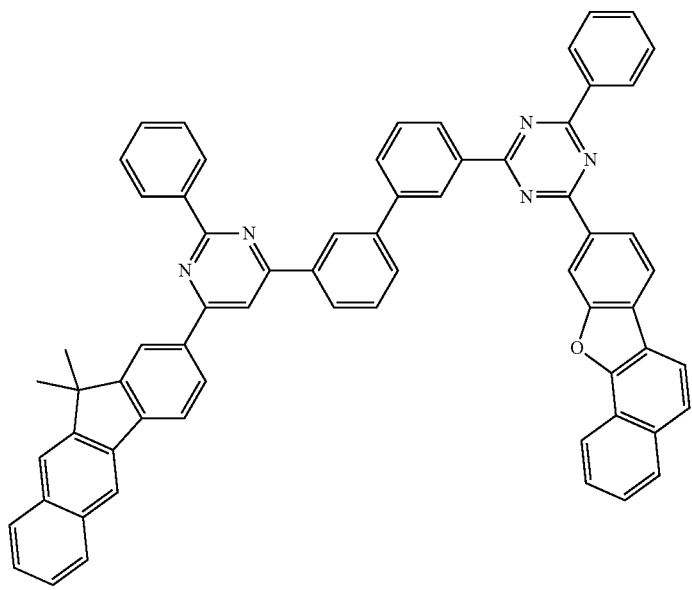
586
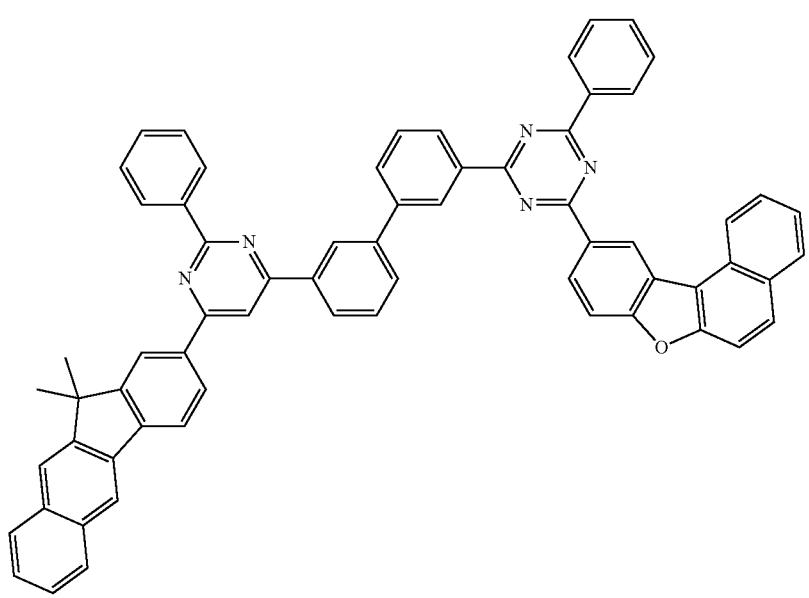

587
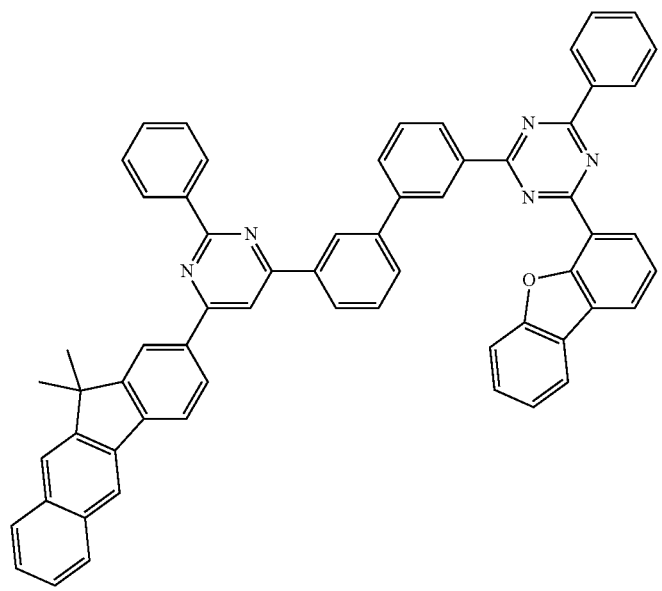
588
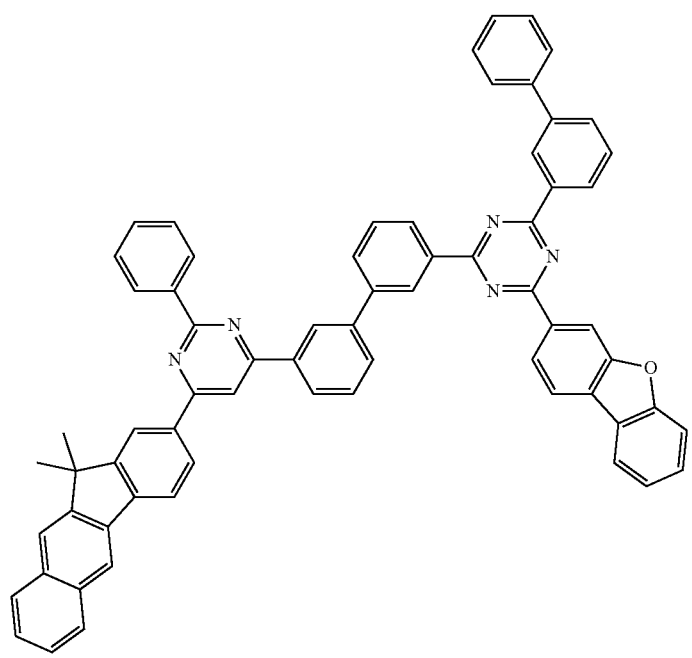

589
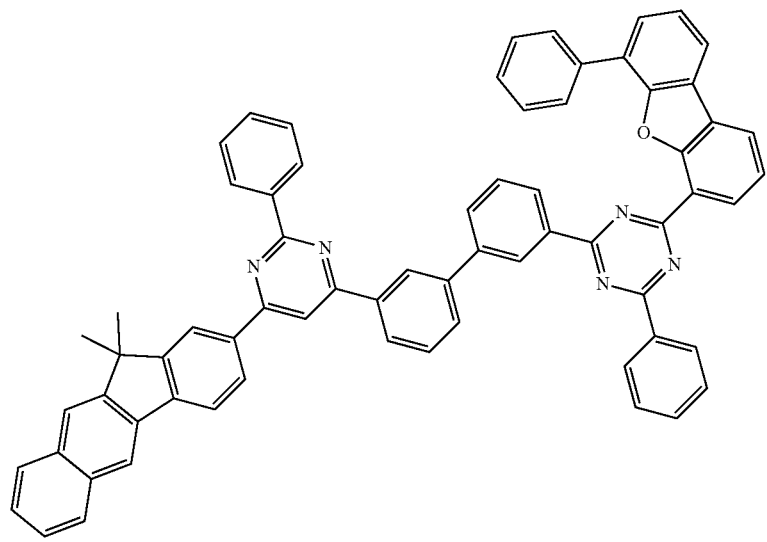
590
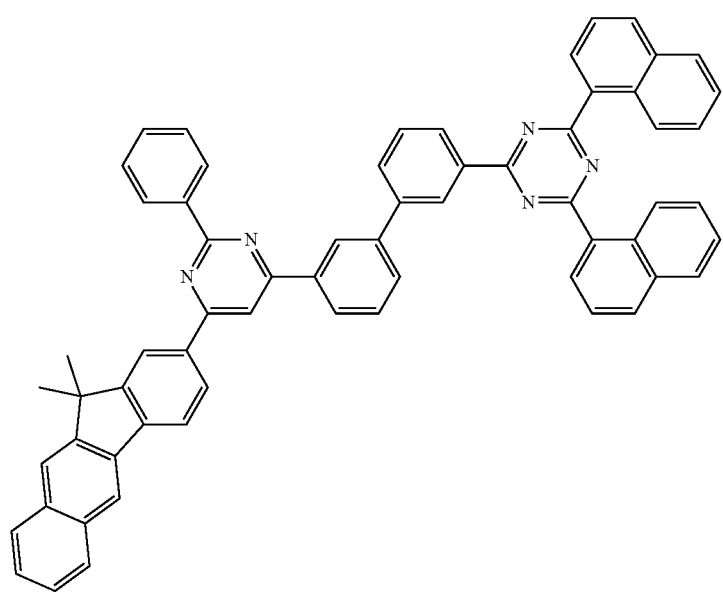
591
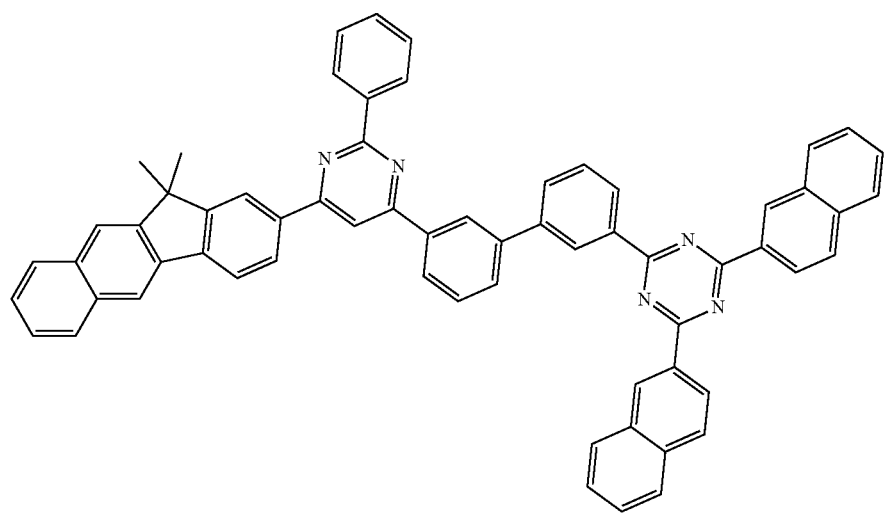

592
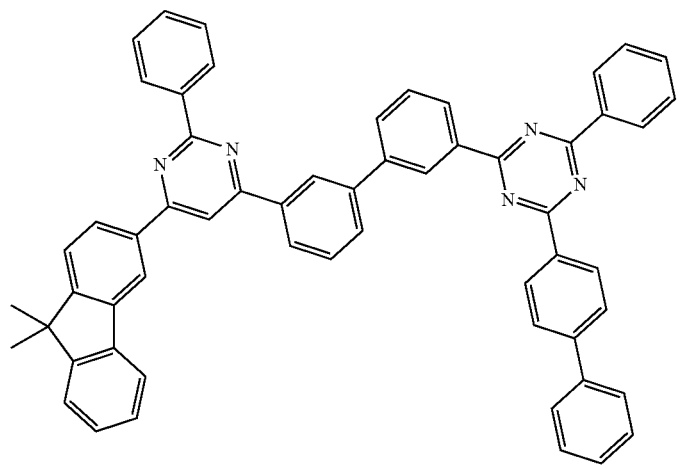
593
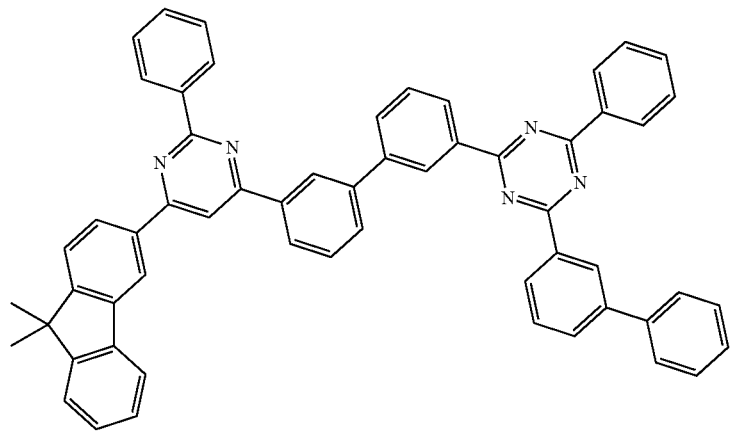
594
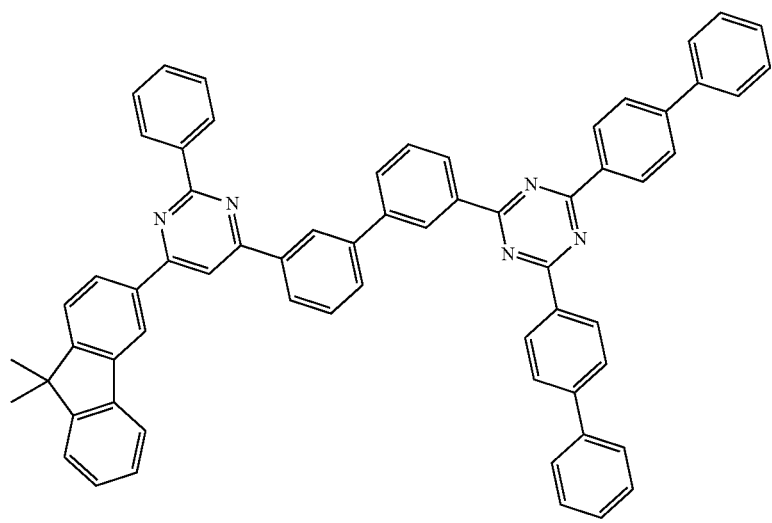

595
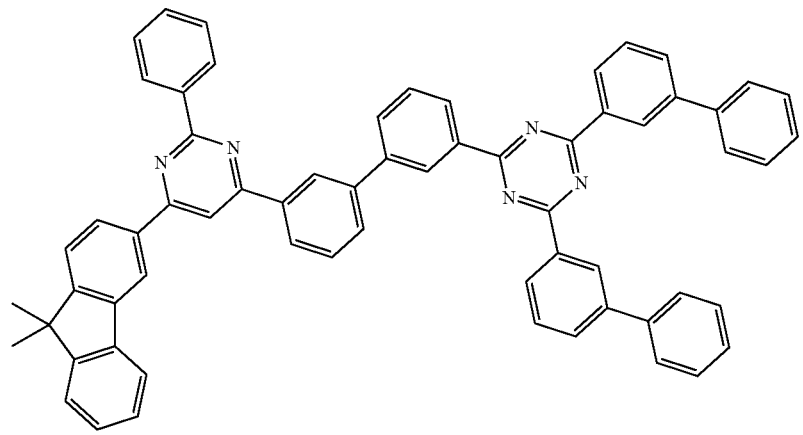
596
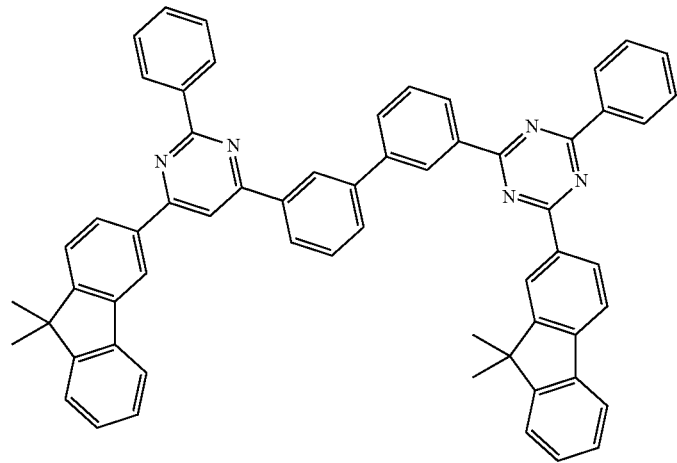
597
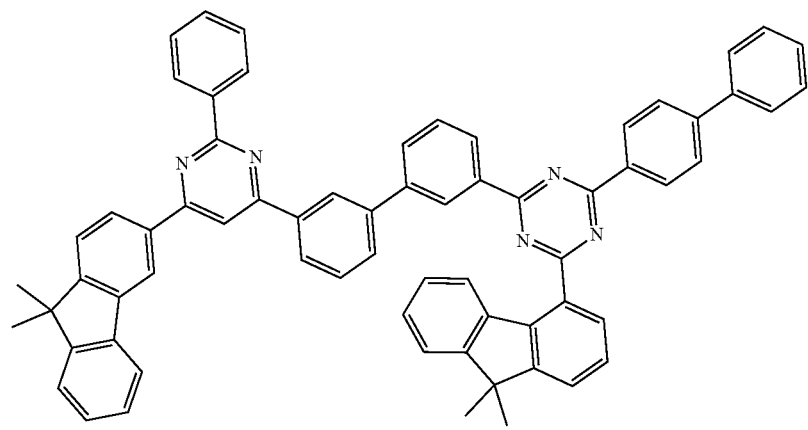

598
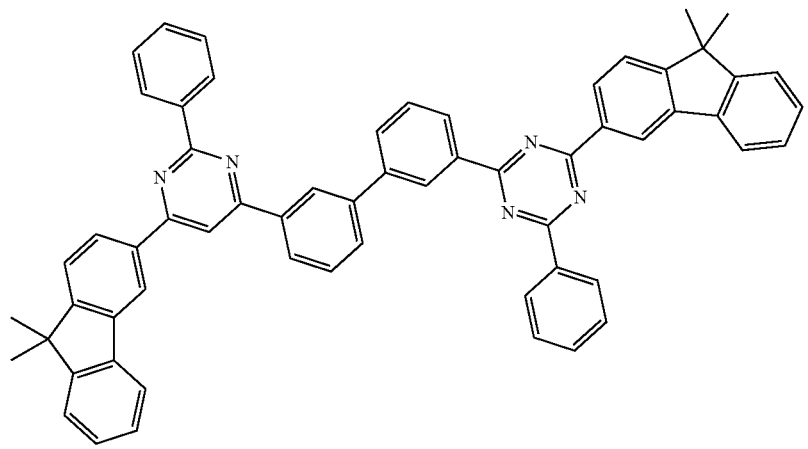
599
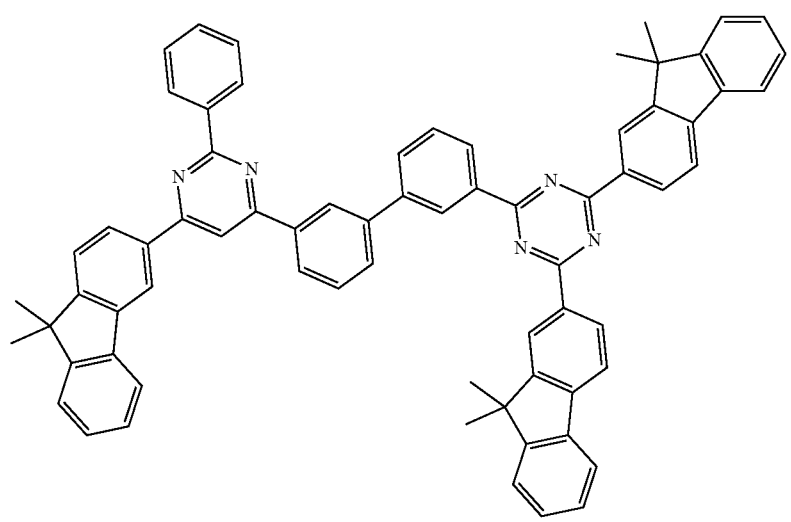
600
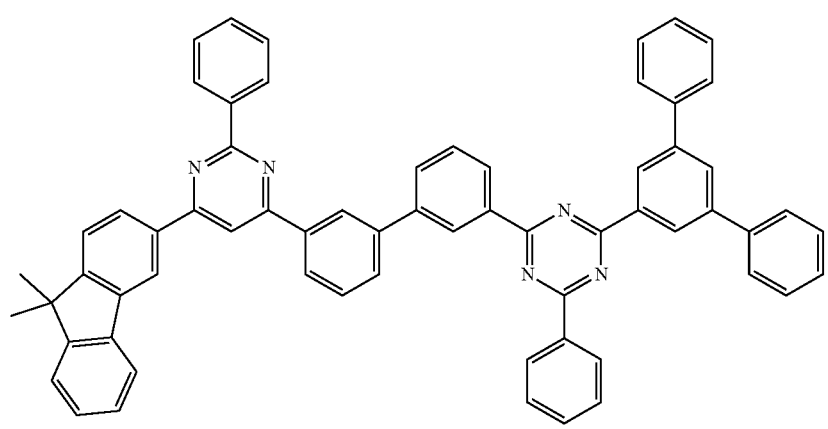

-continued
601
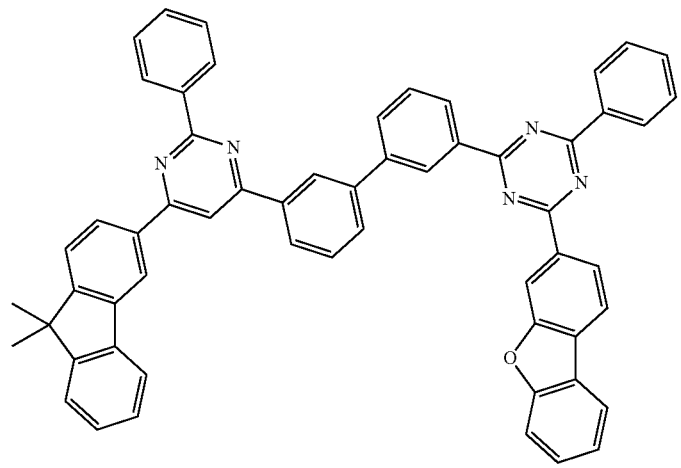
602
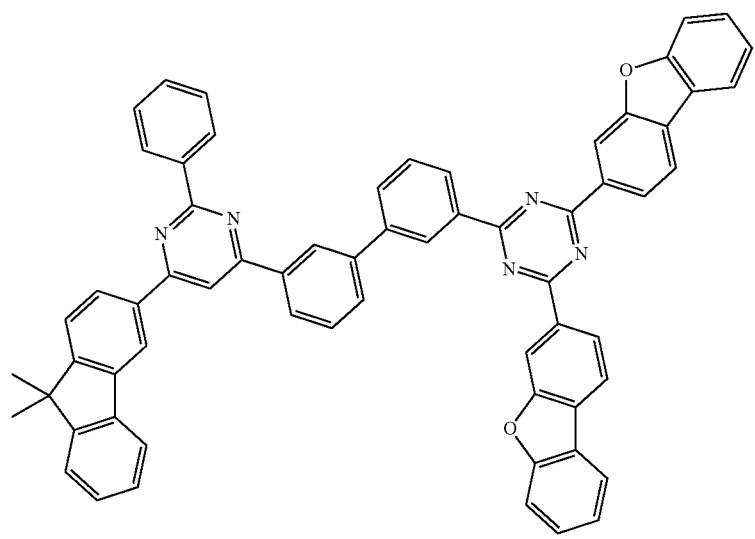
603
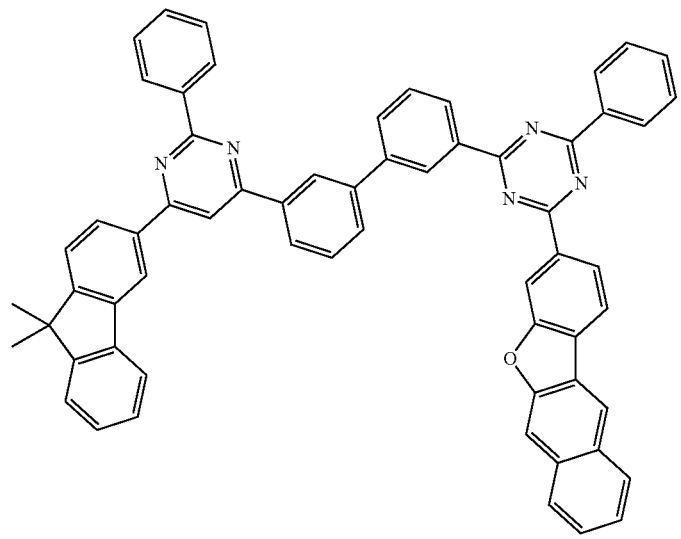

604
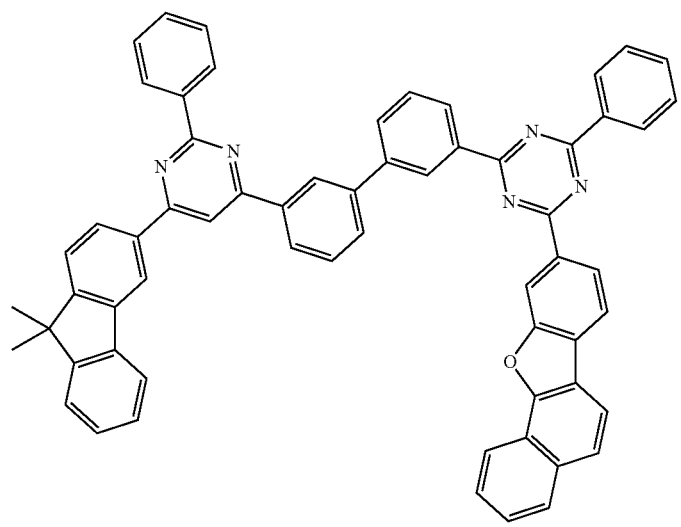
605
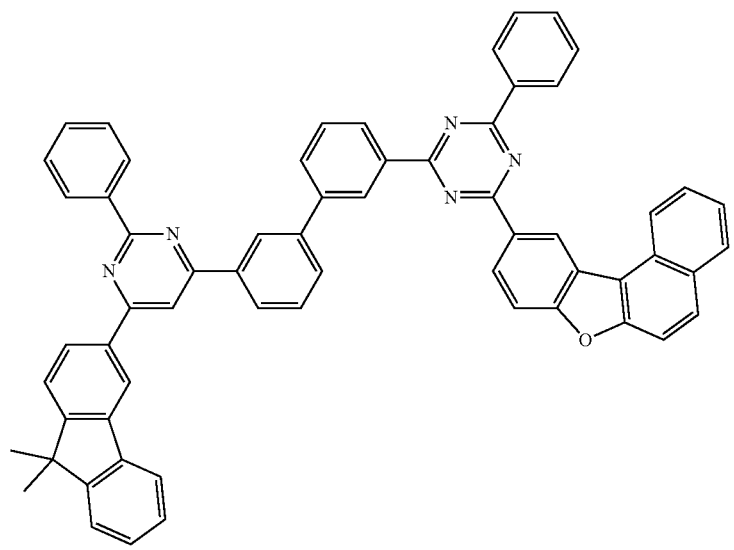
606
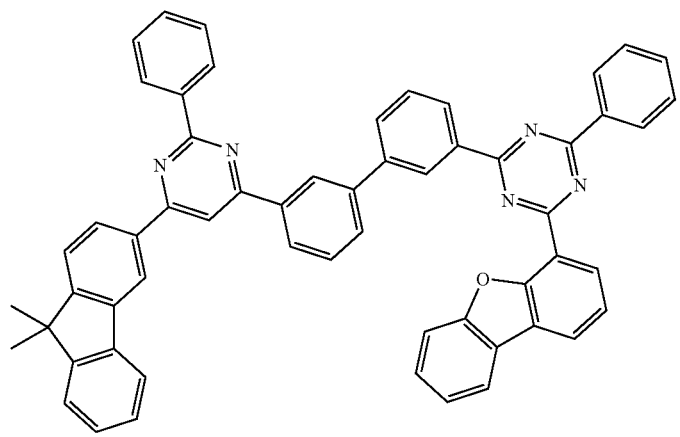

607
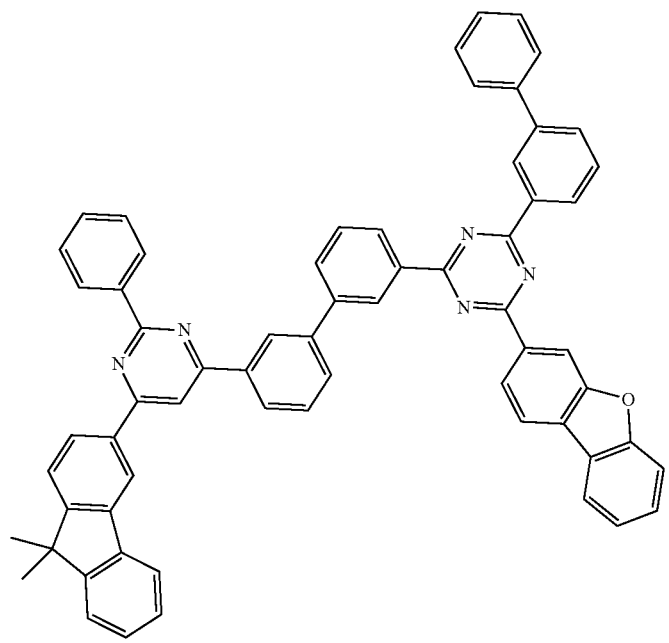
608
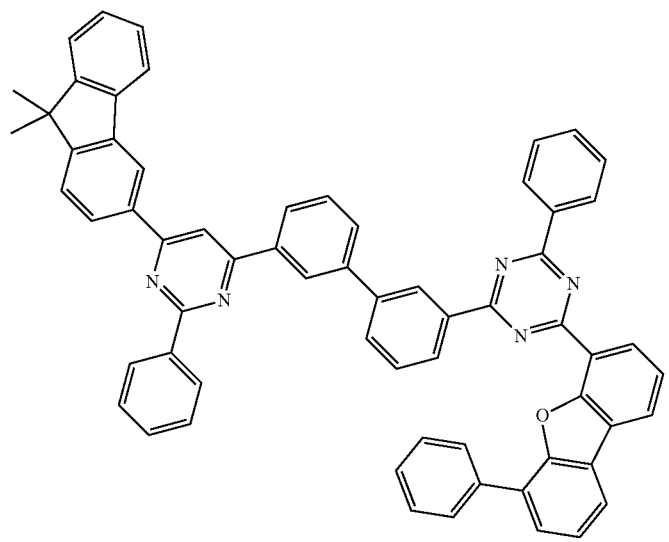
609
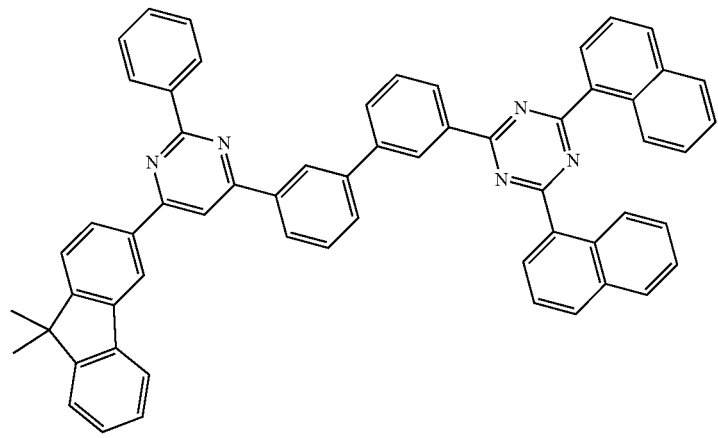

610
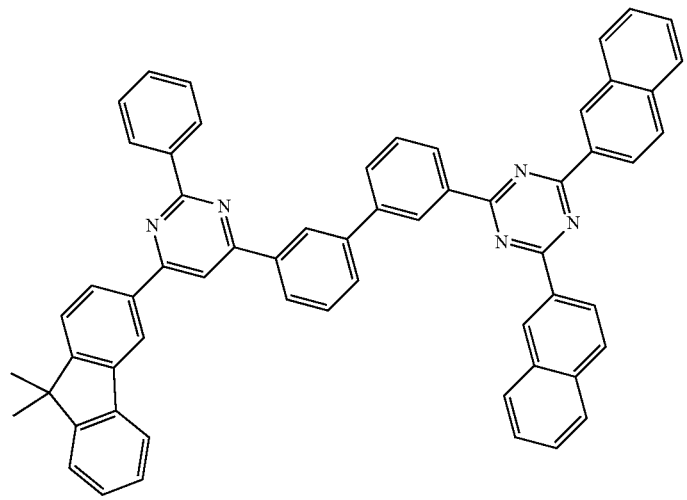
611
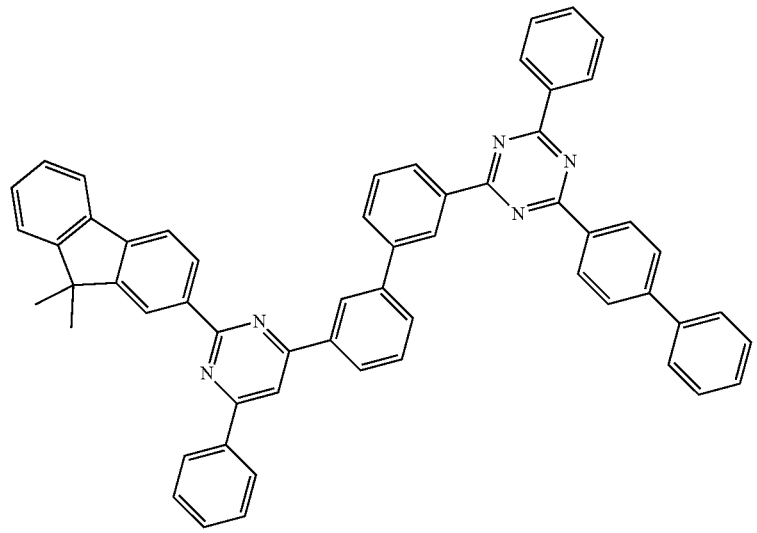
612
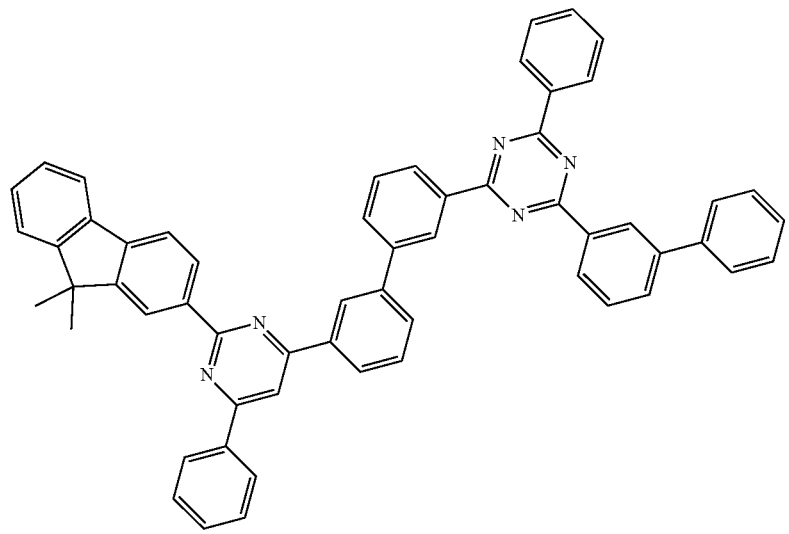

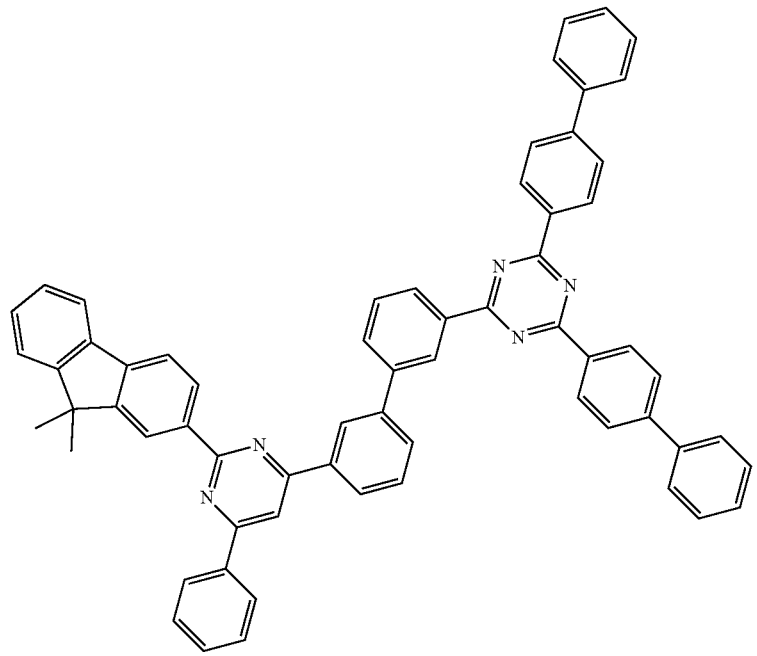
613
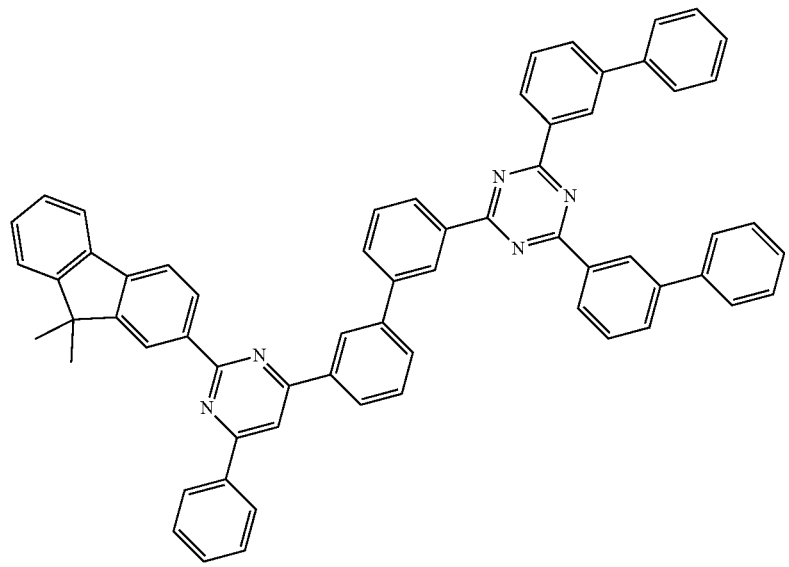
614

-continued
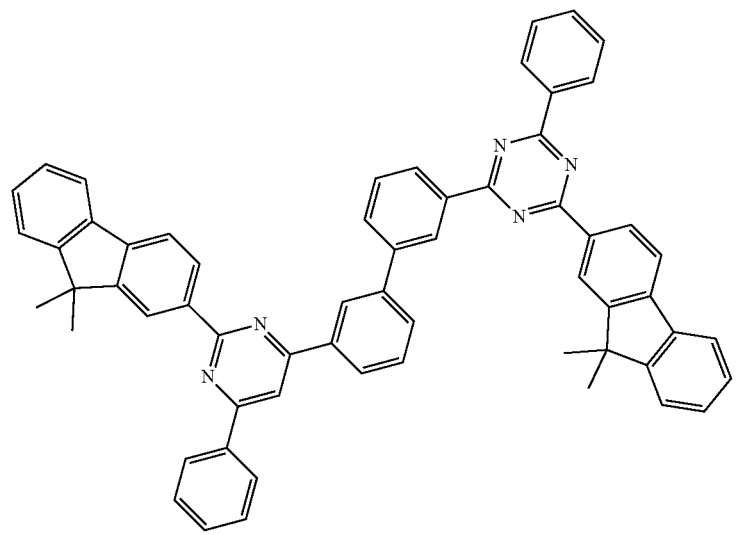
615
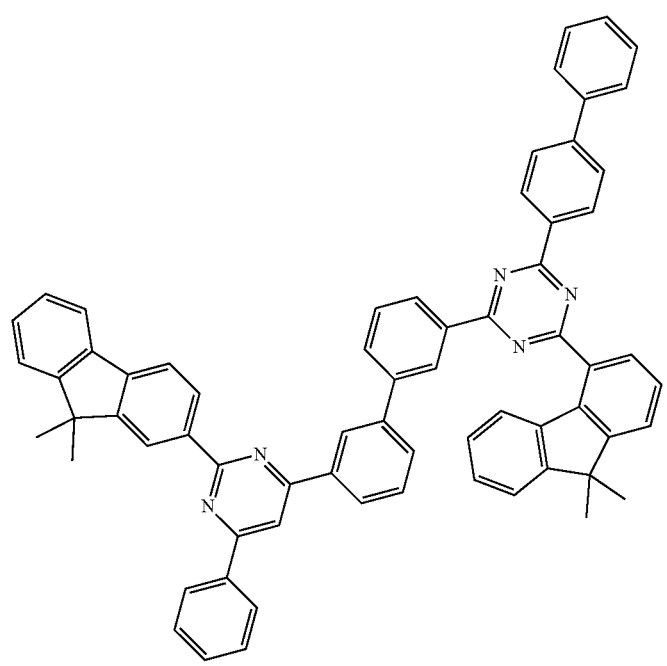
616

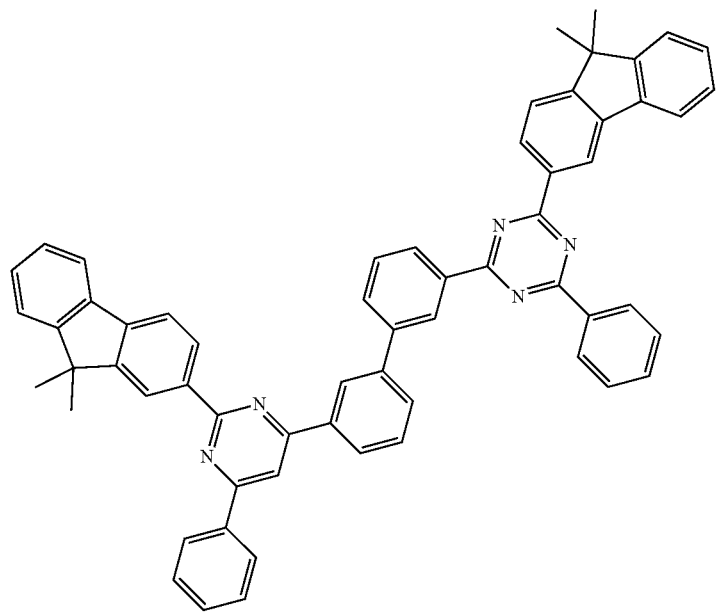
617
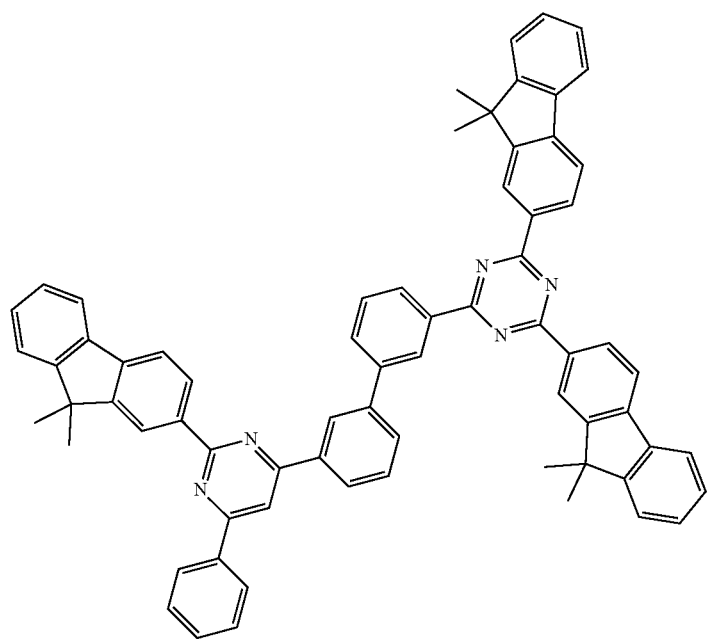
618

619
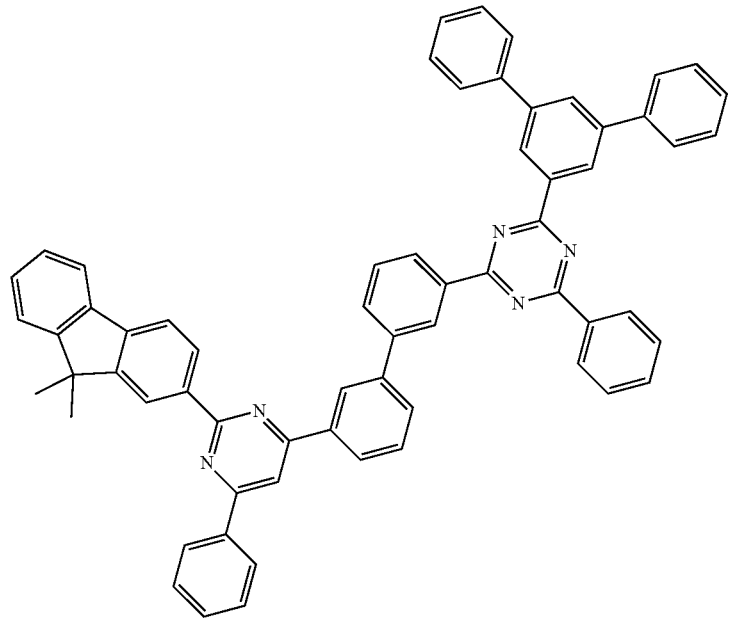
620
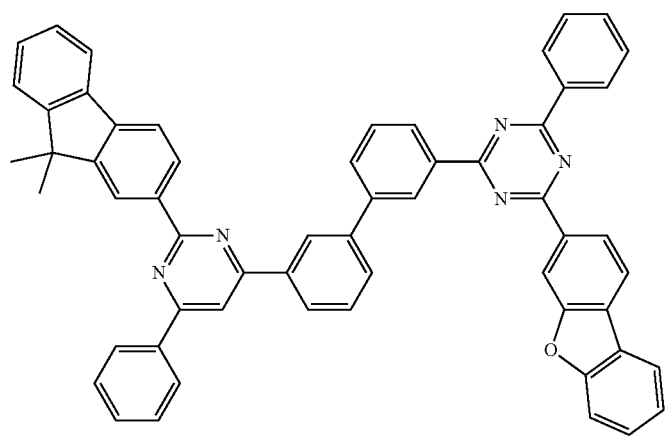
621
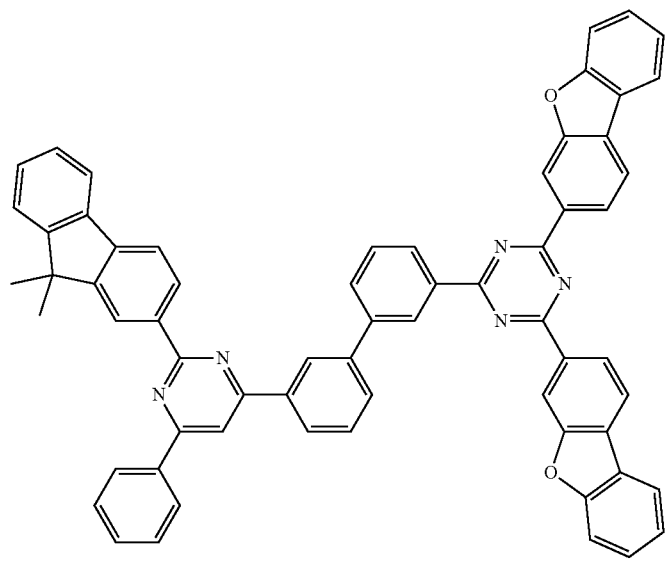

-continued
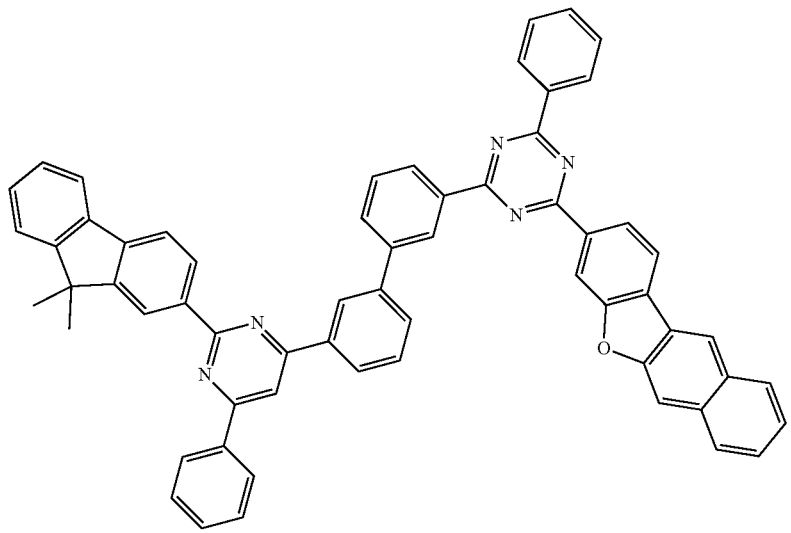
622
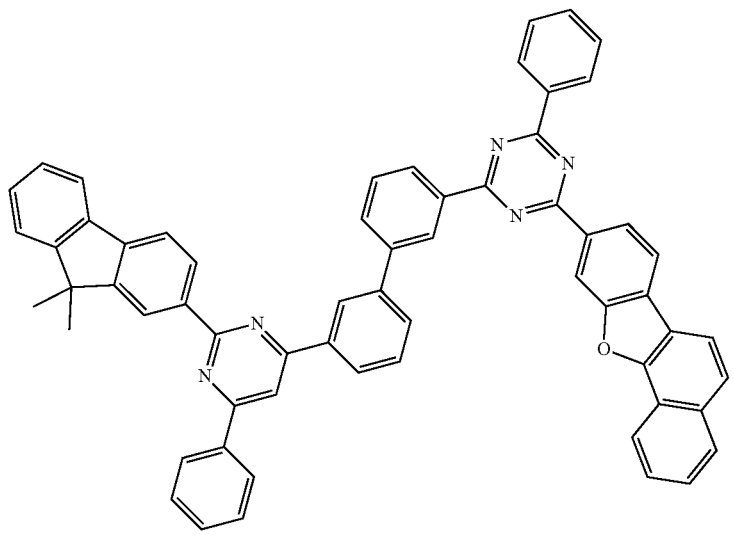
623
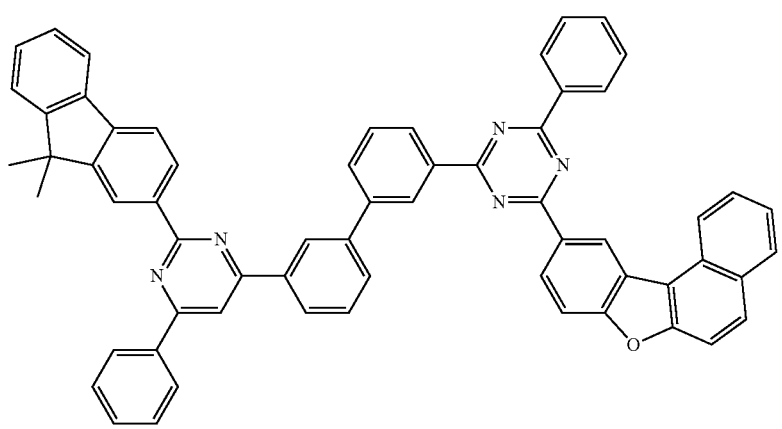
624

625
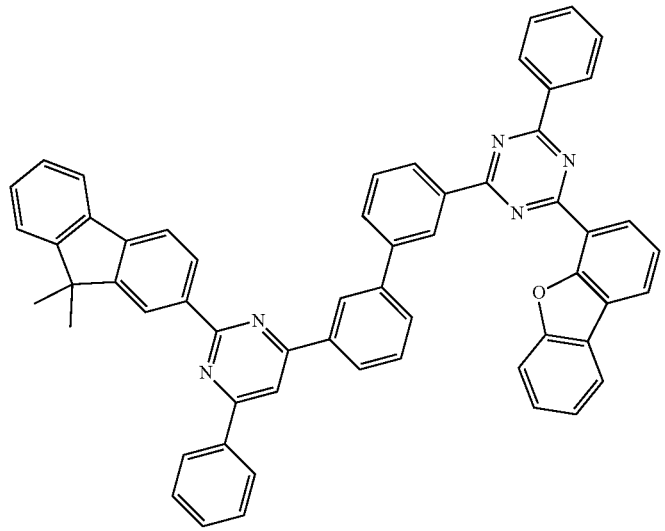
626
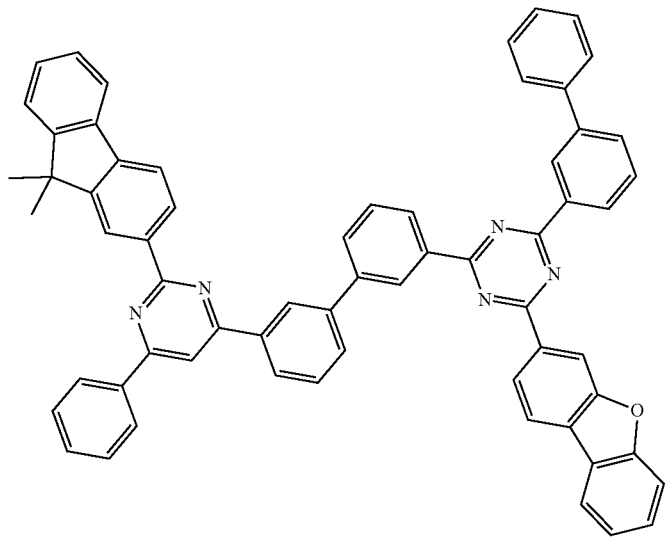
627
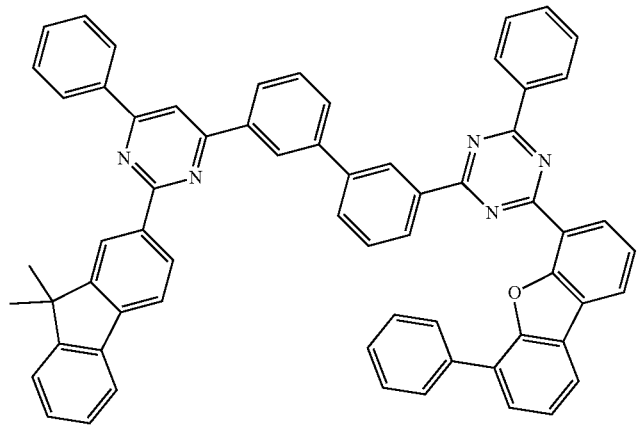

628
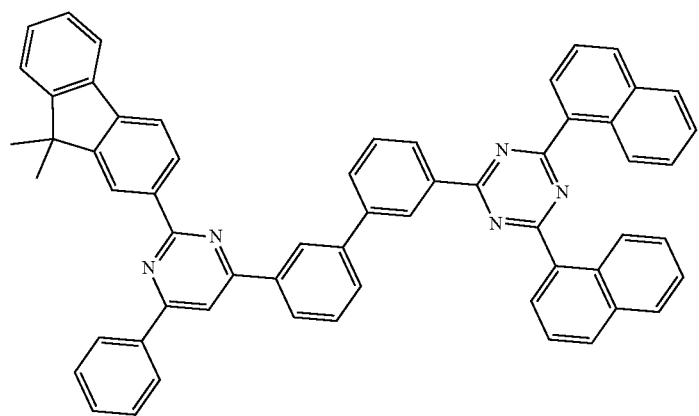
629
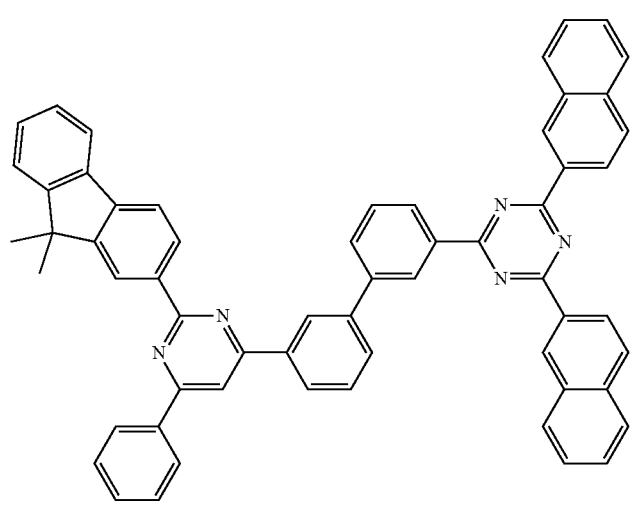
630
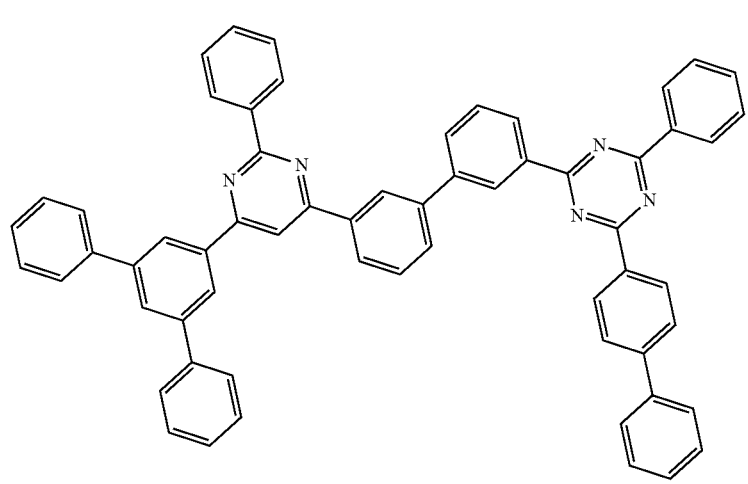

-continued
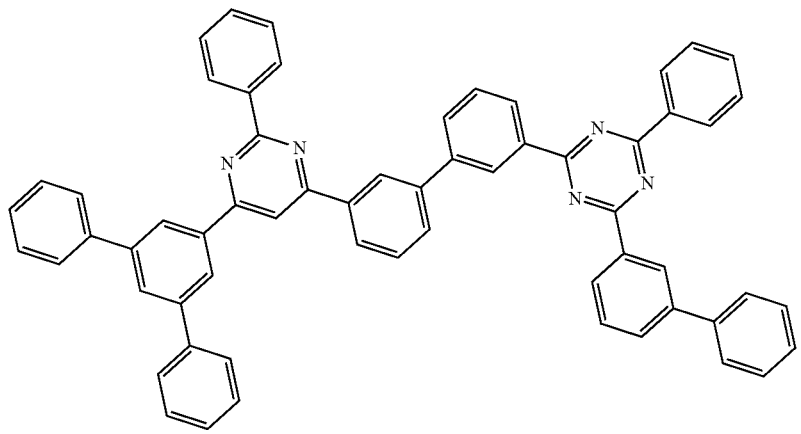
631
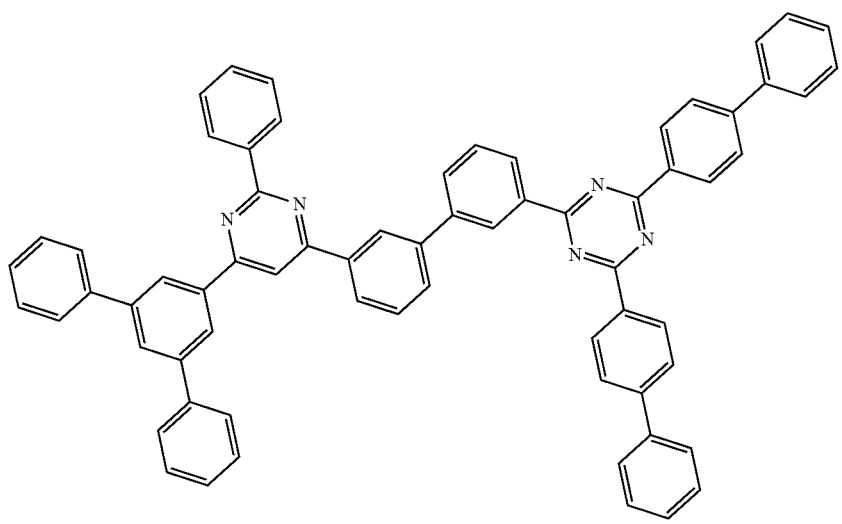
632
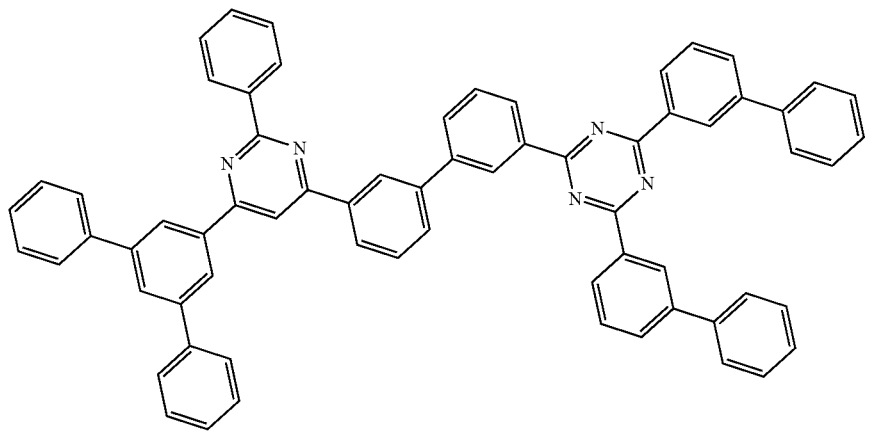
633

634
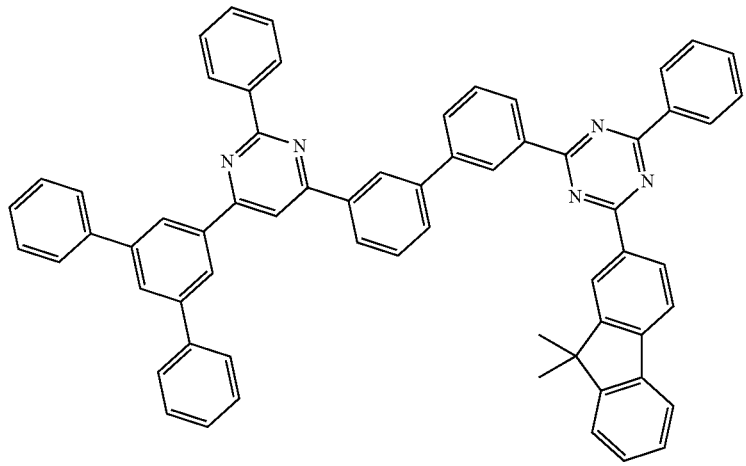
635
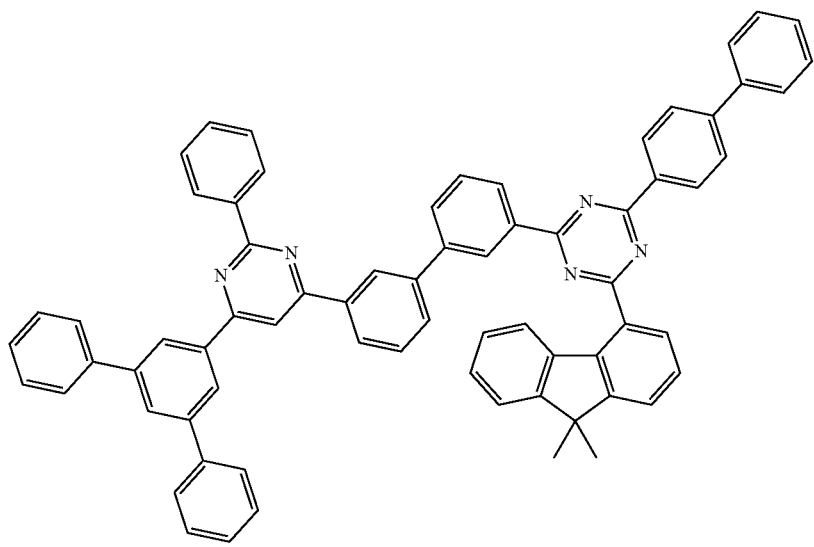
636
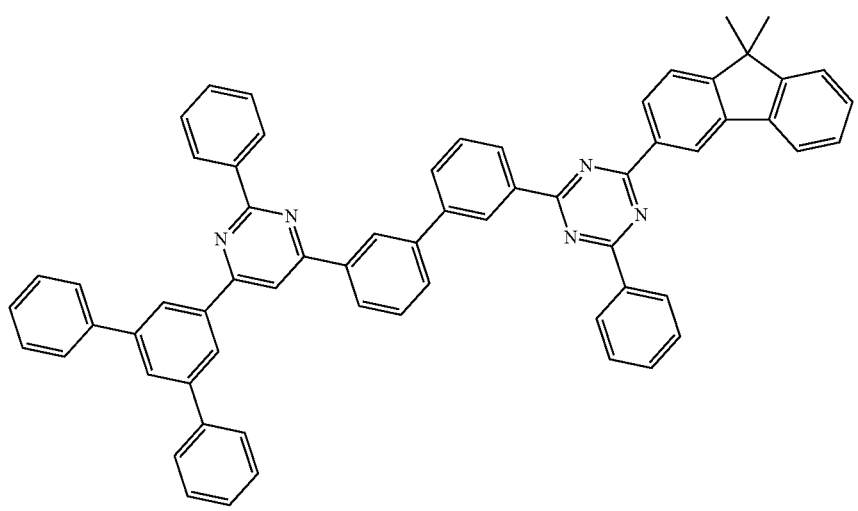

637
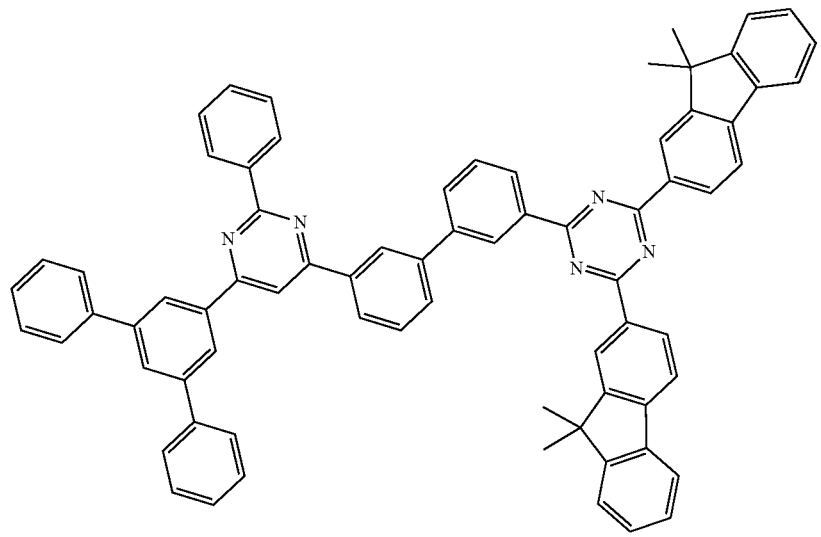
638
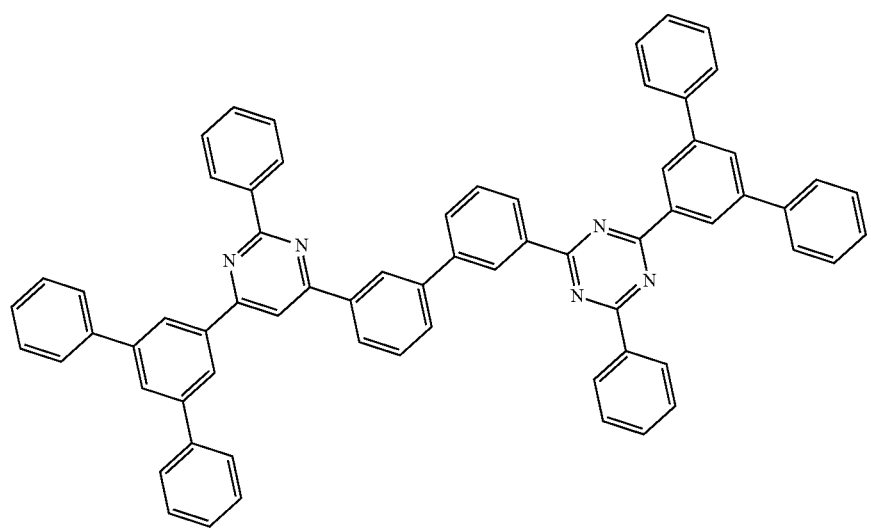
639
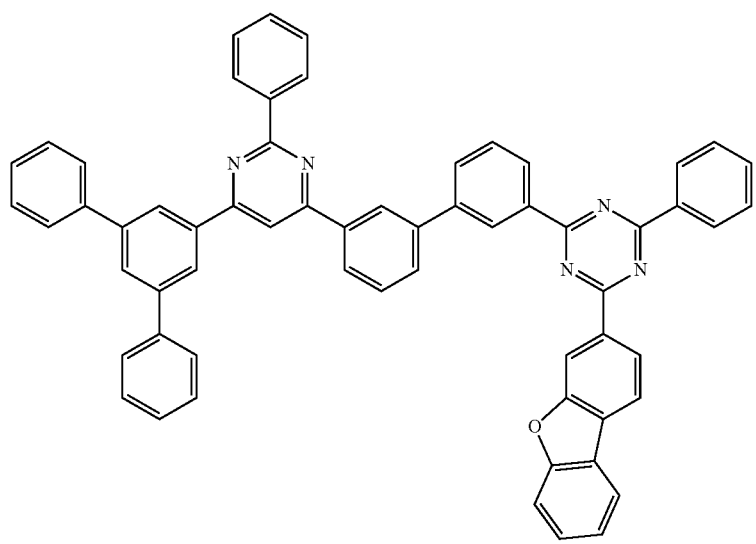

-continued
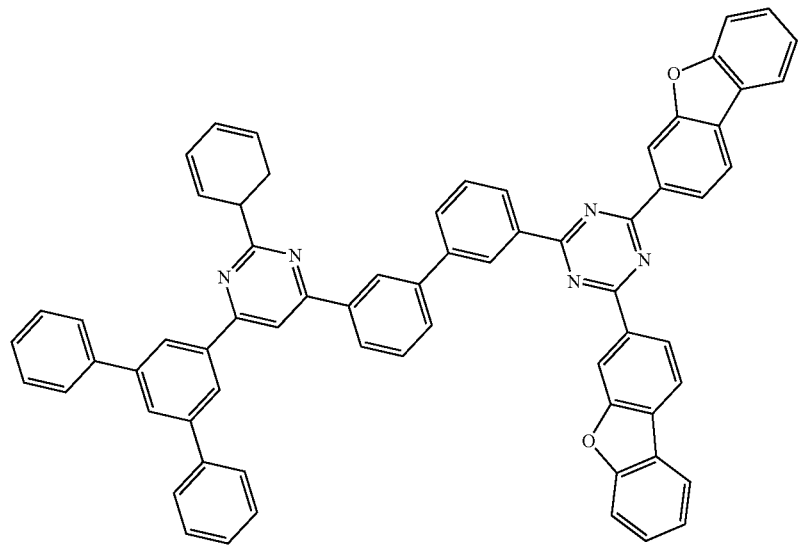
640
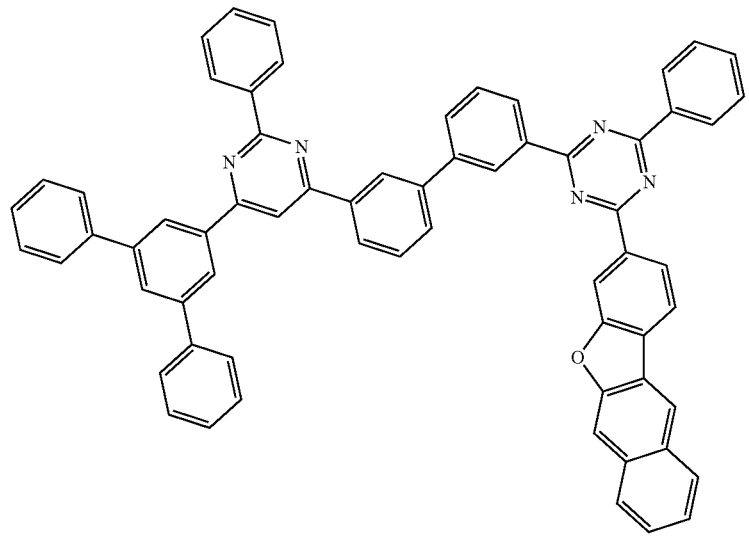
641
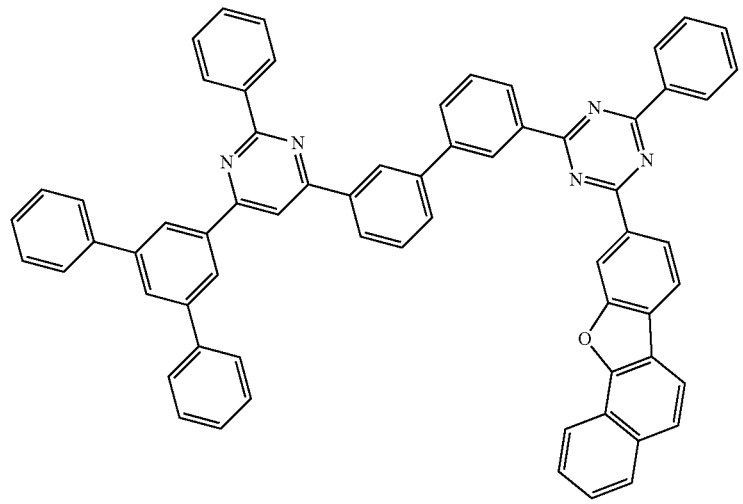
642

643
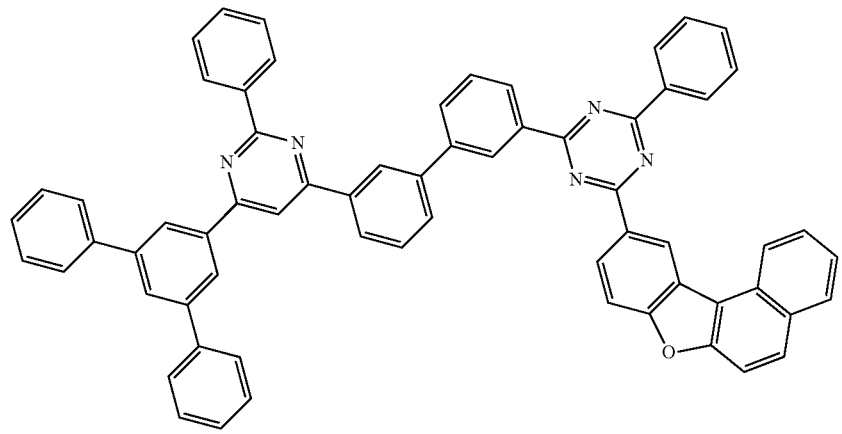
644
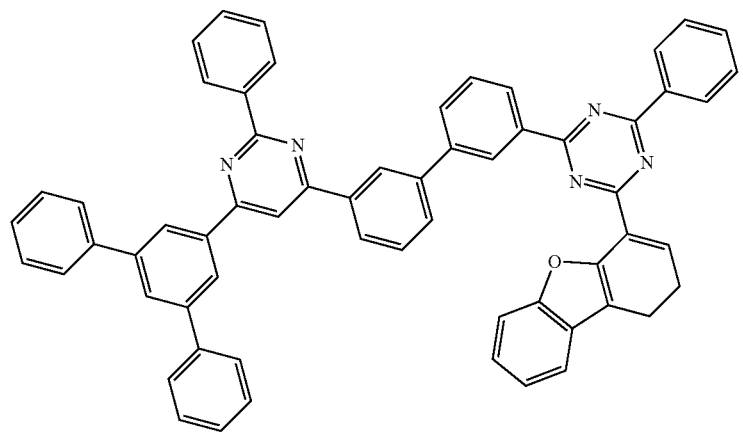
645
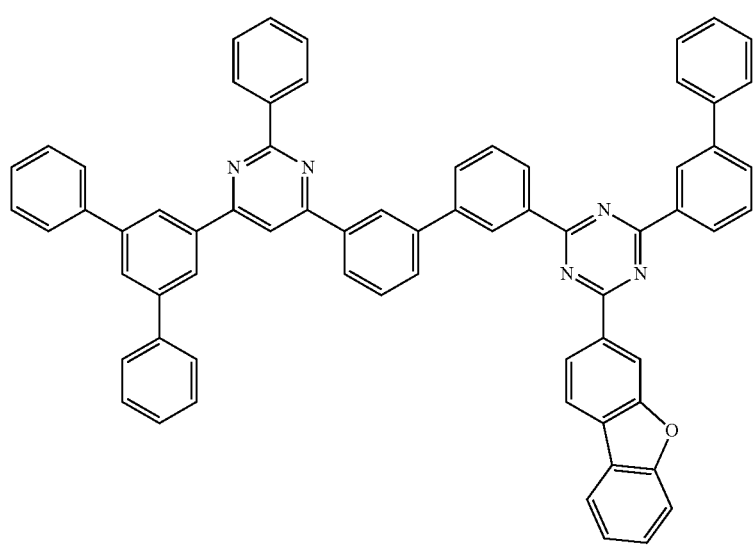

646
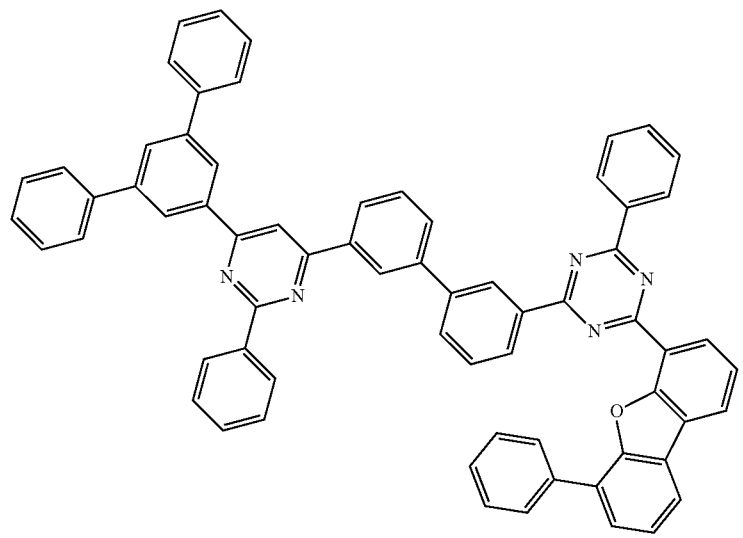
647
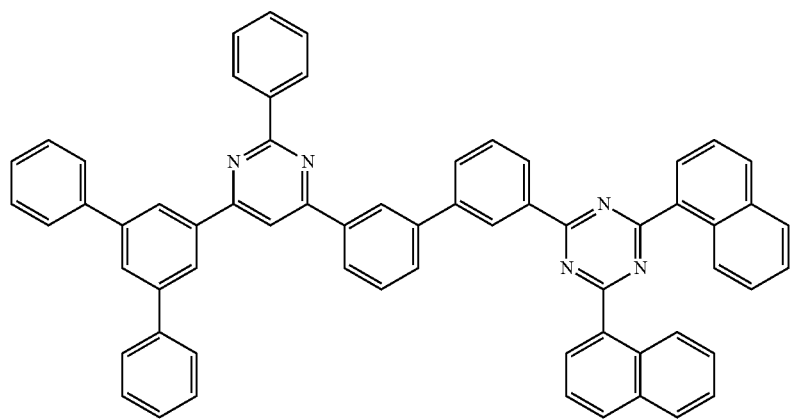
648
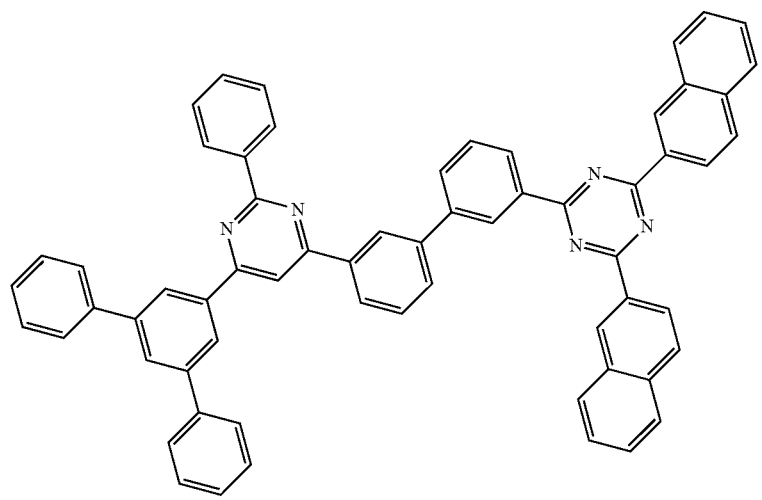

-continued
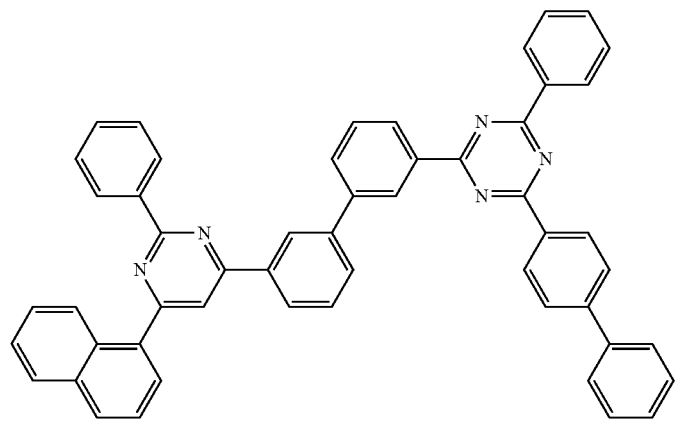
649
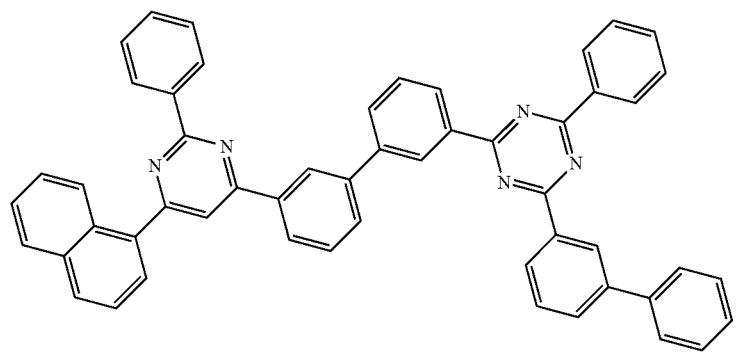
650
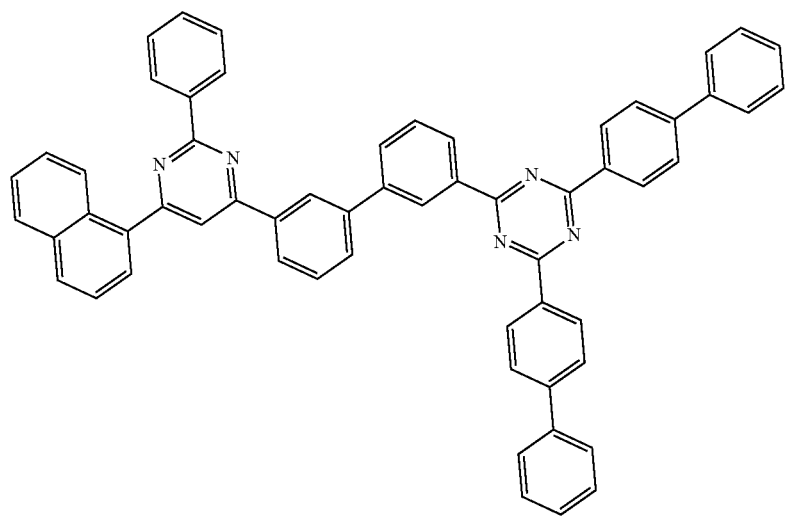
651

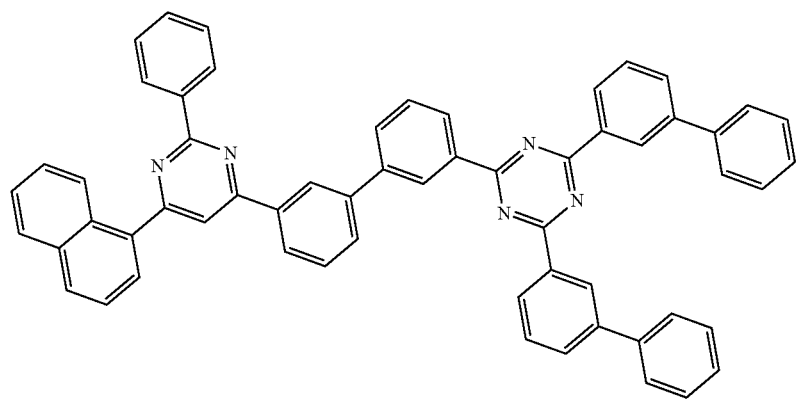
652
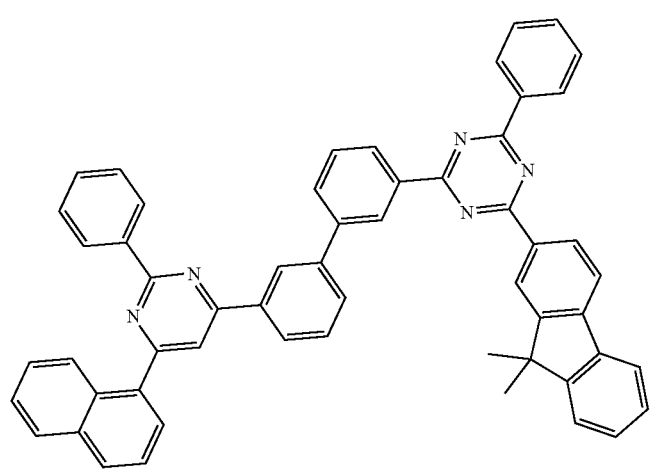
653
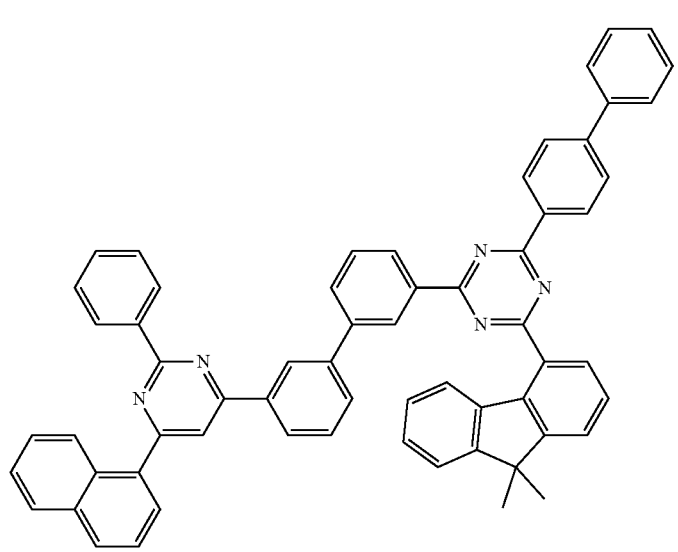
654

655
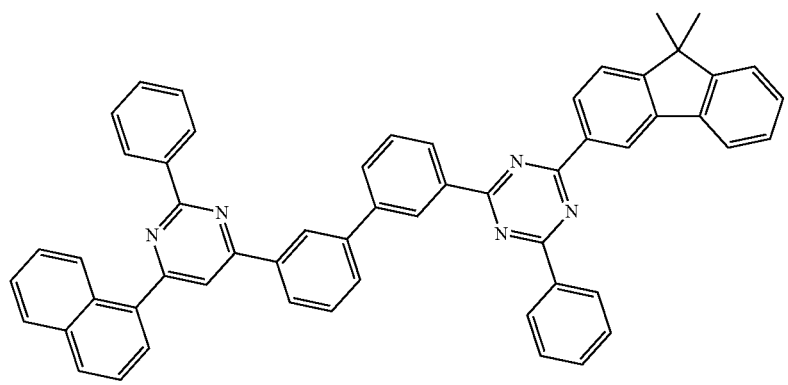
656
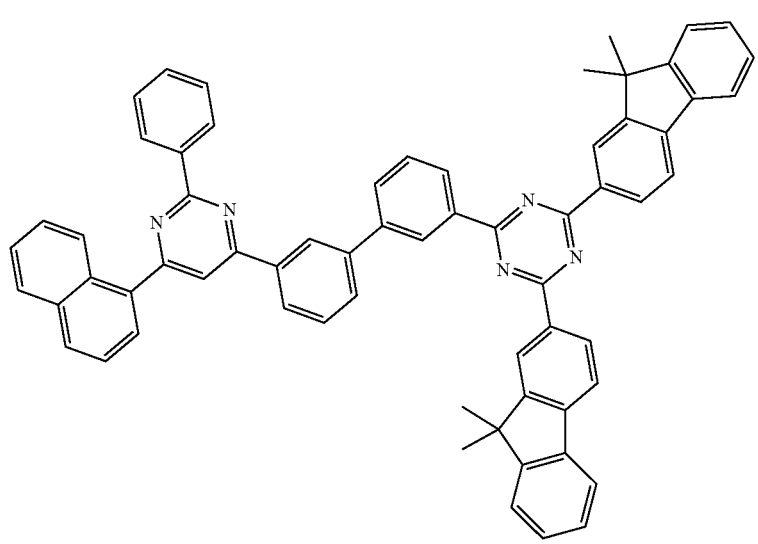
657
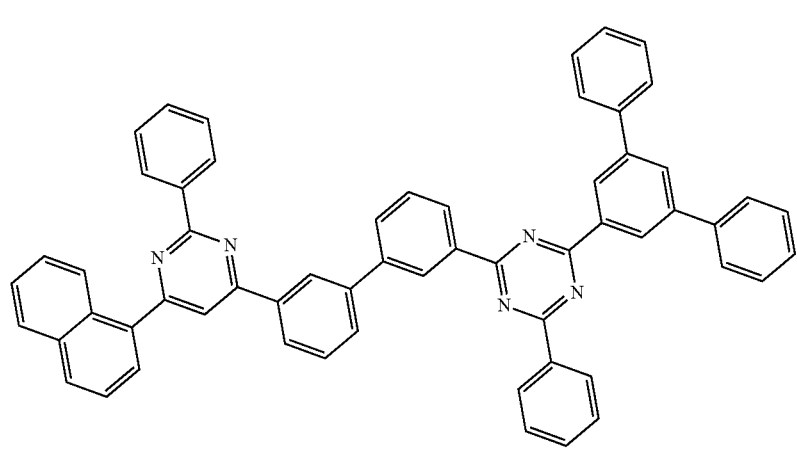

658
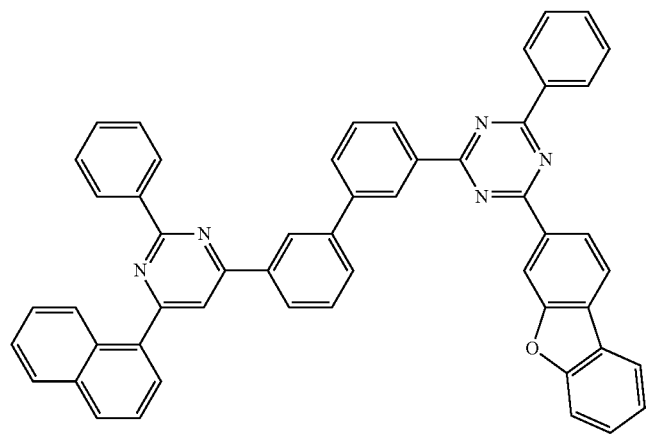
659
660
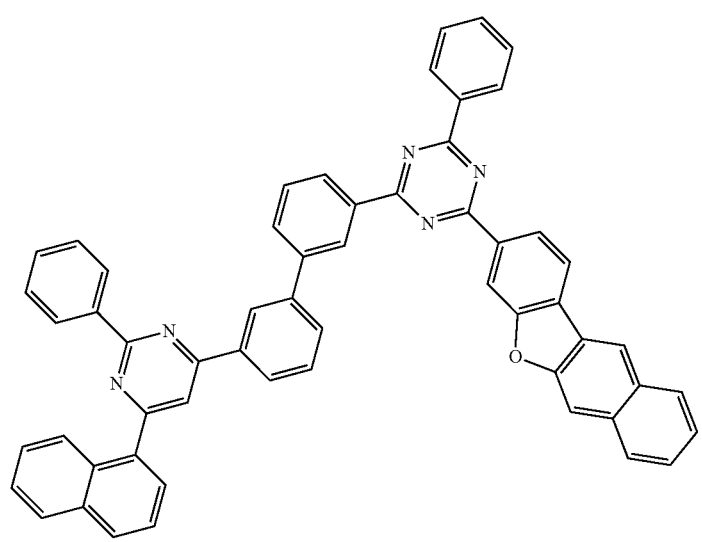

661
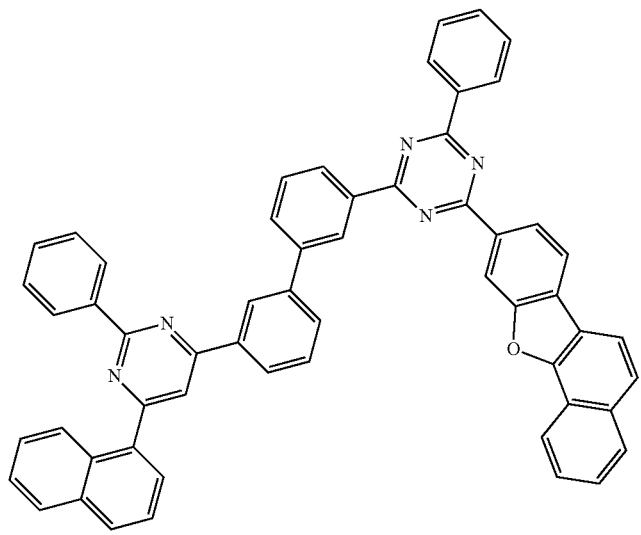
662
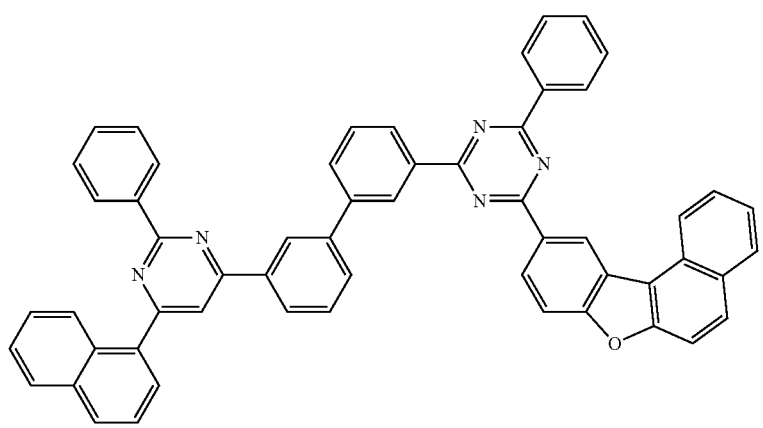
663
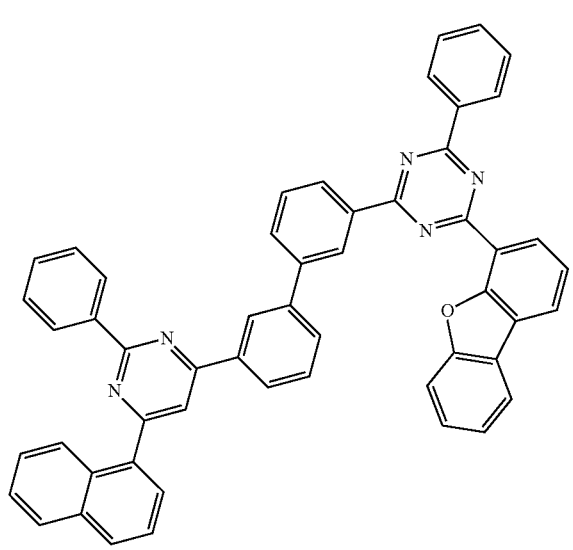

664
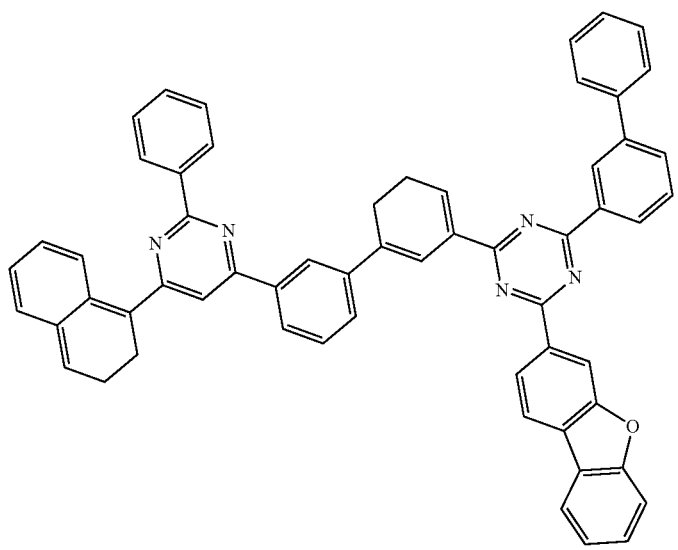
665
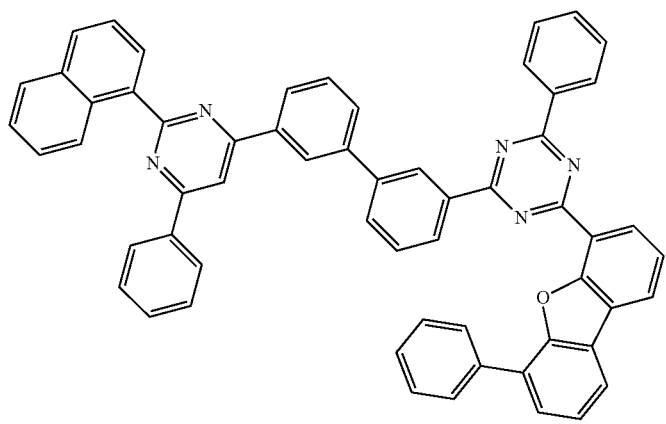
666
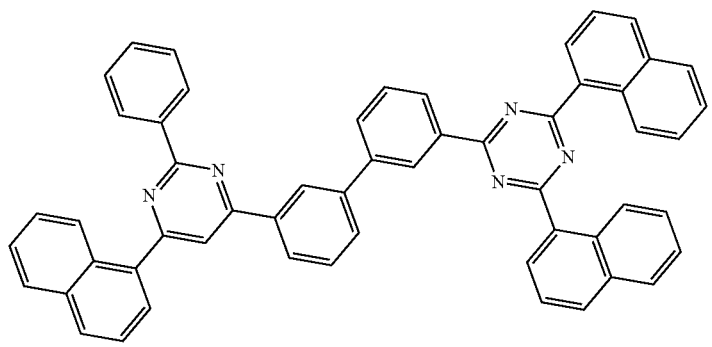

667
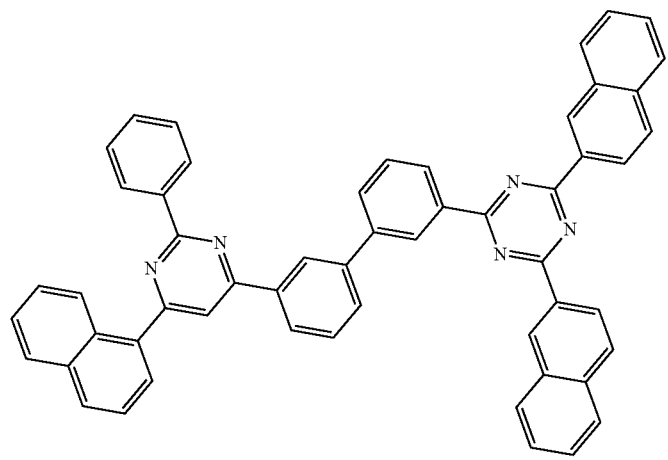
668
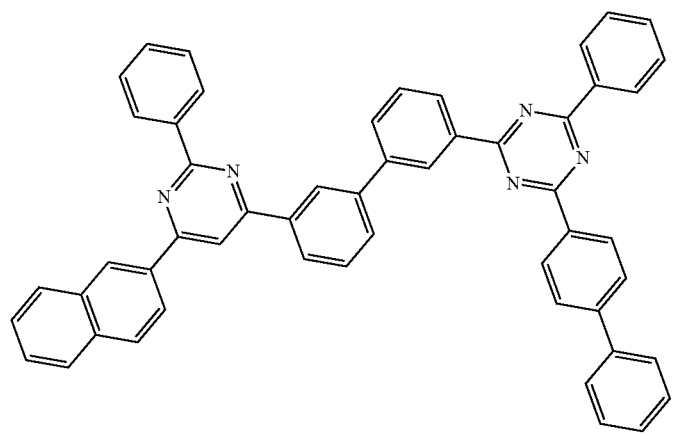
669
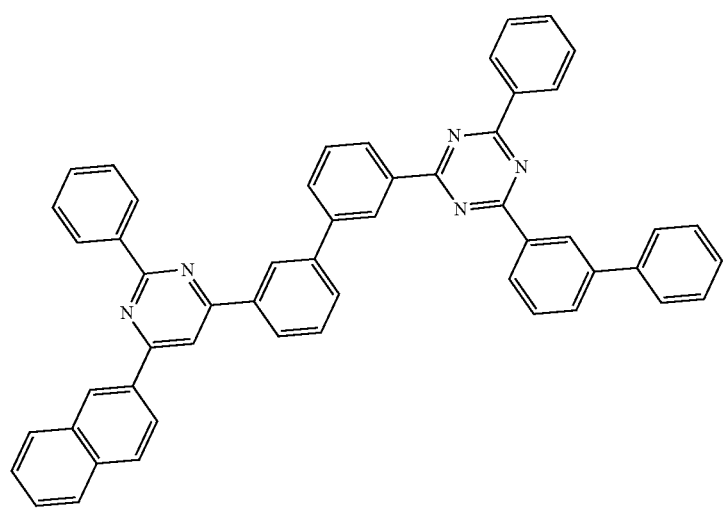

670
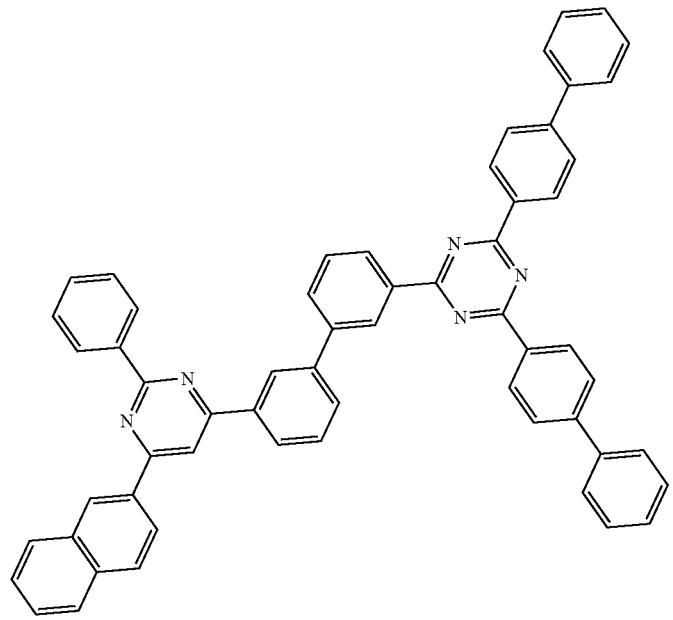
671
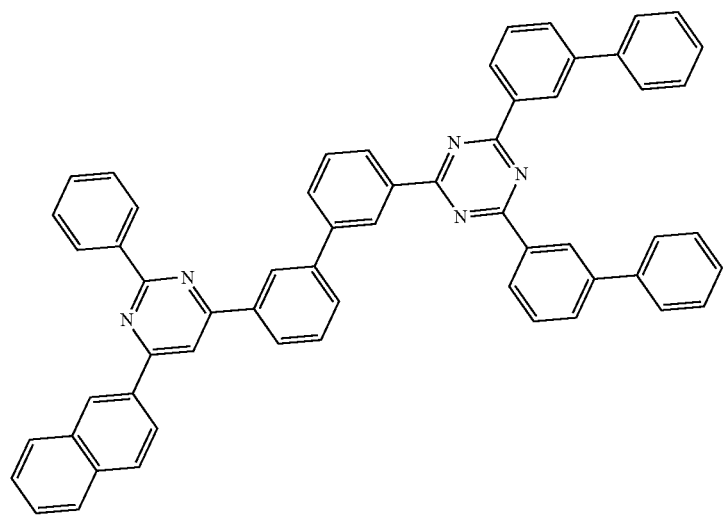
672
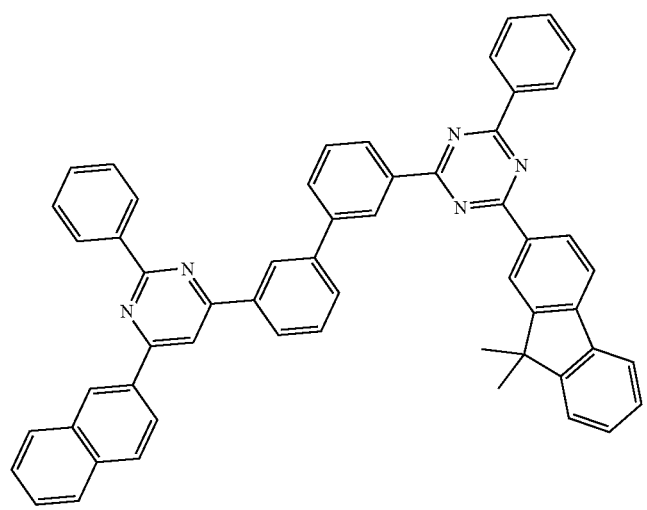

673
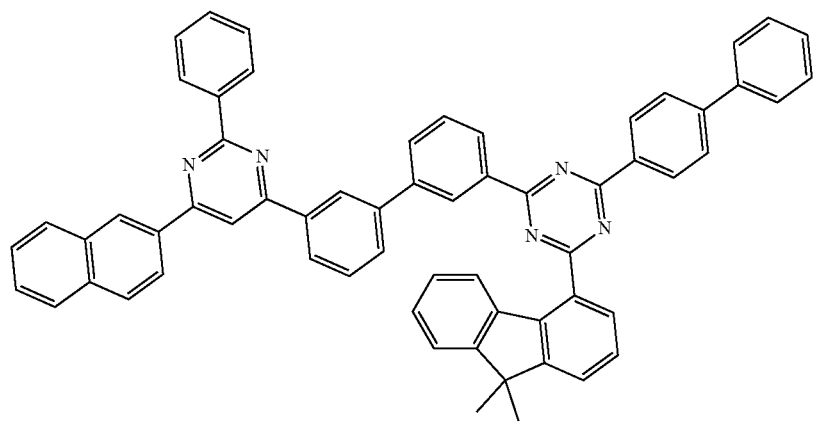
674
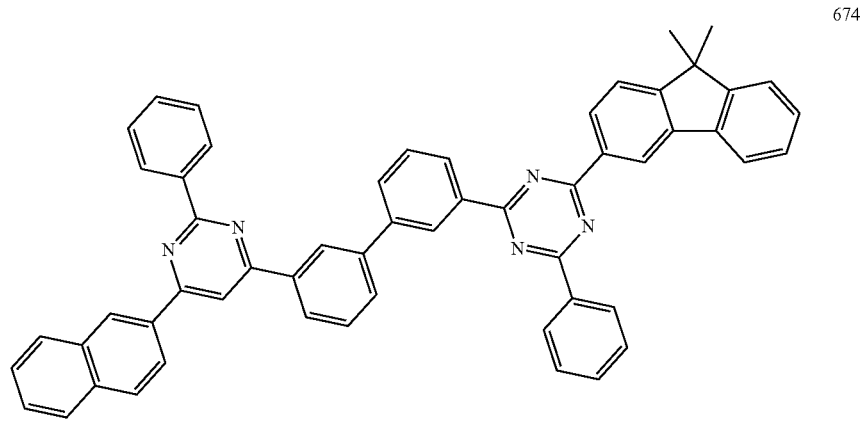
675
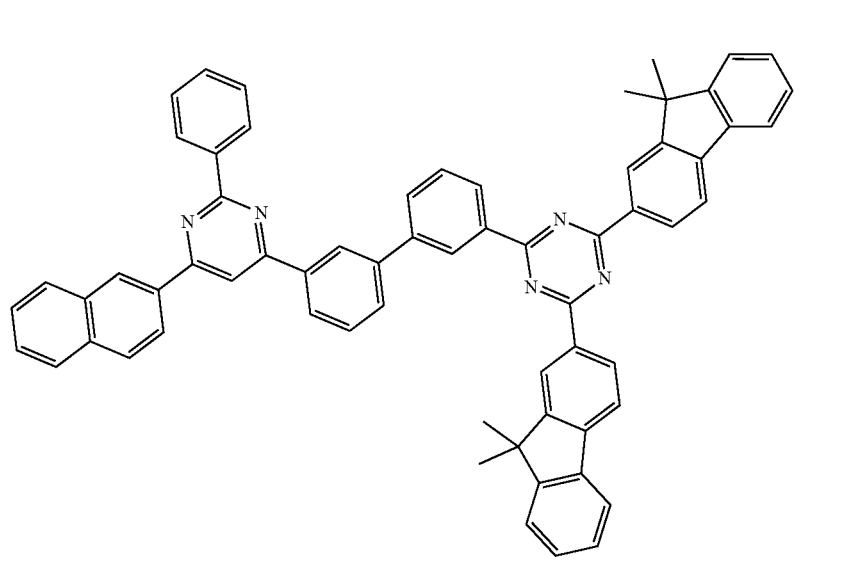

-continued
676
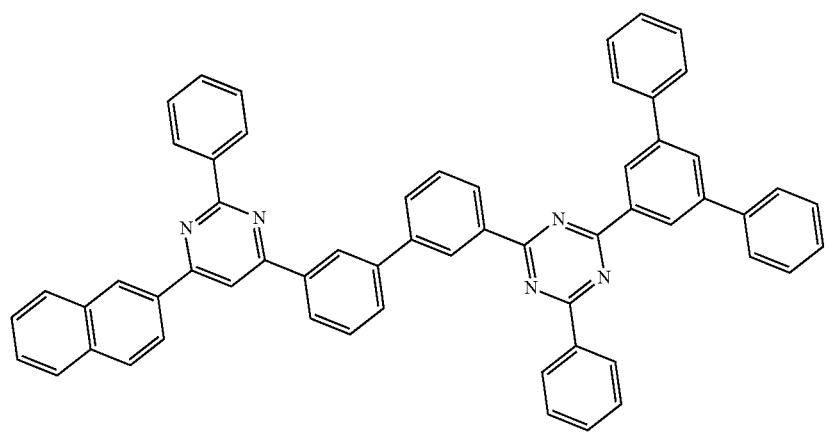
677
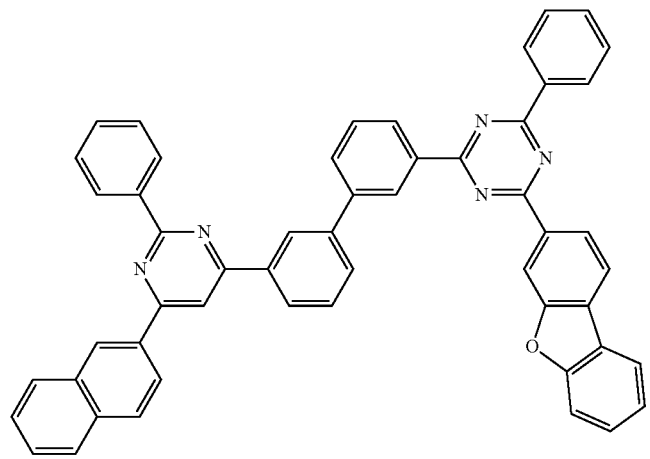
678
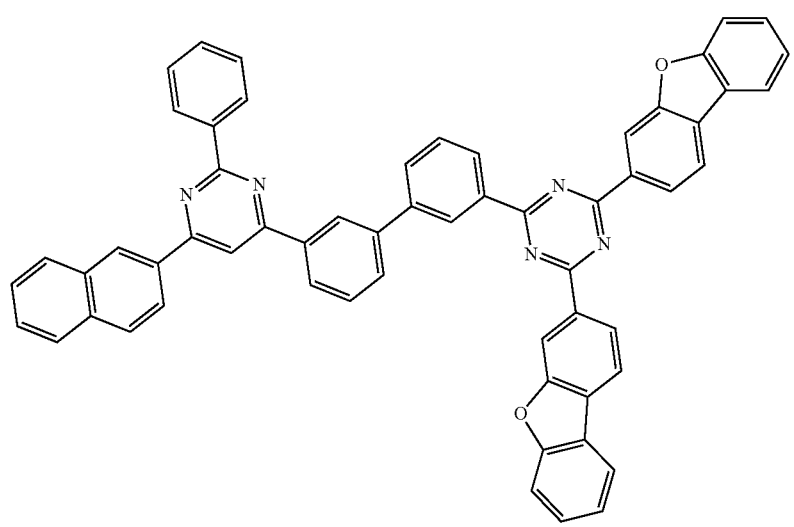

679
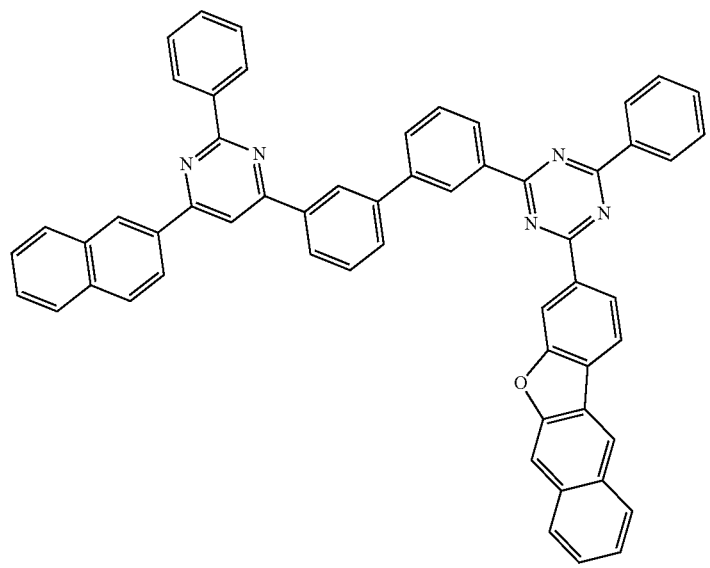
680
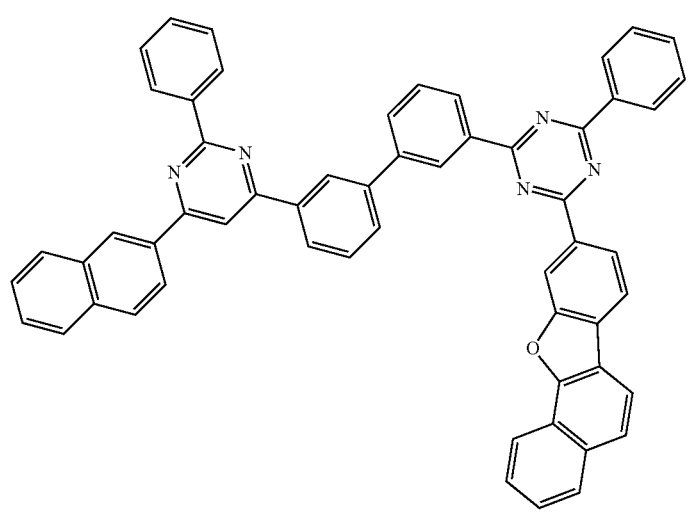
681
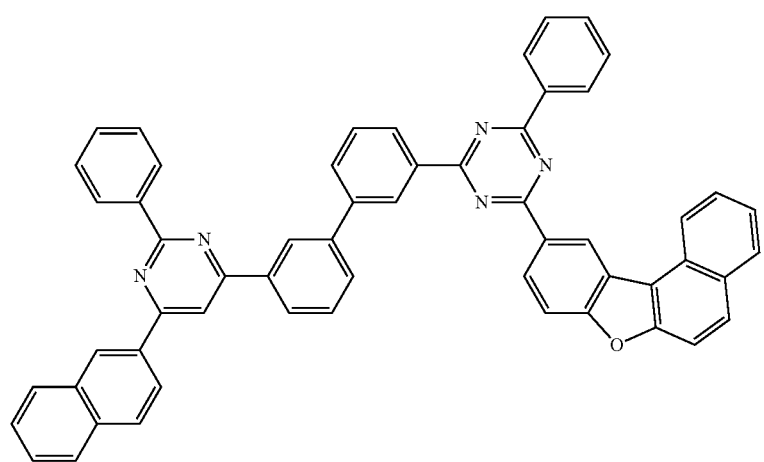

682
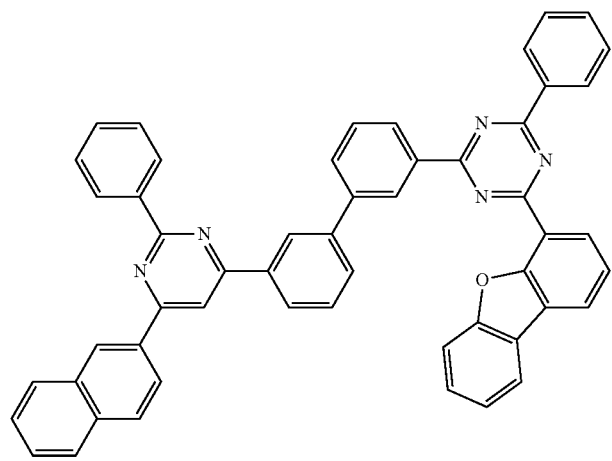
683
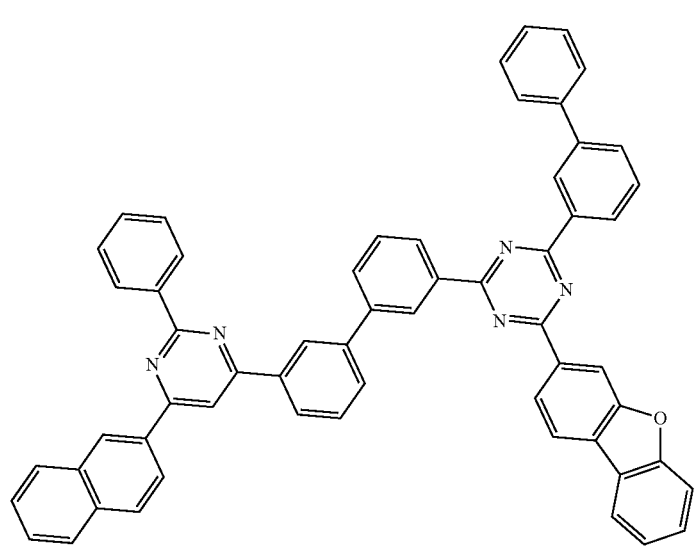
684
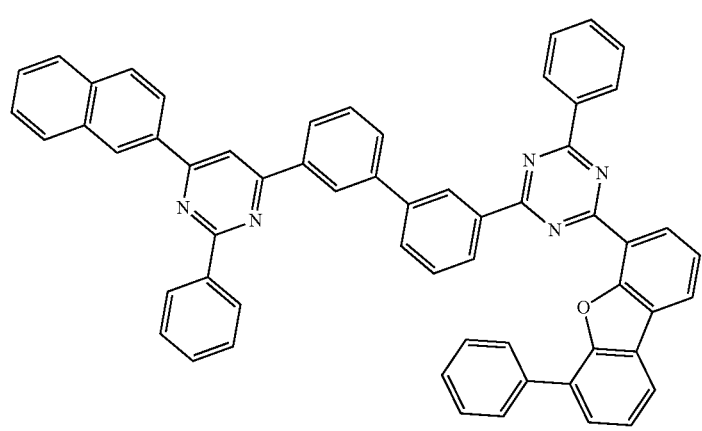

685
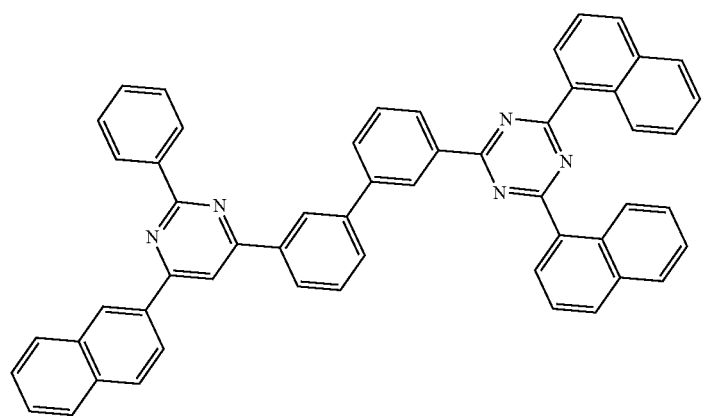
686
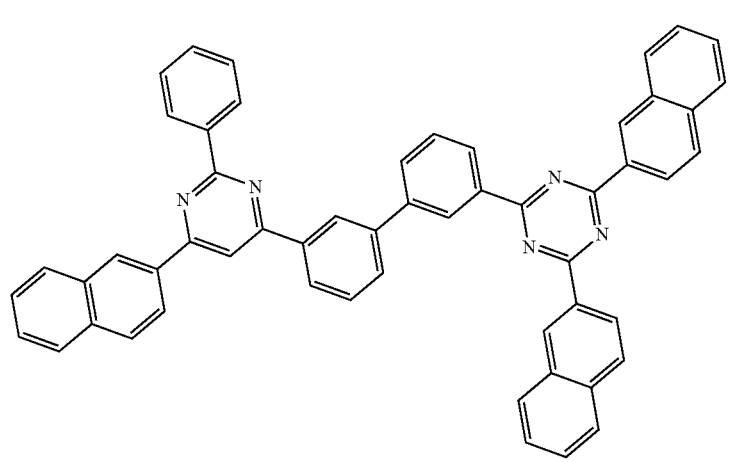
687
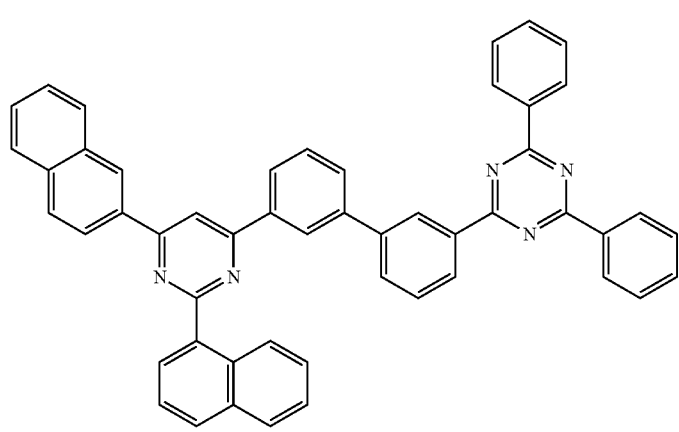

688
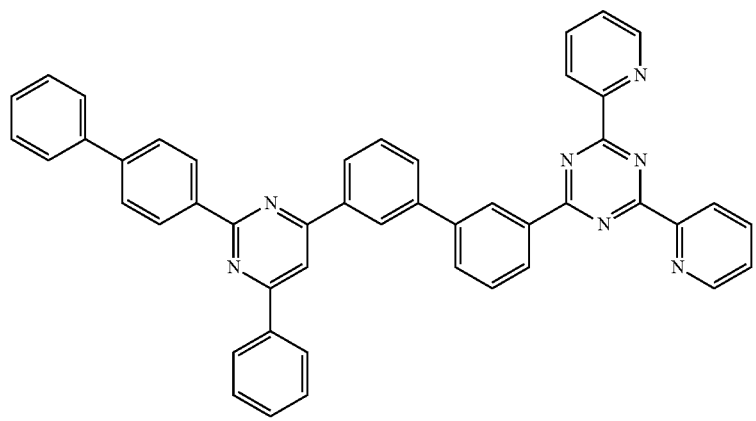
689
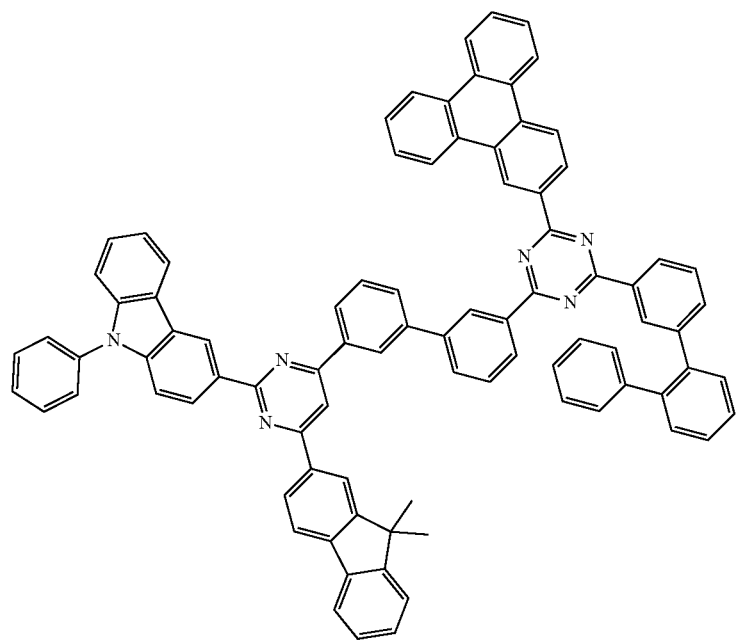

-continued
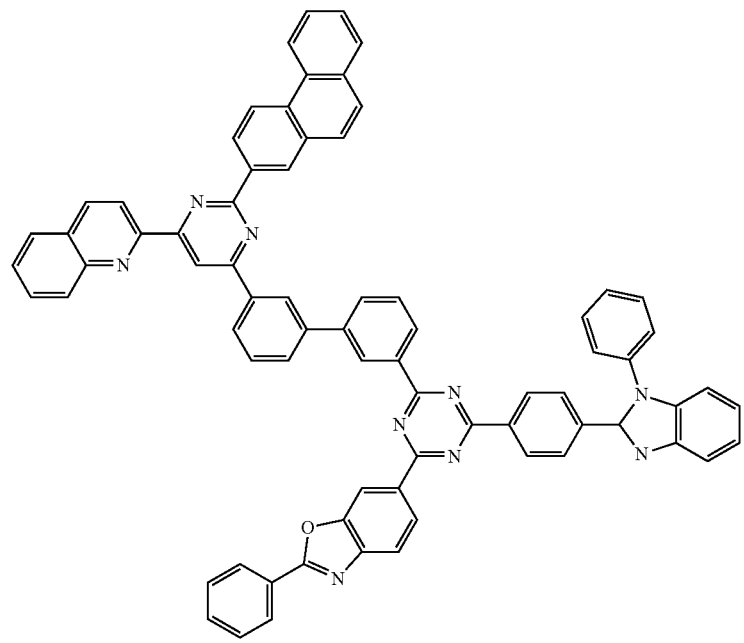
690
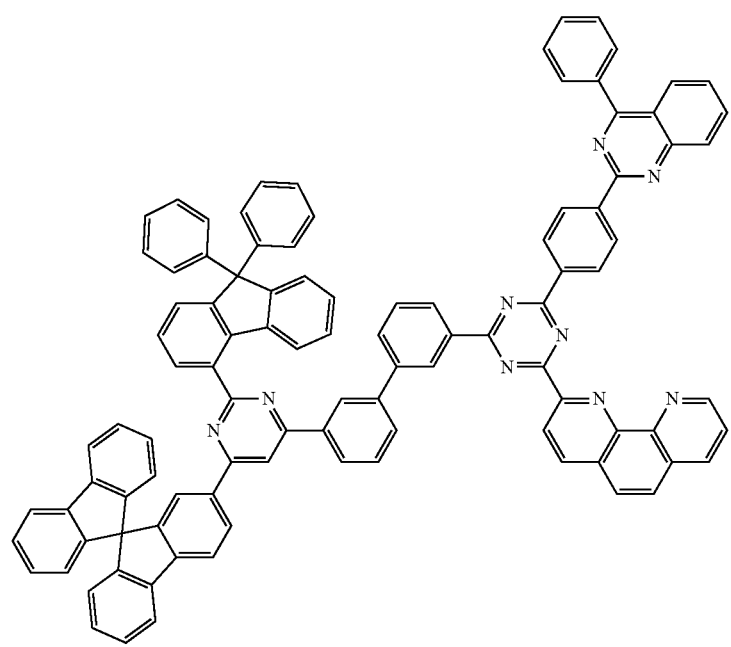
691

-continued
692
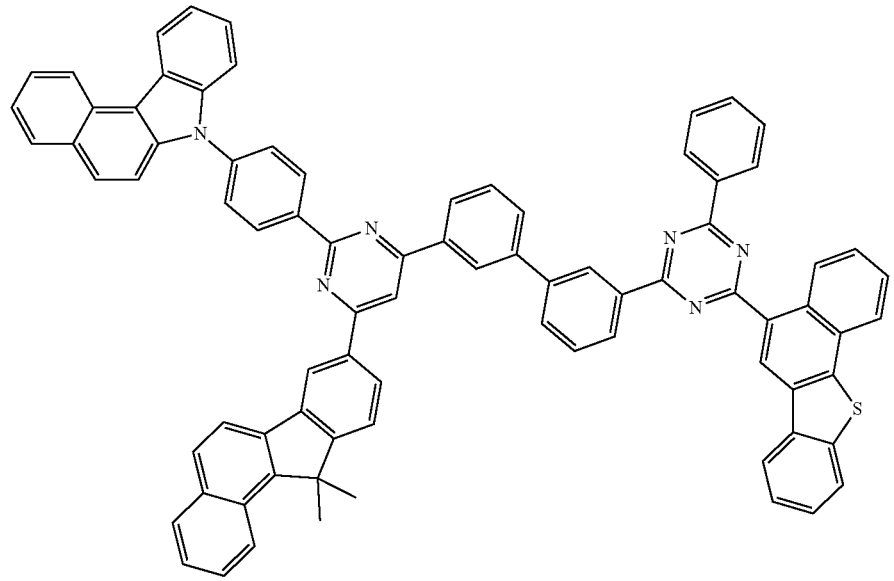
693
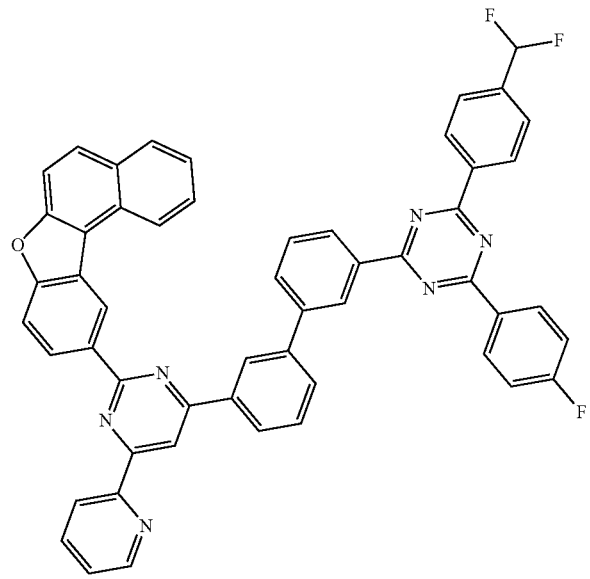
694
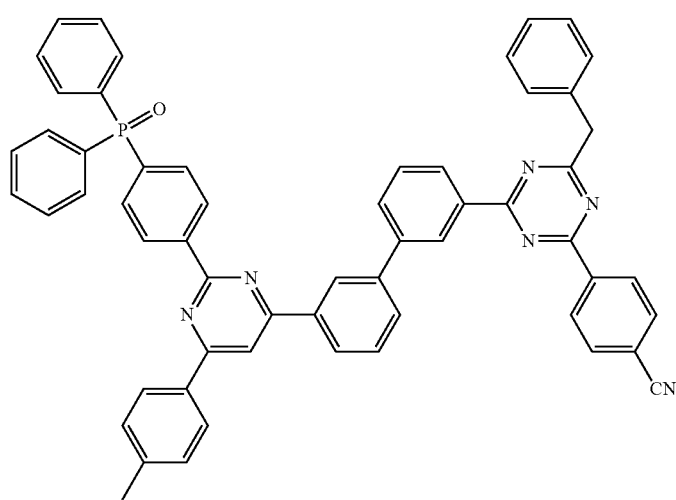

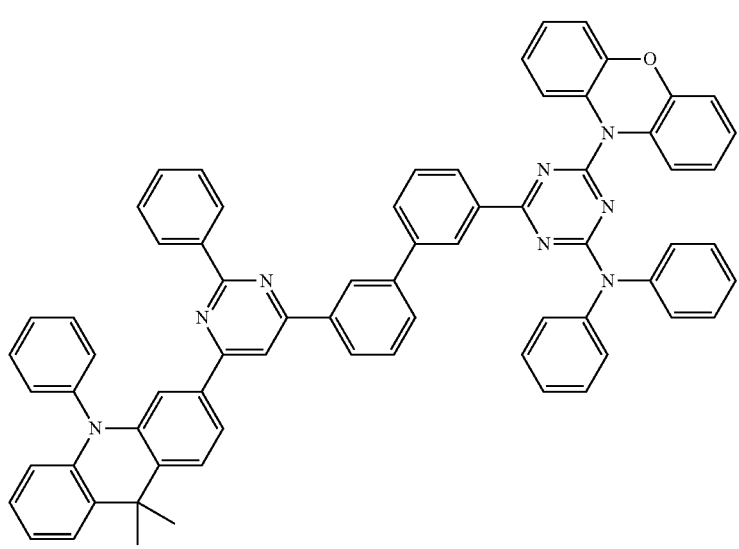

695

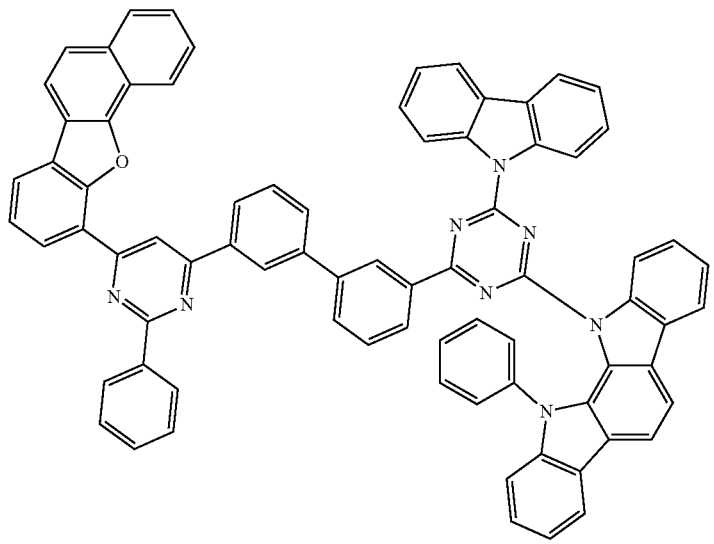

696

As used herein, "alkyl" refers to a monovalent substituent derived from a saturated, linear or branched hydrocarbon having 1 to 40 carbon atoms. Examples of such alkyl may include, but are not limited to, methyl, ethyl, propyl, isobutyl, sec-butyl, pentyl, iso-amyl, hexyl or the like.

As used herein, "alkenyl" refers to a monovalent substituent derived from an unsaturated, linear or branched hydrocarbon having 2 to 40 carbon atoms, having at least one carbon-carbon double bond. Examples of such alkenyl may include, but are not limited to, vinyl, allyl, isopropenyl, 2-butenyl or the like.

As used herein, "alkynyl" refers to a monovalent substituent derived from an unsaturated, linear or branched hydrocarbon having 2 to 40 carbon atoms, having at least one carbon-carbon triple bond. Examples of such alkynyl may include, but are not limited to, ethynyl, 2-propynyl or the like.

As used herein, "aryl" refers to a monovalent substituent derived from a $C_6$ to $C_{60}$ aromatic hydrocarbon which is in a structure with a single ring or two or more rings combined with each other. In addition, a form in which two or more rings are pendant (e.g., simply attached) to or condensed with each other may also be included. Examples of such aryl may include, but are not limited to, phenyl, naphthyl, phenanthryl, anthryl or the like.

As used herein, "heteroaryl" refers to a monovalent substituent derived from a monoheterocyclic or polyheterocyclic aromatic hydrocarbon having 5 to 60 nuclear atoms. In such a case, one or more carbons in the ring, preferably one to three carbons, are substituted with a heteroatom such as N, O, S or Se. In addition, a form in which two or more rings are pendant to or condensed with each other may be included, and a form condensed with an aryl group may be included. Examples of such heteroaryl may include, but are not limited to, a 6-membered monocyclic ring such as pyridyl, pyrazinyl, pyrimidinyl, pyridazinyl and triazinyl; a polycyclic ring such as phenoxathienyl, indolizinyl, indolyl, purinyl, quinolyl, benzothiazole and carbazolyl; 2-furanyl; N-imidazolyl; 2-isoxazolyl; 2-pyridinyl; 2-pyrimidinyl or the like.

As used herein, "aryloxy" refers to a monovalent substituent represented by RO—, where R is aryl having 6 to 60 carbon atoms. Examples of such aryloxy may include, but are not limited to, phenyloxy, naphthyloxy, diphenyloxy or the like.

As used herein, "alkyloxy" refers to a monovalent substituent represented by R'O—, where R' is alkyl having 1 to 40 carbon atoms. Such alkyloxy may include a linear, branched or cyclic structure. Examples of such alkyloxy may include, but are not limited to, methoxy, ethoxy, n-propoxy, 1-propoxy, t-butoxy, n-butoxy, pentoxy or the like.

As used herein, "arylamine" refers to amine substituted with aryl having 6 to 60 carbon atoms.

As used herein, "cycloalkyl" refers to a monovalent substituent derived from a monocyclic or polycyclic non-aromatic hydrocarbon having 3 to 40 carbon atoms. Examples of such cycloalkyl may include, but are not limited to, cyclopropyl, cyclopentyl, cyclohexyl, norbornyl, adamantine or the like.

As used herein, "heterocycloalkyl" refers to a monovalent substituent derived from a non-aromatic hydrocarbon having 3 to 40 nuclear atoms, where one or more carbons in the ring, preferably one to three carbons, are substituted with a heteroatom such as N, O, S or Se. Examples of such heterocycloalkyl may include, but are not limited to, morpholine, piperazine or the like.

As used herein, "alkylsilyl" refers to silyl substituted with alkyl having 1 to 40 carbon atoms, and "arylsilyl" refers to silyl substituted with aryl, having 6 to 60 carbon atoms.

As used herein, "alkylboron" refers to boron substituted with alkyl having 1 to 40 carbon atoms, and "arylboron" refers to boron substituted with aryl, having 6 to 60 carbon atoms.

As used herein, "arylphosphine" refers to phosphine substituted with aryl having 6 to 60 carbon atoms, and "arylphosphine oxide" refers to phosphine, substituted with aryl having 6 to 60 carbon atoms, that has O.

As used herein, the term "condensed ring" refers to a condensed aliphatic ring, a condensed aromatic ring, a condensed heteroaliphatic ring, a condensed heteroaromatic ring, or a combination thereof.

Such a compound represented by Chemical Formula 1 of the present invention may be synthesized in various ways with reference to the synthesis process of the following embodiments.

2. Organic Electroluminescent Device

The present invention provides an organic electroluminescent device including the compound represented by Chemical Formula 1.

More specifically, the organic electroluminescent device according to the present invention includes an anode, a cathode, and one or more organic layers interposed between the anode and the cathode, and at least one of the one or more organic layers include the compound represented by Chemical Formula 1. In such a case, the compound may be used solely or as a combination of two or more kinds thereof.

The one or more organic layers may be any one or more of a hole injection layer, a hole transporting layer, an auxiliary light-emitting layer, a light-emitting layer, an electron transporting layer and an electron injection layer, and at least one of the organic layers may include the compound represented by Chemical Formula 1. Specifically, the organic layer including the compound represented by Chemical Formula 1 is preferably a light-emitting layer and an electron transporting layer.

The light-emitting layer of the organic electroluminescent device of the present invention may include a host material (preferably, a phosphorescent host material). In addition, the light-emitting layer of the organic electroluminescent device of the present invention may include, as a host, a compound other than the compound represented by Chemical Formula 1.

A structure of the organic electroluminescent device of the present invention is not particularly limited, but a non-limiting example thereof may be a structure in which a substrate, an anode, a hole injection layer, a hole transporting layer, an auxiliary light-emitting layer, a light-emitting layer, an electron transporting layer and a cathode are sequentially stacked. In such a case, at least one of the hole injection layer, the hole transporting layer, the auxiliary light-emitting layer, the light-emitting layer, the electron transporting layer and the electron injection layer may include the compound represented by Chemical Formula 1, and preferably, the light-emitting layer may include the compound represented by Chemical Formula 1. In such a case, an electron injection layer may be further stacked on the electron transporting layer. In addition, the structure of the organic electroluminescent device of the present invention may be a structure in which an insulating layer or an adhesive layer is inserted at interfaces between the electrodes and the organic layers.

Meanwhile, the organic electroluminescent device of the present invention may be manufactured by forming organic layers and electrodes with conventional materials and through conventional methods known in the art, except that one or more of the aforementioned organic layers include the compound represented by Chemical Formula 1.

The organic layer may be formed by a vacuum deposition method or a solution coating method. Examples of the solution coating method may include, but are not limited to, spin coating, dip coating, doctor blading, inkjet printing, thermal transfer or the like.

The substrate used for manufacturing the organic electroluminescent device of the present invention is not particularly limited, but silicon wafers, quartz, glass plates, metal plates, plastic films, sheets or the like may be used.

In addition, a material of the anode may include, but is not limited to, a metal such as vanadium, chromium, copper, zinc and gold or an alloy thereof; a metal oxide such as zinc oxide, indium oxide, indium tin oxide (ITO) and indium zinc oxide (IZO); a combination of oxide with metal such as ZnO:Al or $SnO_2$:Sb; a conductive polymer such as polythiophene, poly(3-methylthiophene), poly [3,4-(ethylene-1,2-dioxy)thiophene] (PEDT), polypyrrole and polyaniline; carbon black or the like.

In addition, a material of the cathode may include, but is not limited to, a metal such as magnesium, calcium, sodium, potassium, titanium, indium, yttrium, lithium, gadolinium, aluminum, silver, tin and lead or an alloy thereof; a multi-layered material such as LiF/Al and $LiO_2$/Al or the like.

In addition, materials of the hole injection layer, the hole transporting layer and the auxiliary light-emitting layer are not particularly limited and conventional materials known in the art may be used.

Hereinafter, the present invention will be described in detail with reference to the following embodiments. However, the following embodiments are merely to illustrate the invention, and the present invention is not limited by the following embodiments.

Preparation Example 1 Synthesis of Compound Z-1

<Step 1> Synthesis of 2,4-dichloro-6-(9,9-dimethyl-9H-fluoren-2-yl)pyrimidine

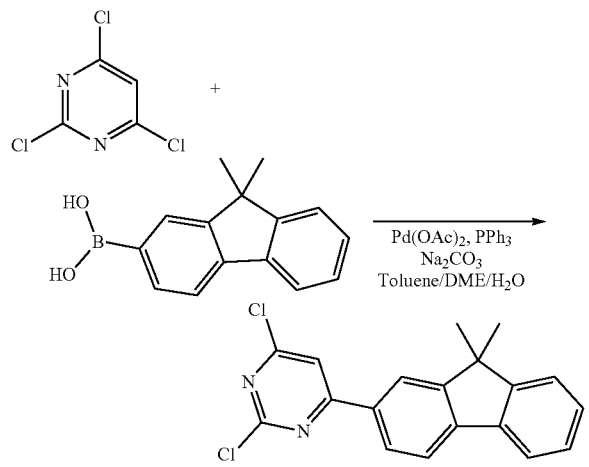

Under nitrogen environment, 2,4,6-trichloropyrimidine (1.83 g, 10 mmol), (9,9-dimethyl-9H-fluoren-2-yl)boronic acid (2.38 g, 10.0 mmol), Pd(OAc)$_2$ (0.11 g, 5 mol %), PPh$_3$ (0.26 g, 1 mmol), Na$_2$CO$_3$ (2.10 g, 20 mmol) and Toluene/DME/H$_2$O (10 ml/30 ml/20 ml) were mixed and then heated to reflux for 8 hours. After the reaction was completed, the mixture was cooled to room temperature, extraction was performed with methylene chloride, MgSO$_4$ was added to the extracted material, and the resultant material was filtered. After removing the solvent from the obtained organic layer, a compound 2,4-dichloro-6-(9,9-dimethyl-9H-fluoren-2-yl)pyrimidine (2.72 g, yield 80%) was obtained through column chromatography.

1H-NMR: δ 1.69 (s, 6H), 7.13 (s, 1H), 7.28 (t, 1H), 7.38 (t, 1H), 7.55 (d, 1H), 7.78 (d, 1H), 7.90 (m, 2H), 8.09 (d, 1H)

<Step 2> Synthesis of 2-chloro-4-(3-chlorophenyl-6-(9,9-dimethyl-9H-fluoren-2-yl)pyrimidine

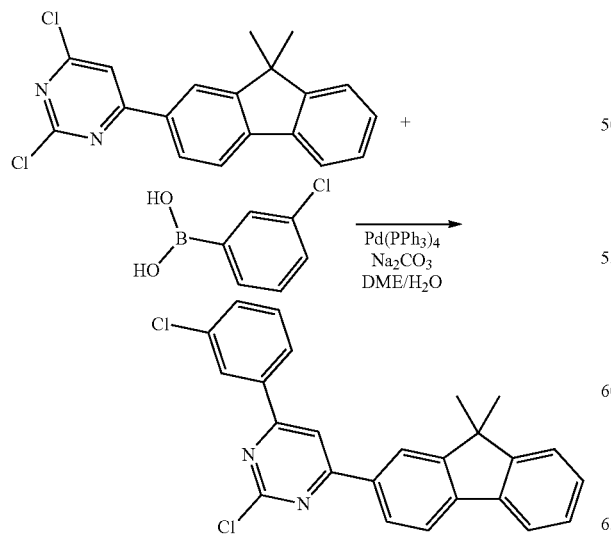

Under nitrogen environment, 2,4-dichloro-6-(9,9-dimethyl-9H-fluoren-2-yl)pyrimidine (3.41 g, 10 mmol), which had been synthesized in <Step 1>, and (3-chlorophenyl)boronic acid (1.56 g, 10.0 mmol), Pd(PPh$_3$)$_4$ (0.57 g, 5 mol %), Na$_2$CO$_3$ (2.10 g, 20 mmol) and DME/H$_2$O (40 ml/20 ml) were mixed and then heated to reflux for 8 hours. After the reaction was completed, the mixture was cooled to room temperature, extraction was performed with methylene chloride, MgSO$_4$ was added to the extracted material, and the resultant material was filtered. After removing the solvent from the obtained organic layer, a compound 2-chloro-4-(3-chlorophenyl)-6-(9,9-dimethyl-9H-fluoren-2-yl)pyrimidine (3.29 g, yield 79%) was obtained through column chromatography.

1H-NMR: δ 1.69 (s, 6H), 7.28 (t, 1H), 7.38 (t, 1H), 7.50 (m, 3H), 7.76 (m, 2H), 7.90 (m, 2H), 7.97 (s, 1H), 8.09 (d, 1H), 8.33 (s, 1H)

<Step 3> Synthesis of 3-(4-(3-chlorophenyl)-6-(9,9-dimethyl-9H-fluoren-2-yl)pyrimidin-2-yl)-9-phenyl-9H-carbazole

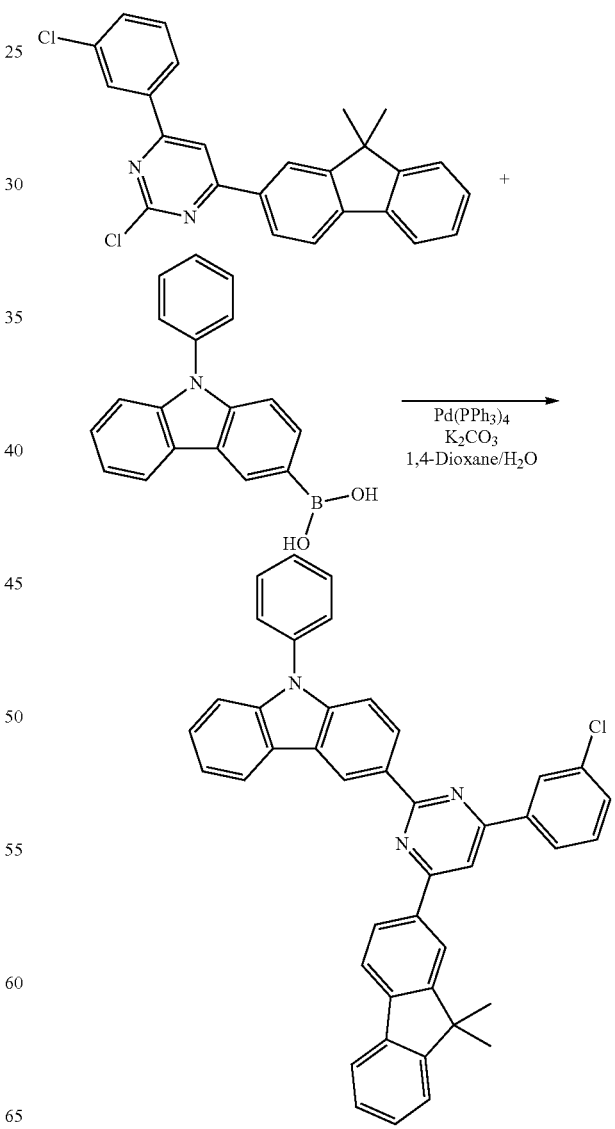

Under nitrogen environment, 2-chloro-4-(3-chlorophenyl)-6-(9,9-dimethyl-9H-fluoren-2-yl)pyrimidine (4.17 g, 10 mmol), which had been synthesized in <Step 2>, and (9-phenyl-9H-carbazol-3-yl)boronic acid (2.87 g, 10.0 mmol), Pd(PPh₃)₄ (0.57 g, 5 mol %), K₂CO₃ (2.76 g, 20 mmol) and 1,4-Dioxane/H₂O (80 m/20 ml) were mixed and then heated to reflux for 8 hours. After the reaction was completed, the mixture was cooled to room temperature, extraction was performed with methylene chloride, MgSO₄ was added to the extracted material, and the resultant material was filtered. After removing the solvent from the obtained organic layer, a compound 3-(4-(3-chlorophenyl)-6-(9,9-dimethyl-9H-fluoren-2-yl)pyrimidin-2-yl)-9-phenyl-9H-carbazole (4.86 g, yield 78%) was obtained through column chromatography.

1H-NMR: δ 1.69 (s, 6H), 7.16 (t, 1H), 7.30 (m, 3H), 7.50 (m, 8H), 7.70 (m, 3H), 7.90 (m, 6H), 8.09 (d, 1H), 8.23 (s, 1H), 8.55 (d, 1H)

<Step 4> Synthesis of Compound Z-1

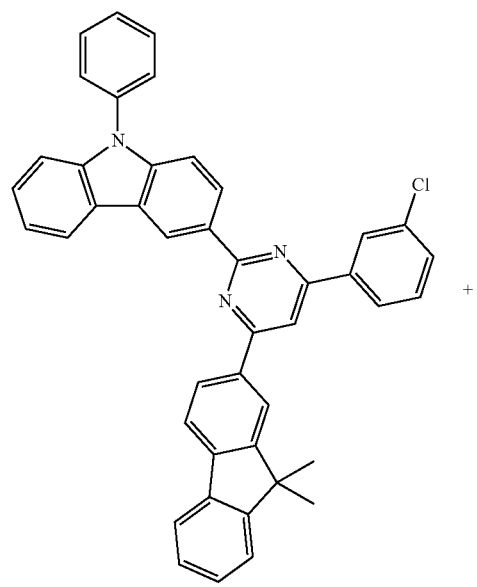

+

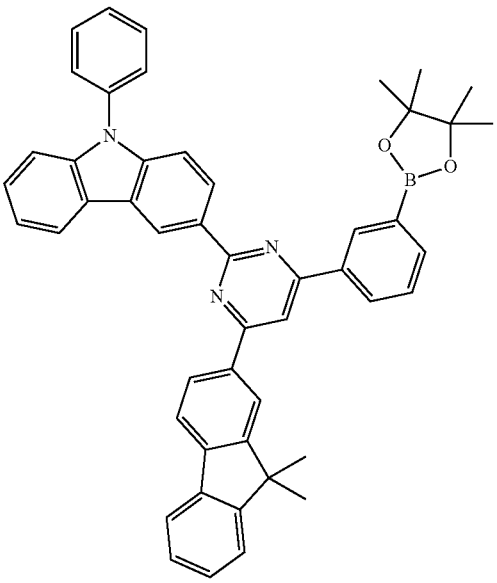

Z-1

Under nitrogen environment, 3-(4(3-chlorophenyl)-6-(9,9-dimethyl-9H-fluoren-2-yl)pyrimidin-2-yl)-9-phenyl-9H-carbazole (6.24 g, 10 mmol), which had been synthesized in <Step 3>, and 4,4,4',4',5,5,5',5'-octamethyl-2,2'-bi(1,3,2-dioxaborolane) (5.07 g, 20.0 mmol), Pd(dppf)Cl₂ (0.36 g, 5 mol %), XPhos (0.47 g, 1 mmol), KOAc (1.96 g, 20 mmol) and 1,4-Dioxane (100 ml) were mixed and then heated to reflux for 8 hours. After the reaction was completed, the mixture was cooled to room temperature, extraction was performed with methylene chloride, MgSO₄ was added to the extracted material, and the resultant material was filtered. After removing the solvent from the obtained organic layer, the target compound, Compound Z-1 (3.57 g, yield 50%), was obtained through column chromatography.

1H-NMR: δ 1.20 (s, 12H), 1.69 (s, 6H), 7.16 (t, 1H), 7.35 (m, 3H), 7.55 (m, 8H), 7.85 (m, 9H), 8.09 (d, 1H), 8.23 (s, 1H), 8.55 (d, 1H)

[Preparation Example 2] Synthesis of Compound Z-2

<Step 1> Synthesis of 2,4-dichloro-6-(triphenylen-2-yl)-1,3,5-triazine

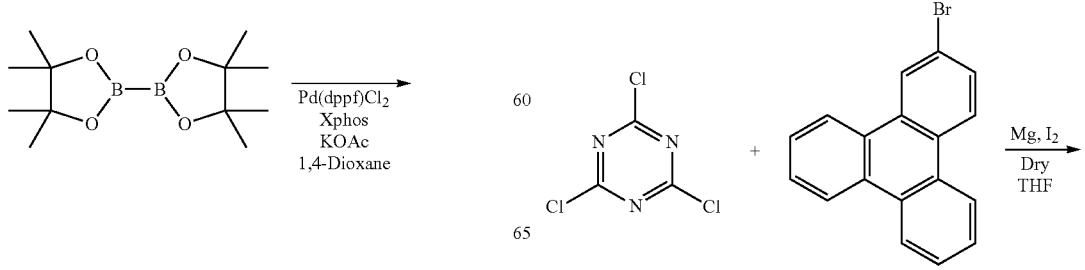

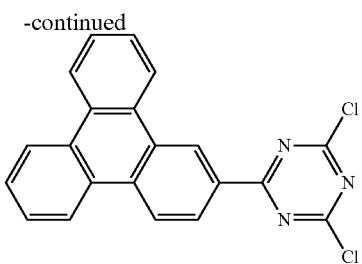

A solution was prepared by dissolving Mg (0.24 g, 10 mmol) and I₂ (0.1 g) in dry THF (30 mL), adding 2-bromotriphenylene (3.07 g, 10 mmol) thereto, and then refluxing the mixture for 2 hours. 2,4,6-trichloro-1,3,5-triazine (1.84 g, 10 mmol) was dissolved in dry THF (30 mL) and cooled to 0° C., the previously prepared solution was then slowly added thereto for 1 hour, and the mixture was stirred for 2 hours. After the reaction was completed, the organic layer was dried over MgSO₄, concentrated under reduced pressure, and purified with hexane, thereby obtaining a compound 2,4-dichloro-6-(triphenylen-2-yl)-1,3,5-triazine (2.06 g, yield 55%).

1H-NMR: δ 7.60 (m, 6H), 8.15 (d, 1H), 8.30 (m, 2H), 9.27 (s, 1H), 9.60 (d, 1H)

<Step 2> Synthesis of 2-([1,1':2',1''-terphenyl]-3-yl)-4-chloro-6-(triphenylen-2-yl)-1,3,5-triazine

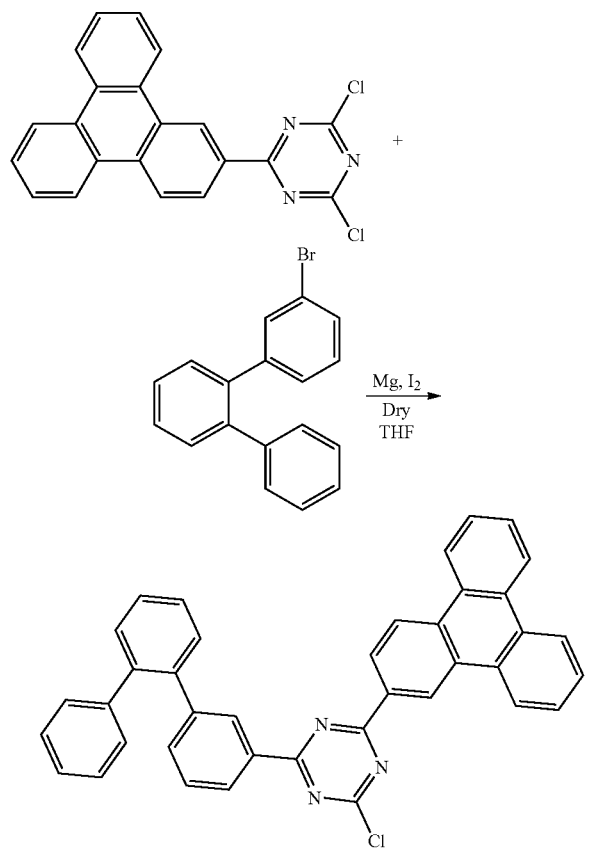

A solution was prepared by dissolving Mg (0.24 g, 10 mmol) and I₂ (0.1 g) in dry THF (30 mL), adding 3-bromo-1,1':2',1''-terphenyl (3.09 g, 10 mmol) thereto, and then refluxing the mixture for 2 hours. 2,4-dichloro-6-(triphenylen-2-yl)-1,3,5-triazine (3.76 g, 10 mmol), which had been synthesized in <Step 1> was dissolved in dry THF (30 mL) and cooled to 0° C., the previously prepared solution was then slowly added thereto for 1 hour, and the mixture was stirred for 2 hours. After the reaction was completed, the organic layer was dried over MgSO₄, concentrated under reduced pressure, and recrystallized with methanol, thereby obtaining a compound 2-([1,1':2',1''-terphenyl]-3-yl)-4-chloro-6-(triphenylen-2-yl)-1,3,5-triazine (2.85 g, yield 50%).

1H-NMR: δ 7.50 (m, 15H), 7.95 (m, 3H), 8.15 (d, 1H), 8.31 (m, 3H), 9.27 (s, 1H), 9.60 (d, 1H)

<Step 3> Synthesis of Compound Z-2

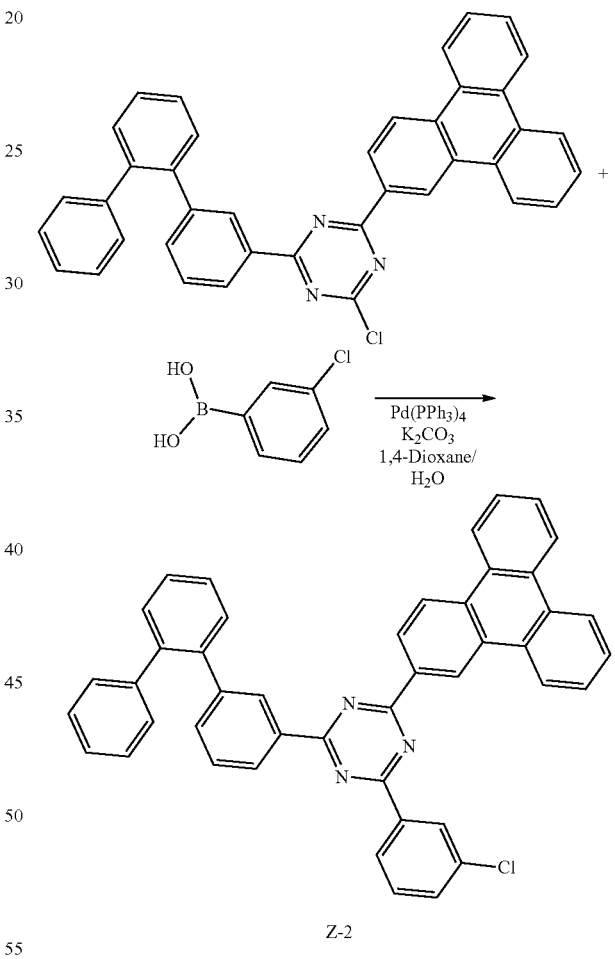

The same process as in <Step 3> of [Preparation Example 1] was carried out, except that 2-([1,1':2',1''-terphenyl]-3-yl)-4-chloro-6-(triphenylen-2-yl)-1,3,5-triazine (5.70 g, 10.0 mmol) was used instead of 2-chloro-4-(3-chlorophenyl)-6-(9,9-dimethyl-9H-fluoren-2-yl)pyrimidine, and that (3-chlorophenyl)boronic acid (1.56 g, 10.0 mmol) was used instead of (9-phenyl-9H-carbazol-3-yl)boronic acid, such that the target compound, Compound Z-2 (3.87 g, yield 60%), was obtained.

1H-NMR: δ 7.50 (m, 17H), 7.95 (m, 4H), 8.15 (m, 2H), 8.31 (m, 3H), 9.27 (s, 1H), 9.60 (d, 1H)

[Preparation Example 3] Synthesis of Compound Z-3

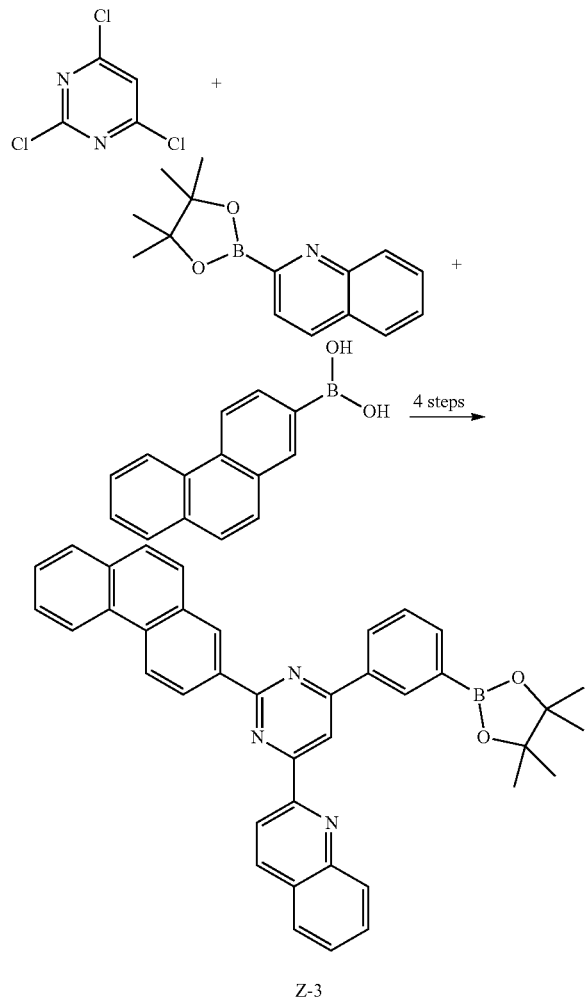

Z-3

The same process as in [Preparation Example 1] was carried out, except that 2-(4,4,5,5-tetramethyl-1,3,2-dioxaborolan-2-yl)quinoline (2.55 g, 10.0 mmol) was used instead of (9,9-dimethyl-9H-fluoren-2-yl)boronic acid, and that phenanthren-2-ylboronic acid (2.22 g, 10.0 mmol) was used instead of (9-phenyl-9H-carbazol-3-yl)boronic acid, such that the target compound, Compound Z-3 (3.45 g, yield 59%), was obtained.

1H-NMR: δ 1.20 (s, 12H), 7.54 (m, 2H), 7.66 (m, 5H), 7.85 (m, 7H), 8.21 (d, 1H), 8.46 (s, 1H), 8.70 (m, 2H), 9.11 (d, 1H), 9.19 (s, 1H)

[Preparation Example 4] Synthesis of Compound Z-4

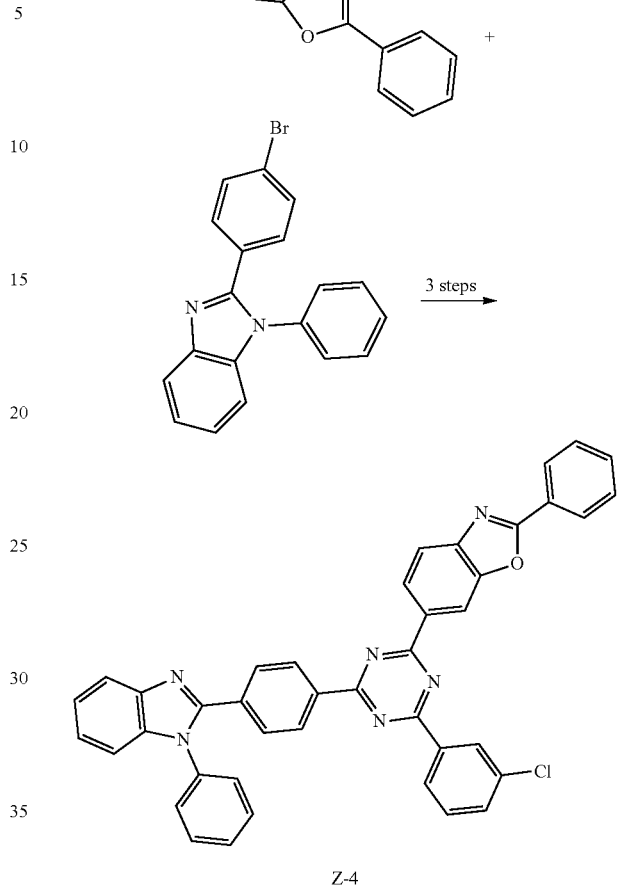

Z-4

The same process as in [Preparation Example 2] was carried out, except that 6-bromo-2-phenylbenzo[d]oxazole (2.74 g, 10.0 mmol) was used instead of 2-bromotriphenylene, and that 2-(4-bromophenyl)-1-phenyl-1H-benzo[d]imidazole (3.49 g, 10.0 mmol) was used instead of 3-bromo-1,1':2',1''-terphenyl, such that the target compound, Compound Z-4 (3.78 g, yield 58%), was obtained.

1H-NMR: δ 7.30 (m, 3H), 7.50 (m, 10H), 7.80 (m, 3H), 7.96 (m, 5H), 8.16 (m, 3H), 8.56 (d, 1H)

[Preparation Example 5] Synthesis of Compound Z-5

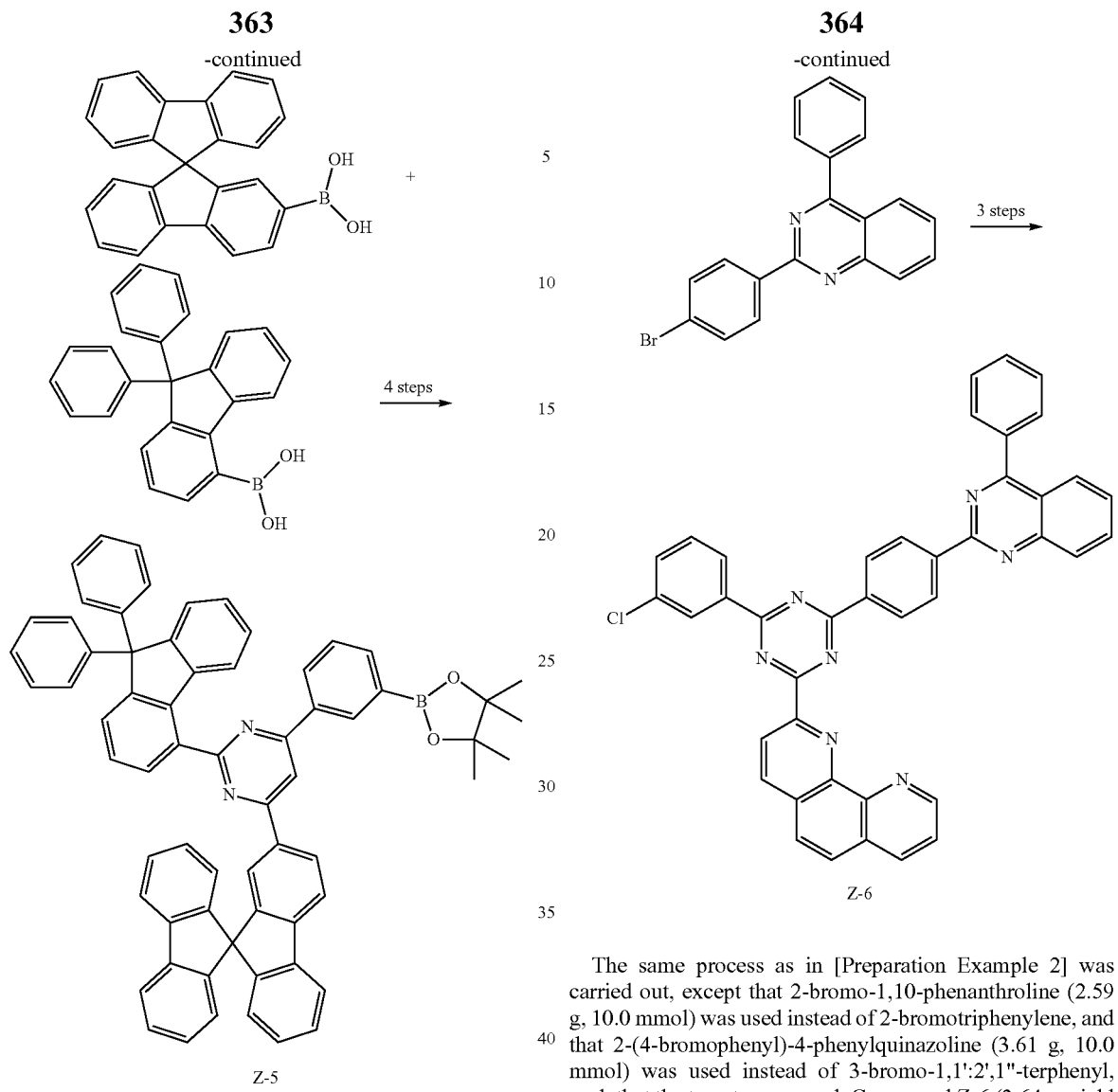

Z-5

Z-6

The same process as in [Preparation Example 1] was carried out, except that 9,9'-spirobi[fluoren]-2-ylboronic acid (3.60 g, 10.0 mmol) was used instead of (9,9-dimethyl-9H-fluoren-2-yl)boronic acid, and that (9,9-diphenyl-9H-fluoren-4-yl)boronic acid (3.62 g, 10.0 mmol) was used instead of (9-phenyl-9H-carbazol-3-yl)boronic acid, such that the target compound, Compound Z-5 (5.20 g, yield 57%), was obtained.

1H-NMR: δ 1.20 (s, 12H), 7.20 (m, 16H), 7.40 (m, 8H), 7.67 (m, 2H), 7.89 (m, 9H), 8.09 (d, 1H), 8.23 (s, 1H)

[Preparation Example 6] Synthesis of Compound Z-6

The same process as in [Preparation Example 2] was carried out, except that 2-bromo-1,10-phenanthroline (2.59 g, 10.0 mmol) was used instead of 2-bromotriphenylene, and that 2-(4-bromophenyl)-4-phenylquinazoline (3.61 g, 10.0 mmol) was used instead of 3-bromo-1,1':2',1"-terphenyl, such that the target compound, Compound Z-6 (3.64 g, yield 56%), was obtained.

1H-NMR: δ 7.50 (m, 8H), 7.90 (m, 10H), 8.10 (m, 3H), 8.45 (d, 1H), 8.65 (d, 1H), 8.80 (d, 1H)

[Preparation Example 7] Synthesis of Compound Z-7

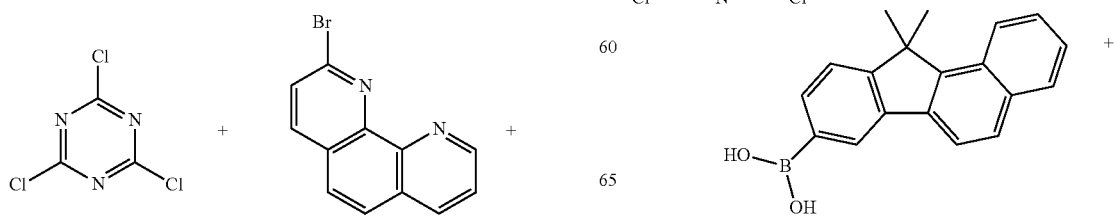

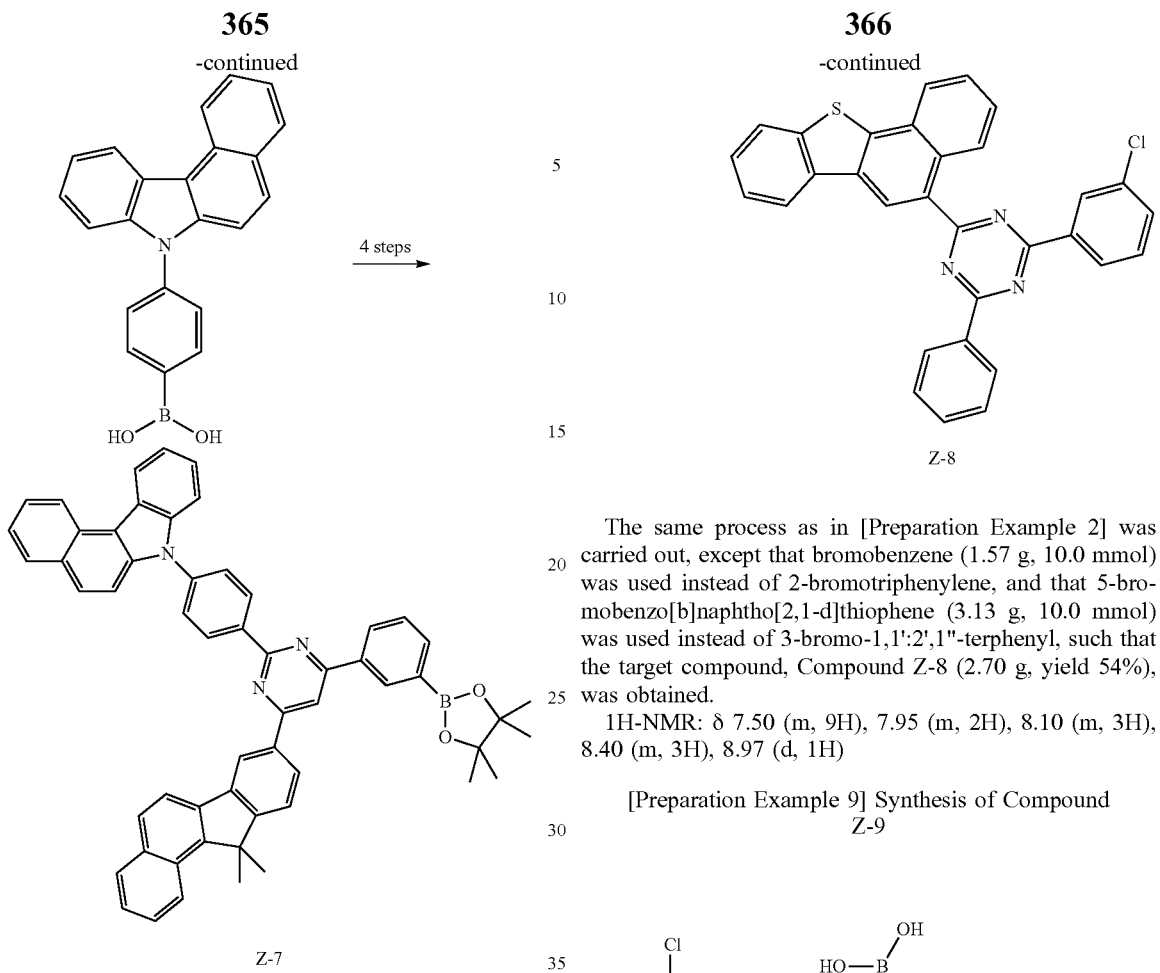

The same process as in [Preparation Example 1] was carried out, except that (11,11-dimethyl-11H-benzo[a]fluoren-8-yl)boronic acid (2.88 g, 10.0 mmol) was used instead of (9,9-dimethyl-9H-fluoren-2-yl)boronic acid, and that (4-(7H-benzo[c]carbazol-7-yl)phenyl)boronic acid (3.37 g, 10.0 mmol) was used instead of (9-phenyl-9H-carbazol-3-yl)boronic acid, such that the target compound, Compound Z-7 (4.48 g, yield 55%), was obtained.

1H-NMR: δ 1.20 (s, 12H), 1.82 (s, 6H), 7.30 (m, 2H), 7.50 (m, 8H), 7.90 (m, 11H), 8.05 (m, 2H), 8.19 (m, 3H), 8.50 (m, 2H)

[Preparation Example 8] Synthesis of Compound Z-8

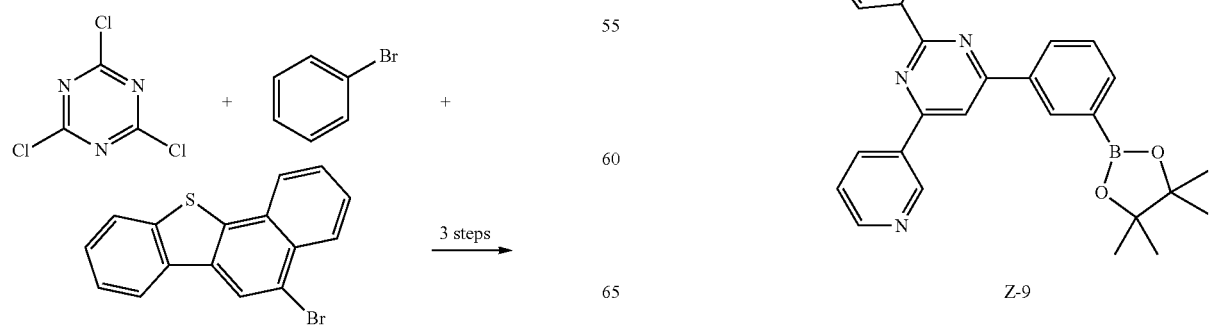

The same process as in [Preparation Example 2] was carried out, except that bromobenzene (1.57 g, 10.0 mmol) was used instead of 2-bromotriphenylene, and that 5-bromobenzo[b]naphtho[2,1-d]thiophene (3.13 g, 10.0 mmol) was used instead of 3-bromo-1,1':2',1''-terphenyl, such that the target compound, Compound Z-8 (2.70 g, yield 54%), was obtained.

1H-NMR: δ 7.50 (m, 9H), 7.95 (m, 2H), 8.10 (m, 3H), 8.40 (m, 3H), 8.97 (d, 1H)

[Preparation Example 9] Synthesis of Compound Z-9

The same process as in [Preparation Example 1] was carried out, except that pyridin-3-ylboronic acid (1.22 g, 10.0 mmol) was used instead of (9,9-dimethyl-9H-fluoren-2-yl)boronic acid, and that naphtho[2,1-b]benzofuran-10-ylboronic acid (2.62 g, 10.0 mmol) was used instead of (9-phenyl-9H-carbazol-3-yl)boronic acid, such that the target compound, Compound Z-9 (3.05 g, yield 53%), was obtained.

1H-NMR: δ 1.20 (s, 12H), 7.50 (m, 7H), 7.80 (m, 5H), 7.99 (d, 1H), 8.50 (m, 4H), 9.24 (s, 1H)

[Preparation Example 10] Synthesis of Compound Z-10

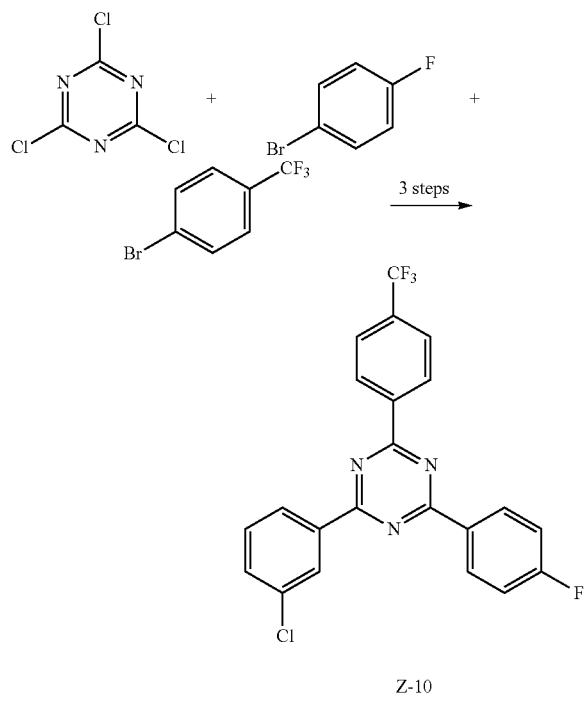

Z-10

The same process as in [Preparation Example 2] was carried out, except that 1-bromo-4-fluorobenzene (1.75 g, 10.0 mmol) was used instead of 2-bromotriphenylene, and that 1-bromo-4-(trifluoromethyl)benzene (2.25 g, 10.0 mmol) was used instead of 3-bromo-1,1':2',1''-terphenyl, such that the target compound, Compound Z-10 (2.23 g, yield 52%), was obtained.

1H-NMR: δ 7.31 (m, 2H), 7.48 (m, 2H), 7.70 (m, 4H), 7.97 (s, 1H), 8.17 (d, 1H), 8.50 (m, 2H)

[Preparation Example 11] Synthesis of Compound Z-11

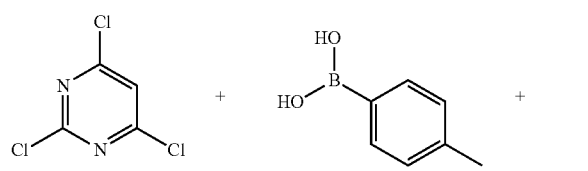

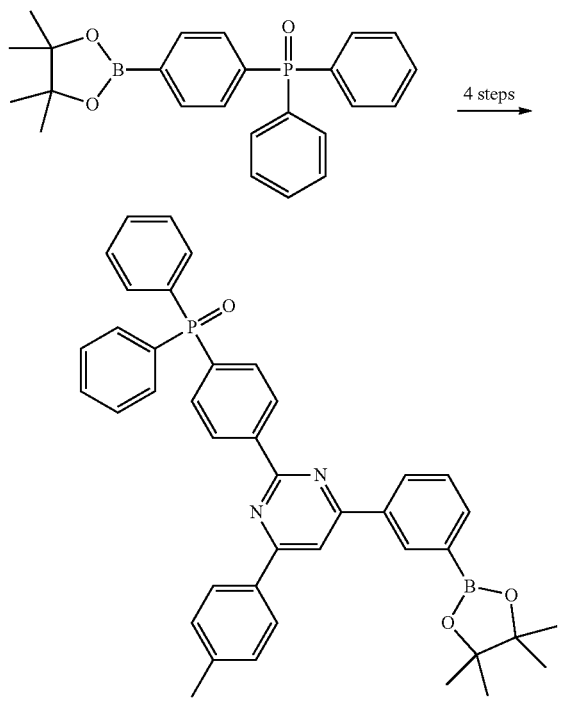

Z-11

The same process as in [Preparation Example 1] was carried out, except that p-tolylboronic acid (1.35 g, 10.0 mmol) was used instead of (9,9-dimethyl-9H-fluoren-2-yl) boronic acid, and that diphenyl(4-(4,4,5,5-tetramethyl-1,3,2-dioxaborolan-2-yl)phenyl)phosphine oxide (4.04 g, 10.0 mmol) was used instead of (9-phenyl-9H-carbazol-3-yl) boronic acid, such that the target compound, Compound Z-11 (3.30 g, yield 51%), was obtained.

1H-NMR: δ 1.20 (s, 12H), 2.34 (s, 3H), 7.15 (m, 2H), 7.50 (m, 9H), 7.67 (s, 1H), 7.80 (m, 6H), 7.96 (m, 4H), 8.23 (s, 1H)

[Preparation Example 12] Synthesis of Compound Z-12

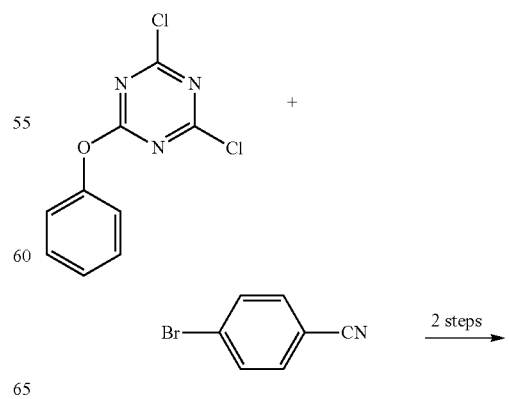

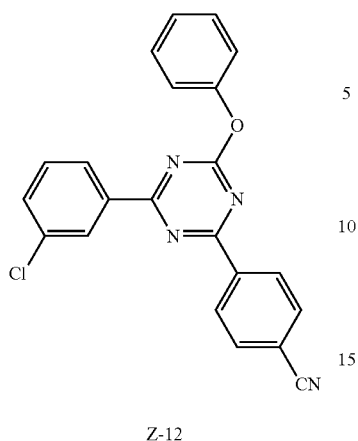

Z-12

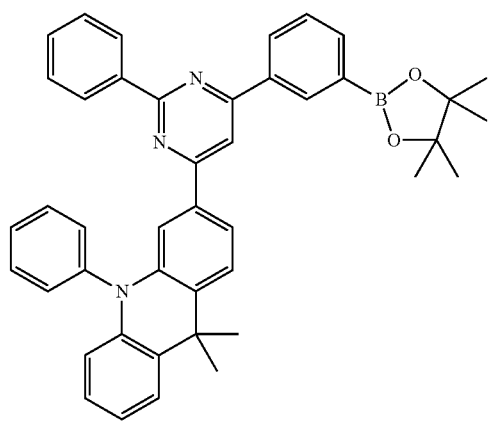

Z-13

The same process as in <Steps 2 and 3> of (Preparation Example 2] was carried out, except that 2,4-dichloro-6-phenoxy-1,3,5-triazine (2.42 g, 10.0 mmol) was used instead of 2,4-dichloro-6-(triphenylen-2-yl)-1,3,5-triazine, and that 4-bromobenzonitrile (1.82 g, 10.0 mmol) was used instead of 3-bromo-1,1':2',1''-terphenyl, such that the target compound, Compound Z-12 (1.92 g, yield 50%), was obtained.

1H-NMR: δ 7.00 (m, 3H), 7.29 (m, 2H), 7.48 (m, 2H), 7.82 (m, 2H), 7.95 (m, 3H), 8.16 (m, 1H)

[Preparation Example 13] Synthesis of Compound Z-13

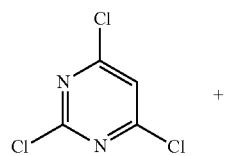

+

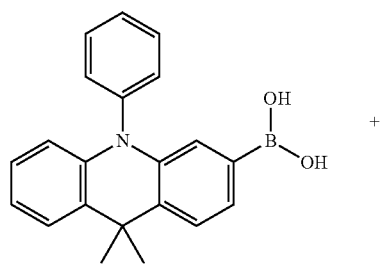

+

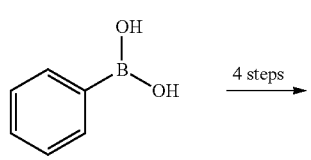

4 steps

The same process as in [Preparation Example 1] was carried out, except that (9,9-dimethyl-10-phenyl-9,10-dihydroacridin-3-yl)boronic acid (3.29 g, 10.0 mmol) was used instead of (9,9-dimethyl-9H-fluoren-2-yl)boronic acid, and that phenylboronic acid (1.21 g, 10.0 mmol) was used instead of (9-phenyl-9H-carbazol-3-yl)boronic acid, such that the target compound, Compound Z-13 (3.27 g, yield 51%), was obtained.

1H-NMR: δ 1.20 (s, 12H), 1.69 (s, 6H), 7.00 (m, 2H), 7.20 (m, 10H), 7.50 (m, 4H), 7.67 (s, 1H), 7.80 (m, 2H), 8.23 (s, 1H), 8.35 (m, 2H)

[Preparation Example 14] Synthesis of Compound Z-14

<Step 1> Synthesis of 4-chloro-6-(10H-phenoxazin-10-yl)-N,N-diphenyl-1,3,5-triazin-2-amine

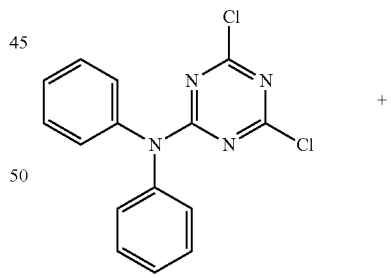

+

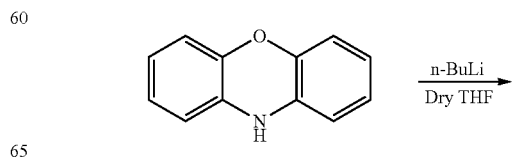

n-BuLi
Dry THF

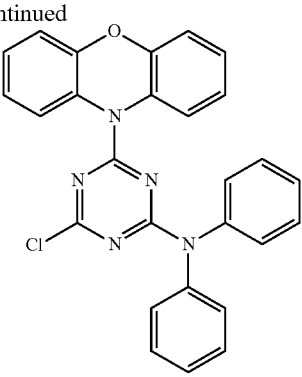

Under argon environment, after 10H-phenoxazine (1.83 g, 10.0 mmol) was dissolved in dry THF (60 ml), n-Butyl-lithium (1.6 M in hexane solution) (6.25 ml, 10.0 mmol) was slowly added thereto, and the mixture was stirred for 10 minutes. 4,6-dichloro-N,N-diphenyl-1,3,5-triazin-2-amine (3.17 g, 10.0 mmol) was dissolved in dry THF (50 mL), the previously prepared solution was then slowly added thereto for 10 minutes, and the mixture was heated to reflux for 6 hours and then cooled to room temperature. Water in an amount of 100 ml was added to the mixture, and the resultant mixture was filtered, washed with water and hexane, and purified with ethanol, such that a compound 4-chloro-6-(10H-phenoxazin-10-yl)-N,N-diphenyl-1,3,5-triazin-2-amine (2.41 g, yield 52%), was obtained.

1H-NMR: δ 7.00 (m, 4H), 7.20 (m, 14H)

<Step 2> Synthesis of Compound Z-14

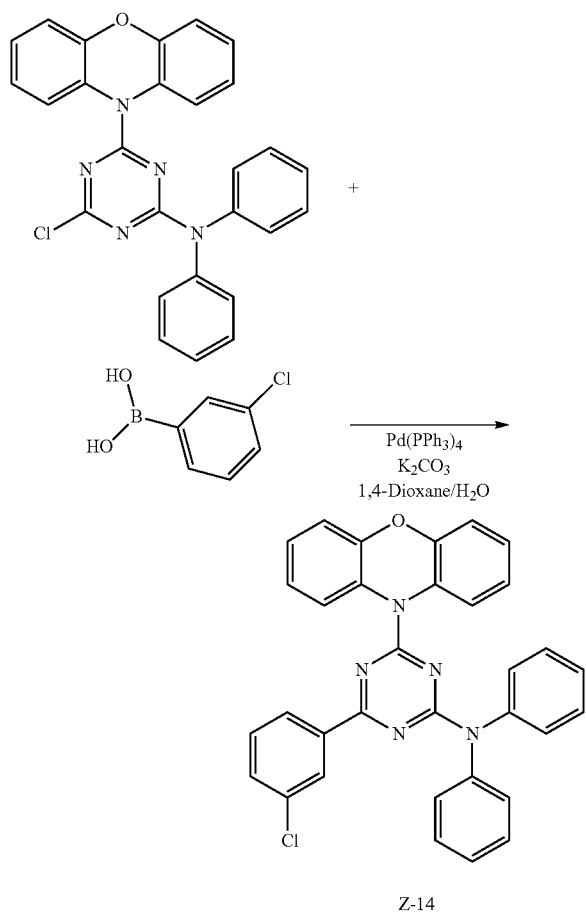

The same process as in <Step 3> of [Preparation Example 1] was carried out, except that 4-chloro-6-(10H-phenoxazin-10-yl)-N,N-diphenyl-1,3,5-triazin-2-amine (4.63 g, 10.0 mmol), which had been synthesized in <Step 1>, was used instead of 2-chloro-4-(3-chlorophenyl)-6-(9,9-dimethyl-9H-fluoren-2-yl)pyrimidine, and that (3-chlorophenyl)boronic acid (1.56 g, 10.0 mmol) was used instead of (9-phenyl-9H-carbazol-3-yl)boronic acid, such that the target compound, Compound Z-14 (2.86 g, yield 53%), was obtained.

1H-NMR: δ 7.00 (m, 4H), 7.20 (m, 14H), 7.48 (m, 2H), 7.97 (s, 1H), 8.16 (m, 1H)

[Preparation Example 15] Synthesis of Compound Z-15

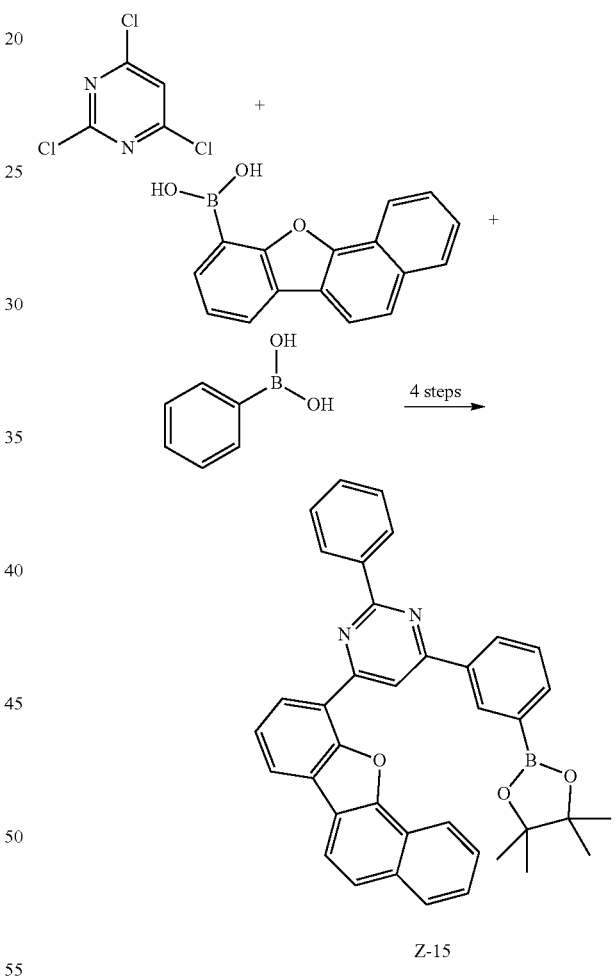

The same process as in [Preparation Example 1] was carried out, except that naphtho[1,2-b]benzofuran-10-ylboronic acid (2.62 g, 10.0 mmol) was used instead of (9,9-dimethyl-9H-fluoren-2-yl)boronic acid, and that phenylboronic acid (1.21 g, 10.0 mmol) was used instead of (9-phenyl-9H-carbazol-3-yl)boronic acid, such that the target compound, Compound Z-15 (3.10 g, yield 54%), was obtained.

1H-NMR: δ 1.20 (s, 12H), 7.50 (m, 6H), 7.70 (m, 3H), 7.85 (m, 3H), 8.10 (m, 3H), 8.23 (s, 1H), 8.35 (m, 2H)

[Preparation Example 16] Synthesis of Compound Z-16

[Synthesis Example 1] Synthesis of Compound 1

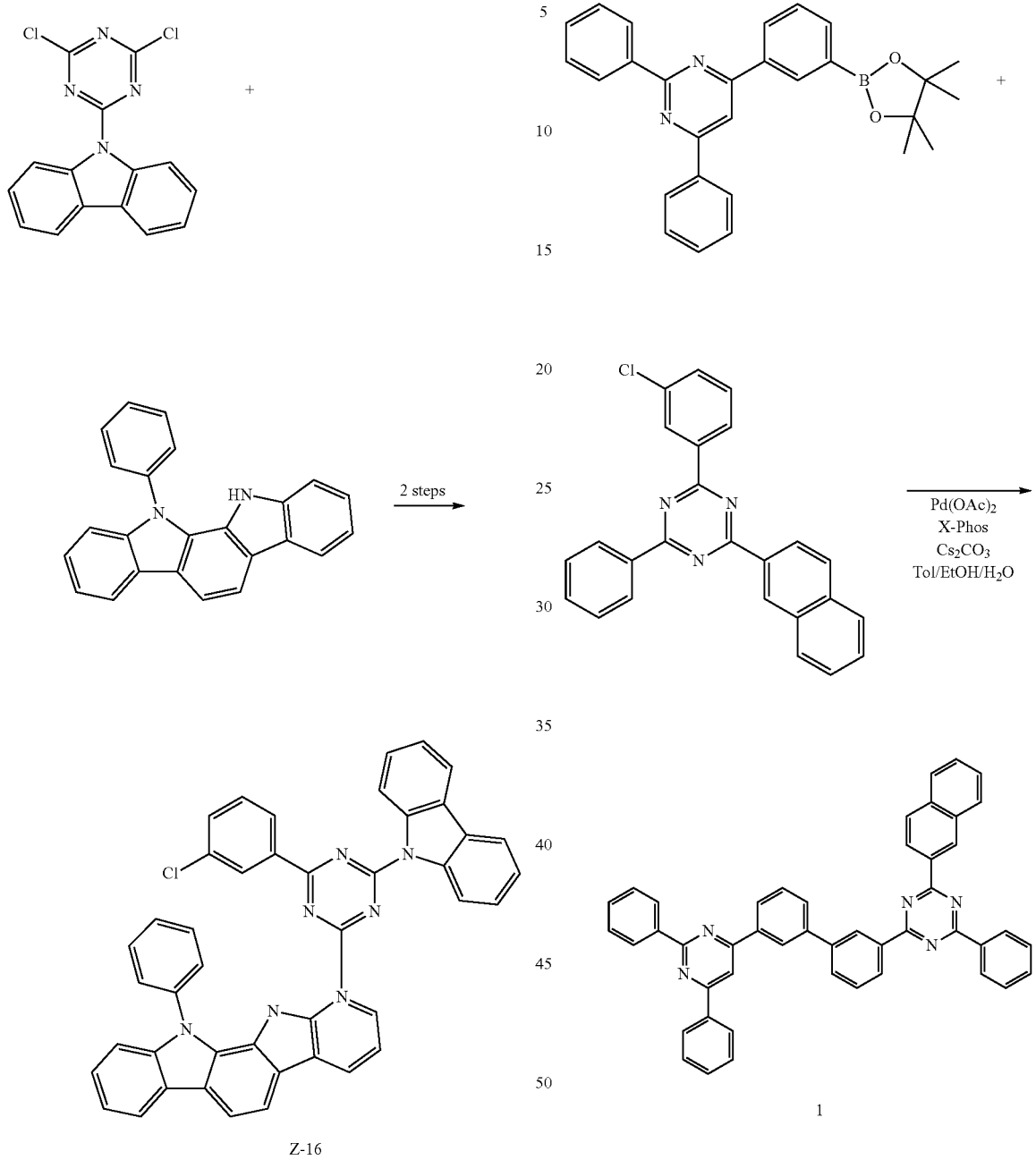

Z-16

1

The same process as in [Preparation Example 14] was carried out, except that 9-(4,6-dichloro-1,3,5-triazin-2-yl)-9H-carbazole (3.15 g, 10.0 mmol) was used instead of 4,6-dichloro-N,N-diphenyl-1,3,5-triazin-2-amine, and that 11-phenyl-11,12-dihydroindolo[2,3-a]carbazole (3.32 g, 10.0 mmol) was used instead of 10H-phenoxazine, such that the target compound, Compound Z-16 (3.77 g, yield 55%), was obtained.

1H-NMR: δ 7.20 (m, 4H), 7.35 (m, 3H), 7.50 (m, 10H), 7.95 (m, 4H), 8.15 (m, 3H), 8.55 (m, 3H)

Under nitrogen environment, 2,4-diphenyl-6-(3-(4,4,5,5-tetramethyl-1,3,2-dioxaborolan-2-yl)phenyl)pyrimidine (4.34 g, 10 mmol), 2-(3-chlorophenyl)-4-(naphthalen-2-yl)-6-phenyl-1,3,5-triazine (3.93 g, 10.0 mmol), Pd(OAc)$_2$ (0.11 g, 5 mol %), Xphos (0.47 g, 2 mmol), Cs$_2$CO$_3$ (6.51 g, 20 mmol) and Toluene/EtOH/H$_2$O (80 ml/40 ml/20 ml) were mixed and stirred at 100° C. for 6 hours. After the reaction was completed, extraction was performed with methylene chloride, MgSO$_4$ was added to the extracted material, and the resultant material was filtered. After removing the solvent from the obtained organic layer, the target compound, Compound 1 (3.72 g, yield 56%), was obtained through column chromatography.

[LCMS]: 665

[Synthesis Example 2] Synthesis of Compound 8

[Synthesis Example 3] Synthesis of Compound 186

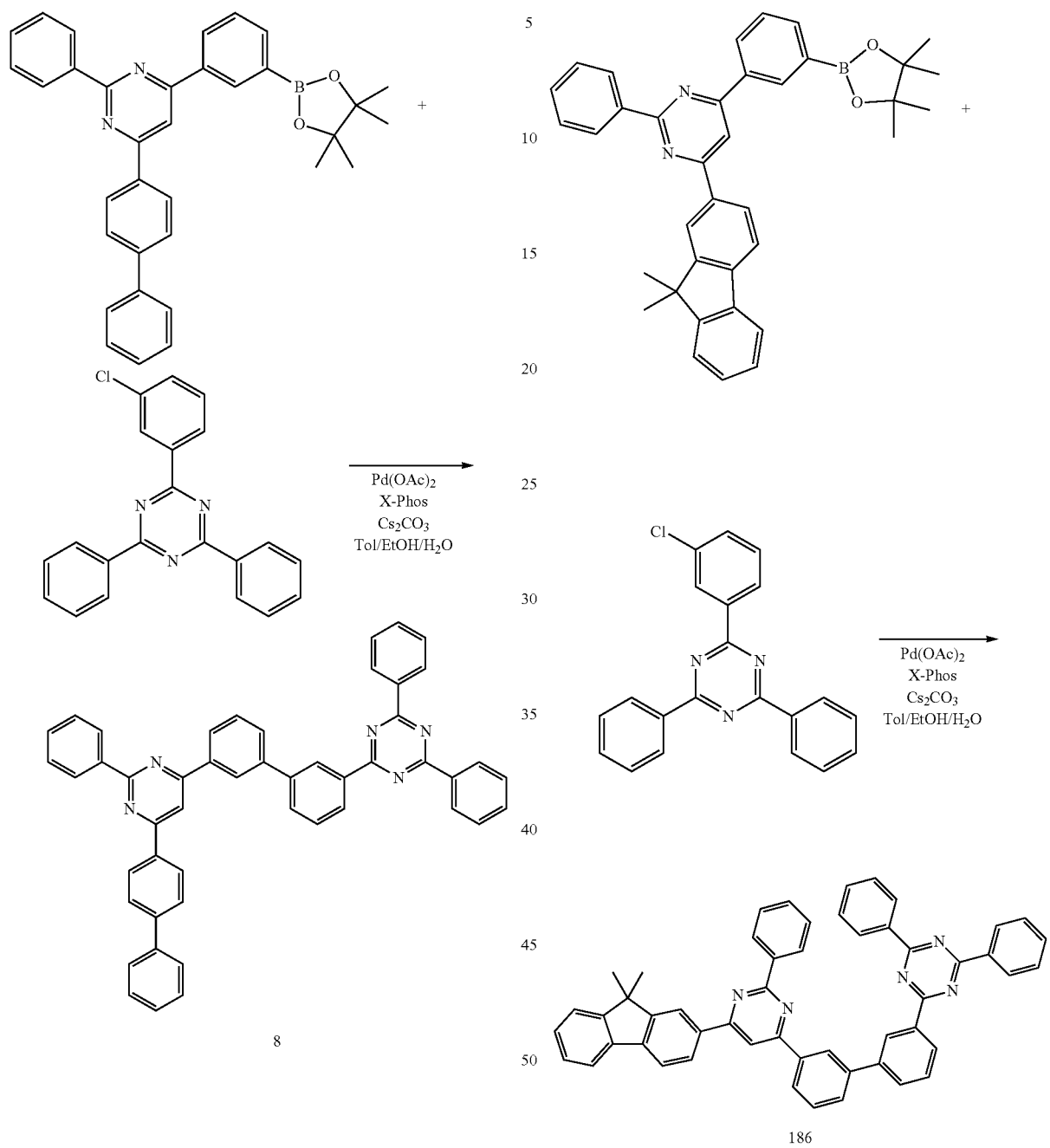

The same process as in [Synthesis Example 1] was carried out, except that 4-([1,1'-biphenyl]-4-yl)-2-phenyl-6-(3-(4,4,5,5-tetramethyl-1,3,2-dioxaborolan-2-yl)phenyl)pyrimidine (5.10 g, 10.0 mmol) was used instead of 2,4-diphenyl-6-(3-(4,4,5,5-tetramethyl-1,3,2-dioxaborolan-2-yl)pyrimidine, and that 2-(3-chlorophenyl)-4,6-diphenyl-1,3,5-triazine (3.43 g, 10.0 mmol) was used instead of 2-(3-chlorophenyl)-4-(naphthalen-2-yl)-6-phenyl-1,3,5-triazine, such that the target compound, Compound 8 (3.94 g, yield 57%), was obtained.

[LCMS]: 691

The same process as in [Synthesis Example 1] was carried out, except that 4-(9,9-dimethyl-9H-fluoren-2-yl)-2-phenyl-6-(3-(4,4,5,5-tetramethyl-1,3,2-dioxaborolan-2-yl)phenyl)pyrimidine (5.50 g, 10.0 mmol) was used instead of 2,4-diphenyl-6-(3-(4,4,5,5-tetramethyl-1,3,2-dioxaborolan-2-yl)phenyl)pyrimidine, and that 2-(3-chlorophenyl)-4,6-diphenyl-1,3,5-triazine (3.43 g, 10.0 mmol) was used instead of 2-(3-chlorophenyl)-4-(naphthalen-2-yl)-6-phenyl-1,3,5-triazine, such that the target compound, Compound 186 (4.24 g, yield 58%), was obtained.

[LCMS]: 731

[Synthesis Example 4] Synthesis of Compound 206

[Synthesis Example 5] Synthesis of Compound 219

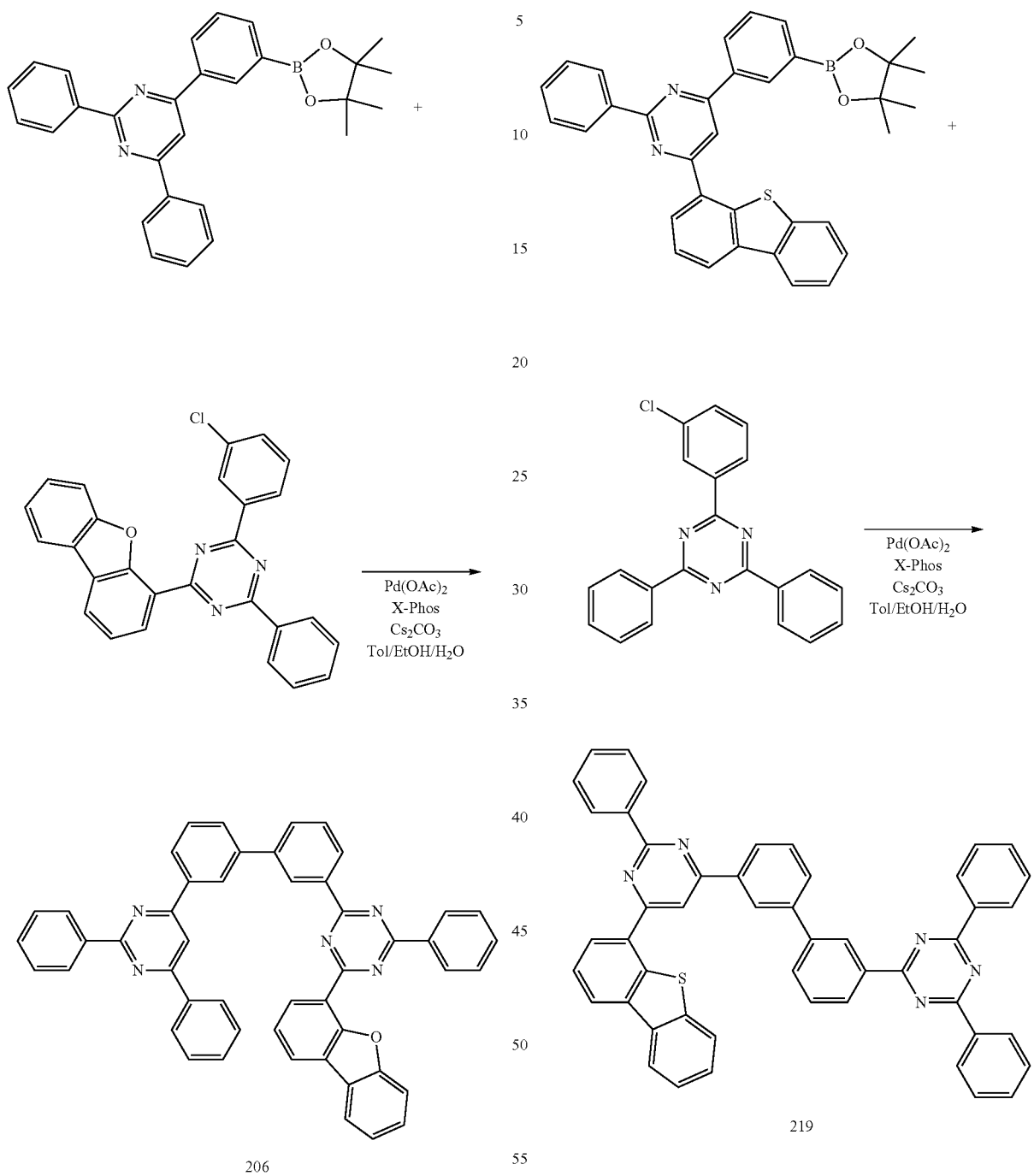

The same process as in [Synthesis Example 1] was carried out, except that 2-(3-chlorophenyl)-4-(dibenzo[b,d]furan-4-yl)-6-phenyl-1,3,5-triazine (4.33 g, 10.0 mmol) was used instead of 2-(3-chlorophenyl)-4-(naphthalen-2-yl)-6-phenyl-1,3,5-triazine, such that the target compound, Compound 206 (4.82 g, yield 59%), was obtained.

[LCMS]: 705

The same process as in [Synthesis Example 1] was carried out, except that 4-(dibenzo[b,d]thiophen-4-yl)-2-phenyl-6-(3-(4,4,5,5-tetramethyl-1,3,2-dioxaborolan-2-yl)phenyl)pyrimidine (5.40 g, 10.0 mmol) was used instead of 2,4-diphenyl-6-(3-(4,4,5,5-tetramethyl-1,3,2-dioxaborolan-2-yl)phenyl)pyrimidine, and that 2-(3-chlorophenyl)-4,6-diphenyl-1,3,5-triazine (3.43 g, 10.0 mmol) was used instead of 2-(3-chlorophenyl)-4-(naphthalen-2-yl)-6-phenyl-1,3,5-triazine, such that the target compound, Compound 219 (4.33 g, yield 60%), was obtained.

[LCMS]: 721

[Synthesis Example 6] Synthesis of Compound 311

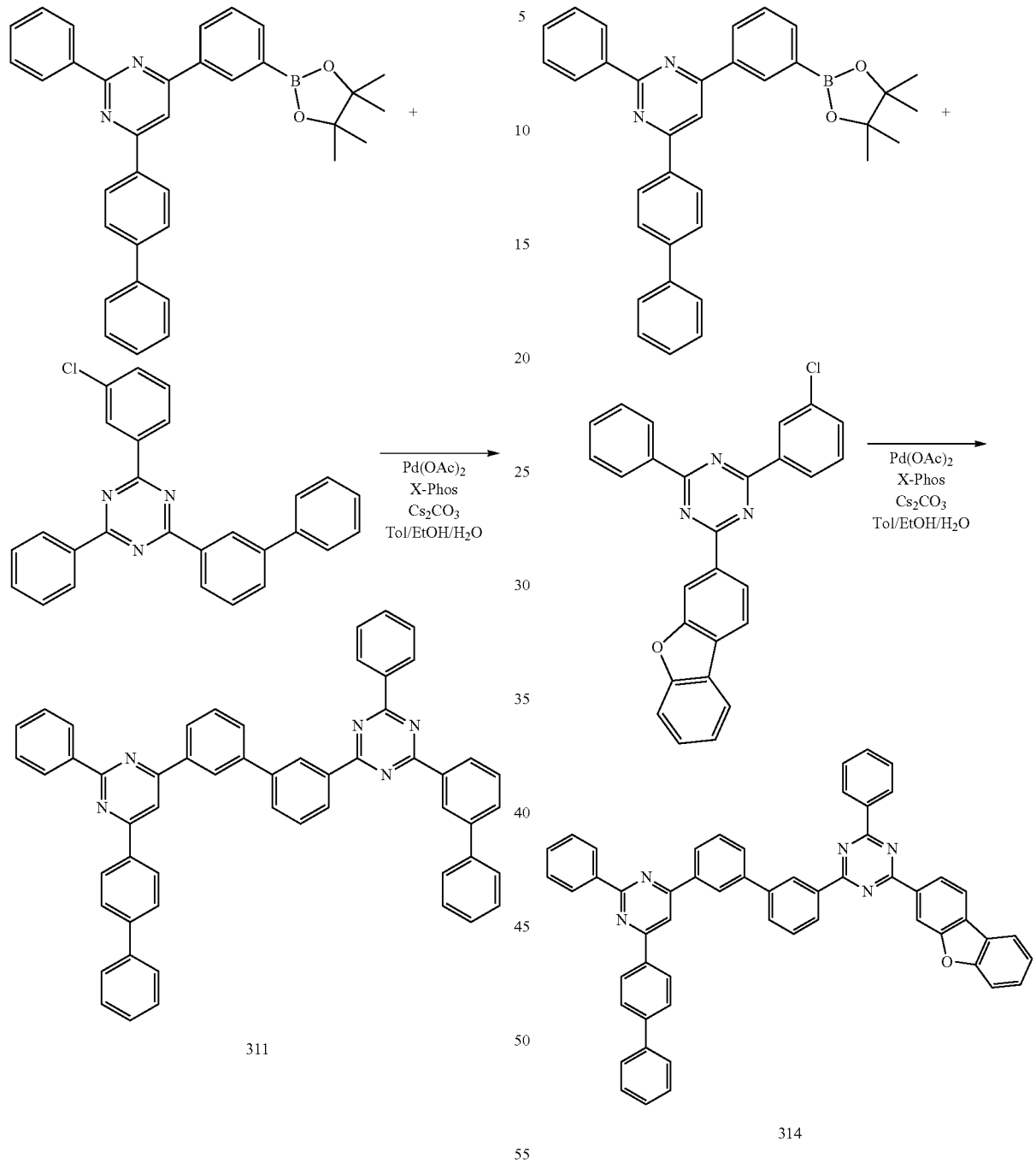

[Synthesis Example 7] Synthesis of Compound 314

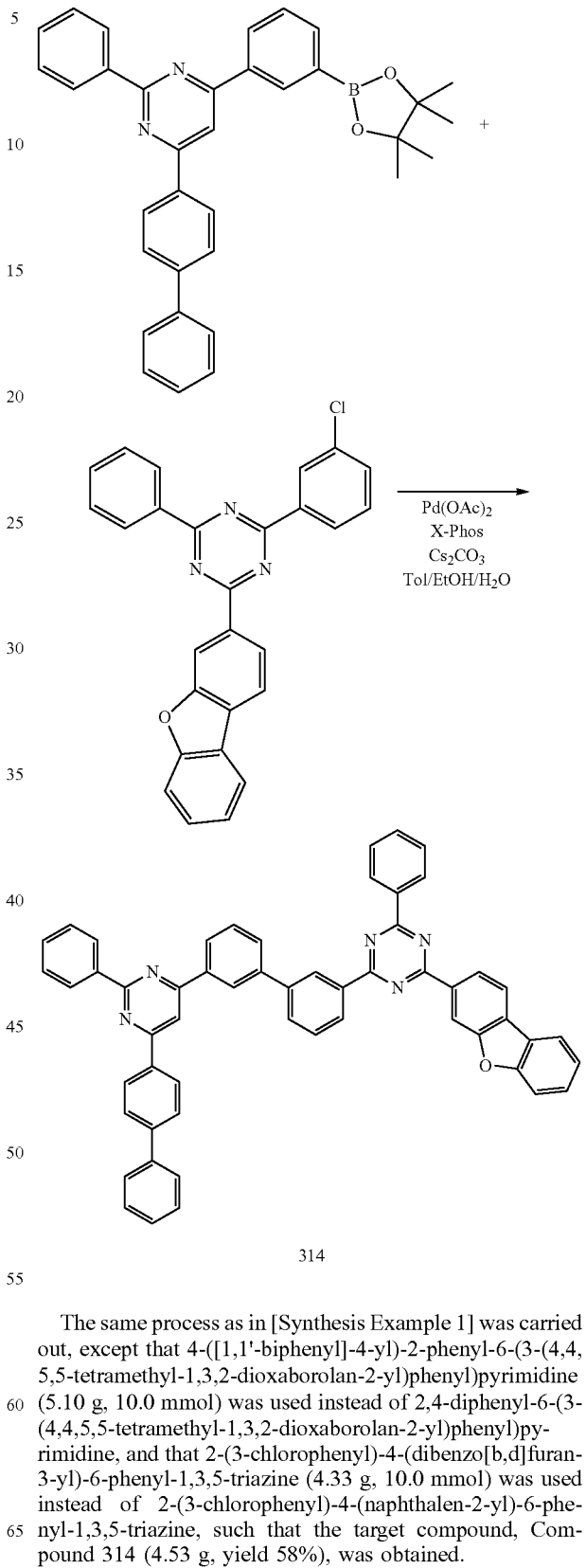

The same process as in [Synthesis Example 1] was carried out, except that 4-([1,1'-biphenyl]-4-yl)-2-phenyl-6-(3-(4,4,5,5-tetramethyl-1,3,2-dioxaborolan-2-yl)phenyl)pyrimidine (5.10 g, 10.0 mmol) was used instead of 2,4-diphenyl-6-(3-(4,4,5,5-tetramethyl-1,3,2-dioxaborolan-2-yl)phenyl)pyrimidine, and that 24 ([1,1'-biphenyl]-3-yl)-4-(3-chlorophenyl)-6-phenyl-1,3,5-triazine (4.19 g, 10.0 mmol) was used instead of 2-(3-chlorophenyl)-4-(naphthalen-2-yl)-6-phenyl-1,3,5-triazine, such that the target compound, Compound 311 (4.53 g, yield 59%), was obtained.

[LCMS]: 767

The same process as in [Synthesis Example 1] was carried out, except that 4-([1,1'-biphenyl]-4-yl)-2-phenyl-6-(3-(4,4,5,5-tetramethyl-1,3,2-dioxaborolan-2-yl)phenyl)pyrimidine (5.10 g, 10.0 mmol) was used instead of 2,4-diphenyl-6-(3-(4,4,5,5-tetramethyl-1,3,2-dioxaborolan-2-yl)phenyl)pyrimidine, and that 2-(3-chlorophenyl)-4-(dibenzo[b,d]furan-3-yl)-6-phenyl-1,3,5-triazine (4.33 g, 10.0 mmol) was used instead of 2-(3-chlorophenyl)-4-(naphthalen-2-yl)-6-phenyl-1,3,5-triazine, such that the target compound, Compound 314 (4.53 g, yield 58%), was obtained.

[LCMS]: 781

381
[Synthesis Example 8] Synthesis of Compound 687

382
[Synthesis Example 9] Synthesis of Compound 688

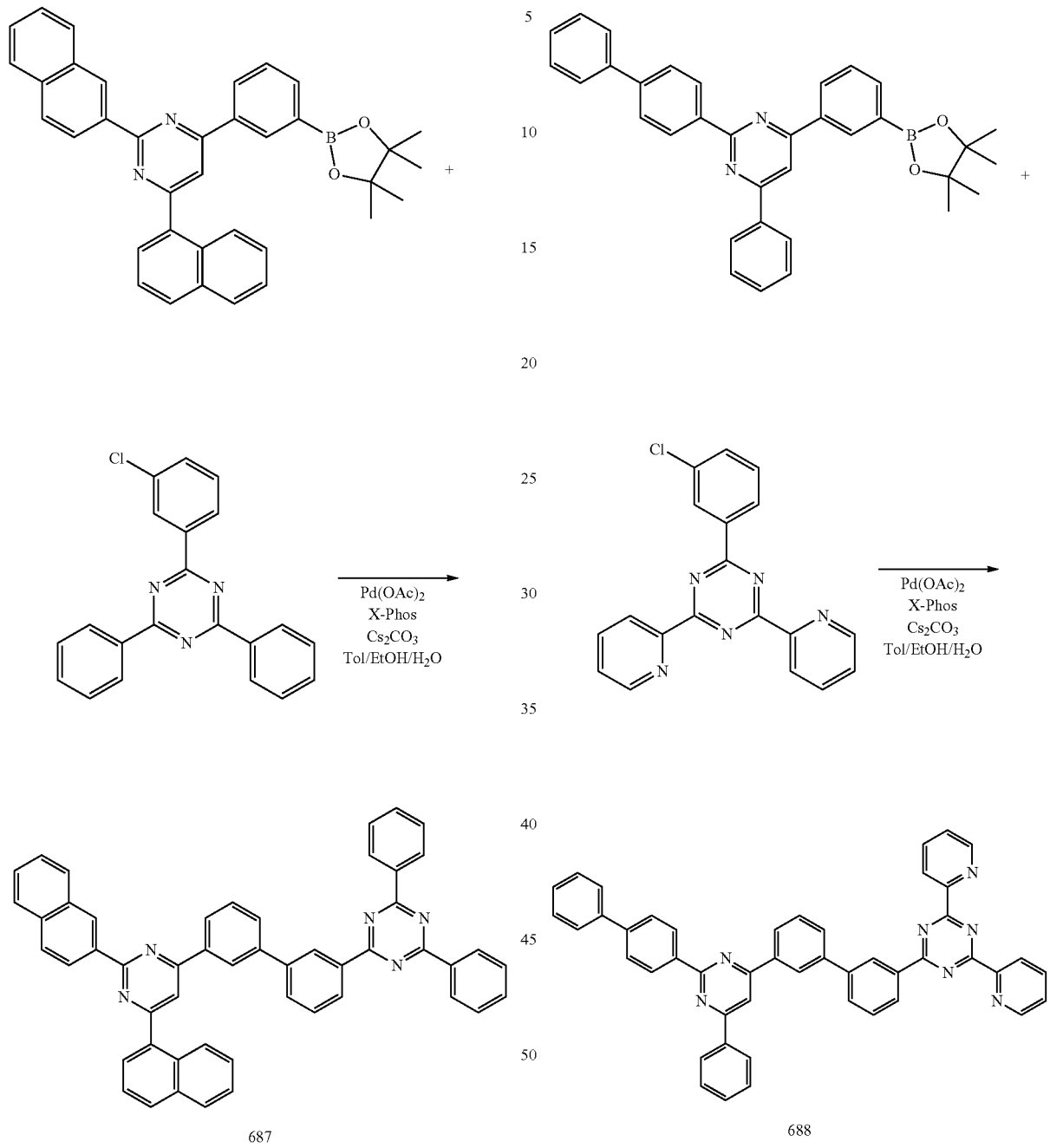

The same process as in [Synthesis Example 1] was carried out, except that 4-(naphthalen-1-yl)-2-(naphthalen-2-yl)-6-(3-(4,4,5,5-tetramethyl-1,3,2-dioxaborolan-2-yl)phenyl)pyrimidine (5.34 g, 10.0 mmol) was used instead of 2,4-diphenyl-6-(3-(4,4,5,5-tetramethyl-1,3,2-dioxaborolan-2-yl)phenyl)pyrimidine, and that 2-(3-chlorophenyl)-4,6-diphenyl-1,3,5-triazine (3.43 g, 10.0 mmol) was used instead of 2-(3-chlorophenyl)-4-(naphthalen-2-yl)-6-phenyl-1,3,5-triazine, such that the target compound, Compound 687 (4.08 g, yield 57%), was obtained.

[LCMS]: 715

The same process as in [Synthesis Example 1] was carried out, except that 2-([1,1'-biphenyl]-4-yl)-4-phenyl-6-(3-(4,4,5,5-tetramethyl-1,3,2-dioxaborolan-2-yl)phenyl)pyrimidine (5.10 g, 10.0 mmol) was used instead of 2,4-diphenyl-6-(3-(4,4,5,5-tetramethyl-1,3,2-dioxaborolan-2-yl)phenyl)pyrimidine, and that 2-(3-chlorophenyl)-4,6-di(pyridin-2-yl)-1,3,5-triazine (3.45 g, 10.0 mmol) was used instead of 2-(3-chlorophenyl)-4-(naphthalen-2-yl)-6-phenyl-1,3,5-triazine, such that the target compound, Compound 688 (3.88 g, yield 56%), was obtained.

[LCMS]: 693

[Synthesis Example 10] Synthesis of Compound 689
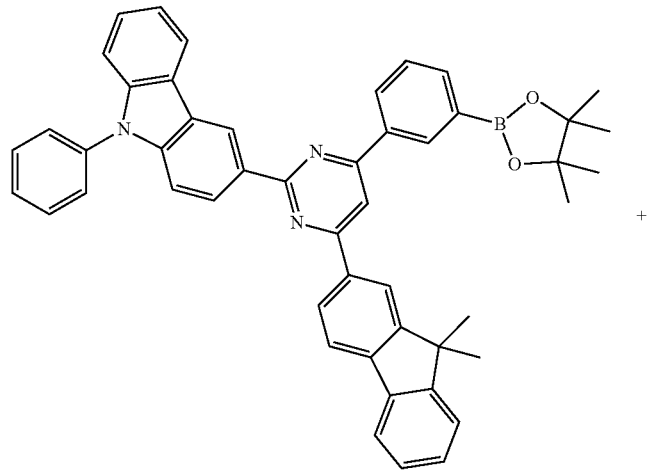
Z-1
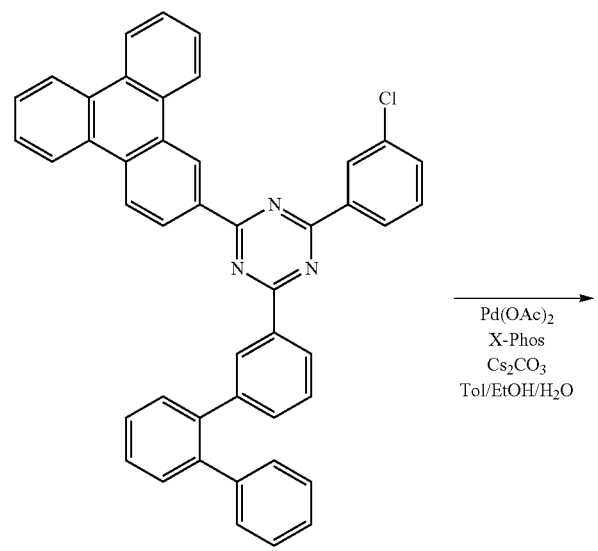
Z-2
Pd(OAc)₂
X-Phos
Cs₂CO₃
Tol/EtOH/H₂O

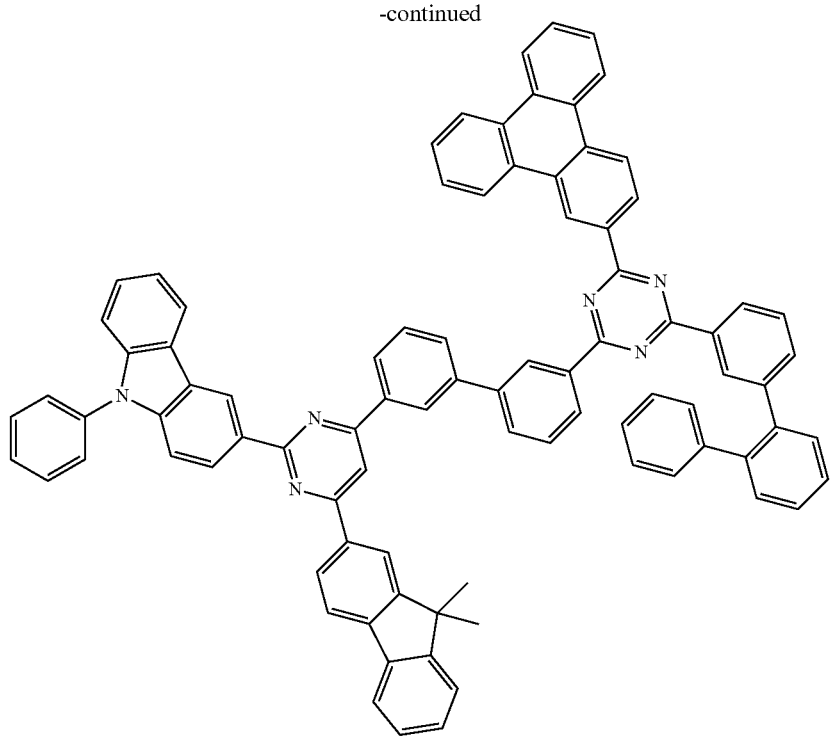

689

The same process as in [Synthesis Example 1] was carried out, except that Compound Z-1 (7.15 g, 10.0 mmol) was used instead of 2,4-diphenyl-6-(3-(4,4,5,5-tetramethyl-1,3,2-dioxaborolan-2-yl)phenyl)pyrimidine, and that Compound Z-2 (6.46 g, 10.0 mmol) was used instead of 2-(3-chlorophenyl)-4-(naphthalen-2-yl)-6-phenyl-1,3,5-triazine, such that the target compound, Compound 689 (6.59 g, yield 55%), was obtained.

[LCMS]: 1199

[Synthesis Example 11] Synthesis of Compound 690

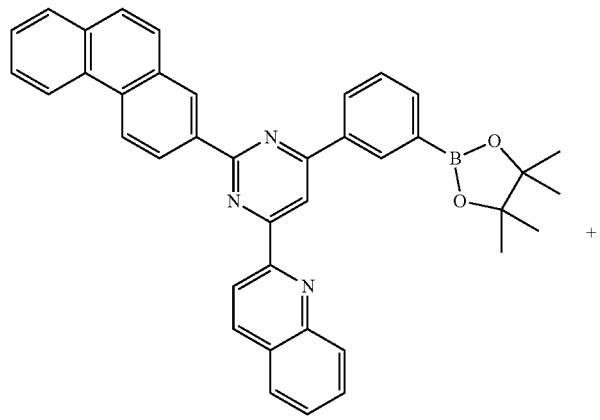

Z-3

-continued
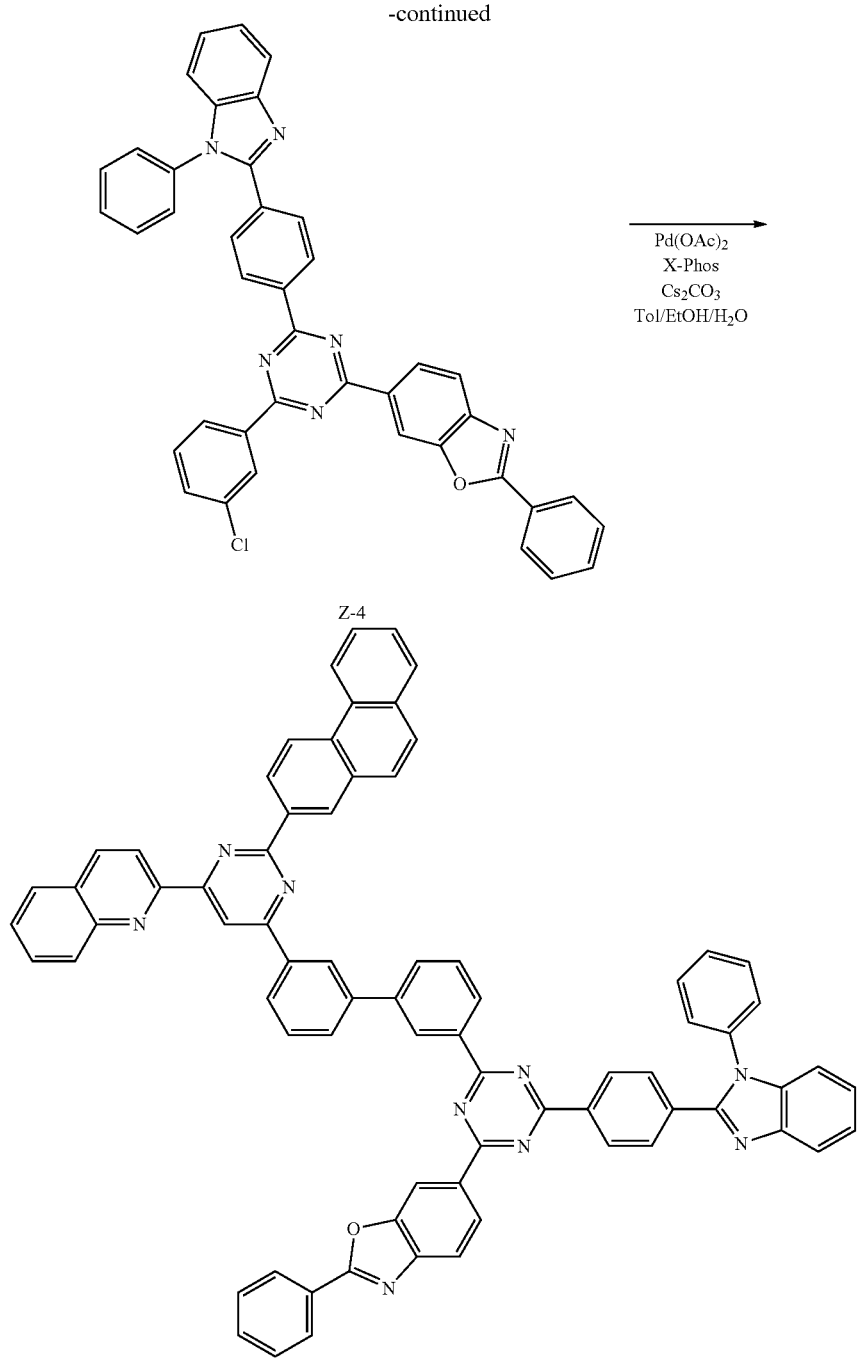
The same process as in [Synthesis Example 1] was carried out, except that Compound Z-3 (5.85 g, 10.0 mmol) was used instead of 2,4-diphenyl-6-(3-(4,4,5,5-tetramethyl-1,3,2-dioxaborolan-2-yl)phenyl)pyrimidine, and that Compound Z-4 (6.53 g, 10.0 mmol) was used instead of 2-(3-chlorophenyl)-4-(naphthalen-2-yl)-6-phenyl-1,3,5-triazine, such that the target compound, Compound 690 (5.81 g, yield 54%), was obtained.
[LCMS]: 1076

[Synthesis Example 12] Synthesis of Compound 691
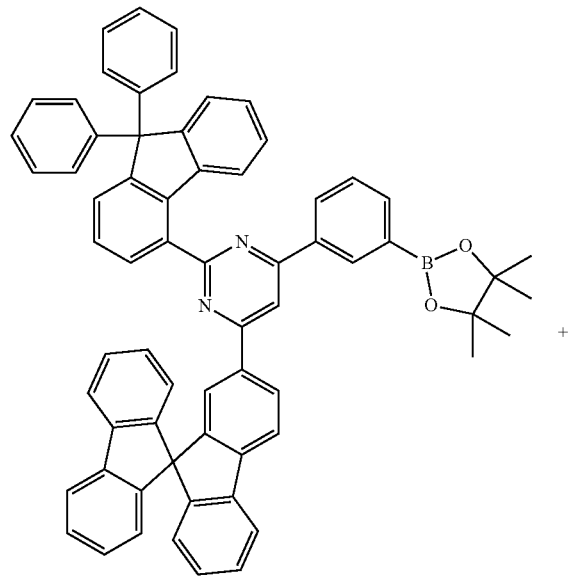
Z-5
+
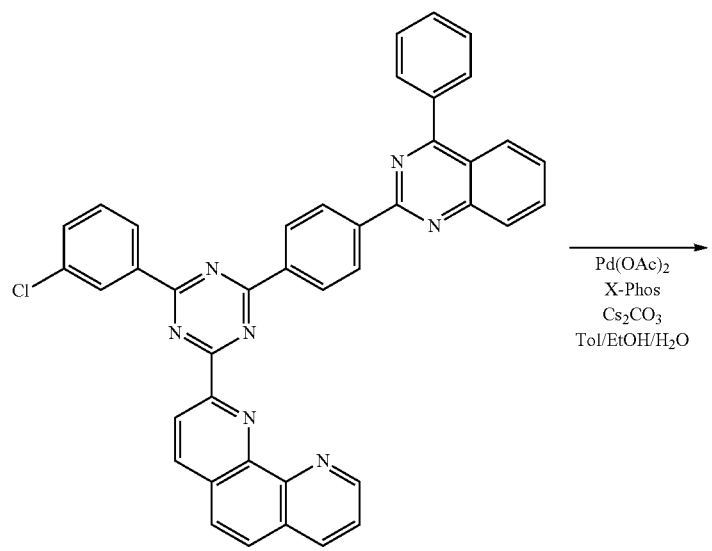
Z-6
→ Pd(OAc)₂
X-Phos
Cs₂CO₃
Tol/EtOH/H₂O

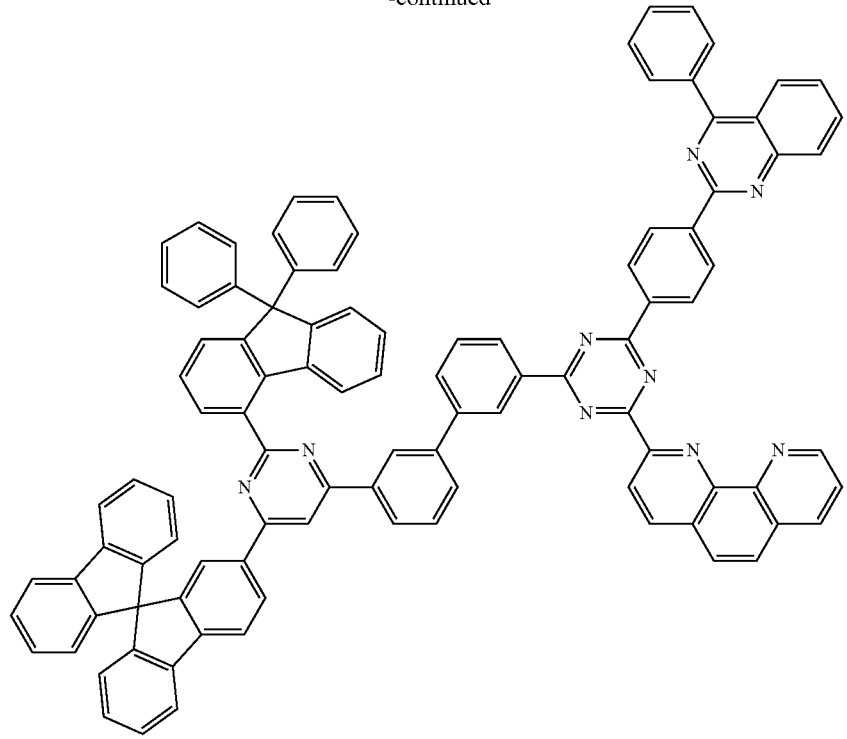

691

The same process as in [Synthesis Example 1] was carried out, except that Compound Z-5 (9.12 g, 10.0 mmol) was used instead of 2,4-diphenyl-6-(3-(4,4,5,5-tetramethyl-1,3,2-dioxaborolan-2-yl)phenyl)pyrimidine, and that Compound Z-6 (6.50 g, 10.0 mmol) was used instead of 2-(3-chlorophenyl)-4-(naphthalen-2-yl)-6-phenyl-1,3,5-triazine, such that the target compound, Compound 691 (7.42 g, yield 53%), was obtained.

[LCMS]: 1400

[Synthesis Example 13] Synthesis of Compound 692

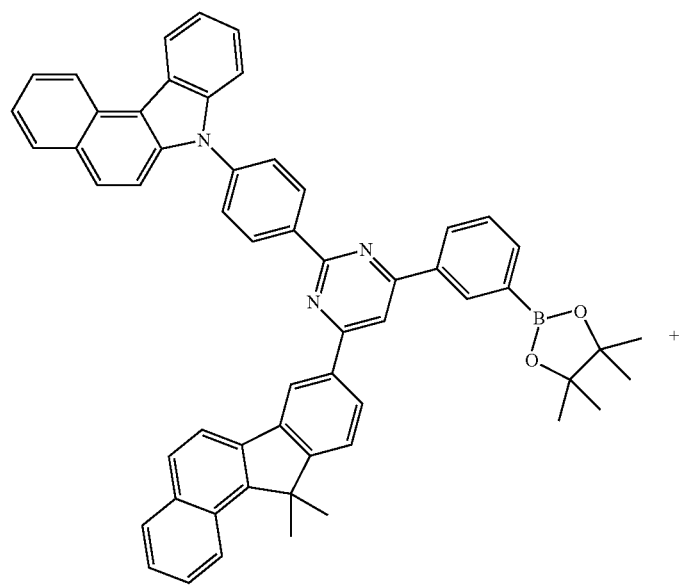

Z-7

-continued
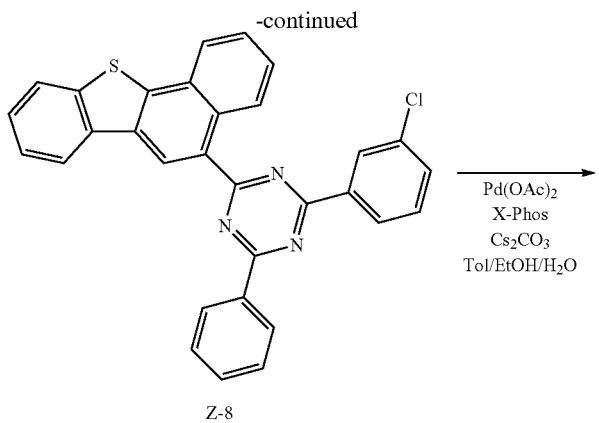
Z-8
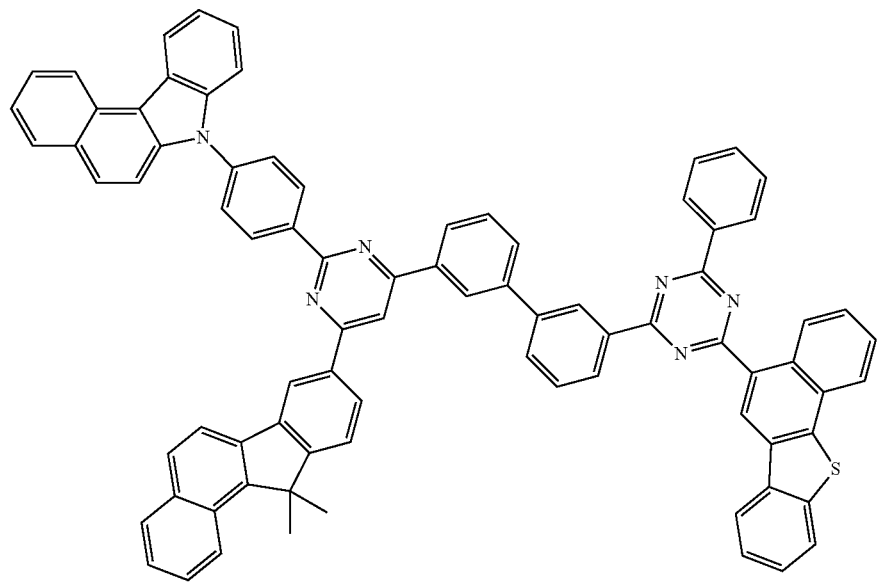
692
The same process as in [Synthesis Example 1] was carried out, except that Compound Z-7 (8.15 g, 10.0 mmol) was used instead of 2,4-diphenyl-6-(3-(4,4,5,5-tetramethyl-1,3,2-dioxaborolan-2-yl)phenyl)pyrimidine, and that Compound Z-8 (5.00 g, 10.0 mmol) was used instead of 2-(3-chlorophenyl)-4-(naphthalen-2-yl)-6-phenyl-1,3,5-triazine, such that the target compound, Compound 692 (5.99 g, yield 52%), was obtained.
[LCMS]: 1153

[Synthesis Example 14] Synthesis of Compound 693

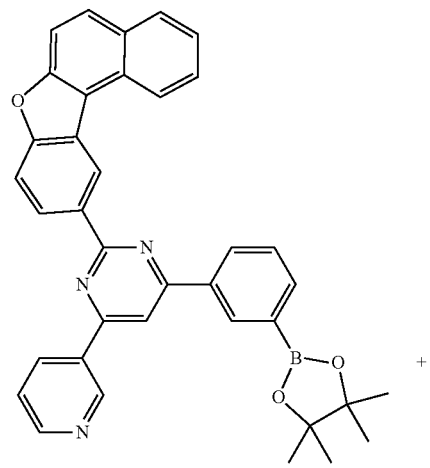

Z-9

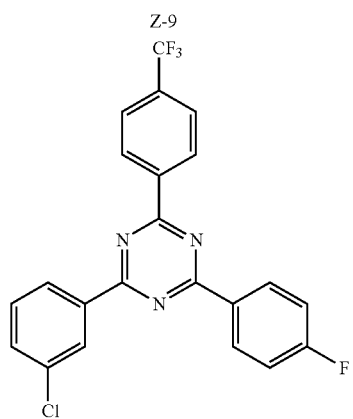

Z-10

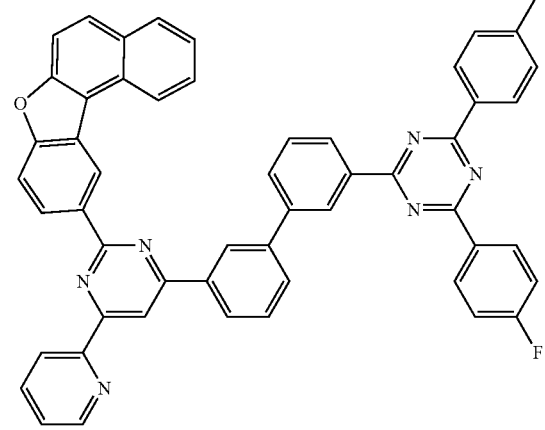

693

The same process as in [Synthesis Example 1] was carried out, except that Compound Z-9 (5.75 g, 10.0 mmol) was used instead of 2,4-diphenyl-6-(3-(4,4,5,5-tetramethyl-1,3,2-dioxaborolan-2-yl)phenyl)pyrimidine, and that Compound Z-10 (4.29 g, 10.0 mmol) was used instead of 2-(3-chlorophenyl)-4-(naphthalen-2-yl)-6-phenyl-1,3,5-triazine, such that the target compound, Compound 693 (4.29 g, yield 51%), was obtained.

[LCMS]: 842

[Synthesis Example 15] Synthesis of Compound 694

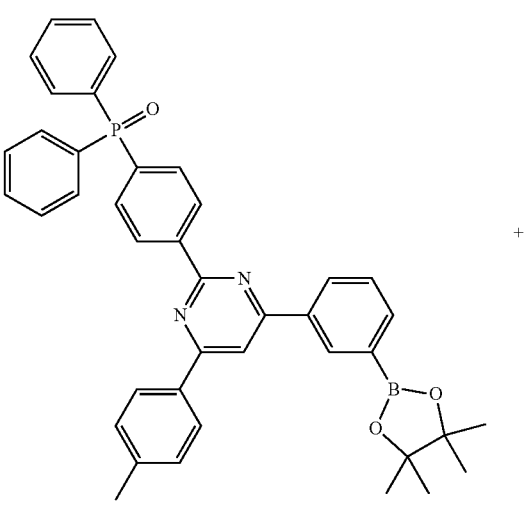

Z-11

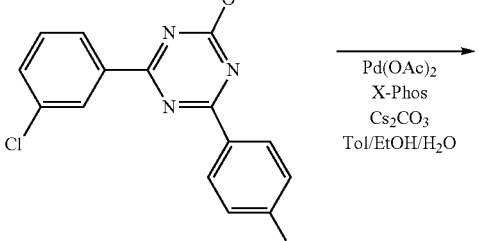

Z-12

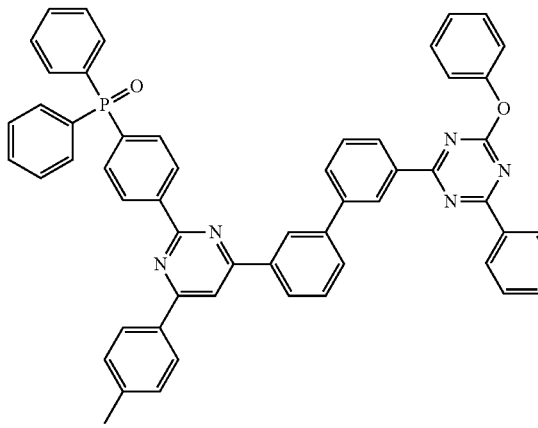

694

The same process as in [Synthesis Example 1] was carried out, except that Compound Z-11 (5.75 g, 10.0 mmol) was used instead of 2,4-diphenyl-6-(3-(4,4,5,5-tetramethyl-1,3,2-dioxaborolan-2-yl)phenyl)pyrimidine, and that Compound Z-12 (4.29 g, 10.0 mmol) was used instead of 2-(3-chlorophenyl)-4-(naphthalen-2-yl)-6-phenyl-1,3,5-triazine, such that the target compound, Compound 694 (4.35 g, yield 50%), was obtained.

[LCMS]: 870

[Synthesis Example 16] Synthesis of Compound 695

2-dioxaborolan-2-yl)phenyl)pyrimidine, and that Compound Z-14 (5.40 g, 10.0 mmol) was used instead of 2-(3-chlorophenyl)-4-(naphthalen-2-yl)-6-phenyl-1,3,5-triazine, such that the target compound, Compound 695 (5.19 g, yield 51%), was obtained.

[LCMS]: 1019

[Synthesis Example 17] Synthesis of Compound 696

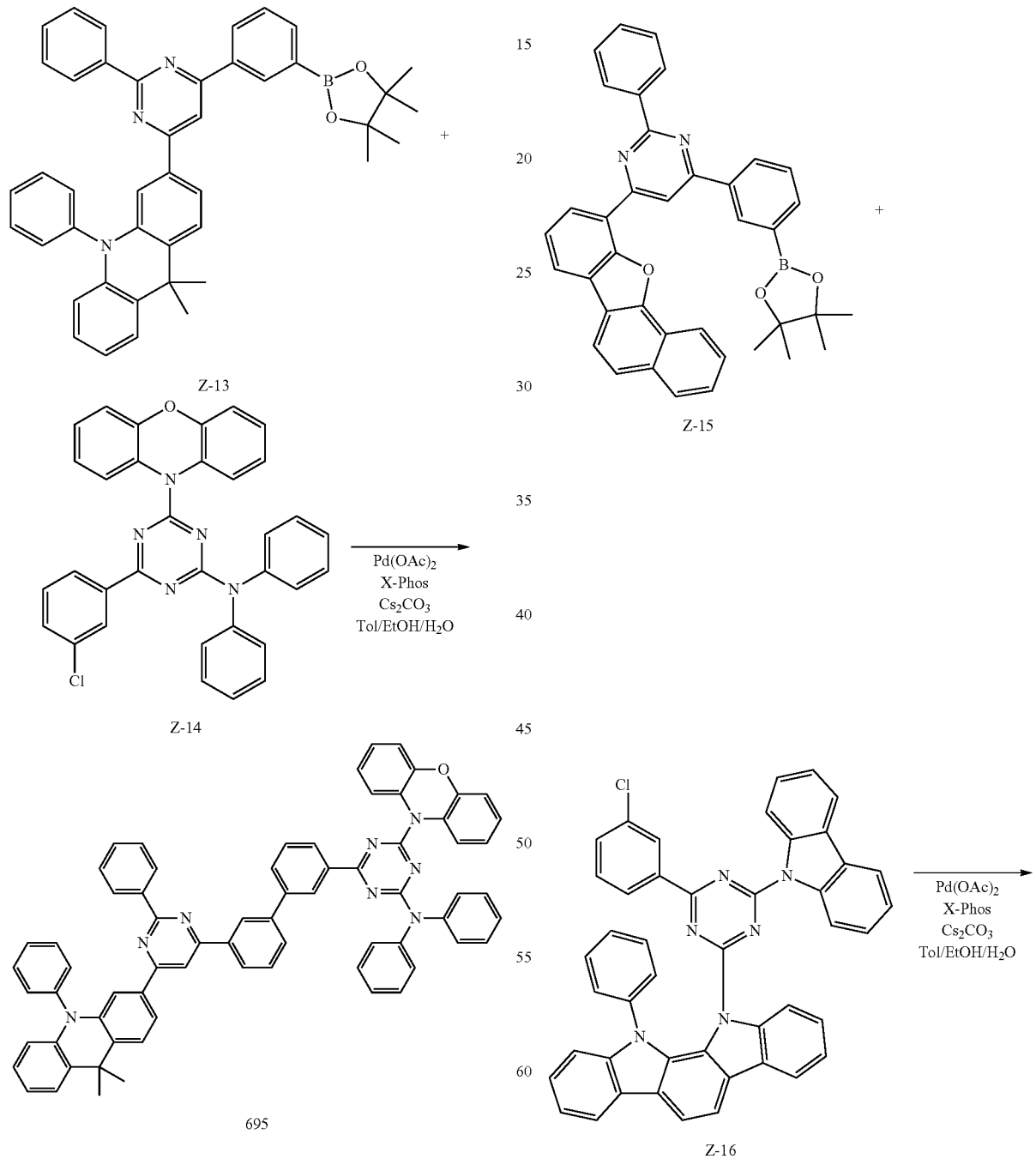

The same process as in [Synthesis Example 1] was carried out, except that Compound Z-13 (6.41 g, 10.0 mmol) was used instead of 2,4-diphenyl-6-(3-(4,4,5,5-tetramethyl-1,3, -continued

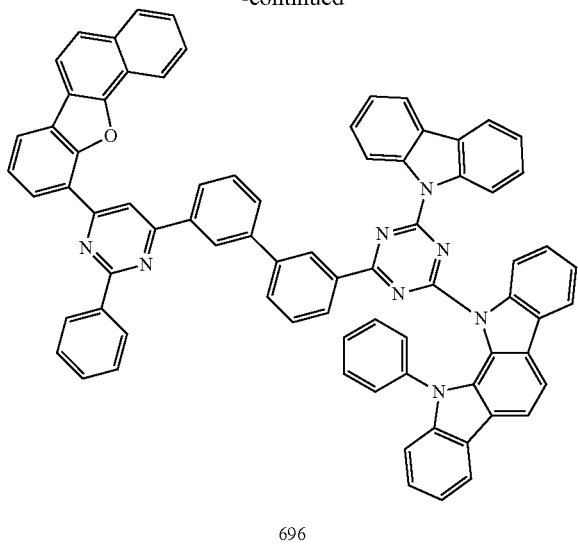

696

The same process as in [Synthesis Example 1] was carried out, except that Compound Z-15 (5.74 g, 10.0 mmol) was used instead of 2,4-diphenyl-6-(3-(4,4,5,5-tetramethyl-1,3,2-dioxaborolan-2-yl)phenyl)pyrimidine, and that Compound Z-16 (6.87 g, 10.0 mmol) was used instead of 2-chloro-4-(naphthalen-2-yl)-6-phenyl-1,3,5-triazine, such that the target compound, Compound 696 (5.71 g, yield 52%), was obtained.

[LCMS]: 1099

[Embodiments 1 to 17] Fabrication of Blue Organic Electroluminescent Device

Compounds 1, 8, 186, 206, 219, 311, 314 and 687 to 696 synthesized in the above Synthesis Examples were subjected to high purity sublimation purification by a commonly known method and then blue organic electroluminescent devices were fabricated as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics CO., LTD., 80 nm)/NPB (15 nm)/ADN+5% DS-405 (Doosan Electronics CO., LTD., 30 nm)/material of electron transporting layer in Table 1 (30 nm)/LiF (1 nm)/Al (200 nm) were laminated in order to fabricate an organic electroluminescent device.

[Comparative Example 1] Fabrication of Blue Organic Electroluminescent Device

A blue organic electroluminescent device was manufactured in the same manner as in Embodiment 1, except that $Alq_3$, instead of Compound 1, was used as the material of the electron transporting layer.

[Comparative Example 2] Fabrication of Blue Organic Electroluminescent Device

A blue organic electroluminescent device was manufactured in the same manner as in Embodiment 1, except that a compound T-1, instead of Compound 1, was used as the material of the electron transporting layer.

[Comparative Example 3] Fabrication of Blue Organic Electroluminescent Device

A blue organic electroluminescent device was manufactured in the same manner as in Embodiment 1, except that a compound T-2, instead of Compound 1, was used as the material of the electron transporting layer.

The structures of NPB, ADN, $Alq_3$, T-1 and T-2 used in Embodiments 1 to 17 and Comparative Examples 1 to 3 are as follows.

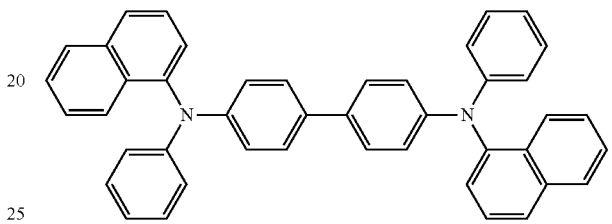

NPB

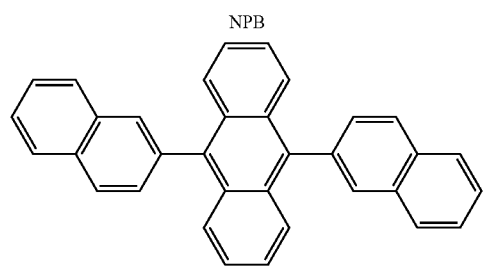

ADN

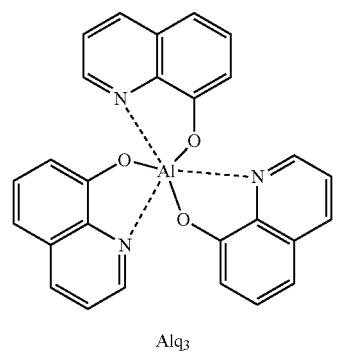

$Alq_3$

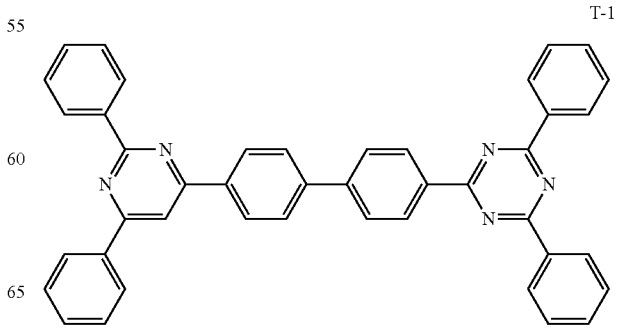

T-1

T-2

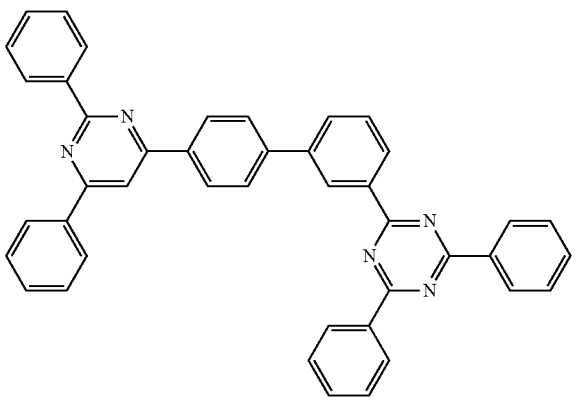

Evaluation Example 1

For each of the blue organic electroluminescent devices fabricated in Embodiments 1 to 17 and Comparative Examples 1 to 3, a driving voltage, a current efficiency and a light emission peak at a current density of 10 mA/cm² were measured and the results are shown in Table 1 below.

TABLE 1

| Sample | Material for electron transporting layer | Driving voltage (V) | Emission peak (nm) | Current efficiency (cd/A) |
|---|---|---|---|---|
| Embodiment 1 | Compound 1 | 3.9 | 454 | 8.0 |
| Embodiment 2 | Compound 8 | 3.5 | 456 | 8.9 |
| Embodiment 3 | Compound 186 | 3.8 | 457 | 8.3 |
| Embodiment 4 | Compound 206 | 3.7 | 452 | 8.6 |
| Embodiment 3 | Compound 219 | 4.3 | 455 | 8.5 |
| Embodiment 6 | Compound 311 | 3.7 | 452 | 8.3 |
| Embodiment 7 | Compound 314 | 3.8 | 453 | 7.7 |
| Embodiment 8 | Compound 687 | 3.9 | 454 | 7.8 |
| Embodiment 9 | Compound 688 | 4.0 | 455 | 7.9 |
| Embodiment 10 | Compound 689 | 4.2 | 456 | 6.0 |
| Embodiment 11 | Compound 690 | 4.4 | 458 | 6.0 |
| Embodiment 12 | Compound 691 | 4.2 | 457 | 6.1 |
| Embodiment 13 | Compound 692 | 4.0 | 454 | 6.2 |
| Embodiment 14 | Compound 693 | 3.8 | 453 | 7.0 |
| Embodiment 15 | Compound 694 | 4.0 | 457 | 6.1 |
| Embodiment 16 | Compound 695 | 4.1 | 458 | 6.1 |
| Embodiment 17 | Compound 696 | 4.2 | 459 | 6.1 |
| Comparative Example 1 | Alq₃ | 5.4 | 458 | 5.5 |
| Comparative Example 2 | T-1 | 4.5 | 459 | 5.9 |
| Comparative Example 3 | T-2 | 4.4 | 458 | 6.0 |

As shown in Table 1, it was appreciated that the blue organic electroluminescent devices (Embodiments 1 to 17) in which the compounds 1, 8, 186, 206, 219, 311, 314 and 687 to 696, synthesized in the Synthesis Examples, were used in the electron transporting layer exhibited excellent performance in terms of driving voltage, light emission peak and current efficiency, as compared with a conventional blue organic electroluminescent device (Comparative Example 1) in which Alq₃ was used in the electron transporting layer.

In addition, the blue organic electroluminescent devices (Embodiments 1 to 17) in which the compounds 1, 8, 186, 206, 219, 311, 314 and 687 to 696, synthesized in the Synthesis Examples, were used in the electron transporting layer exhibited excellent performance in terms of driving voltage, light emission peak and current efficiency by including m,m-biphenylene as a linker, as compared with blue organic electroluminescent devices (Comparative Examples 2 and 3) in which the compound having p,p-biphenylene or m,p-biphenylene was used in the electron transporting layer.

[Embodiments 18 to 34] Fabrication of Blue Organic Electroluminescent Device

Compounds 1, 8, 186, 206, 219, 311, 314 and 687 to 696 synthesized in the above Synthesis Examples were subjected to high purity sublimation purification by a commonly known method and then blue organic electroluminescent devices were manufactured as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics CO., LTD., 80 nm)/NPB (15 nm)/ADN+5% DS-405 (Doosan Electronics CO., LTD., 30 nm)/material of auxiliary electron transporting layer in Table 2 (5 nm)/Alq₃ (25 nm)/LiF (1 nm)/Al (200 nm) were laminated in order to fabricate an organic electroluminescent device.

[Comparative Example 4] Fabrication of Blue Organic Electroluminescent Device

A blue organic electroluminescent device was manufactured in the same manner as in Embodiment 18, except that Compound 1 was not used as the material of the auxiliary electron transporting layer, and that Alq₃, which is a material of the electron transporting layer, was laminated to 30 nm, rather than 25 nm.

[Comparative Example 5] Fabrication of Blue Organic Electroluminescent Device

A blue organic electroluminescent device was manufactured in the same manner as in Embodiment 18, except that a compound T-1, instead of Compound 1, was used as the material of the auxiliary electron transporting layer.

[Comparative Example 6] Fabrication of Blue Organic Electroluminescent Device

A blue organic electroluminescent device was manufactured in the same manner as in Embodiment 18, except that a compound T-2, instead of Compound 1, was used as the material of the auxiliary electron transporting layer.

Evaluation Example 2

For each of the blue organic electroluminescent devices fabricated in Embodiments 18 to 34 and Comparative Examples 4 to 6, a driving voltage, a light emission peak and a current efficiency at a current density of 10 mA/cm² were measured and the results are shown in Table 2 below.

TABLE 2

| Sample | Material of auxiliary electron transporting layer | Driving voltage (V) | Emission peak (nm) | Current efficiency (cd/A) |
|---|---|---|---|---|
| Embodiment 18 | Compound 1 | 4.3 | 452 | 8.0 |
| Embodiment 19 | Compound 8 | 3.7 | 451 | 8.4 |
| Embodiment 20 | Compound 186 | 4.5 | 452 | 7.6 |
| Embodiment 21 | Compound 206 | 3.8 | 454 | 8.2 |
| Embodiment 22 | Compound 219 | 3.7 | 451 | 7.3 |
| Embodiment 23 | Compound 311 | 4.2 | 452 | 8.0 |
| Embodiment 24 | Compound 314 | 4.5 | 453 | 7.6 |
| Embodiment 25 | Compound 687 | 4.4 | 454 | 7.5 |
| Embodiment 26 | Compound 688 | 4.1 | 455 | 7.4 |
| Embodiment 27 | Compound 689 | 4.6 | 456 | 6.2 |
| Embodiment 28 | Compound 690 | 4.4 | 457 | 6.2 |
| Embodiment 29 | Compound 691 | 4.2 | 458 | 6.3 |
| Embodiment 30 | Compound 692 | 4.0 | 457 | 7.5 |
| Embodiment 31 | Compound 693 | 4.1 | 456 | 7.4 |
| Embodiment 32 | Compound 694 | 4.2 | 455 | 7.0 |
| Embodiment 33 | Compound 695 | 4.3 | 454 | 6.6 |
| Embodiment 34 | Compound 696 | 4.4 | 453 | 6.5 |
| Comparative Example 4 | — | 4.8 | 458 | 6.0 |
| Comparative Example 5 | T-1 | 4.7 | 457 | 6.1 |
| Comparative Example 6 | T-2 | 4.6 | 456 | 6.2 |

As shown in Table 2, it was appreciated that the blue organic electroluminescent devices (Embodiments 18 to 34) in which the compounds 1, 8, 186, 206, 219, 311, 314 and 687 to 696, synthesized in the Synthesis Examples, were used in the auxiliary electron transporting layer exhibited excellent performance in terms of driving voltage, light emission peak and current efficiency, as compared with a conventional blue organic electroluminescent device (Comparative Example 4) without the auxiliary electron transporting layer.

In addition, the blue organic electroluminescent devices (Embodiments 18 to 34) in which the compounds 1, 8, 186, 206, 219, 311, 314 and 687 to 696, synthesized in the Synthesis Examples, were used in the auxiliary electron transporting layer exhibited excellent performance in terms of driving voltage, light emission peak and current efficiency by including m,m-biphenylene as a linker, as compared with blue organic electroluminescent devices (Comparative Examples 5 and 6) in which the compound having p,p-biphenylene or m,p-biphenylene was used in the auxiliary electron transporting layer.

[Embodiments 35 to 51] Fabrication of Green Organic Electroluminescent Device Compounds 1, 8, 186, 206, 219, 311, 314 and 687 to 696 synthesized in the above Synthesis Examples were subjected to high purity sublimation purification by a commonly known method and then green organic electroluminescent devices were manufactured as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, m-MTDATA (60 nm)/TCTA (80 nm)/90% of host material in Table 3+10% of Ir(ppy)$_3$ (300 nm)/BCP (10 nm)/Alq$_3$ (30 nm)/LiF (1 nm)/Al (200 nm) were laminated in order to fabricate an organic electroluminescent device.

[Comparative Example 7] Fabrication of Green Organic Electroluminescent Device An organic electroluminescent device was manufactured in the same manner as in Embodiment 35, except that CBP, instead of Compound 1, was used as a light emission host material when forming the light-emitting layer.

[Comparative Example 8] Fabrication of Green Organic Electroluminescent Device An organic electroluminescent device was manufactured in the same manner as in Embodiment 35, except that a compound T-1, instead of Compound 1, was used as a light emission host material when forming the light-emitting layer.

[Comparative Example 9] Fabrication of Green Organic Electroluminescent Device An organic electroluminescent device was manufactured in the same manner as in Embodiment 35, except that a compound T-2, instead of Compound 1, was used as a light emission host material when forming the light-emitting layer.

The structures of m-MTDATA, TCTA, Ir(ppy)$_3$, CBP and BCP used in Embodiments 35 to 51 and Comparative Examples 7 to 9 are as follows.

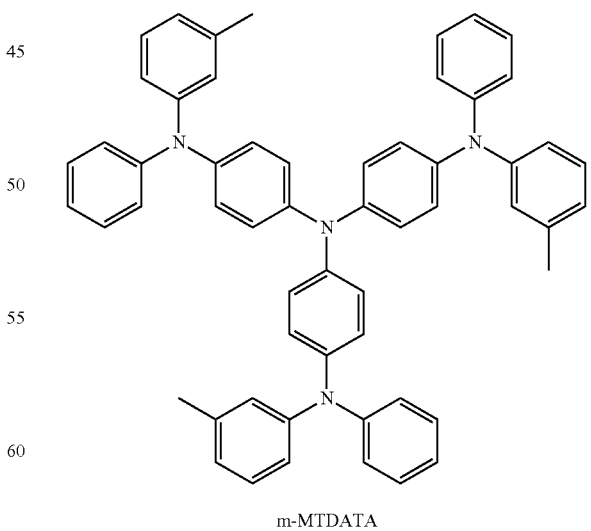

m-MTDATA

-continued

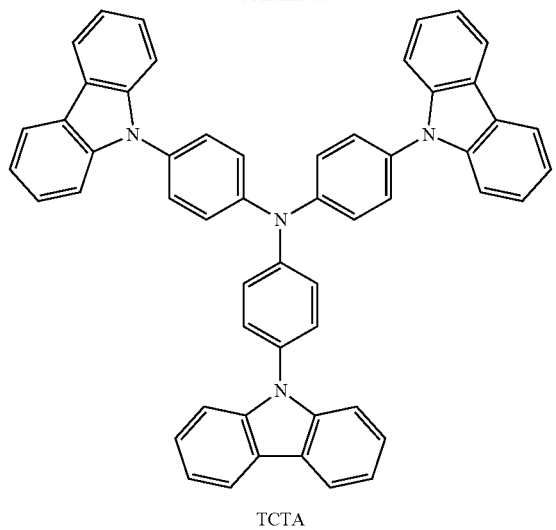

TCTA

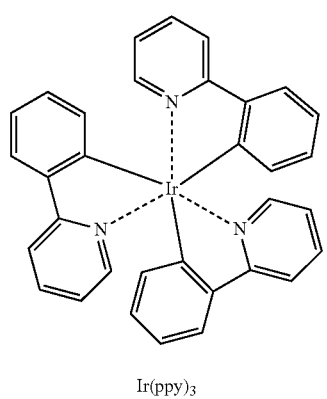

Ir(ppy)₃

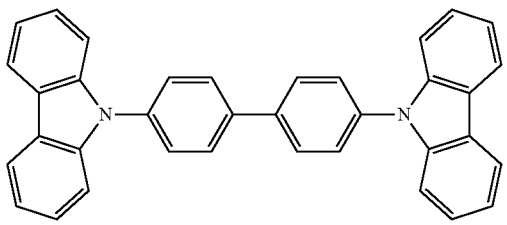

CBP

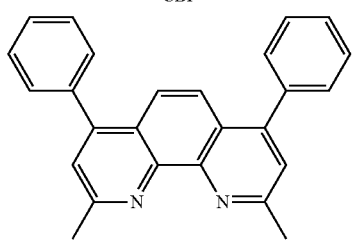

BCP

Evaluation Example

For each of the green organic electroluminescent devices fabricated in Embodiments 35 to 51 and Comparative Examples 7 to 9, a driving voltage, a current efficiency and alight emission peak at a current density of 10 mA/cm² were measured and the results are shown in Table 3 below.

TABLE 3

| Sample | Host material | Driving voltage (V) | Emission peak (nm) | Current efficiency (cd/A) |
|---|---|---|---|---|
| Embodiment 35 | Compound 1 | 6.81 | 518 | 39.7 |
| Embodiment 36 | Compound 8 | 6.48 | 518 | 44.9 |
| Embodiment 37 | Compound 186 | 6.66 | 518 | 41.3 |
| Embodiment 38 | Compound 206 | 6.70 | 517 | 41,3 |
| Embodiment 39 | Compound 219 | 6.70 | 515 | 43.1 |
| Embodiment 40 | Compound 311 | 6.51 | 518 | 43.5 |
| Embodiment 41 | Compound 314 | 6.77 | 518 | 41.4 |
| Embodiment 42 | Compound 687 | 6.82 | 517 | 41.3 |
| Embodiment 43 | Compound 688 | 6.66 | 515 | 41.3 |
| Embodiment 44 | Compound 689 | 6.86 | 516 | 41.2 |
| Embodiment 45 | Compound 690 | 6.79 | 518 | 40.3 |
| Embodiment 46 | Compound 691 | 6.80 | 518 | 40.4 |
| Embodiment 47 | Compound 692 | 6.67 | 517 | 39.9 |
| Embodiment 48 | Compound 693 | 6.66 | 516 | 41.1 |
| Embodiment 49 | Compound 694 | 6.49 | 515 | 42.4 |
| Embodiment 50 | Compound 695 | 6.56 | 516 | 40.0 |
| Embodiment 51 | Compound 696 | 6.57 | 517 | 40.1 |
| Comparative Example 7 | CBP | 6.93 | 516 | 38.2 |
| Comparative Example 8 | T-1 | 6.9 | 517 | 39.5 |
| Comparative Example 9 | T-2 | 6.87 | 517 | 39.2 |

As shown in Table 3, it was appreciated that the green organic electroluminescent devices (Embodiments 35 to 51) in which the compounds 1, 8, 186, 206, 219, 311, 314 and 687 to 696, synthesized in the Synthesis Examples, were used in the light-emitting layer exhibited excellent performance in terms of driving voltage and current efficiency, as compared with a conventional green organic electroluminescent device (Comparative Example 7) in which CBP was used in the light-emitting layer.

In addition, the green organic electroluminescent devices (Embodiments 35 to 51) in which the compounds 1, 8, 186, 206, 219, 311, 314 and 687 to 696, synthesized in the Synthesis Examples, were used in the light-emitting layer exhibited excellent performance in terms of driving voltage, light emission peak and current efficiency by including m,m-biphenylene as a linker, as compared with green organic electroluminescent devices (Comparative Examples 8 and 9) in which the compound having p,p-biphenylene or m,p-biphenylene was used in the light-emitting layer.

The invention claimed is:

1. A compound selected from any one of the following compounds:

1

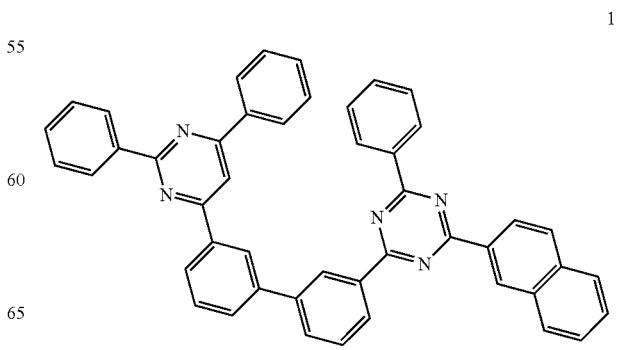

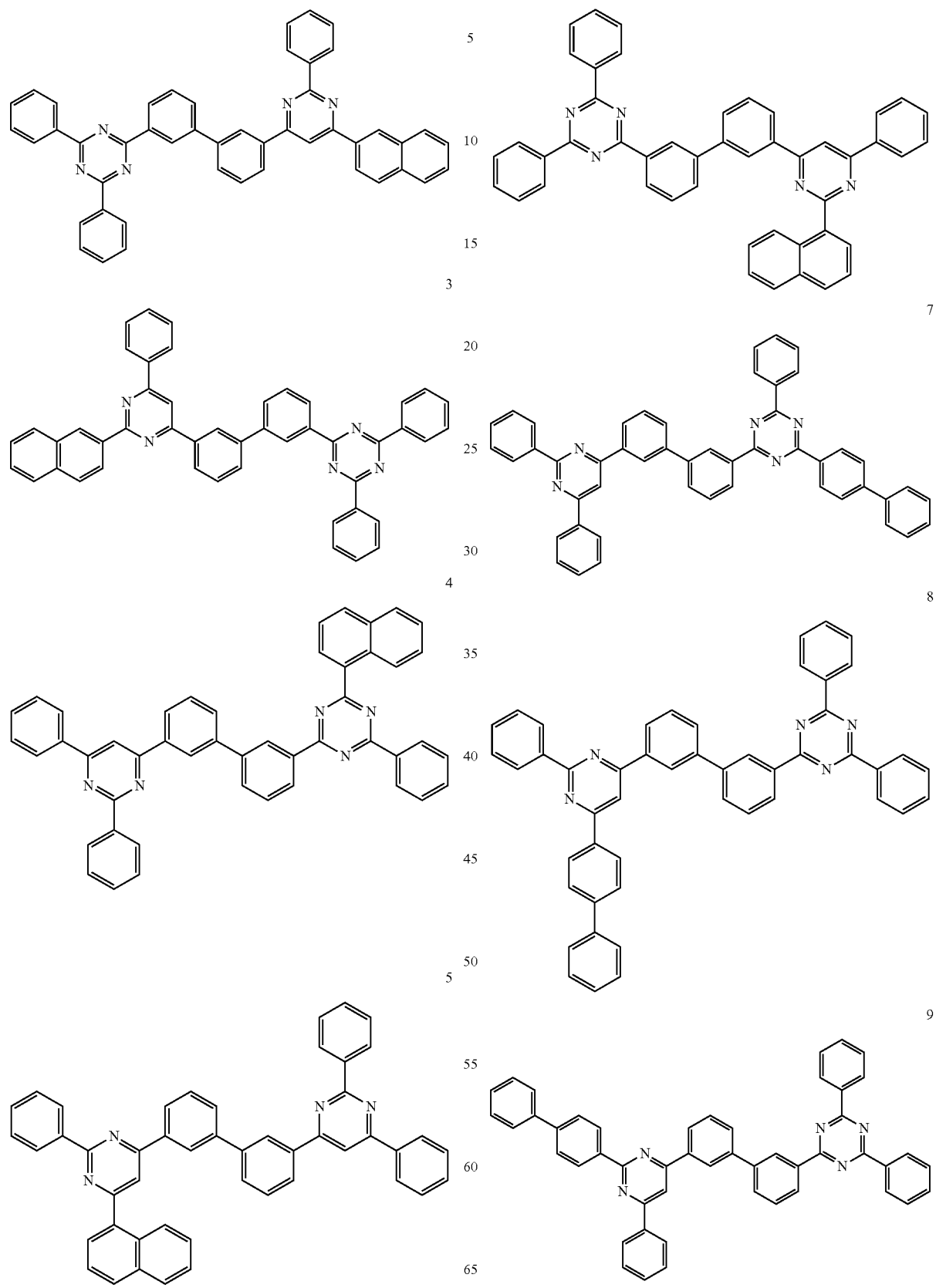

10
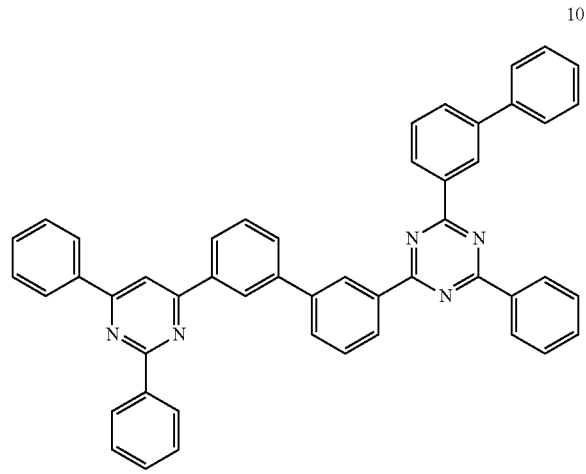
11
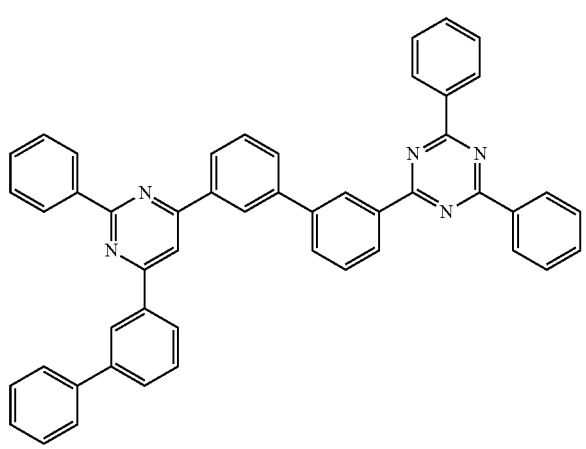
12
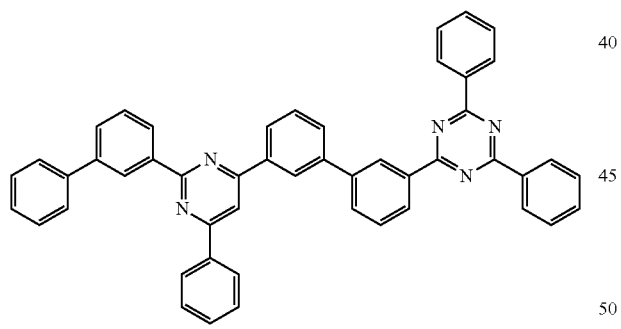
13
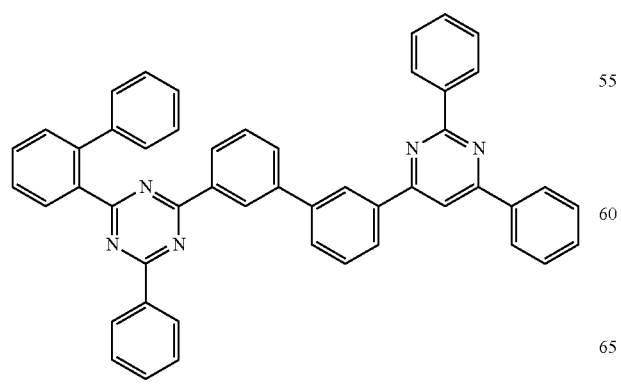
14
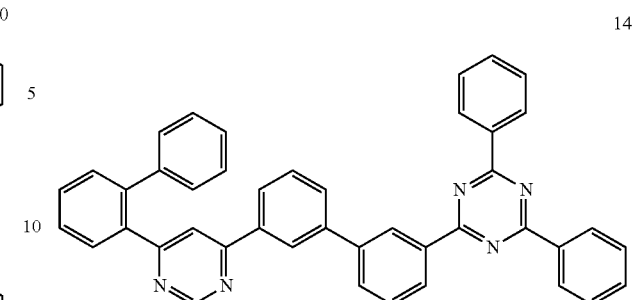
15
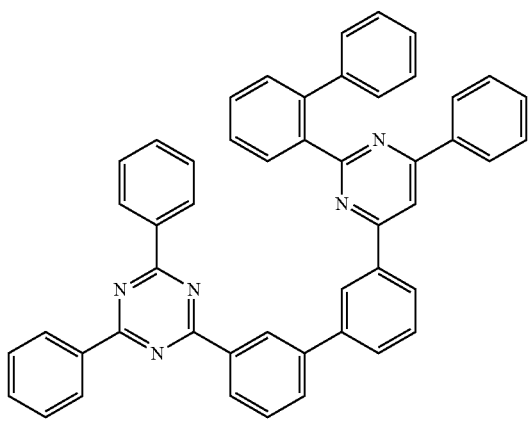
16
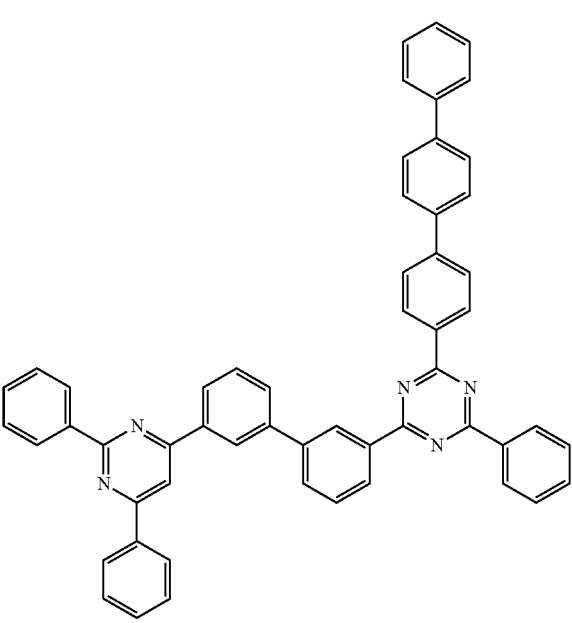

17
-continued
18
19
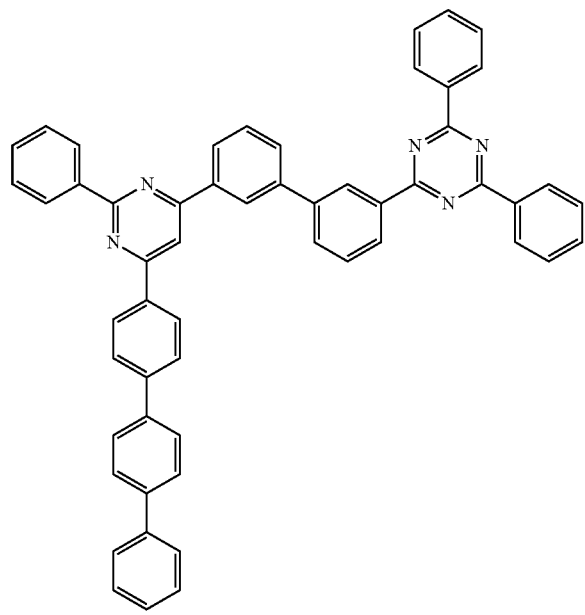
20
-continued
21
22
23
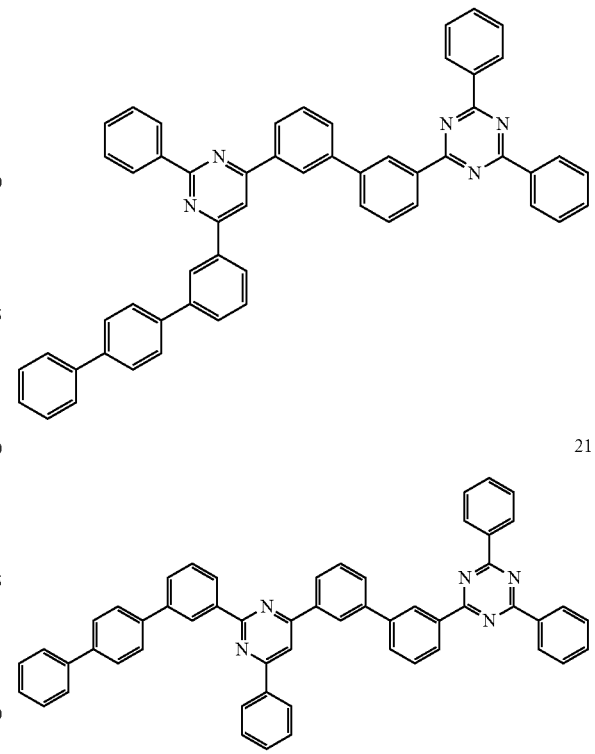
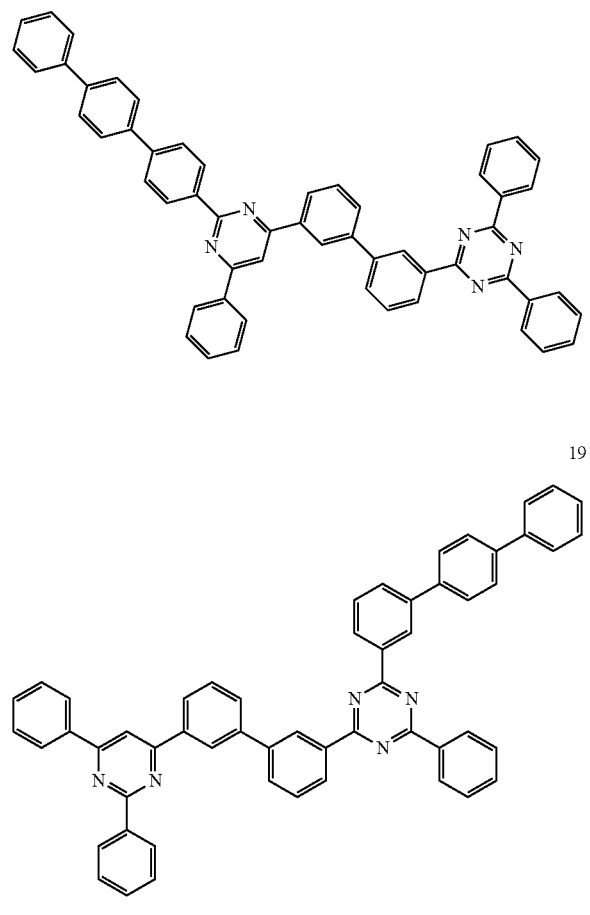

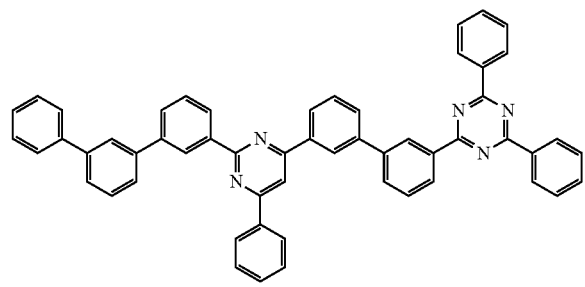
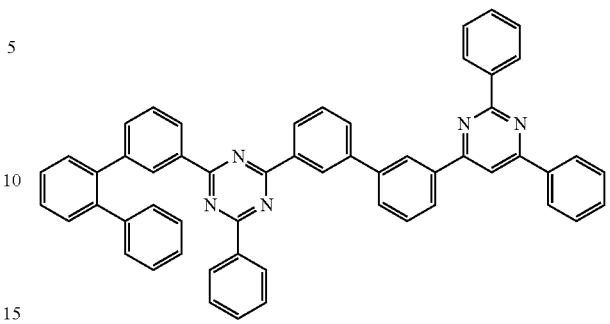
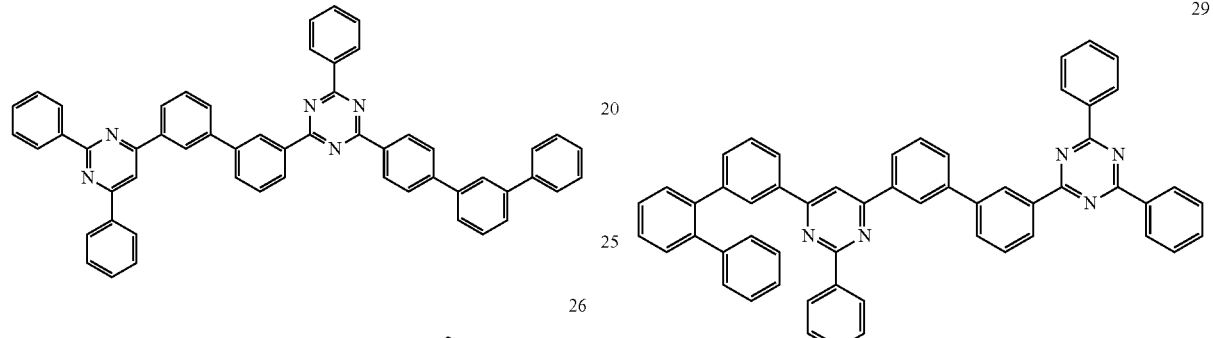
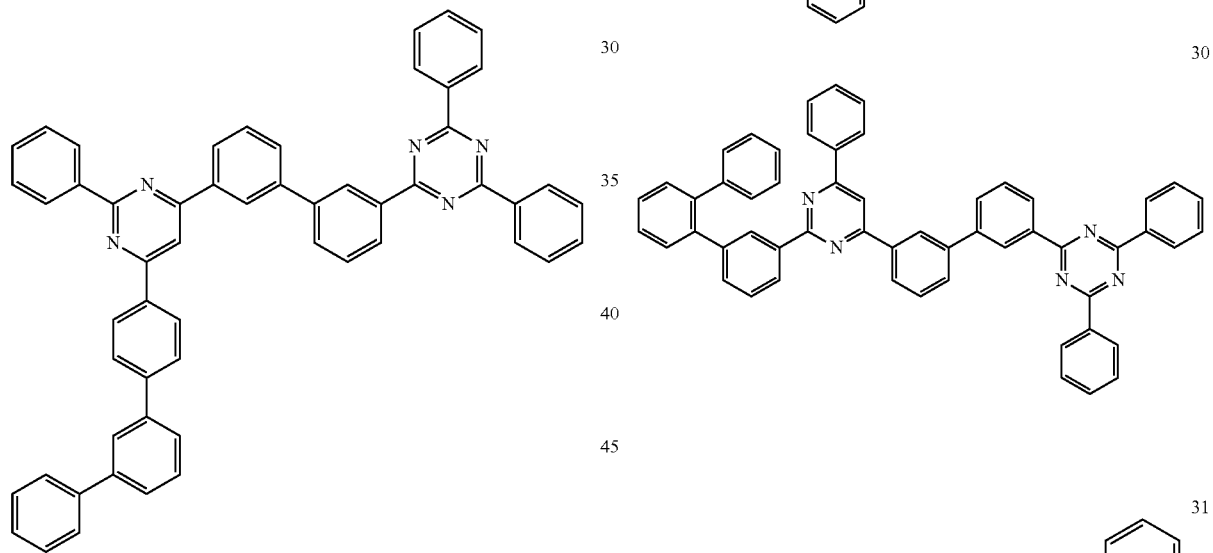
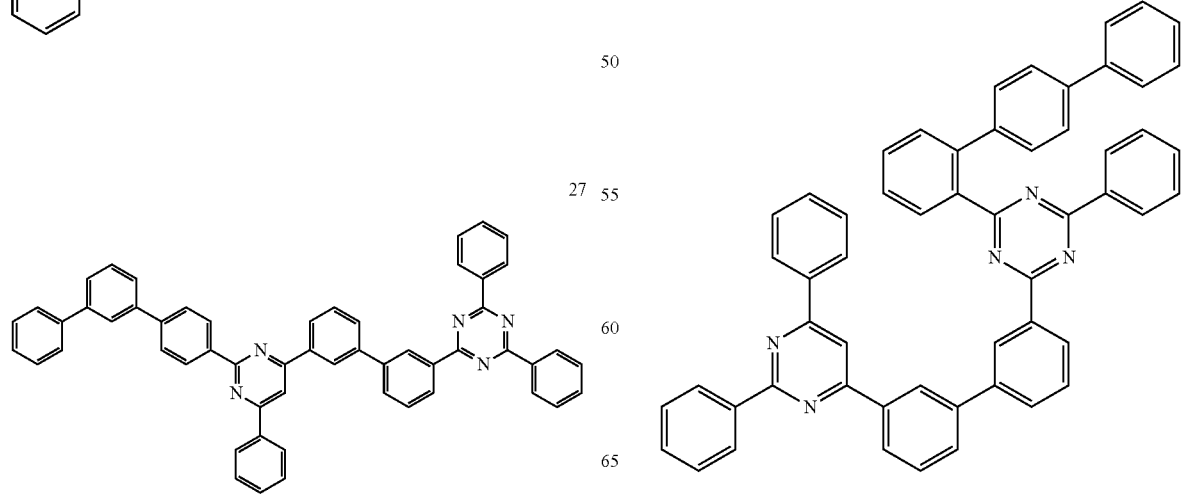

32
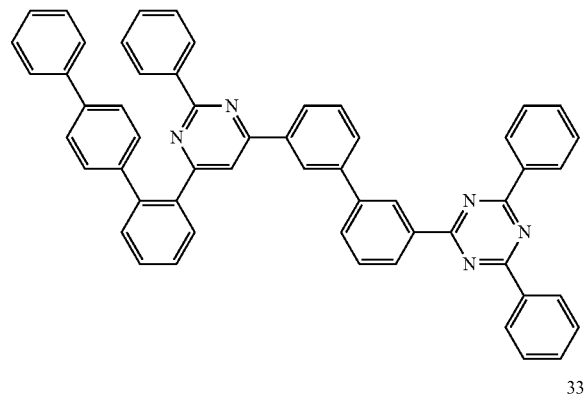
33
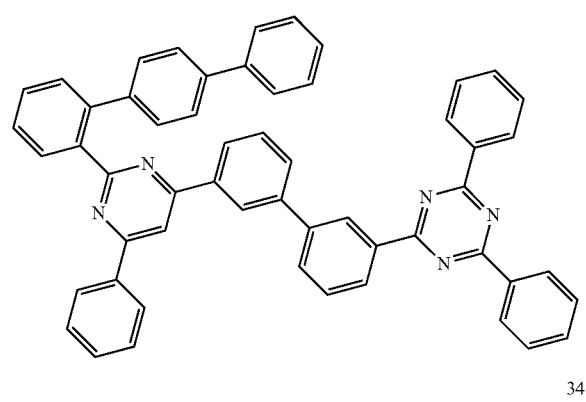
34
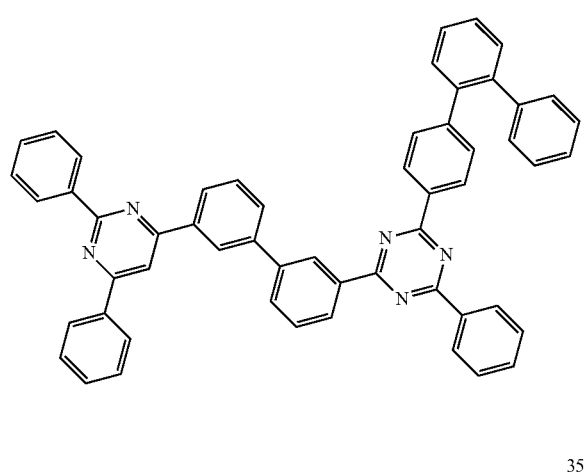
35
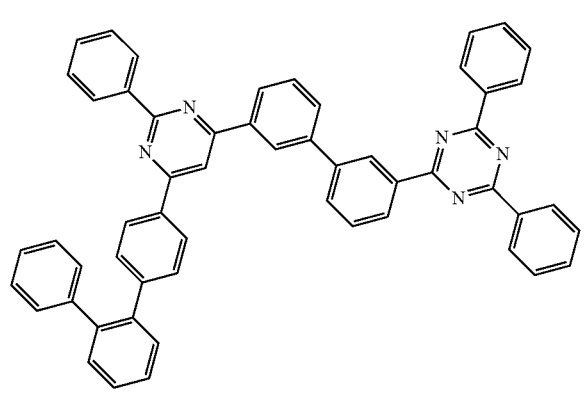
36
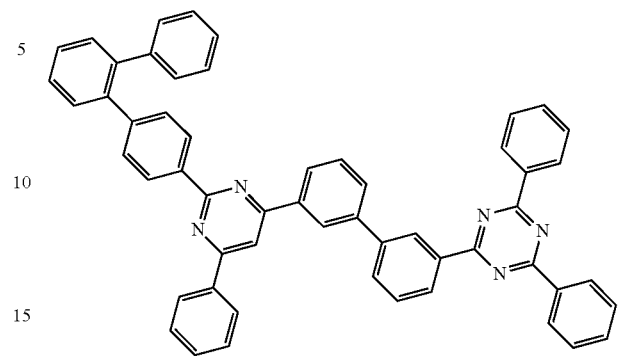
37
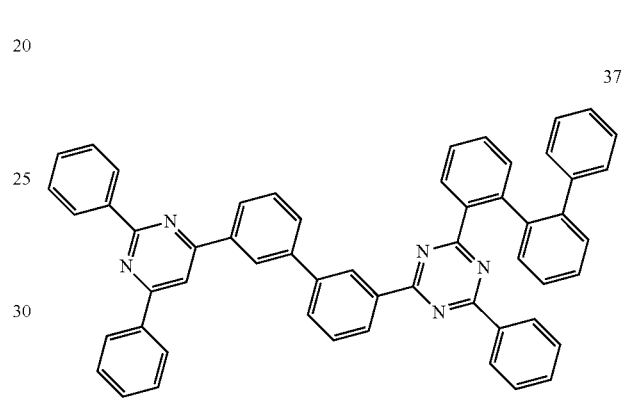
38
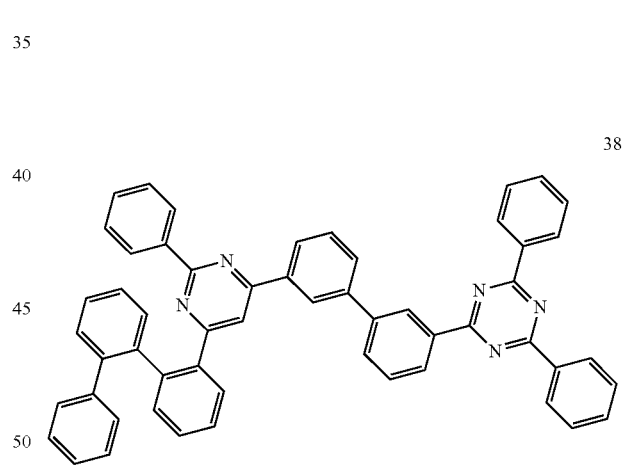
39
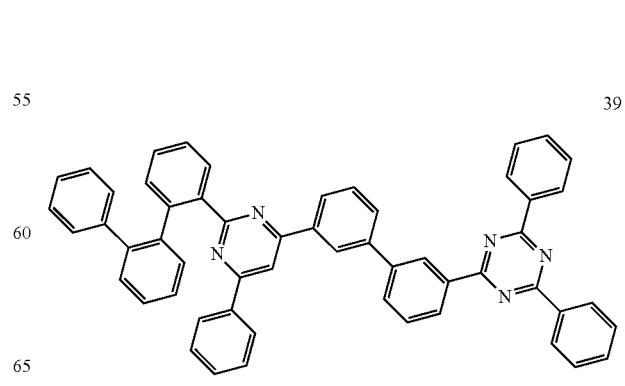

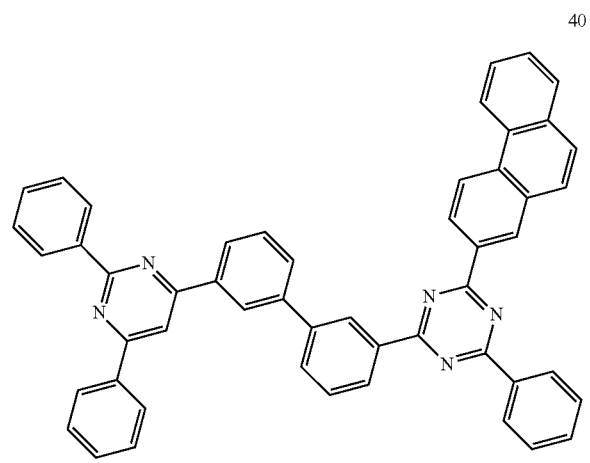
40
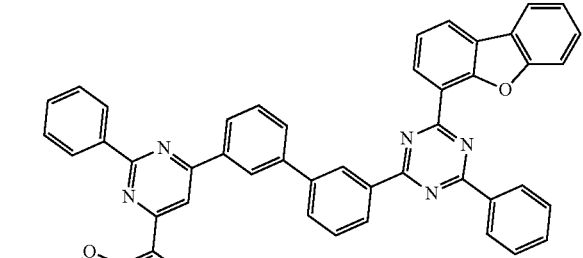
41
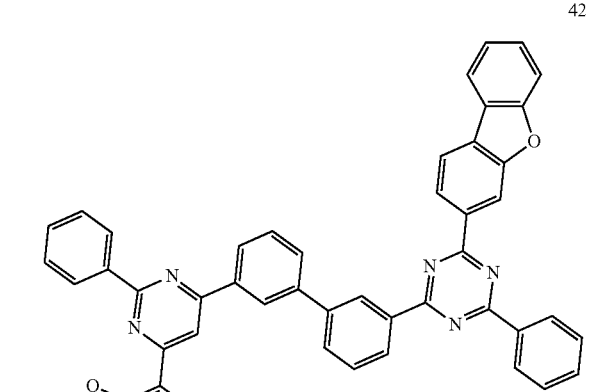
42
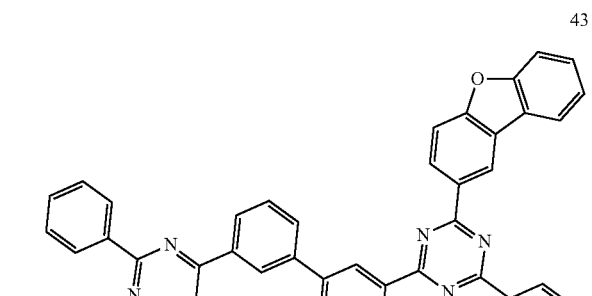
43
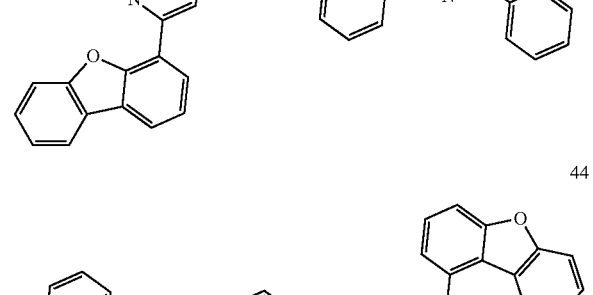
44
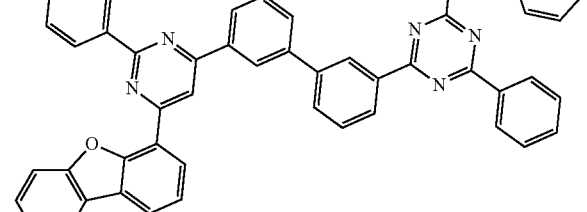
45
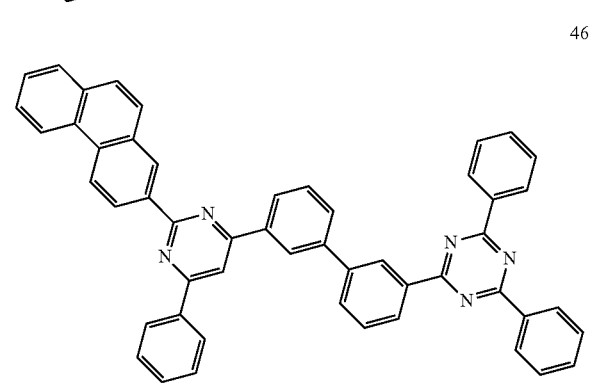
46

47
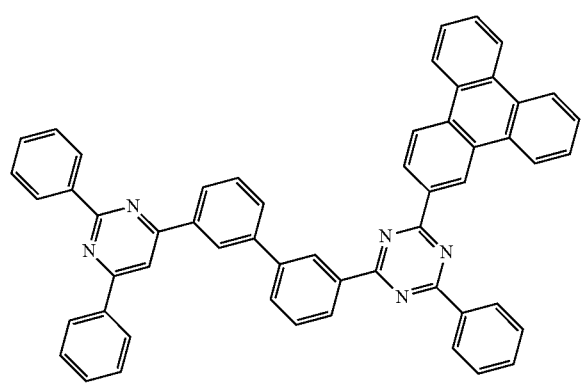
48
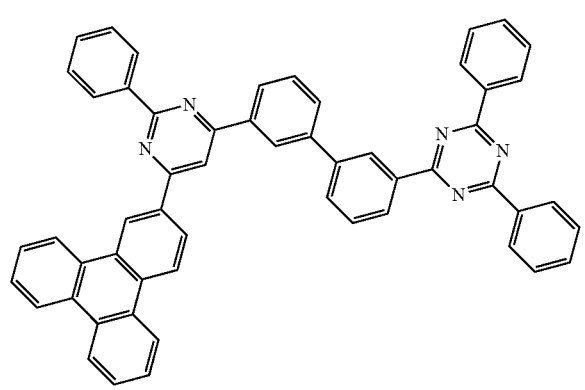
49
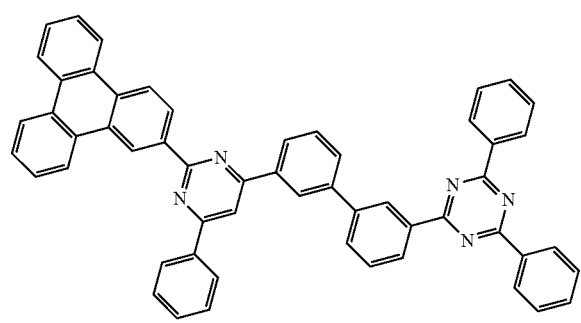
50
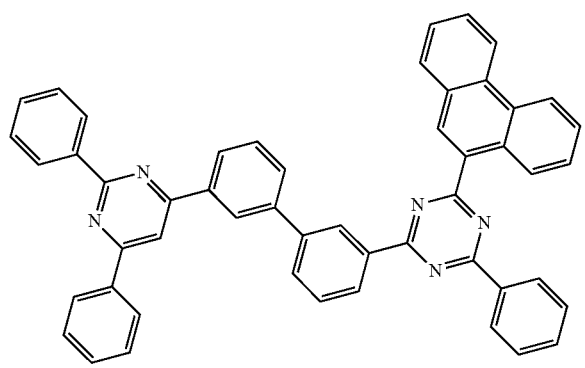
51
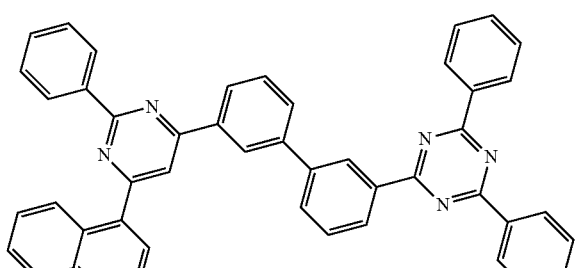
52
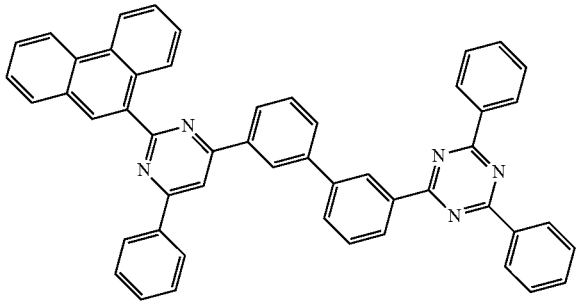
53
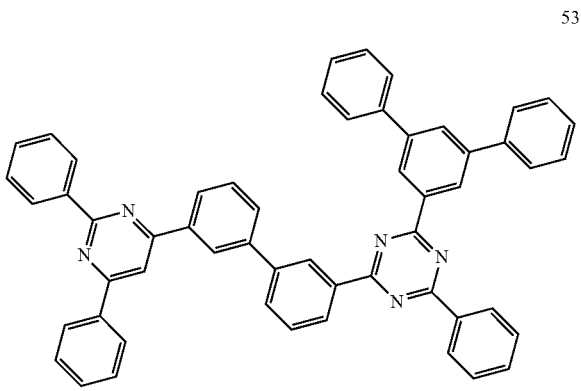
54
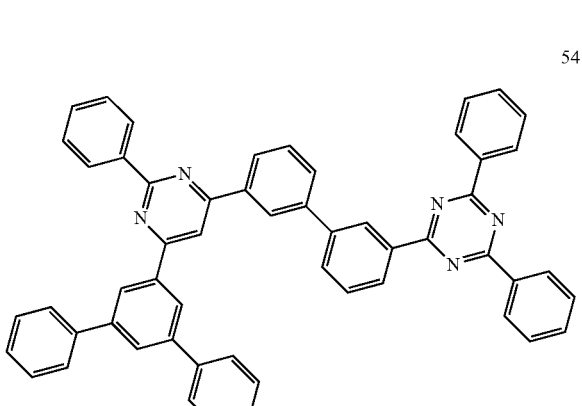

55
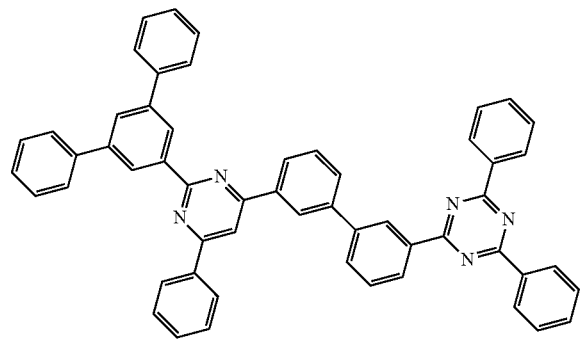
56
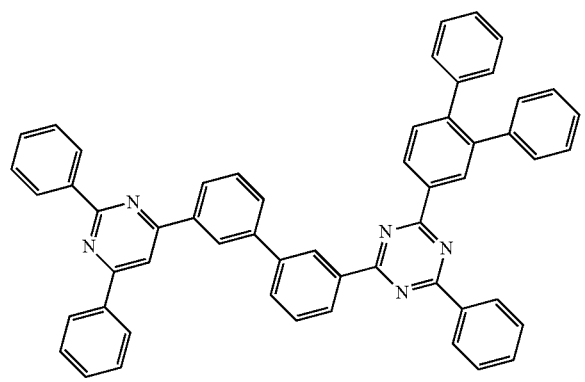
57
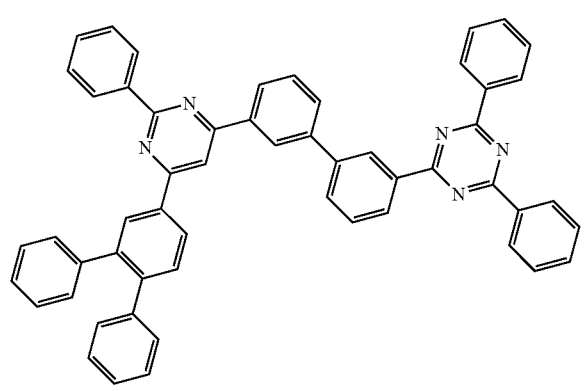
58
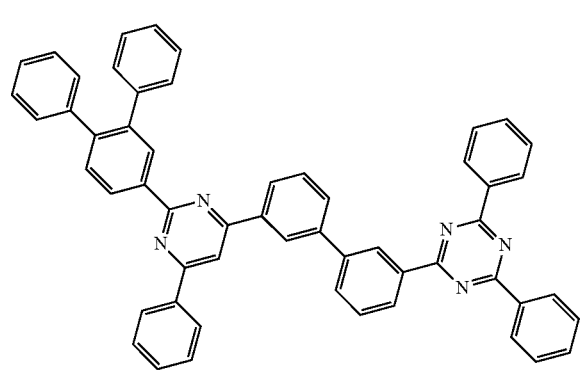
59
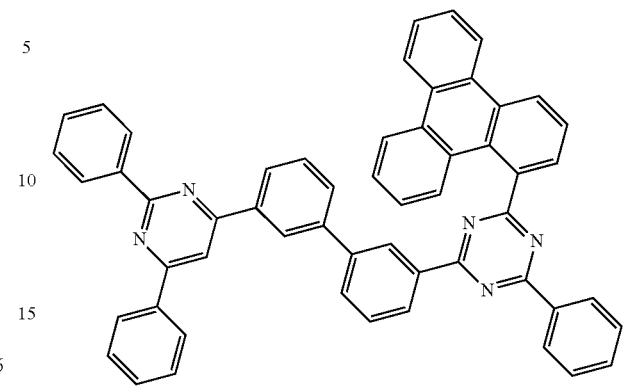
60
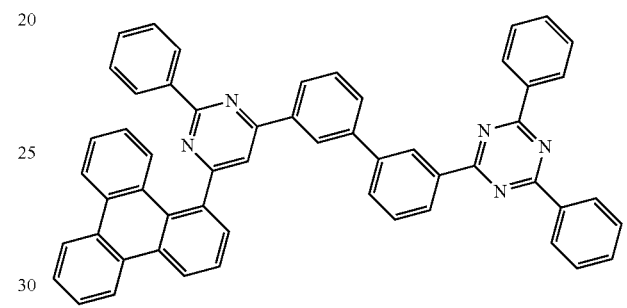
61
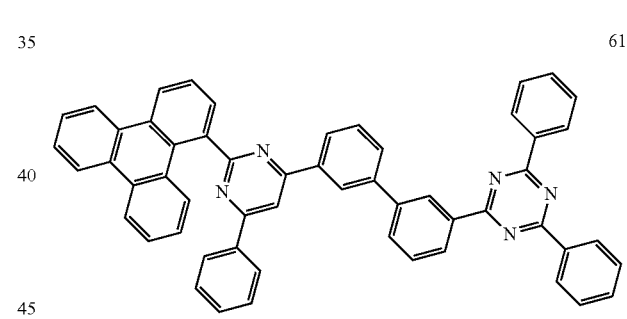
62
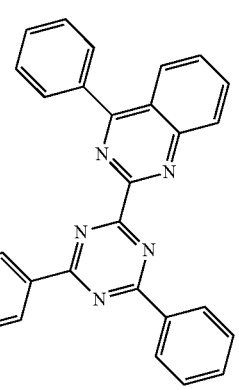

423
-continued
63
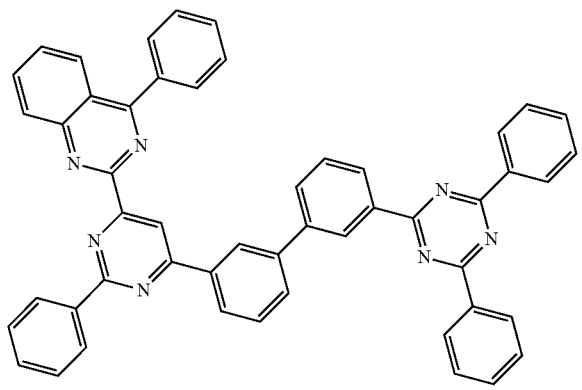
64
65
66
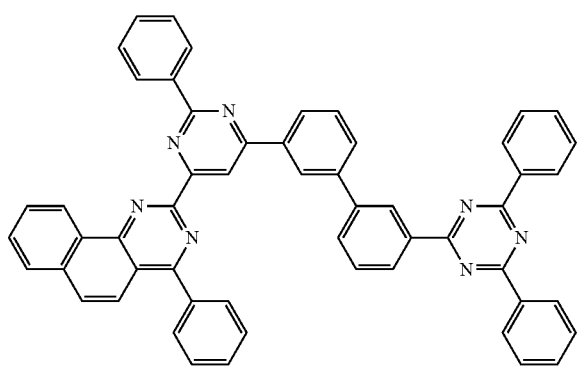
424
-continued
67
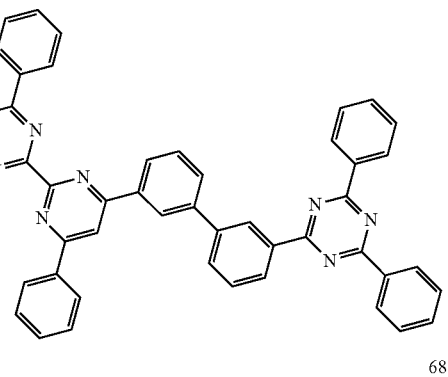
68
69
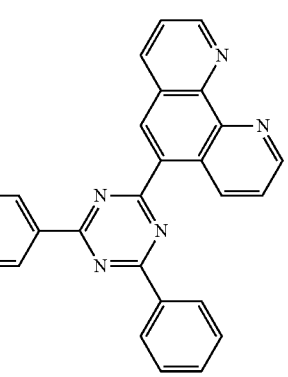
70
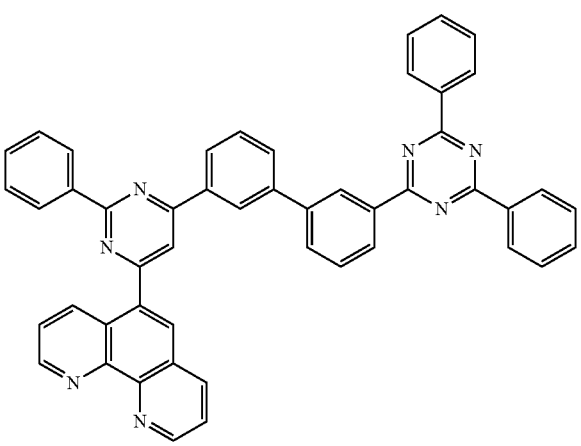

71
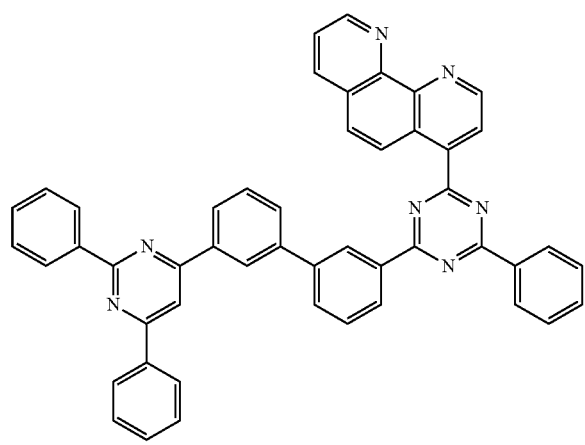
72
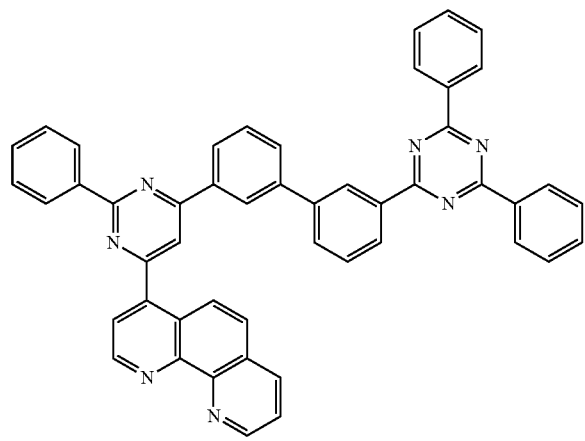
73
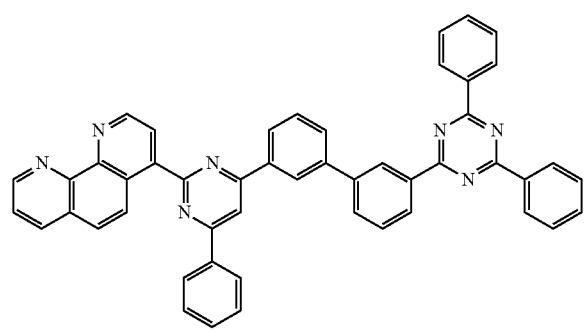
74
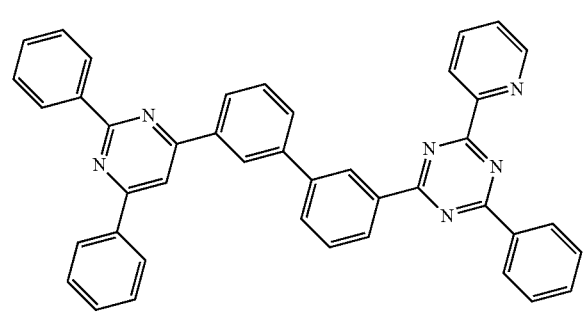
75
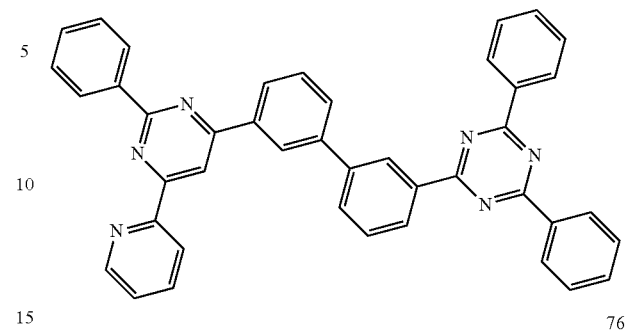
76
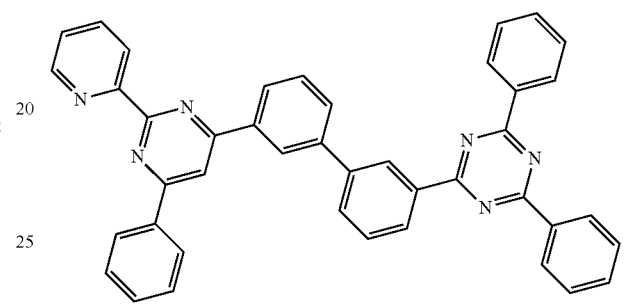
77
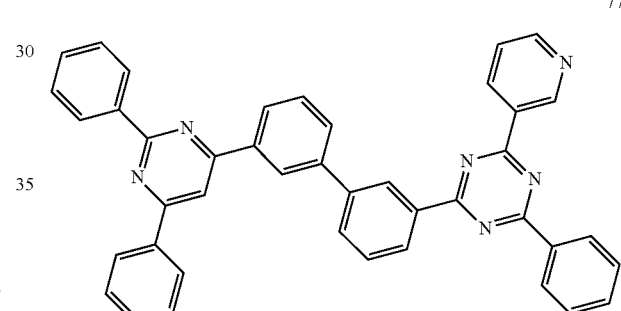
78
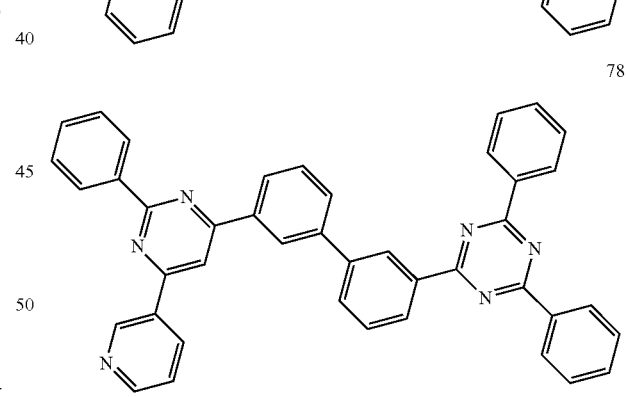
79
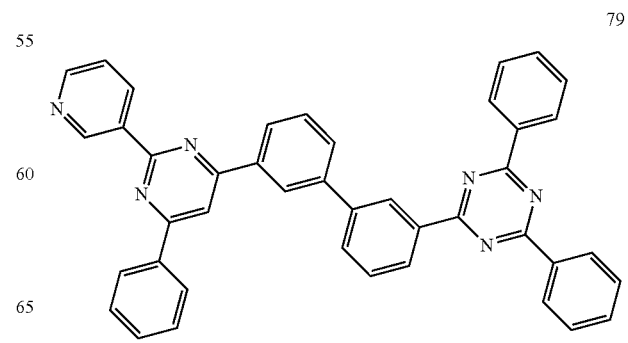

80
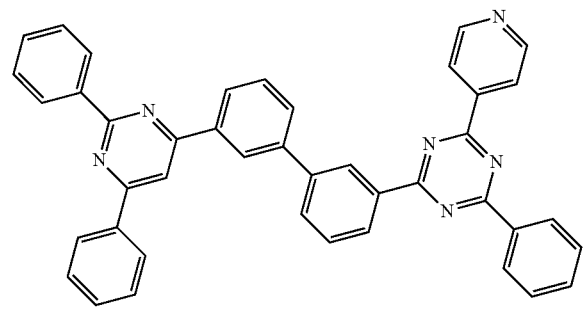
81
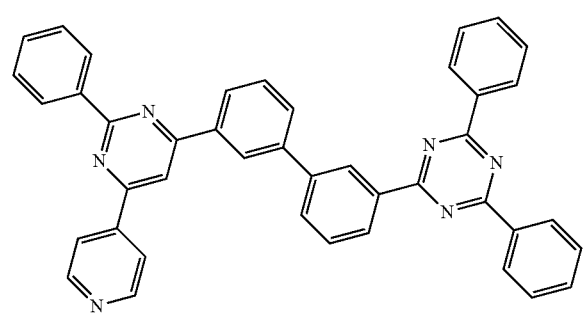
82
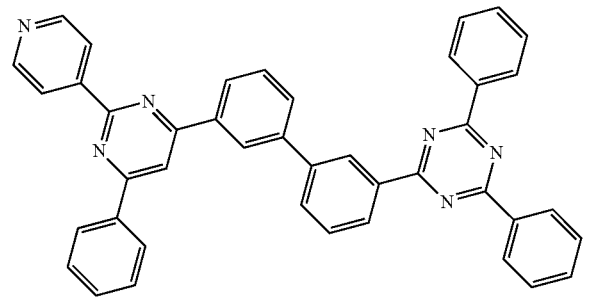
83
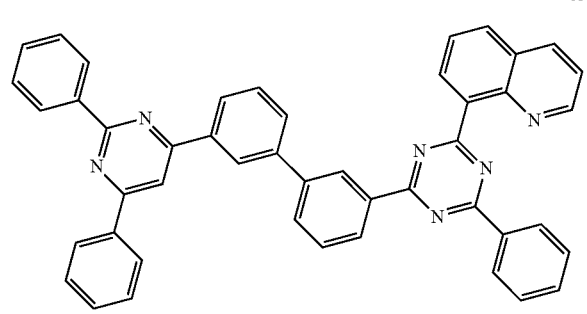
84
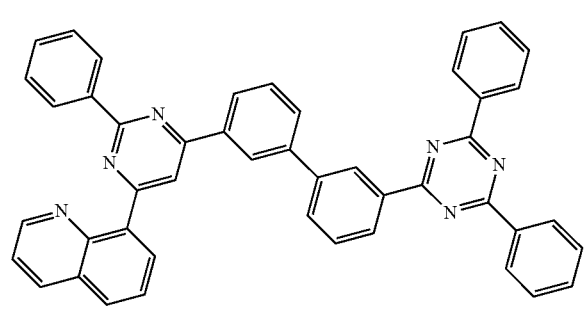
85
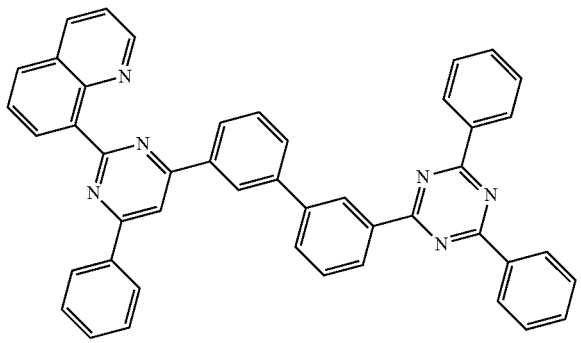
86
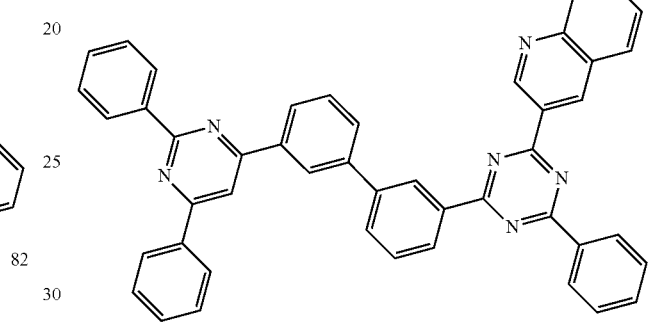
87
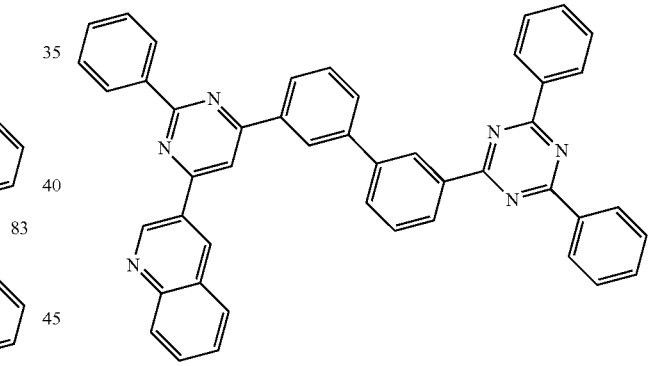
88
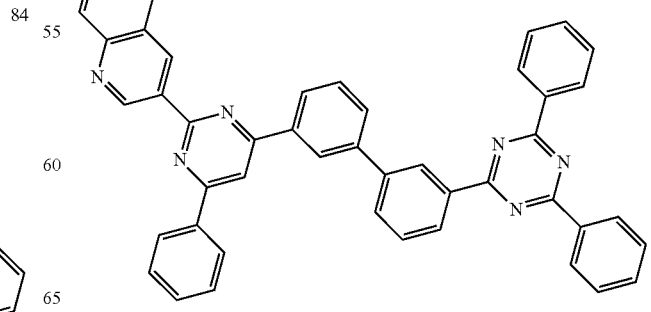

89
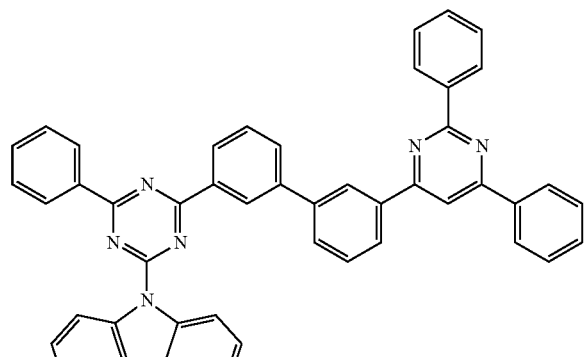
90

91
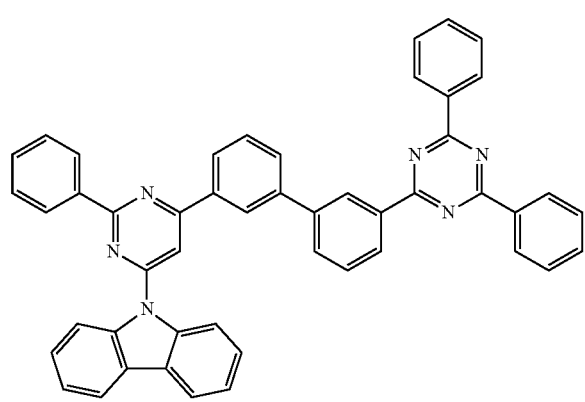
92
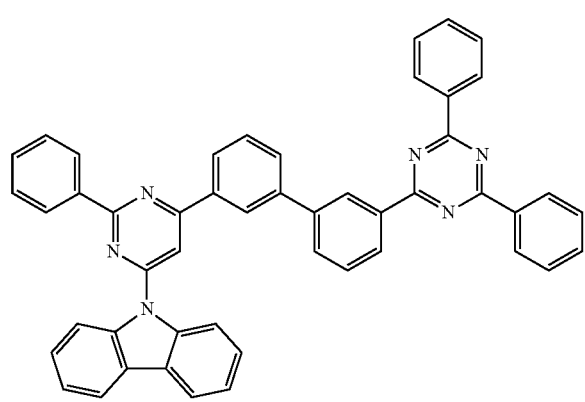
93
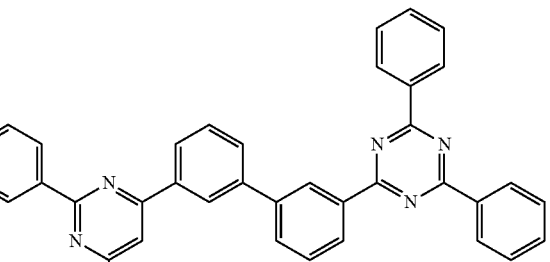
94
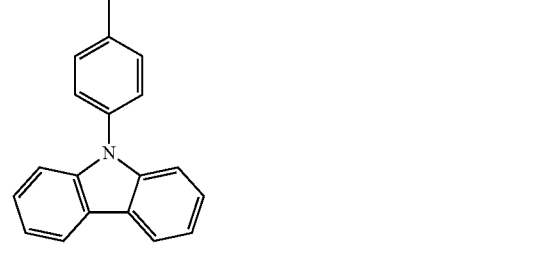
95
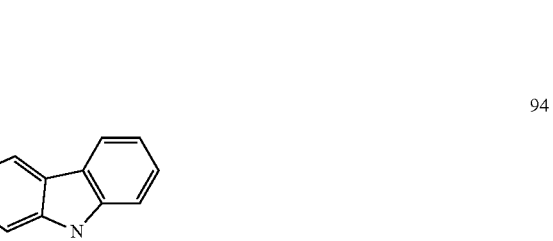

96
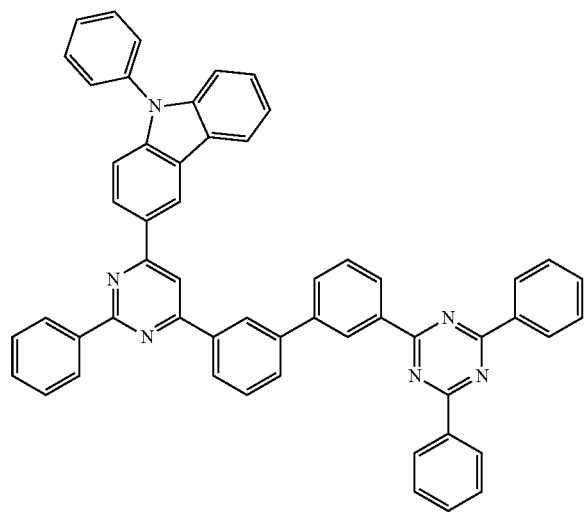
97
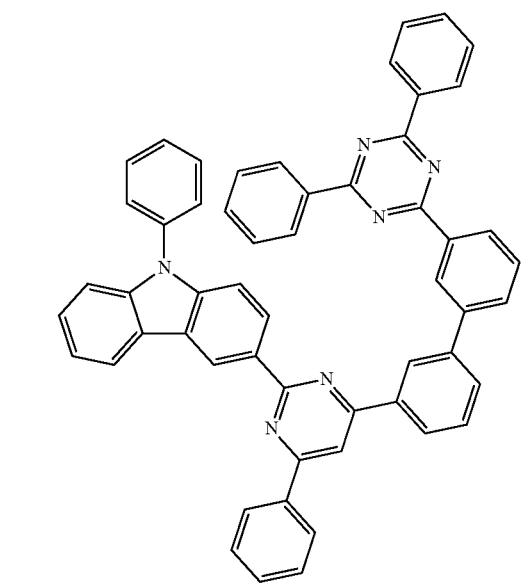
98
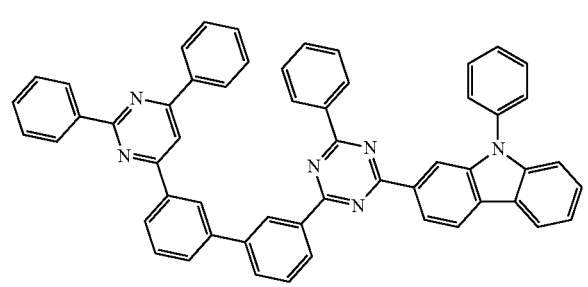
99
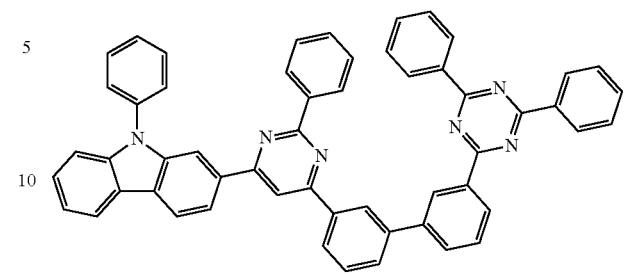
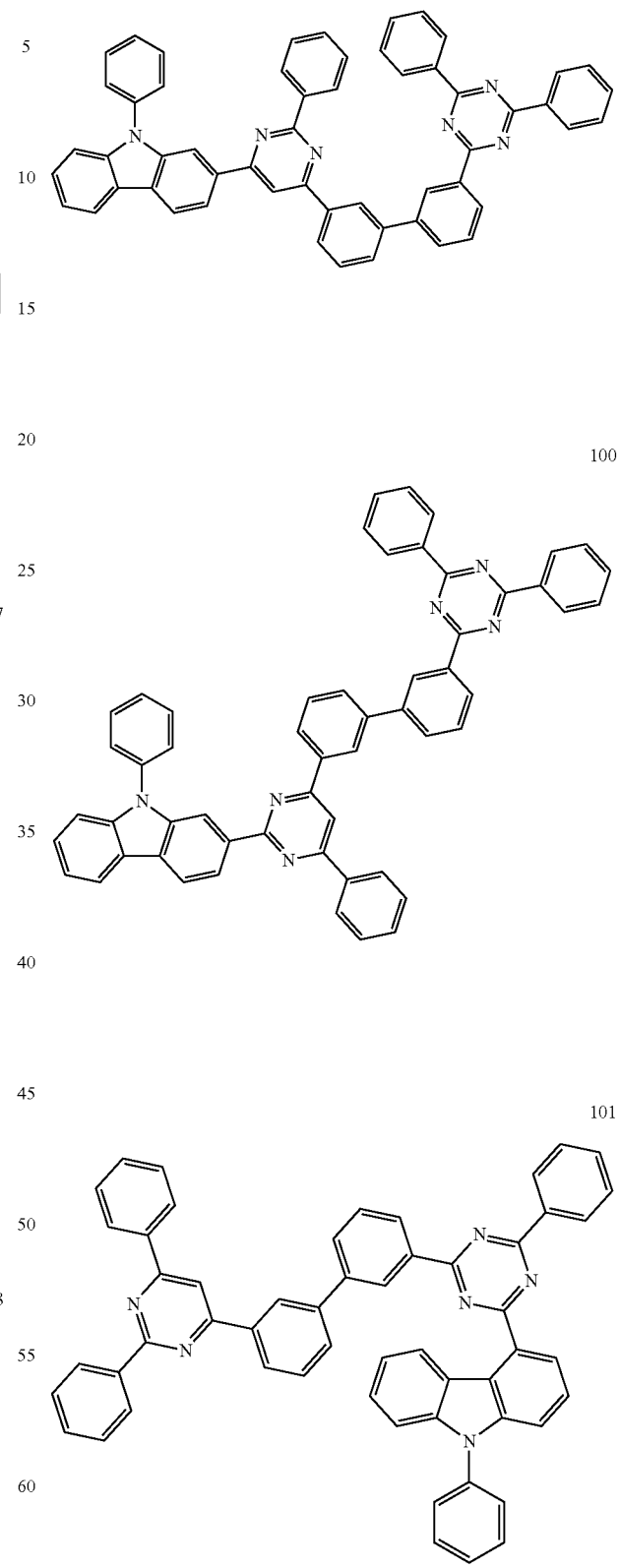

102
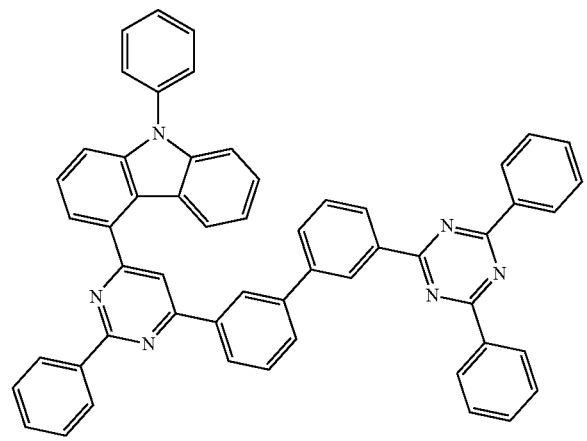
103
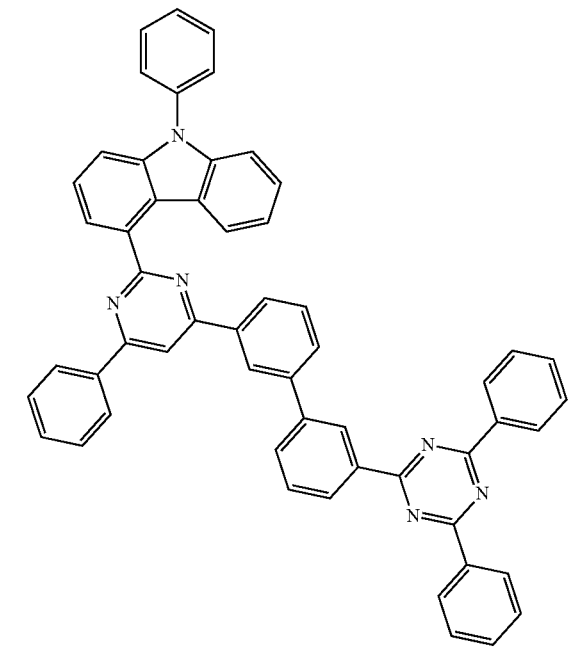
104
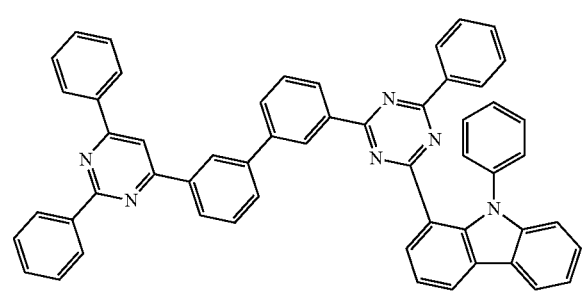
105
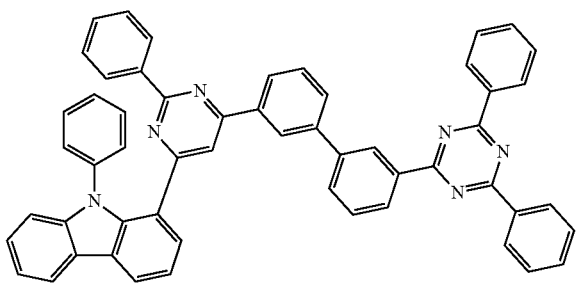
106
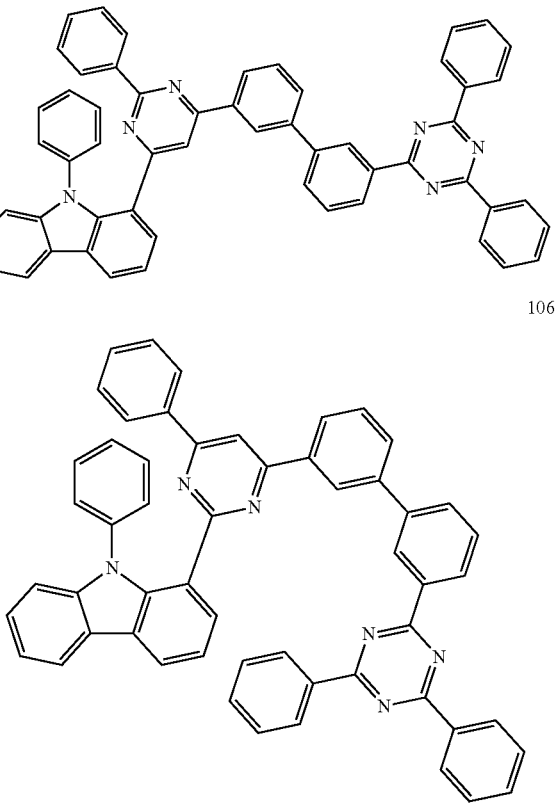
107
108
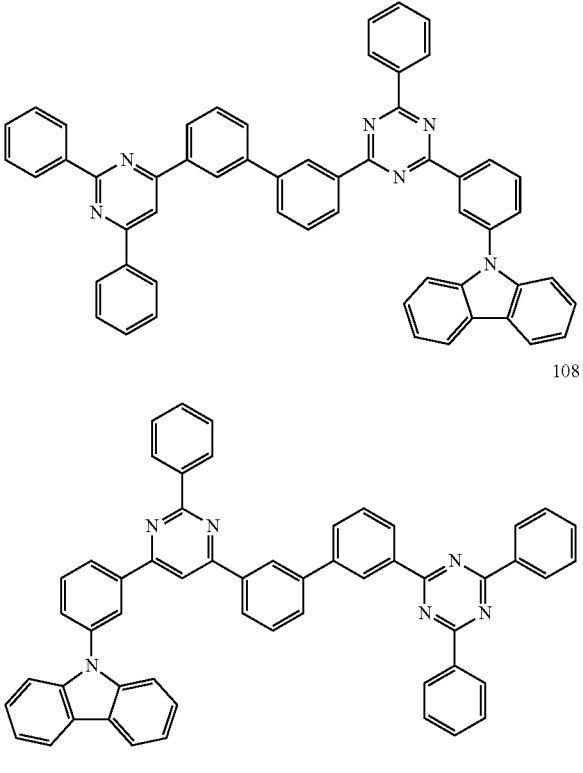

-continued
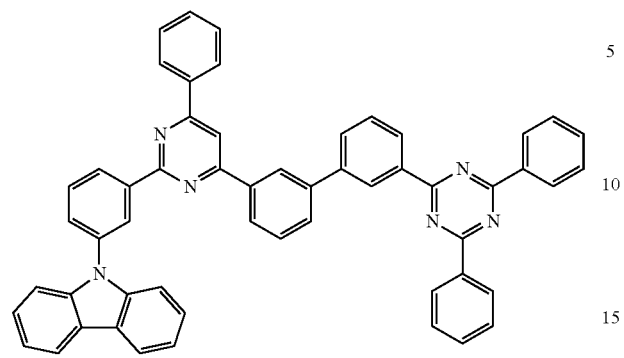
109
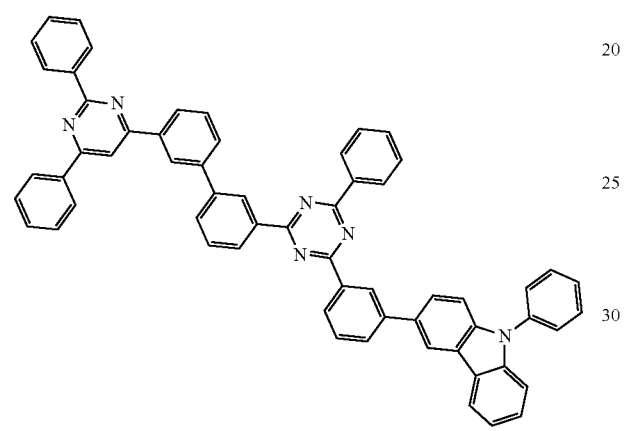
110
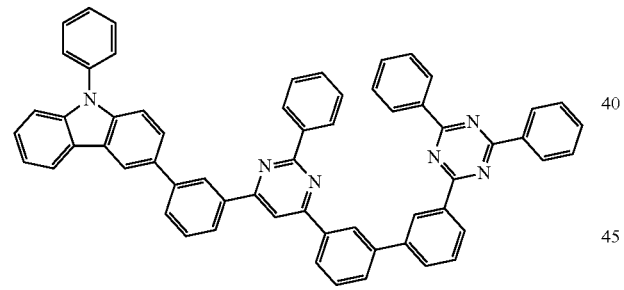
111
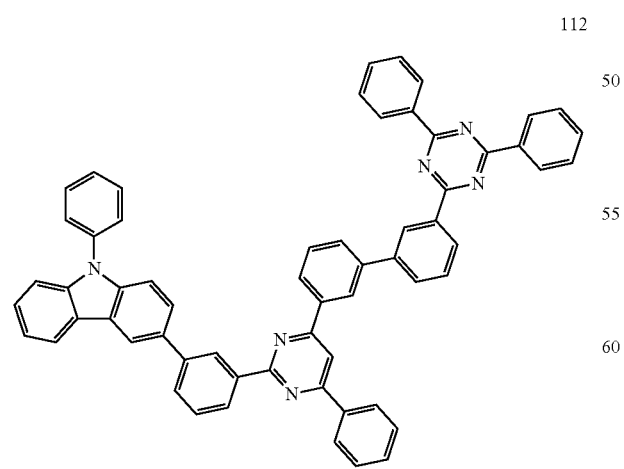
112
-continued
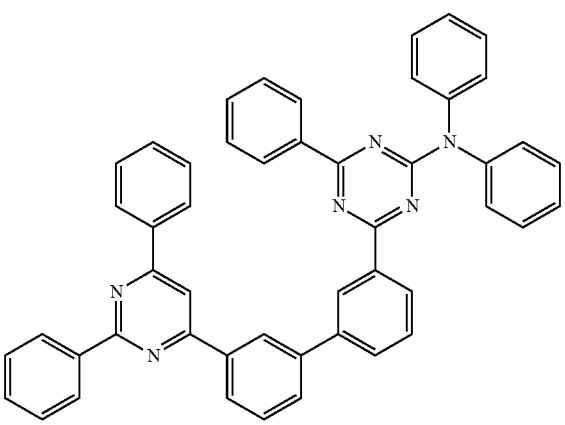
113
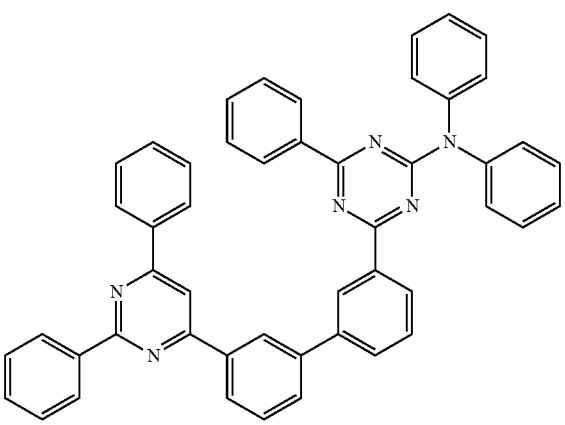
114
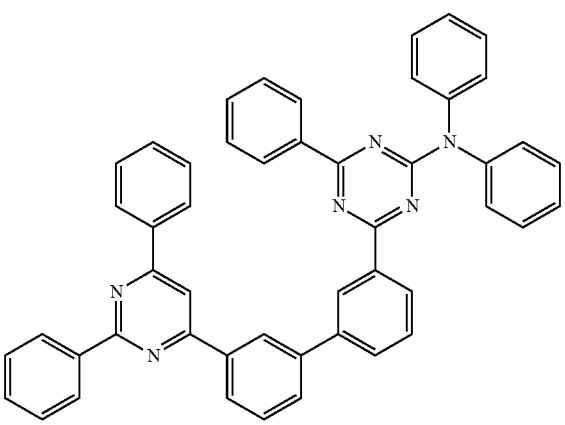
115

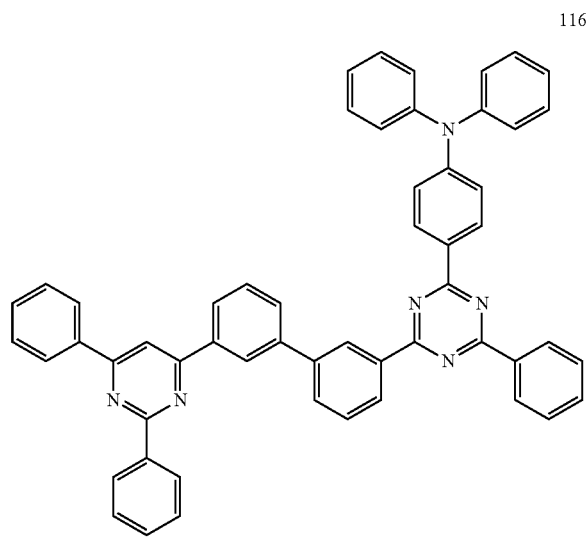
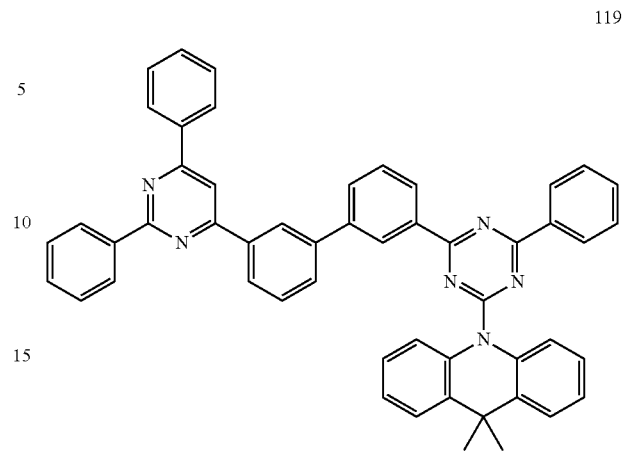
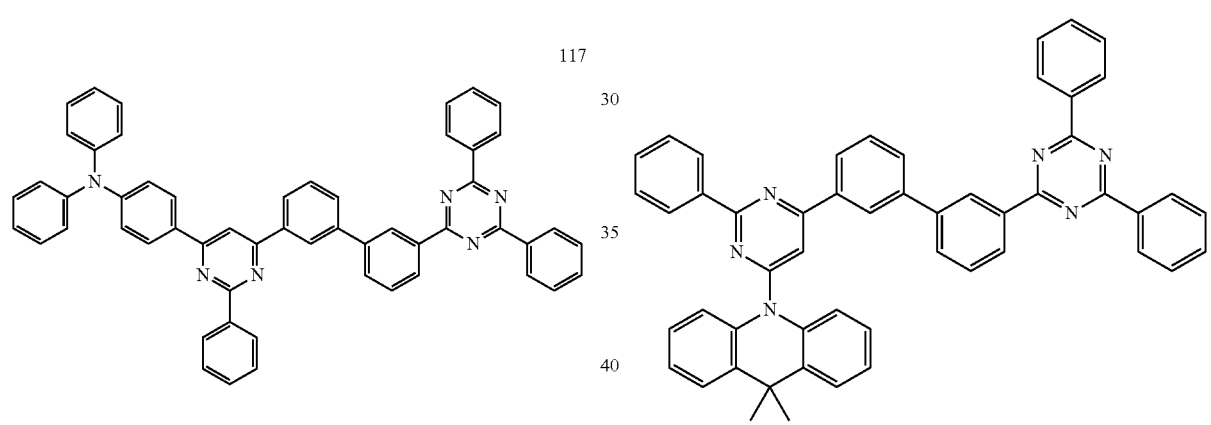
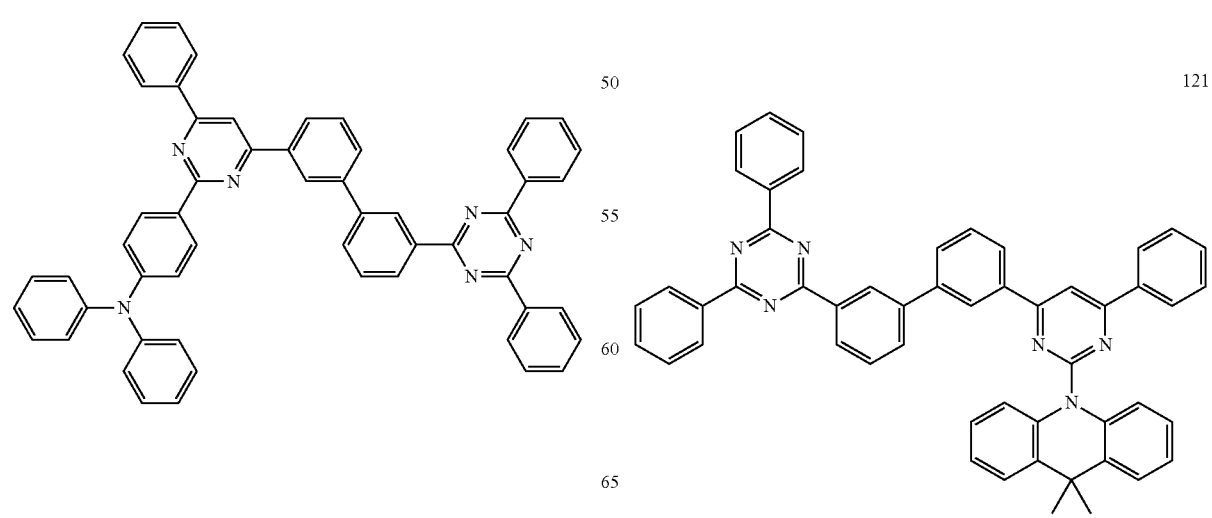

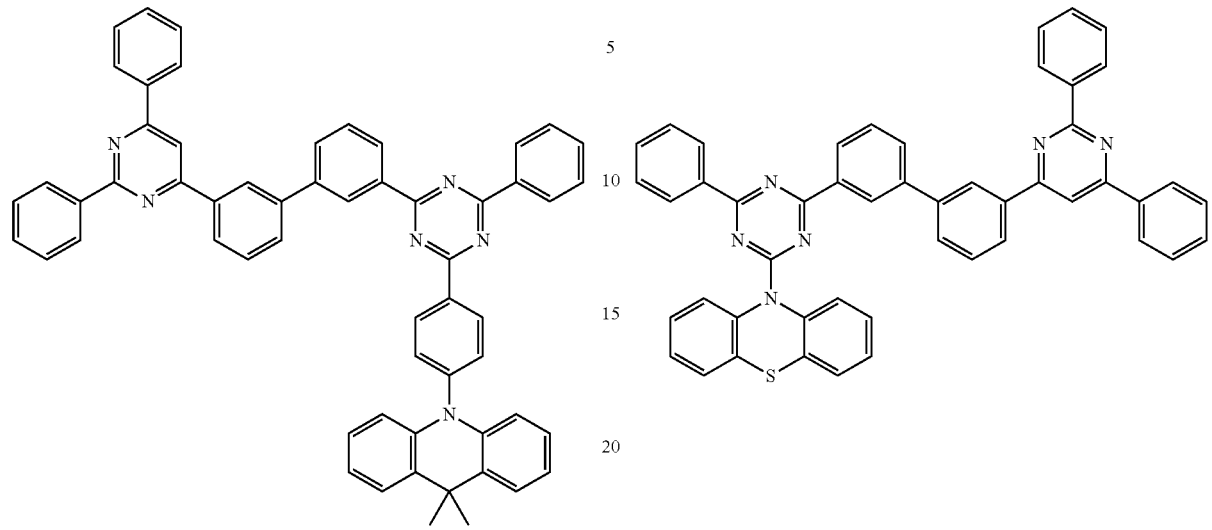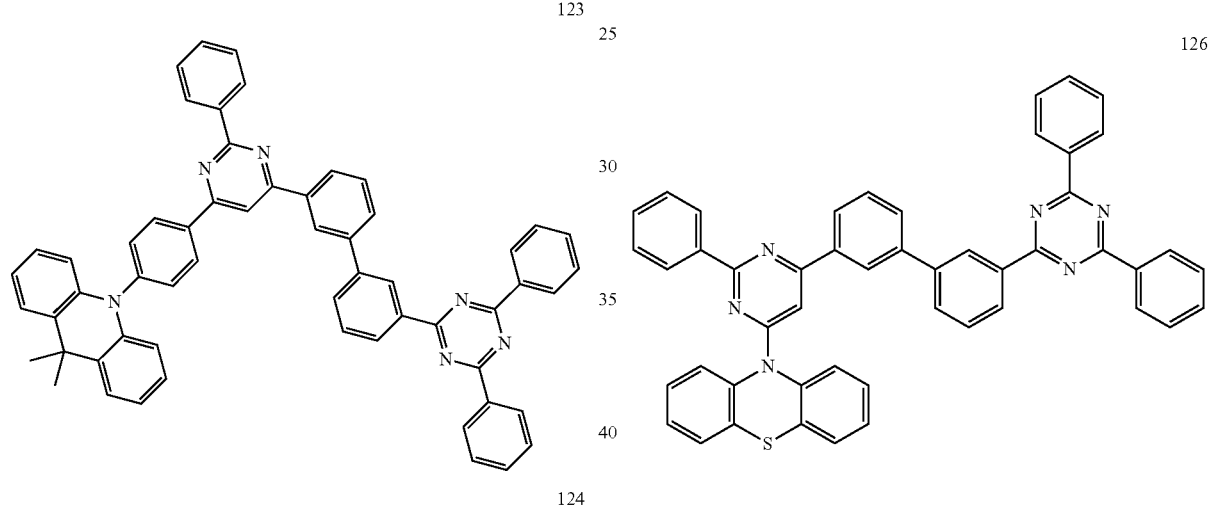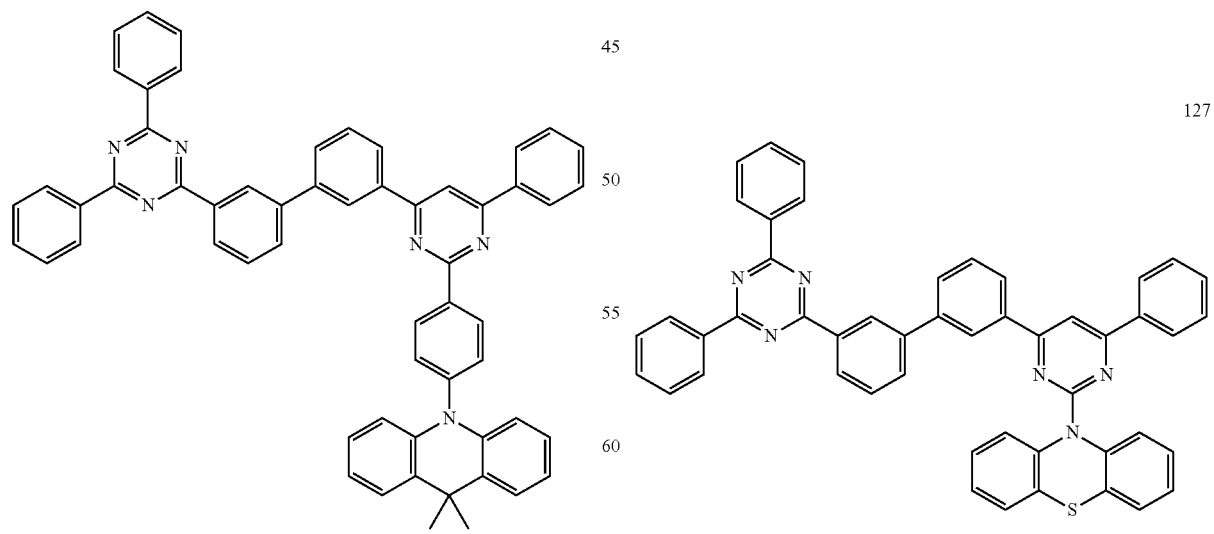

128
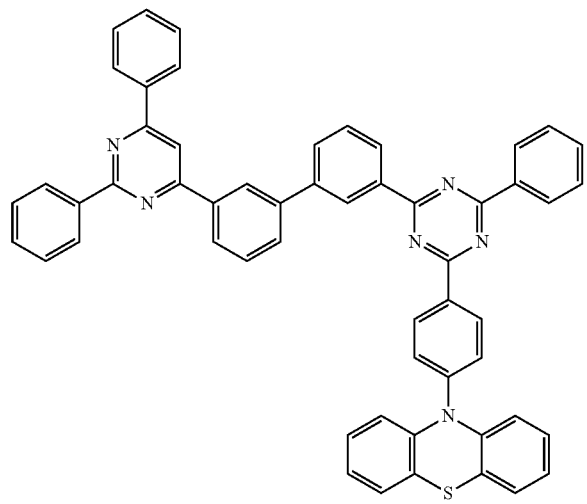
129
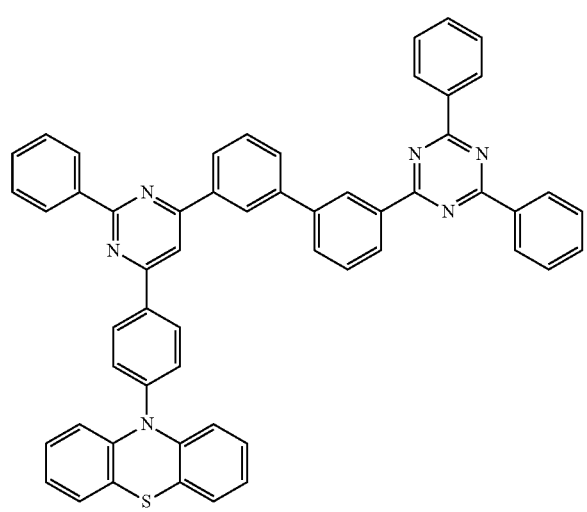
130
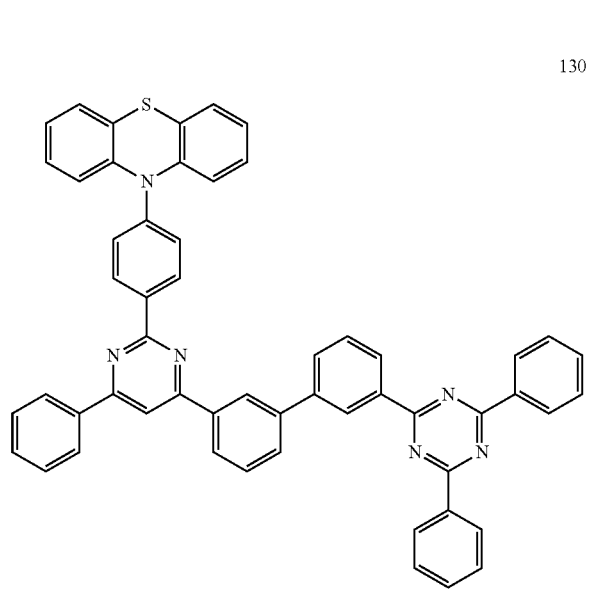
131
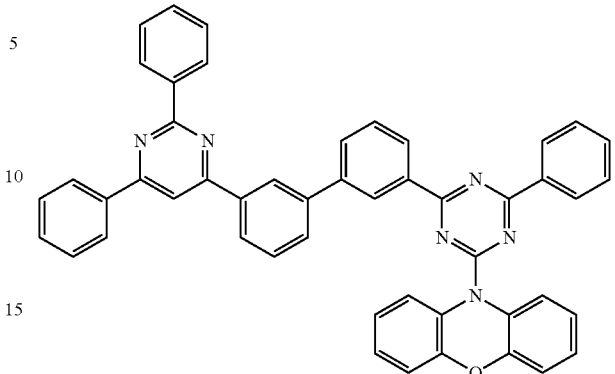
132
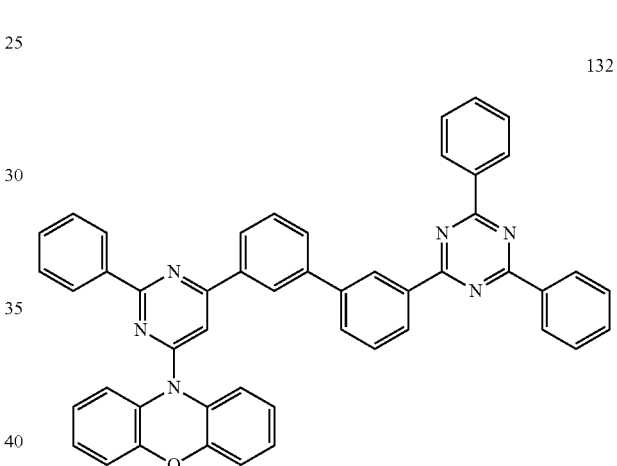
133
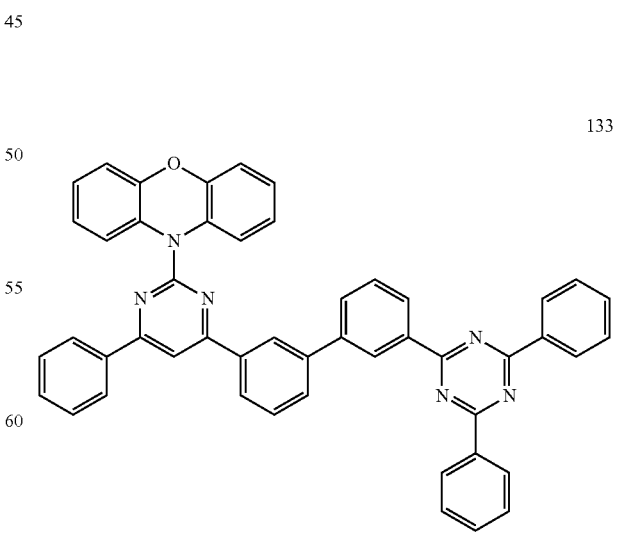

134
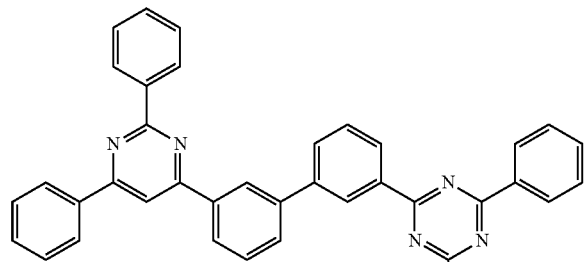
135
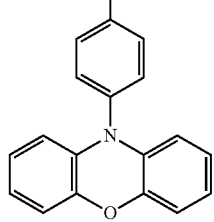
136
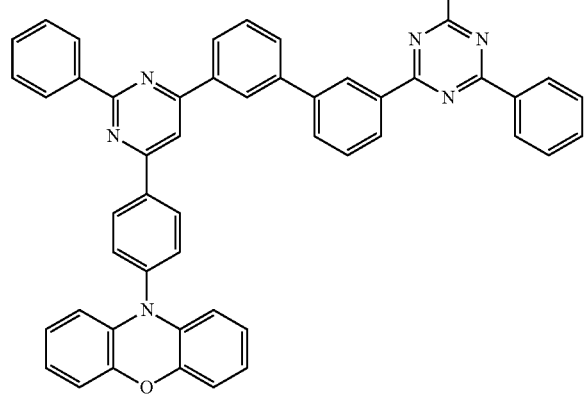
137
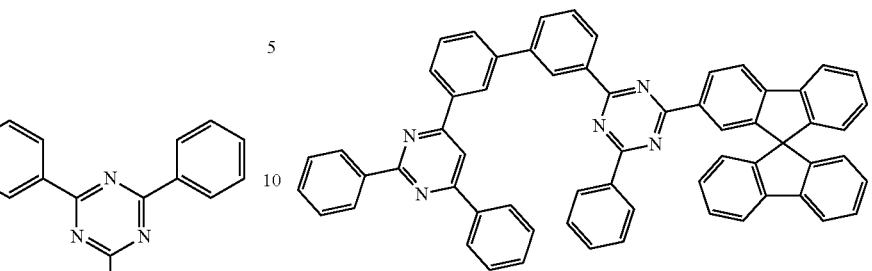
138
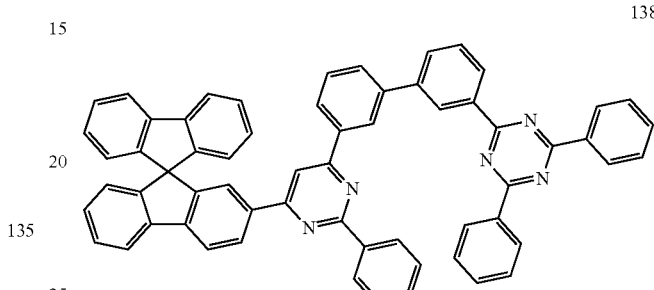
139
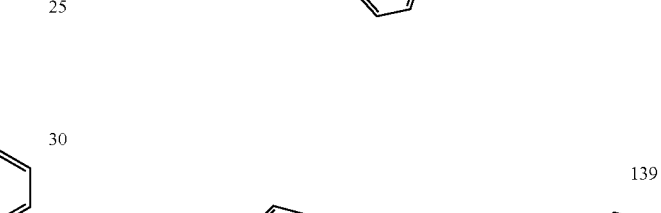
140
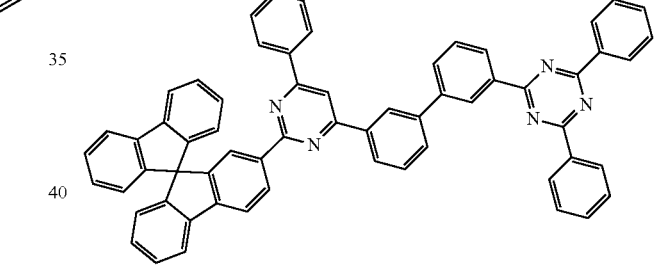

141
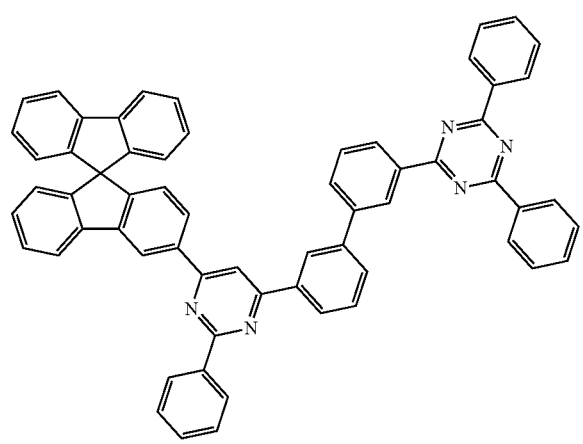
142
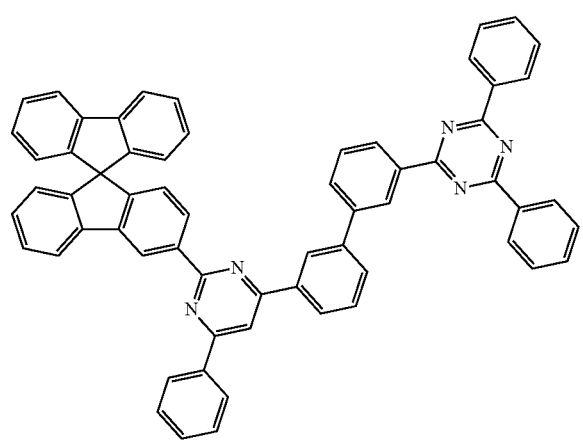
143
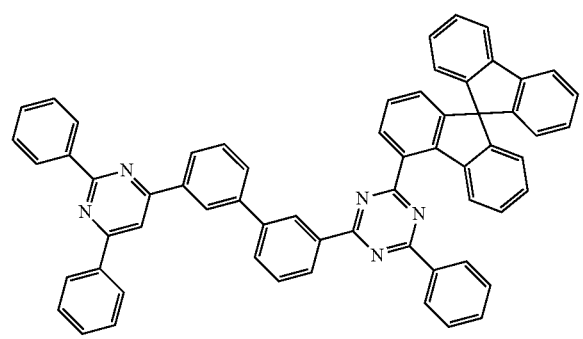
144
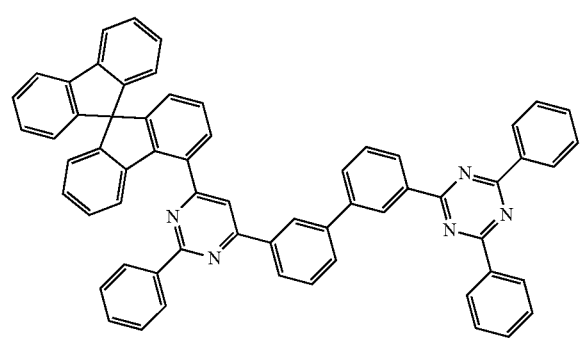
145
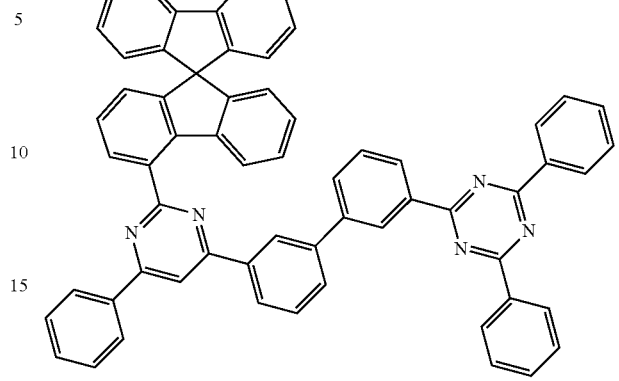
146
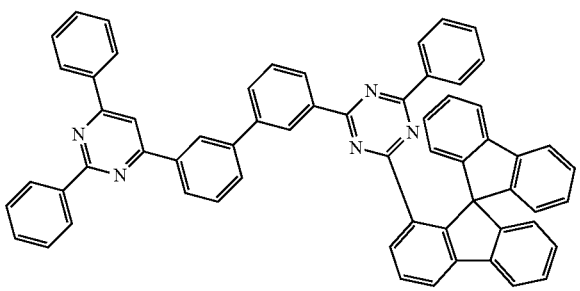
147
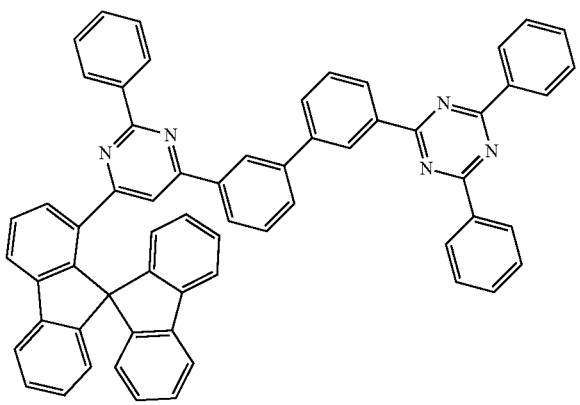
148
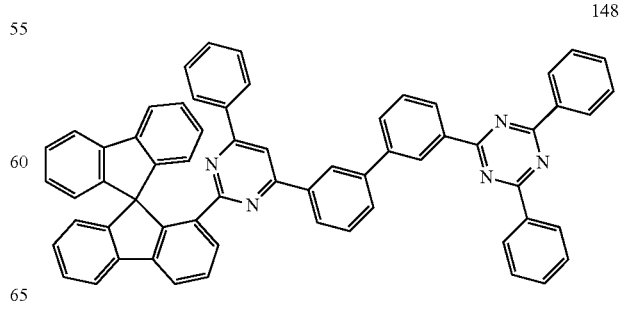

149
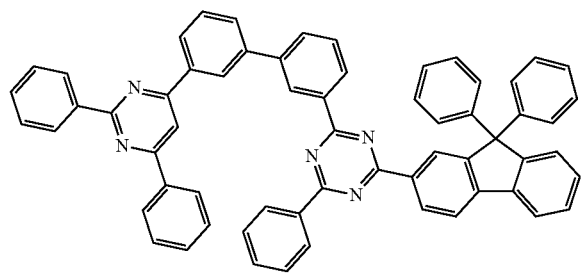
150
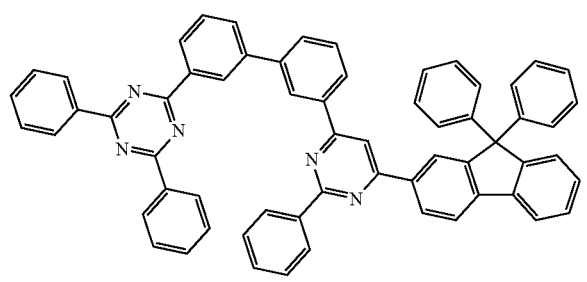
151
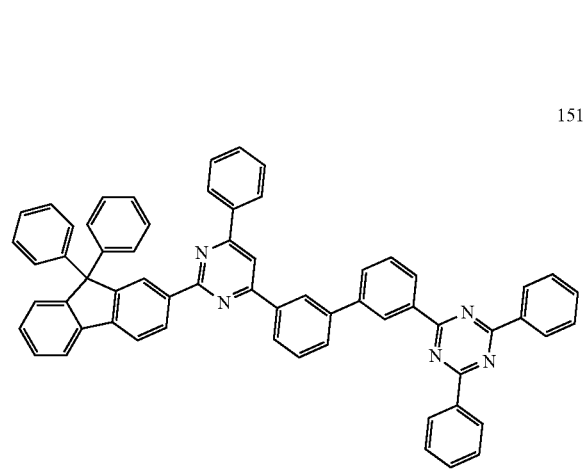
152
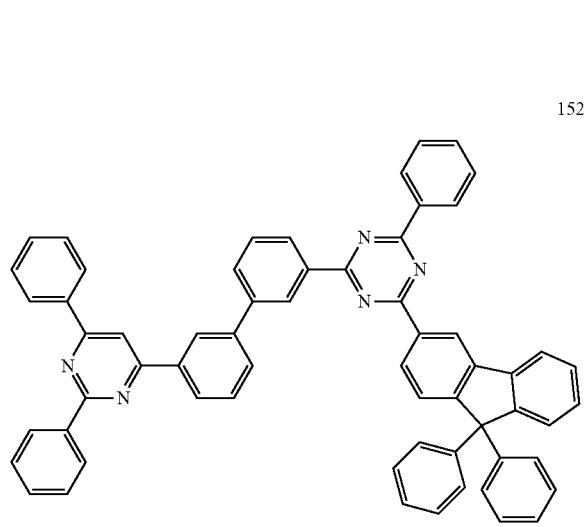
153
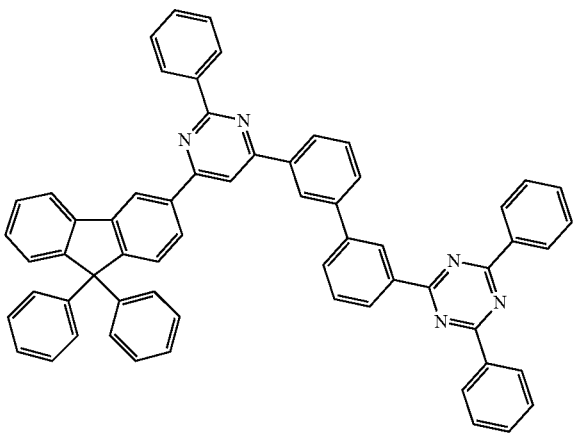
154
155
156
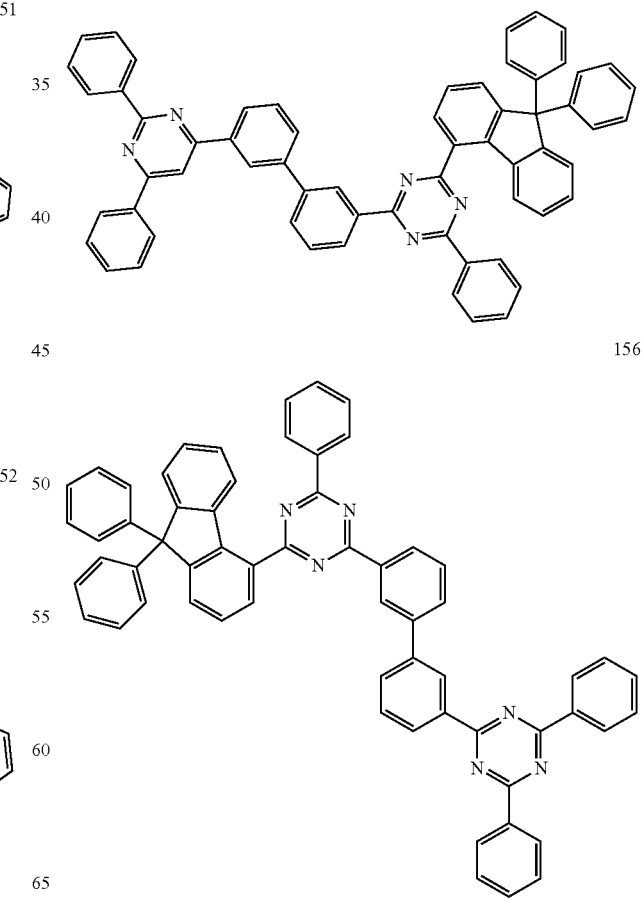

157
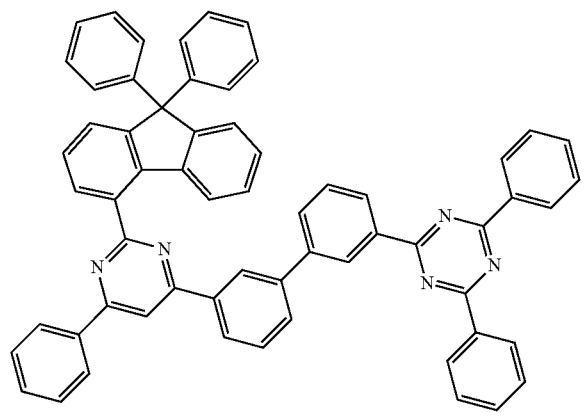
158
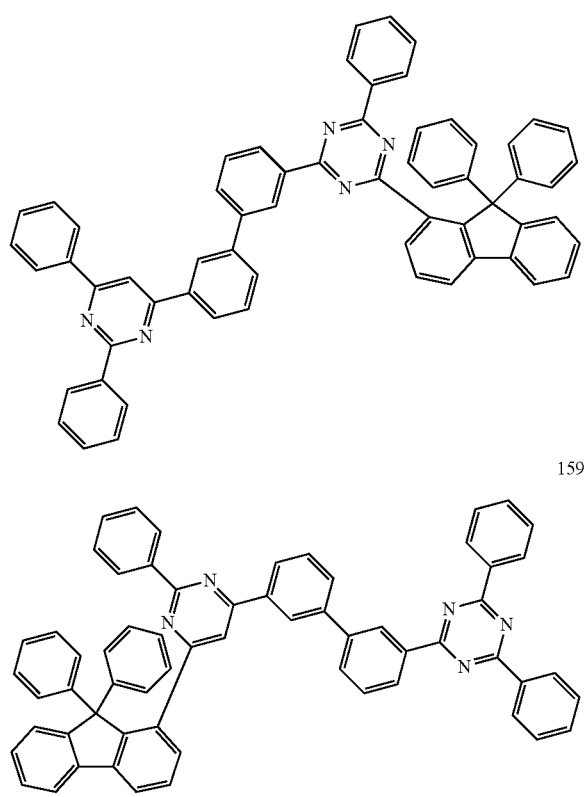
159
160
161
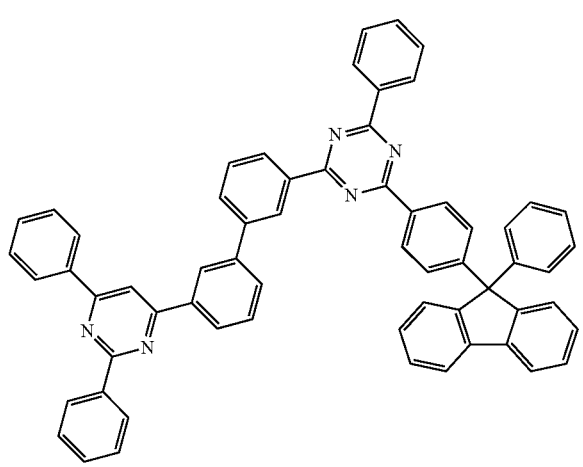
162
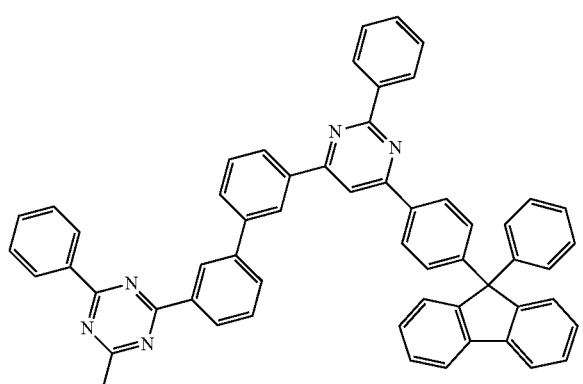
163
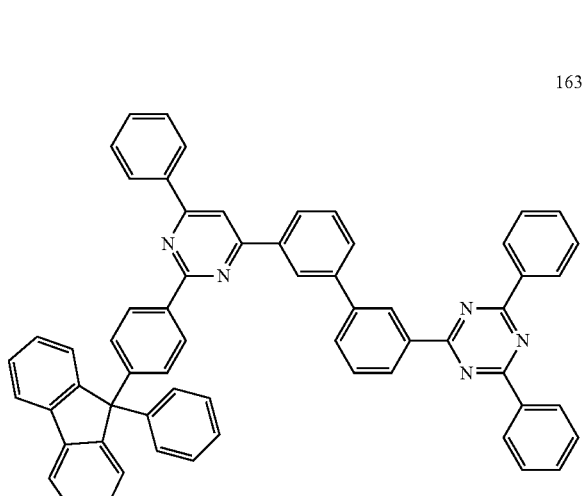

164
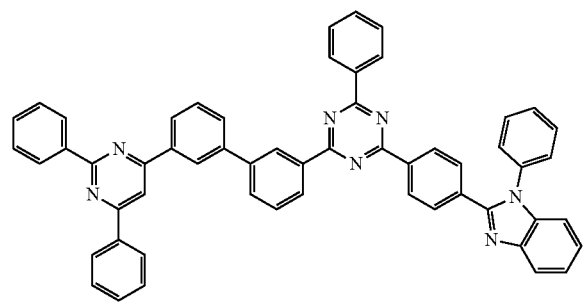
165
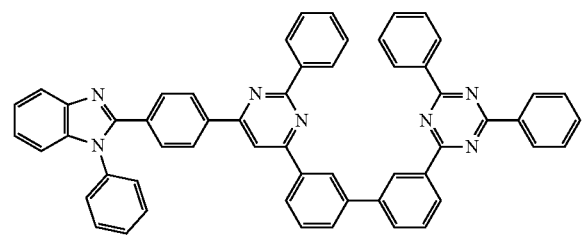
166
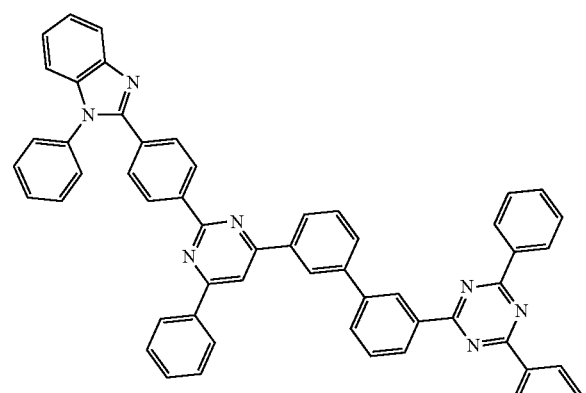
167
168
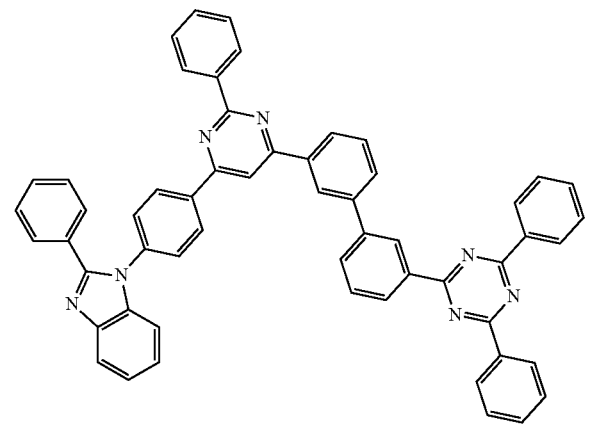
169
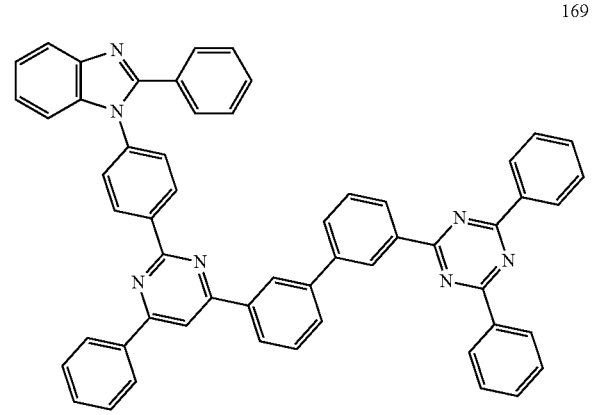
170
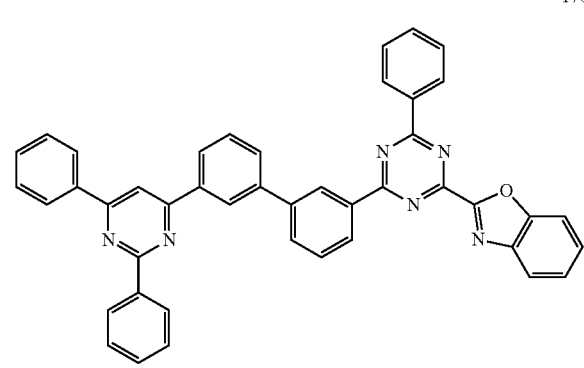
171
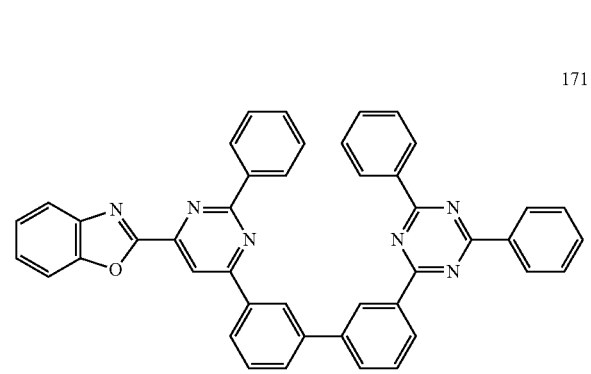

172
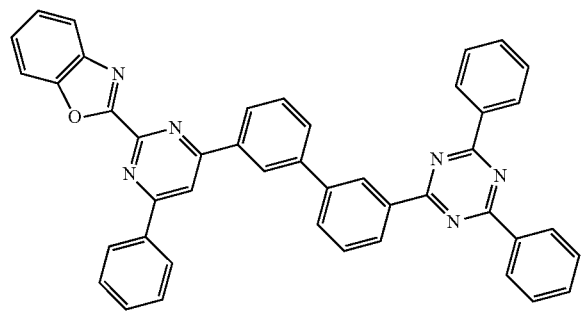
173
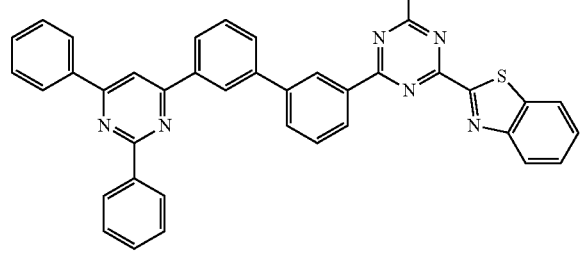
174
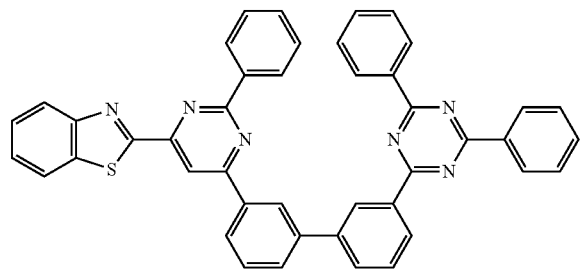
175
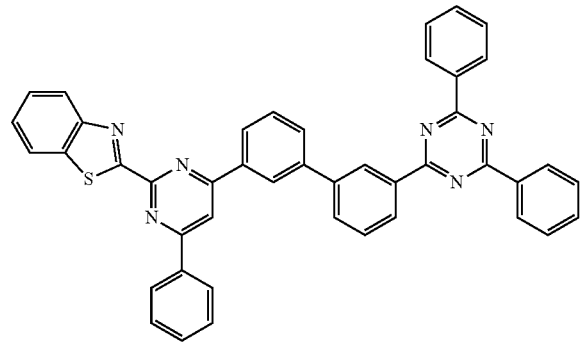
176
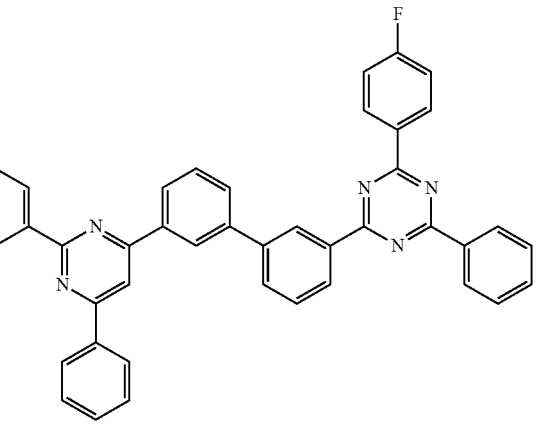
177
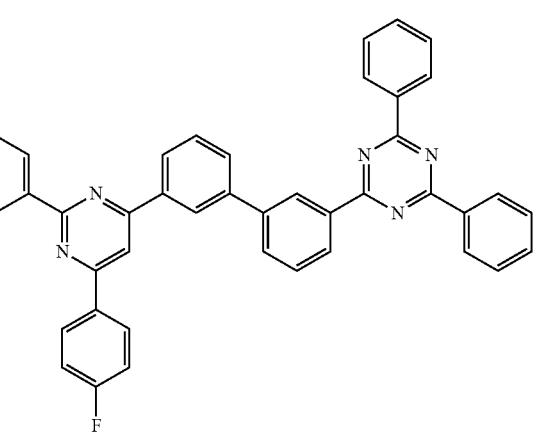
178
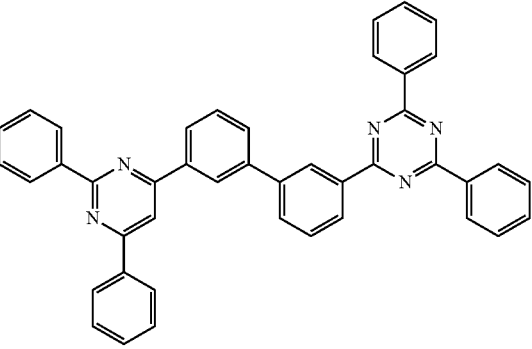
179
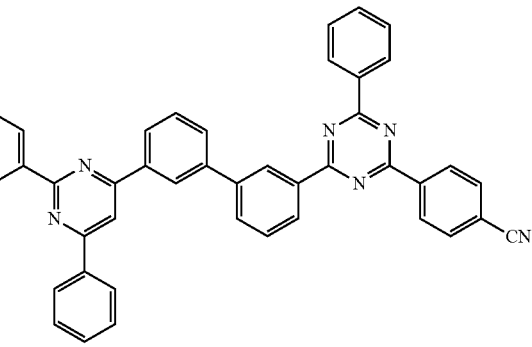

180
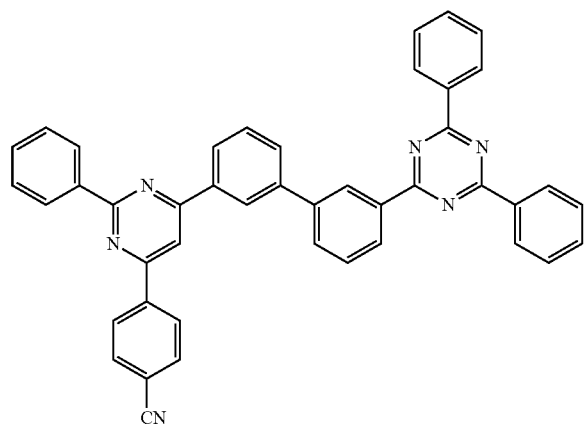
181
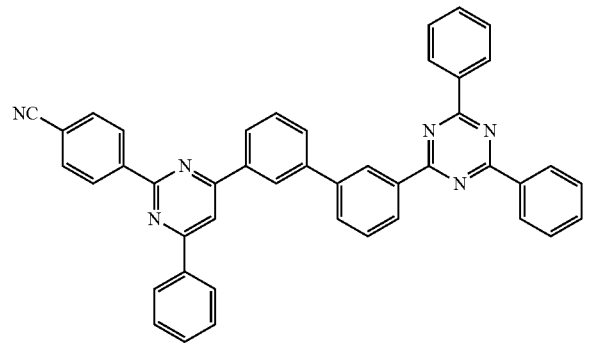
182
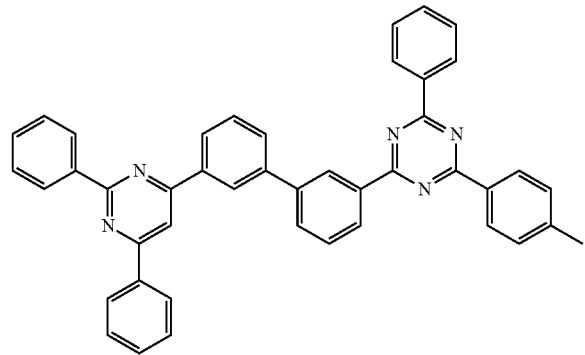
183
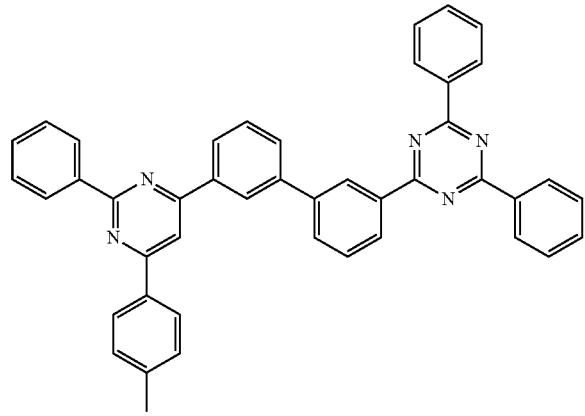
184
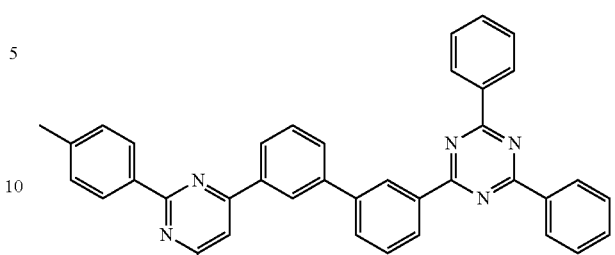
185
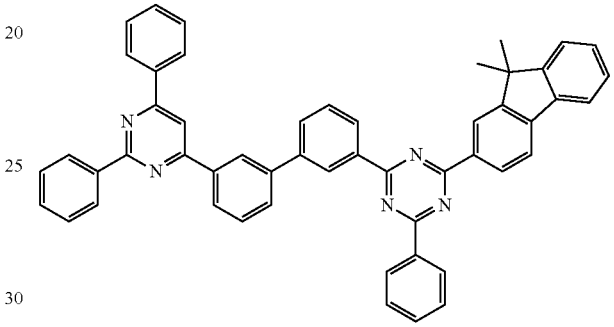
186
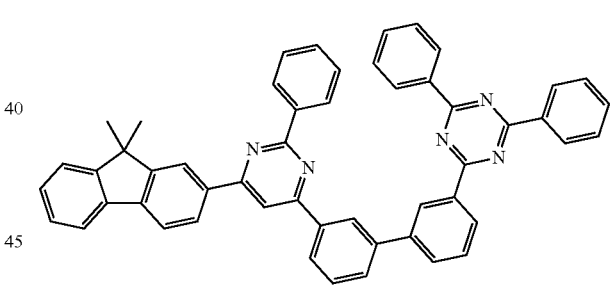
187
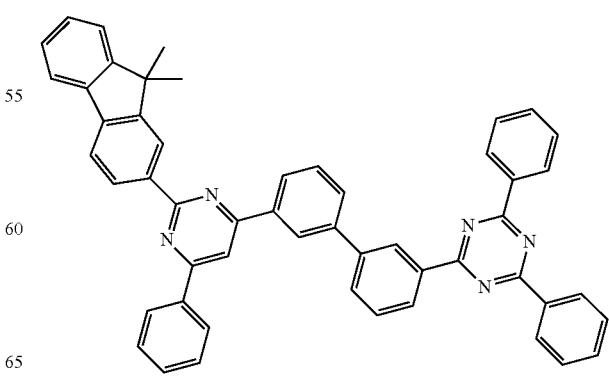

188
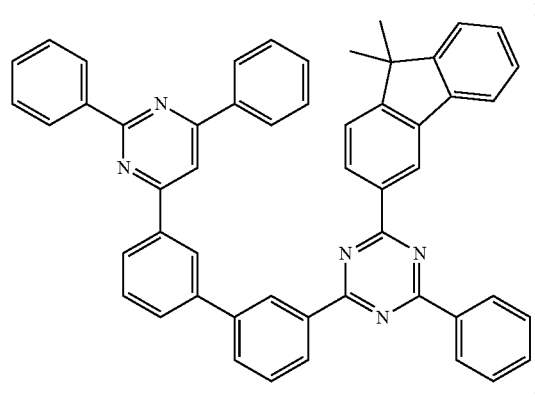
189
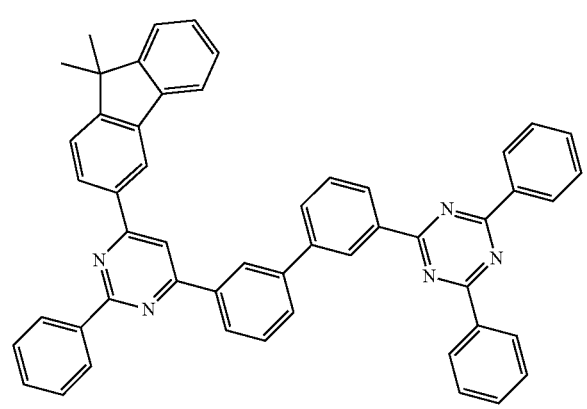
190
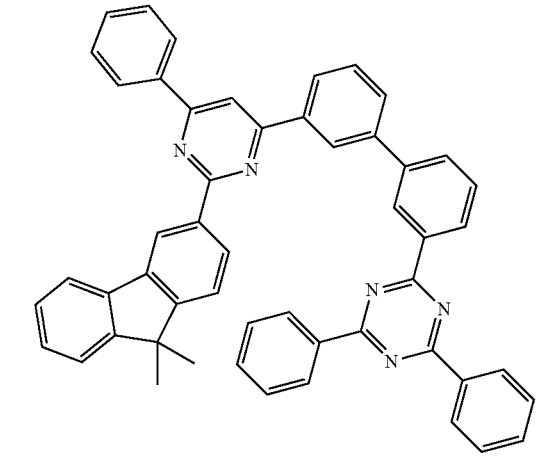
191
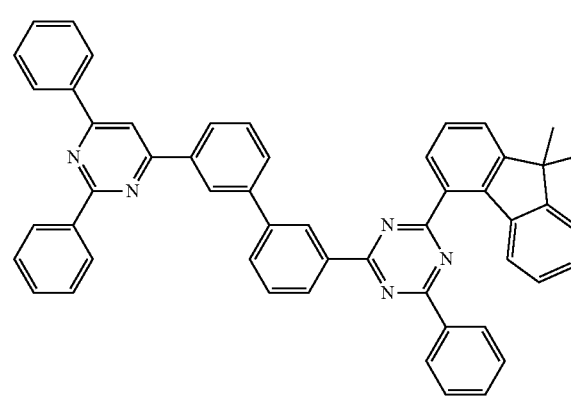
192
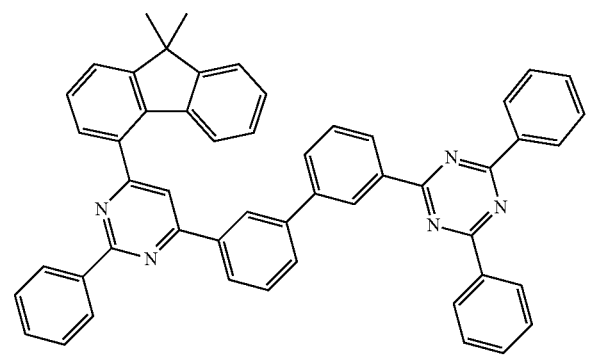
193
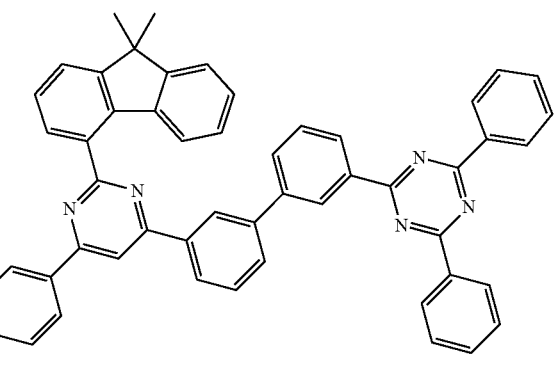
194
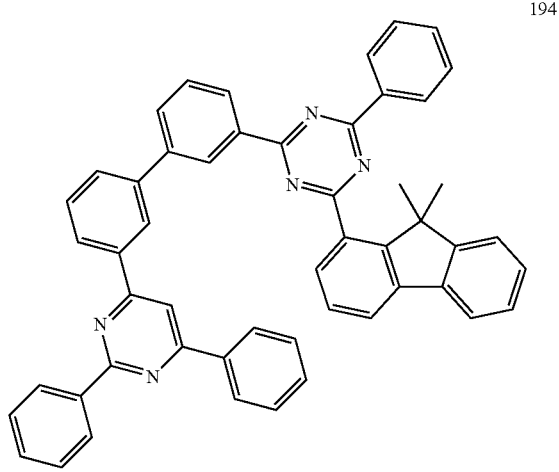

459
-continued
195
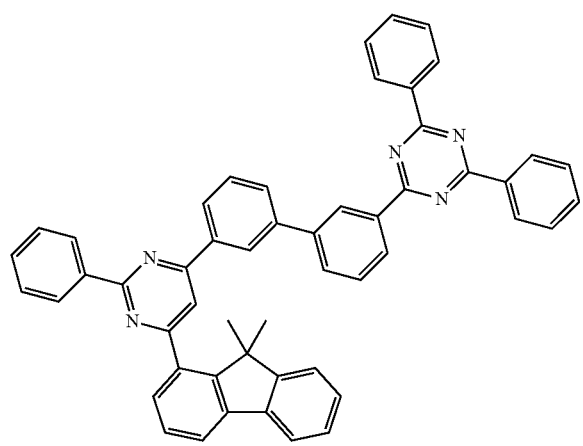
196
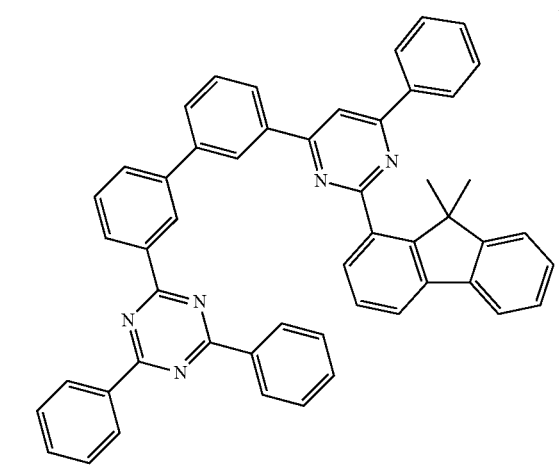
221
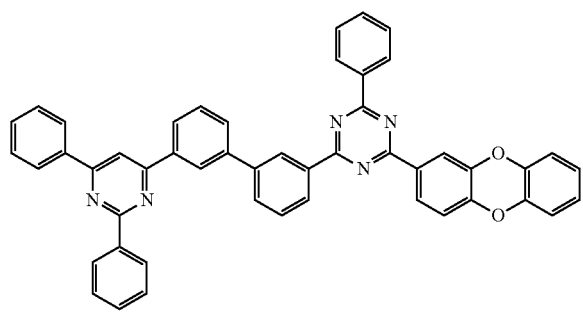
460
-continued
222
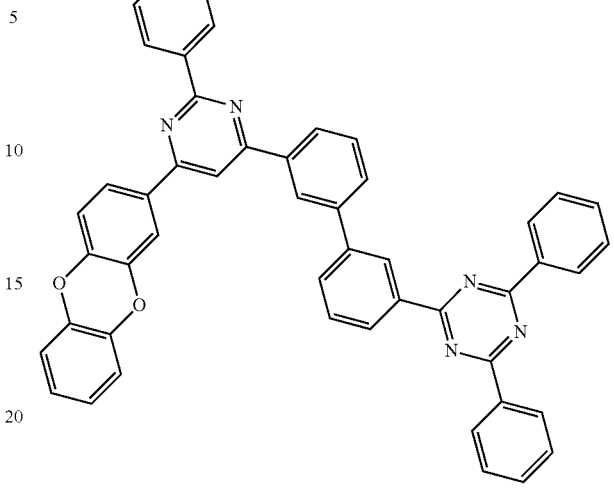
223
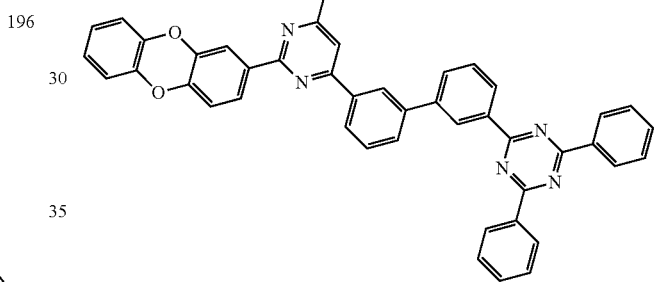
224
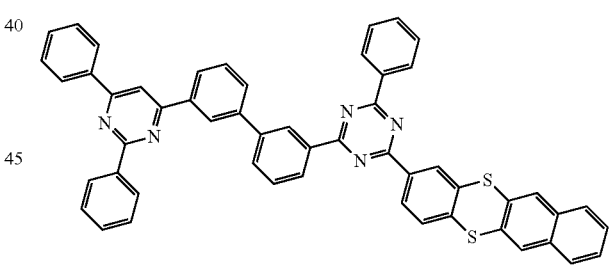
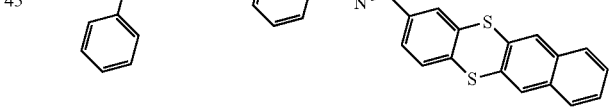
225
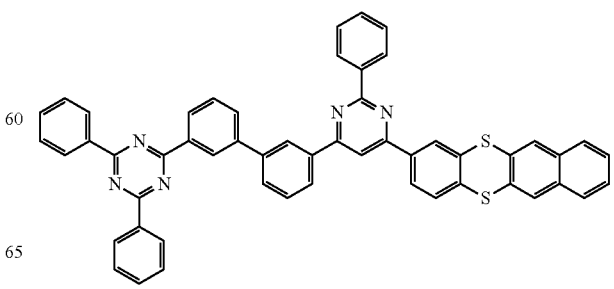

-continued

226

227

228

229

-continued

230

231

232

233
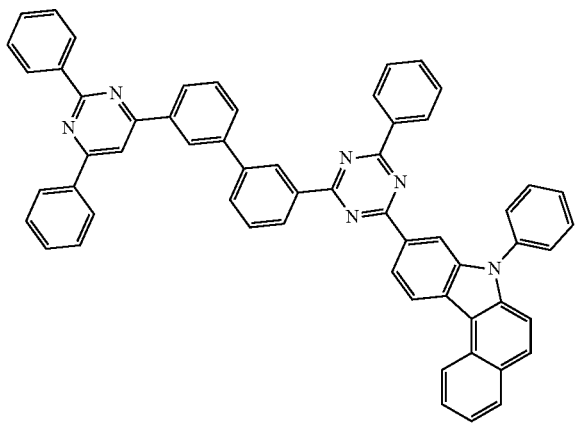
234
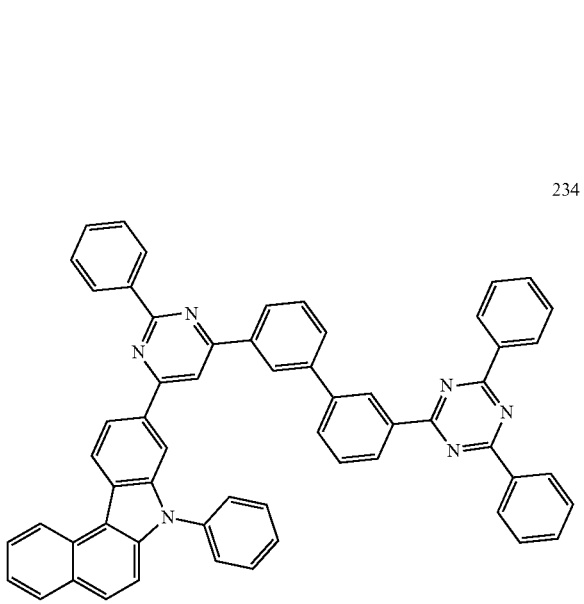
235
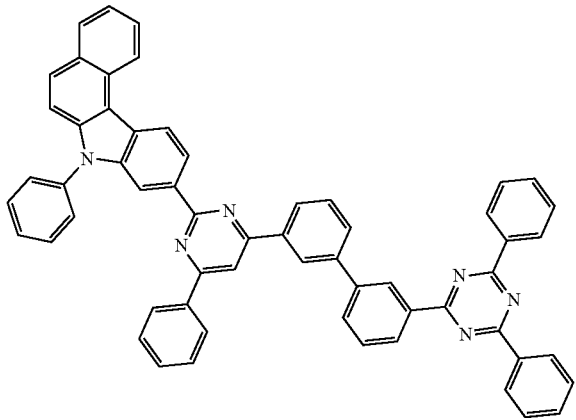
236
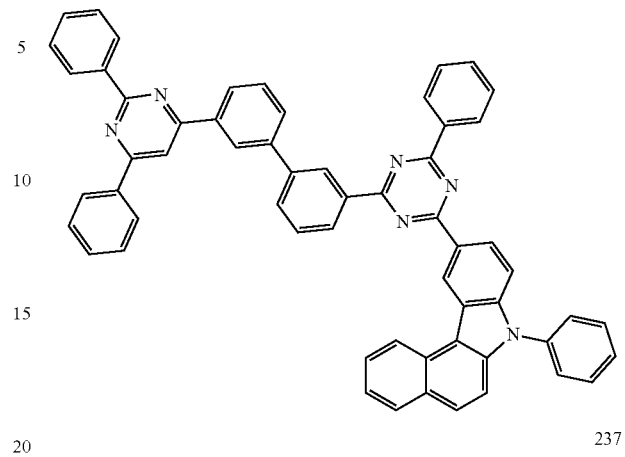
237
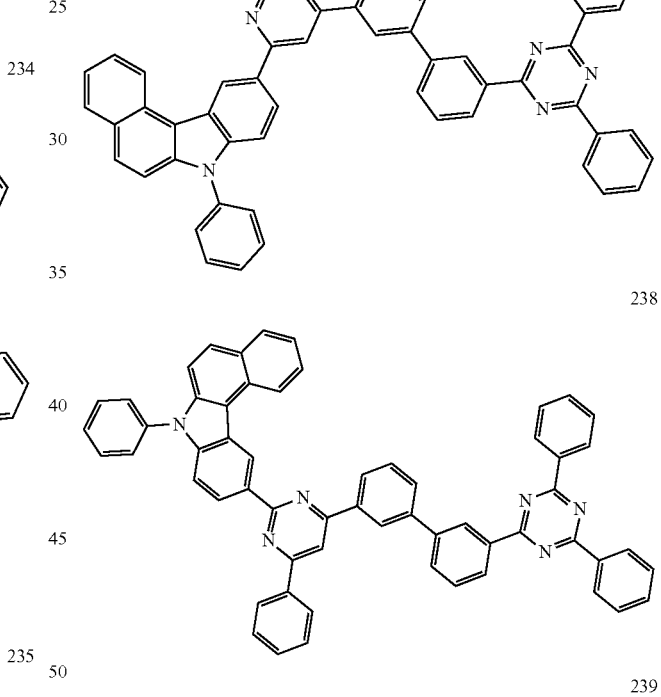
238
239
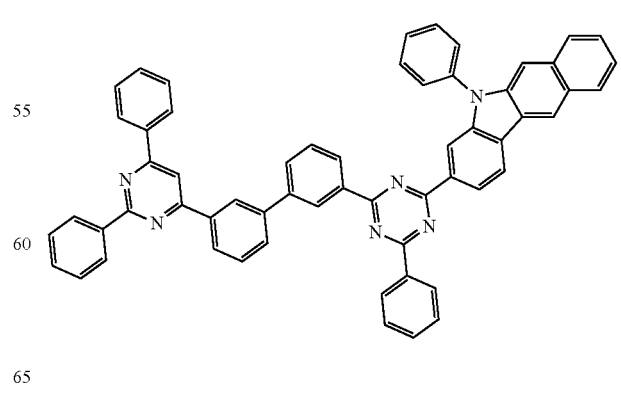

465
-continued
240
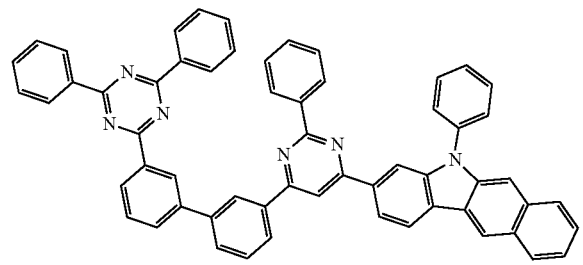
241
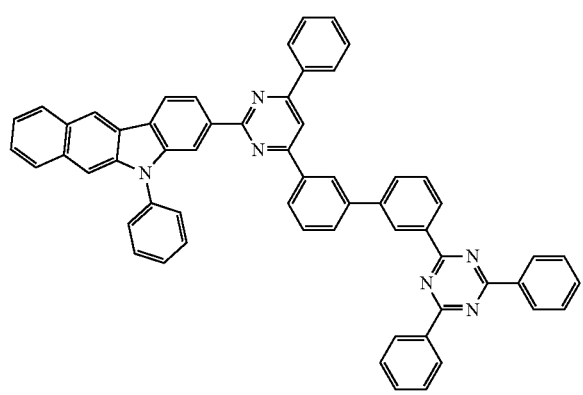
242
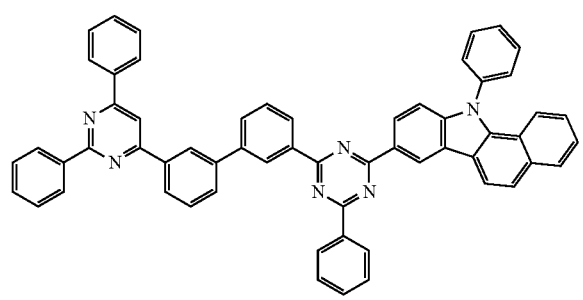
243
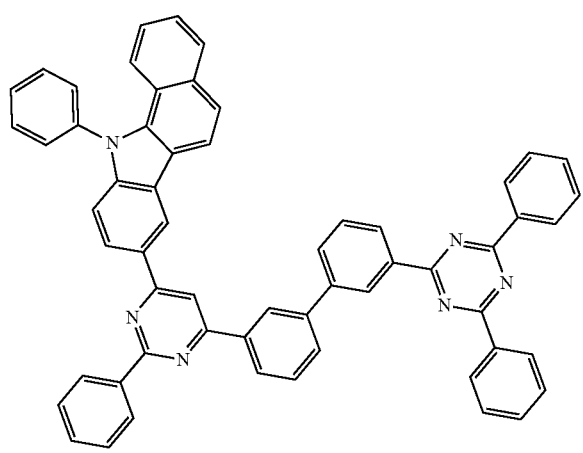
466
-continued
244
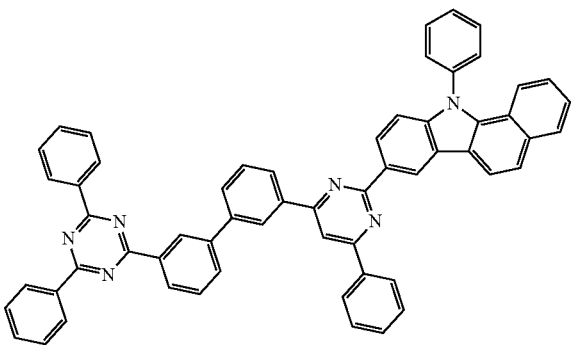
245
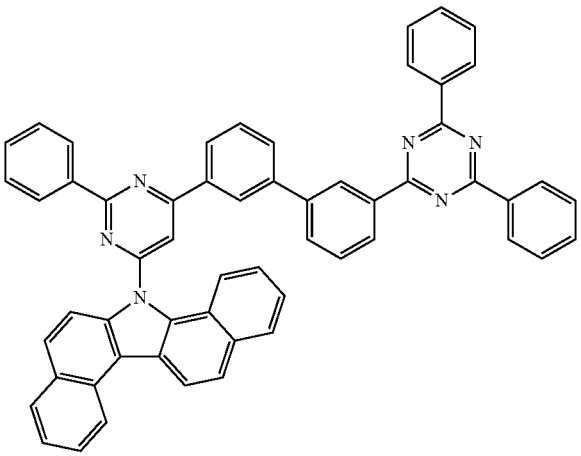
246

467  468
-continued  -continued
247
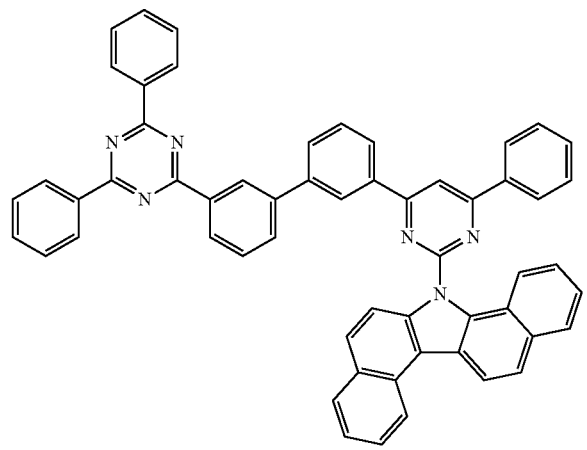
250
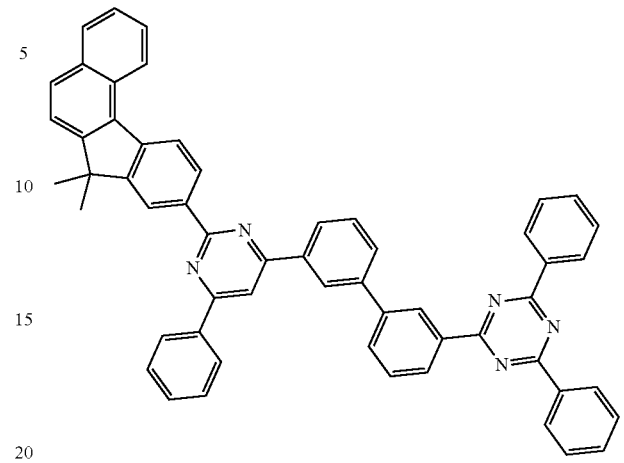
248
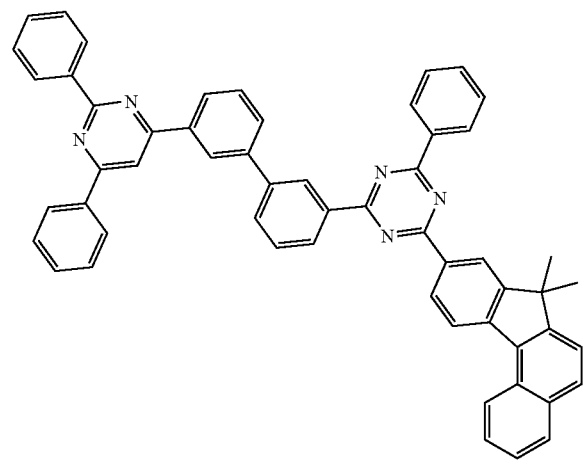
251
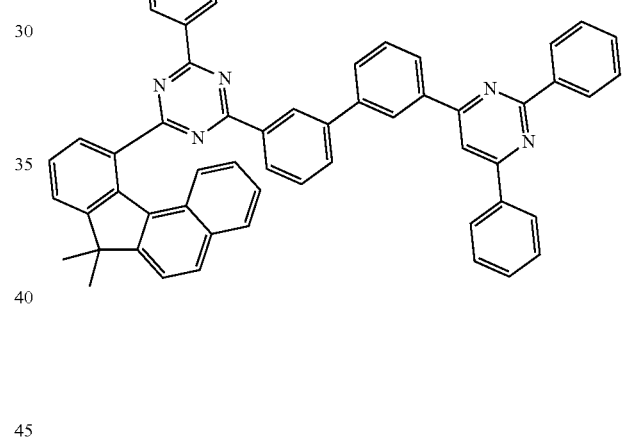
249
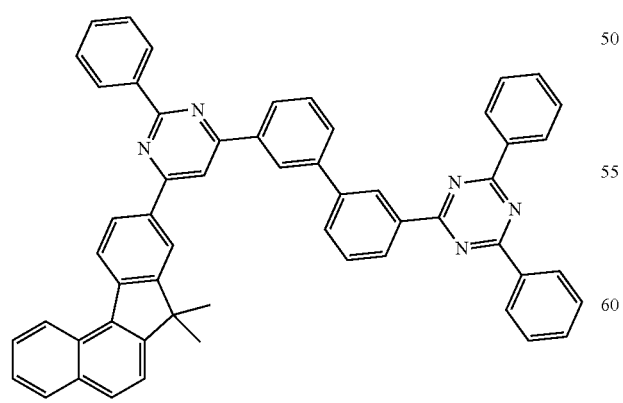
252

253
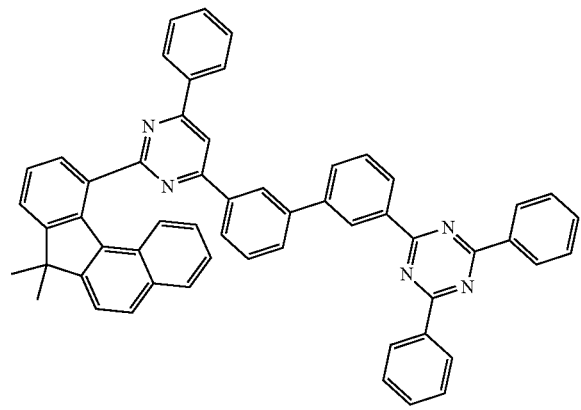
254
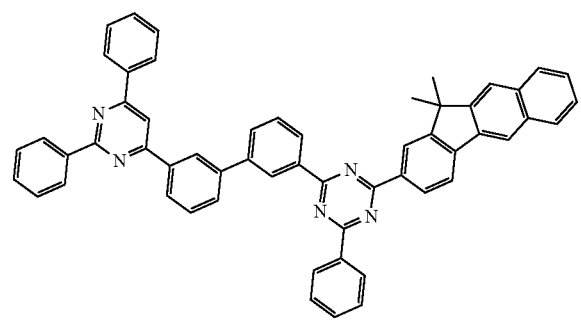
255
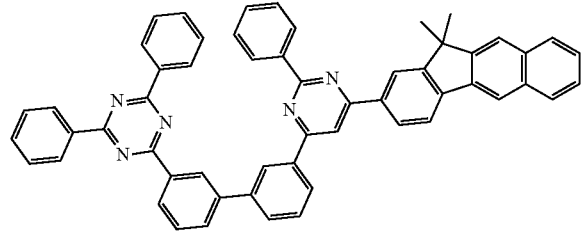
256
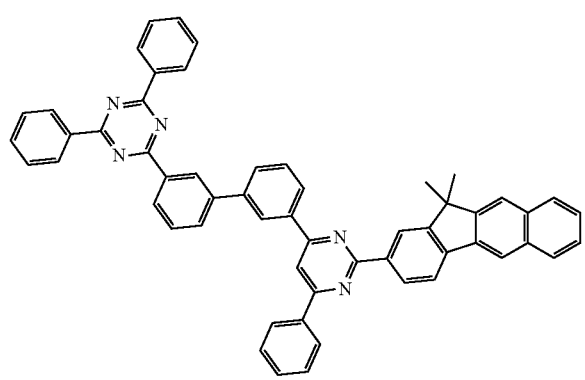
257
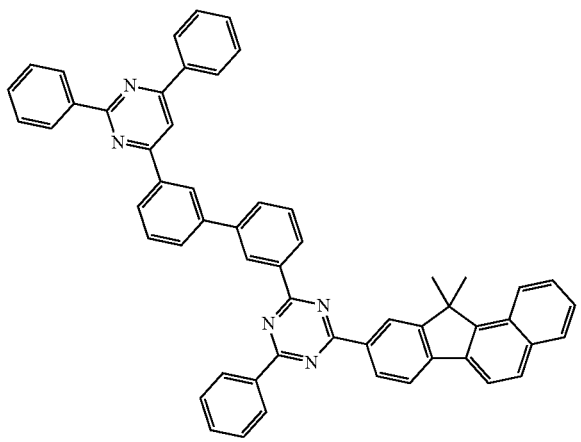
258
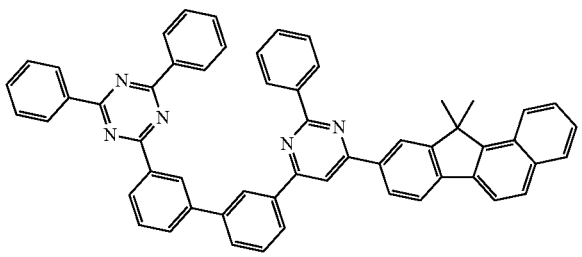
259
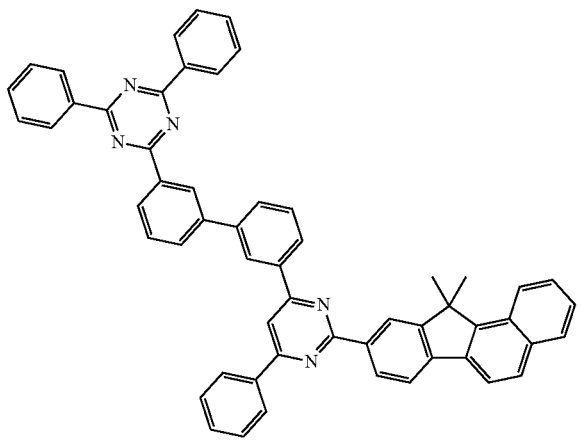
260
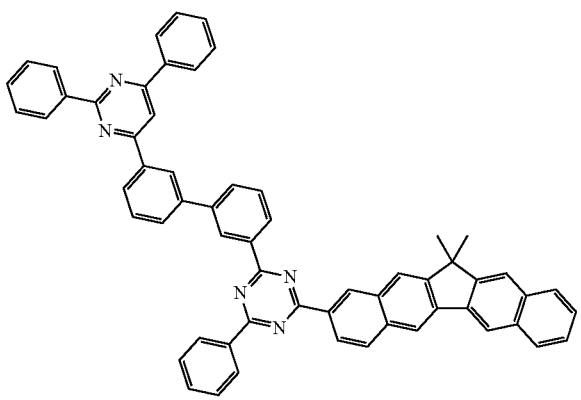

261
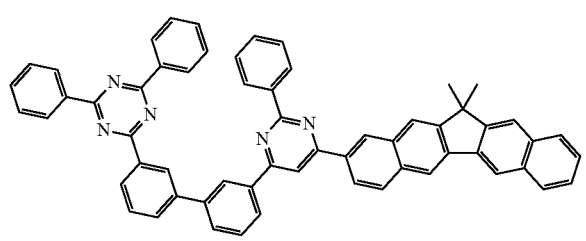
262
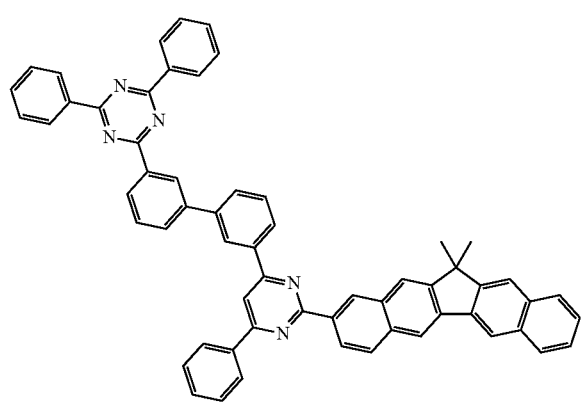
263
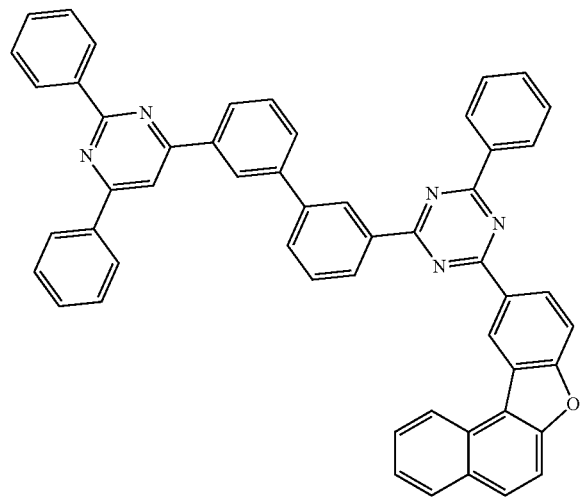
264
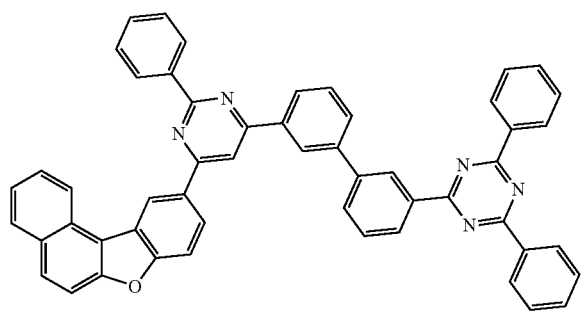
265
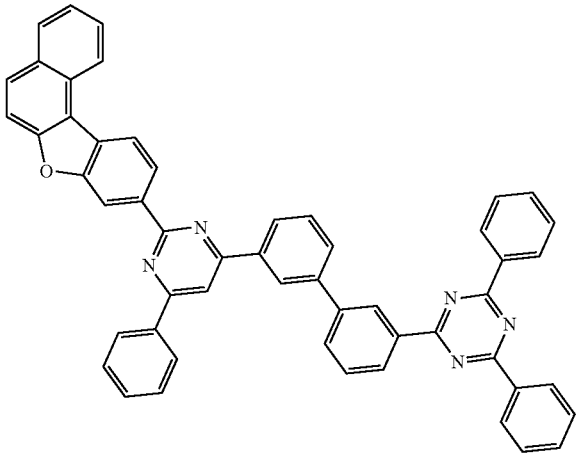
266
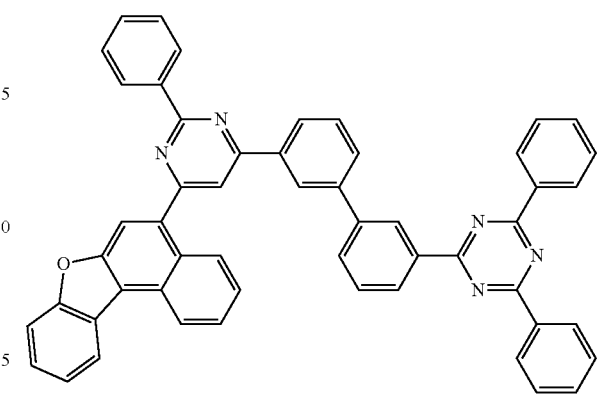
267

268
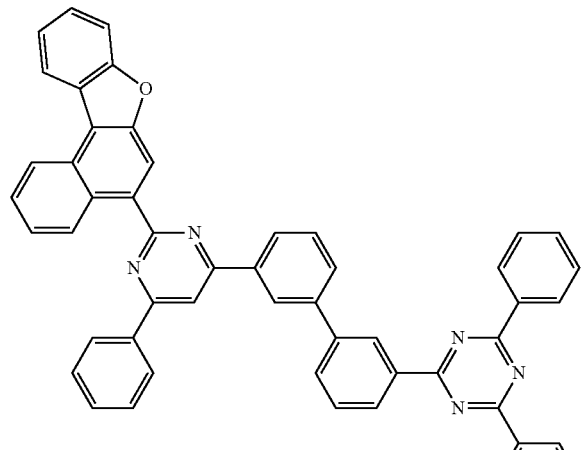
269
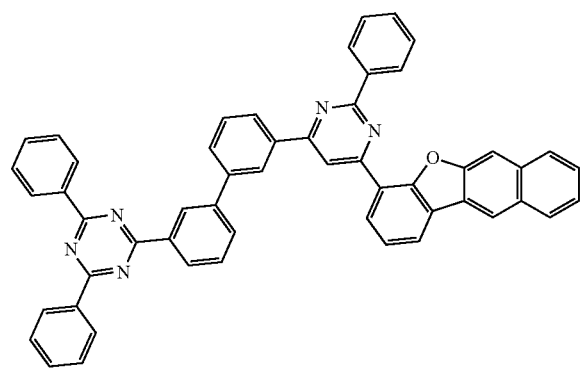
270
271
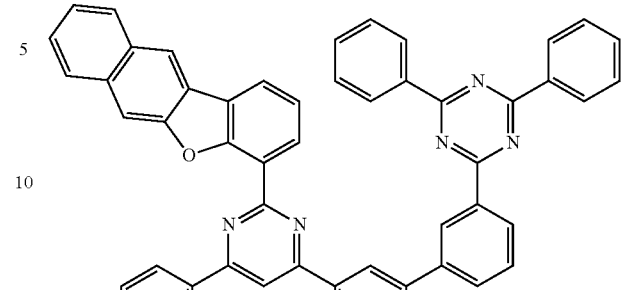
272
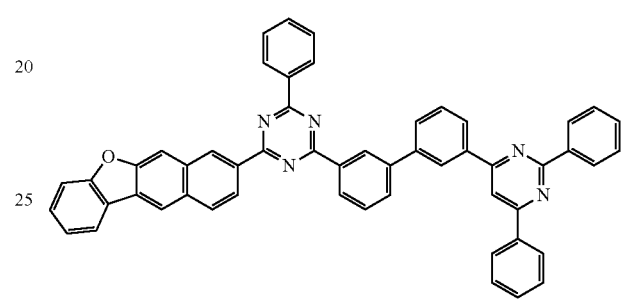
273
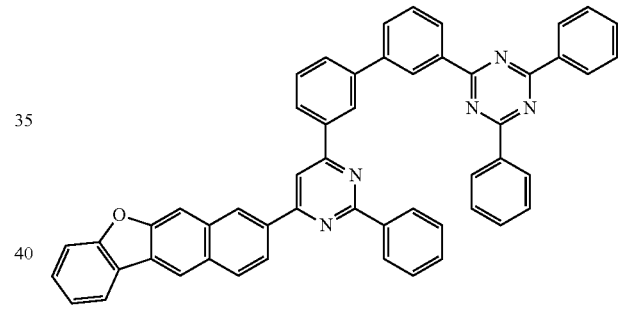
274
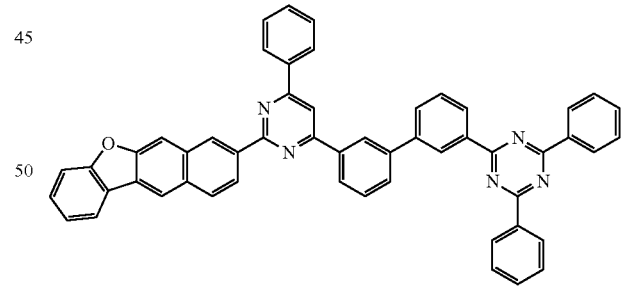
275
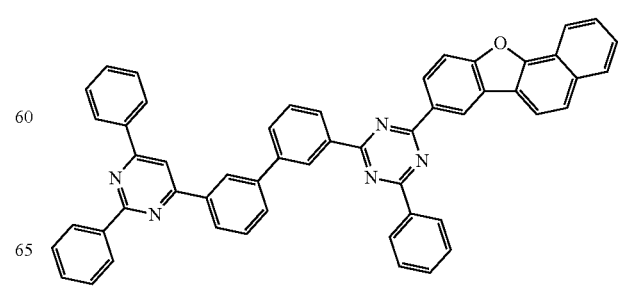

276
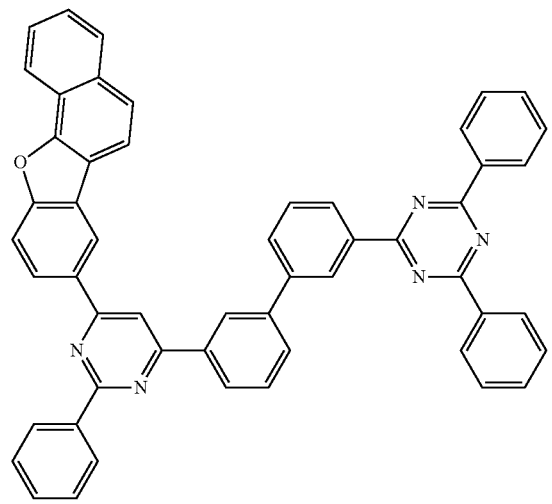
277
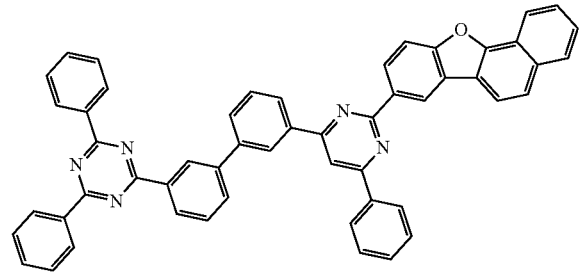
278
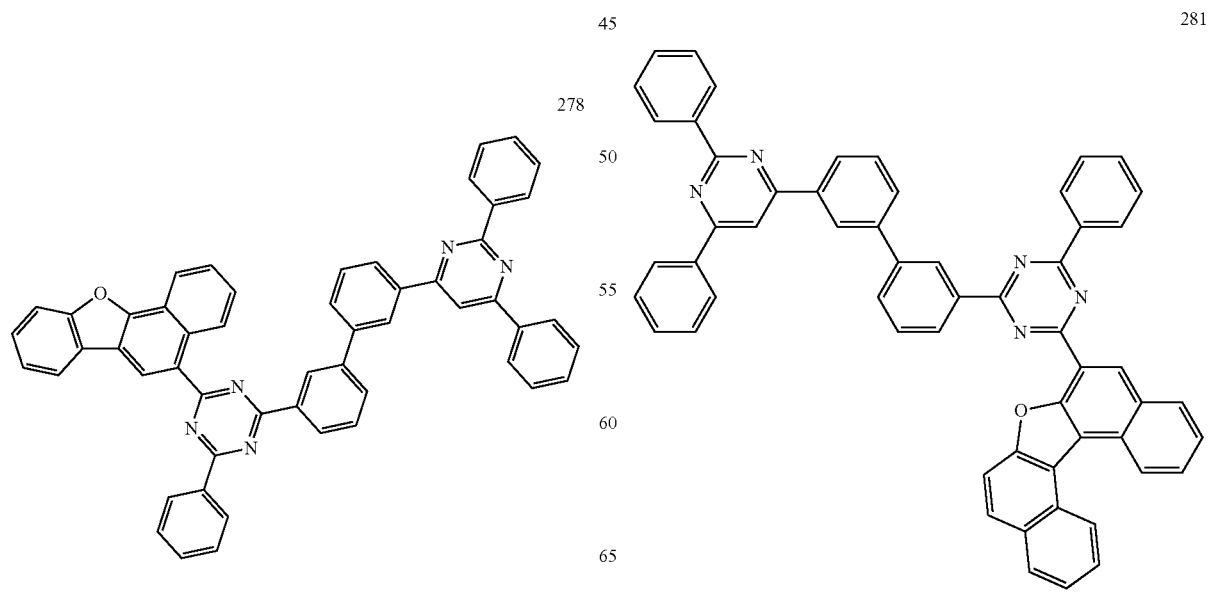
279
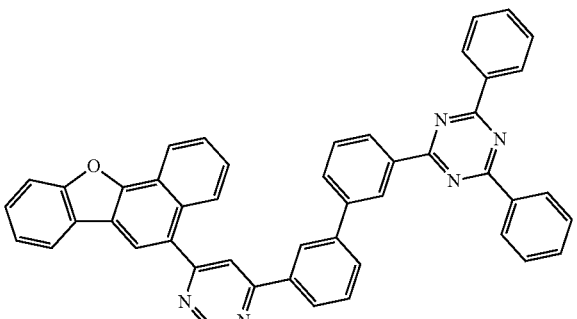
280
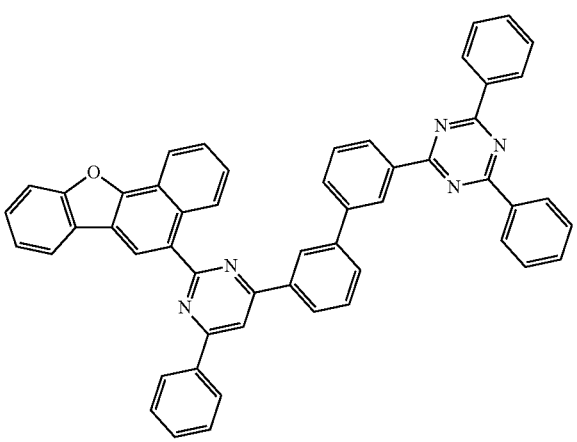
281

282
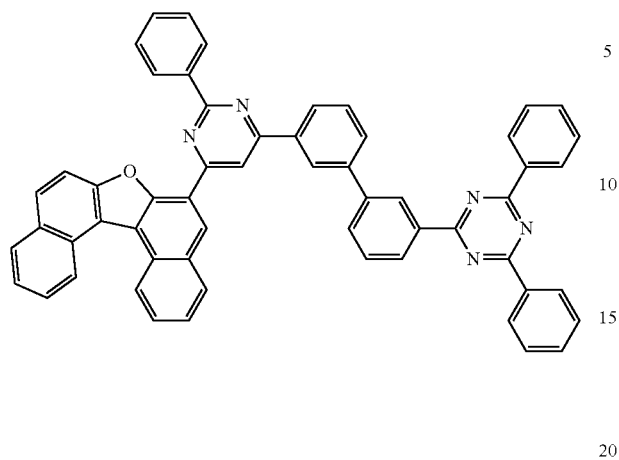
285
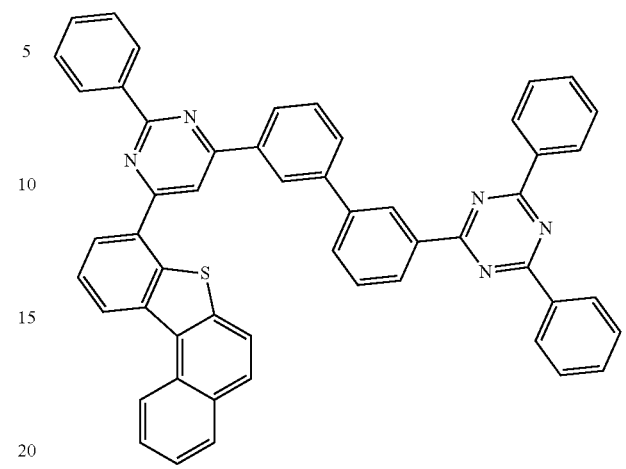
283
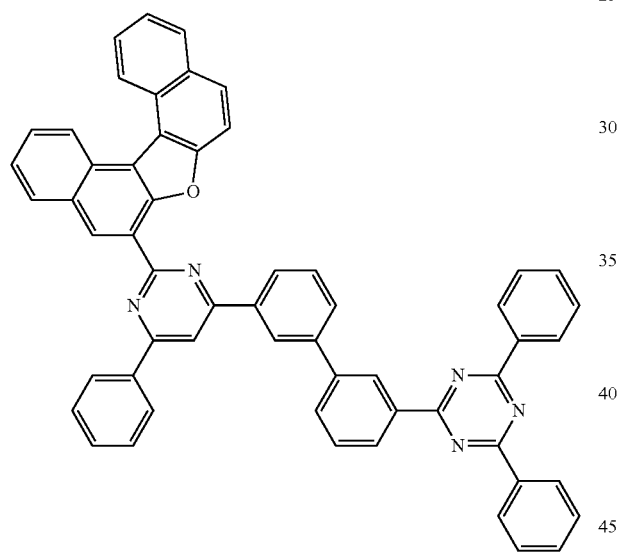
286
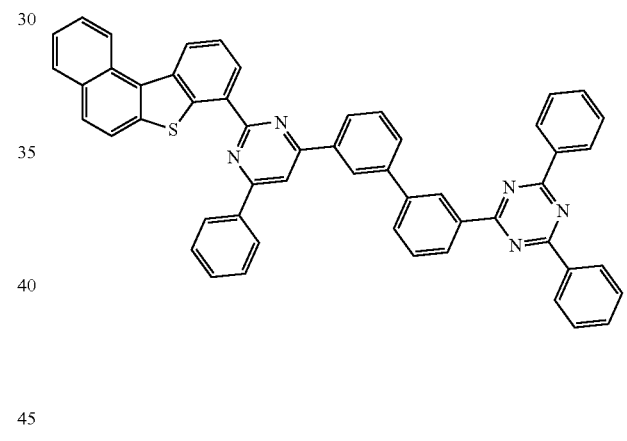
284
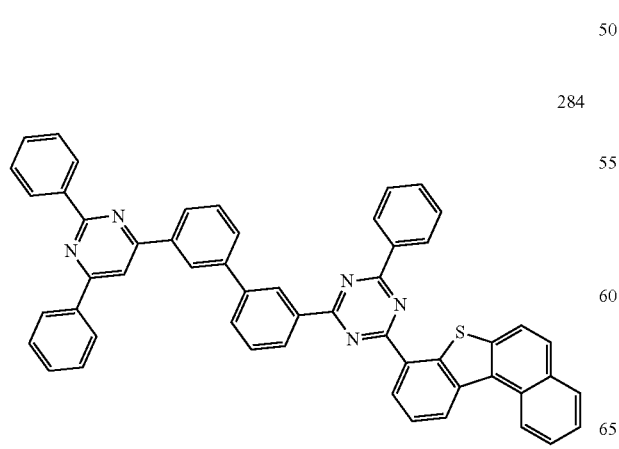
287
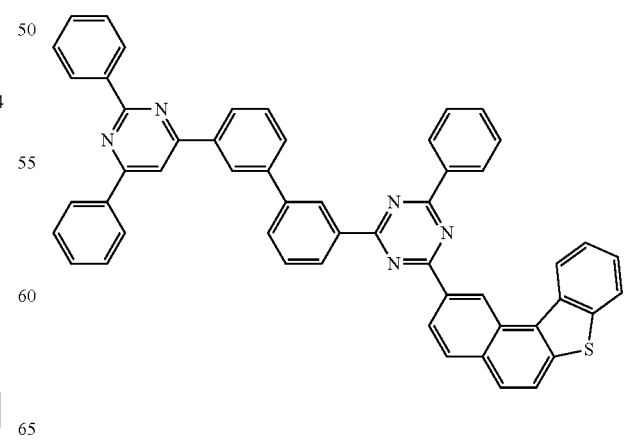

288
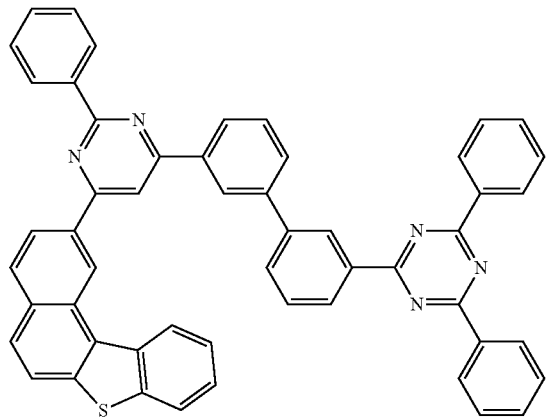
289
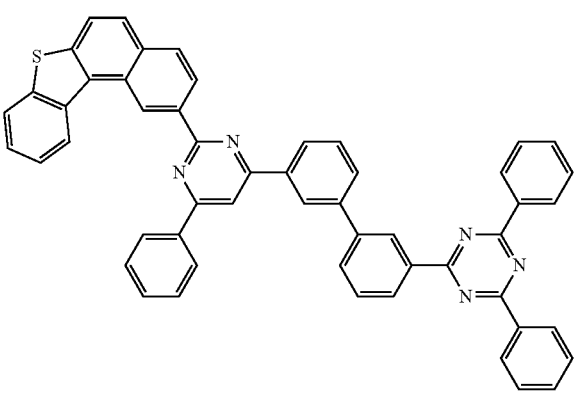
290
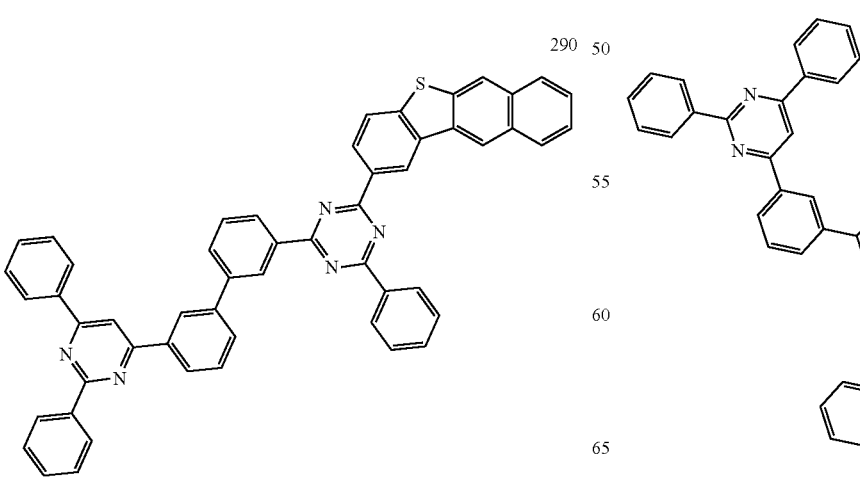
291
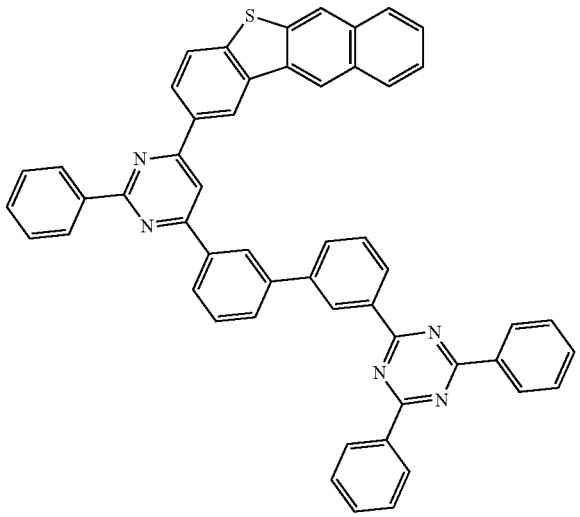
292
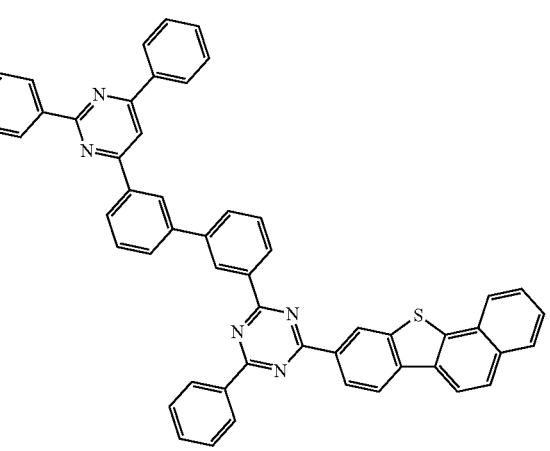
293

294
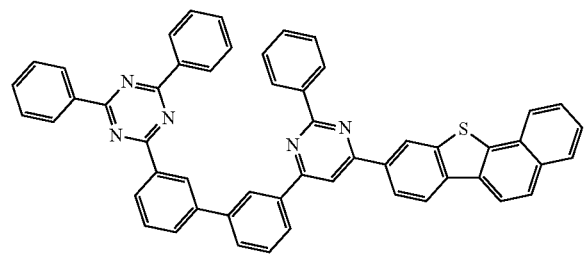
295
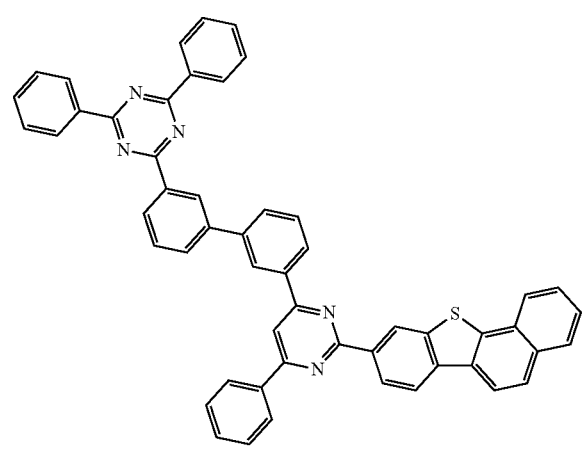
296
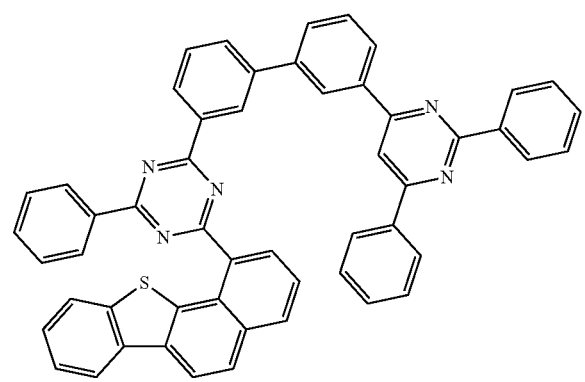
297
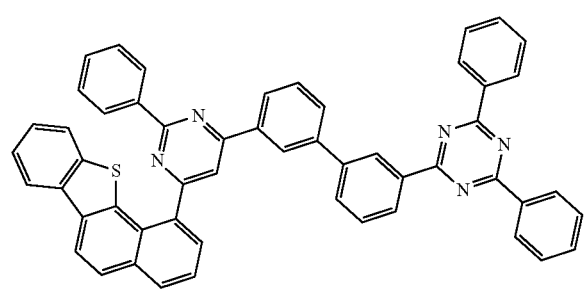
298
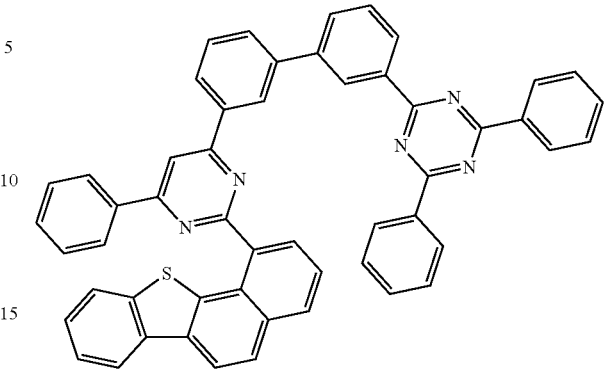
299
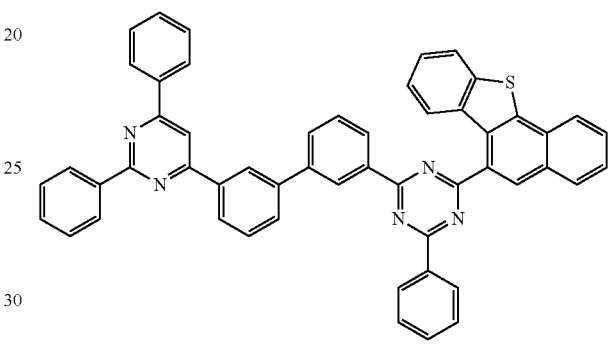
300
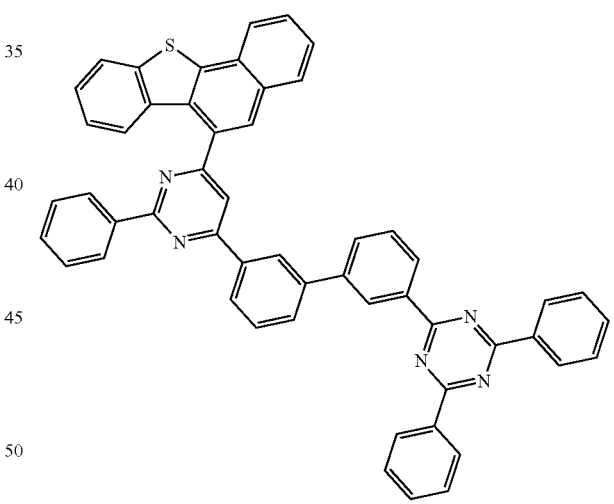
301
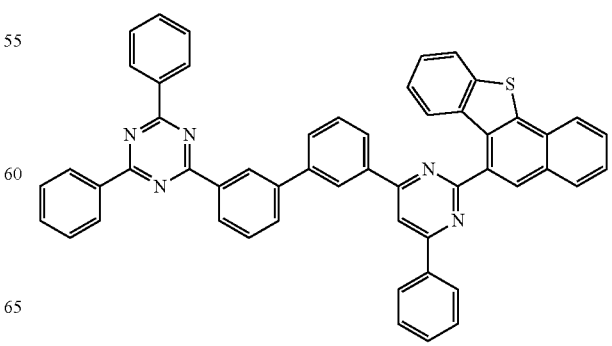

483
-continued
302
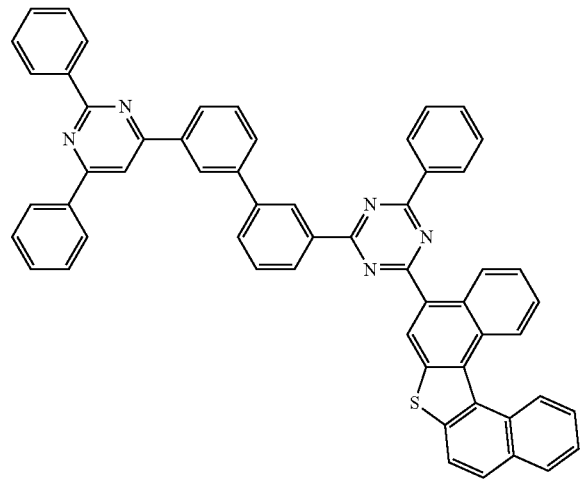
303
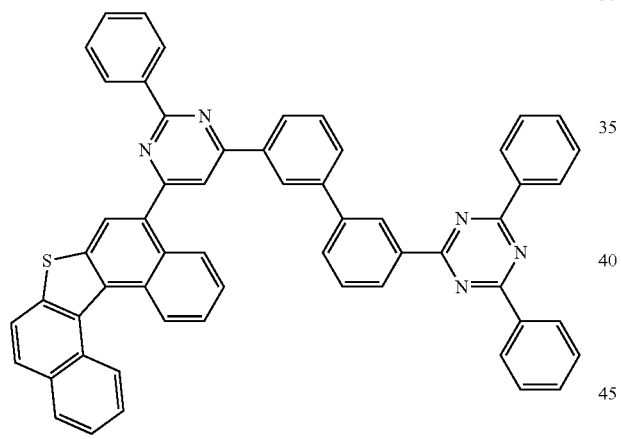
304
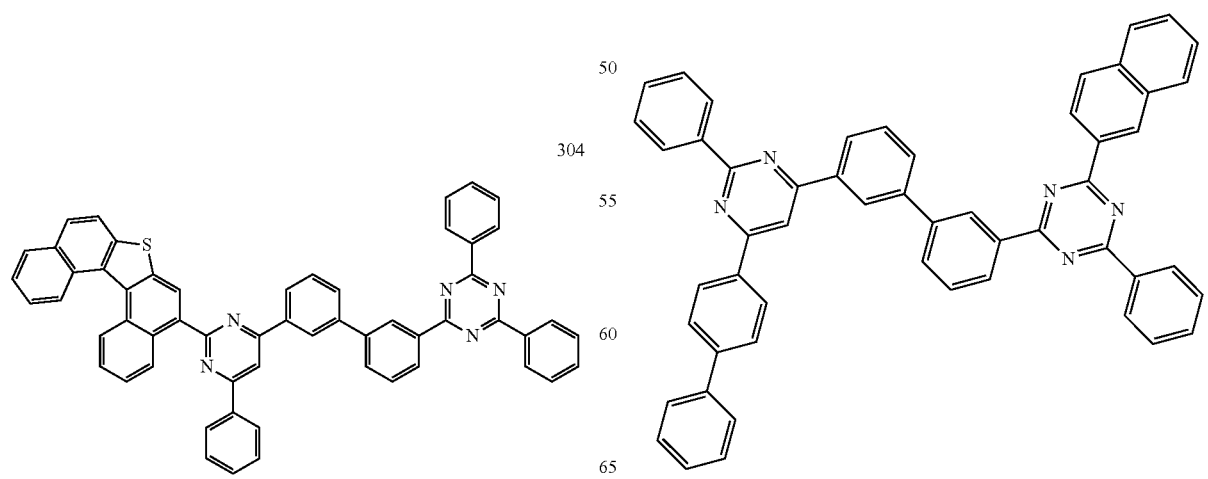
484
-continued
305
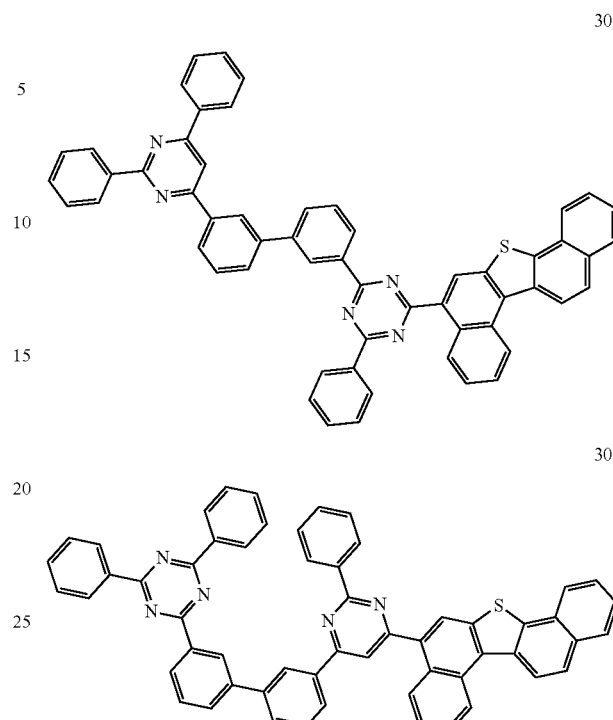
306
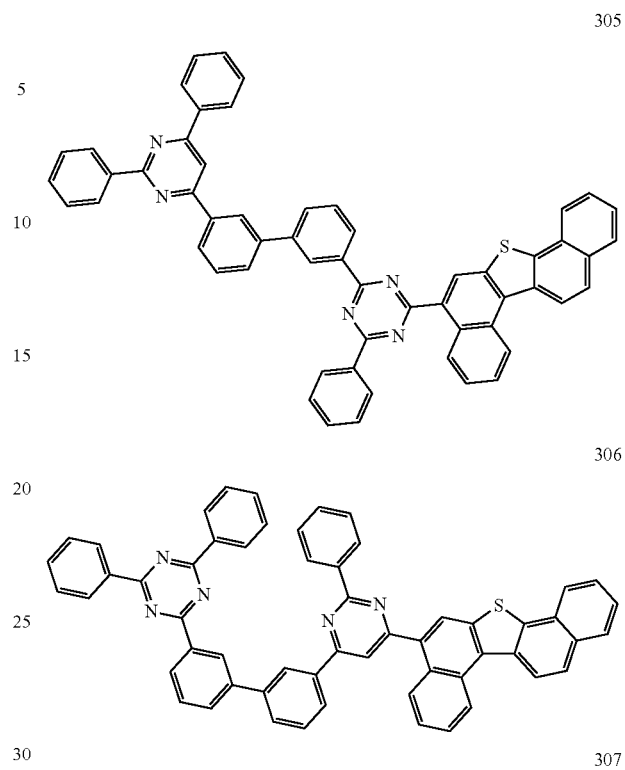
307
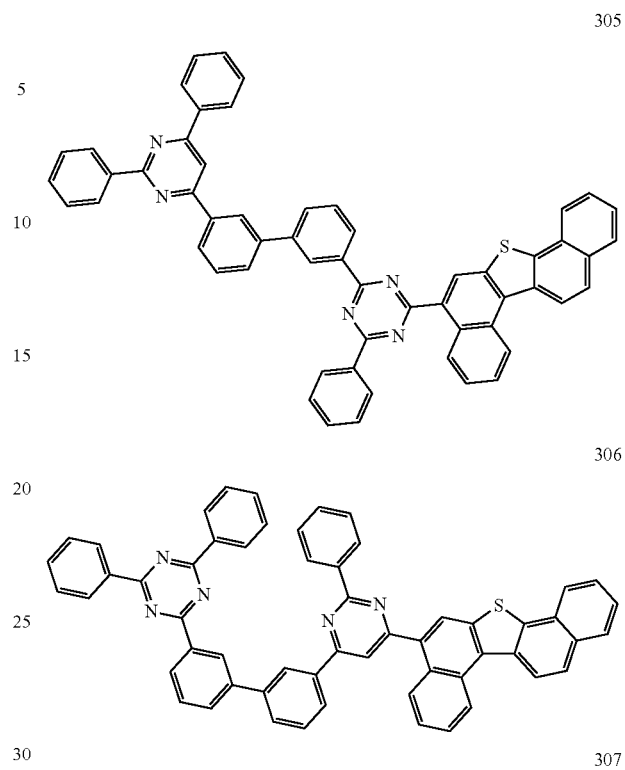
308
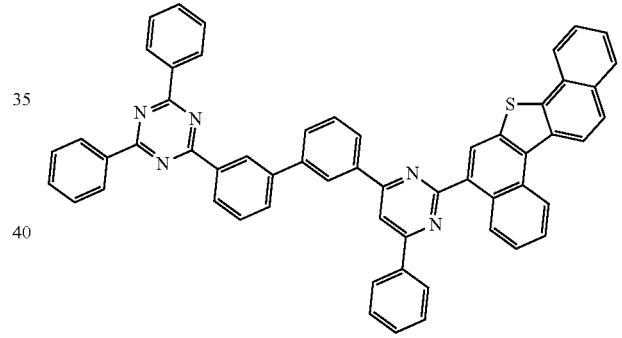

309
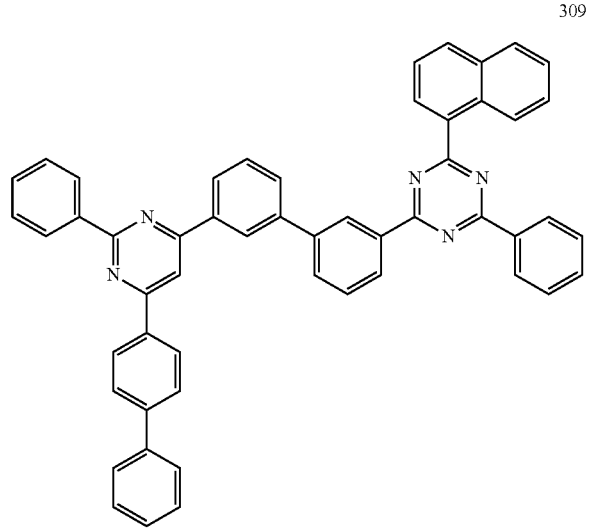
310
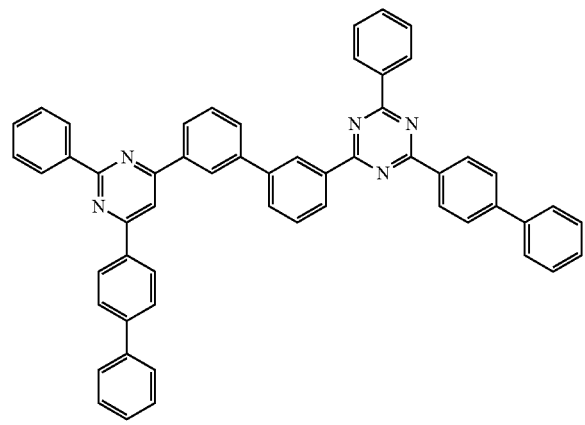
311
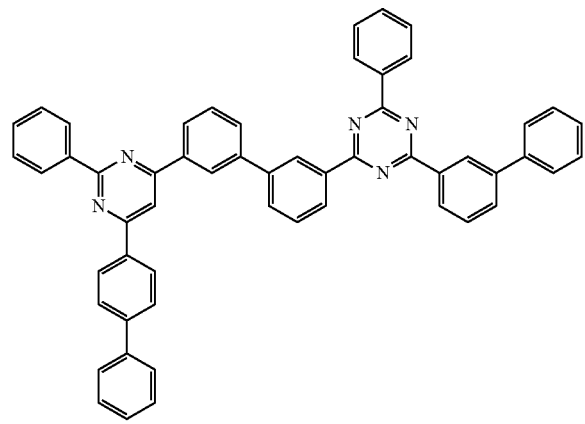
312
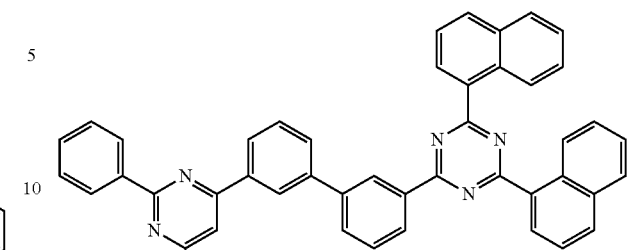
313
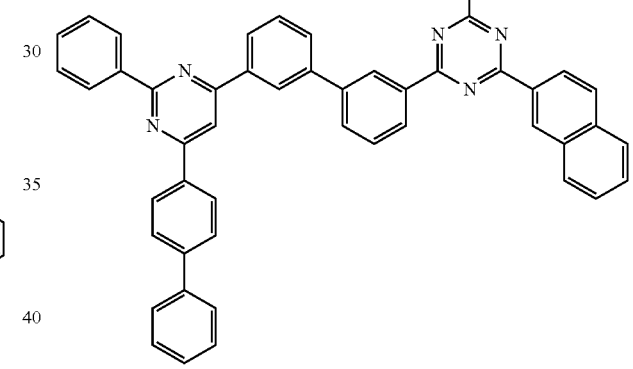
316
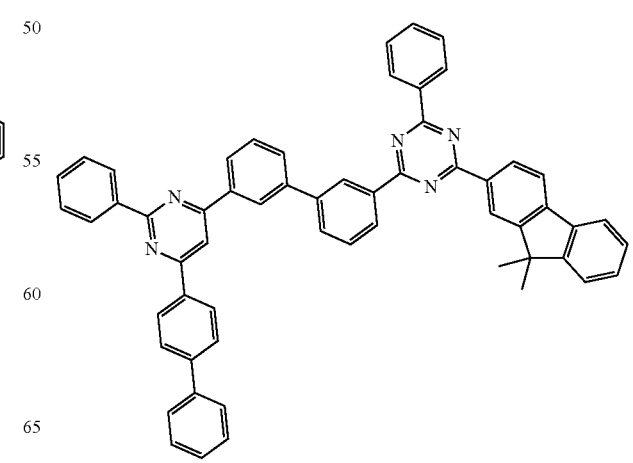

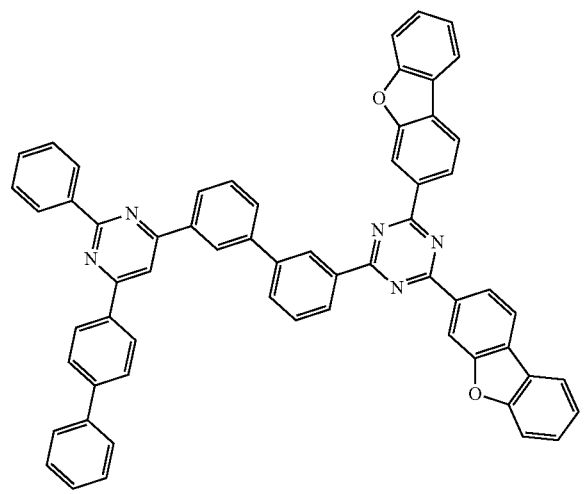
317
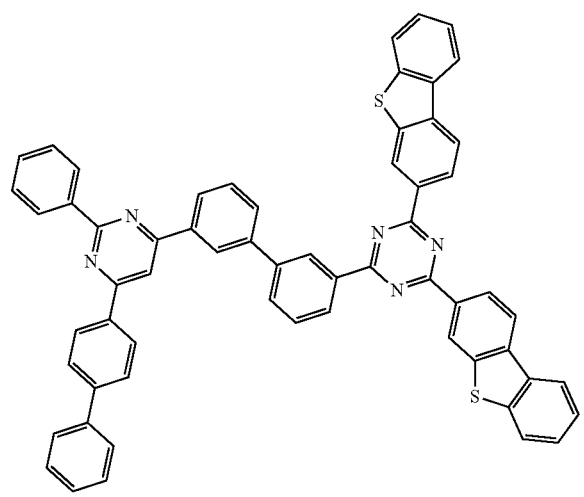
318
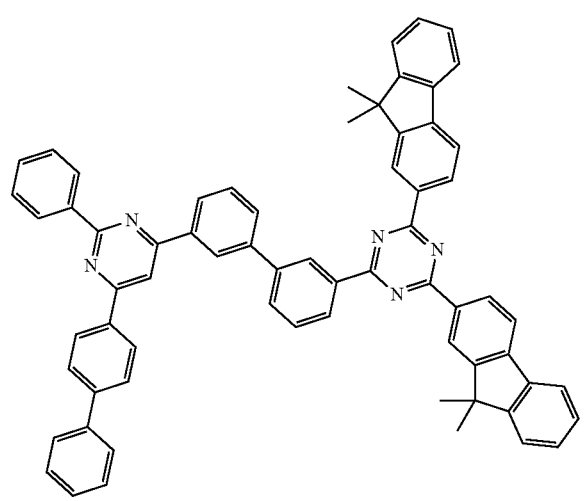
319
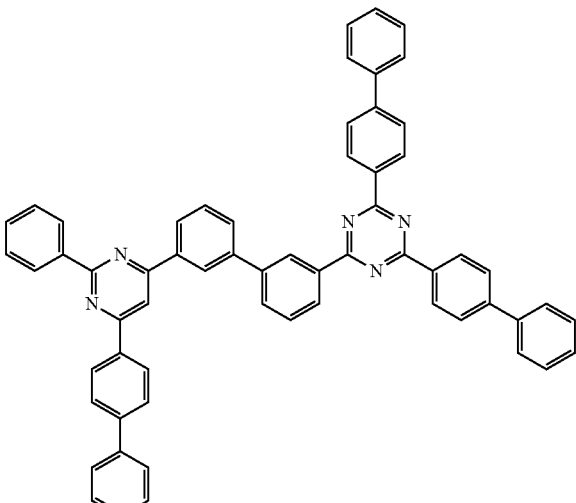
321
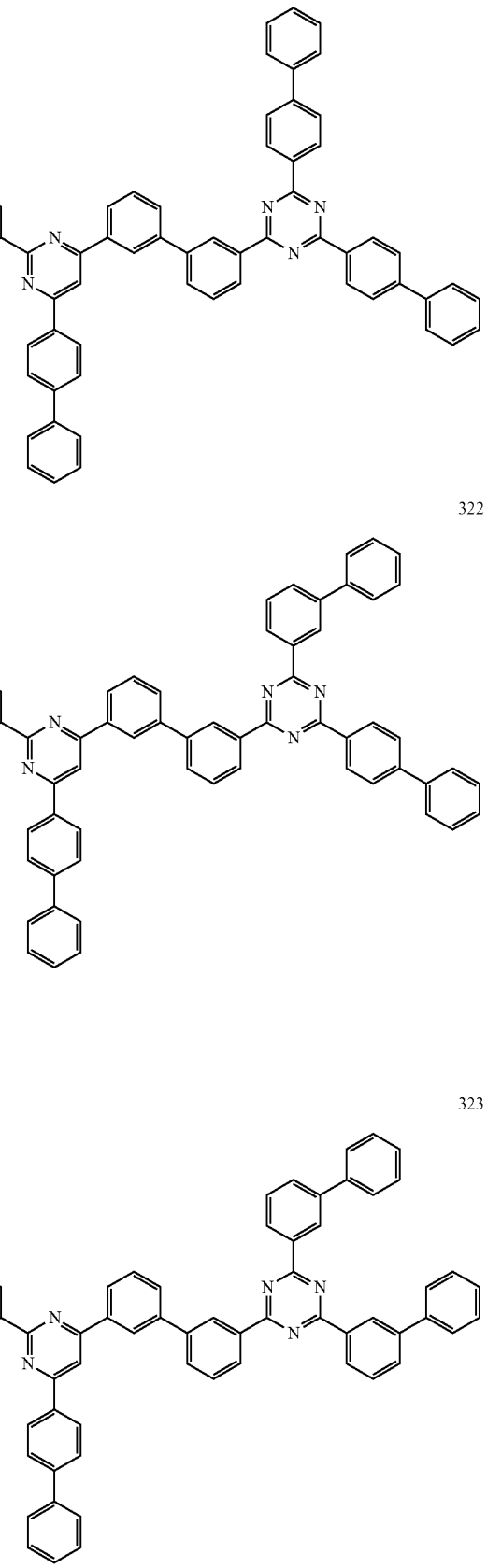

489
-continued
490
-continued
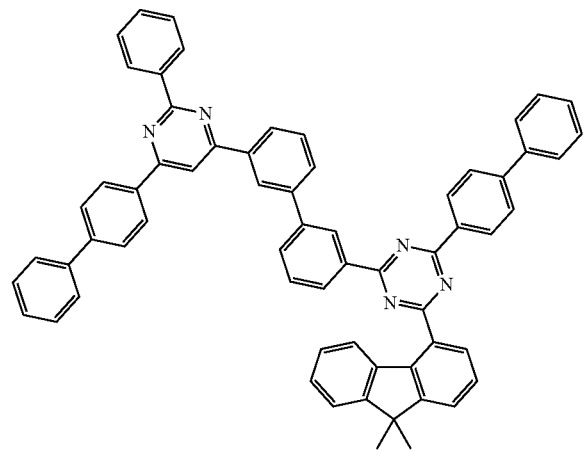
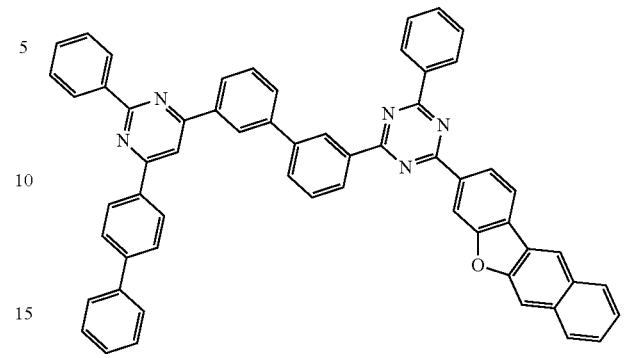
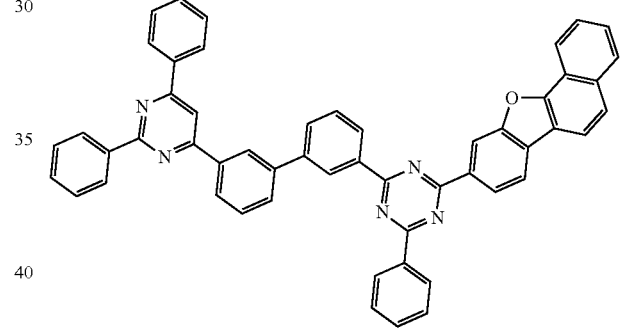
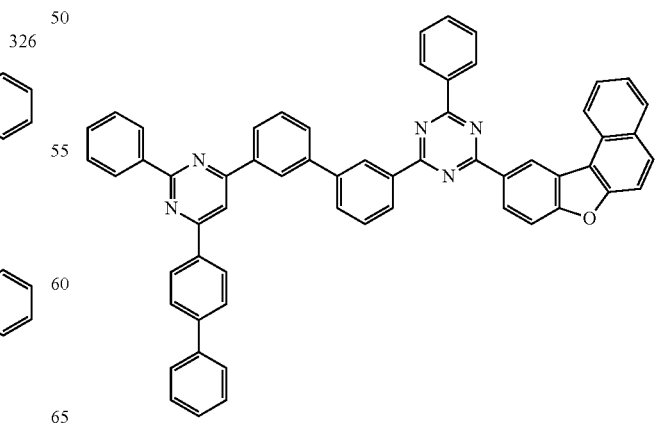

332
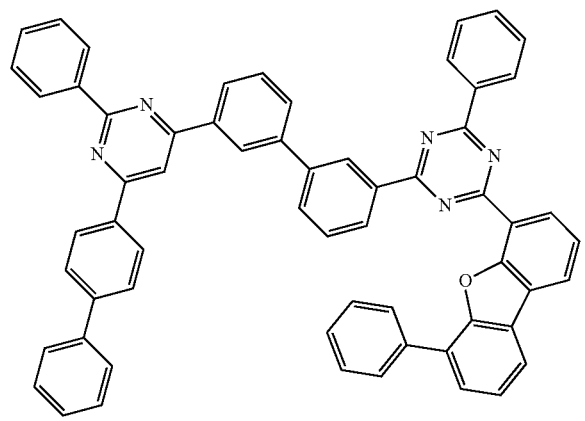
333
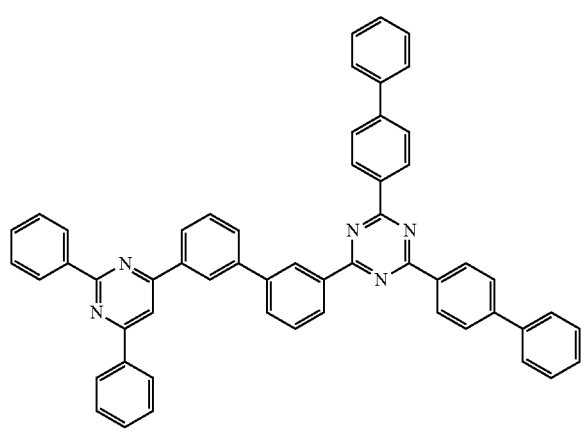
334
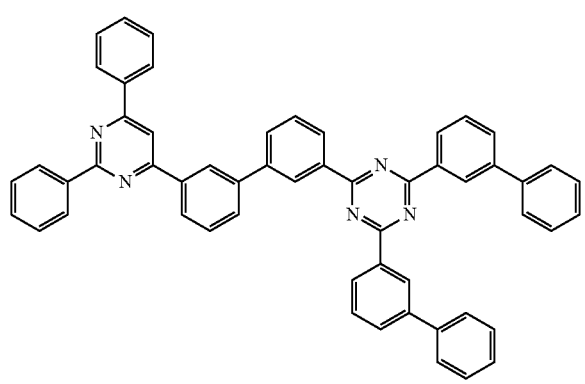
335
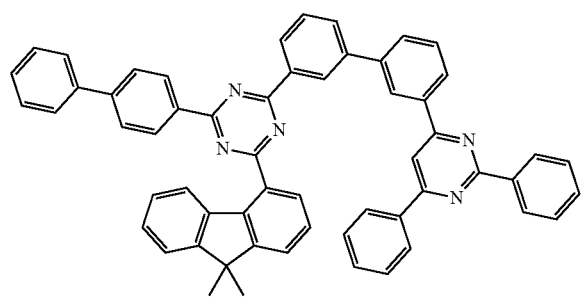
336
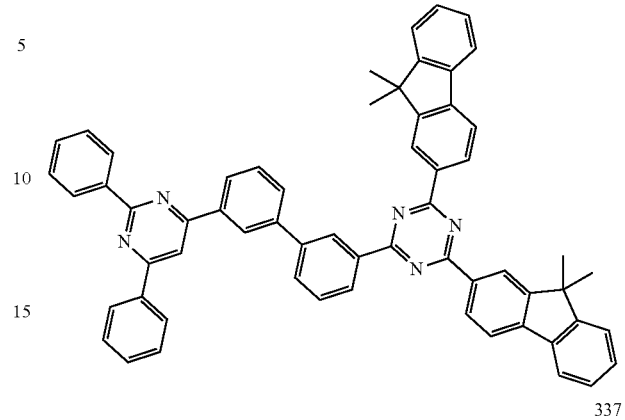
337
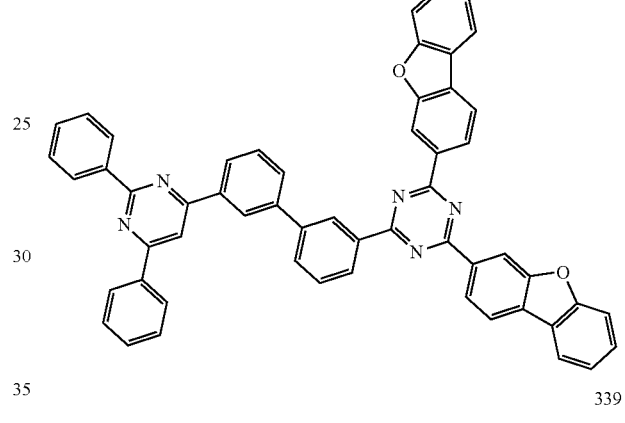
339
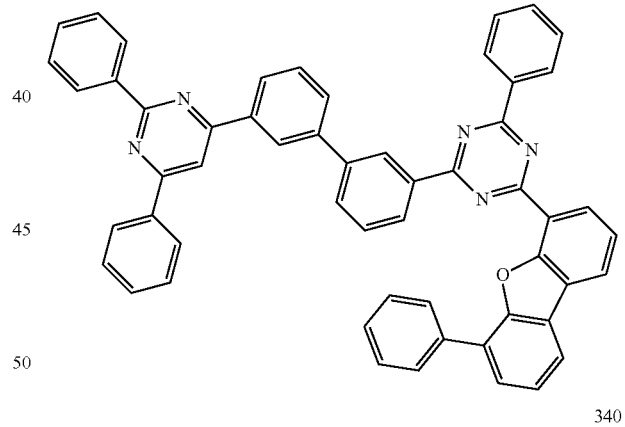
340
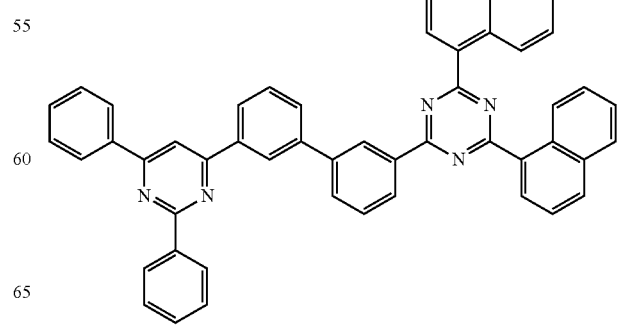

341
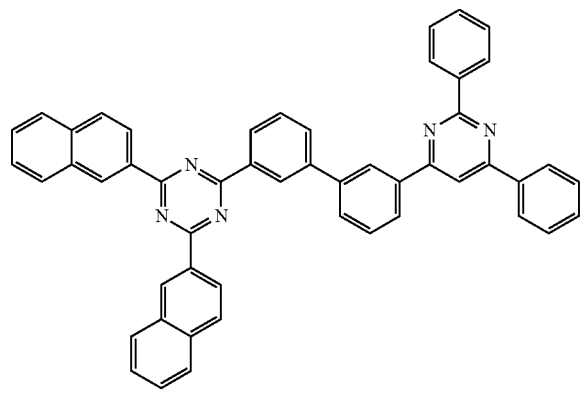
342
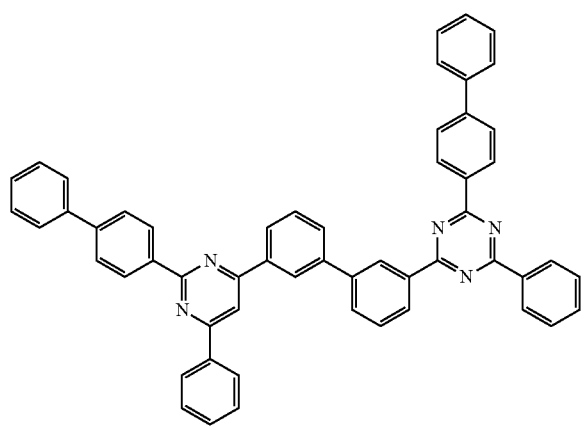
343
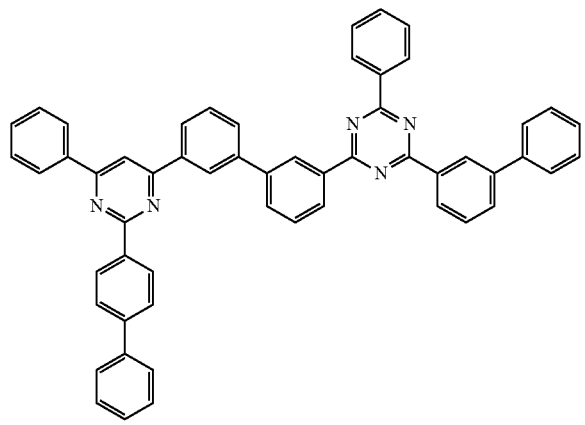
344
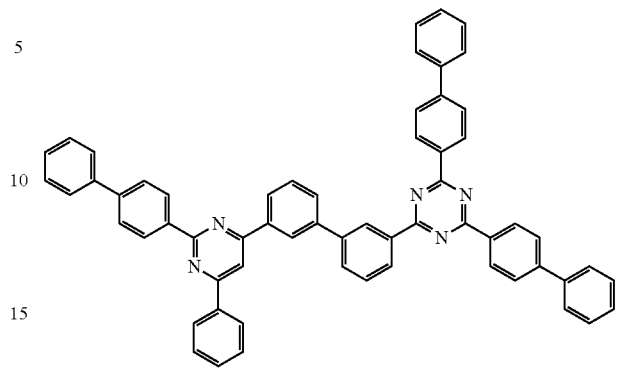
345
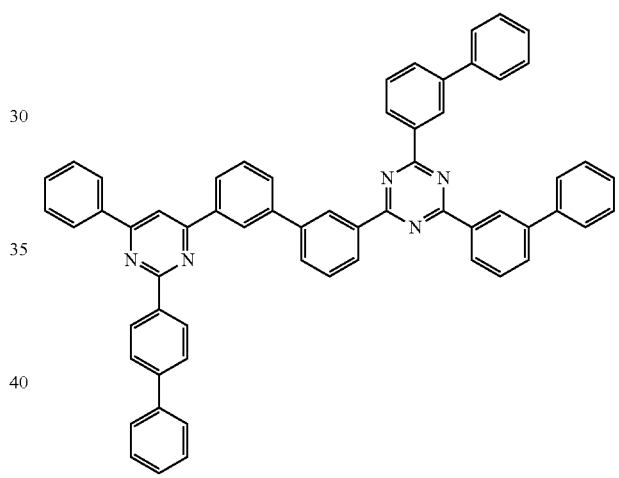
346
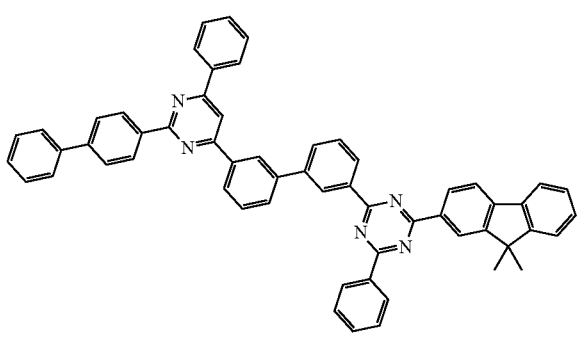

347
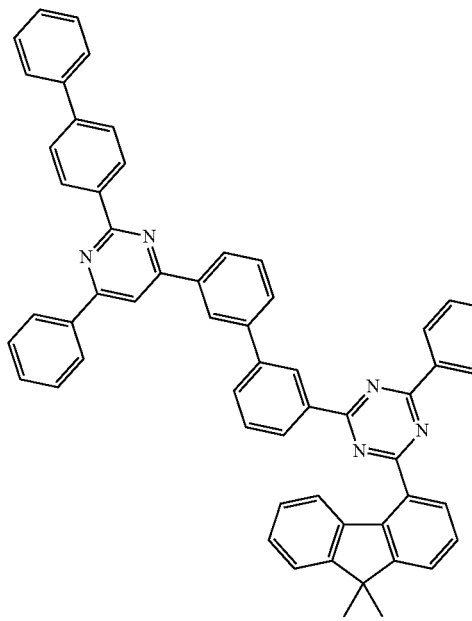
348
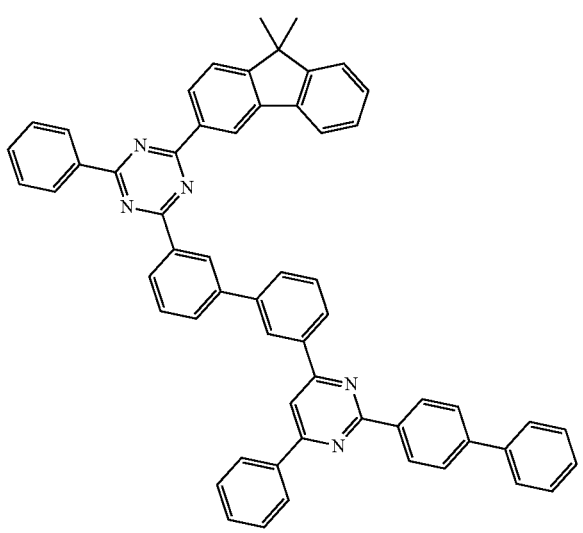
349
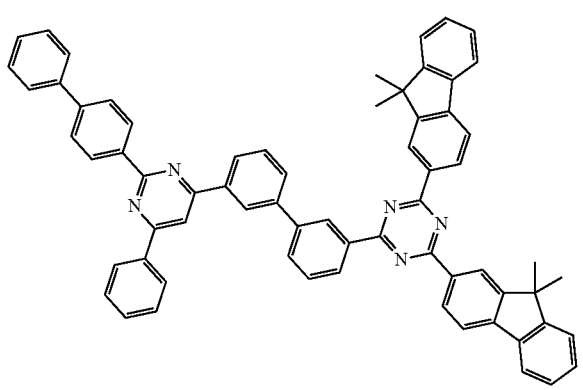
350
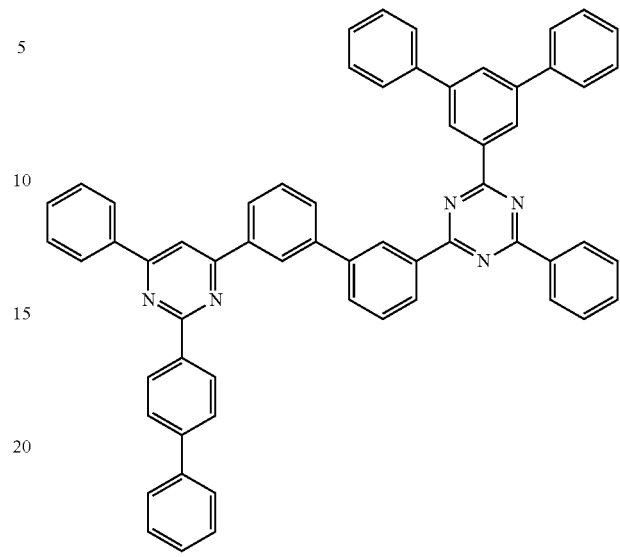
352
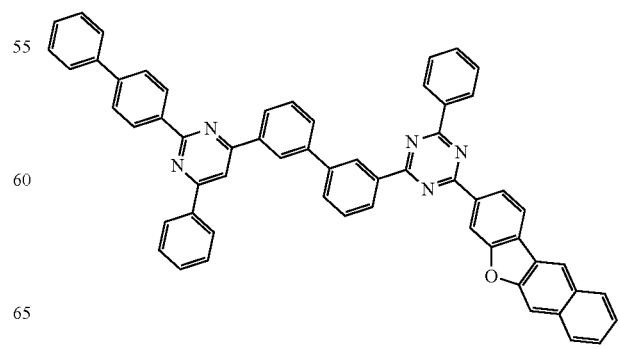
353

354
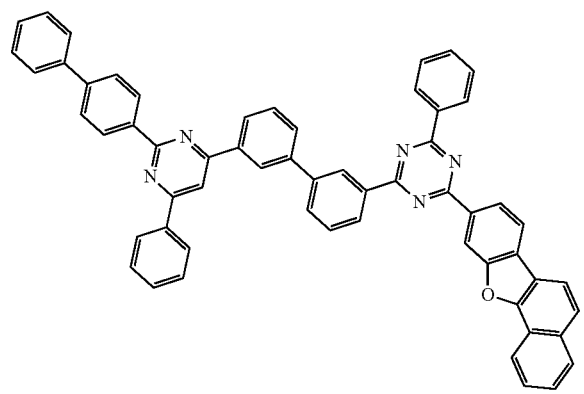
355
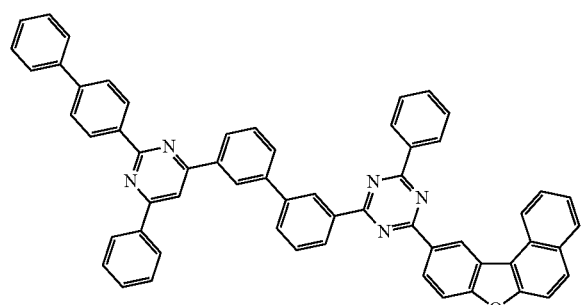
358
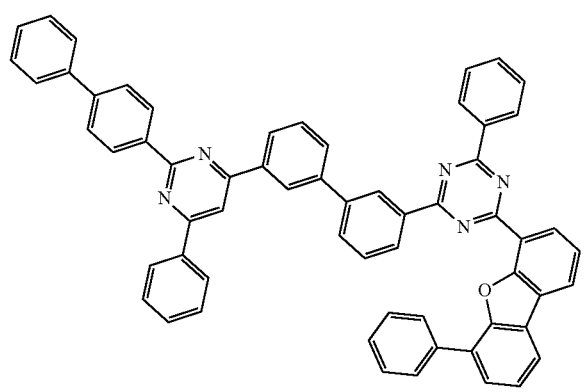
359
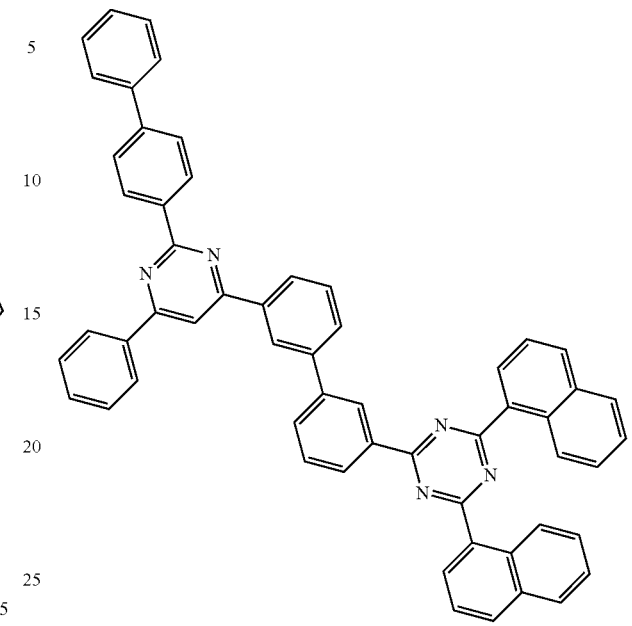
360
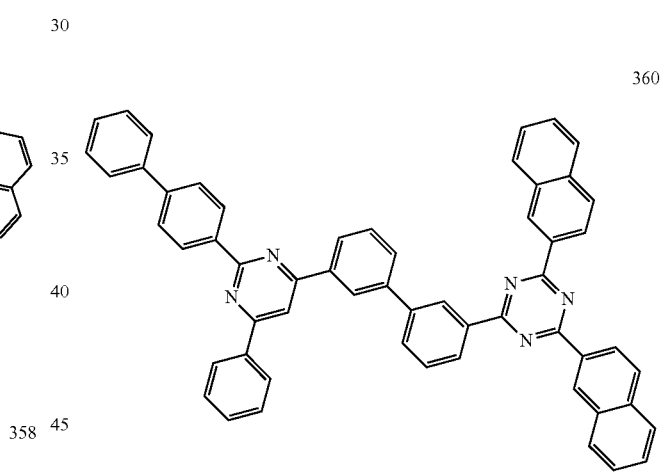
361
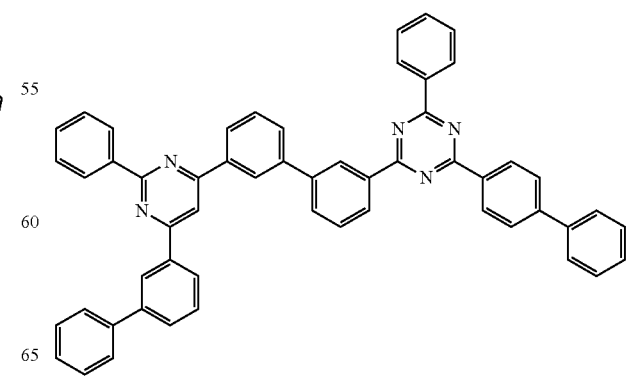

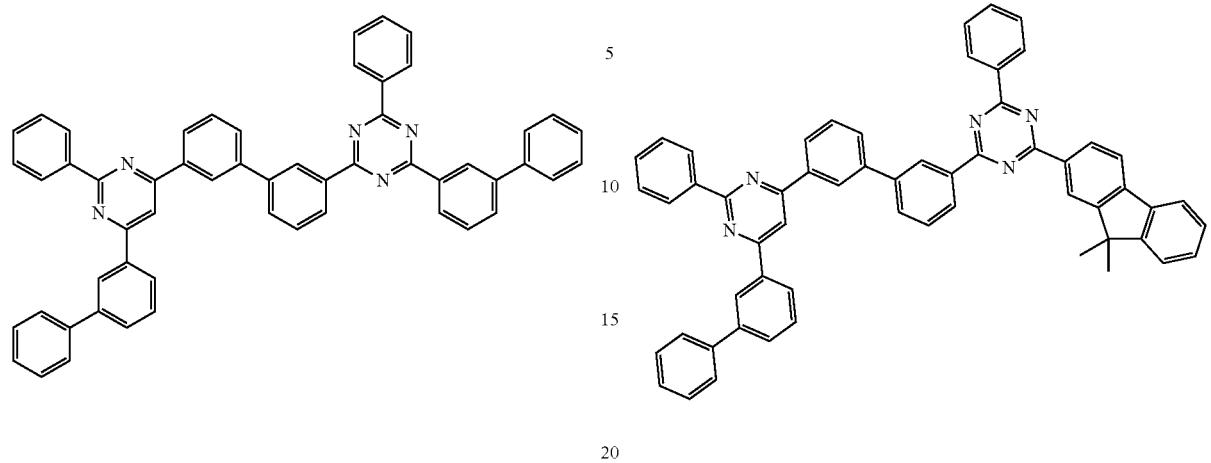
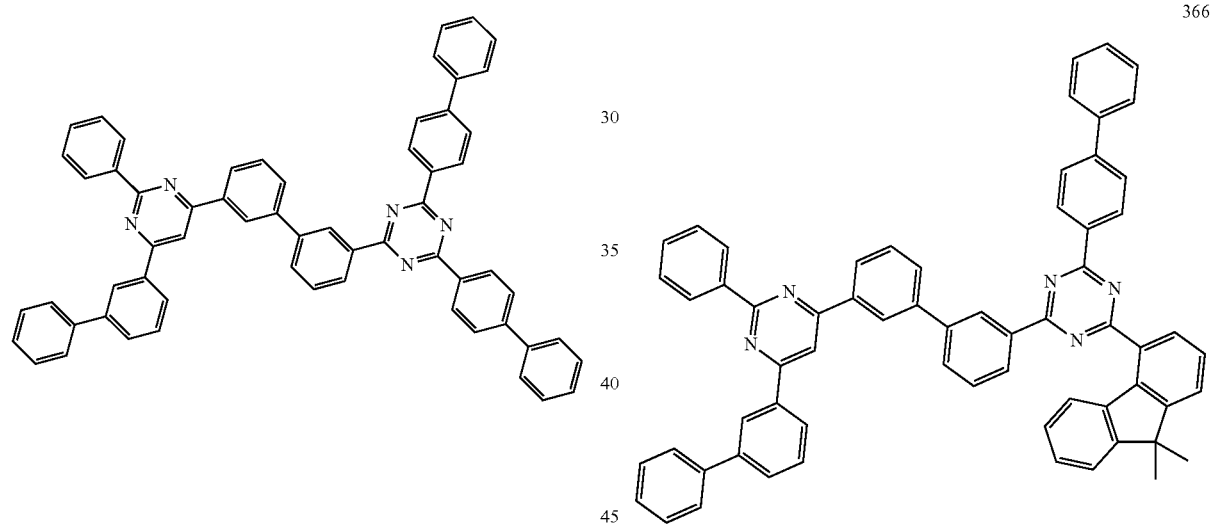
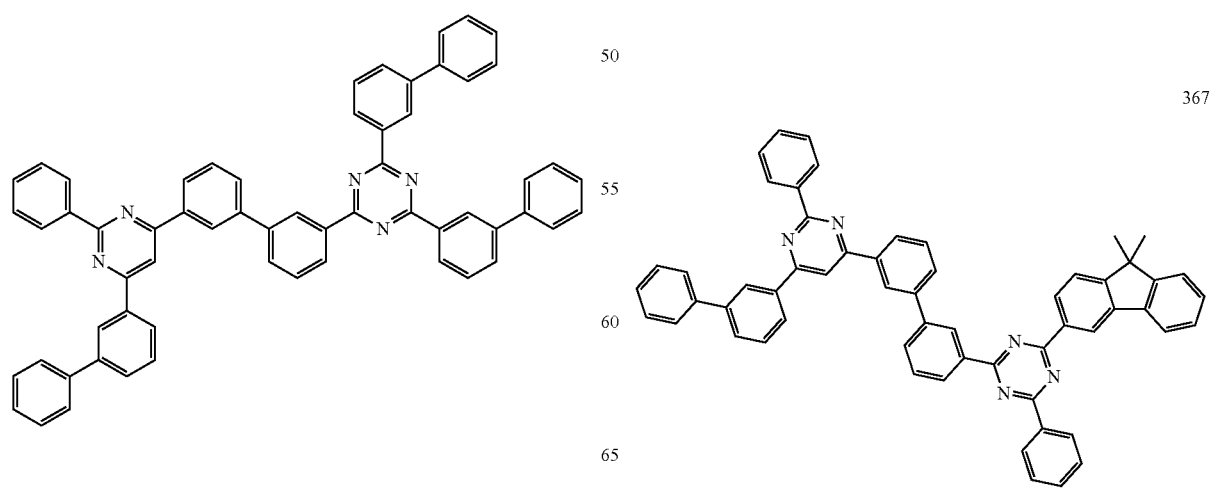

501
-continued
368
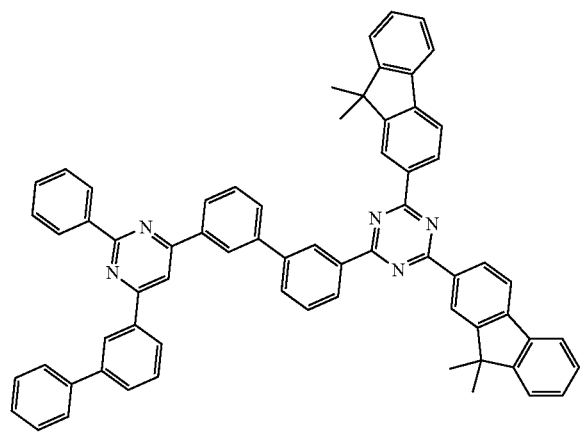
369
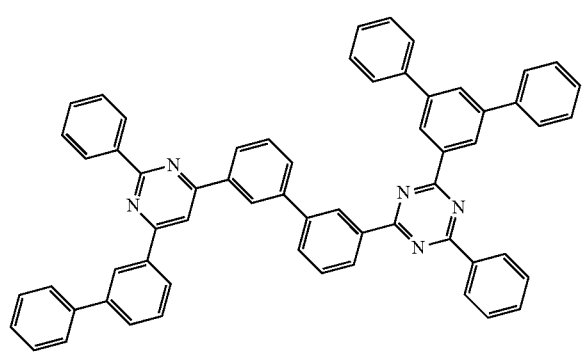
371
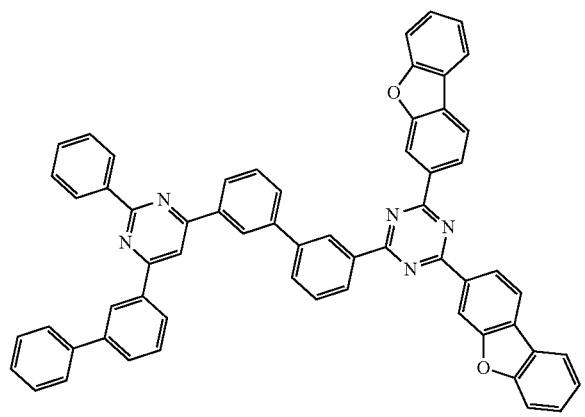
372
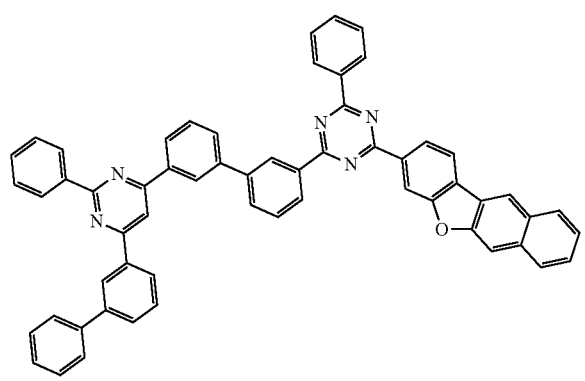
502
-continued
373
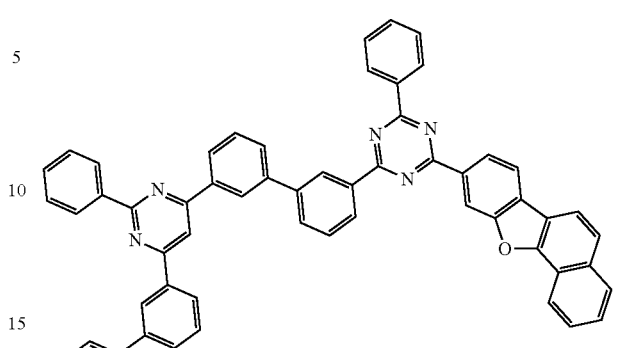
374
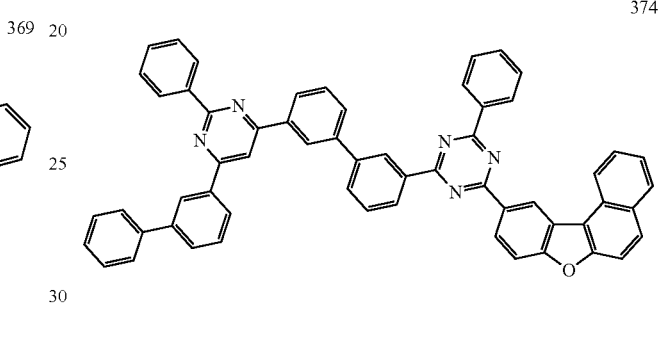
377
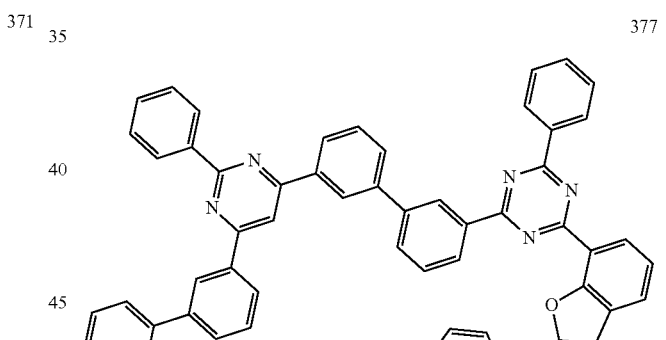
378
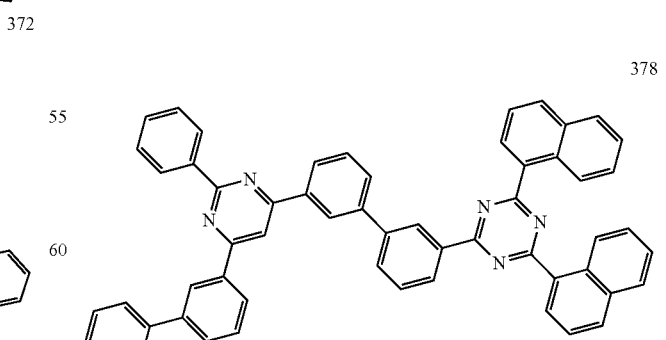

379
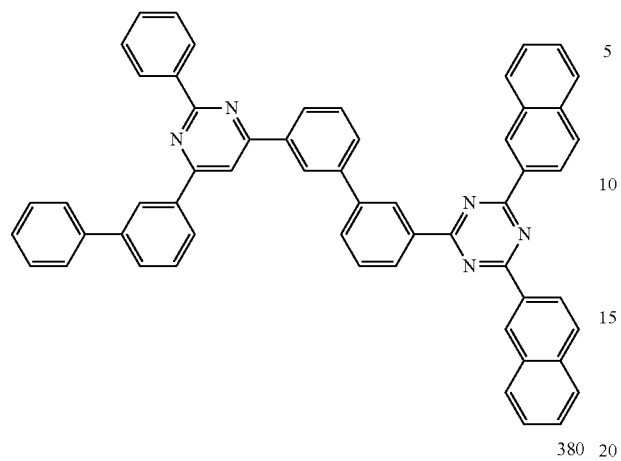
380
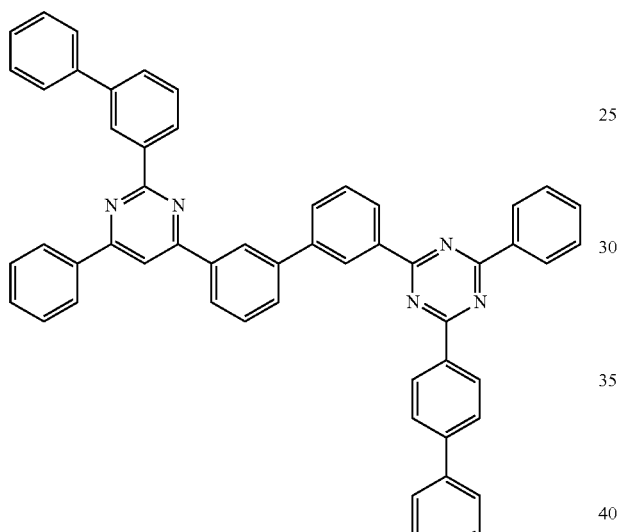
381
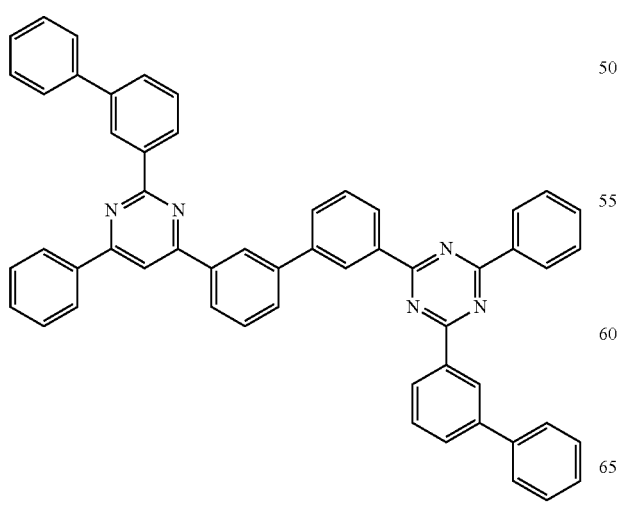
382
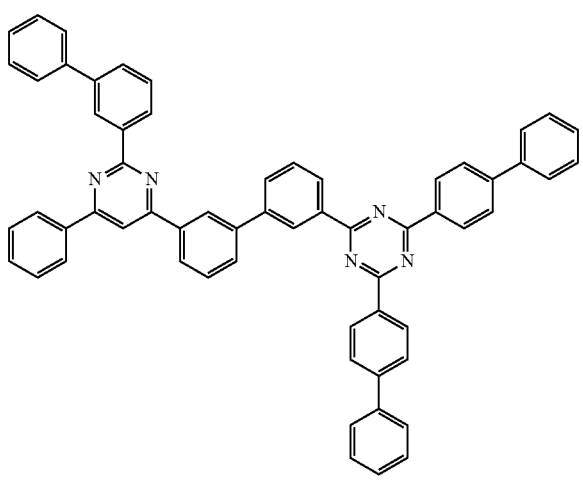
383
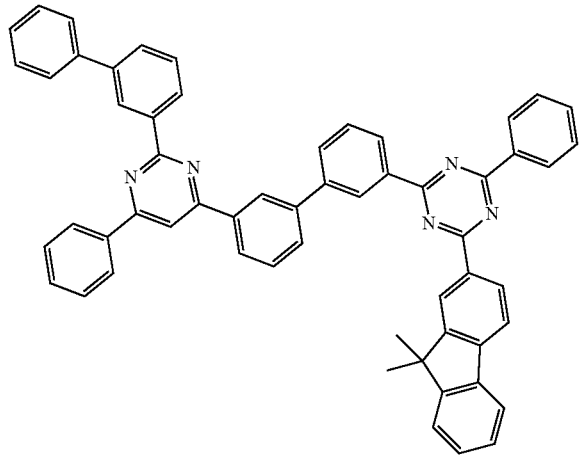
384

385
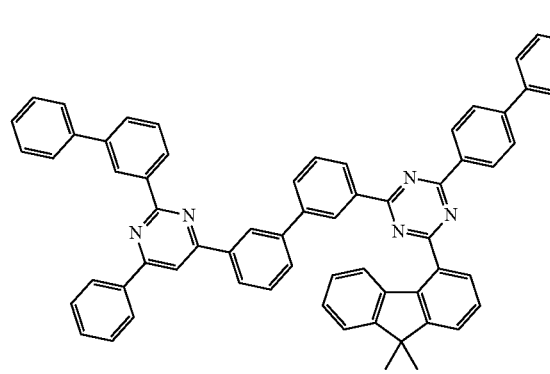
386
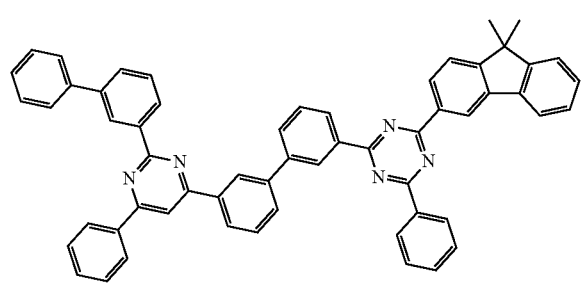
387
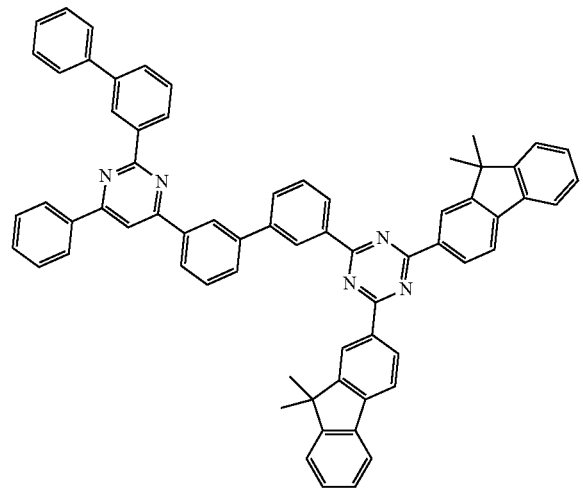
388
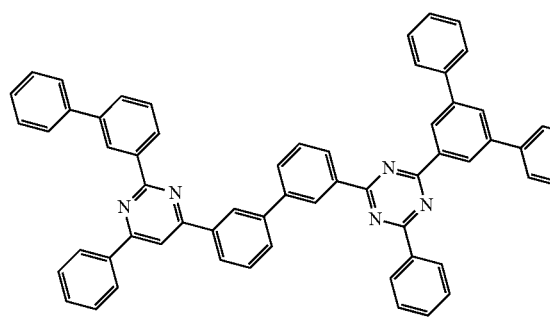
390
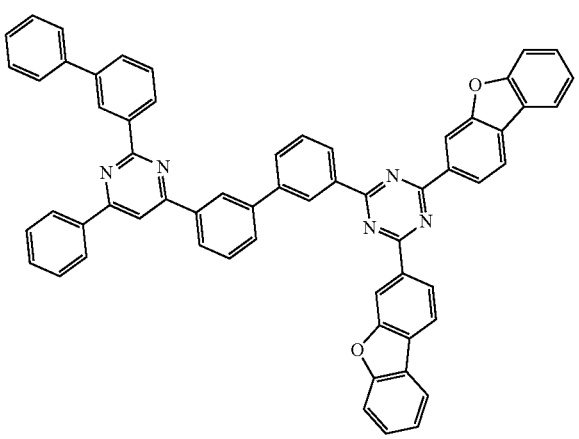
391
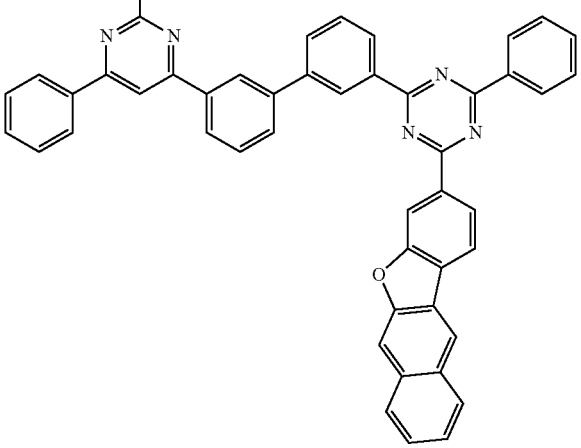
392
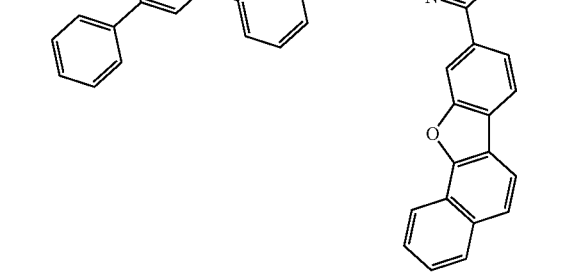

393
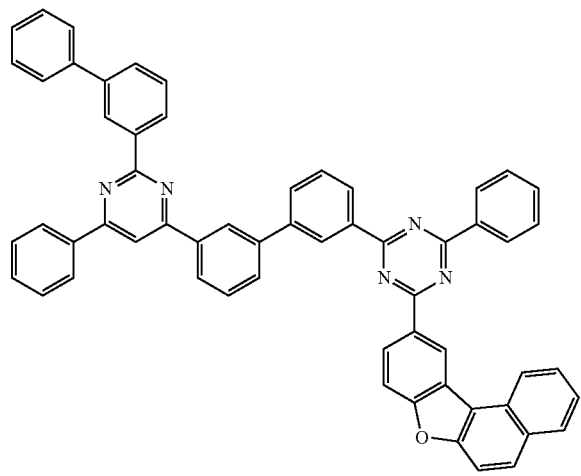
398
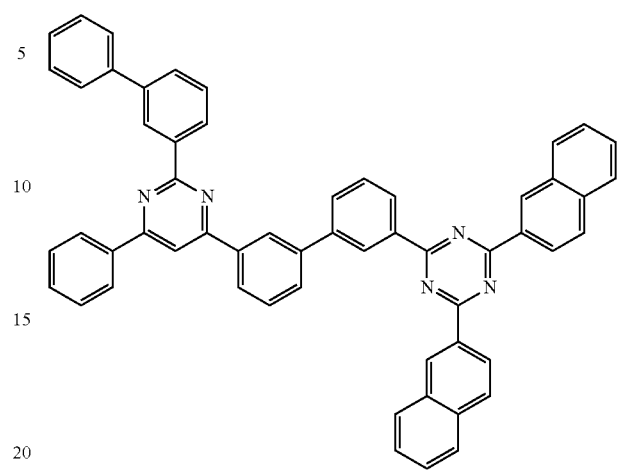
396
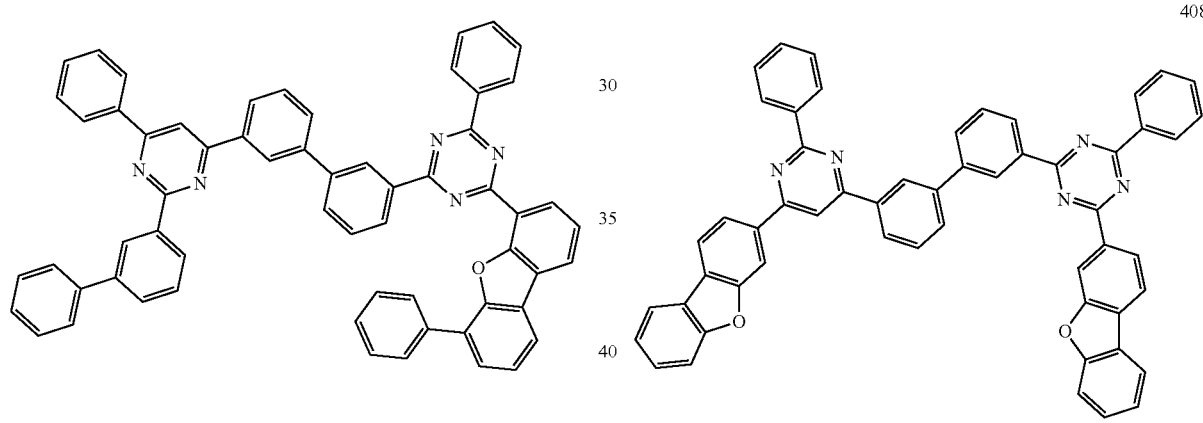
408
397
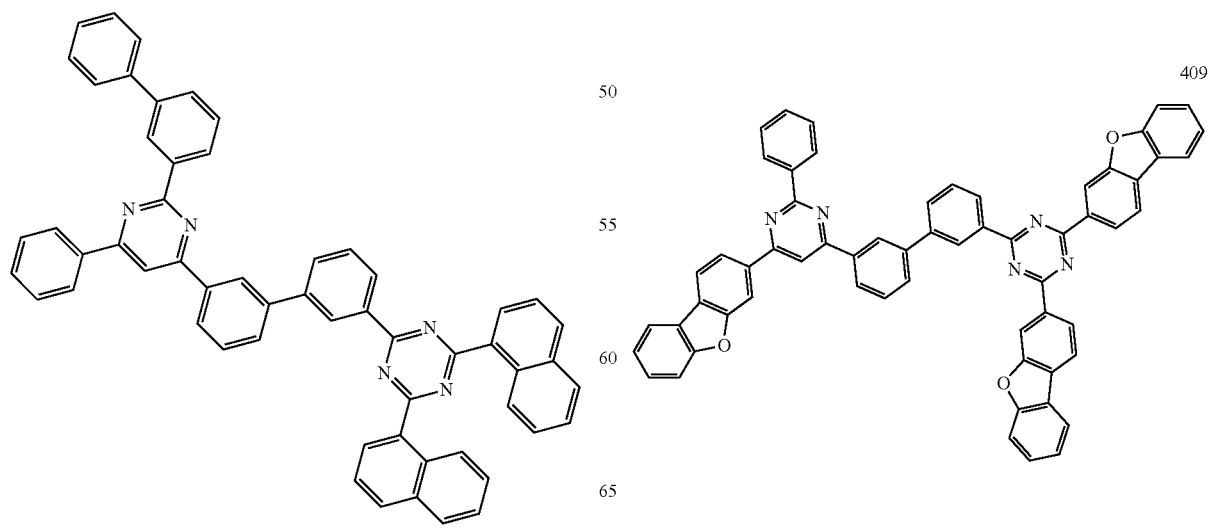
409

509
-continued
410
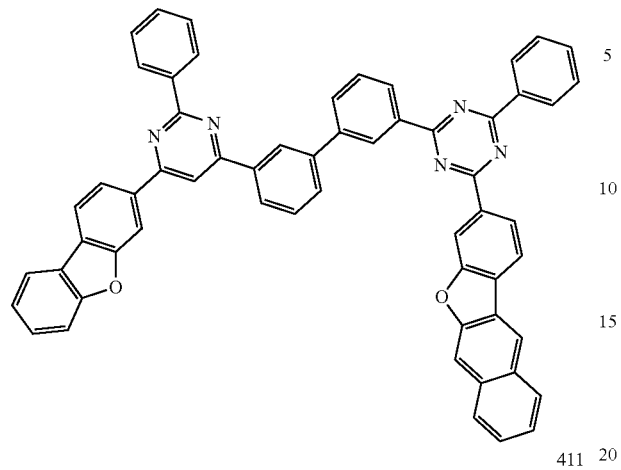
411
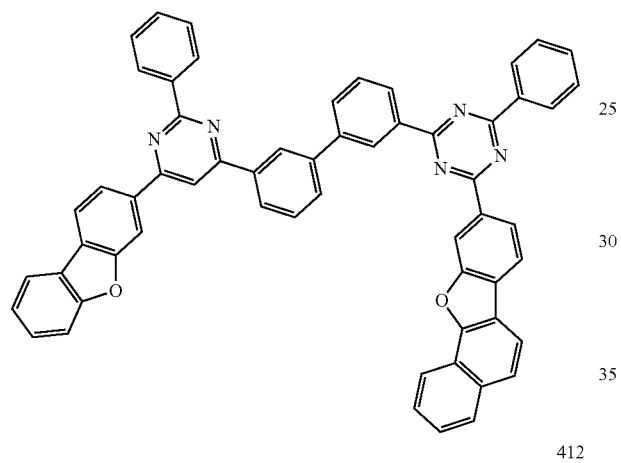
412
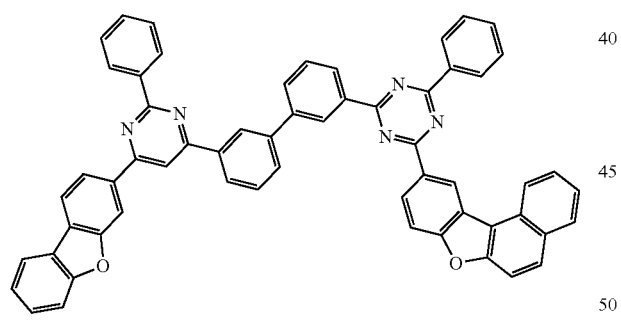
413
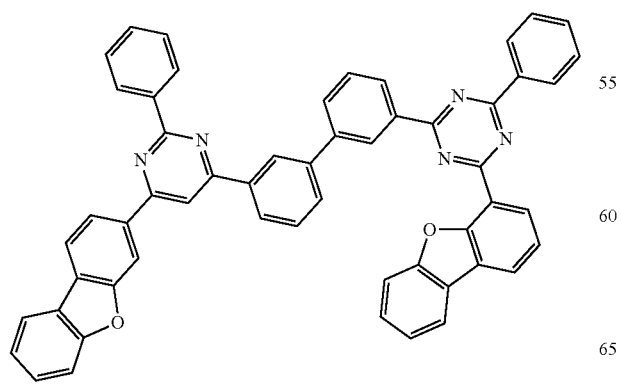
510
-continued
414
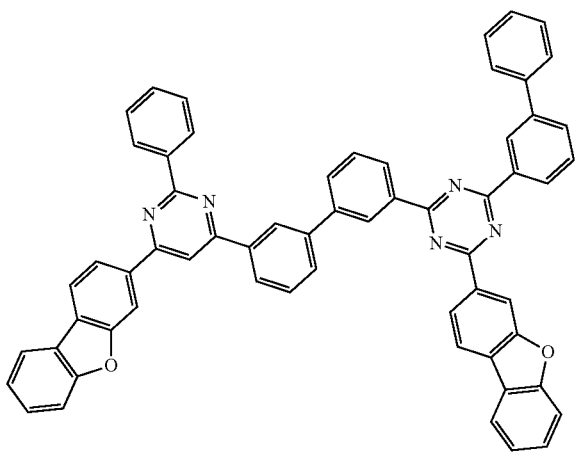
415
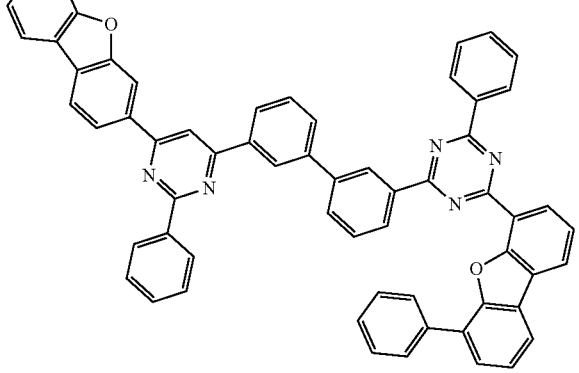
428
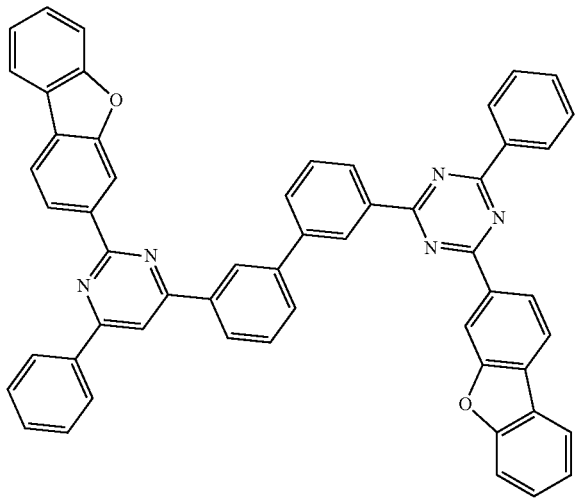

429
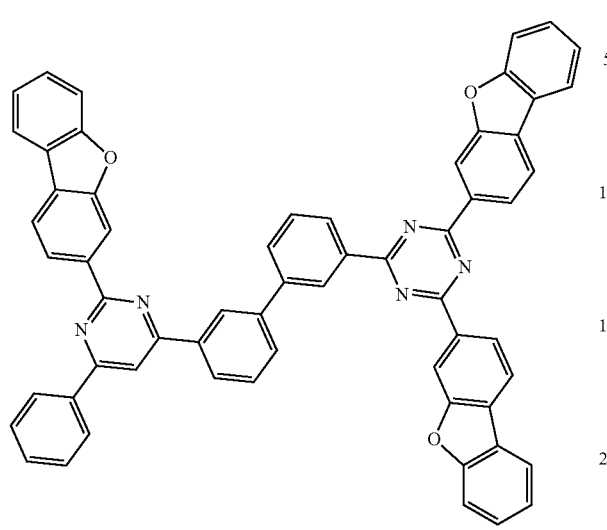
430
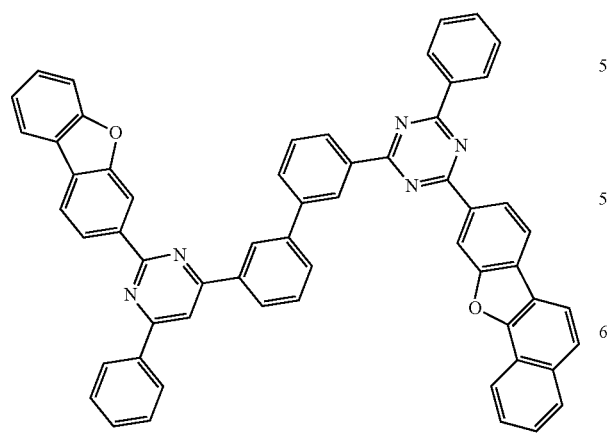
432
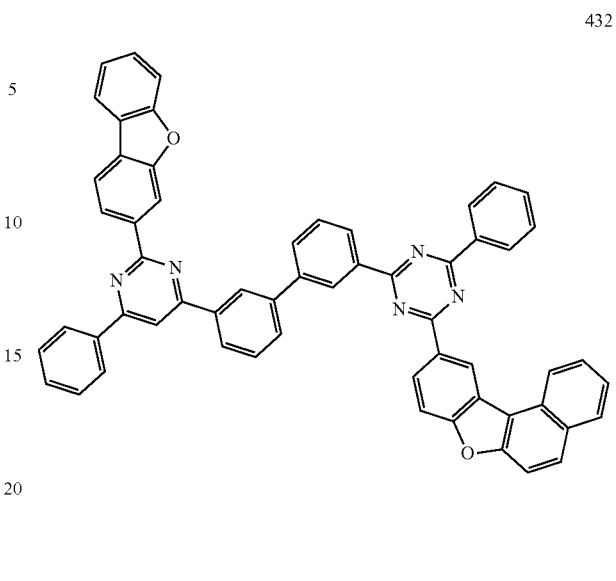
433
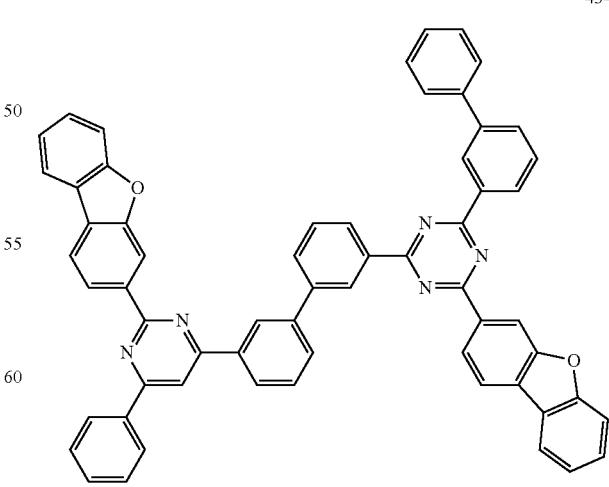
431
434

513
-continued
435
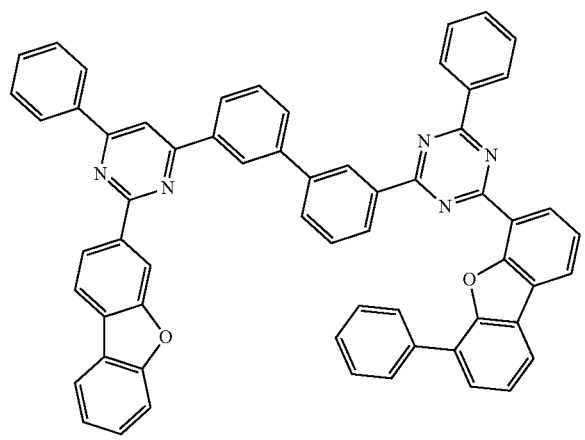
447
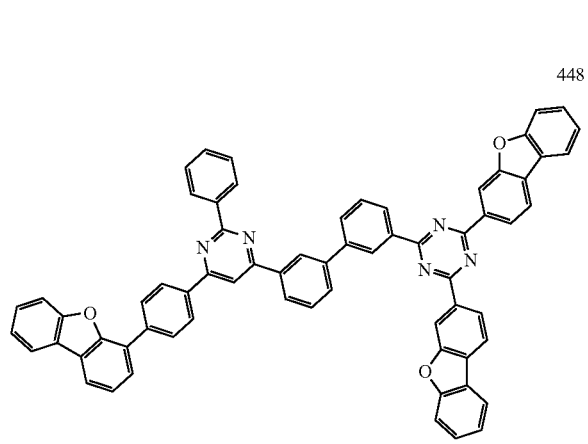
448
514
-continued
449
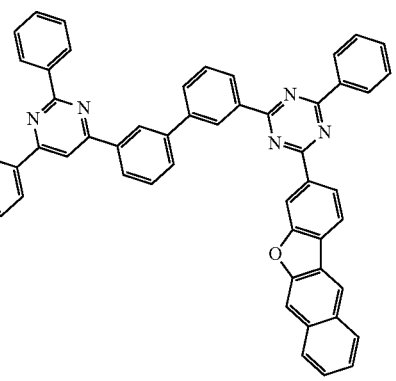
450
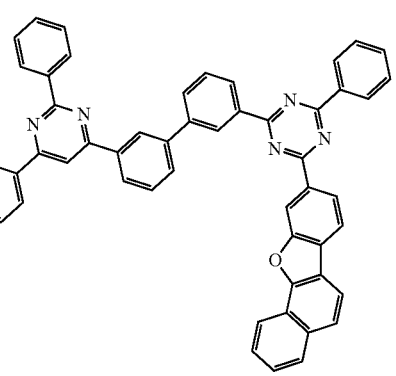
451
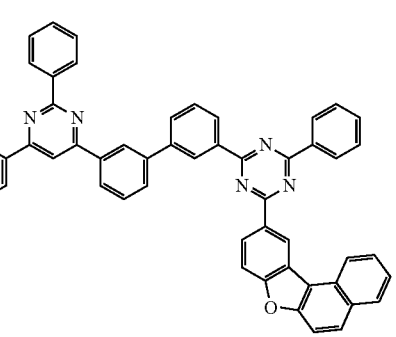
452
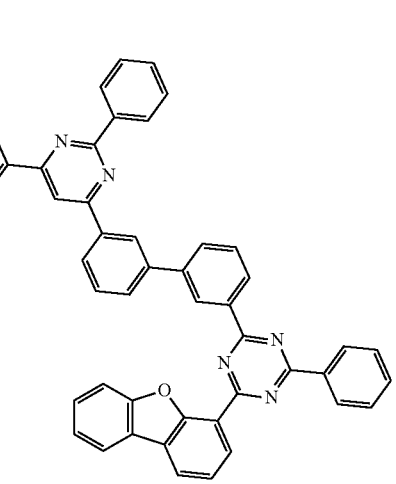

515
-continued
516
-continued
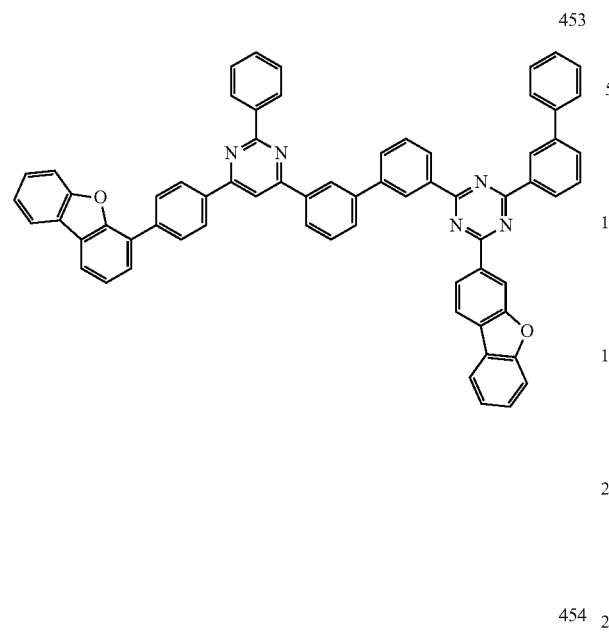
453
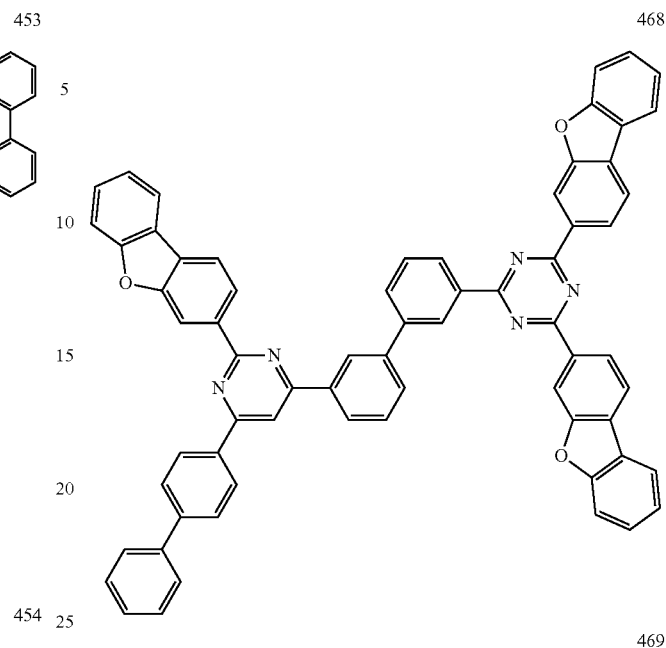
468
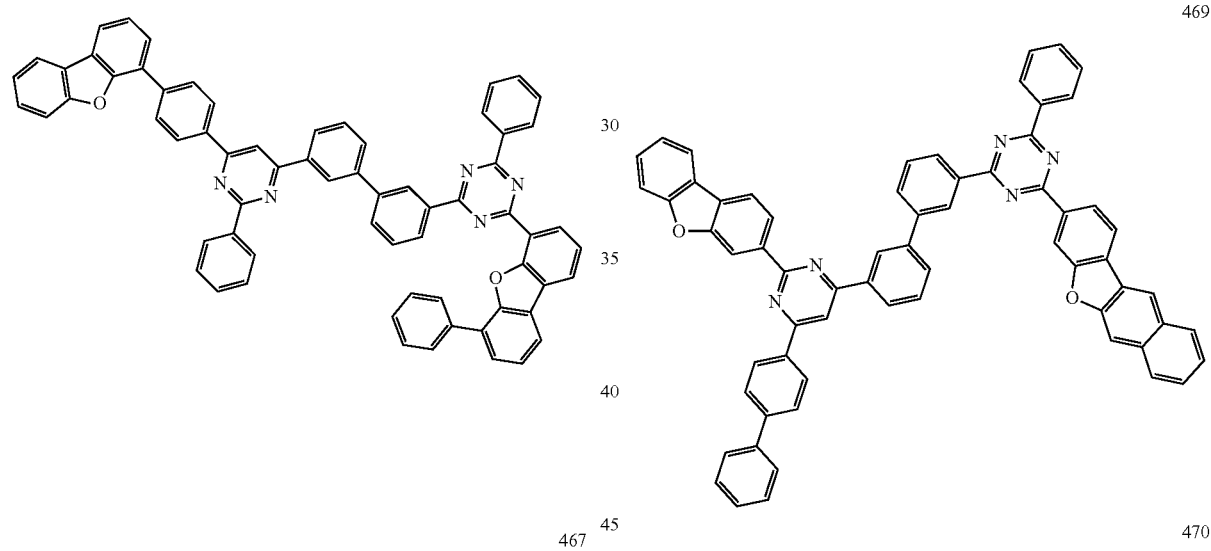
454
467
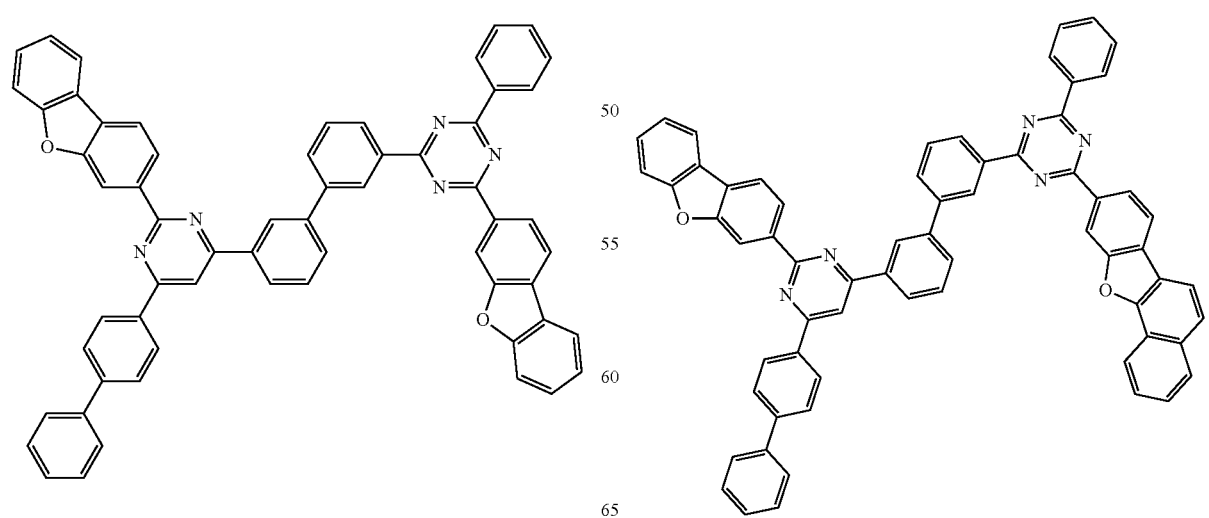
469
470

471
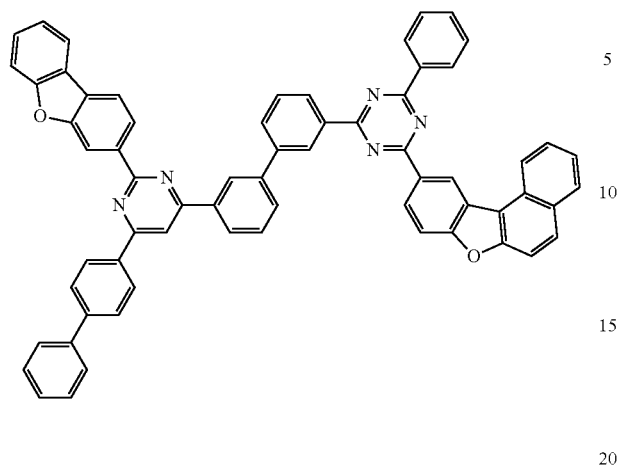
472
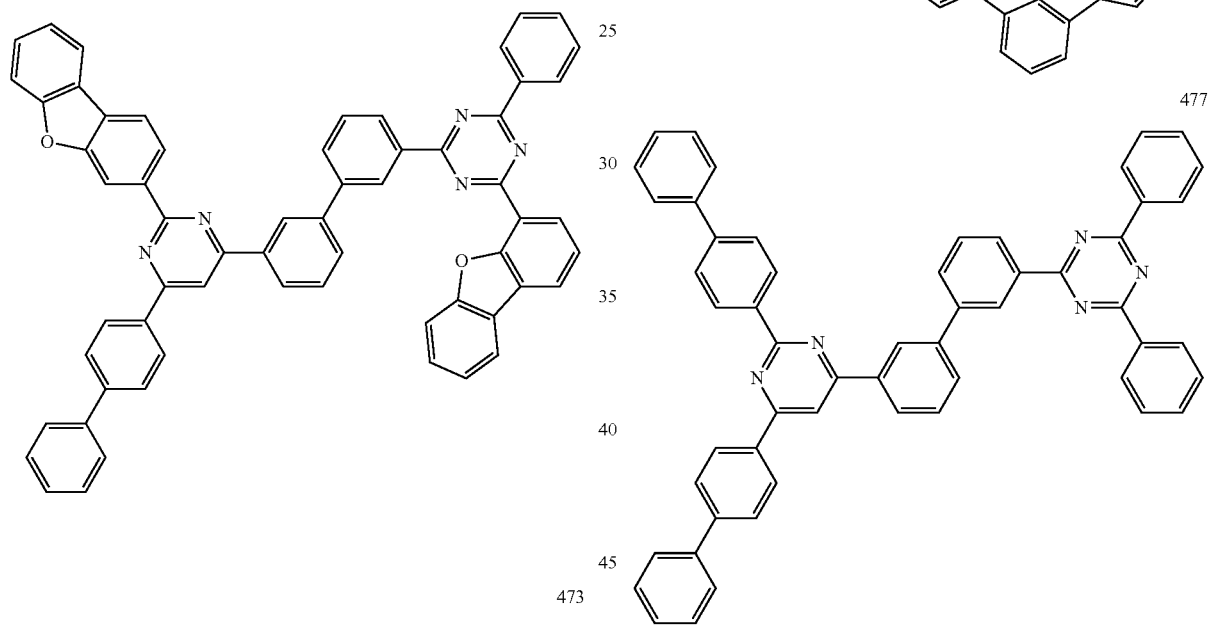
473
474
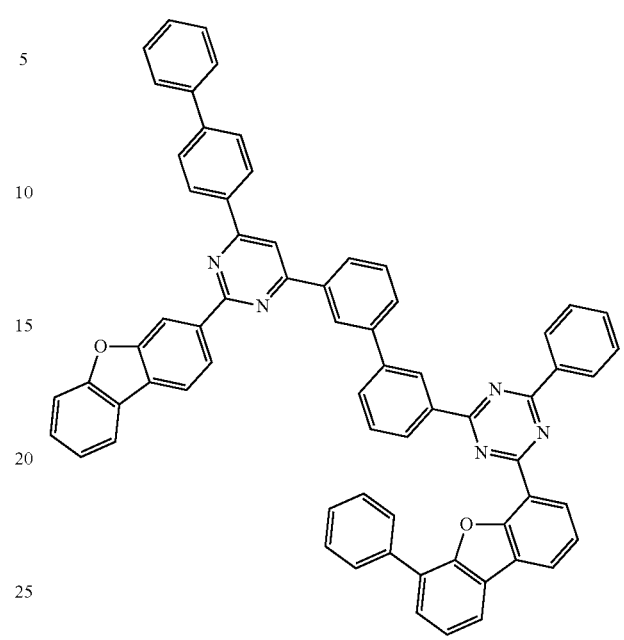
477
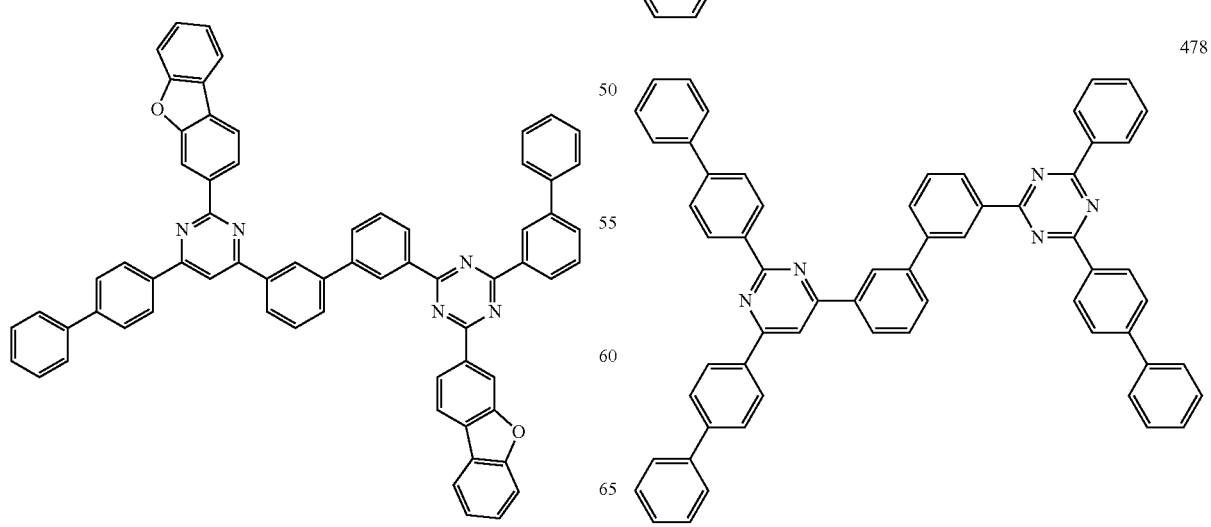
478

-continued
479
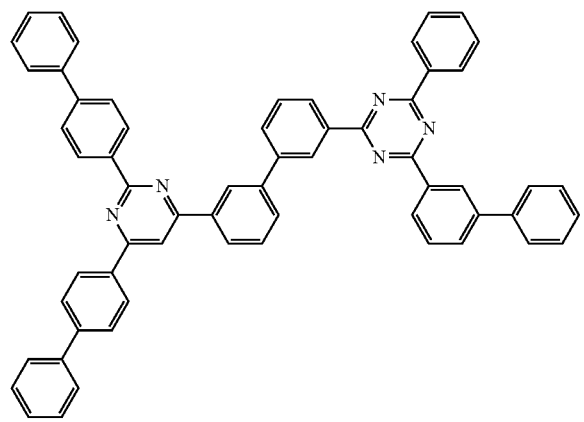
480
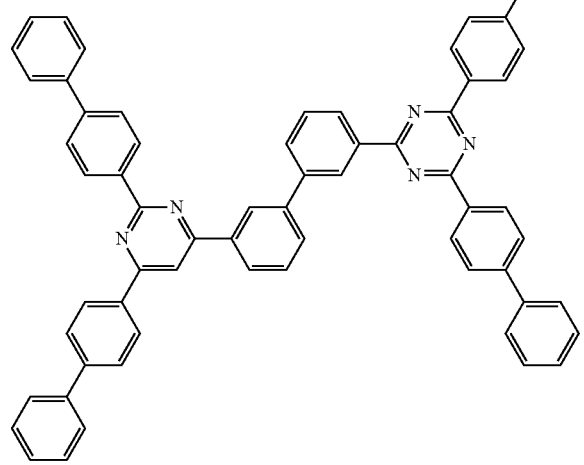
481
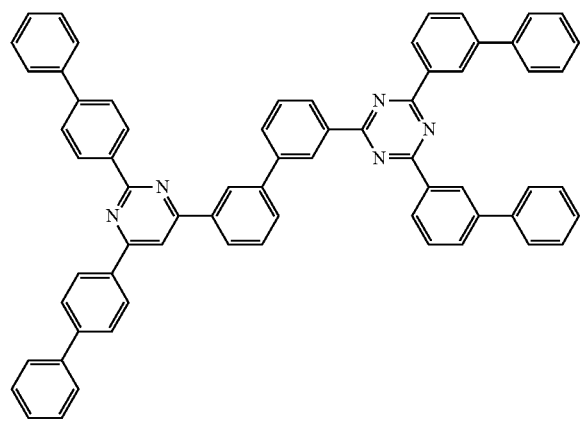
-continued
482
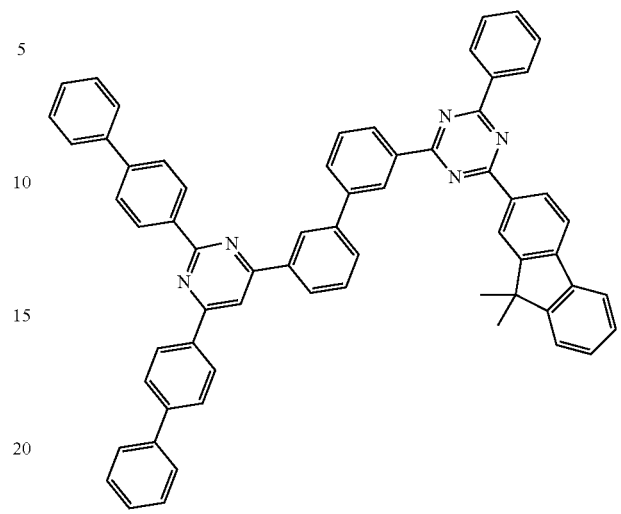
483
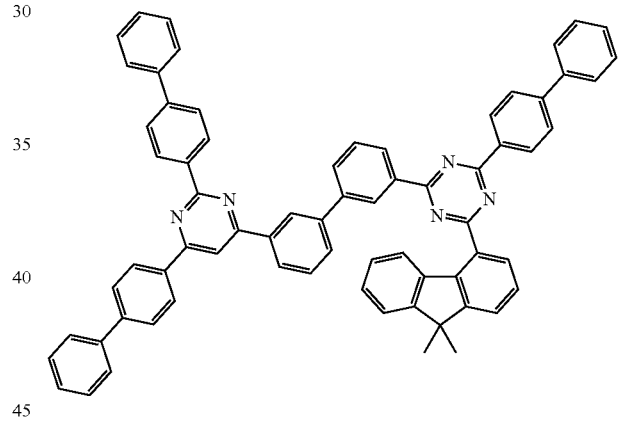
484
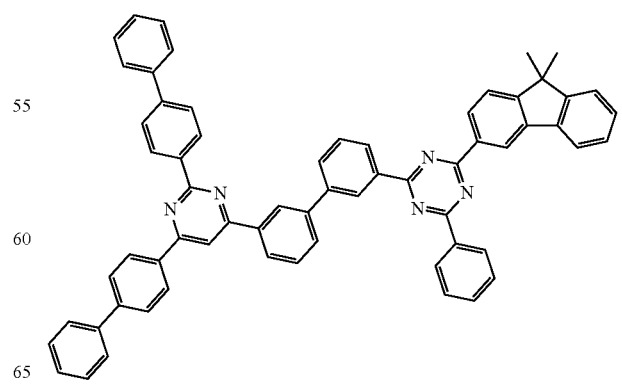

521
-continued
485
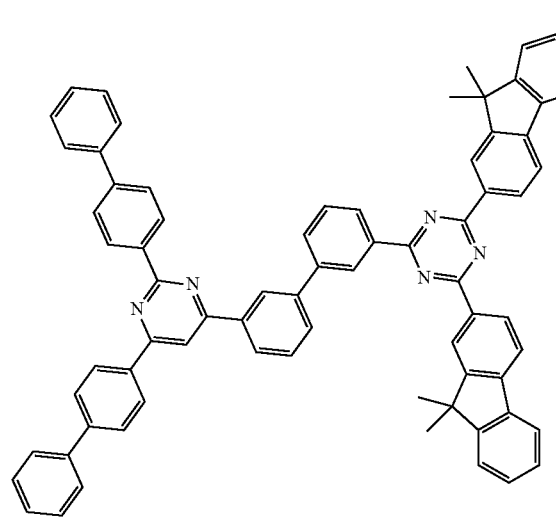
486
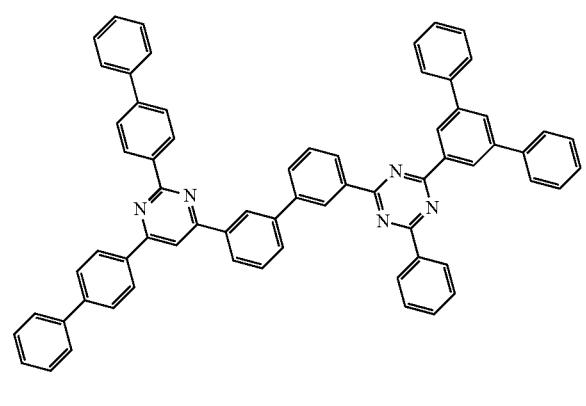
488
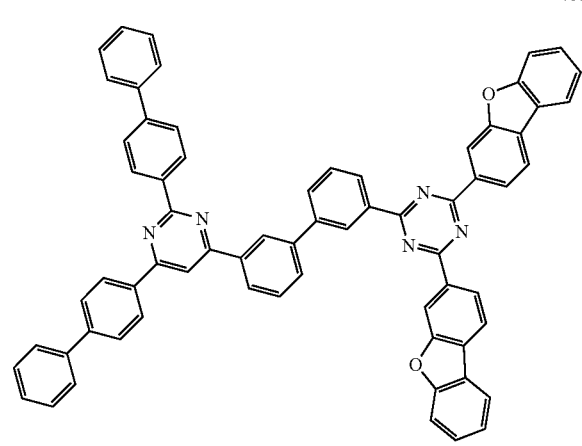
522
-continued
489
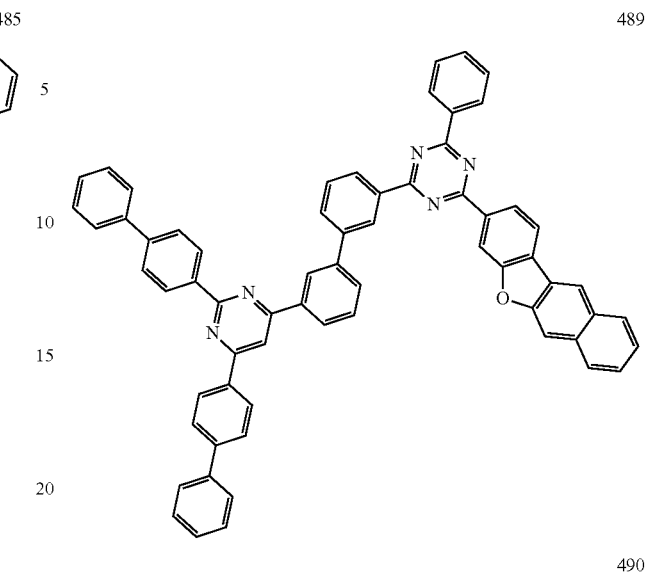
490
491

494
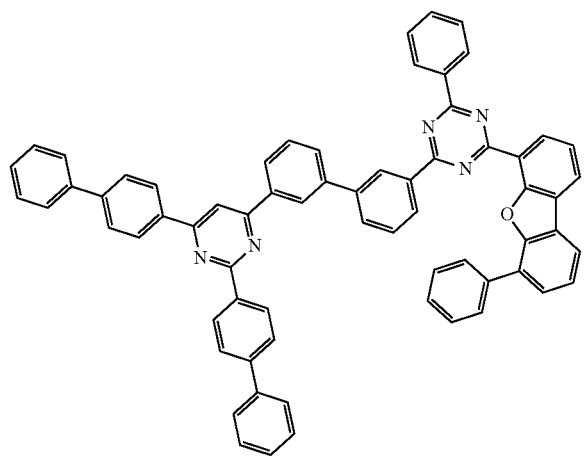
495
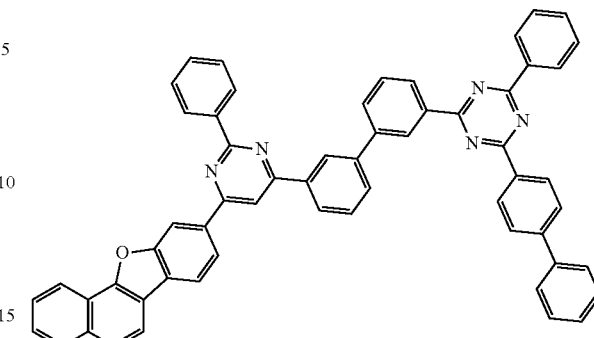
496
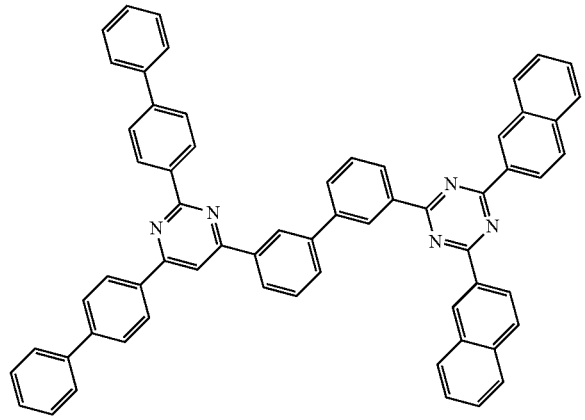
497
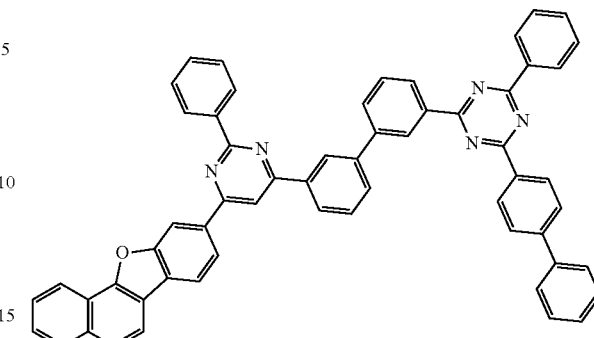
498
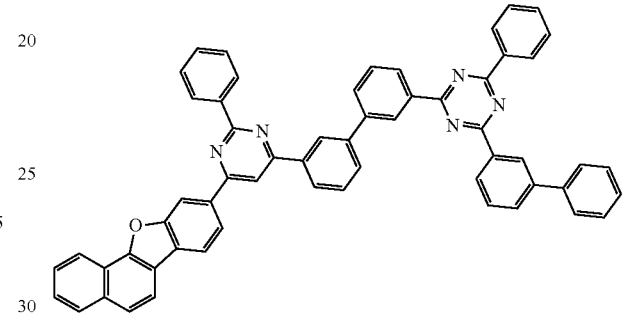
499
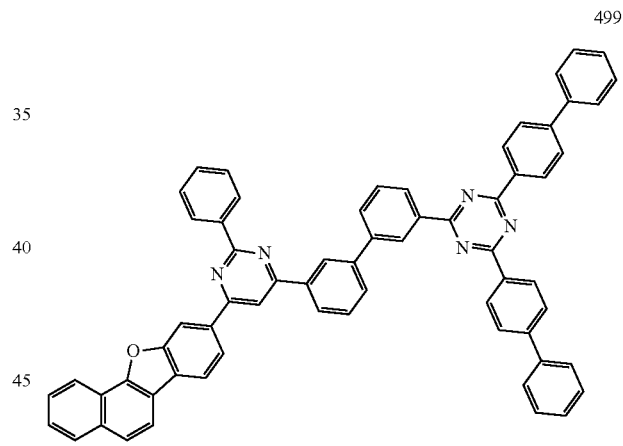
500
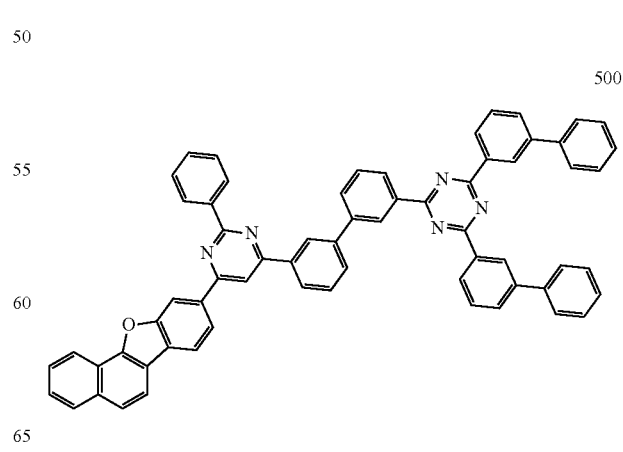

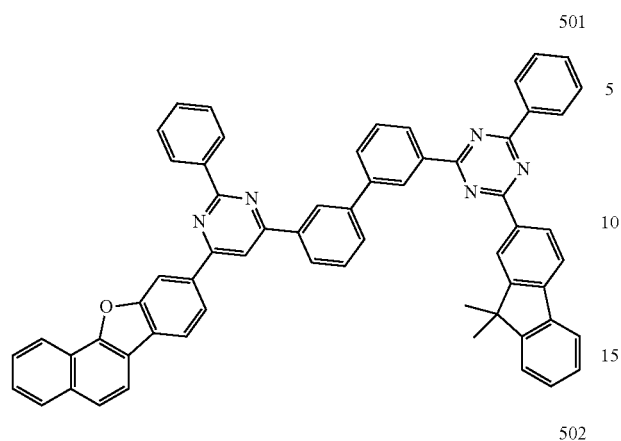
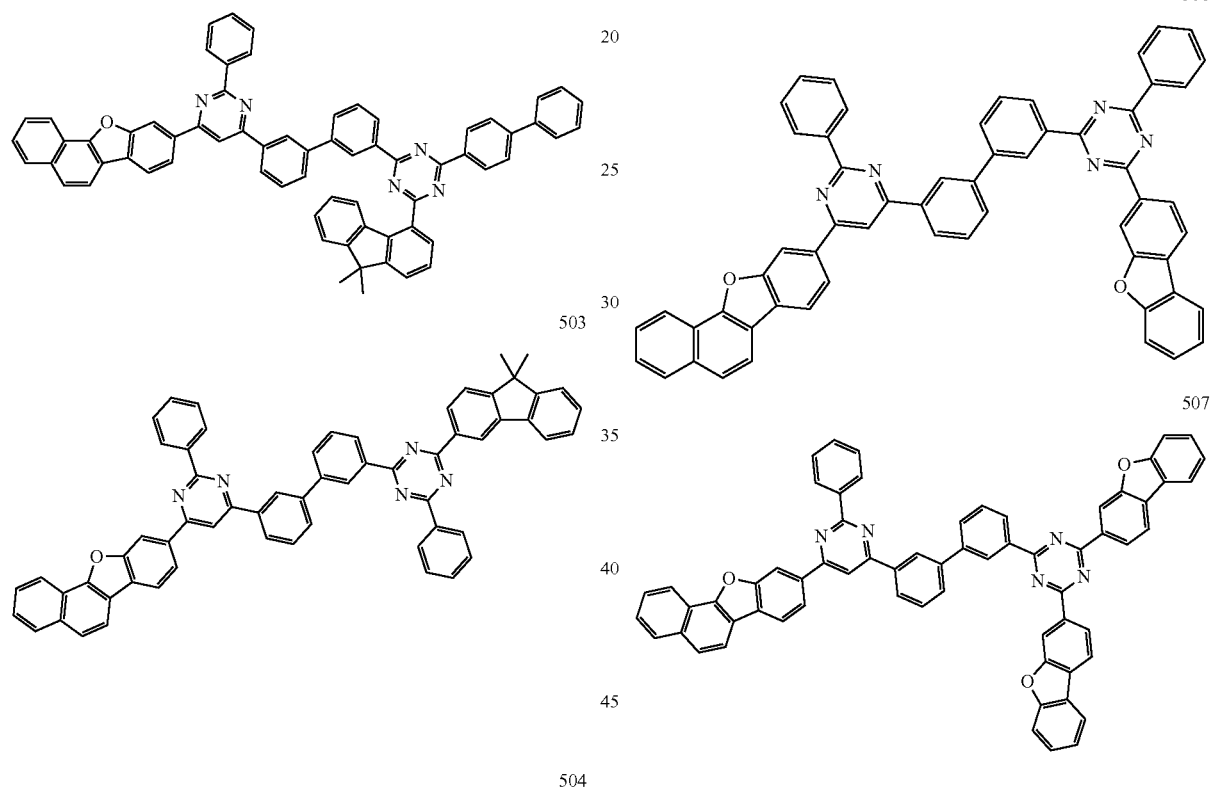
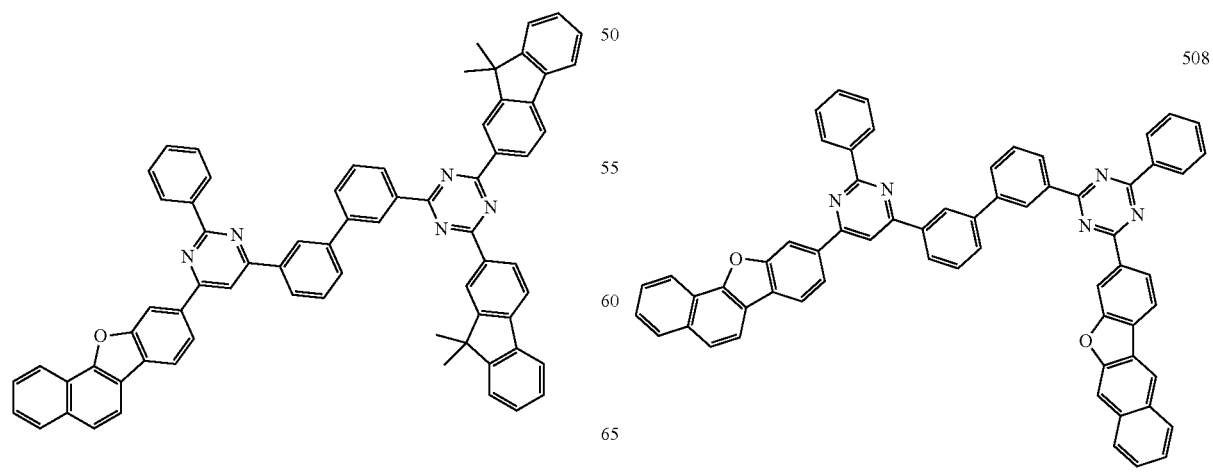

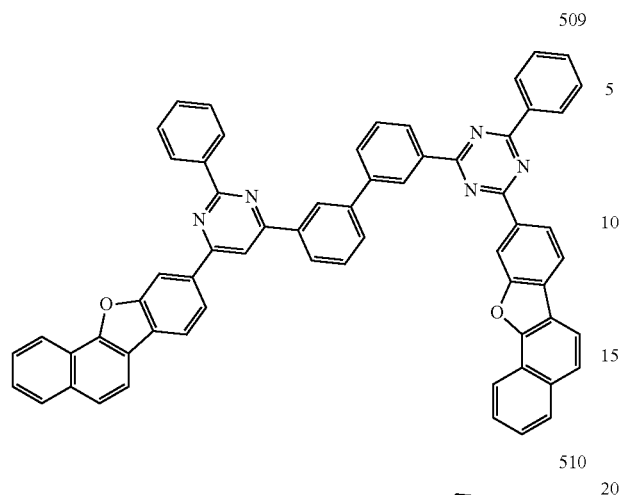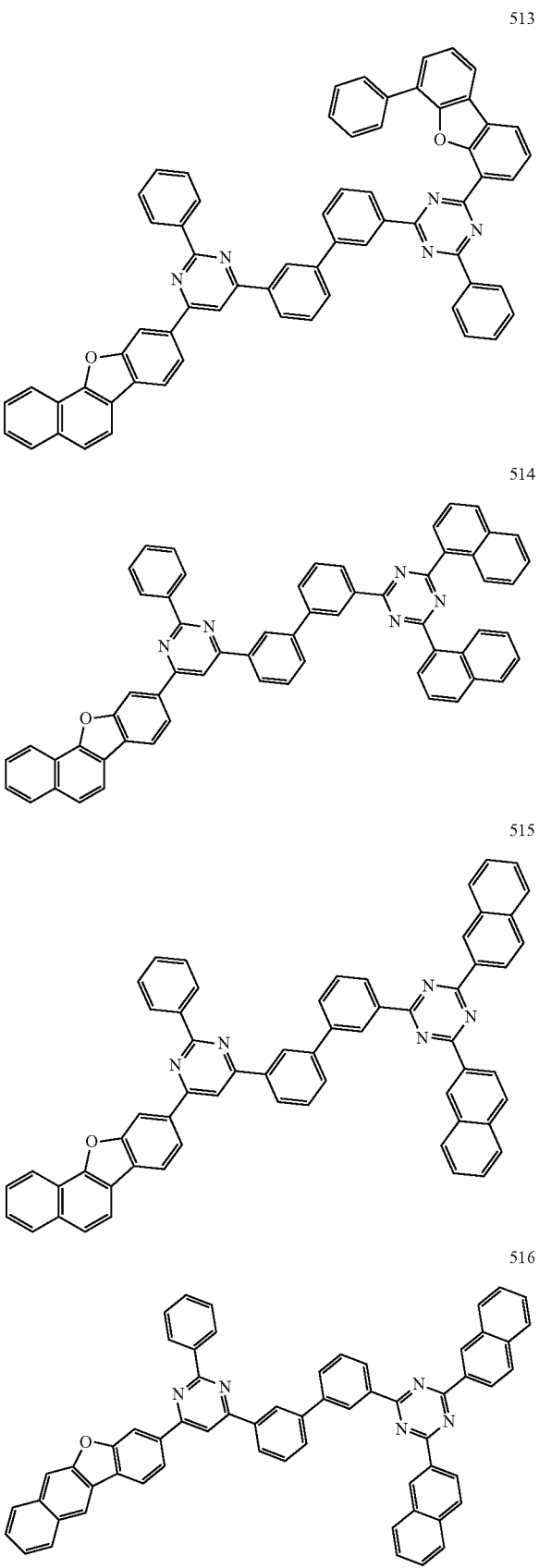

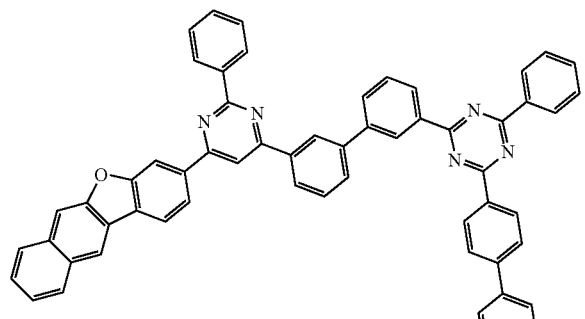
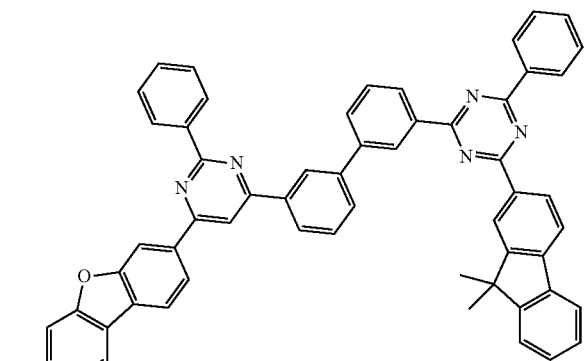
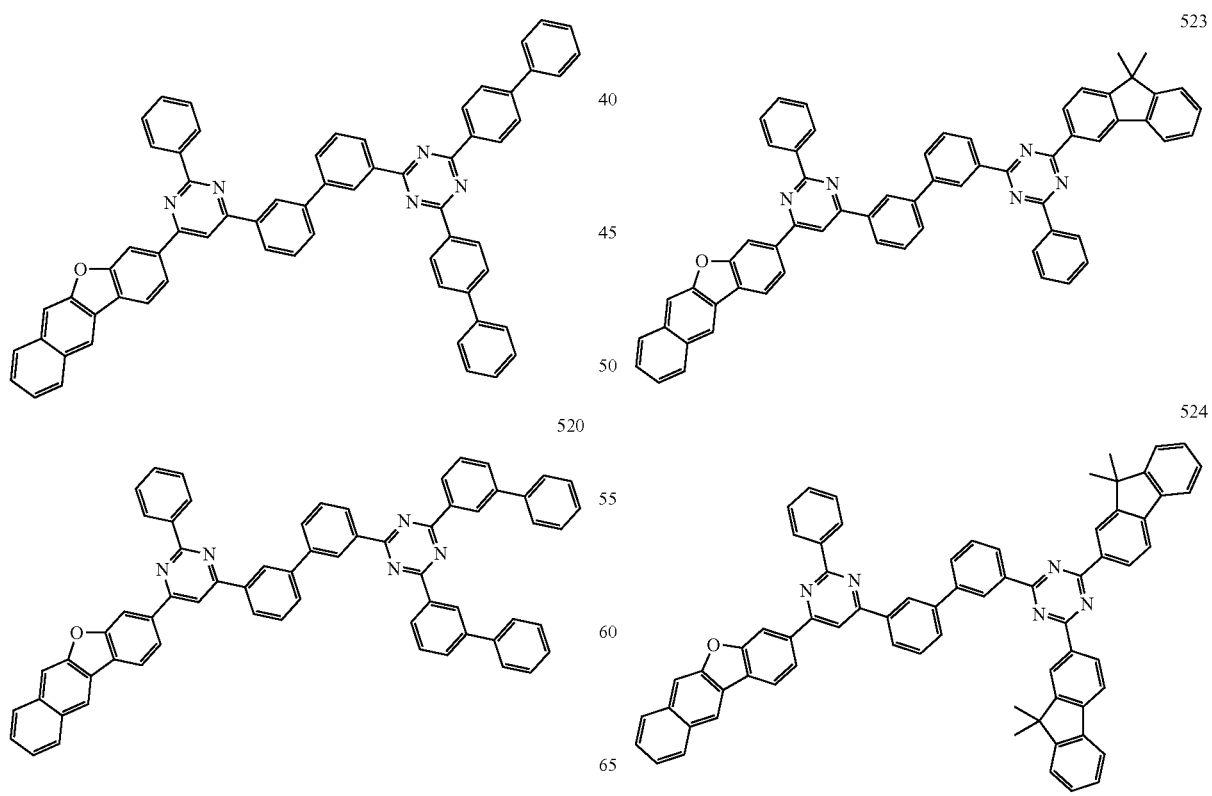

525
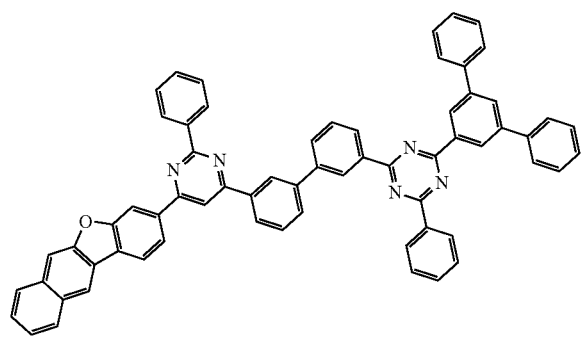
526
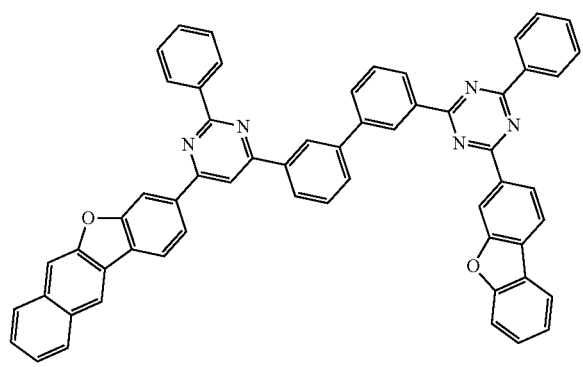
527
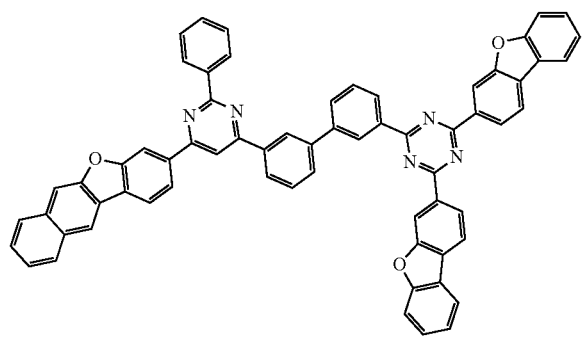
528
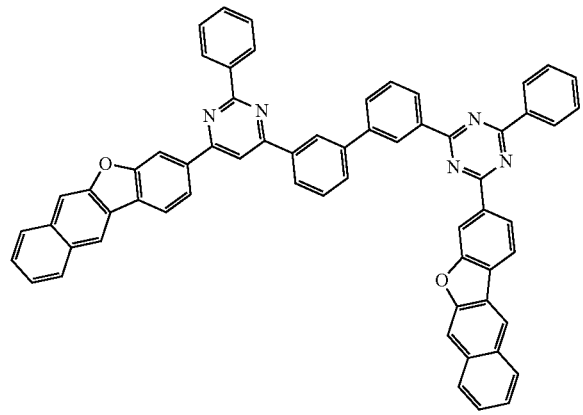
529
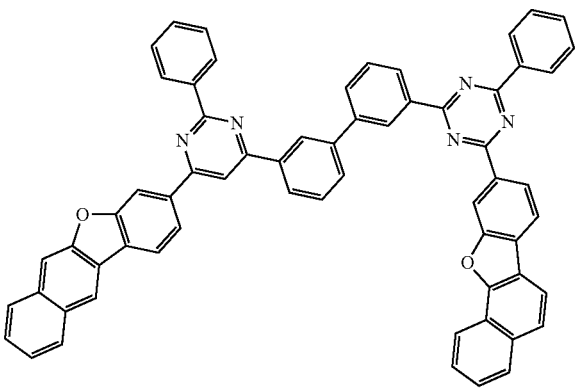
530
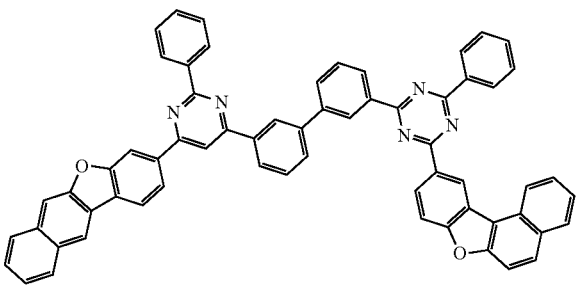
531
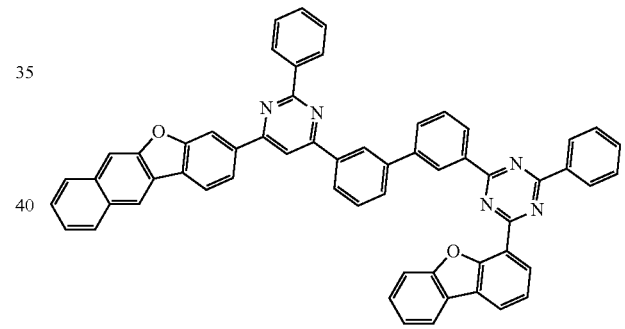
532
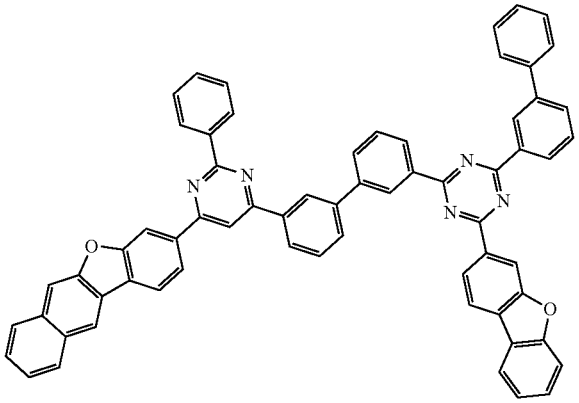

533
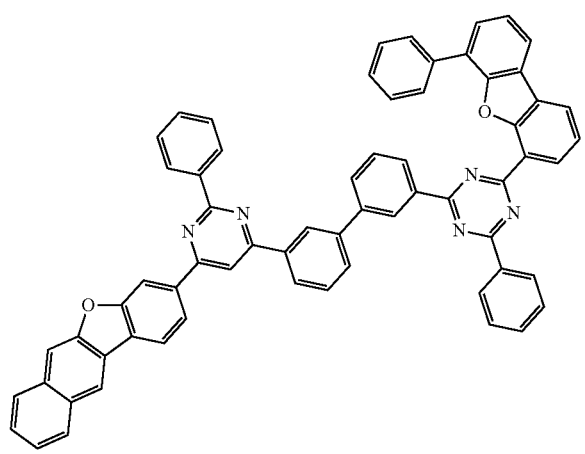
534
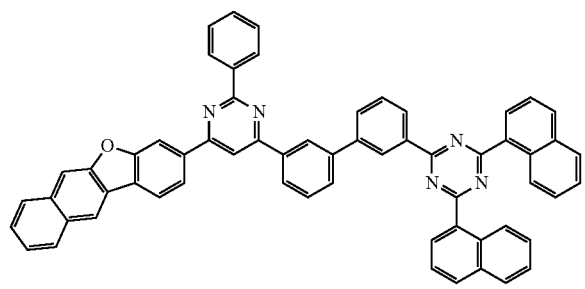
535
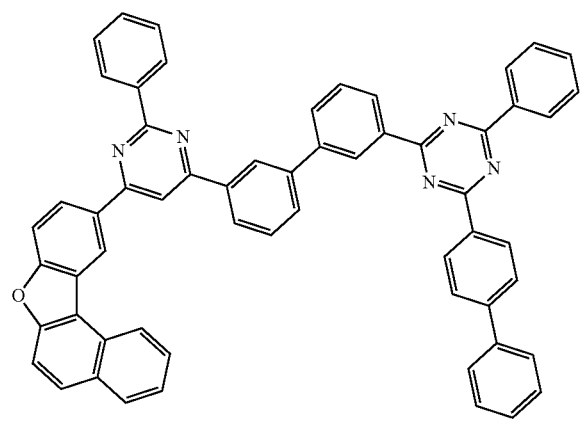
536
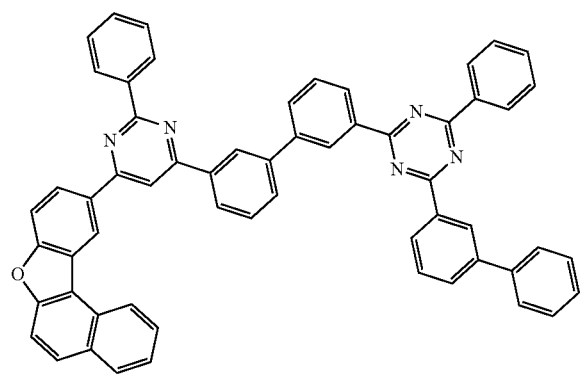
537
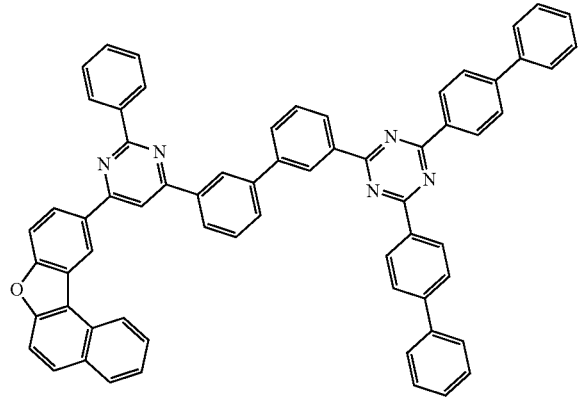
538
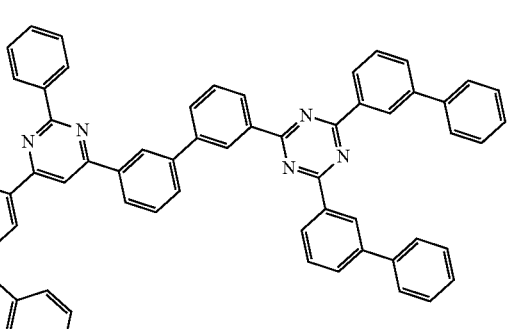
539
540
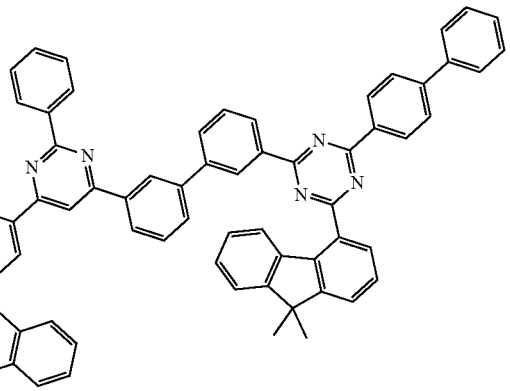

535
-continued
541
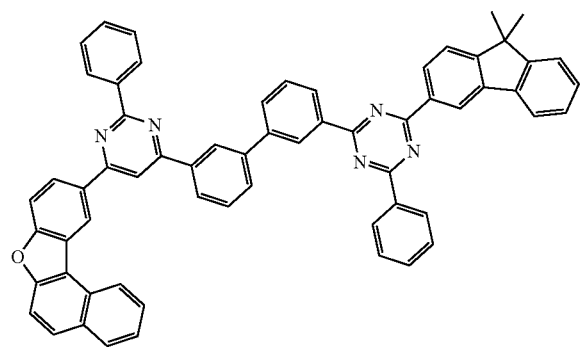
542
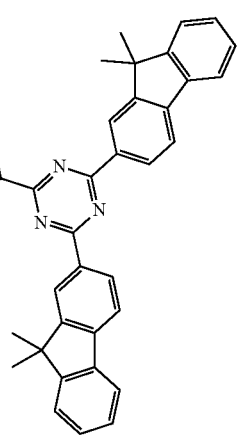
543
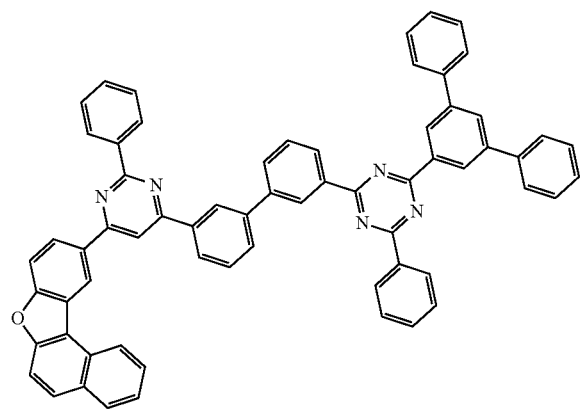
536
-continued
544
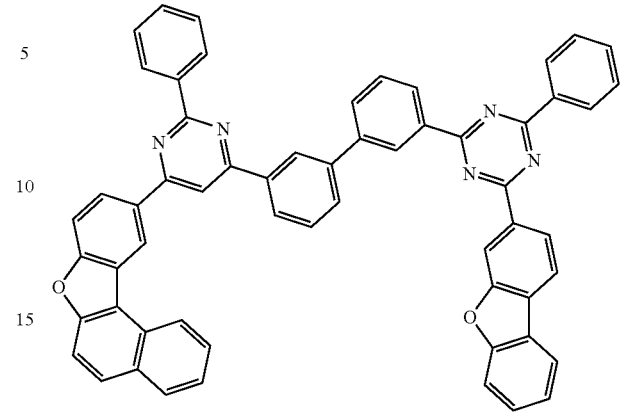
545
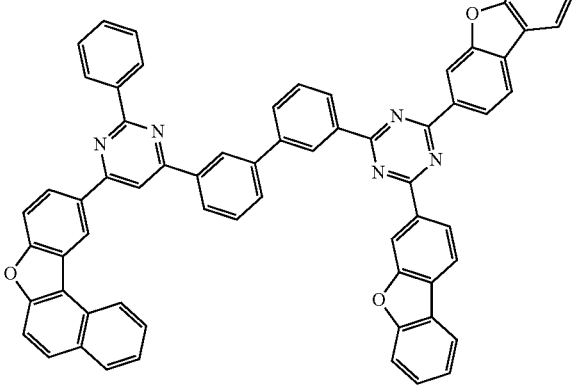
546
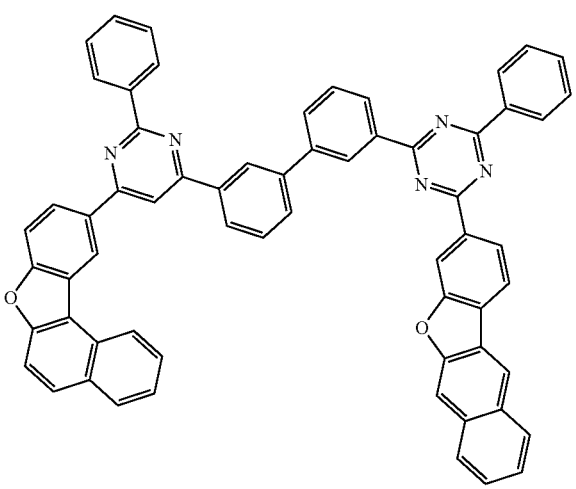

547
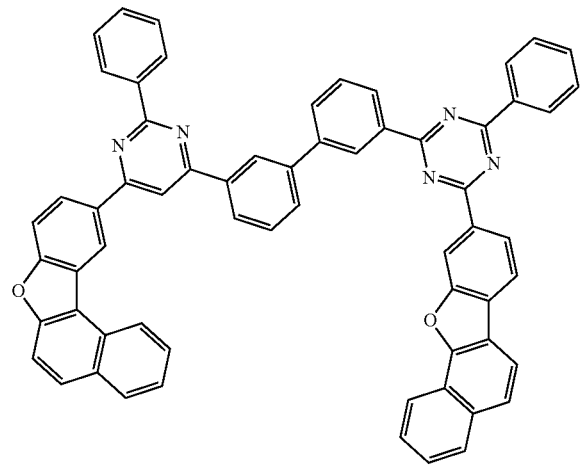
550
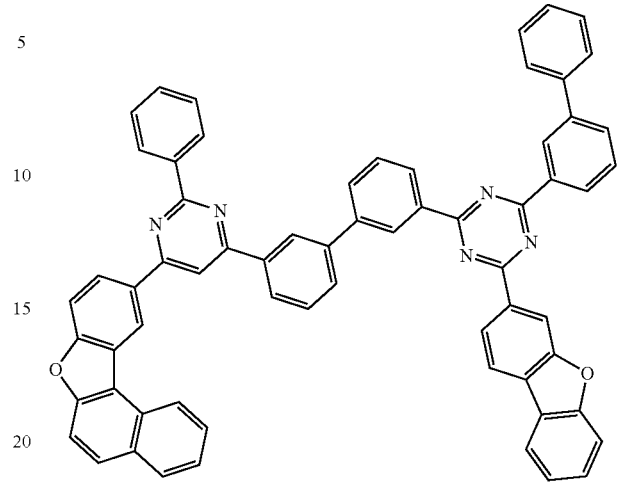
548
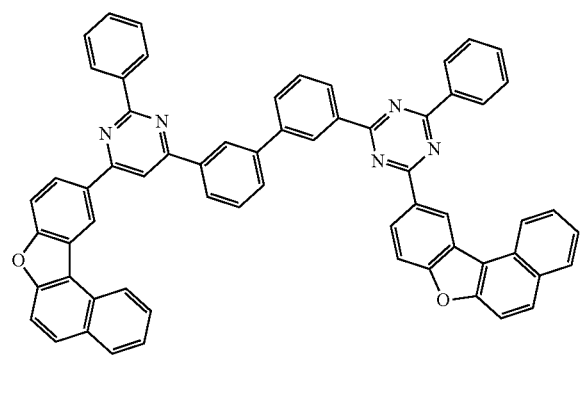
551
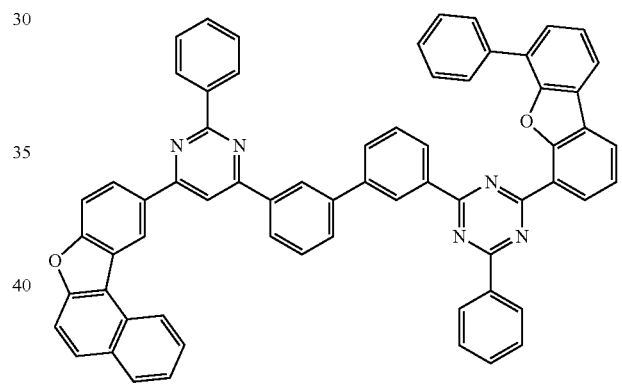
549
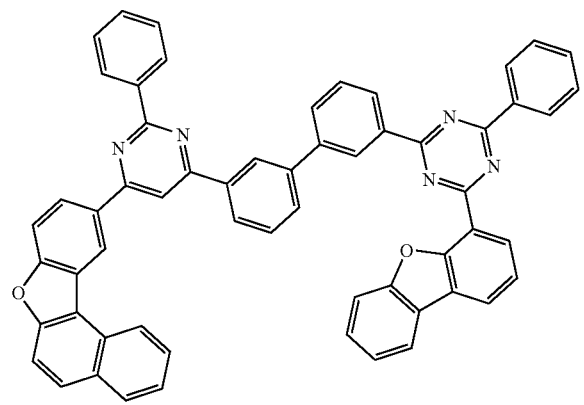
552
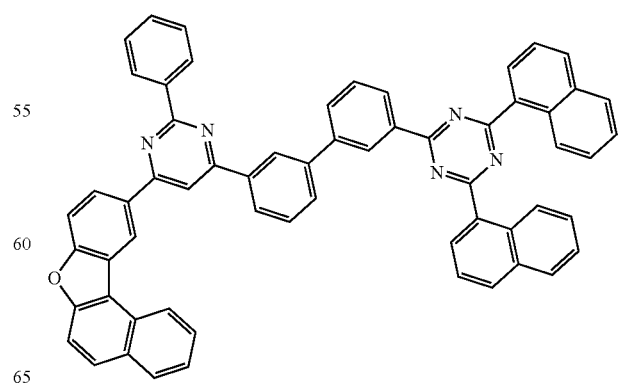

539
-continued
540
-continued
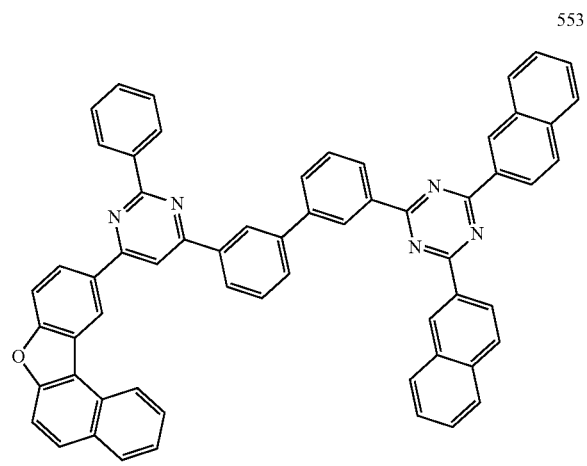
553
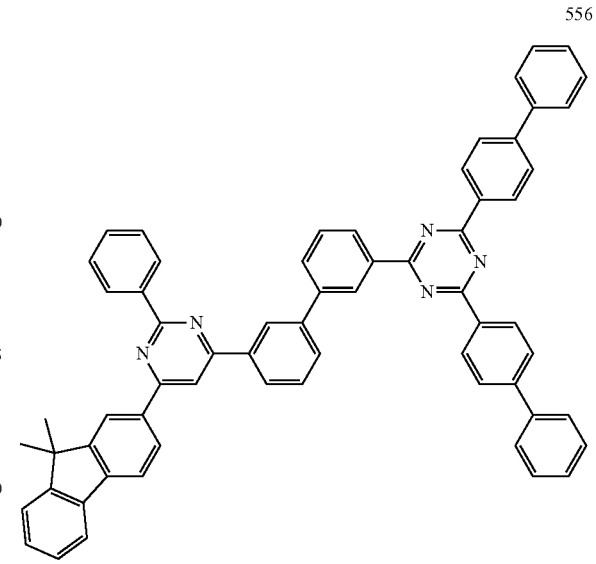
556
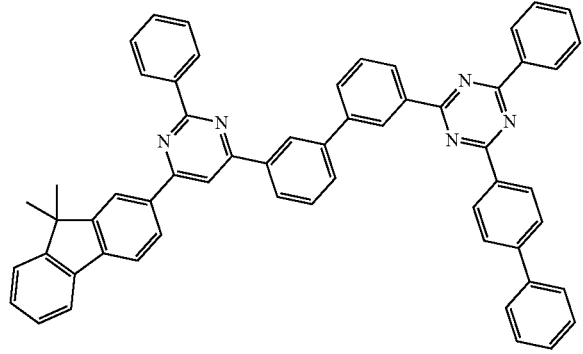
554
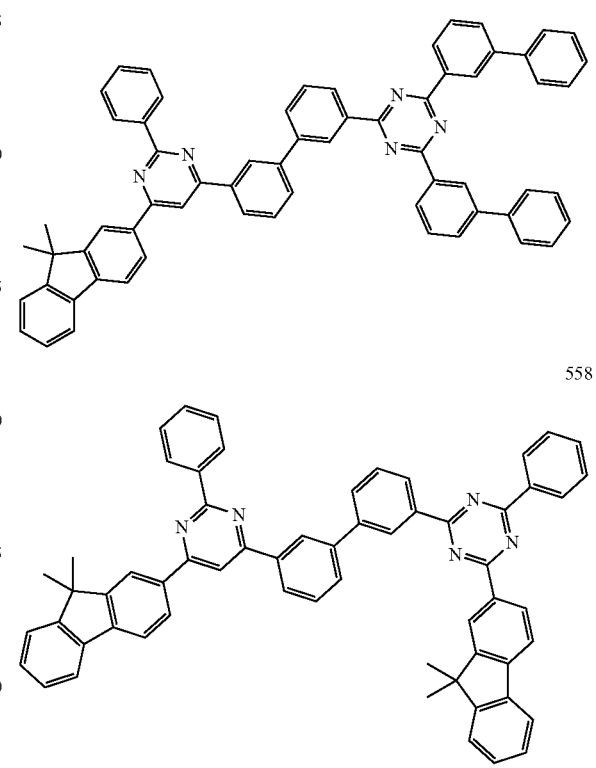
557
558
559
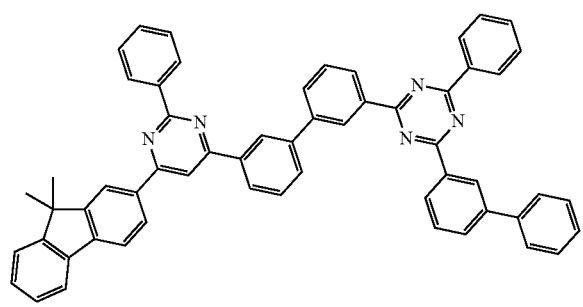
555

541
-continued
560
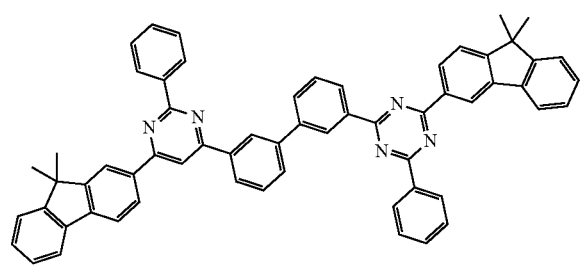
561
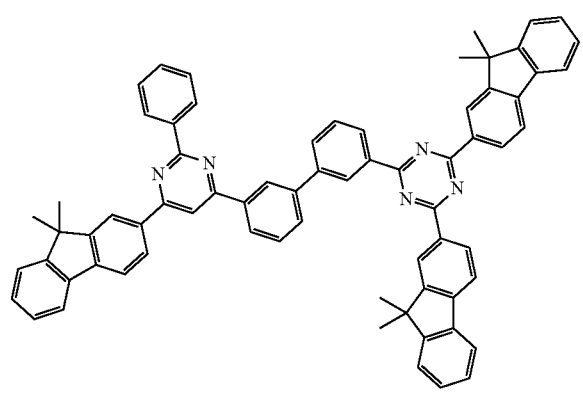
562
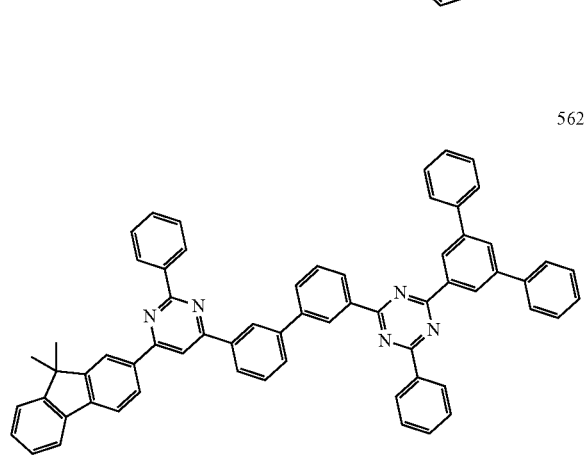
564
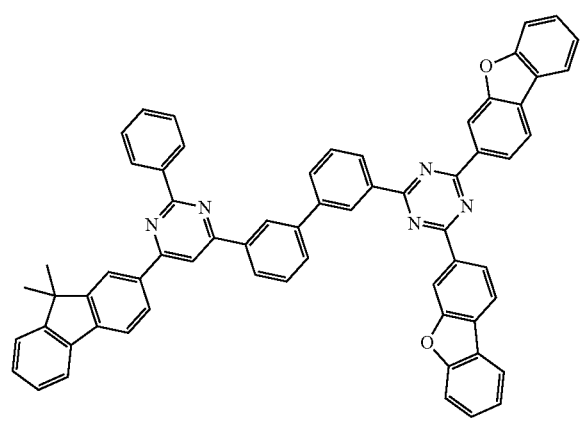
542
-continued
565
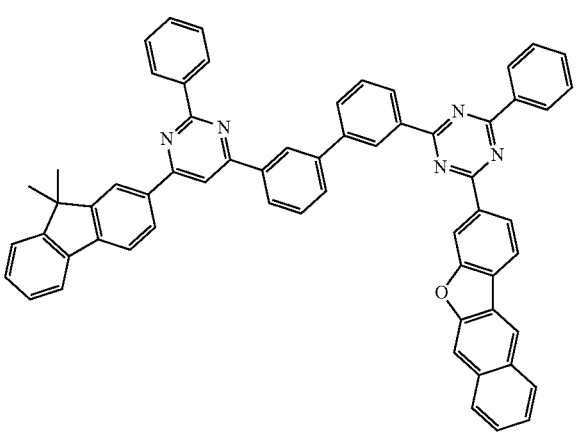
566
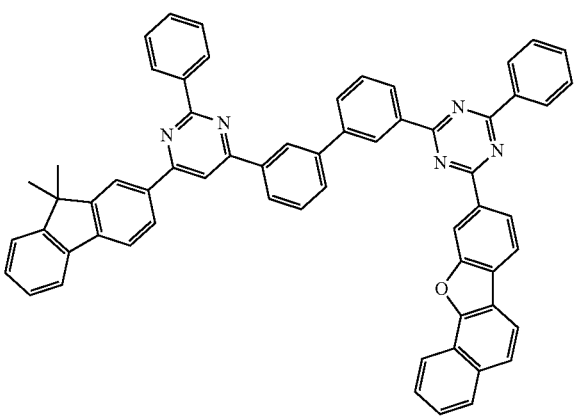
567

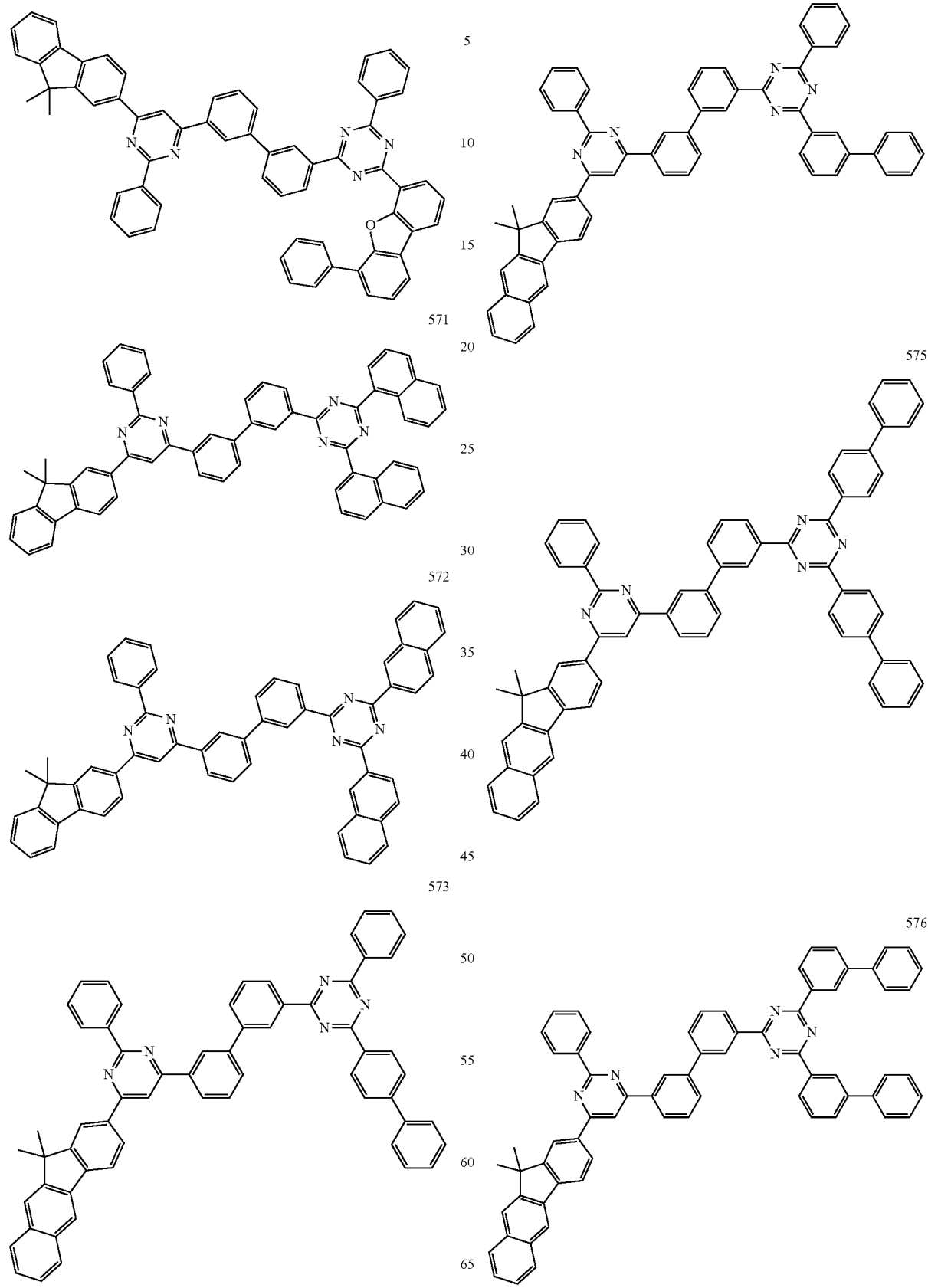

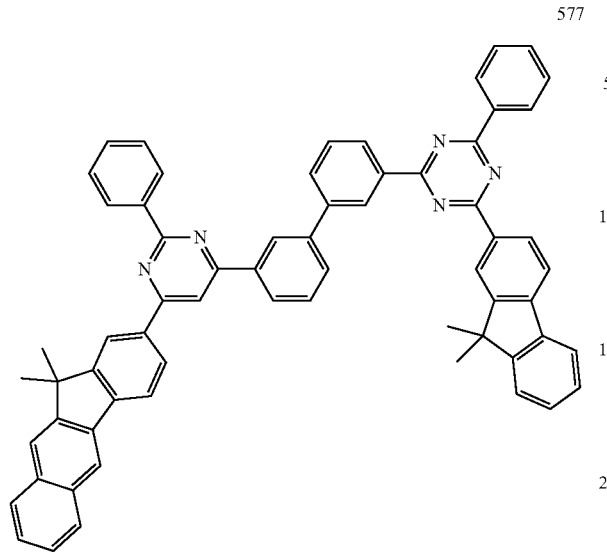
577
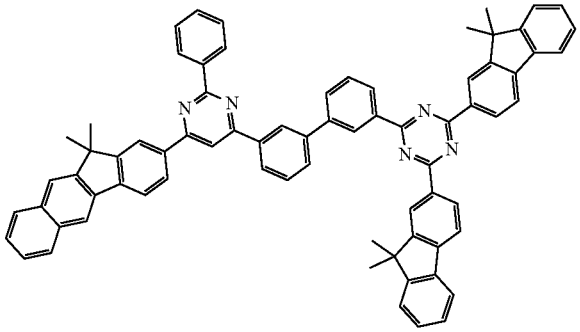
580
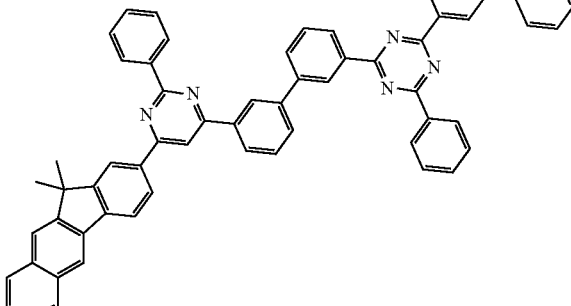
581
578
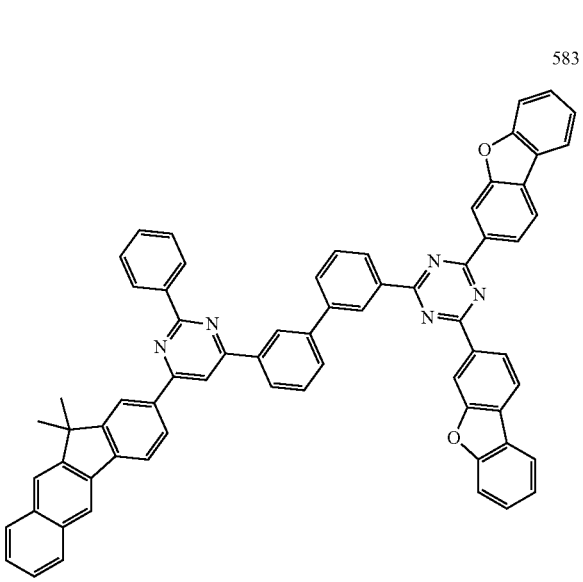
583
579

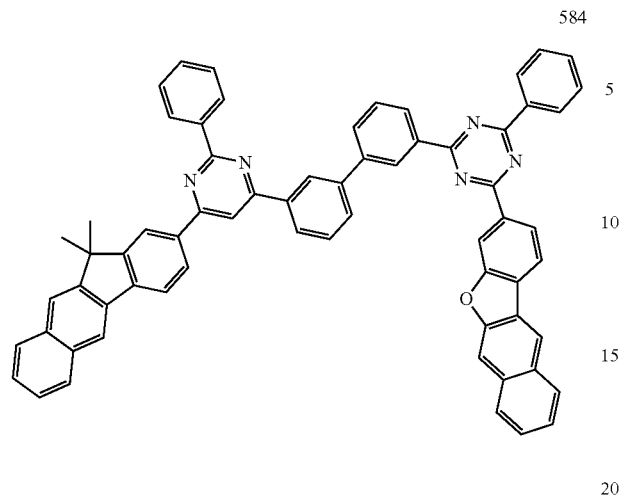
584
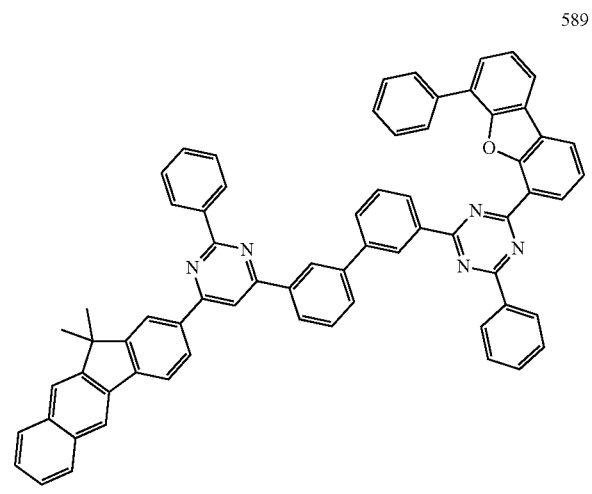
589
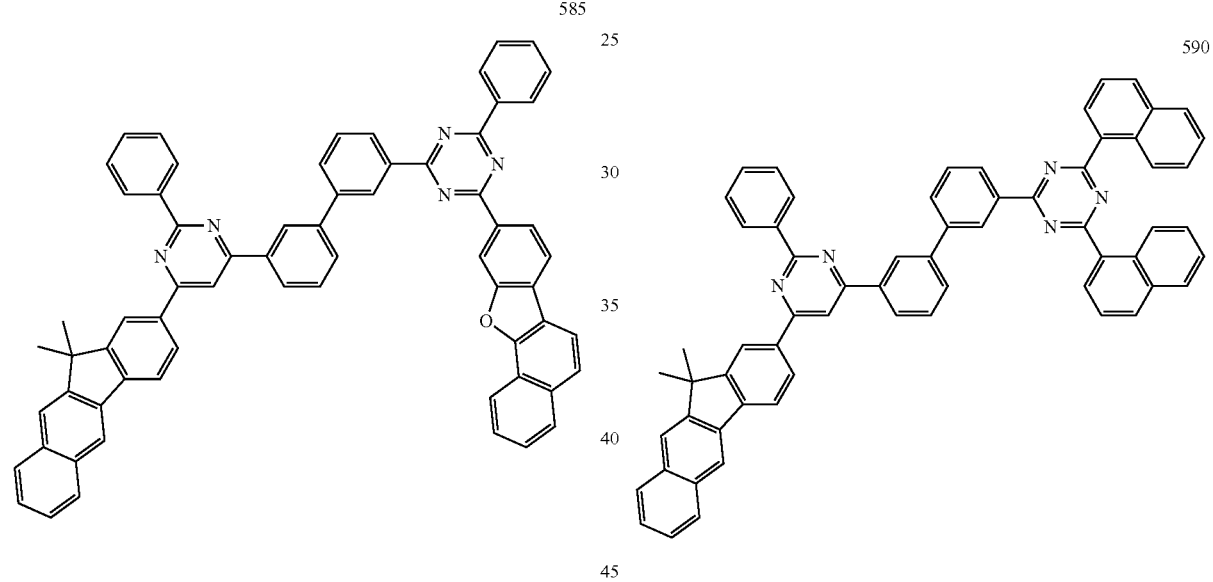
585
590
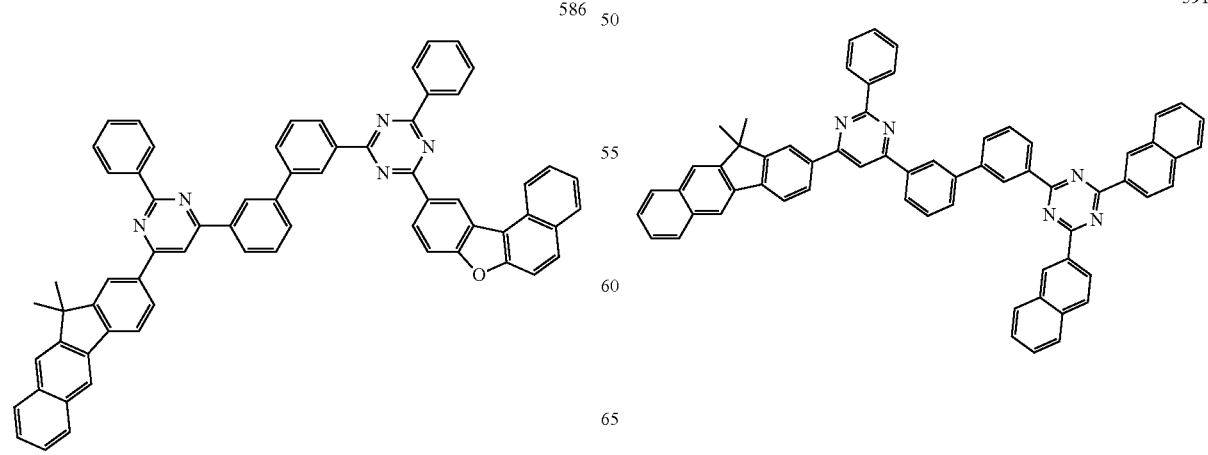
586
591

-continued
592
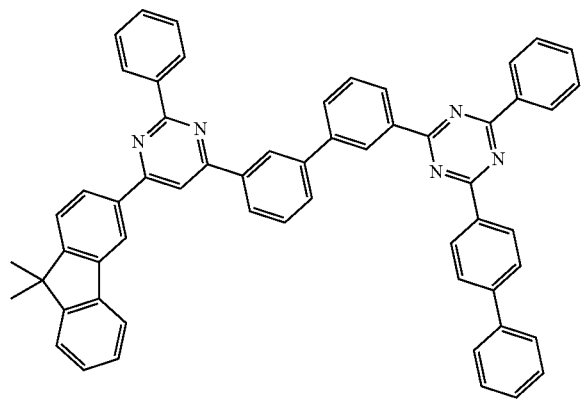
593
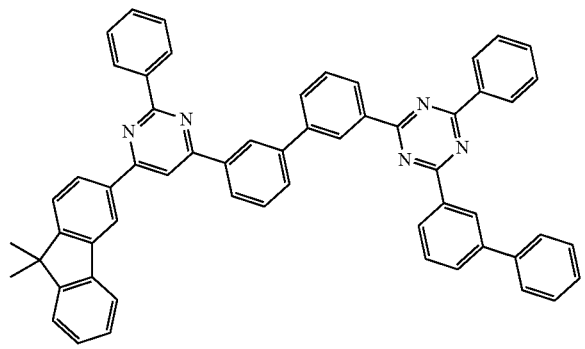
594
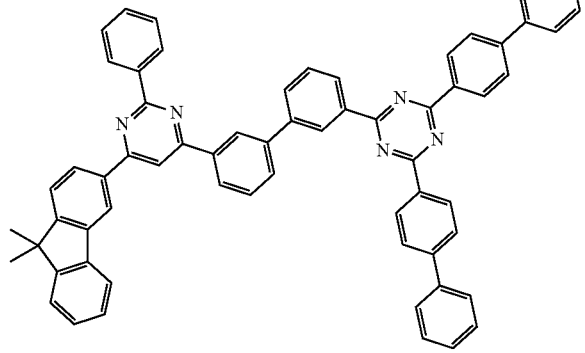
595
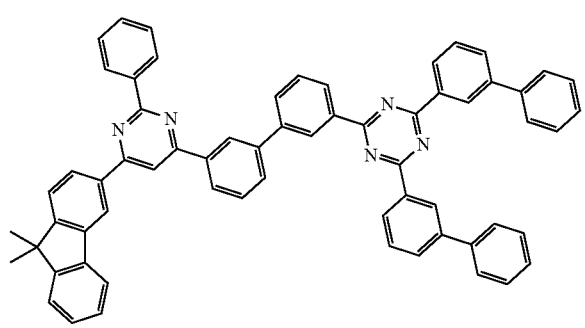
-continued
596
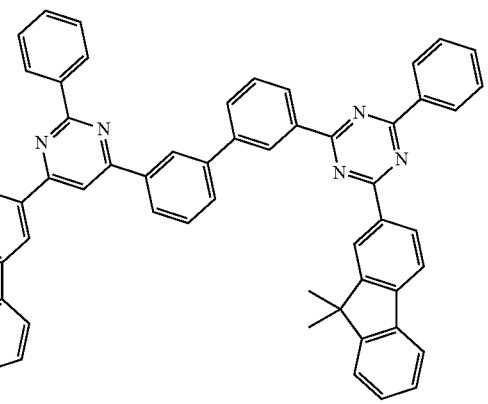
597
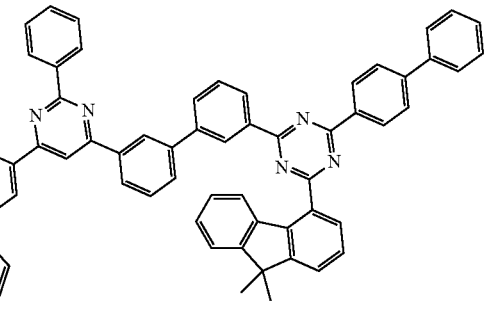
598
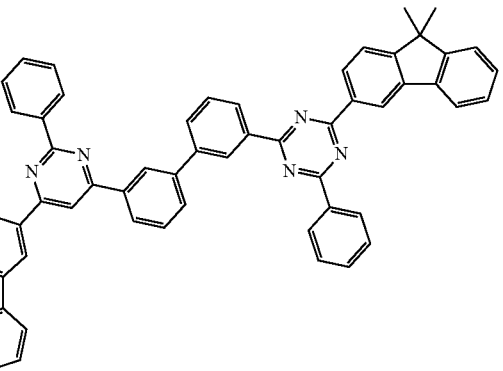
599
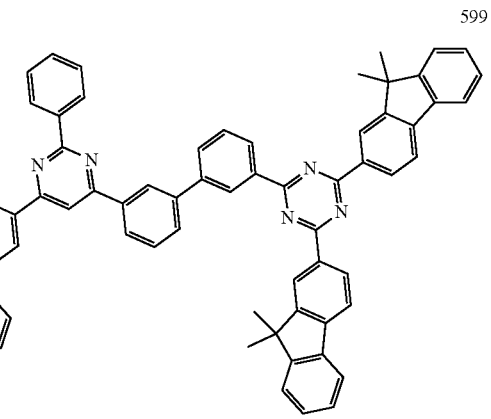

600
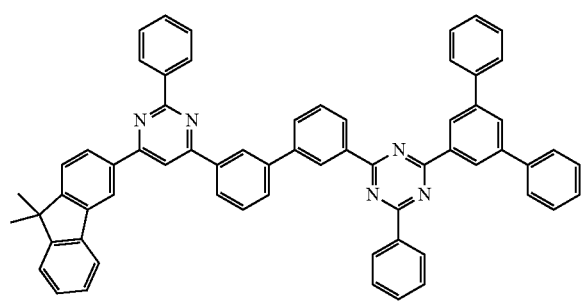
602
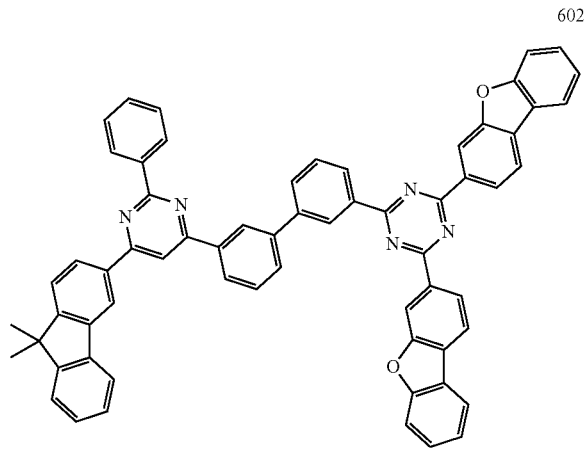
603
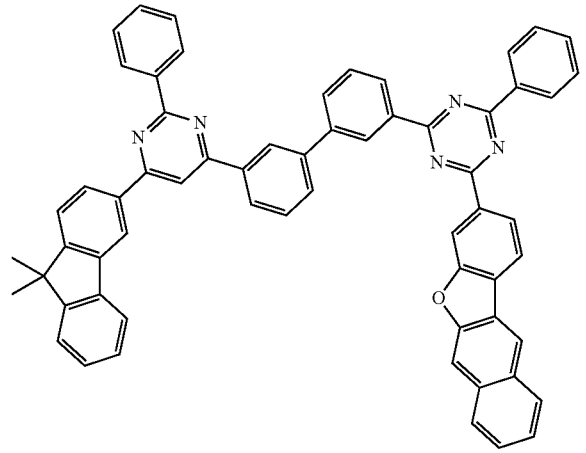
604
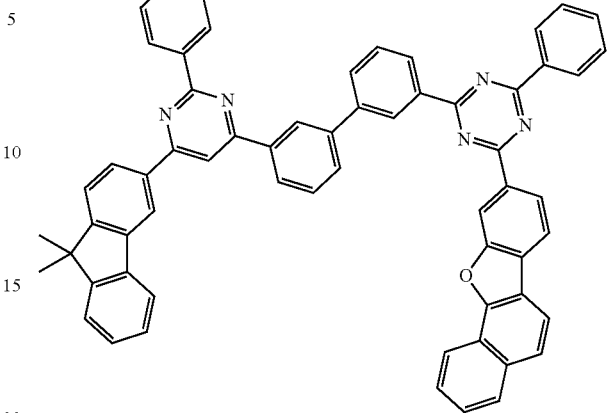
605
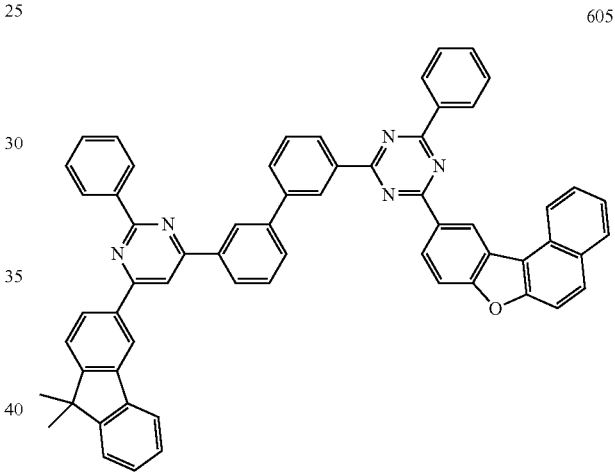
608
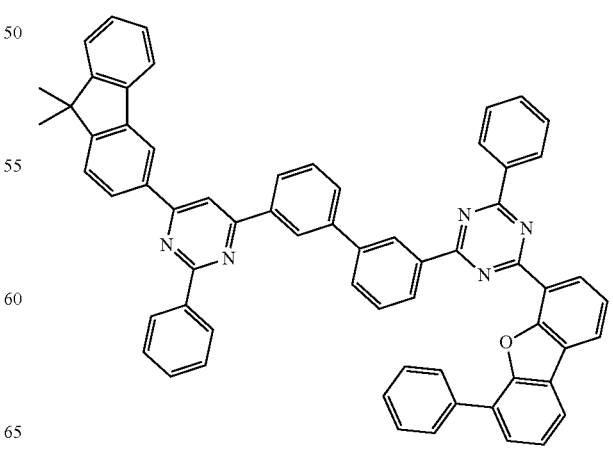

553
-continued
554
-continued
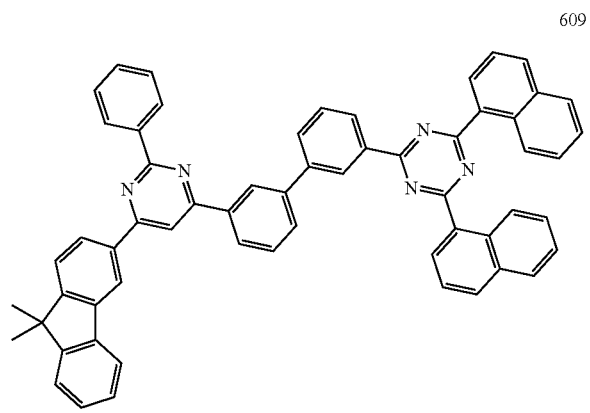
609
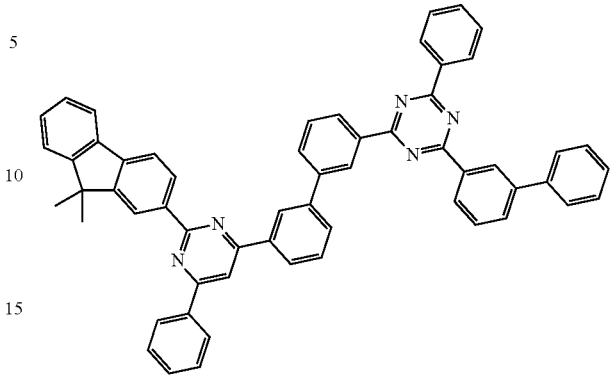
612
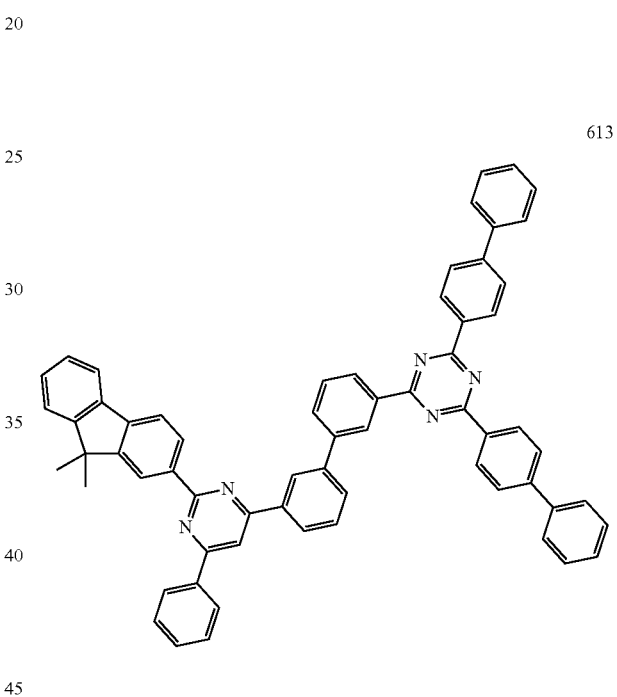
610
613
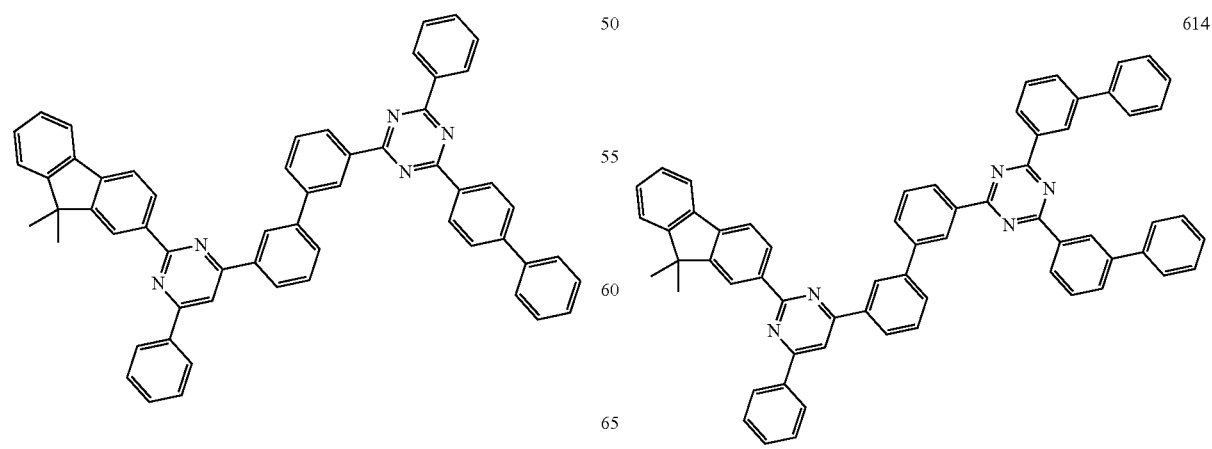
611
614

555
-continued
615
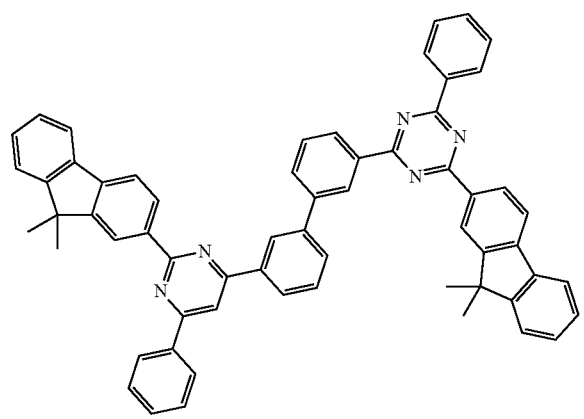
616
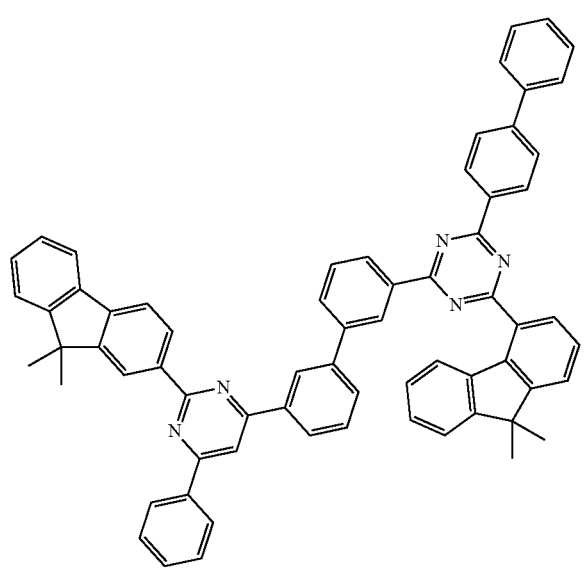
617
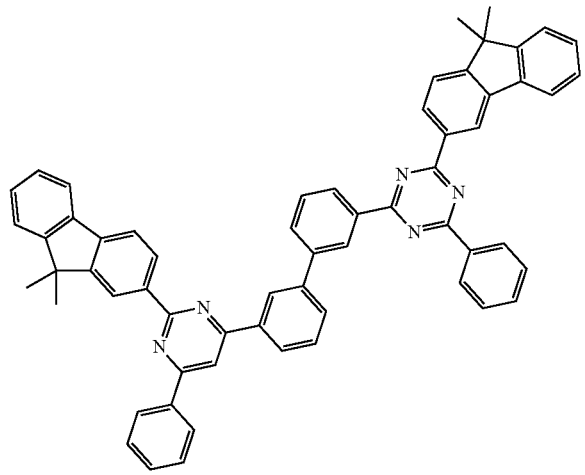
556
-continued
618
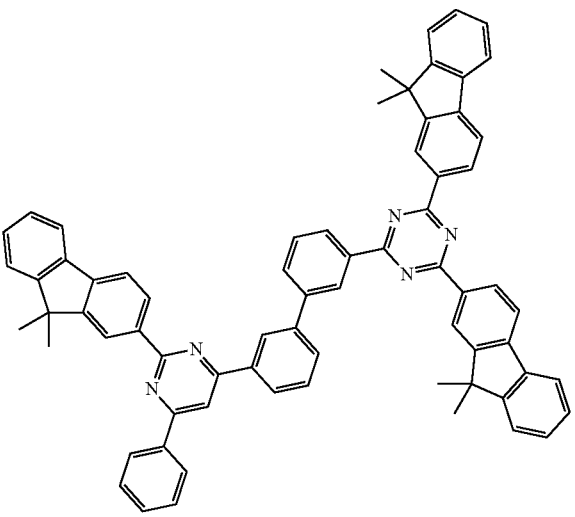
619
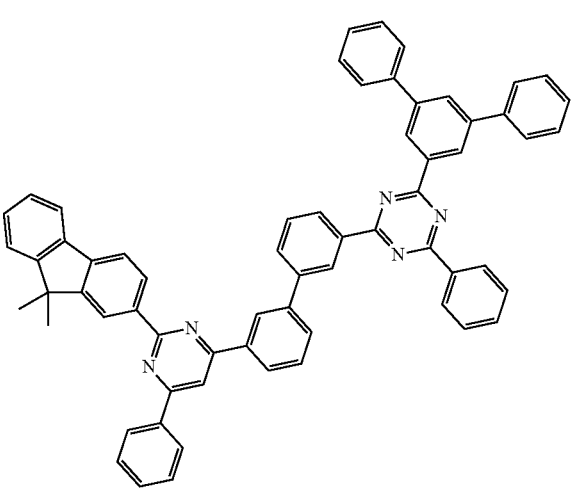
621
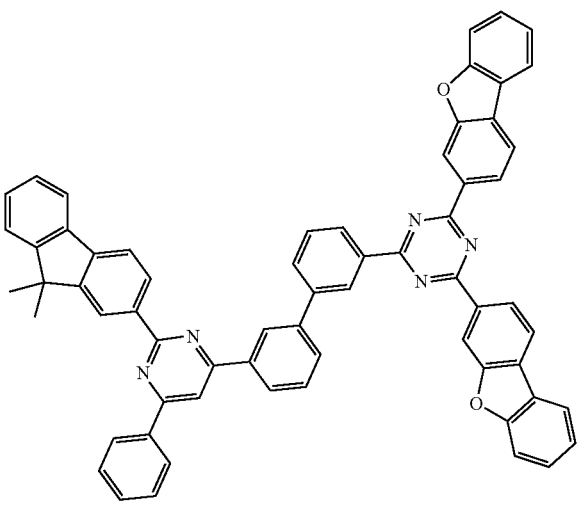

622
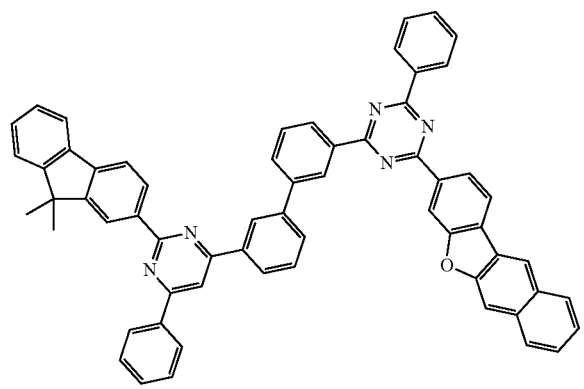
623
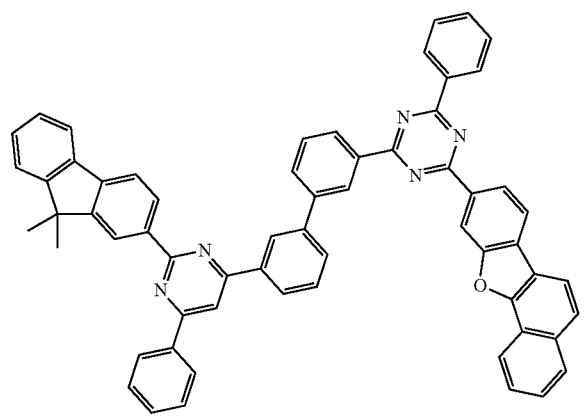
624
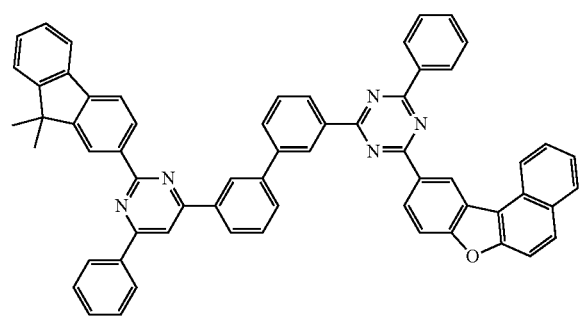
627
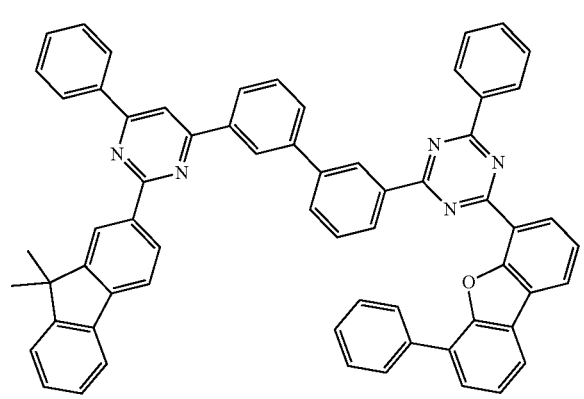
628
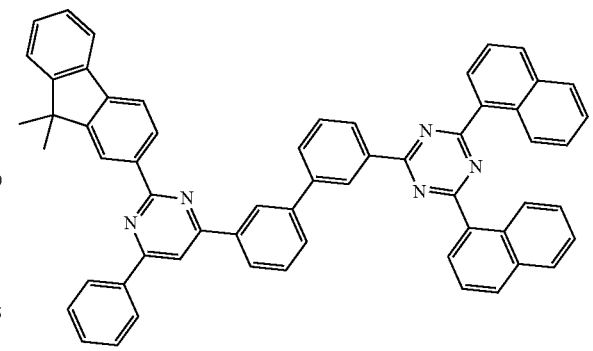
629
630
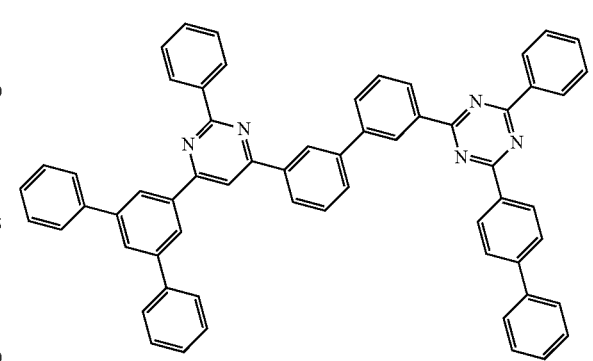
631
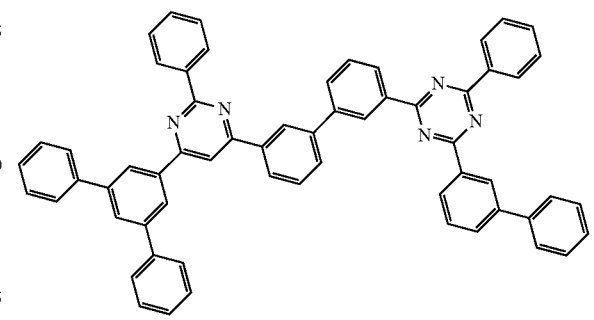

632
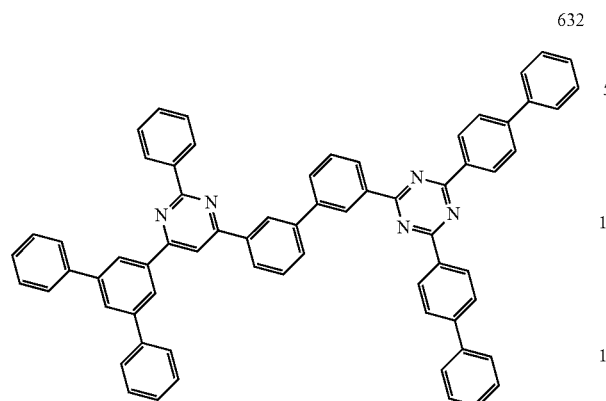
636
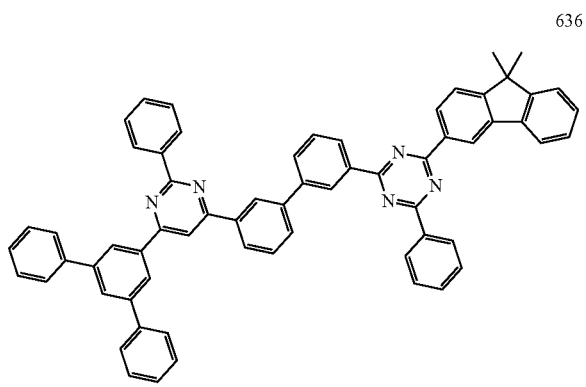
633
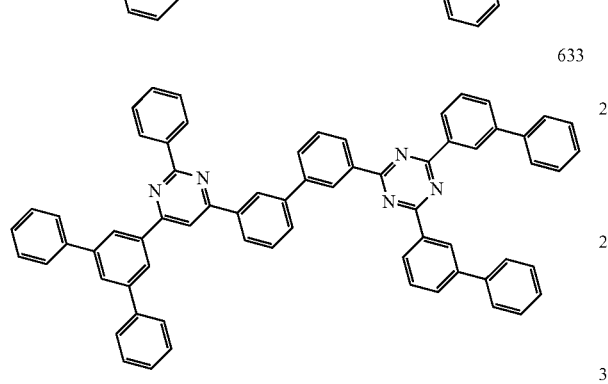
637
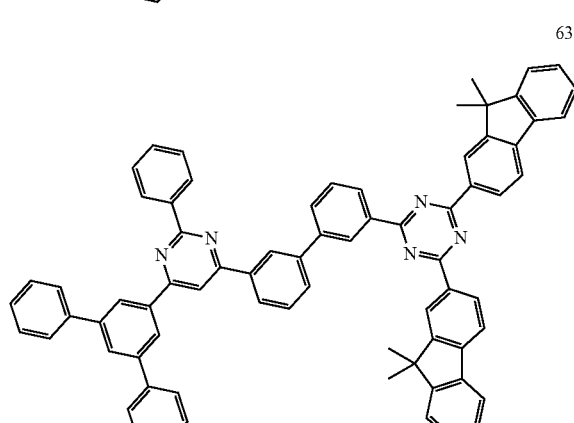
634
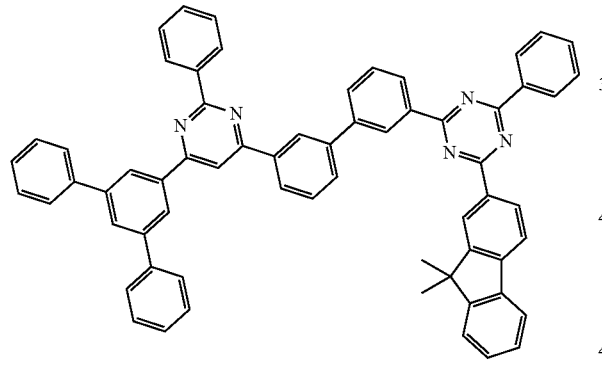
638
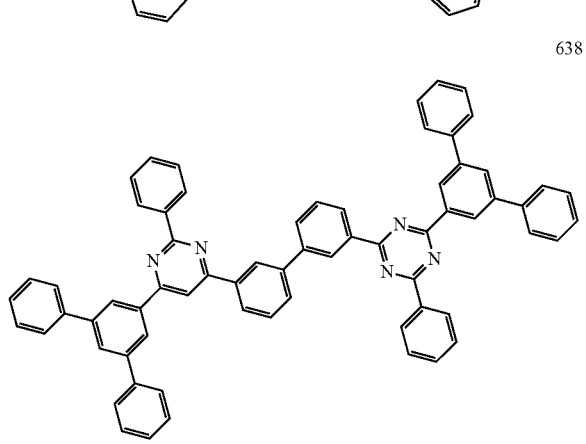
635
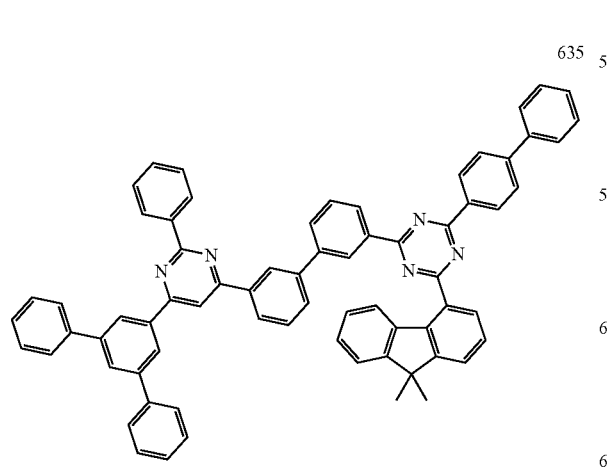
640
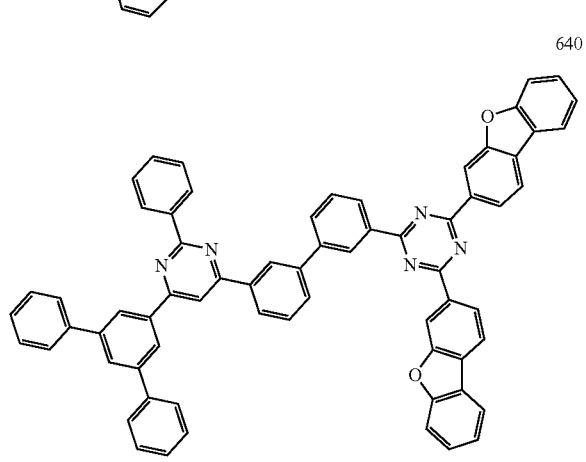

561
-continued
641
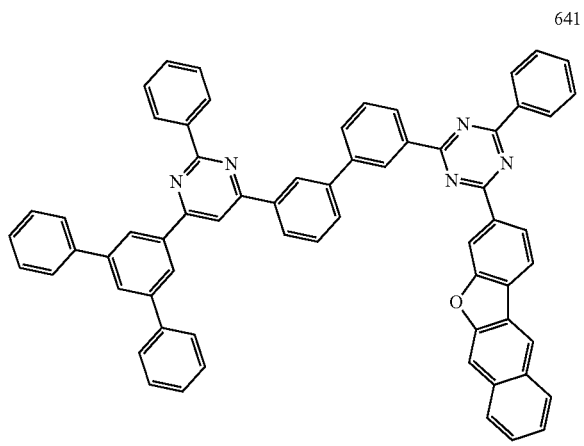
642
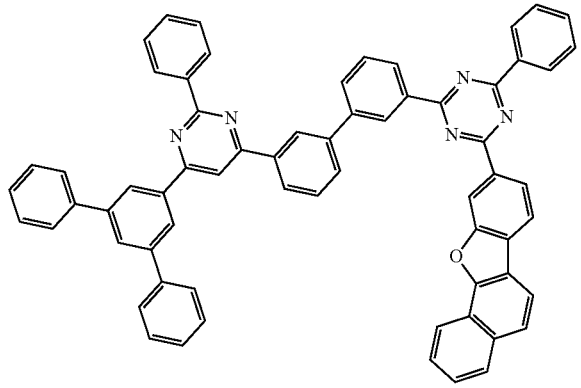
643
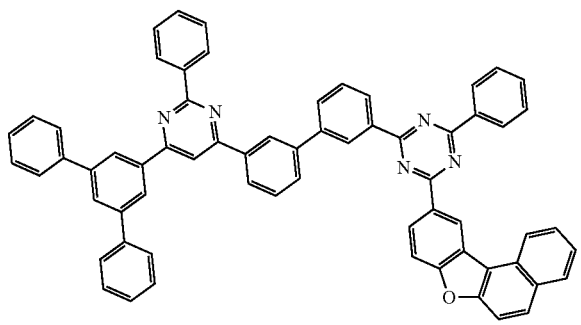
646
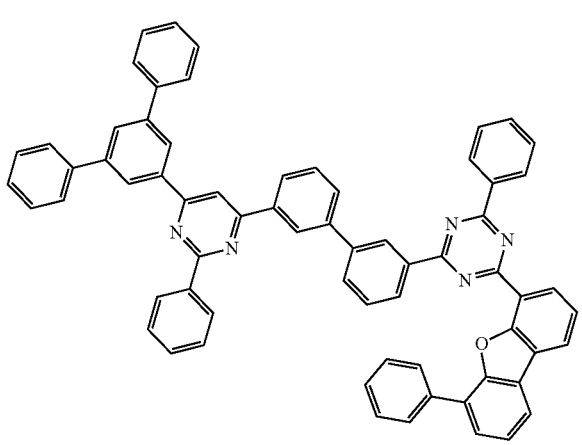
562
-continued
647
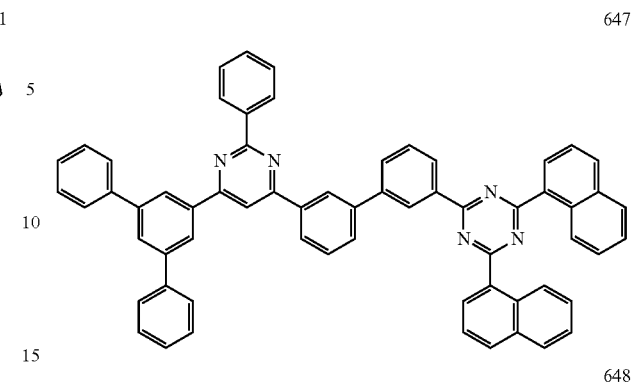
648
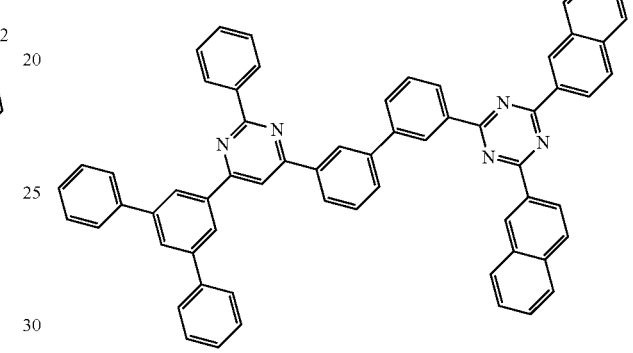
649
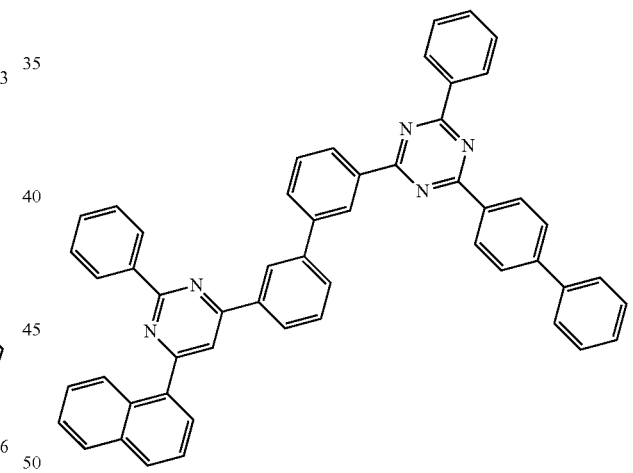
650
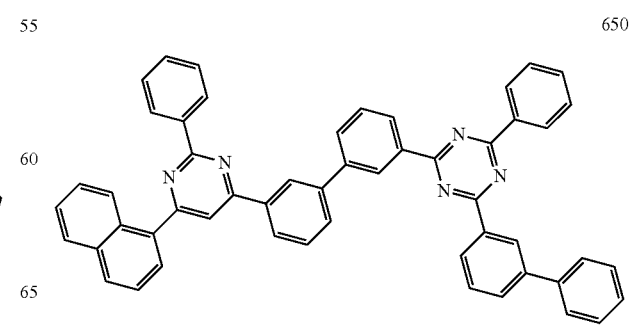

563
-continued
651
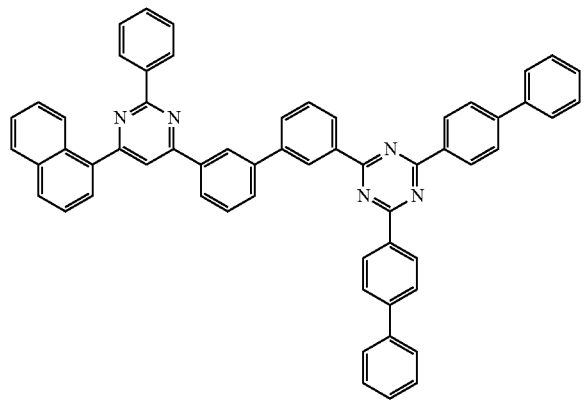
652
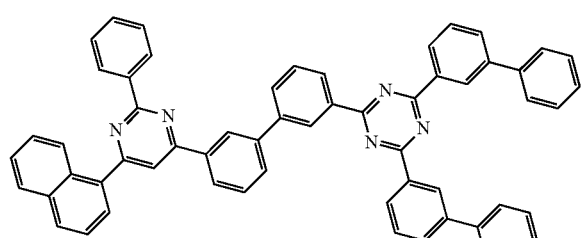
653
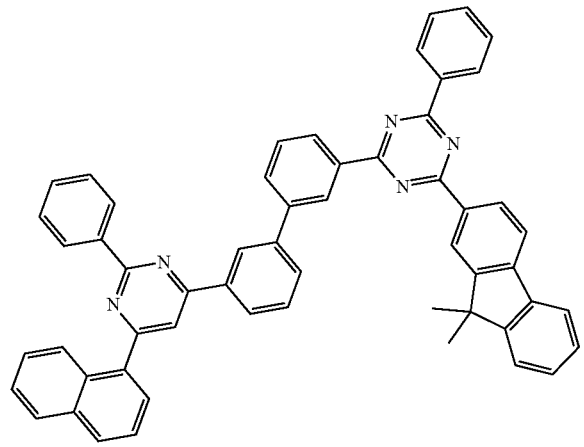
654
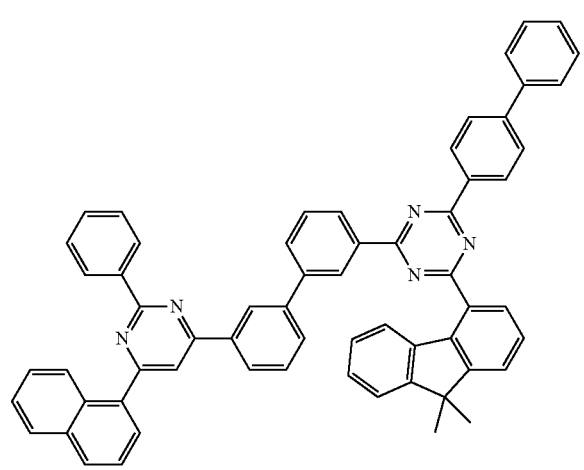
564
-continued
655
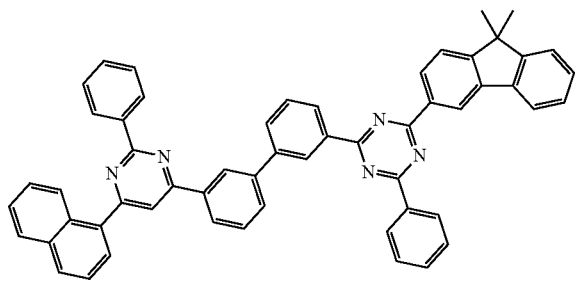
656
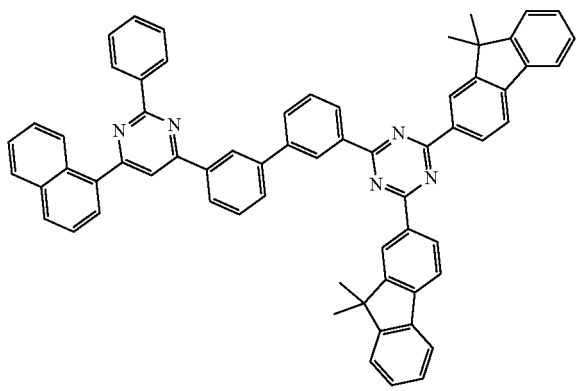
657
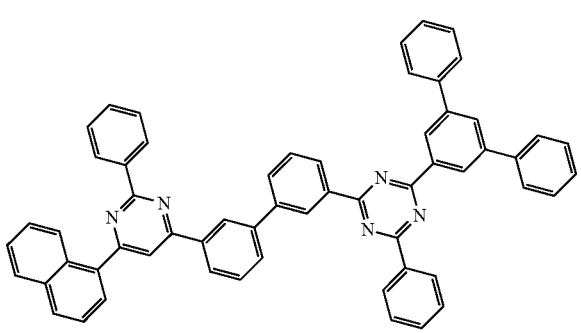
659
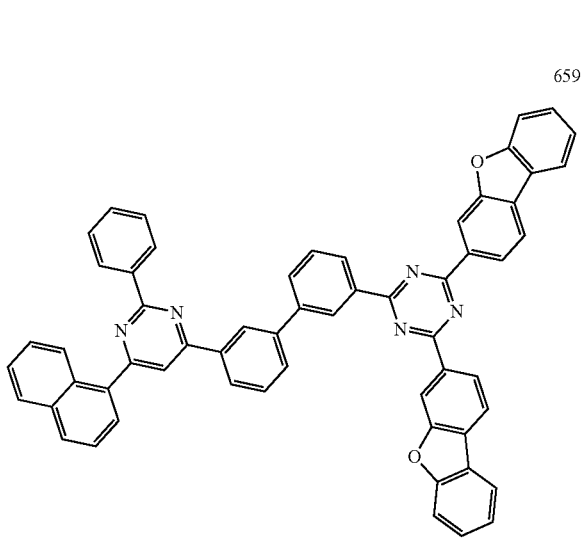

660
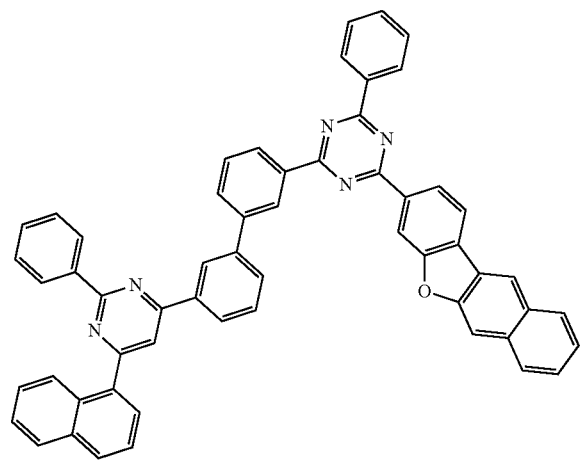
661
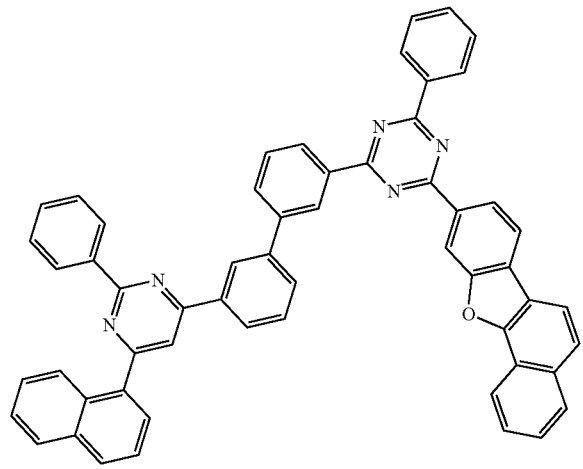
662
665
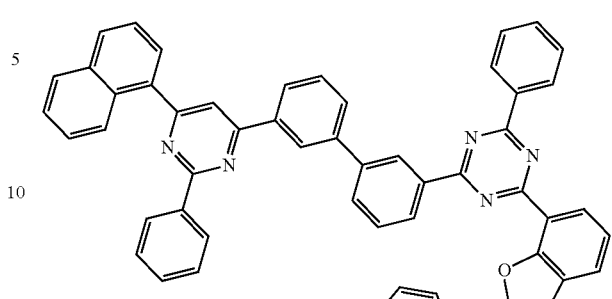
666
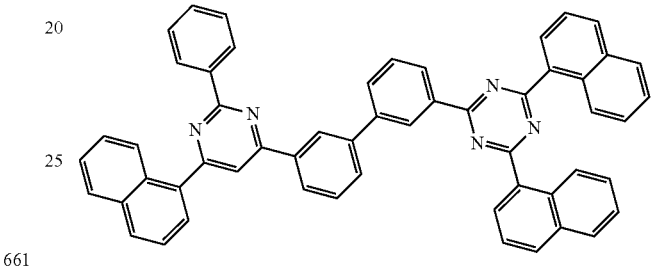
667
668
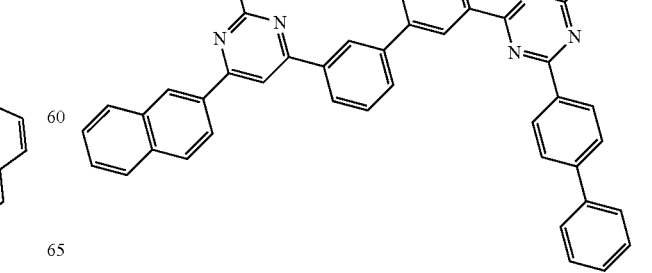

-continued
669
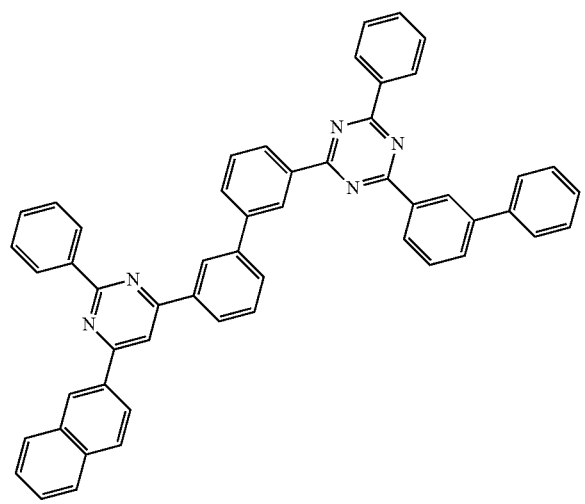
-continued
671
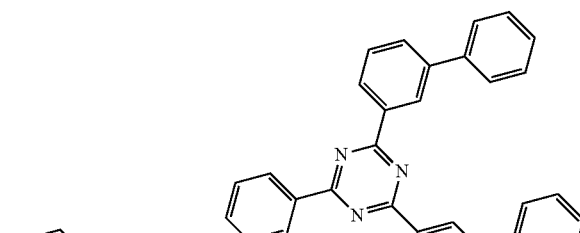
672
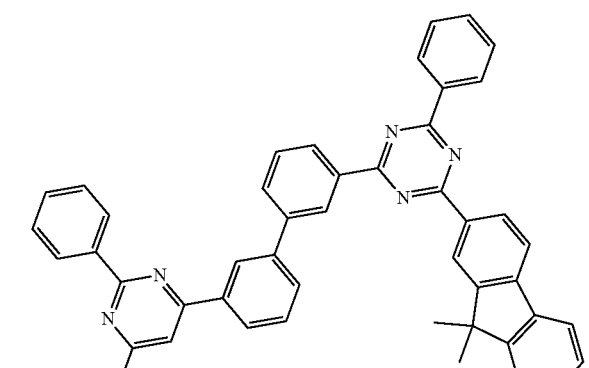
670
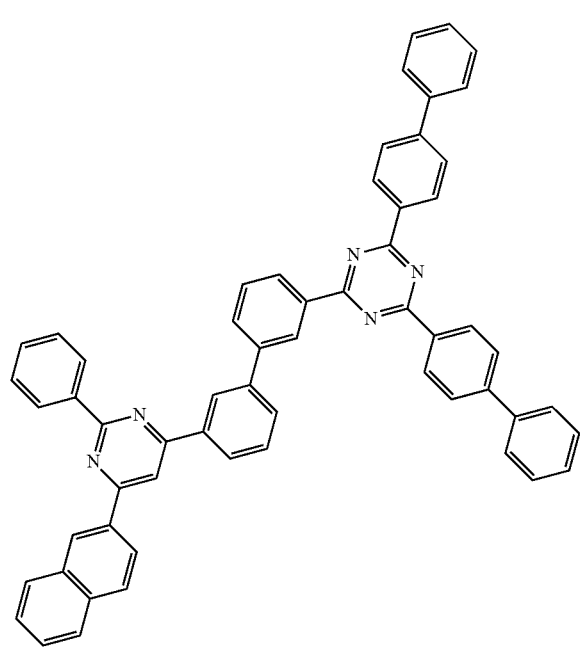
673
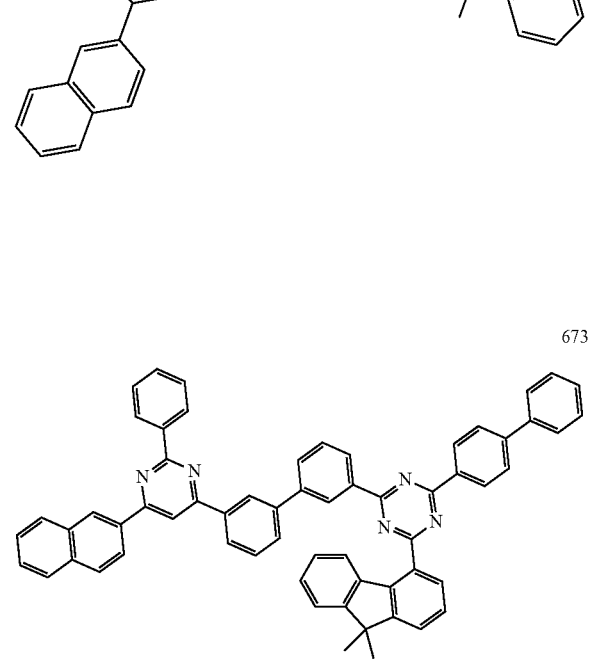

569
-continued
674
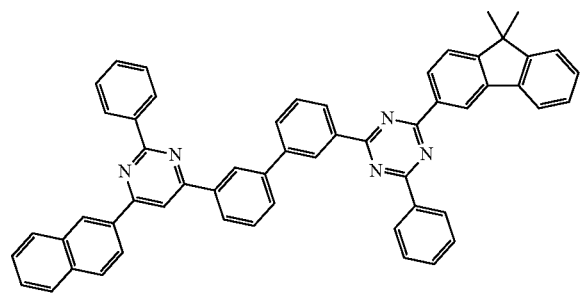
675
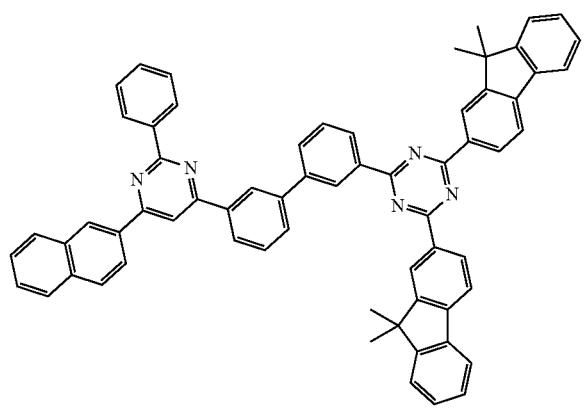
676
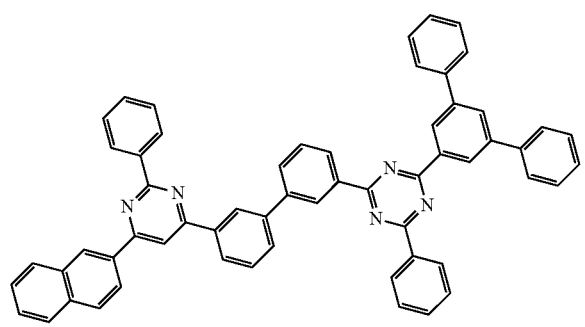
678
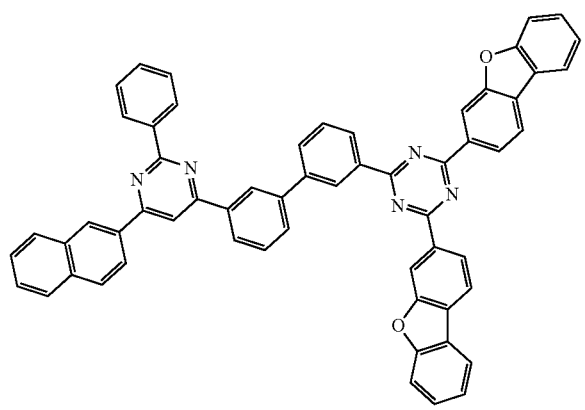
570
-continued
679
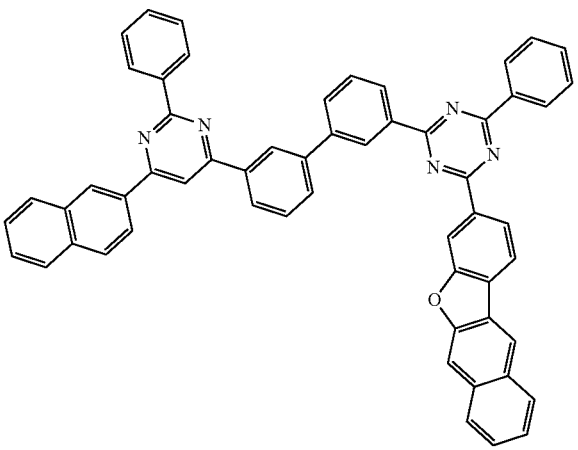
680
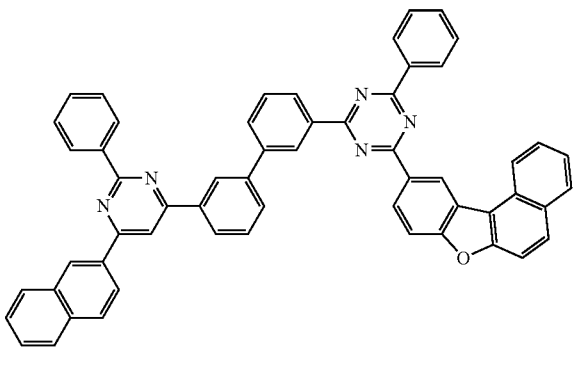
681

684
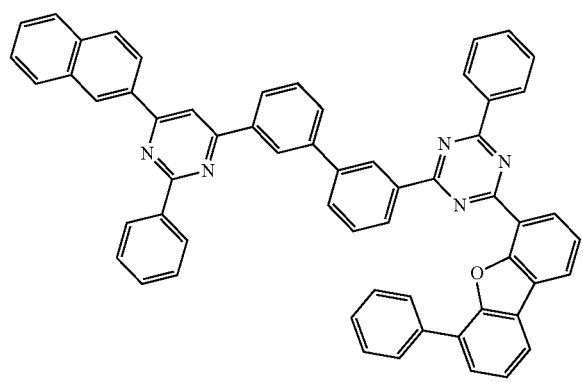
685
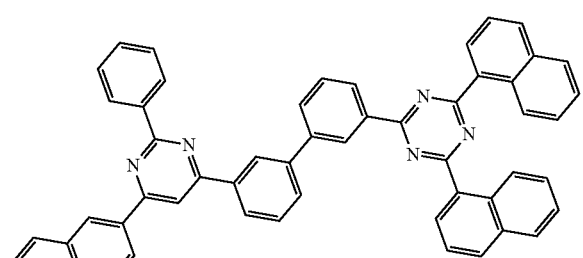
686
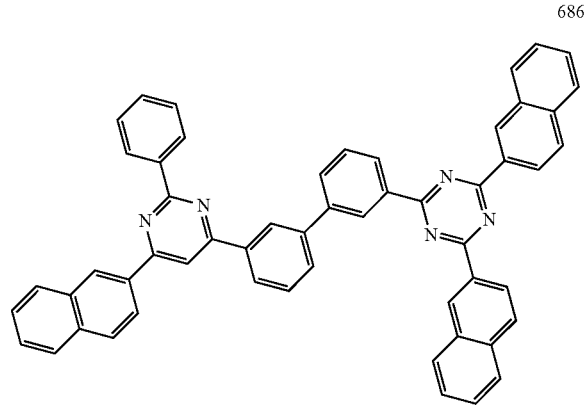
687
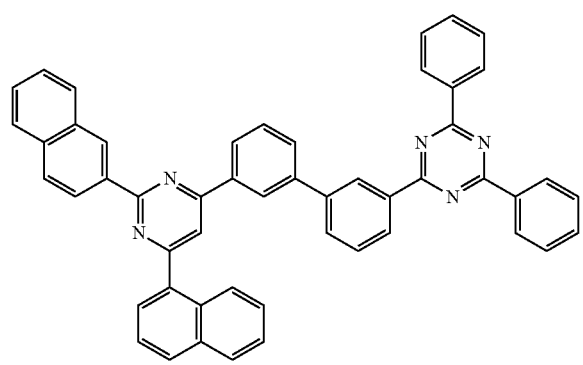
688
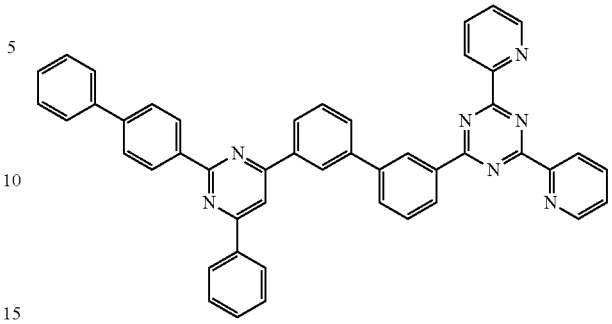
689
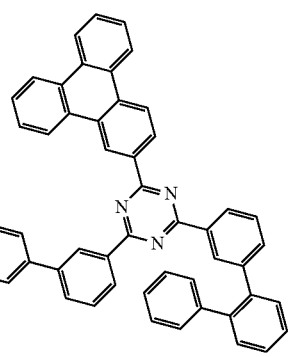
690
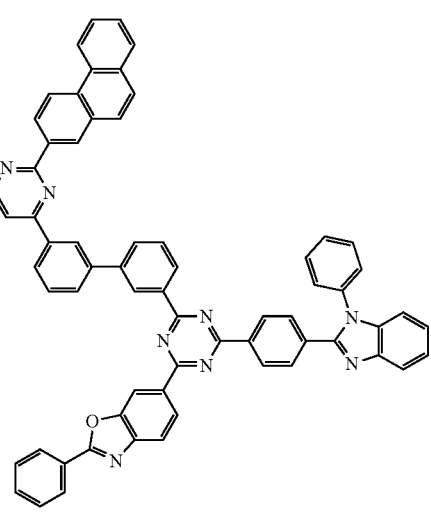

691
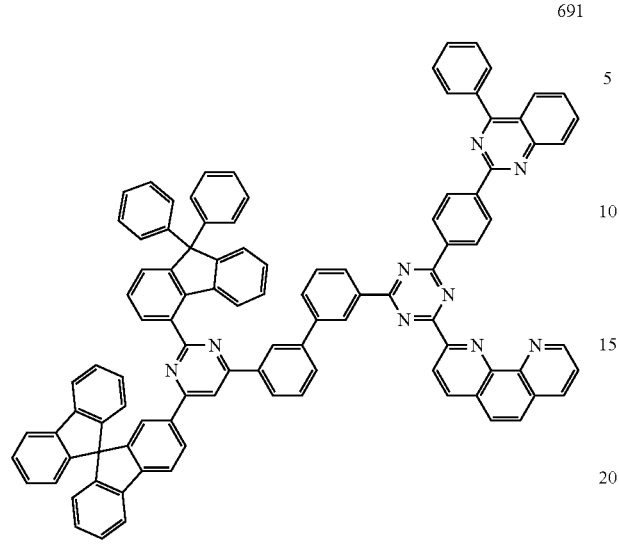
692
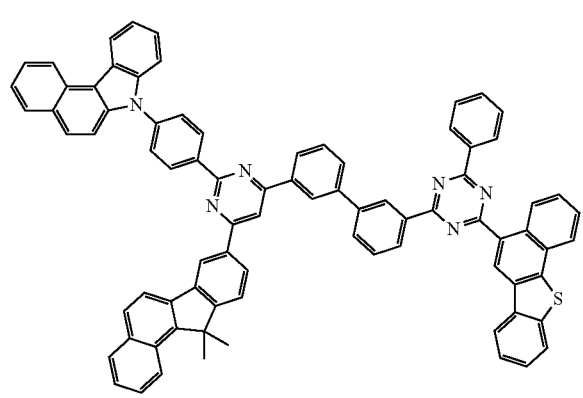
693
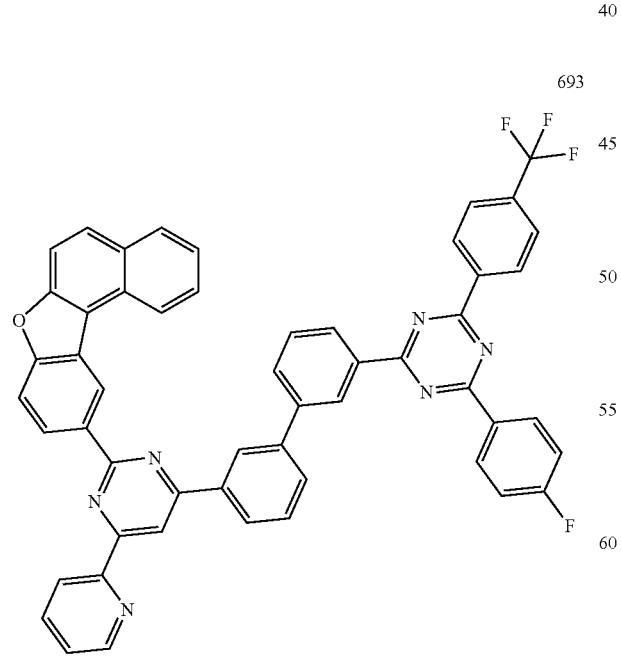
694
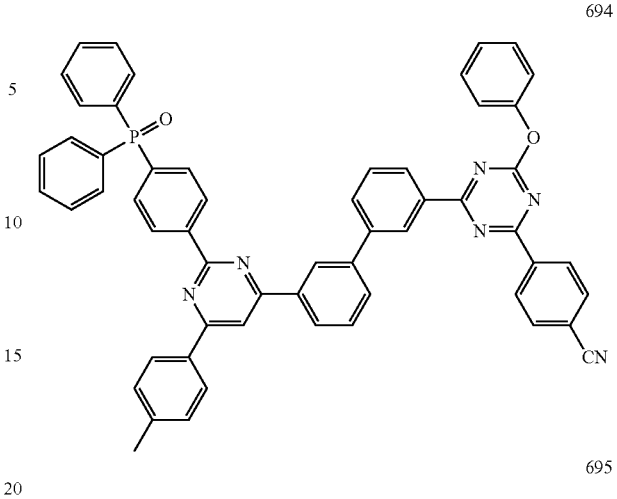
695
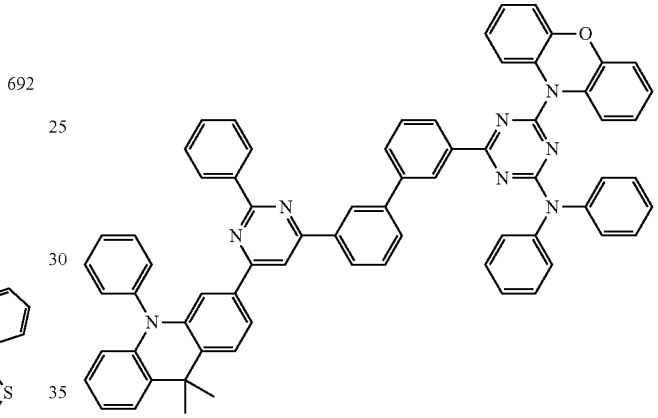
696
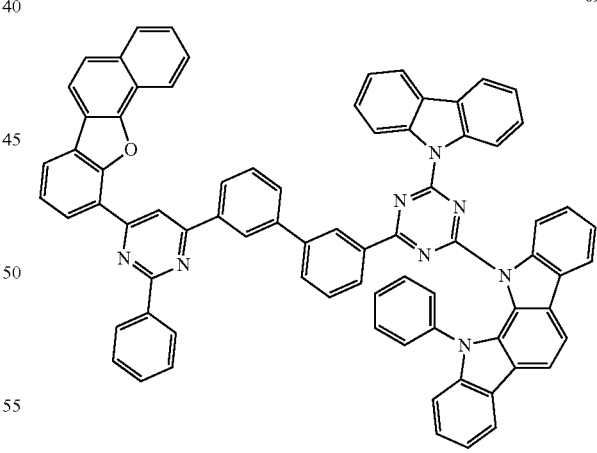
2. An organic electroluminescent device, comprising an anode, a cathode and one or more organic layers interposed between the anode and the cathode,
wherein at least one of the one or more organic layers comprises any one of the following compounds:

575 576
1
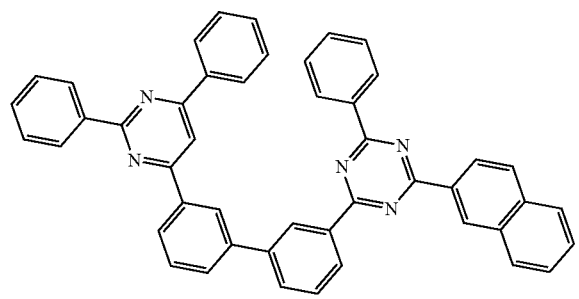
2
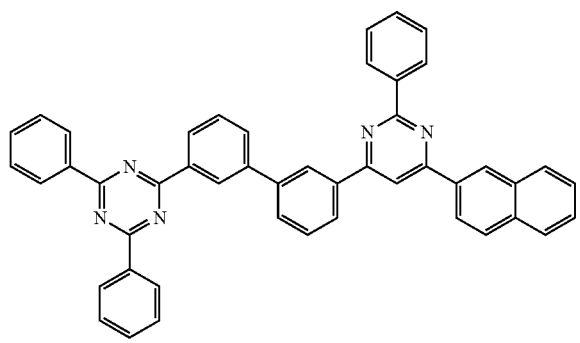
3
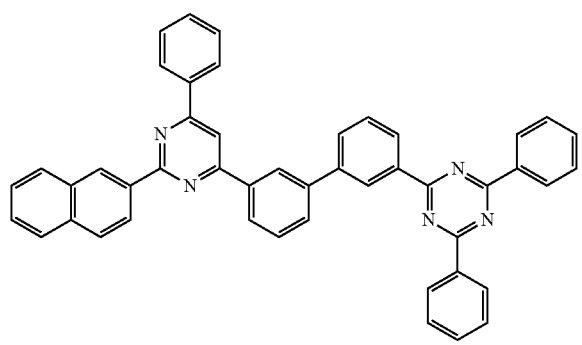
4
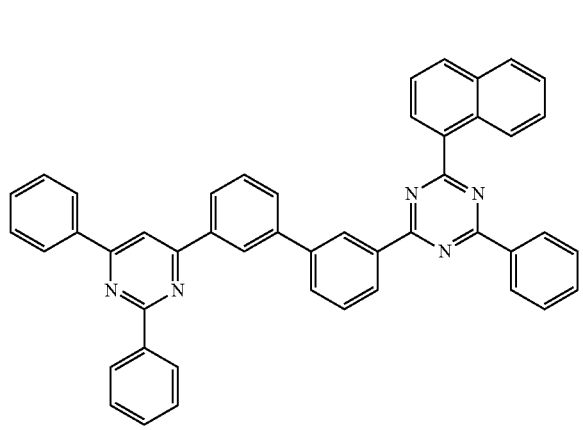
5
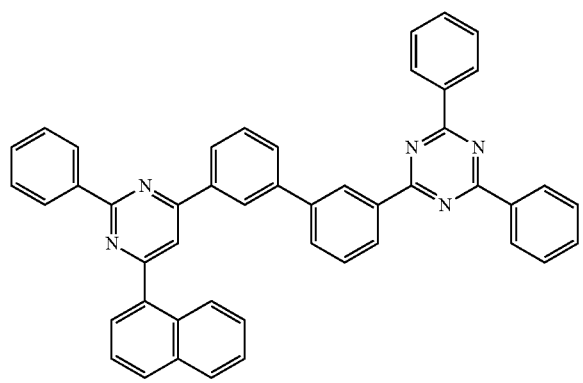
6
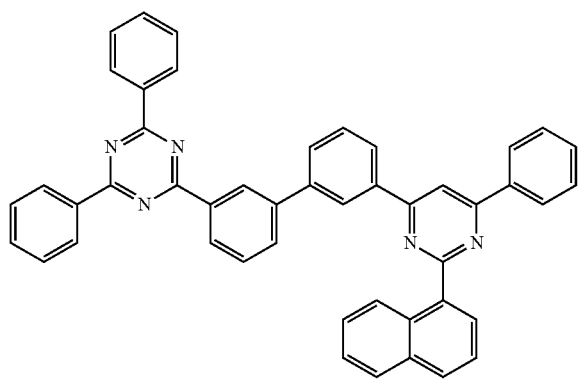

-continued
7
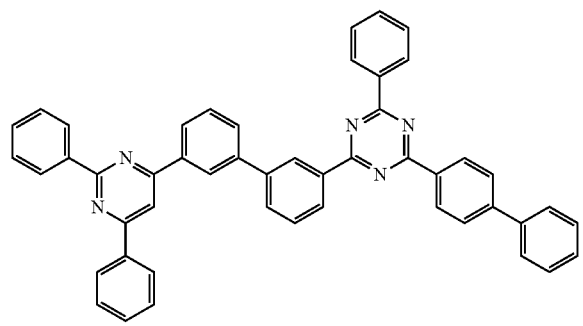
8
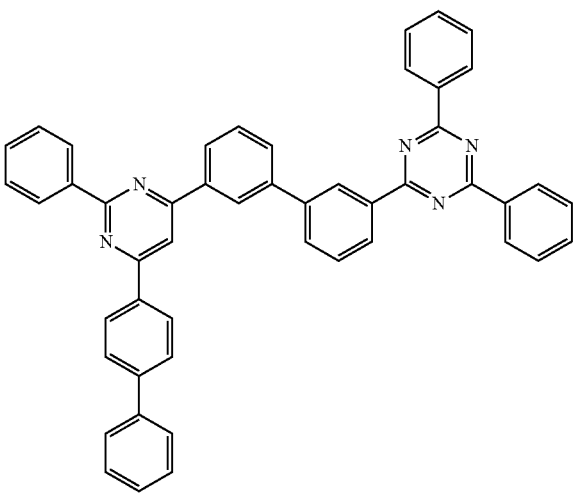
9
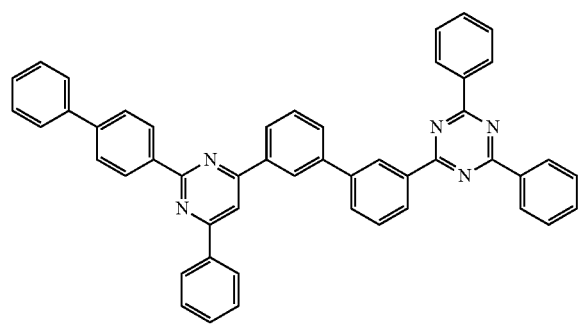
10
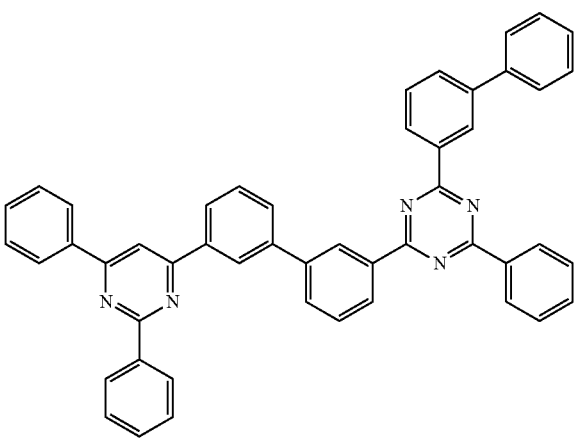
11
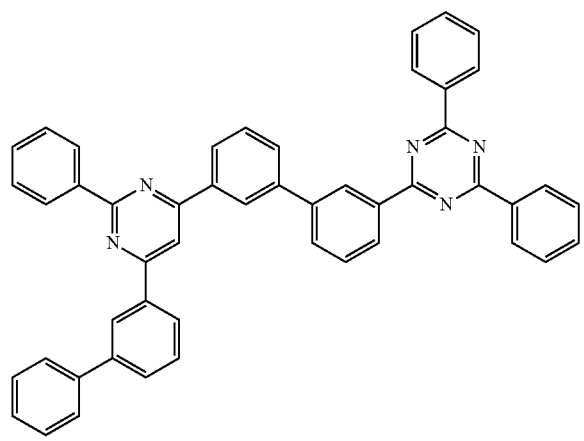
12
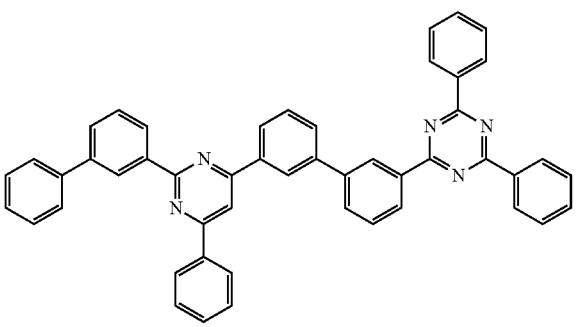

-continued
13
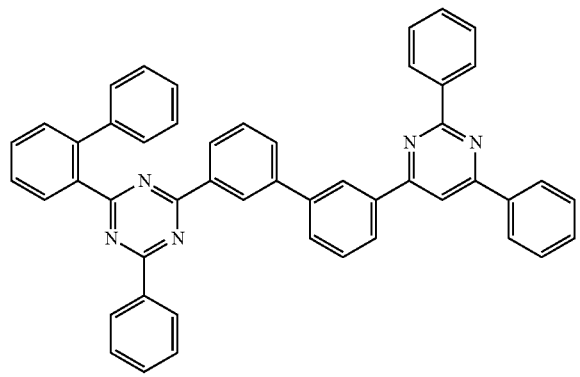
14
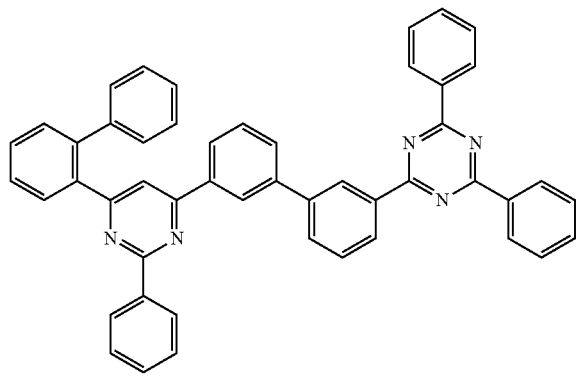
15
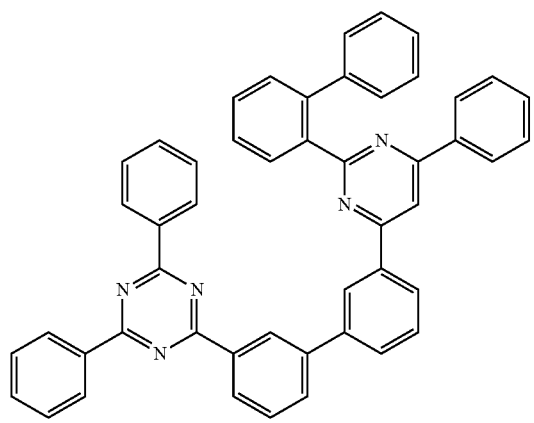
16
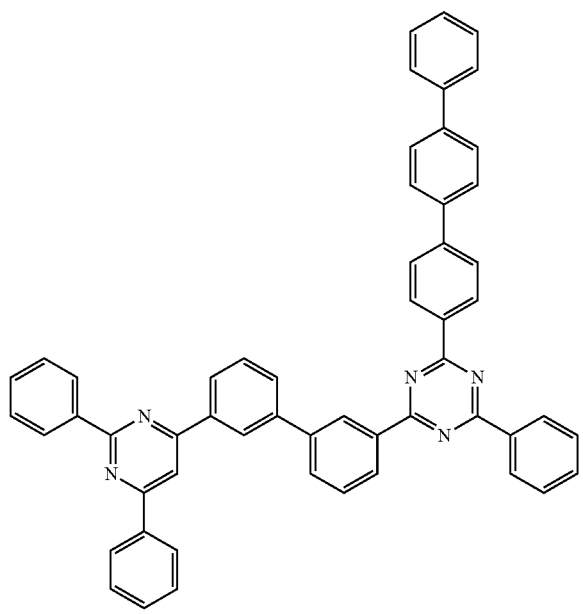
17
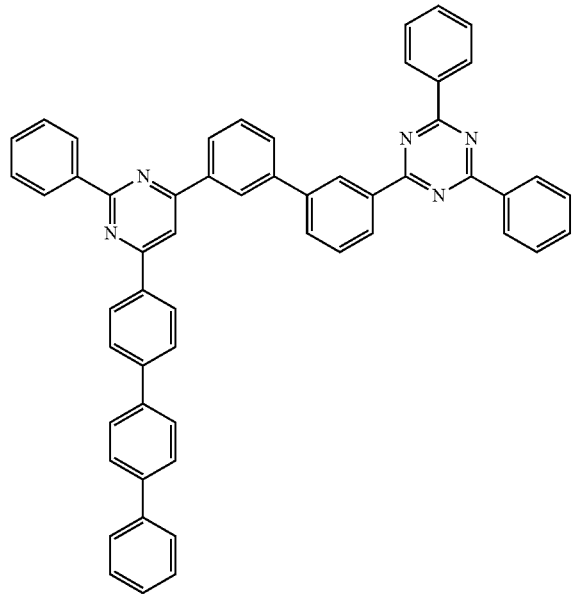

-continued
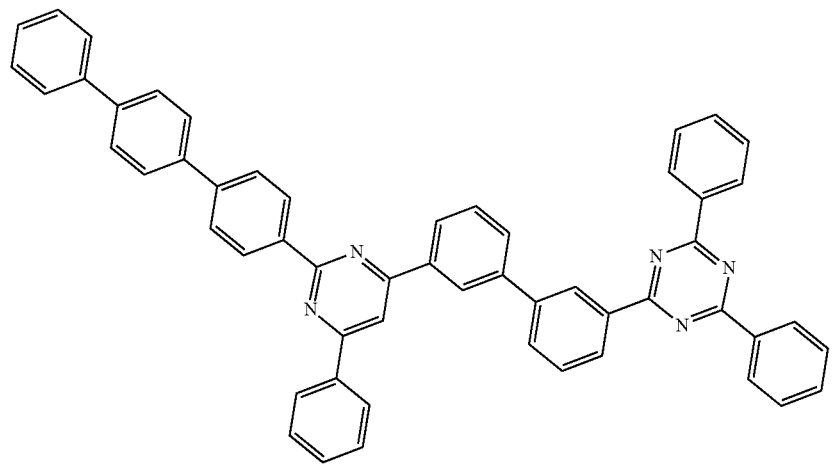
18
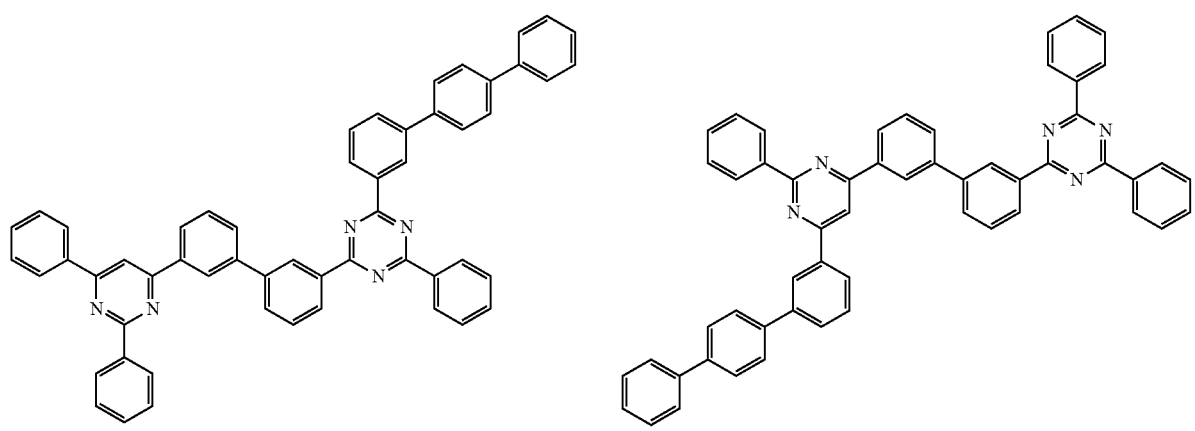
19 20
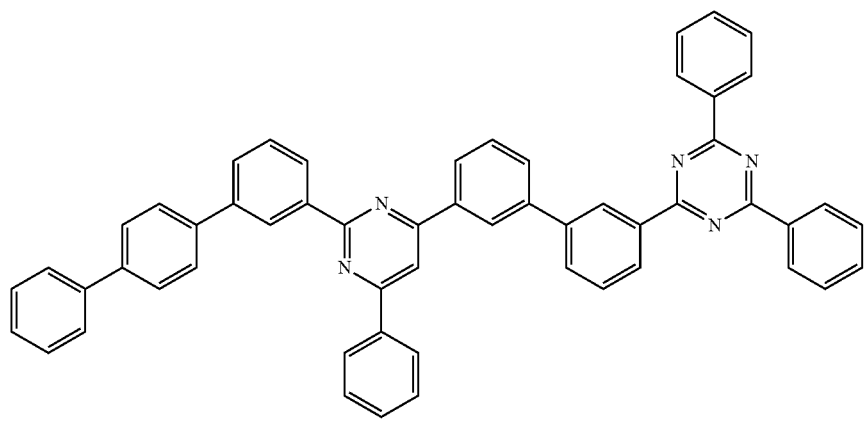
21

-continued
22
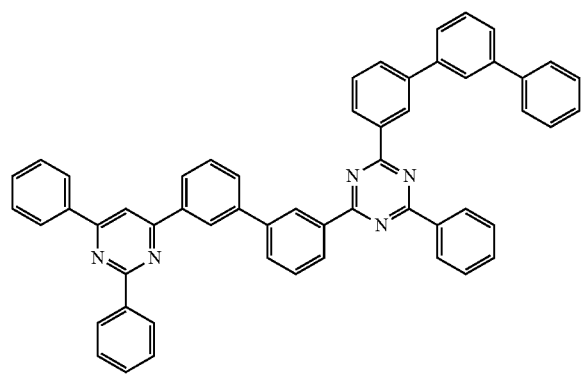
23
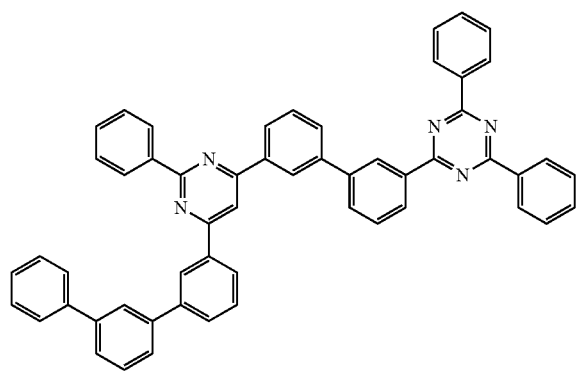
24
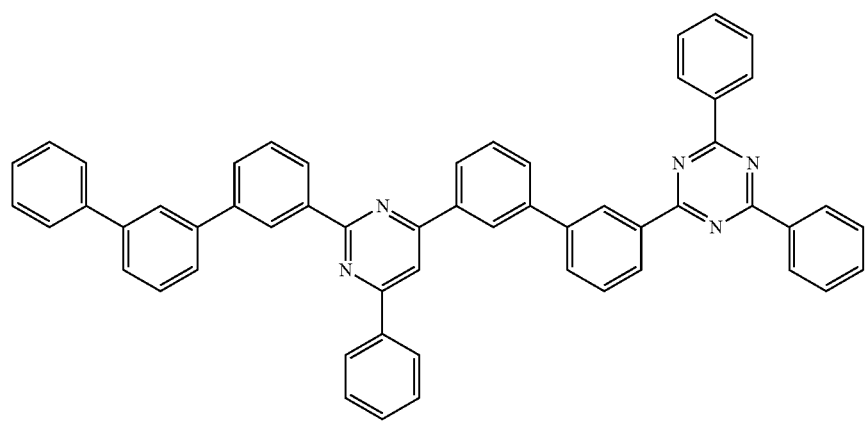
25
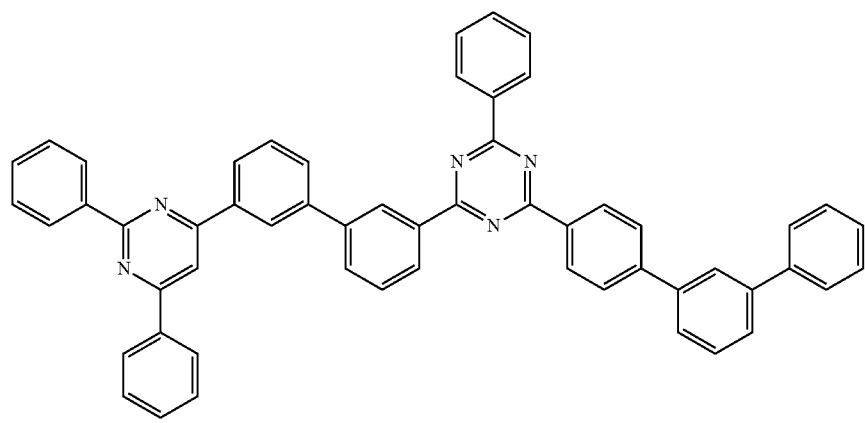

26
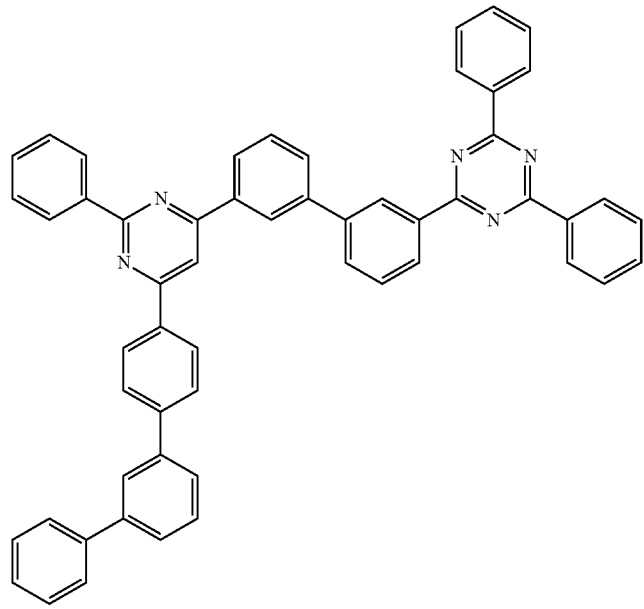
27
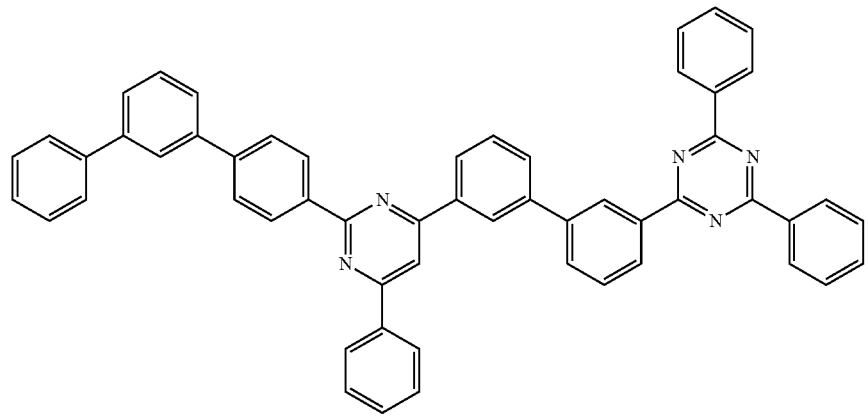
28
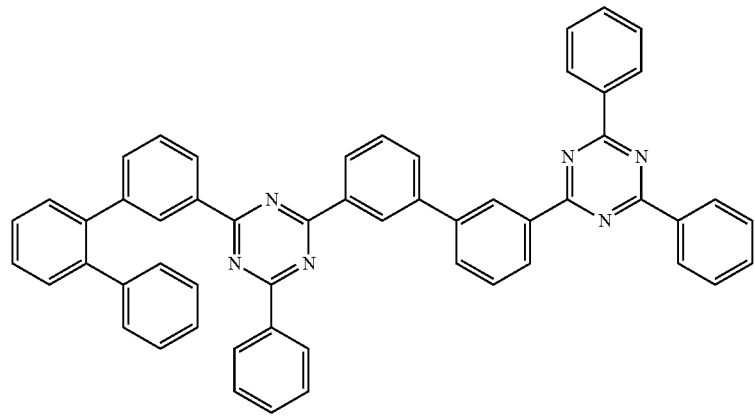

-continued
29
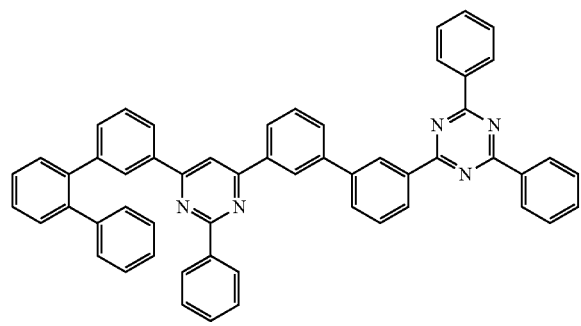
30
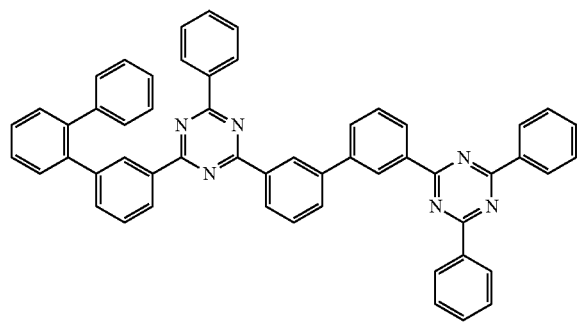
31
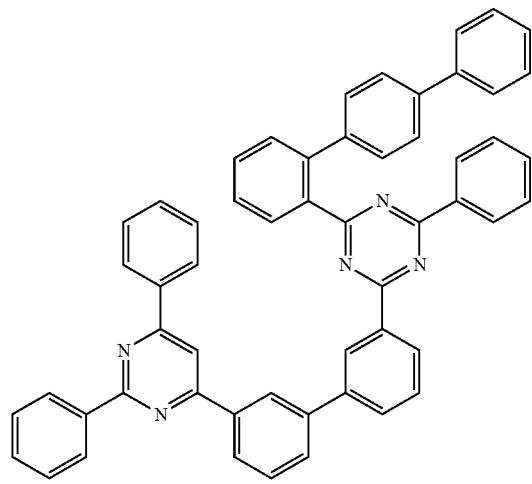
32
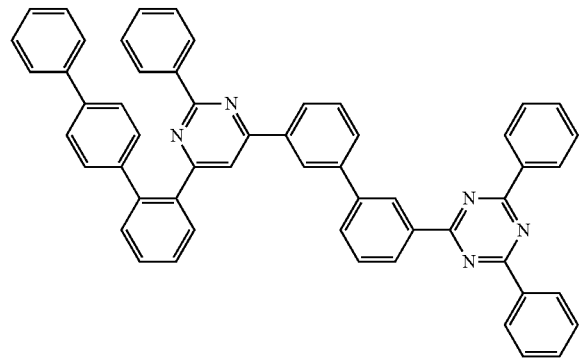
33
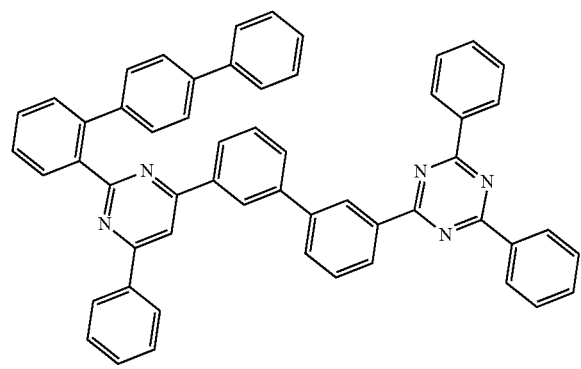
34
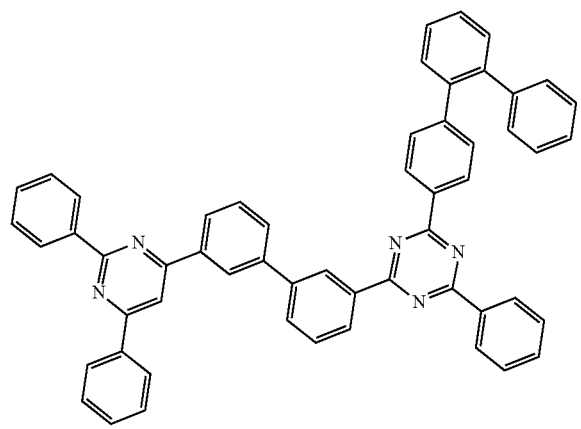

35
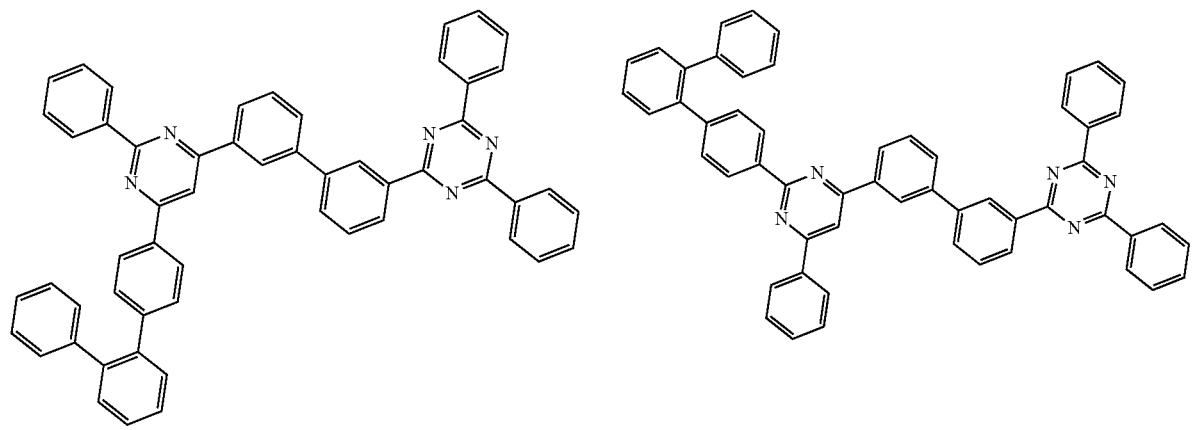
37
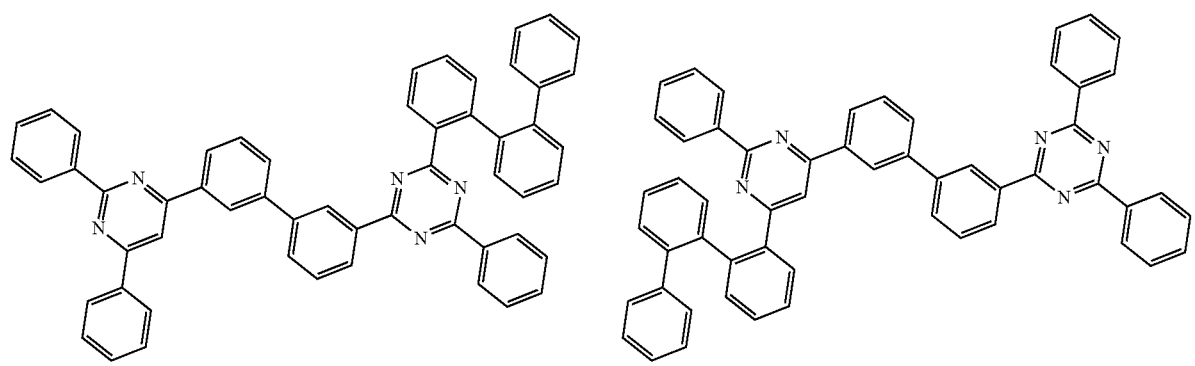
39
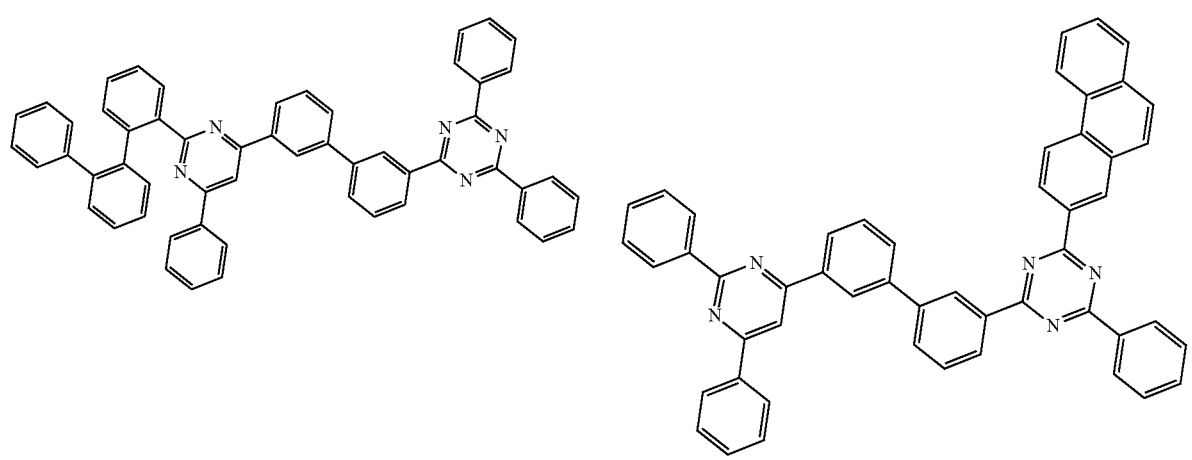

-continued
41
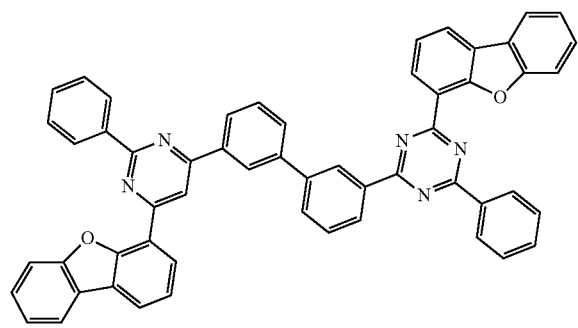
42
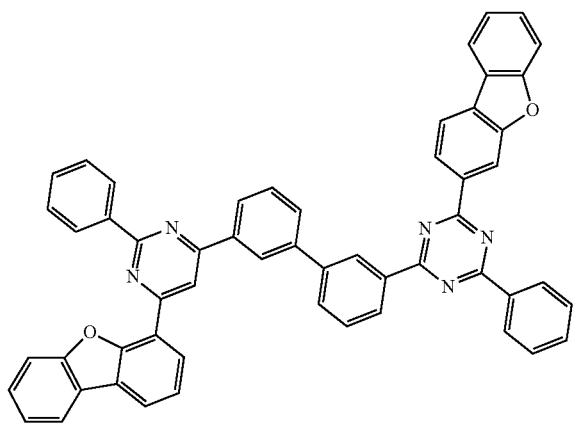
43
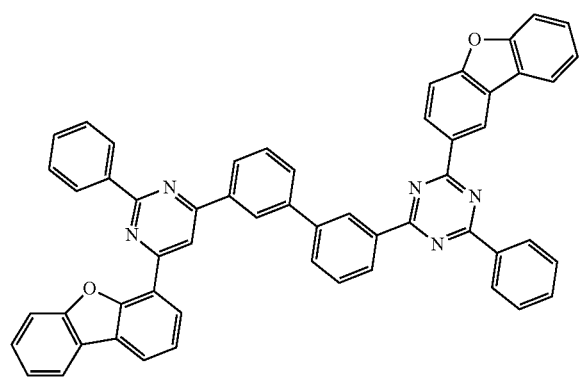
44
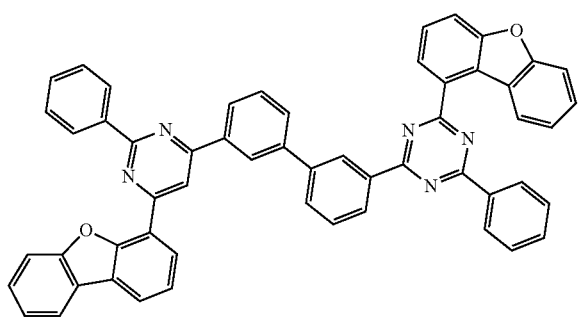
45
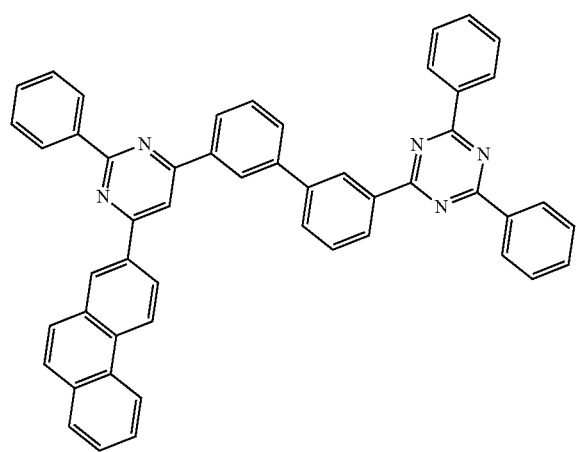
46
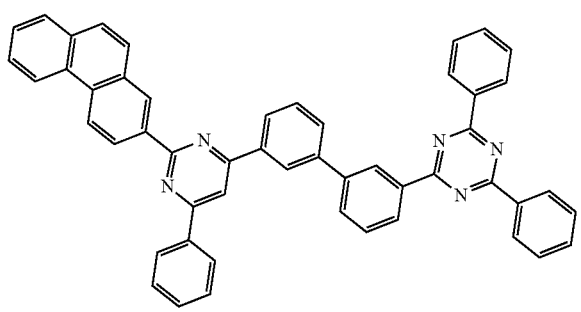

-continued
47
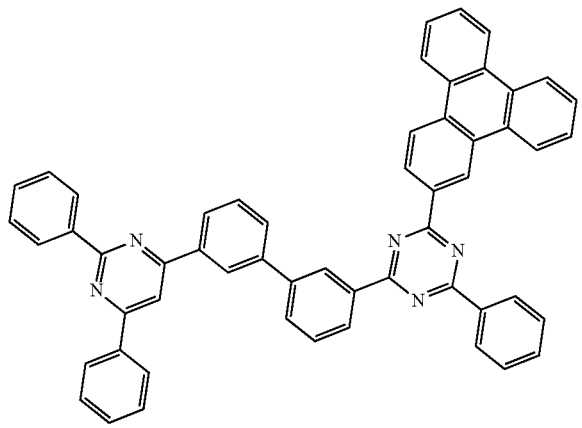
48
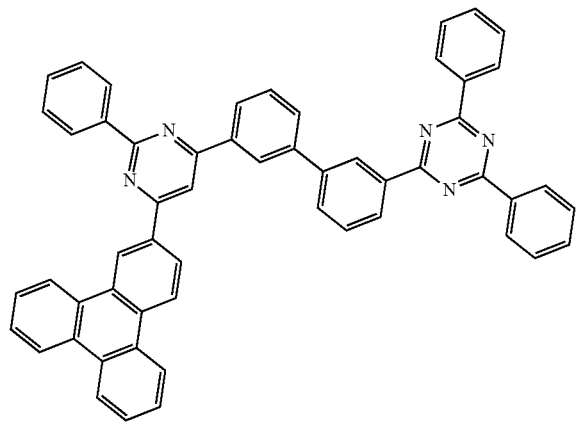
49
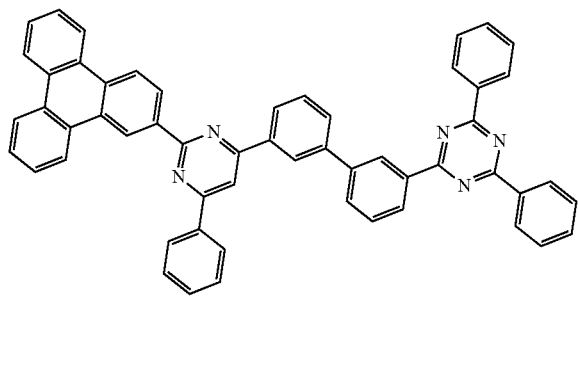
50
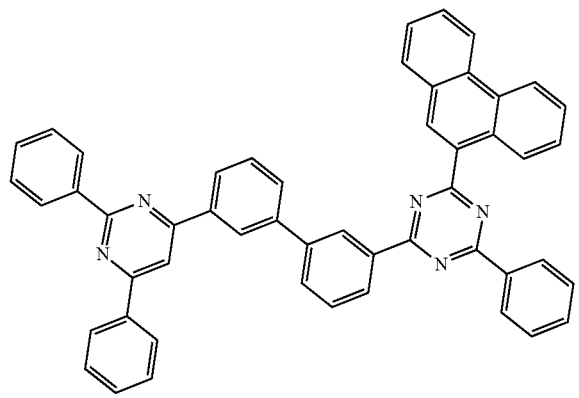
51
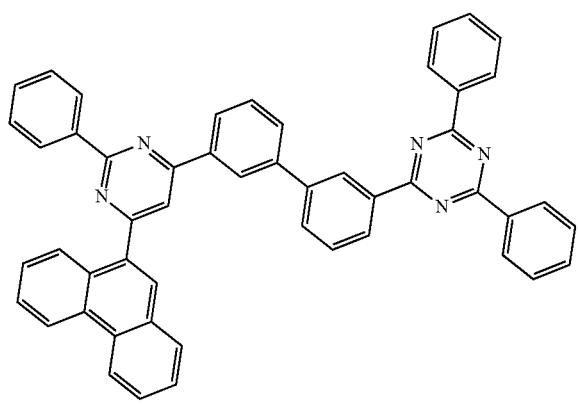
52
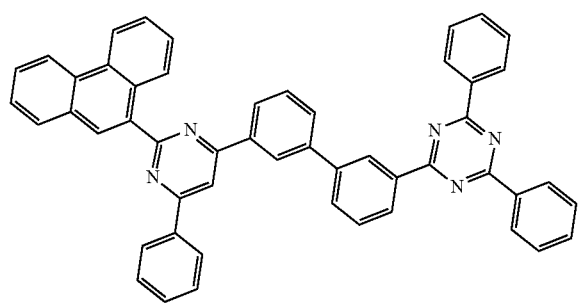

-continued
53
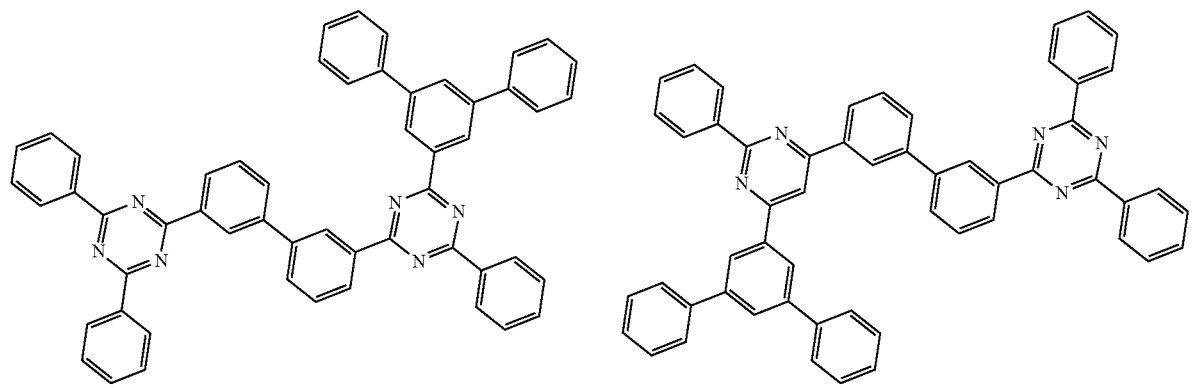
54
55
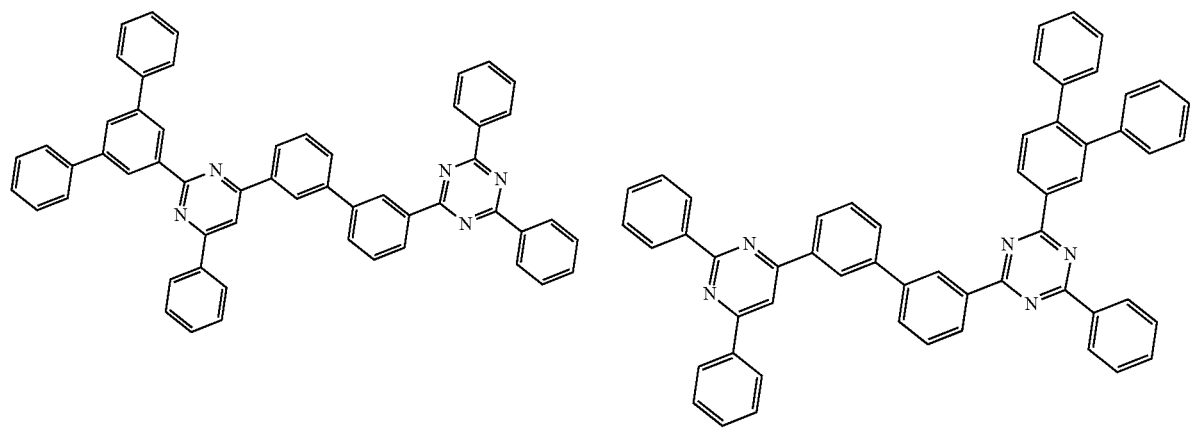
56
57
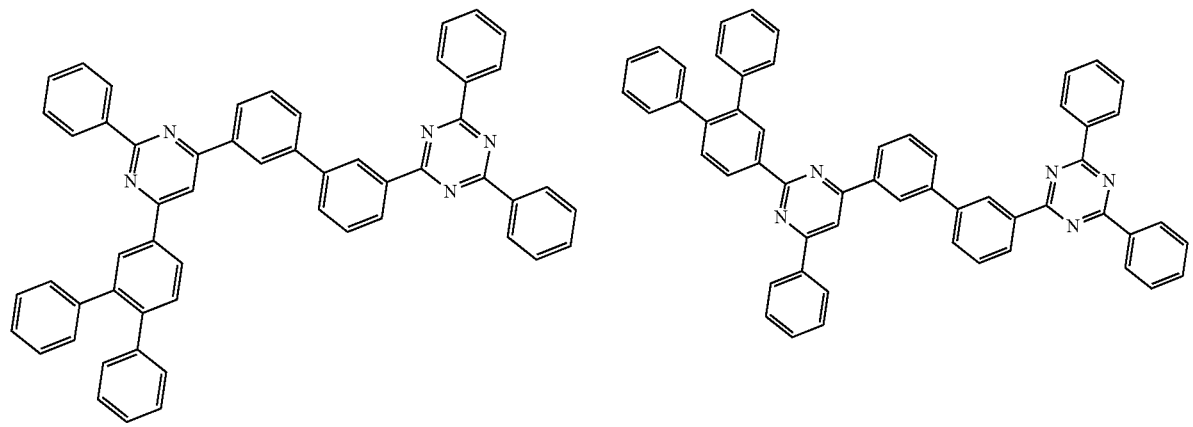
58

-continued
59
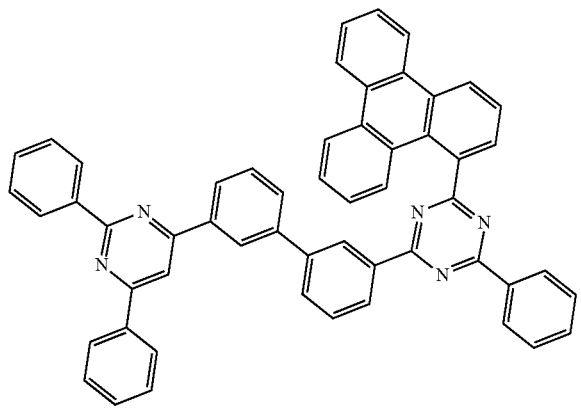
60
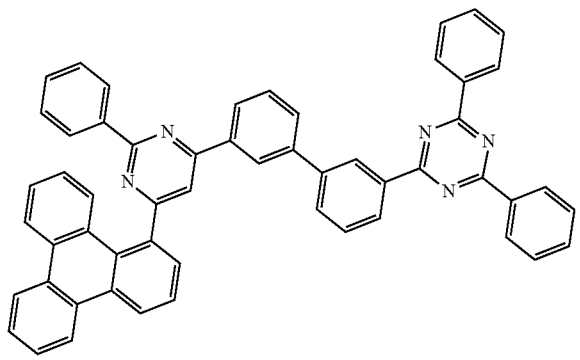
61
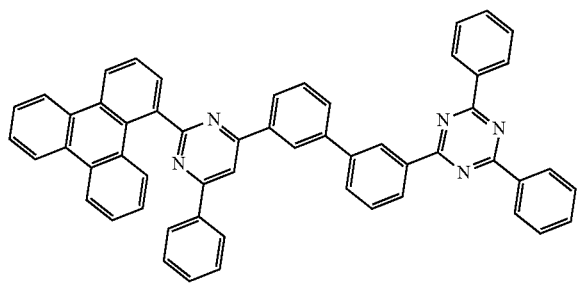
62
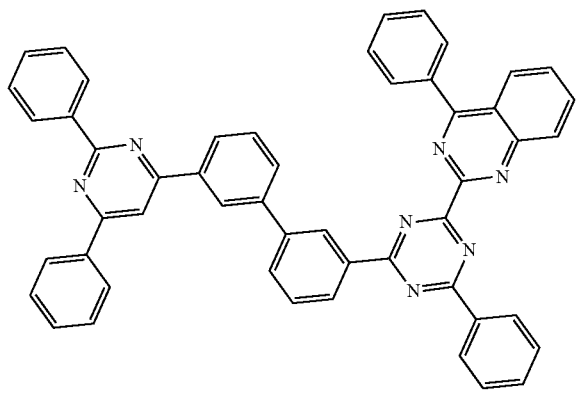
63
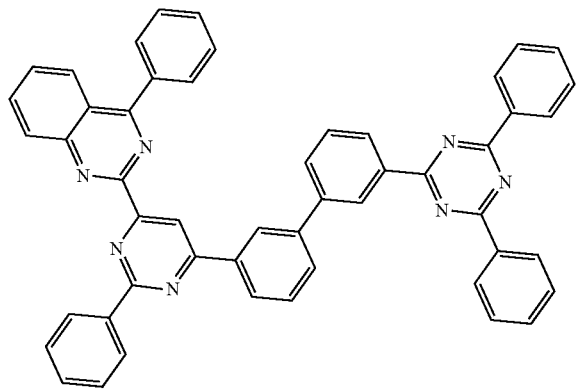
64
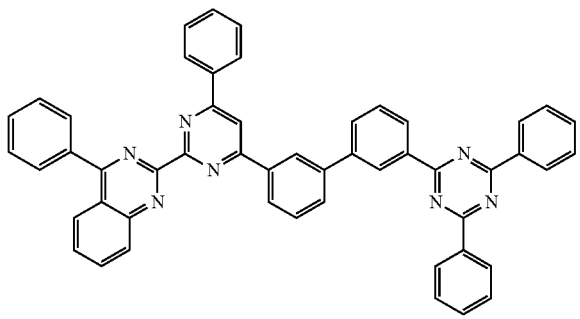
65
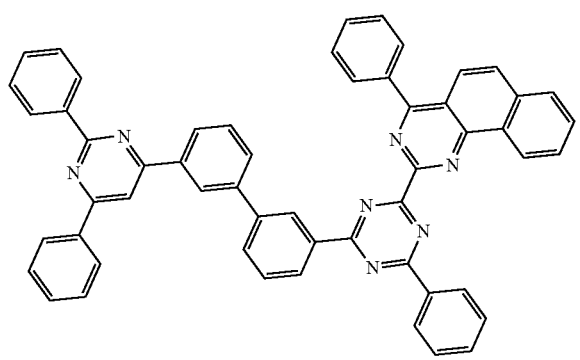
66
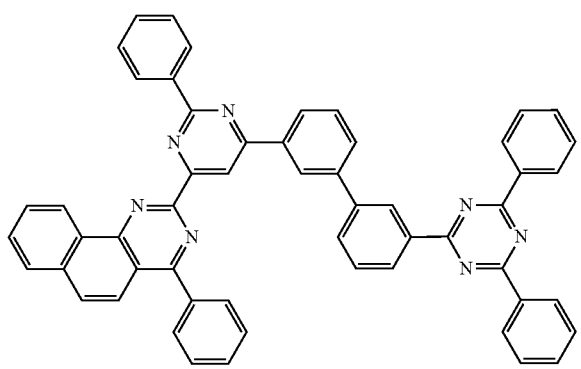

67
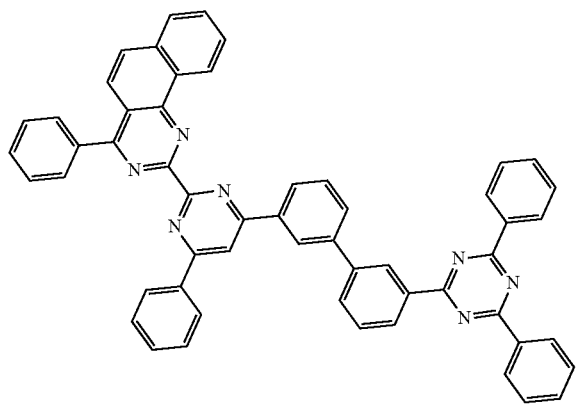
68
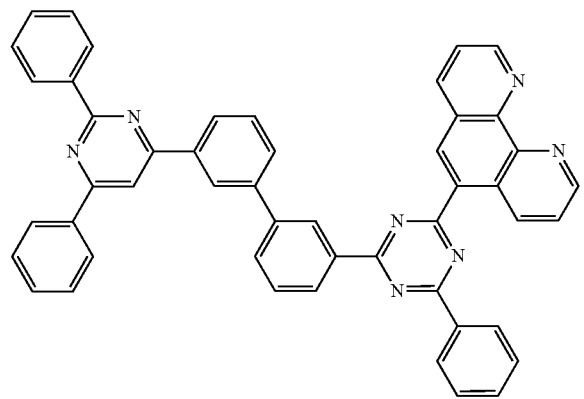
69
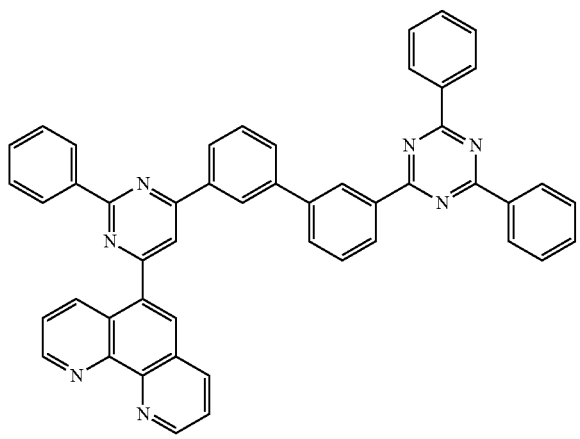
70
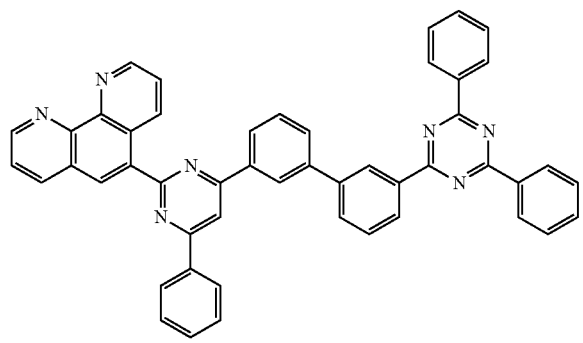
71
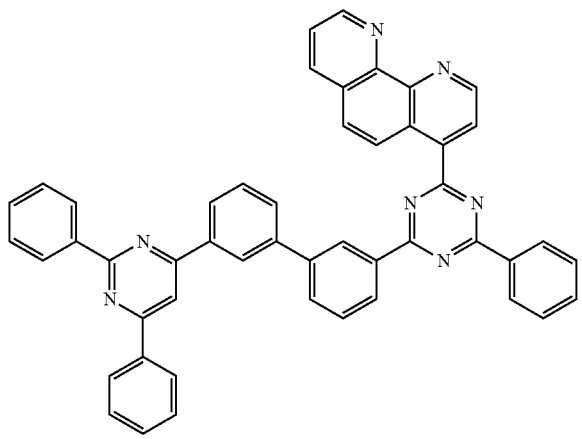
72
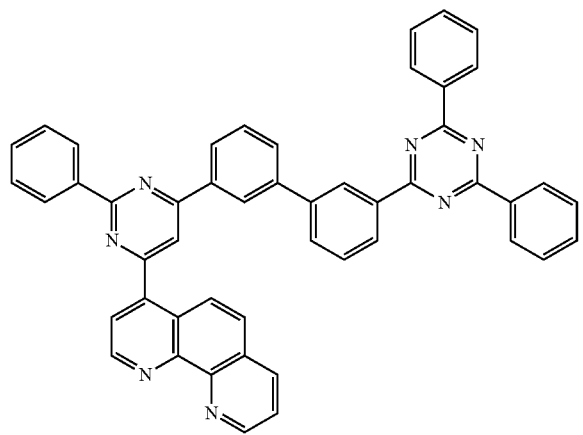

-continued
73
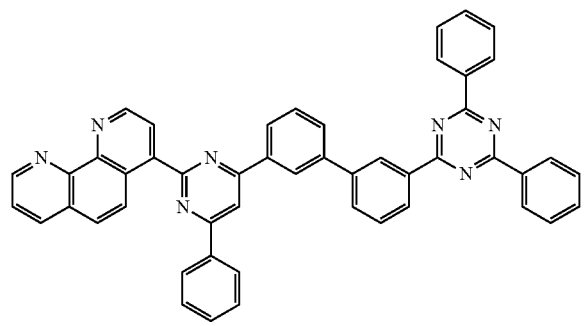
74
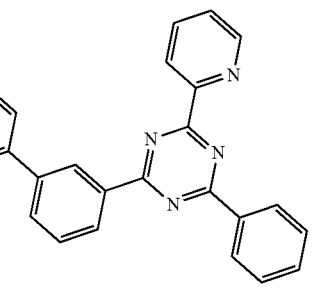
75
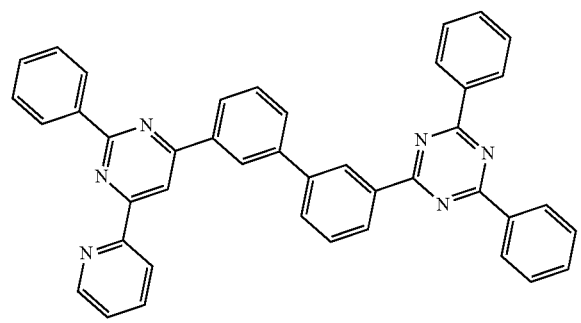
76
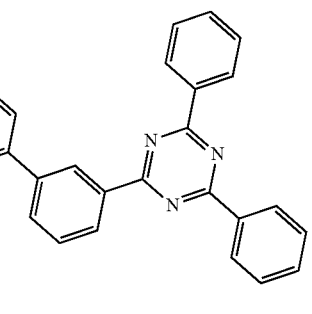
77
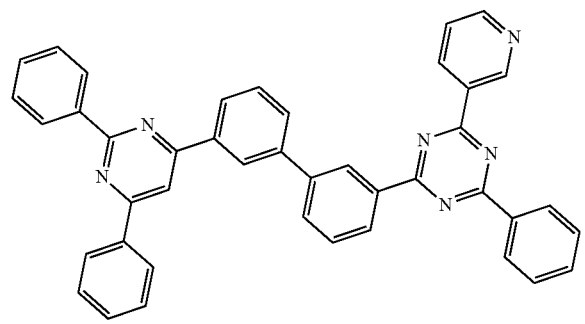
78
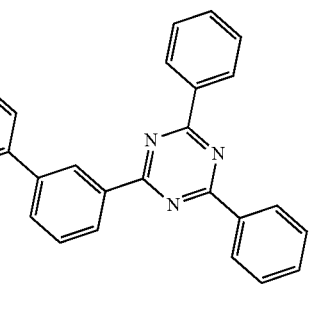
79
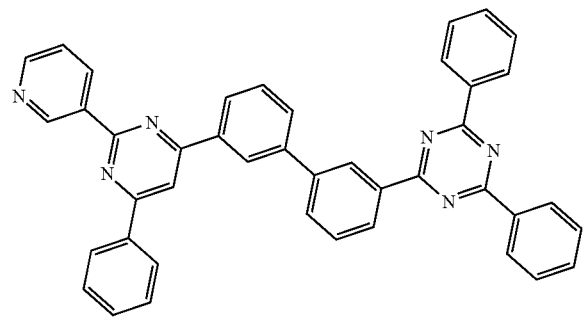
80
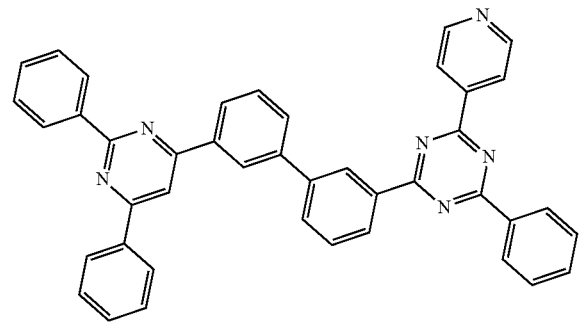

-continued
81
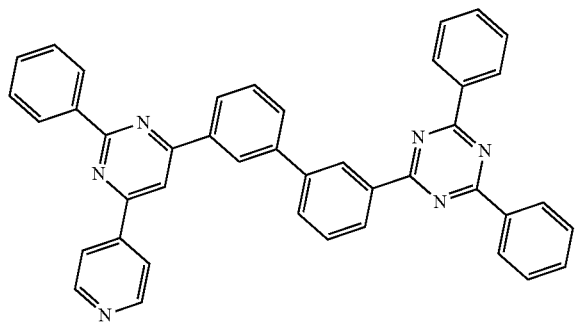
82
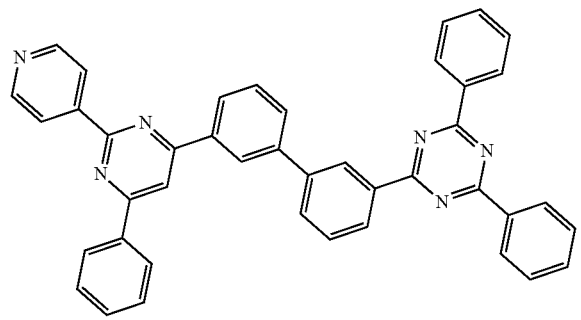
83
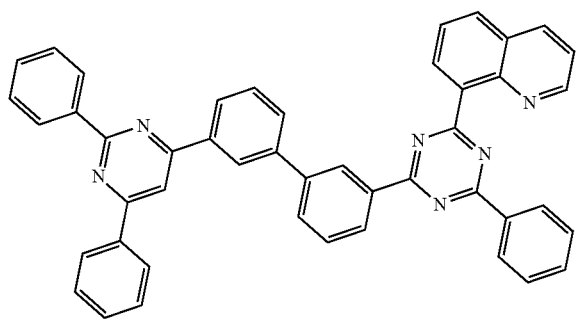
84
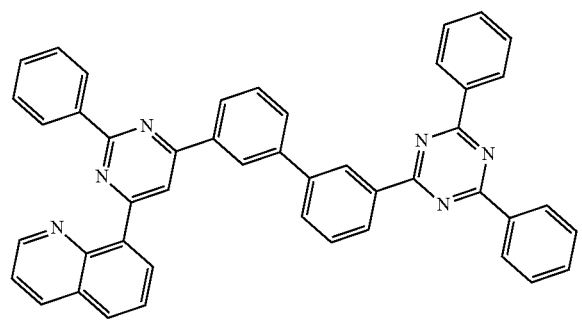
85
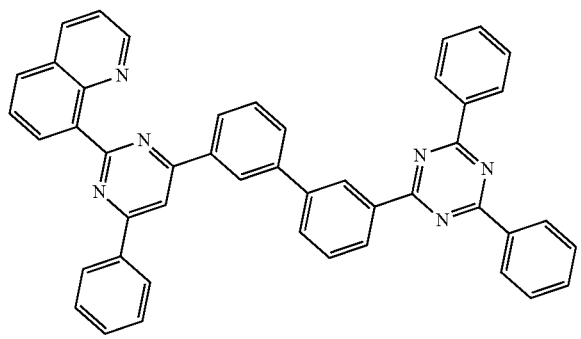
86
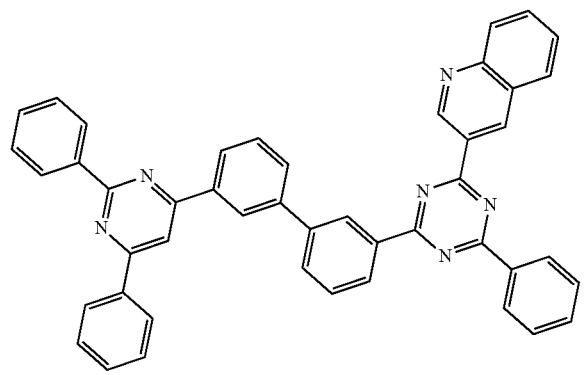
87
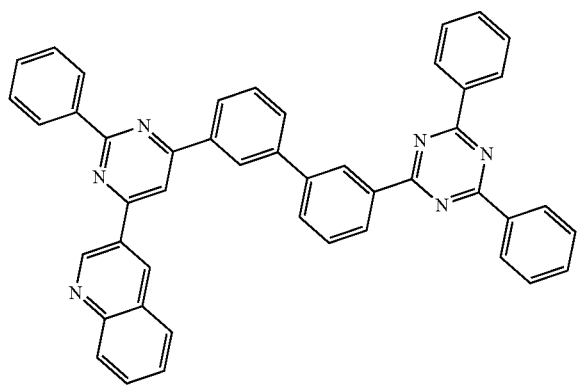
88
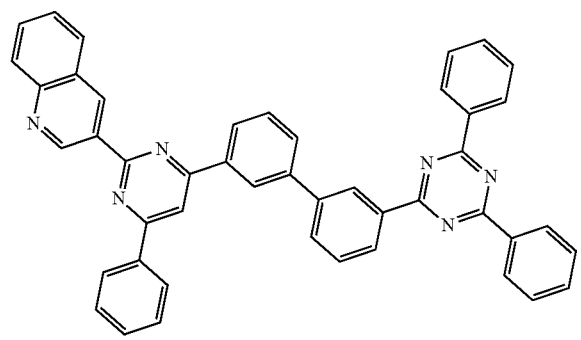

89
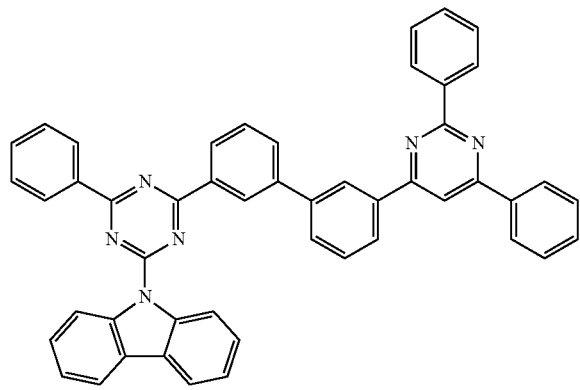
90
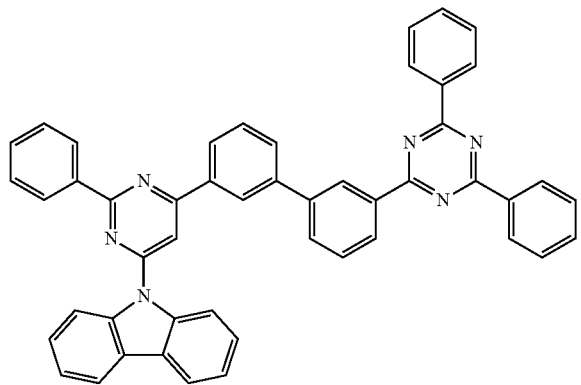
91
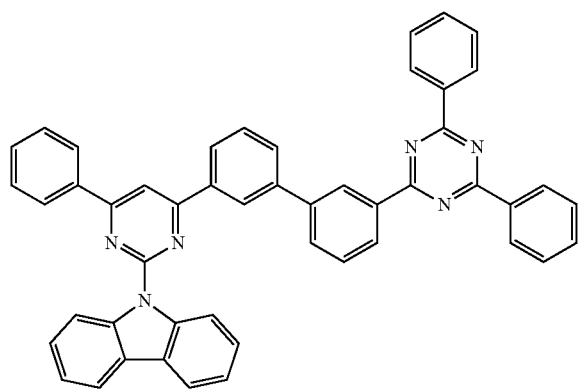
92
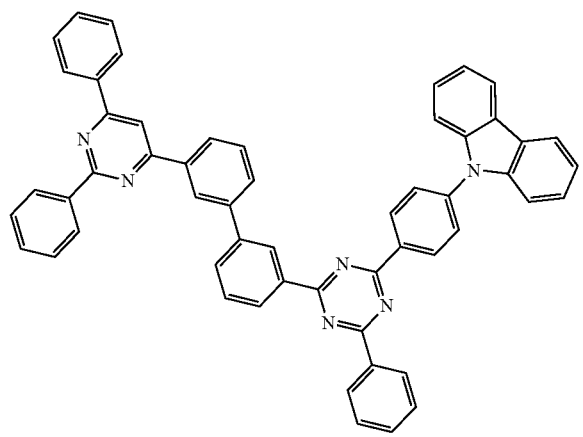
93
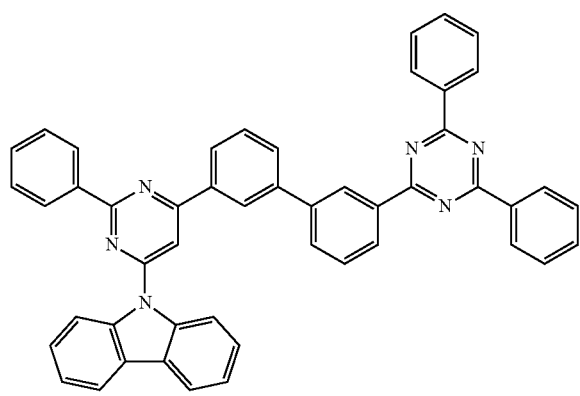
94
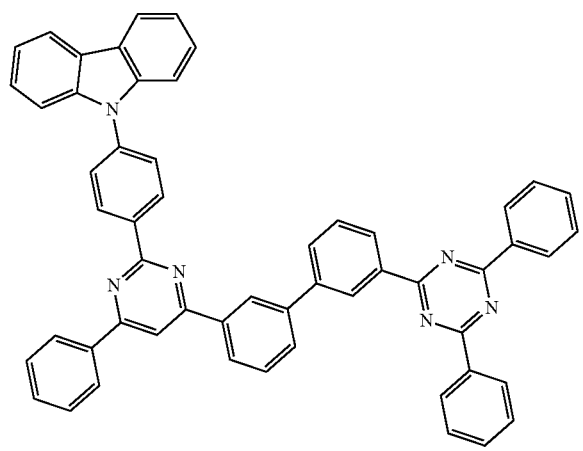

-continued
95
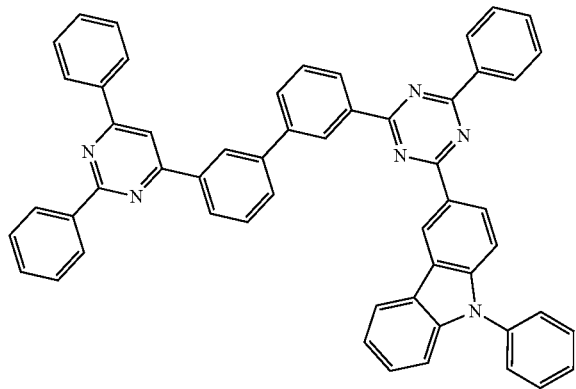
96
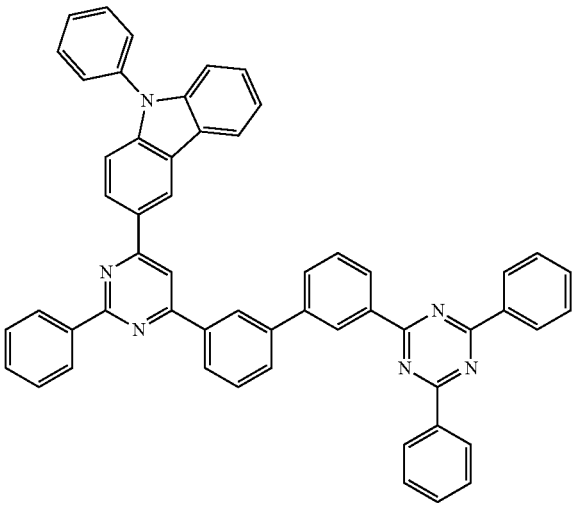
97
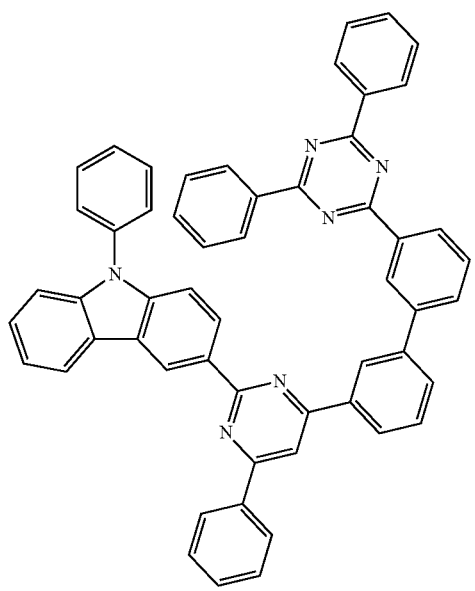
98
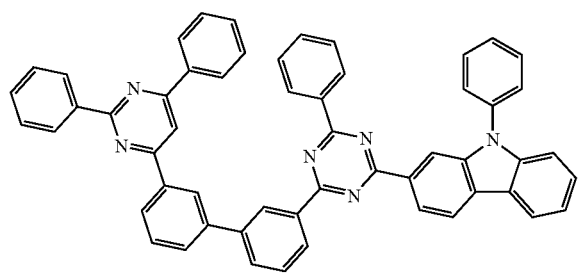
99
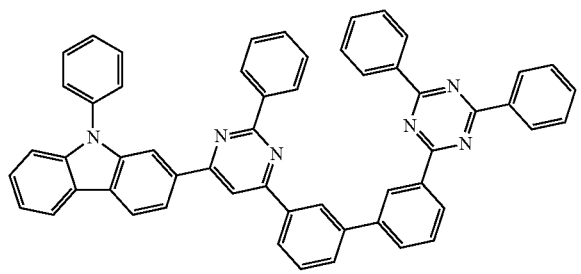
100
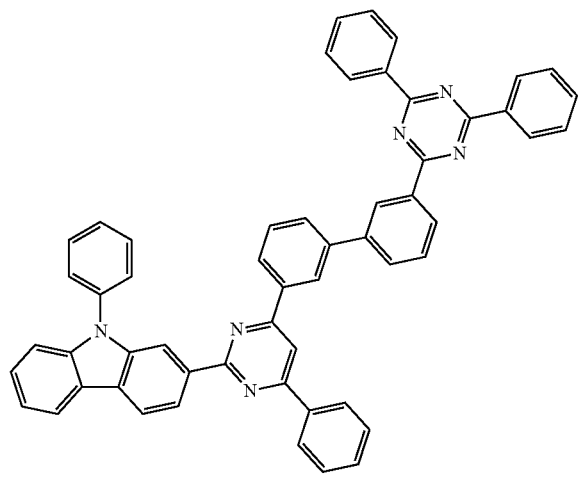

-continued
101
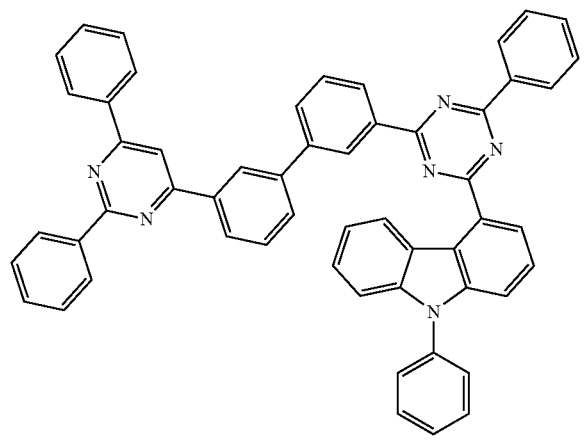
102
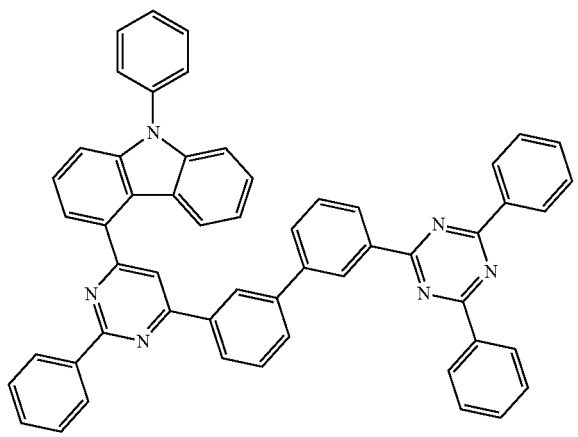
103
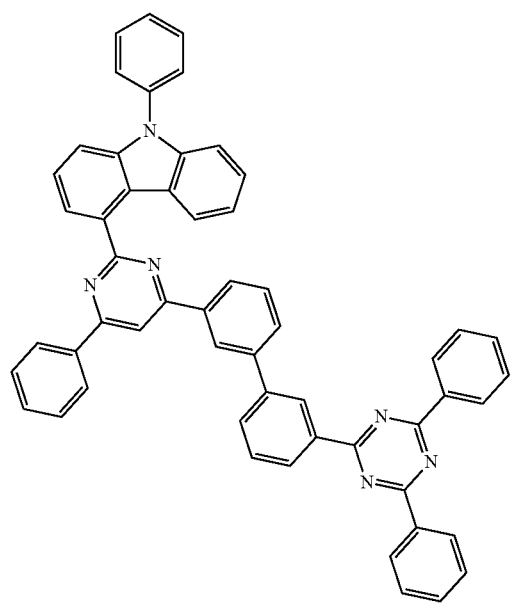
104
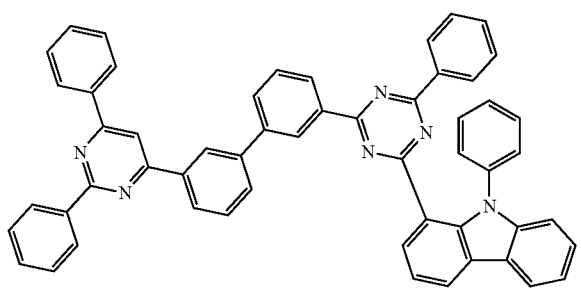
105
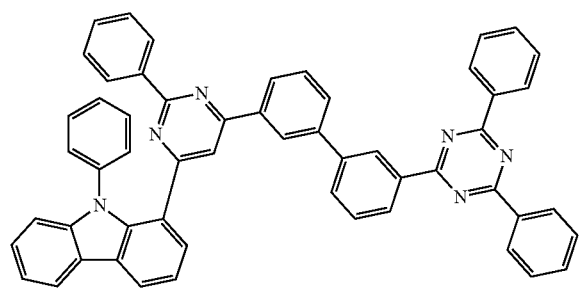
106
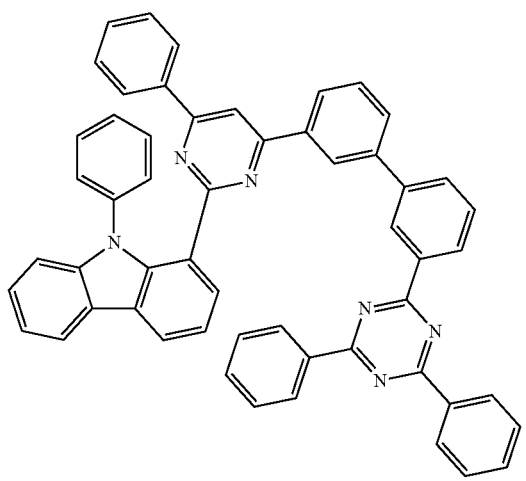

107
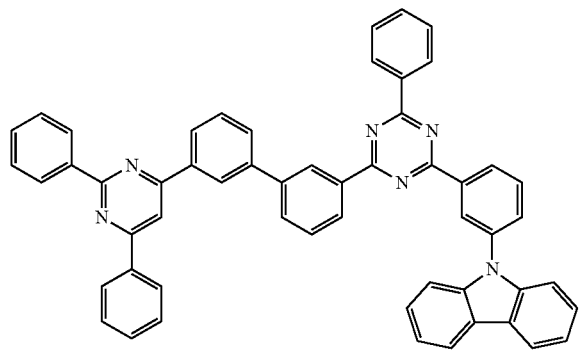
108
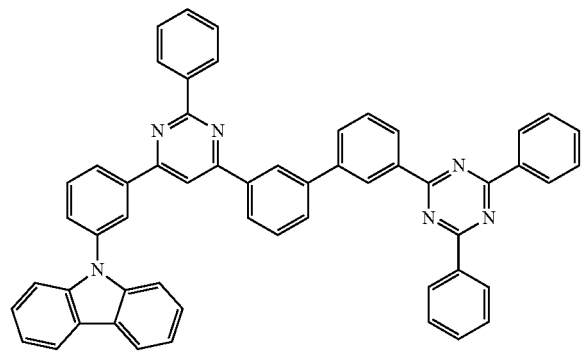
109
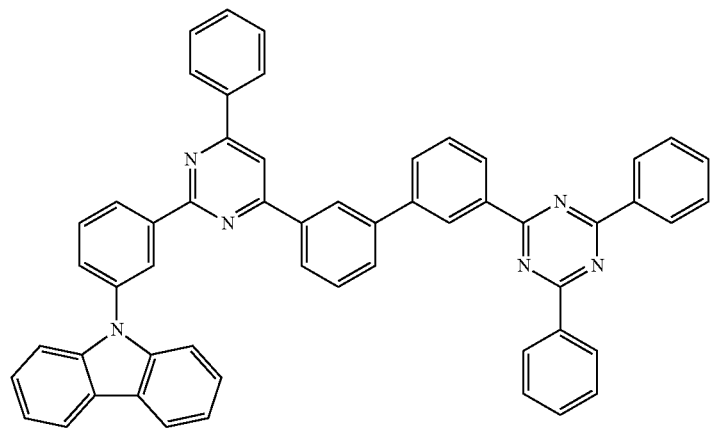
110
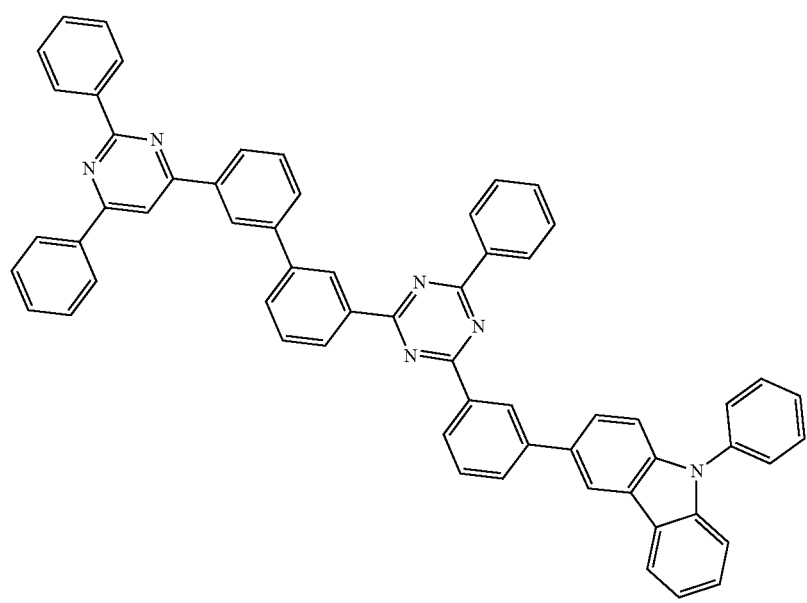

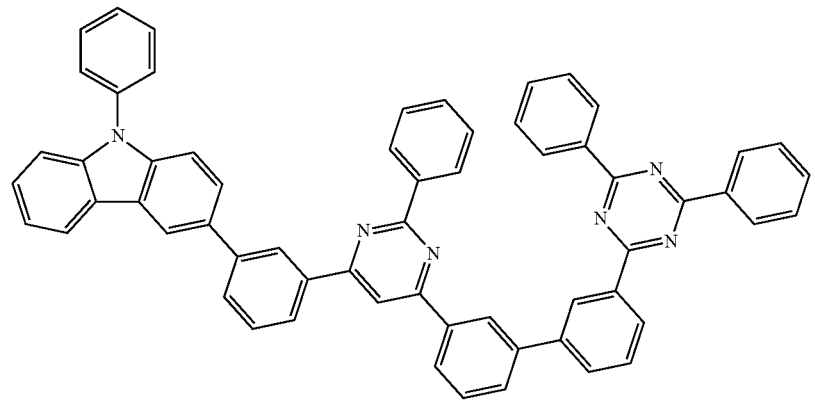
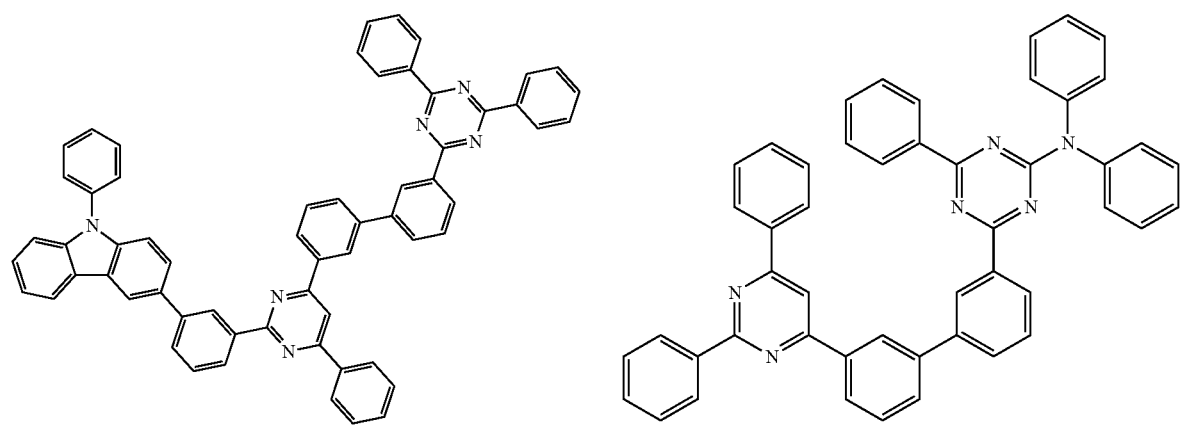
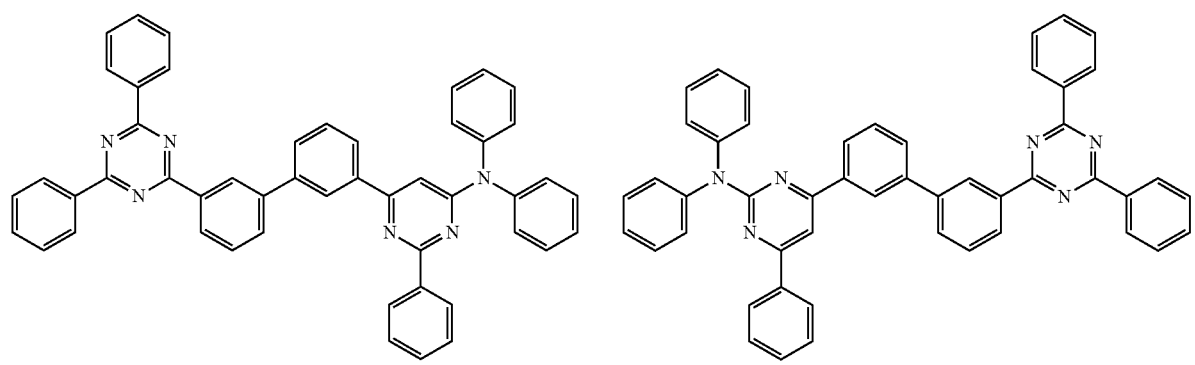

116
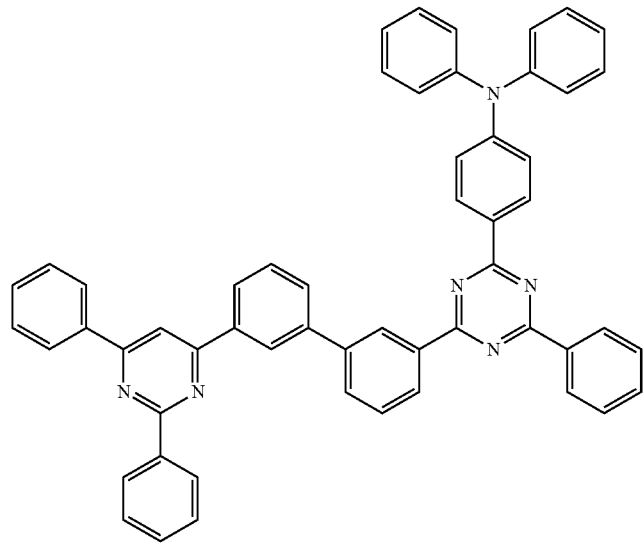
117
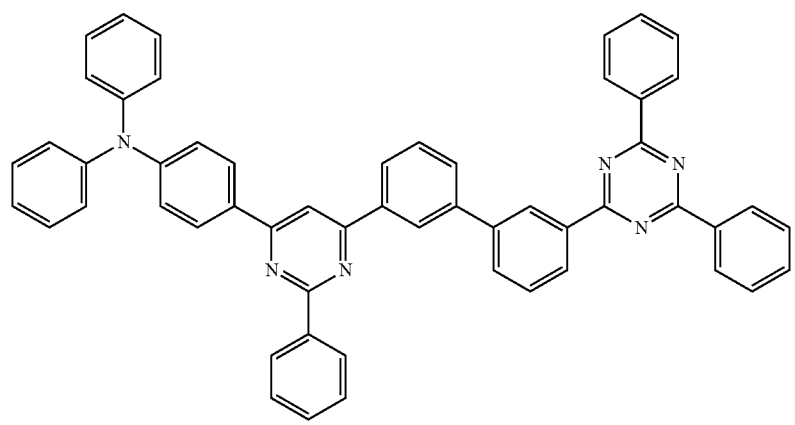
118 119
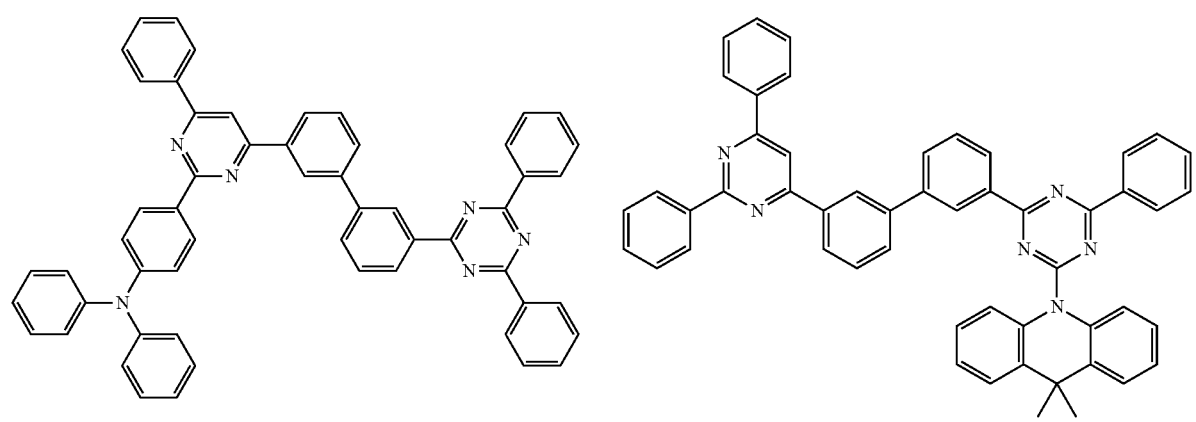

120
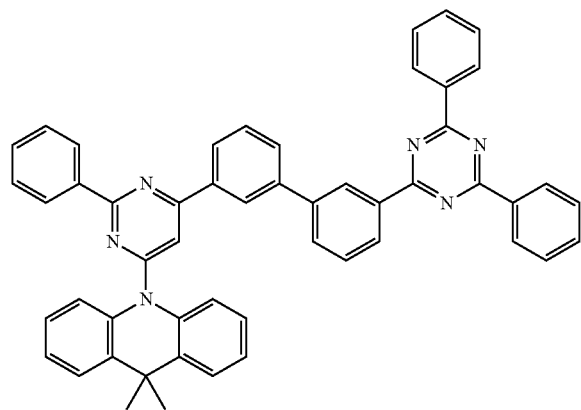
121
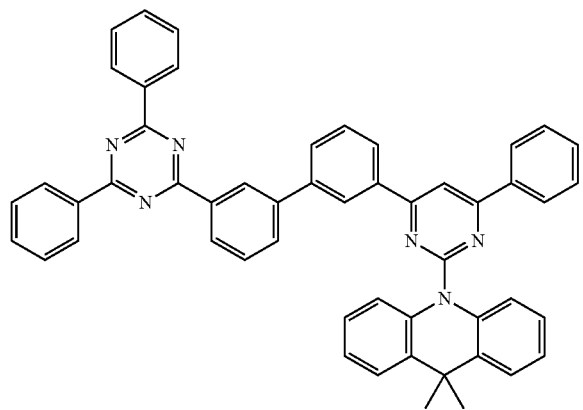
122
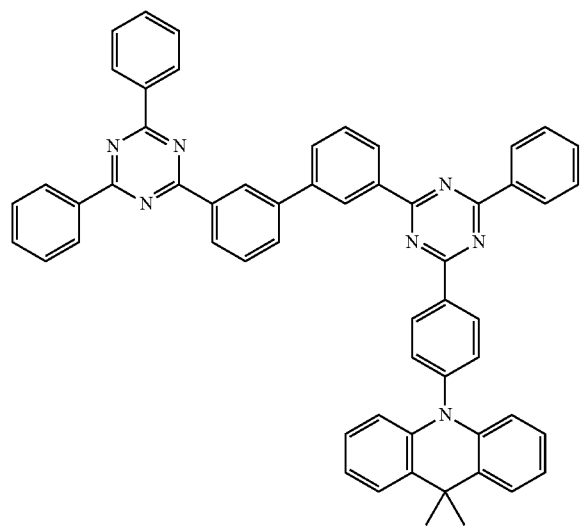
123
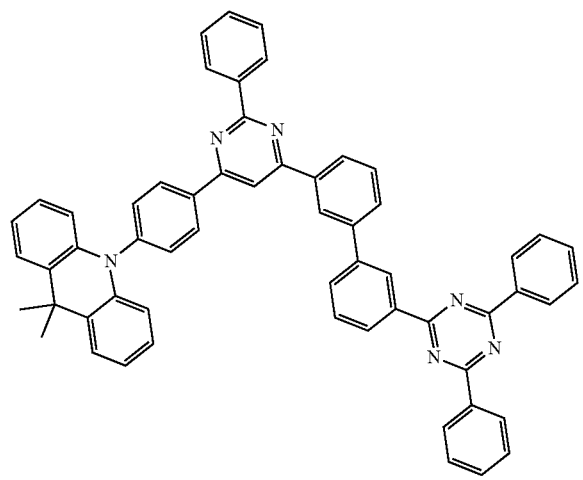
124
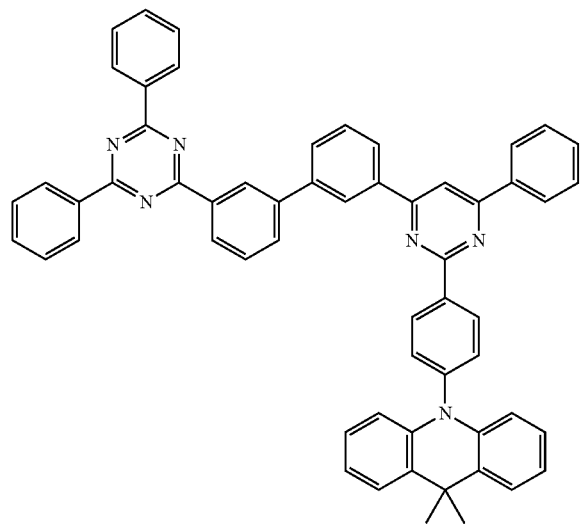
125
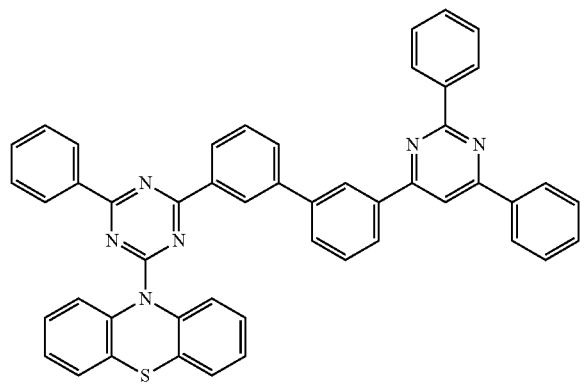

-continued
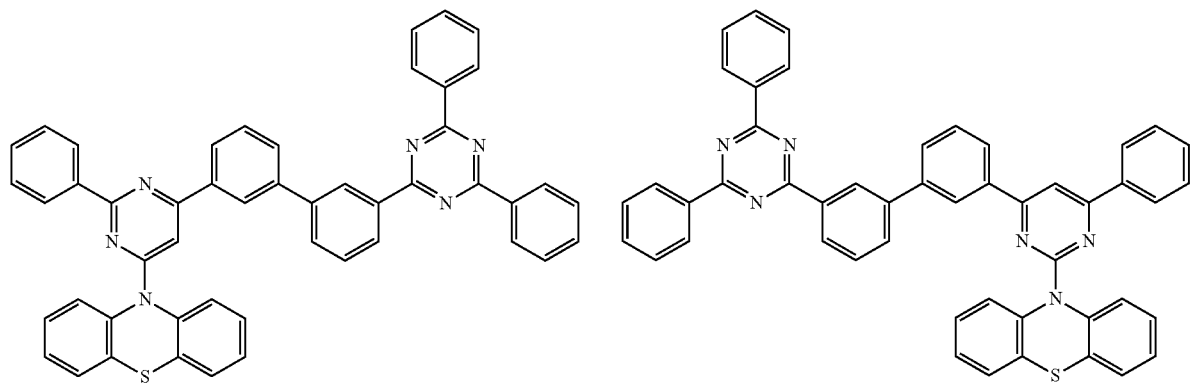
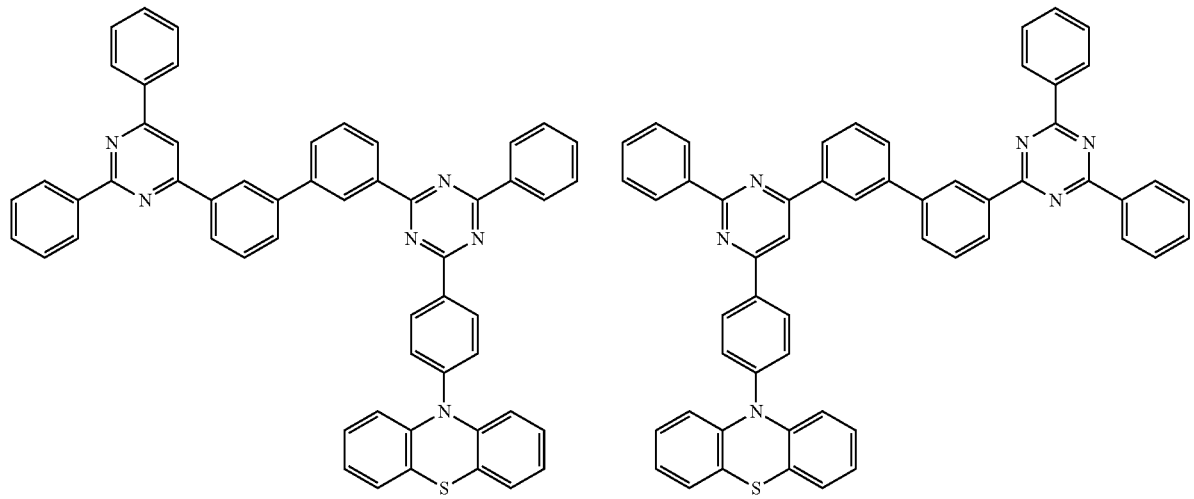
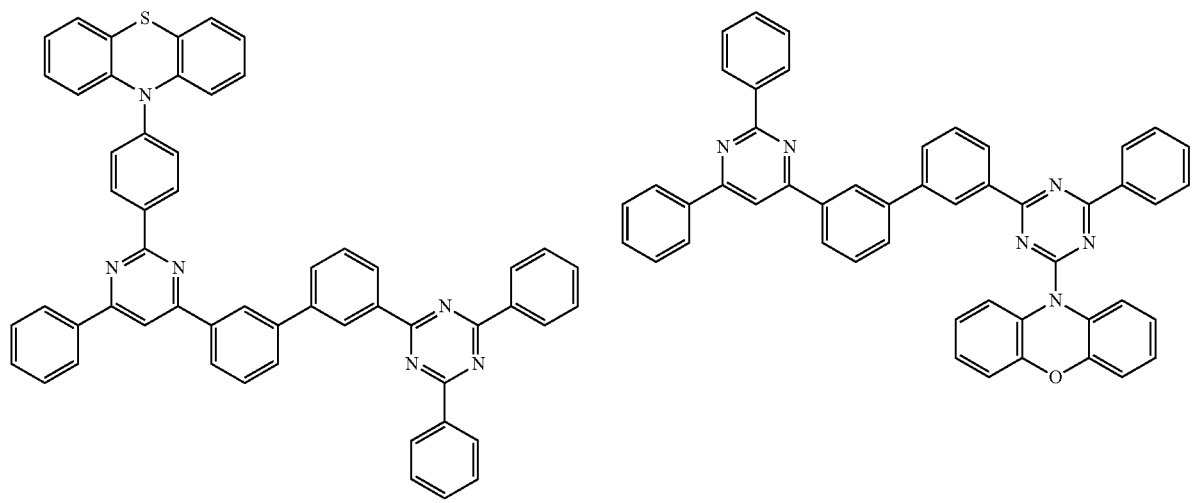

-continued
132
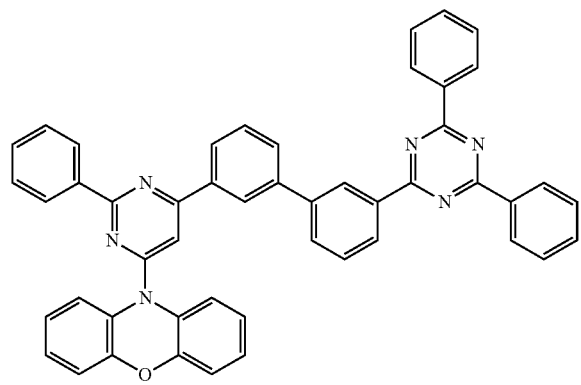
133
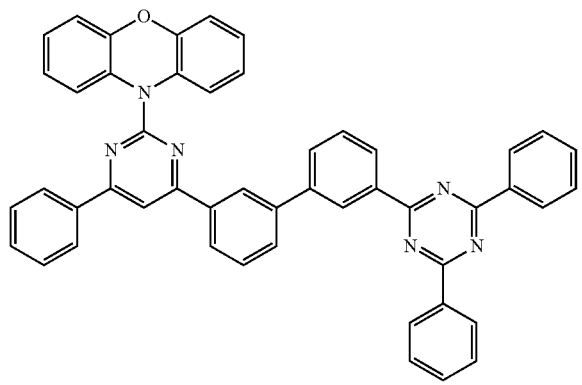
134
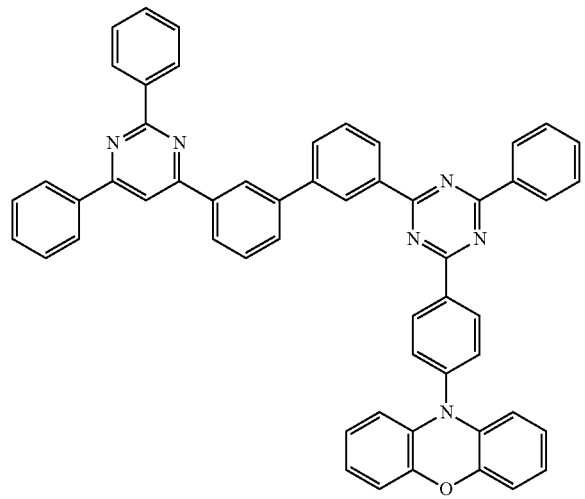
135
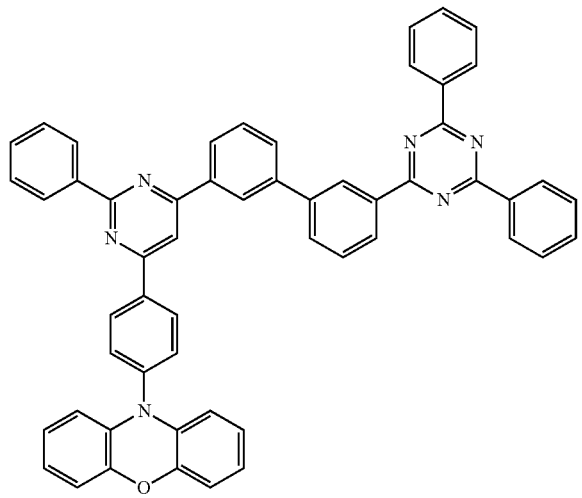
136
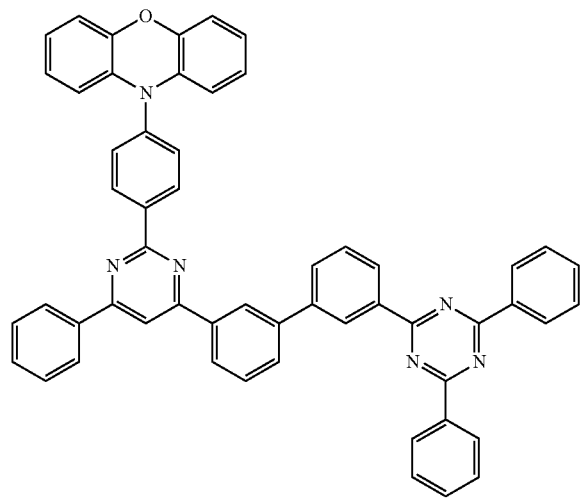
137
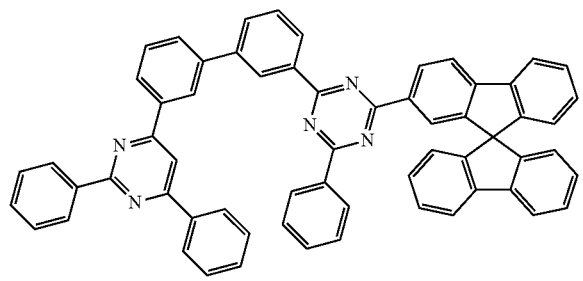

138
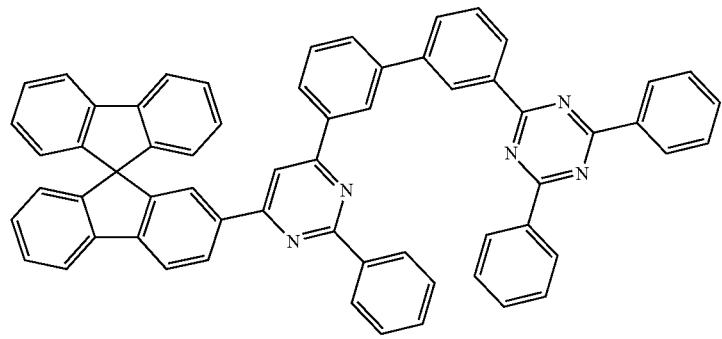
139
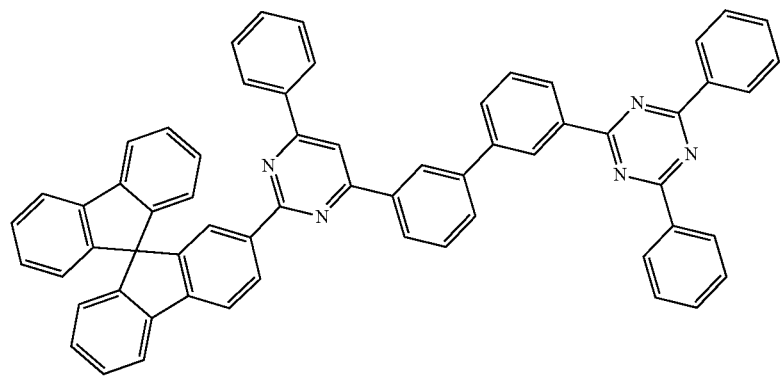
140 141
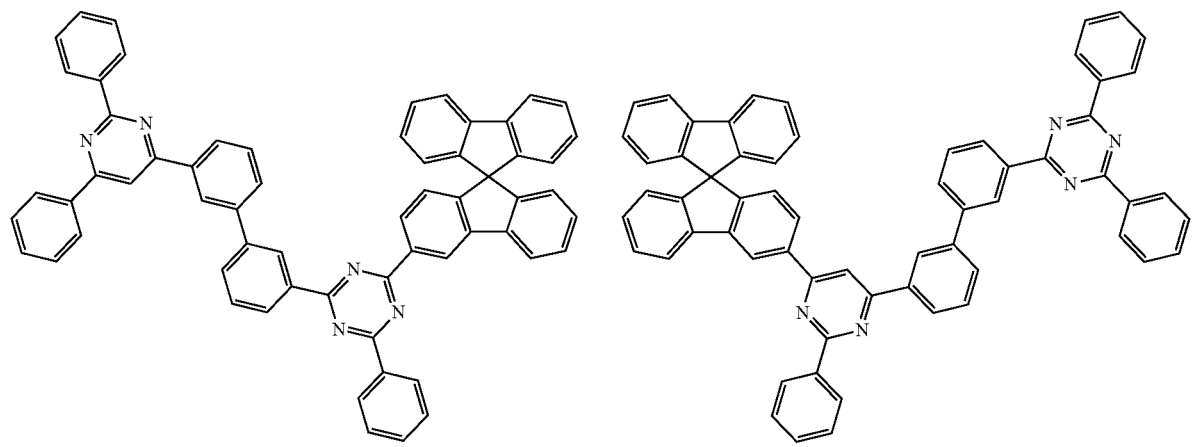
142 143
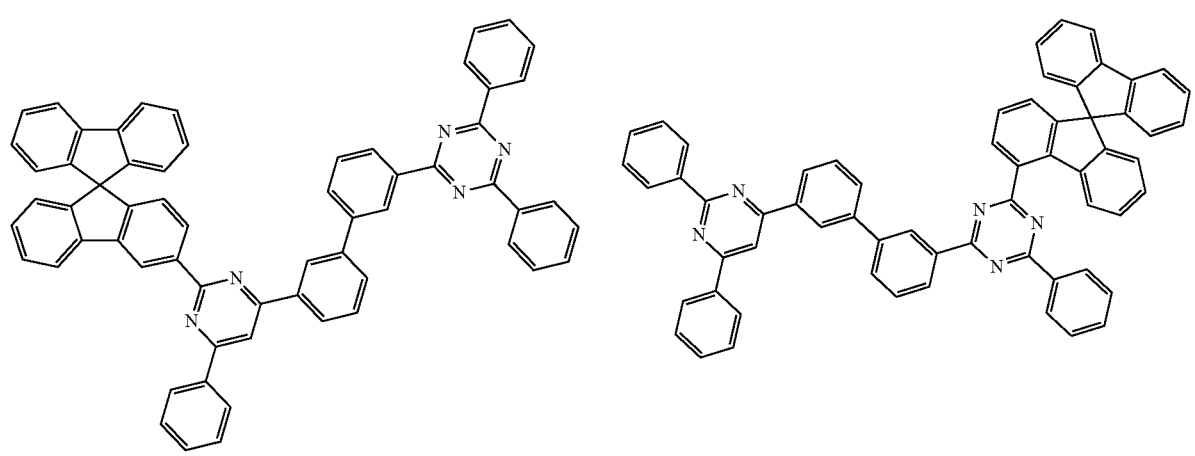

-continued
144
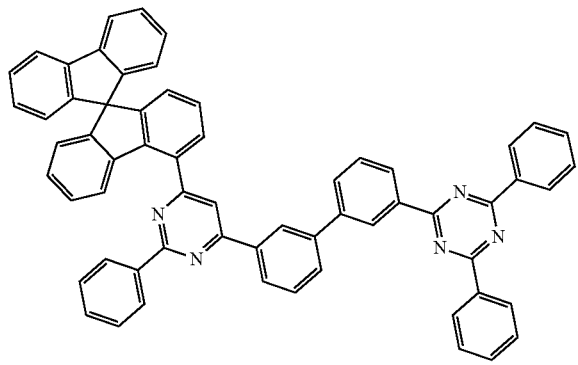
145
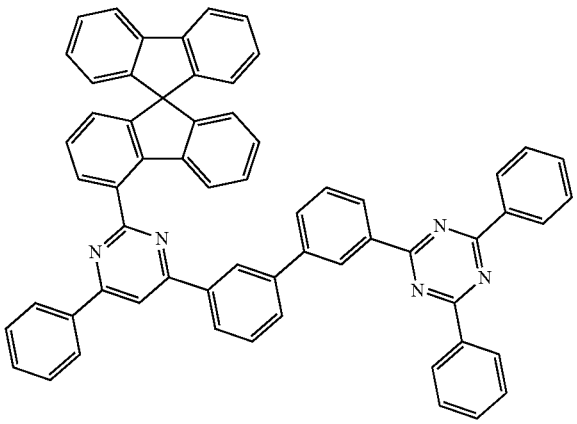
146
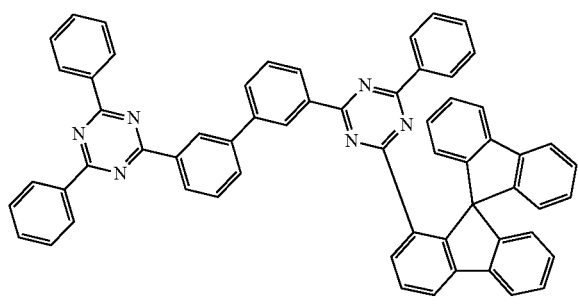
147
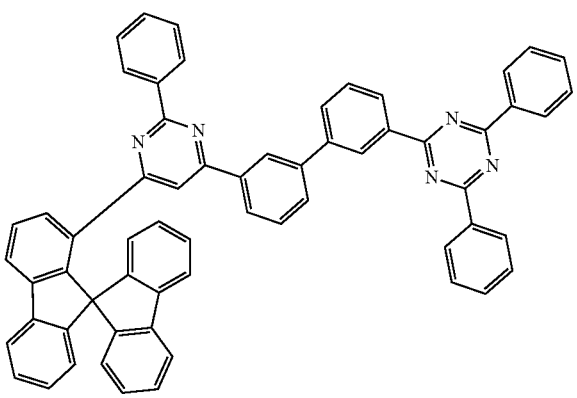
148
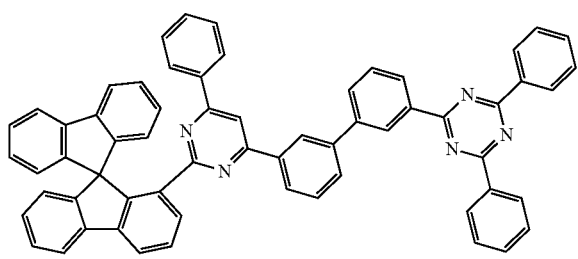
149
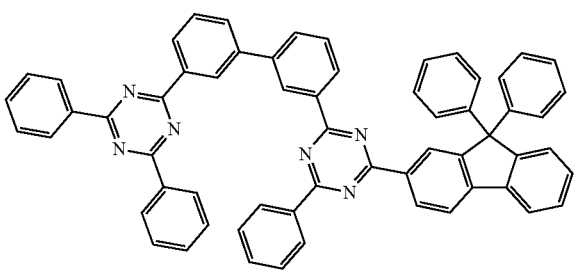
150
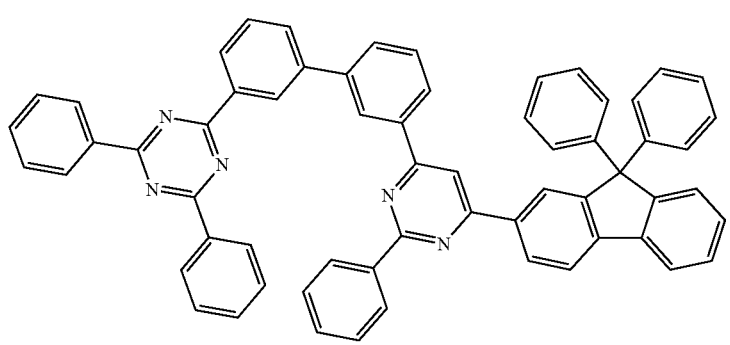

151
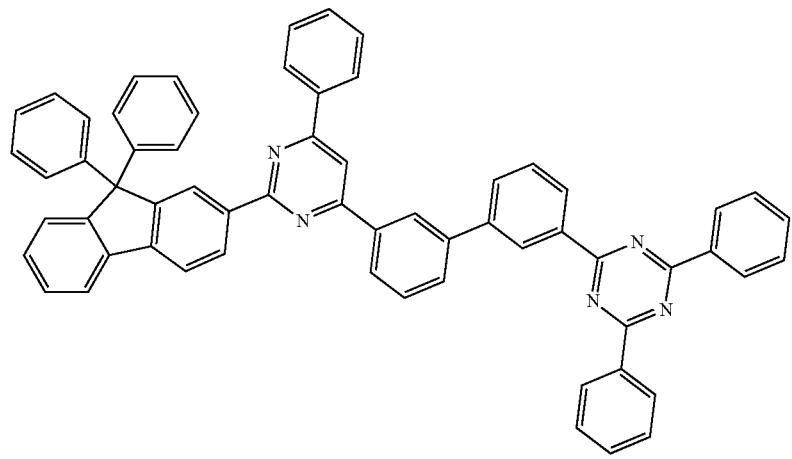
152
153
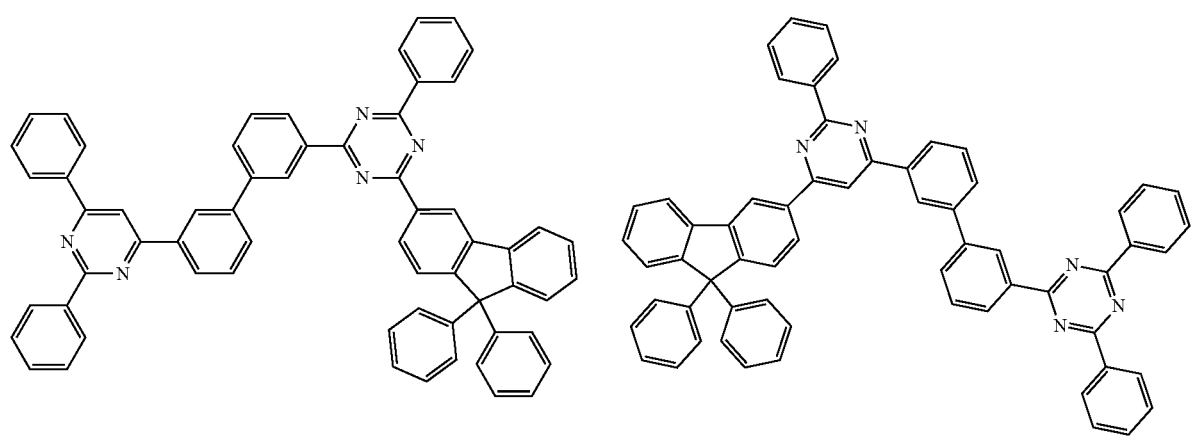
154
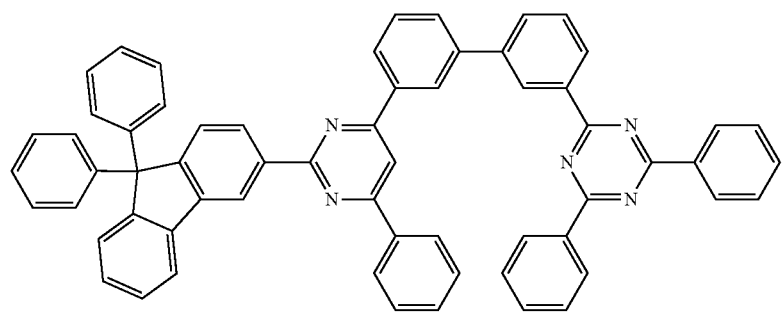

-continued
155
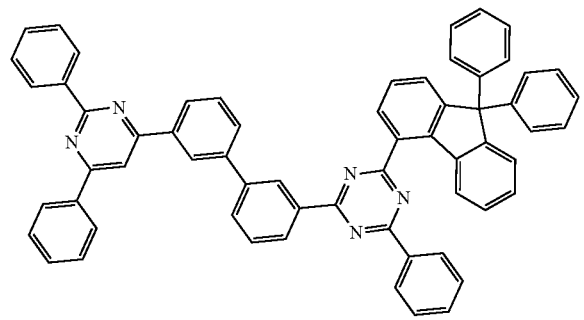
156
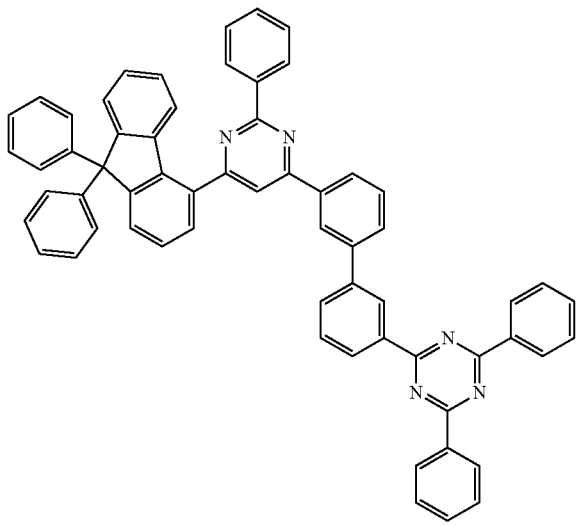
157
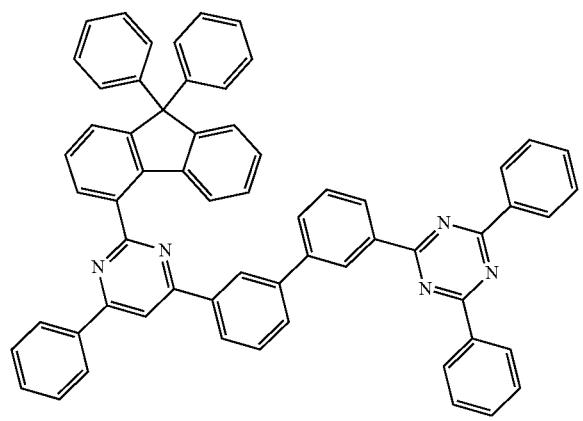
158
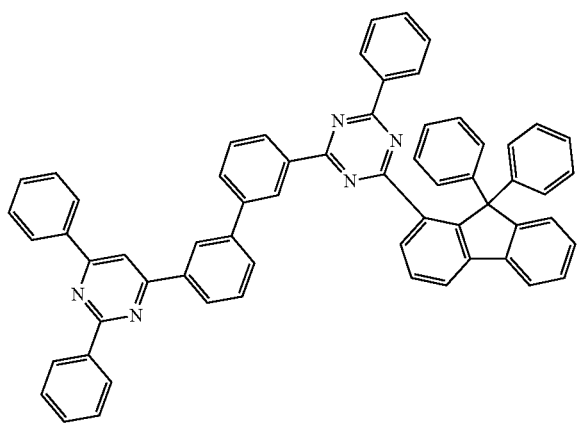
159
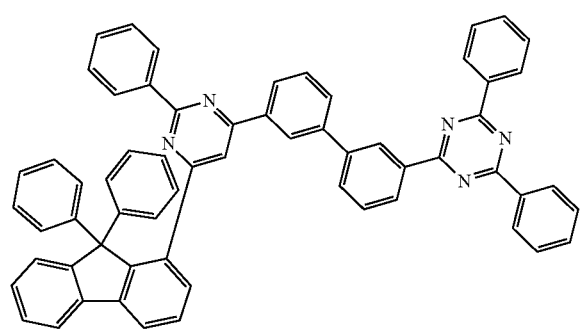
160
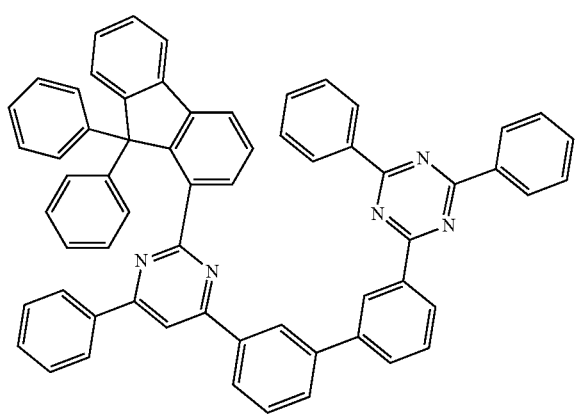

-continued
161
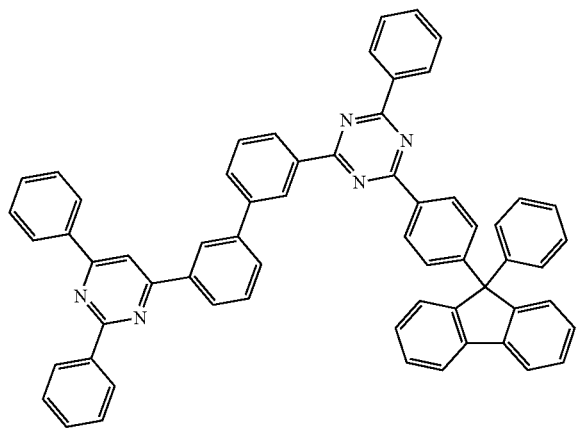
162
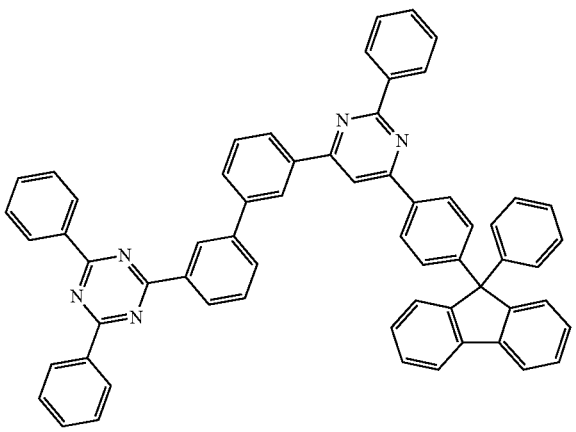
163
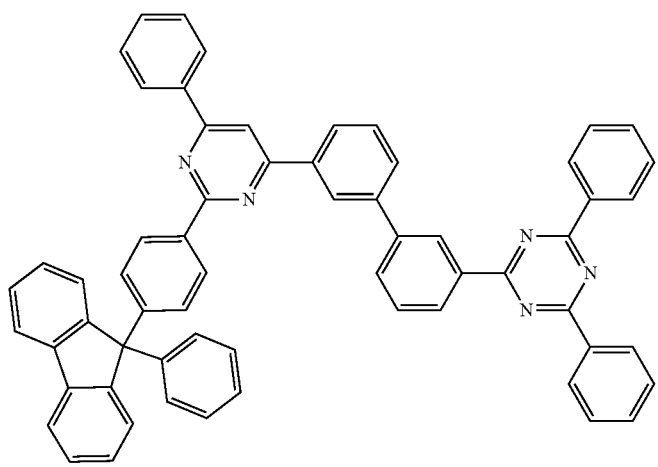
164
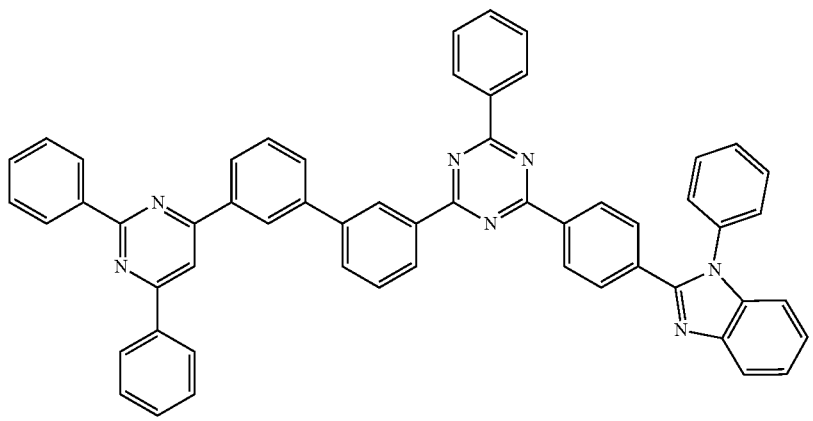
165
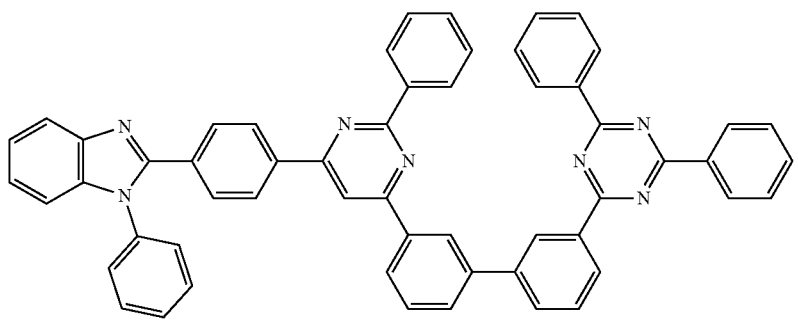

-continued
166
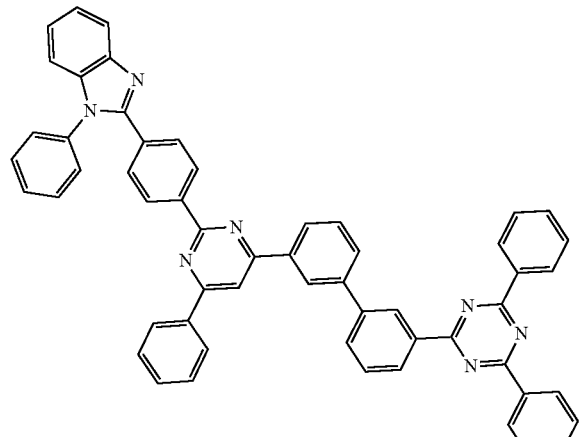
167
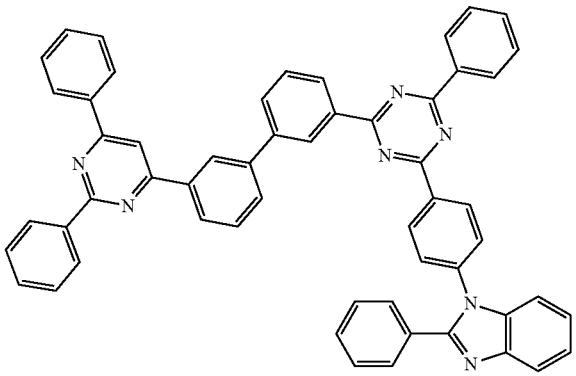
169
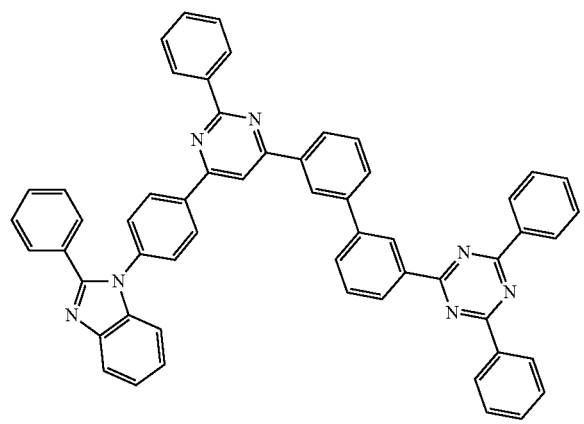
168
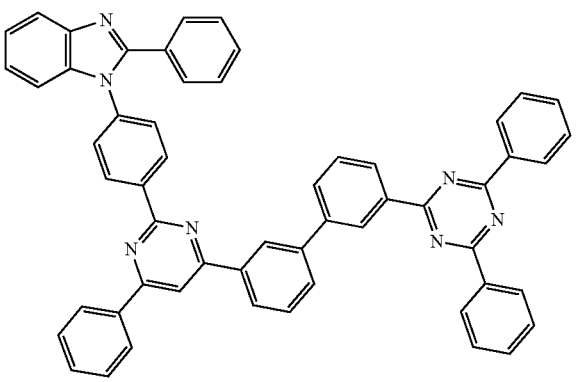
170
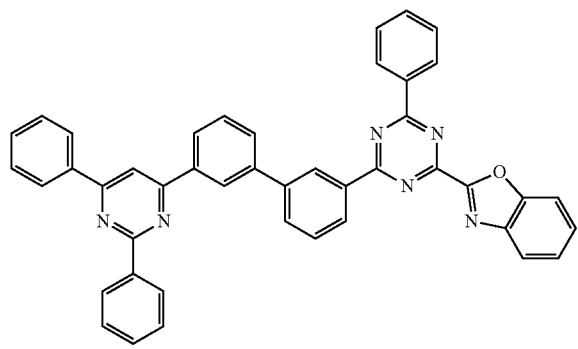
171
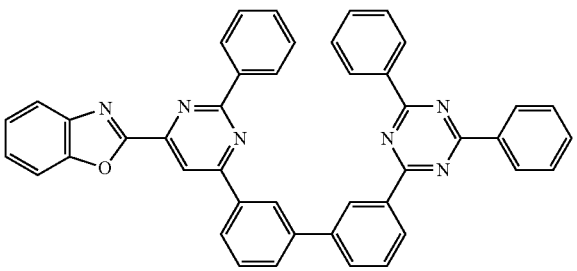
172
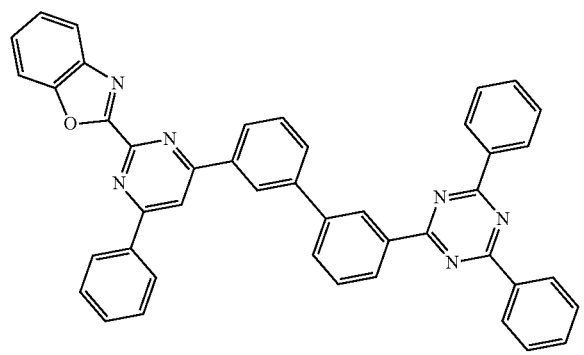
173
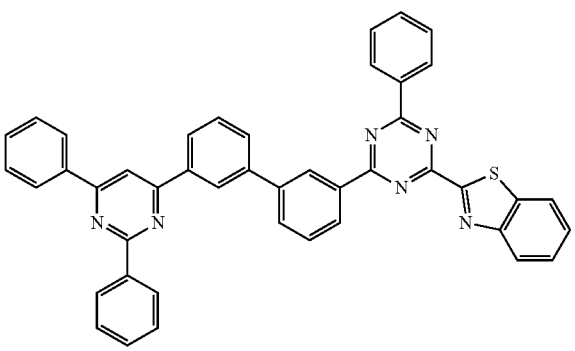

-continued
174
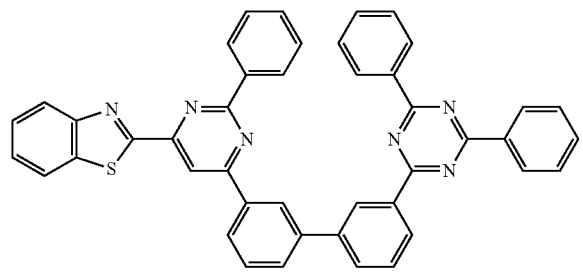
175
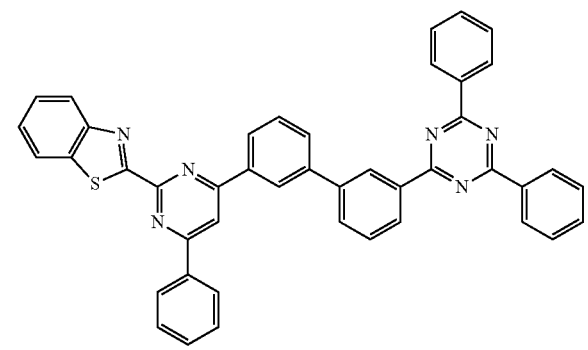
176
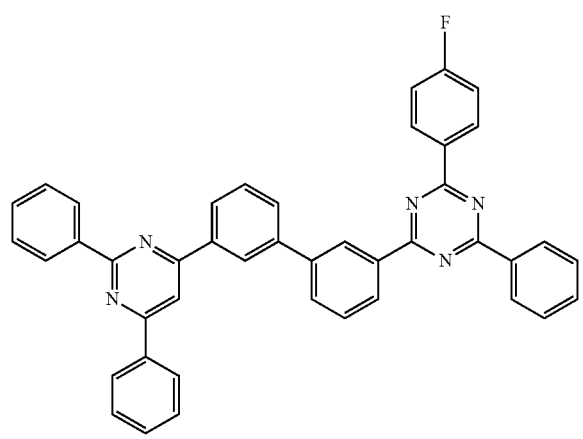
177
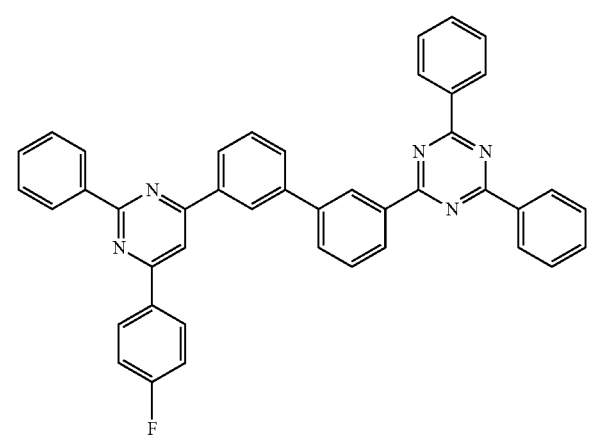
178
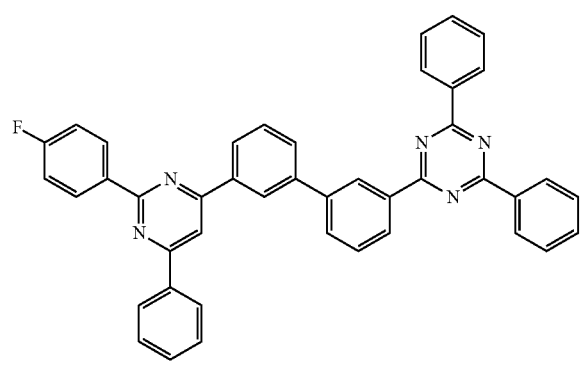
179
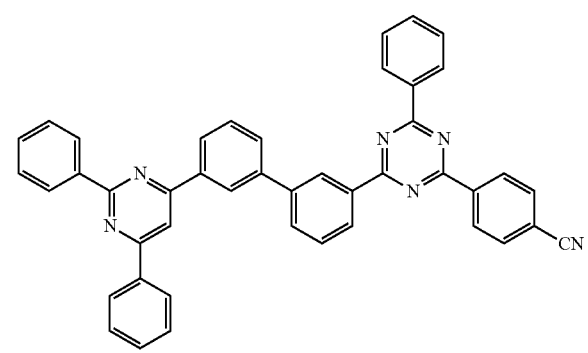
180
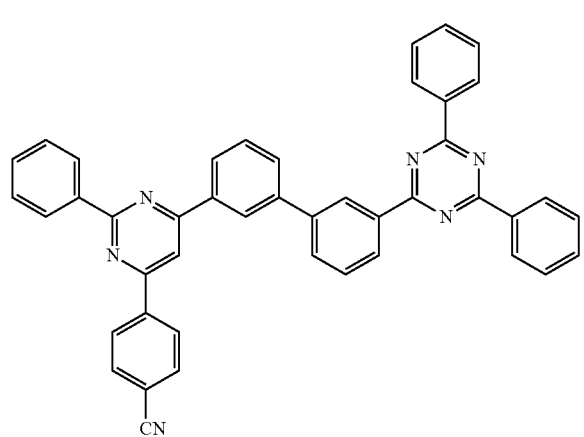
181
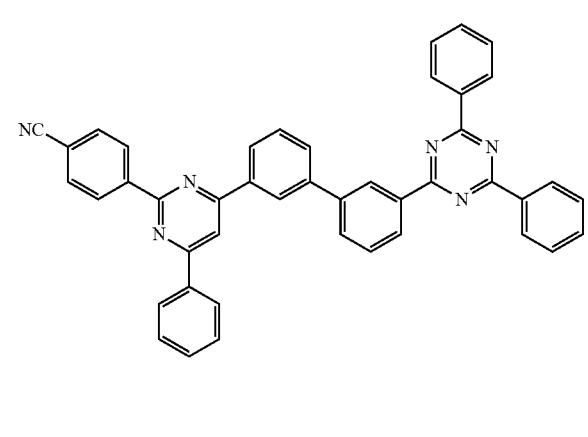

-continued
182
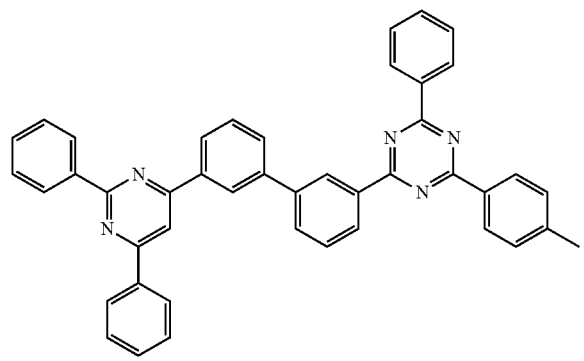
183
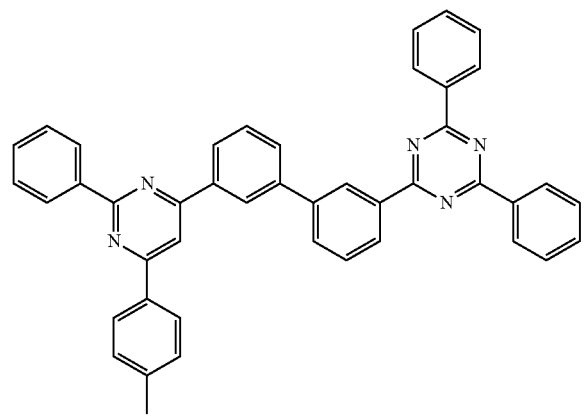
184
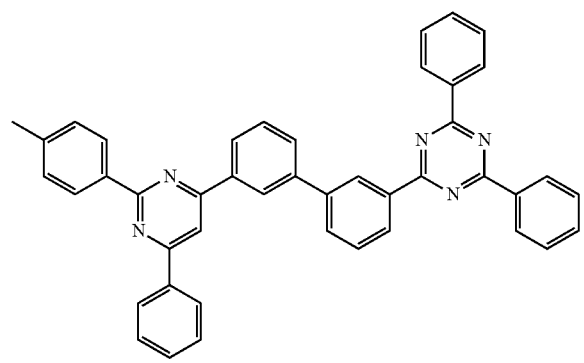
185
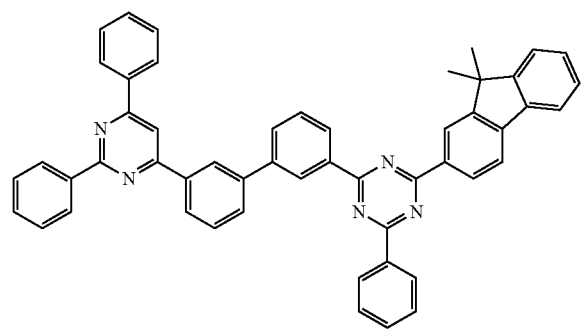
186
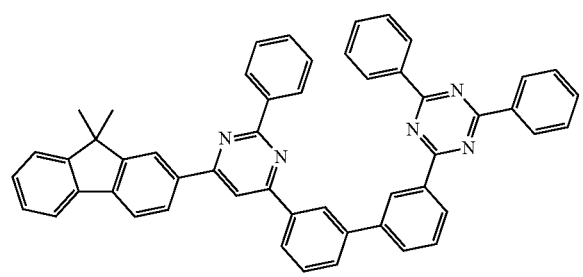
187
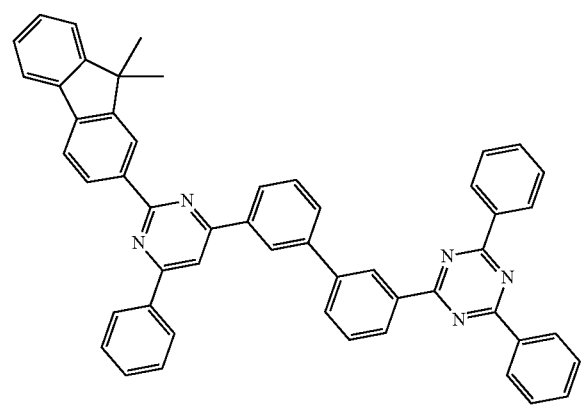

188
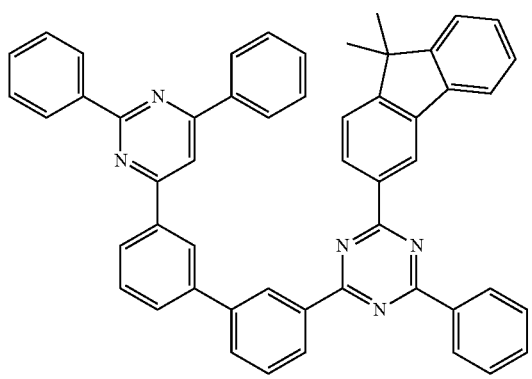
189
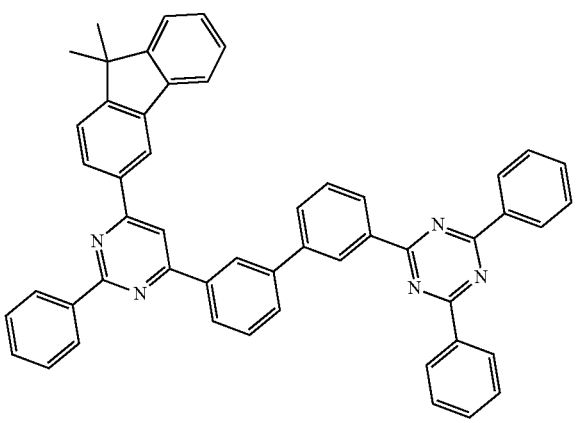
190
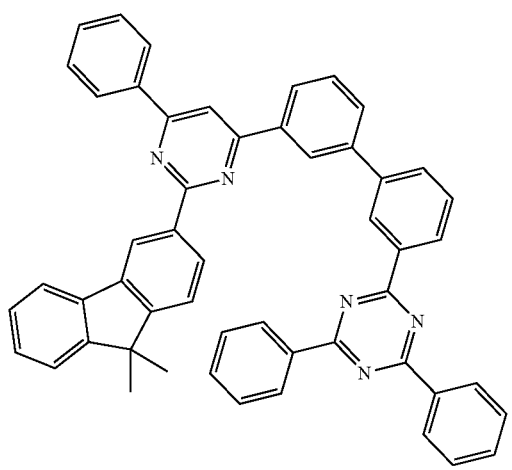
191
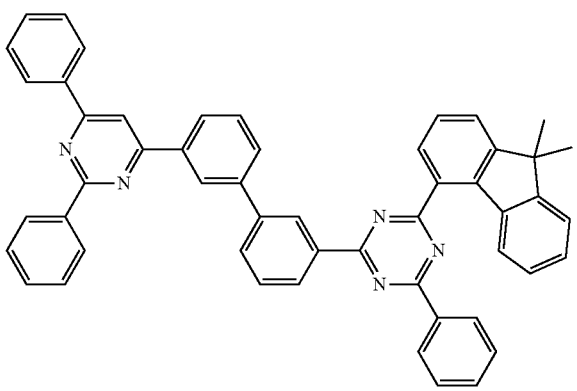
192
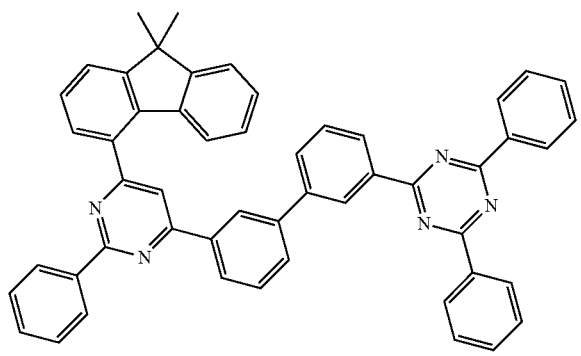
193
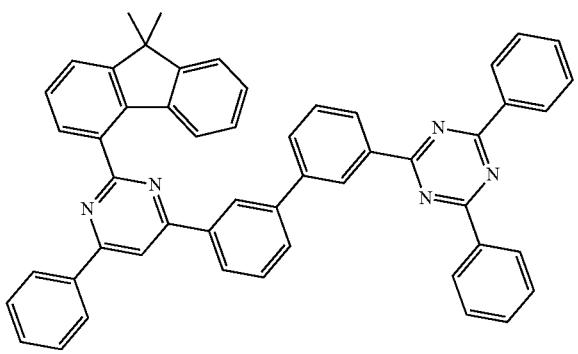

194
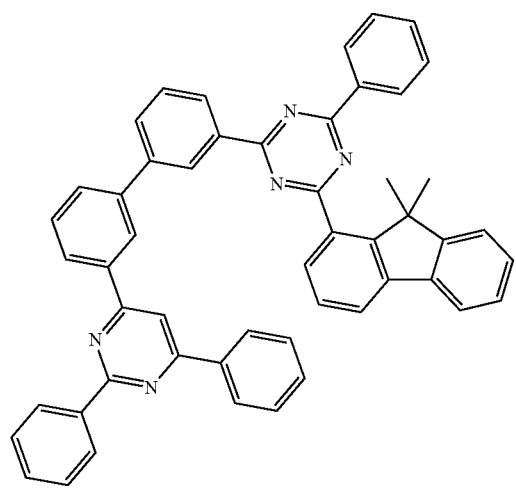
195
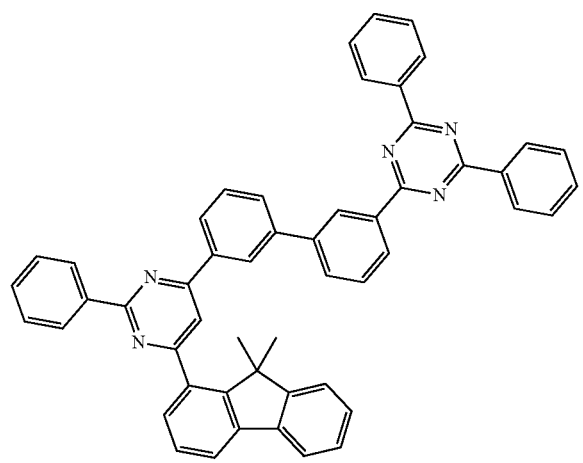
196
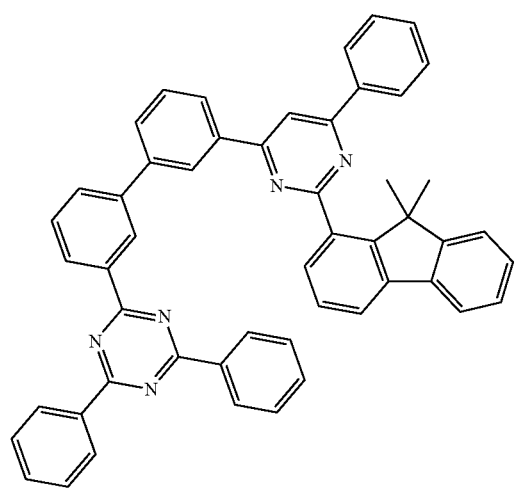
221
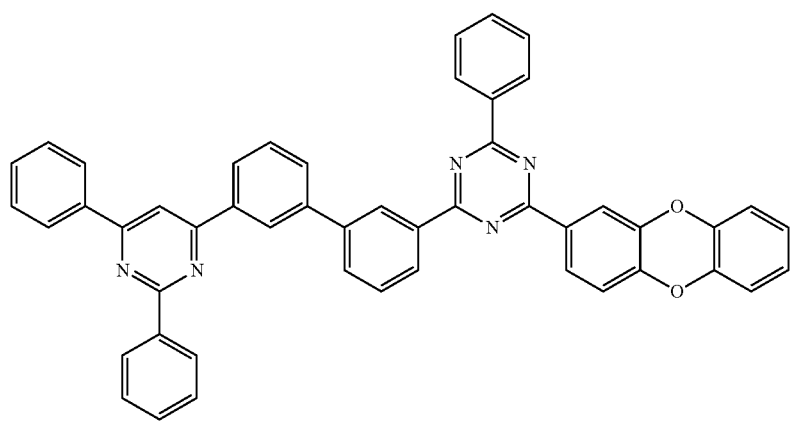

222
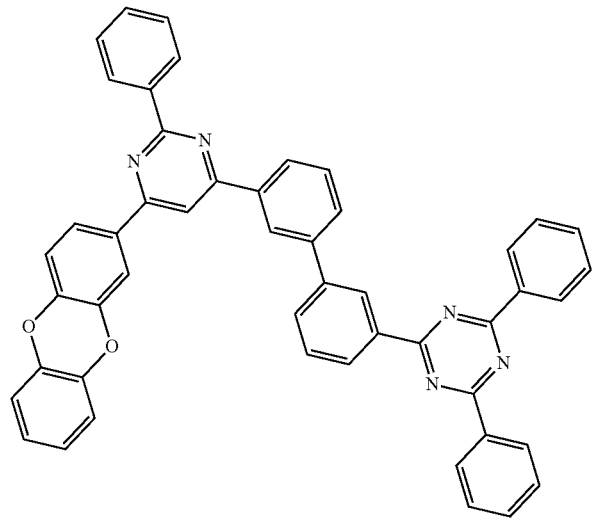
223
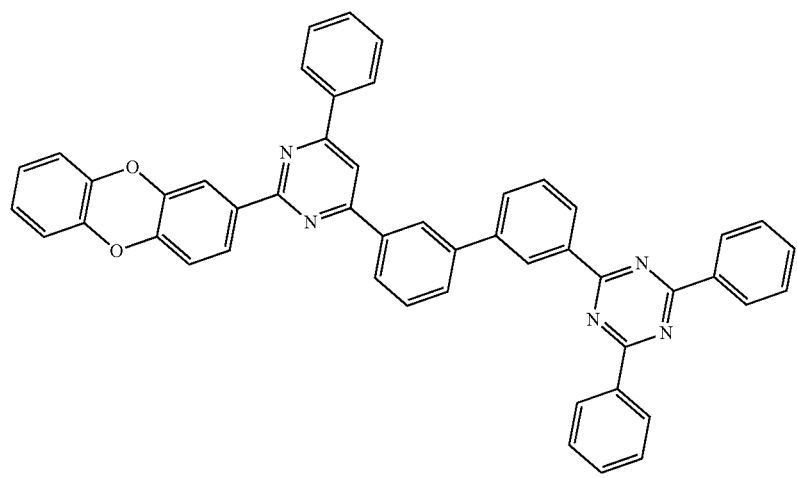
224
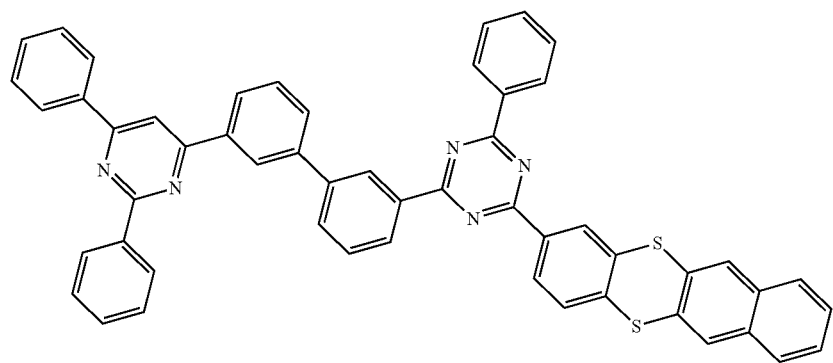

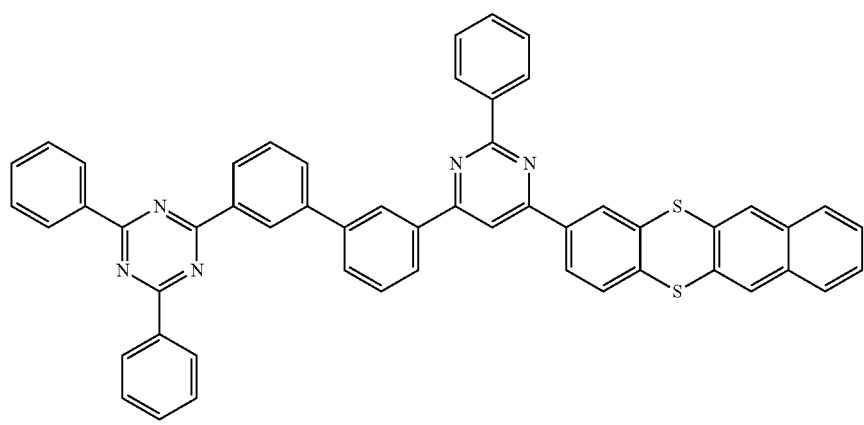
225
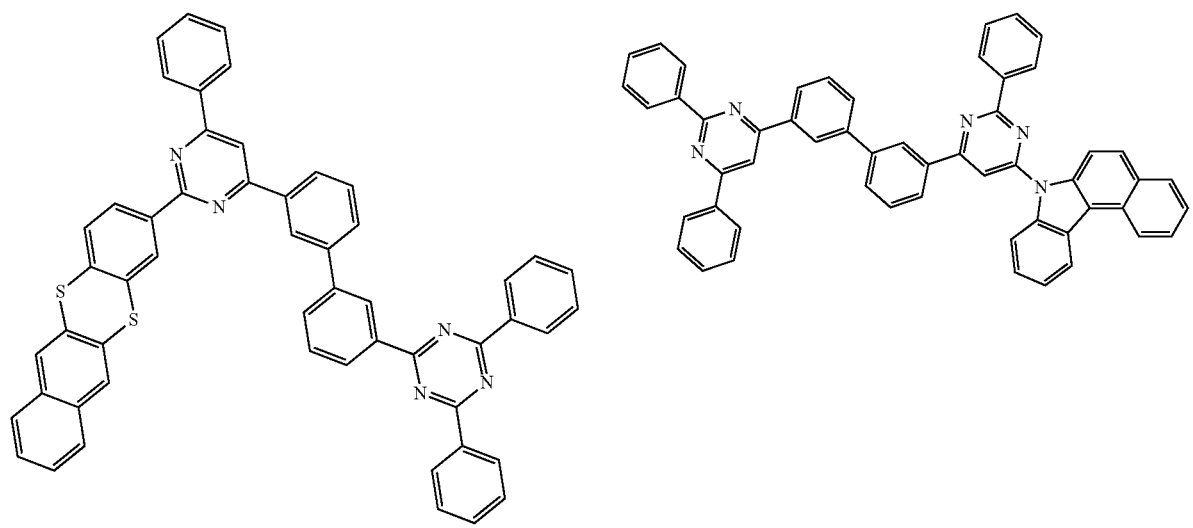
226 227
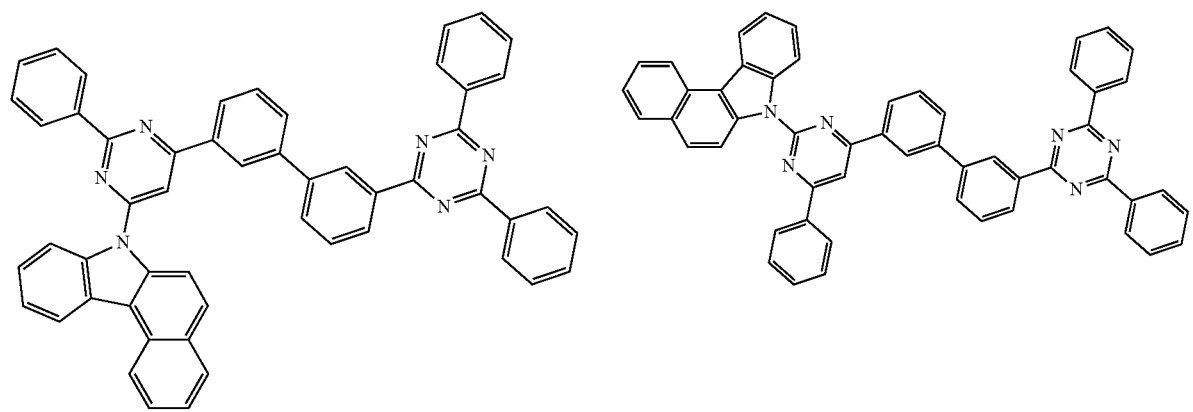
228 229

230
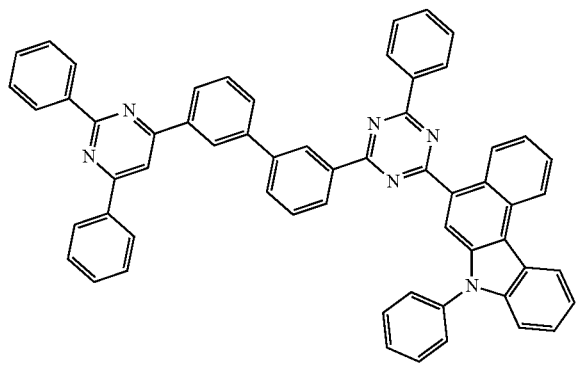
231
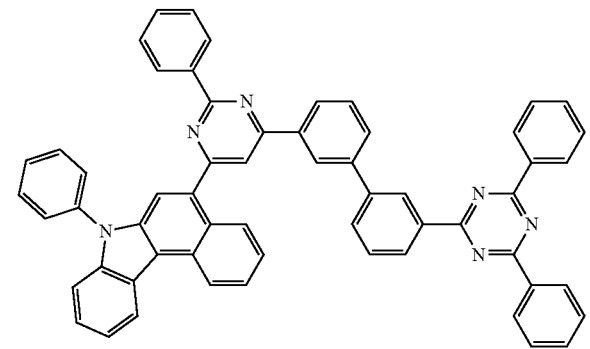
232
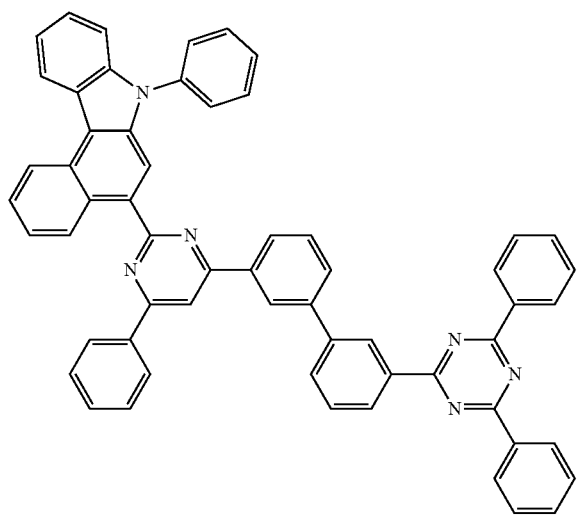
233
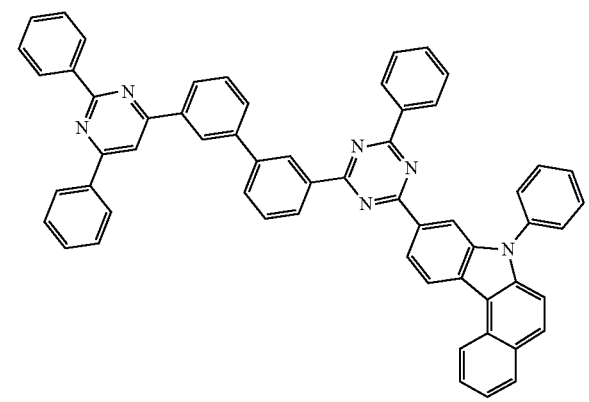
234
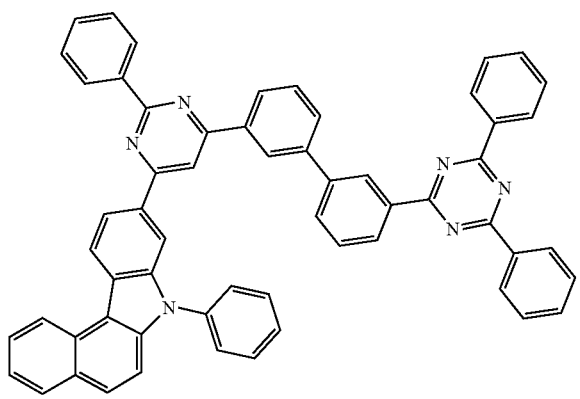
235
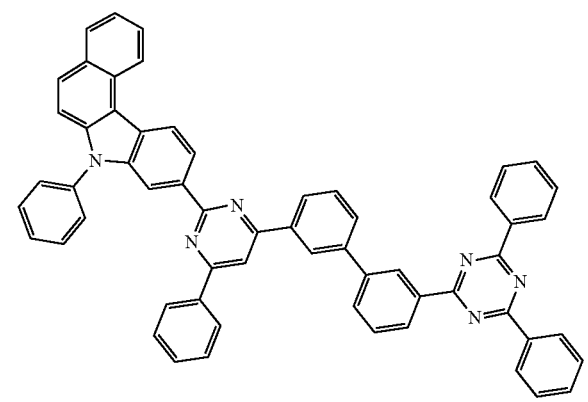

-continued
236
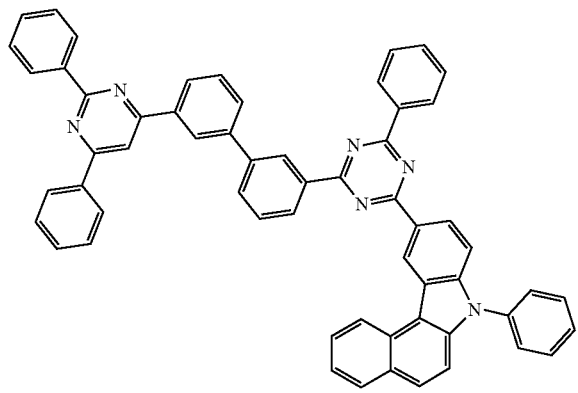
237
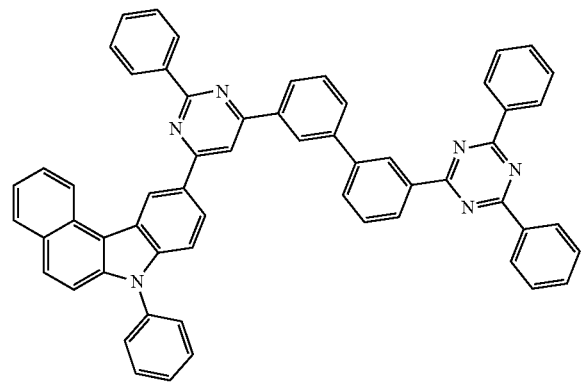
238
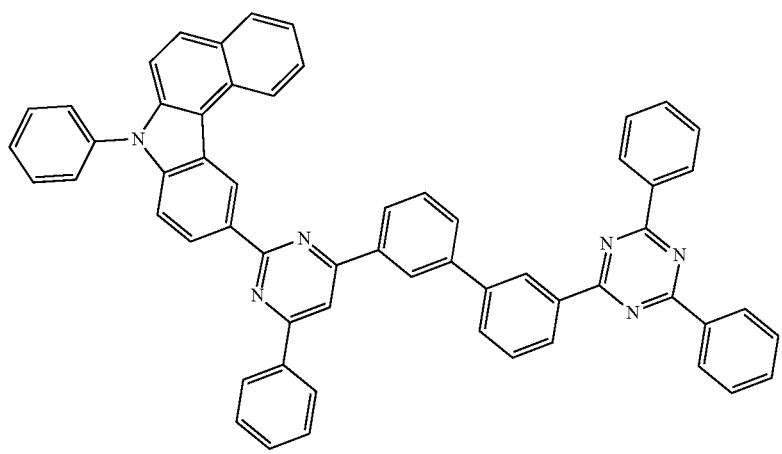
239
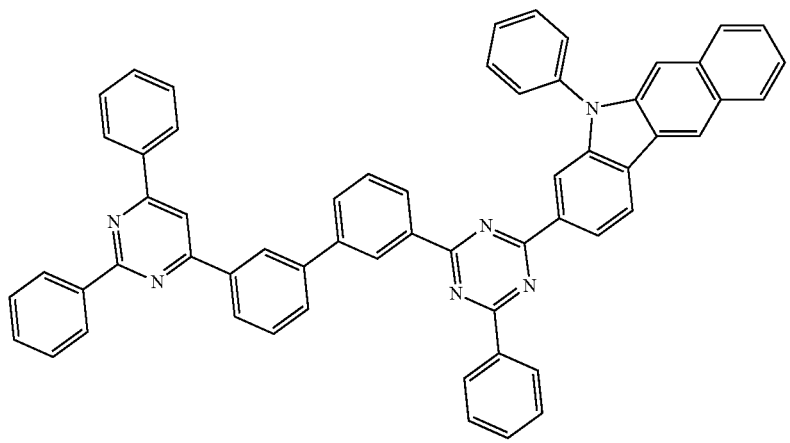
240
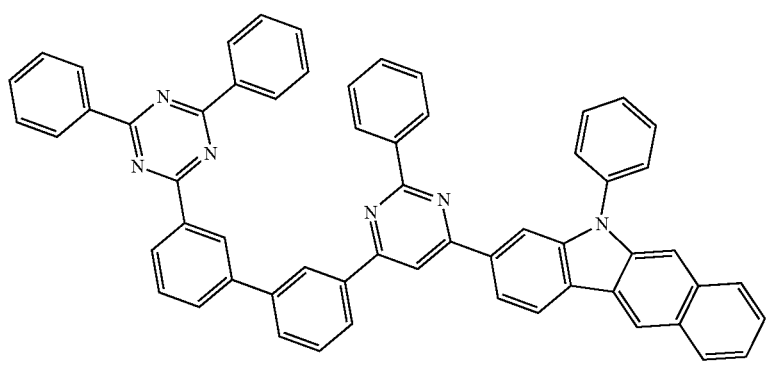

241
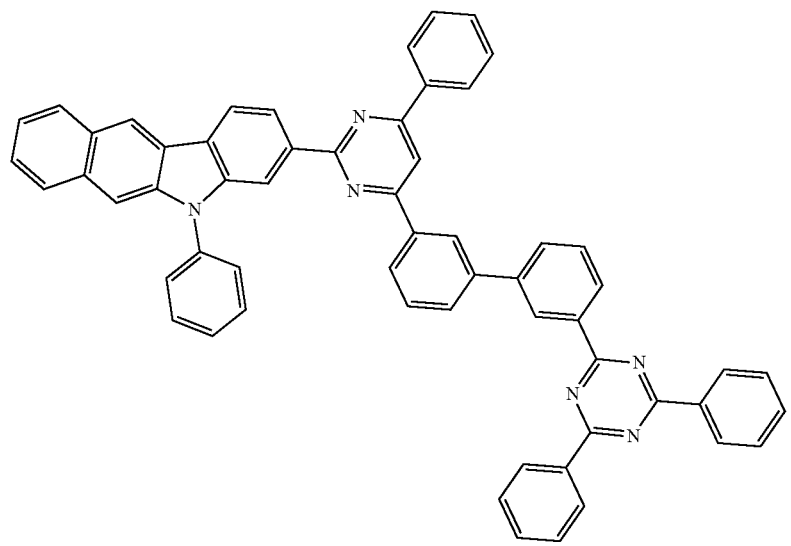
242
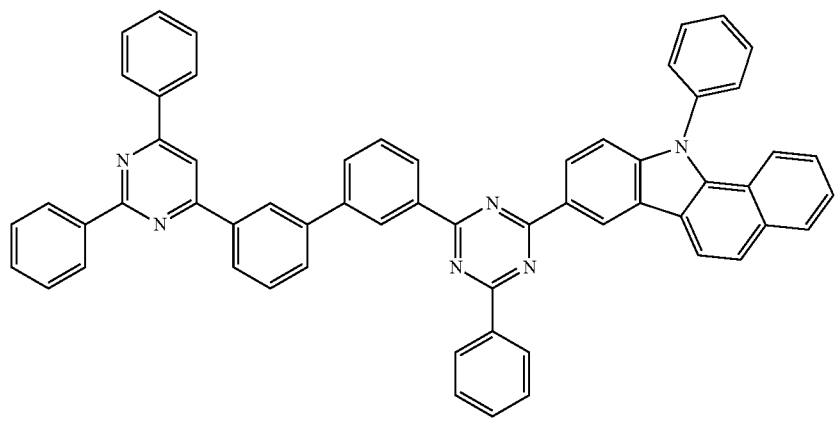
243
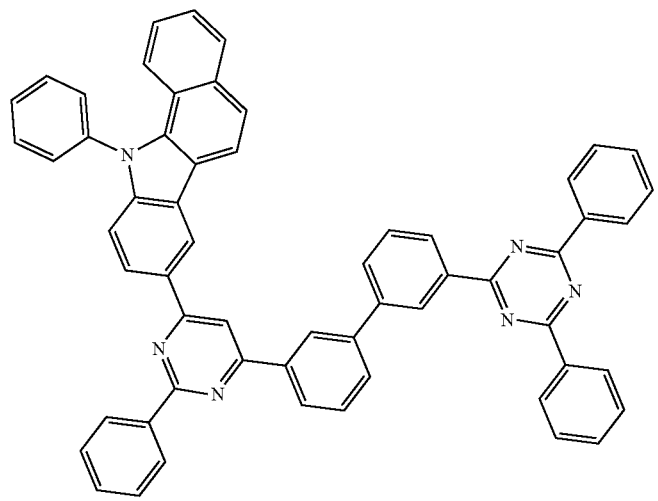

244
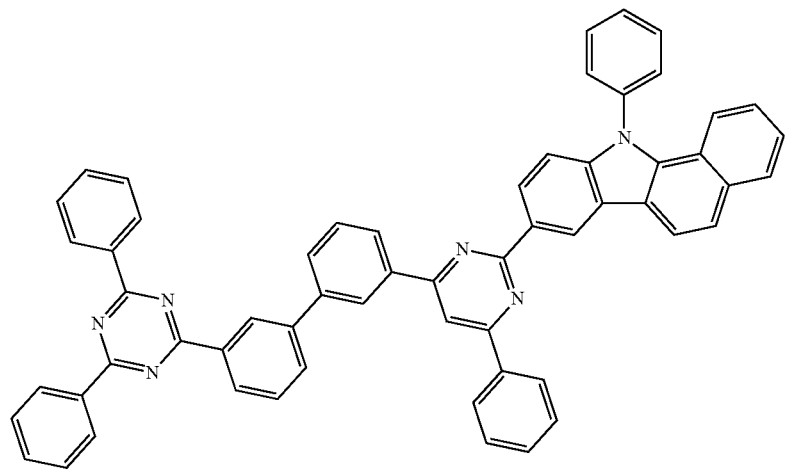
245 246
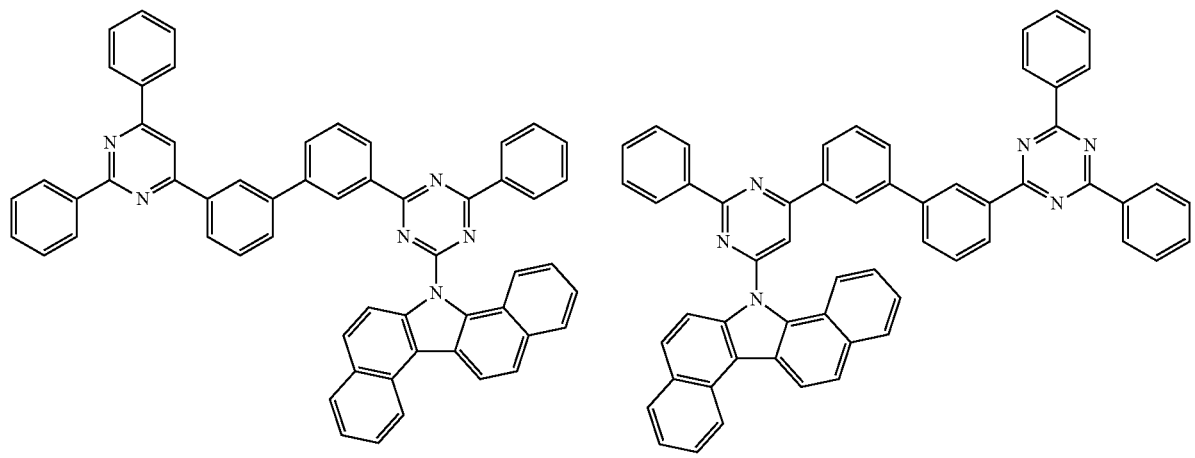
247 248
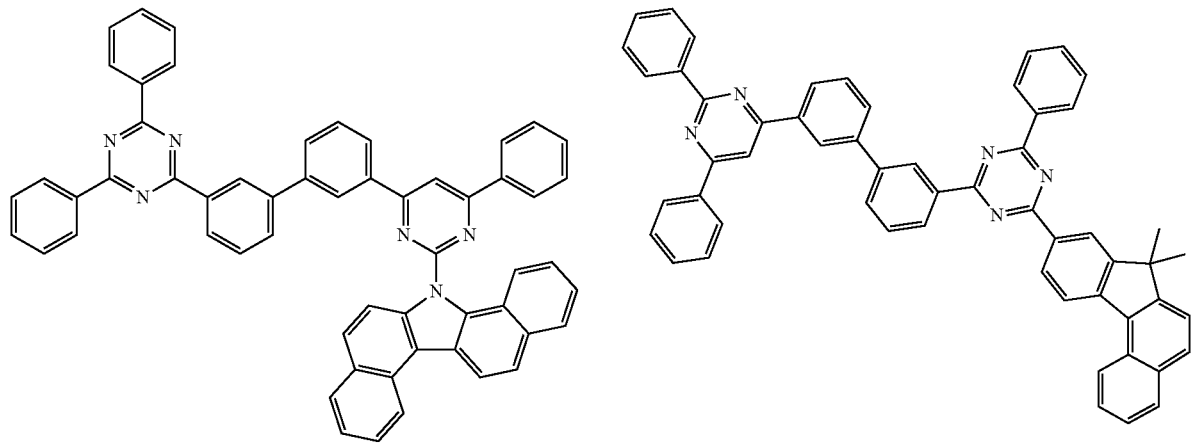

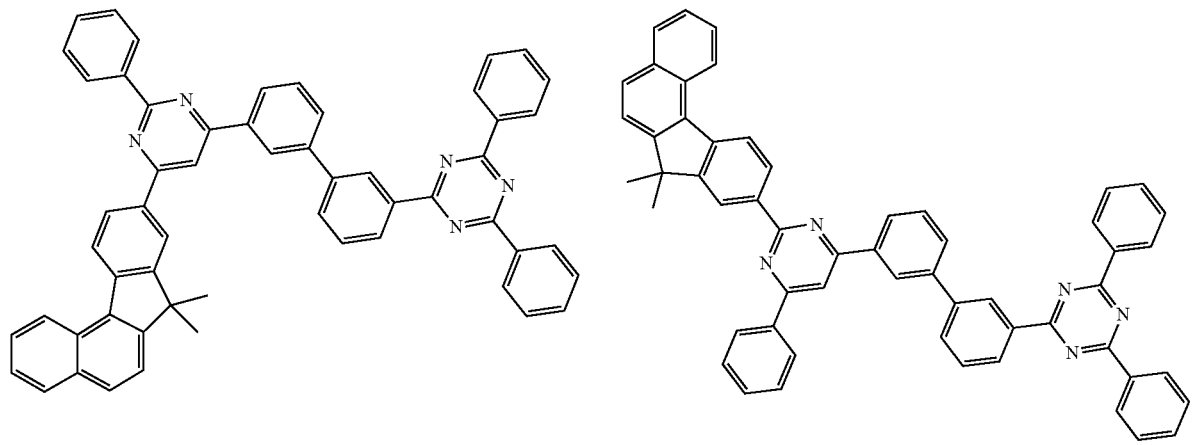
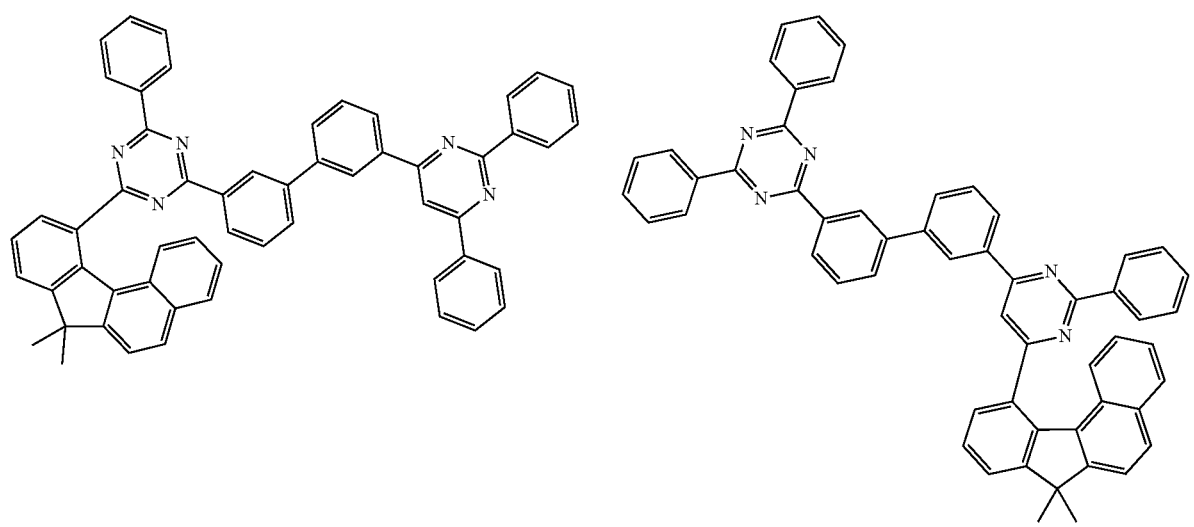
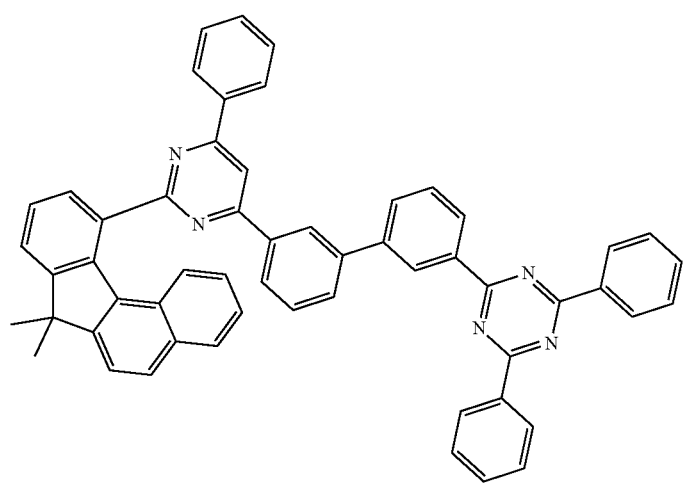

254
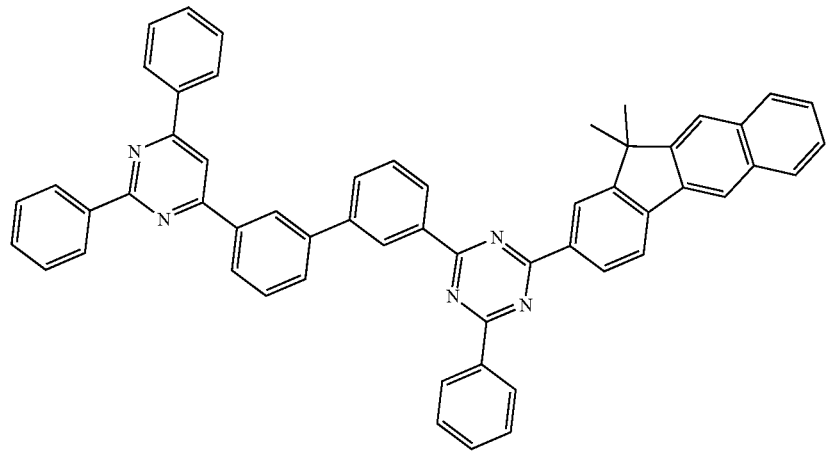
255
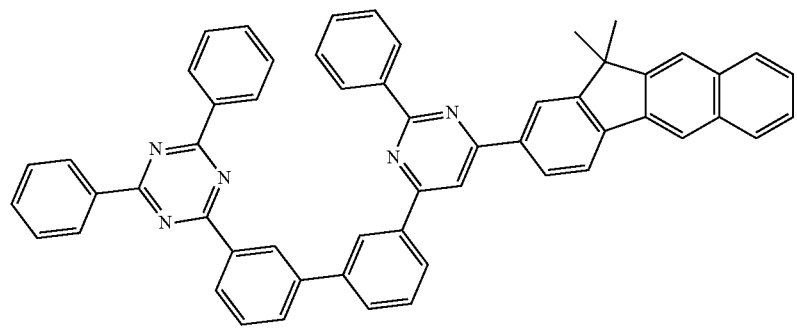
256
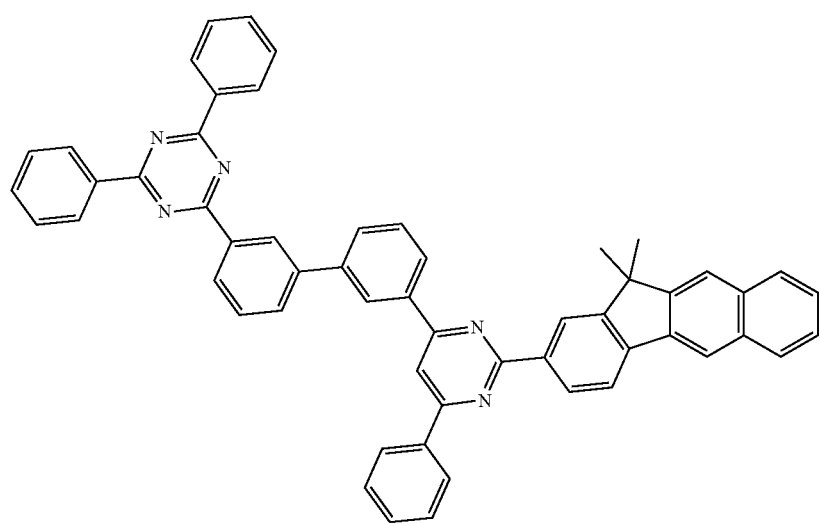

257
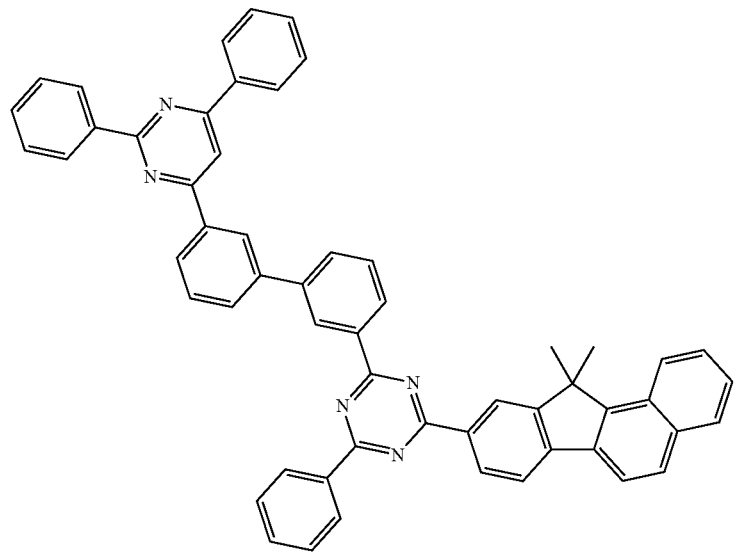
258
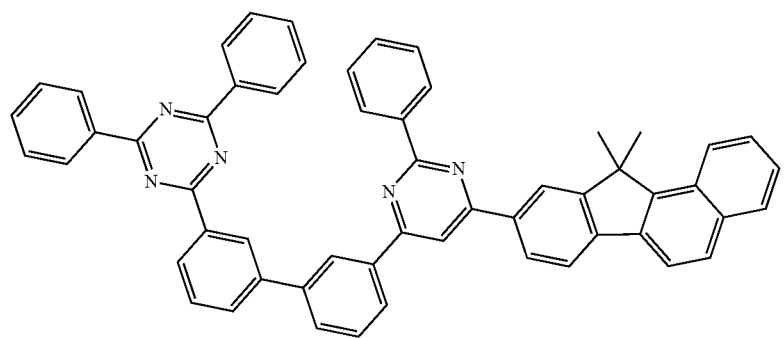
259
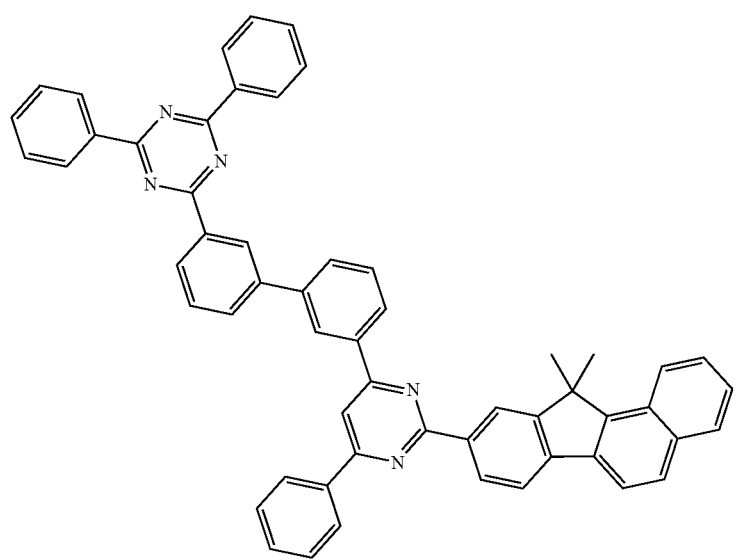

260
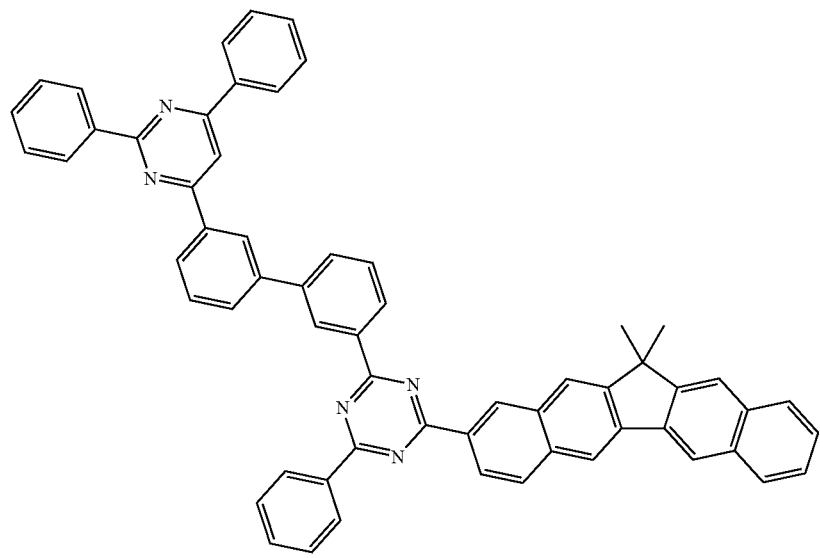
261
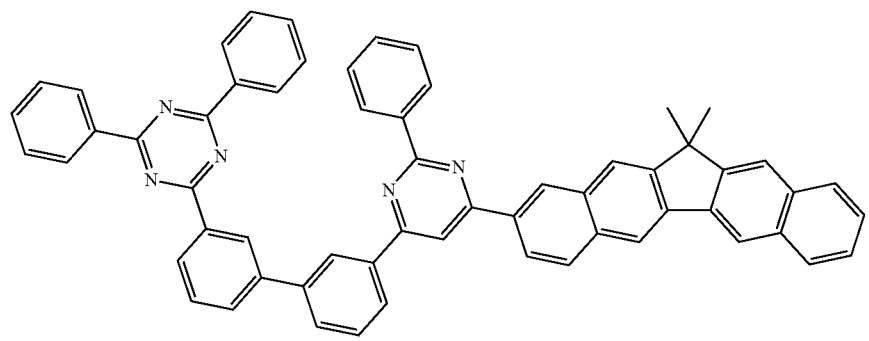
262
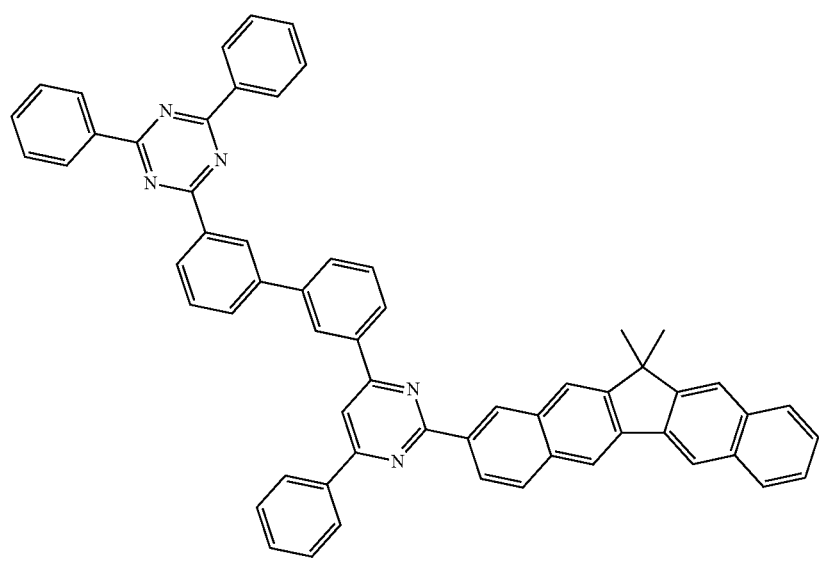

-continued
263
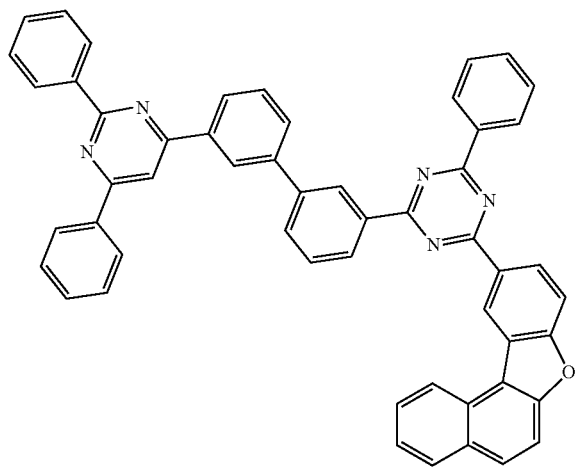
264
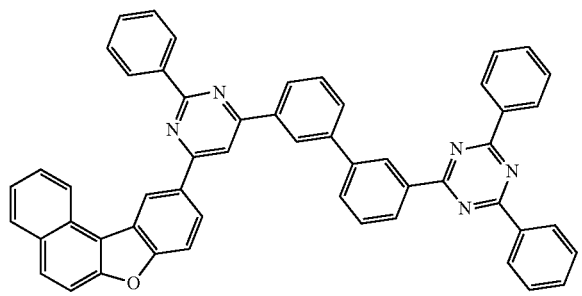
265
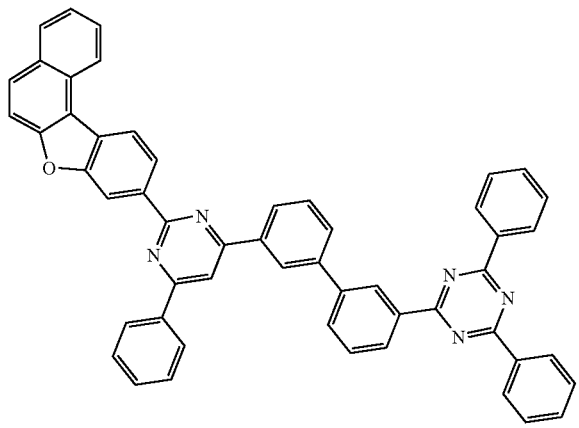
266
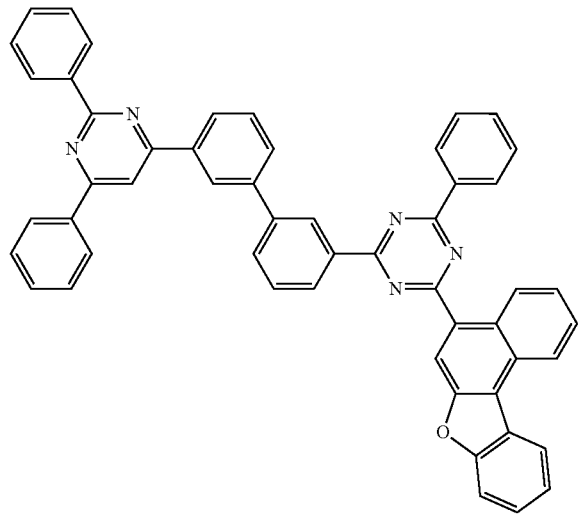
267
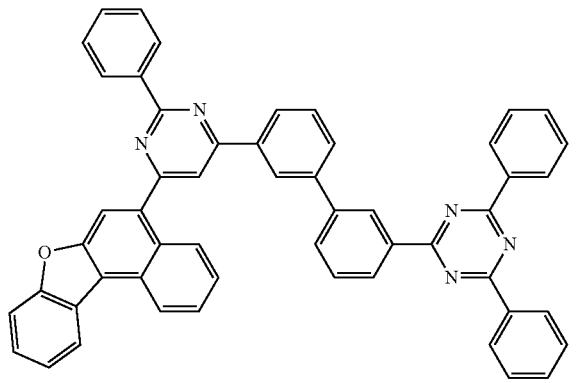
268
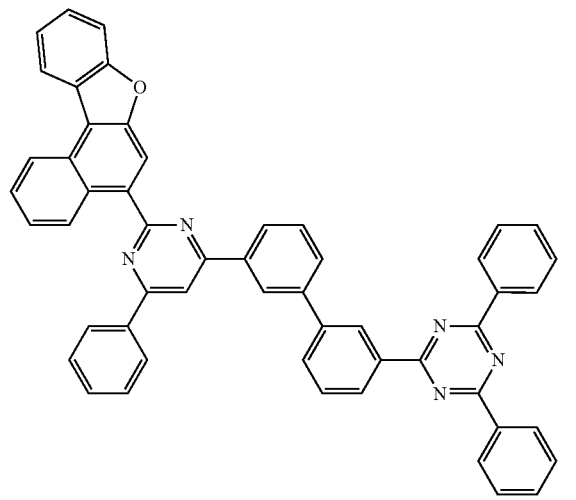

269
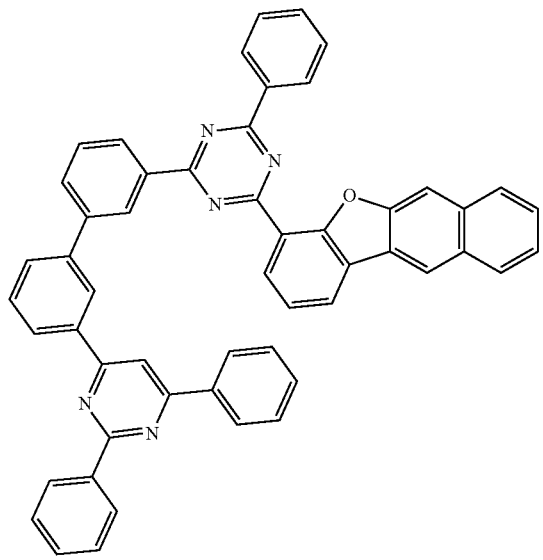
270
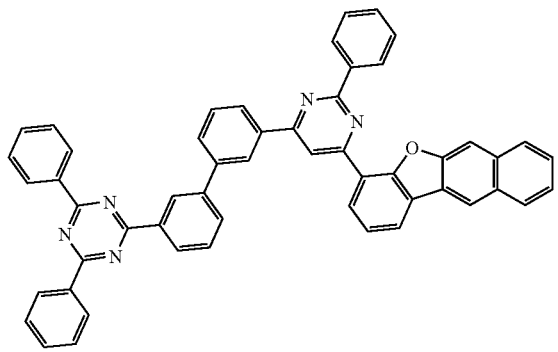
271
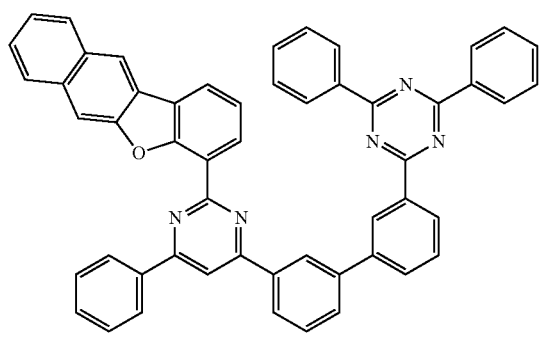
272
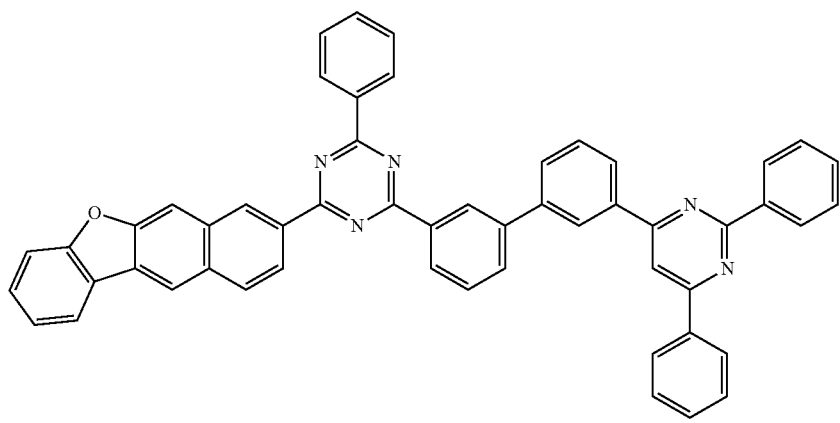

273
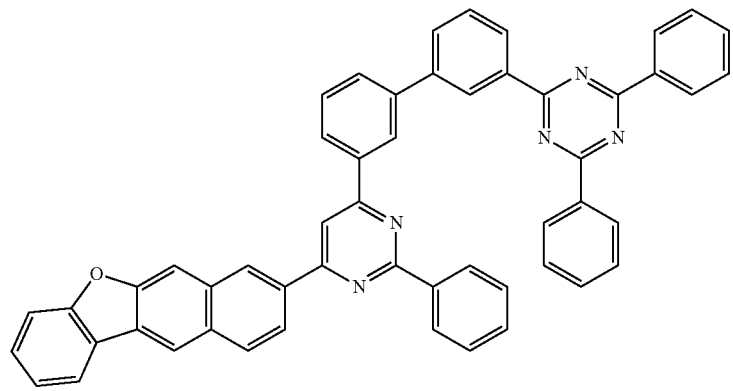
274
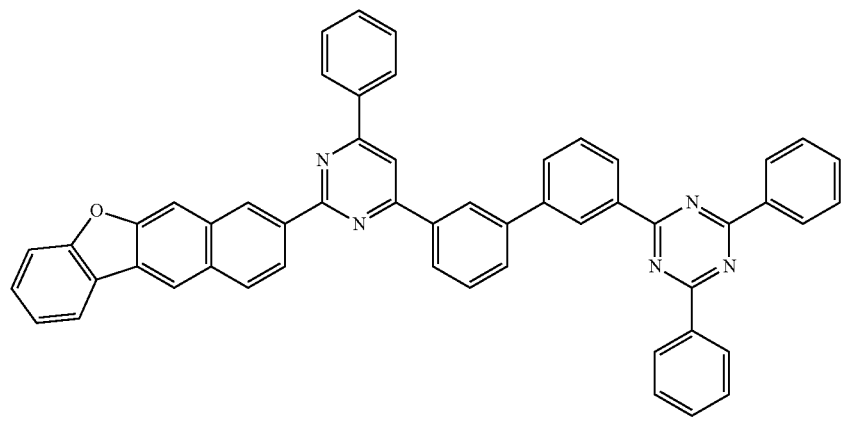
275
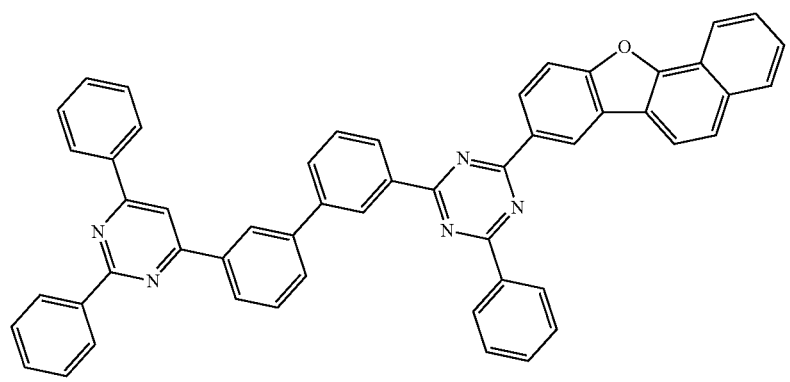
276
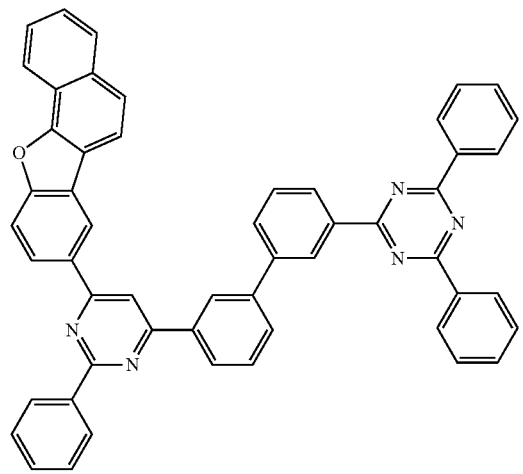

277
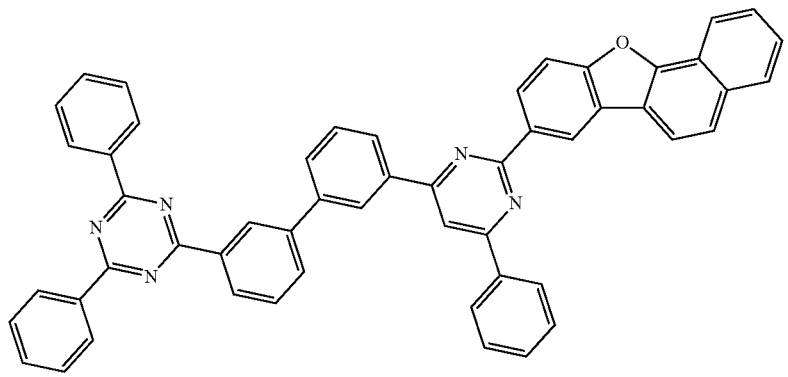
278 279
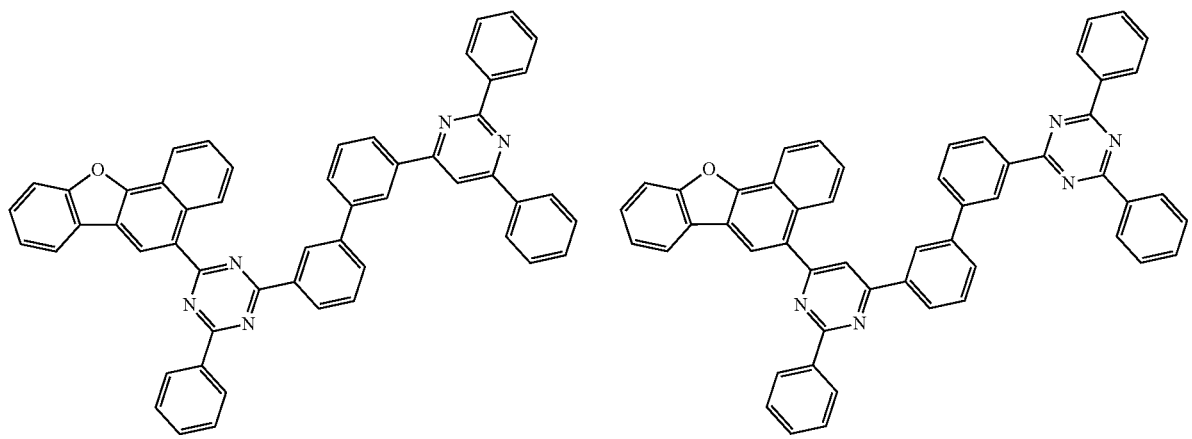
280 281
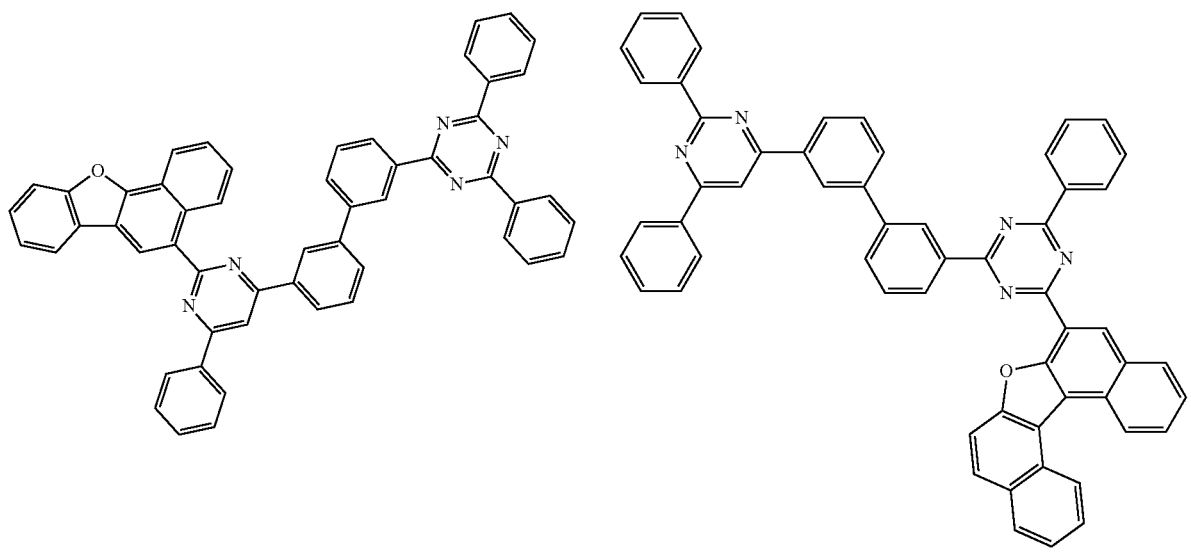

-continued
282
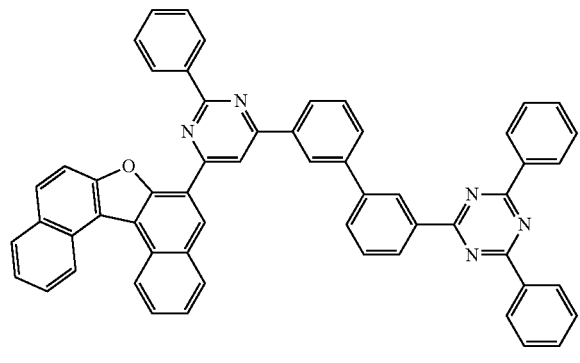
283
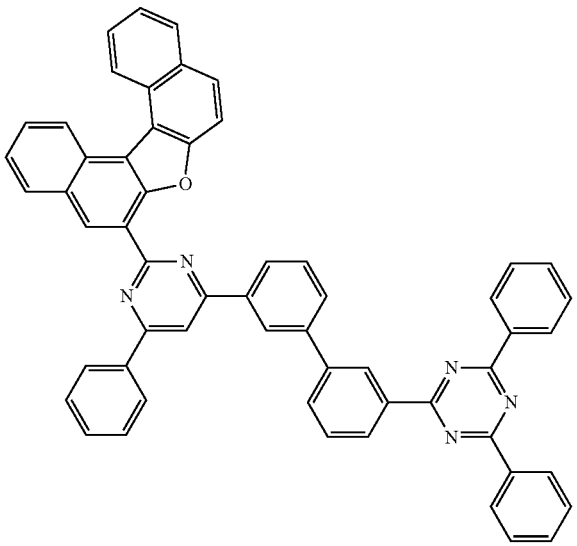
284
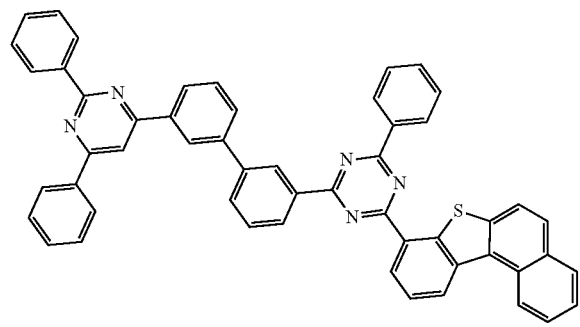
285
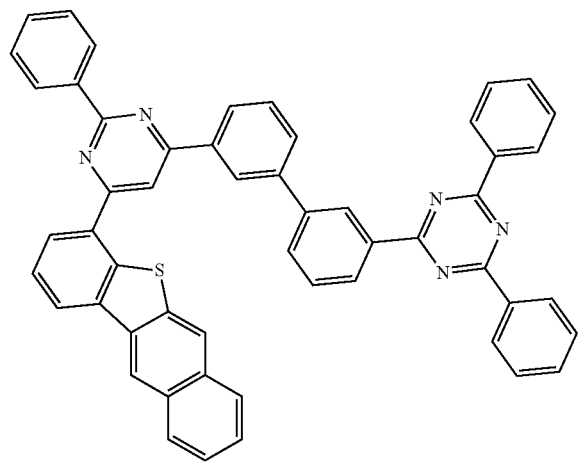
286
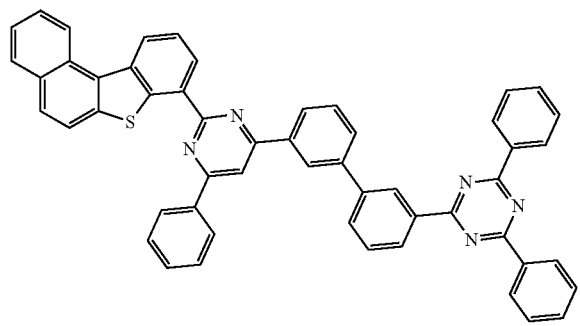
287
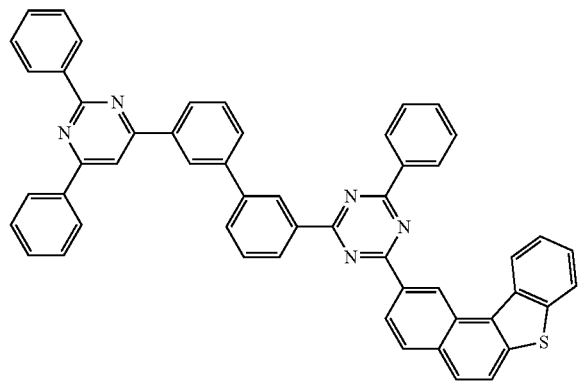

288
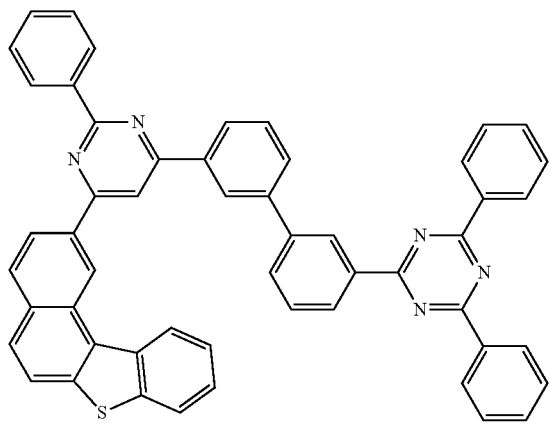
289
290
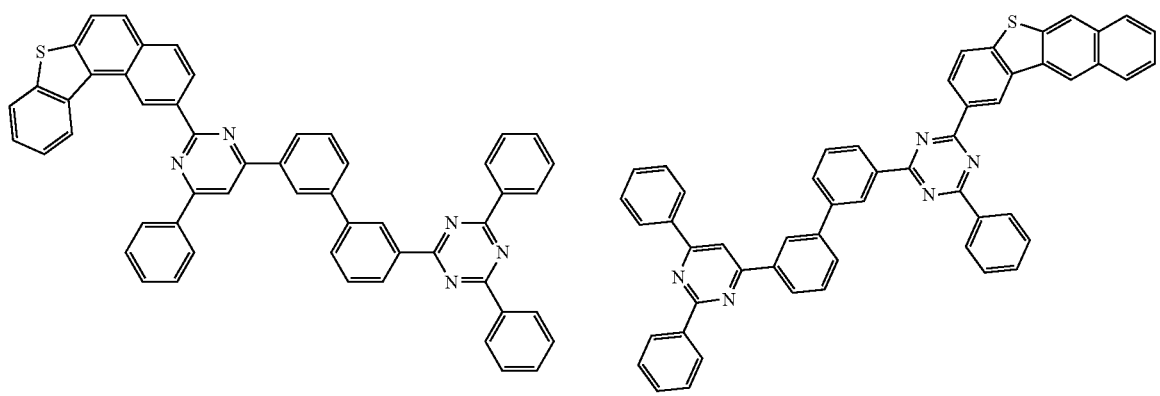
291
292
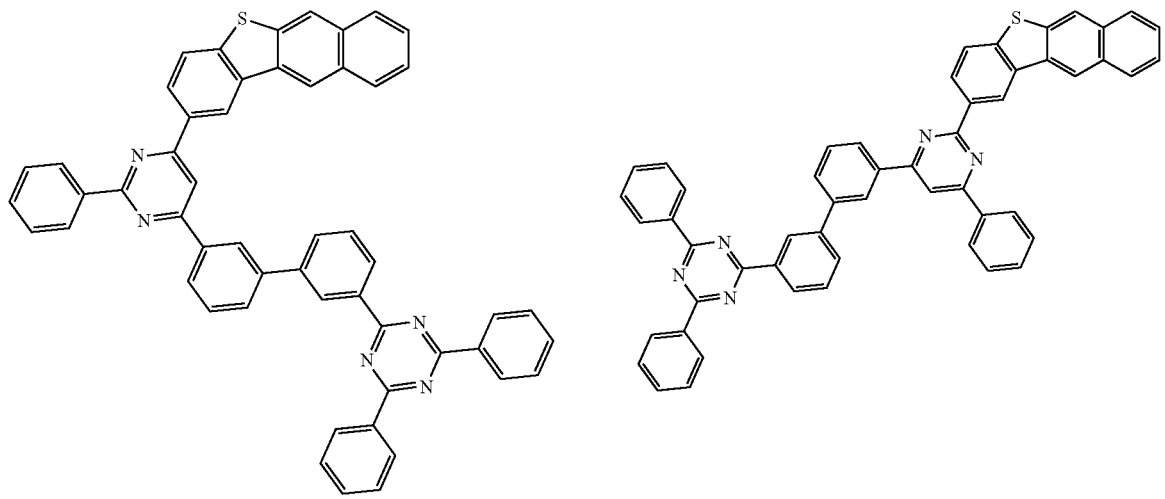

293
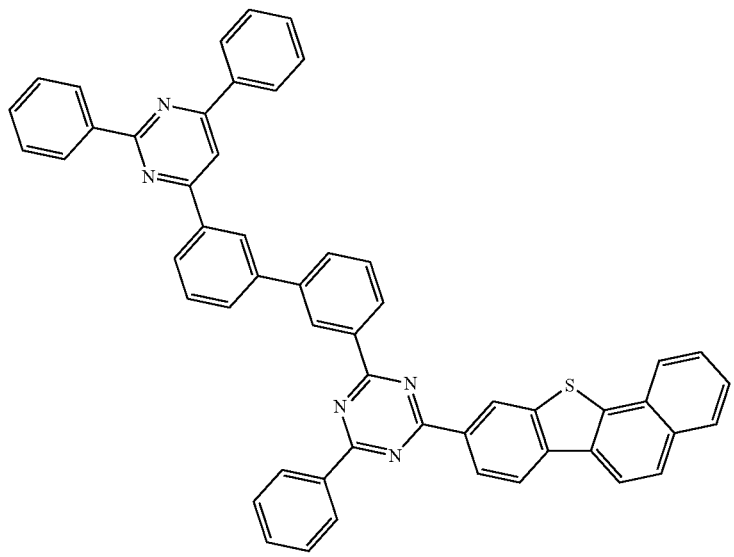
294
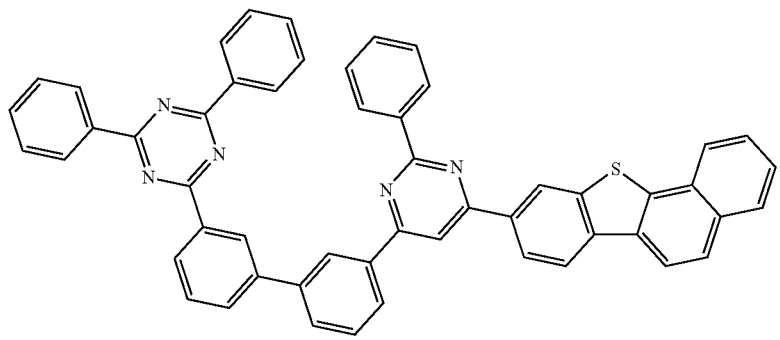
295
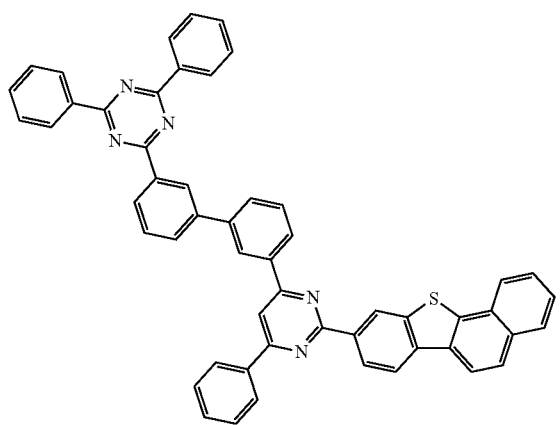
296
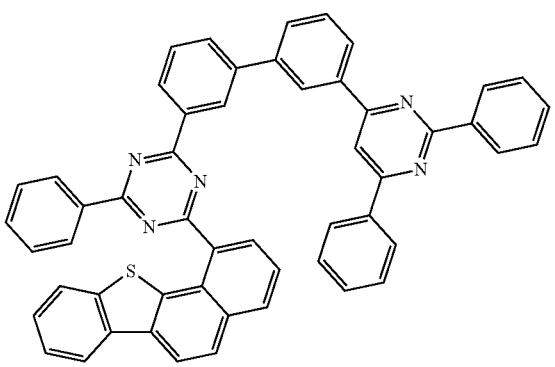

-continued
297
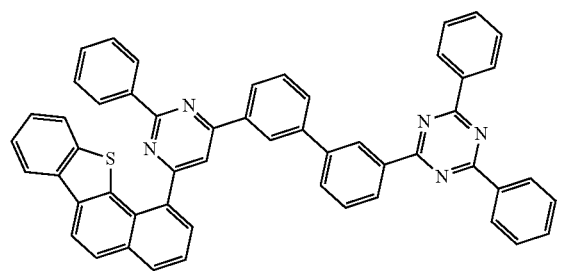
298
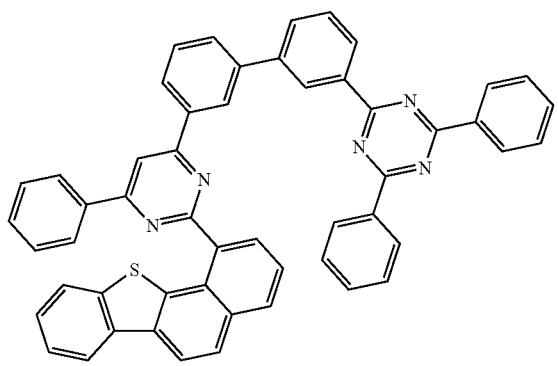
299
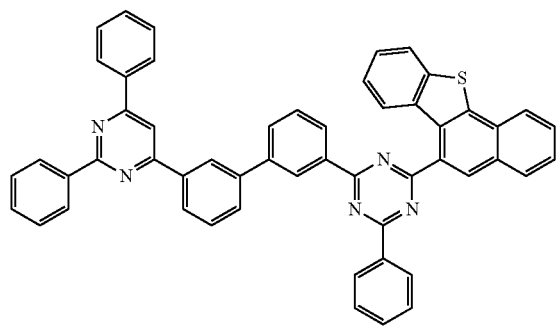
300
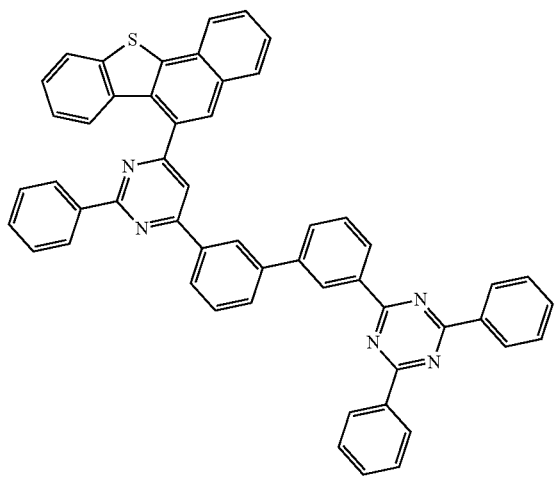
301
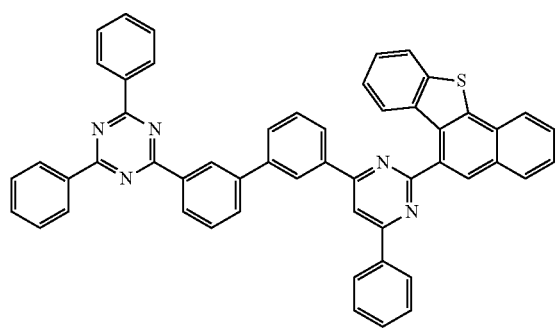
302
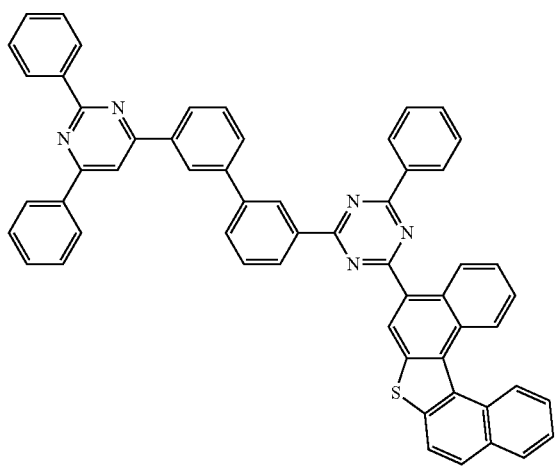

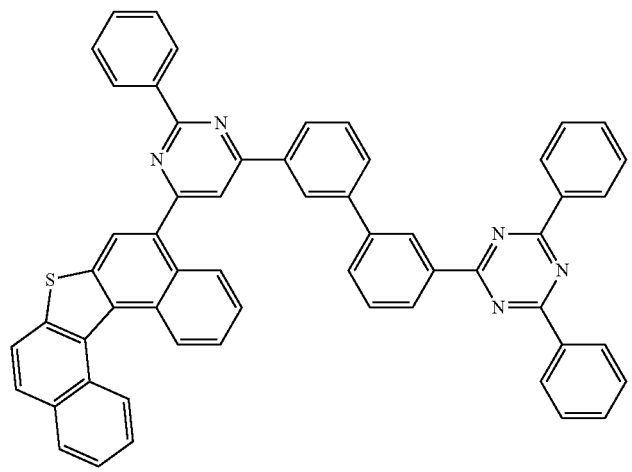
303
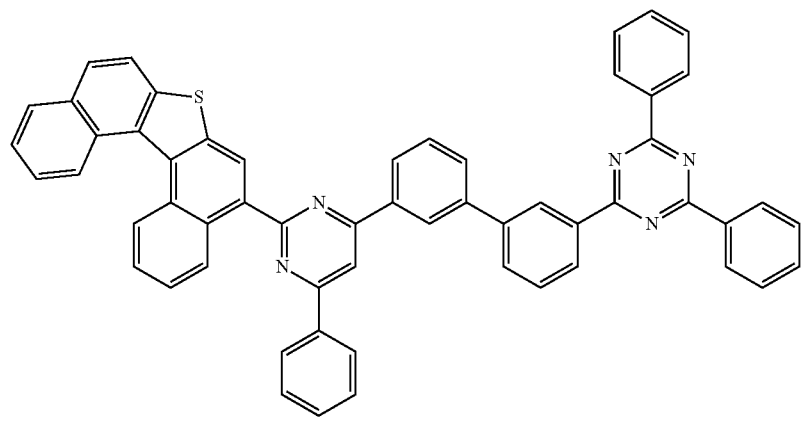
304
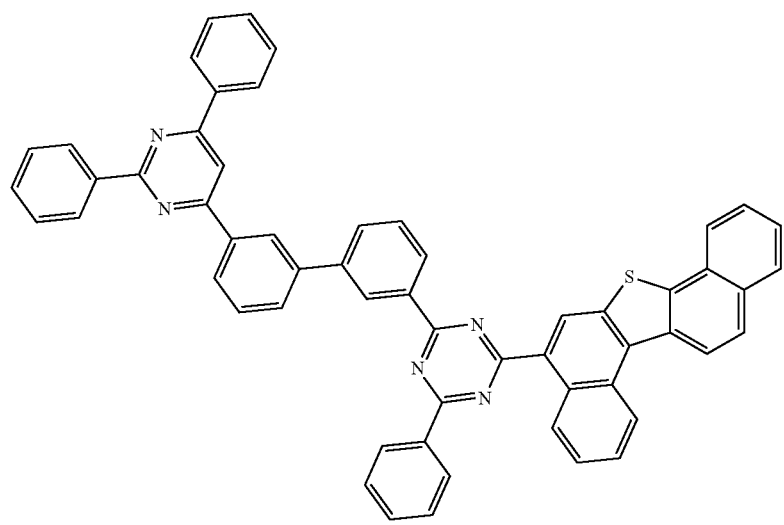
305

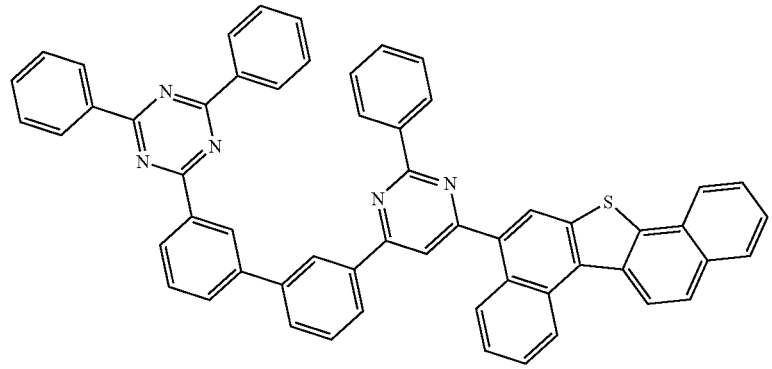
306
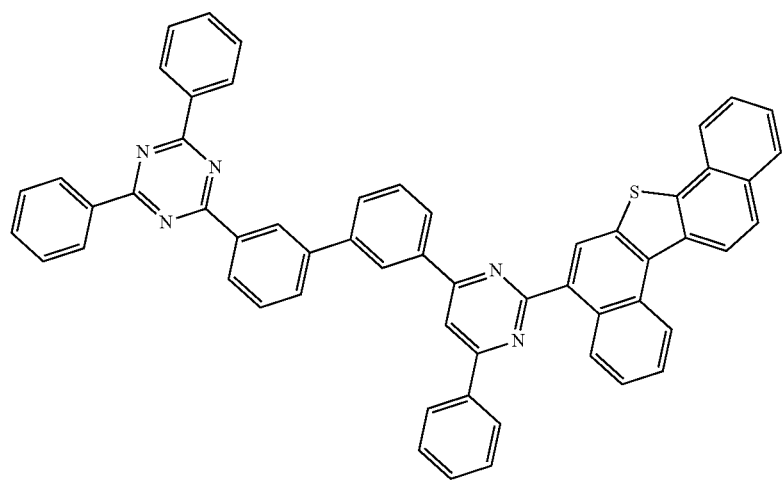
307
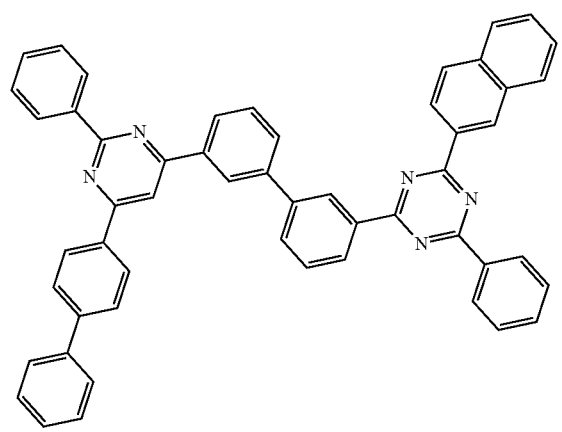
308
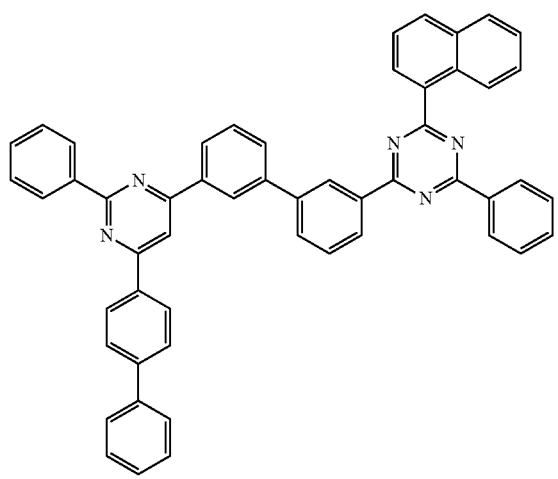
309

| 310 | 311 |
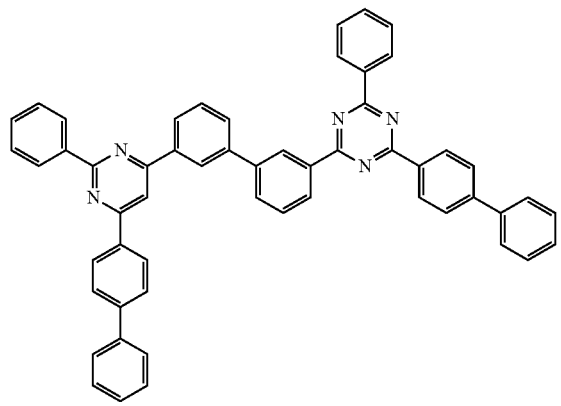 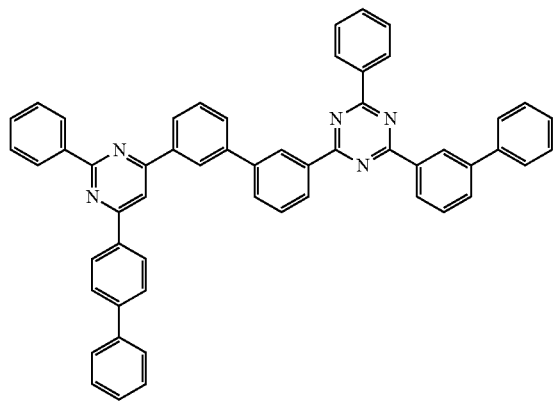
| 312 | 313 |
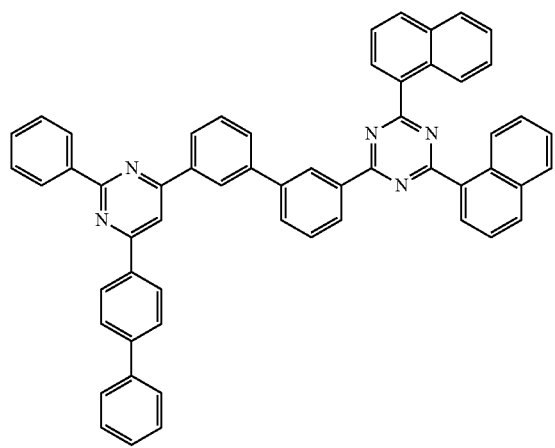 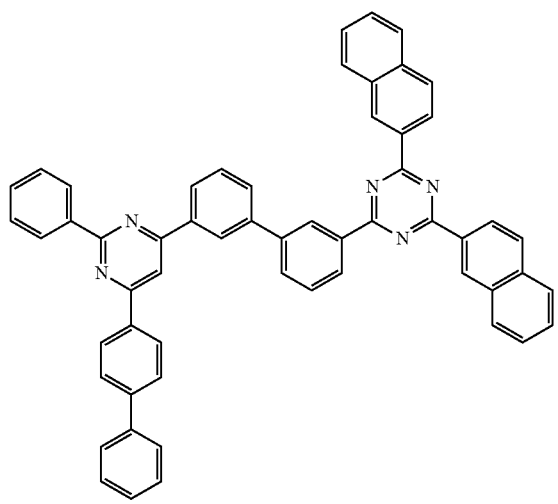
| 316 | 317 |
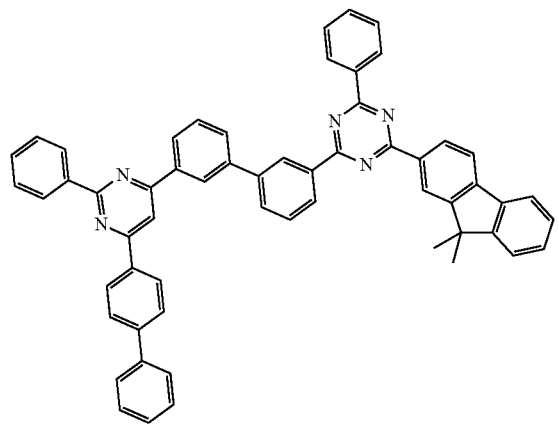 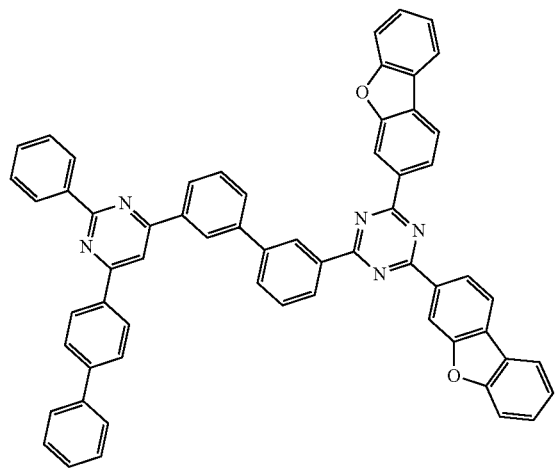

318
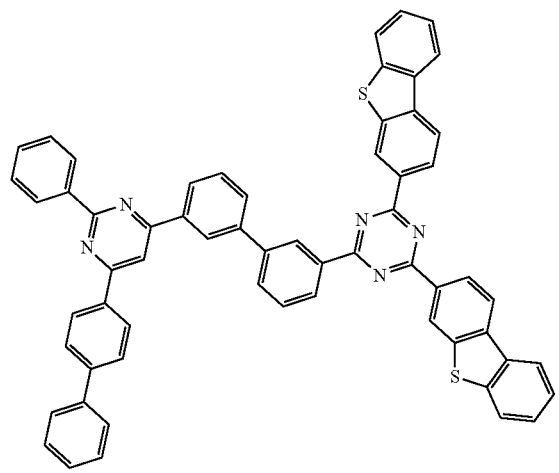
319
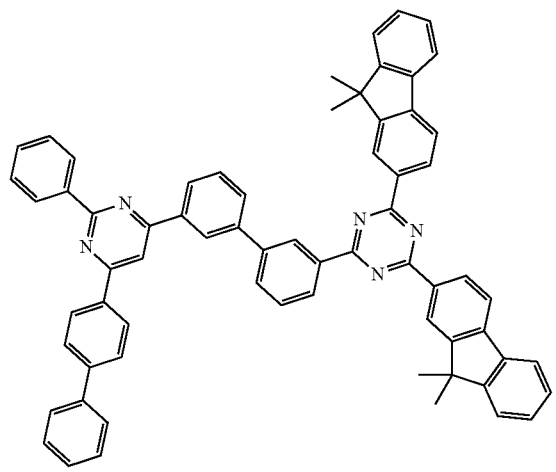
321
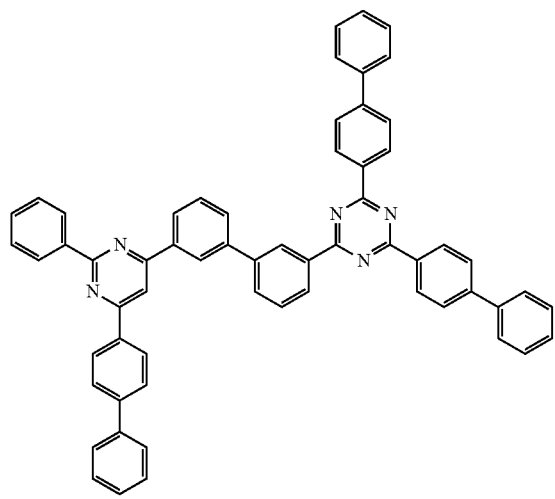
322
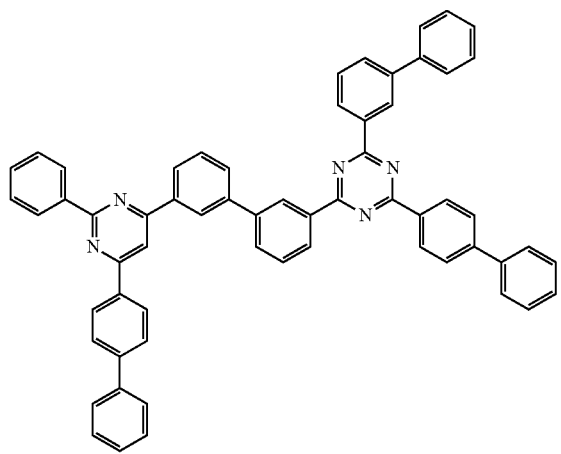
323
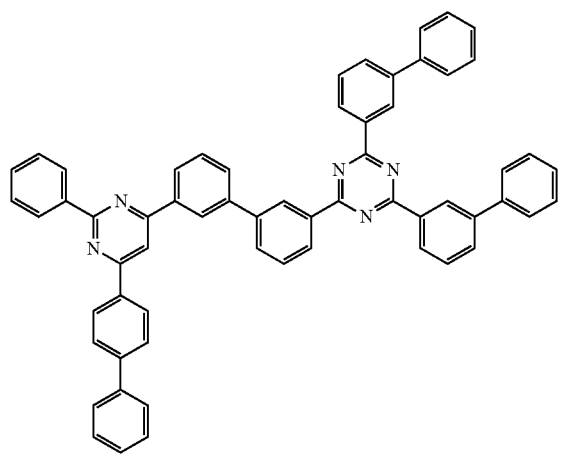
324
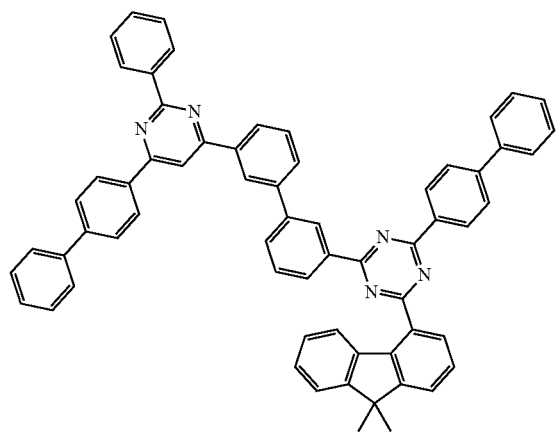

-continued
325
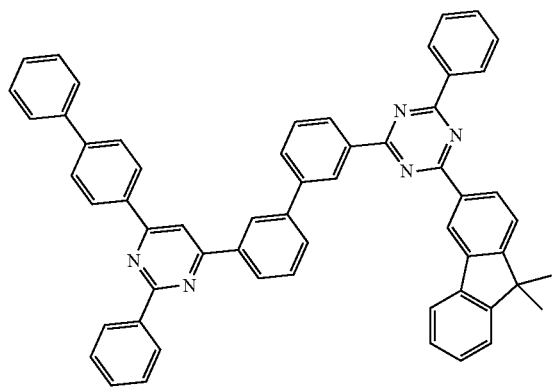
326
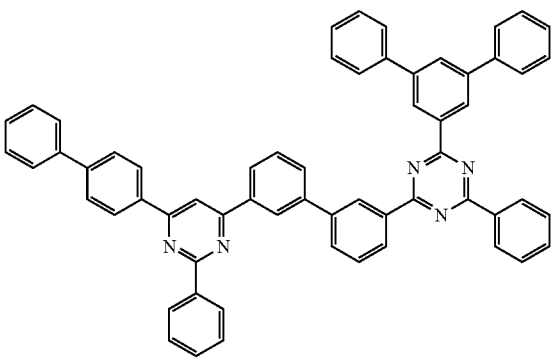
327
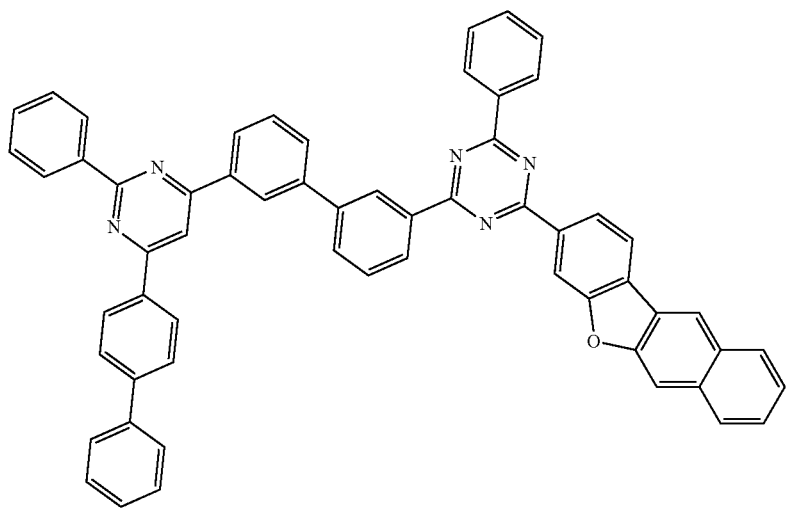
328
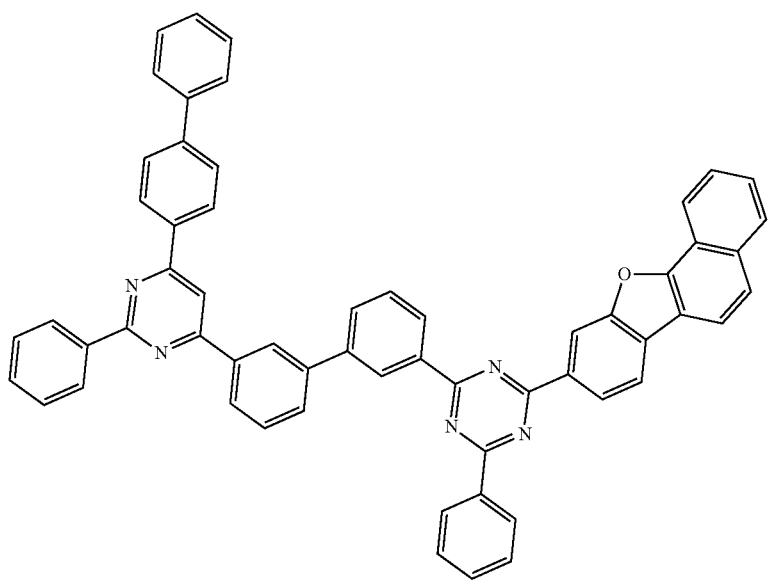

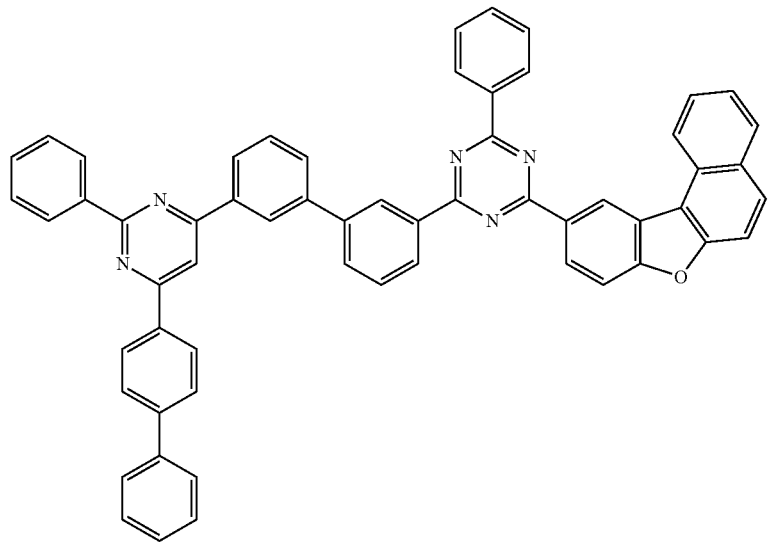
329
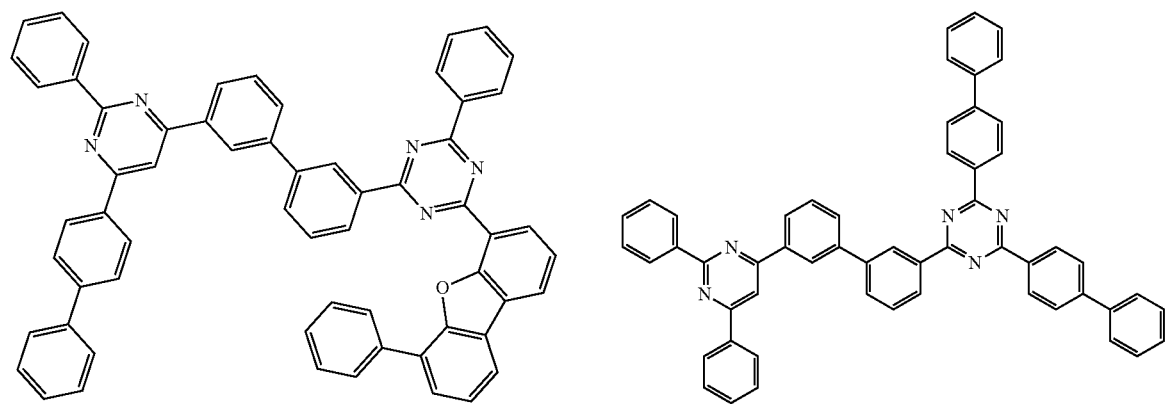
332
333
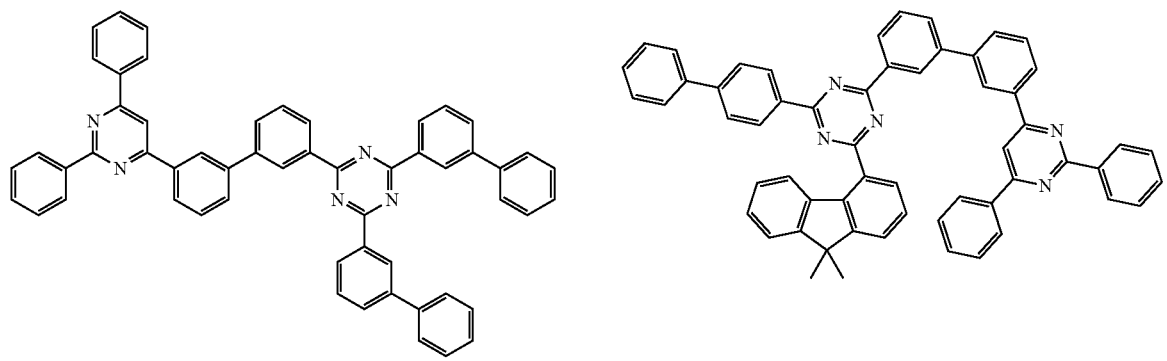
334
335

| 336 | 337 |
|---|---|
| 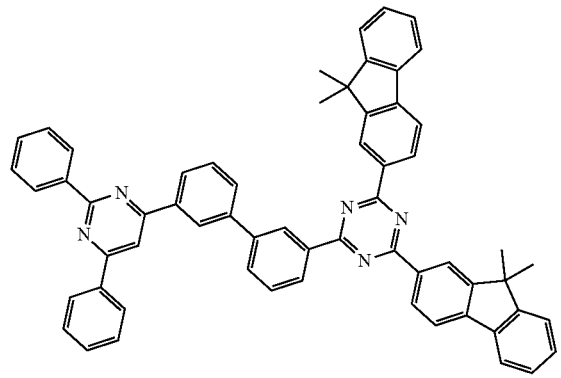 | 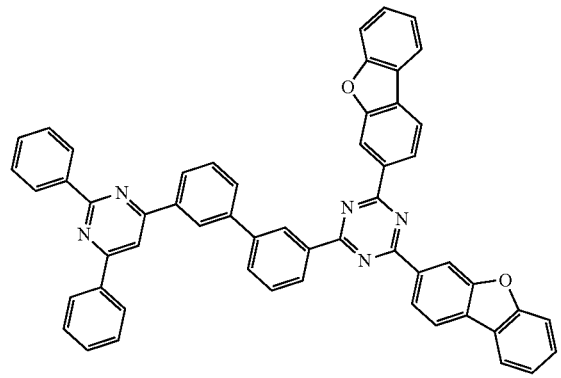 |
| 339 | 340 |
| 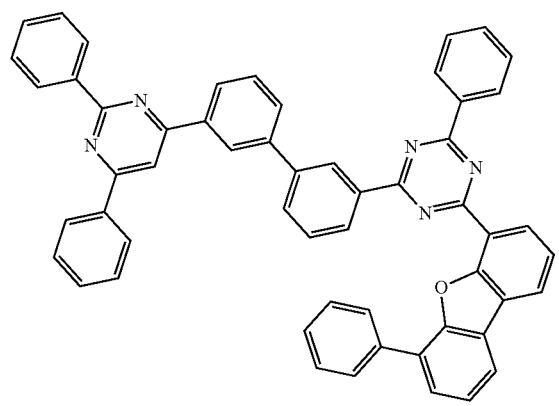 | 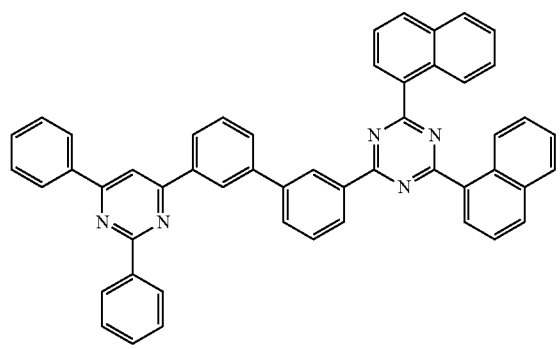 |
| 341 | 342 |
| 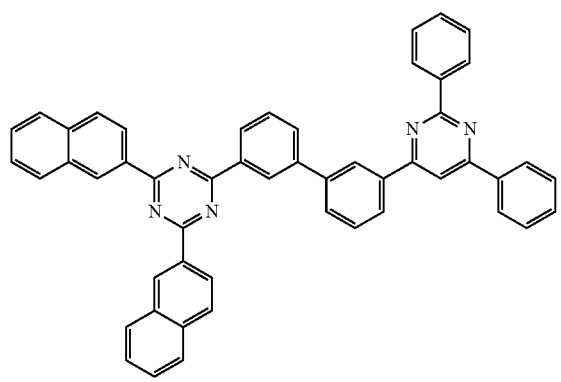 | 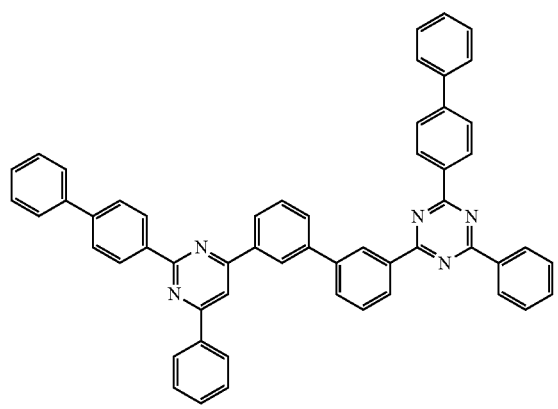 |

343
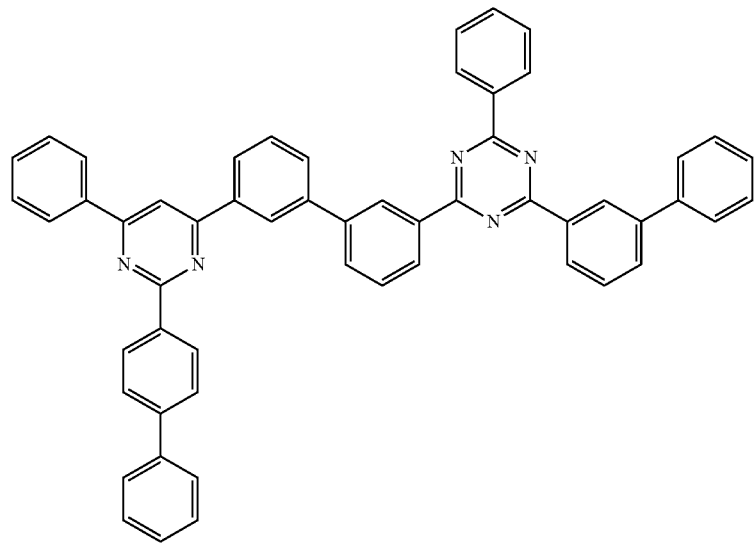
344
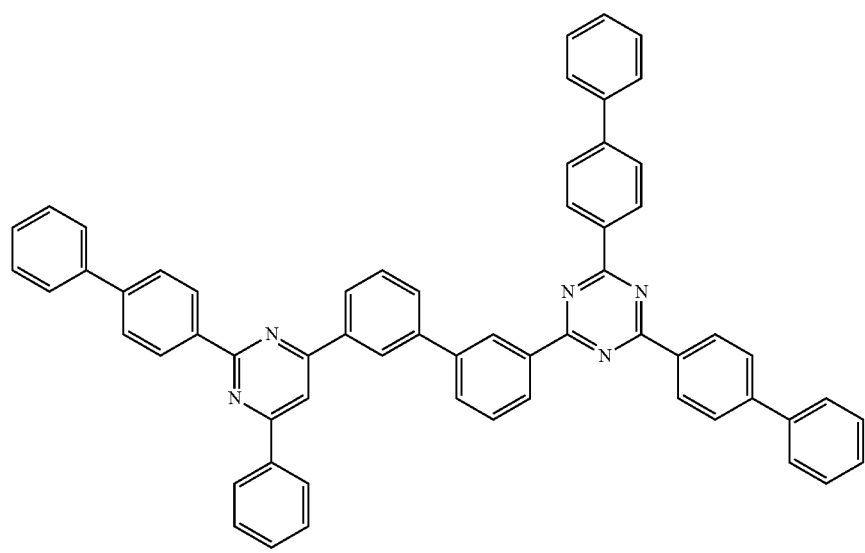

345
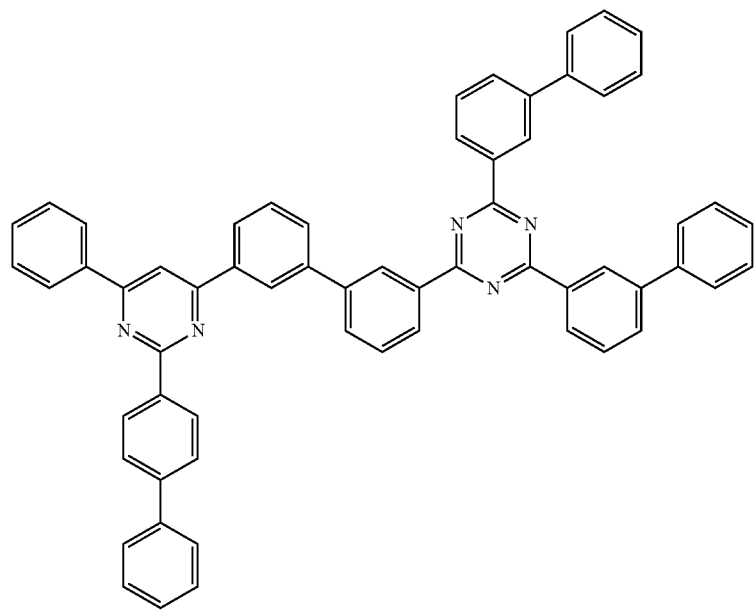
346
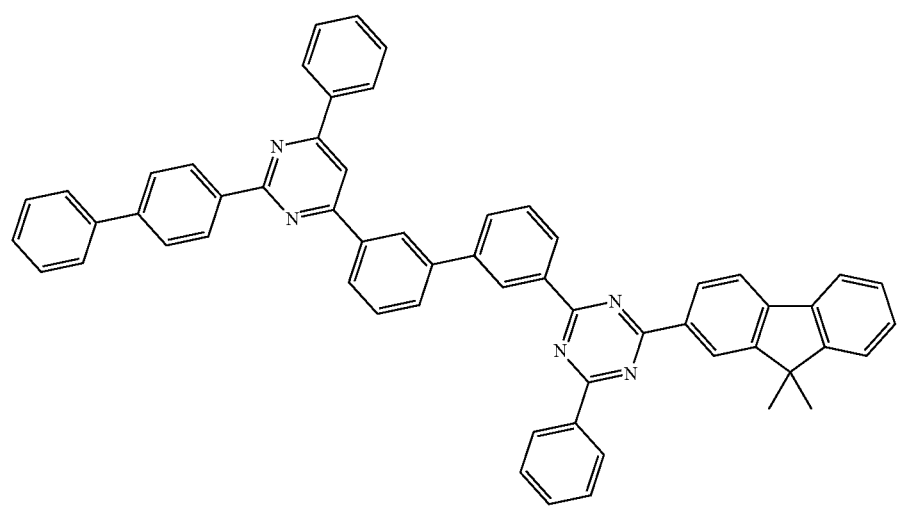

-continued
347
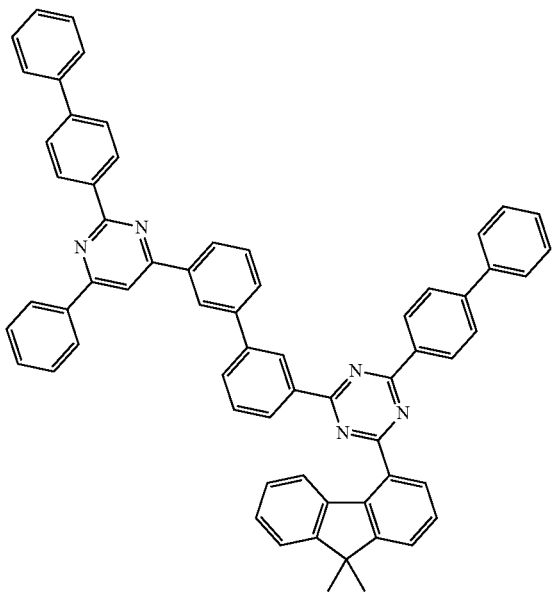
348
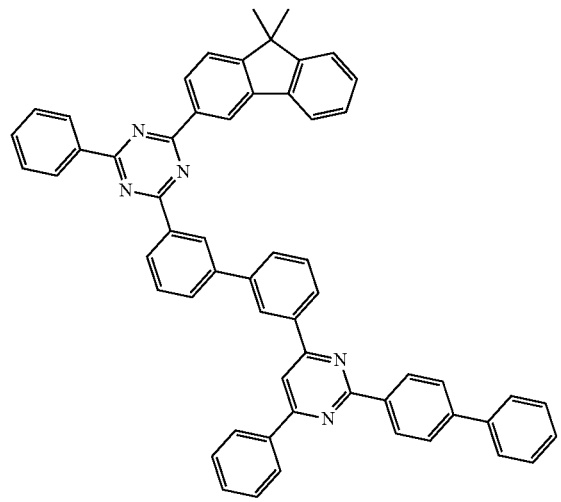
349
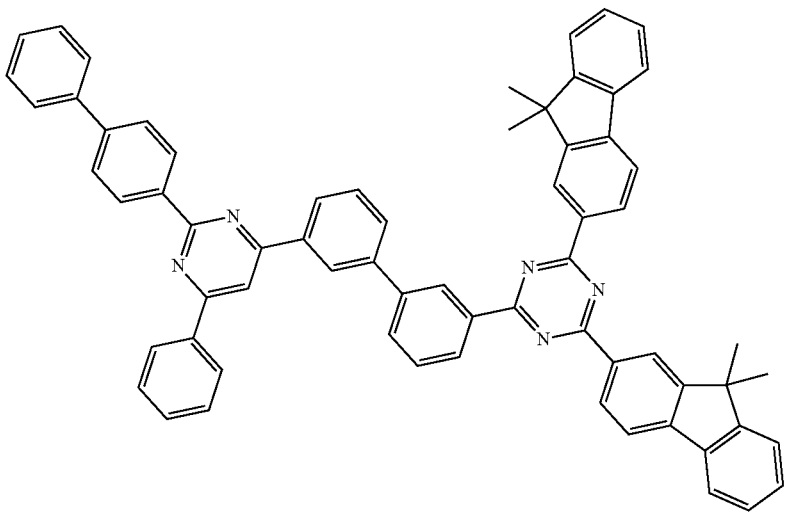
350
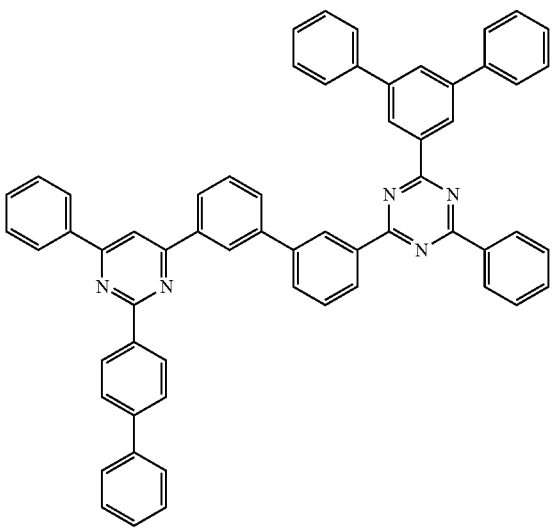
352
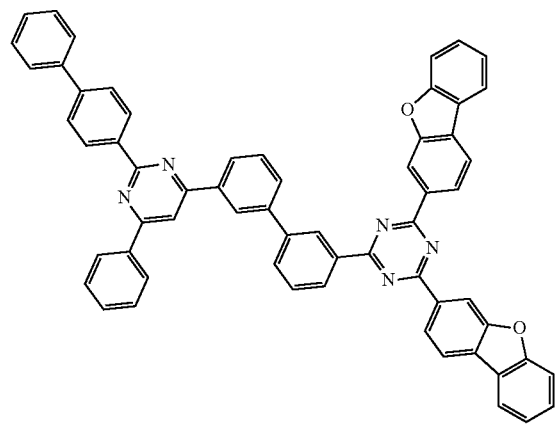

-continued
353
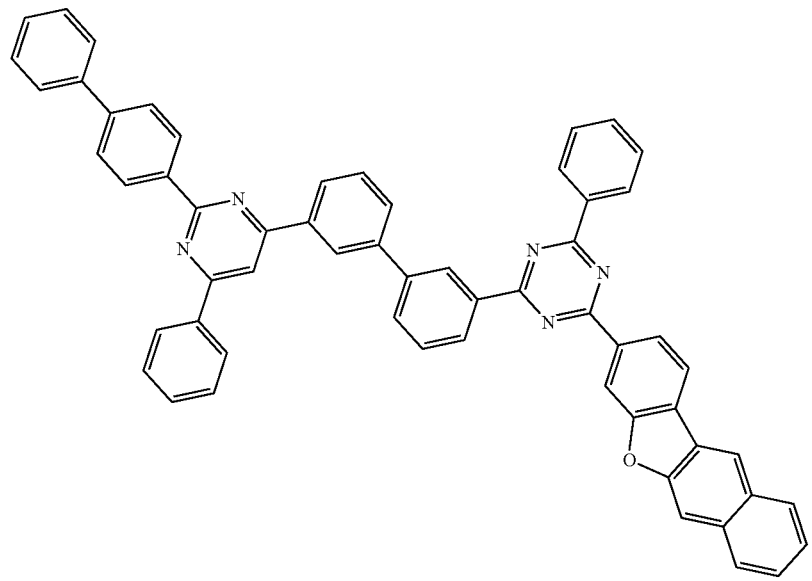
354
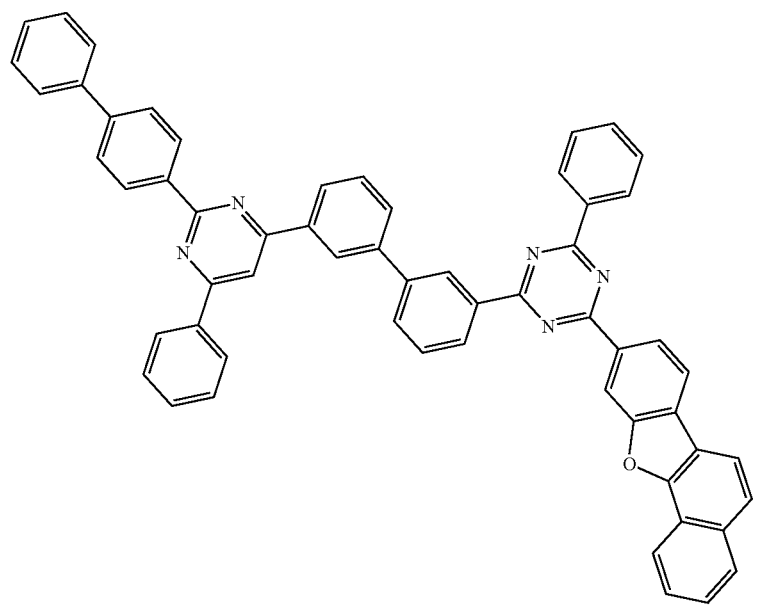
355
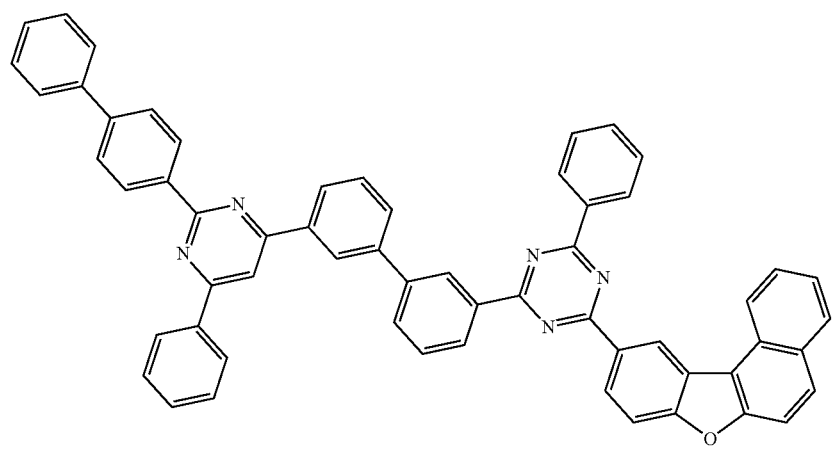

-continued
358
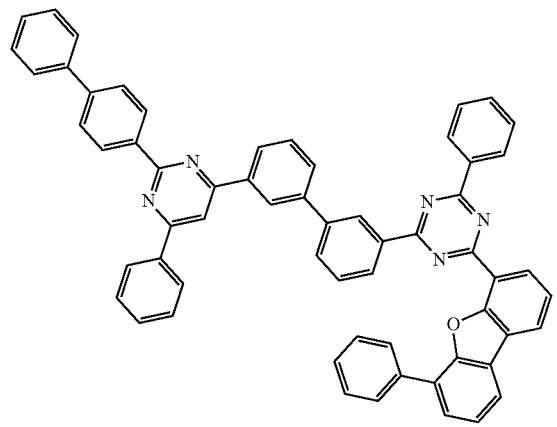
359
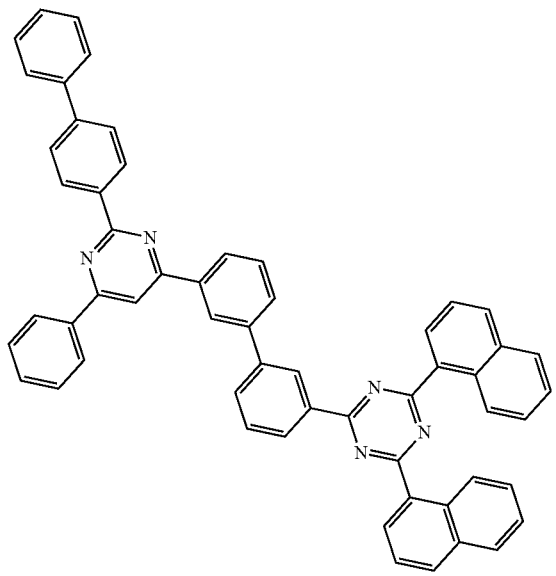
360
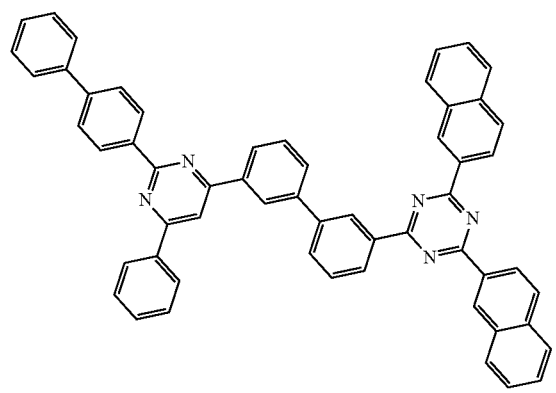
361
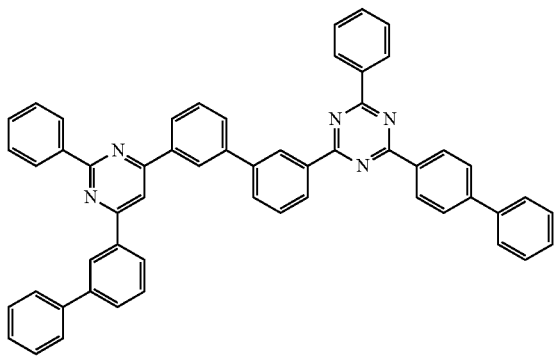
362
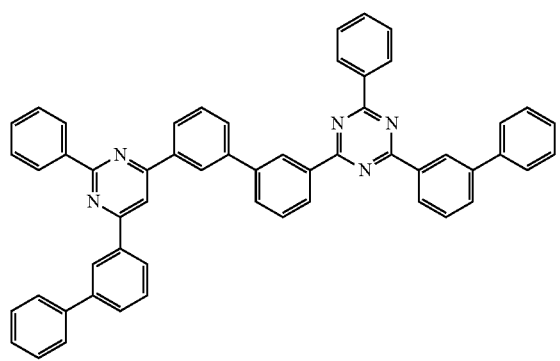
363
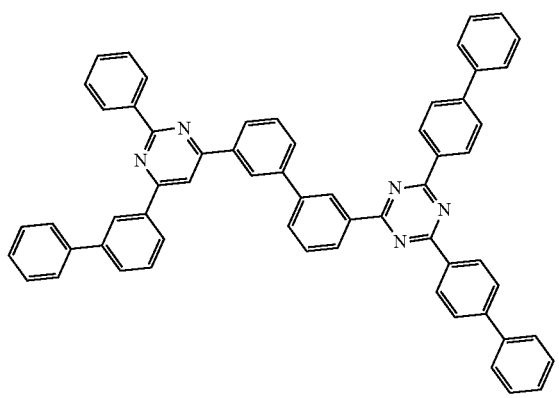

-continued
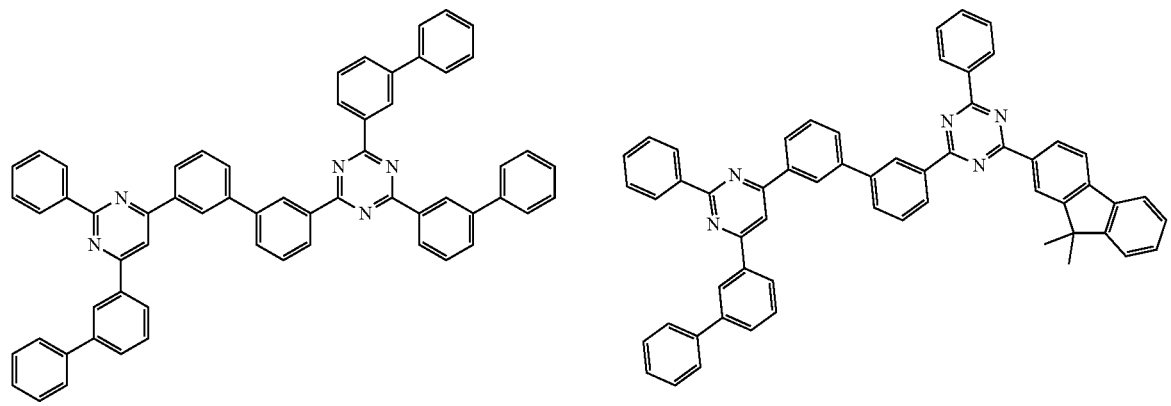
364
365
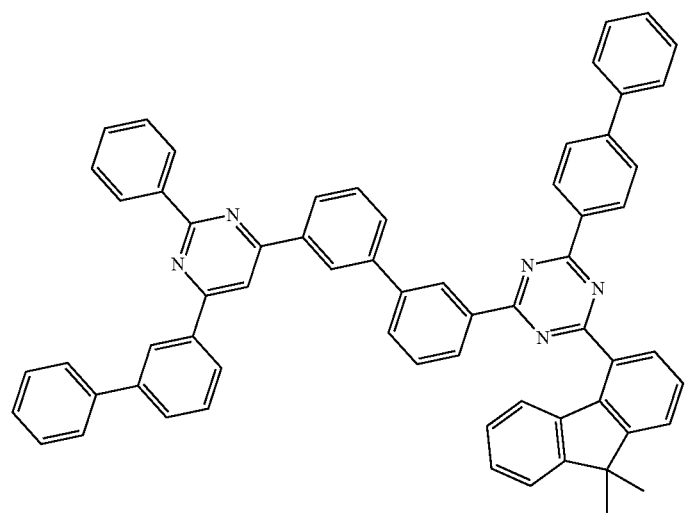
366
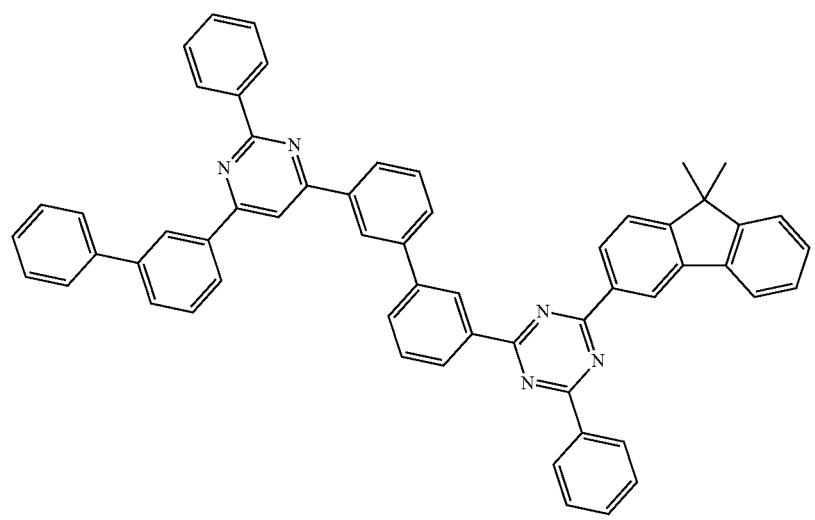
367

-continued
368
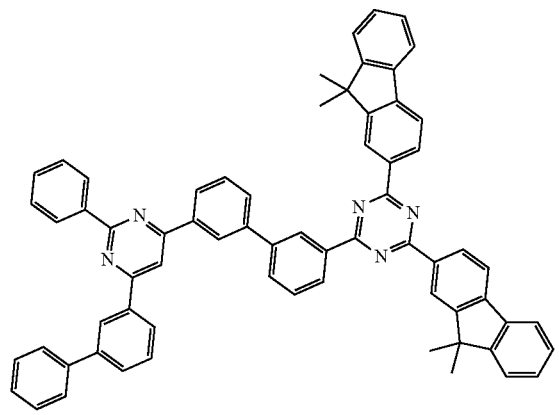
369
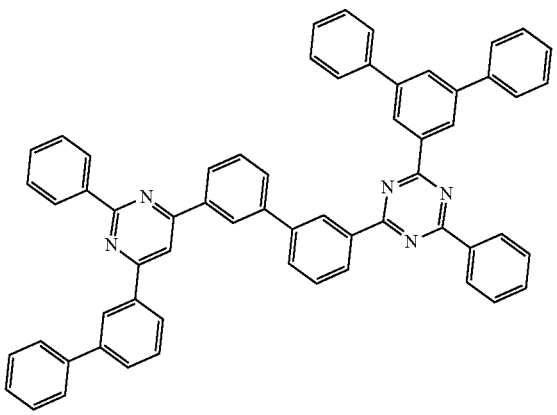
371
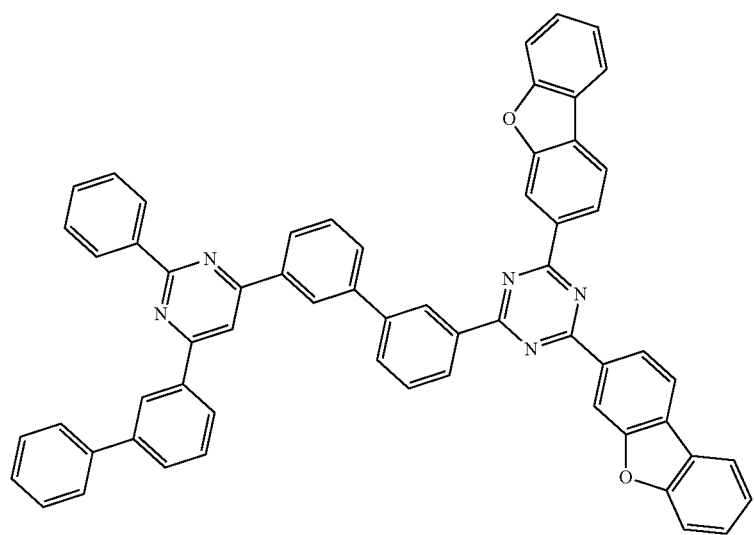
372
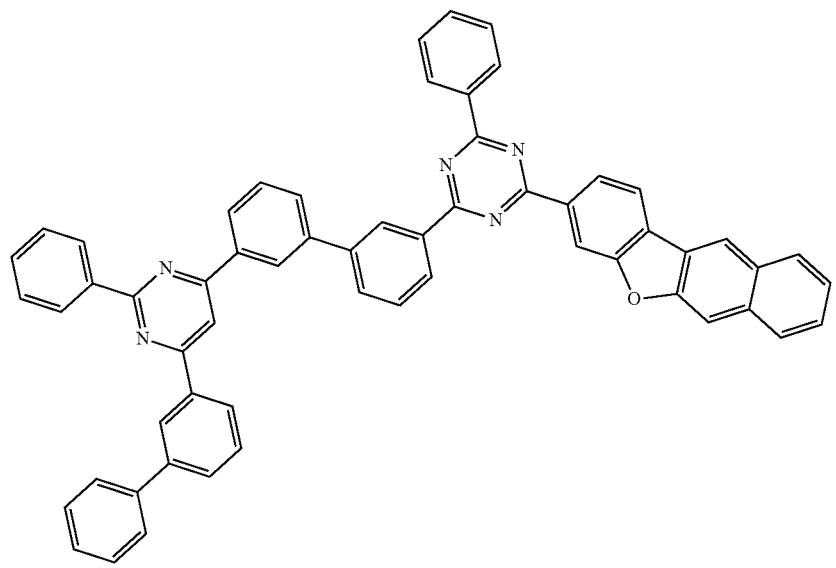

373
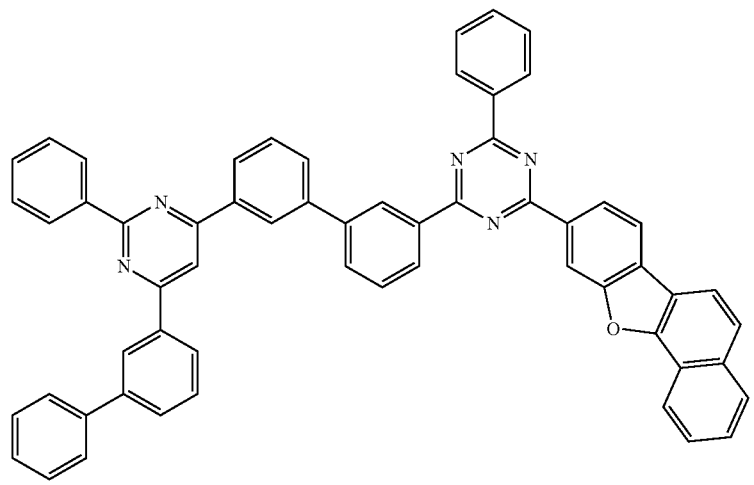
374
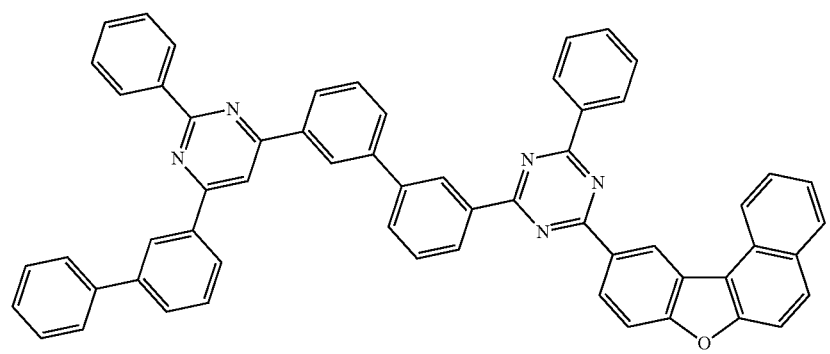
377
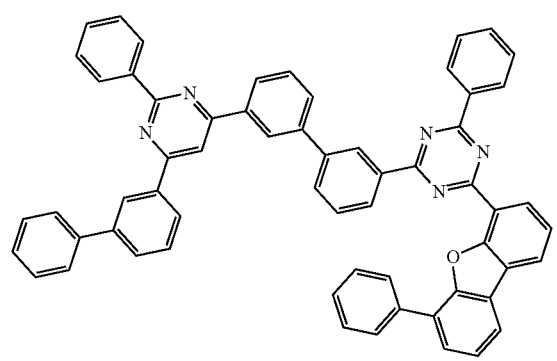
378
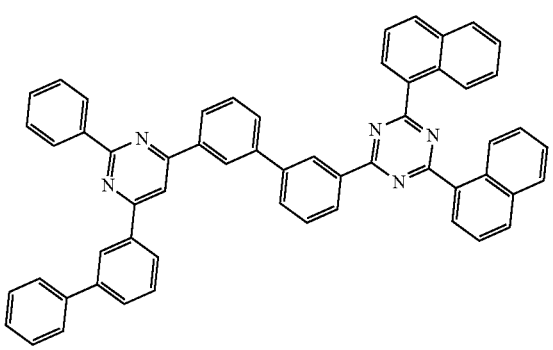

-continued
379
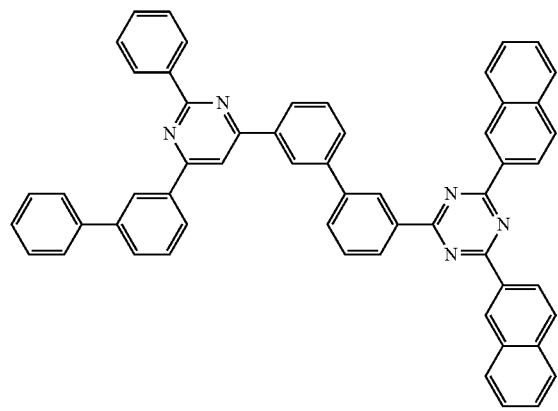
380
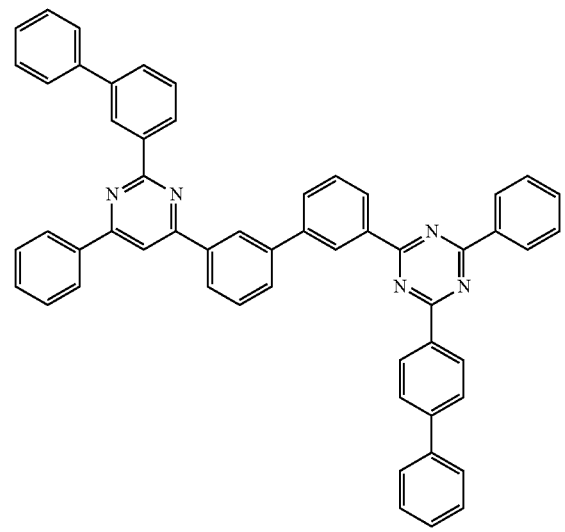
381
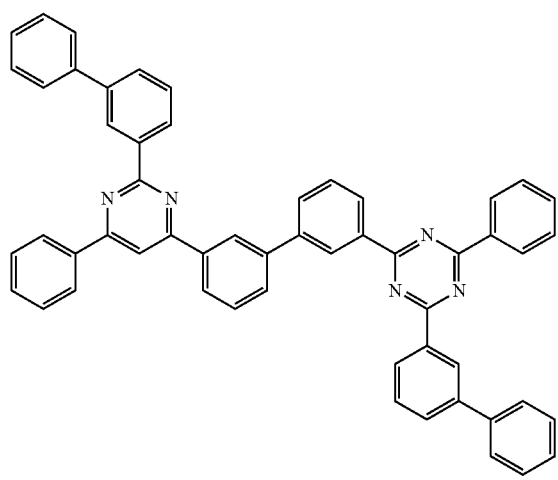
382
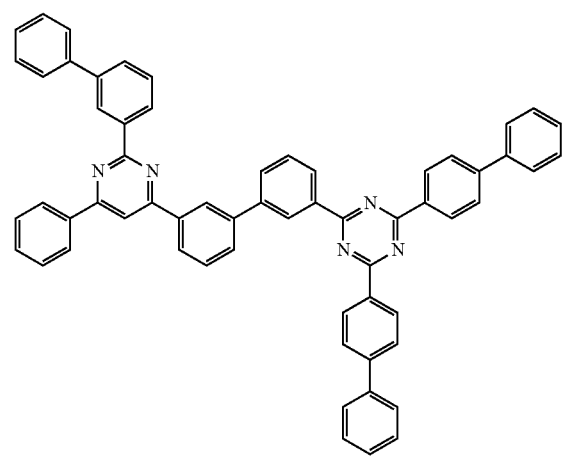
383
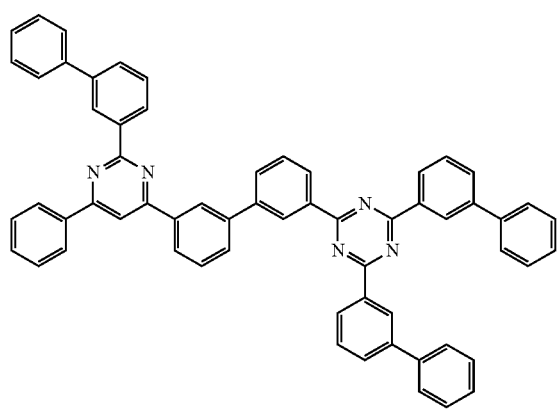
384
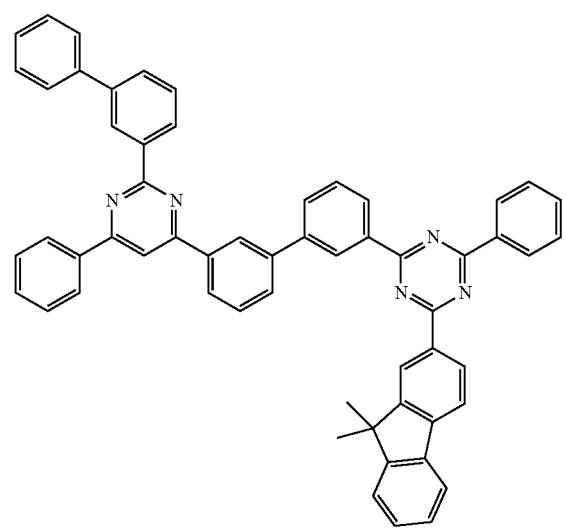

385
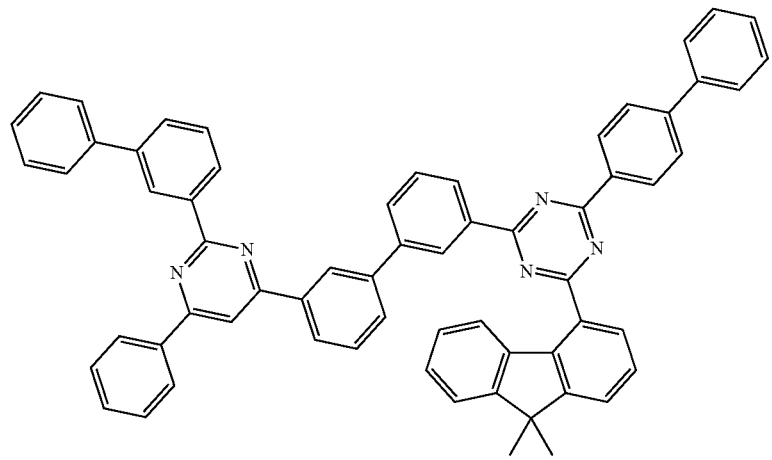
386
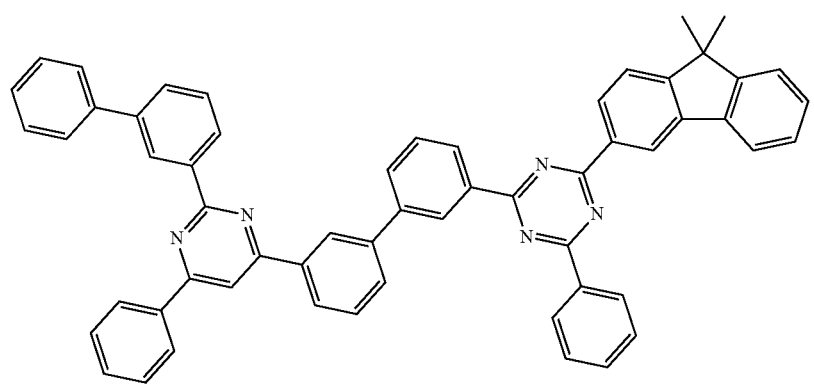
387
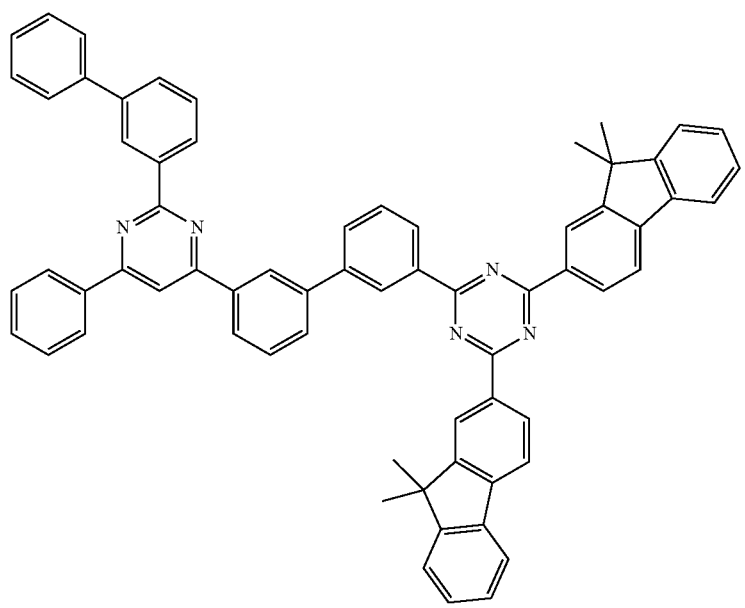

713
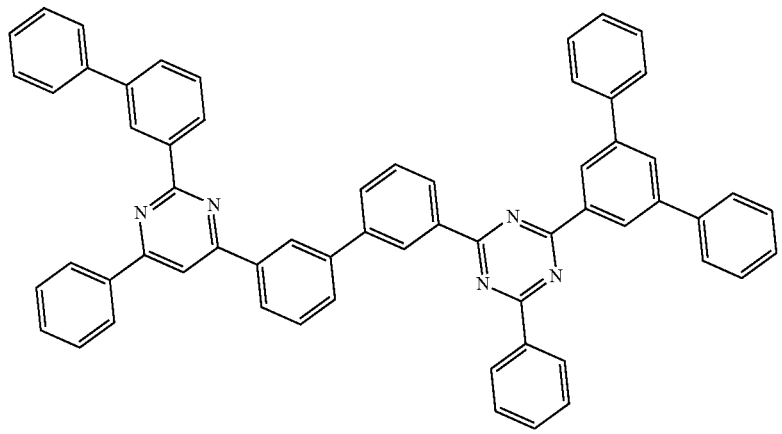
388
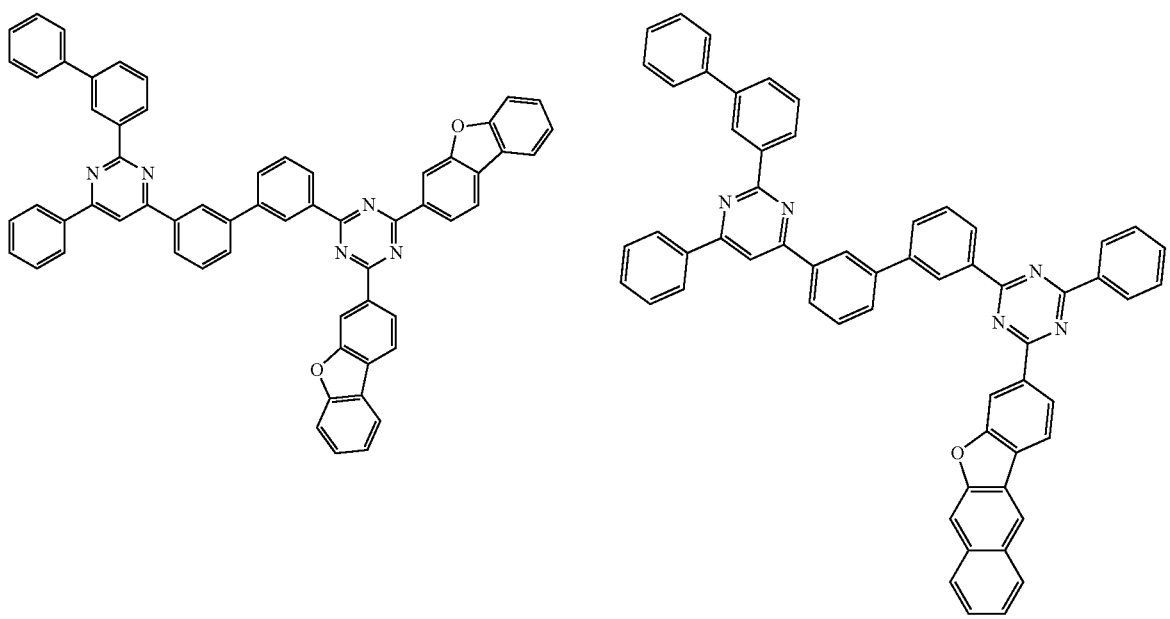
390
391
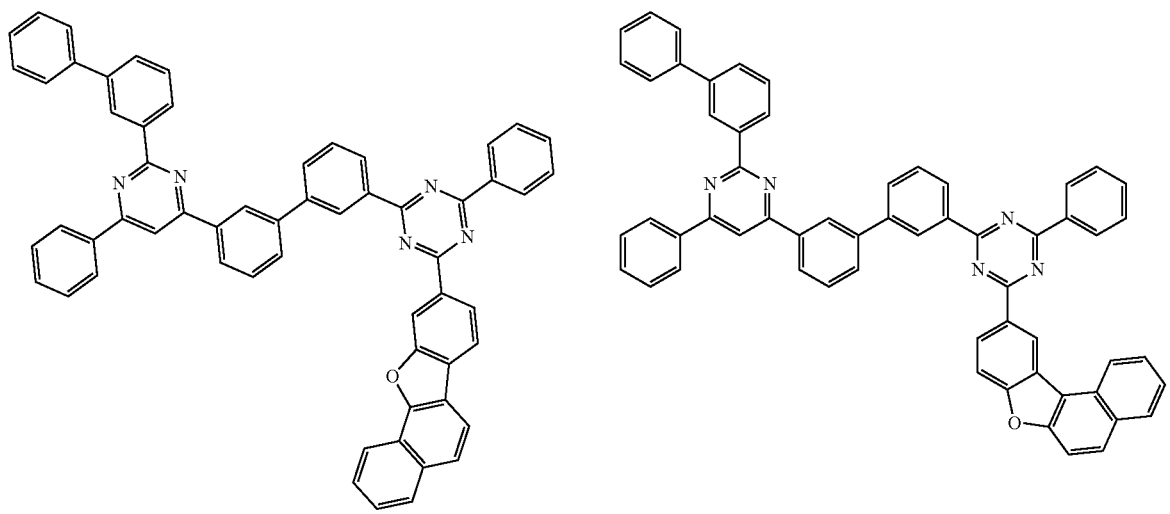
392
393

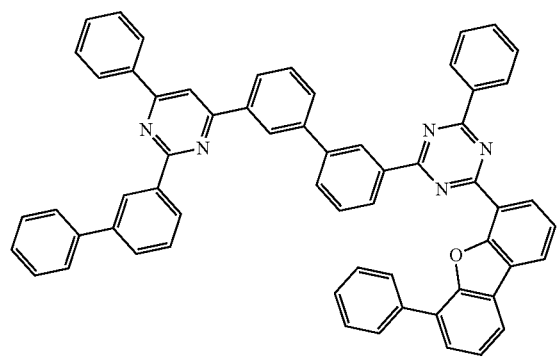
396
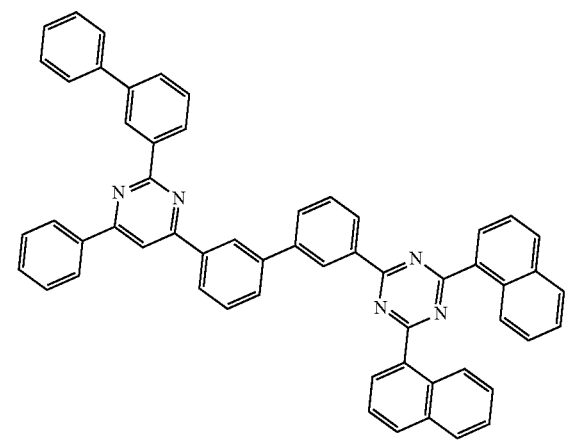
397
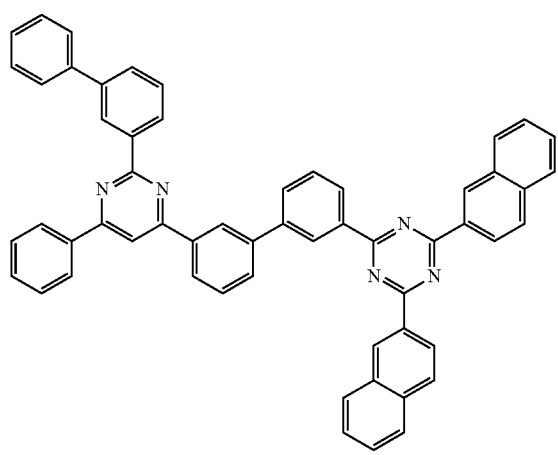
398
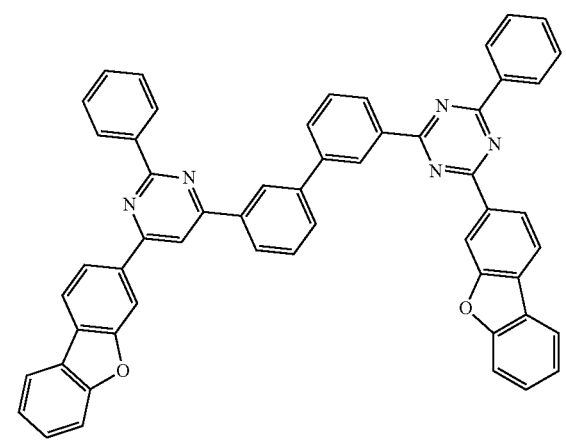
408
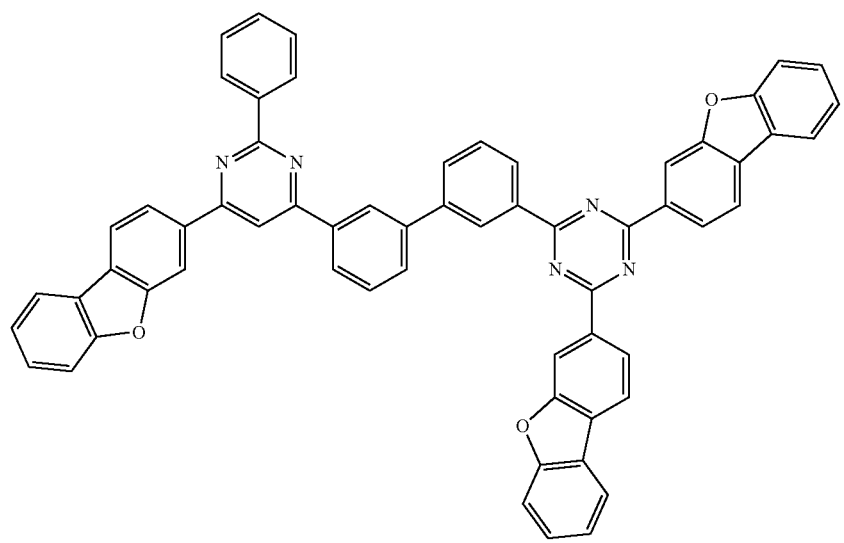
409

717 718
-continued
410
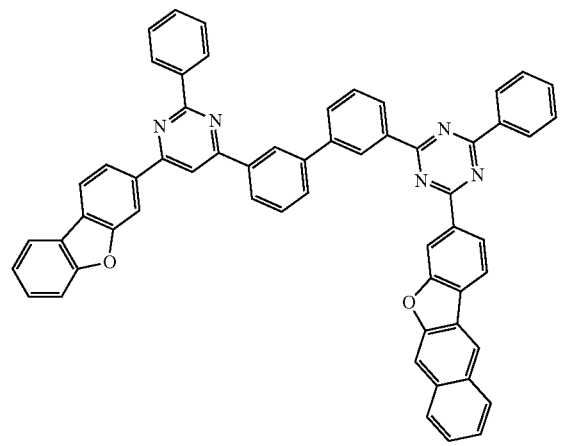
411
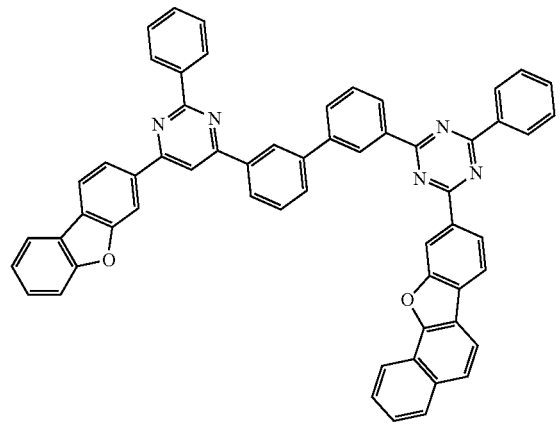
412
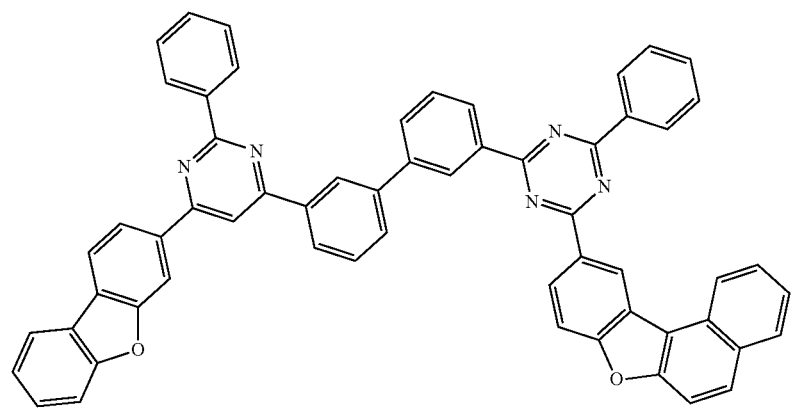
413
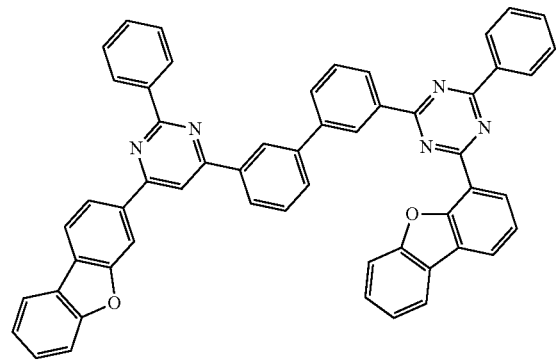
414
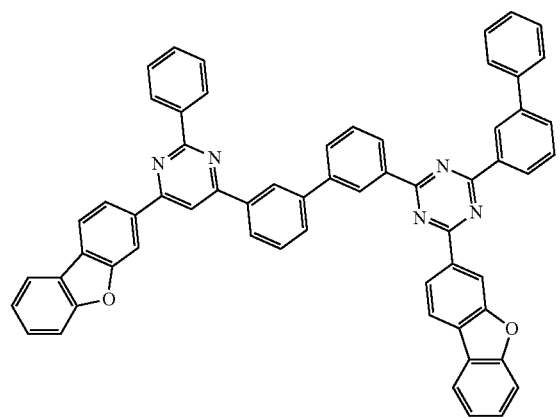

-continued
415
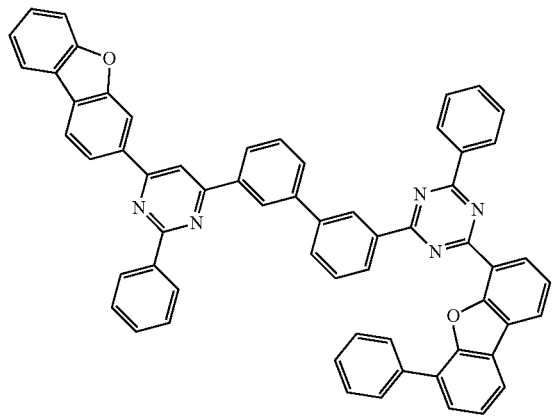
428
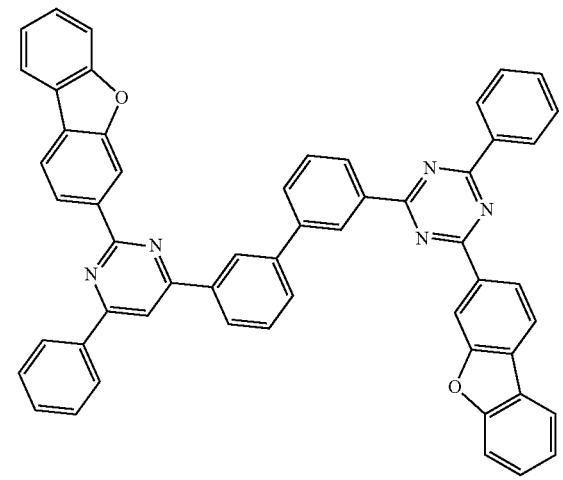
429
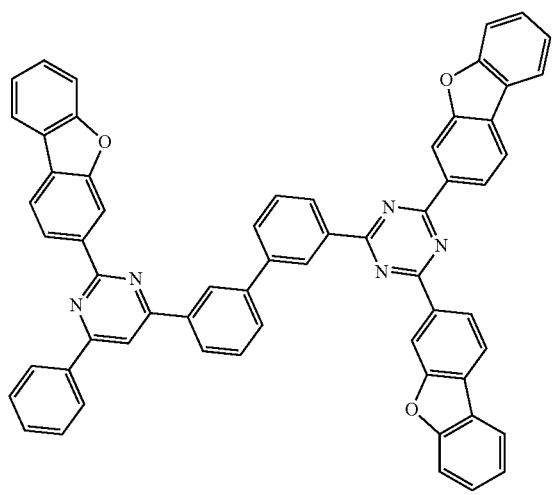
430
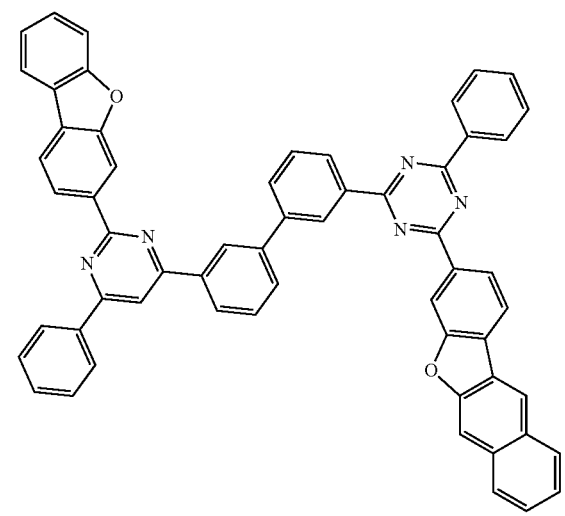
431
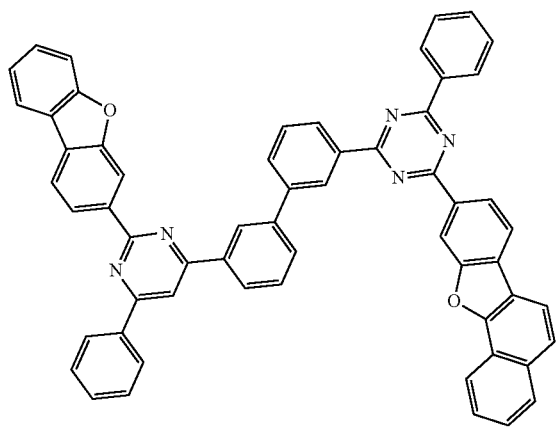
432
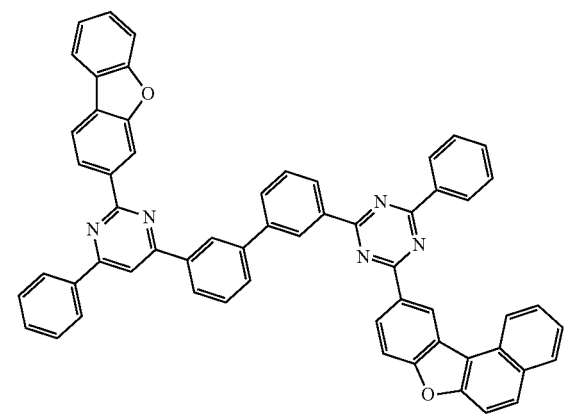

-continued
433
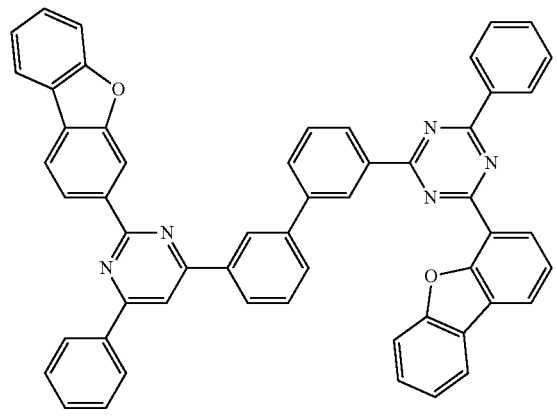
434
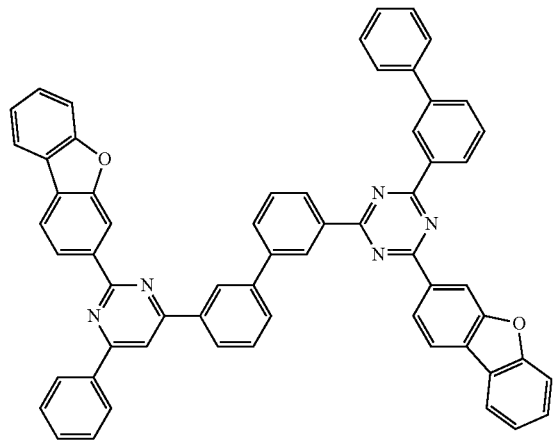
435
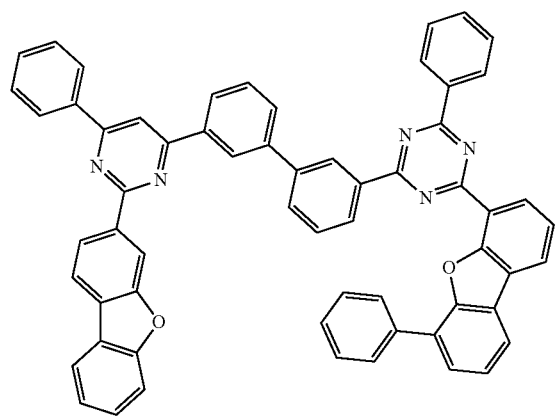
447
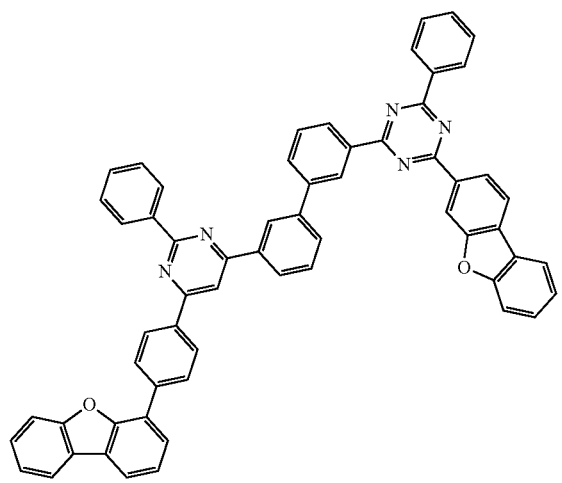
448
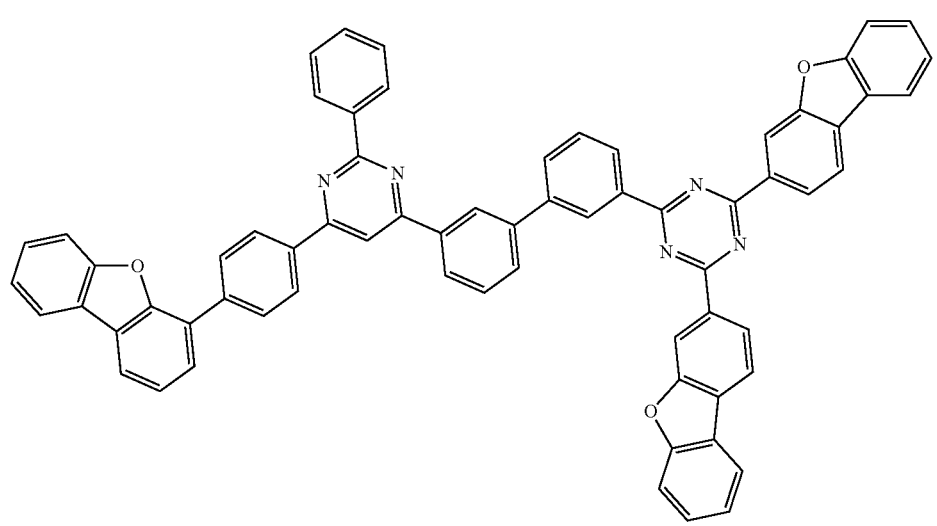

449
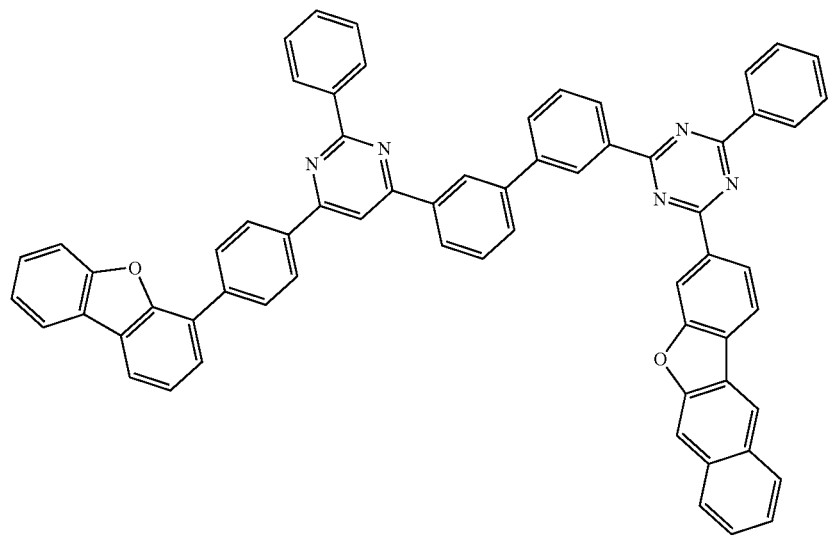
450
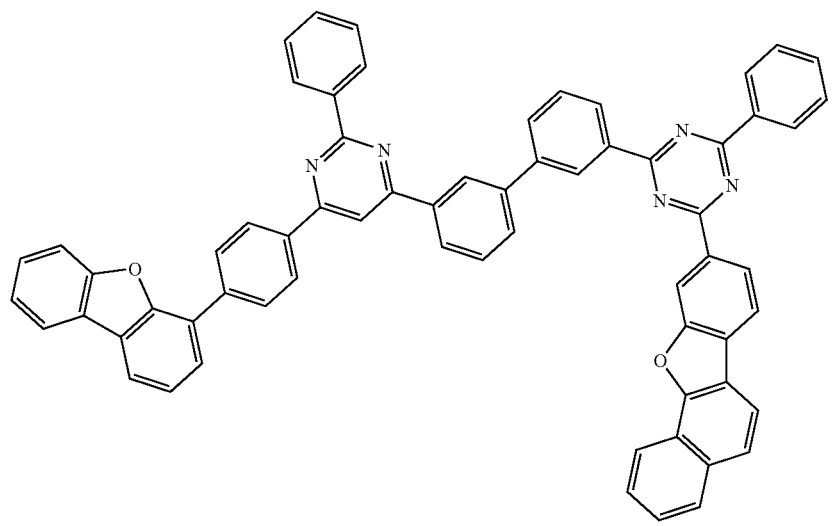
451
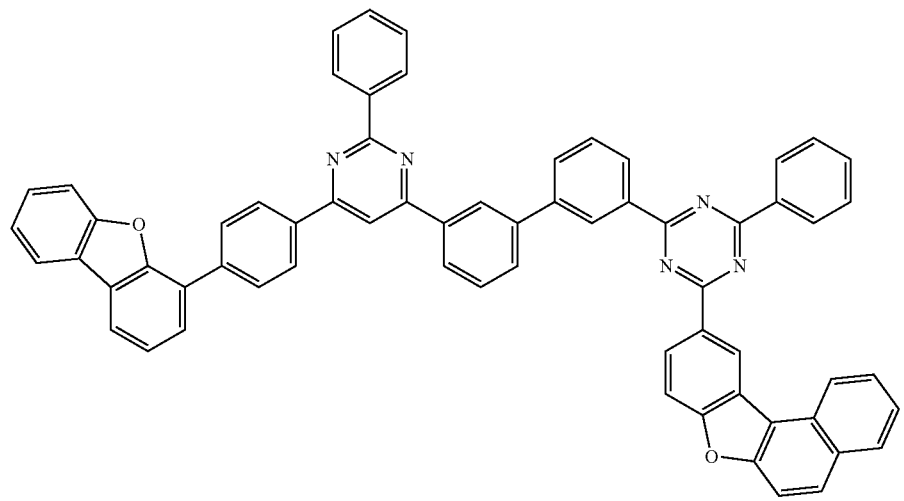

-continued
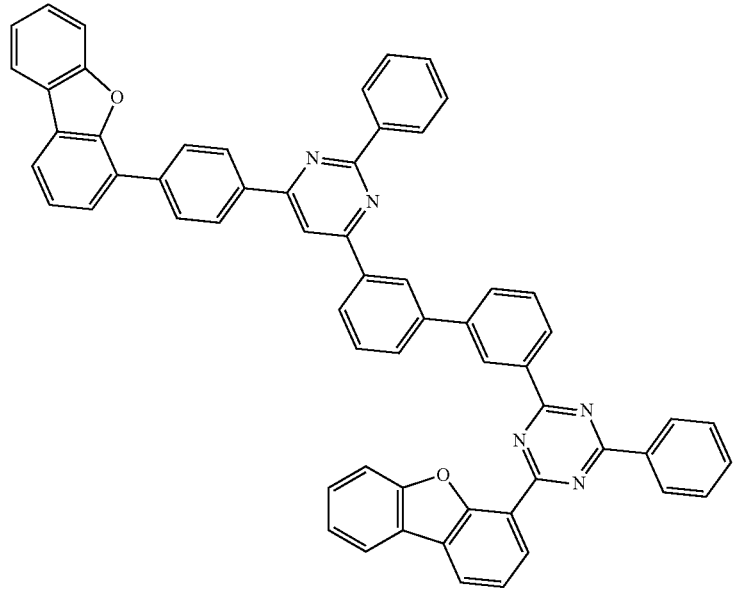
452
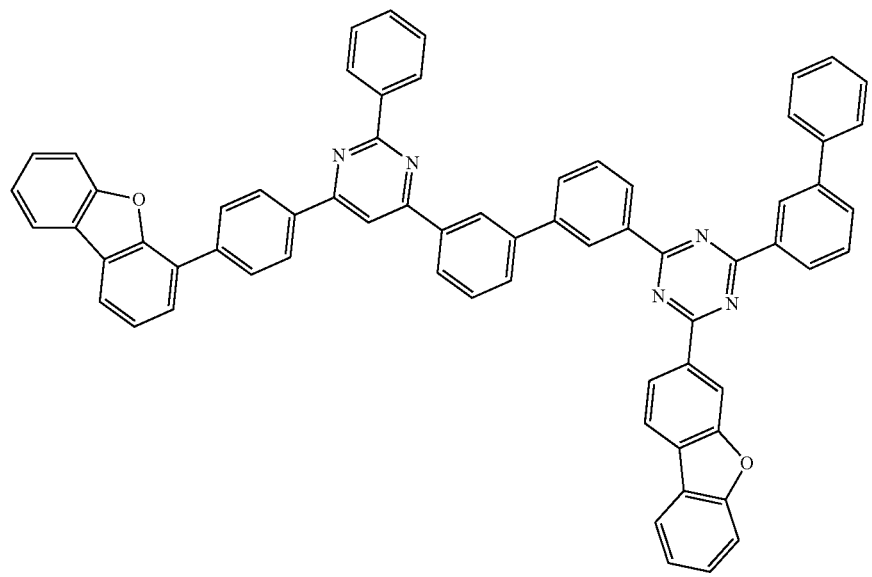
453
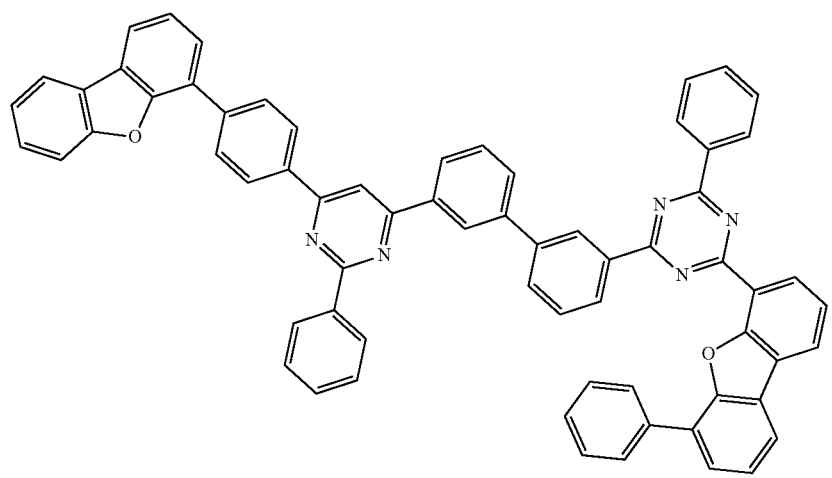
454

-continued
727
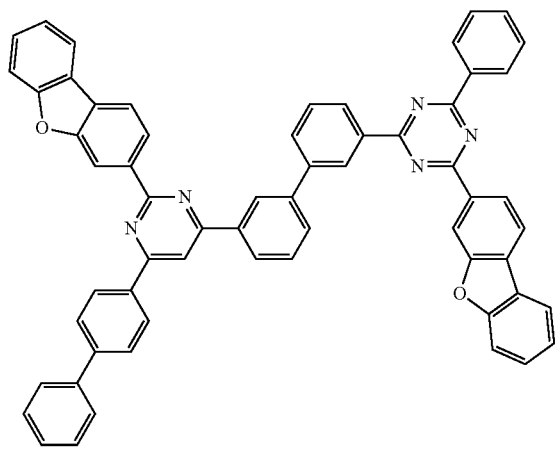
728
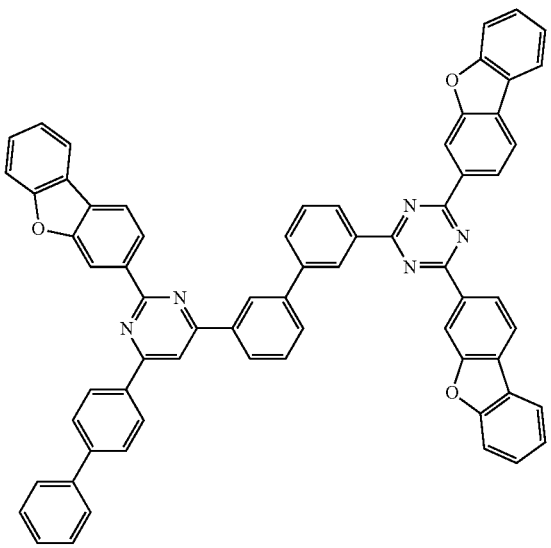
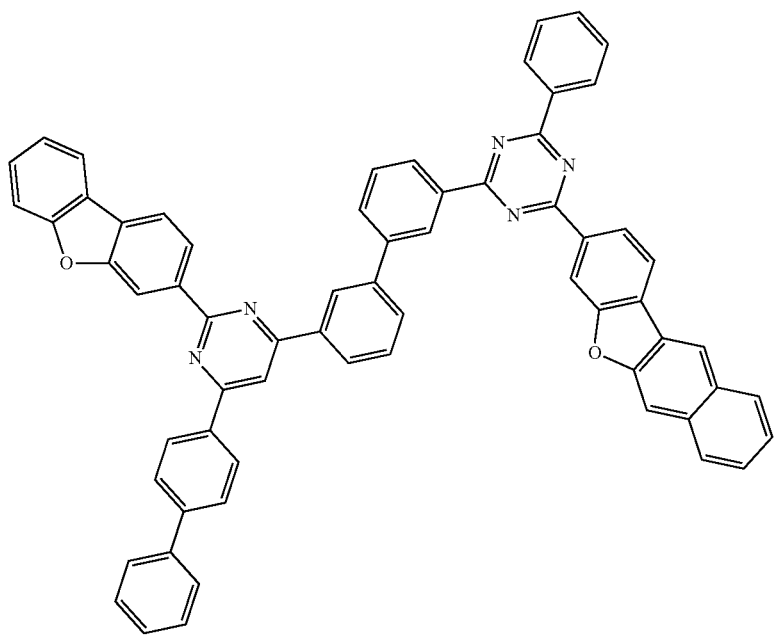

-continued
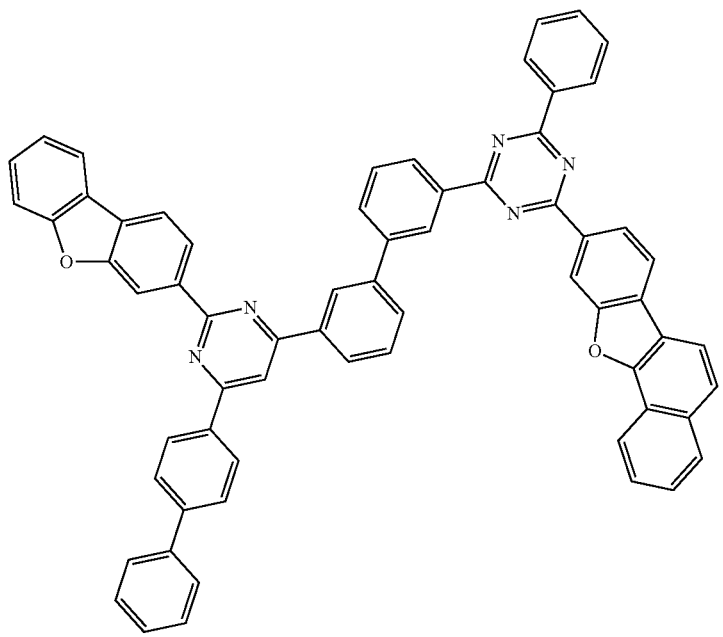
470
471
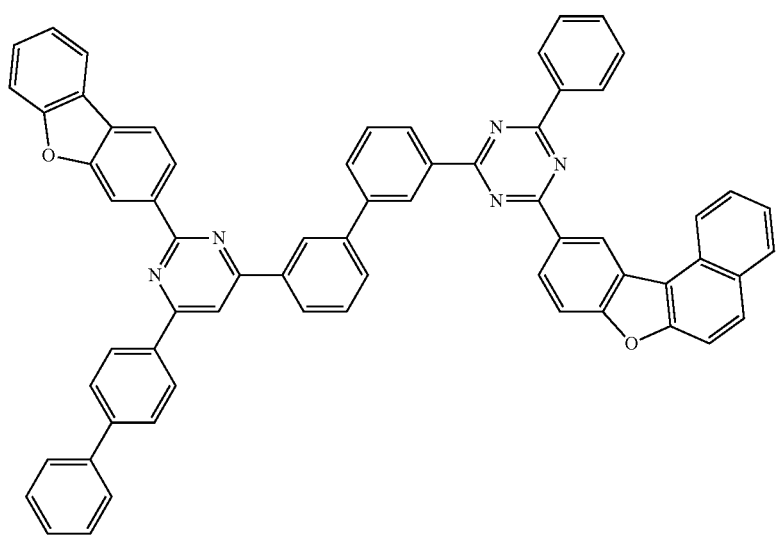
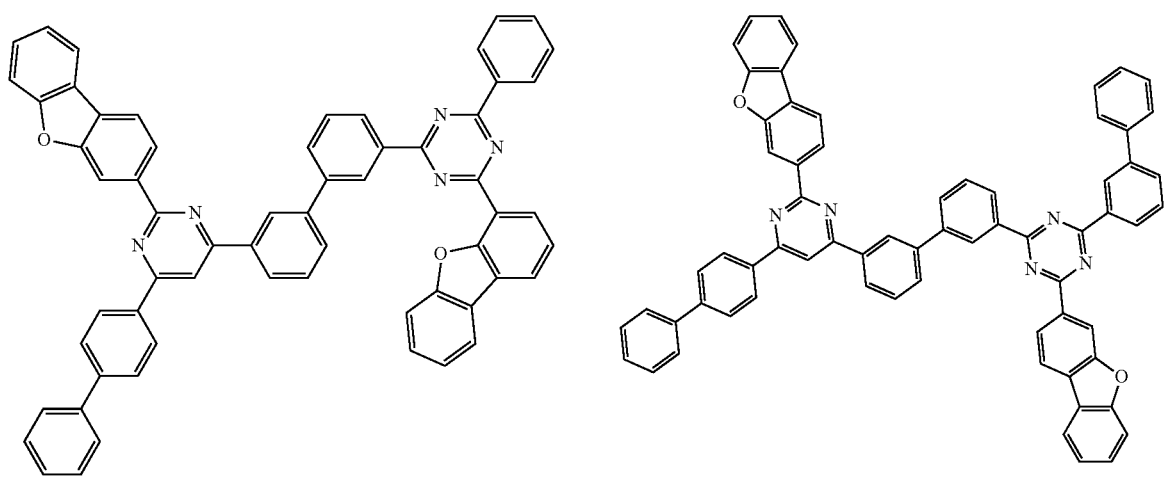
472
473

-continued
474
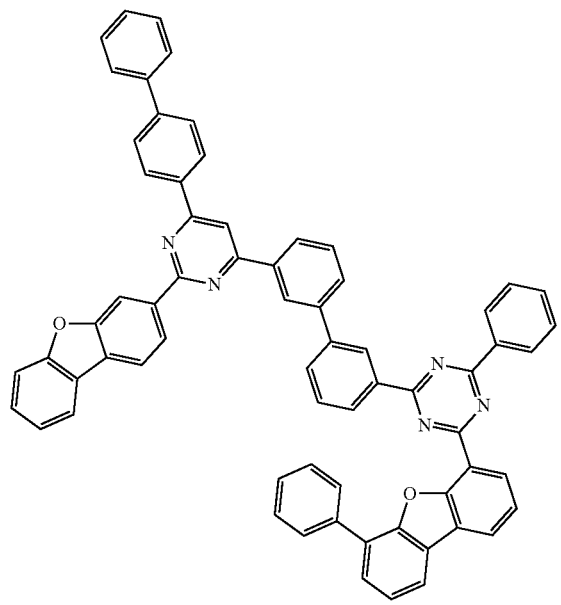
477
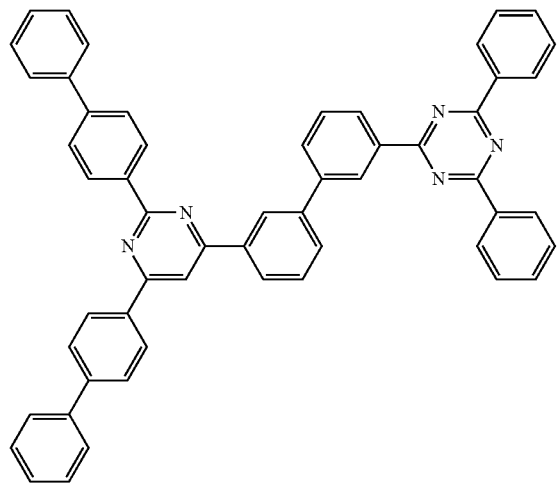
478
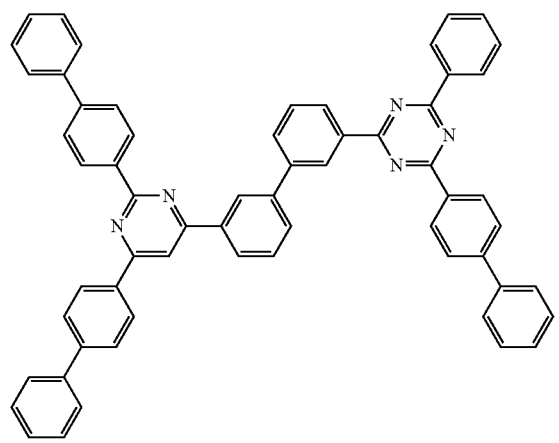
479
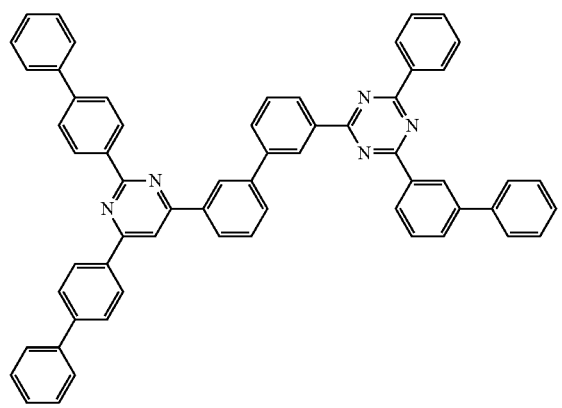
480
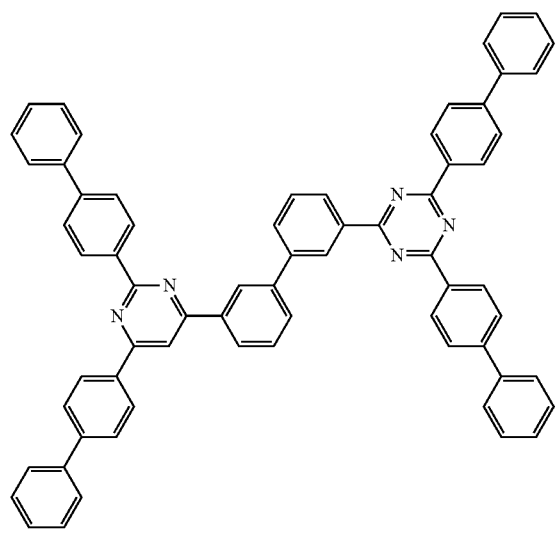
481
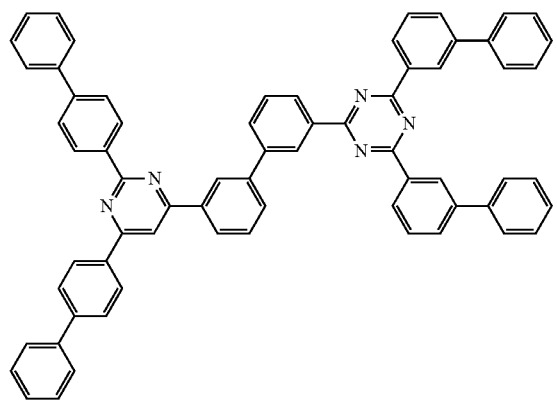

-continued
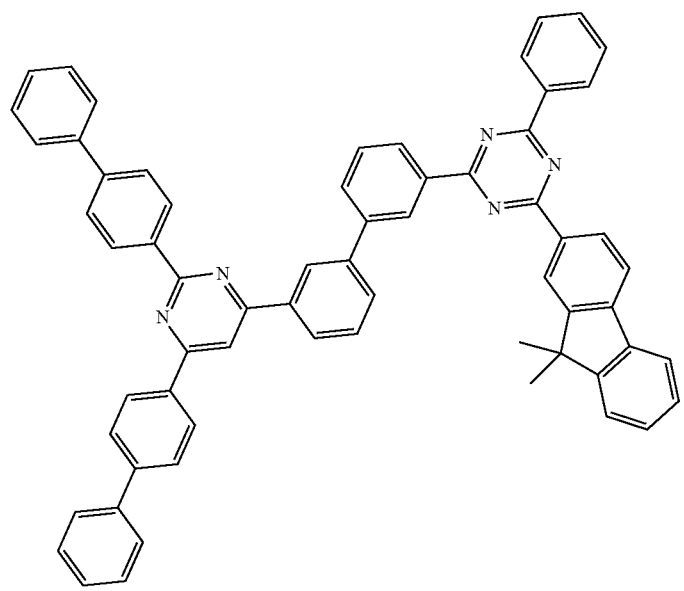
482
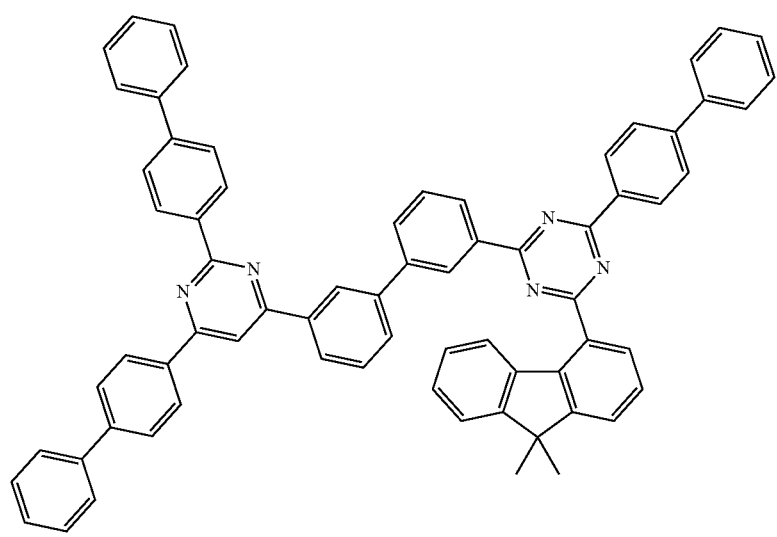
483
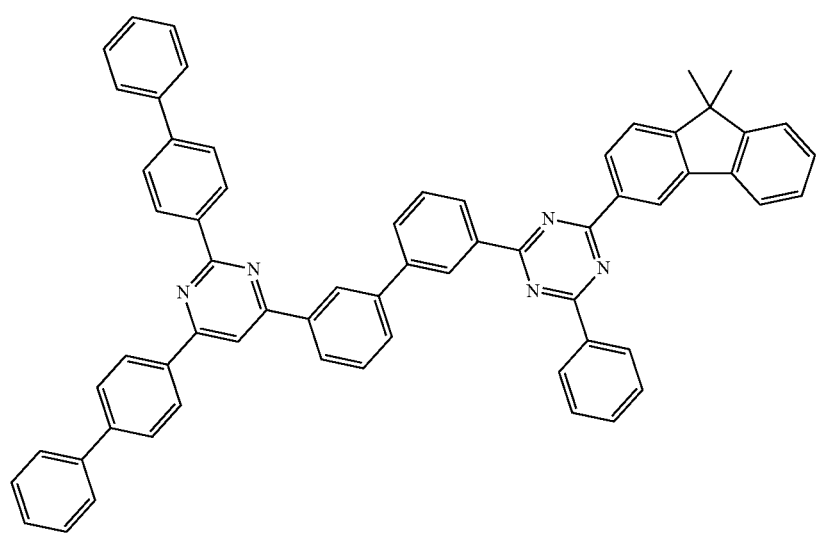
484

-continued
485
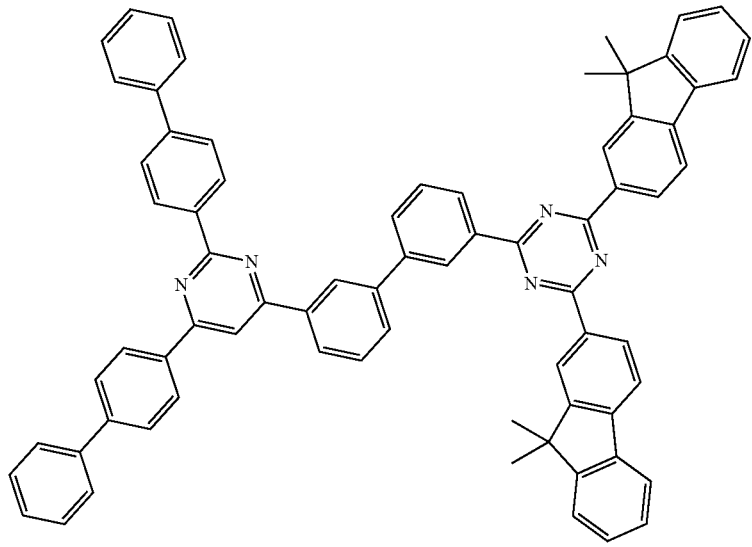
486
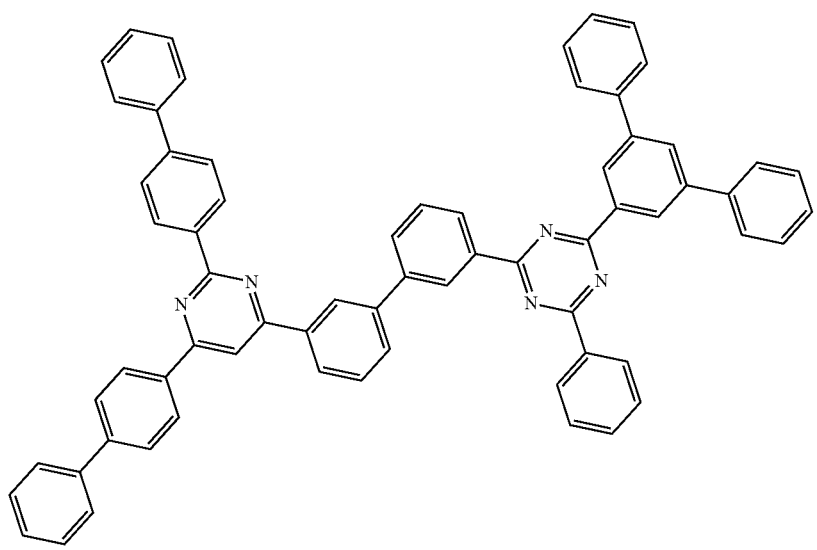
488 489
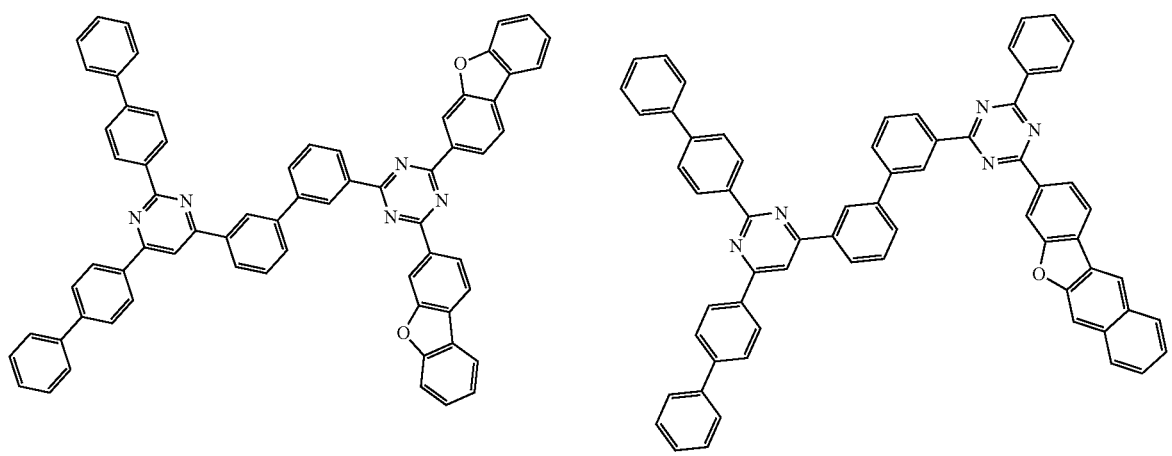

-continued
490
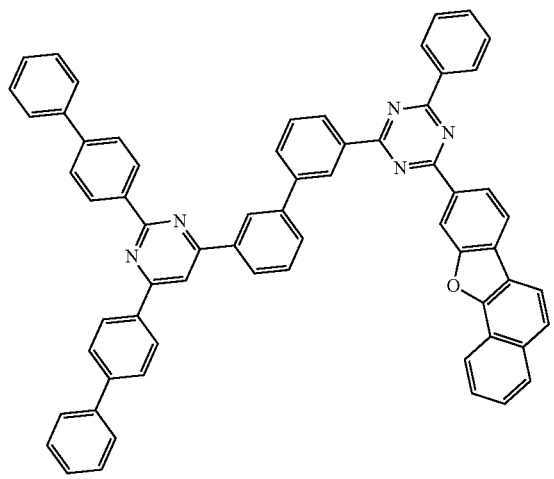
491
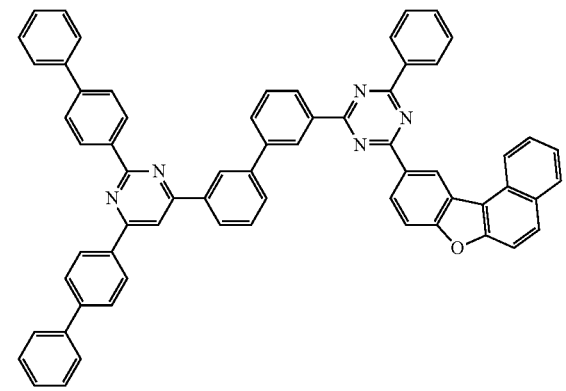
494
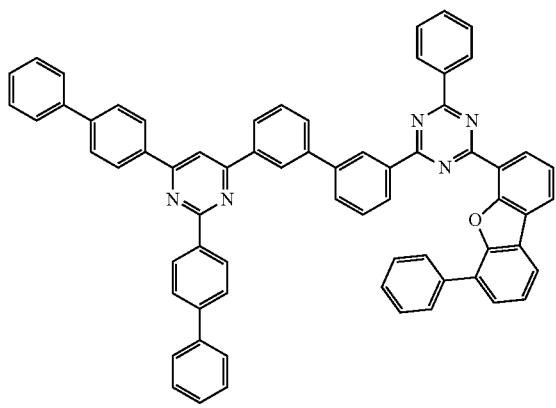
495
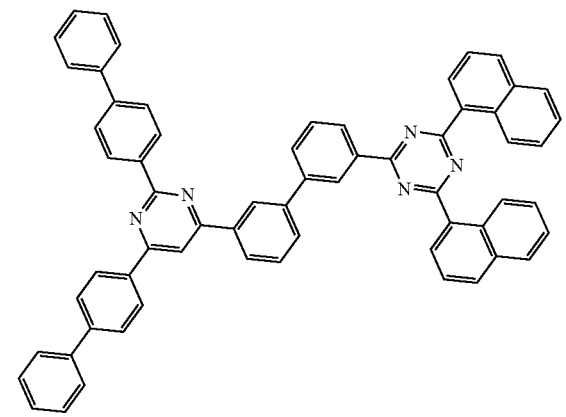
496
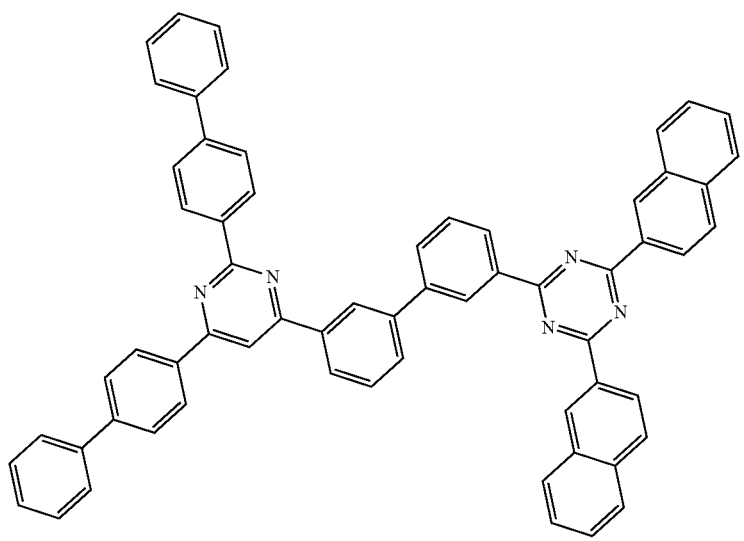

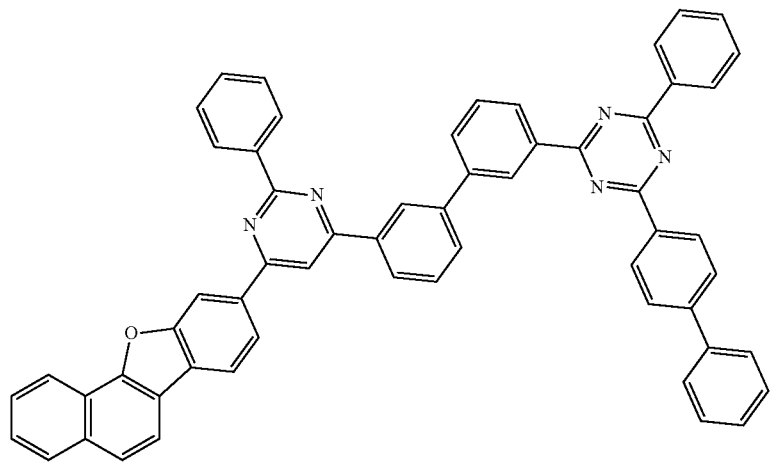
497
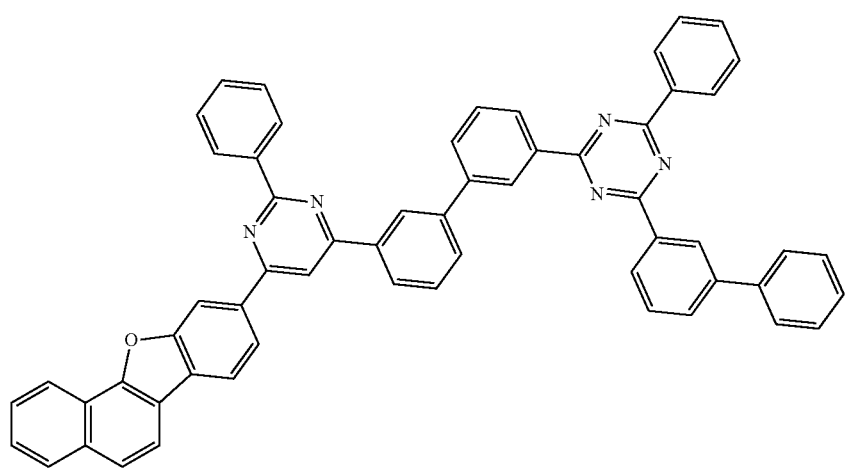
498
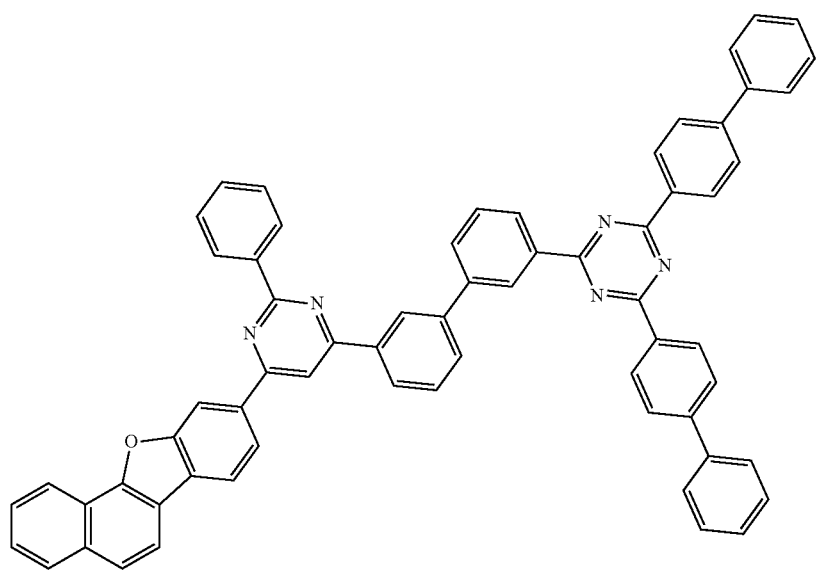
499

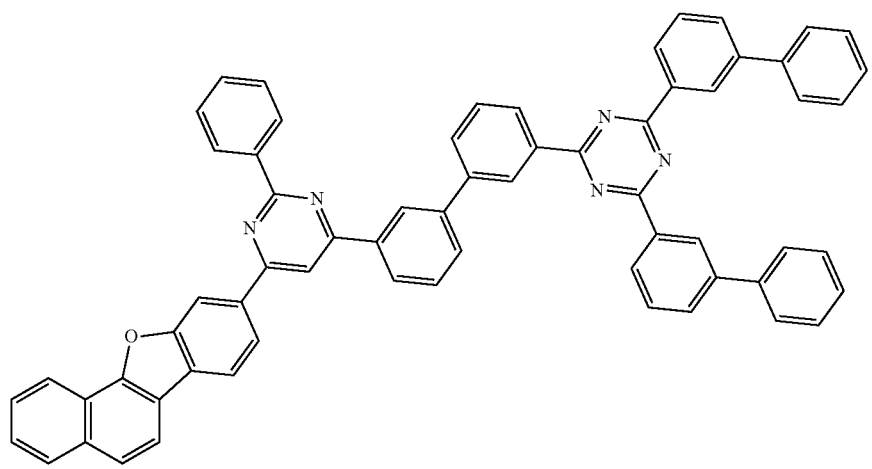
500
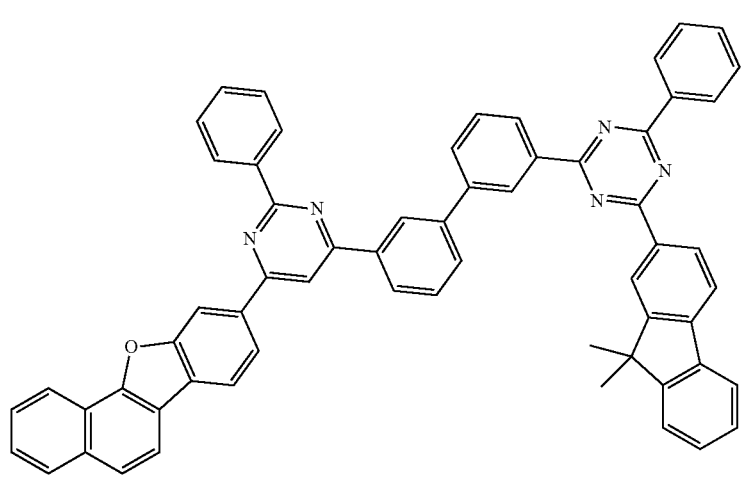
501
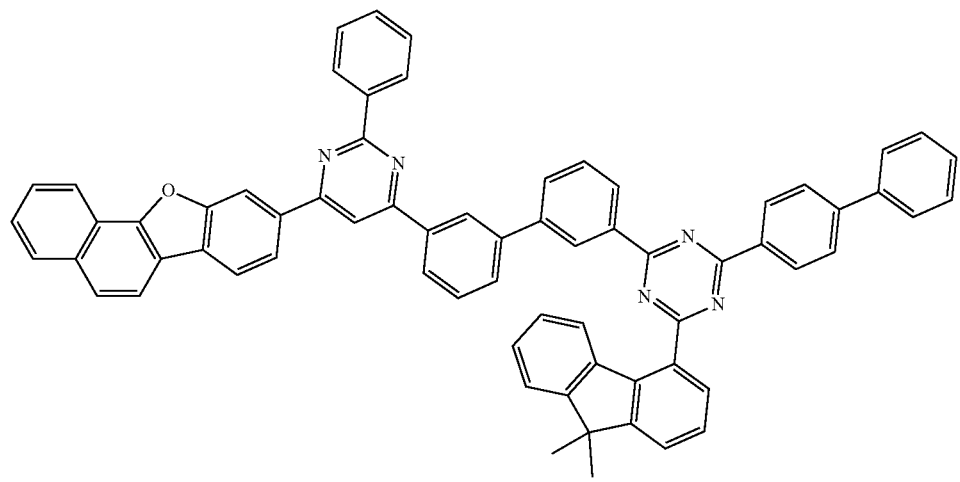
502

-continued
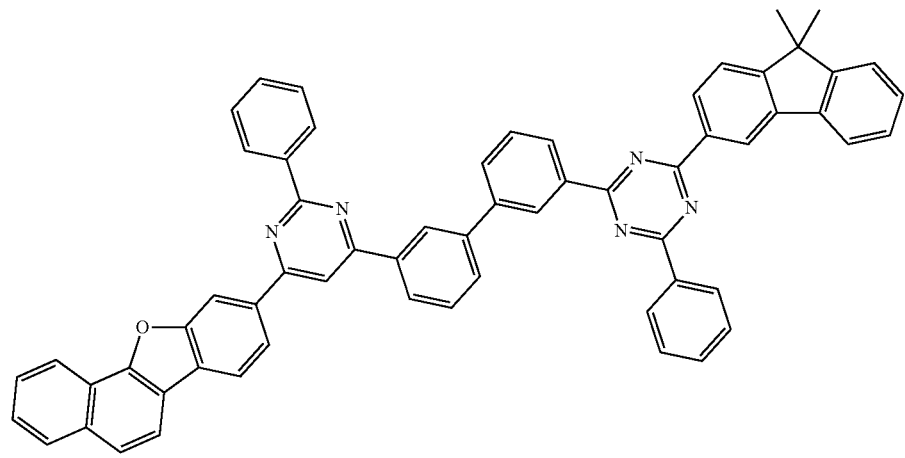
503
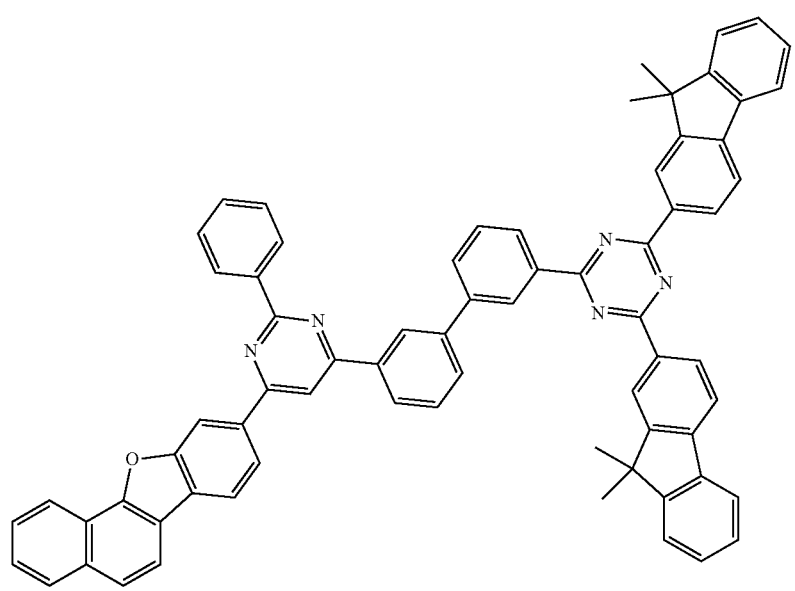
504
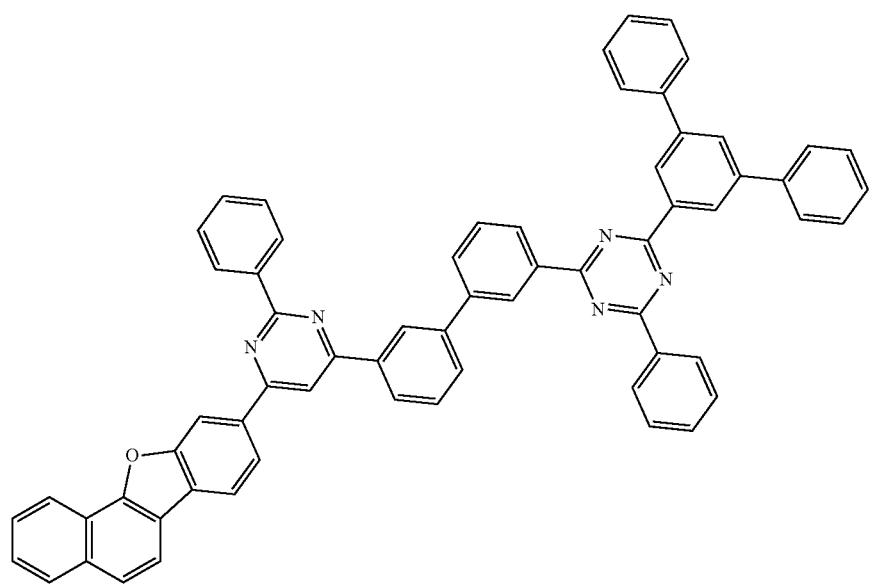
505

506
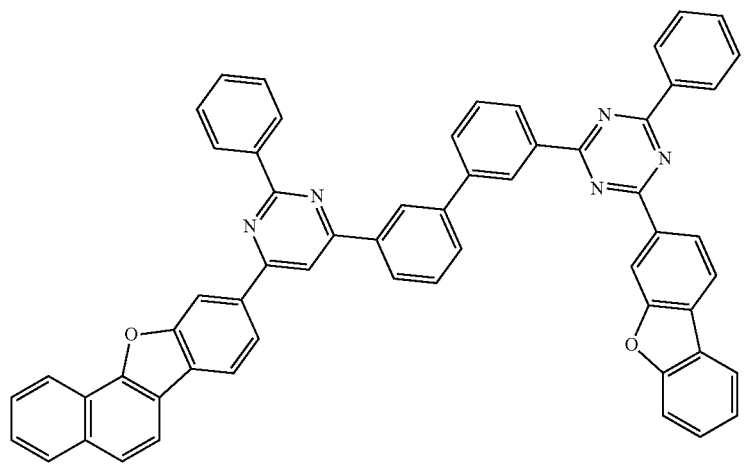
507
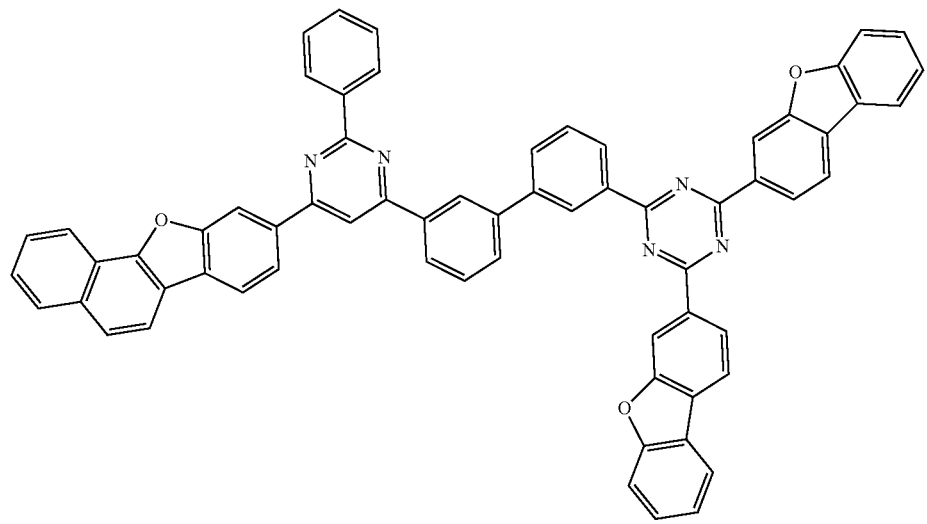
508
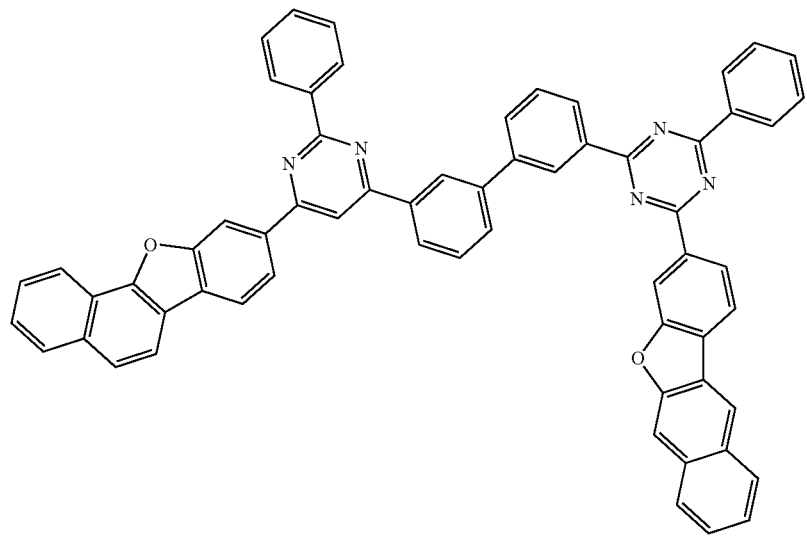

509
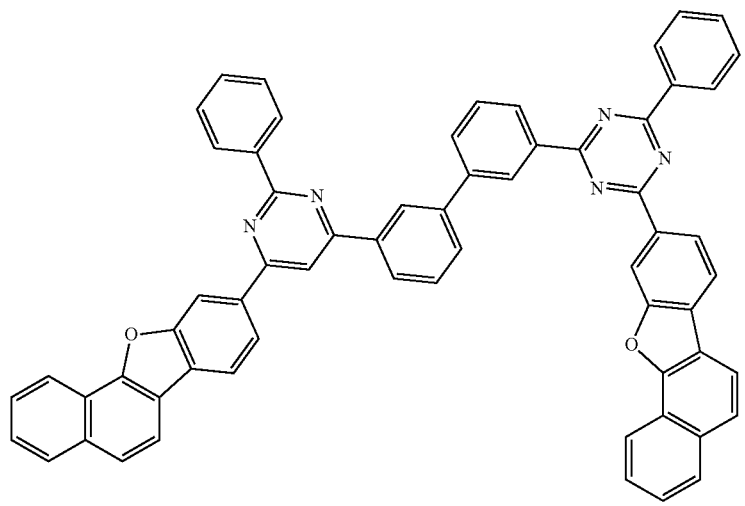
510
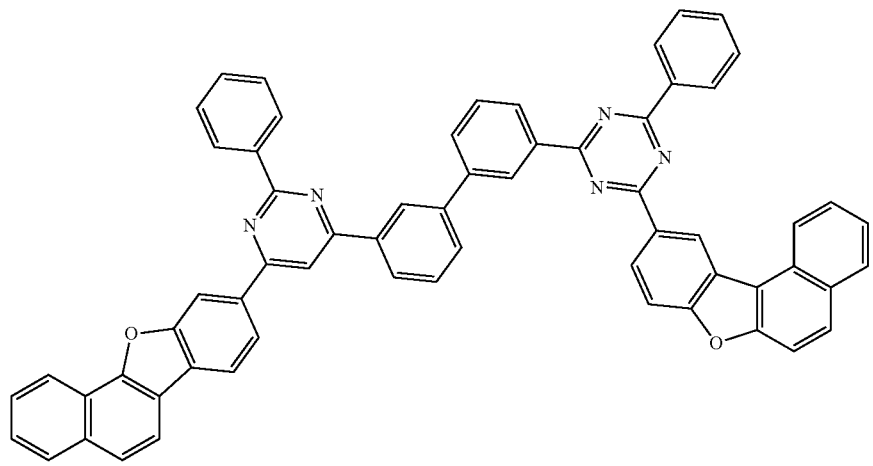
511
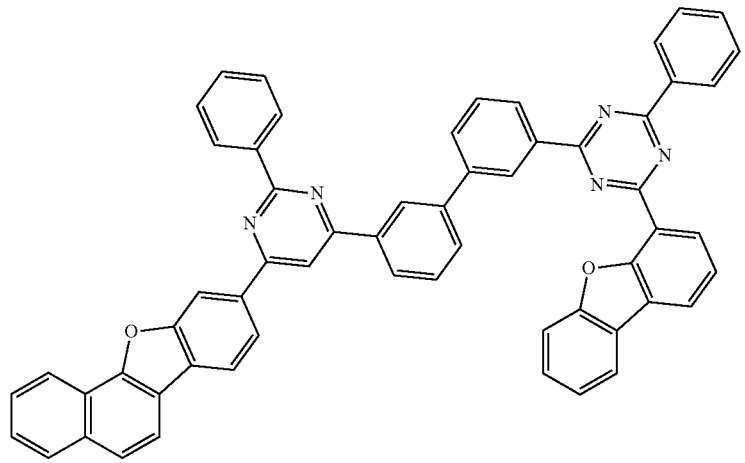

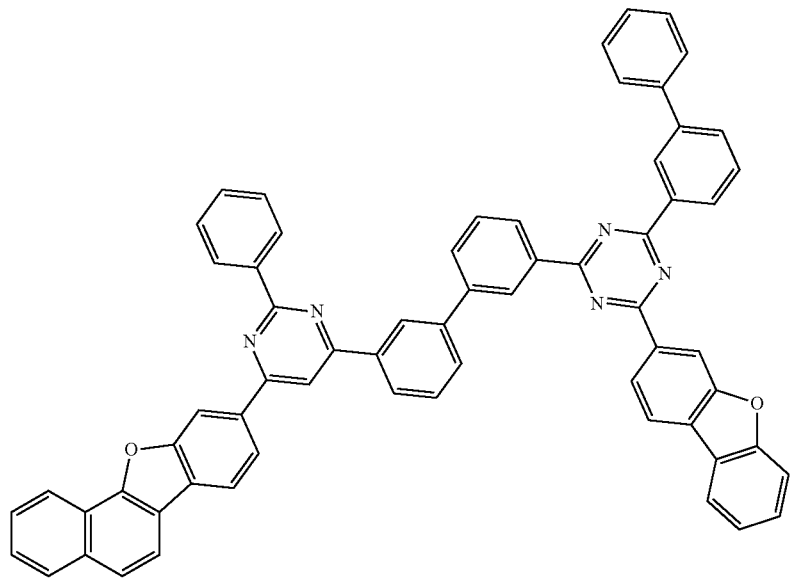
512
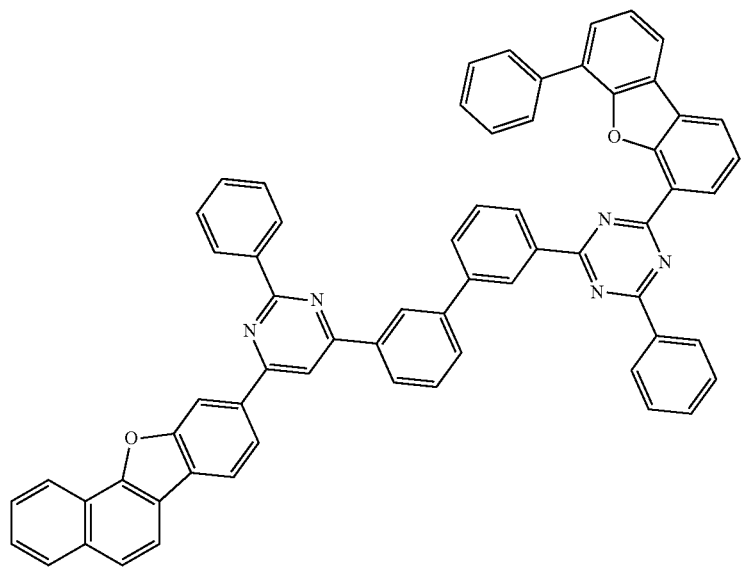
513
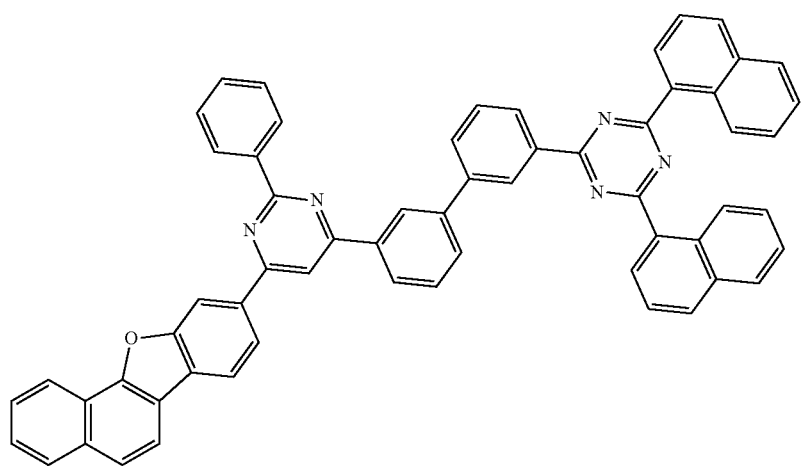
514

-continued
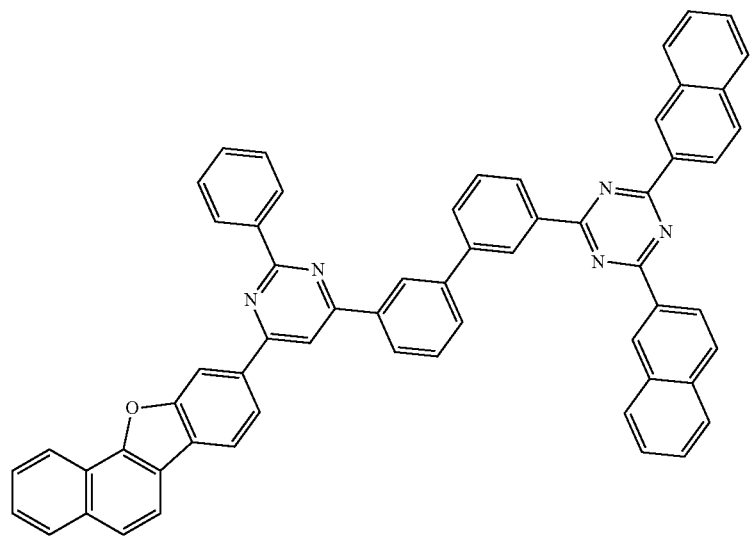
515
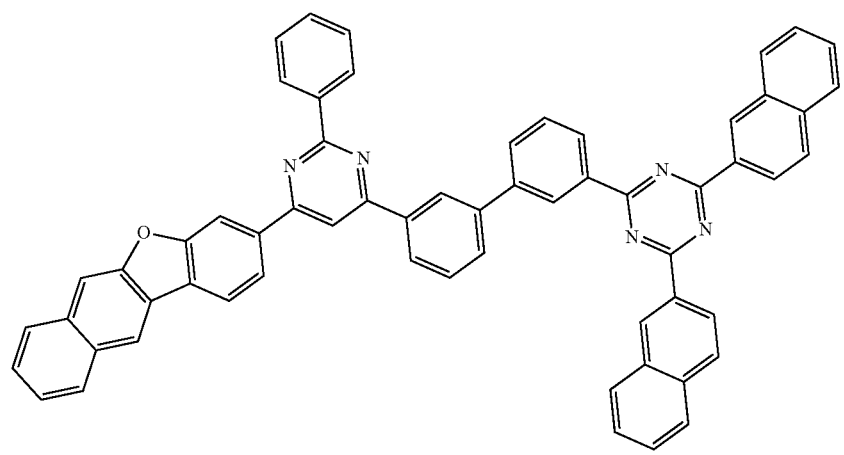
516
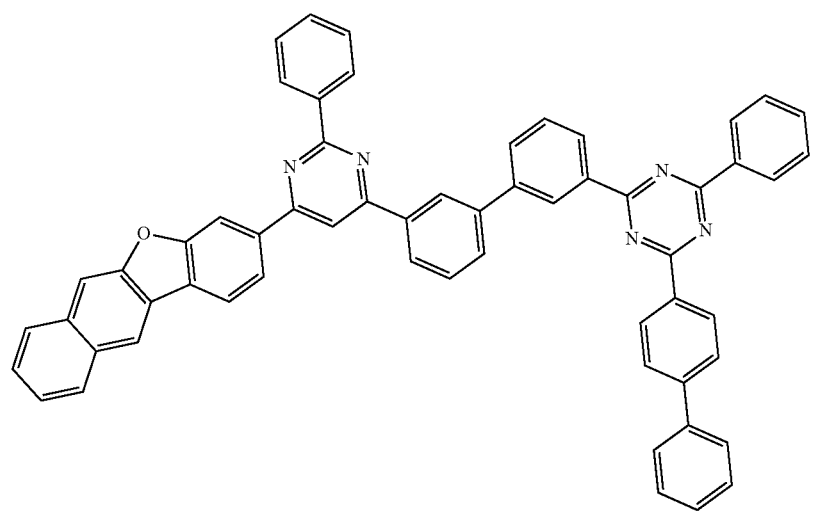
517

-continued
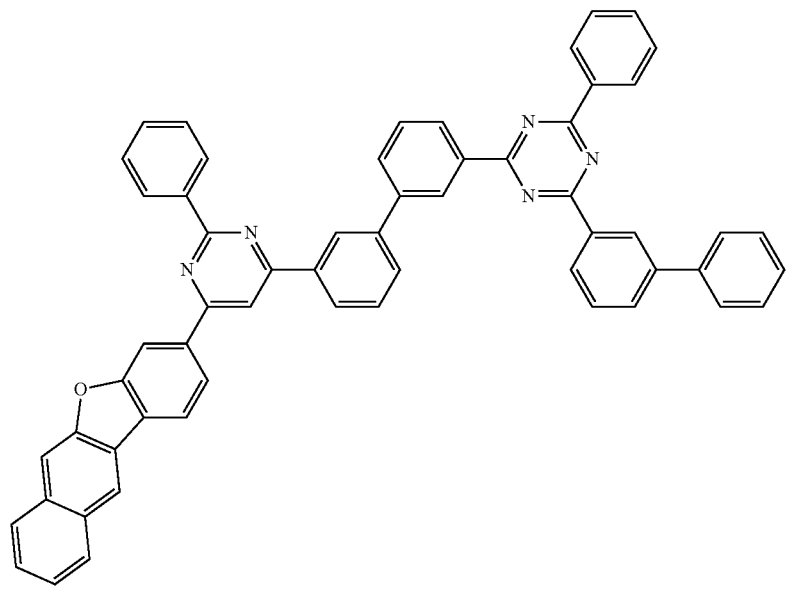
518
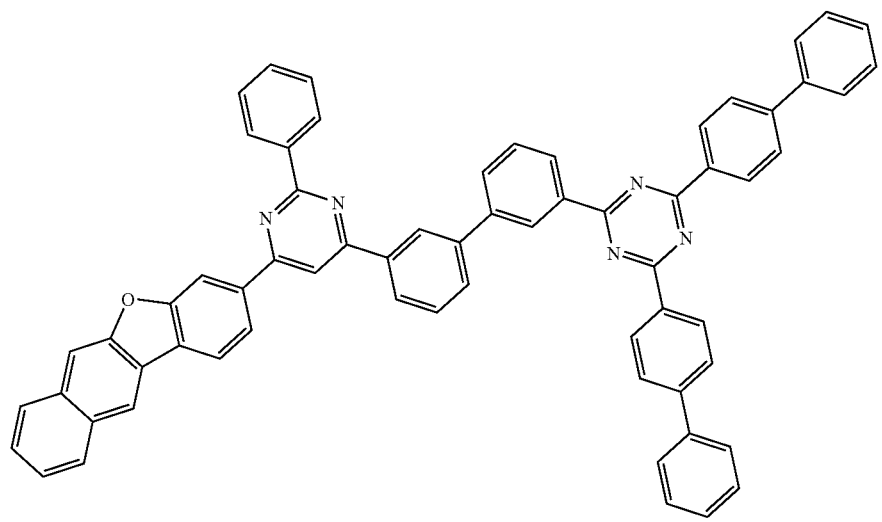
519
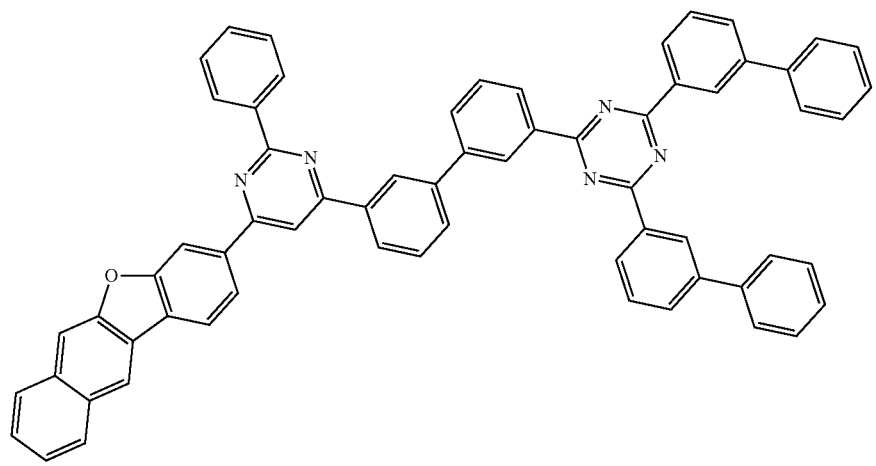
520

521
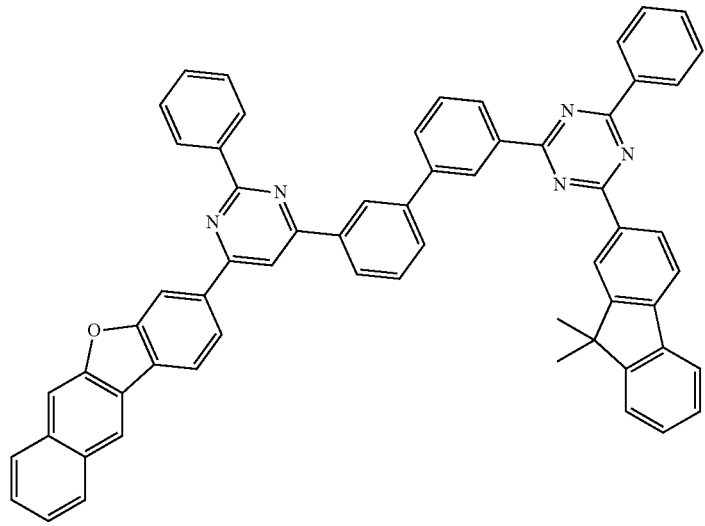
522
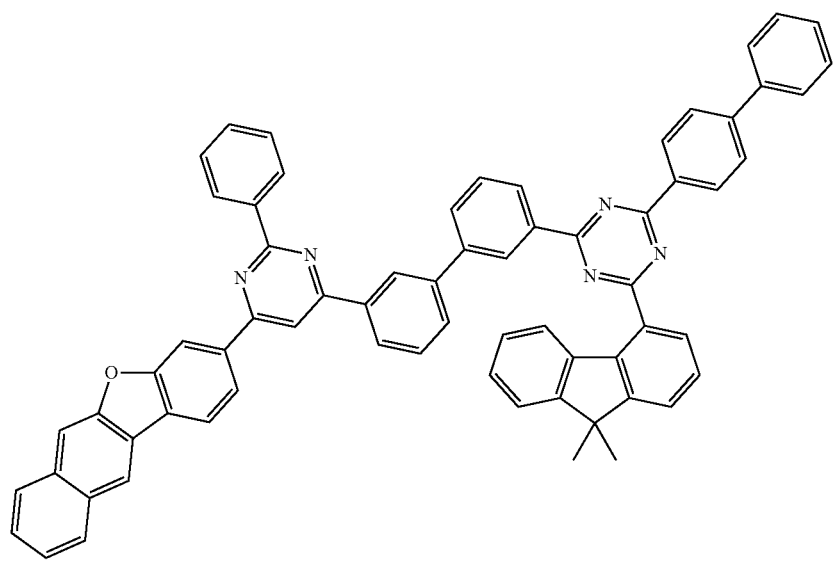
523
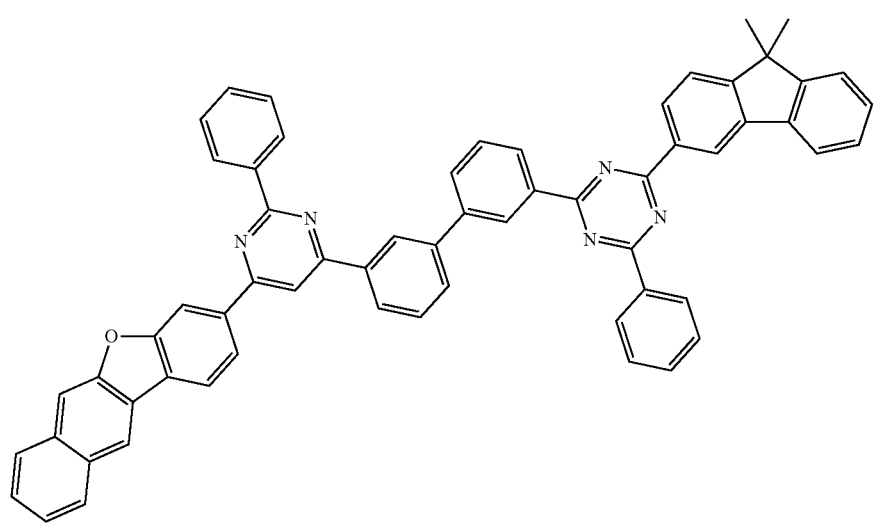

524
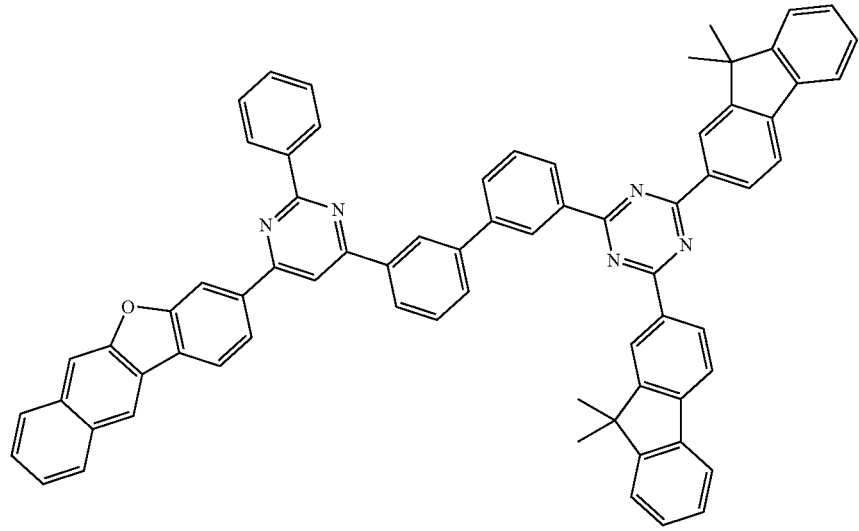
525
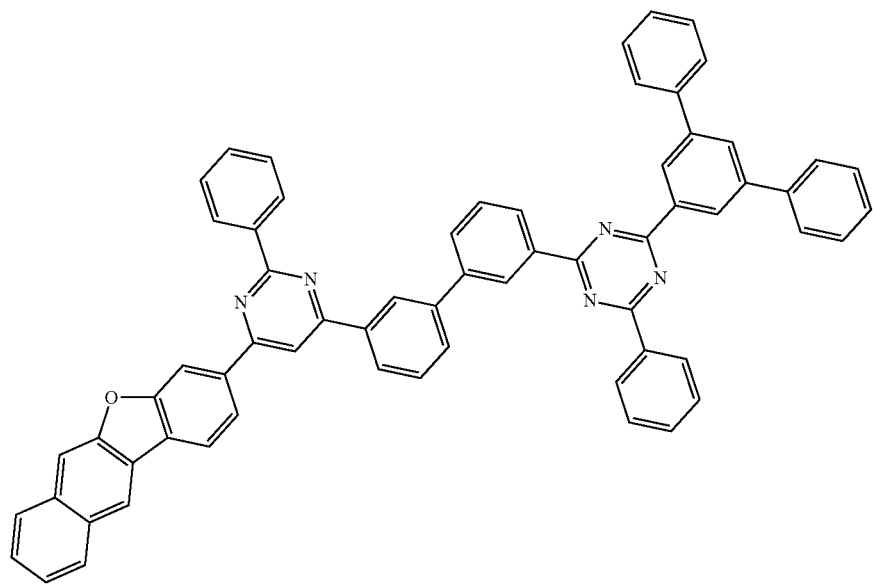
526
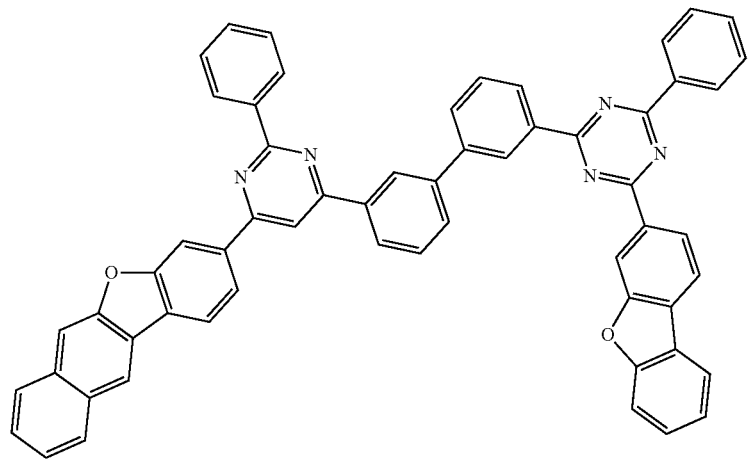

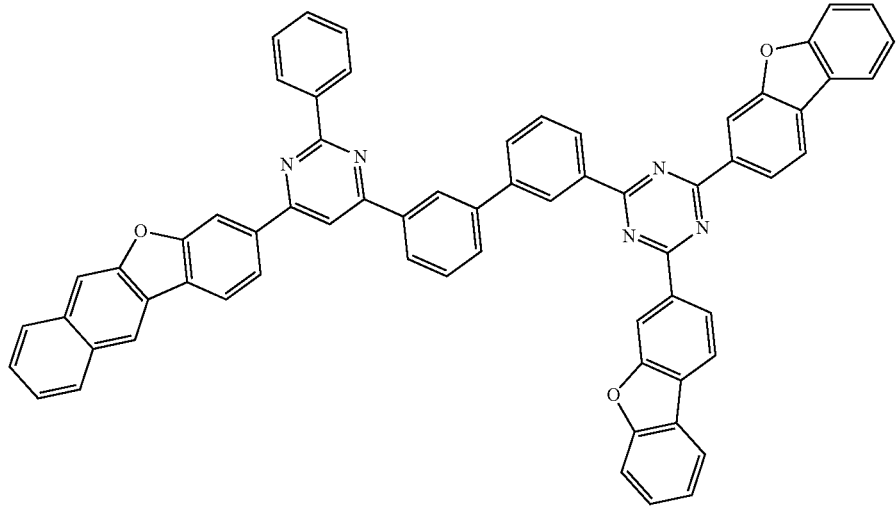
527
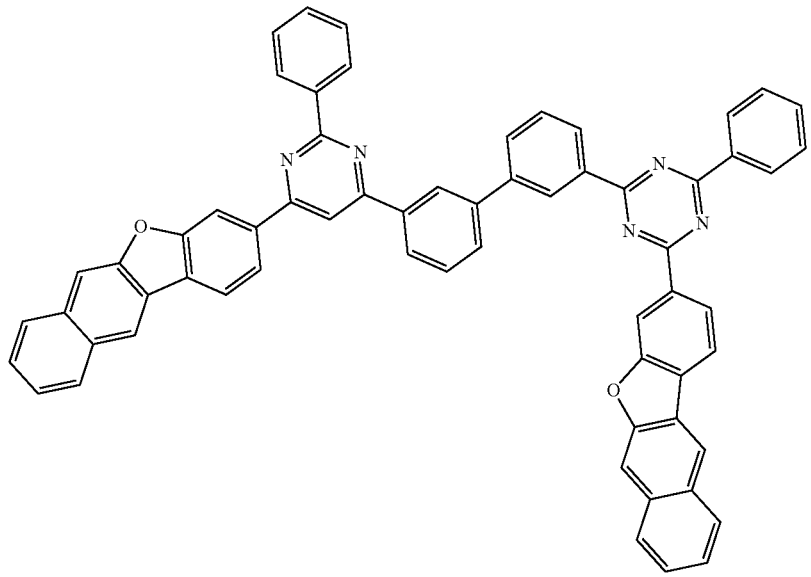
528
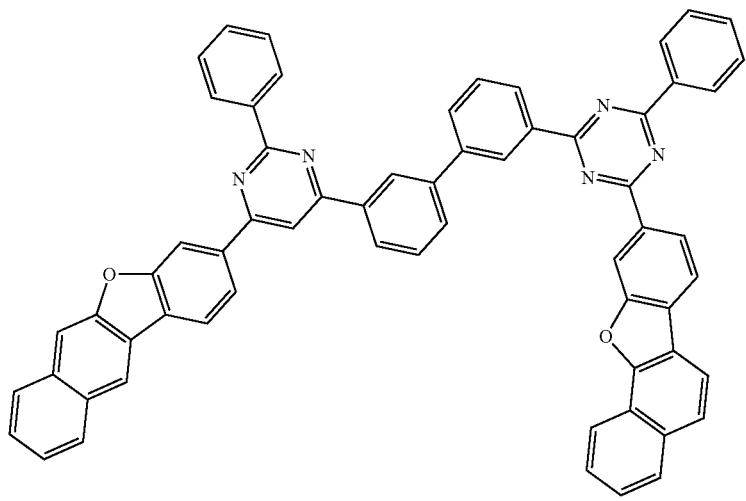
529

530
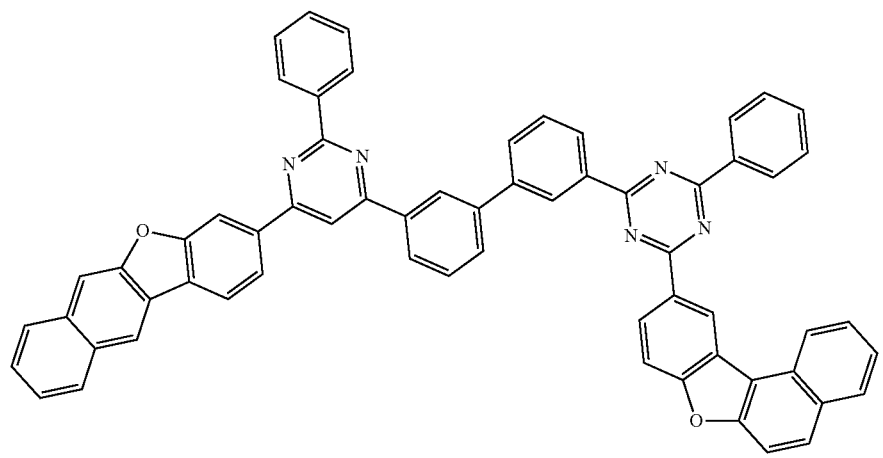
531
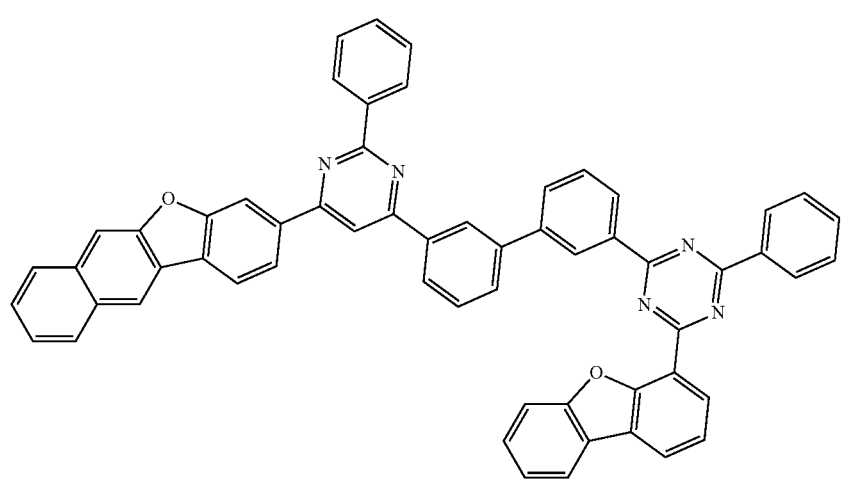
532
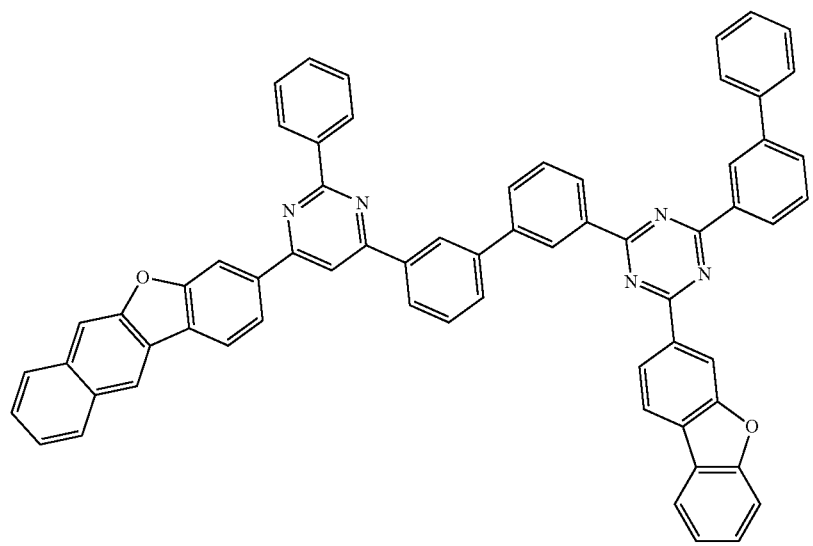

533
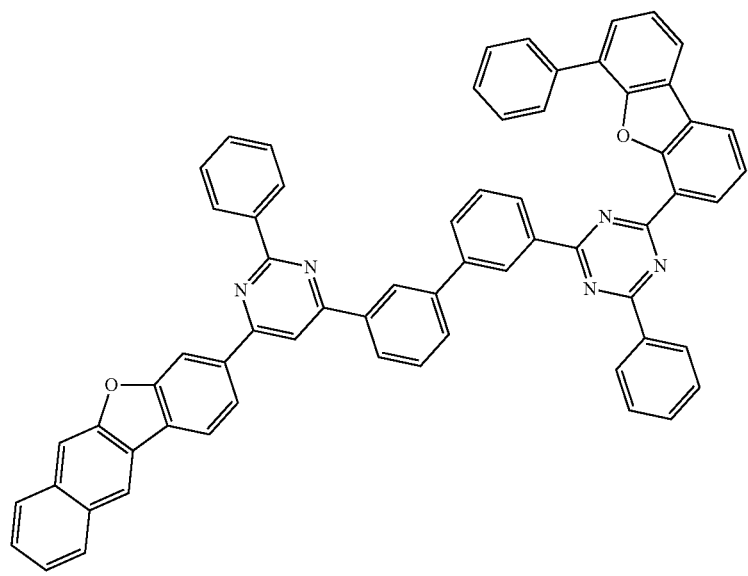
534
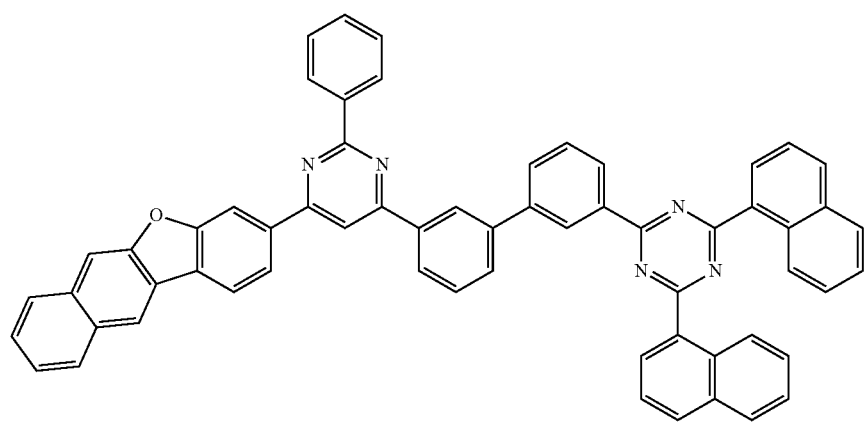
535
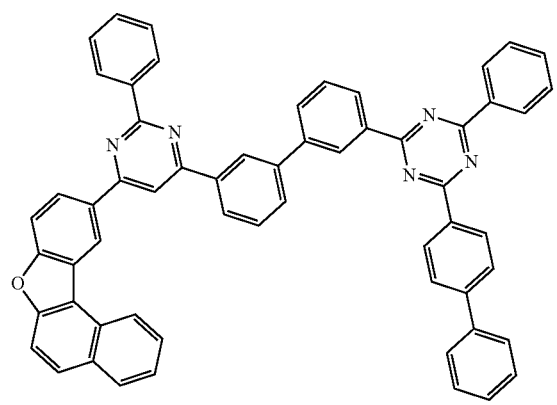
536
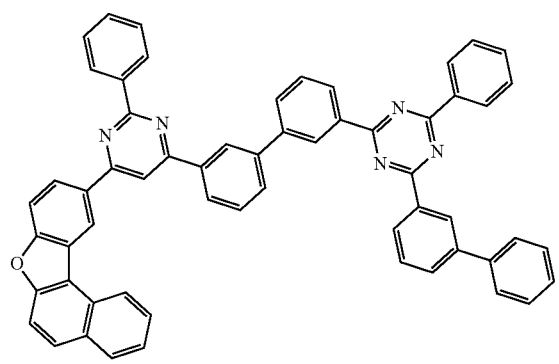

-continued
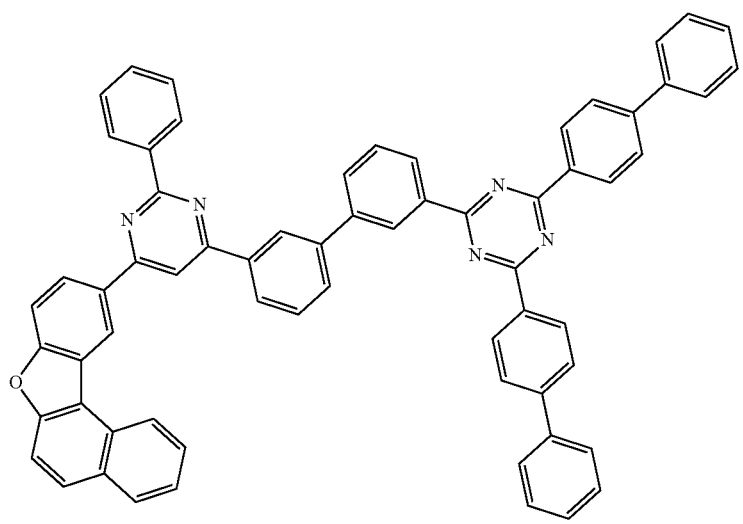
537
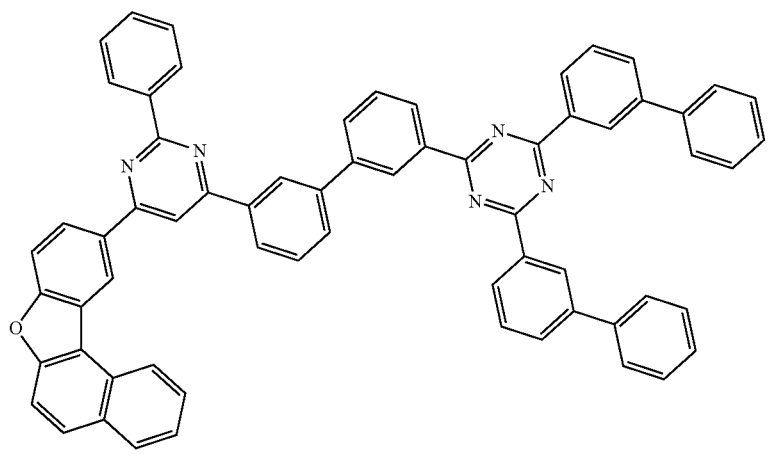
538
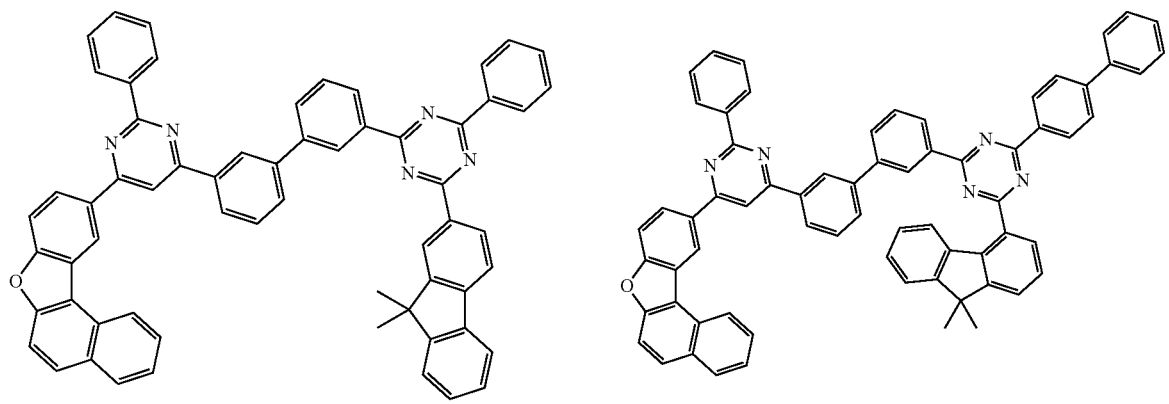
539        540

-continued
541
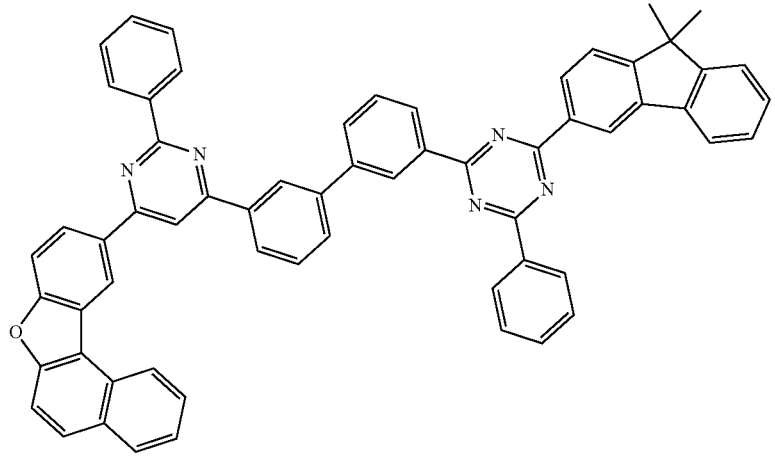
542
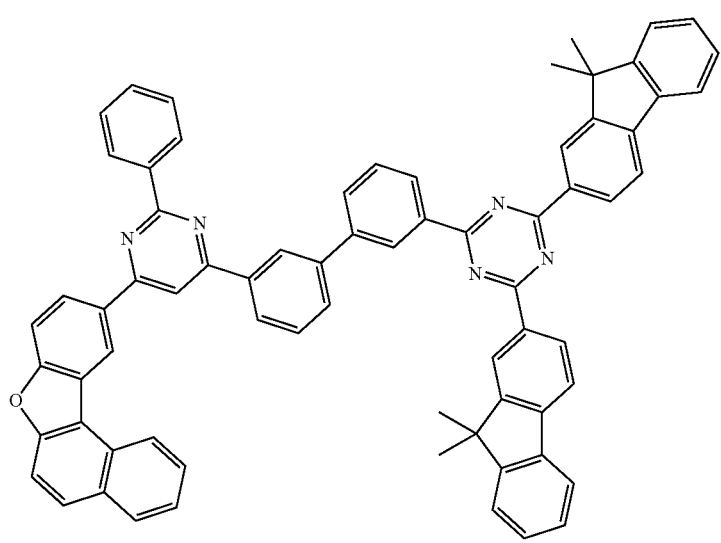
543
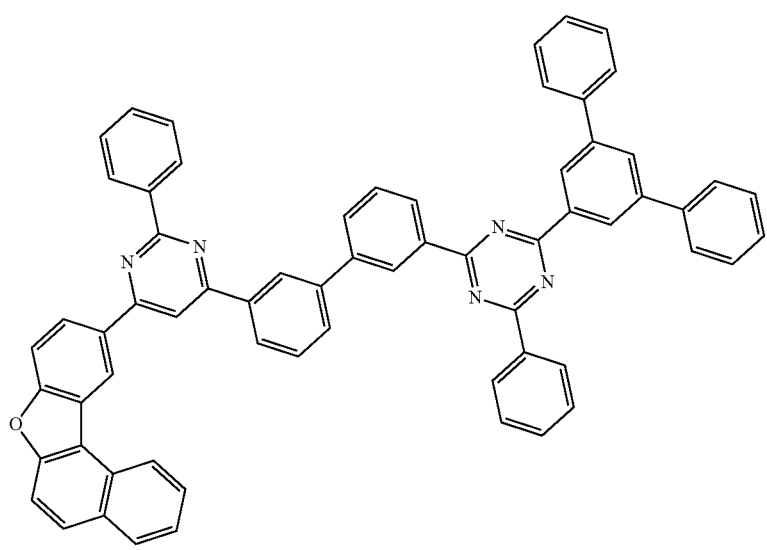

-continued
544
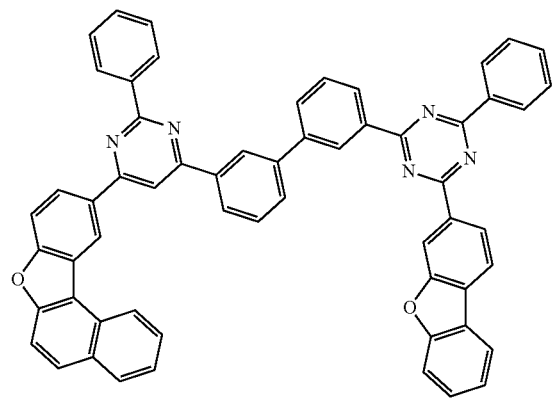
545
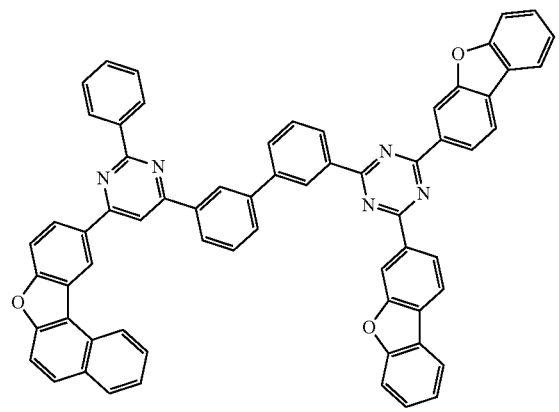
546
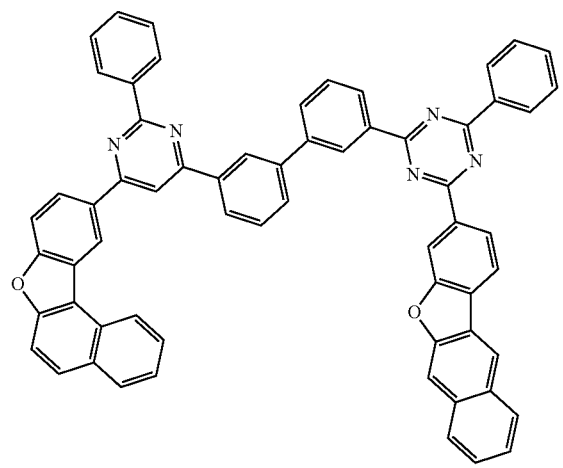
547
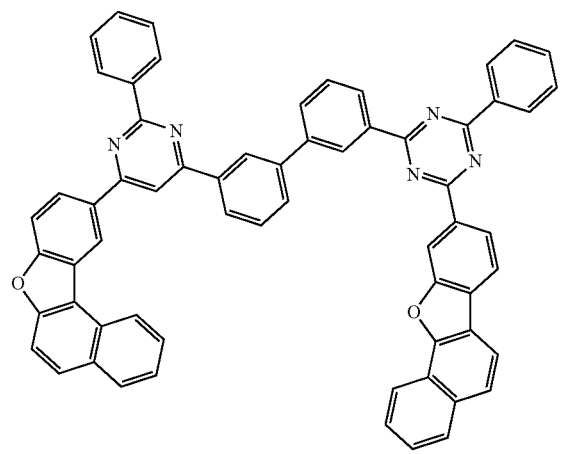
548
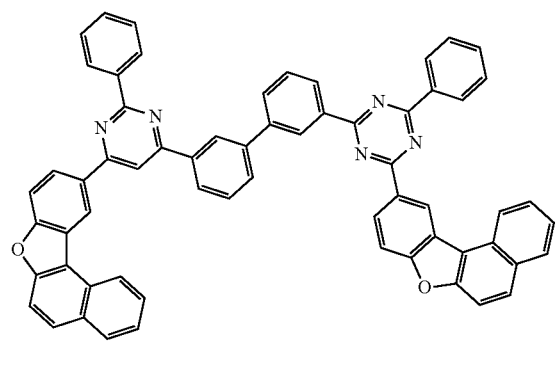
549
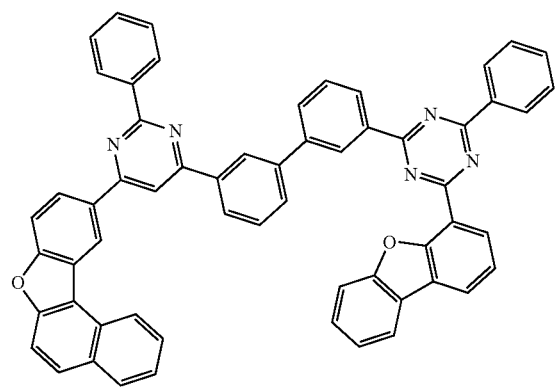

-continued
771 550
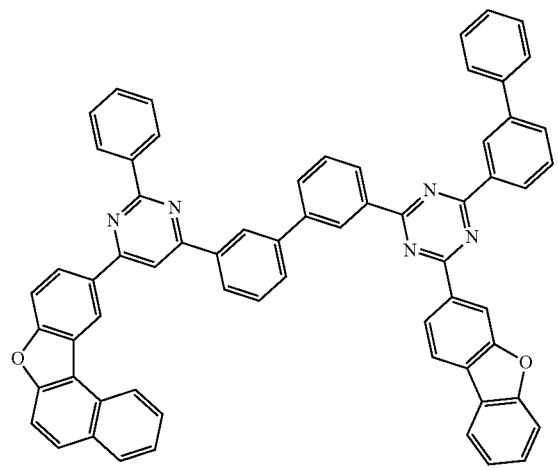
772 551
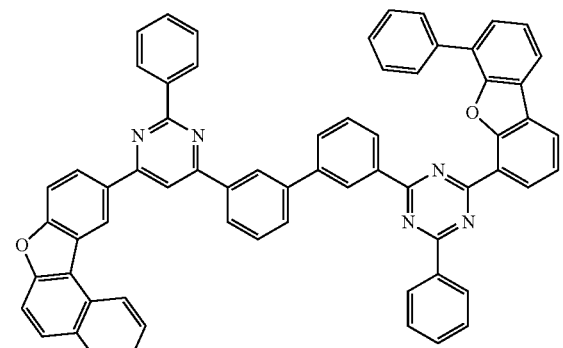
552
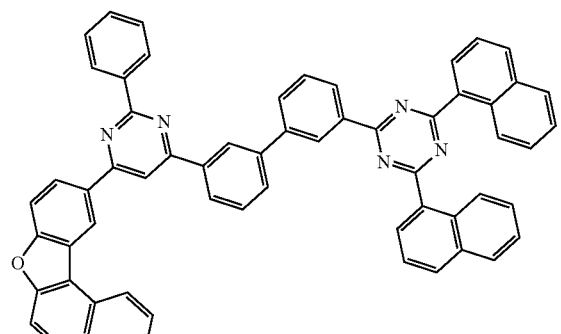
553
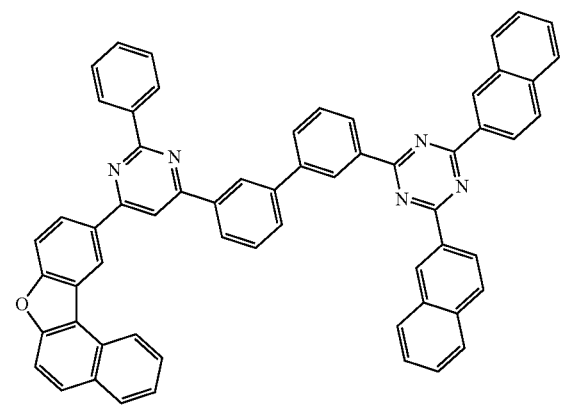
554
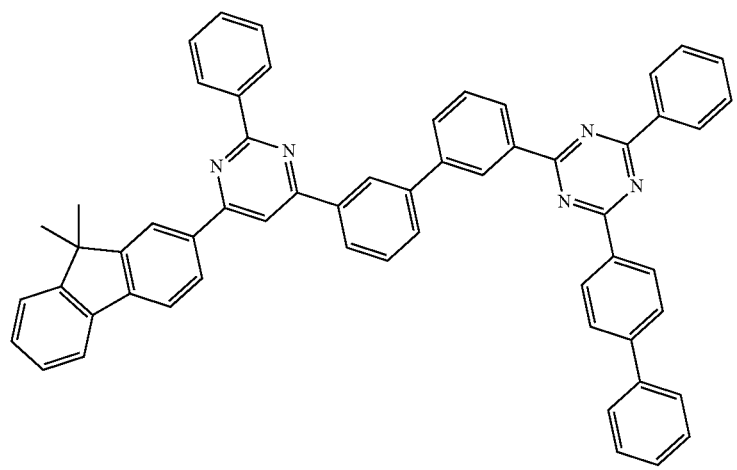

555
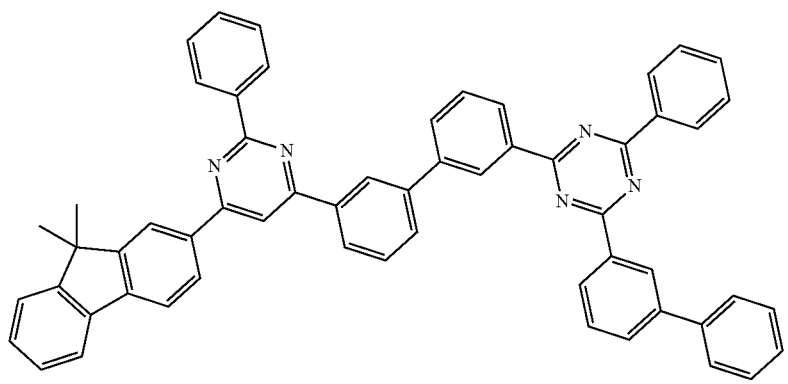
556
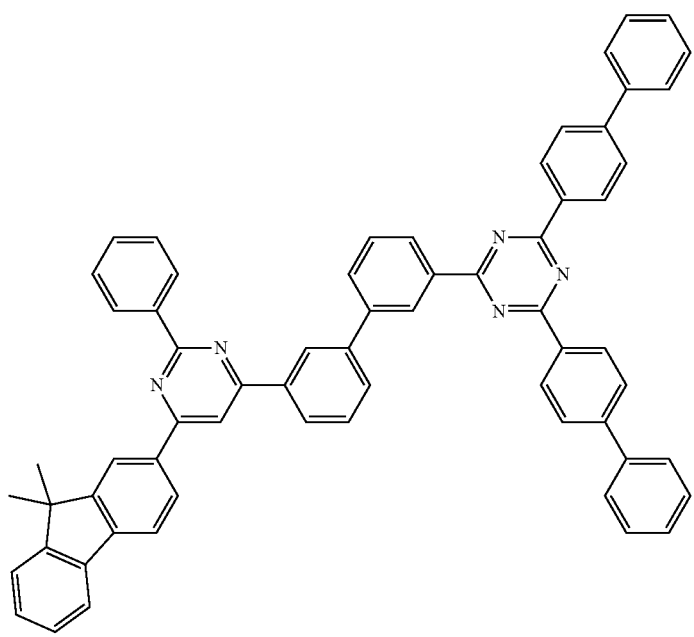
557
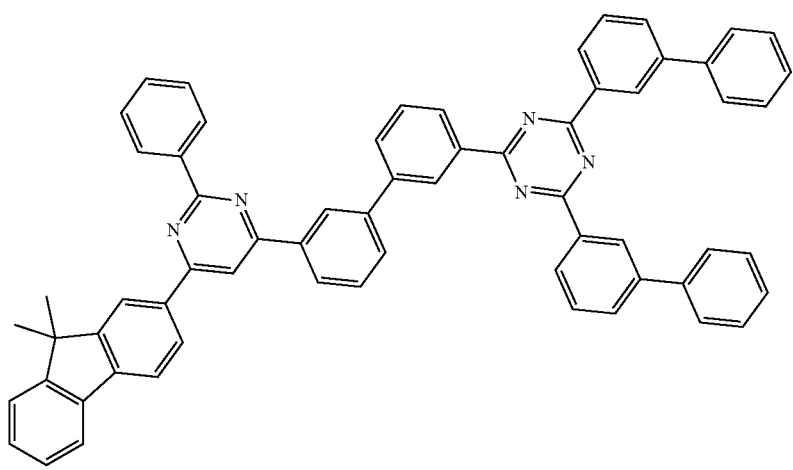

558
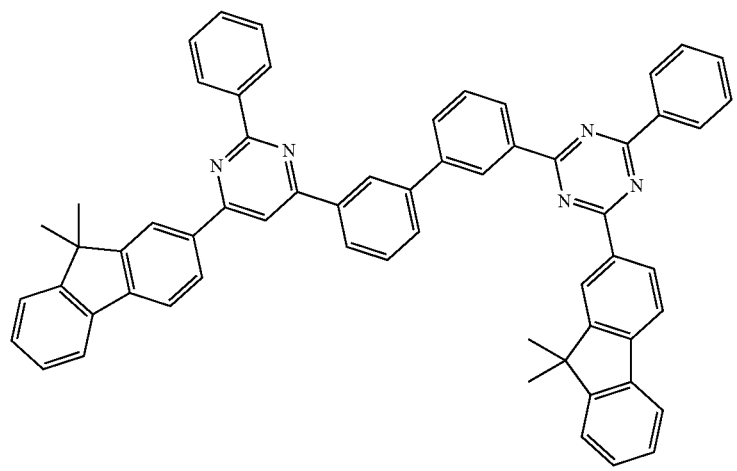
559
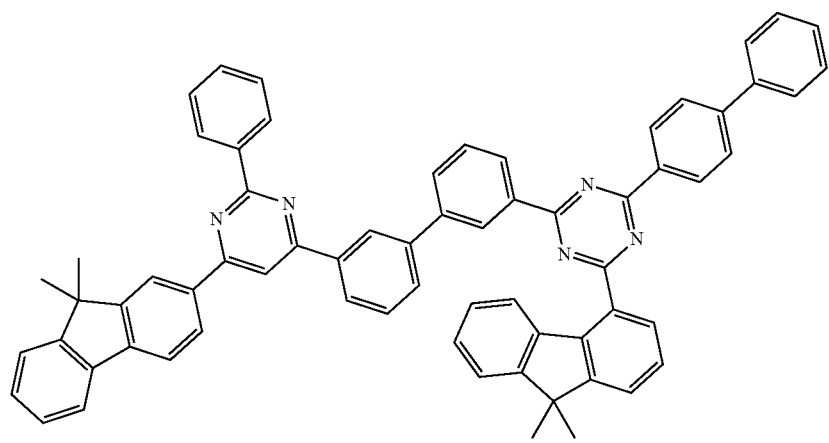
560
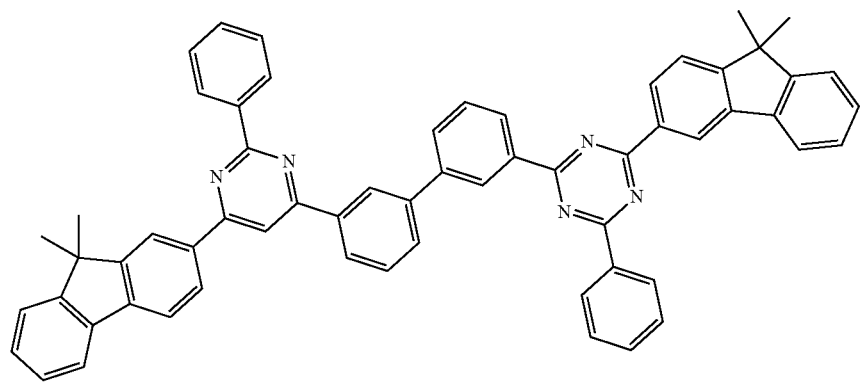

561
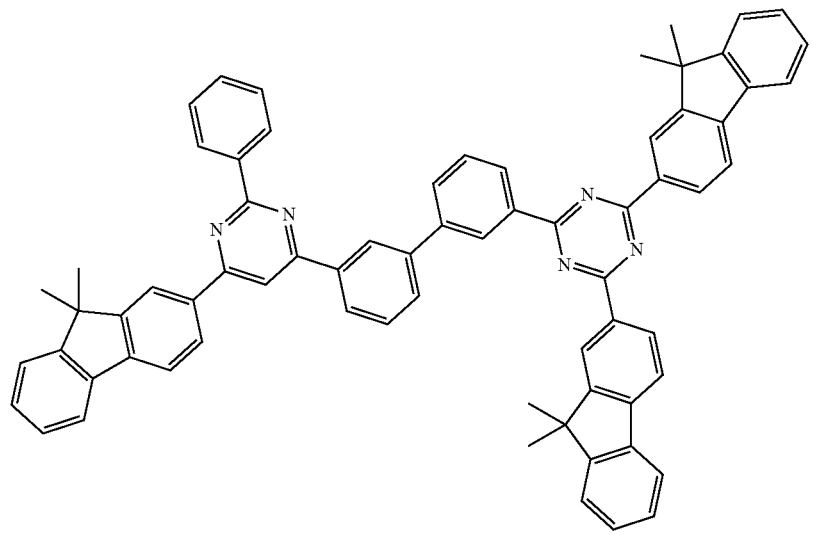
562
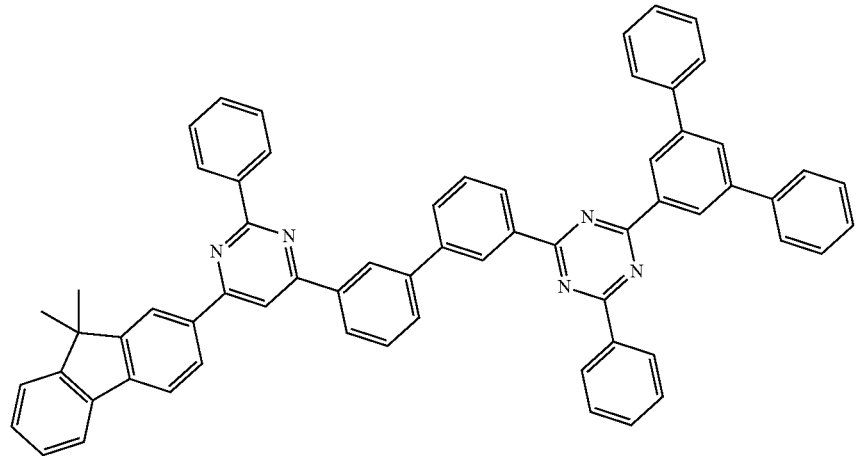
564
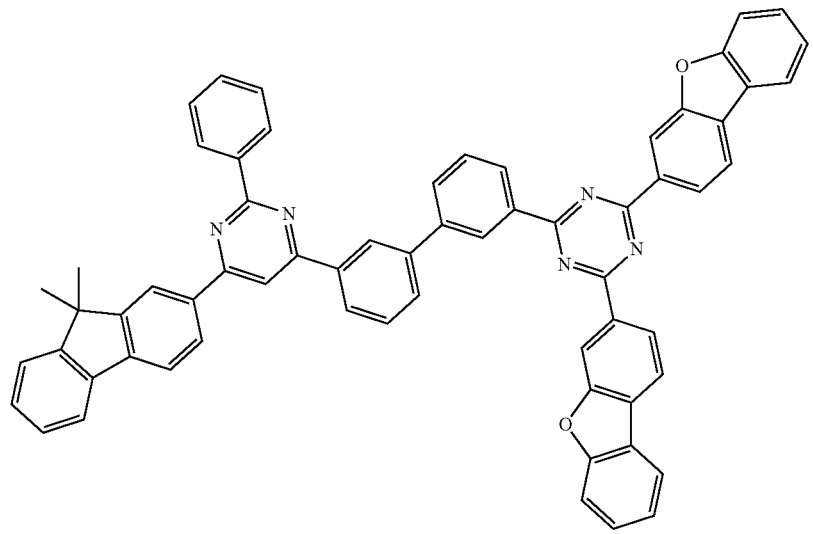

-continued
565
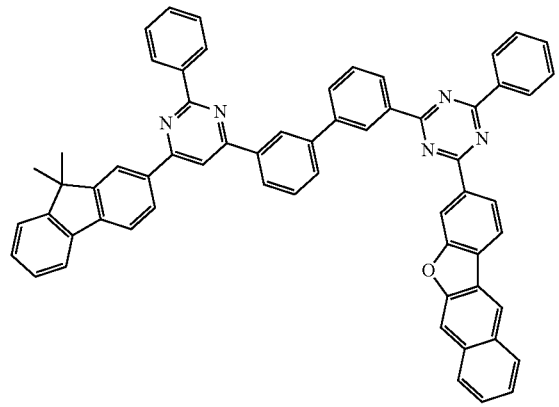
566
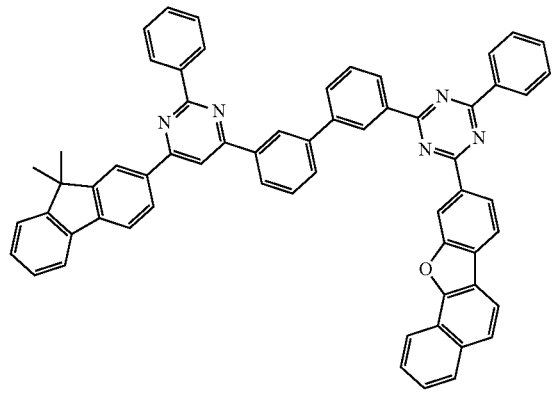
567
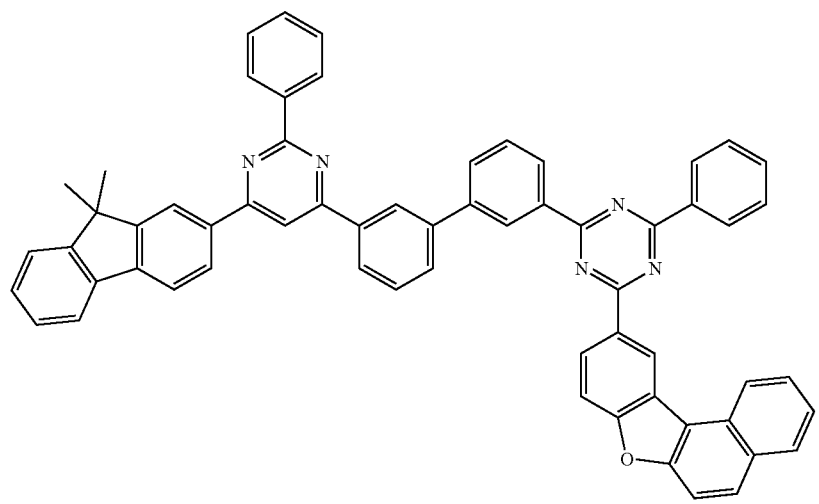
570
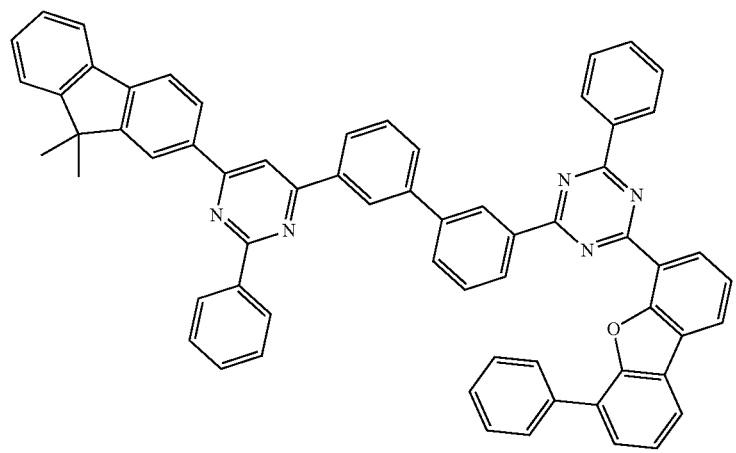

-continued
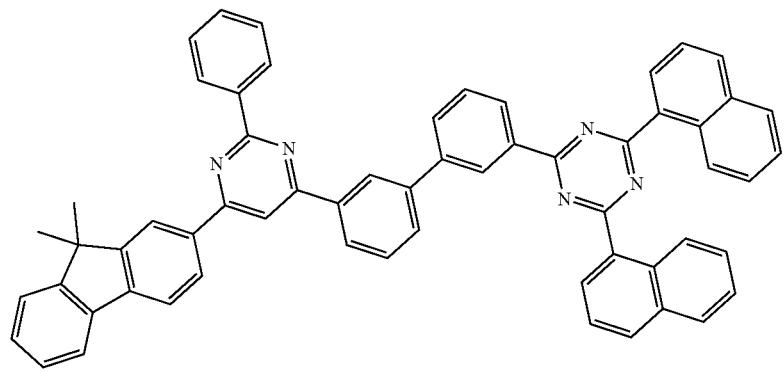
571
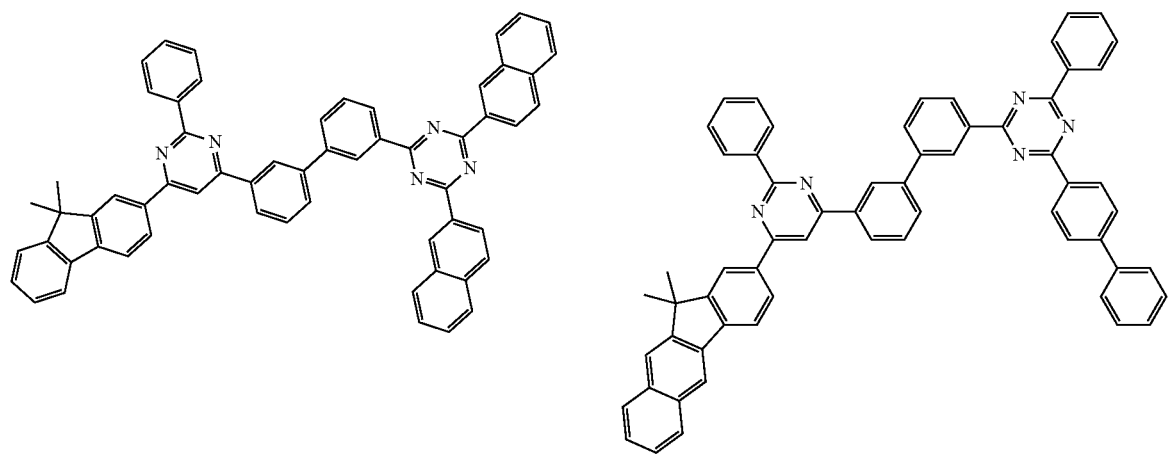
572
573
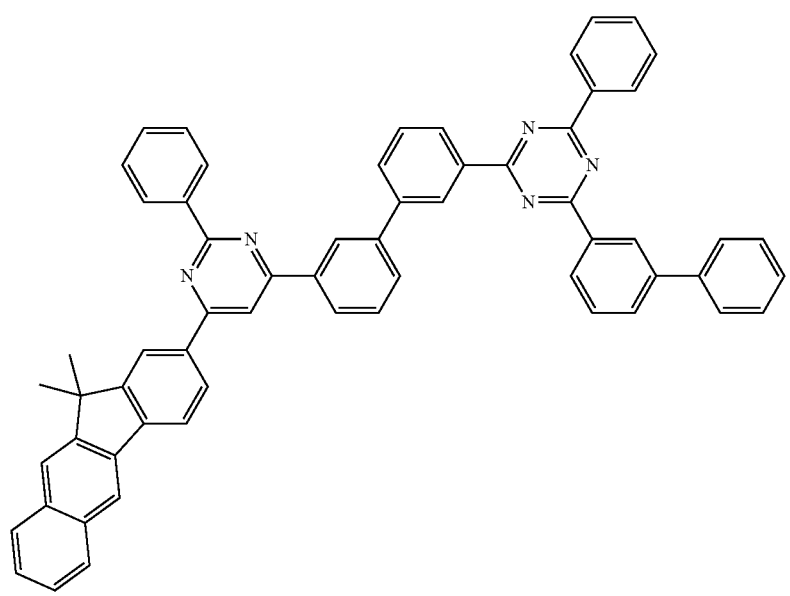
574

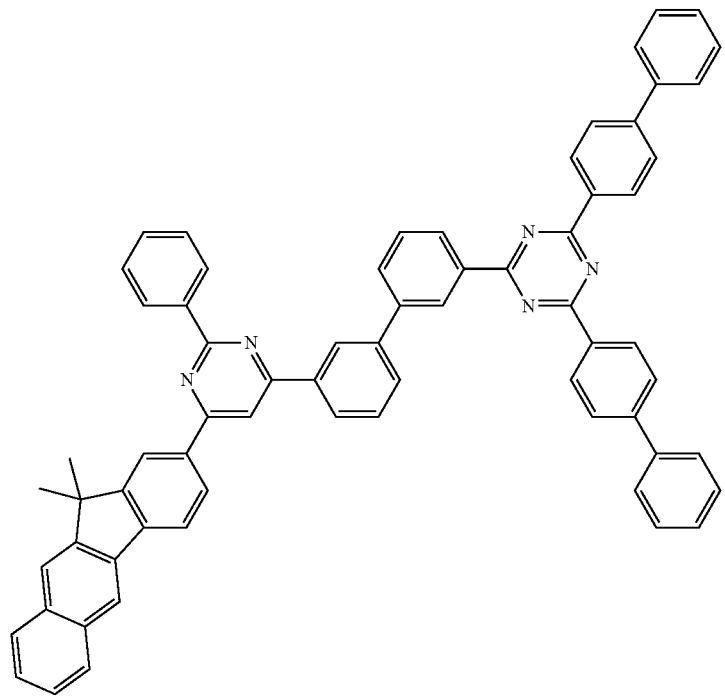
575
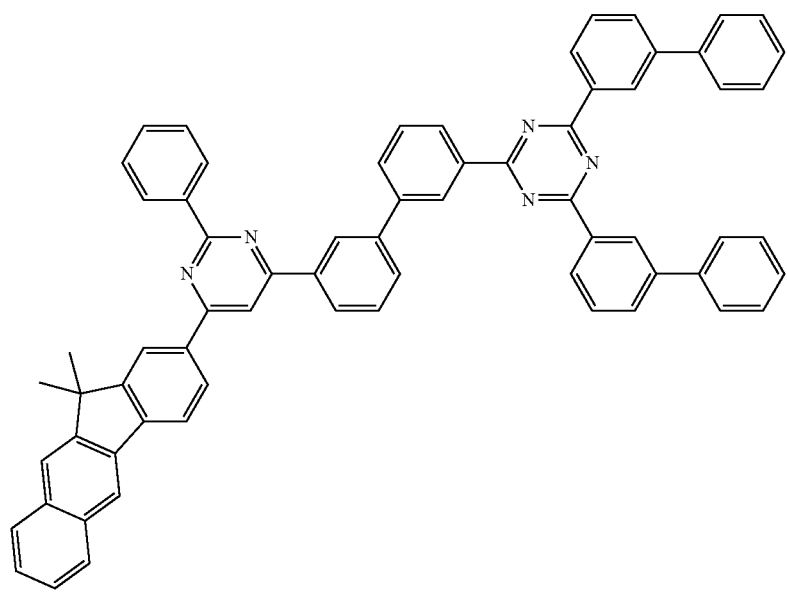
576

785 786
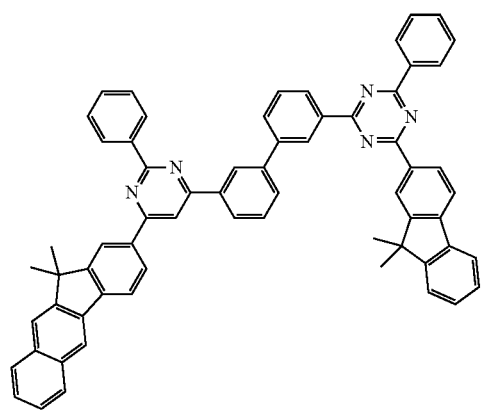
577
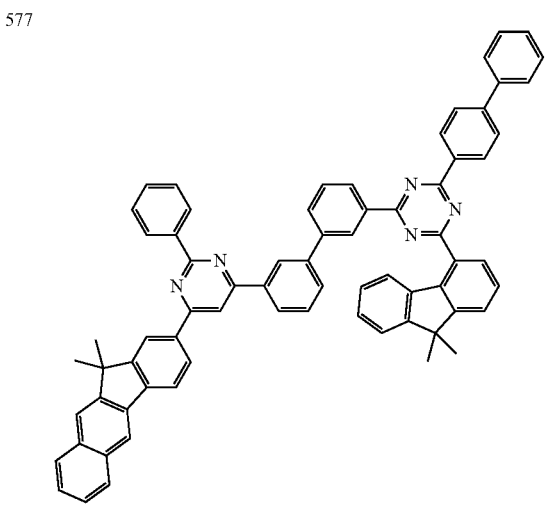
578
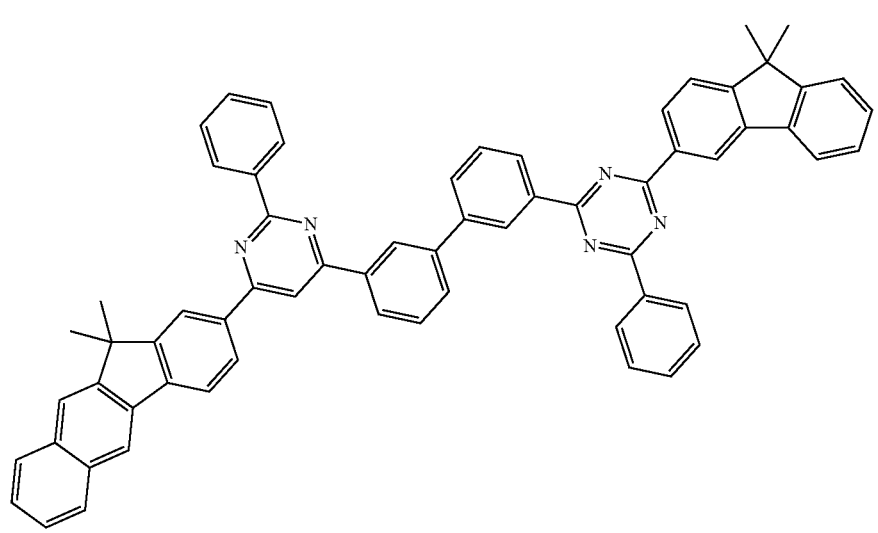
579
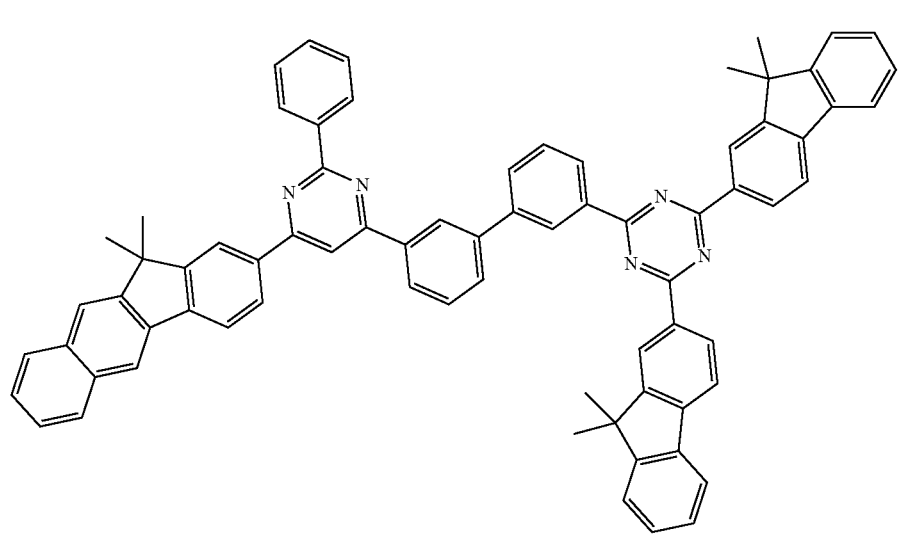
580

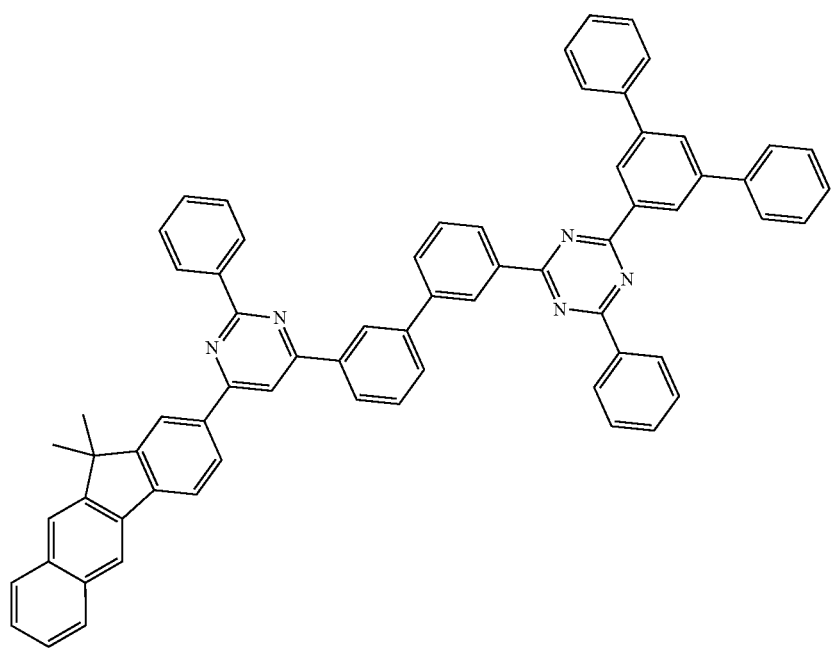
581
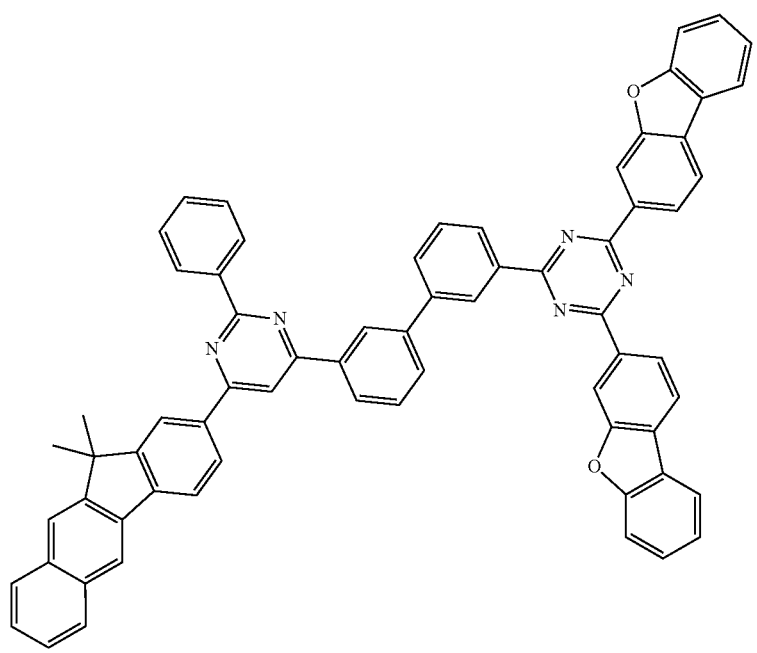
583

584
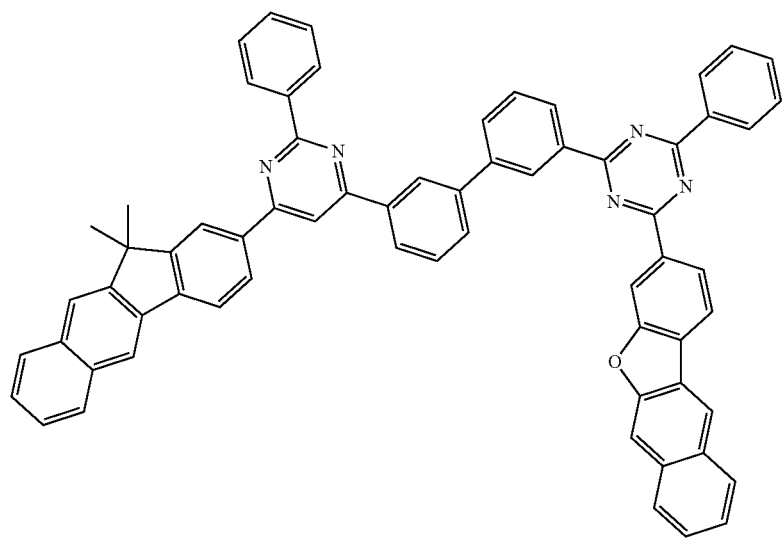
585
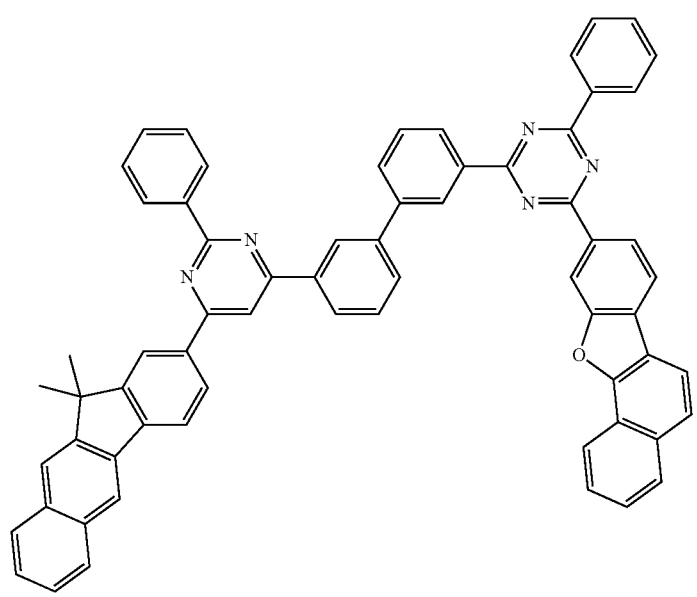

586
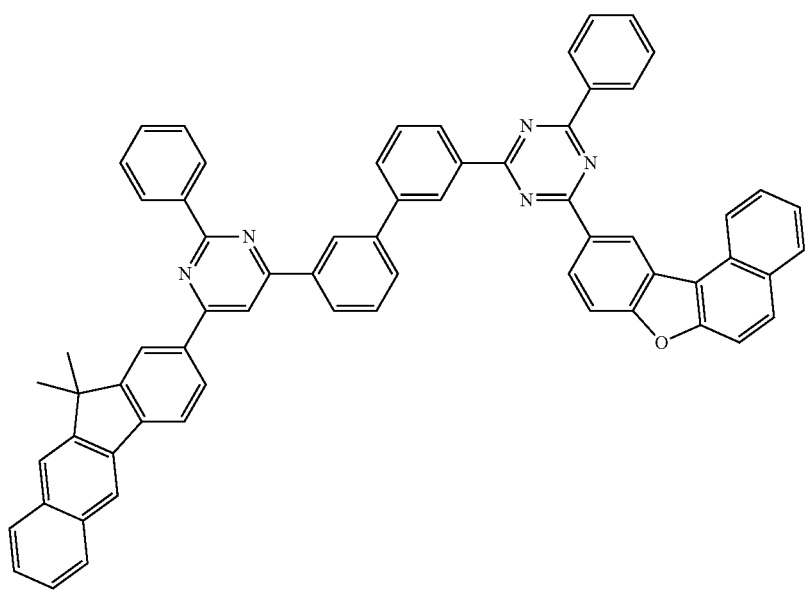
589
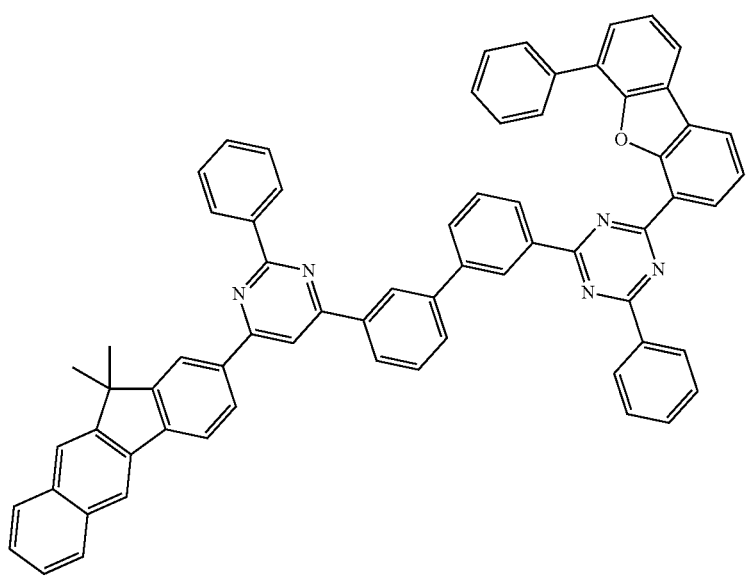

-continued
590
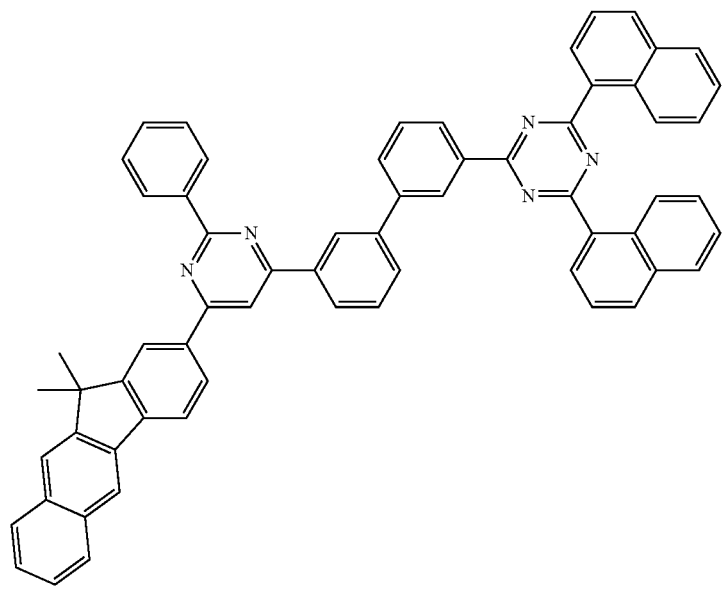
591
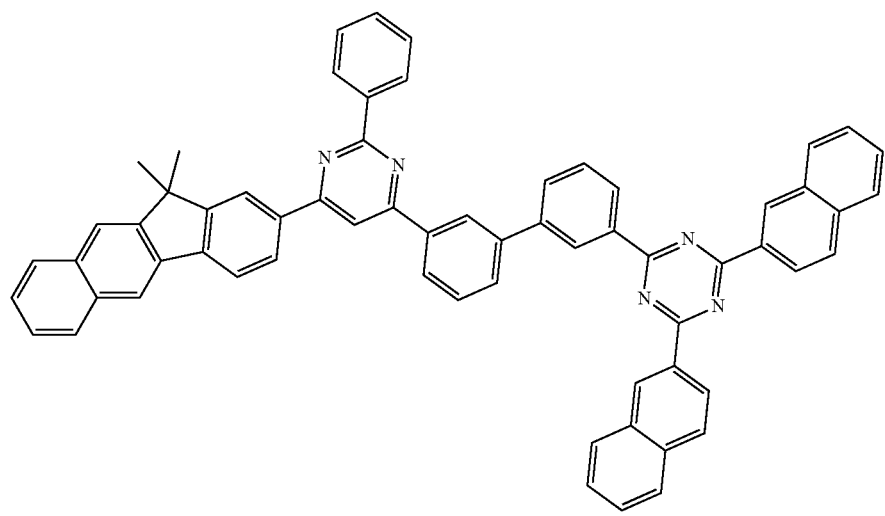
592
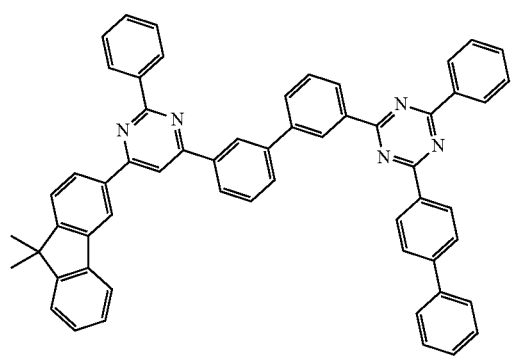
593
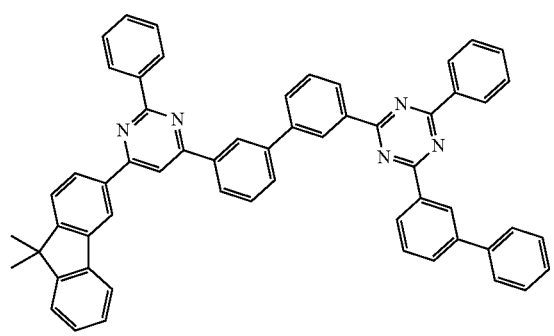

-continued
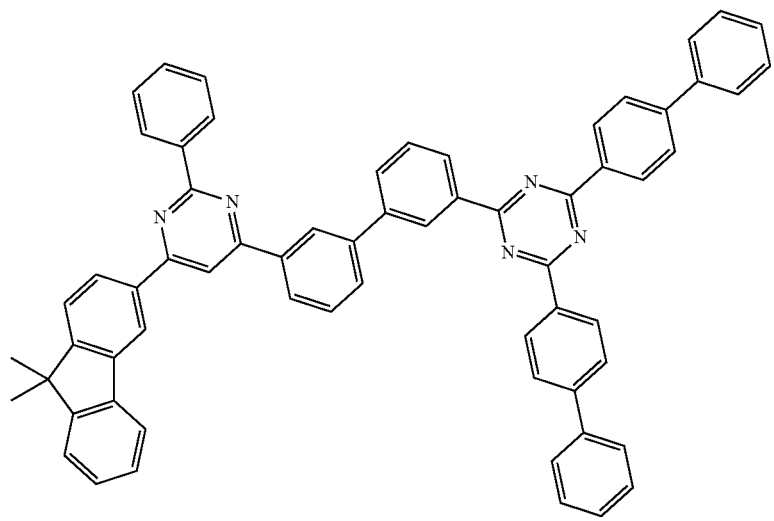
594
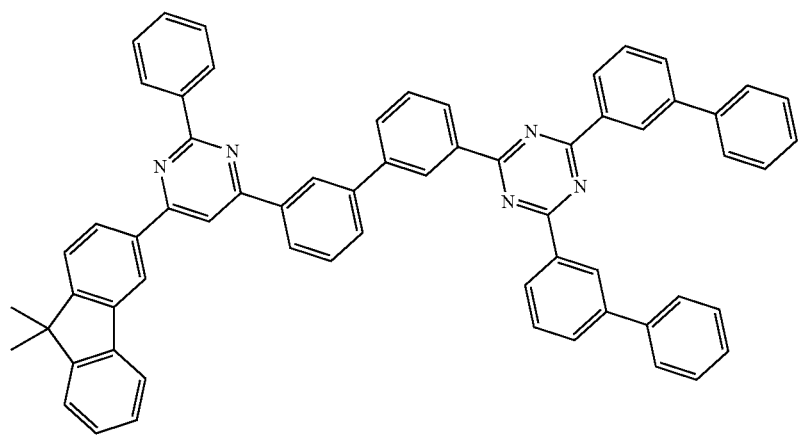
595
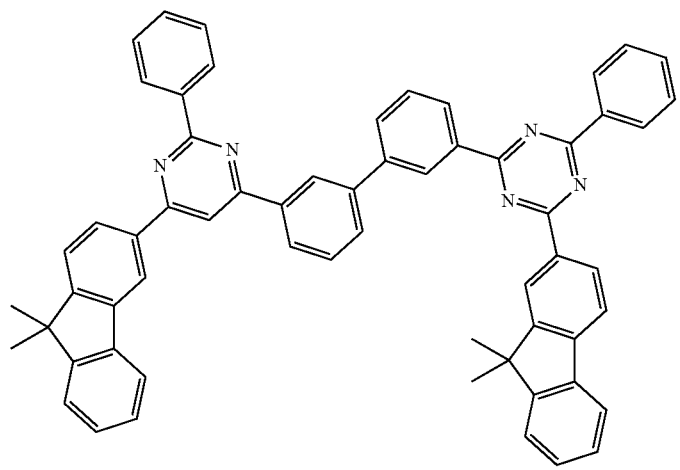
596

597
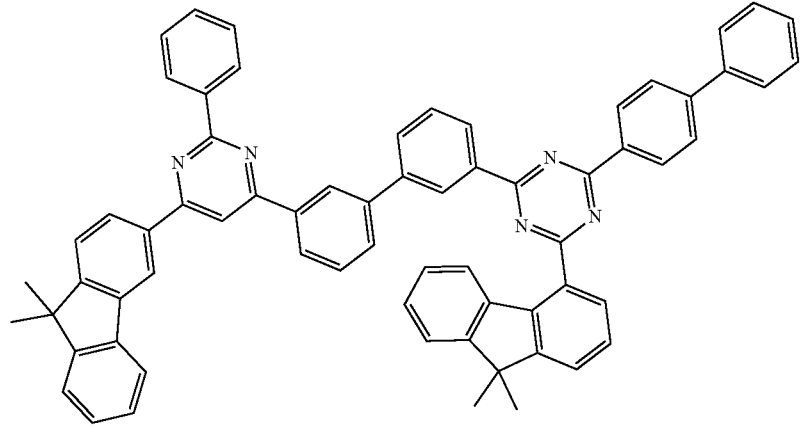
598
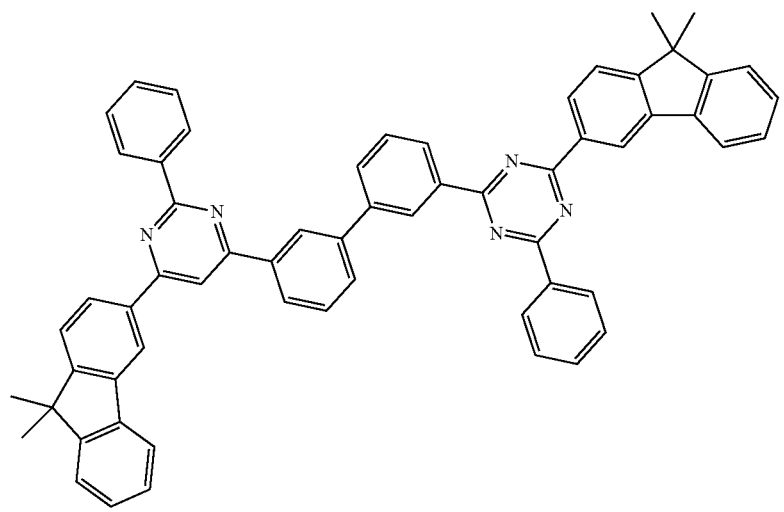
599
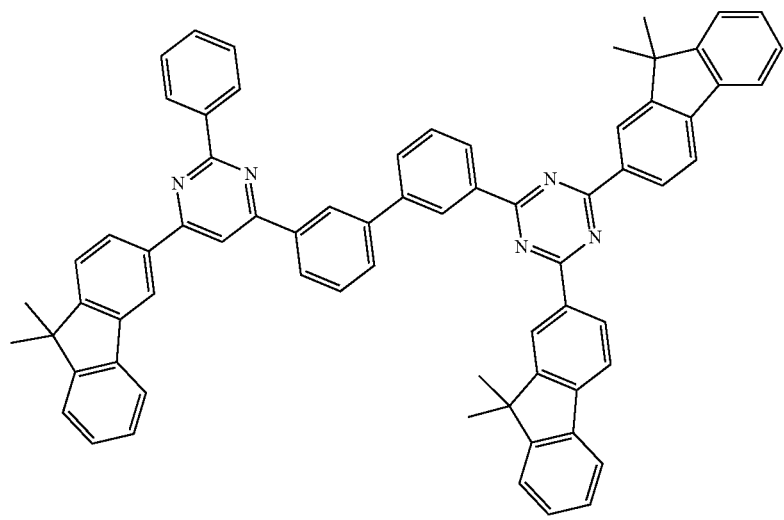

600
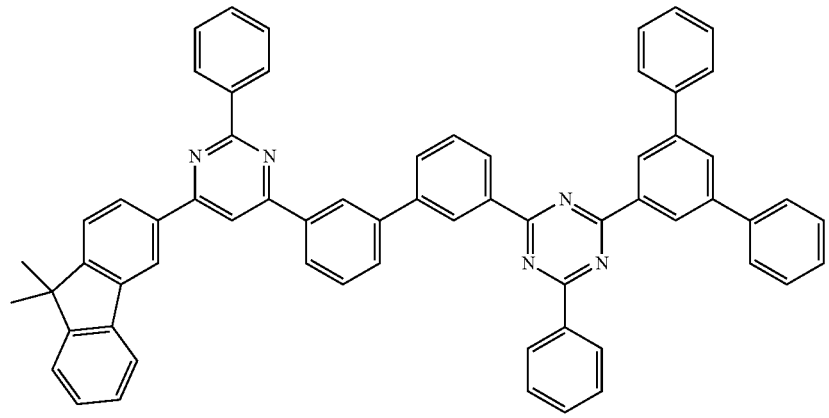
601 602
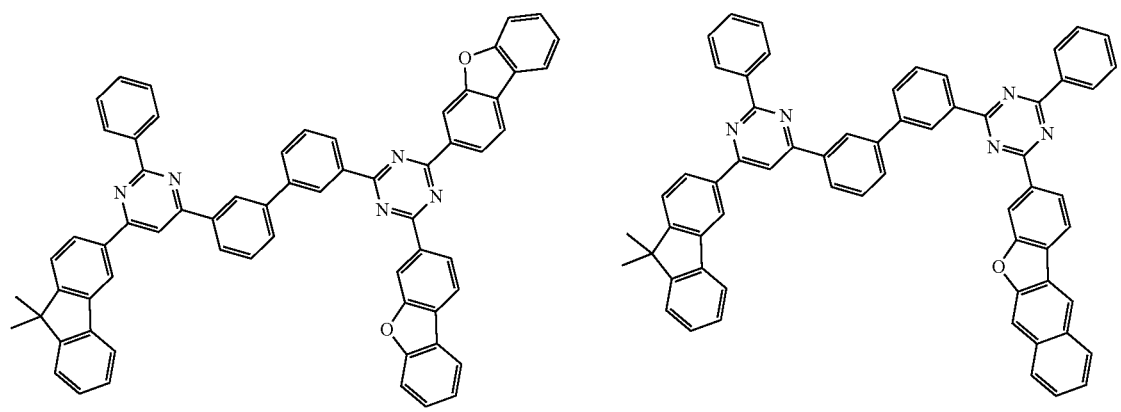
604 605
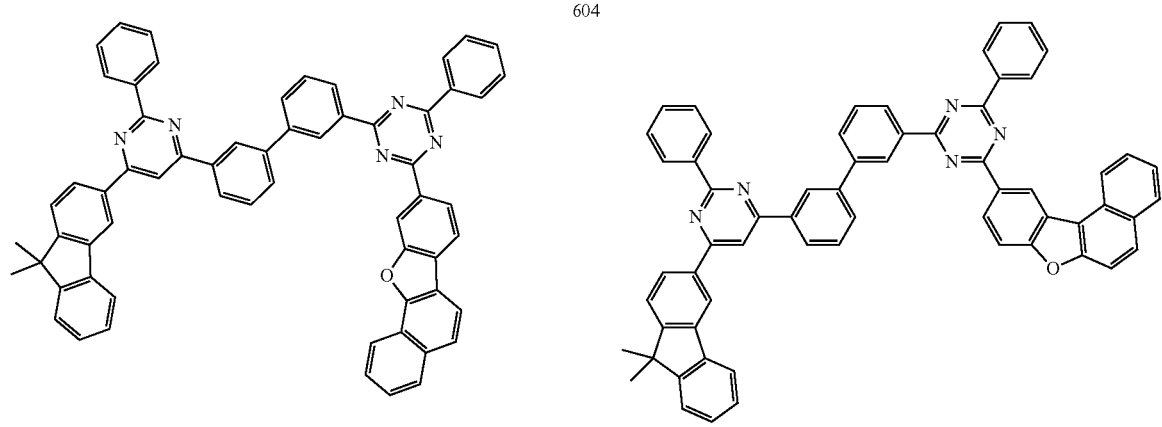
608 609
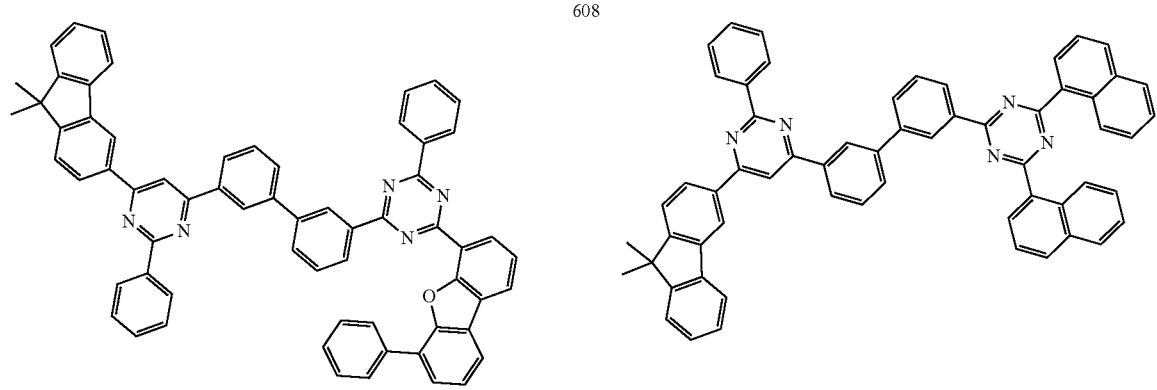

-continued
610
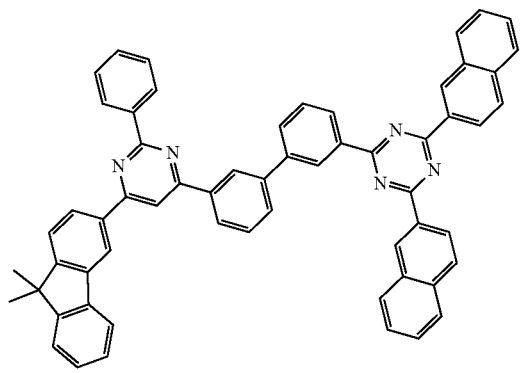
611
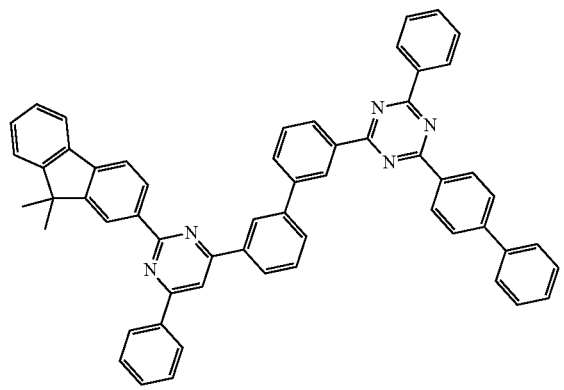
612
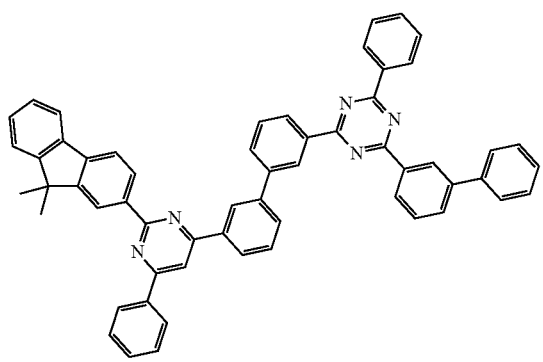
613
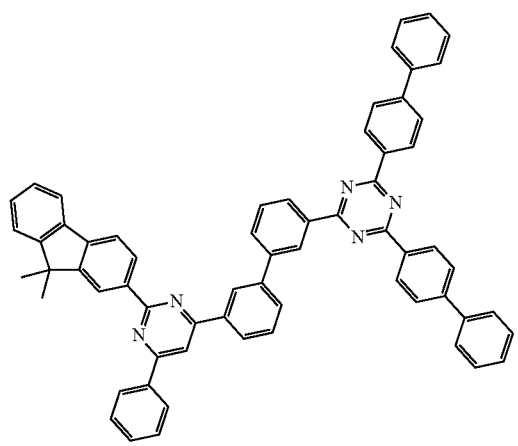
614
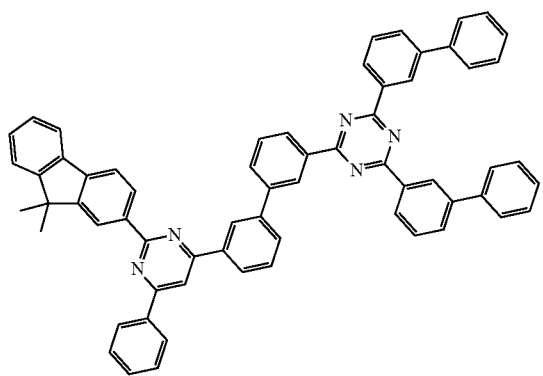
615
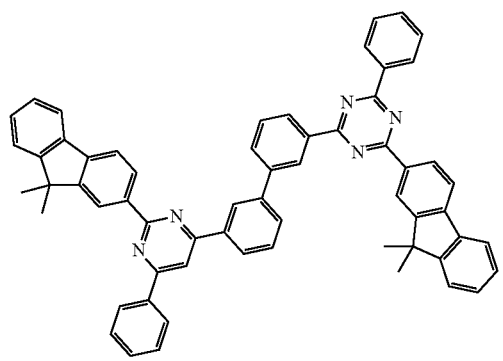

-continued
616
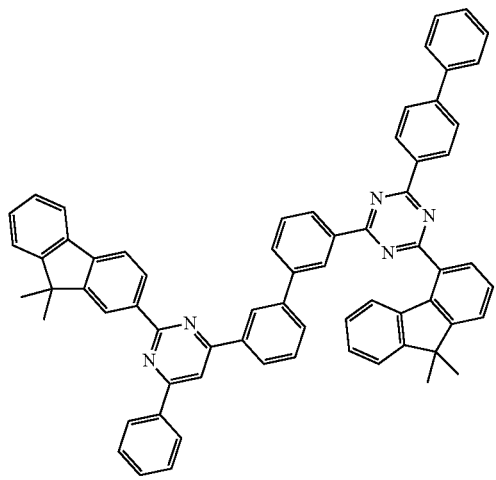
617
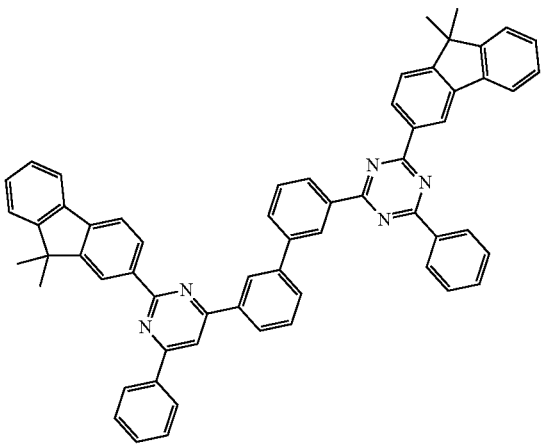
618
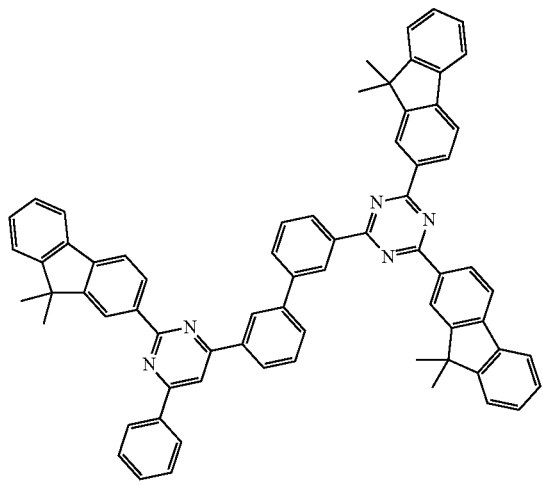
619
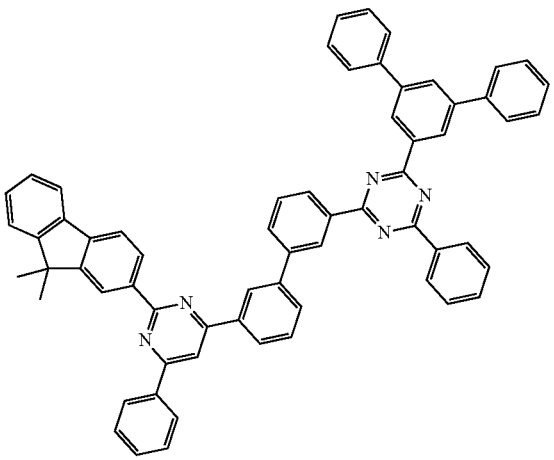
621
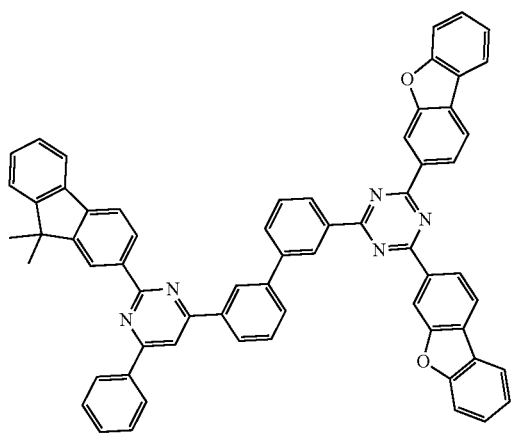
622
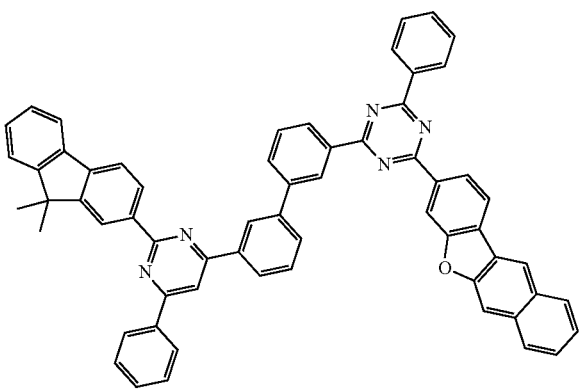

-continued
623
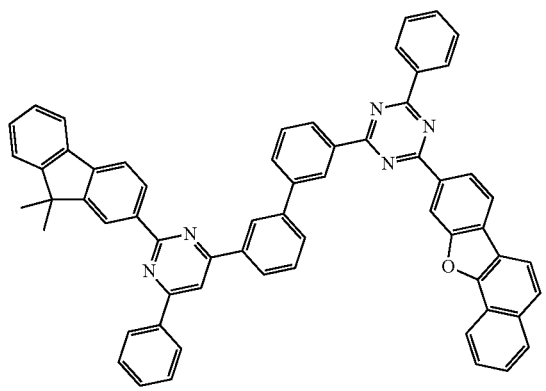
624
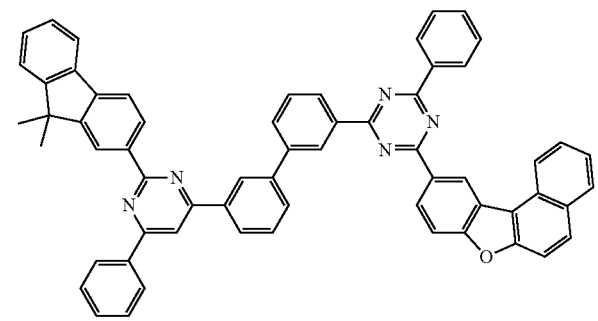
627
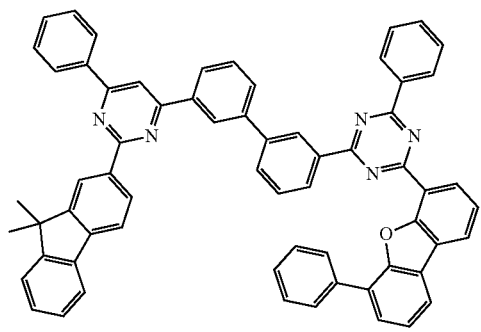
628
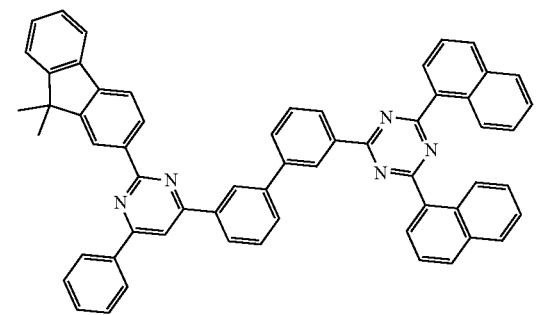
629
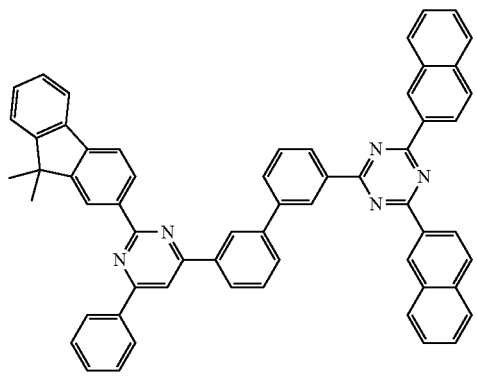
630
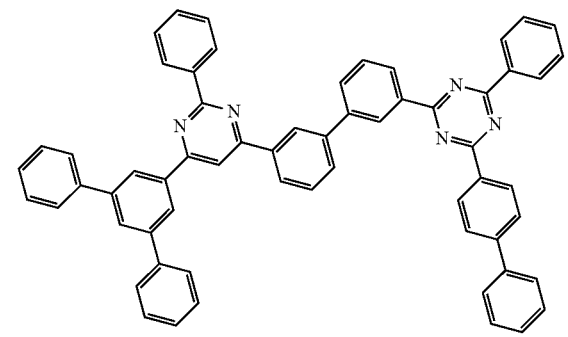
631
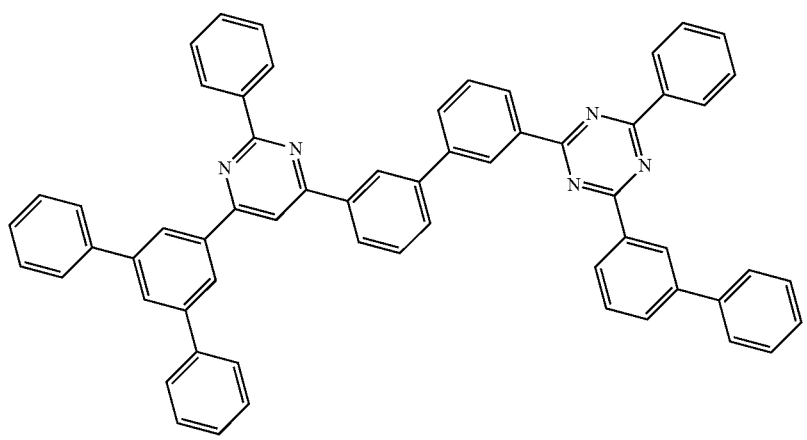

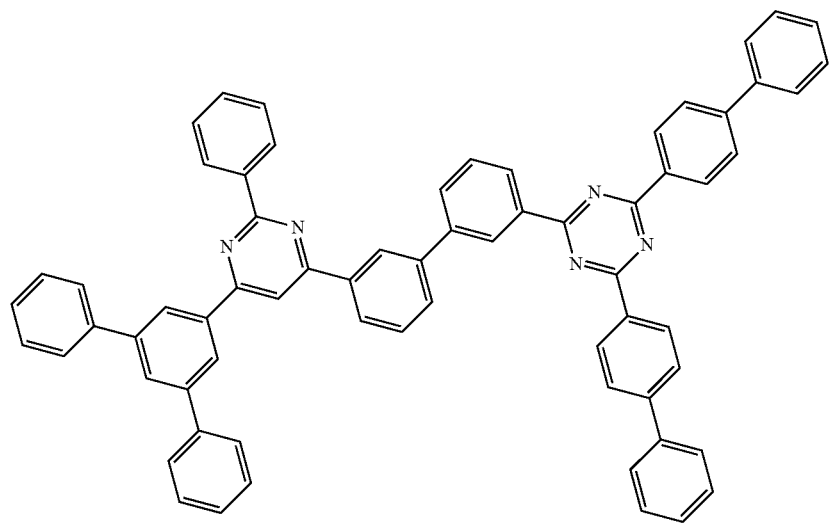
632
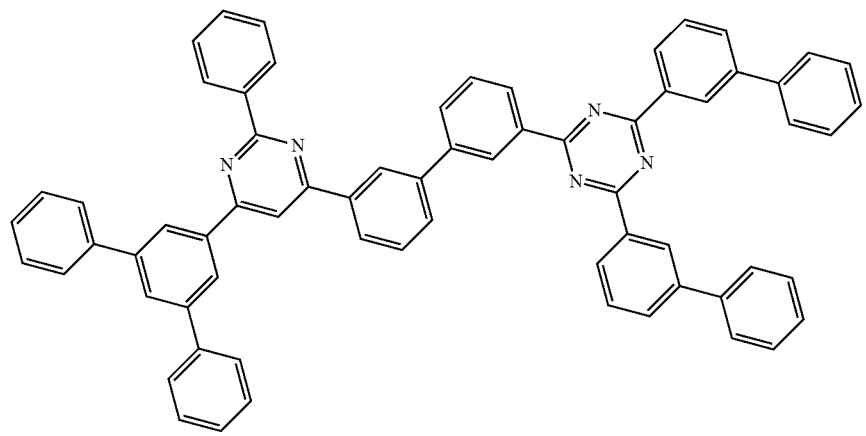
633
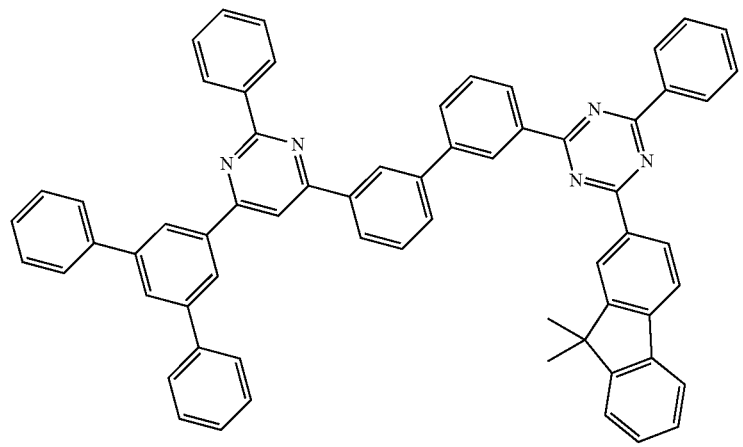
634

635
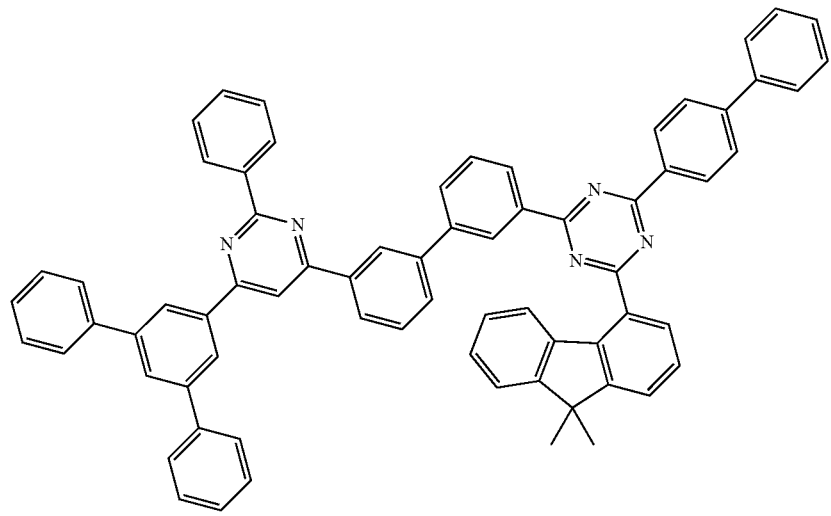
636
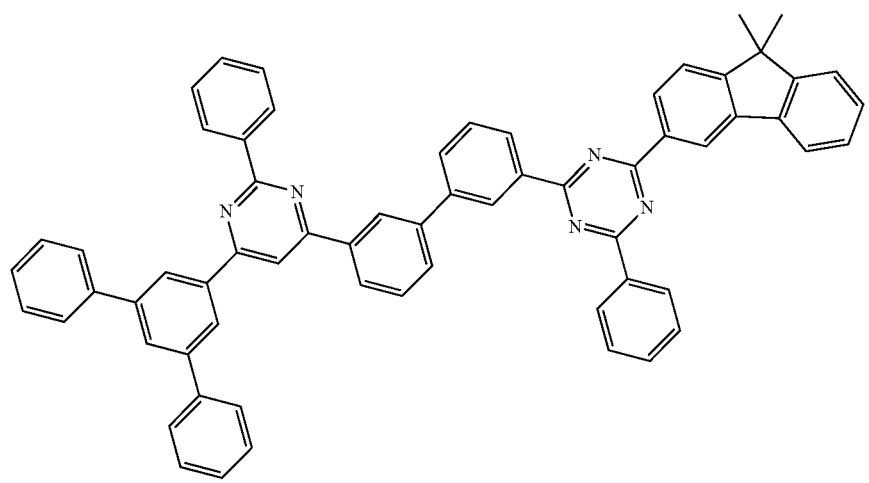
637
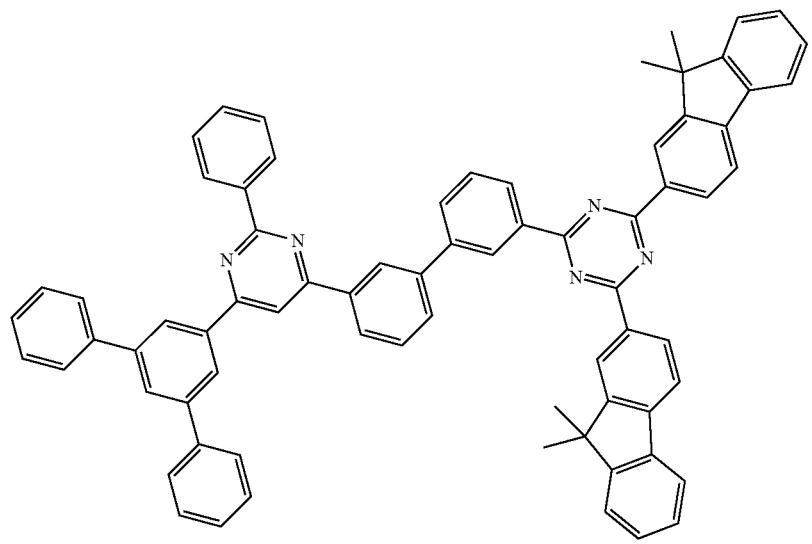

-continued
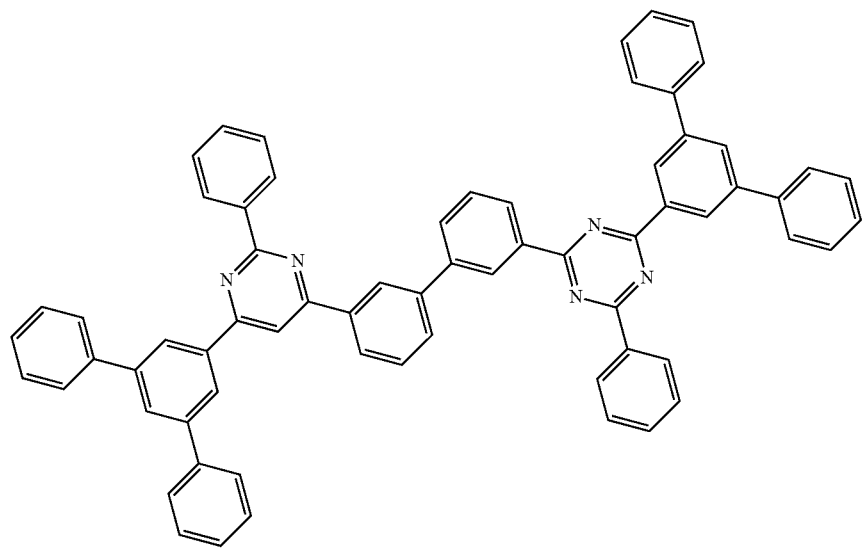
638
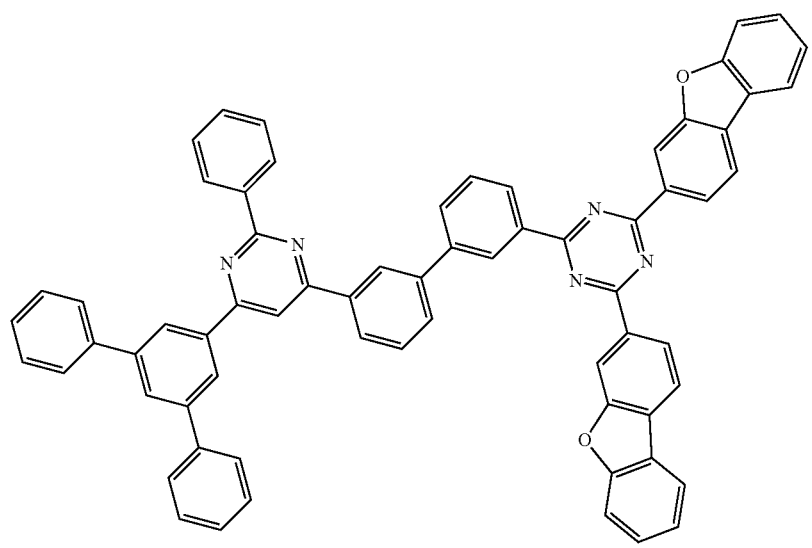
640
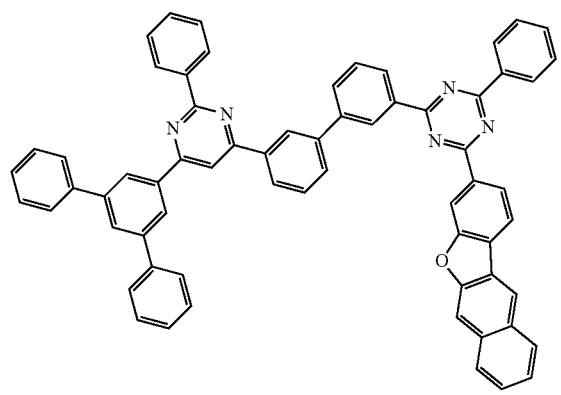
641
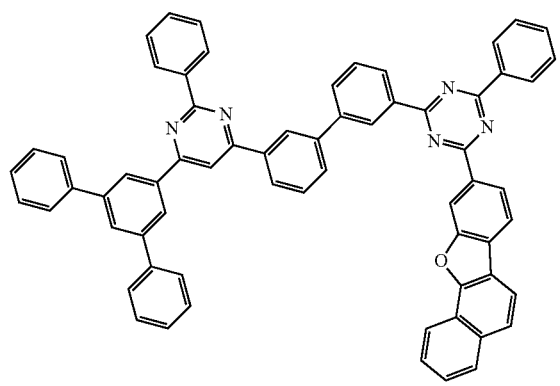
642

813 814
-continued
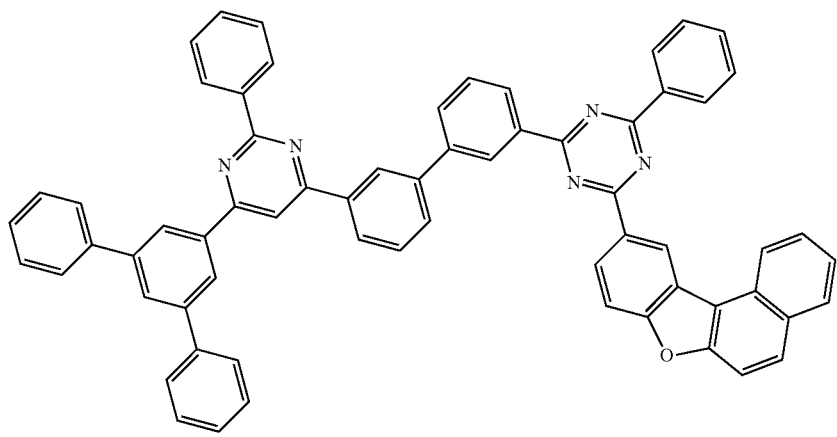
643
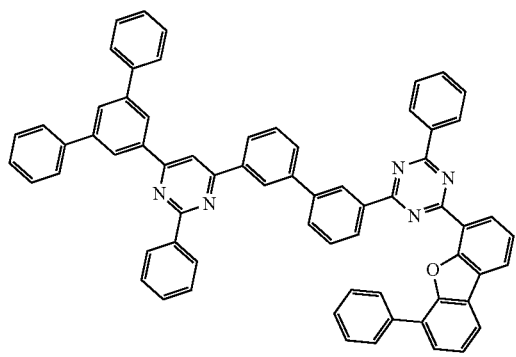
646
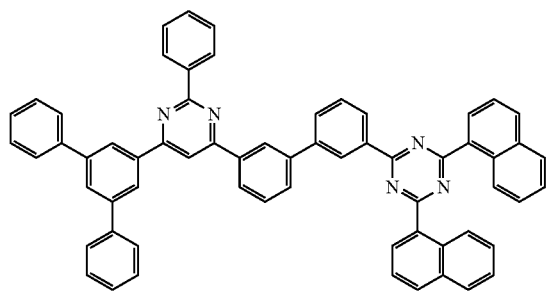
647
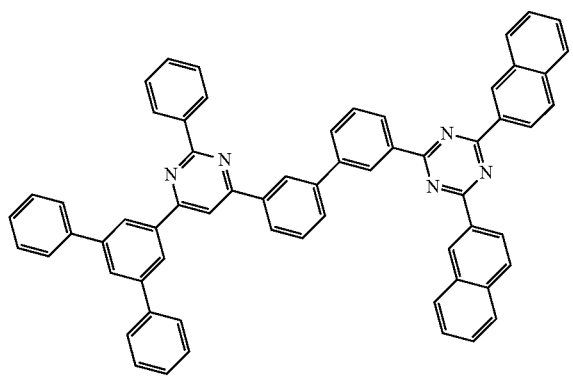
648
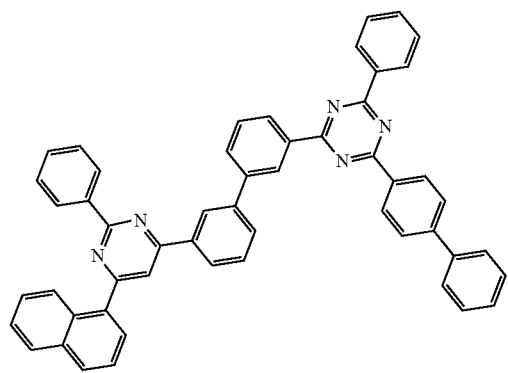
649
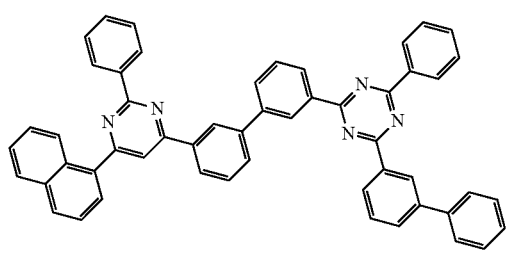
650
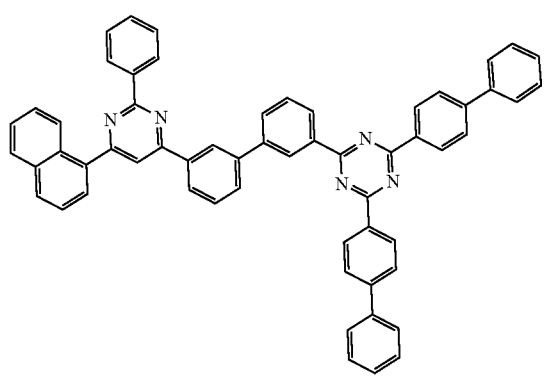
651

-continued
652
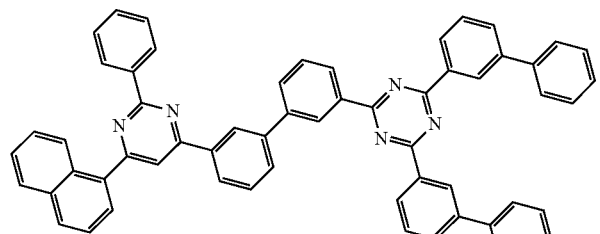
653
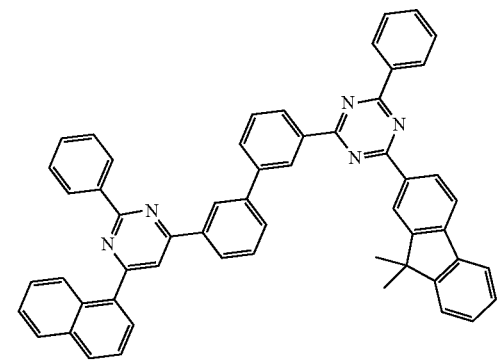
654
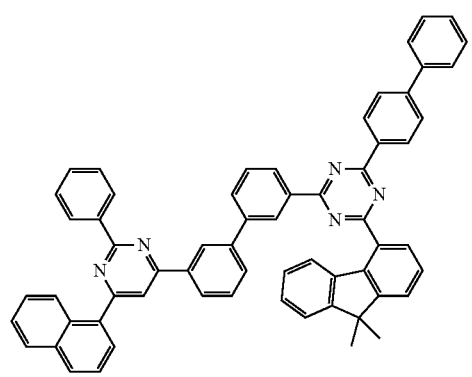
655
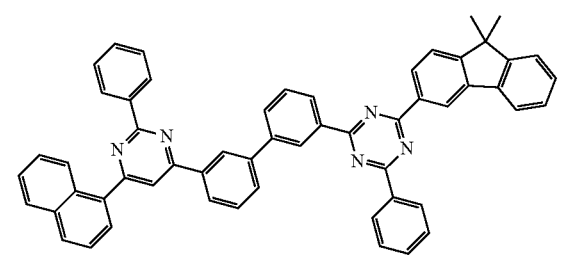
656
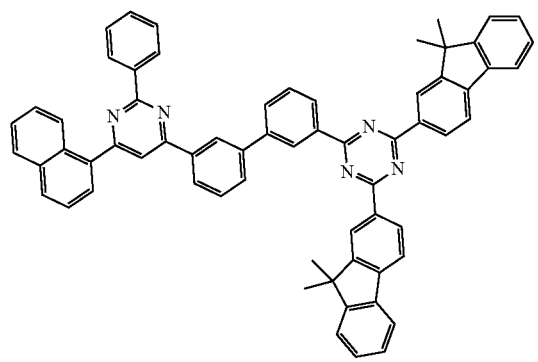
657
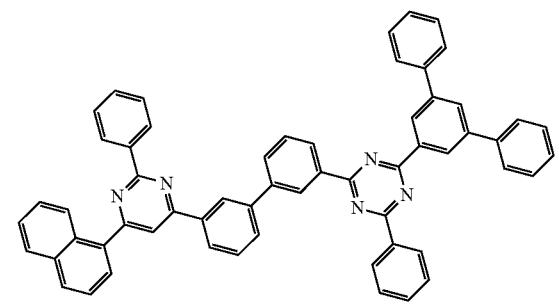
659
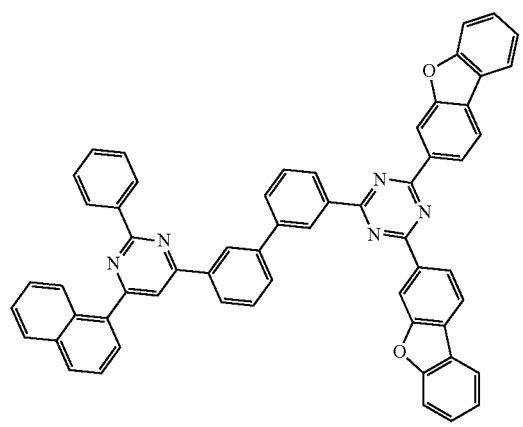
660
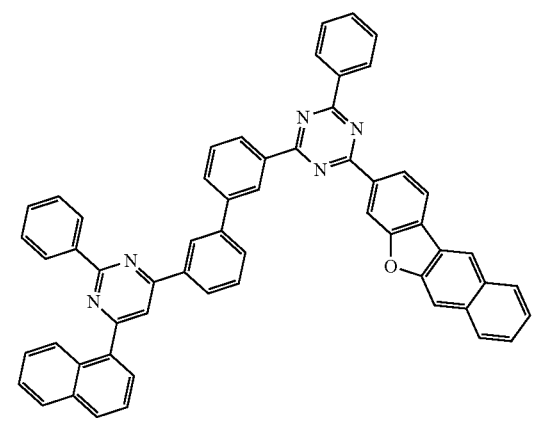

-continued
661
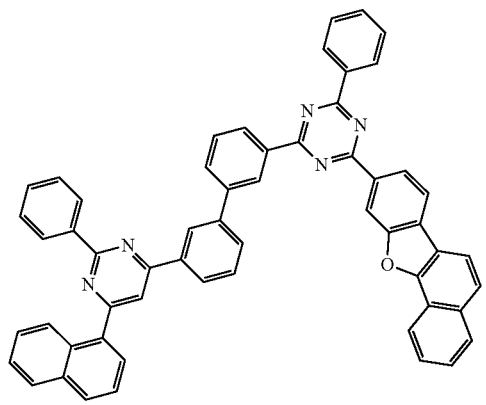
662
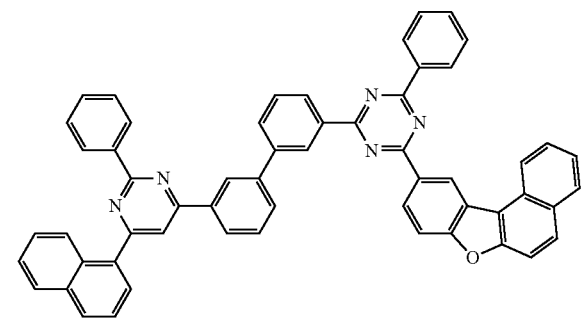
665
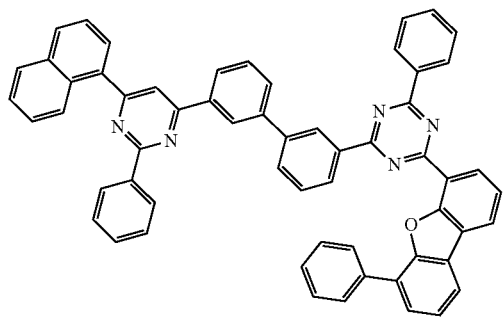
666
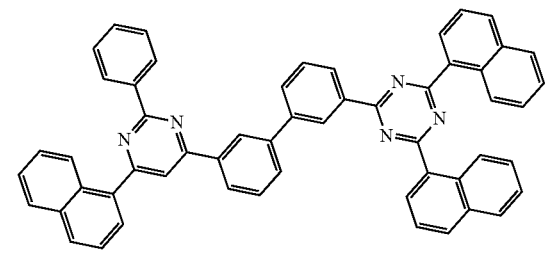
667
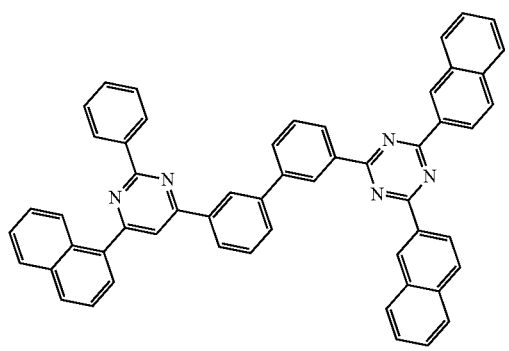
668
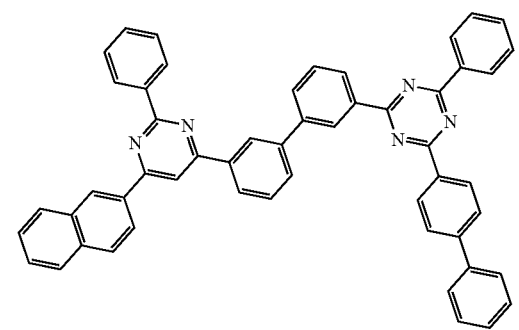
669
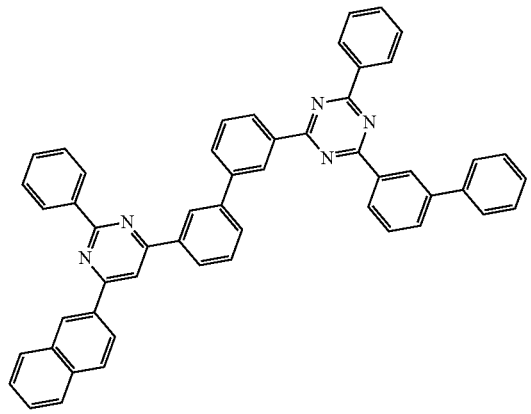
670
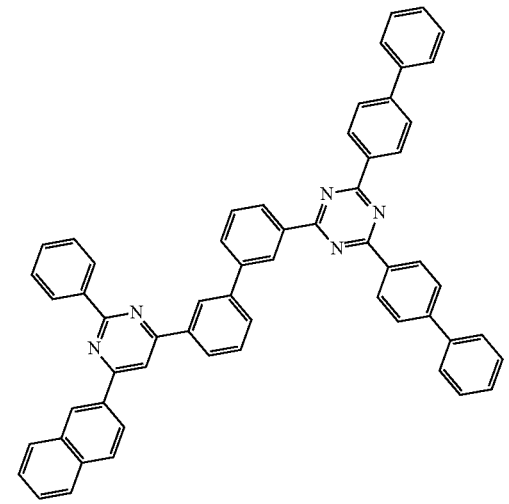

-continued
671
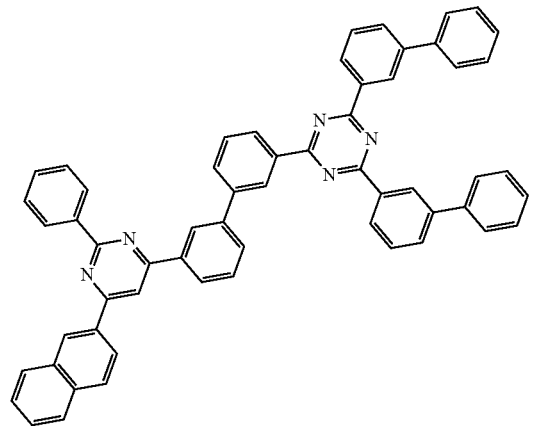
672
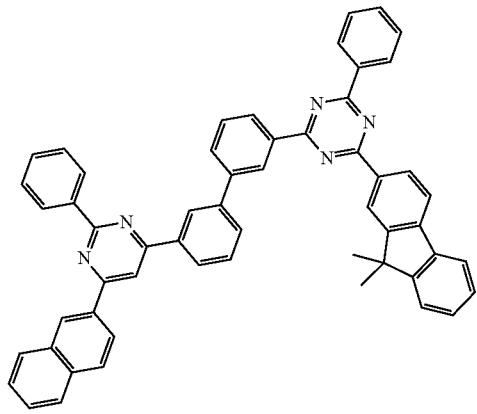
673
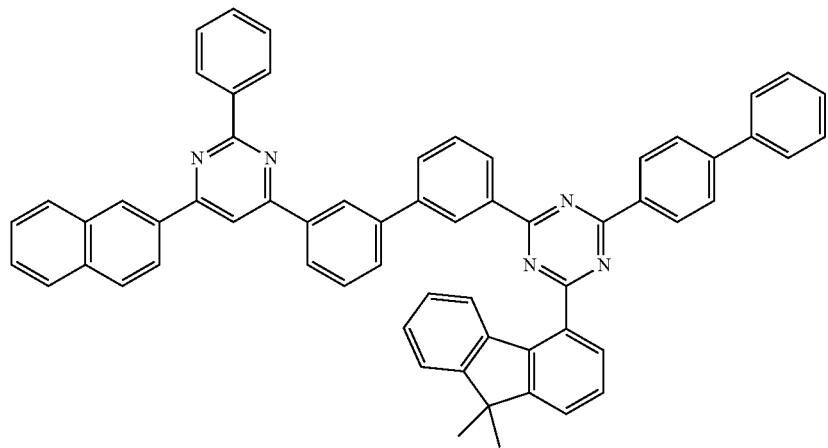
674
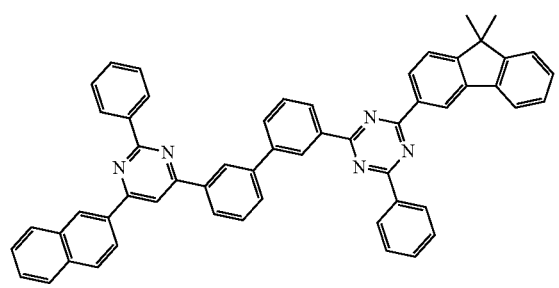
675
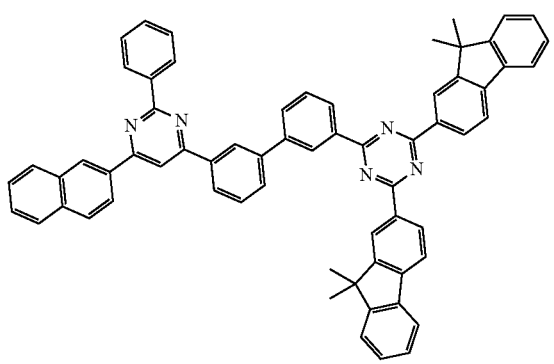

-continued
676
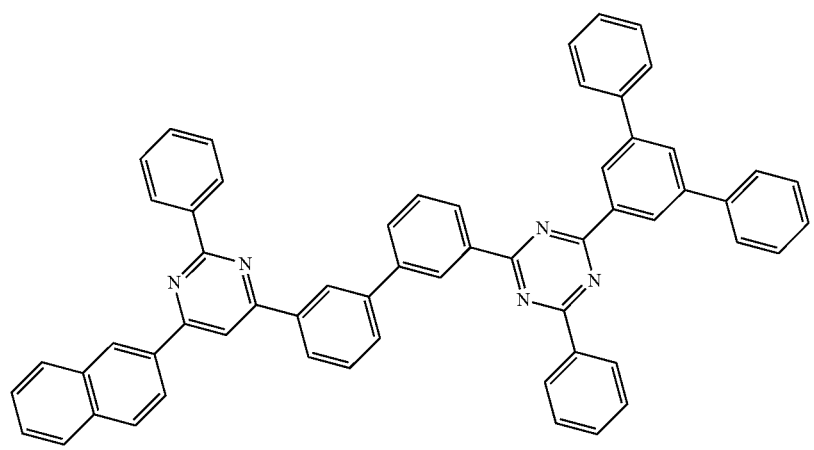
678
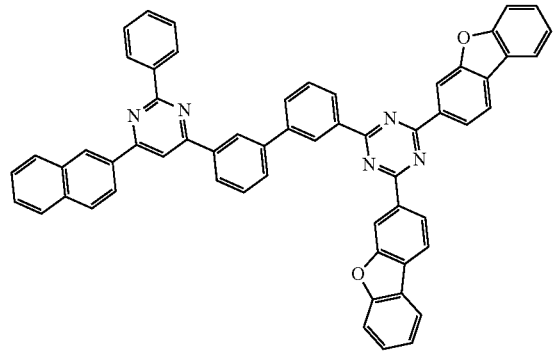
679
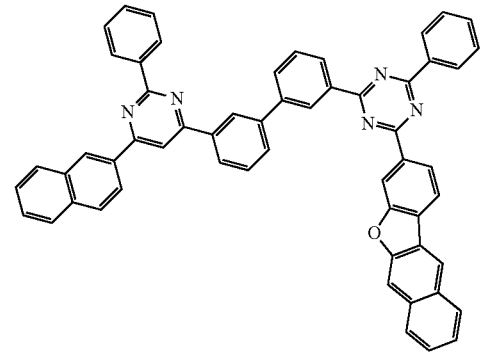
680
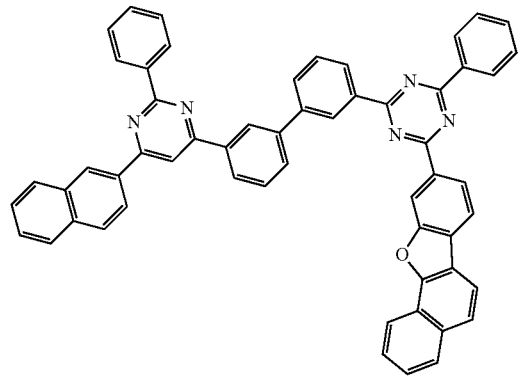
681
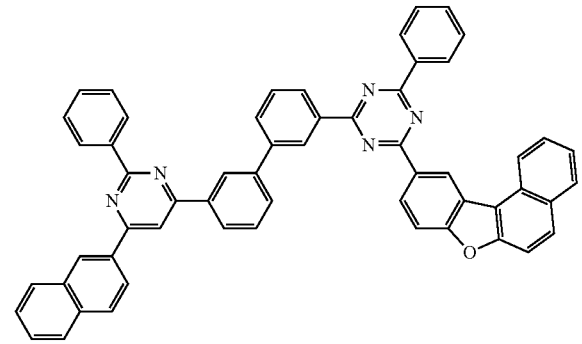
684
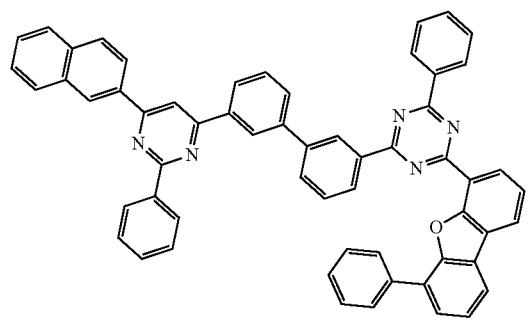
685
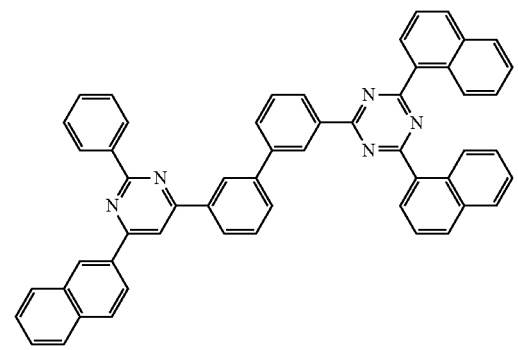

823 824
-continued
686 687
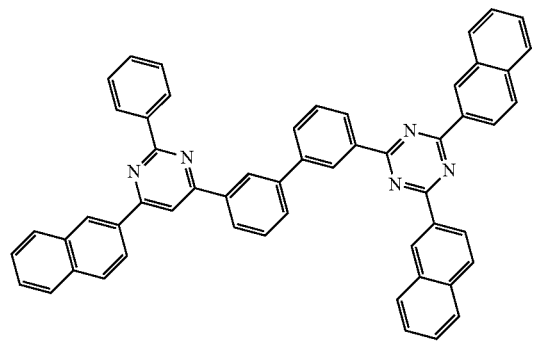 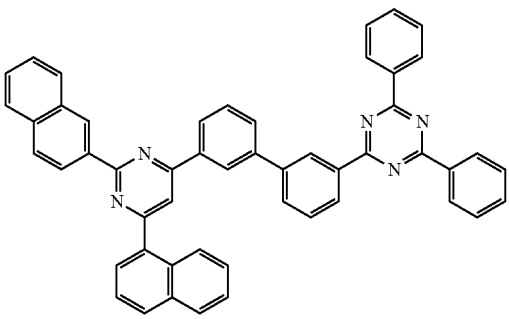
688
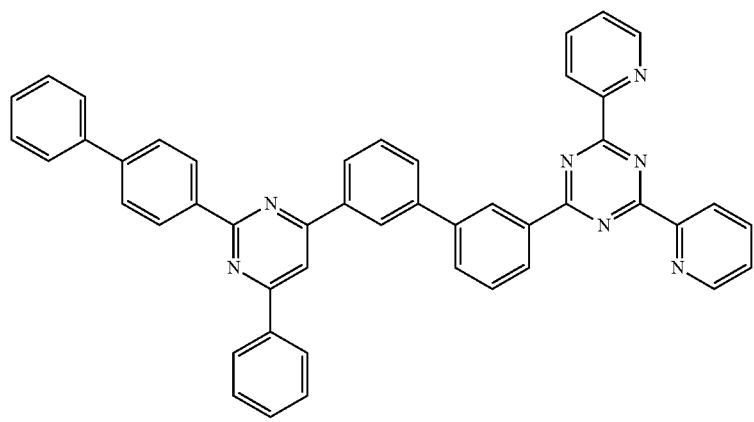
689
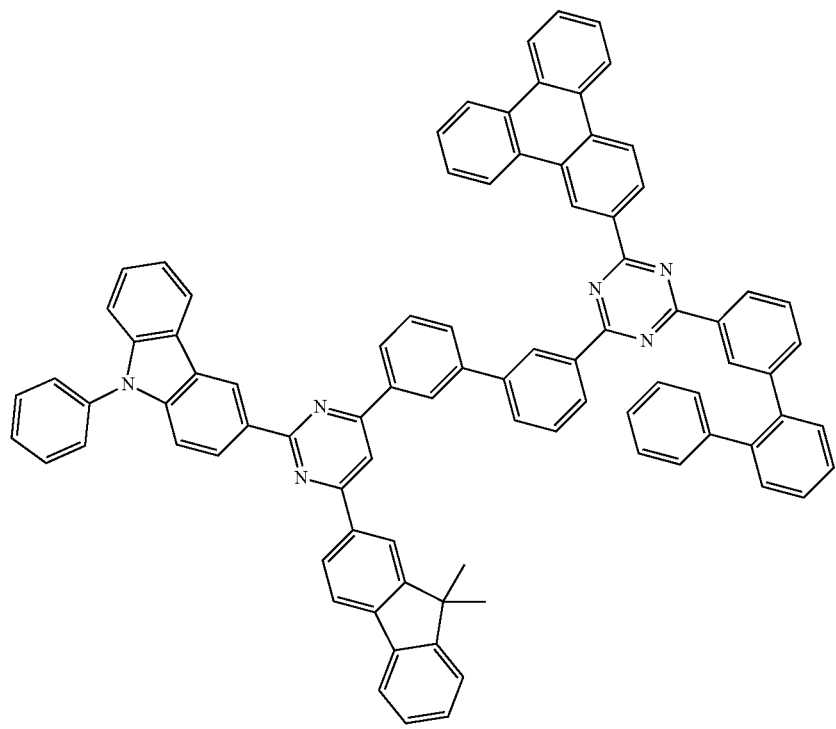

-continued
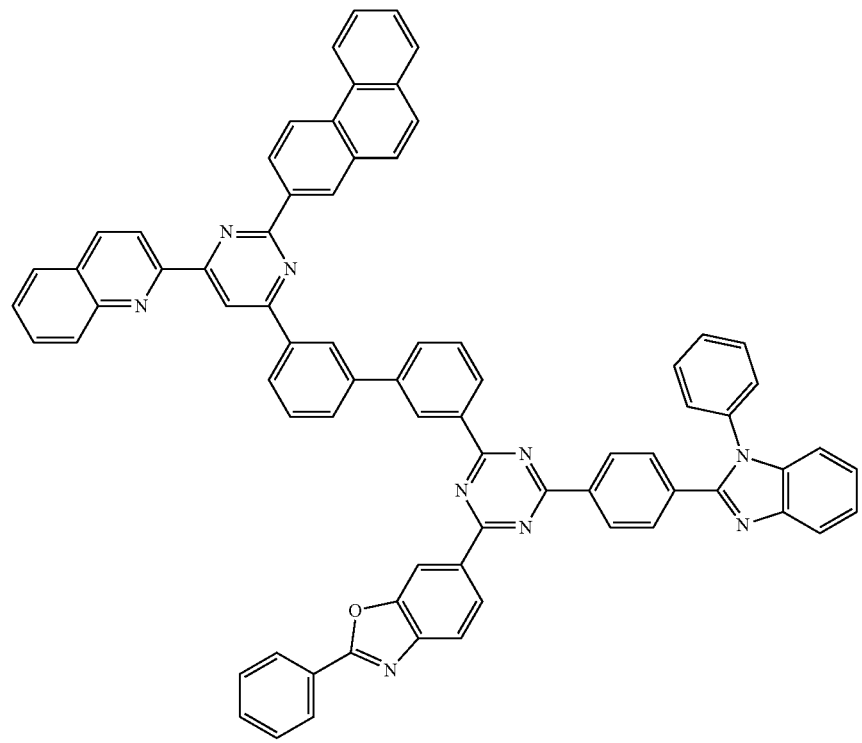
690
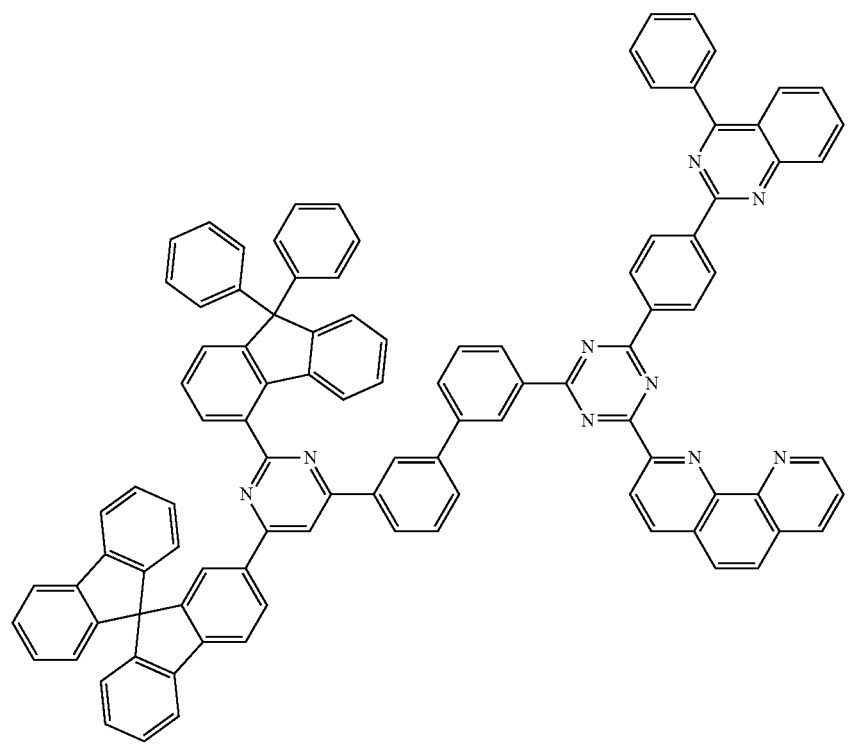
691

827 828
-continued
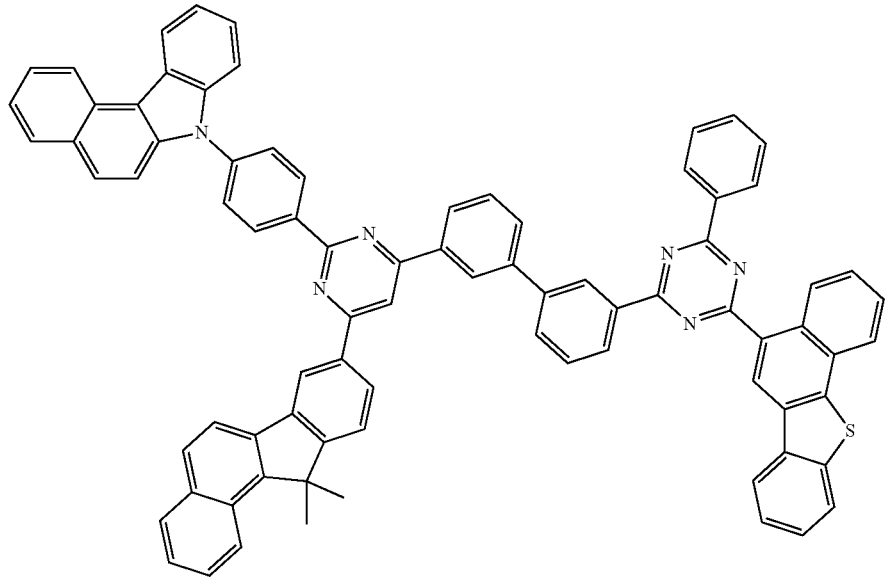
692
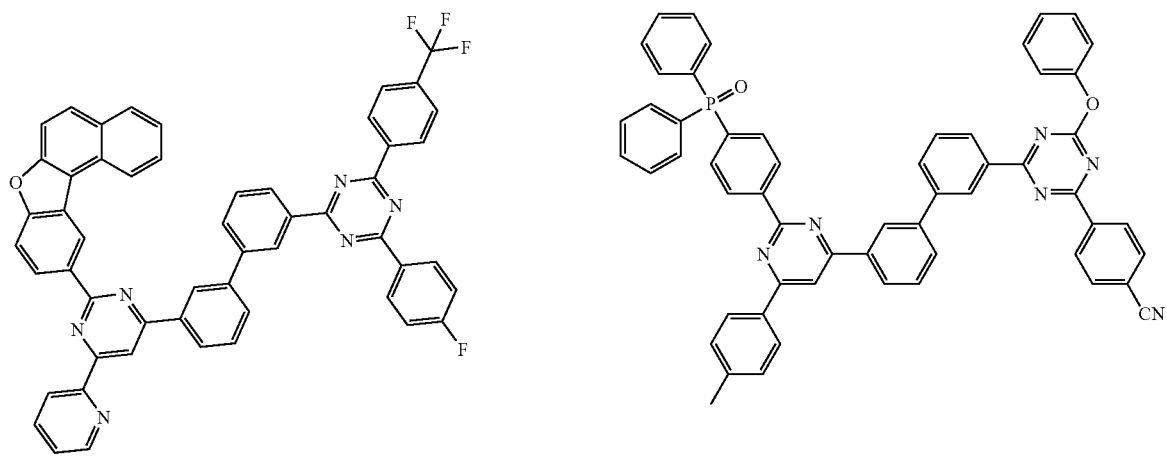
693 694
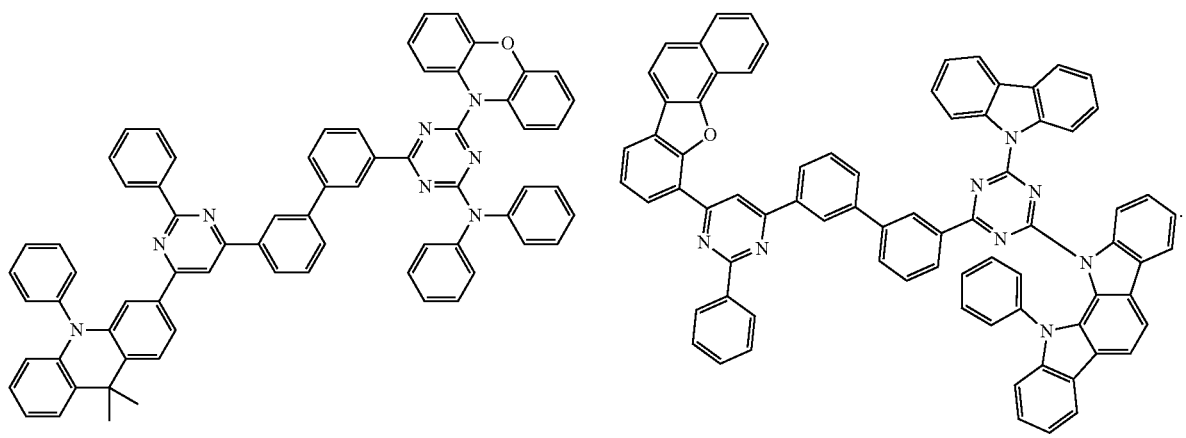
695 696

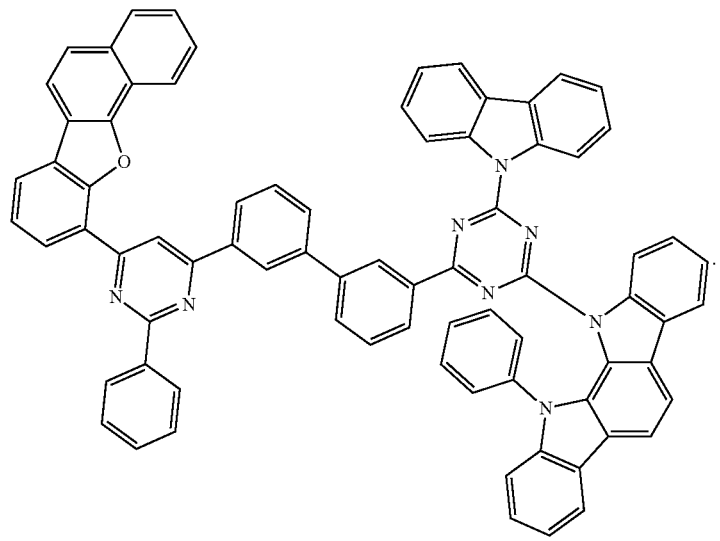

696

3. The organic electroluminescent device of claim 2, wherein the organic layer comprising the compound is selected from the group consisting of: a hole injection layer, a hole transporting layer, an auxiliary luminescent layer, a luminescent layer, an electron transporting layer, an auxiliary electron transporting layer and an electron injection layer.

4. The organic electroluminescent device of claim 2, wherein the organic layer comprising the compound is selected from the group consisting of: a phosphorescent luminescent layer, an electron transporting layer and an auxiliary electron transporting layer.

* * * * *